(12) United States Patent
Hornberger et al.

(10) Patent No.: US 12,180,193 B2
(45) Date of Patent: Dec. 31, 2024

(54) ACCELERATING FIBROSARCOMA PROTEIN DEGRADING COMPOUNDS AND ASSOCIATED METHODS OF USE

(71) Applicant: Arvinas Operations, Inc., New Haven, CT (US)

(72) Inventors: Keith R. Hornberger, Southbury, CT (US); Jing Wang, Milford, CT (US)

(73) Assignee: Arvinas Operations, Inc., New Haven, CT (US)

( * ) Notice: Subject to any disclaimer, the term of this patent is extended or adjusted under 35 U.S.C. 154(b) by 79 days.

(21) Appl. No.: 17/459,179

(22) Filed: Aug. 27, 2021

(65) Prior Publication Data

US 2023/0081501 A1    Mar. 16, 2023

Related U.S. Application Data

(60) Provisional application No. 63/219,254, filed on Jul. 7, 2021, provisional application No. 63/071,824, filed on Aug. 28, 2020.

(51) Int. Cl.
*C07D 403/14* (2006.01)

(52) U.S. Cl.
CPC ................... *C07D 403/14* (2013.01)

(58) Field of Classification Search
CPC ................................ C07D 403/14
See application file for complete search history.

(56) References Cited

U.S. PATENT DOCUMENTS

| | | | |
|---|---|---|---|
| 6,268,391 B1 | 7/2001 | Dickerson et al. | |
| 6,306,663 B1 | 10/2001 | Kenten et al. | |
| 6,670,348 B1 | 12/2003 | Rosen et al. | |
| 7,030,141 B2 | 4/2006 | Bigge et al. | |
| 7,041,298 B2 | 5/2006 | Deshaies et al. | |
| 7,208,157 B2 | 4/2007 | Dashaies et al. | |
| 7,244,851 B2 | 7/2007 | Cohen et al. | |
| 7,345,081 B2 | 3/2008 | Cohen et al. | |
| 7,419,975 B2 | 9/2008 | Palermo et al. | |
| 7,517,906 B2 | 4/2009 | Condon et al. | |
| 7,915,293 B2 | 3/2011 | Ramesh | |
| 9,447,070 B2 | 9/2016 | Muller et al. | |
| 9,500,653 B2 | 11/2016 | Crews et al. | |
| 9,632,089 B2 | 4/2017 | Crews et al. | |
| 10,604,506 B2 | 3/2020 | Crew et al. | |
| 10,723,717 B2 | 7/2020 | Crew et al. | |
| 11,173,211 B2 * | 11/2021 | Crew | A61K 47/55 |
| 11,266,653 B2 | 3/2022 | Cooke | |
| 11,338,012 B2 | 5/2022 | Wang et al. | |
| 11,414,404 B2 | 8/2022 | Barbour et al. | |
| 2003/0096841 A1 | 5/2003 | Robarge et al. | |
| 2006/0128632 A1 | 6/2006 | Sharma et al. | |
| 2008/0051432 A1 | 2/2008 | Zhang | |
| 2008/0214501 A1 | 9/2008 | Pan et al. | |
| 2008/0269140 A1 | 10/2008 | Wang et al. | |
| 2010/0203012 A1 | 8/2010 | Laurent et al. | |
| 2011/0195043 A1 | 8/2011 | Sun et al. | |
| 2011/0230457 A1 | 9/2011 | Berghausen et al. | |
| 2012/0270800 A1 | 10/2012 | Verdine et al. | |
| 2013/0029993 A1 | 1/2013 | Stadtmueller | |
| 2014/0088143 A1 | 3/2014 | Jain | |
| 2014/0235629 A1 | 8/2014 | Bartberger et al. | |
| 2014/0243372 A1 | 8/2014 | Rew | |
| 2014/0302523 A1 | 10/2014 | Crews et al. | |
| 2014/0356322 A1 | 12/2014 | Crews et al. | |
| 2015/0119435 A1 | 4/2015 | Crews et al. | |
| 2015/0141470 A1 | 5/2015 | Garraway et al. | |
| 2015/0259288 A1 | 9/2015 | Nam et al. | |
| 2015/0291562 A1 | 10/2015 | Crew et al. | |
| 2015/0344473 A1 | 12/2015 | Du et al. | |
| 2016/0022642 A1 | 1/2016 | Crews et al. | |
| 2016/0045607 A1 | 2/2016 | Crew et al. | |
| 2016/0058872 A1 | 3/2016 | Crew et al. | |

(Continued)

FOREIGN PATENT DOCUMENTS

| | | |
|---|---|---|
| CN | 1844118 A | 10/2006 |
| CN | 102050793 A | 5/2011 |

(Continued)

OTHER PUBLICATIONS

Takle, A. K., et al., (378) The identification of potent and selective imidazole-based inhibitors of B-Raf kinase, Bioorganic & Medicinal Chemistry Letters 16 (2006) 378-381, (Jan. 2006).

Kim, Minjung, et al., Design, synthesis and biological evaluation of benzyl 2-(1H-imidazole-1-yl) pyrimidine analogues as selective and potent Raf inhibitors, Bioorganic & Medicinal Chemistry Letters, 24 (May 17, 2014) 3600-3604.

Ahn et al., HIF-1 alpha peptide derivatives with modifications at the hydroxyproline residue as activators of HIF-1alpha. Bioorg Med Chem Lett. Aug. 1, 2009;19(15):4403-5.

Ammar et al., Recent advances of RAF (rapidly accelerated fibrosarcoma) inhibitors as anti-cancer agents. Eur J Med Chem. Oct. 5, 2018;158:144-166.

Ardecky et al., Design, synthesis and evaluation of inhibitor of apoptosis protein (IAP) antagonists that are highly selective for the BIR2 domain of XIAP. Bioorg Med Chem Lett. Jul. 15, 2013;23(14):4253-7.

Arora et al., Design, synthesis and characterisation of a novel type II B-RAF paradox breaker inhibitor. Eur J Med Chem. Mar. 15, 2023;250:115231, 44 pages. Pre-publication edition.

(Continued)

*Primary Examiner* — James D. Anderson
(74) *Attorney, Agent, or Firm* — McCarter & English, LLP; Michael J. DeGrazia; James M. Alburger

(57) ABSTRACT

Bifunctional compounds, which find utility as modulators of Rapidly Accelerated Fibrosarcoma (Raf, such as c-Raf, A-Raf, and/or B-Raf), are described herein. In particular, the hetero-bifunctional compounds of the present disclosure contain on one end a moiety that binds to the cereblon E3 ubiquitin ligase and on the other end a moiety which binds Raf, such that the target protein is placed in proximity to the ubiquitin ligase to effect degradation (and inhibition) of target protein. The hetero-bifunctional compounds of the present disclosure exhibit a broad range of pharmacological activities associated with degradation/inhibition of target protein. Diseases or disorders that result from aberrant regulation of the target protein are treated or prevented with compounds and compositions of the present disclosure.

4 Claims, 1 Drawing Sheet

(56) References Cited

U.S. PATENT DOCUMENTS

| | | |
|---|---|---|
| 2016/0136230 A1 | 5/2016 | Campos et al. |
| 2016/0214972 A1 | 7/2016 | Jin et al. |
| 2016/0243247 A1 | 8/2016 | Bradner et al. |
| 2016/0272639 A1 | 9/2016 | Crew et al. |
| 2016/0368911 A1 | 12/2016 | Campos et al. |
| 2017/0008904 A1 | 1/2017 | Crew et al. |
| 2017/0037004 A1 | 2/2017 | Crew et al. |
| 2017/0065719 A1 | 3/2017 | Qian et al. |
| 2017/0121321 A1 | 5/2017 | Crews et al. |
| 2017/0281784 A1 | 10/2017 | Wang et al. |
| 2017/0307614 A1 | 10/2017 | Crews et al. |
| 2017/0327469 A1 | 11/2017 | Crew et al. |
| 2018/0015087 A1 | 1/2018 | Liu et al. |
| 2018/0072711 A1 | 3/2018 | Crew et al. |
| 2018/0099940 A1 | 4/2018 | Crew et al. |
| 2018/0125821 A1 | 5/2018 | Crew et al. |
| 2018/0147202 A1 | 5/2018 | Crew et al. |
| 2018/0155322 A1 | 6/2018 | Crew et al. |
| 2018/0177750 A1 | 6/2018 | Crew et al. |
| 2018/0179183 A1 | 6/2018 | Crew et al. |
| 2018/0193470 A1 | 7/2018 | Crew et al. |
| 2018/0215731 A1 | 8/2018 | Crew et al. |
| 2018/0228907 A1 | 8/2018 | Crew et al. |
| 2018/0256586 A1 | 9/2018 | Crew et al. |
| 2018/0353501 A1 | 12/2018 | Crew et al. |
| 2019/0151295 A1 | 5/2019 | Crew et al. |
| 2020/0129627 A1* | 4/2020 | Crew .................. A61K 47/555 |
| 2021/0087171 A1 | 3/2021 | Fan et al. |
| 2022/0125936 A1 | 4/2022 | Sicheri et al. |
| 2022/0144809 A1 | 5/2022 | Dong et al. |
| 2022/0217979 A1 | 7/2022 | Tsuruda et al. |
| 2023/0000994 A1 | 1/2023 | Crew et al. |

FOREIGN PATENT DOCUMENTS

| | | |
|---|---|---|
| CN | 103159736 A | 6/2013 |
| CN | 103688176 A | 3/2014 |
| CN | 108276352 A | 7/2018 |
| CN | 114805303 A | 7/2022 |
| EP | 2985285 A1 | 2/2016 |
| JP | 2004-525889 A | 8/2004 |
| JP | 2010-502627 A | 1/2010 |
| JP | 2020-189891 A | 11/2020 |
| KR | 20180011759 A | 2/2018 |
| RU | 2008112221 A | 10/2009 |
| RU | 2418800 C2 | 5/2011 |
| RU | 2448101 C2 | 4/2012 |
| RU | 2011121567 A | 12/2012 |
| RU | 2012138709 A | 3/2014 |
| WO | WO-1998/003502 A1 | 1/1998 |
| WO | WO-2000/066119 A1 | 11/2000 |
| WO | WO-2002/048115 A2 | 6/2002 |
| WO | WO-2002/066512 A1 | 8/2002 |
| WO | WO-2002/096873 A1 | 12/2002 |
| WO | WO-2002/100845 A1 | 12/2002 |
| WO | WO-2003/033480 A1 | 4/2003 |
| WO | WO-2004/113307 A1 | 12/2004 |
| WO | WO-2005/016326 A2 | 2/2005 |
| WO | WO-2005/042502 A1 | 5/2005 |
| WO | WO-2005/097791 A1 | 10/2005 |
| WO | WO-2006/024834 A1 | 3/2006 |
| WO | WO-2006/069063 A1 | 6/2006 |
| WO | WO-2006/084015 A2 | 8/2006 |
| WO | WO-2006/090143 A1 | 8/2006 |
| WO | WO-2006/113942 A2 | 10/2006 |
| WO | WO-2007/056167 A2 | 5/2007 |
| WO | WO-2007/101347 A1 | 9/2007 |
| WO | WO-2007/106670 A2 | 9/2007 |
| WO | WO-2007/115289 A2 | 10/2007 |
| WO | WO-2007/130626 A2 | 11/2007 |
| WO | WO-2008/011392 A2 | 1/2008 |
| WO | WO-2008/014236 A1 | 1/2008 |
| WO | WO-2008/044688 A1 | 4/2008 |
| WO | WO-2008/109057 A1 | 9/2008 |
| WO | WO-2008/128121 A1 | 10/2008 |
| WO | WO-2008/128171 A2 | 10/2008 |
| WO | WO-2008/134679 A1 | 11/2008 |
| WO | WO-2009/015254 A1 | 1/2009 |
| WO | WO-2009/060292 A2 | 5/2009 |
| WO | WO-2010/063784 A1 | 6/2010 |
| WO | WO-2010/107485 A1 | 9/2010 |
| WO | WO-2010/141805 A1 | 12/2010 |
| WO | WO-2011/008260 A2 | 1/2011 |
| WO | WO-2011/045258 A1 | 4/2011 |
| WO | WO-2012/003281 A2 | 1/2012 |
| WO | WO-2012/007409 A1 | 1/2012 |
| WO | WO-2012/040527 A2 | 3/2012 |
| WO | WO-2012/078559 A2 | 6/2012 |
| WO | WO-2012/090104 A1 | 7/2012 |
| WO | WO-2012/118492 A1 | 9/2012 |
| WO | WO-2013/071035 A1 | 5/2013 |
| WO | WO-2013/071039 A1 | 5/2013 |
| WO | WO-2013/097224 A1 | 7/2013 |
| WO | WO-2013/106643 A2 | 7/2013 |
| WO | WO-2013/106646 A2 | 7/2013 |
| WO | WO-2013/170147 A1 | 11/2013 |
| WO | WO-2013/175417 A1 | 11/2013 |
| WO | WO-2013/178570 A1 | 12/2013 |
| WO | WO-2014/011712 A1 | 1/2014 |
| WO | WO-2014/020502 A2 | 2/2014 |
| WO | WO-2014/025759 A1 | 2/2014 |
| WO | WO-2014/038606 A1 | 3/2014 |
| WO | WO-2014/047024 A1 | 3/2014 |
| WO | WO-2014/055461 A1 | 4/2014 |
| WO | WO-2014/074658 A1 | 5/2014 |
| WO | WO-2014/100065 A1 | 6/2014 |
| WO | WO-2014/100071 A2 | 6/2014 |
| WO | WO-2014/107713 A1 | 7/2014 |
| WO | WO-2014/108452 A1 | 7/2014 |
| WO | WO-2014/123418 A1 | 8/2014 |
| WO | WO-2014/134201 A1 | 9/2014 |
| WO | WO-2014/151863 A1 | 9/2014 |
| WO | WO-2014/182643 A2 | 11/2014 |
| WO | WO-2015/000868 A1 | 1/2015 |
| WO | WO-2015/006524 A1 | 1/2015 |
| WO | WO-2015/040169 A1 | 3/2015 |
| WO | WO-2015/097621 A2 | 7/2015 |
| WO | WO-2015/160845 A2 | 10/2015 |
| WO | WO-2016/045765 A1 | 3/2016 |
| WO | WO-2016/105518 A1 | 6/2016 |
| WO | WO-2016/118666 A1 | 7/2016 |
| WO | WO-2016/146985 A1 | 9/2016 |
| WO | WO-2016/149668 A1 | 9/2016 |
| WO | WO-2016/151144 A1 | 9/2016 |
| WO | WO-2016/169989 A1 | 10/2016 |
| WO | WO-2016/172134 A2 | 10/2016 |
| WO | WO-2016/197114 A1 | 12/2016 |
| WO | WO-2017/007612 A1 | 1/2017 |
| WO | WO-2017/011590 A1 | 1/2017 |
| WO | WO-2017/024317 A2 | 2/2017 |
| WO | WO-2017/024318 A1 | 2/2017 |
| WO | WO-2017/024319 A1 | 2/2017 |
| WO | WO-2017/030814 A1 | 2/2017 |
| WO | WO-2017/046036 A1 | 3/2017 |
| WO | WO-2017/079267 A1 | 5/2017 |
| WO | WO-2017/117473 A1 | 7/2017 |
| WO | WO-2017/117474 A1 | 7/2017 |
| WO | WO-2017/161119 A1 | 9/2017 |
| WO | WO-2017/176957 A1 | 10/2017 |
| WO | WO-2017/176958 A1 | 10/2017 |
| WO | WO-2017/185023 A1 | 10/2017 |
| WO | WO-2017/185031 A1 | 10/2017 |
| WO | WO-2017/185034 A1 | 10/2017 |
| WO | WO-2017/185036 A1 | 10/2017 |
| WO | WO-2017/197051 A1 | 11/2017 |
| WO | WO-2017/197055 A1 | 11/2017 |
| WO | WO-2017/197056 A1 | 11/2017 |
| WO | WO-2017/223415 A1 | 12/2017 |
| WO | WO-2017/223452 A1 | 12/2017 |
| WO | WO-2018/052949 A1 | 3/2018 |
| WO | WO-2018/064589 A1 | 4/2018 |
| WO | WO-2018/098275 A1 | 5/2018 |
| WO | WO-2018/098280 A1 | 5/2018 |
| WO | WO-2018/098288 A1 | 5/2018 |

(56) References Cited

FOREIGN PATENT DOCUMENTS

| | | |
|---|---|---|
| WO | WO-2018/106870 A1 | 6/2018 |
| WO | WO-2018/119448 A1 | 6/2018 |
| WO | WO-2018/148440 A1 | 8/2018 |
| WO | WO-2018/200981 A1 | 11/2018 |
| WO | WO-2020/051564 A1 | 3/2020 |
| WO | WO-2020/203763 A1 | 10/2020 |
| WO | WO-2020/261156 A1 | 12/2020 |
| WO | WO-2021/16055 A1 | 1/2021 |
| WO | WO-2021/25052 A1 | 2/2021 |
| WO | WO-2021/061644 A1 | 4/2021 |
| WO | WO-2021/116050 A1 | 6/2021 |
| WO | WO-2021/129653 A1 | 7/2021 |
| WO | WO-2021/207532 A1 | 10/2021 |
| WO | WO-2021/224927 A1 | 11/2021 |
| WO | WO-2021/250521 A1 | 12/2021 |
| WO | WO-2021/255212 A1 | 12/2021 |
| WO | WO-2021/255213 A1 | 12/2021 |
| WO | WO-2022/011204 A1 | 1/2022 |
| WO | WO-2022/047145 A1 | 3/2022 |
| WO | WO-2022/061348 A1 | 3/2022 |
| WO | WO-2022/098544 A1 | 5/2022 |
| WO | WO-2022/129259 A1 | 6/2022 |
| WO | WO-2022/129260 A1 | 6/2022 |
| WO | WO-2022/258584 A1 | 12/2022 |
| WO | WO-2022/258600 A1 | 12/2022 |
| WO | WO-2022/258612 A1 | 12/2022 |
| WO | WO-2022/259157 A1 | 12/2022 |
| WO | WO-2022/261250 A1 | 12/2022 |
| WO | WO-2023/076991 A1 | 5/2023 |
| WO | WO-2023/078881 A1 | 5/2023 |

OTHER PUBLICATIONS

Asano et al., Design, stereoselective synthesis, and biological evaluation of novel tri-cyclic compounds as inhibitor of apoptosis proteins (IAP) antagonists. Bioorg Med Chem. Sep. 15, 2013;21(18):5725-37.
Avery et al., Onco-immunomodulatory properties of pharmacological interference with RAS-RAF-MEK-ERK pathway hyperactivation. Front Oncol. Jul. 27, 2022;12:931774, 30 pages.
Bargagna-Mohan et al., Use of PROTACS as molecular probes of angiogenesis. Bioorg Med Chem Lett. Jun. 2, 2005;15(11):2724-7.
Bondeson et al., Catalytic in vivo protein knockdown by small-molecule PROTACs. Nat Chem Biol. Aug. 2015;11(8):611-7.
Bondeson et al., Lessons in PROTAC Design from Selective Degradation with a Promiscuous Warhead. Cell Chem Biol. Jan. 1, 20188;25(1):78-87.e5.
Bondeson et al., Targeted Protein Degradation by Small Molecules. Annu Rev Pharmacol Toxicol. Jan. 6, 2017;57:107-123.
Buckley et al., HaloPROTACS: Use of Small Molecule PROTACs to Induce Degradation of Halo Tag Fusion Proteins. ACS Chem Biol. Aug. 21, 2015;10(8):1831-7.
Buckley et al., Small-molecule inhibitors of the interaction between the E3 ligase VHL and HIF1a. Angew Chem Int Ed Engl. Nov. 12, 2012;51(46):11463-7.
Buckley et al., Targeting the von Hippel-Lindau E3 ubiquitin ligase using small molecules to disrupt the VHL/HIF-1a interaction. J Am Chem Soc. Mar. 14, 2012;134(10):4465-8.
Burslem et al., Small-Molecule Modulation of Protein Homeostasis. Chem Rev. Sep. 13, 2017;117(17):11269-11301.
Burslem et al., The Advantages of Targeted Protein Degradation Over Inhibition: An RTK Case Study. Cell Chem Biol. Jan. 18, 2018;25(1):67-77.e3.
Capitosti et al., Thalidomide analogues demonstrate dual inhibition of both angiogenesis and prostate cancer. Bioorg Med Chem. Jan. 15, 2004;12(2):327-36.
Carmony et al., PROTAC-induced proteolytic targeting. Methods Mol Biol. 2012;832:627-38.
CAS Registry No. 1004933-70-3, STN, dated Feb. 21, 2008, 1 page.
CAS Registry No. 1226974-40-8, STN, dated Jun. 4, 2010, 1 page.
CAS Registry No. 1542127-97-8, STN, dated Feb. 11, 2014, 5 pages.
CAS Registry No. 871986-52-6, 1 page, Jan. 16, 2006.
Chan et al., Impact of Target Warhead and Linkage Vector on Inducing Protein Degradation: Comparison of Bromodomain and Extra-Terminal (BET) Degraders Derived from Triazolodiazepine (JQ1) and Tetrahydroquinoline (I-BET726) Bet Inhibitor Scaffolds. J Med Chem. Jan. 2, 20185;61(2):504-513.
Chene, Inhibiting the p53-MDM2 interaction: an important target for cancer therapy. Nat Rev. Cancer. Feb. 2003;3(2):102-9.
Churcher, Protac-Induced Protein Degradation in Drug Discovery: Breaking the Rules or Just Making New Ones? J Med Chem. Jan. 25, 2018;61(2):444-452.
Cohen et al., Antagonists of inhibitor of apoptosis proteins based on thiazole amide isosteres. Bioorg Med Chem Lett. Apr. 1, 2010;20(7):2229-33.
Cohen et al., Orally bioavailable antagonists of inhibitor of apoptosis proteins based on an azabicyclooctane scaffold. J Med Chem. Mar. 26, 2009;52(6):1723-30.
Contino-Pepin et al., Preliminary biological evaluations of new thalidomide analogues for multiple sclerosis application. Bioorg Med Chem Lett. Feb. 1, 2009;19(3):878-81.
Corson et al., Design and Applications of Bifunctional Small Molecules: Why Two Heads Are Better Than One. ACS Chem Biol. Nov. 21, 2008;3(11):677-692.
Crew et al., Identification and Characterization of Von Hippel-Lindau-Recruiting Proteolysis Targeting Chimeras (PROTACs) of TANK-Binding Kinase 1. J Med Chem. Jan. 25, 2018;61(2):583-598.
Crews. Targeting the undruggable proteome: the small molecules of my dreams. Chem Biol. Jun. 25, 2010;17(6):551-5.
Cromm et al., Targeted Protein Degradation: from Chemical Biology to Drug Discovery. Cell Chem Biol. Sep. 21, 2017;24(9):1181-1190.
Cyrus et al., Impact of linker length on the activity of PROTACs. Mol Biosyst. Feb. 2011;7(2):359-64.
Cyrus et al., Jostling for position: optimizing linker location in the design of estrogen receptor-targeting PROTACs. ChemMedChem. Jul. 5, 2010;5(7):979-85.
Cyrus et al., Two-headed PROTAC: an effective new tool for targeted protein degradation. Chembiochem. Jul. 26, 2010;11(11):1531-4.
Di et al., Reactivation of p53 by inhibiting Mdm2 E3 ligase: a novel antitumor approach. Curr Cancer Drug Targets. Oct. 2011; 11(8):987-94.
Ding et al., Discovery of RG7388, a potent and selective p53-MDM2 inhibitor in clinical development. J Med Chem. Jul. 25, 2013;56(14):5979-83.
Dixon et al., Identifying druggable disease-modifying gene products. Curr Opin Chem Biol. Dec. 2009;13(5-6):549-55.
Fischer et al., Structure of the DDB1-CRBN E3 ubiquitin ligase in complex with thalidomide. Nature. Aug. 7, 2014;512(7512):49-53.
Flygare et al., Small-molecule pan-IAP antagonists: a patent review. Expert Opin Ther Pat. Feb. 2010;20(2):251-67.
Gadd et al., Structural basis of PROTAC cooperative recognition for selective protein degradation. Nat Chem Biol. May 2017;13(5):514-521.
Galdeano et al., Structure-guided design and optimization of small molecules targeting the protein-protein interaction between the von Hippel-Lindau (VHL) E3 ubiquitin ligase and the hypoxia inducible factor (HIF) alpha subunit with in vitro nanomolar affinities. J Med Chem. Oct. 23, 2014;57(20):8657-63.
Golub et al., Molecular classification of cancer: class discovery and class prediction by gene expression monitoring. Science. Oct. 15, 1999;286(5439):531-7.
Gosink et al., Redirecting the specificity of ubiquitination by modifying ubiquitin-conjugating enzymes. Proc Natl Acad Sci U S A. Sep. 26, 1995;92(20):9117-21.
Grasso et al., Chemically Linked Vemurafenib Inhibitors Promote an Inactive BRAFV600E Conformation. ACS Chem Biol. Oct. 21, 2016;11(10):2876-2888.
Graves et al., The dynamic nature of the kinome. Biochem J. Feb. 15, 2013;450(1):1-8.

(56) References Cited

OTHER PUBLICATIONS

Han et al., Discovery of ARD-69 as a Highly Potent Proteolysis Targeting Chimera (PROTAC) Degrader of Androgen Receptor (AR) for the Treatment of Prostate Cancer. J Med Chem. Jan. 24, 2019;62(2):941-964.
Han et al., Discovery of Selective Small Molecule Degraders of BRAF-V600E. J Med Chem. Apr. 23, 2020;63(8):4069-4080. Pre-publication edition.
Hansen et al., Potent and selective pyrazole-based inhibitors of B-Raf kinase. Bioorg Med Chem Lett. Aug. 15, 2008;18(16):4692-5.
Haupt et al., Mdm2 promotes the rapid degradation of p53. Nature. May 15, 1997;387(6630):296-9.
Hennessy et al., Discovery of aminopiperidine-based Smac mimetics as IAP antagonists. Bioorg Med Chem Lett. Feb. 15, 2012;22(4):1690-4.
Hines et al., Posttranslational protein knockdown coupled to receptor tyrosine kinase activation with phosphoPROTACs. Proc Natl Acad Sci U S A. May 28, 2013;110(22):8942-7.
Hird et al., Structure-based design and synthesis of tricyclic IAP (Inhibitors of Apoptosis Proteins) inhibitors. Bioorg Med Chem Lett. Apr. 1, 2014;24(7):1820-4.
Hon et al., Structural basis for the recognition of hydroxyproline in HIF-1 alpha by pVHL. Nature. Jun. 27, 2002;417(6892):975-8.
Hu et al., Discovery of ERD-308 as a Highly Potent Proteolysis Targeting Chimera (PROTAC) Degrader of Estrogen Receptor (ER). J Med Chem. Feb. 14, 2019;62(3):1420-1442.
Huang et al., A Chemoproteomic Approach to Query the Degradable Kinome Using a Multi-kinase Degrader. Cell Chem Biol. Jan. 18, 2018;25(1):88-99.e6.
Huang et al., Drugging the undruggables: exploring the ubiquitin system for drug development. Cell Res. Apr. 2016;26(4):484-98.
Hughes et al., Molecular recognition of ternary complexes: a new dimension in the structure-guided design of chemical degraders. Essays Biochem. Nov. 8, 2017;61(5):505-516.
Ishikawa et al., Design and synthesis of novel human epidermal growth factor receptor 2 (HER2)/epidermal growth factor receptor (EGFR) dual inhibitors bearing a pyrrolo[3,2- d]pyrimidine scaffold. J Med Chem. Dec. 8, 2011;54(23):8030-50.
Itoh et al., Development of target protein-selective degradation inducer for protein knockdown. Bioorg Med Chem. May 15, 2011;19(10):3229-41.
Itoh et al., Protein knockdown using methyl bestatin-ligand hybrid molecules: design and synthesis of inducers of ubiquitination-mediated degradation of cellular retinoic acid-binding proteins. J Am Chem Soc. Apr. 28, 2018;132(16):5820-6.
Ivan et al., HIFalpha targeted for VHL-mediated destruction by proline hydroxylation: implications for O2 sensing. Science. Apr. 20, 2001;292(5516):464-8.
Jang et al., Targeted Degradation of Proteins by PROTACs. Curr Protoc Chem Biol. Jun. 1, 2010;2(2):71-87.
Kim et al., Design, synthesis and biological evaluation of benzyl 2-(1H-imidazole-1-yl) pyrimidine analogues as selective and potent Raf inhibitors. Bioorg Med Chem Lett. Aug. 1, 2014;24(15):3600-4.
Kim et al., Discovery of tetrahydroisoquinoline-based bivalent heterodimeric IAP antagonists. Bioorg Med Chem Lett. Nov. 1, 2014;24(21):5022-9.
Knott, Compounds containing sulphur chromophores. Part I. The action of bases on heterocyclic sulphide quarternary salts. Journal of the Chemical Society. 1955, pp. 916-927.
Knott, Compounds containing sulphur chromophores. Part V. Complex Cyanines. The Journal of the Chemical Society. 1955;949-954.
Kronke et al., Lenalidomide causes selective degradation of IKZF1 and IKZF3 in multiple myeloma cells. Science. Jan. 17, 2014;343(6168):301-5.
Lackey et al., The discovery of potent cRaf1 kinase inhibitors. Bioorg Med Chem Lett. Feb. 7, 2000;10(3):223-6.
Lai et al., Induced protein degradation: an emerging drug discovery paradigm. Nat Rev Drug Discov. Feb. 2017; 16(2):101-114.
Lai et al., Modular PROTAC Design for the Degradation of Oncogenic BCR-ABL. Angew Chem Int Ed Engl. Jan. 11, 2016;55(2):807-10.
Lala et al., Role of nitric oxide in tumor progression: lessons from experimental tumors. Cancer Metastasis Rev. Mar. 1998; 17(1):91-106.
Lebraud et al., Protein Degradation by In-Cell Self-Assembly of Proteolysis Targeting Chimeras. ACS Cent Sci. Dec. 28, 2016;2(12):927-934.
Lee et al., Targeted degradation of the aryl hydrocarbon receptor by the PROTAC approach: a useful chemical genetic tool. Chembiochem. Nov. 23, 2007;8(17):2058-62.
Levine et al., Targeting the androgen receptor with steroid conjugates. J Med Chem. Oct. 23, 2014;57(20):8224-37.
Li et al., Single Polymer-drug Conjugate Carrying Two Drugs for Fixed-dose Codelivery. Medicinal Chemistry, 2014;4(10):676-683.
Liang et al., The Discovery and Characterization of CFT-18442: A Potent, Selective, and Orally Bioavailable Degrader of BRAF V600E. 16th Winter Conference on Medicinal & Bioorganic Chemistry. 1 page, Feb. 1, 2023.
Liu et al., Design and biological characterization of hybrid compounds of curcumin and thalidomide for multiple myeloma. Org Biomol Chem. Aug. 7, 2013;11(29):4757-63.
Lopez-Girona et al., Cereblon is a direct protein target for immunomodulatory and antiproliferative activities of lenalidomide and pomalidomide. Leukemia. Nov. 2012;26(11):2326-35.
Lu et al., Hijacking the E3 Ubiquitin Ligase Cereblon to Efficiently Target BRD4. Chem Biol. Jun. 18, 2015;22(6):755-63.
Lu et al., The myeloma drug lenalidomide promotes the cereblon-dependent destruction of Ikaros proteins. Science. Jan. 17, 2014;343(6168):305-9.
Mahalingam et al., Targeting HSP90 for cancer therapy. Br J Cancer. May 19, 2009;100(10):1523-9.
Maniaci et al., Homo-PROTACs: bivalent small-molecule dimerizers of the VHL E3 ubiquitin ligase to induce self-degradation. Nat Commun. Oct. 10, 2017;8(1):830, 14 pages.
Mannhold et al., IAP antagonists: promising candidates for cancer therapy. Drug Discov Today. Mar. 2010;15(5-6):210-9.
Medlineplus, Cancer. Retrieved online at: www.nlm.nih.gov/medlineplus/cancer.html. 10 page, Jun. 27, 2007.
Min et al., Structure of an HIF-1alpha-pVHL complex: hydroxyproline recognition in signaling. Science. Jun. 7, 2002;296(5574):1886-9.
Miyazaki et al., Discovery of DS-5272 as a promising candidate: A potent and orally active p53-MDM2 interaction inhibitor. Bioorg Med Chem. May 15, 2015;23(10):2360-7.
Muller et al., Amino-substituted thalidomide analogs: potent inhibitors of TNF-alpha production. Bioorg Med Chem Lett. Jun. 7, 1999;9(11):1625-30.
Ndubaku et al., Antagonism of c-IAP and XIAP proteins is required for efficient induction of cell death by small-molecule IAP antagonists. ACS Chem Biol. Jul. 17, 2009;4(7):557-66.
Neklesa et al., Greasy tags for protein removal. Nature. Jul. 18, 2012;487(7407):308-9.
Neklesa et al., Targeted protein degradation by PROTACs. Pharmacol Ther. Jun. 2017;174:138-144.
Nikolovska-Coleska et al., Interaction of a cyclic, bivalent smac mimetic with the x-linked inhibitor of apoptosis protein. Biochemistry. Sep. 16, 2008;47(37):9811-24.
Noguchi-Yachide, Bet Bromodomain as a Target of Epigenetic Therapy. Chem Pharm Bull (Tokyo). 2016;64(6):540-7.
Ohoka et al., SNIPER(TACC3) induces cytoplasmic vacuolization and sensitizes cancer cells to Bortezomib. Cancer Sci. May 2017;108(5):1032-1041.
Oost et al., Discovery of potent antagonists of the antiapoptotic protein XIAP for the treatment of cancer. J Med Chem. Aug. 26, 2004;47(18):4417-26.
Ottis et al., Assessing Different E3 Ligases for Small Molecule Induced Protein Ubiquitination and Degradation. ACS Chem Biol. Oct. 20, 2017;12(10):2570-2578.
Ottis et al., Proteolysis-Targeting Chimeras: Induced Protein Degradation as a Therapeutic Strategy. ACS Chem Biol. Apr. 21, 2017;12(4):892-898.

(56) References Cited

OTHER PUBLICATIONS

Perez et al., Discovery of potent heterodimeric antagonists of inhibitor of apoptosis proteins (IAPs) with sustained antitumor activity. J Med Chem. Feb. 12, 2015;58(3):1556-62.
Posternak et al., Functional characterization of a PROTAC directed against BRAF mutant V600E. Nat Chem Biol. Nov. 2020;16(11):1170-1178.
Poulikakos et al., RAF inhibitors transactivate RAF dimers and ERK signalling in cells with wild-type BRAF. Nature. Mar. 18, 2010;464(7287):427-30.
Powell et al., Chemically Induced Degradation of Anaplastic Lymphoma Kinase (Alk). J Med Chem. May 10, 2018;61(9):4249-4255.
Puppala et al., Development of an aryl hydrocarbon receptor antagonist using the proteolysis-targeting chimeric molecules approach: a potential tool for chemoprevention. Mol Pharmacol. Apr. 2008;73(4):1064-71.
Raina et al., Chemical inducers of targeted protein degradation. J Biol Chem. Apr. 9, 2010;285(15):11057-60.
Raina et al., PROTAC-induced BET protein degradation as a therapy for castration-resistant prostate cancer. Proc Natl Acad Sci U S A. Jun. 28, 2016;113(26):7124-9.
Raina et al., Targeted protein knockdown using small molecule degraders. Curr Opin Chem Biol. Aug. 2017;39:46-53.
Remillard et al., Degradation of the BAF Complex Factor BRD9 by Heterobifunctional Ligands. Angew Chem Int Ed Engl. May 15, 2017;56(21):5738-5743.
Rew et al., Discovery of AM-7209, a potent and selective 4-amidobenzoic acid inhibitor of the MDM2-p53 interaction. J Med Chem. Dec. 26, 2014;57(24):10499-511.
Rodriguez-Gonzalez et al., Targeting steroid hormone receptors for ubiquitination and degradation in breast and prostate cancer. Oncogene. Dec. 4, 2008;27(57):7201-11.
Rotili et al., Photoactivable peptides for identifying enzyme-substrate and protein-protein interactions. Chem Commun (Camb). Feb. 7, 2011;47(5):1488-90.
Ruchelman et al., Isosteric analogs of lenalidomide and pomalidomide: synthesis and biological activity. Bioorg Med Chem Lett. Jan. 1, 2013;23(1):360-5.
Sakamoto et al., Development of Protacs to target cancer-promoting proteins for ubiquitination and degradation. Mol Cell Proteomics. Dec. 2003;2(12):1350-8.
Sakamoto et al., Protacs: chimeric molecules that target proteins to the Skp1-Cullin-F box complex for ubiquitination and degradation. Proc Natl Acad Sci U S A. Jul. 17, 2001;98(15):8554-9.
Salami et al., Waste disposal-An attractive strategy for cancer therapy. Science. Mar. 17, 2017;355(6330):1163-1167.
Schiedel et al., Chemically Induced Degradation of Sirtuin 2 (Sirt2) by a Proteolysis Targeting Chimera (PROTAC) Based on Sirtuin Rearranging Ligands (SirReals). J Med Chem. Jan. 25, 2018;61(2):482-491.
Schneekloth et al., Chemical genetic control of protein levels: selective in vivo targeted degradation. J Am Chem Soc. Mar. 31, 2004;126(12):3748-54.
Schneekloth et al., Targeted intracellular protein degradation induced by a small molecule: En route to chemical proteomics. Bioorg Med Chem Lett. Nov. 15, 2008;18(22):5904-8.
Shangary et al., Temporal activation of p53 by a specific MDM2 inhibitor is selectively toxic to tumors and leads to complete tumor growth inhibition. Proc Natl Acad Sci U S A. Mar. 11, 2008;105(10):3933-8.
Smith et al., Targeted Intracellular Protein Degradation Induced by a Small Molecule: En Route to Chemical Proteomics. Bioorg Med Chem Lett. Nov. 15, 2008;18(22):5904-5908.
Stanton et al., Chemically induced proximity in biology and medicine. Science. Mar. 9, 2018;359(6380):eaao5902, 9 pages.
Stanton et al., Chemically induced proximity in biology and medicine. Science. Mar. 9, 2018;359:1117.
Stewart et al., Efforts toward elucidating Thalidomide's molecular target: an expedient synthesis of the first Thalidomide biotin analogue. Org Biomol Chem. Sep. 21, 2010;8(18):4059-62.
STN Accession No. 1957:56724, Compounds containing sulfur Chromophores v. Complex cyanines. 1 page, (2017).
STN Registry No. 1004933-70-3, 2-Pyrrolidinecarboxamide, N-(4-bromo-2-fluorophenyl)-4-hydroxy-1-(2-naphthalenylsulfonyl). 1 page, Feb. 21, 2008.
Stoppler, Endometriosis, Endometriosis definition and facts. Retrieved online at: http://www.medicinenet.com/endometriosis/article.htm. 7 pages, retrieved on Apr. 5, 2017.
Stoppler, Endometriosis, What about surgery for Endometriosis. Retrieved online at: http://www.medicinenet.com/endometriosis/article.htm. 7 pages, retrieved on Apr. 5, 2017.
Sun et al., BET protein proteolysis targeting chimera (PROTAC) exerts potent lethal activity against mantle cell lymphoma cells. Leukemia. Feb. 2018;32(2):343-352.
Sun et al., Discovery of AMG 232, a potent, selective, and orally bioavailable MDM2-p53 inhibitor in clinical development. J Med Chem. Feb. 27, 2014;57(4):1454-72.
Sun et al., Potent bivalent Smac mimetics: effect of the linker on binding to inhibitor of apoptosis proteins (IAPs) and anticancer activity. J Med Chem. May 12, 2011;54(9):3306-18.
Takeuchi et al., Receptor tyrosine kinases and targeted cancer therapeutics. Biol Pharm Bull. 2011;34(12):1774-80.
Toure et al., Small-Molecule PROTACS: New Approaches to Protein Degradation. Angew Chem Int Ed Engl. Feb. 5, 2016;55(6):1966-73.
Turk et al., Binding of thalidomide to alpha1-acid glycoprotein may be involved in its inhibition of tumor necrosis factor alpha production. Proc Natl Acad Sci U S A. Jul. 23, 1996;93(15):7552-6.
Vallee et al., Tricyclic series of heat shock protein 90 (Hsp90) inhibitors part I: discovery of tricyclic imidazo[4,5-c]pyridines as potent inhibitors of the Hsp90 molecular chaperone. J Med Chem. Oct. 27, 2011;54(20):7206-19.
Vamos et al., Expedient synthesis of highly potent antagonists of inhibitor of apoptosis proteins (IAPs) with unique selectivity for ML-Iap. ACS Chem Biol. Apr. 19, 2013;8(4):725-32.
Van Molle et al., Dissecting fragment-based lead discovery at the von Hippel-Lindau protein:hypoxia inducible factor 1a protein-protein interface. Chem Biol. Oct. 26, 2012;19(10):1300-12.
Vassilev et al., In vivo activation of the p53 pathway by small-molecule antagonists of MDM2. Science. Feb. 6, 2004;303(5659):844-8.
Vazquez et al., The genetics of the p53 pathway, apoptosis and cancer therapy. Nat Rev Drug Discov. Dec. 2008;7(12):979-87.
Vu et al., Discovery of RG7112: A Small-Molecule MDM2 Inhibitor in Clinical Development. ACS Med Chem Lett. Apr. 2, 2013;4(5):466-9.
Waizenegger et al., A Novel RAF Kinase Inhibitor with DFG-Out-Binding Mode: High Efficacy in BRAF-Mutant Tumor Xenograft Models in the Absence of Normal Tissue Hyperproliferation. Mol Cancer Ther. Mar. 2016;15(3):354-65.
Wang et al., Discovery of novel second mitochondria-derived activator of caspase mimetics as selective inhibitor of apoptosis protein inhibitors. J Pharmacol Exp Ther. May 2014;349(2):319-29.
Wenglowsky et al., Highly potent and selective 3-N-methylquinazoline-4(3H)-one based inhibitors of B-Raf(V600E) kinase. Bioorg Med Chem Lett. Apr. 15, 2014;24(8):1923-7.
Wichmann et al., Preclinical Characterization of a Next-Generation Brain Permeable, Paradox Breaker BRAF Inhibitor. Clin Cancer Res. Feb. 15, 2022;28(4):770-780.
Winter et al., Phthalimide conjugation as a strategy for in vivo target protein degradation. Science. Jun. 19, 2015;348(6241):1376-81.
Yao et al., BRAF Mutants Evade ERK-Dependent Feedback by Different Mechanisms that Determine Their Sensitivity to Pharmacologic Inhibition. Cancer Cell. Sep. 14, 2015;28(3):370-83.
Yao et al., Tumours with class 3 BRAF mutants are sensitive to the inhibition of activated RAS. Nature. Aug. 10, 2017;548(7666):234-238.
Zengerle et al., Selective Small Molecule Induced Degradation of the BET Bromodomain Protein BRD4. ACS Chem Biol. Aug. 21, 2015;10(8):1770-7.
Zhang et al., RAF inhibitors that evade paradoxical MAPK pathway activation. Nature. Oct. 22, 2015;526(7574):583-6.

(56) References Cited

OTHER PUBLICATIONS

Zhang et al., Small-molecule MDM2-p53 inhibitors: recent advances. Future Med Chem. 2015;7(5):631-45.

Zhang et al., Targeted degradation of proteins by small molecules: a novel tool for functional proteomics. Comb Chem High Throughput Screen. Nov. 2004;7(7):689-97.

Zhao et al., Small-molecule inhibitors of the MDM2-p53 protein-protein interaction (MDM2 Inhibitors) in clinical trials for cancer treatment. J Med Chem. Feb. 12, 2015;58(3):1038-52.

Zhou et al., Discovery of a Small-Molecule Degrader of Bromodomain and Extra-Terminal (BET) Proteins with Picomolar Cellular Potencies and Capable of Achieving Tumor Regression. J Med Chem. Jan. 25, 2018;61(2):462-481.

International Search Report and Written Opinion for Application No. PCT/US2023/032225, dated Jan. 3, 2024, 15 pages.

International Search Report and Written Opinion for Application No. PCT/US2019/050114, dated Jan. 2, 2020, 10 pages.

International Search Report and Written Opinion for Application No. PCT/US2021/047929, dated Dec. 20, 2021, 8 pages.

International Preliminary Report on Patentability for Application No. PCT/US2021/047929, dated Mar. 9, 2023, 7 pages.

\* cited by examiner

ACCELERATING FIBROSARCOMA PROTEIN DEGRADING COMPOUNDS AND ASSOCIATED METHODS OF USE

CROSS-REFERENCE TO RELATED APPLICATIONS

The present application claims priority and benefit to U.S. Provisional Application No. 63/071,824, filed 28 Aug. 2020 and titled: RAPIDLY ACCELERATING FIBROSARCOMA PROTEIN DEGRADING COMPOUNDS AND ASSOCIATED METHODS OF USE, and U.S. Provisional Application No. 63/219,254, filed 7 Jul. 2021 and titled: RAPIDLY ACCELERATING FIBROSARCOMA PROTEIN DEGRADING COMPOUNDS AND ASSOCIATED METHODS OF USE, which are incorporated herein by reference in their entirety for all purposes.

INCORPORATION BY REFERENCE

All cited references are hereby incorporated herein by reference in their entirety, including U.S. patent application Ser. No. 15/074,820, filed on 18 Mar. 2016, published as U.S. Patent Application Publication No. 2016/0272639; and U.S. patent application Ser. No. 14/371,956, filed on 11 Jul. 2014, published as U.S. Patent Application Publication No. 2014/0356322; and U.S. patent application Ser. No. 16/224,088, filed on 18 Dec. 2018, published as U.S. Patent Application Publication No. 2019/0127359; and U.S. patent application Ser. No. 16/375,643, filed on 4 Apr. 2019, published as U.S. Patent Application Publication No. 2019/0315732; and U.S. patent application Ser. No. 15/853,166, filed on 22 Dec. 2017, published as U.S. Patent Application Publication No. 2018/0179183, and U.S. patent application Ser. No. 16/563,842, filed on 7 Sep. 2019.

FIELD OF THE INVENTION

The invention provides hetero-bifunctional compounds comprising a target protein binding moiety and an E3 ubiquitin ligase binding moiety, and associated methods of use. The bifunctional compounds are useful as modulators of targeted ubiquitination of Rapidly Accelerated Fibrosarcoma (RAF), and mutant forms thereof, which is then degraded and/or inhibited.

BACKGROUND

Most small molecule drugs bind enzymes or receptors in tight and well-defined pockets. On the other hand, protein-protein interactions are notoriously difficult to target using small molecules due to their large contact surfaces and the shallow grooves or flat interfaces involved. E3 ubiquitin ligases (of which hundreds are known in humans) confer substrate specificity for ubiquitination, and therefore are more attractive therapeutic targets than general proteasome inhibitors due to their specificity for certain protein substrates. The development of ligands of E3 ligases has proven challenging, in part due to the fact that they must disrupt protein-protein interactions. However, recent developments have provided specific ligands that bind to these ligases. For example, since the discovery of nutlins, the first small molecule E3 ligase inhibitors, additional compounds have been reported that target E3 ligases.

Cereblon is a protein that in humans is encoded by the CRBN gene. CRBN orthologs are highly conserved from plants to humans, which underscores its physiological importance. Cereblon forms an E3 ubiquitin ligase complex with damaged DNA binding protein 1 (DDB1), Cullin-4A (CUL4A), and regulator of cullins 1 (ROC1). This complex ubiquitinates a number of other proteins. Through a mechanism which has not been completely elucidated, cereblon ubiquitination of target proteins results in increased levels of fibroblast growth factor 8 (FGF8) and fibroblast growth factor 10 (FGF10). FGF8 in turn regulates a number of developmental processes, such as limb and auditory vesicle formation. The net result is that this ubiquitin ligase complex is important for limb outgrowth in embryos. In the absence of cereblon, DDB1 forms a complex with DDB2 that functions as a DNA damage-binding protein.

Bifunctional compounds such as those described in U.S. Patent Application Publications 2015/0291562 and 2014/0356322 (incorporated herein by reference), function to recruit endogenous proteins to an E3 ubiquitin ligase for ubiquitination and subsequent degradation in the proteasome degradation pathway. In particular, the publications cited above describe bifunctional or proteolysis-targeting chimeric (PROTAC®) protein degrader compounds, which find utility as modulators of targeted ubiquitination of a variety of polypeptides and proteins, which are then degraded and/or inhibited by the bifunctional compounds.

An ongoing need exists in the art for effective treatments for disease associated with overexpression or aggregation of Rapidly Accelerated Fibrosarcoma (RAF), or the overactivation of RAF (such as constitutively active RAF). For example, current B-Raf inhibitors (such as, vemurafenib and dabrafenib) may target V600 mutant BRaf. Thus, a need exists for diseases or disorders (such as, melanoma, lung cancer, pancreatic cancer, and/or colorectal cancers) that have different B-Raf mutations that are insensitive to currently marketed agents. Furthermore, resistance mutations can emerge in response to BRaf/MEK inhibitor therapy. For example, the p61 splice variant can emerge in melanoma patients treated with BRaf/MEK inhibitor therapy, which leaves these patients with no clinical options. Currently marketed agents also bind to and cause paradoxical activation of wild-type BRaf, which results in clinical complications. In addition, the family of hypoactive Class III B-Raf mutants that signal through heterodimerization with CRaf, constitute 40% of B-Raf mutations in non-small cell lung cancer (NSCLC), and also appear sporadically across other cancers, cannot be targeted with any currently approved or clinical-stage B-Raf inhibitors. Class I BRaf mutants (V600E, V600K, V600D) have high kinase activity, are Ras and dimerization independent, and are sensitive to vemurafenib. Class II B-Raf mutants have high to intermediate kinase activity, are Ras-independent and dimerization dependent, and are insensitive to vemurafenib. Class III B-Raf mutants have varying levels of kinase activity (e.g., some Class III B-raf mutants have high levels of kinase activity while other mutants have no kinase activity), are Ras and dimerization dependent, and are insensitive to vemurafenib.

Thus, non-specific effects and the inability to target and modulate RAF remain an obstacle to the development of effective treatments. As such, an ongoing need exists in the art for effective treatments for RAF-related disease and disorders, e.g., cancer, cardiofaciocutaneous syndrome, neurofibromatosis type 1, Costello syndrome, Noonan Syndrome, LEOPARD (Lentigo, Electrocardiographic abnormalities, Ocular hypertelorism, Pulmonary stenosis, Abnormal genitalia, Retarded growth, Deafness) syndrome associated with RAF accumulation and aggregation, renal cell carcinoma, pancreatic cancer, colorectal cancer, lung cancer, ovarian cancer, breast cancer, thyroid cancer, pilocytic astrocytoma, prostate cancer, gastric cancer, hepatocellular carcinoma, or melanoma.

SUMMARY

The present disclosure describes hetero-bifunctional compounds that function to recruit Rapidly Accelerated Fibrosarcoma (RAF) protein, such as B-Raf or a mutated version thereof, to an E3 ubiquitin ligase for targeted ubiquitination and subsequent proteasomal degradation, and methods of making and using the same. In addition, the description provides methods of using an effective amount of a compound of the present disclosure for the treatment or amelioration of a disease condition, such as a RAF-related disease or disorder, e.g., accumulation or overactivity of a RAF protein, cancer, such as renal cell carcinoma, pancreatic cancer, colorectal cancer, lung cancer, ovarian cancer, breast cancer, thyroid cancer, pilocytic astrocytoma, prostate cancer, gastric cancer, hepatocellular carcinoma, and melanoma, cardiofaciocutaneous syndrome, neurofibromatosis type 1, Costello syndrome, Noonan Syndrome, or LEOPARD (Lentigo, Electrocardiographic abnormalities, Ocular hypertelorism, Pulmonary stenosis, Abnormal genitalia, Retarded growth, Deafness) syndrome.

In one aspect, the disclosure provides hetero-bifunctional compounds, which comprise an E3 ubiquitin ligase binding moiety (i.e., a ligand for an E3 ubiquitin ligase (a "ULM" group)), and a moiety that binds RAF or a mutated version thereof (i.e., a protein targeting moiety or "PTM" group, that is, a RAF-targeting ligand/moiety or a "RTM" group) such that the RAF protein, such as B-Raf or a mutated version thereof, is thereby placed in proximity to the ubiquitin ligase to effect ubiquitination and subsequent degradation (and/or inhibition) of the B-Raf protein. In a preferred embodiment, the ULM (ubiquitination ligase binding moiety) is a cereblon E3 ubiquitin ligase binding moiety (CLM). For example, the structure of the bifunctional compound can be depicted as follows where PTM and ULM are directly covalently linked together:

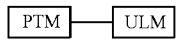

The respective positions of the PTM and ULM moieties (e.g., CLM), as well as their number as illustrated herein, is provided by way of example only and is not intended to limit the compounds in any way. As would be understood by the skilled artisan, the bifunctional compounds as described herein can be synthesized such that the number and position of the respective functional moieties can be varied as desired.

In certain embodiments, the bifunctional compound further comprises a chemical linker ("L"). In this example, the structure of the bifunctional compound can be depicted as:

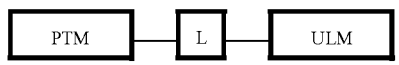

where PTM is a RAF-targeting moiety, L is a linker, e.g., a chemical linking group coupling PTM to ULM, and ULM is a cereblon E3 ubiquitin ligase binding moiety (CLM).

For example, the structure of the bifunctional compound can be depicted as:

wherein: PTM is a RAF-targeting moiety; "L" is a linker (e.g. a bond or a chemical linking group) coupling the PTM and CLM; and CLM is a cereblon E3 ubiquitin ligase binding moiety.

In any aspect or embodiment described herein, the compounds as described herein comprise multiple independently selected ULMs, multiple PTMs, multiple chemical linkers or a combination thereof.

In any of the aspects or embodiments described herein, the PTM is a small molecule that binds RAF or a mutant form thereof. In any of the aspects or embodiments described herein, the PTM is a small molecule that binds B-Raf or a mutant version thereof. In any of the aspects or embodiments described herein, the PTM is a small molecule that binds both a RAF wild-type protein and a RAF mutant. In any of the aspects or embodiments described herein, the PTM is a small molecule that binds both a RAF wild-type protein and RAF mutant such as, but not limited to, a RAF mutant with increased kinase activity. In any of the aspects or embodiments described herein, the small molecule capable of binding RAF protein, is a small molecule that binds RAF protein. In any aspect or embodiment described herein, the small molecule binds the RAF as described herein.

In any aspect or embodiment described herein, the CLM comprises a chemical group derived from an imide, a thioimide, an amide, or a thioamide. In a particular embodiment, the chemical group is a phthalimido group, or an analog or derivative thereof. In a certain embodiment, the CLM is selected from thalidomide, lenalidomide, pomalidomide, analogs thereof, isosteres thereof, and derivatives thereof. Other contemplated CLMs are described in U.S. Patent Application Publication No. 2015/0291562, which is incorporated herein by reference in its entirety.

In any aspect or embodiment described herein, "L" is a bond. In additional embodiments, the linker "L" is a chemical linking moiety/group with a linear non-hydrogen atom number in the range of 1 to 40 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40). The connector "L" can contain, but is not limited to one or more functional groups such as ether, amide, alkane, alkene, alkyne, ketone, hydroxyl, carboxylic acid, thioether, sulfoxide, and sulfone. The linker can contain aromatic, heteroaromatic, cyclic, bicyclic or tricyclic moieties. Substitution with halogen, such as Cl, F, Br and I, or alkyl, such as methyl, ethyl, isopropyl, and tert-butyl, can be included in the linker. In the case of fluorine substitution, single or multiple fluorines can be included.

In an additional aspect, the present disclosure provides therapeutic compositions comprising an effective amount of a compound as described herein, or a pharmaceutically acceptable salt form thereof, and a pharmaceutically acceptable carrier. The therapeutic compositions can be used to trigger targeted degradation of RAF, such as B-Raf, or a mutated version thereof and/or inhibition of RAF, such as B-Raf, or a mutated version thereof, in a patient or subject, for example, an animal such as a human, and can be used for treating or ameliorating one or more disease states, conditions, or symptoms causally related to RAF or mutated version thereof, which treatment is accomplished through degradation or inhibition of the RAF protein or mutated version thereof, or controlling or lowering RAF protein levels or protein levels of a mutated version thereof, in a patient or subject. In certain embodiments, the therapeutic compositions as described herein may be used to effectuate the degradation of RAF, or a mutant or mis-folded form thereof, for the treatment or amelioration of a disease or condition causally related, e.g., to accumulation, aggregation, or overreactivity of a RAF protein, a mis-folded, or a mutated form thereof (such as a RAF or B-Raf protein with increase kinase activity relative to wild-type RAF or B-Raf, cancer, such as, e.g., renal cell carcinoma, pancreatic cancer, colorectal cancer, lung cancer, ovarian cancer, thyroid cancer, pilocytic astrocytoma, prostate cancer, gastric cancer, hepatocellular carcinoma, and melanoma), cardiofaciocutaneous syndrome, neurofibromatosis type 1, Costello syndrome, Noonan Syndrome, LEOPARD (Lentigo, Electrocardiographic abnormalities, Ocular hypertelorism, Pulmonary stenosis, Abnormal genitalia, Retarded growth, Deafness) syndrome.

In yet another aspect, the present disclosure provides a method of ubiquitinating RAF or a mutated form thereof in a cell (e.g., in vitro or in vivo). In any aspect or embodiment described herein, the method comprises administering a hetero-bifunctional compound as described herein comprising a PTM that binds RAF or a mutant form thereof, and a CLM, preferably linked through a chemical linker moiety, as described herein, to effectuate degradation of the RAF protein or mutant form thereof. Though not wanting to be limited by theory, the inventors believe that, pursuant to the invention, poly-ubiquitination of the RAF (such as B-Raf) wild-type or mutant protein will occur when it is placed in proximity to the E3 ubiquitin ligase via use of the heterobifunctional compound, thereby triggering subsequent degradation of the RAF or mutant protein via the proteasomal pathway and control or reduction of RAF protein levels in cells, such as cells of a subject in need of such treatment. The control or reduction in levels of the RAF protein or mutated form thereof afforded by the present disclosure provides treatment of a RAF causally related disease state, condition or related symptom, as modulated, e.g., through a lowering of the amount of RAF protein or mutated form thereof in cells of the subject.

In still another aspect, the present disclosure provides methods for treating or ameliorating a disease, condition, or symptom thereof causally related to RAF or mutated form thereof in a subject or a patient, e.g., an animal such as a human, comprising administering to a subject in need thereof a composition comprising an effective amount, e.g., a therapeutically effective amount, of a hetero-bifunctional compound as described herein or pharmaceutically acceptable salt form thereof, and a pharmaceutically acceptable carrier, wherein the composition is effective for treating or ameliorating the disease or disorder or symptom thereof in the subject.

In some aspects or embodiments described herein, the method further includes, prior to the step of administering a composition or compound of the present disclosure to a subject, the step of identifying a subject as having a mutant RAF protein (e.g., B-Raf mutant having a V600 mutation and/or a G466V mutation).

In another aspect, the present disclosure provides methods for identifying the effects of the degradation of RAF protein in a biological system using compounds according to the present disclosure.

In another aspect, the present disclosure provides processes and intermediates for making a hetero-bifunctional compound of the present disclosure capable of targeted ubiquitination and degradation of the RAF protein in a cell (e.g., in vivo or in vitro).

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating embodiments of the disclosure and are not to be construed as limiting the disclosure. Further objects, features and advantages of the disclosure will become apparent from the following detailed description taken in conjunction with the accompanying figures showing illustrative embodiments of the disclosure.

FIG. 1A. Exemplary hetero-biofunctional protein degrading compounds comprise a protein targeting moiety (PTM; darkly shaded rectangle), a ubiquitin ligase binding moiety (ULM; lightly shaded triangle), and optionally a linker moiety (L; black line) coupling the PTM to the ULM. FIG. 1B Illustrates the functional use of the hetero-bifunctional protein degrading compounds (commercially known as PROTAC® protein degrader compounds) as described herein. Briefly, the ULM (triangle) recognizes and binds to a specific E3 ubiquitin ligase, and the PTM (large rectangle) binds and recruits a target protein bringing it into close proximity to the E3 ubiquitin ligase. Typically, the E3 ubiquitin ligase is complexed with an E2 ubiquitin-conjugating protein (E2), and either alone or via the E2 protein catalyzes attachment of multiple ubiquitin molecules (black circles) to a lysine on the target protein via an isopeptide bond. The poly-ubiquitinated protein (far right) has thereby been targeted for degradation by the proteosomal machinery of the cell.

DETAILED DESCRIPTION

Figure 1A:
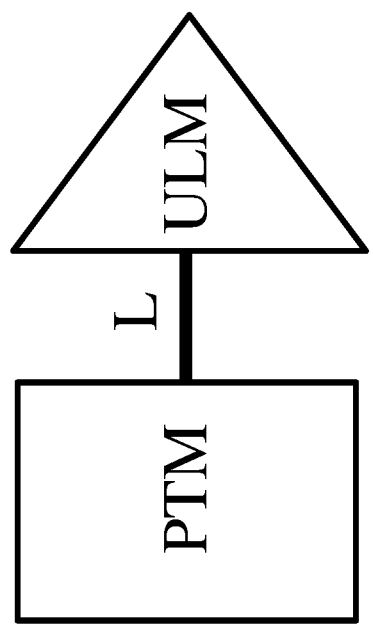
FIGS. 1A and 1B. Illustration of general principle for hetero-bifunctional protein-degrading compounds.
Figure 1B:
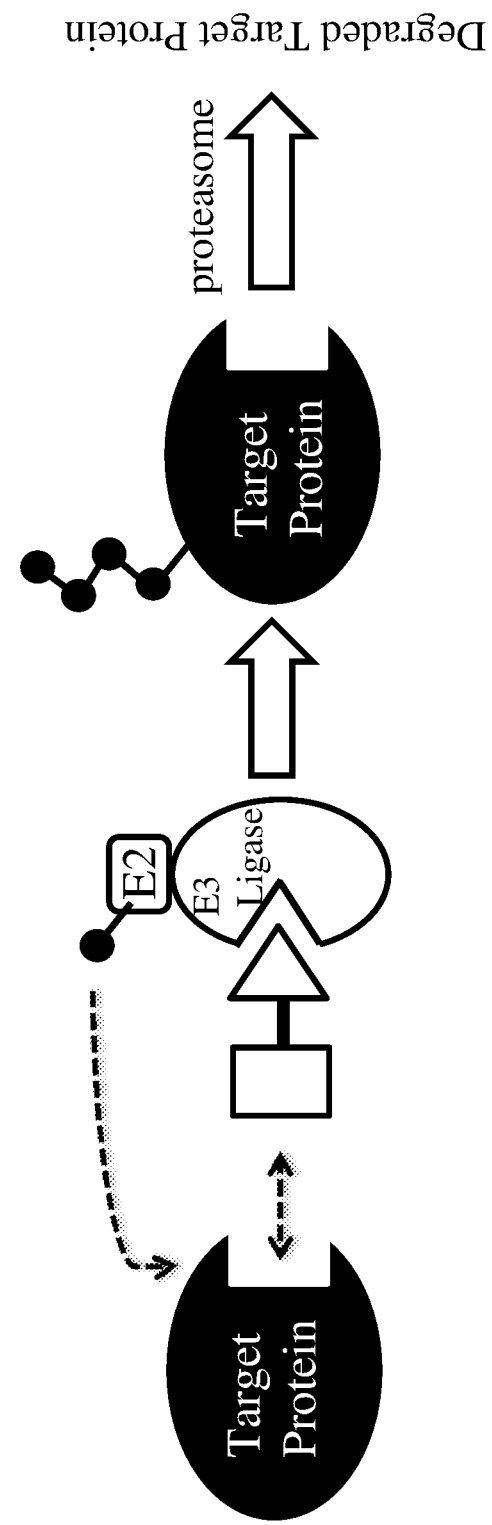

Presently described are compounds, compositions and methods that relate to the surprising discovery that an E3 ubiquitin ligase (e.g., a Von Hippel-Lindau (VHL) E3 ubiquitin ligase or a cereblon E3 ubiquitin ligase) ubiquitinates the RAF protein or mutated form thereof once the E3 ubiquitin ligase and the RAF protein are placed in proximity via a bifunctional compound that binds both the E3 ubiquitin ligase and the RAF protein. Accordingly the present disclosure provides compounds and compositions comprising an E3 ubiquitin ligase binding moiety ("ULM") coupled by a bond or chemical linking group (L) to a protein targeting moiety ("PTM") that targets the RAF protein, which results in the ubiquitination of the RAF protein, and which leads to degradation of the RAF protein by the proteasome (see FIGS. 1A and 1B).

In an aspect, the description provides compounds in which the PTM binds to the RAF protein and/or a mutated form thereof. The present disclosure also provides a library of compositions and the use thereof to produce targeted degradation of the RAF protein in a cell.

In certain aspects, the present disclosure provides heterobifunctional compounds which comprise a ligand, e.g., a small molecule ligand (i.e., having a molecular weight of below 2,000, 1,000, 500, or 200 Daltons), which is capable of binding to an E3 ubiquitin ligase, such as the cereblon E3 ubiquitin ligase. The compounds also comprise a small molecule moiety that is capable of binding to the RAF protein or mutated form thereof in such a way that the RAF protein or mutated form is placed in proximity to the ubiquitin ligase to effect ubiquitination and degradation (and/or inhibition) of the RAF protein or mutated form. "Small molecule" means, in addition to the above, that the molecule is non-peptidyl, that is, it is not considered a peptide, e.g., comprises fewer than 4, 3, or 2 amino acid residues. In accordance with the present description, each of the PTM, ULM and hetero-bifunctional molecule is a small molecule.

The term "RAF" as used herein, unless specifically indicated to the contrary, is intended to include both wild-type RAF (such as, A-Raf, B-Raf, or c-Raf) and mutant forms therefore, such as a RAF mutant protein having increased kinase activity relative to wild-type RAF protein, a B-Raf mutant protein having increased kinase activity relative to wild-type B-Raf protein or a B-Raf protein having one or more mutations selected from V600E, V600K, V600D, R461I, I462S, G463E, G463V, G465A, G465E, G465V, G466V, G468A, G468E, N580S, E585K, D593V, F594L, G595R, L596V, T598I, V599D, V599E, V599K, V599R, A727V, and combinations thereof Unless otherwise defined, all technical and scientific terms used herein have the same meaning as commonly understood by one of ordinary skill in the art to which this disclosure belongs. The terminology used in the description is for describing particular embodiments only and is not intended to be limiting of the disclosure.

Where a range of values is provided, it is understood that each intervening value in the range, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either/or both of those included limits are also included in the disclosure.

The following terms are used to describe the present disclosure. In instances where a term is not specifically defined herein, that term is given an art-recognized meaning by those of ordinary skill applying that term in context to its use in describing the present disclosure.

The articles "a" and "an" as used herein and in the appended claims are used herein to refer to one or to more than one (i.e., to at least one) of the grammatical object of the article unless the context clearly indicates otherwise. By way of example, "an element" means one element or more than one element, unless otherwise indicated.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

It should also be understood that, in certain methods or processes described herein that include more than one step or act, the order of the steps or acts of the method is not necessarily limited to the order in which the steps or acts of the method are recited unless the context indicates otherwise.

The terms "co-administration" and "co-administering" or "combination therapy" refer to both concurrent administration (administration of two or more therapeutic agents at the same time) and time-varied administration (administration of one or more therapeutic agents at a time different from that of the administration of an additional therapeutic agent or agents), as long as the two or more therapeutic agents are present in the patient to some extent, preferably at effective amounts, at the same time. In certain preferred aspects, one or more of the hetero-bifunctional compounds described herein are coadministered with at least one additional bioactive agent, e.g., another anticancer agent. In particularly preferred aspects, the co-administration of such compounds results in synergistic activity and/or therapy such as, e.g., anticancer activity.

The term "compound", as used herein, unless otherwise indicated, refers to any specific hetero-bifunctional compound disclosed herein, pharmaceutically acceptable salts and solvates thereof, and deuterated forms of any of the aforementioned molecules, where applicable. Deuterated compounds contemplated are those in which one or more of the hydrogen atoms contained in the drug molecule have been replaced by deuterium. Such deuterated compounds preferably may have one or more improved pharmacokinetic or pharmacodynamic properties (e.g., longer half-life) compared to the equivalent "un-deuterated" compound.

The term "ubiquitin ligase" refers to a family of proteins that facilitate the transfer of one or more ubiquitins to a specific substrate protein. Addition of a chain of several ubiquitins (poly-ubiquitination) targets the substrate protein for degradation. For example, cereblon is an E3 ubiquitin ligase that alone, or in combination with an E2 ubiquitin-conjugating enzyme, can ultimately cause the attachment of a chain of four ubiquitins to a lysine residue on the target protein, thereby targeting the protein for degradation by the proteasome. The ubiquitin ligase is involved in poly-ubiquitination such that a first ubiquitin is attached to a lysine on the target protein; a second ubiquitin is attached to the first; a third is attached to the second, and a fourth is attached to the third. Such poly-ubiquitination marks proteins for degradation by the proteasome.

The term "patient" or "subject" is used throughout the specification to describe an animal, preferably a human or a domesticated animal, to whom treatment, including prophylactic treatment, with the compositions according to the present disclosure is provided. For treatment of those diseases, conditions or symptoms that are specific for a specific animal, such as a human patient, the term "patient" refers to that specific animal, including a domesticated animal such as a dog or cat, or a farm animal such as a horse, cow, sheep, etc. In general, in the present disclosure, the terms "patient" and "subject" refer to a human patient unless otherwise stated or implied from the context of the use of the term.

The terms "effective" and "therapeutically effective" are used to describe an amount of a compound or composition which, when used within the context of its intended use, and either in a single dose or, more preferably after multiple doses within the context of a treatment regimen, effects an intended result such as an improvement in a disease or condition, or amelioration or reduction in one or more symptoms associated with a disease or condition. The terms "effective" and "therapeutically effective" subsume all other "effective amount" or "effective concentration" terms, which are otherwise described or used in the present application.

Compounds and Compositions

In one aspect, the description provides hetero-bifunctional compounds comprising an E3 ubiquitin ligase binding moiety ("ULM") that is a cereblon E3 ubiquitin ligase binding moiety (a "CLM"), The CLM is covalently coupled to a protein targeting moiety (PTM) that binds to the protein, which coupling is either directly by a bond or via a chemical linking group (L) according to the structure:

PTM-L-CLM (A)

wherein L is the bond or chemical linking group, and PTM is a protein targeting moiety that binds to the protein RAF or a mutant form thereof, as described herein, where the PTM is a RAF targeting moiety (RTM). The term CLM is inclusive of all CLM binding moieties that function according to the invention of the present disclosure.

In any of the aspects or embodiments, the CLM demonstrates a half maximal inhibitory concentration ($IC_{50}$) for the E3 ubiquitin ligase (e.g., cereblon E3 ubiquitin ligase) of less than about 200 μM. The $IC_{50}$ can be determined according to any suitable method known in the art, e.g., a fluorescent polarization assay.

In certain embodiments, the hetero-bifunctional compounds described herein demonstrate an $IC_{50}$ or a half maximal degradation concentration ($DC_{50}$) of less than about 100, 50, 10, 1, 0.5, 0.1, 0.05, 0.01, 0.005, or 0.001 mM, or less than about 100, 50, 10, 1, 0.5, 0.1, 0.05, 0.01, 0.005, or 0.001 μM, or less than about 100, 50, 10, 1, 0.5, 0.1, 0.05, 0.01, 0.005, 0.001 nM, or less than about 100, 50, 10, 1, 0.5, 0.1, 0.05, 0.01, 0.005, or 0.001 pM.

In any aspect or embodiment described herein, the PTM is represented by the chemical structure:

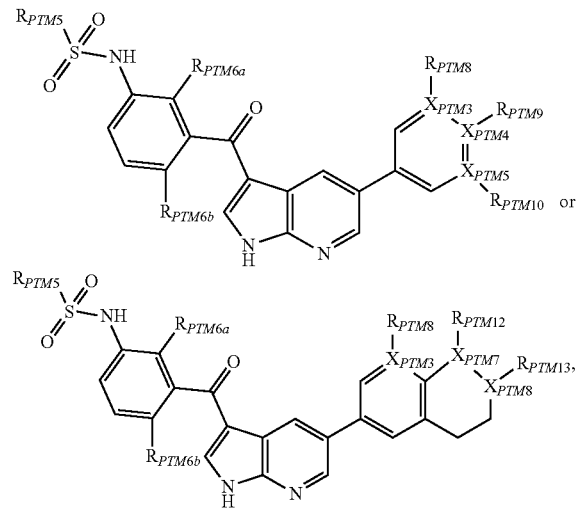

wherein:

$X_{PTM3}$, $X_{PTM4}$, $X_{PTM5}$, $X_{PTM7}$, and $X_{PTM8}$ are independently selected from CH or N;

$R_{PTM5}$ is selected from the group consisting of:

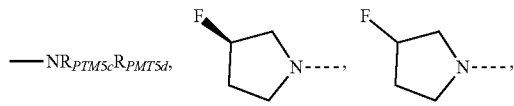

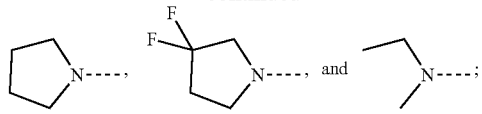

$R_{PTM5c}$ and $R_{PMT5d}$ are each independently selected from an optionally substituted alkyl (e.g., optionally substituted with one, two, or three halogens), or $R_{PTM5c}$, $R_{PMT5d}$, and the nitrogen they are attached form an optionally substituted 4-6 membered heterocycloalkyl (e.g., optionally substituted with one, two, or three halogens, an optionally substituted 5-membered heterocycloalky, or a combination thereof);

$R_{PTM6a}$ and $R_{PTM6b}$ are independently a halogen or C1-C3 alkyl (e.g., methyl or ethyl);

$R_{PTM8}$ is absent (a bond), hydrogen, halogen (e.g., F, Cl, or Br), or C1-C3 alkyl (e.g., methyl or ethyl);

$R_{PTM9}$ and $R_{PTM10}$ are each independently absent (e.g., hydrogen), halogen (e.g., F, Cl, or Br) or C1-C3 alkyl (e.g., methyl or ethyl); or $R_{PTM9}$, $R_{PTM10}$ and the ring they are attached form 5-7 membered (e.g., 6-membered) cycloalkyl or heterocycloalkyl optionally substituted with one or two groups selected from halogen (e.g., F, Cl, or Br) and C1-C3 alkyl (e.g., methyl or ethyl);

$R_{PTM12}$ is absent (a bond), hydrogen, halogen (e.g., F, Cl, or Br), or C1-C3 alkyl (e.g., methyl or ethyl);

$R_{PTM13}$ is absent (a bond), hydrogen, halogen (e.g., F, Cl, or Br), or C1-C3 alkyl (e.g., methyl or ethyl); and one of $R_{PTM8}$, $R_{PTM9}$, $R_{PTM10}$, $R_{PTM12}$, $R_{PTM13}$ or the cycloalkyl or heterocycloalkyl formed from $R_{PTM9}$ and $R_{PTM10}$ is modified to be covalently joined to a chemical linker group (L) or a CLM.

The term "alkyl" shall mean within its context a linear, branch-chained or cyclic fully saturated hydrocarbon radical, preferably a $C_1$-$C_{10}$, preferably a $C_1$-$C_6$, or more preferably a $C_1$-$C_3$ alkyl group, which may be optionally substituted with any suitable functional group or groups. Examples of alkyl groups are methyl, ethyl, n-butyl, sec-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopentylethyl, cyclohexylethyl and cyclohexyl, among others. In certain embodiments, the alkyl group is end-capped with a halogen group (At, Br, Cl, F, or I).

The term "Alkenyl" refers to linear, branch-chained or cyclic $C_2$-$C_{10}$ (preferably $C_2$-$C_6$) hydrocarbon radicals containing at least one C=C bond.

The term "Alkynyl" refers to linear, branch-chained or cyclic $C_2$-$C_{10}$ (preferably $C_2$-$C_6$) hydrocarbon radicals containing at least one C≡C bond.

The term "alkylene" when used, refers to a —(CH$_2$)$_n$— group (n is an integer generally from 0-6), which may be optionally substituted. When substituted, the alkylene group preferably is substituted on one or more of the methylene groups with a $C_1$-$C_6$ alkyl group (including a cyclopropyl group or a t-butyl group), but may also be substituted with one or more halo groups, preferably from 1 to 3 halo groups or one or two hydroxyl groups, O—($C_1$-$C_6$ alkyl) groups or amino acid sidechains as otherwise disclosed herein. In certain embodiments, an alkylene group may be substituted with a urethane or alkoxy group (or other suitable functional group) which may be further substituted with a polyethylene glycol chain (of from 1 to 10, preferably 1 to 6, or more preferably 1 to 4 ethylene glycol units) to which is substituted (preferably, but not exclusively on the distal end of the polyethylene glycol chain) an alkyl chain substituted with a single halogen group, preferably a chlorine group. In still other embodiments, the alkylene (e.g., methylene) group, may be substituted with an amino acid sidechain group such as a sidechain group of a natural or unnatural amino acid, for example, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine.

The term "unsubstituted" shall mean substituted only with hydrogen atoms. A range of carbon atoms which includes $C_0$ means that carbon is absent and is replaced with H. Thus, a range of carbon atoms which is $C_0$-$C_6$ includes carbons atoms of 1, 2, 3, 4, 5 and 6 and for $C_0$, H stands in place of carbon.

The term "substituted" or "optionally substituted" shall mean independently (i.e., where more than one substituent occurs, each substituent is selected independent of another substituent) one or more substituents (independently up to five substituents, preferably up to three substituents, more preferably 1 or 2 substituents on a moiety in a compound according to the present disclosure and may include substituents which themselves may be further substituted) at a carbon (or nitrogen) position anywhere on a molecule within context, and includes as possible substituents hydroxyl, thiol, carboxyl, cyano (C≡N), nitro ($NO_2$), halogen (preferably, 1, 2 or 3 halogens, especially on an alkyl, especially a methyl group such as a trifluoromethyl), an alkyl group (preferably, $C_1$-$C_{10}$, more preferably, $C_1$-$C_6$), aryl (especially phenyl and substituted phenyl, for example benzyl or benzoyl), alkoxy group (preferably, $C_1$-$C_6$ alkyl or aryl, including phenyl and substituted phenyl), thioether (preferably, $C_1$-$C_6$ alkyl or aryl), acyl (preferably, $C_1$-$C_6$ acyl), ester or thioester (preferably, $C_1$-$C_6$ alkyl or aryl) including alkylene ester (such that attachment is on the alkylene group, rather than at the ester function which is preferably substituted with a $C_1$-$C_6$ alkyl or aryl group), halogen (preferably, F or Cl), amine (including a five- or six-membered cyclic alkylene amine, further including a $C_1$-$C_6$ alkyl amine or a $C_1$-$C_6$ dialkyl amine which alkyl groups may be substituted with one or two hydroxyl groups) or an optionally substituted —N($C_0$-$C_6$ alkyl)C(O)(O—$C_1$-$C_6$ alkyl) group (which may be optionally substituted with a polyethylene glycol chain to which is further bound an alkyl group containing a single halogen, preferably chlorine substituent), hydrazine, amido, which are preferably independently substituted with one or two $C_1$-$C_6$ alkyl groups (including a carboxamide which is optionally substituted with one or two $C_1$-$C_6$ alkyl groups), alkanol (preferably, $C_1$-$C_6$ alkyl or aryl), or alkanoic acid (preferably, $C_1$-$C_6$ alkyl or aryl). Substituents according to the present disclosure may include, for example —Si$R_1R_2R_3$ groups where each of $R_1$ and $R_2$ is as otherwise described herein and $R_3$ is H or a $C_1$-$C_6$ alkyl group, preferably $R_1$, $R_2$, $R_3$ together is a $C_1$-$C_3$ alkyl group (including an isopropyl or t-butyl group). Each of the above-described groups may be linked directly to the substituted moiety or alternatively, the substituent may be linked to the substituted moiety (preferably in the case of an aryl or heteroaryl moiety) through an optionally substituted —(CH$_2$)$_m$— or alternatively an optionally substituted —(OCH$_2$)$_m$—, —(OCH$_2$CH$_2$)$_m$— or —(CH$_2$CH$_2$O)$_m$— group, which may be substituted with any one or more of the above-described substituents. Alkylene groups —(CH$_2$)$_m$— or —(CH$_2$)$_n$— groups or other chains such as ethylene glycol chains, as identified above, may be substituted anywhere on the chain. Preferred substituents on alkylene groups include halogen or $C_1$-$C_6$ (preferably $C_1$-$C_3$) alkyl groups, which may be optionally substituted with one or two hydroxyl groups, one or two ether groups (O—$C_1$-$C_6$ groups), up to three halo groups (preferably F), or a side chain of an amino acid as otherwise described herein and optionally substituted amide (preferably carboxamide substituted as described above) or urethane groups (often with one or two $C_0$-$C_6$ alkyl substituents, which group(s) may be further substituted). In certain embodiments, the alkylene group (often a single methylene group) is substituted with one or two optionally substituted $C_1$-$C_6$ alkyl groups, preferably $C_1$-$C_4$ alkyl group, most often methyl or O-methyl groups or a sidechain of an amino acid as otherwise described herein. In the present disclosure, a moiety in a molecule may be optionally substituted with up to five substituents, preferably up to three substituents. Most often, in the present disclosure moieties which are substituted are substituted with one or two substituents.

The term "substituted" (each substituent being independent of any other substituent) shall also mean within its context of use $C_1$-$C_6$ alkyl, $C_1$-$C_6$ alkoxy, halogen, amido, carboxamido, sulfone, including sulfonamide, keto, carboxy, $C_1$-$C_6$ ester (oxyester or carbonylester), $C_1$-$C_6$ keto, urethane —O—C(O)—NR$_1$R$_2$ or —N(R$_1$)—C(O)—O—R$_1$, nitro, cyano and amine (especially including a $C_1$-$C_6$ alkylene-NR$_1$R$_2$, a mono- or di-$C_1$-$C_6$ alkyl substituted amines which may be optionally substituted with one or two hydroxyl groups). Each of these groups contain unless otherwise indicated, within context, between 1 and 6 carbon atoms. In certain embodiments, preferred substituents will include for example, —NH—, —NHC(O)—, —O—, =O, —(CH$_2$)$_m$— (here, m and n are in context, 1, 2, 3, 4, 5 or 6), —S—, —S(O)—, SO$_2$— or —NH—C(O)—NH—, —(CH$_2$)$_n$OH, —(CH$_2$)$_n$SH, —(CH$_2$)$_n$COOH, $C_1$-$C_6$ alkyl, —(CH$_2$)$_n$C—($C_1$-$C_6$ alkyl), —(CH$_2$)$_n$C(O)—($C_1$-$C_6$ alkyl), —(CH$_2$)$_n$OC(O)—($C_1$-$C_6$ alkyl), —(CH$_2$)$_n$C(O)O—($C_1$-$C_6$ alkyl), —(CH$_2$)$_n$NHC(O)—R$_1$, —(CH$_2$)$_n$C(O)—NR$_1$R$_2$, —(OCH$_2$)$_n$OH, —(CH$_2$O)$_n$COOH, $C_1$-$C_6$ alkyl, —(OCH$_2$)$_n$O—($C_1$-$C_6$ alkyl), —(CH$_2$O)$_n$C(O)—($C_1$-$C_6$ alkyl), —(OCH$_2$)$_n$NHC(O)—R$_1$, —(CH$_2$O)$_n$C(O)—NR$_1$R$_2$, —S(O)$_2$—R$_s$, —S(O)—R$_s$ (R$_s$ is $C_1$-$C_6$ alkyl or a —(CH$_2$)$_m$—NR$_1$R$_2$ group), NO$_2$, CN or halogen (F, Cl, Br, I, preferably F or Cl), depending on the context of the use of the substituent. R$_1$ and R$_2$ are each, within context, H or a $C_1$-$C_6$ alkyl group (which may be optionally substituted with one or two hydroxyl groups or up to three halogen groups, preferably fluorine). The term "substituted" shall also mean, within the chemical context of the compound defined and substituent used, an optionally substituted aryl or heteroaryl group or an optionally substituted heterocyclic group as otherwise described herein. Alkylene groups may also be substituted as otherwise disclosed herein, preferably with optionally substituted $C_1$-$C_6$ alkyl groups (methyl, ethyl or hydroxymethyl or hydroxyethyl is preferred, thus providing a chiral center), a sidechain of an amino acid group as otherwise described herein, an amido group as described hereinabove, or a urethane group O—C(O)—NR$_1$R$_2$ group where R$_1$ and R$_2$ are as otherwise described herein, although numerous other groups may also be used as substituents. Various optionally substituted moieties may be substituted with 3 or more substituents, preferably no more than 3 substituents and preferably with 1 or 2 substituents. It is noted that in instances where, in a compound at a particular position of the molecule substitution is required (principally, because of valency), but no substitution is indicated, then that substituent is construed or understood to be H, unless the context of the substitution suggests otherwise.

The term "aryl" or "aromatic", in context, refers to a substituted (as otherwise described herein) or unsubstituted monovalent aromatic radical (e.g., a 5-16 membered ring) having a single ring (e.g., benzene, phenyl, benzyl, or 5, 6, 7 or 8 membered ring) or condensed rings (e.g., naphthyl, anthracenyl, phenanthrenyl, 10-16 membered ring, etc.) and can be bound to the compound according to the present disclosure at any available stable position on the ring(s) or as otherwise indicated in the chemical structure presented. Other examples of aryl groups, in context, may include heterocyclic aromatic ring systems, "heteroaryl" groups having one or more nitrogen, oxygen, or sulfur atoms in the ring (moncyclic) such as imidazole, furyl, pyrrole, furanyl, thiene, thiazole, pyridine, pyrimidine, pyrazine, triazole, oxazole or fused ring systems such as indole, quinoline, indolizine, azaindolizine, benzofurazan, etc., among others, which may be optionally substituted as described above. Among the heteroaryl groups which may be mentioned include nitrogen-containing heteroaryl groups such as pyrrole, pyridine, pyridone, pyridazine, pyrimidine, pyrazine, pyrazole, imidazole, triazole, triazine, tetrazole, indole, isoindole, indolizine, azaindolizine, purine, indazole, quinoline, dihydroquinoline, tetrahydroquinoline, isoquinoline, dihydroisoquinoline, tetrahydroisoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, pyrimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

The term "substituted aryl" refers to an aromatic carbocyclic group comprised of at least one aromatic ring or of multiple condensed rings at least one of which being aromatic, wherein the ring(s) are substituted with one or more substituents. For example, an aryl group can comprise a substituent(s) selected from: —(CH$_2$)$_n$OH, —(CH$_2$)$_n$—O—(C$_1$-C$_6$)alkyl, —(CH$_2$)$_n$—O—(CH$_2$)$_n$—(C$_1$-C$_6$)alkyl, —(CH$_2$)$_n$—C(O)(C$_0$-C$_6$) alkyl, —(CH$_2$)$_n$—C(O)O(C$_0$-C$_6$) alkyl, —(CH$_2$)$_n$—OC(O)(C$_0$-C$_6$)alkyl, amine, mono- or di-(C$_1$-C$_6$ alkyl) amine wherein the alkyl group on the amine is optionally substituted with 1 or 2 hydroxyl groups or up to three halo (preferably F, Cl) groups, OH, COOH, C$_1$-C$_6$ alkyl, preferably CH$_3$, CF$_3$, OMe, OCF$_3$, NO$_2$, or CN group (each of which may be substituted in ortho-, meta- and/or para-positions of the phenyl ring, preferably para-), an optionally substituted phenyl group (the phenyl group itself is preferably connected to a PTM group, including a ULM group, via a linker group), and/or at least one of F, Cl, OH, COOH, CH$_3$, CF$_3$, OMe, OCF$_3$, NO$_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methyl substituted isoxazole, an optionally substituted oxazole including a methyl substituted oxazole, an optionally substituted thiazole including a methyl substituted thiazole, an optionally substituted isothiazole including a methyl substituted isothiazole, an optionally substituted pyrrole including a methyl substituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo- (preferably, F) or methyl substituted pyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, and combinations thereof.

"Carboxyl" denotes the group —C(O)OR, where R is hydrogen, alkyl, substituted alkyl, aryl, substituted aryl, heteroaryl or substituted heteroaryl, whereas these generic substituents have meanings which are identical with definitions of the corresponding groups defined herein.

The term "heteroaryl" or "hetaryl" can mean but is in no way limited to a 5-16 membered heteroaryl (e.g., 5, 6, 7 or 8 membered monocyclic ring or a 10-16 membered heteroaryl having multiple condensed rings), an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted —(CH$_2$)$_m$—O—C$_1$-C$_6$ alkyl group or an optionally substituted —(CH$_2$)$_m$—C(O)—O—C$_1$-C$_6$ alkyl group), an optionally substituted pyridine (2-, 3-, or 4-pyridine) or a group according to the chemical structure:

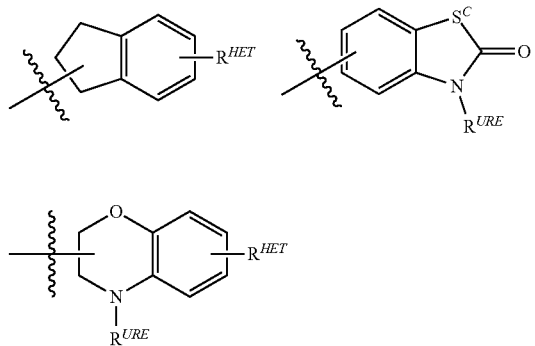

-continued

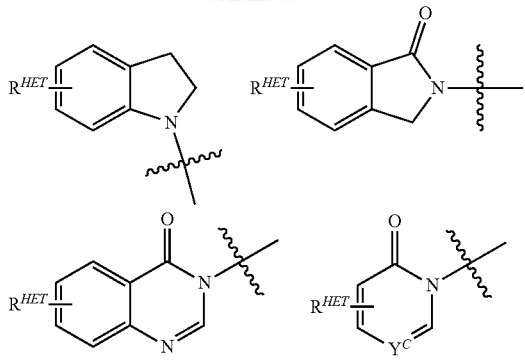

wherein:
$S^c$ is $CHR^{SS}$, $NR^{URE}$ or O;
$R^{HET}$ is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);
$R^{SS}$ is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O) ($C_1$-$C_6$ alkyl) (preferably substituted with one or two hydroxyl groups or up to three halo groups);
$R^{URE}$ is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and
$Y^C$ is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where R a is H or a $C_1$-$C_6$ alkyl group (preferably $C_1$-$C_3$ alkyl).

The terms "aralkyl" and "heteroarylalkyl" refer to groups that comprise both aryl or, respectively, heteroaryl as well as alkyl and/or heteroalkyl and/or carbocyclic and/or heterocycloalkyl ring systems according to the above definitions.

The term "arylalkyl" as used herein refers to an aryl group as defined above appended to an alkyl group defined above. The arylalkyl group is attached to the parent moiety through an alkyl group wherein the alkyl group is one to six carbon atoms. The aryl group in the arylalkyl group may be substituted as defined above.

The term "Heterocycle" refers to a cyclic group which contains at least one heteroatom, e.g., N, O or S, and may be aromatic (heteroaryl) or non-aromatic. Thus, the heteroaryl moieties are subsumed under the definition of heterocycle, depending on the context of its use. Exemplary heteroaryl groups are described hereinabove.

Exemplary heterocyclics include: azetidinyl, benzimidazolyl, 1,4-benzodioxanyl, 1,3-benzodioxolyl, benzoxazolyl, benzothiazolyl, benzothienyl, dihydroimidazolyl, dihydropyranyl, dihydrofuranyl, dioxanyl, dioxolanyl, ethyleneurea, 1,3-dioxolane, 1,3-dioxane, 1,4-dioxane, furyl, homopiperidinyl, imidazolyl, itnidazolinyl, imidazolidinyl, indolinyl, indolyl, isoquinolinyl, isothiazolidinyl, isothiazolyl, isoxazolidinyl, isoxazolyl, morpholinyl, naphthyridinyl, oxazolidinyl, oxazolyl, pyridone, 2-pyrrolidone, pyridine, piperazinyl, N-methylpiperazinyl, piperidinyl, phthalimide, succinimide, pyrazinyl, pyrazolinyl, pyridyl, pyrimidinyl, pyrrolidinyl, pyrrolinyl, pyrrolyl, quinolinyl, tetrahydrofuranyl, tetrahydropyranyl, tetrahydroquinoline, thiazolidinyl, thiazolyl, thienyl, tetrahydrothiophene, oxane, oxetanyl, oxathiolanyl, thiane among others.

Heterocyclic groups can be optionally substituted with a member selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SOaryl, —SO-heteroaryl, —$SO_2$-alkyl, —$SO_2$-substituted alkyl, —$SO_2$-aryl, oxo (=O), and —$SO_2$-heteroaryl. Such heterocyclic groups can have a single ring or multiple condensed rings. Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxynitrogen containing heterocycles. The term "heterocyclic" also includes bicyclic groups in which any of the heterocyclic rings is fused to a benzene ring or a cyclohexane ring or another heterocyclic ring (for example, indolyl, quinolyl, isoquinolyl, tetrahydroquinolyl, and the like).

The term "cycloalkyl" can mean but is in no way limited to univalent groups derived from monocyclic or polycyclic alkyl groups or cycloalkanes, as defined herein, e.g., saturated monocyclic hydrocarbon groups having from three to twenty carbon atoms in the ring, including, but not limited to, cyclopropyl, cyclobutyl, cyclopentyl, cyclohexyl, cycloheptyl and the like. The term "substituted cycloalkyl" can mean but is in no way limited to a monocyclic or polycyclic alkyl group and being substituted by one or more substituents, for example, amino, halogen, alkyl, substituted alkyl, carbyloxy, carbylmercapto, aryl, nitro, mercapto or sulfo, whereas these generic substituent groups have meanings which are identical with definitions of the corresponding groups as defined in this legend.

"Heterocycloalkyl" refers to a monocyclic or polycyclic alkyl group in which at least one ring carbon atom of its cyclic structure being replaced with a heteroatom selected from the group consisting of N, O, S or P. "Substituted heterocycloalkyl" refers to a monocyclic or polycyclic alkyl group in which at least one ring carbon atom of its cyclic structure being replaced with a heteroatom selected from the group consisting of N, O, S or P and the group is containing one or more substituents selected from the group consisting of halogen, alkyl, substituted alkyl, carbyloxy, carbylmercapto, aryl, nitro, mercapto or sulfo, whereas these generic substituent group have meanings which are identical with definitions of the corresponding groups as defined in this legend.

The term "hydrocarbyl" shall mean a compound which contains carbon and hydrogen and which may be fully saturated, partially unsaturated or aromatic and includes aryl groups, alkyl groups, alkenyl groups and alkynyl groups.

The term "independently" is used herein to indicate that the variable, which is independently applied, varies independently from application to application.

The term "lower alkyl" refers to methyl, ethyl or propyl

The term "lower alkoxy" refers to methoxy, ethoxy or propoxy.

Exemplary CLMs

In one aspect the description provides CLMs useful for binding and recruiting cereblon. In any aspect or embodiment described herein, the CLM is selected from the group consisting of chemical structures:

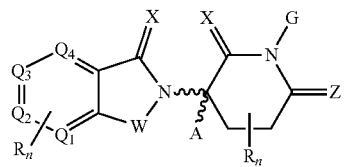
(a1)

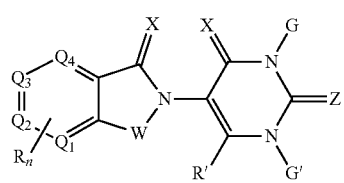
(b)

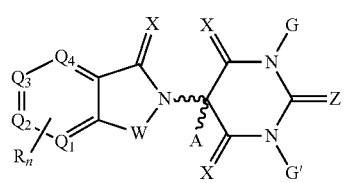
(c)

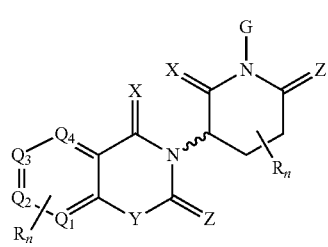
(d1)

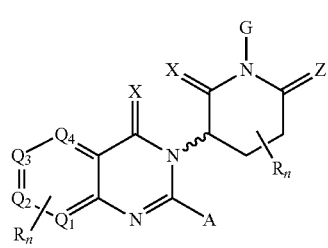
(e)

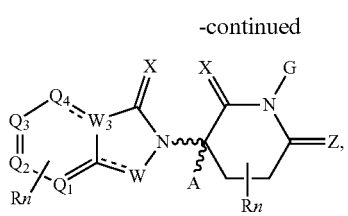
(a2)

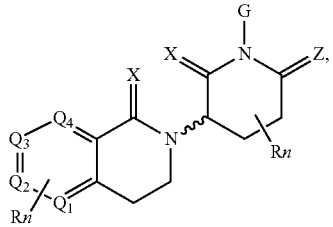
(d2)

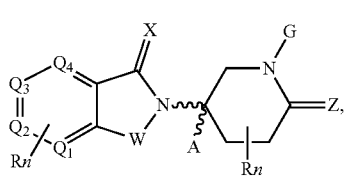
(a3)

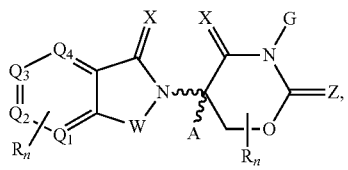
(a4)

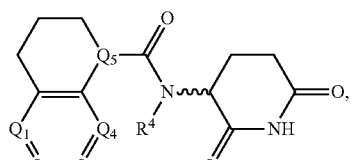
(f)

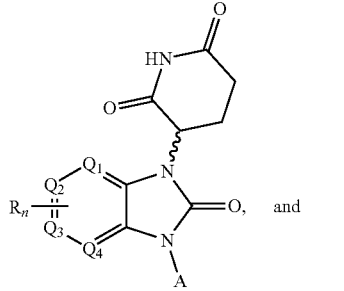
(g)

(h)

wherein:

W of Formulae (a1) through (e) (i.e., (a1), (a2), (a3), (a4), (b), (c), (d1), (d2), and (e)) is independently selected from CH$_2$, O, CHR, C=O, SO$_2$, NH, N, optionally substituted cyclopropyl group, optionally substituted cyclobutyl group, and N-alkyl;

W$_3$ of Formula (a2) is selected from C and N;

each X of Formulas (a1) through (e) is independently selected from absent, O, S and CH$_2$, each Y of Formula (d1) is independently selected from CH$_2$, C=CR', NH, N-alkyl, N-aryl, N-heteroaryl, N-cycloalkyl, N-heterocyclyl, O, and S;

each Z of Formulae (a1) through (e) is independently selected from absent, O, S, and CH$_2$, except that both X and Z cannot be CH$_2$ or absent;

each G and G' of Formulae (a1) through (e) is independently selected from H, optionally substituted linear or branched alkyl, OH, R'OCOOR, R'OCONRR", CH$_2$-heterocyclyl optionally substituted with R', and benzyl optionally substituted with R';

each of Q1, Q2, Q3, Q4, and Q5 of Formulae (a1) through (h) represent a nitrogen or a carbon substituted with a group independently selected from H, R, N and N-oxide;

each A of Formulae (a1) through (h) is independently selected from H, optionally substituted linear or branched alkyl, cycloalkyl, Cl and F;

each n of Formulae (a1) through (e) represents an integer independently selected from 1 to 10 (e.g., 1-4, 1, 2, 3, 4, 5, 6, 7, 8, 9, or 10);

each R of Formulae (a1) through (e) is independently selected from: H, —C(=O)R' (e.g., a carboxy group), —CONR'R" (e.g., an amide group), —OR' (e.g., OH), —NR'R" (e.g., an amine group), —SR', —SO$_2$R', —SO$_2$NR'R", —CR'R"—, —CR'NR'R"—, (—CR'O)$_{n'}$R", optionally substituted aryl, (e.g., an optionally substituted C5-C7 aryl), optionally substituted heteroaryl, (e.g., an optionally substituted 5-7 membered heteroaryl), optionally substituted alkyl-aryl (e.g., an alkyl-aryl comprising at least one of an optionally substituted C1-C6 alkyl, an optionally substituted C5-C7 aryl, or a combination thereof), optionally substituted heteroaryl, optionally substituted alkyl (e.g., a C1-C6 linear or branched alkyl optionally substituted with one or more halogen, cycloalkyl (e.g., a C3-C6 cycloalkyl), or aryl (e.g., C5-C7 aryl)), optionally substituted alkoxyl group (e.g., a methoxy, ethoxy, butoxy, propoxy, pentoxy, or hexoxy; wherein the alkoxyl may be substituted with one or more halogen, alkyl, haloalky, fluoroalkyl, cycloalkyl (e.g., a C3-C6 cycloalkyl), or aryl (e.g., C5-C7 aryl)), optionally substituted cycloalkyl, optionally substituted heterocyclyl, —P(O)(OR')R", —P(O)R'R", —OP(O)(OR')R", —OP(O)R'R", —Cl, —F, —Br, —I, —CF$_3$, —CN, —NR'SO$_2$NR'R", —NR'CONR'R", —CONR'COR", —NR'C(=N—CN)NR'R", —C(=N—CN)NR'R", —NR'C(=N—CN)R", —NR'C(=C—NO$_2$)NR'R", —SO$_2$NR'COR", —NO$_2$, —CO$_2$R', —C(C=N—OR')R", —CR'=CR'R", —CCR', —S(C=O)(C=N—R')R", —SF$_5$ or —OCF$_3$, wherein at least one W, X, Y, Z, G, G', R, R', R", Q1, Q2, Q3, Q4, or A is modified to be covalently joined to a PTM, a chemical linking group (L), a ULM, CLM, or a combination thereof;

R' and R" of Formulae (a1) through (e) are each independently selected from H, optionally substituted linear or branched alkyl, optionally substituted cycloalkyl, optionally substituted aryl, optionally substituted heteroaryl, optionally substituted heterocyclic, —C(=O)R, and optionally substituted heterocyclyl;

R$^4$ is selected from H, alkyl, and substituted alkyl;

n' of Formulae (a1) through (e) is an integer selected from 1-10 (e.g., 1-4, 1, 2, 3, 4, 5, 6, 7, 8, 9, or 10);

⋯⋯ represents a single bond or a double bond; and each ∿∿ of Formulae (a1) through (h) independently represents a bond that is stereospecific ((R) or (S)) or non-stereospecific.

In any aspect or embodiment described herein, the CLM comprises a chemical structure selected from the group consisting of:

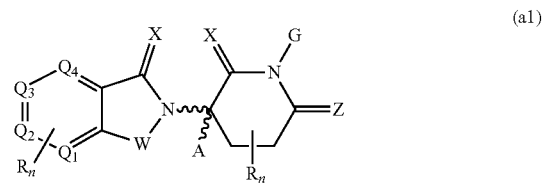

(a1)

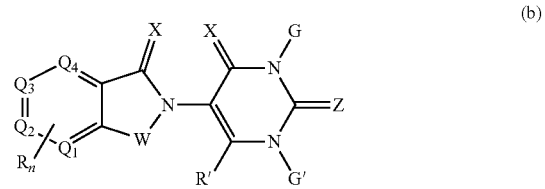

(b)

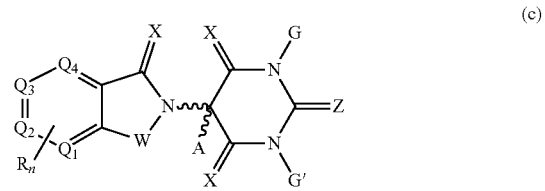

(c)

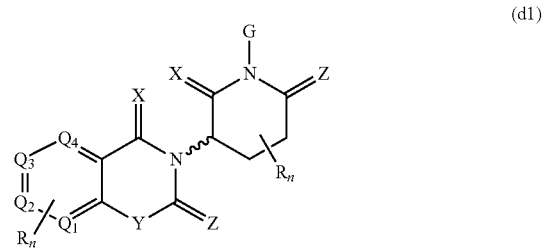

(d1)

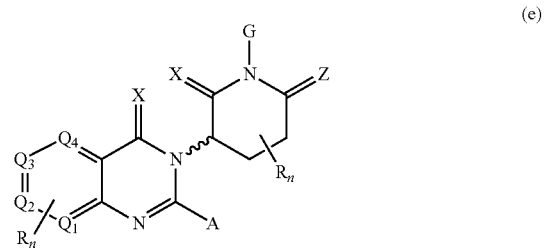

(e)

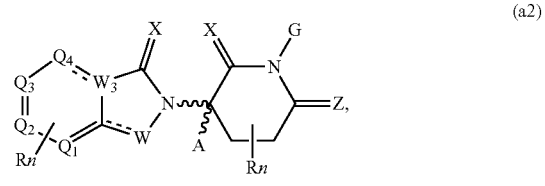

(a2)

-continued

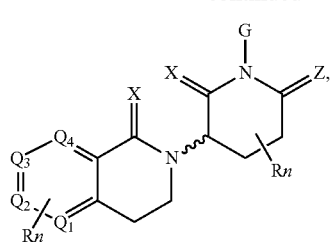
(d2)

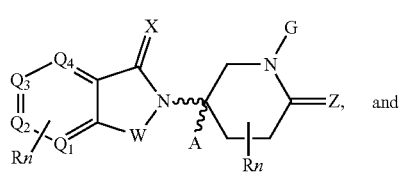
(a3)

and

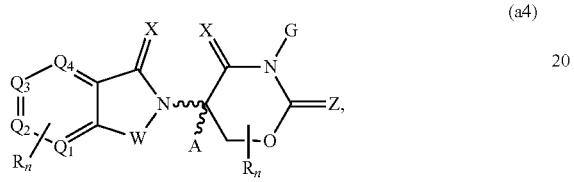
(a4)

wherein:
each W of Formulae (a1) through (e) (i.e., (a1), (a2), (a3), (a4), (b), (c), (d1), (d2), and (e)) is independently selected from CH$_2$, O, CHR, C=O, SO$_2$, NH, N, optionally substituted cyclopropyl group, optionally substituted cyclobutyl group, and N-alkyl;
W$_3$ of Formula (a2) is selected from C and N;
each X of Formulae (a1) through (e) is independently selected from absent, O, S and CH$_2$;
each Y of Formula (d1) through (e) is independently selected from CH$_2$, C=CR', NH, N-alkyl, N-aryl, N-hetaryl, N-cycloalkyl, N-heterocyclyl, O, and S;
each Z of Formulae (a1) through (e) is independently selected from absent, O, and S or CH$_2$, except that both X and Z cannot be CH$_2$ or absent;
each of G and G' of Formulae (a1) through (e) are independently selected from H, optionally substituted linear or branched alkyl, OH, R'OCOOR, R'OCONRR", CH$_2$-heterocyclyl optionally substituted with R', and benzyl optionally substituted with R';
Q1, Q2, Q3 and Q4 of Formulas (a1) through (e) each independently represent a nitrogen or a carbon with a group independently selected from H, R, N and N-oxide;
A of Formulae (a1) through (e) is independently selected from H, optionally substituted linear or branched alkyl, cycloalkyl, Cl and F;
n of Formulae (a1) through (e) represents an integer independently selected from 1 to 10 (e.g., 1-4, 1, 2, 3, 4, 5, 6, 7, 8, 9, or 10);
R of Formulae (a1) through (e) is selected from the group consisting of: H, —C(=O)R' (e.g., a carboxy group), —CONR'R" (e.g., an amide group), —OR' (e.g., OH), —NR'R" (e.g. an amine group), —SR', —SO$_2$R', —SO$_2$NR'R", —CR'R"—, —CR'NR'R"—, (—CR'O)$_n$, R", optionally substituted aryl (e.g., an optionally substituted C5-C7 aryl), optionally substituted alkyl-aryl (e.g., an alkyl-aryl comprising at least one of an optionally substituted C1-C6 alkyl, an optionally substituted C5-C7 aryl, or a combination thereof), optionally substituted heteroaryl (e.g., an optionally substituted 5-7 membered heteroaryl), -optionally substituted linear or branched alkyl (e.g., a C1-C6 linear or branched alkyl optionally substituted with one or more halogen, cycloalkyl (e.g., a C3-C6 cycloalkyl), or aryl (e.g., C5-C7 aryl)), optionally substituted alkoxyl group (e.g., a methoxy, ethoxy, butoxy, propoxy, pentoxy, or hexoxy; wherein the alkoxyl may be substituted with one or more halogen, alkyl, haloalky, fluoroalkyl, cycloalkyl (e.g., a C3-C6 cycloalkyl), or aryl (e.g., C5-C7 aryl)), optionally substituted cycloalkyl, optionally substituted heterocyclyl, —P(O)(OR')R", —P(O)R'R", —OP(O)(OR'—OP(O)R'R", —Cl, —F, —Br, —I, —CF3, —CN, —NR'SO2NR'R", —NR-'CONR'R", —CONR'COR", —NR'C(=N—CN)NR'R", —C(=N—CN)NR'R", —NR'C(=N—CN)R", —NR'C(=C—NO2)NR'R", —SO2NR'COR", —NO2, —CO2R', —C(C=N—OR')R", —CR'=CR'R", —CCR', —S(C=O)(C=N—R')R", —SF5 and —OCF$_3$, wherein at least one of W, X, Y, Z, G, G', R, R', R", Q1-Q4, or A is covalently joined (directly or indirectly, e.g., via a functional group or an atom, such as O, S, N) to a PTM, a chemical linking group (L), a ULM, CLM, or combination thereof;
R' and R" of Formulae (a1) through (e) are each independently selected from a bond, H, optionally substituted linear or branched alkyl, optionally substituted cycloalkyl, optionally substituted aryl, optionally substituted heteroaryl, optionally substituted heterocyclic, —C(=O)R, optionally substituted heterocyclyl;
n' of Formulae (a1) through (e) is an integer selected from 1-10 (e.g., 1-4, 1, 2, 3, 4, 5, 6, 7, 8, 9, or 10);
represents a single bond or a double bond; and
each ⟿ of Formulae (a1) through (e) independently represents a bond that is stereospecific ((R) or (S)) or non-stereospecific.
In any aspect or embodiment described herein, the CLM or ULM has the chemical structure of Formula (g):

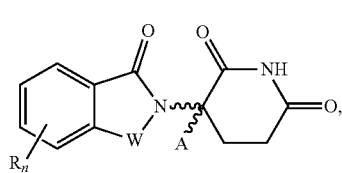
Formula (g)

wherein:
W of Formula (g) is selected from CH$_2$, O, C=O, NH, and N-alkyl;
A of Formula (g) is selected from H, methyl, or optionally substituted linear or branched alkyl; n is an integer selected from 1 to 4;
R of Formula (g) is independently selected from H, O, OH, N, NH, NH$_2$, —Cl, —F, —Br, —I, methyl, optionally substituted linear or branched alkyl (e.g., optionally substituted linear or branched C1-C6 alkyl), optionally substituted linear or branched alkoxy (e.g., optionally substituted linear or branched C1-C6 alkoxy), -alkyl-aryl (e.g., an -alkyl-aryl comprising at least one of C1-C6 alkyl, C4-C7 aryl, or a combination thereof), aryl (e.g., C5-C7 aryl), amine, amide, or carboxy), wherein at least one R or W is modified to be covalently joined to a PTM, a chemical linking group (L), a ULM, CLM, or combination thereof; and each ⌇ of Formula (g) independently represents a bond that is stereospecific ((R) or (S)) or non-stereospecific.

In any aspect or embodiment described herein, the CLM or ULM is selected from the group consisting of:

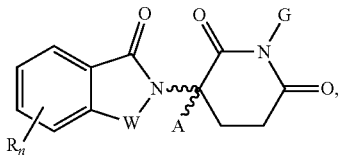

wherein:
W is selected from CH$_2$ and C=O;
A is a H or linear or branched C$_{1-3}$ alkyl (e.g., a methyl or ethyl);
n is an integer selected from 1 to 2;
G is a H or a linear or branched C$_{1-3}$ alkyl (e.g., methyl);
each R is independently selected from a H, O, OH, N, NH, NH$_2$, —Cl, —F, —Br, linear or branched C$_{1-3}$ alkyl (e.g., methyl or ethyl), or a linear or branched C$_{1-3}$ alkoxy (e.g., methoxy or ethoxy), wherein one R is modified to be covalently joined to a PTM via a chemical linking group (L); and
each ⌇ independently represents a bond that is stereospecific ((R) or (S)) or non-stereospecific.

In any aspect or embodiment described herein, the CLM or ULM is selected from the group consisting of:

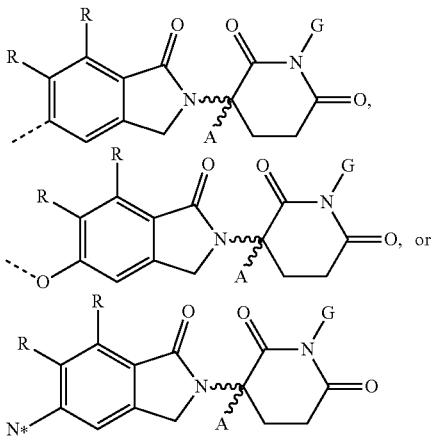

wherein:
A is a H or linear or branched C$_{1-3}$ alkyl (e.g., a methyl or ethyl);
G is a H or a linear or branched C$_{1-3}$ alkyl (e.g., methyl);
each R is independently a H, OH, NH$_2$, —Cl, —F, —Br, linear or branched C$_{1-3}$ alkyl (e.g., methyl or ethyl), or a linear or branched C$_{1-3}$ alkoxy (e.g., methoxy or ethoxy); and
N* is a nitrogen atom that is covalently linked to the PTM via the chemical linker group (L) with a H or methyl completing valency or that is shared with the chemical linker group (L) (e.g., a heteroatom shared with an optionally substituted heterocyloalkyl of the chemical linker group (L).

In any aspect or embodiment described herein, the CLM or ULM is selected from the group consisting of:

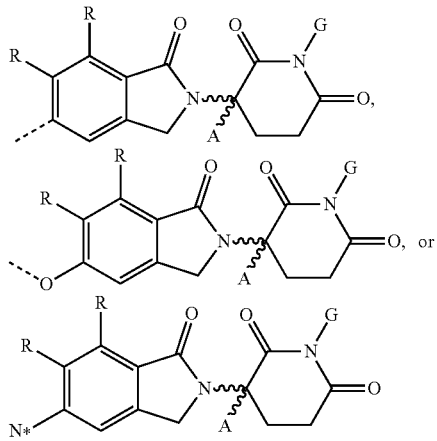

wherein:
A is a H or linear or branched C$_{1-3}$ alkyl (e.g., a methyl or ethyl);
G is a H or a linear or branched C$_{1-3}$ alkyl (e.g., methyl);
one R is a hydrogen and the other R is a H, OH, NH$_2$, —Cl, —F, —Br, linear or branched C$_{1-3}$ alkyl (e.g., methyl or ethyl), or a linear or branched C$_{1-3}$ alkoxy (e.g., methoxy or ethoxy); and
N* is a nitrogen atom that is covalently linked to the PTM via the chemical linker group (L) with a H or methyl completing valency or that is shared with the chemical linker group (L) (e.g., a heteroatom shared with an optionally substituted heterocyloalkyl of the chemical linker group (L).

In any aspect or embodiment described herein, the CLM or ULM is selected from the group consisting of:

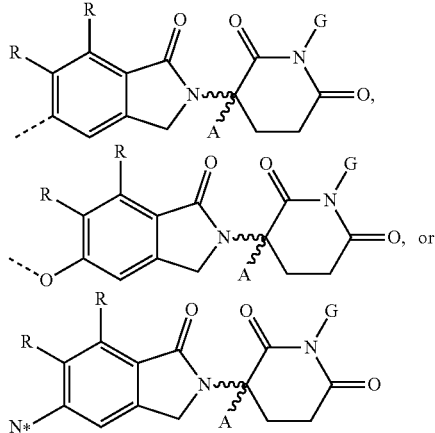

wherein:
A is a H or linear or branched C$_{1-3}$ alkyl (e.g., a methyl or ethyl);
G is a H or a linear or branched C$_{1-3}$ alkyl (e.g., methyl), preferably H;
one R is a hydrogen and the other R is a H, —Cl, —F, —Br, linear or branched C$_{1-3}$ alkyl (e.g., methyl or ethyl), or a linear or branched C$_{1-3}$ alkoxy (e.g., methoxy or ethoxy); and
N* is a nitrogen atom that is covalently linked to the PTM via the chemical linker group (L) with a H or methyl completing valency or that is shared with the chemical linker group (L) (e.g., a heteroatom shared with an optionally substituted heterocyloalkyl of the chemical linker group (L)).

In any aspect or embodiment described herein, the CLM or ULM is selected from the group consisting of:

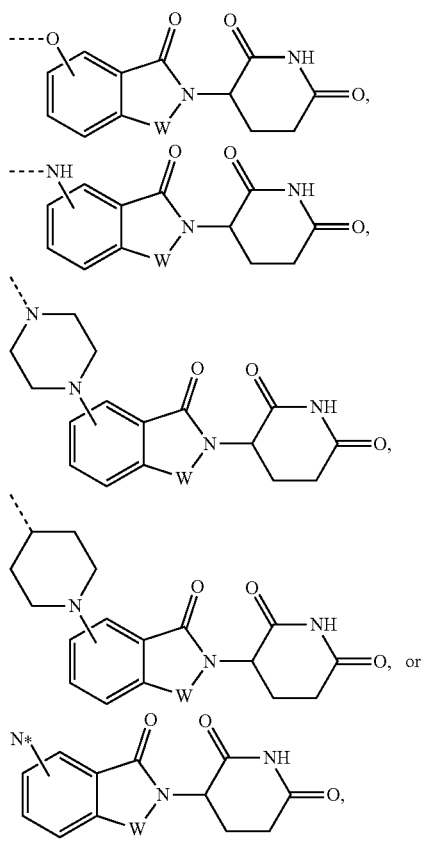

wherein:
W is C=O or CH$_2$;
N* is a nitrogen atom that is covalently linked to the PTM or linker, or that is shared with the the PTM or linker (L) (e.g., a heteroatom shared with an optionally substituted heterocyclyl of the linker (L) or PTM); and ⋰ indicates the point of attachment of the CLM or ULM to the linker (L) or PTM.

In any aspect or embodiment described herein, R is selected from: H, O, OH, N, NH, NH$_2$, C1-C6 alkyl, C1-C6 alkoxy, -alkyl-aryl (e.g., an -alkyl-aryl comprising at least one of C1-C6 alkyl, C4-C7 aryl, or a combination thereof), aryl (e.g., C5-C7 aryl), amine, amide, and carboxy).

In any aspect or embodiment described herein, at least one R (e.g. an R group selected from the following H, O, OH, N, NH, NH$_2$, C1-C6 alkyl, C1-C6 alkoxy, -alkyl-aryl (e.g., an -alkyl-aryl comprising at least one of C1-C6 alkyl, C4-C7 aryl, or a combination thereof), aryl (e.g., C5-C7 aryl), amine, amide, or carboxy) or W is modified to be covalently joined to a PTM, a chemical linker group (L), a ULM, a CLM, or a combination thereof.

In any aspect or embodiment described herein, the W, X, Y, Z, G, G', R, R', R", Q1-Q4, and A of Formulas (a) through (g) can independently be covalently coupled to a linker and/or a linker to which is attached one or more PTM, ULM, or CLM groups.

In any of the aspect or embodiment described herein, n is an integer from 1 to 4, and each R is independently selected functional group or atom, for example, O, OH, N, —Cl, —F, C1-C6 alkyl, C1-C6 alkoxy, -alkyl-aryl (e.g., an -alkyl-aryl comprising at least one of C1-C6 alkyl, C4-C7 aryl, or a combination thereof), aryl (e.g., C5-C7 aryl), amine, amide, or carboxy, on the aryl or heteroaryl of the CLM, and optionally, one of which is modified to be covalently joined to a PTM, a chemical linker group (L), a ULM, CLM or combination thereof.

More specifically, non-limiting examples of CLMs include those shown below as well as those "hybrid" molecules that arise from the combination of one or more of the different features shown in the molecules below wherein at least one R or W is modified to be covalently joined to a PTM, a chemical linking group (L), a ULM, CLM, or combination thereof.

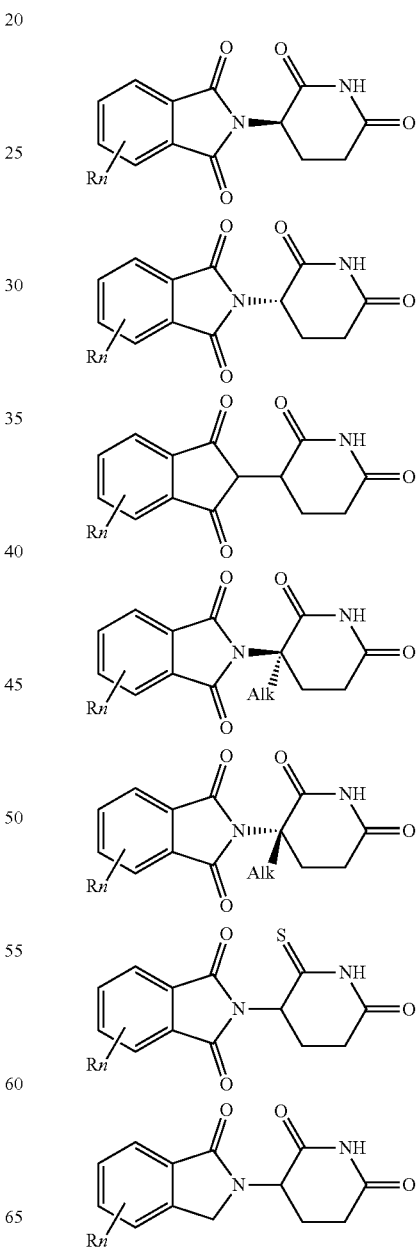

-continued
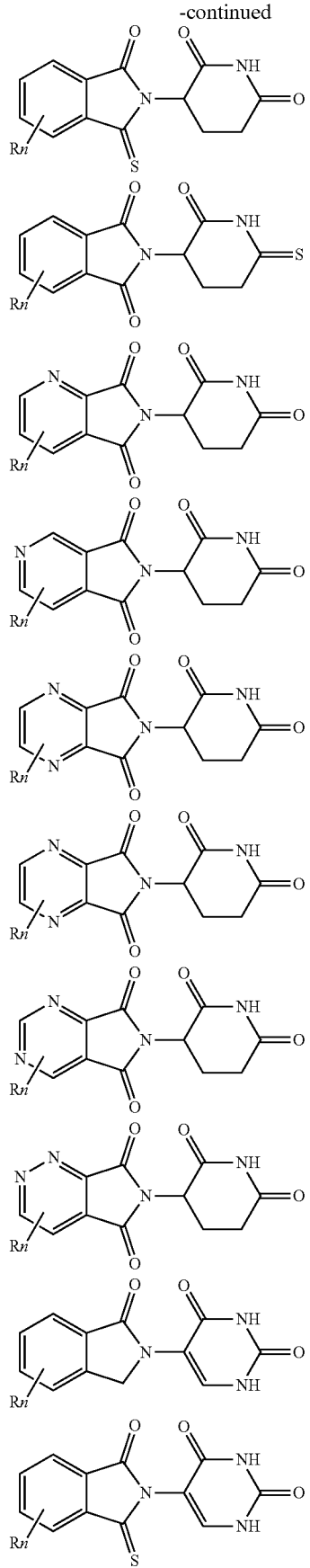
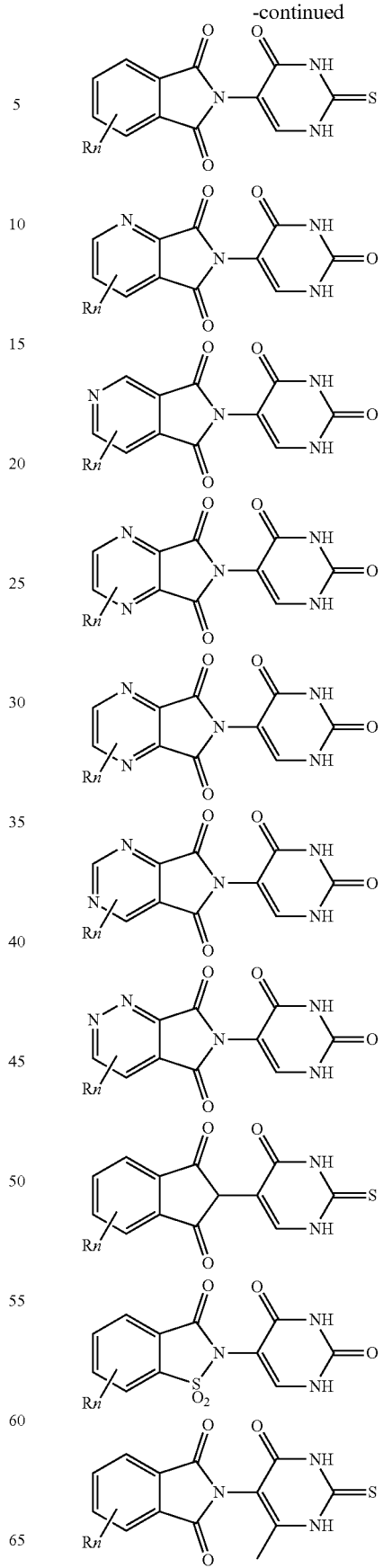

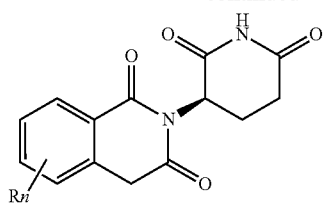
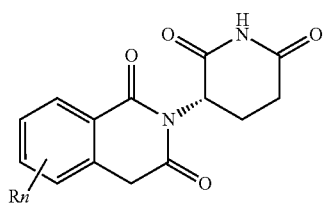
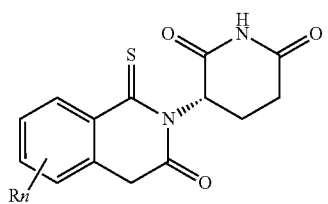
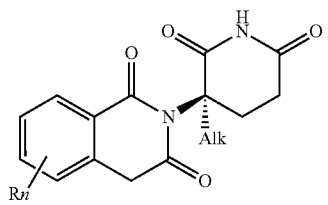
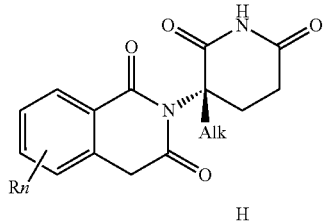
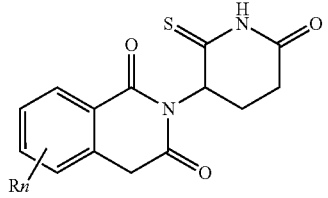
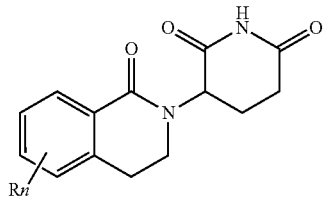
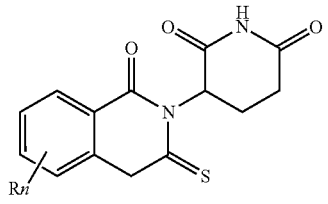
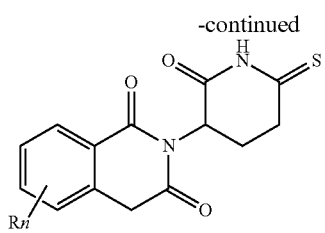
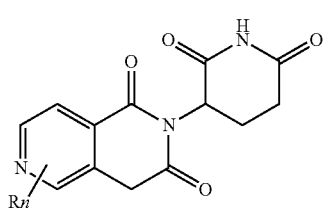
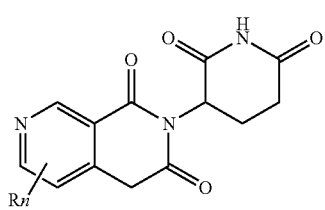
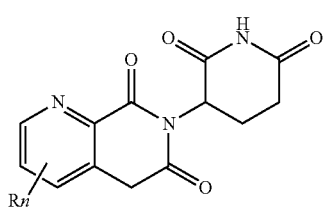
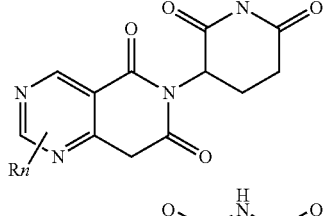
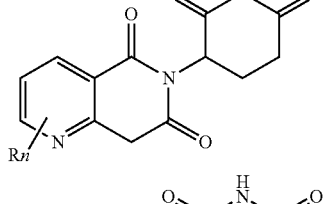
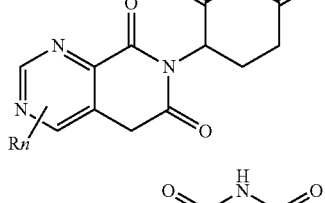
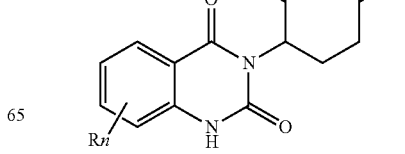

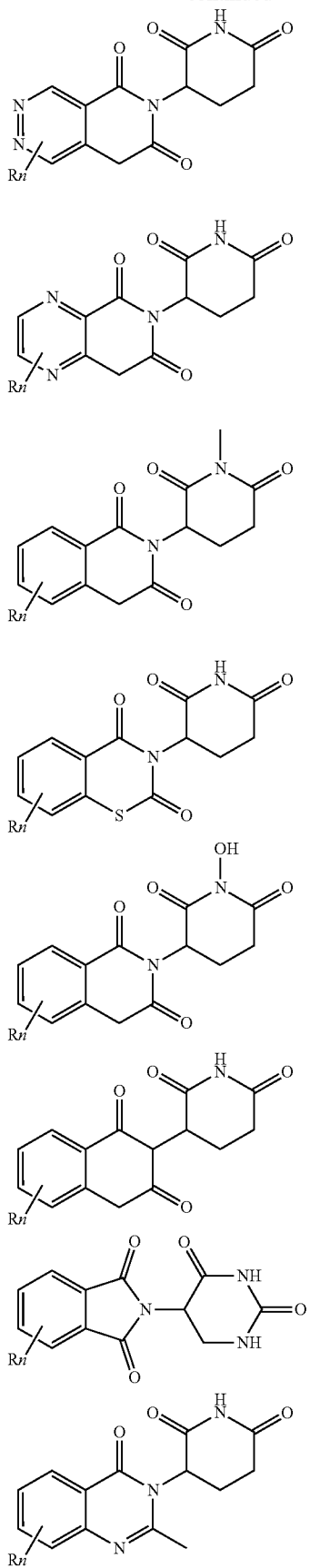
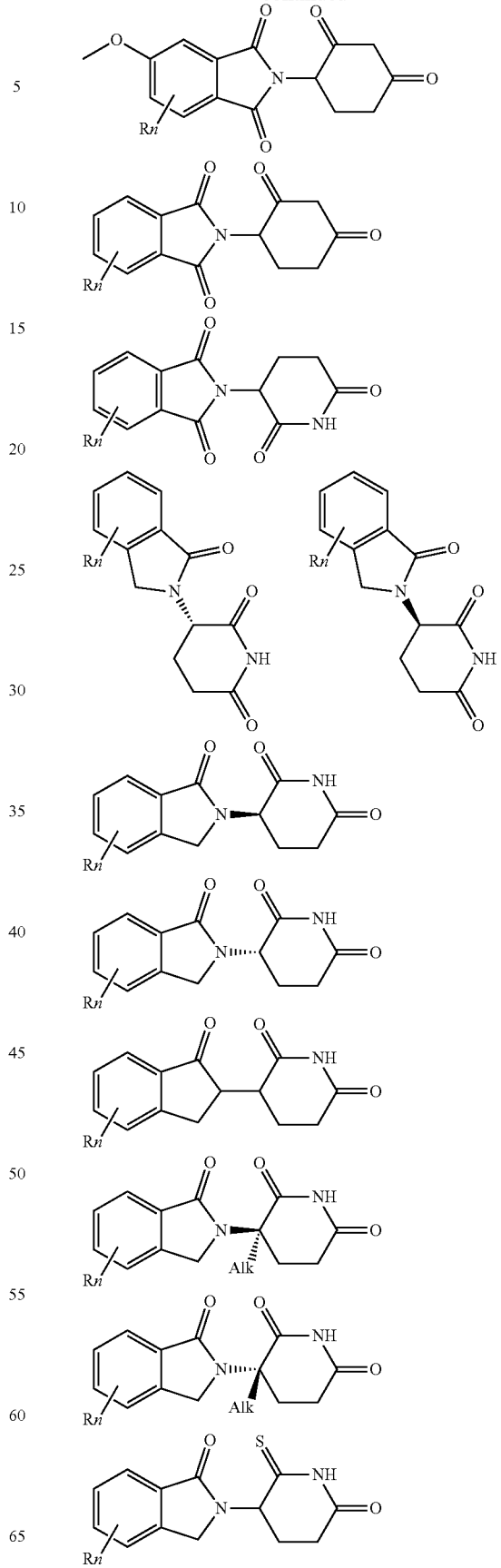

-continued
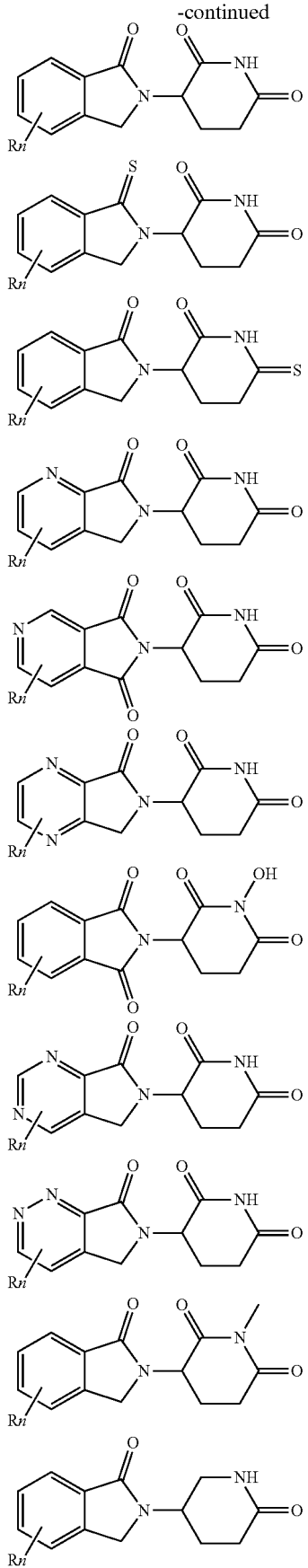
-continued
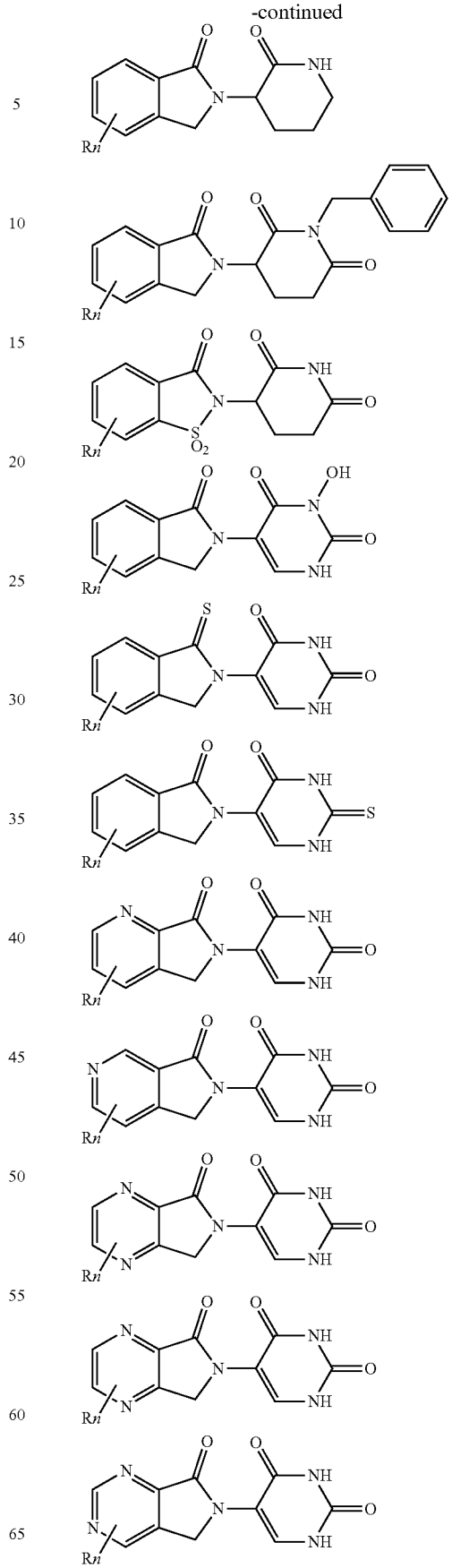

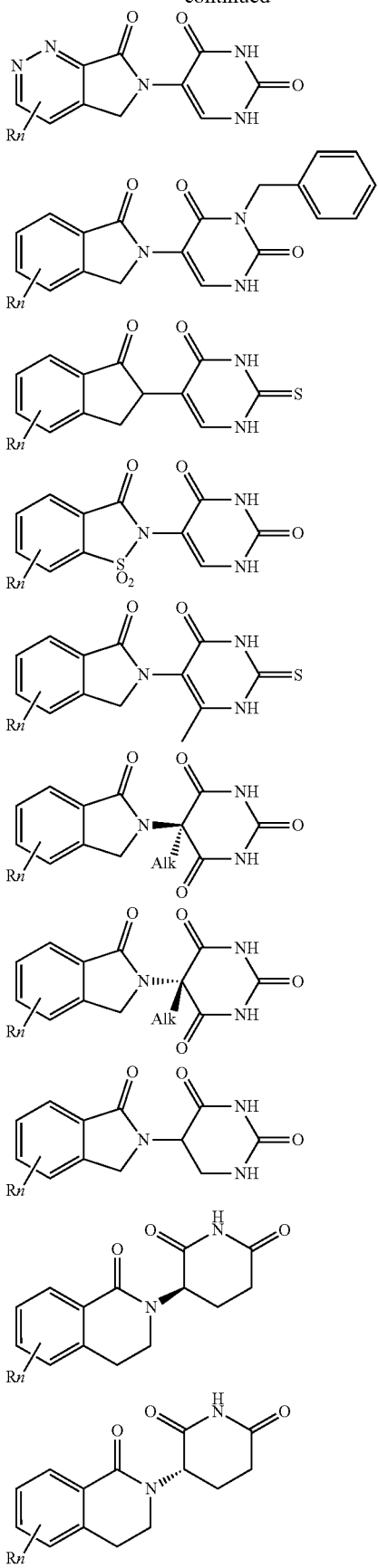

37
-continued
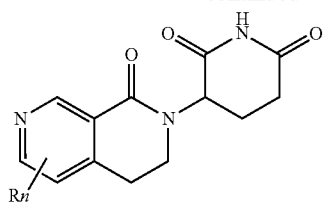
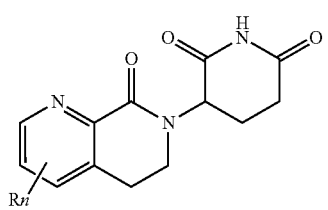
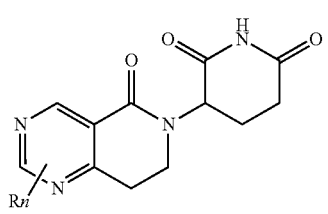
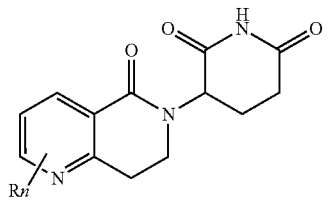
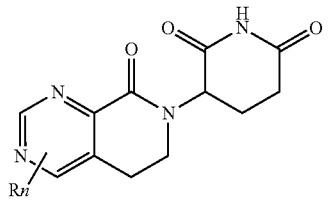
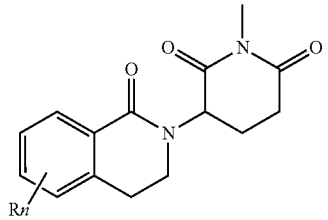
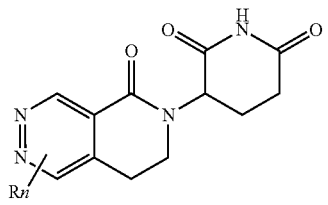
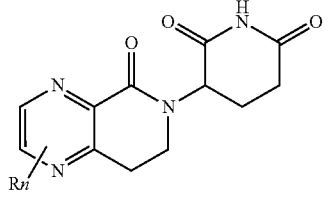
38
-continued
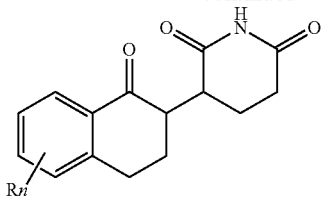
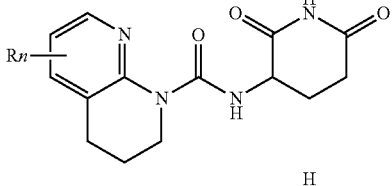
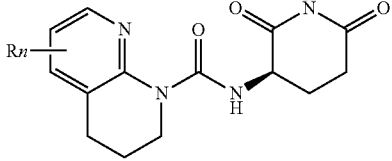
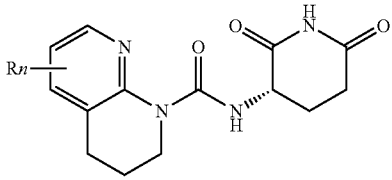
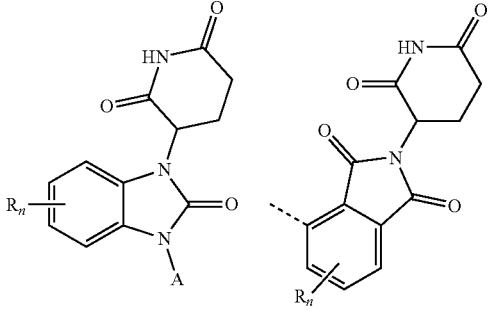
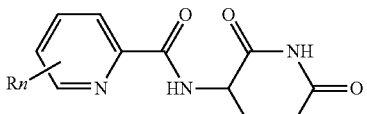
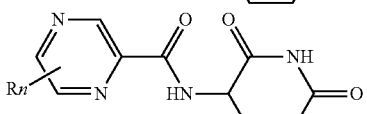
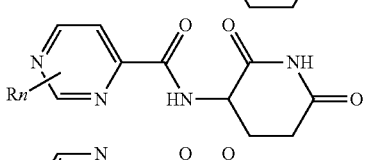
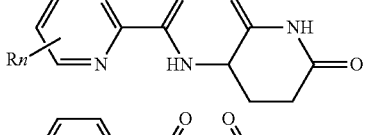
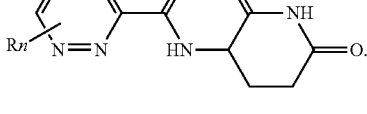

In any aspect or embodiment described herein, the CLM comprises a chemical structure selected from the group:
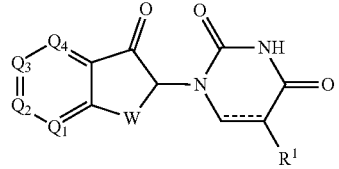
(h)
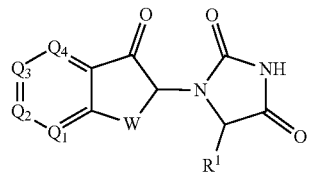
(i)
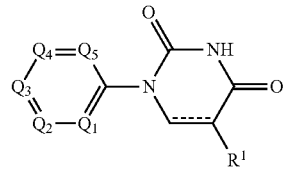
(j)
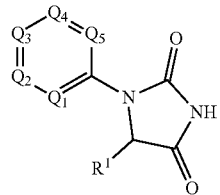
(k)
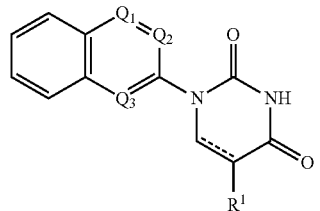
(l)
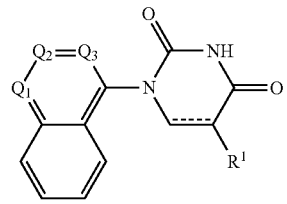
(m)
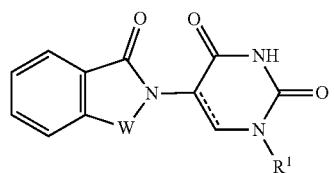
(n)
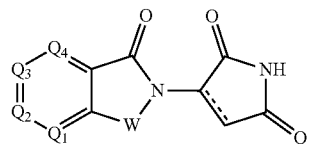
(o)
-continued
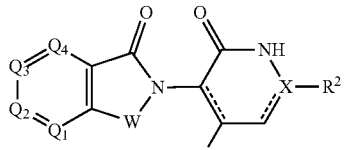
(p)
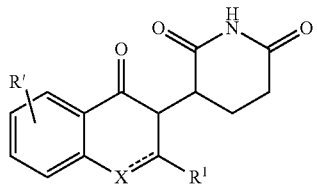
(q)
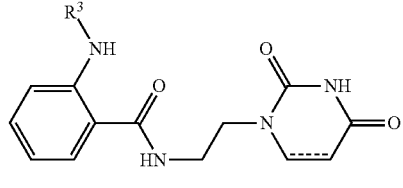
(r)
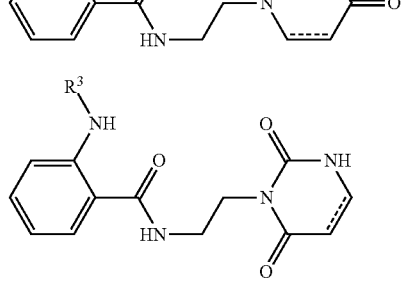
(s)
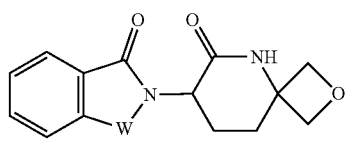
(t)
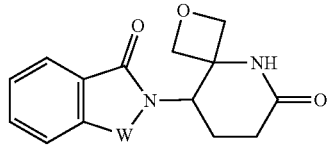
(u)
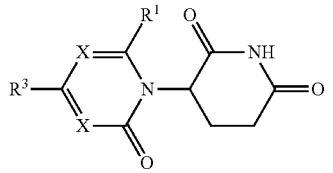
(v)
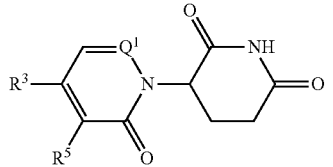
(w)
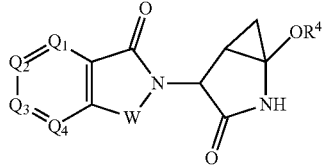
(x)

-continued
(y)
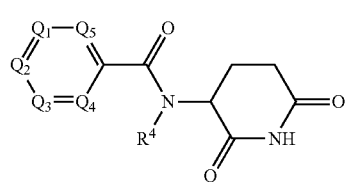
(z)
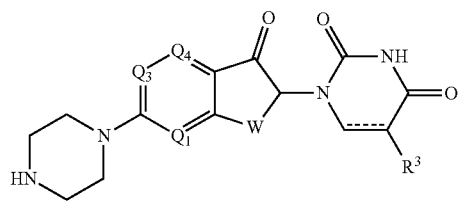
(aa)
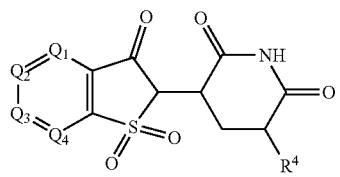
(ab)
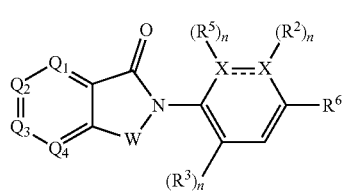
(ac)
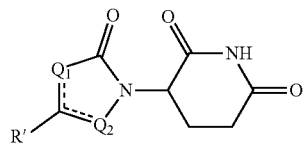
(ad)
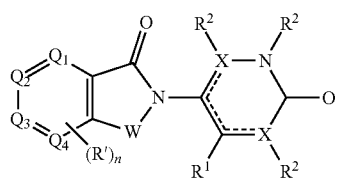
(ae)
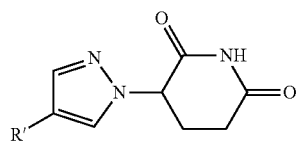
(af)
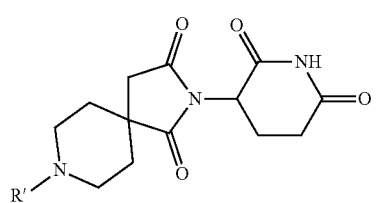
-continued
(ag)
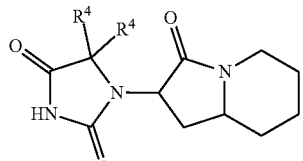
(ah)
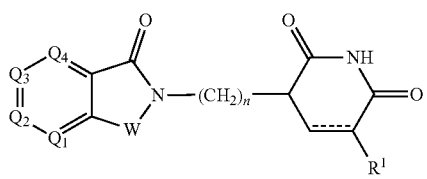
(ai)
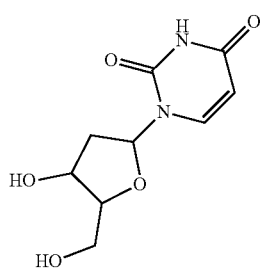
(aj)
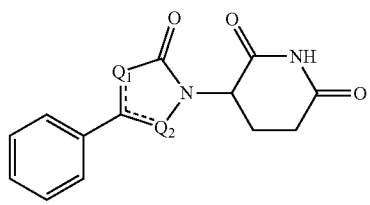
(ak)
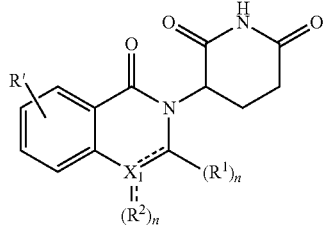
(al)
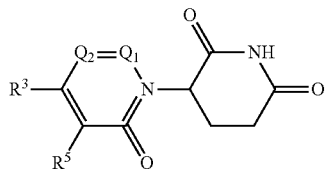
(am)
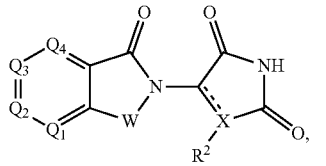
(an)
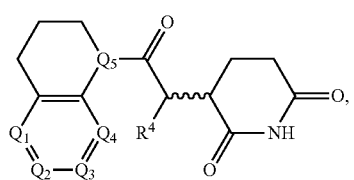

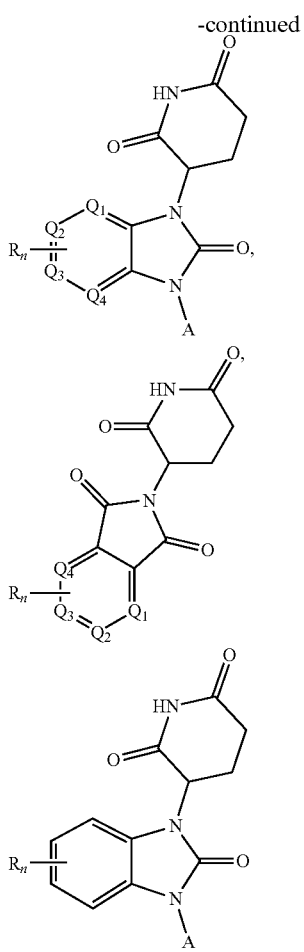

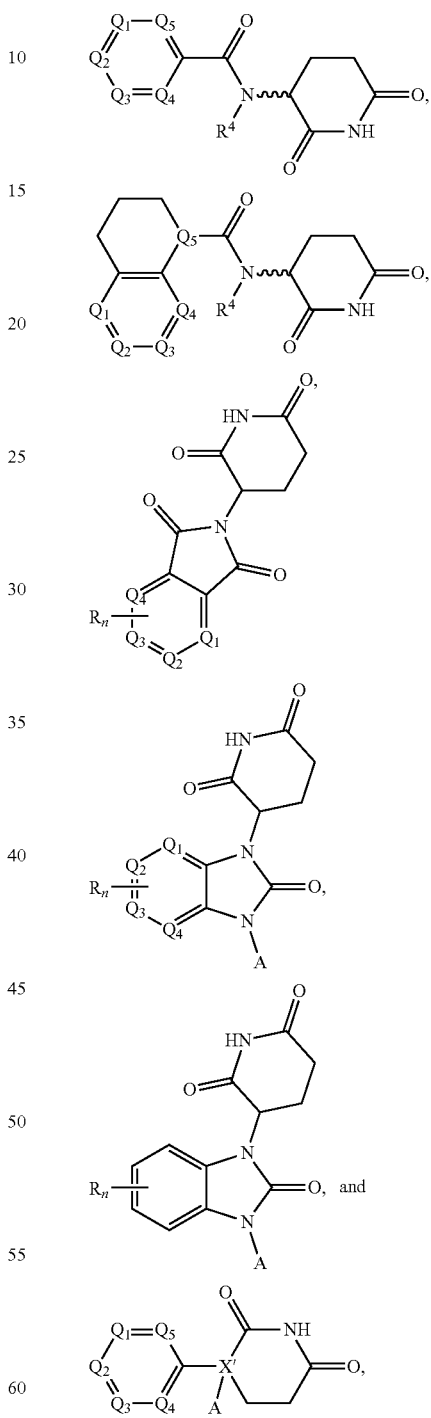

wherein:
- W is independently selected from $CH_2$, O, CHR, C=O, $SO_2$, NH, N, optionally substituted cyclopropyl group, optionally substituted cyclobutyl group, and N-alkyl (e.g., $CH_2$, CHR, C=O, $SO_2$, NH, and N-alkyl);
- $Q_1$, $Q_2$, $Q_3$, $Q_4$, $Q_5$ are each independently C or N substituted with a group independently selected from R', N and N-oxide;
- $R^1$ is selected from absent, H, OH, CN, C1-C3 alkyl, and C=O;
- $R^2$ is selected from the group absent, H, OH, CN, C1-C3 alkyl, $CHF_2$, $CF_3$, CHO, and $C(=O)NH_2$;
- $R^3$ is selected from H, alkyl (e.g., C1-C6 or C1-C3 alkyl), substituted alkyl (e.g., substituted C1-C6 or C1-C3 alkyl), alkoxy (e.g., C1-C6 or C1-C3 alkoxyl), and substituted alkoxy (e.g., substituted C1-C6 or C1-C3 alkoxyl);
- $R^4$ is selected from H, alkyl, and substituted alkyl;
- $R^5$ and $R^6$ are each independently selected from H, halogen, C(=O)R', CN, OH, and $CF_3$;
- X is C, CH, C=O, or N;
- $X_1$ is C=O, N, CH, or $CH_2$;
- R' is selected from H, halogen, amine, alkyl (e.g., C1-C3 alkyl), substituted alkyl (e.g., substituted $C_1$-C3 alkyl), alkoxy (e.g., C1-C3 alkoxyl), substituted alkoxy (e.g., substituted C1-C3 alkoxyl), $NR^2R^3$, $C(=O)OR^2$, and optionally substituted phenyl;
- n is 0-4;
- ⫽ is a single or double bond; and
- the CLM is covalently joined to a PTM either by a covalent bond or through a chemical linker group (L), wherein L is a chemical linking moiety that covalently couples the CLM to the PTM via a member selected from $Q_1$, $Q_2$, $Q_3$, $Q_4$, $Q_5$, R, and R'.

In any aspect or embodiment described herein, the CLM or ULM is selected from:

wherein:
- $Q_1$, $Q_2$, $Q_3$, $Q_4$, $Q_5$ are each independently N or C substituted with a group independently selected from R, N or N-oxide;

X' is N or C;

A is a H or linear or branched $C_{1-3}$ alkyl (e.g., a methyl or ethyl);

$R^4$ is a H or methyl;

R is a H, halogen (e.g., F, Cl, Br), a $C_{1-3}$ alkyl (e.g., methyl or ethyl), or $C_{1-3}$ alkoxyl (e.g., a methoxy or ethoxy);

⫽ is a single or double bond; and

⌇⌇⌇ represents a bond that is stereospecific ((R) or (S)) or non-stereospecific.

In any aspect or embodiment described herein, the CLM or ULM is:

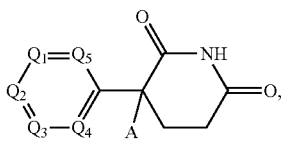

wherein:

$Q_1$, $Q_2$, $Q_3$, $Q_4$, $Q_5$ are each independently N or C substituted with a group independently selected from R, N or N-oxide;

A is a H or linear or branched $C_{1-3}$ alkyl (e.g., a methyl or ethyl); and

R is a H, halogen (e.g., F, Cl, Br), a $C_{1-3}$ alkyl (e.g., methyl or ethyl), or $C_{1-3}$ alkoxyl (e.g., a methoxy or ethoxy).

In any aspect or embodiment described herein, the CLM or ULM is:

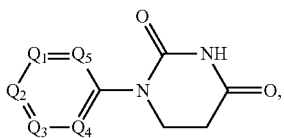

wherein:

$Q_1$, $Q_2$, $Q_3$, $Q_4$, $Q_5$ are each independently N or C substituted with a group independently selected from R, N or N-oxide;

A is a H or linear or branched $C_{1-3}$ alkyl (e.g., a methyl or ethyl); and

R is a H, halogen (e.g., F, Cl, Br), a $C_{1-3}$ alkyl (e.g., methyl or ethyl), or $C_{1-3}$ alkoxyl (e.g., a methoxy or ethoxy).

In any aspect or embodiment described herein, the CLM or ULM is selected from:

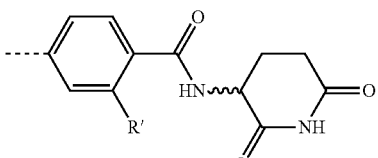

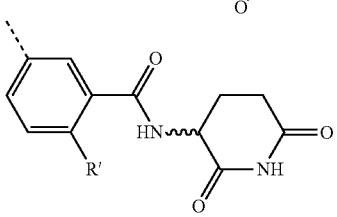

-continued

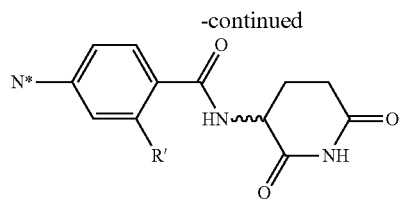

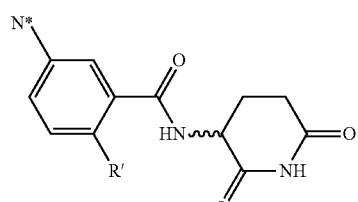

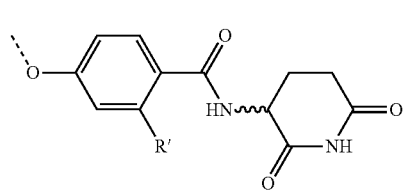

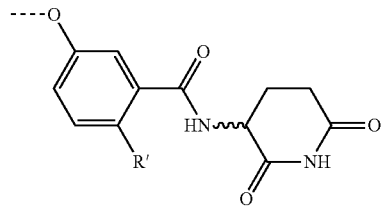

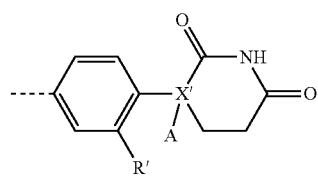

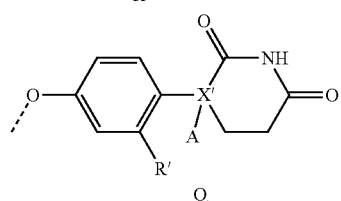

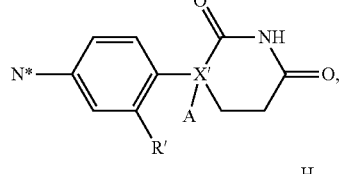

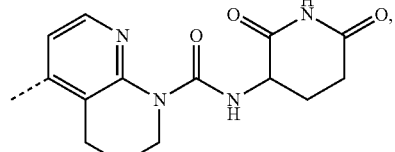

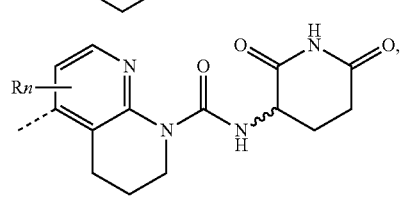

-continued

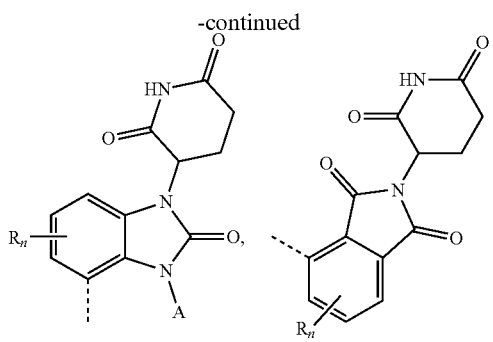

wherein:

X' is N, C or CH;

A is a H or linear or branched $C_{1-3}$ alkyl (e.g., a methyl or ethyl);

R' is a H, halogen (e.g., F, Cl, Br), a $C_{1-3}$ alkyl (e.g., methyl or ethyl), or $C_{1-3}$ alkoxyl (e.g., a methoxy or ethoxy);

∿∿ represents a bond that is stereospecific ((R) or (S)) or non-stereospecific;

N* is a nitrogen atom (i) that is covalently linked to the PTM via a chemical linker group (L) with a H or methyl completing valency or (ii) that is shared with the chemical linker group (L) (e.g., a heteroatom shared with an optionally substituted heterocyloalkyl of the chemical linker group (L);

⫽ is a single or double bond; and the ⌐--⌐ indicates the site of attachment of a PTM via the chemical linker group.

In any aspect or embodiment described herein, the CLM is covalently joined directly to a PTM, or through a chemical linker group (L) via an R group (such as, R, $R^1$, $R^2$, $R^3$, $R^4$ or R'), W, X, or a Q group (such as, $Q_1$, $Q_2$, $Q_3$, $Q_4$, or $Q_5$), for example, L is a chemical linking moiety that covalently couples the CLM to the PTM via a member selected from $Q_1$, $Q_2$, $Q_3$, $Q_4$, $Q_5$, R, and R'.

In any aspect or embodiment described herein, the CLM is covalently joined directly to a PTM via a bond, or through a chemical linker group (L) via W, X, $R^1$, $R^2$, $R^3$, $R^4$, $R^5$, R', $Q_1$, $Q_2$, $Q_3$, $Q_4$, and $Q_5$.

In any aspect or embodiment described herein, the W, X, $R^1$, $R^2$, $R^3$, $R^4$, R', $Q_1$, $Q_2$, $Q_3$, $Q_4$, or $Q_5$ can independently be covalently coupled to a linker to which is attached one or more PTM, ULM, or CLM groups.

More specifically, non-limiting examples of CLMs include those shown below as well as "hybrid" molecules or compounds that arise from combining one or more features of the following compounds:

(an)

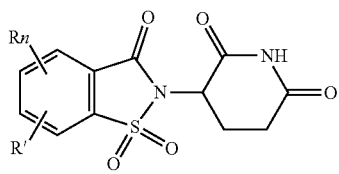

(ao)

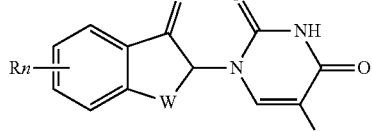

(ap)

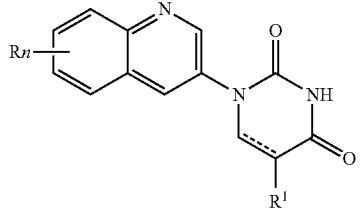

(aq)

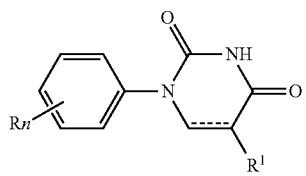

(ar)

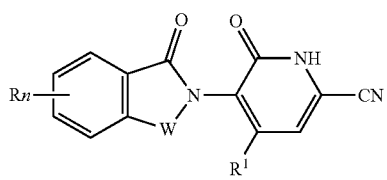

(as)

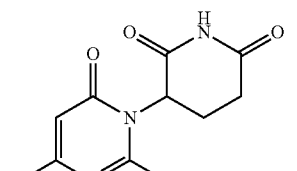

(at)

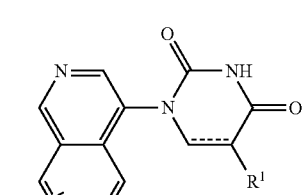

(au)

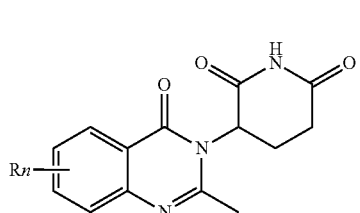

(av)

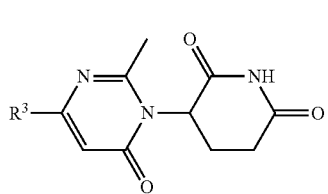

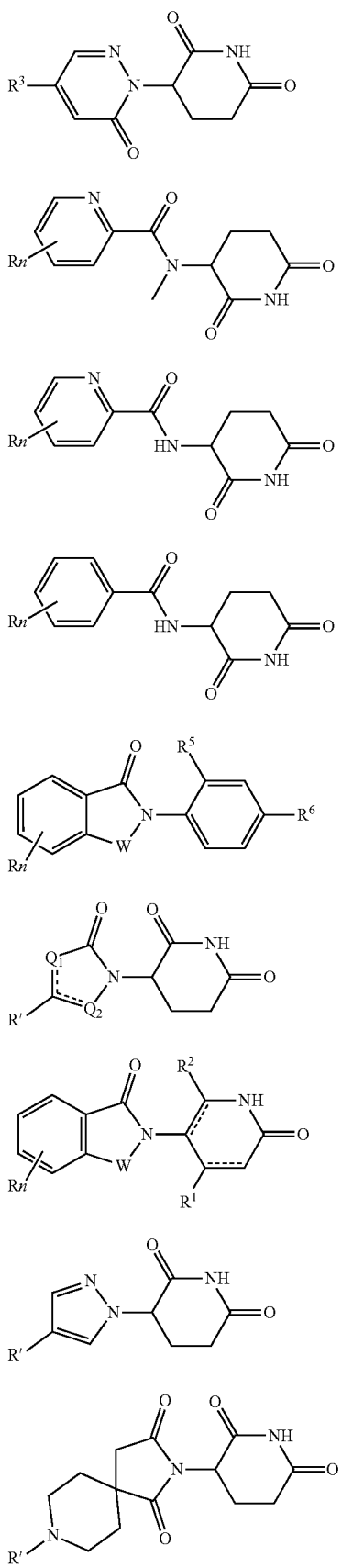

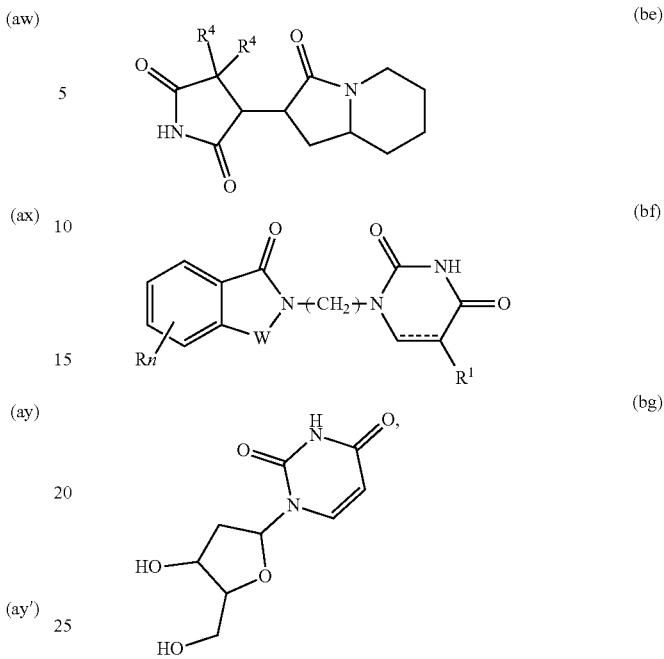

wherein:

W is independently selected from the group $CH_2$, CHR, C=O, $SO_2$, NH, and N-alkyl;

$R^1$ is selected from the group absent, H, CH, CN, and C1-C3 alkyl;

$R^2$ is H or a C1-C3 alkyl;

$R^3$ is selected from H, alkyl, substituted alkyl, alkoxy, and substituted alkoxy;

$R^4$ is methyl or ethyl;

$R^5$ is H or halo;

$R^6$ is H or halo;

n is an integer from 0-4;

R and R' are independently H, a functional group or an atom (e.g., H, halogen (e.g., —Cl or —F), amine, C1-C3 alkyl, C1-C3 alkoxyl, $NR^2R^3$, or C(=O)$OR^2$); or an attachment point for a PTM, or a chemical linker group (L), $Q_1$ and $Q_2$ are each independently C or N substituted with a group independently selected from H and C1-C3 alkyl; and ⤳ is a single or double bond.

In any aspect or embodiment described herein, the W, $R^1$, $R^2$, $Q_1$, $Q_2$, $Q_3$, $Q_4$, R, or R' can independently be covalently coupled to a linker to which is attached one or more PTM groups.

In any aspect or embodiment described herein, the $R^1$, $R^2$, $Q_1$, $Q_2$, $Q_3$, $Q_4$, R, or R' can independently be covalently coupled to a linker to which is attached one or more PTM groups.

In any aspect or embodiment described herein, the $Q_1$, $Q_2$, $Q_3$, $Q_4$, R, or R' can independently be covalently coupled to a linker to which is attached one or more PTM groups.

In any aspect or embodiment described herein, R is modified to be covalently joined to the linker group (L) or directly to a PTM, or combination thereof.

In any aspect or embodiment described herein, the CLM is selected from:

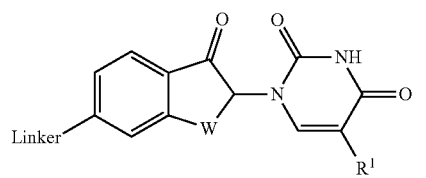
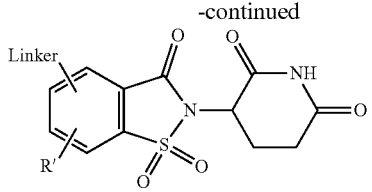
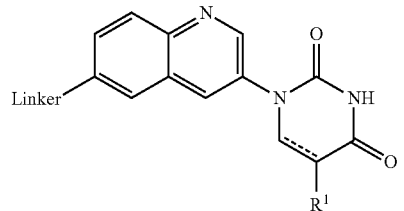
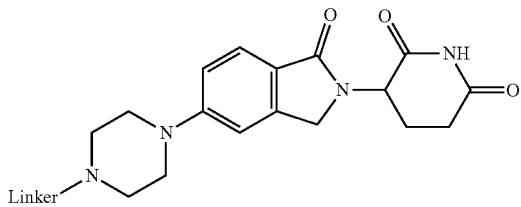
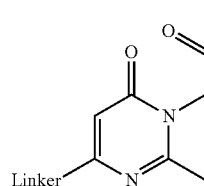
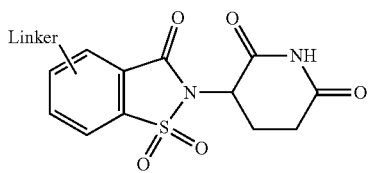
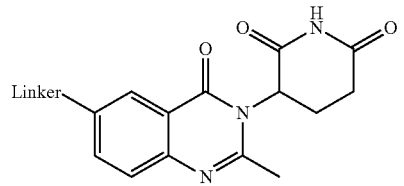
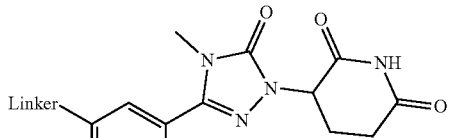
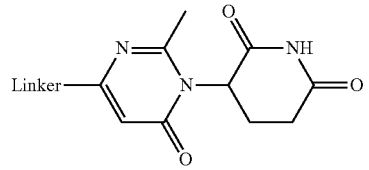
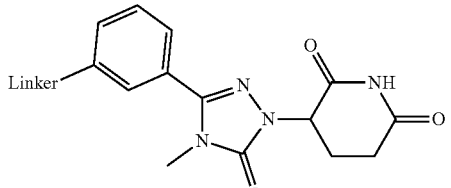
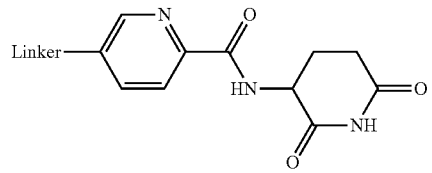
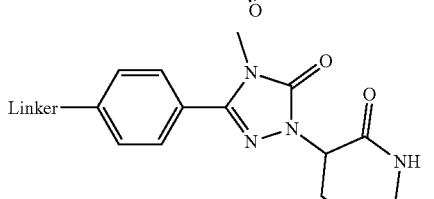
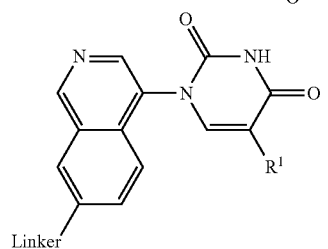
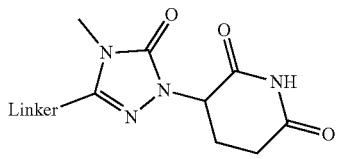
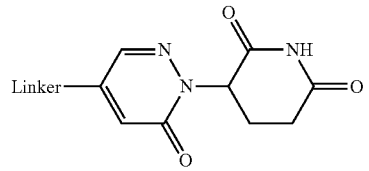
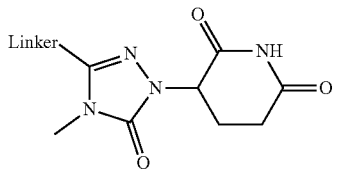
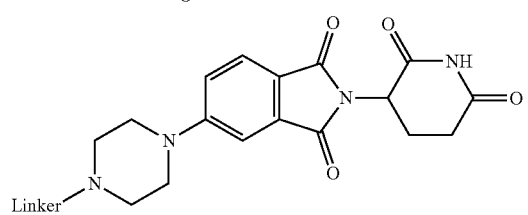
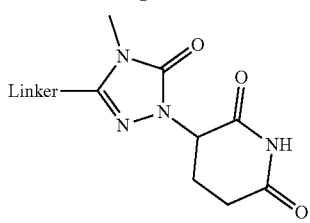

-continued
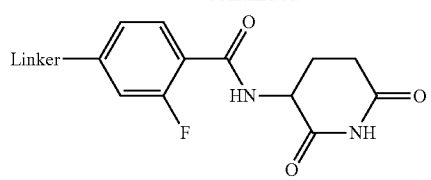
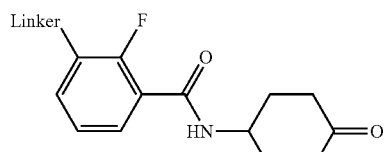
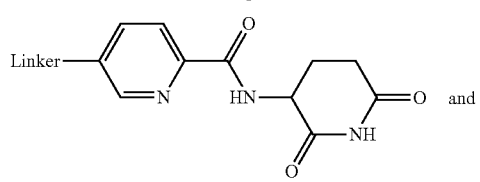 and
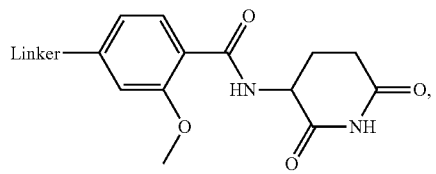,
wherein R' is a halogen and R¹ is as described herein.
In any aspect or embodiment described herein, "CLM" can be an imide that binds to cereblon E3 ligase. These imides and linker attachment point can be, but not be limited to one of the following structures:

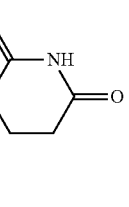
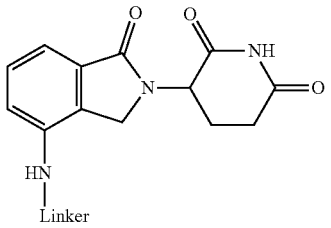
-continued
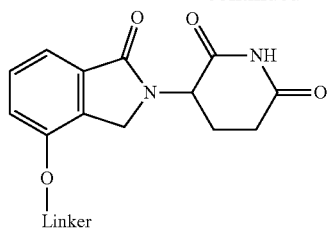
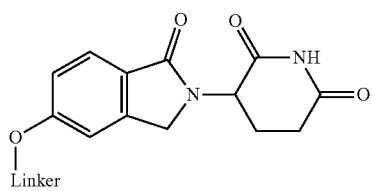
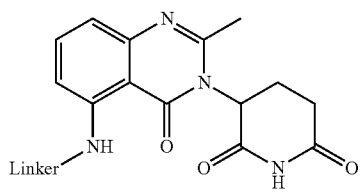
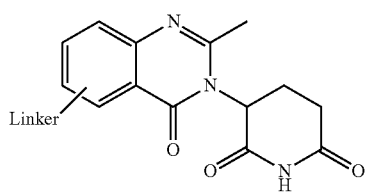
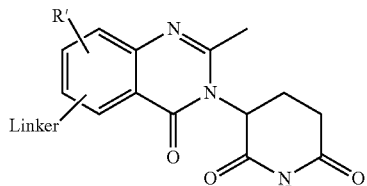
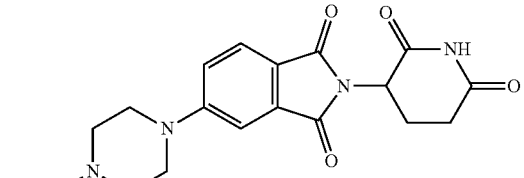
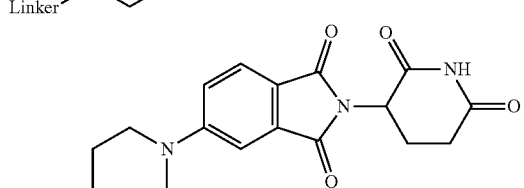
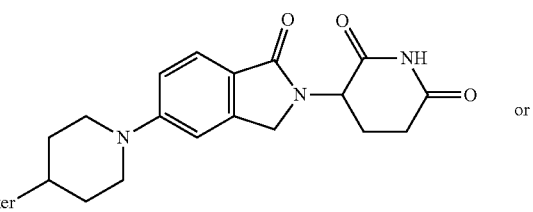 or

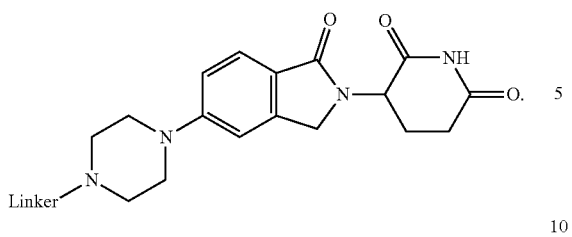
In any aspect or embodiment described herein, the CLM or ULM is selected from the group consisting of:
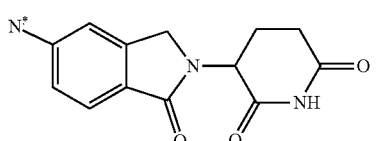
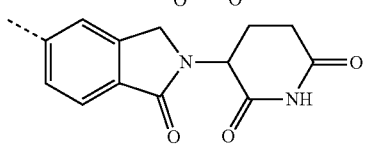
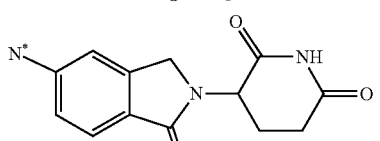
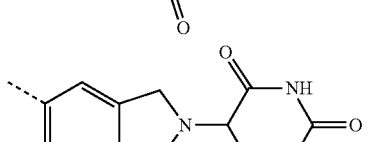
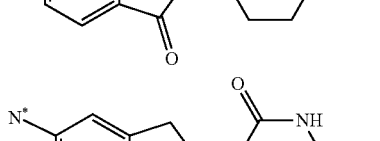
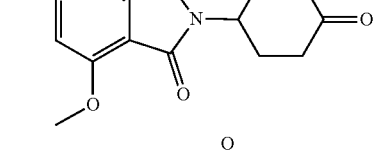
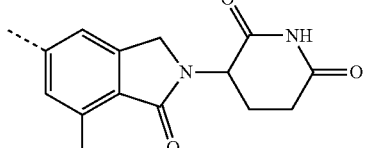
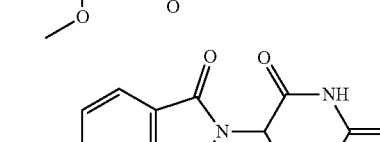
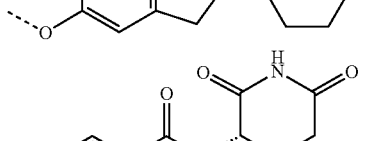
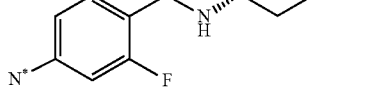
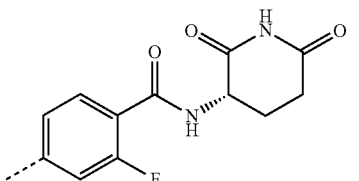

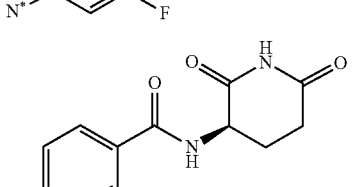
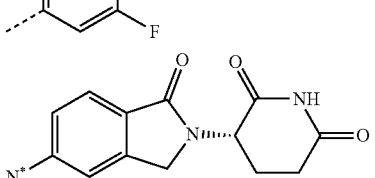
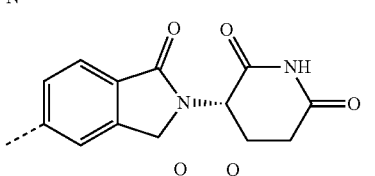
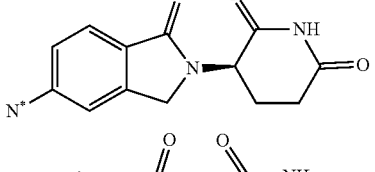
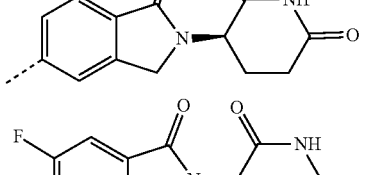
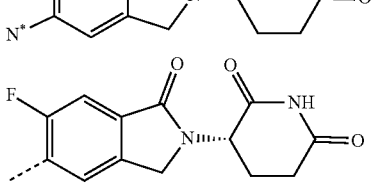
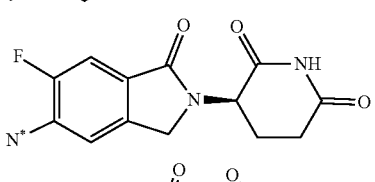
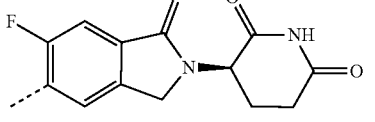

-continued
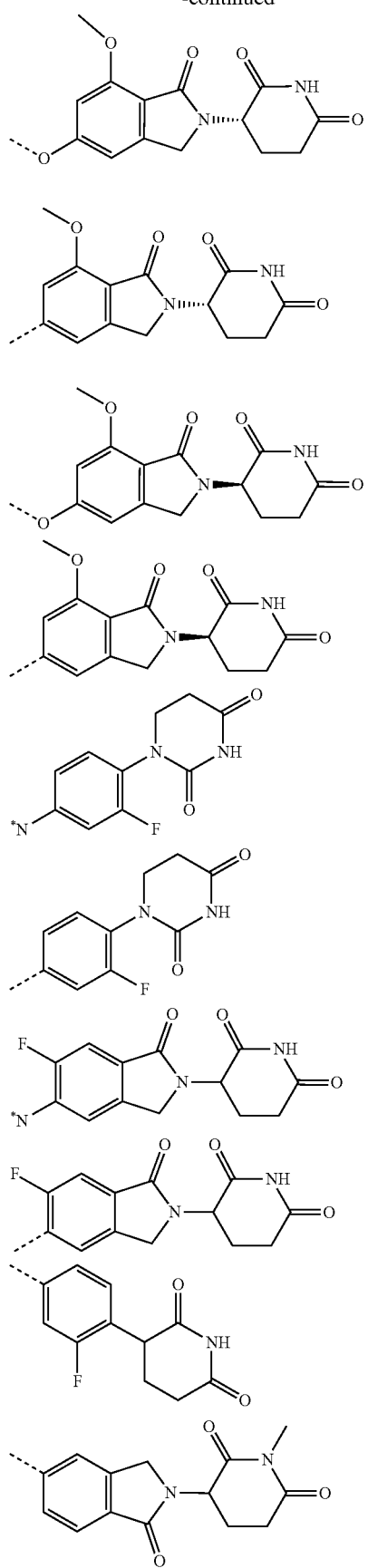
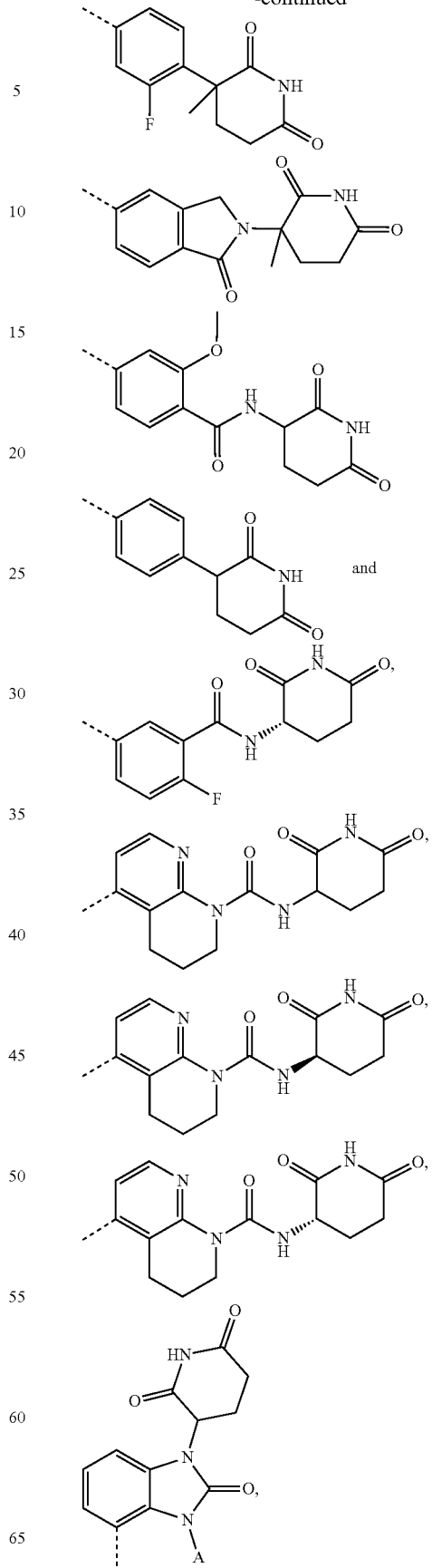
and

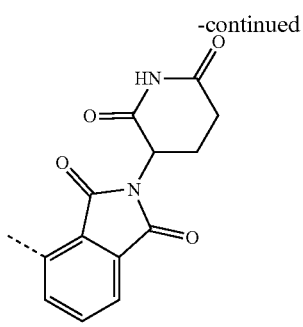

wherein:
  N* is a nitrogen atom (i) that is covalently linked to the PTM via the chemical linker group (L) with a H or methyl completing valency or (ii) that is shared with the chemical linker group (L) (e.g., a heteroatom shared with an optionally substituted heterocyloalkyl of the chemical linker group (L); and
  ⌇ of the CLM indicates the point of attachment with a linker group or a PTM.

In any aspect or embodiment described herein, the CLM is selected from the group consisting of:

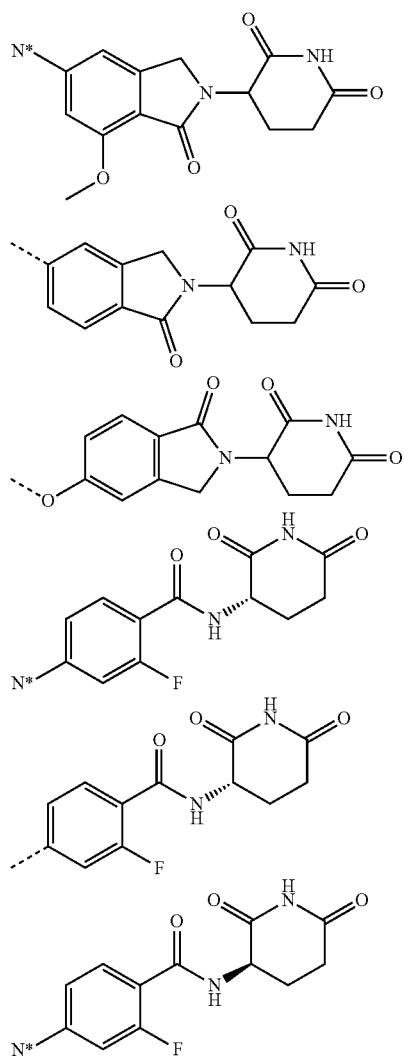

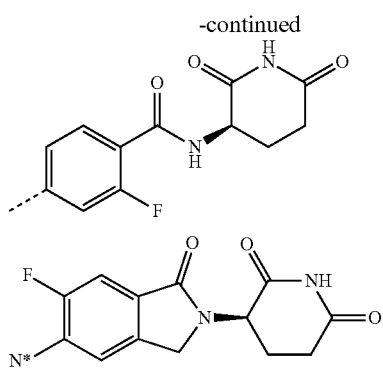

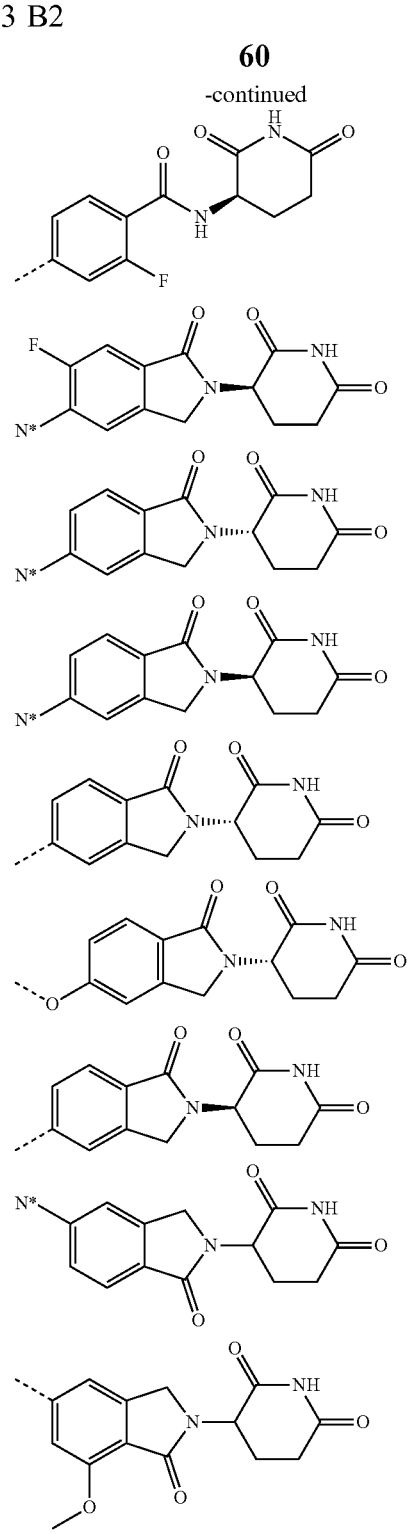

wherein:
  N* is a nitrogen atom that is shared with the chemical linker group (L) (e.g., a heteroatom shared with an optionally substituted heterocyloalkyl of the chemical linker group (L); and
  ⌇ of the CLM indicates the point of attachment with a linker group or a PTM.

In any aspect or embodiment described herein, the CLM is selected from the group consisting of:

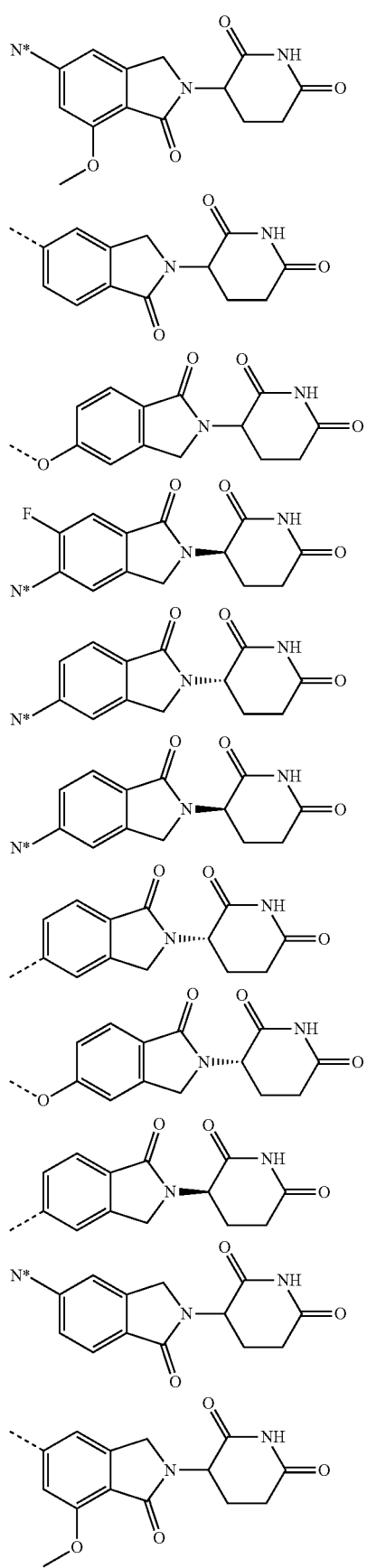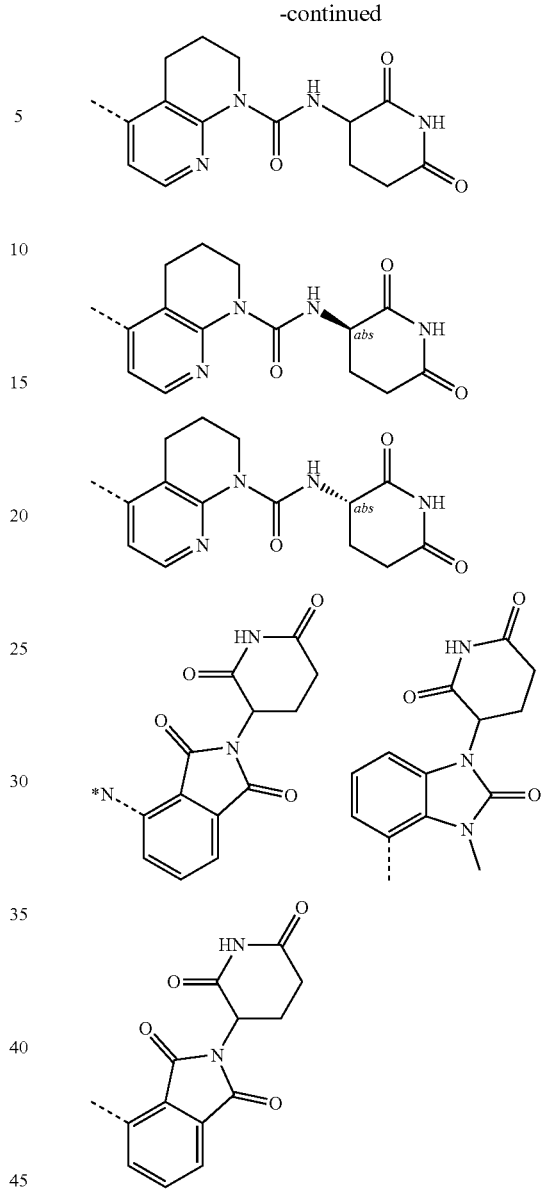
wherein:
N* is a nitrogen atom that is shared with the chemical linker group (L) (e.g., a heteroatom shared with an optionally substituted heterocyloalkyl of the chemical linker group (L); and
⸺ of the CLM indicates the point of attachment with a linker group or a PTM.
In any aspect or embodiment described herein, the CLM is selected from the group consisting of:
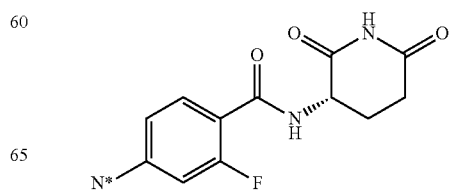

-continued
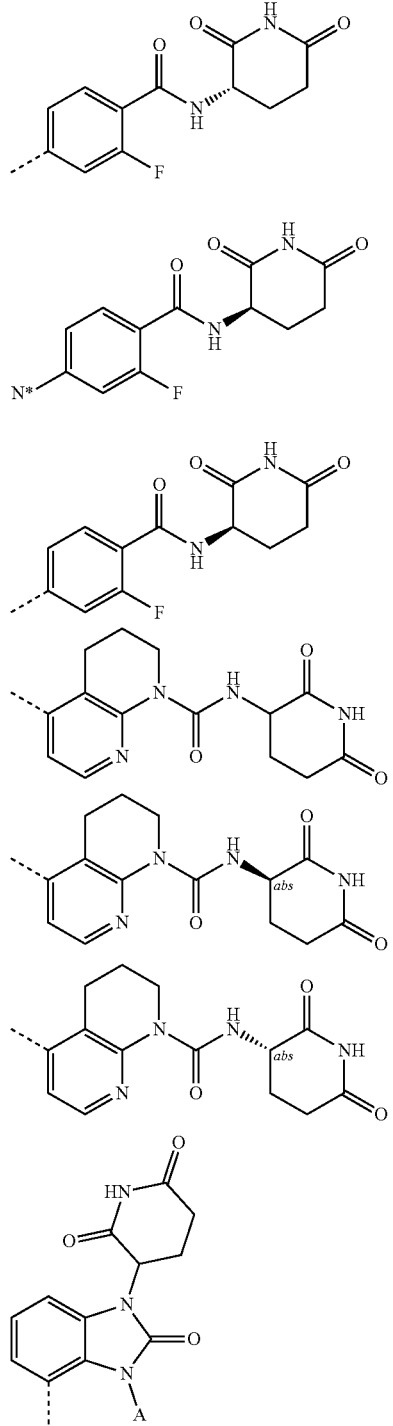
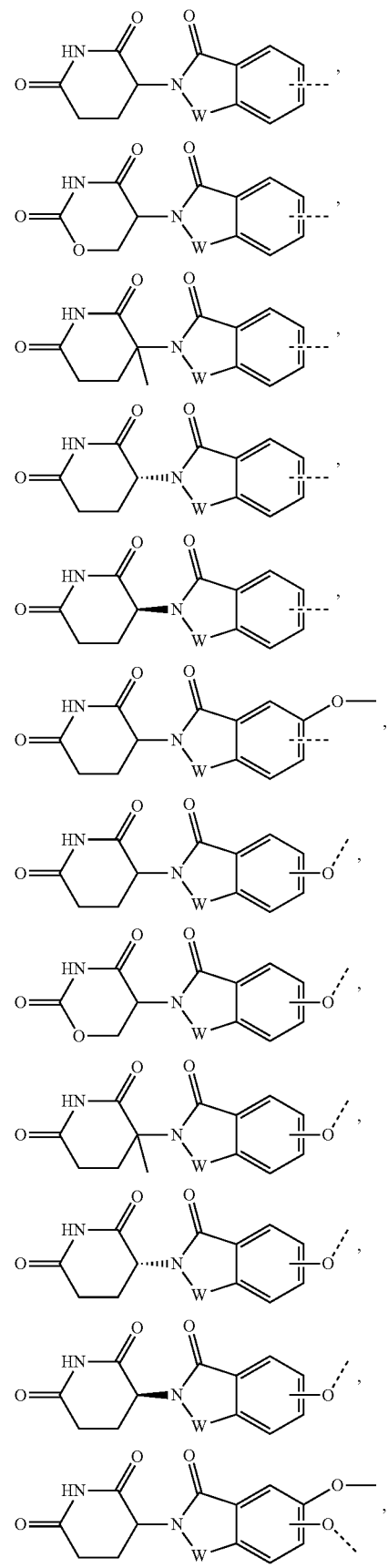
wherein:
N* is a nitrogen atom that is shared with the chemical linker group (L) (e.g., a heteroatom shared with an optionally substituted heterocyloalkyl of the chemical linker group (L); and
⸺ of the CLM indicates the point of attachment with a linker group or a PTM.
In any aspect or embodiment described herein, the CLM is selected from the group consisting of:

-continued

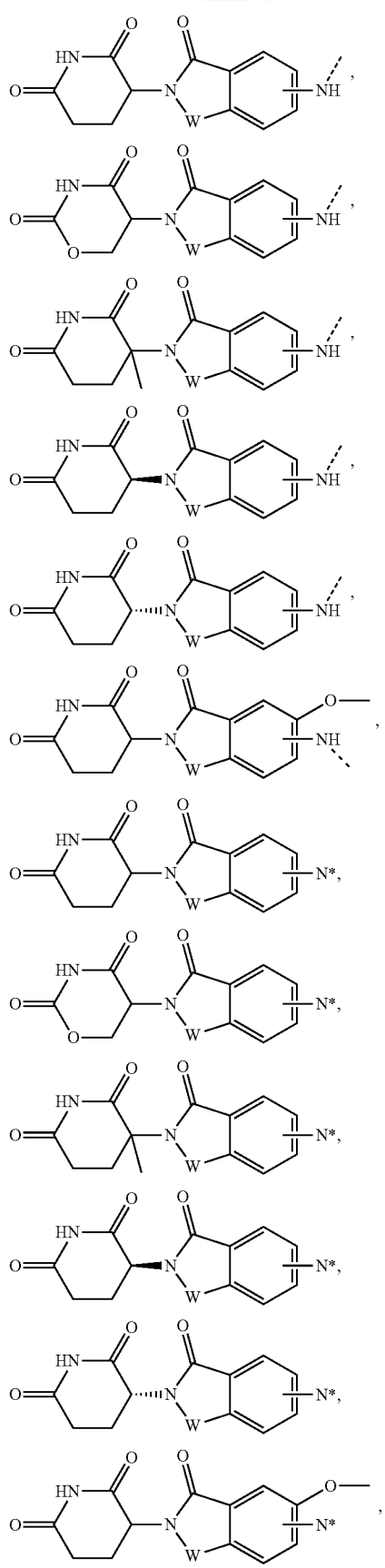

-continued

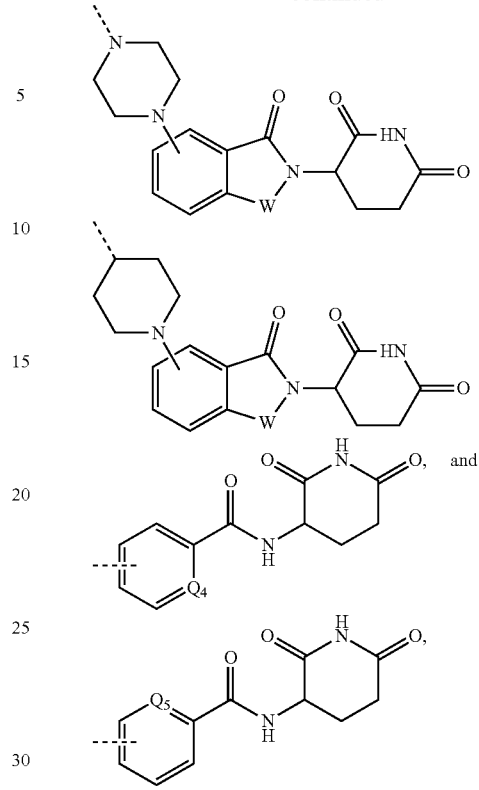

wherein:
- - - of the CLM indicates the point of attachment with a linker group or a PTM;
N* is a nitrogen atom that is shared with the chemical linker group or PTM; and
W, Q4, and Q5 are each defined as described in any aspect or embodiment described herein.

Exemplary Linkers

In some aspects or embodiments described herein, the compounds as described herein include a PTM chemically linked to a ULM (e.g., CLM) via a chemical linker (L). In certain embodiments, the linker group L comprises one or more covalently connected structural units (e.g., -$A^L_1$ ... $(A^L)_q$- or -$(A^L)_q$-), wherein $A^L_1$ is a group coupled to PTM, and $(A^L)_q$ is a group coupled to ULM.

In some aspects or embodiments described herein, the linker (L) to a ULM (e.g., CLM) connection is a stable L-ULM connection. For example, in any aspect or embodiment described herein, when a linker (L) and a ULM are connected via a heteroatom (e.g., N, O, S), any additional heteroatom, if present, is separated by at least a carbon atom (e.g., —CH$_2$—), such as with an acetal or aminal group. By way of further example, in any aspect or embodiment described herein, when a linker (L) and a ULM are connected via a heteroatom, the heteroatom is not part of an ester.

In any aspect or embodiment described herein, the linker group L is a bond or a chemical linker group represented by the formula -$(A^L)_q$-, wherein A is a chemical moiety and q is an integer from 1-100 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80), and wherein L is covalently bound to both the PTM and the ULM, and provides for binding of the PTM to the protein target and the ULM to an E3 ubiquitin ligase to effectuate target protein ubiquitination.

In any aspect or embodiment described herein, the linker group L is a bond or a chemical linker group represented by the formula $-(A^L)_q-$, wherein A is a chemical moiety and q is an integer from 6-30 (e.g., 1, 2, 3, 4, 5, 6, 7, 8, 9, 10, 11, 12, 13, 14, 15, 16, 17, 18, 19, 20, 21, 22, 23, 24, or 25), and wherein L is covalently bound to both the PTM and the ULM, and provides for binding of the PTM to the protein target and the ULM to an E3 ubiquitin ligase in sufficient proximity to result in target protein ubiquitination.

In any aspect or embodiment described herein, the linker group L is $-(A^L)_q-$, wherein:

$(A^L)_q$ is a group which connects a ULM (e.g., CLM), to PTM (RTM);

q of the linker is an integer greater than or equal to 1;

each A L is independently selected from the group consisting of a bond, $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, C=O, $CR^{L1}$=$CR^{L2}$, C≡C, $SiR^{L1}R^{L2}$, $P(O)R^{L1}$, $P(O)OR^{L1}$, $NR^{L3}C$(=NCN)$NR^{L4}$, $NR^{L3}C$(=NCN), $NR^{L3}C$(=$CNO_2$)$NR^{L4}$, $C_{3-11}$cycloalkyl optionally substituted with 1-6 $R^{L1}$ and/or $R^{L2}$ groups, $C_{5-13}$ spirocycloalkyl optionally substituted with 1-9 $R^{L1}$ and/or $R^{L2}$ groups, $C_{3-11}$heterocyclyl optionally substituted with 1-6 $R^{L1}$ and/or $R^{L2}$ groups, $C_{5-13}$ spiroheterocyclyl optionally substituted with 1-8 $R^{L1}$ and/or $R^{L2}$ groups, aryl optionally substituted with 1-6 $R^{L1}$ and/or $R^{L2}$ groups, and heteroaryl optionally substituted with 1-6 $R^{L1}$ and/or $R^{L2}$ groups, where $R^{L1}$ or $R^{L2}$, each independently are optionally linked to other groups to form cycloalkyl and/or heterocyclyl moiety, optionally substituted with 1-4 $R^{L5}$ groups; and $R^{L1}$, $R^{L2}$, $R^{L3}$, $R^{L4}$ and $R^{L5}$ are each independently selected from H, halo, $C_{1-8}$alkyl, $OC_{1-8}$alkyl, $SC_{1-8}$alkyl, $NHC_{1-8}$alkyl, $N(C_{1-8}$alkyl$)_2$, $C_{3-11}$cycloalkyl, aryl (e.g., 5-, 6-, 7-, or 8-membered aryl), heteroaryl (e.g., 5-, 6-, 7-, or 8-membered heteroaryl), $C_{3-11}$heterocyclyl, $OC_{3-8}$cycloalkyl, $SC_{3-8}$cycloalkyl, $NHC_{3-8}$cycloalkyl, $N(C_{3-8}$cycloalkyl$)_2$, $N(C_{3-8}$cycloalkyl)($C_{1-8}$ alkyl), OH, $NH_2$, SH, $SO_2C_{1-8}$alkyl, $P(O)(OC_{1-8}$alkyl)($C_{1-8}$alkyl), $P(O)(OC_{1-8}$alkyl$)_2$, C≡C—$C_{1-8}$alkyl, C≡CH, CH=CH($C_{1-8}$alkyl), C($C_{1-8}$alkyl)=CH($C_{1-8}$ alkyl), C($C_{1-8}$alkyl)=C($C_{1-8}$alkyl$)_2$, Si(OH$)_3$, Si($C_{1-8}$ alkyl$)_3$, Si(OH)($C_{1-8}$alkyl$)_2$, $COC_{1-8}$alkyl, $CO_2H$, halogen, CN, $CF_3$, $CHF_2$, $CH_2F$, $NO_2$, $SF_5$, $SO_2NHC_{1-8}$ alkyl, $SO_2N(C_{1-8}$alkyl$)_2$, $SONHC_{1-8}$alkyl, $SON(C_{1-8}$ alkyl$)_2$, $CONHC_{1-8}$alkyl, $CON(C_{1-8}$alkyl$)_2$, $N(C_{1-8}$alkyl)CONH($C_{1-8}$alkyl), $N(C_{1-8}$alkyl)$CON(C_{1-8}$alkyl$)_2$, $NHCONH(C_{1-8}$alkyl), $NHCON(C_{1-8}$alkyl$)_2$, $NHCONH_2$, $N(C_{1-8}$alkyl)$SO_2NH(C_{1-8}$alkyl), $N(C_{1-8}$alkyl) $SO_2N(C_{1-8}$alkyl$)_2$, NH $SO_2NH(C_{1-8}$alkyl), NH $SO_2N(C_{1-8}$alkyl$)_2$, and NH $SO_2NH_2$.

In any aspect or embodiment described herein, q is an integer greater than or equal to 1.

In any aspect or embodiment described herein, e.g., where q of the linker is greater than 2, $(A^L)_q$ is a group which is $A^L_1$ and $(A^L)_q$ wherein the linker couples a PTM to a ULM.

In any aspect or embodiment described herein, e.g., where q of the linker is 2, $A^L_2$ is a group which is connected to $A^L_1$ and to a ULM.

In any aspect or embodiment described herein, q of the chemical linking group (L) is an integer from 1-100 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80).

In any aspect or embodiment described herein, e.g., where q of the linker is 1, the structure of the linker group L is $-A^L_1-$, and $A^L_1$ is a group which connects a ULM moiety to a PTM moiety.

In any aspect or embodiment described herein, the unit A L of linker (L) comprises a group represented by a general structure selected from the group consisting of:

$NR(CH_2)_n$-(lower alkyl)-, —$NR(CH_2)_n$-(lower alkoxyl)-, —$NR(CH_2)_n$-(lower alkoxyl)-$OCH_2$—, —$NR(CH_2)_n$-(lower alkoxyl)-(lower alkyl)-$OCH_2$—, —$NR(CH_2)_n$-(cycloalkyl)-(lower alkyl)-$OCH_2$—, —$NR(CH_2)_n$-(heterocycloalkyl)-, —$NR(CH_2CH_2O)_n$-(lower alkyl)-O—$CH_2$—, —$NR(CH_2CH_2O)_n$-(heterocycloalkyl)-O—$CH_2$—, —$NR(CH_2CH_2O)_n$-Aryl-O—$CH_2$—, —$NR(CH_2CH_2O)_n$-(heteroaryl)-O—$CH_2$—, —NR $(CH_2CH_2O)_n$-(cyclo alkyl)-O-(heteroaryl)-O—$CH_2$—, —$NR(CH_2CH_2O)_n$-(cyclo alkyl)-O-Aryl-O—$CH_2$—, —$NR(CH_2CH_2O)_n$-(lower alkyl)-NH-Aryl-O—$CH_2$—, —$NR(CH_2CH_2O)_n$-(lower alkyl)-O-Aryl-$CH_2$, —$NR(CH_2CH_2O)_n$-cycloalkyl-O-Aryl-, —NR $(CH_2CH_2O)_n$-cycloalkyl-O-(heteroaryl)l-, —NR $(CH_2CH_2)_n$-(cycloalkyl)-O-(heterocycly)-$CH_2$, —NR $(CH_2CH_2)_n$-(heterocyclyl)-(heterocyclyl)-$CH_2$, and —N(R1R2)-(heterocyclyl)-$CH_2$; where n of the linker can be 0 to 10;

R of the linker can be H, or lower alkyl; and

R1 and R2 of the linker can form a ring with the connecting N.

In any aspect or embodiment described herein, the linker (L) includes an optionally substituted $C_1$-$C_{50}$ alkyl (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ alkyl, and including all implied subranges, e.g., C1-C10, C1-C20; C2-C10, C2-20; C10-C20, C10-C50 etc.), wherein each carbon is optionally independently substituted or replaced with (1) a heteroatom selected from N, O, S, P, or Si atoms that has an appropriate number of hydrogens, substitutions, or both to complete valency, (2) an optionally substituted cycloalkyl or bicyclic cycloalkly, (3) an optionally substituted heterocycloalkyl or bicyclic heterocycloalkyl, (4) an optionally substituted aryl or bicyclic aryl, or (5) optionally substituted heteroaryl or bicyclic heteroaryl. In any aspect or embodiment described herein, the linker (L) does not have heteroatom-heteroatom bonding (e.g., no heteroatoms are covalently linked or adjacently located).

In any aspect or embodiment described herein, the linker (L) includes an optionally substituted $C_1$-$C_{50}$ alkyl (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ alkyl), wherein:

each carbon is optionally independently substituted or replaced with a group independently selected from $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, C=O, $CR^{L1}$=$CR^{L2}$, $SiR^{L1}R^{L2}$, $P(O)R^{L1}$, $P(O)OR^{L1}$, $NR^{L3}C$(=NCN)$NR^{L4}$, $NR^{L3}C$(=NCN), $NR^{L3}C$(=$CNO_2$)$NR^{L4}$, $C_{3-11}$cycloalkyl optionally substituted with 1-6 $R^{L1}$ and/or $R^{L2}$ groups, $C_{5-13}$ spirocycloalkyl optionally substituted with 1-9 $R^{L1}$ and/or $R^{L2}$ groups, $C_{3-11}$ heterocyclyl optionally substituted with 1-6 $R^{L1}$ and/or $R^{L2}$ groups, $C_{5-13}$ spiroheterocyclyl optionally substituted with 1-8 $R^{L1}$ and/or $R^{L2}$ groups, aryl optionally substituted with 1-6 $R^{L1}$ and/or $R^{L2}$ groups, or heteroaryl optionally substituted with 1-6 $R^{L1}$ and/or $R^{L2}$ groups, where $R^{L1}$ or $R^{L2}$, each independently, are optionally linked to other groups to form a cycloalkyl and/or a heterocyclyl moiety, optionally substituted with 1-4 $R^{L5}$ groups; and $R^{L1}$, $R^{L2}$, $R^{L3}$, $R^{L4}$ and $R^{L5}$ are, each independently, H, halo, $C_{1-8}$alkyl, $OC_{1-8}$alkyl, $SC_{1-8}$alkyl, $NHC_{1-8}$alkyl, $N(C_{1-8}alkyl)_2$, $C_{3-11}$cycloalkyl, 5-8 membered aryl (e.g., 5-, 6-, 7-, or 8-membered aryl), 5-8 membered heteroaryl (e.g., 5-, 6-, 7-, or 8-membered heteroaryl), $C_{3-11}$heterocyclyl, $OC_{3-8}$cycloalkyl, $SC_{3-8}$cycloalkyl, $NHC_{3-8}$cycloalkyl, $N(C_{3-8}cycloalkyl)_2$, $N(C_{3-8}cycloalkyl)(C_{1-8}alkyl)$, OH, $NH_2$, SH, $SO_2C_{1-8}$alkyl, $P(O)(OC_{1-8}alkyl)(C_{1-8}alkyl)$, $P(O)(OC_{1-8}alkyl)_2$, C≡C—$C_{1-8}$ alkyl, C≡CH, CH=CH($C_{1-8}$alkyl), C($C_{1-8}$alkyl)=CH($C_{1-8}$alkyl), C($C_{1-8}$alkyl)=C($C_{1-8}$alkyl)$_2$, $Si(OH)_3$, $Si(C_{1-8}alkyl)_3$, $Si(OH)(C_{1-8}alkyl)_2$, $COC_{1-8}$alkyl, $CO_2H$, halogen, CN, $CF_3$, $CHF_2$, $CH_2F$, $NO_2$, $SF_5$, $SO_2NHC_{1-8}$alkyl, $SO_2N(C_{1-8}alkyl)_2$, $SONHC_{1-8}$alkyl, $SON(C_{1-8}alkyl)_2$, $CONHC_{1-8}$alkyl, $CON(C_{1-8}alkyl)_2$, $N(C_{1-8}alkyl)CONH(C_{1-8}alkyl)$, $N(C_{1-8}alkyl)CON(C_{1-8}alkyl)_2$, $NHCONH(C_{1-8}alkyl)$, $NHCON(C_{1-8} alkyl)_2$, $NHCONH_2$, $N(C_{1-8}alkyl)SO_2NH(C_{1-8} alkyl)$, $N(C_{1-8}alkyl) SO_2N(C_{1-8}alkyl)_2$, $NH SO_2NH(C_{1-8}alkyl)$, $NH SO_2N(C_{1-8}alkyl)_2$, or $NH SO_2NH_2$.

In any aspect or embodiment described herein, the linker group is an optionally substituted $C_1$-$C_{50}$ alkyl (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ alkyl, and including all subranges, e.g., C1-C10, C1-C20; C2-C10, C2-20; C10-C20, C10-C50 etc.), wherein each carbon atom is optionally substituted or replaced with:

- a O, N, S, P or Si atom that has an appropriate number of hydrogens, substitutions (e.g., OH, halo, $C_{1-8}$alkyl, methyl, ethyl, $C_{1-8}$haloalkyl, $C_{1-8}$hydroxyalkyl, $C_{1-8}$alkoxy, or methoxy), or both to complete valency;
- an optionally substituted aryl (e.g., an optionally substituted 5- or 6-membered aryl) or bicyclic aryl (e.g., an optionally substituted 9-20 membered bicyclic heteroaryl), such as an optionally substituted aryl or bicyclic aryl optionally substituted with OH, halo, $C_{1-8}$alkyl, methyl, ethyl, $C_{1-8}$haloalkyl, $C_{1-8}$hydroxyalkyl, $C_{1-8}$alkoxy, or methoxy;
- an optionally substituted heteroaryl (e.g., an optionally substituted 5- or 6-membered heteroaryl) or bicyclic heteroaryl (e.g., an optionally substituted 9-20 membered bicyclic heteroaryl), such as an optionally substituted heteroaryl or bicyclic heteroaryl having one or more heteroatoms selected from N, O, S, P, and Si that has an appropriate number of hydrogens, substitutions (e.g., OH, halo, $C_{1-8}$alkyl, methyl, ethyl, $C_{1-8}$haloalkyl, $C_{1-8}$hydroxyalkyl, $C_{1-8}$alkoxy, or methoxy), or both to complete valency);
- an optionally substituted C1-C6 alkyl, such as optionally substituted with OH, halo, $C_{1-8}$alkyl, methyl, ethyl, $C_{1-8}$haloalkyl, $C_{1-8}$hydroxyalkyl, $C_{1-8}$alkoxy, or methoxy;
- an optionally substituted $C_2$-$C_6$ alkenyl, such as optionally substituted with OH, halo, $C_{1-8}$alkyl, methyl, ethyl, $C_{1-8}$haloalkyl, $C_{1-8}$hydroxyalkyl, $C_{1-8}$alkoxy, or methoxy;
- an optionally substituted C2-C6 alkynyl, such as optionally substituted with OH, halo, $C_{1-8}$alkyl, methyl, ethyl, $C_{1-8}$haloalkyl, $C_{1-8}$hydroxyalkyl, $C_{1-8}$alkoxy, or methoxy;
- an optionally substituted cycloalkyl (e.g., an optionally substituted C3-C7 cycloalkyl) or bicyclic cycloalkyl (e.g., an optionally substituted C5-C20 bicyclic cycloalkyl), such as an optionally substituted cycloalkyl or bicyclic cycloalkyl optionally substituted with OH, halo, $C_{1-8}$alkyl, methyl, ethyl, $C_{1-8}$haloalkyl, $C_{1-8}$hydroxyalkyl, $C_{1-8}$alkoxy, or methoxy; or
- an optionally substituted heterocycloalkyl (e.g., an optionally substituted 3-, 4-, 5-, 6-, or 7-membered heterocyclic group) or bicyclic heterocycloalkyl (e.g., an optionally substituted 5-20 membered bicyclic heterocycloalkyl), such as an optionally substituted heterocycloalkyl or bicyclic heterocycloalkyl having one or more heteroatoms independently selected from N, O, S, P, or Si atoms that has an appropriate number of hydrogens, substitutions (e.g., OH, halo, $C_{1-8}$alkyl, methyl, ethyl, $C_{1-8}$haloalkyl, $C_{1-8}$hydroxyalkyl, $C_{1-8}$alkoxy, or methoxy), or both to complete valency.

In any aspect or embodiment described herein, the optionally substituted alkyl linker is optionally substituted with one or more OH, halo, linear or branched C1-C6 alkyl (such as methyl or ethyl), linear or branched C1-C6 haloalkyl, linear or branched C1-C6 hydroxyalkyl, or linear or branched C1-C6 alkoxy (e.g., methoxy).

In any aspect or embodiment described herein, the linker (L) does not have heteroatom-heteroatom bonding (e.g., no heteroatoms are covalently linked or adjacently located).

In any aspect or embodiment described herein, the linker (L) includes 1 to 50 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) alkylene glycol units that are optionally substituted, wherein carbon or oxygen may be substituted or replaced with a heteroatom selected from N, S, P, or Si atoms with an appropriate number of hydrogens to complete valency.

In any aspect or embodiment described herein, the linker (L) is represented by the chemical structure:

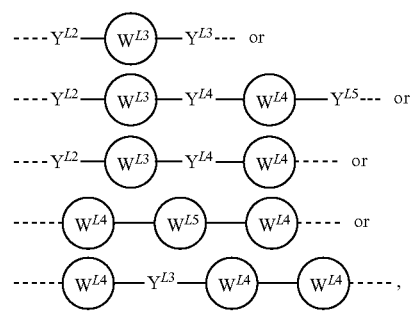

$Y^{L2}$ is a bond, O,

a 4-6 membered heterocycloalkyl-$C_{1-2}$ alkyl, an unsubstituted or substituted linear or branched C1-C6 alkyl (e.g., optionally substituted with one or more (e.g., 1, 2, or 3) halogen (e.g., F, Cl, Br), OH, C1-C3 alkyl, C1-C2 hydroxyalkyl, methyl, or ethyl), a unsubstituted or substituted linear or branched C₂-C6 alkenyl (e.g., an optionally substituted C—C4 alkenyl and/or optionally substituted with one or more (e.g., 1, 2, or 3) halogen, OH, C1-C3 alkyl, C1-C2 hydroxyalkyl, methyl, or ethyl), or an unsubstituted or substituted linear or branched C1-C6 alkynyl (e.g., an optionally substituted C2-C₄ alkynyl and/or optionally substituted with one or more (e.g., 1, 2, or 3) halogen, OH, C1-C3 alkyl, C1-C2 hydroxyalkyl, methyl, or ethyl), each of the alkyl, the alkenyl, and the alkyl optionally having one or more (e.g., 1, 2, or 3) C atoms replaced with O, NH, or NCH₃;

$W^{L3}$ is a 3-7 membered ring (e.g., 4-6 membered cycloalkyl or heterocycloalkyl), a 8-12 membered spirocyclic, or a 8-10 membered non-aromatic bicyclic group, each with 0-4 heteroatoms and optionally substituted with one or more (e.g., 1, 2, or 3) halogen, OH, C1-C3 alkyl, C1-C2 hydroxyalkyl, methyl, or ethyl;

$Y^{L3}$ is a bond or a C1-C6 alkyl ($C_1$, $C_2$, $C_3$, $C_4$, $C_5$, or $C_6$ alkyl), wherein one or more (e.g., 1, 2, or 3) C atoms are optionally replaced with 0 and each carbon is optionally substituted with one or more (e.g., 1, 2, or 3) halogen, OH, C1-C3 alkyl, C1-C2 hydroxyalkyl, methyl, or ethyl;

$Y^{L4}$ is bond, O, or an unsubstituted or substituted linear or branched C1-C4 alkyl, wherein one or more carbons are optionally replaced O, NH, or NCH₃, and optionally substituted with one or more (e.g., 1, 2, or 3) halogen, OH, C1-C3 alkyl, C1-C2 hydroxyalkyl, methyl, or ethyl;

each $W^{L4}$ is a 3-8 membered cycloalkyl or heterocycloalkyl (e.g., 4-6 membered cycloalkyl or heterocycloalkyl) with 0-4 heteroatoms and optionally substituted with one or more (e.g., 1, 2, or 3) halogen, OH, C1-C3 alkyl, C1-C2 hydroxyalkyl, methyl, or ethyl;

$Y^{L5}$ is a bond or an unsubstituted or substituted C1-C₃ alkyl, wherein one or two C atoms are optionally replaced with O and optionally substituted with one or more (e.g., 1, 2, or 3) halogen, OH, C1-C3 alkyl, C1-C2 hydroxyalkyl, methyl, or ethyl; and $W^{L5}$ is a 5-6 membered aromatic ring with 0-4 heteroatoms.

In any aspect or embodiment described herein, the linker (L) is represented by the chemical structure:

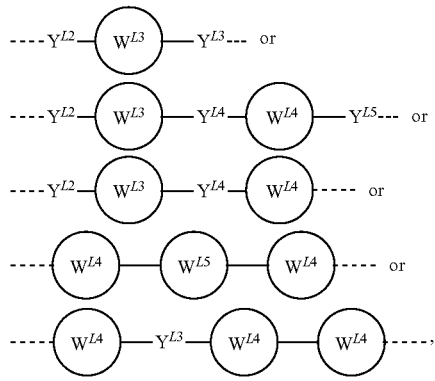

$Y^{L2}$ is a bond, O, N—C1-C6 alkyl,

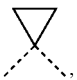

a 4-6 membered cycloalkyl, a 4-6 membered heterocycloalkyl, a 4-6 membered heterocycloalkyl-$C_{1-2}$ alkyl, an unsubstituted or substituted linear or branched C1-C6 alkyl (e.g., optionally substituted with one or more (e.g., 1, 2, or 3) halogen (e.g., F, Cl, Br), OH, C1-C3 alkyl, C1-C2 hydroxyalkyl, methyl, or ethyl), a unsubstituted or substituted linear or branched C2-C6 alkenyl (e.g., an optionally substituted C—C4 alkenyl and/or optionally substituted with one or more (e.g., 1, 2, or 3) halogen, OH, C1-C3 alkyl, C1-C2 hydroxyalkyl, methyl, or ethyl), or an unsubstituted or substituted linear or branched C1-C6 alkynyl (e.g., an optionally substituted C2-C4 alkynyl and/or optionally substituted with one or more (e.g., 1, 2, or 3) halogen, OH, C1-C3 alkyl, C1-C2 hydroxyalkyl, methyl, or ethyl), each of the alkyl, the alkenyl, and the alkyl optionally having one or more (e.g., 1, 2, or 3) C atoms replaced with O, NH, or NCH₃;

$W^{L3}$ is a 3-7 membered ring (e.g., 4-6 membered cycloalkyl or heterocycloalkyl), a 8-12 membered spirocyclic, or a 8-10 membered non-aromatic bicyclic group, each with 0-4 heteroatoms and optionally substituted with one or more (e.g., 1, 2, or 3) halogen, OH, C1-C3 alkyl, C1-C2 hydroxyalkyl, methyl, or ethyl;

$Y^{L3}$ is a bond or a C1-C6 alkyl ($C_1$, $C_2$, $C_3$, $C_4$, $C_5$, or $C_6$ alkyl), wherein one or more (e.g., 1, 2, or 3) C atoms are optionally replaced with 0 and each carbon is optionally substituted with one or more (e.g., 1, 2, or 3) halogen, OH, C1-C3 alkyl, C1-C2 hydroxyalkyl, methyl, or ethyl;

$Y^{L4}$ is bond, O, or an unsubstituted or substituted linear or branched C1-C4 alkyl, wherein one or more carbons are optionally replaced O, NH, or NCH₃, and optionally substituted with one or more (e.g., 1, 2, or 3) halogen, OH, $C_1$-$C_3$ alkyl, $C_1$-$C_2$ hydroxyalkyl, methyl, or ethyl;

each $W^{L4}$ is a 3-8 membered cycloalkyl or heterocycloalkyl (e.g., 4-6 membered cycloalkyl or heterocycloalkyl) with 0-4 heteroatoms and optionally substituted with one or more (e.g., 1, 2, or 3) halogen, OH, C1-C3 alkyl, C1-C2 hydroxyalkyl, methyl, or ethyl;

$Y^{L5}$ is a bond or an unsubstituted or substituted C1-C3 alkyl, wherein one or two C atoms are optionally replaced with O and optionally substituted with one or more (e.g., 1, 2, or 3) halogen, OH, C1-C3 alkyl, C1-C2 hydroxyalkyl, methyl, or ethyl; and $W^{L5}$ is a 5-6 membered aromatic ring with 0-4 heteroatoms.

In any aspect or embodiment described herein, the unit A L of the linker (L) comprises a structure selected from the group consisting of:

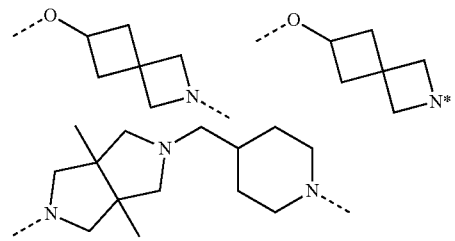

-continued
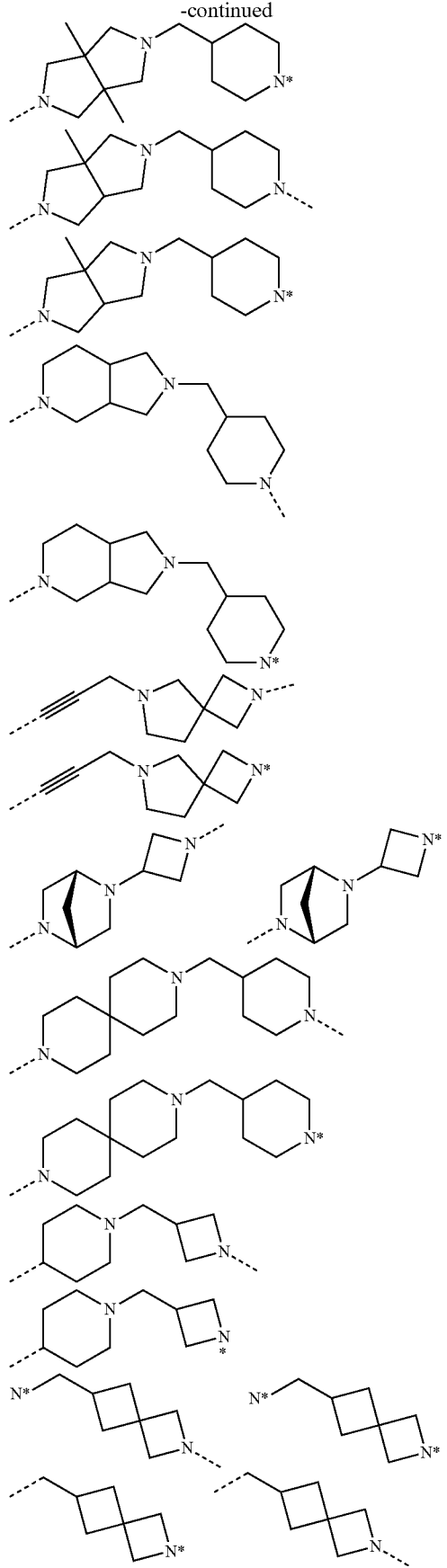
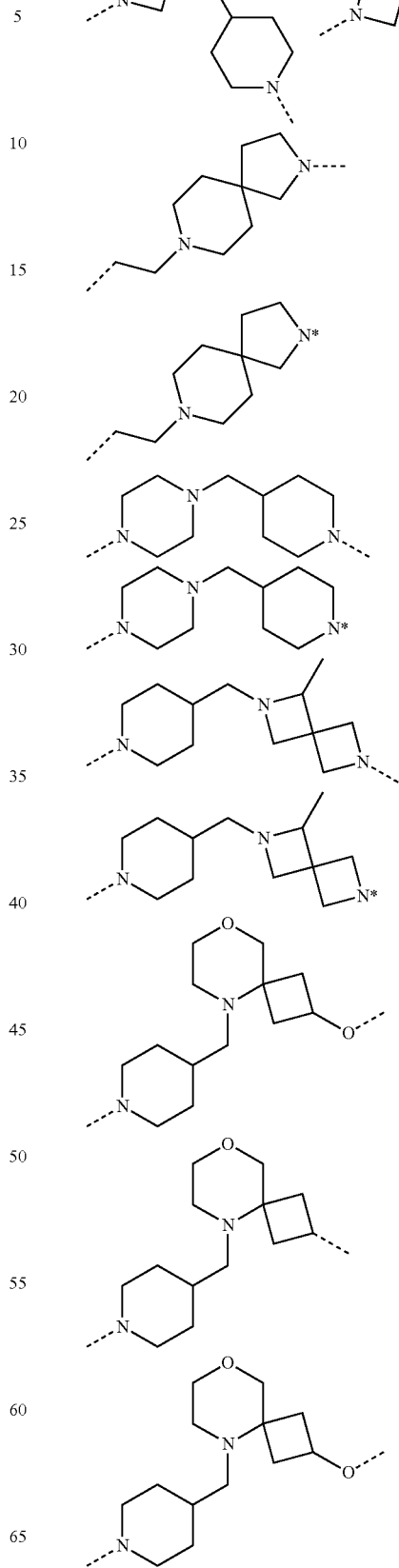

-continued
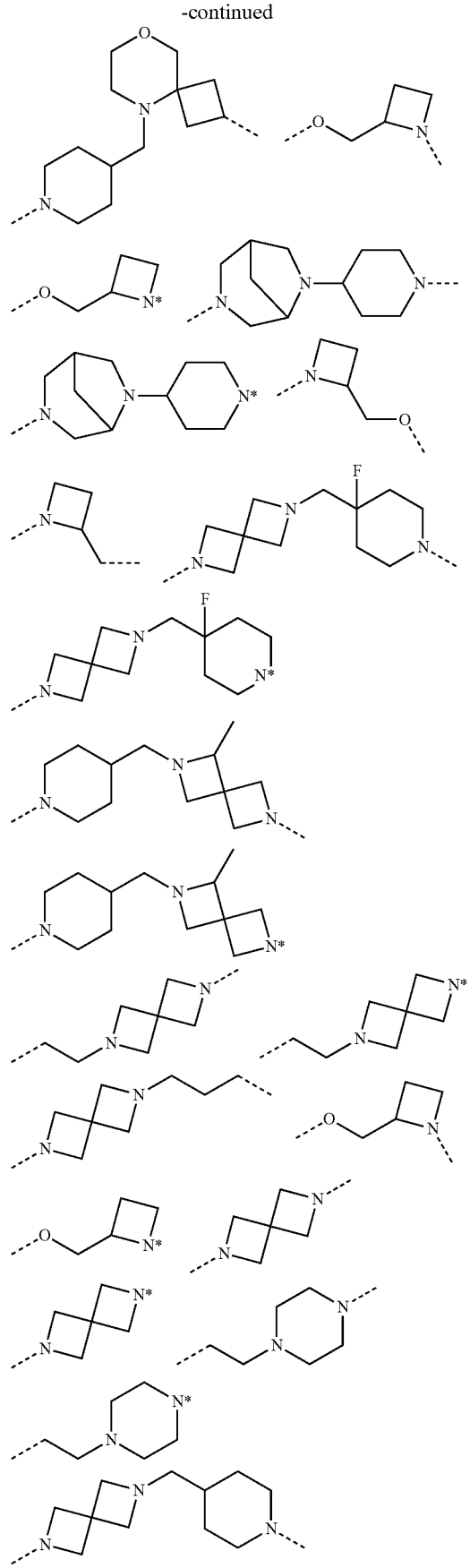
-continued
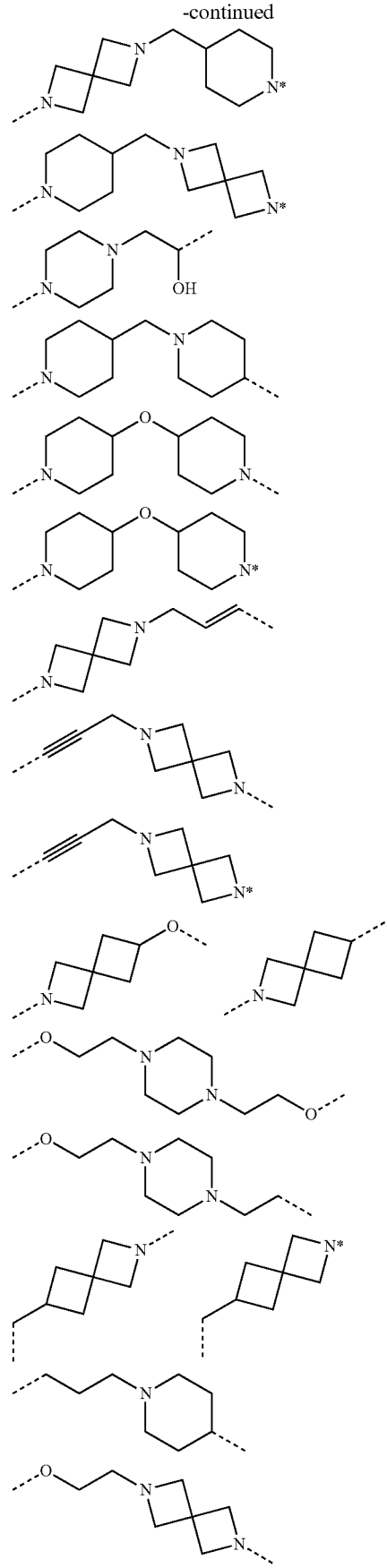

77
-continued
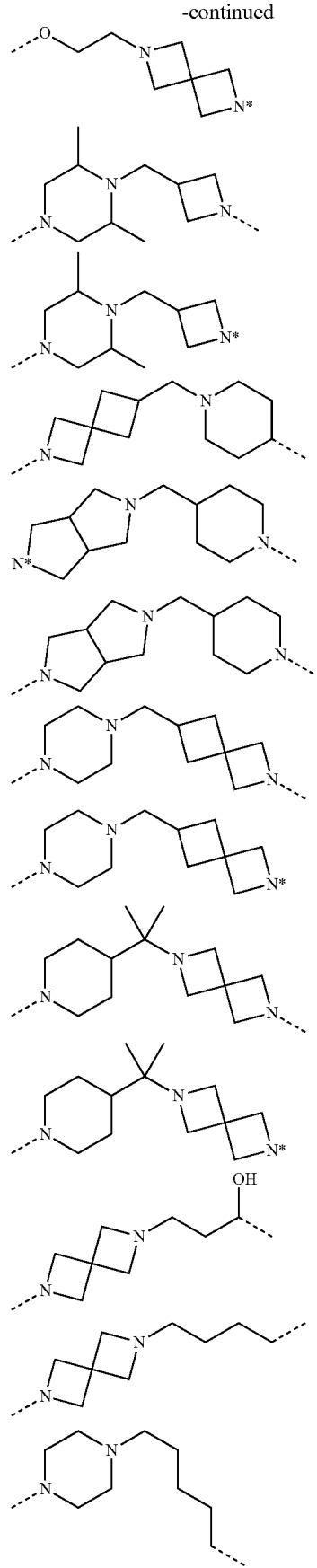
78
-continued
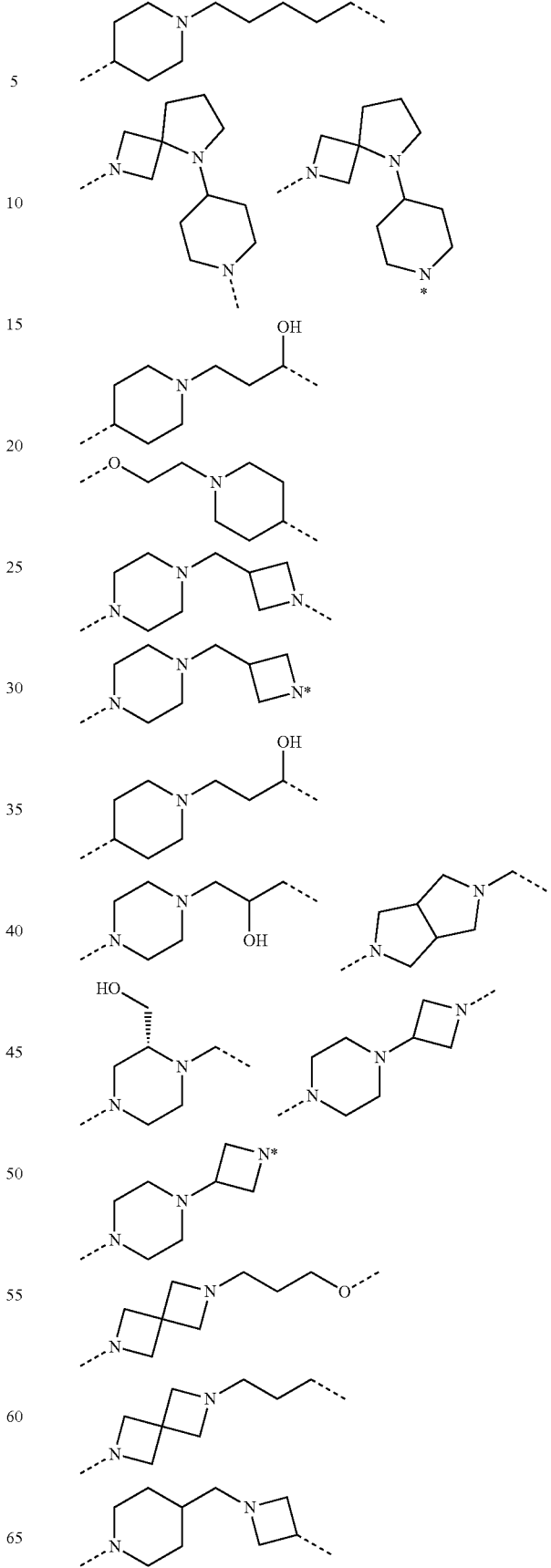

-continued
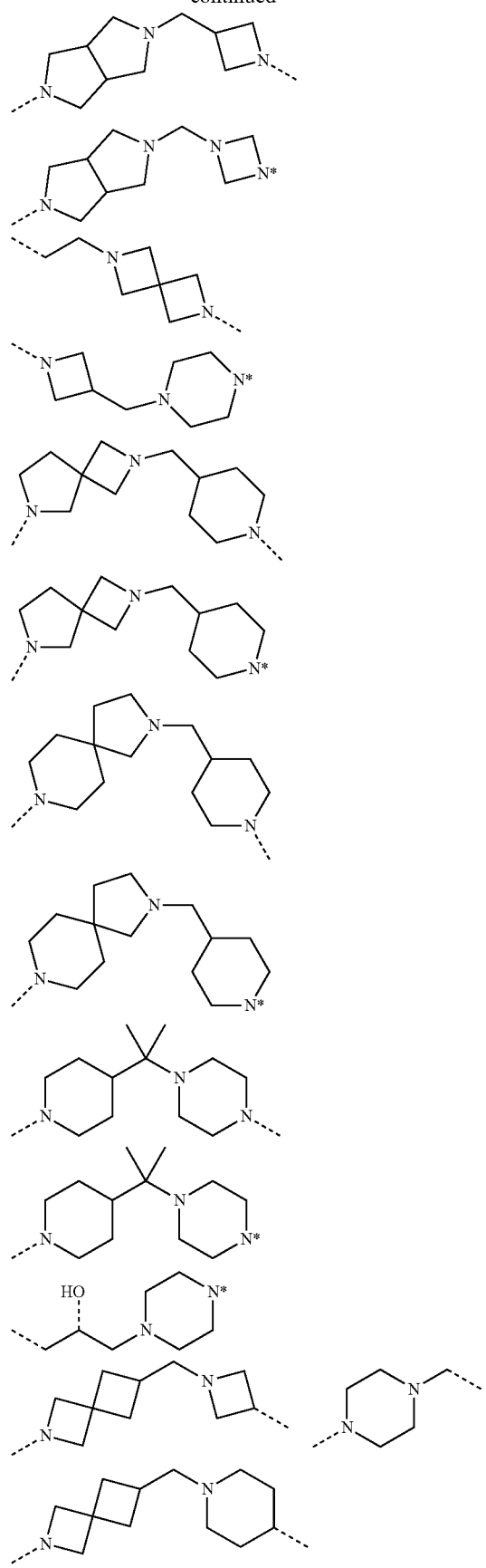
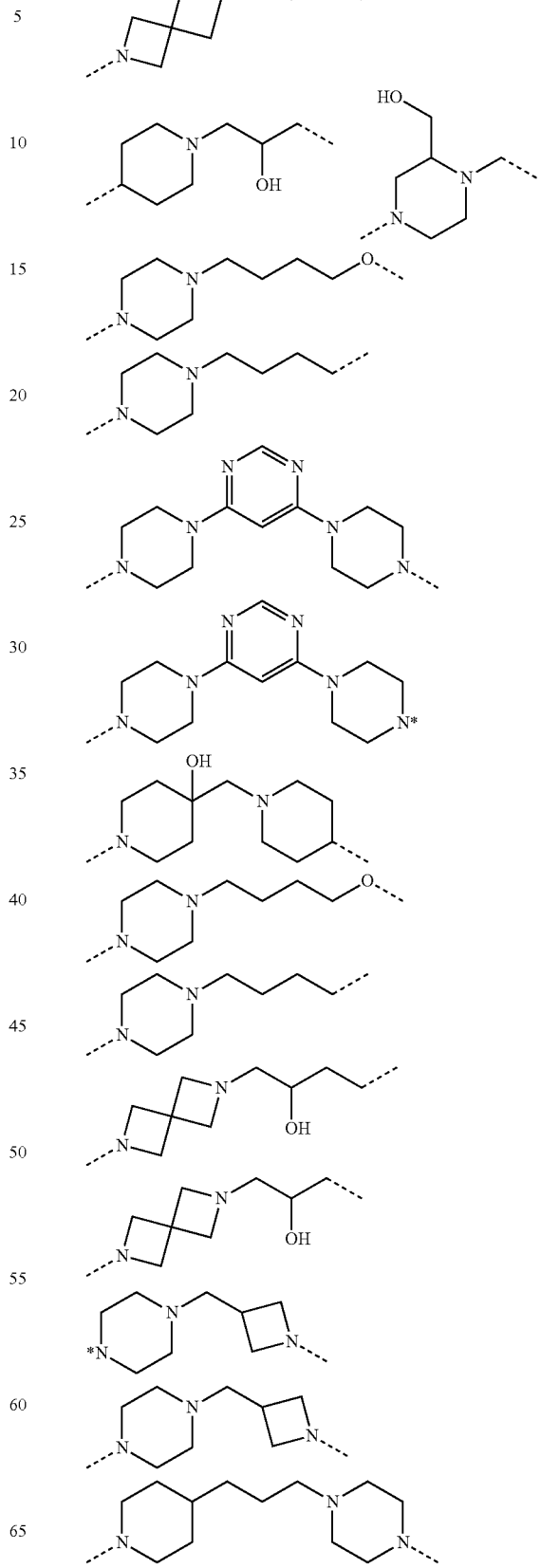

-continued
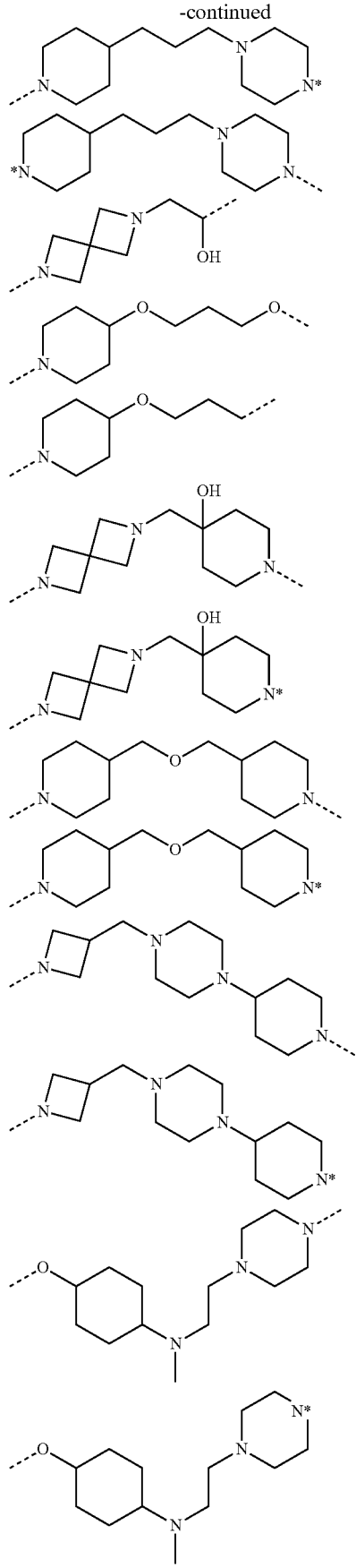
-continued
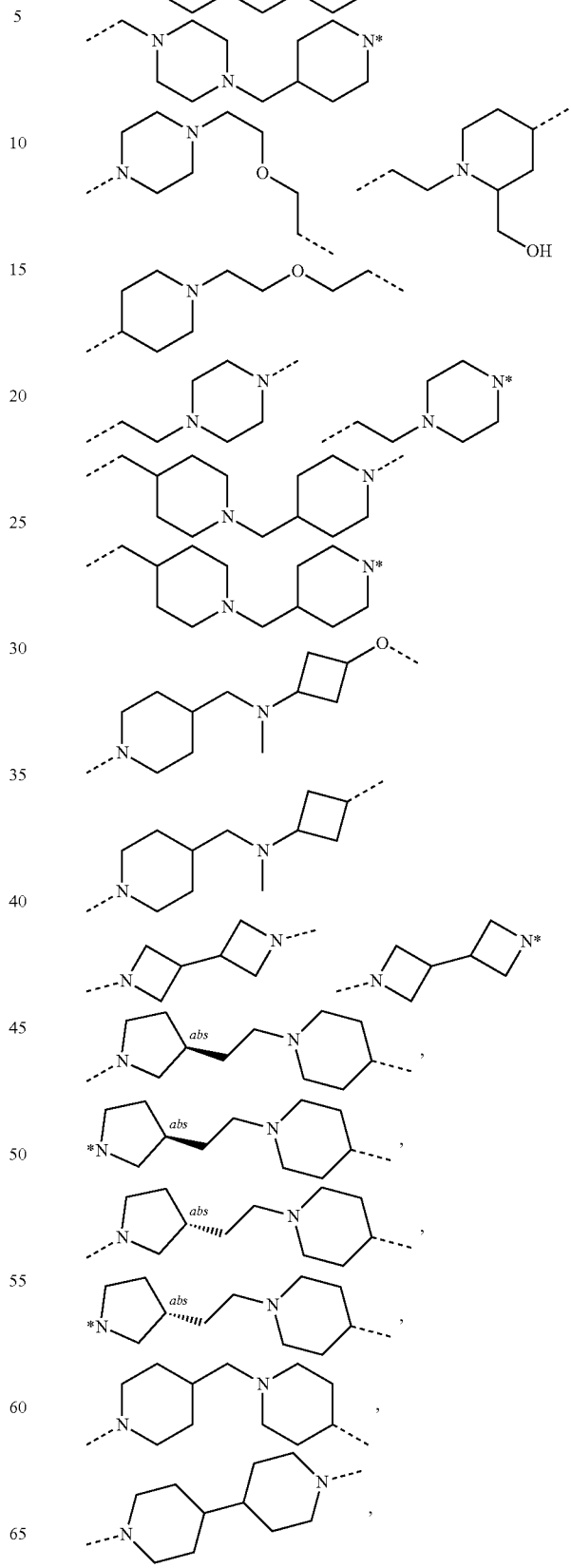

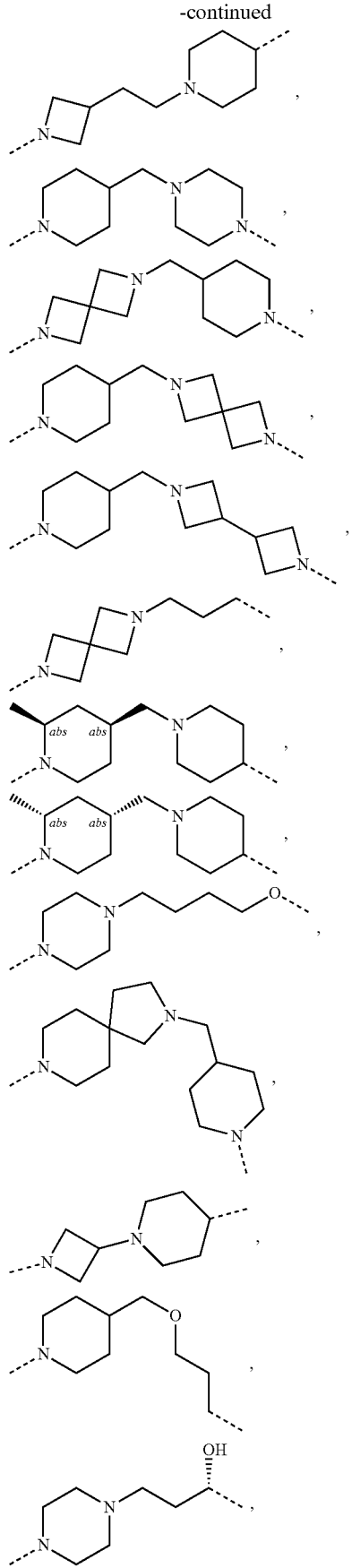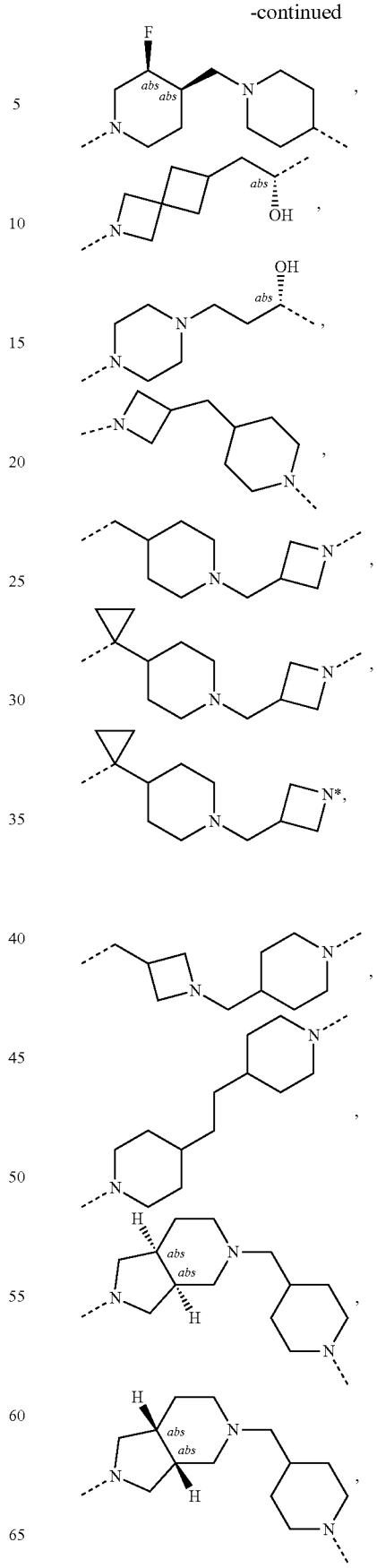

-continued
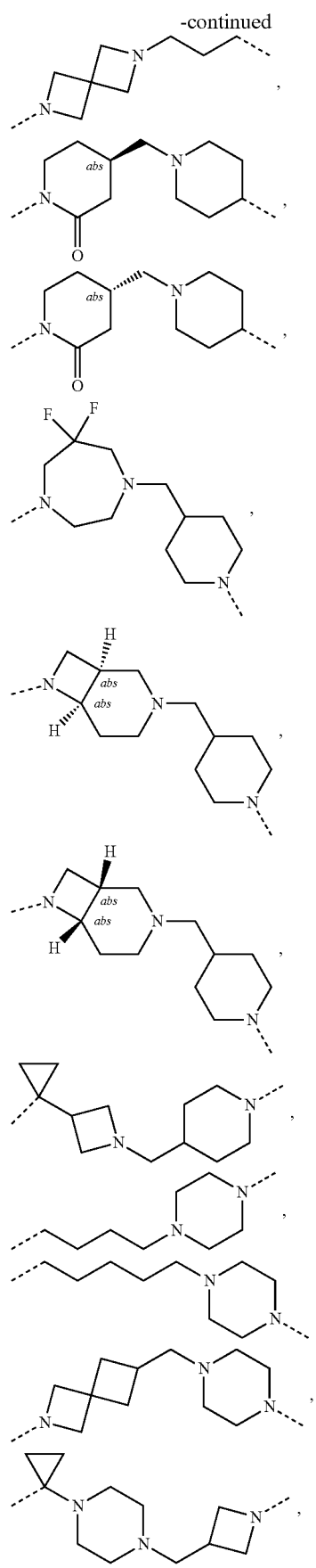
-continued
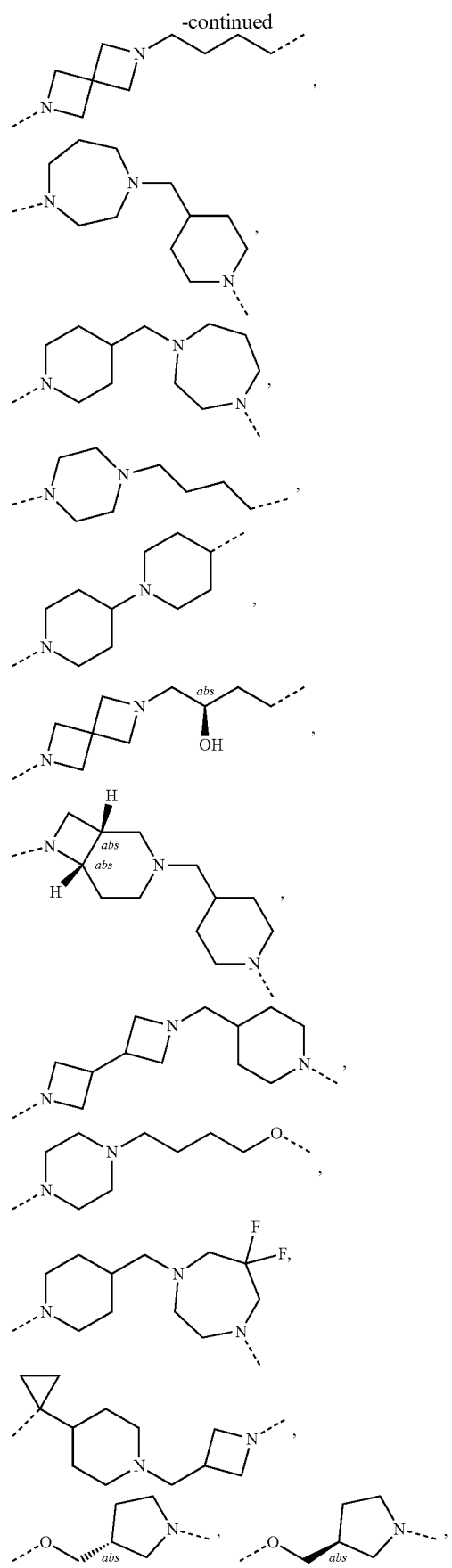

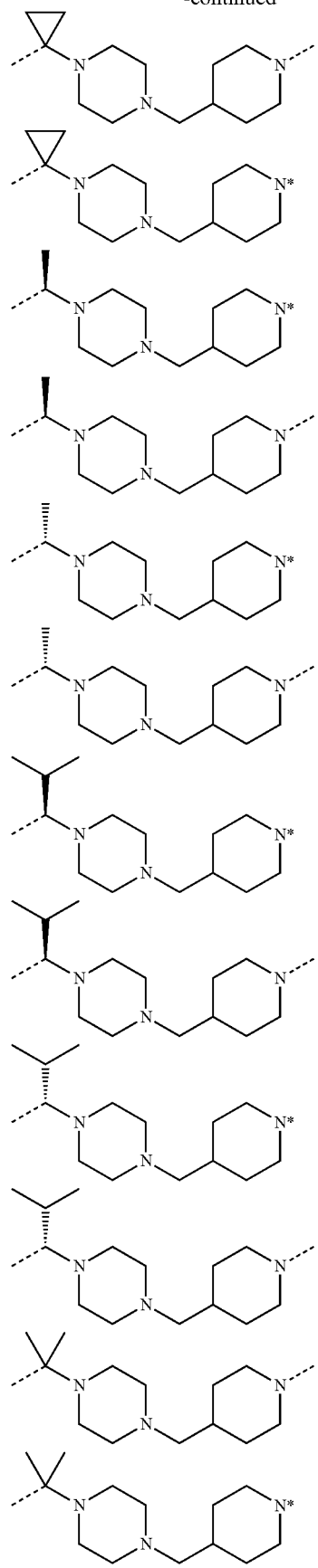
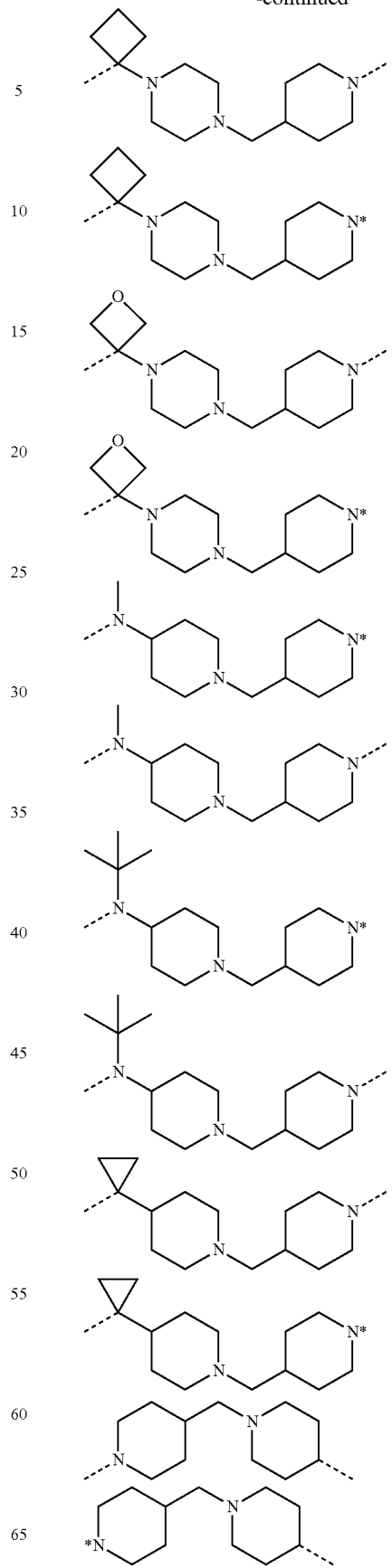

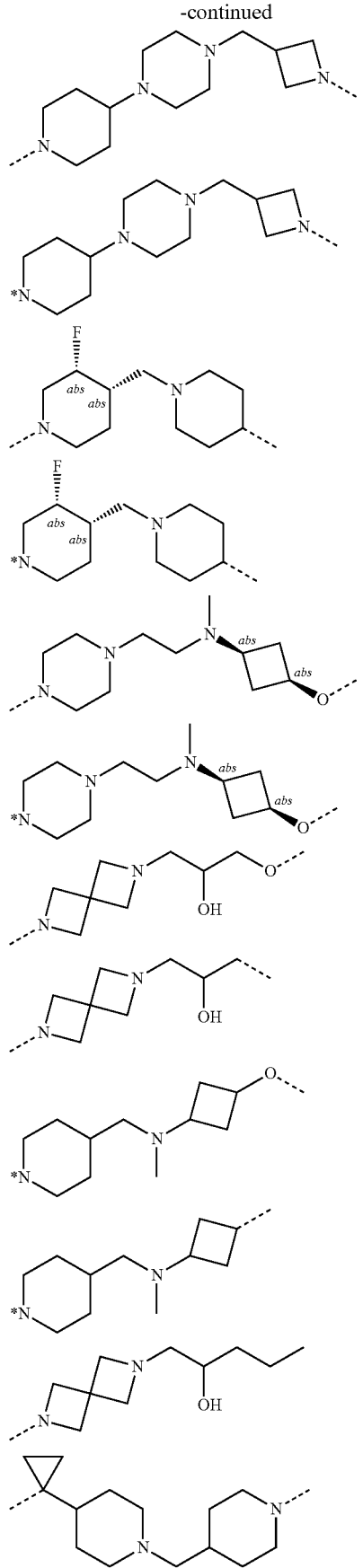
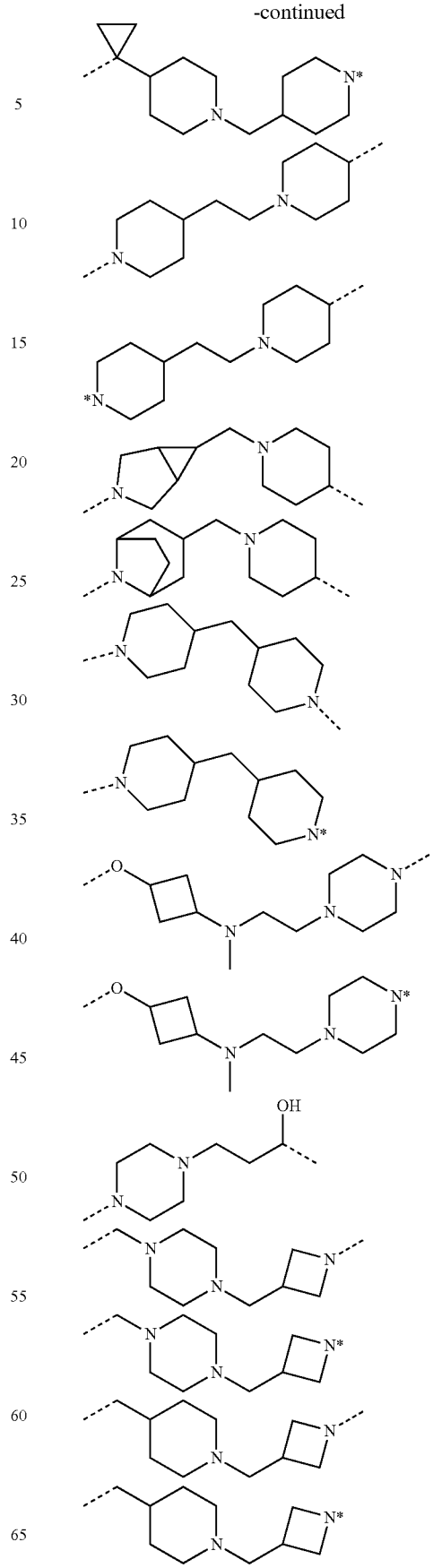

-continued
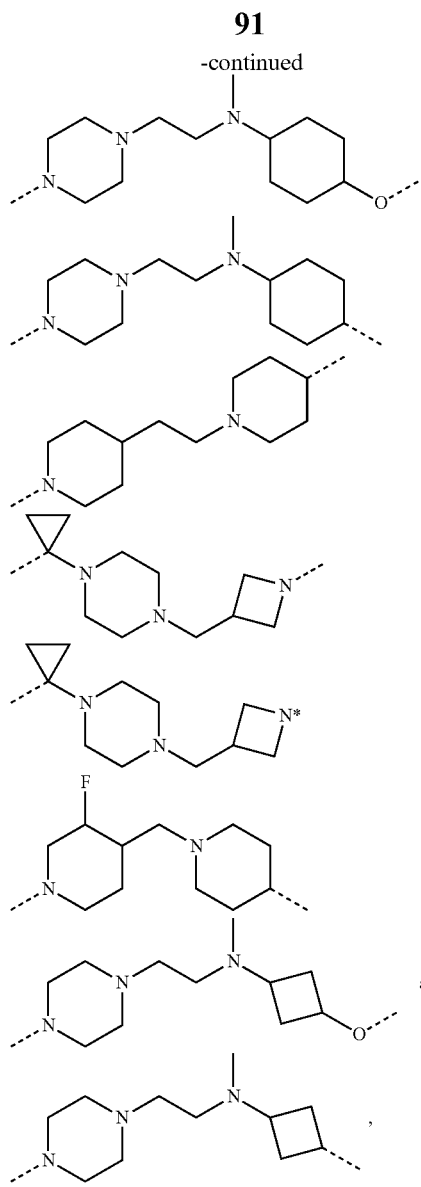
wherein:
~~~ indicates the site that is covalently linked to the CLM or PTM; and
\* indicates the site that is covalently linked to the CLM or PTM, or is an atom that is shared with the CLM or PTM.
In any aspect or embodiment described herein, the unit $A^L$ of the linker (L) comprises a structure selected from the group consisting of:
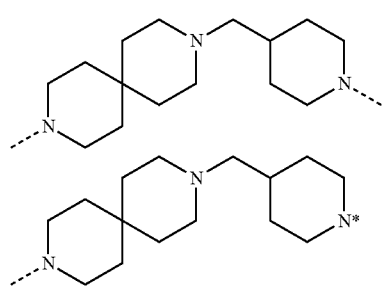
-continued
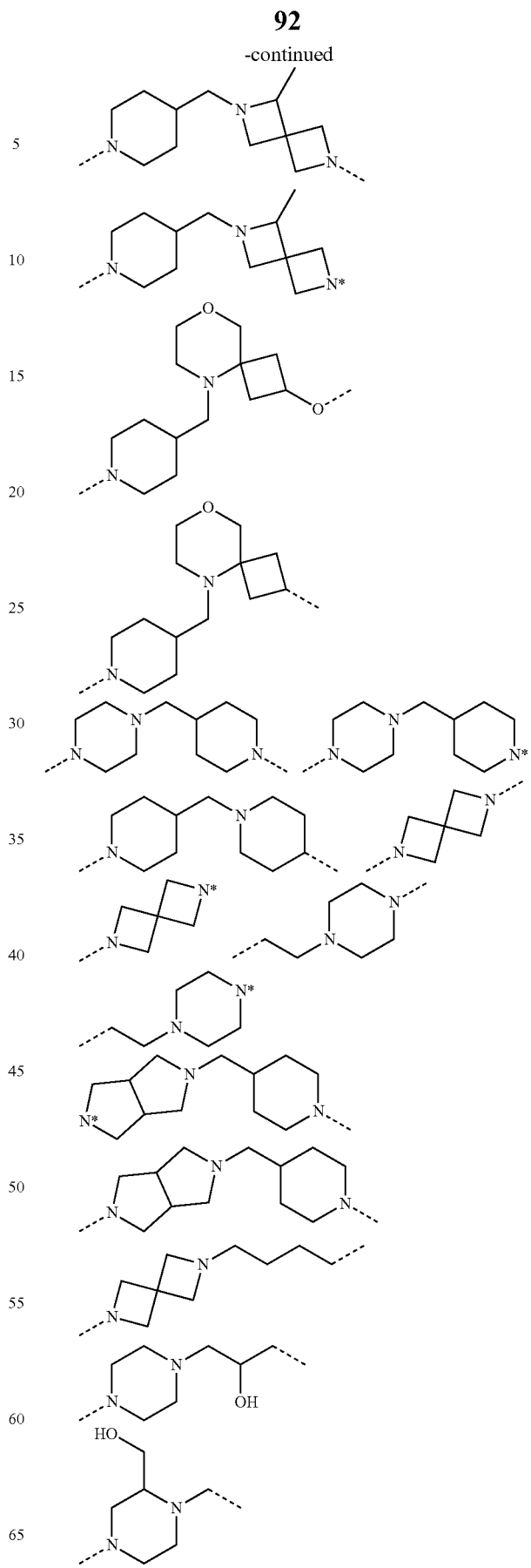

-continued
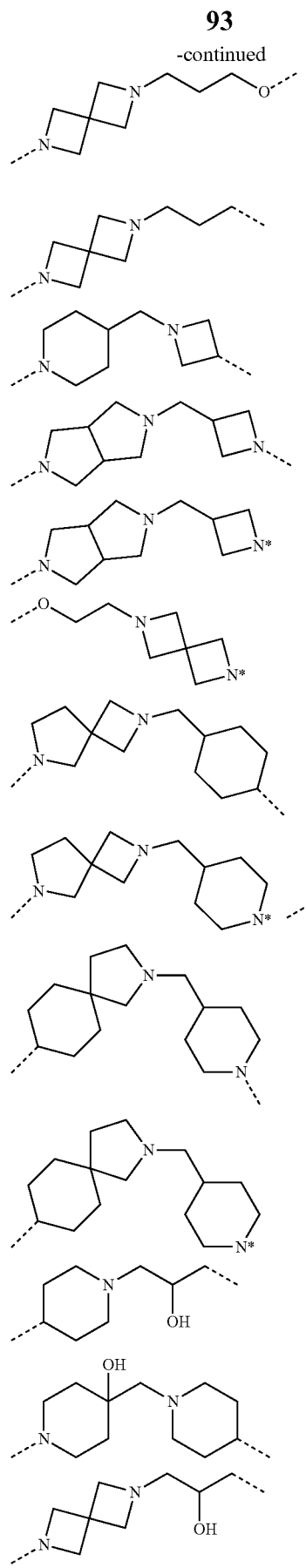
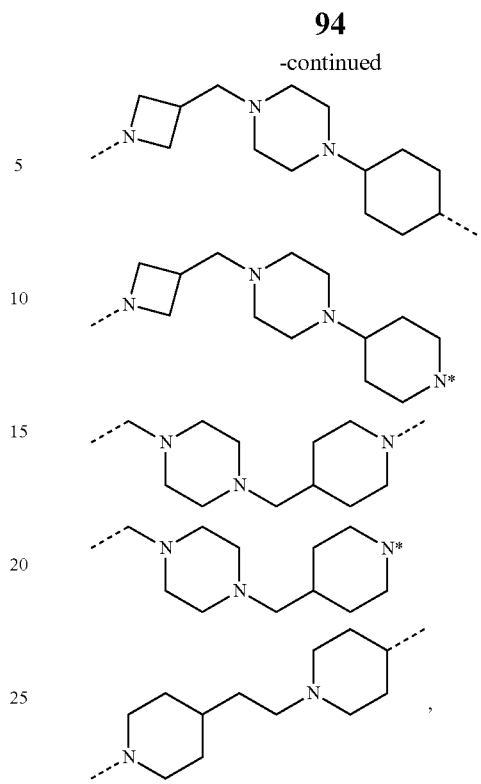
wherein:
- - - indicates the site that is covalently linked to the CLM or PTM; and
* indicates the site that is covalently linked to the CLM or PTM, or is an atom that is shared with the CLM or PTM.
In any aspect or embodiment described herein, the unit A L of the linker (L) comprises a structure selected from the group consisting of:
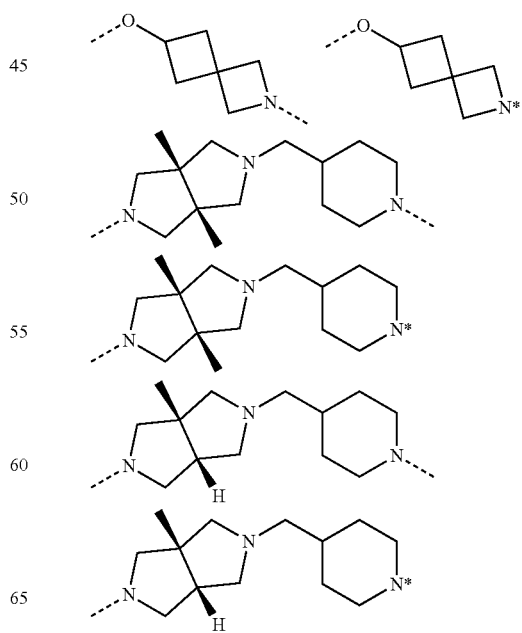

95
-continued
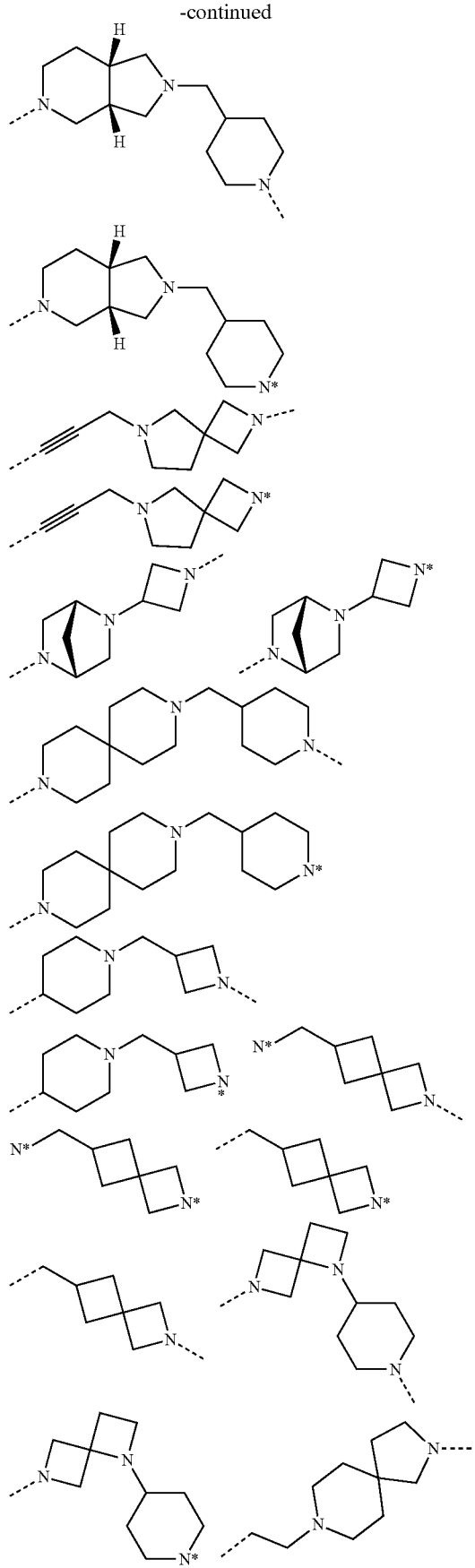
96
-continued
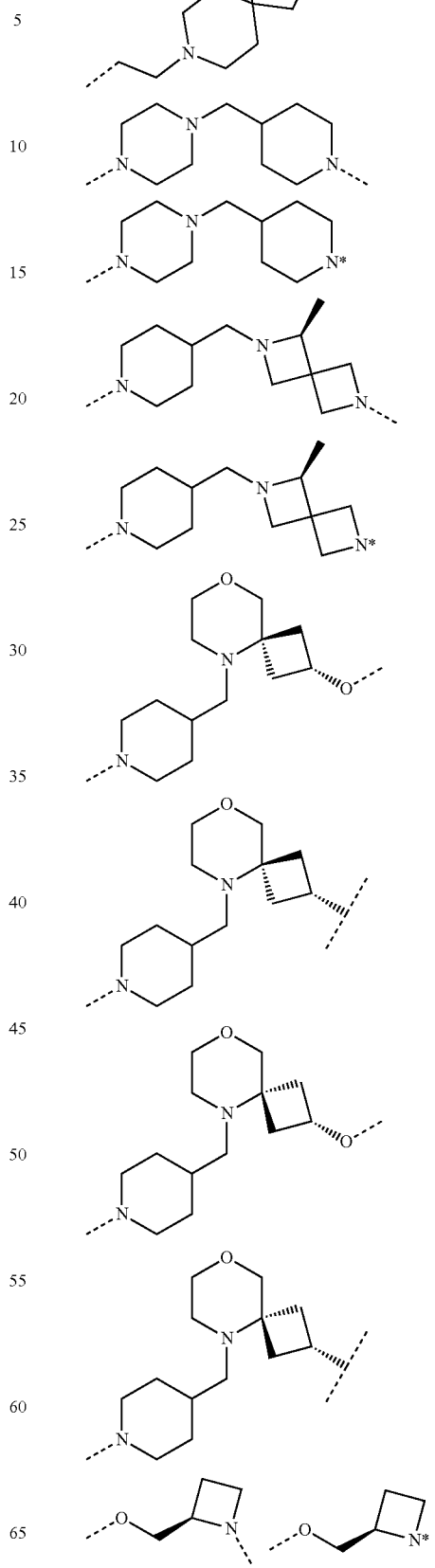

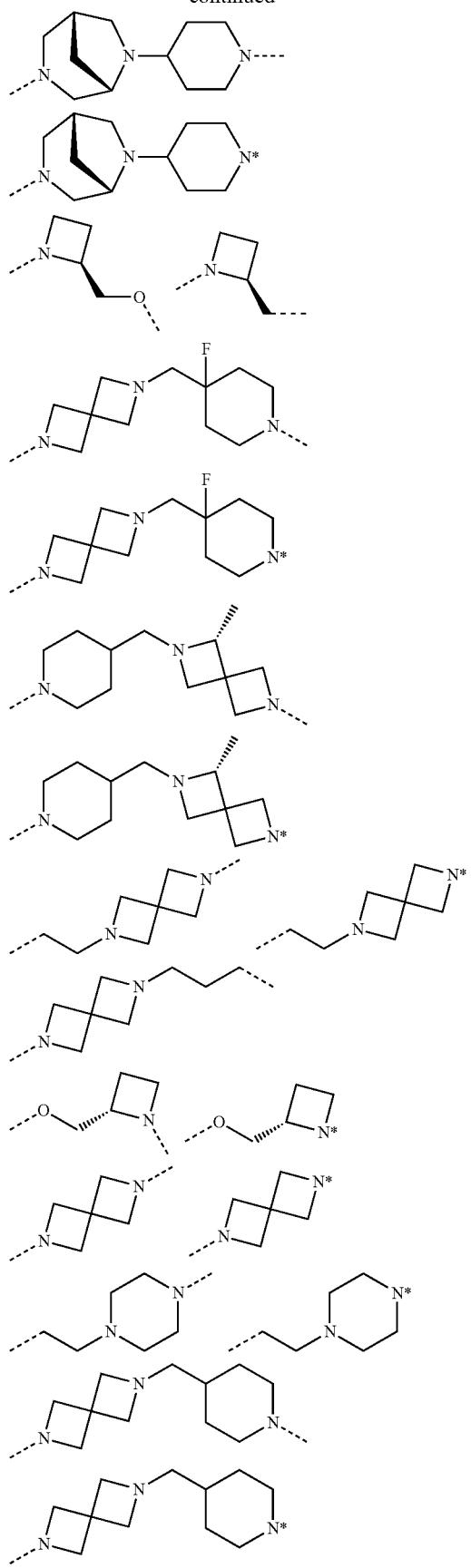
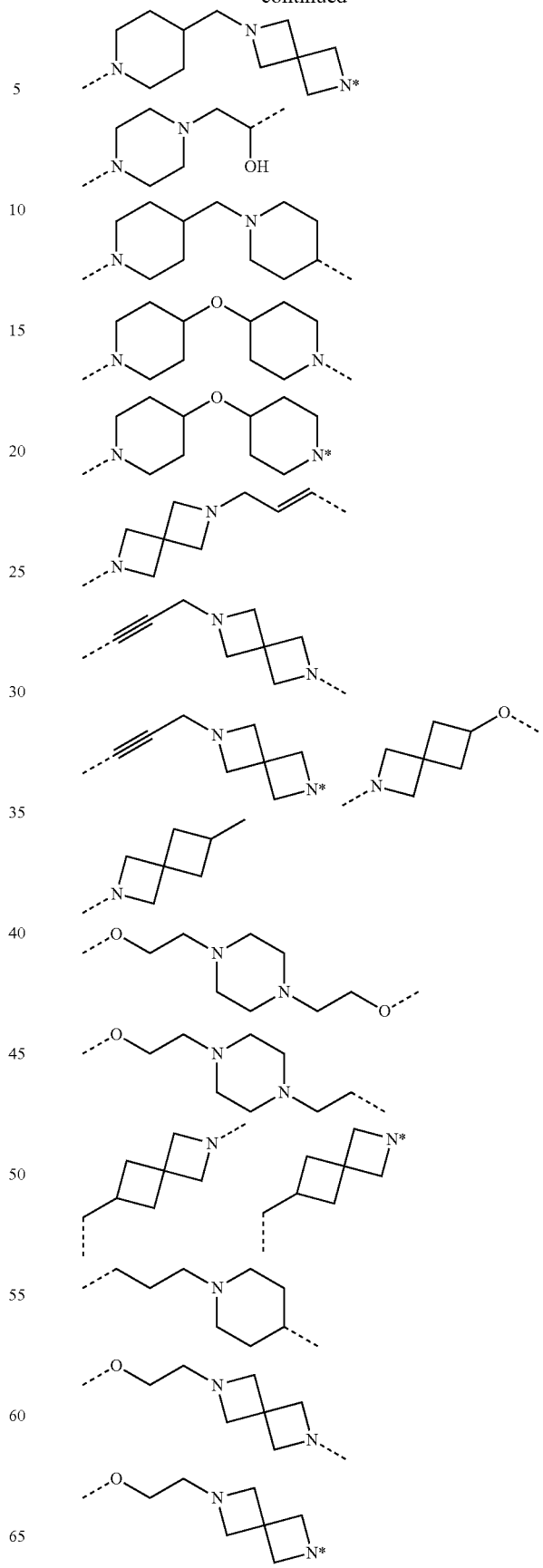

99
-continued
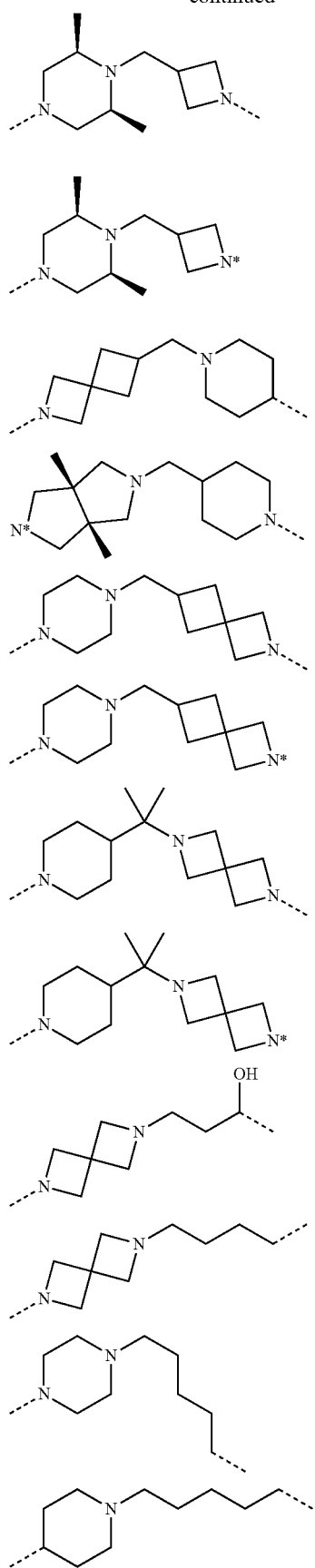
100
-continued
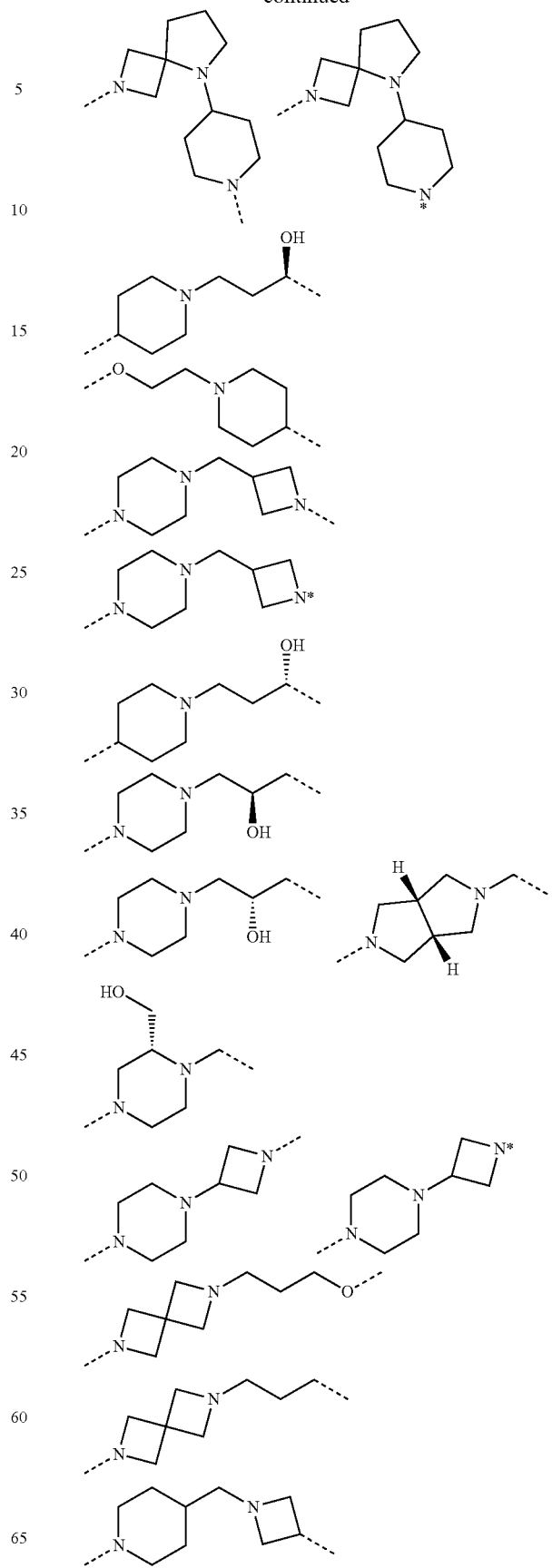

101
-continued
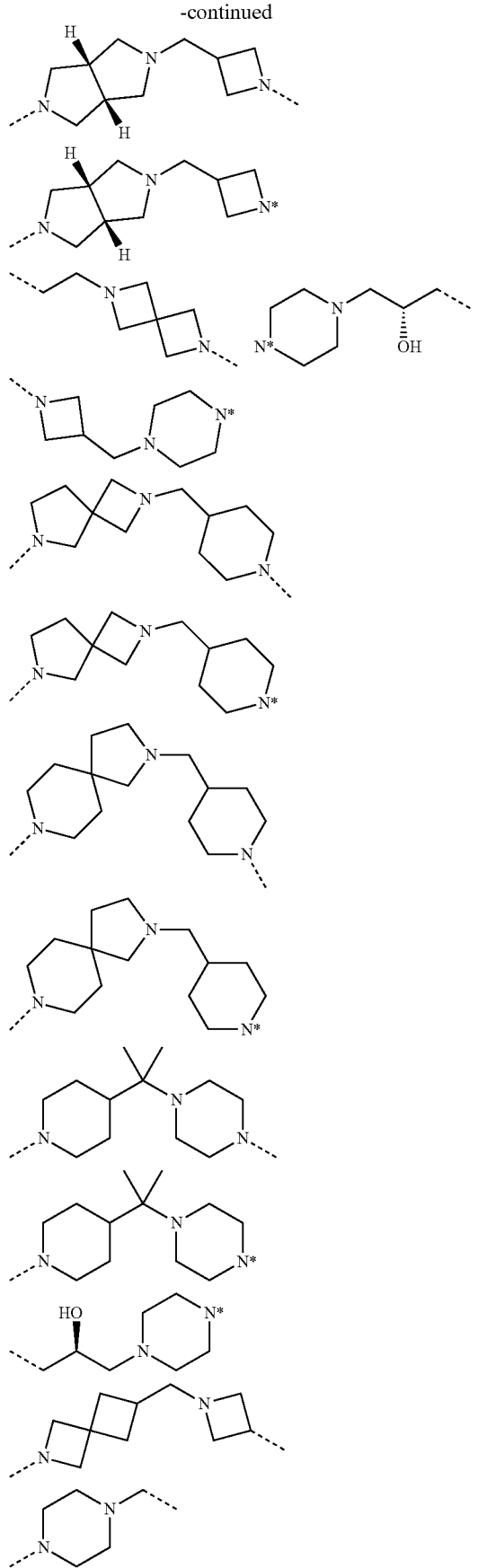
102
-continued
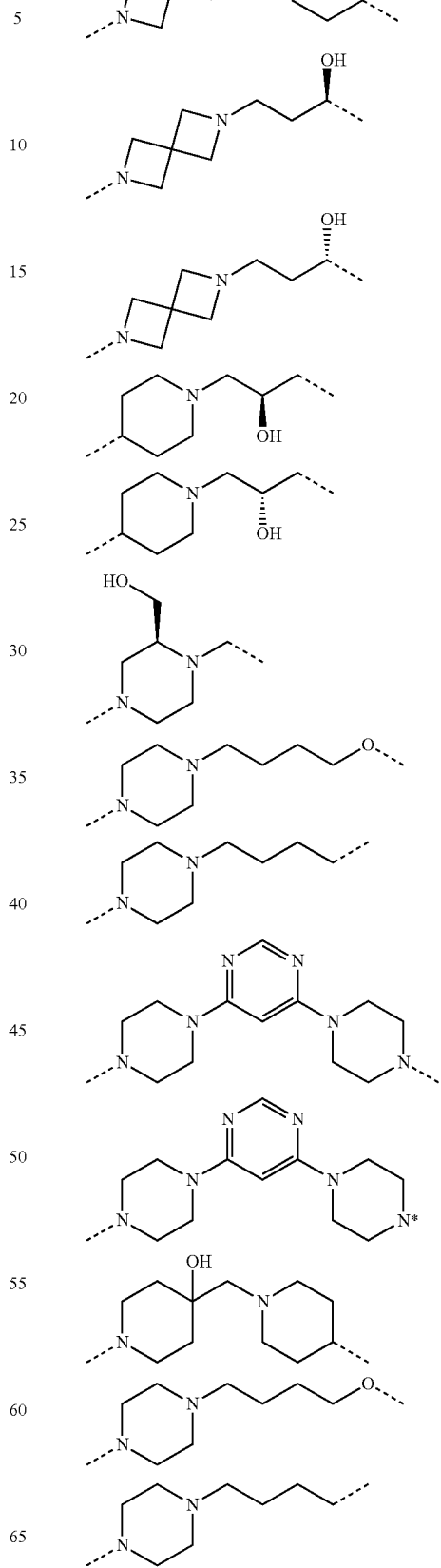

103
-continued
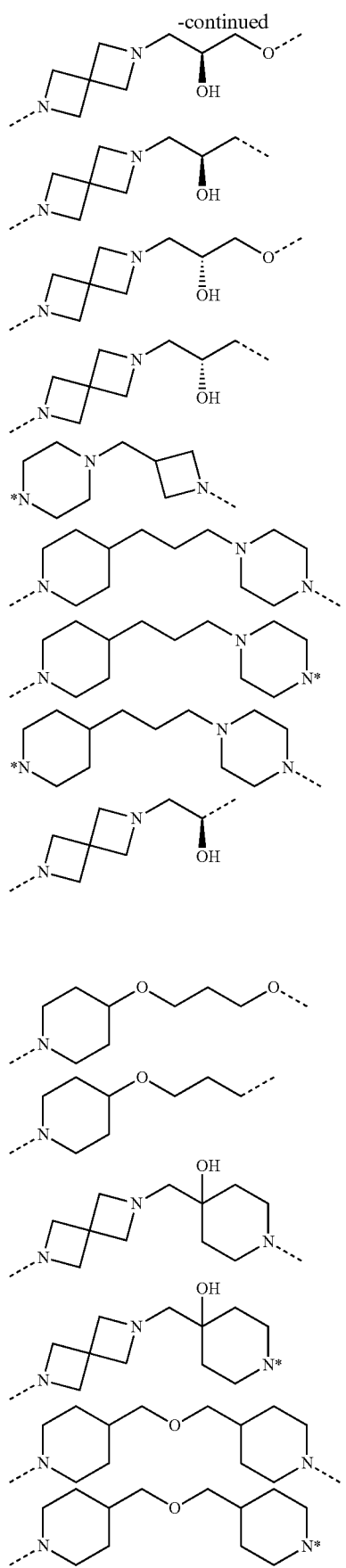
104
-continued
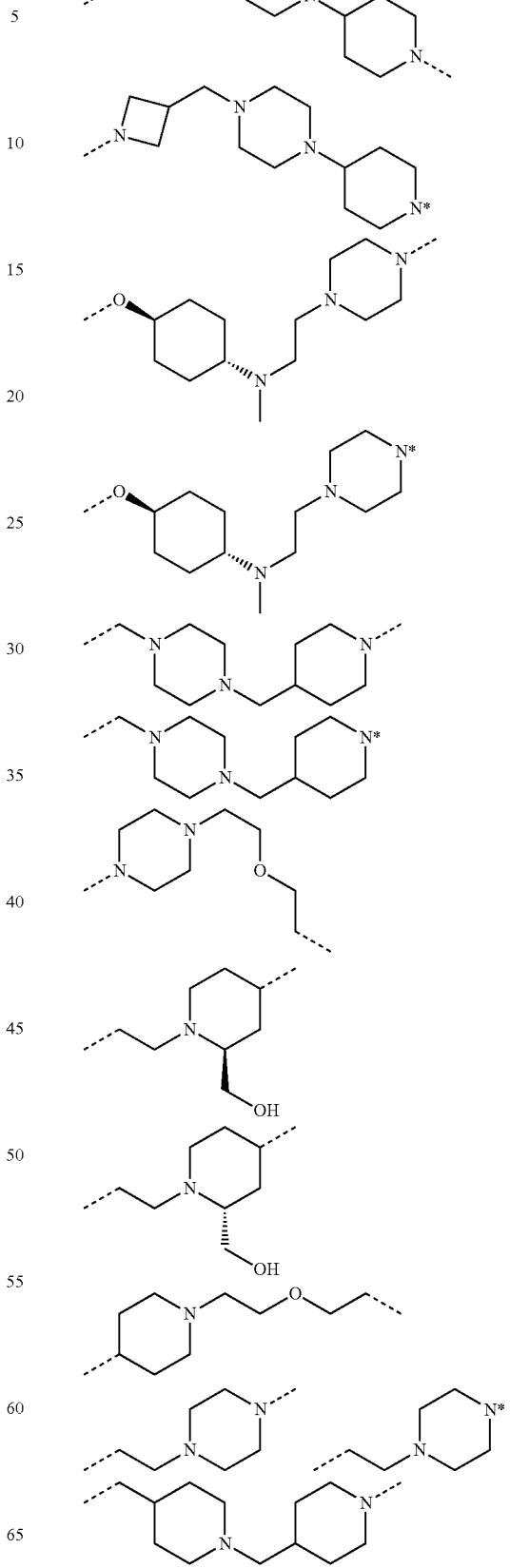

105
-continued
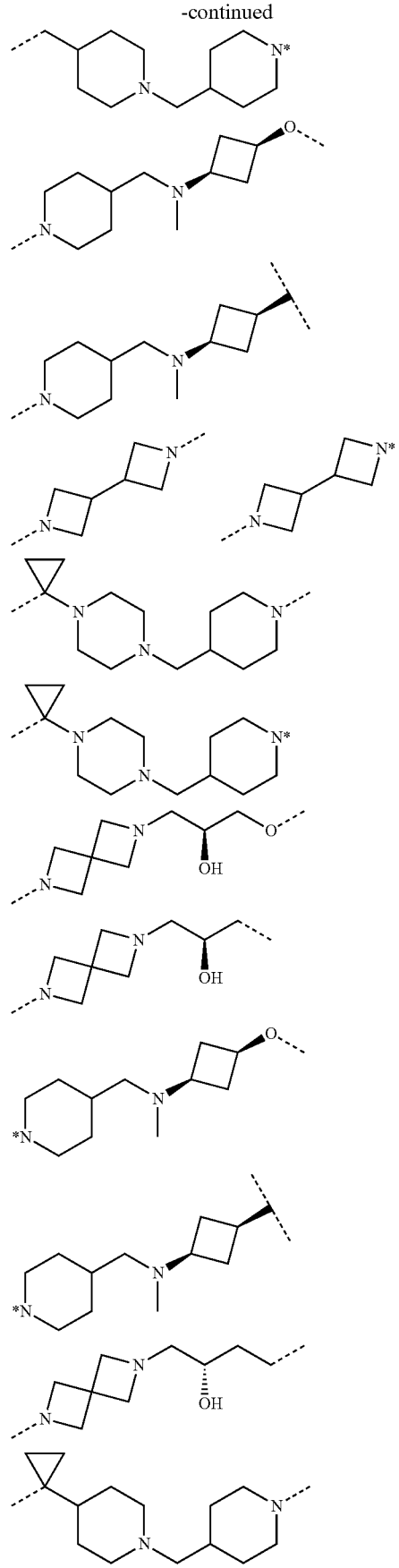
106
-continued
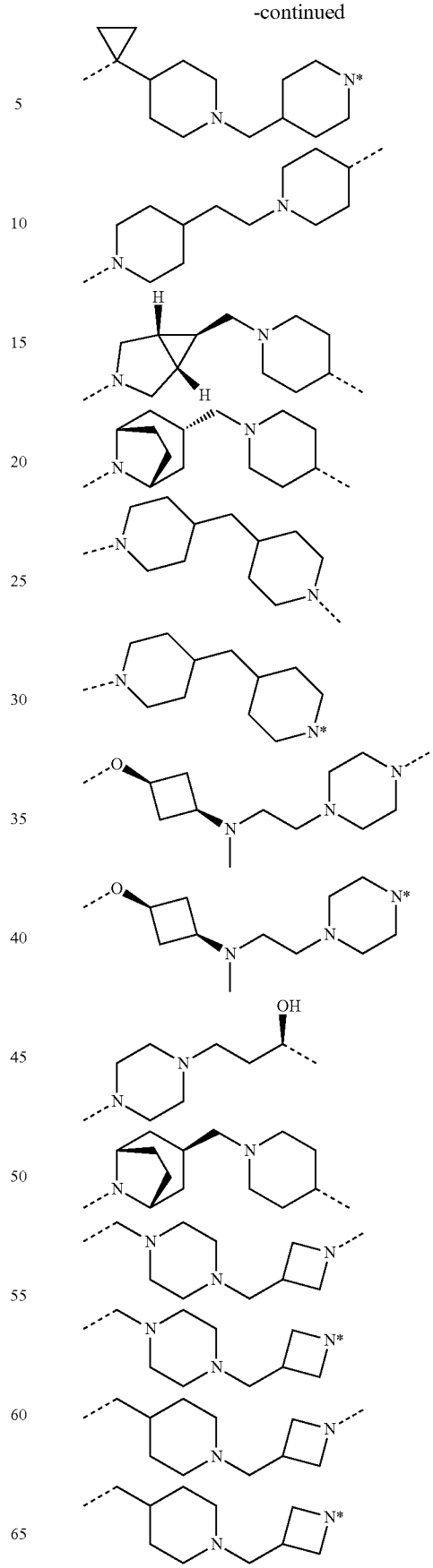

107
-continued
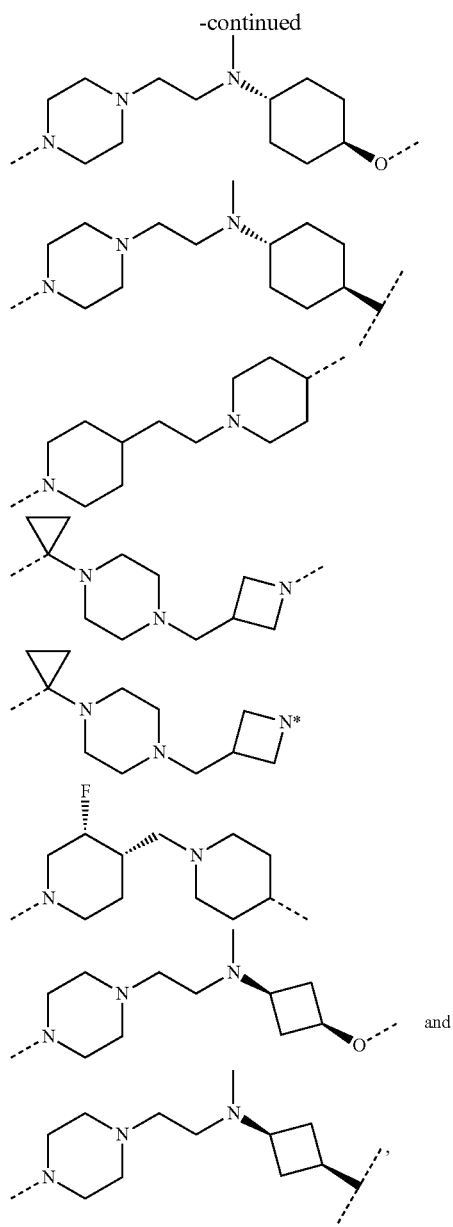
108
-continued
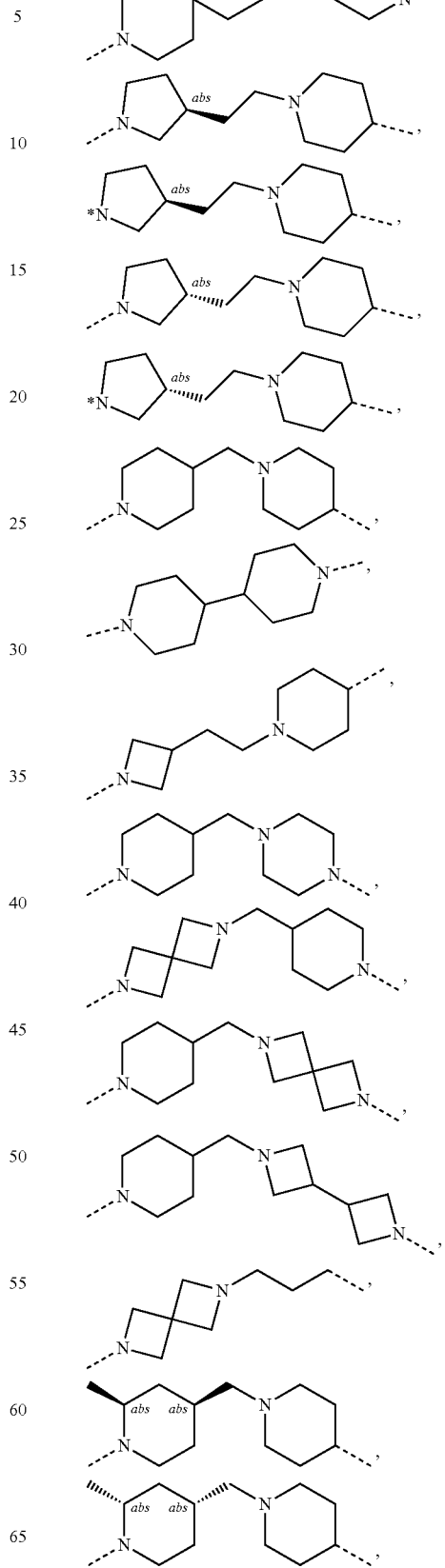
wherein:
  ⌇ indicates the site that is covalently linked to the CLM or PTM; and
  * indicates the site that is covalently linked to the CLM or PTM, or is an atom that is shared with the CLM or PTM.
In any aspect or embodiment described herein, the unit A L of the linker (L) comprises a structure selected from the group consisting of:
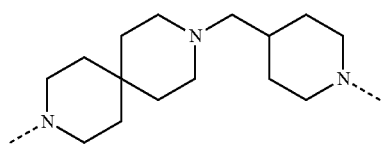

-continued
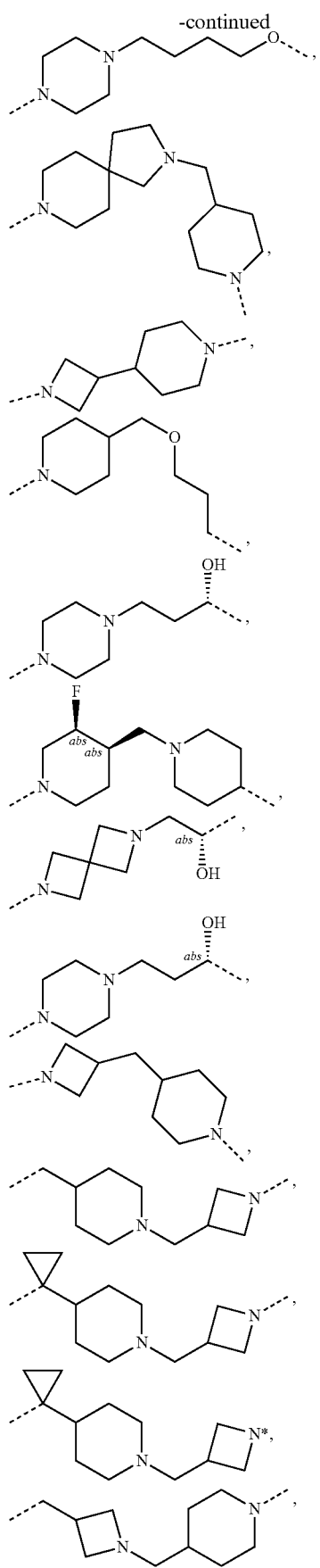
-continued
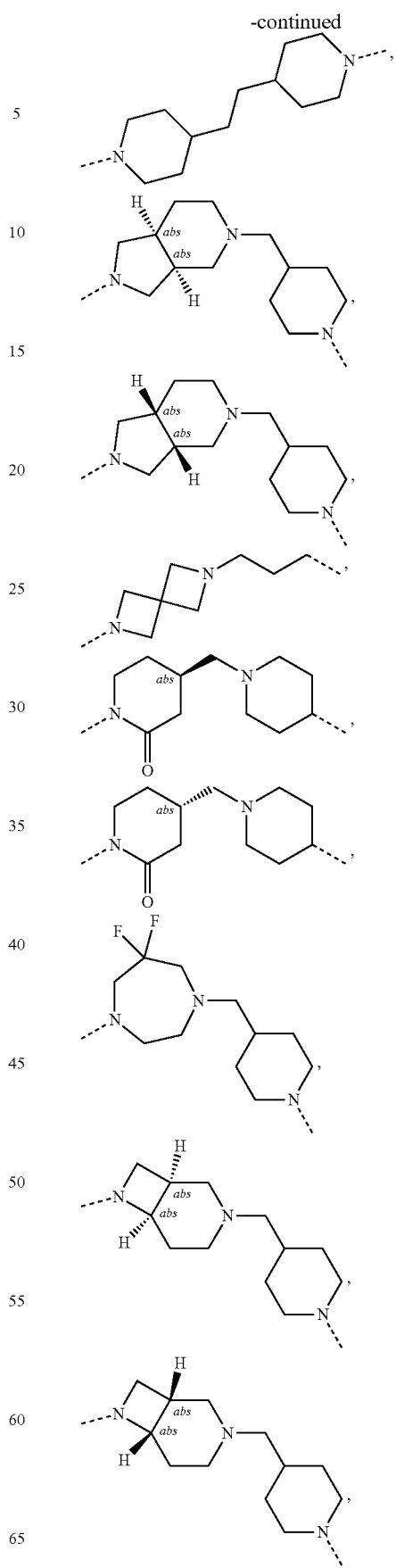

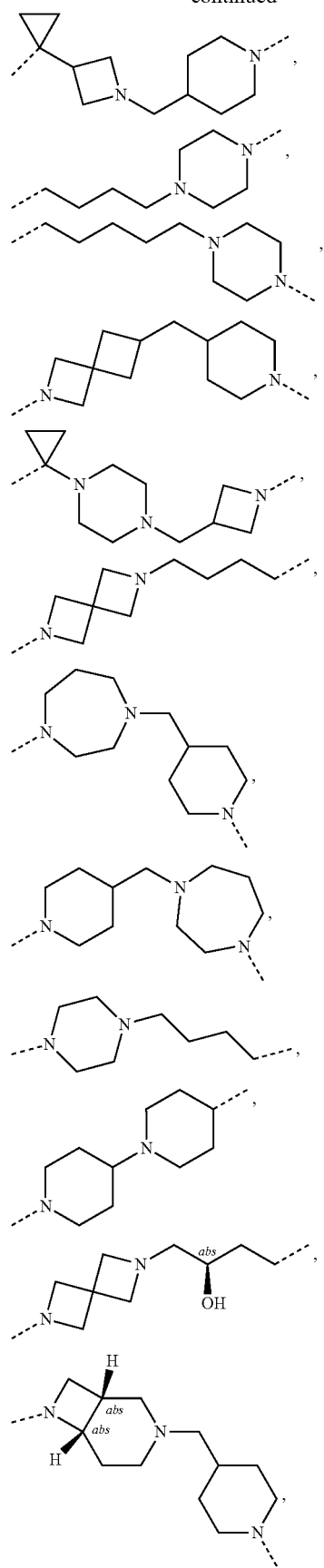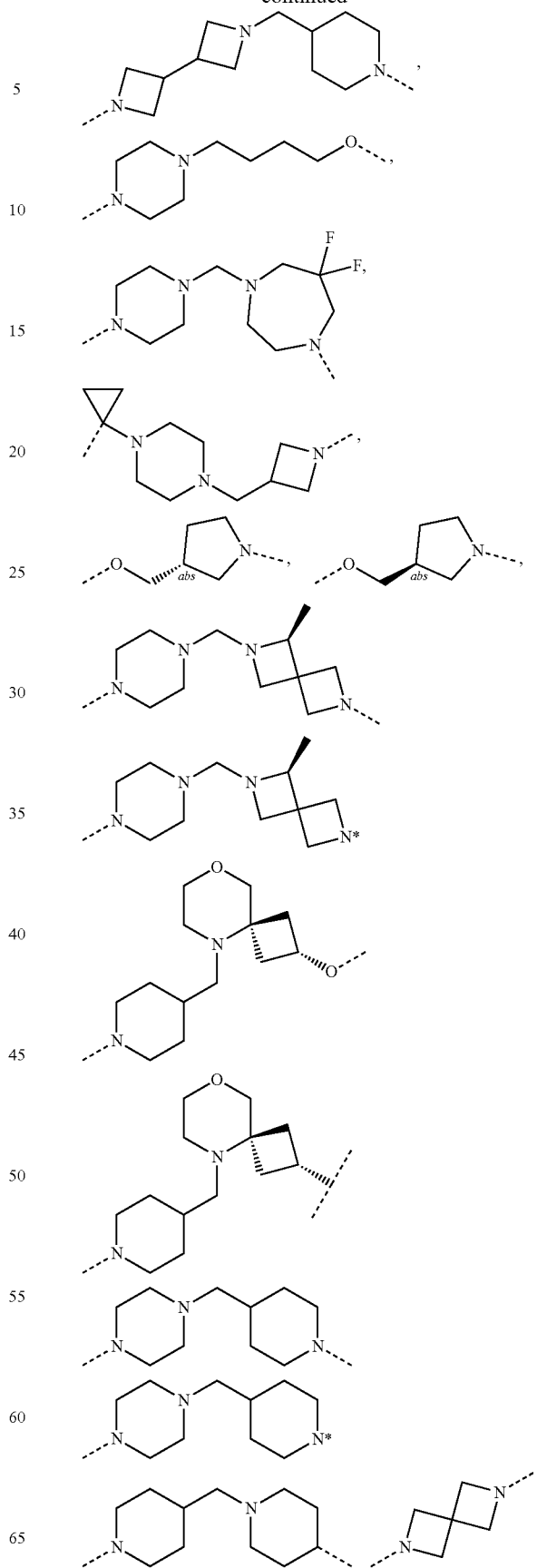

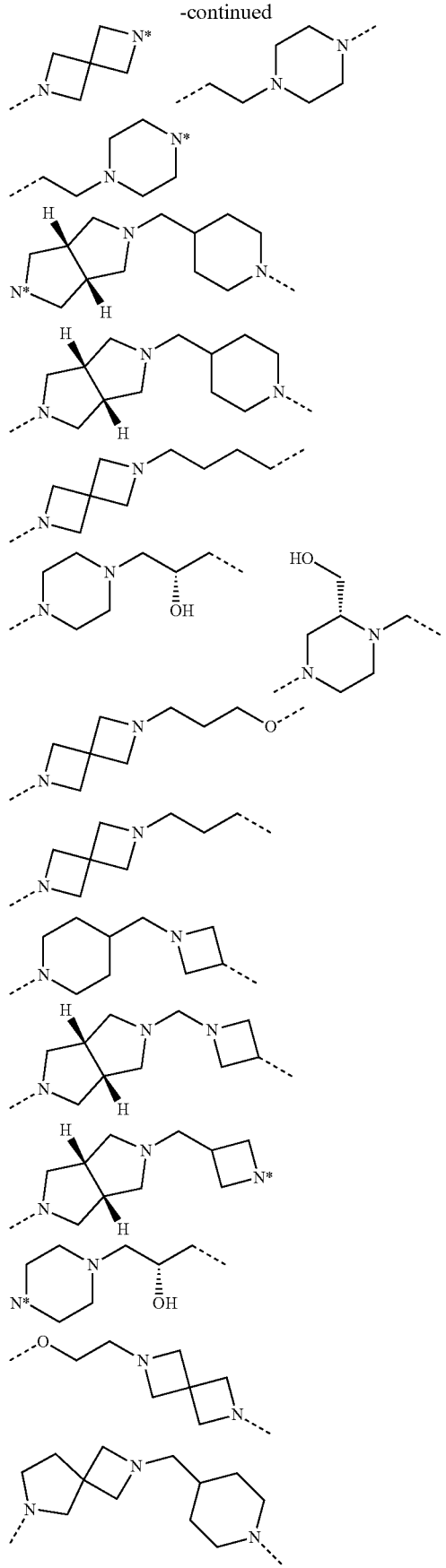
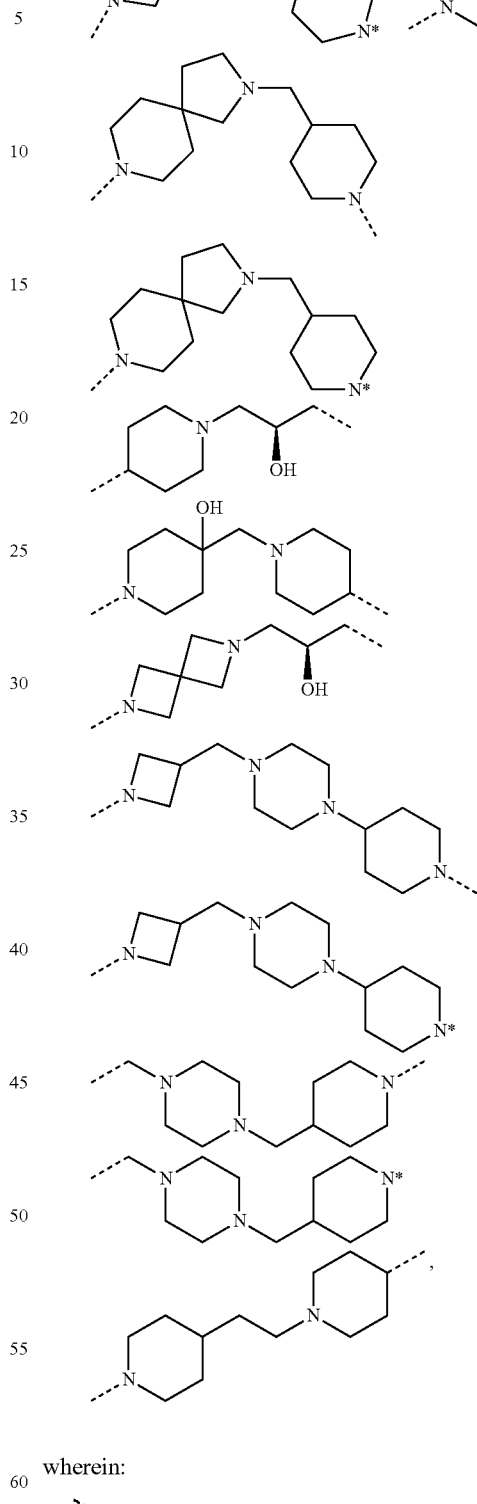
wherein:
- - - indicates the site that is covalently linked to the CLM or PTM; and
\* indicates the site that is covalently linked to the CLM or PTM, or is an atom that is shared with the CLM or PTM. In certain embodiments, the linker (L) includes any subset of the structures listed above.

In any aspect or embodiment described herein, the linker (L) comprises a structure selected from the structure shown below:

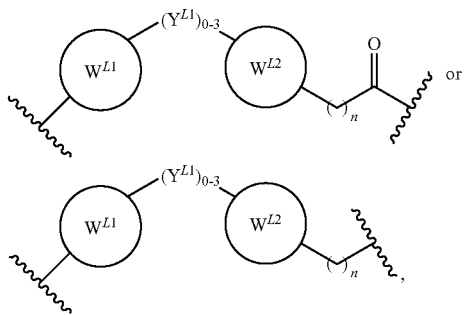

wherein:
- $W^{L1}$ and $W^{L2}$ are each independently absent, a 4-8 membered ring with 0-4 heteroatoms, optionally substituted with $R^Q$, each $R^Q$ is independently a H, halo, OH, CN, $CF_3$, optionally substituted linear or branched $C_1$-$C_6$ alkyl, optionally substituted linear or branched $C_1$-$C_6$ alkoxy, or 2 $R^Q$ groups taken together with the atom they are attached to, form a 4-8 membered ring system containing 0-4 heteroatoms;
- $Y^{L1}$ is each independently a bond, optionally substituted linear or branched $C_1$-$C_6$ alkyl and optionally one or more C atoms are replaced with O or $NR^{YL1}$, optionally substituted $C_1$-$C_6$ alkene and optionally one or more C atoms are replaced with O, optionally substituted $C_1$-$C_6$ alkyne, and optionally one or more C atoms are replaced with O, or optionally substituted linear or branched $C_1$-$C_6$ alkoxy;
- $R^{YL1}$ is H, or optionally substituted linear or branched $C_{1-6}$ alkyl;
- n is 0-10; and
- ⥇ and ⤳ indicates the attachment point to the PTM or ULM moieties.

In any aspect or embodiment described herein, the linker (L) comprises a structure selected from the structure shown below:

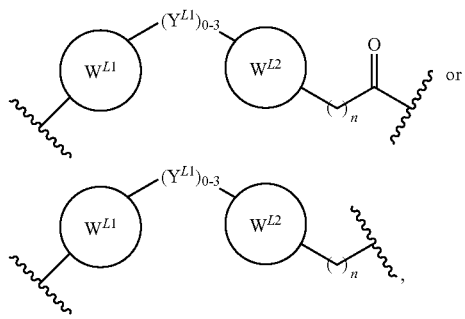

wherein:
- $W^{L1}$ and $W^{L2}$ are each independently absent, piperazine, piperidine, morpholine, optionally substituted with $R^Q$, each $R^Q$ is independently a H, —Cl—, —F—, OH, CN, $CF_3$, optionally substituted linear or branched $C_1$-$C_6$ alkyl (e.g. methyl, ethyl), optionally substituted linear or branched $C_1$-$C_6$ alkoxy (e.g. methoxy, ethoxy);
- $Y^{L1}$ is each independently a bond, optionally substituted linear or branched $C_1$-$C_6$ alkyl and optionally one or more C atoms are replaced with O or $NR^{YL1}$; optionally substituted $C_1$-$C_6$ alkene and optionally one or more C atoms are replaced with O, optionally substituted $C_1$-$C_6$ alkyne and optionally one or more C atoms are replaced with O, or optionally substituted linear or branched $C_1$-$C_6$ alkoxy;
- $R^{YL1}$ is H, or optionally substituted linear or branched $C_{1-6}$ alkyl (e.g. methyl, ethyl);
- n is 0-10; and
- ⥇ and ⤳ indicates the attachment point to the PTM or ULM moieties.

In any aspect or embodiment described herein, the linker (L) comprises a structure selected from the structure shown below:

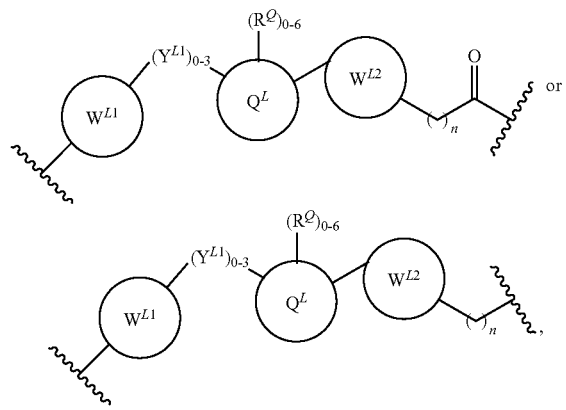

wherein:
- $W^{L1}$ and $W^{L2}$ are each independently absent, aryl, heteroaryl, cyclic, heterocyclic, $C_{1-6}$ alkyl and optionally one or more C atoms are replaced with O or $NR^{YL1}$, $C_{1-6}$ alkene and optionally one or more C atoms are replaced with O, $C_{1-6}$ alkyne and optionally one or more C atoms are replaced with O, bicyclic, biaryl, biheteroaryl, or biheterocyclic, each optionally substituted with $R^Q$, each $R^Q$ is independently a H, halo, OH, CN, $CF_3$, hydroxyl, nitro, C≡CH, $C_{2-6}$ alkenyl, $C_{2-6}$ alkynyl, optionally substituted linear or branched $C_1$-$C_6$ alkyl, optionally substituted linear or branched $C_1$-$C_6$ alkoxy, optionally substituted $OC_{1-3}$alkyl (e.g., optionally substituted by 1 or more —F), OH, $NH_2$, $NR^{Y1}R^{Y2}$, CN, or 2 $R^Q$ groups taken together with the atom they are attached to, form a 4-8 membered ring system containing 0-4 heteroatoms;
- $Y^{L1}$ is each independently a bond, $NR^{YL1}$, O, S, $NR^{YL2}$, $CR^{YL1}R^{YL2}$, C=O, C=S, SO, $SO_2$, optionally substituted linear or branched $C_1$-$C_6$ alkyl and optionally one or more C atoms are replaced with O; optionally substituted linear or branched $C_1$-$C_6$ alkoxy;
- $Q^L$ is a 3-6 membered alicyclic, bicyclic or aromatic ring with 0-4 heteroatoms, optionally bridged, optionally substituted with 0-6 $R^Q$, each $R^Q$ is independently H, optionally substitute linear or branched $C_{1-6}$ alkyl (e.g., optionally substituted by 1 or more halo, $C_{1-6}$ alkoxyl), or 2 $R^Q$ groups taken together with the atom they are attached to, form a 3-8 membered ring system containing 0-2 heteroatoms;

$R^{YL1}$, $R^{YL2}$ are each independently H, OH, optionally substituted linear or branched $C_{1-6}$ alkyl (e.g., optionally substituted by 1 or more halo, $C_{1-6}$ alkoxyl), or $R^1$, $R^2$ together with the atom they are attached to, form a 3-8 membered ring system containing 0-2 heteroatoms; n is 0-10; and ⤤ and ⤳ indicates the attachment point to the PTM or ULM moieties.

In any aspect or embodiment described herein, the linker (L) comprises a structure selected from the structure shown below:

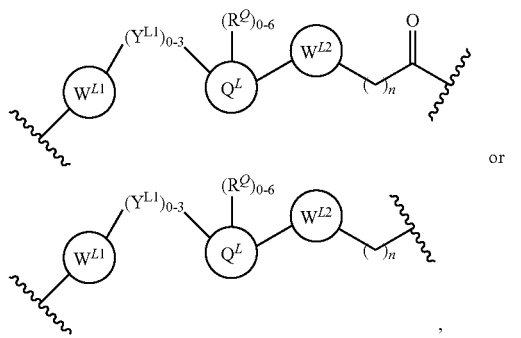

or wherein:
- $W^{L1}$ and $W^{L2}$ are each independently absent, cyclohexane, cyclopentane, piperazine, piperidine, morpholine, $C_{1-6}$ alkyl and optionally one or more C atoms are replaced with O or $NR^{YL1}$, $C_{1-6}$ alkene and optionally one or more C atoms are replaced with O, $C_{1-6}$ alkene and optionally one or more C atoms are replaced with O, or $C_{1-6}$ alkyne and optionally one or more C atoms are replaced with O, each optionally substituted with $R^Q$, each $R^Q$ is independently a H, —Cl, —F, OH, CN, $CF_3$, hydroxyl, optionally substituted linear or branched $C_1$-$C_6$ alkyl (e.g., methyl, ethyl), or optionally substituted linear or branched $C_1$-$C_6$ alkoxy;
- $Y^{L1}$ is each independently a bond, $NR^{YL1}$, O, $CR^{YL1}R^{YL2}$, C=O optionally substituted linear or branched $C_1$-$C_6$ alkyl and optionally one or more C atoms are replaced with O or $NR^{YL1}$, $C_{1-6}$ alkene and optionally one or more C atoms are replaced with O, $C_{1-6}$ alkyne and optionally one or more C atoms are replaced with O, or optionally substituted linear or branched $C_1$-$C_6$ alkoxy;
- $Q^L$ is a 3-6 membered heterocyclic, heterobicyclic, or heteroaryl ring, optionally substituted with 0-6 $R^Q$, each $R^Q$ is independently H, or optionally substituted linear or branched $C_{1-6}$ alkyl (e.g., optionally substituted by 1 or more halo, $C_{1-6}$ alkoxyl); $R^{YL1}$, $R^{YL2}$ are each independently H, optionally substituted linear or branched $C_{1-6}$ alkyl (e.g., methyl, ethyl, optionally substituted by 1 or more halo, $C_{1-6}$ alkoxyl);
- n is 0-10; and ⤤ and ⤳ indicates the attachment point to the PTM or ULM moieties.

Exemplary PTMs

In one aspect of the disclosure, the PTM group (also referred as the RTM group) binds to the target protein, RAF or a mutated form thereof such as a B-Raf mutant having V600E and/or G466V.

The compositions described below exemplify members of RAF binding moieties (e.g., V600 mutant B-Raf binding moiety or B-Raf G466V biding moiety) that can be used according to the present invention. These binding moieties are linked to the ubiquitin ligase binding moiety (e.g., CLM) preferably through a chemical linking group in order to recruit the RAF protein, such as the wild-type B-Raf protein, or a mutant B-Raf having a V600 mutation and/or a G466V mutation, and present it in proximity to the ubiquitin ligase for ubiquitination and subsequent degradation.

In certain contexts, the term "target protein" is used to refer to the RAF protein or kinase (such as A-Raf, B-Raf, or C-Raf), which are serine/threonine-specific protein kinases related to retroviral oncogenes, and which are target proteins to be ubiquitinated and degraded. In some contexts, the term "target protein" is used to refer to the wild-type RAF (e.g., B-RAF) protein. In other contexts, the term "target protein" is used to refer to a mutated form of the RAF protein, such as RAF mutant protein having increased kinase activity relative to wild-type RAF, or a B-Raf mutant protein having increased kinase activity relative to wild-type B-Raf protein, or a B-Raf protein having one or more mutations selected from the group consisting of V600E, V600K, V600D, R461I, I462S, G463E, G463V, G465A, G465E, G465V, G466V, G468A, G468E, N580S, E585K, D593V, F594L, G595R, L596V, T598I, V599D, V599E, V599K, V599R, A727V, and combinations thereof.

In any of the aspects or embodiments described herein, the PTM is a small molecule that selectively or preferentially binds to a B-Raf protein having at least one mutation that is a V600 mutation (e.g., V600E, V600K, or V600D) and/or G466V mutation compared to the PTM binding to a wildtype B-Raf. In any of the aspects or embodiments described herein, the PTM is a small molecule capable of selectively binding the B-Raf protein having at least one mutation that is a V600 mutation (e.g., V600E, V600K, or V600D) and/or G466V, wherein selectivity towards the B-Raf protein having at least one mutation that is a V600 mutation and/or a G466V mutation is at least 1-60 times (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 times) compared to the wild-type B-Raf. In any of the aspects or embodiments described herein, the PTM is a small molecule that binds the B-Raf protein having at least one mutation that is a V600 mutation (e.g., V600E, V600K, or V600D) and/or a G466V mutation, wherein selectivity towards the B-Raf protein having at least one mutation that is a V600 mutation and/or G466V mutation is at least 1-1000 times (e.g., 1, 5, 10, 20, 50, 100, 200, 300, 400, 500, 600, 700, 800, 900 times) compared to the wild-type B-Raf.

The compositions described herein exemplify the use of these PTMs.

In any aspect or embodiment described herein, the PTM is represented by the chemical structure:

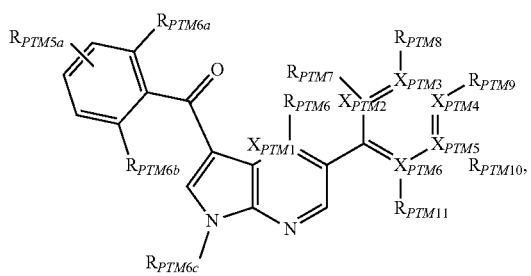

wherein:

$X_{PTM1}$, $X_{PTM2}$, $X_{PTM3}$, $X_{PTM4}$, $X_{PTM5}$, and $X_{PTM6}$ are each independently selected from CH or N;

$R_{PTM5a}$ is selected from the group consisting of: bond, optionally substituted amine, optionally substituted amide (e.g., optionally substituted with an alkyl, methyl, ethyl, propyl, or butyl group), H,

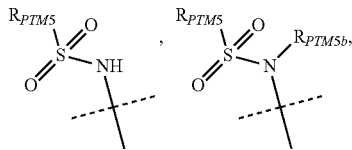

—NHC(O)$R^{PTM5}$;

$R_{PTM5}$ is selected from the group consisting of optionally substituted alkyl, optionally substituted cycloalkyl, —NR$_{PTM5c}$R$_{PMT5d}$,

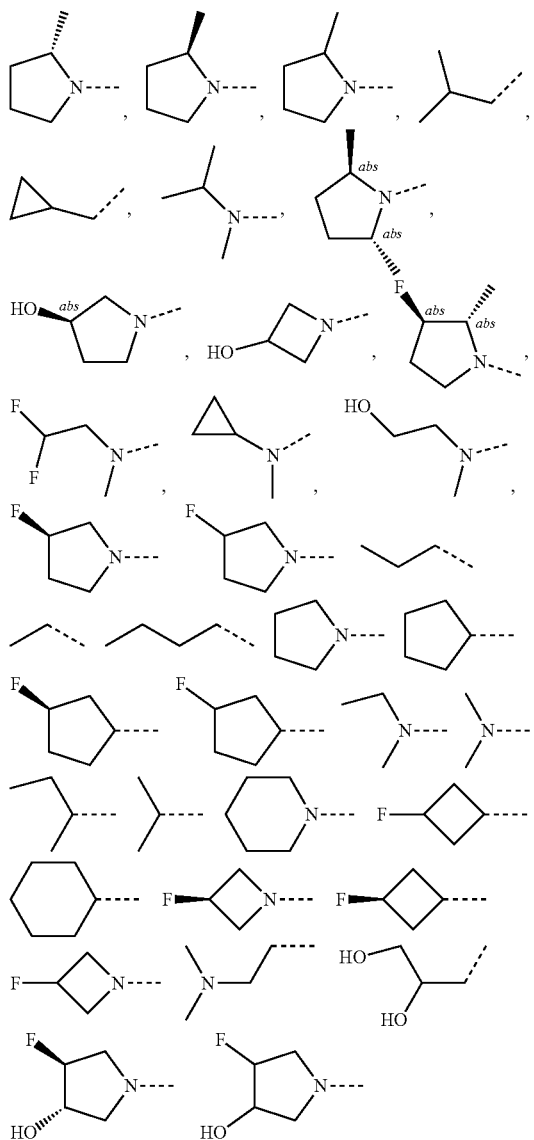

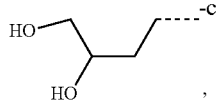

$R_{PTM5b}$ is hydrogen or a linear or branched C1-C4 alkyl (e.g., methyl or ethyl);

$R_{PTM6a}$ and $R_{PTM6b}$ are each independently selected from hydrogen, halogen, or optionally substituted linear or branched $C_1$-$C_6$ alkyl;

$R_{PTM6}$ is absent, hydrogen, halogen, aryl, methyl, ethyl, OCH$_3$, NHCH$_3$ or M1-CH$_2$—CH$_2$-M2, wherein M1 is CH$_2$, O and NH, and M2 is hydrogen, alkyl, cyclic alkyl, aryl or heterocycle;

$R_{PTM6c}$ is hydrogen or a linear or branched C1-C4 alkyl (e.g., methyl or ethyl);

$R_{PTM7}$ is absent, hydrogen, halogen, aryl, methyl, ethyl, OCH$_3$, NHCH$_3$ or M1-CH$_2$—CH$_2$-M2, wherein M1 is CH$_2$, O or NH, and M2 is hydrogen, alkyl, cyclic alkyl, aryl or heterocycle;

$R_{PTM8}$, $R_{PTM9}$ or $R_{PTM10}$ are independently selected from the group consisting of absent, hydrogen, halogen, aryl, heteroaryl, alkyl, cycloalkyl, heterocycle, methyl, ethyl, OCH$_3$, NHCH$_3$ or M1-CH$_2$—CH$_2$-M2, wherein M1 is CH$_2$, O and NH, and M2 is hydrogen, alkyl, cyclic alkyl, aryl or heterocycle;

$R_{PTM11}$ is absent, hydrogen, halogen, methyl, ethyl, OCH$_3$, NH CH$_3$ or M1-CH$_2$—CH$_2$-M2, wherein M1 is CH$_2$, O or NH, and M2 is hydrogen, alkyl, cyclic alkyl, aryl or heterocycle; and at least one of $R_{PTM8}$, $R_{PTM9}$ or $R_{PTM10}$ is modified to be covalently joined to a chemical linker group (L) or a CLM, or two of $R_{PTM8}$, $R_{PTM9}$, and $R_{PTM10}$ are modified to form a polycyclic (e.g., bicyclic) fused ring that is covalently joined to a chemical linker group (L) or a CLM.

In any aspect or embodiment described herein, the PTM is represented by the chemical structure:

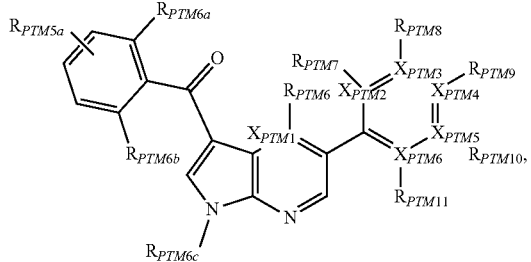

wherein:

$X_{PTM1}$, $X_{PTM2}$, $X_{PTM3}$, $X_{PTM4}$, $X_{PTM5}$, and $X_{PTM6}$ are each independently selected from CH or N;

$R_{PTM5a}$ is selected from the group consisting of: bond, optionally substituted amine, optionally substituted amide (e.g., optionally substituted with an alkyl, methyl, ethyl, propyl, or butyl group), H,

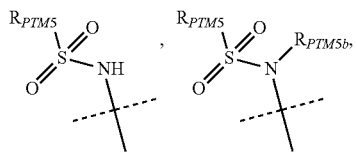

—NHC(O)$R_{PTM5}$;

$R_{PTM5}$ is selected from the group consisting of optionally substituted alkyl, optionally substituted cycloalkyl, $-NR_{PTM5c}R_{PMT5d}$,
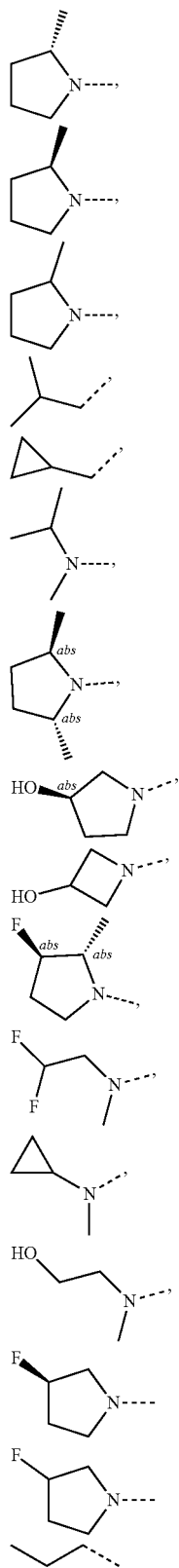
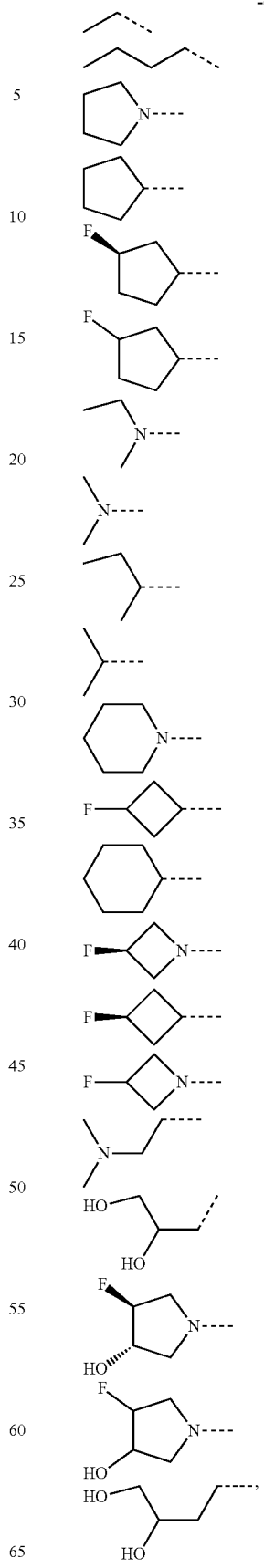

$R_{PTM5b}$ is hydrogen or a linear or branched C1-C4 alkyl (e.g., methyl or ethyl);

$R_{PTM5c}$ and $R_{PMT5d}$ are each independently selected from H, an optionally substituted alkyl (e.g., optionally substituted, linear or branched, with one, two, or three halogens), or $R_{PTM5c}$, $R_{PMT5d}$ and the nitrogen they are attached form an optionally substituted 4-6 membered heterocycloalkyl (e.g., optionally substituted with one, two, or three halogens, an optionally substituted 5-membered heterocycloalky, or a combination thereof);

$R_{PTM6a}$ and $R_{PTM6b}$ are each independently selected from hydrogen, halogen (e.g., F, Cl, or Br), C1-C3 alkoxy (e.g. methoxy or ethoxy), or optionally substituted linear or branched $C_1$-$C_6$ alkyl;

$R_{PTM6}$ is absent (a bond), hydrogen, halogen, aryl, methyl, ethyl, $OCH_3$, $NHCH_3$ or M1-$CH_2$—$CH_2$-M2, wherein M1 is $CH_2$, O and NH, and M2 is hydrogen, alkyl, cyclic alkyl, aryl or heterocycle;

$R_{PTM6}$ is hydrogen or a linear or branched C1-C4 alkyl (e.g., methyl or ethyl);

$R_{PTM7}$ is absent, hydrogen, halogen, aryl, methyl, ethyl, $OCH_3$, $NHCH_3$ or M1-$CH_2$—$CH_2$-M2, wherein M1 is $CH_2$, O or NH, and M2 is hydrogen, alkyl, cyclic alkyl, aryl or heterocycle;

$R_{PTM8}$, $R_{PTM9}$ or $R_{PTM10}$ are independently selected from the group consisting of absent, hydrogen, halogen, aryl, heteroaryl, alkyl, cycloalkyl, heterocycle, methyl, ethyl, CN, $OCH_3$, —$NR_{PTM12}R_{PMT13}$, $NHCH_3$ or M1-$CH_2$—$CH_2$-M2, wherein M1 is $CH_2$, O and NH, and M2 is hydrogen, alkyl, cyclic alkyl, aryl or heterocycle;

$R_{PTM11}$ is absent, hydrogen, halogen, methyl, ethyl, $OCH_3$, NH $CH_3$ or M1-$CH_2$—$CH_2$-M2, wherein M1 is $CH_2$, O or NH, and M2 is hydrogen, alkyl, cyclic alkyl, aryl or heterocycle;

$R_{PTM12}$ and $R_{PTM13}$ are each independently absent (a bond), hydrogen, or C1-C3 alkyl (e.g., methyl or ethyl); or $R_{PTM12}$, $R_{PTM13}$ and the nitrogen they are attached form 5-7 membered (e.g., 6-membered) heterocycloalkyl optionally substituted with one or two groups selected from halogen (e.g., F, Cl, or Br) and C1-C3 alkyl (e.g., methyl or ethyl); and at least one of $R_{PTM8}$, $R_{PTM9}$ or $R_{PTM10}$ is modified to be covalently joined to a chemical linker group (L) or a CLM, or two of $R_{PTM8}$, $R_{PTM9}$, and $R_{PTM10}$ are modified to form a polycyclic (e.g., bicyclic) fused ring that is covalently joined to a chemical linker group (L) or a CLM.

In any aspect or embodiment described herein, the PTM is represented by the chemical structure:

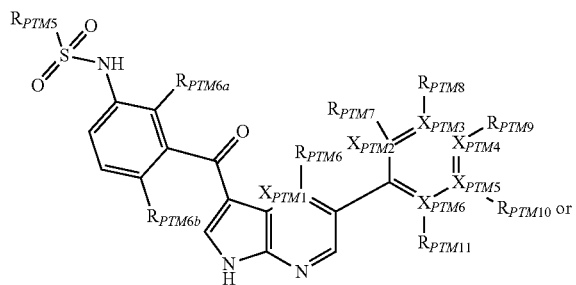

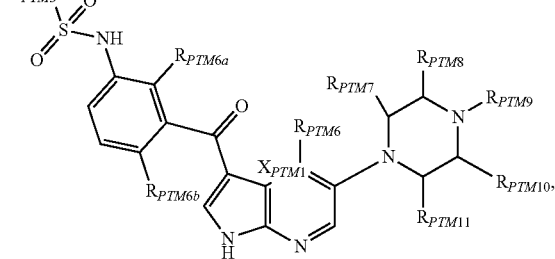

wherein $R_{PTM5}$, $R_{PTM6a}$, $R_{PTM6b}$, $R_{PTM6}$, $R_{PTM7}$, $R_{PTM8}$, $R_{PTM9}$, $R_{PTM10}$, $R_{PTM11}$ are as described herein.

In some embodiments, when $R_{PTM9}$ is the covalently joined position, $R_{PTM7}$ and $R_{PTM8}$ can be connected together via a covalent bond in a way to form a bicyclic group with the ring to which $R_{PTM7}$ and $R_{PTM8}$ are attached.

In other embodiments, when $R_{PTM8}$ is the covalently joined position, $R_{PTM9}$ and $R_{PTM10}$ can be connected together via a covalent bond in a way to form a bicyclic group with the ring to which $R_{PTM9}$ and $R_{PTM10}$ are attached.

In further embodiments, when $R_{PTM10}$ is the covalently joined position, $R_{PTM8}$ and $R_{PTM9}$ can be connected together via a covalent bond in a way to form a bicyclic group with the ring to which $R_{PTM8}$ and $R_{PTM9}$ are attached.

In any aspect or embodiment described herein, the PTM is represented by the chemical structure:

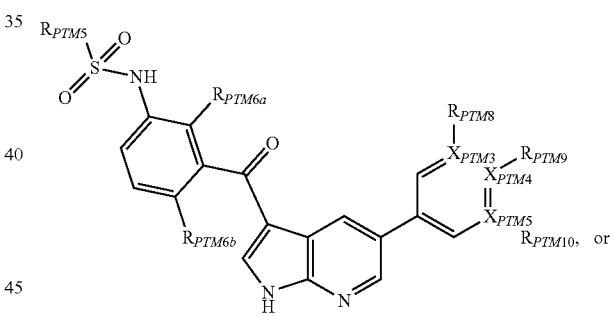

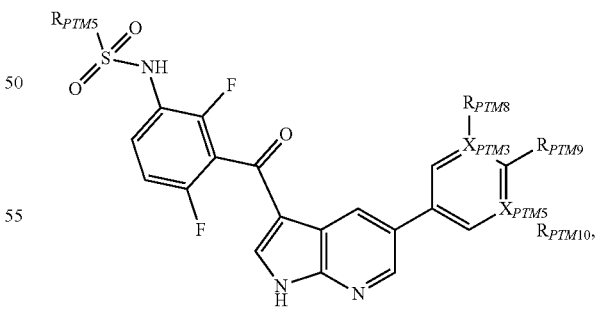

wherein $X_{PTM3}$, $X_{PTM4}$, $X_{PTM5}$, are independently selected from CH or N;

$R_{PTM5}$ is selected from the group consisting of:
optionally substituted alkyl, optionally substituted cycloalkyl,

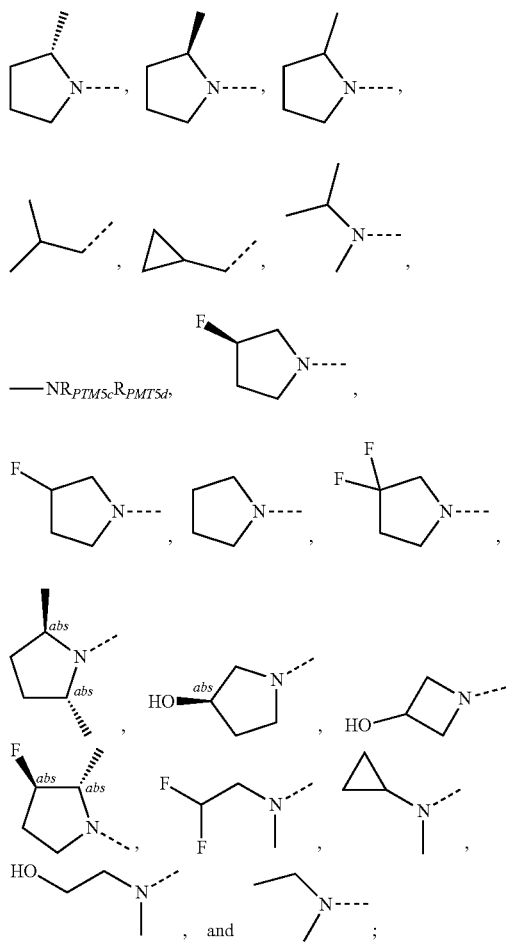

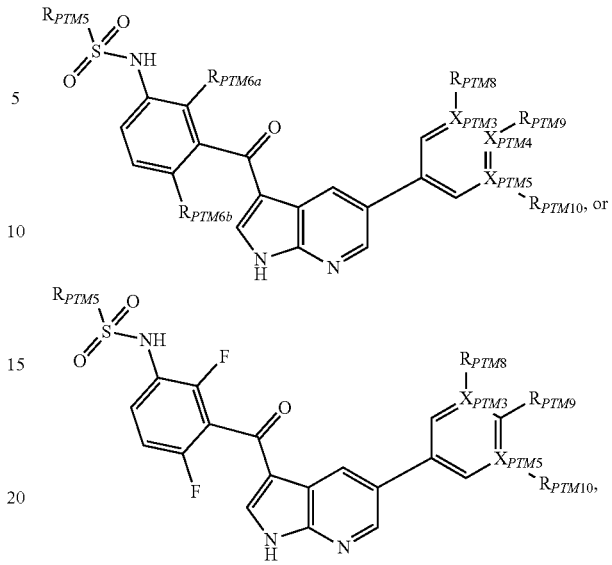

wherein
$X_{PTM3}$, $X_{PTM4}$, $X_{PTM5}$, are independently selected from CH or N;
$R_{PTM5}$ is selected from the group consisting of:
optionally substituted alkyl, optionally substituted cycloalkyl,

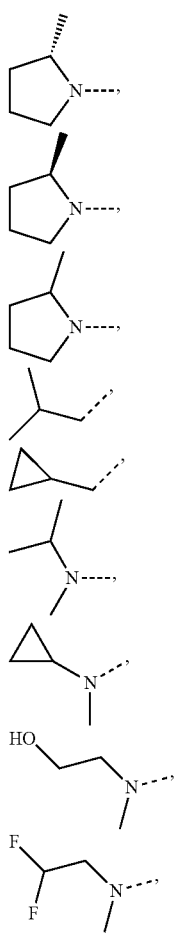

$R_{PTM5c}$ and $R_{PMT5d}$ are each independently selected from an optionally substituted alkyl (e.g., optionally substituted with one, two, or three halogens), or $R_{PTM5c}$, $R_{PMT5d}$, and the nitrogen they are attached form an optionally substituted 4-6 membered heterocycloalkyl (e.g., optionally substituted with one, two, or three halogens, an optionally substituted 5-membered heterocycloalky, or a combination thereof);

$R_{PTM6a}$ and $R_{PTM6b}$ are each independently a halogen, C1-C3 alkoxy, or C1-C3 alkyl (e.g., methyl or ethyl);

$R_{PTM8}$, is absent (a bond), hydrogen, halogen (e.g., F, Cl, or Br), or C1-C3 alkyl (e.g., methyl or ethyl);

$R_{PTM9}$ and $R_{PTM10}$ are each independently absent (a bond), hydrogen, halogen (e.g., F, Cl, or Br), CN, NHCH$_3$, or C1-C3 alkyl (e.g., methyl or ethyl); or); or $R_{PTM9}$, $R_{PTM10}$ and the ring they are attached form 5-7 membered (e.g., 6-membered) cycloalkyl or heterocycloalkyl optionally substituted with one or two groups selected from halogen (e.g., F, Cl, or Br) and C1-C3 alkyl (e.g., methyl or ethyl);

one of $R_{PTM8}$, $R_{PTM9}$, $R_{PTM10}$, or the cycloalkyl or heterocycloalkyl formed from $R_{PTM9}$ and $R_{PTM10}$ is modified to be covalently joined to a chemical linker group (L) or a CLM.

In any aspect or embodiment described herein, the PTM is represented by the chemical structure:

-continued

—NR_{PTM5c}R_{PTM5d},

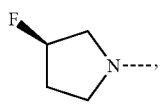

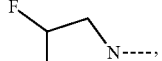

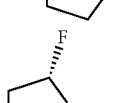



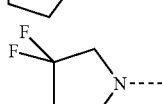

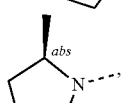

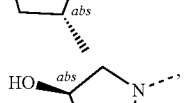

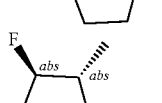

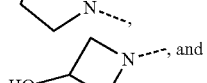

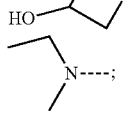

$R_{PTM5c}$ and $R_{PMT5d}$ are each independently selected from an optionally substituted alkyl (e.g., optionally substituted with one, two, or three halogens), or $R_{PTM5c}$, $R_{PMT5d}$, and the nitrogen they are attached form an optionally substituted 4-6 membered heterocycloalkyl (e.g., optionally substituted with one, two, or three halogens, an optionally substituted 5-membered heterocycloalky, or a combination thereof);

$R_{PTM6a}$ and $R_{PTM6b}$ are each independently a halogen, C1-C3 alkoxy, or C1-C3 alkyl (e.g., methyl or ethyl);

$R_{PTM8}$, is absent (a bond), hydrogen, halogen (e.g., F, Cl, or Br), or C1-C3 alkyl (e.g., methyl or ethyl);

$R_{PTM9}$ and $R_{PTM10}$ are each independently absent (a bond), hydrogen, halogen (e.g., F, Cl, or Br), CN, NHCH$_3$, or C1-C3 alkyl (e.g., methyl or ethyl); or); or $R_{PTM9}$, $R_{PTM10}$ and the ring they are attached form 5-7 membered (e.g., 6-membered) cycloalkyl or heterocycloalkyl optionally substituted with one or two groups selected from halogen (e.g., F, Cl, or Br) and C1-C3 alkyl (e.g., methyl or ethyl);

one of $R_{PTM8}$, $R_{PTM9}$, $R_{PTM10}$, or the cycloalkyl or heterocycloalkyl formed from $R_{PTM9}$ and $R_{PTM10}$ is modified to be covalently joined to a chemical linker group (L) or a CLM.

In any aspect or embodiment described herein, the PTM is represented by the chemical structure:

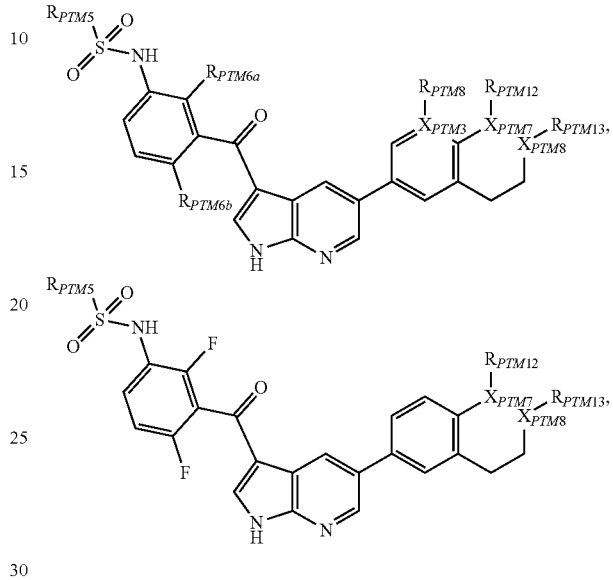

wherein $X_{PTM3}$, $X_{PTM7}$, and $X_{PTM8}$ are independently selected from CH or N;

$R_{PTM5}$ is selected from the group consisting of:

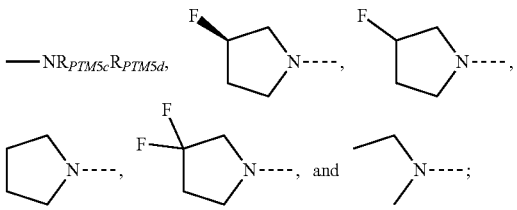

$R_{PTM5c}$ and $R_{PMT5d}$ are each independently selected from an optionally substituted alkyl (e.g., optionally substituted with one, two, or three halogens), or $R_{PTM5c}$, $R_{PMT5d}$, and the nitrogen they are attached form an optionally substituted 4-6 membered heterocycloalkyl (e.g., optionally substituted with one, two, or three halogens, an optionally substituted 5-membered heterocycloalky, or a combination thereof);

$R_{PTM6a}$ and $R_{PTM6b}$ are each independently a halogen or C1-C3 alkyl (e.g., methyl or ethyl);

$R_{PTM8}$, is absent (a bond), hydrogen, halogen (e.g., F, Cl, or Br), or C1-C3 alkyl (e.g., methyl or ethyl);

$R_{PTM12}$ is absent (a bond), hydrogen, halogen (e.g., F, Cl, or Br), or C1-C3 alkyl (e.g., methyl or ethyl);

$R_{PTM13}$ is absent (a bond), hydrogen, halogen (e.g., F, Cl, or Br), or C1-C3 alkyl (e.g., methyl or ethyl); and one of $R_{PTM8}$, $R_{PTM12}$, or $R_{PTM13}$ is modified to be covalently joined to a chemical linker group (L) or a CLM.

In any aspect or embodiment described herein, the PTM is represented by the chemical structure:

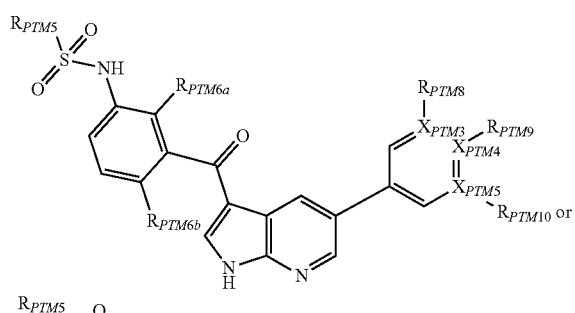
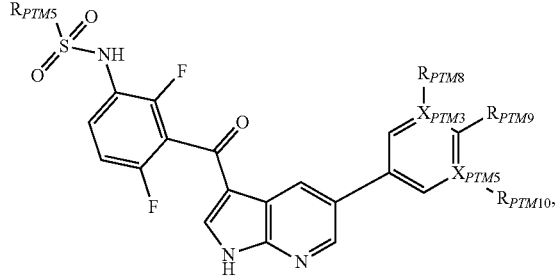
wherein $R_{PTM5}$, $R_{PTM6a}$, $R_{PTM6b}$, $R_{PTM8}$, $R_{PTM8'}$, $R_{PTM9}$, $R_{PTM10}$, $X_{PTM3}$, $X_{PTM4}$, and $X_{PTM5}$ are each individually defined as in any aspect or embodiment described herein or is modified to be covalently joined to a chemical linker group (L) or a CLM.
In any aspect or embodiment described herein, the PTM is represented by the chemical structure:
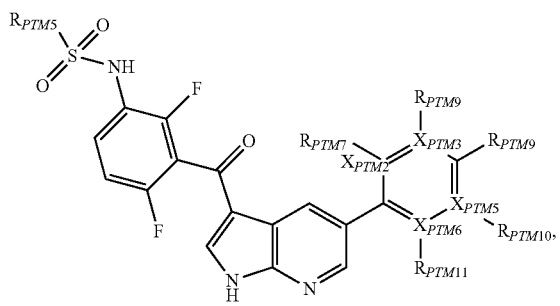
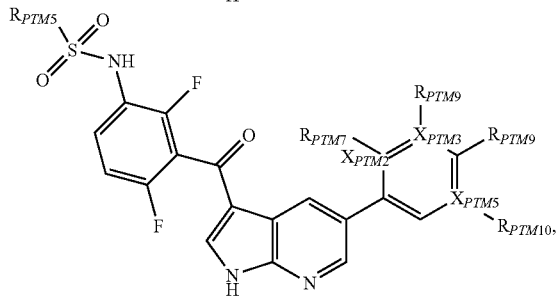
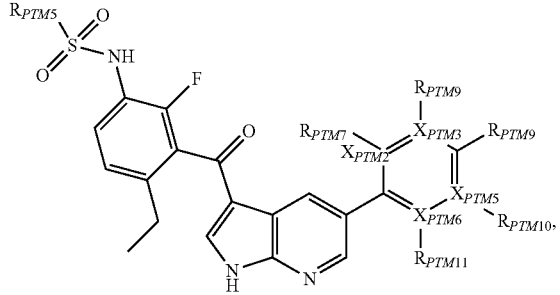
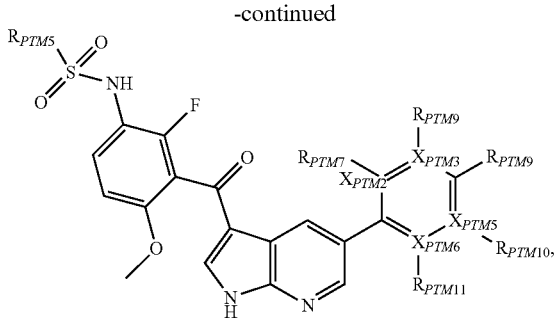
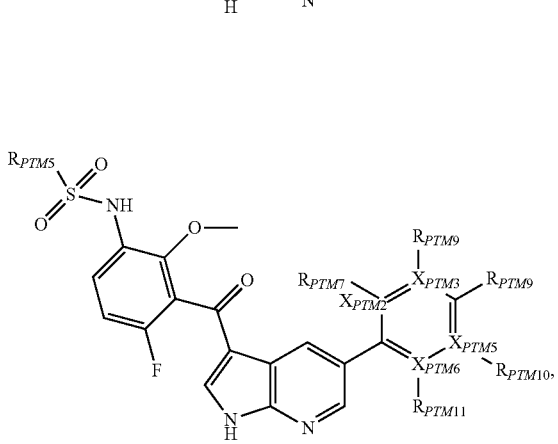
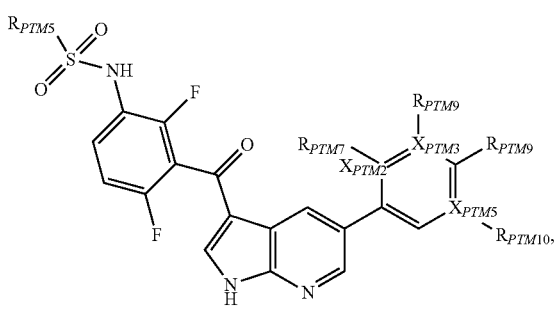
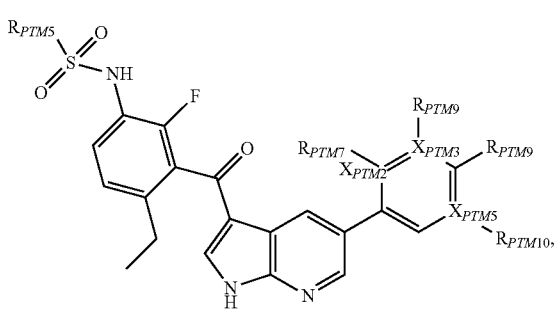
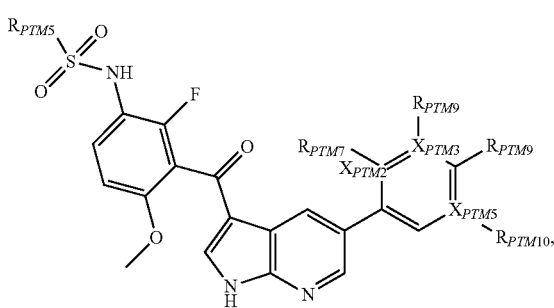

-continued

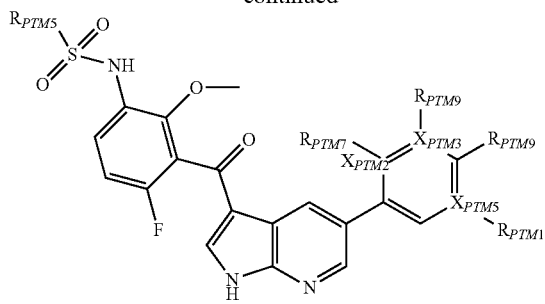

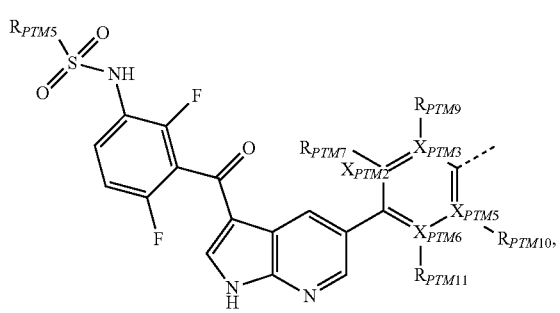

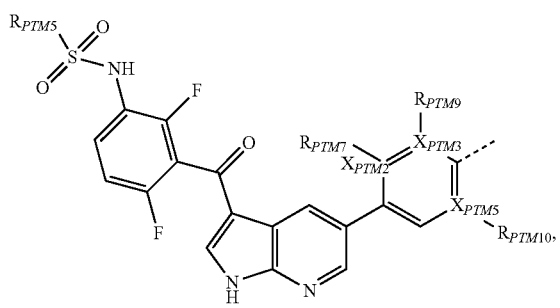

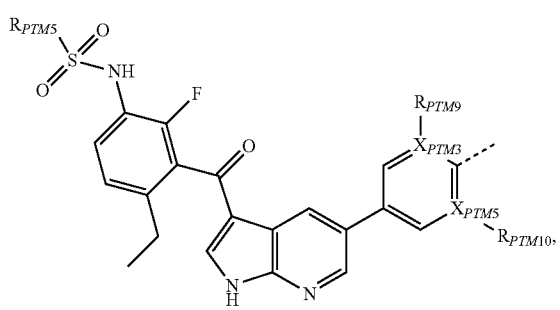

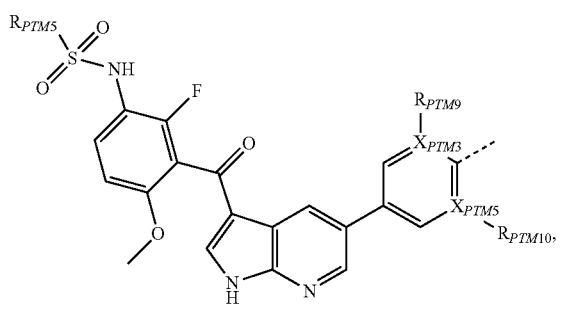

-continued

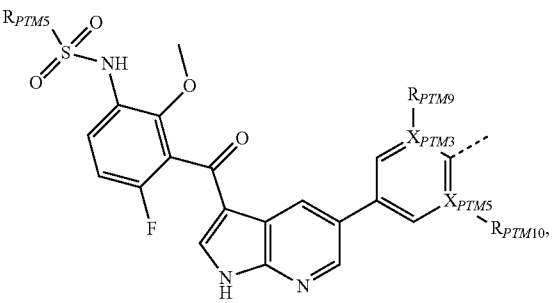

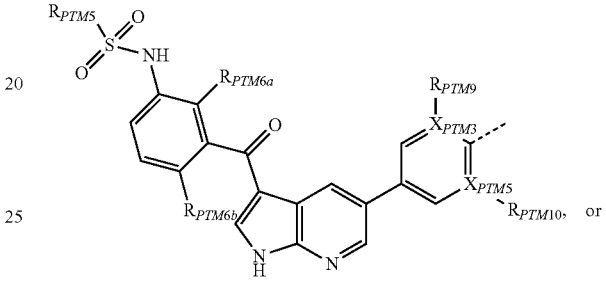

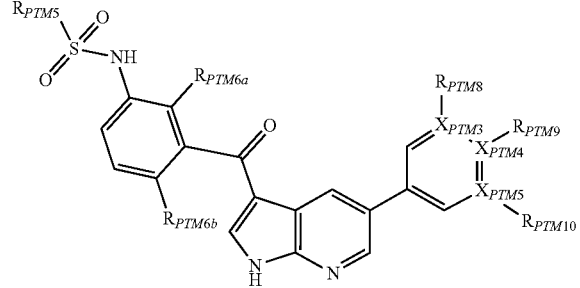

wherein $R_{PTM5}$, $R_{PTM6a}$, $R_{PTM6b}$, $R_{PTM7}$, $R_{PTM8}$, $R_{PTM9}$, $R_{PTM10}$, $R_{PTM11}$, $X_{PTM2}$, $X_{PTM3}$, $X_{PTM4}$, $X_{PTM5}$, and $X_{PTM6}$ are each individually defined as in any aspect or embodiment described herein or is modified to be covalently joined to a chemical linker group (L) or a CLM.

In any aspect or embodiment described herein, the PTM is represented by the chemical structure:

or

133
-continued

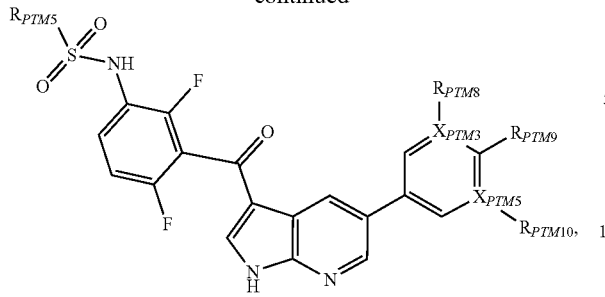

wherein:

X<sub>PTM3</sub> and X<sub>PTM5</sub> are independently selected from C or N;

R<sub>PTM5</sub> is selected from the group consisting of:

optionally substituted alkyl, optionally substituted cycloalkyl, —NR$_{PTM5c}$R$_{PMT5d}$,

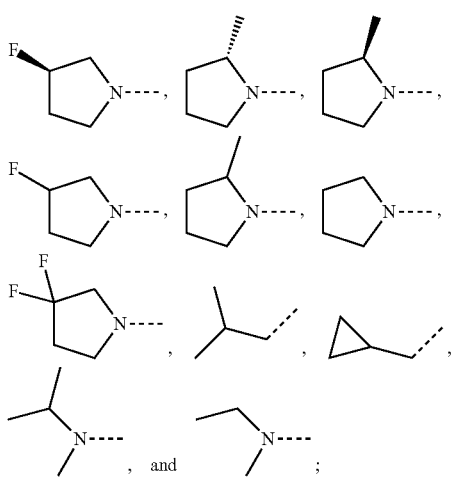

R$_{PTM6a}$ and R$_{PTM6b}$ are each independently a halogen (e.g., F, Cl, or Br);

R$_{PTM8}$, R$_{PTM9}$, or R$_{PTM10}$ are each independently selected from the group consisting of absent (a bond), hydrogen, or halogen (e.g., F, Cl, or Br); and one of R$_{PTM8}$, R$_{PTM9}$, or R$_{PTM10}$ is modified to be covalently joined to a chemical linker group (L) or a CLM.

In any aspect or embodiment described herein, the PTM is represented by the chemical structure:

134
-continued

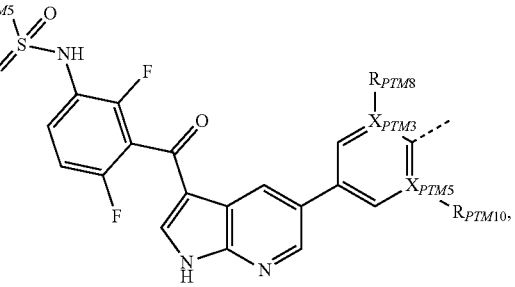

wherein R$_{PTM5}$, R$_{PTM6a}$, R$_{PTM6b}$, R$_{PTM8}$, R$_{PTM8}$, R$_{PTM9}$, R$_{PTM12}$, R$_{PTM13}$, R$_{PTM10}$, X$_{PTM3}$, X$_{PTM4}$, X$_{PTM5}$, X$_{PTM7}$, and X$_{PTM8}$ are each individually defined as in any aspect or embodiment described herein, and ⟋⟋ is the point of attachment of the PTM to a chemical linker group (L) or directly to a CLM.

In any aspect or embodiment described herein, the PTM is represented by the chemical structure:

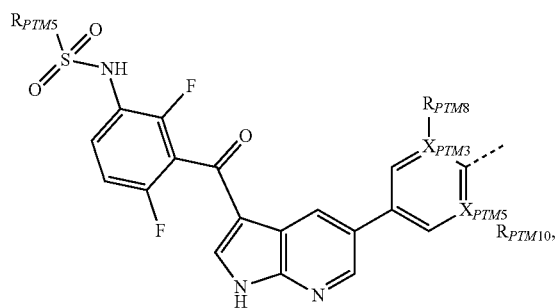

wherein:

$X_{PTM3}$ and $X_{PTM5}$ are independently selected from C or N;

$R_{PTM5}$ is selected from the group consisting of:

optionally substituted alkyl, optionally substituted cycloalkyl, $-NR_{PTM5c}R_{PMT5d}$,

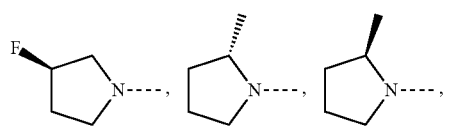

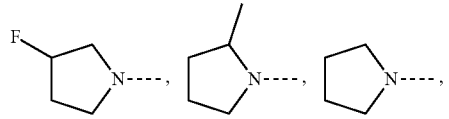

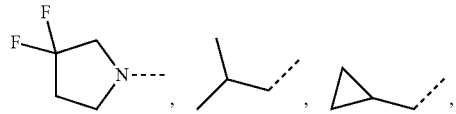

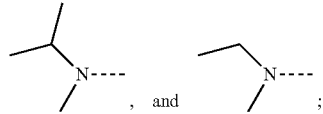

$R_{PTM8}$ or $R_{PTM10}$ are each independently selected from the group consisting of absent (a bond), hydrogen, or halogen (e.g., F, Cl, or Br); and ⸺ is the point of attachment of the PTM to a chemical linker group (L) or directly to a CLM In any aspect or embodiment described herein, the PTM is represented by the chemical structure:

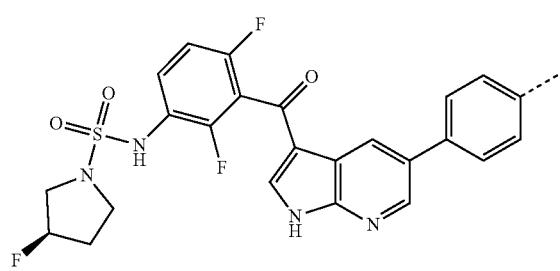

-continued

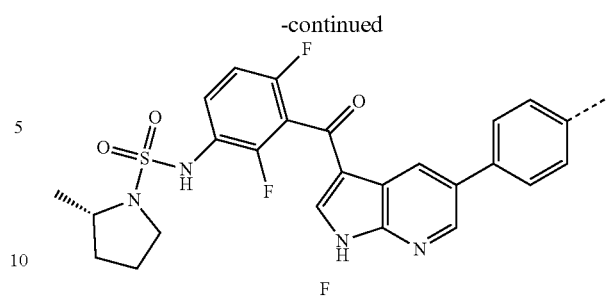

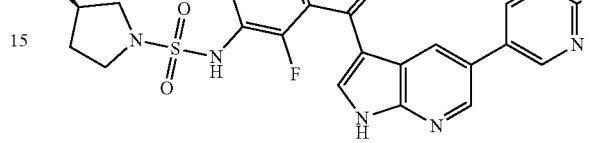

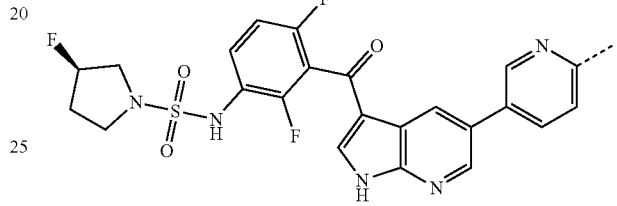

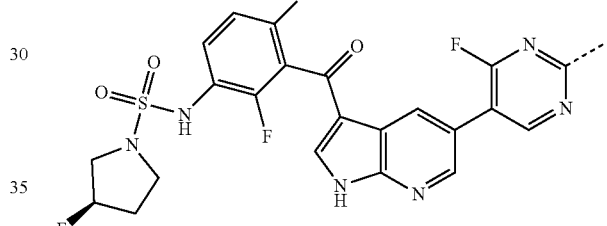

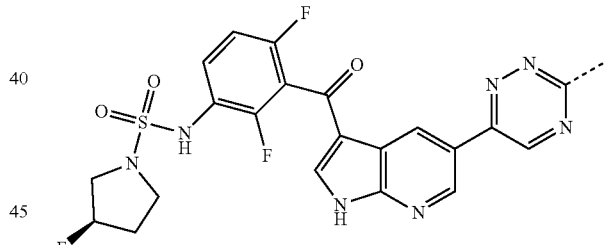

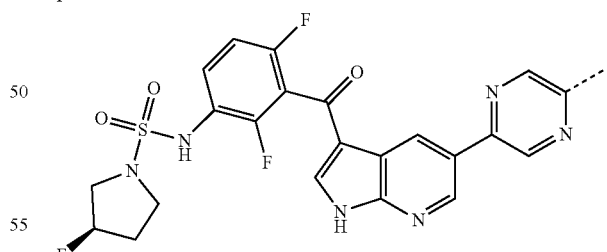

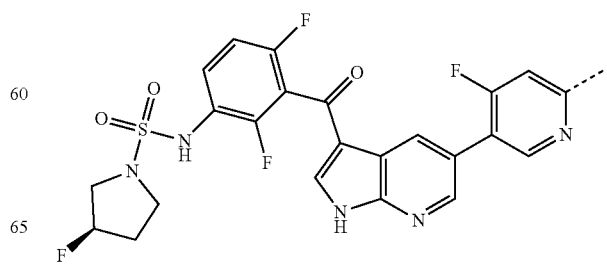

137
-continued
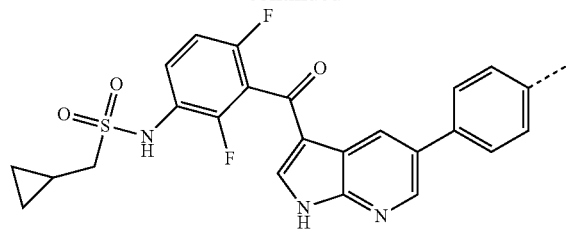
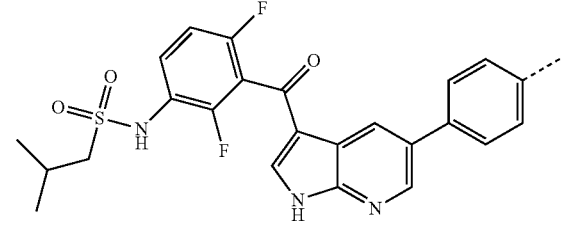
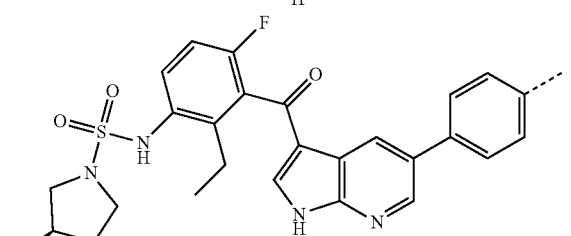
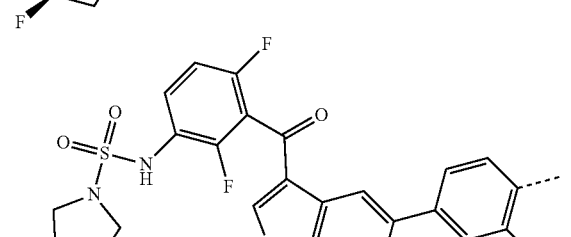
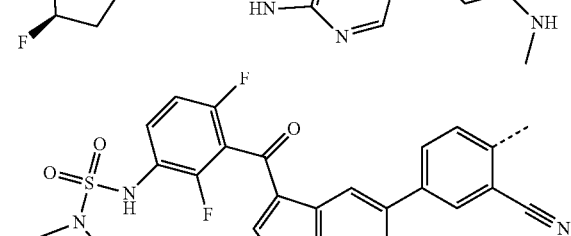
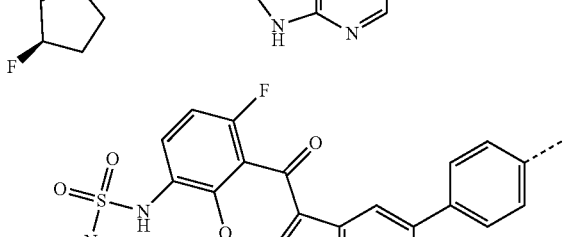
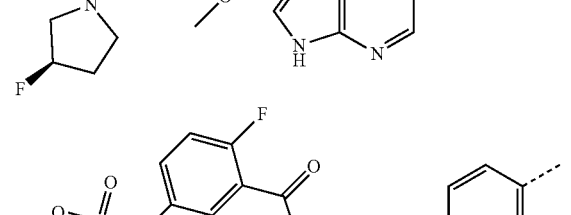
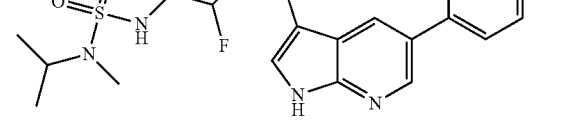
138
-continued
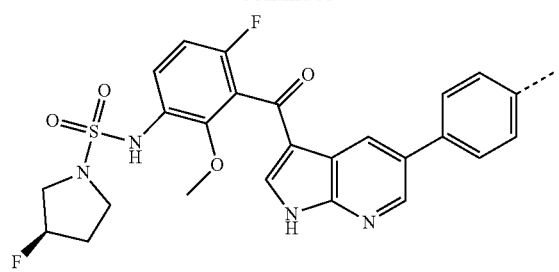
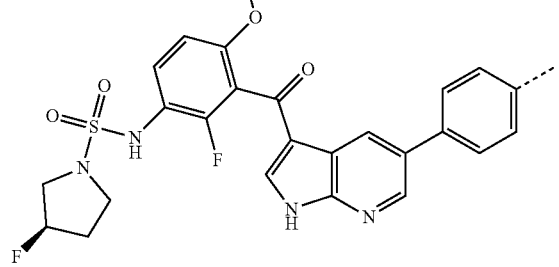
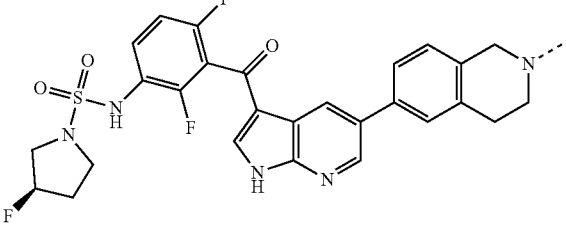
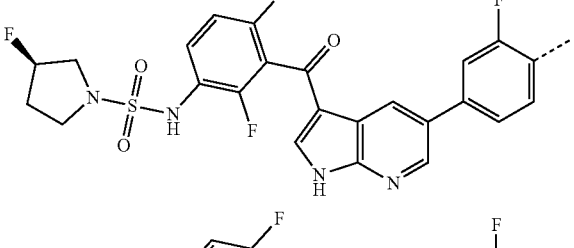
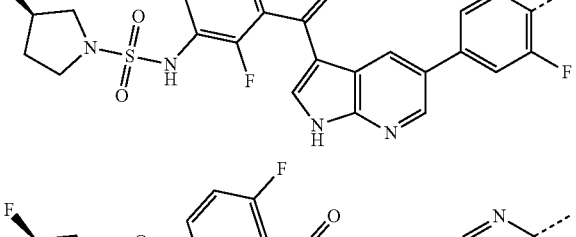
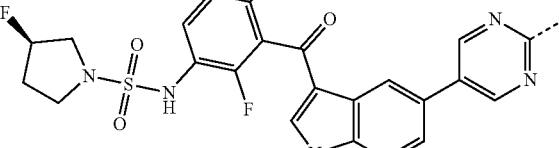
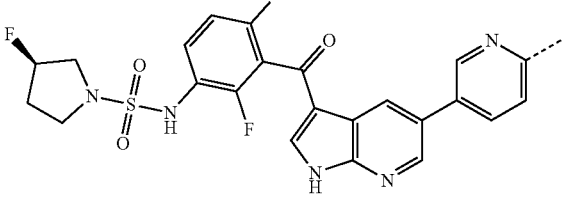

139
-continued
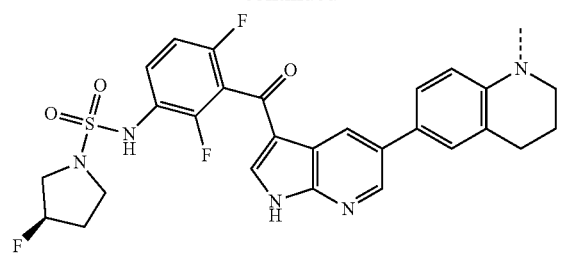
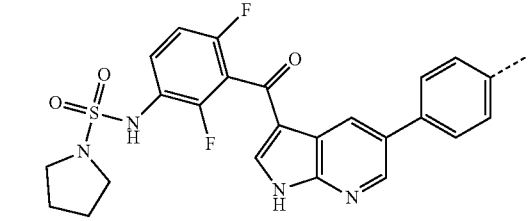
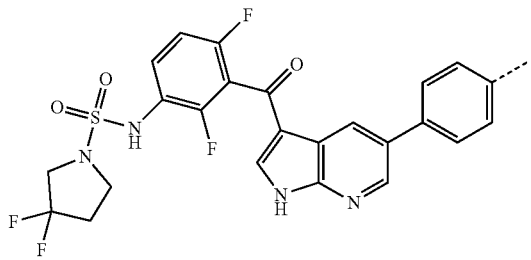
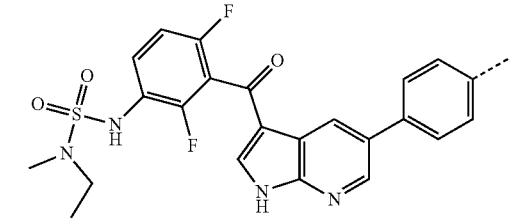
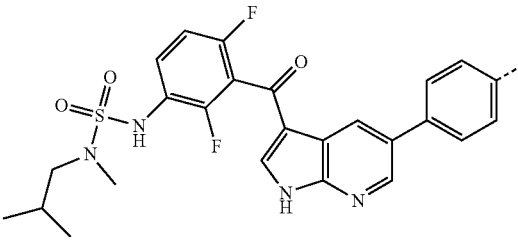
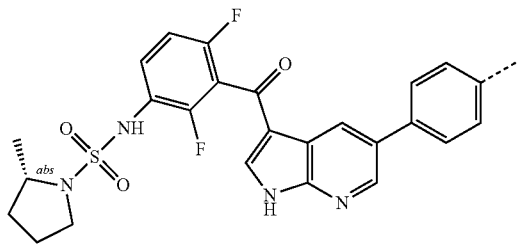
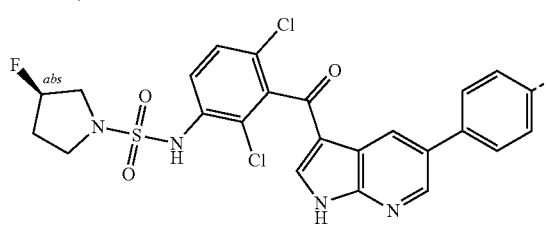
140
-continued
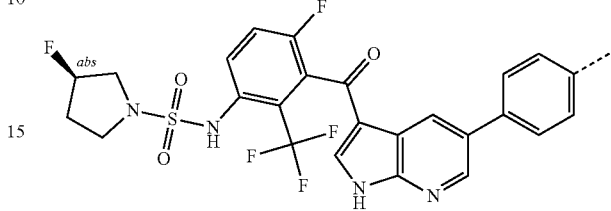
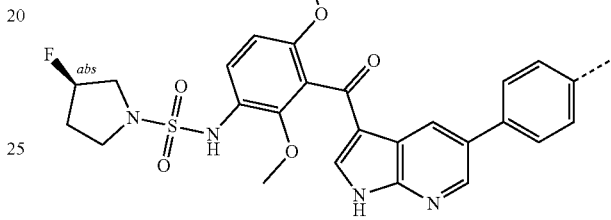
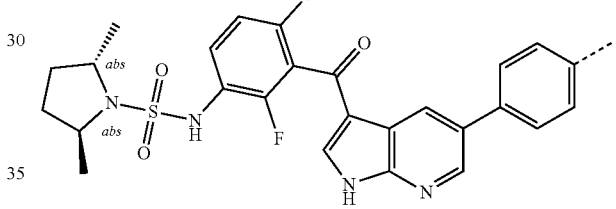
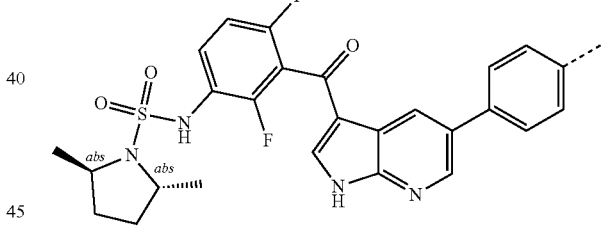
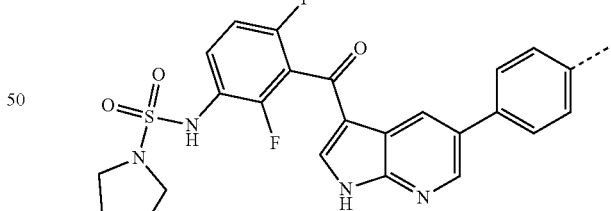
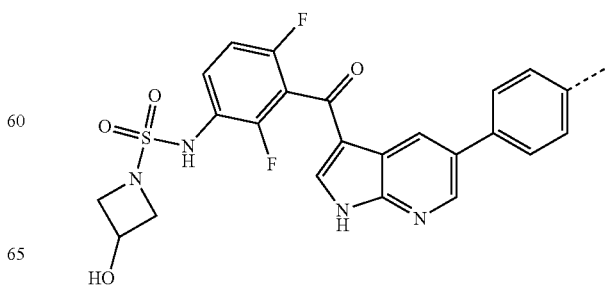

-continued
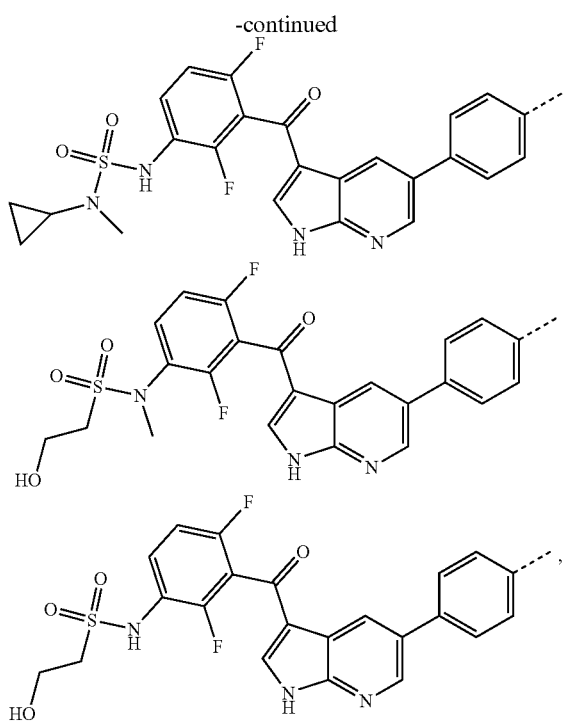
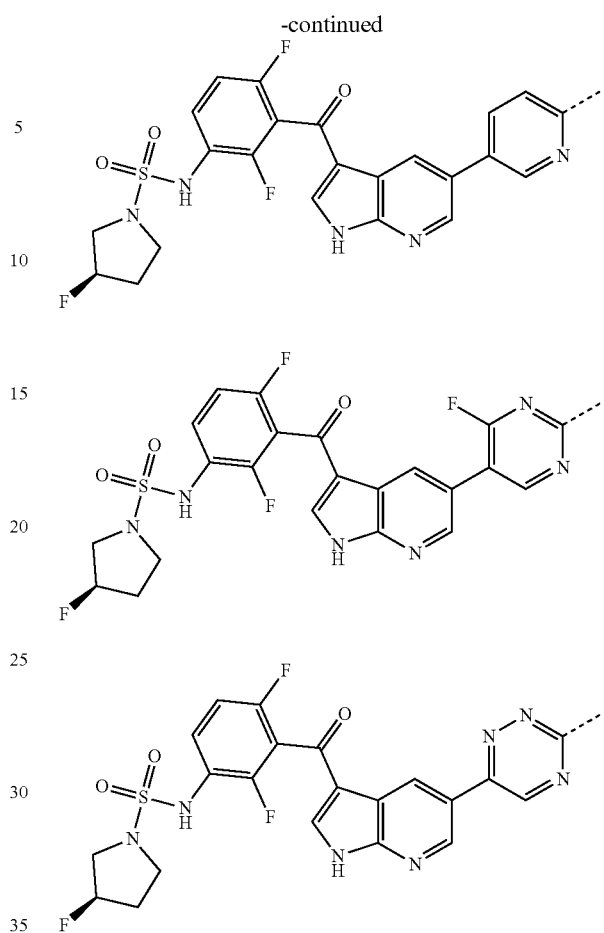
wherein ⌇ is the point of attachment of the PTM to a chemical linker group (L) or directly to a CLM.
In any aspect or embodiment described herein, the PTM is represented by the chemical structure:
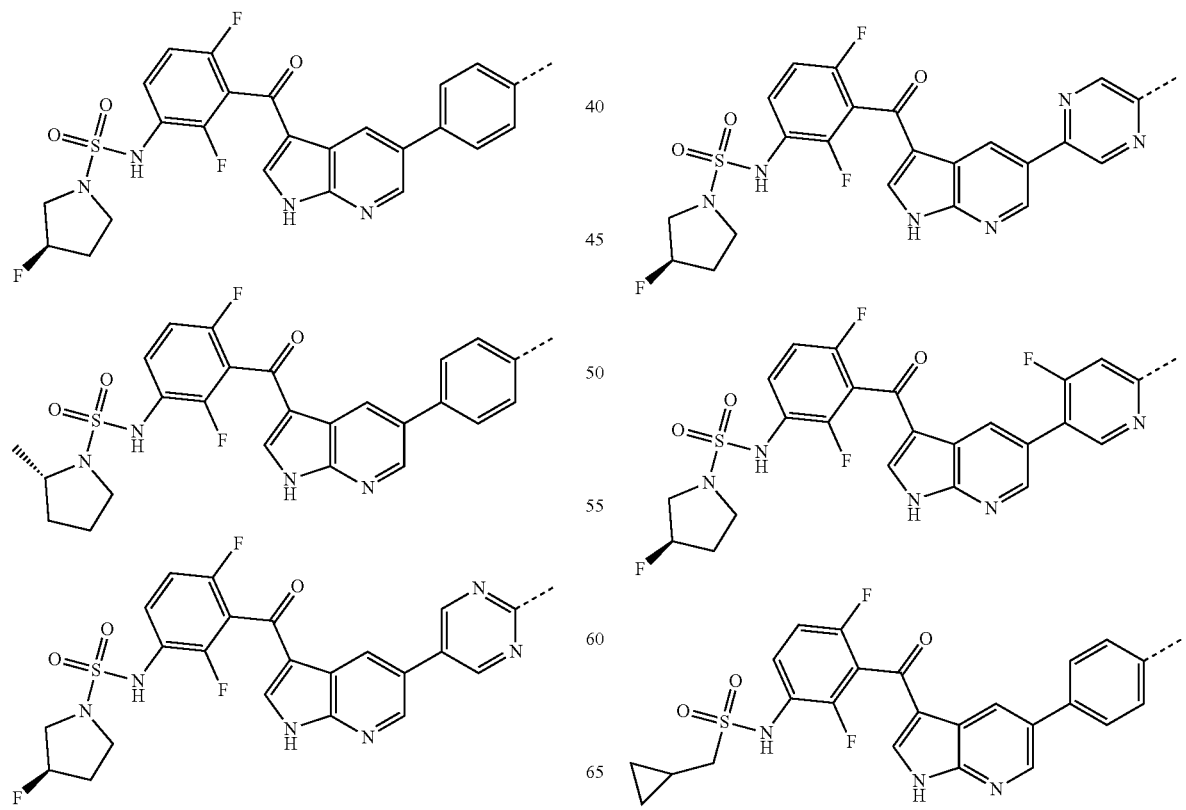

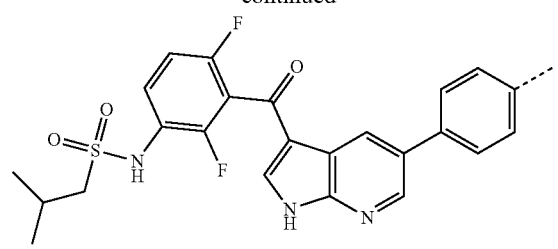
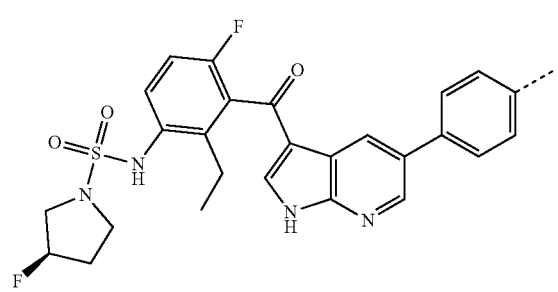
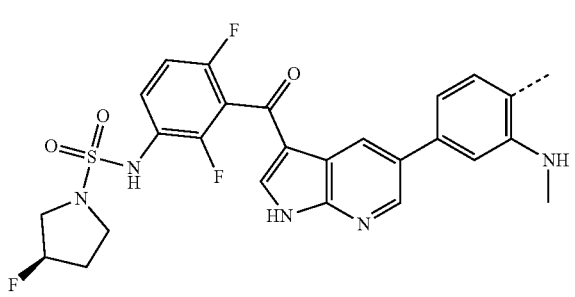
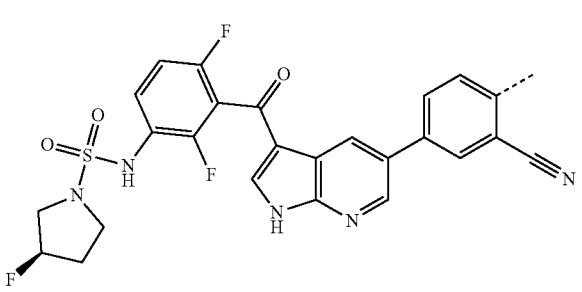
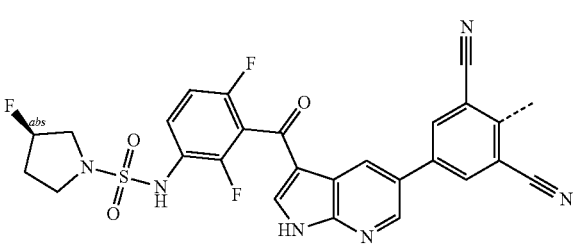
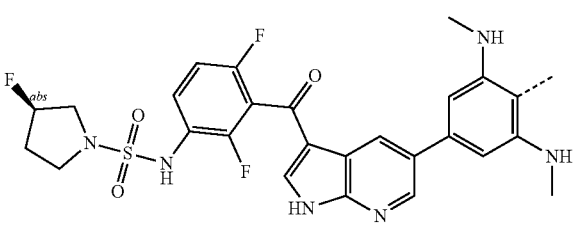
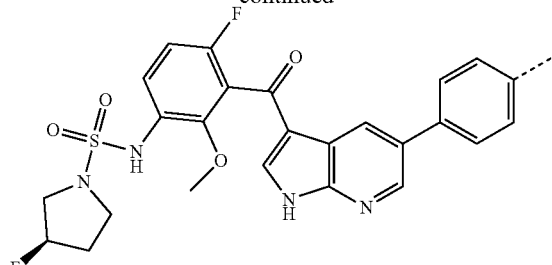
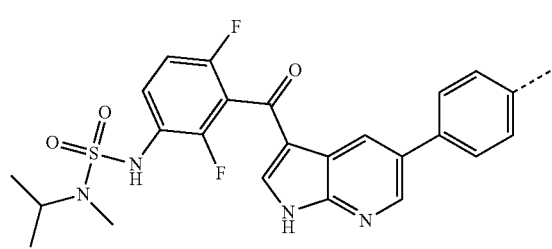
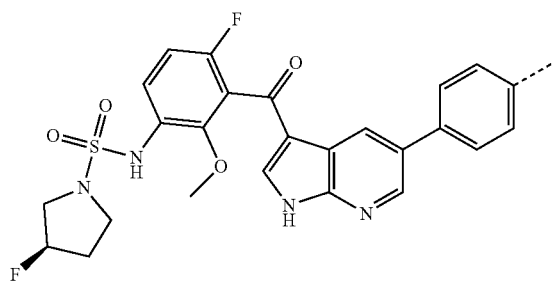
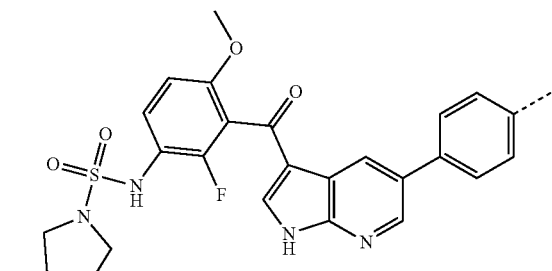
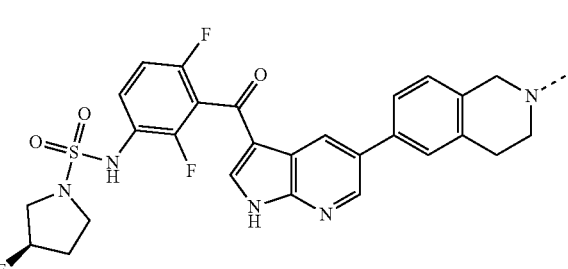
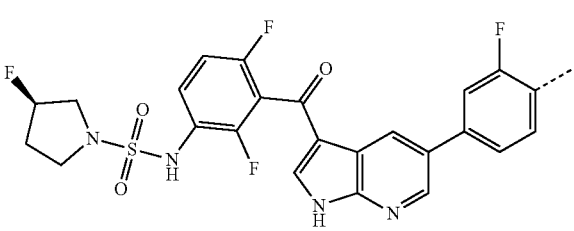

-continued

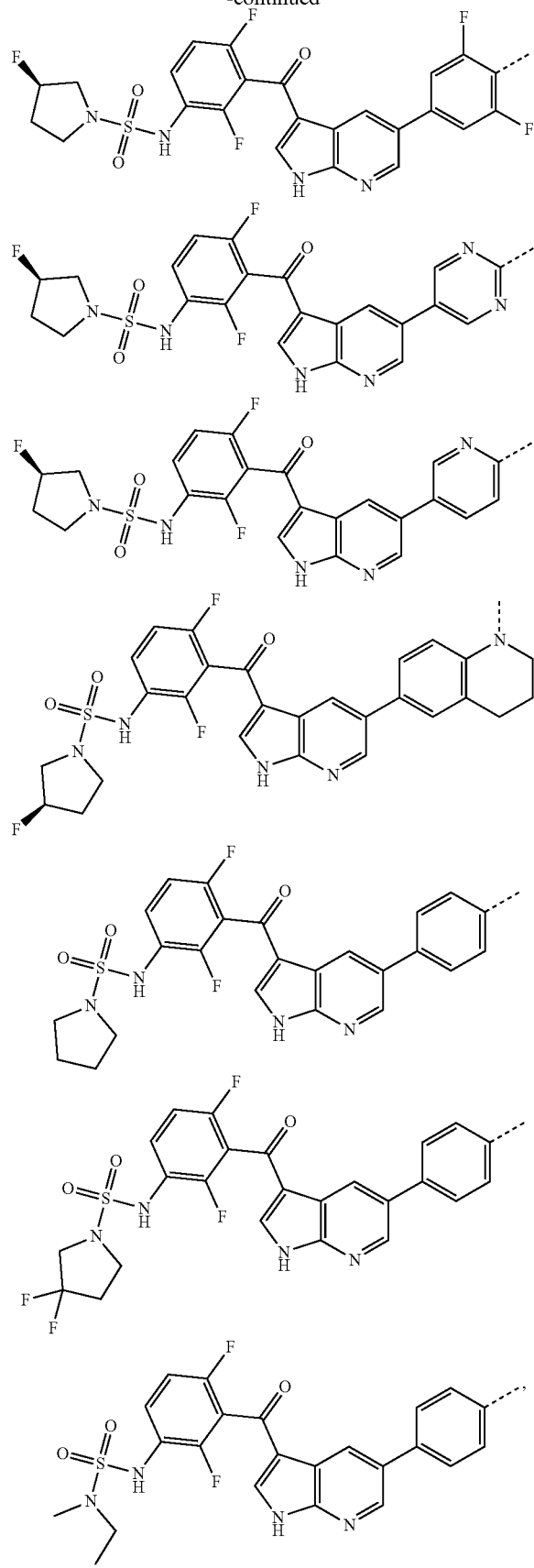

wherein [dashed line] is the point of attachment of the PTM to a chemical linker group (L) or directly to a CLM.

In any aspect or embodiment described herein, the PTM is represented by the chemical structure:

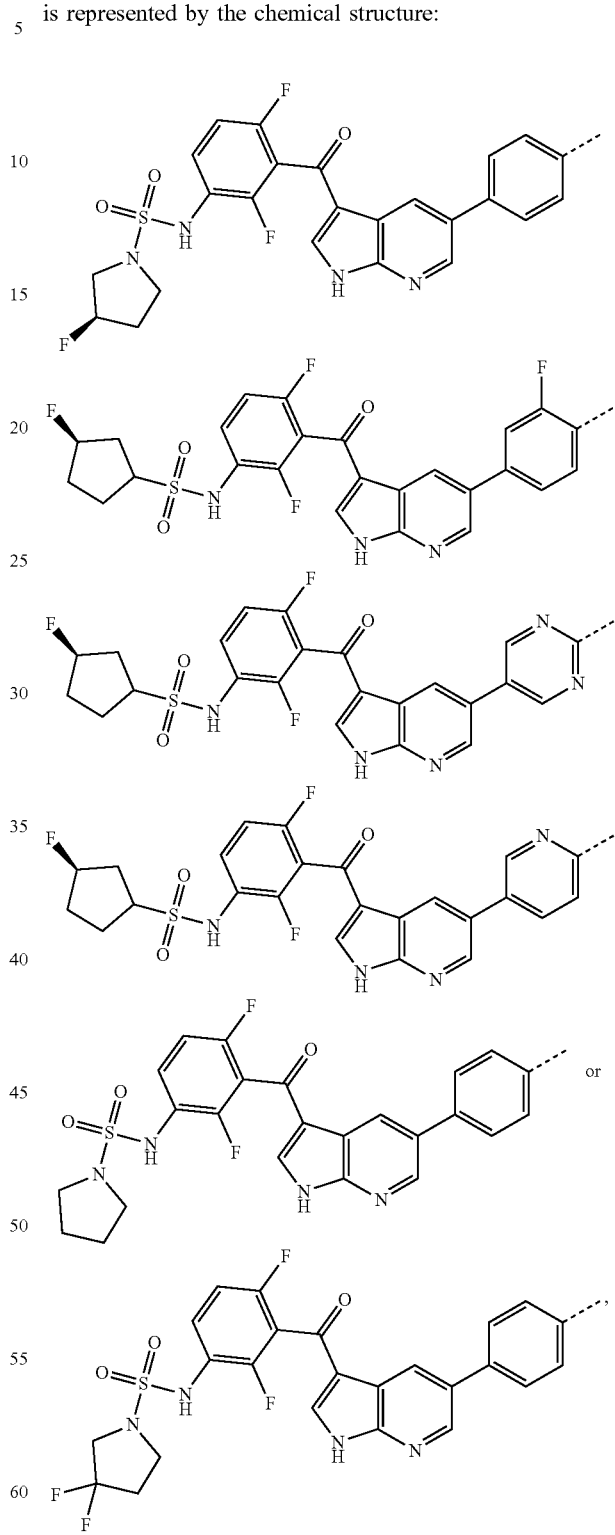

wherein [dashed line] is the point of attachment of the PTM to a chemical linker group (L) or directly to a CLM.

In any aspect or embodiment described herein, the hetero-bifunctional compounds of the present disclosure

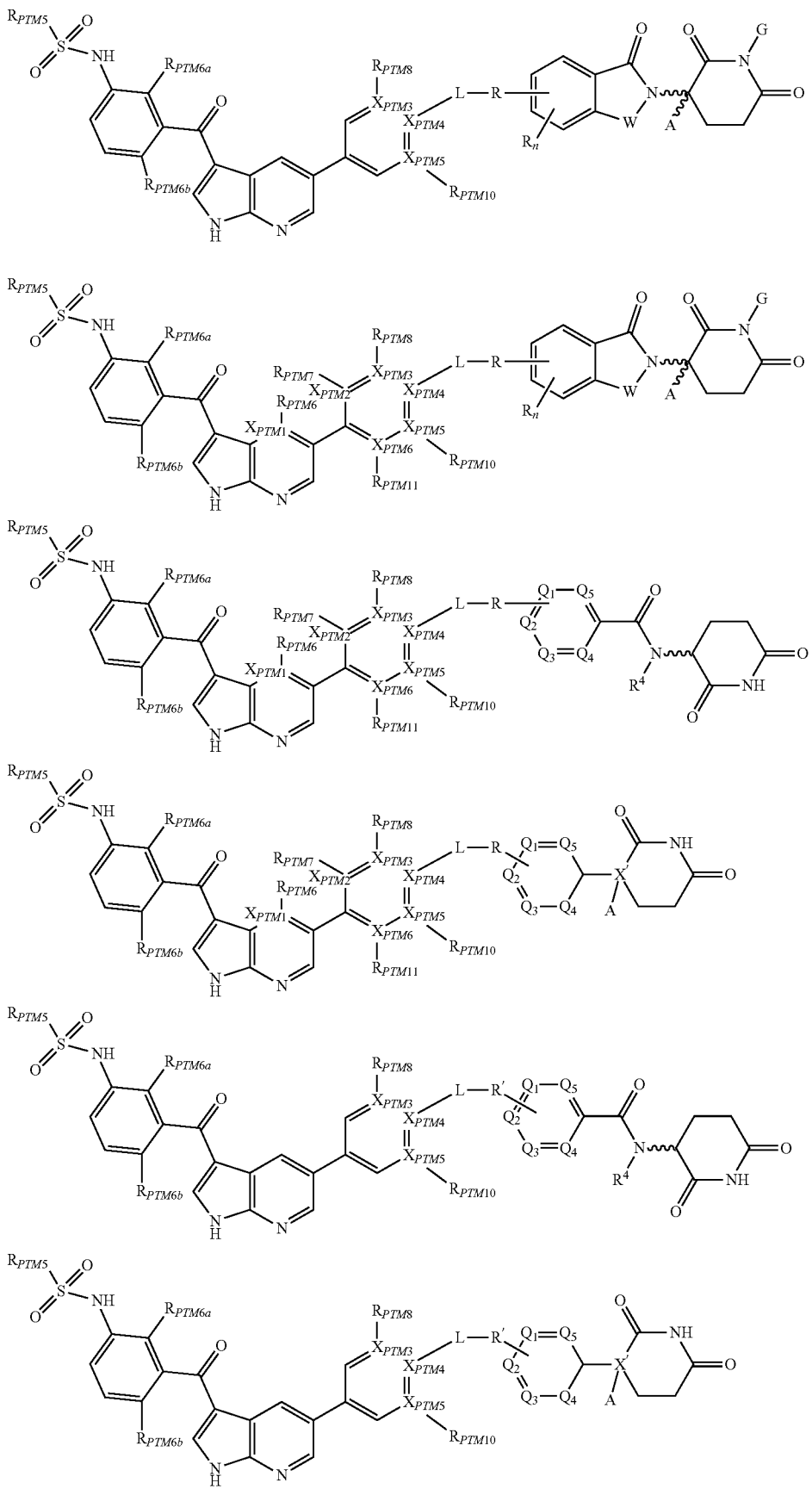

-continued
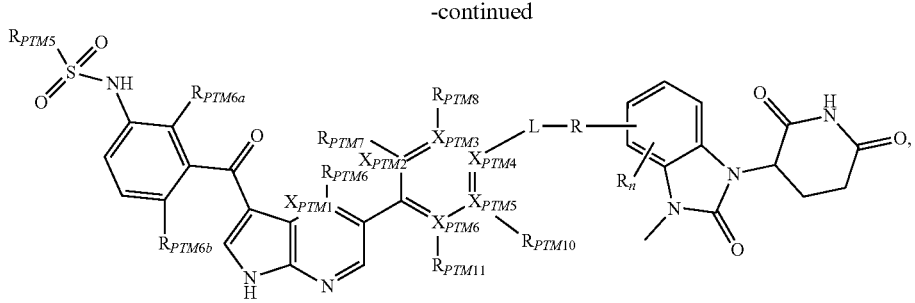
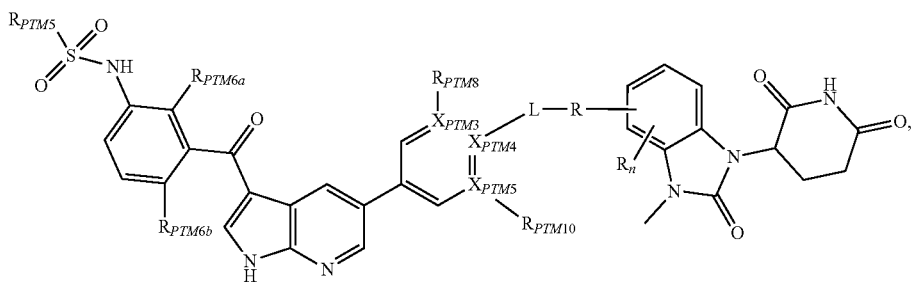
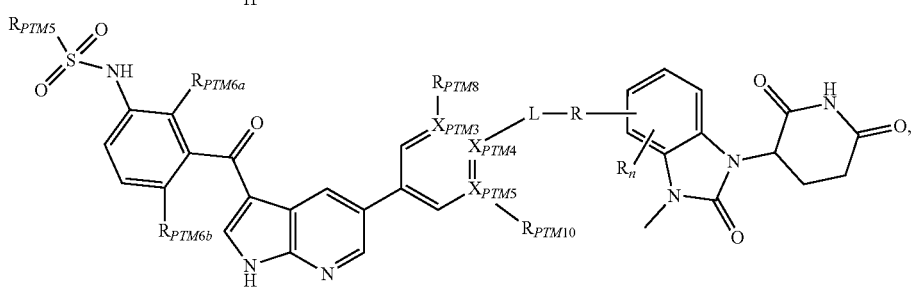
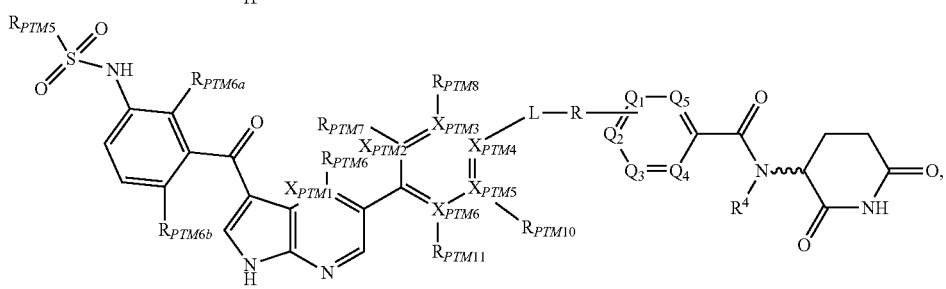
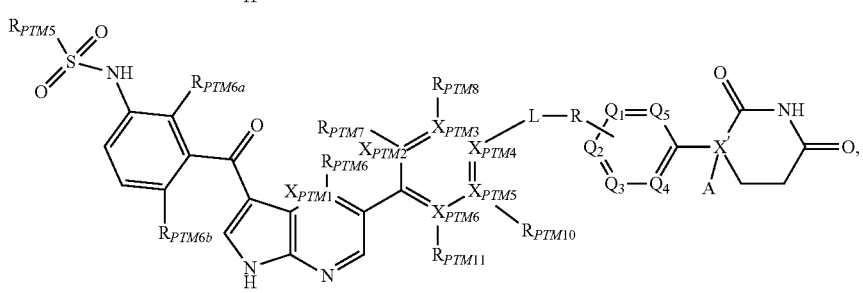
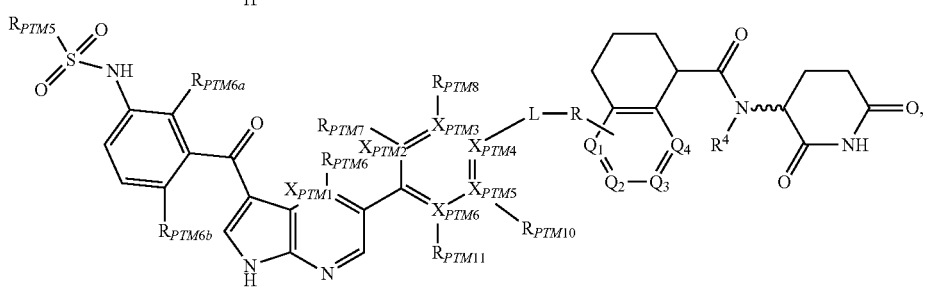

-continued
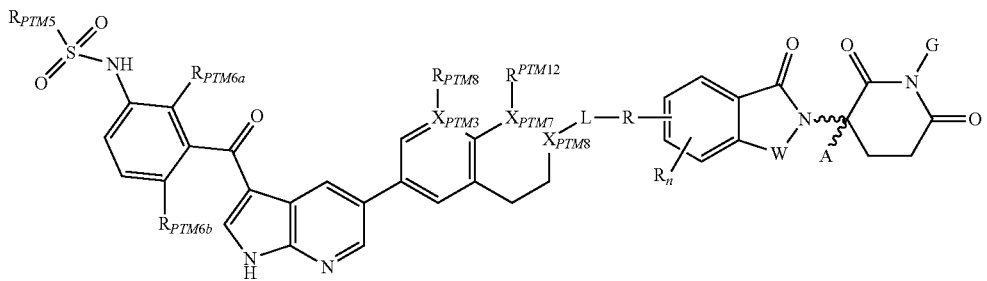
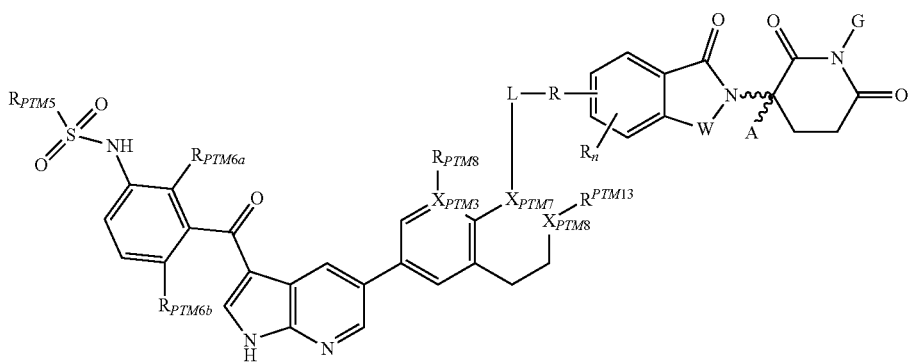
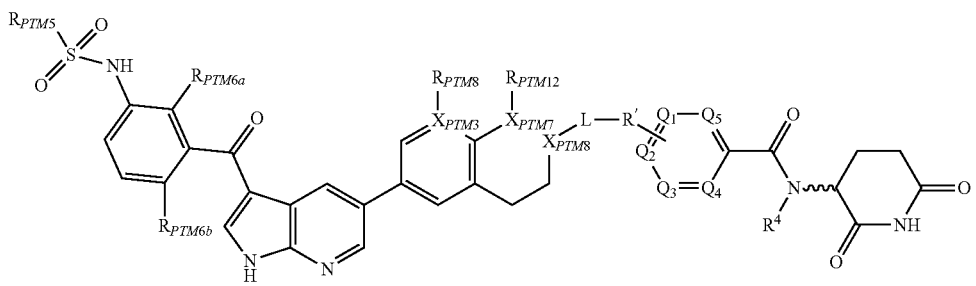
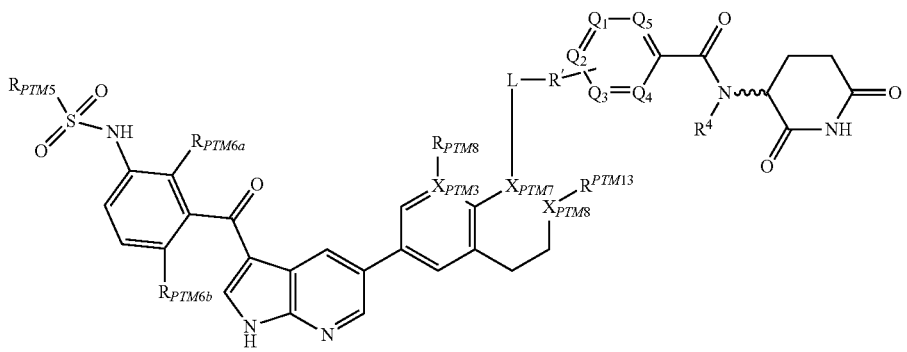
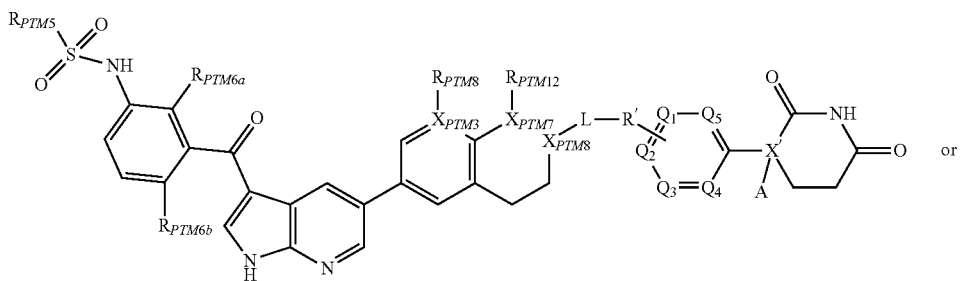 or

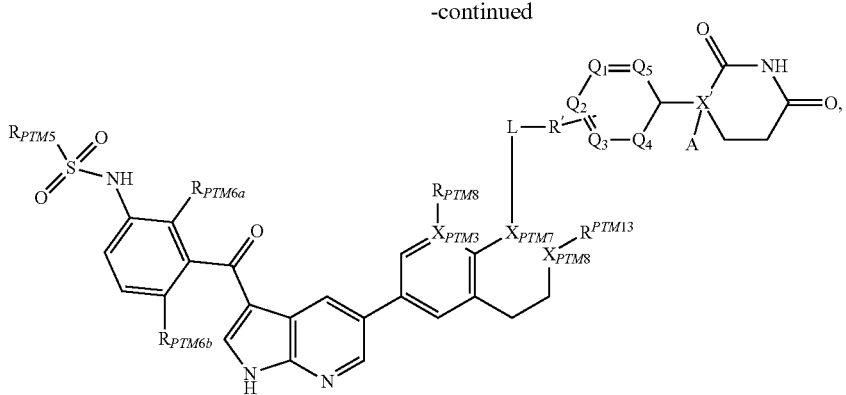
wherein each variable (e.g., $R_{PTM5}$, $R_{PTM6a}$, $R_{PTM6b}$, $R_{PTM8}$, $R_{PTM8}$, $R_{PTM9}$, $R_{PTM12}$, $R_{PTM13}$, $R_{PTM10}$, $X_{PTM3}$, $X_{PTM4}$, $R_{PTM5}$, $X_{PTM7}$, $R_{PTM8}$, L, R', R, n, $Q_1$, $Q_2$, $Q_3$, $Q_4$, $Q_5$, W, A, G, X', $R^4$) is individually defined as in any aspect or embodiment described herein.
In any aspect or embodiment described herein, the heterobifunctional compounds of the present disclosure
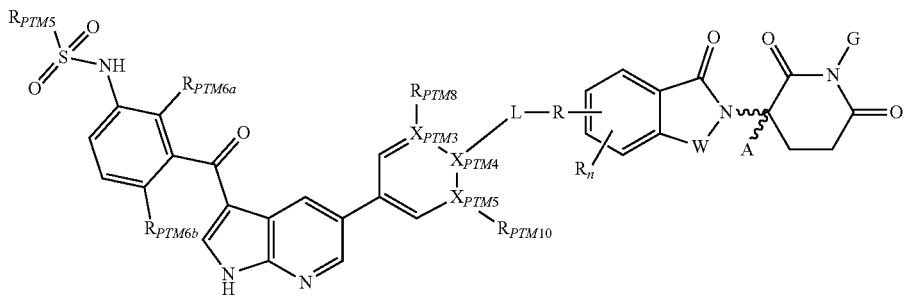
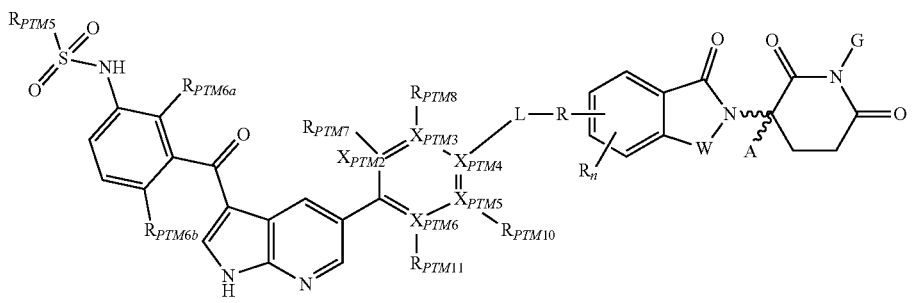
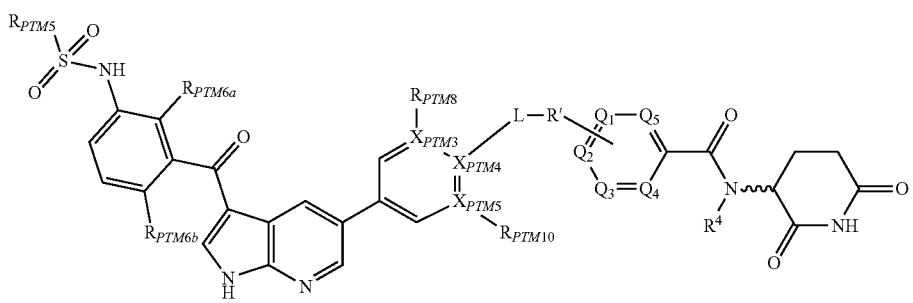

-continued
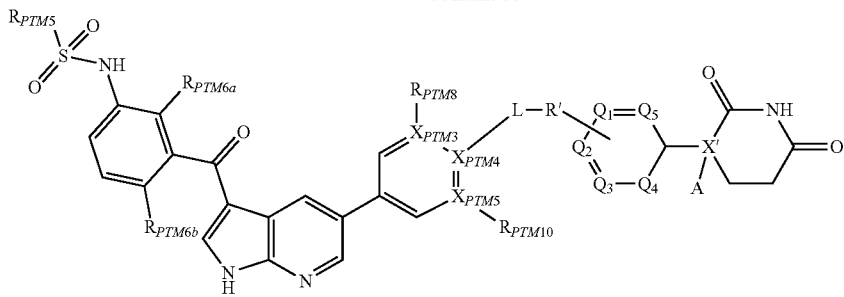
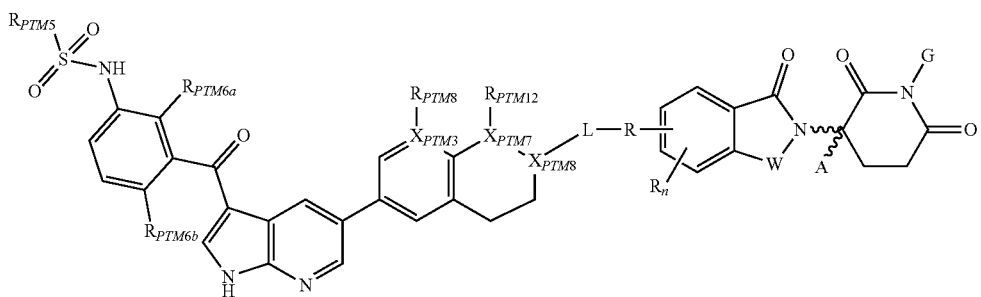
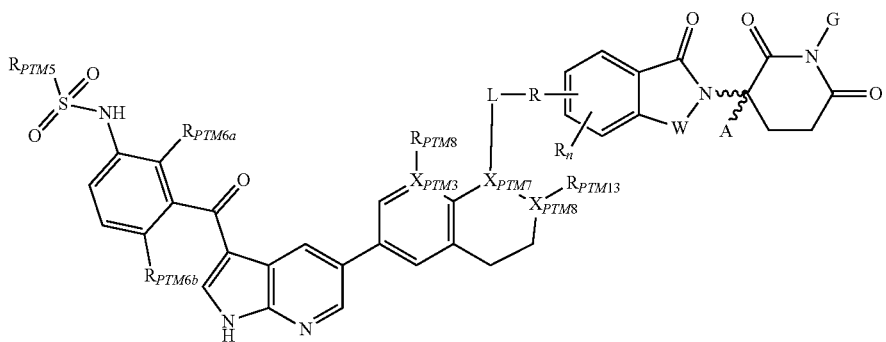
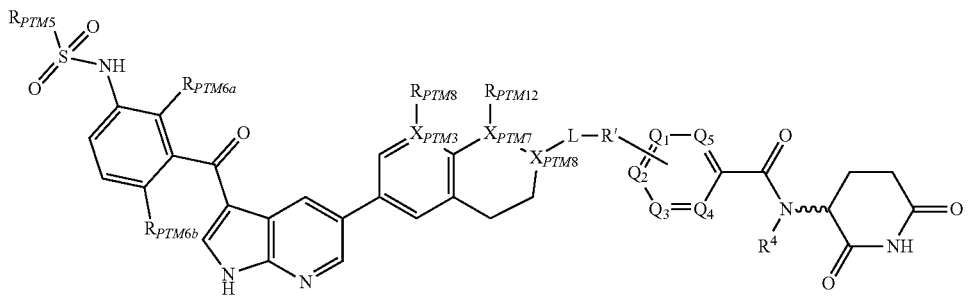
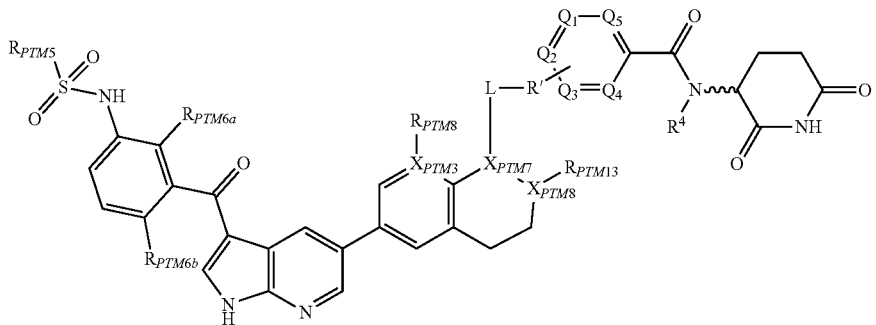

-continued

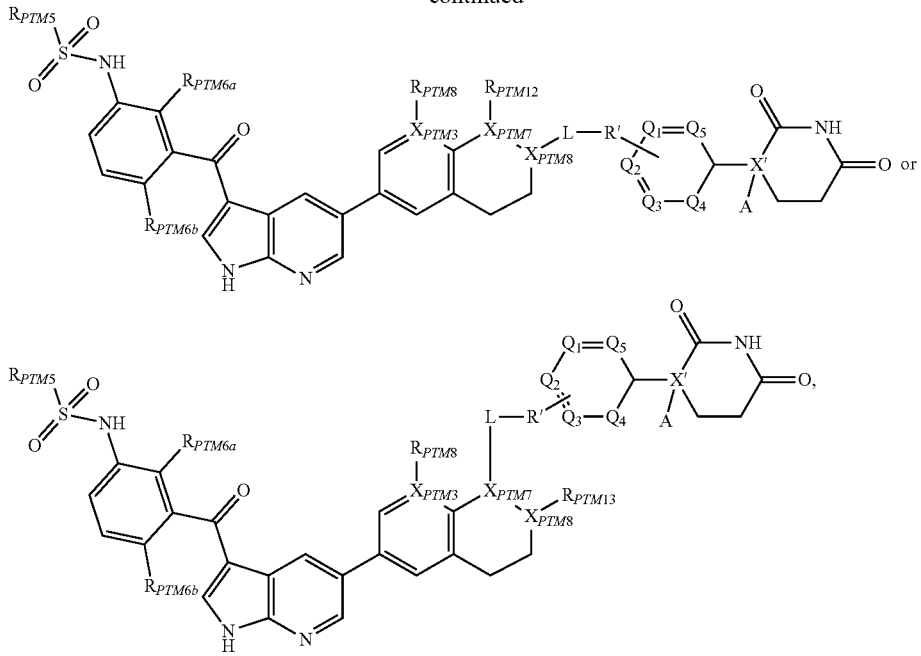

wherein each variable (e.g., $R_{PTM5}$, $R_{PTM6a}$, $R_{PTM6b}$, $R_{PTM8}$, $R_{PTM8}$, $R_{PTM9}$, $R_{PTM12}$, $R_{PTM13}$, $R_{PTM10}$, $X_{PTM3}$, $X_{PTM4}$, $R_{PTM5}$, $X_{PTM7}$, $R_{PTM8}$, L, R', R, n, $Q_1$, $Q_2$, $Q_3$, $Q_4$, $Q_5$, W, A, G, X', $R^4$) is individually defined as in any aspect or embodiment described herein.

Therapeutic Compositions

The present invention further provides pharmaceutical compositions comprising therapeutically effective amounts of at least one bifunctional compound as described herein, in combination with a pharmaceutically acceptable carrier, additive or excipient.

In an additional aspect, the description provides therapeutic compositions comprising an effective amount of a compound as described herein or a pharmaceutically acceptable salt form thereof, and a pharmaceutically acceptable carrier, additive or excipient, and optionally an additional bioactive agent. The therapeutic compositions effect targeted protein degradation in a patient or subject, for example, an animal such as a human, and can be used for treating or ameliorating disease states or conditions which are modulated by degrading the target protein. In certain embodiments, the therapeutic compositions as described herein may be used to effectuate the degradation of protein for the treatment or amelioration of a RAF-related disease or disorder, e.g., accumulation or overactivity of a RAF protein or a mutated RAF, or a mutated RAF protein having increased kinase activity relative to wild-type RAF, or a mutated B-Raf protein having increased kinase activity relative to wild-type B-Raf, or a mis-folded B-Raf protein, or a disease or disorder selected from cancer, renal cell carcinoma, pancreatic cancer, colorectal cancer, lung cancer, ovarian cancer, breast cancer, thyroid cancer, pilocytic astrocytoma, prostate cancer, gastric cancer, hepatocellular carcinoma, melanoma, cardiofaciocutaneous syndrome, neurofibromatosis type 1, Costello syndrome, Noonan Syndrome, LEOPARD (Lentigo, Electrocardiographic abnormalities, Ocular hypertelorism, Pulmonary stenosis, Abnormal genitalia, Retarded growth, Deafness) syndrome.

In alternative aspects, the present disclosure relates to a method for treating a disease state or ameliorating one or more symptoms of a disease or condition in a subject in need thereof by degrading the RAF protein (e.g., a wildtype RAF protein or a RAF mutant protein (e.g., RAF mutant protein having increased kinase activity relative to wild-type RAF protein or a RAF protein having one or more mutations selected from V600E, V600K, V600D, R461I, I462S, G463E, G463V, G465A, G465E, G465V, G466V, G468A, G468E, N580S, E585K, D593V, F594L, G595R, L596V, T598I, V599D, V599E, V599K, V599R, A727V, or combinations thereof) comprising administering to said patient or subject an effective amount, e.g., a therapeutically effective amount, of at least one compound as described herein, optionally in combination with a pharmaceutically acceptable carrier, additive or excipient, and optionally coadministered with an additional bioactive agent, wherein the composition is effective for treating or ameliorating the disease or disorder or one or more symptoms thereof in the subject. The method according to the present disclosure may be used to treat certain disease states, conditions or symptoms including inflammatory disease, autoimmune disease, or cancer, by virtue of the administration of effective amounts of at least one therapeutically effective compound described herein. For example, the method according to the present disclosure may be used to treat a condition causally related to the accumulation or overactivity of a RAF protein, a mutated RAF protein having increased kinase activity relative to wide-type RAF protein, a mis-folded RAF protein, such as, e.g., cancer, renal cell carcinoma, pancreatic cancer, colorectal cancer, lung cancer, ovarian cancer, breast cancer, thyroid cancer, pilocytic astrocytoma, prostate cancer, gastric cancer, hepatocellular carcinoma, and melanoma), cardiofaciocutaneous syndrome, neurofibromatosis type 1, Costello syndrome, Noonan Syndrome, or LEOPARD syndrome associated with RAF overactivity, accumulation or aggregation. In any aspect or embodiment described herein, the method further comprises, prior to administering a composition or compound of the present disclosure to a subject, identifying the subject as having a mutant RAF protein (e.g., B-Raf with V600E and/or G466V).

The present disclosure further includes pharmaceutical compositions comprising a pharmaceutically acceptable salt, in particular, an acid or base addition salt, of a compound as described herein. The acids which are used to prepare the pharmaceutically acceptable acid addition salts of the aforementioned compounds useful according to this aspect are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among numerous others.

Pharmaceutically acceptable base addition salts may also be used to produce pharmaceutically acceptable salt forms of the compounds according to the present disclosure. The chemical bases that may be used as reagents to prepare pharmaceutically acceptable base salts of the present compounds are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium, zinc and magnesium), ammonium or water-soluble amine addition salts such as N-methylglucamine-(meglumine), and the lower alkanolammonium and other base salts of pharmaceutically acceptable organic amines, among others.

The therapeutically effective compounds as described herein may, in accordance with the disclosure, be administered in single or divided doses by the oral, parenteral or topical routes. Administration of the active compound may range from continuous (intravenous drip) to several administrations per day (for example, Q.I.D.) and may include administration routes such as oral, topical, parenteral, intramuscular, intravenous, sub-cutaneous, transdermal (which may include a penetration enhancement agent), buccal, sublingual, intranasal, intraocular, intrathecal, vaginal, and suppository administration, among other routes of administration. The term "parenteral" as used herein includes subcutaneous, intravenous, intramuscular, intra-articular, intrasynovial, intrasternal, intrathecal, intrahepatic, intralesional and intracranial injection or infusion techniques. Enteric coated oral tablets may be used to enhance bioavailability of the compounds from an oral route of administration. The most effective dosage form will depend upon the pharmacokinetics of the particular agent chosen as well as the type, location and severity of disease, condition or symptom, and the health of the patient. Administration of compounds according to the present disclosure as sprays, mists, or aerosols for intra-nasal, intra-tracheal or pulmonary administration may also be used. The present disclosure therefore also is directed to pharmaceutical compositions comprising an effective amount of compound as described herein or a pharmaceutically acceptable salt thereof, optionally in combination with a pharmaceutically acceptable carrier, additive or excipient. Compounds according to the present disclosure may be administered in immediate release or sustained or controlled release forms. Sustained or controlled release forms are preferably administered orally, but also in suppository and transdermal or other topical forms. Intramuscular injections in liposomal form or in depot formulation may also be used to control or sustain the release of compound at an injection site.

The compositions as described herein may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium tri silicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat, and combinations thereof.

Sterile injectable forms of the compositions as described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1, 3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions as described herein may be orally administered in any orally acceptable dosage form including, but not limited to, capsules, tablets, aqueous suspensions or solutions. In the case of tablets for oral use, carriers which are commonly used include lactose and corn starch, among others known in the art. For oral administration in a capsule form, useful diluents include lactose and corn starch. When aqueous suspensions are required for oral use, the active ingredient may be combined with emulsifying and suspending agents. If desired, certain sweetening, flavoring or coloring agents may also be added. Lubricating agents, such as magnesium stearate, are also typically added.

Alternatively, the pharmaceutical compositions as described herein may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

The pharmaceutical compositions as described herein may also be administered topically. For topical applications, the pharmaceutical composition can be formulated in a transdermal patch, which can either be a reservoir patch or a matrix patch comprising the active compound combined with one or more carriers, buffers, absorption enhancers, and providing from 1 day to two weeks of continuous administration.

Alternatively, the pharmaceutical compositions of the present disclosure may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax and water.

Alternatively, the pharmaceutical compositions of the present disclosure can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Alternatively, the pharmaceutical compositions of the present disclosure can be formulated for ophthalmic use. For example, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions as described herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of active pharmaceutical ingredient in a pharmaceutical composition as described herein that may be combined with the carrier materials to produce a single dosage form will vary depending upon the condition of the subject and disease, condition or symptom treated, the particular mode of administration, and the condition of the subject. Preferably, the compositions should be formulated to contain between about 0.05 milligram and about 750 milligrams or more, more preferably about 1 milligram to about 600 milligrams, and even more preferably about 10 milligrams to about 500 milligrams of active ingredient, alone or in combination with another compound according to the present disclosure.

It should also be understood that a specific dosage and treatment regimen for any particular patient will depend on the judgment of the treating physician as based upon a variety of factors, including the activity and bioavailability of the specific compound employed, the age, body weight, general health, sex, diet, time of administration, rate of excretion, drug combination, and the severity of the particular disease or condition being treated.

A patient or subject in need of therapy using a compound according to the methods described herein can be treated by administering to the patient (subject) an effective amount of the compound according to the present disclosure, either alone, or in combination with another known therapeutic agent. In any aspect or embodiment described herein, the method may further include, prior to administering a composition or compound of the present disclosure to patient, identifying the patient as having a mutant RAF protin (e.g., B-Raf with a V600 mutation and/or a G466V mutation).

In certain aspects, the active compound is combined with the pharmaceutically acceptable carrier or diluent in an amount sufficient to deliver to a patient a therapeutically effective amount for the desired indication, without causing an undue degree of serious toxic effects in the patient treated. A preferred dose of the active compound for all of the herein-mentioned conditions is in the range from about 10 nanograms per kilograms (ng/kg) to 300 milligrams per kilograms (mg/kg), preferably 0.1 to 100 mg/kg per day, such as 0.5 to about 25 mg per kilogram body weight of the recipient/patient per day.

In certain aspects, the compound is conveniently administered in any suitable unit dosage form, including but not limited to a dosage form containing less than 1 milligrams (mg), 1 mg to 3000 mg, or 5 mg to 500 mg of active ingredient per unit dosage form. An oral dosage of about 25 mg-250 mg is often convenient.

In certain aspects, the active ingredient is preferably administered to achieve peak plasma concentrations of the active compound of about 0.00001-30 millimole (mM), preferably about 0.1-30 micromole (µM). This may be achieved, for example, by the intravenous injection of a solution or formulation of the active ingredient, optionally in saline, or an aqueous medium or administered as a bolus of the active ingredient. Oral administration may also be appropriate to generate effective plasma concentrations of active agent.

The concentration of active compound in the drug composition will depend on absorption, distribution, metabolism, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the physician administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as anti-cancer agents, as described herein among others. In certain preferred aspects of the disclosure, one or more compounds according to the present disclosure are coadministered with another bioactive agent, such as an anti-cancer agent or a wound healing agent, including an antibiotic, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In any aspect or embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

Therapeutic Methods

In an additional aspect, the description provides therapeutic methods comprising administration of an effective amount of a compound as described herein or pharmaceutically acceptable salt form thereof, and a pharmaceutically acceptable carrier. The therapeutic methods are useful to effect protein degradation in a patient or subject in need thereof, for example, an animal such as a human, for treating or ameliorating a disease state, condition or related symptom that may be treated through targeted protein degradation.

The terms "treat", "treating", and "treatment", etc., as used herein, refer to any action providing a benefit to a patient for which the present compounds may be administered, including the treatment of any disease state, condition, or symptom which is related to the protein to which the present compounds bind. Disease states or conditions, including cancer, which may be treated using compounds according to the present disclosure are set forth hereinabove.

The description provides therapeutic methods for effectuating the degradation of proteins of interest for the treatment or amelioration of a disease, e.g., pancreatic cancer, colon cancer, colorectal cancer, lung cancer, non-small cell lung cancer, biliary tract malignancies, endometrial cancer, cervical cancer, bladder cancer, liver cancer, myeloid leukemia, and breast cancer. As such, in another aspect, the description provides a method of ubiquitinating/degrading a target protein in a cell. In certain embodiments, the method comprises administering a bifunctional compound of the invention. The control or reduction of specific protein levels in cells of a subject as afforded by the present disclosure provides treatment of a disease state, condition, or symptom. In any aspect or embodiment, the method comprises administering an effective amount of a compound as described herein, optionally including a pharmaceutically acceptable excipient, carrier, adjuvant, another bioactive agent or combination thereof.

In additional embodiments, the description provides methods for treating or ameliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable excipient, carrier, adjuvant, another bioactive agent or combination thereof, wherein the composition is effective for treating or ameliorating the disease or disorder or symptom thereof in the subject.

In any aspect or embodiment described herein, the method further includes, prior to administering a composition or compound of the present disclosure to a subject, identifying a patient as having a mutant RAF protein (e.g., V600 mutant B-Raf or B-Raf V600E or a mutant B-Raf with a V600 mutation and/or a G466V mutation).

In another aspect, the description provides methods for identifying the effects of the degradation of proteins of interest in a biological system using compounds according to the present disclosure.

In another aspect, the description provides a process for making a molecule that can cause degradation of RAF (such as B-Raf or a mutated version thereof) in a cell (e.g., in vivo or in vitro), comprising the steps of: (i) providing a small molecule that binds to the RAF protein or a mutated form thereof (ii) providing an E3 ubiquitin ligase binding moiety (ULM), preferably a CLM as described herein; and (iii) covalently coupling the small molecule of step (i) to the ULM of step (ii) via a chemical linking group (L) to form a compound which binds to both a cereblon E3 ubiquitin ligase and RAF protein and/or mutated form of RAF protein in the cell, such that the cereblon E3 ubiquitin ligase is brought in proximity to, and ubiquitinates the RAF protein bound thereto, such that the ubiquitinated RAF is then degraded.

In another aspect, the description provides a method for detecting whether a molecule can trigger degradation of a RAF protein in a cell (e.g., in vivo or in vitro), the method comprising the steps of: (i) providing a molecule for which the ability to trigger degradation of RAF protein in a cell is to be detected, said molecule comprising the structure: ULM-L-PTM, wherein ULM is a cereblon E3 ubiquitin ligase binding moiety (CLM) capable of binding a cereblon E3 ubiquitin ligase in a cell, which CLM is as described herein, preferably a CLM such as thalidomide, pomalidomide, lenalidomide or an analog thereof; PTM is a protein targeting moiety, which is a small molecule that binds to RAF and/or mutated RAF form thereof, said RAF having at least one lysine residue available to be ubiquitinated by a cereblon E3 ubiquitin ligase bound to the CLM of the molecule; and L is a chemical linking group that covalently links the CLM to the PTM to form the molecule; (ii) incubating a RAF protein-expressing cell in the presence of the molecule of step (i); and (iii) detecting whether the RAF protein in the cell has been degraded.

In any aspect or embodiment described herein, the small molecule that binds the RAF protein is as described herein.

In another aspect of said treatment, the present disclosure provides a method of treating a human patient in need of said treatment of a disease state, condition, or symptom causally related to RAF and/or a RAF mutated form, (e.g., expression, over-expression, mutation, aggregation, accumulation, misfolding or dysregulation), where the degradation of the RAF protein or mutated form will produce a therapeutic effect in the patient, the method comprising administering to the patient an effective amount of a compound according to the present disclosure, optionally in combination with another bioactive agent.

The disease state, condition, or symptom may be caused by a microbial agent or other exogenous agent such as a virus, bacteria, fungus, protozoa or other microbe, or may be a disease state, which is caused by expression, overexpression, mutation, misfolding, or dysregulation of the RAF protein, which leads to a disease state, condition, or symptom.

In another aspect, the present disclosure provides a method of treating or ameliorating at least one symptom of a disease or condition in a subject, comprising the steps of:
providing a subject identified as having a symptom of a disease or condition causally related to expression, overexpression, mutation, misfolding, or dysregulation of a RAF protein and/or mutated form thereof in the subject, where the symptom of the disease or condition is treated or ameliorated by degrading RAF protein and/or a mutated form thereof in cells of the subject; and administering to the subject therapeutically effective amount of a compound comprising a small molecule of the present invention such that the RAF protein and/or mutated form thereof is degraded, thereby treating or ameliorating at least one symptom of a disease or condition in the subject.

The term "disease state" or "condition" is used to describe any disease state or condition wherein protein expression, overexpression, mutation, misfolding, or dysregulation (e.g., the amount of protein expressed in a patient is elevated) occurs and where degradation of the RAF protein and/or mutated form thereof to reduce or stabilize the level of RAF protein (whether mutated or not) in a patient provides beneficial therapy or relief of symptoms to a patient in need thereof. In certain instances, the disease state, condition, or symptom may be cured.

Disease state, condition, or symptom which may be treated using compounds according to the present disclosure include, for example, cancer, renal cell carcinoma, pancreatic cancer, colorectal cancer, lung cancer, non-small cell lung cancer, ovarian cancer, thyroid cancer, pilocytic astrocytoma, prostate cancer, gastric cancer, hepatocellular carcinoma, melanomacardiofaciocutaneous syndrome, neurofibromatosis type 1, Costello syndrome; Noonan Syndrome, or LEOPARD syndrome associated with RAF accumulation and aggregation.

The term "bioactive agent" is used to describe an agent, other than a compound according to the present disclosure, which is used in combination with a present compound as an agent with biological activity to assist in effecting an intended therapy, inhibition and/or prevention/prophylaxis for which the present compounds are used. Preferred bioactive agents for use herein include those agents which have pharmacological activity similar to that for which the present compounds are used or administered and include for example, anti-cancer agents, antiviral agents, especially including anti-HIV agents and anti-HCV agents, antimicrobial agents, antifungal agents, etc.

The term "additional anti-cancer agent" or "anti-cancer agent" is used to describe an anti-cancer agent, which may be combined with compounds according to the present disclosure to treat cancer. These agents include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a PI3 kinase inhibitor, an AKT inhibitor, an mTORC1/2 inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR 1 KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo [2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, *Bacillus* Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

The term "pharmaceutically acceptable derivative" is used throughout the specification to describe any pharmaceutically acceptable prodrug form (such as an ester, amide other prodrug group), which, upon administration to a patient, provides directly or indirectly the present compound or an active metabolite of the present compound.

EXAMPLES

Abbreviations
ACN Acetonitrile
AcOH Acetic acid
Boc tert-butoxycarbonyl
dba Dibenzylideneacetone
DBU 1,8-Diazabicyclo[5.4.0]undec-7-ene
DCM Dichloromethane
DMA Dimethylacetamide
DME Dimethoxyethane
DMF Dimethylformamide
DMSO Dimethyl Sulfoxide
DMAC/DMA Dimethylacetamide
DIEA N, N-Diisopropylethylamine
EDTA Ethyl enediaminetetraacetic acid
EtOAc/EA Ethyl Acetate
EtOH Ethanol
FA Formic Acid
HPLC High pressure liquid chromatography
Hz Hertz
IBX 2-Iodoxybenzoic acid
LAH Lithium aluminium hydride
LCMS Liquid Chromatography/Mass Spectrometry
LiHMDS Lithium bis(trimethylsilyl)amide
MHz Megahertz
NBS N-Bromosuccinimide
NCS N-Chlorosuccinimide
NMR Nuclear Magnetic Resonance
NMP N-Methyl-2-pyrrolidone
MeOH Methanol
MPLC Medium pressure liquid chromatography
MTBE Methyl tert-butyl ether
PE Petroleum ether
Psi Pound-force per square inch
RT or r.t. Room temperature
SFC Supercritical fluid chromatography
TEA Triethylamine
THF Tetrahydrofuran
TFA Trifluoracetic acid
TLC Thin layer chromatography
TMS Trimethylsilyl
General Synthetic Approach The synthetic realization and optimization of the bifunctional molecules as described herein may be approached in a stepwise or modular fashion. For example, identification of compounds that bind to the target protein, i.e., RAF can involve high or medium throughput screening campaigns if no suitable ligands are immediately available. It is not unusual for initial ligands to require iterative design and optimization cycles to improve suboptimal aspects as identified by data from suitable in vitro and pharmacological and/or ADMET assays. Part of the optimization/SAR campaign would be to probe positions of the ligand that are tolerant of substitution and that might be suitable places on which to attach the chemical linking group previously referred to herein. Where crystallographic or NMR structural data are available, these can be used to focus such a synthetic effort.

In a very analogous way one can identify and optimize ligands for an E3 Ligase.

With PTMs and ULMs (e.g. CLMs) in hand, one skilled in the art can use known synthetic methods for their combination with or without a chemical linking group(s). Chemical linking group(s) can be synthesized with a range of compositions, lengths and flexibility and functionalized such that the PTM and ULM groups can be attached sequentially to distal ends of the linker. Thus, a library of bifunctional molecules can be realized and profiled in in vitro and in vivo pharmacological and ADMET/PK studies. As with the PTM and ULM groups, the final bifunctional molecules can be subject to iterative design and optimization cycles in order to identify molecules with desirable properties.

In some instances, protecting group strategies and/or functional group interconversions (FGIs) may be required to facilitate the preparation of the desired materials. Such chemical processes are well known to the synthetic organic chemist and many of these may be found in texts such as "Greene's Protective Groups in Organic Synthesis" Peter G. M. Wuts and Theodora W. Greene (Wiley), and "Organic Synthesis: The Disconnection Approach" Stuart Warren and Paul Wyatt (Wiley).

Synthetic Procedures
General Synthetic Scheme

Scheme 1.

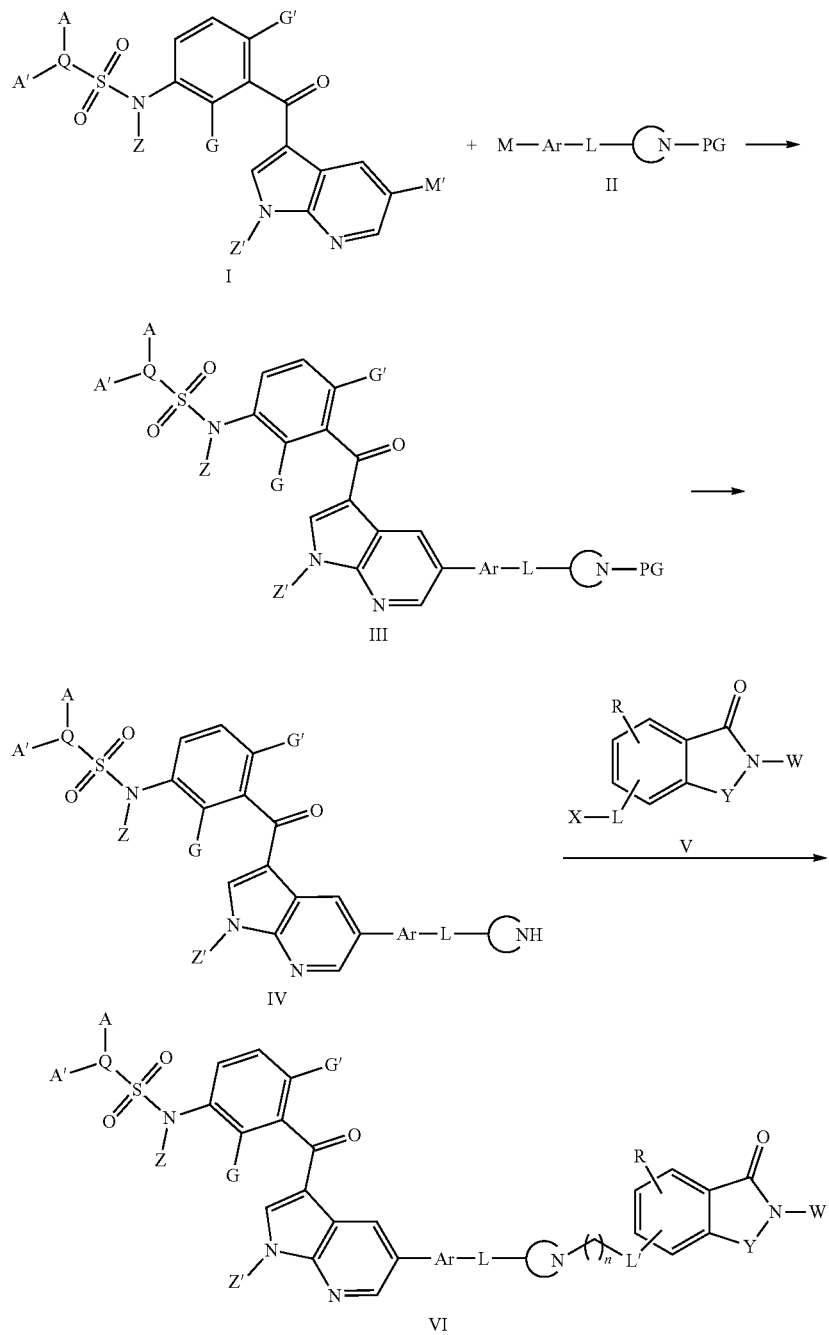

A compound of formula I may be reacted with a reagent II (commercially available or readily prepared using standard reaction techniques known to one skilled in the art) under palladium-catalyzed cross-coupling conditions, e.g. with a suitable palladium catalyst such as bis(di-tert-butyl (4-dimethylaminophenyl)phosphine)dichloropalladium(II), suitable base such as cesium fluoride, suitable solvent such as mixtures of 1,4-dioxane and water, at a suitable temperature such as 100° C., with or without microwave irradiation to produce a compound of formula III. One of M or M' represents a functional group capable of undergoing palladium-catalyzed transmetallation, e.g. a boronic acid, boronic ester, or trialkylstannane; the other of M or M' represents a functional group capable of undergoing palladium-catalyzed oxidative addition, e.g. an iodide, bromide, chloride, or trifluoromethanesulfonate; Z and Z' are each independently H or a suitable protecting group such as t-butoxycarbonyl; Ar represents an aromatic or heteroaromatic ring system with one or more optional substituents; L represents an optional linker or portion of a linker,

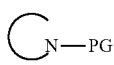

represents a primary or secondary amine, optionally cyclized into a 4 to 8 membered heterocyclic ring and/or fused to Ar, wherein PG represents a suitable protecting group, including but not limited to t-butoxycarbonyl or benzyl; Q is N or CH; and A and A' are each independently H, substituted alkyl, or optionally fused into a ring, which may have further optional substitutions; and G and G' are each independently H, halogen, substituted alkyl, or substituted alkoxy. Compounds of formula III may be converted to a compound of formula IV by treatment with a reagent suitable for the removal of PG, e.g. hydrogen chloride in 1,4-dioxane when PG is t-butoxycarbonyl. Compound IV may then be reacted with compound V to produce compound VI, wherein L' represents an optional linker or portion of a linker, Y is $CH_2$ or C=O, X is either a suitable leaving group (e.g. OMs, OTs, Cl, etc.) or an aldehyde (CHO), and R is an optional substituent (e.g. F or $OCH_3$), and W is:

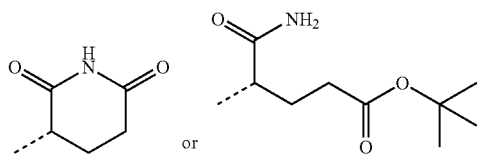

When X is a leaving group, n is 0, and suitable reaction conditions are those for an alkylation reaction, e.g. diisopropylethylamine, potassium iodide, DMSO or acetonitrile, 80° C. When X is an aldehyde, n is 1, and suitable reaction conditions are those for a reductive amination reaction, e.g. sodium cyanoborohydride, methanol, dichloromethane, acetic acid, room temperature. As needed, mixtures of enantiomers or diastereomers of any compounds IV, V, or VI may be resolved into their constituent enantiomers or diastereomers using techniques known to one skilled in the art, including but not limited to preparative high performance liquid chromatography or preparative supercritical fluid chromatography.

In cases where W is

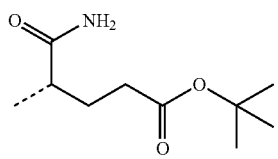

the compound VI may be treated with conditions suitable for imide cyclization, e.g. benzenesulfonic acid in acetonitrile or N-methylpyrrolidone at 100° C. to afford a different compound of formula VI where W is:

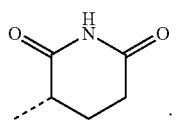

In cases where one or both of Z or Z' are a protecting group, such protecting group may be removed from a compound VI, e.g. by treatment with trifluoroacetic acid when Z and/or Z' are t-butoxycarbonyl, to afford a different compound of formula VI wherein Z and Z' are H.

It will further be apparent to one skilled in the art that the positions of

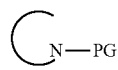

in II and X in V may be reversed throughout the synthetic sequence, such that the positions of

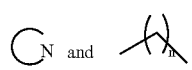

are reversed in compound VI. In such cases, X may also be $CH_2OH$ or an aldehyde protected e.g. as its acetal, and may be converted to a compound where X is CHO by oxidation of the alcohol, e.g. with Dess-Martin periodinane, or deprotection of the acetal, e.g. with Amberlyst 15 in acetone and water at reflux, prior to reaction with V.

Scheme 2.

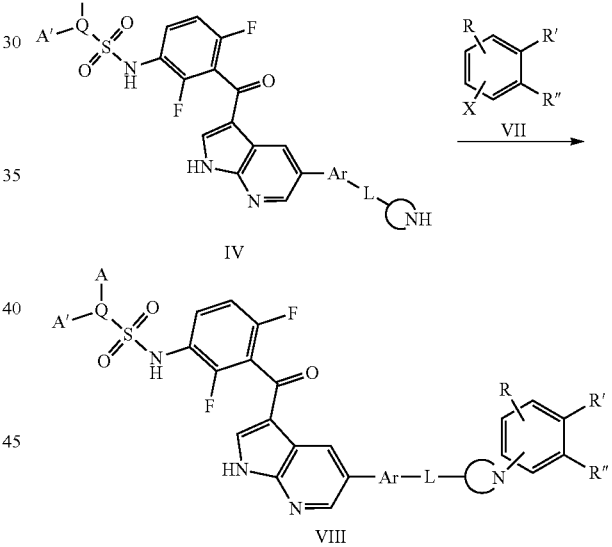

A compound of formula IV as defined in Scheme 1 may also be reacted with a compound of formula VII to provide compounds of formula VIII, wherein X is a suitable leaving group such as fluorine or chlorine, R is one or more optional substituents, R' and R" are either both carboxylic esters, e.g. $CO_2CH_2CH_3$, R is a carboxylic ester e.g. $CO_2CH_3$ and R' is CN, or together R and R' form either:

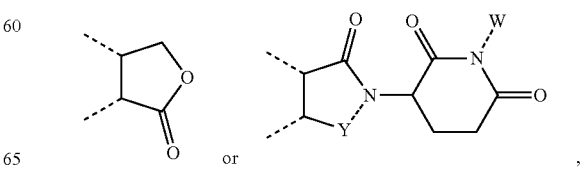

wherein Y is either CH$_2$ or C=O and W is H or CH$_3$, and reaction conditions are those for a nucleophilic aromatic substitution, e.g. triethylamine, DMSO, 70° C.

A compound of formula XXXVI may be further transformed into a different compound of formula XXXVI. When R' is a carboxylic ester and R" is CN, reduction of R" to CHO may be accomplished, e.g. by treatment with sodium hypophosphite and Raney nickel in a mixture of pyridine, acetic acid, and water. When R' and R" together form

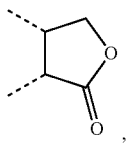

solvolysis e.g. with sodium hydroxide in an alcoholic solvent and tetrahydrofuran may afford a compound where R' is a carboxylic ester and R" is CH$_2$OH. This compound may be further oxidized, e.g. with manganese dioxide, to afford an equivalent compound XXXVI where R' is a carboxylic ester and R" is CHO. Such compounds where R' is a carboxylic ester and R" is CHO may then be reacted with 3-aminoglutarimide in the presence of e.g. sodium triacetoxyborohydride, diisopropylethylamine, and acetic acid in methanol and dichloromethane to afford a new compound of formula XXXVI wherein R' and R" together are:

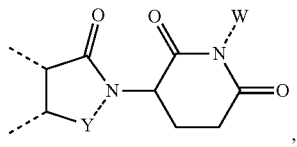

wherein Y is CH$_2$ and W is H or CH$_3$.

Scheme 3.

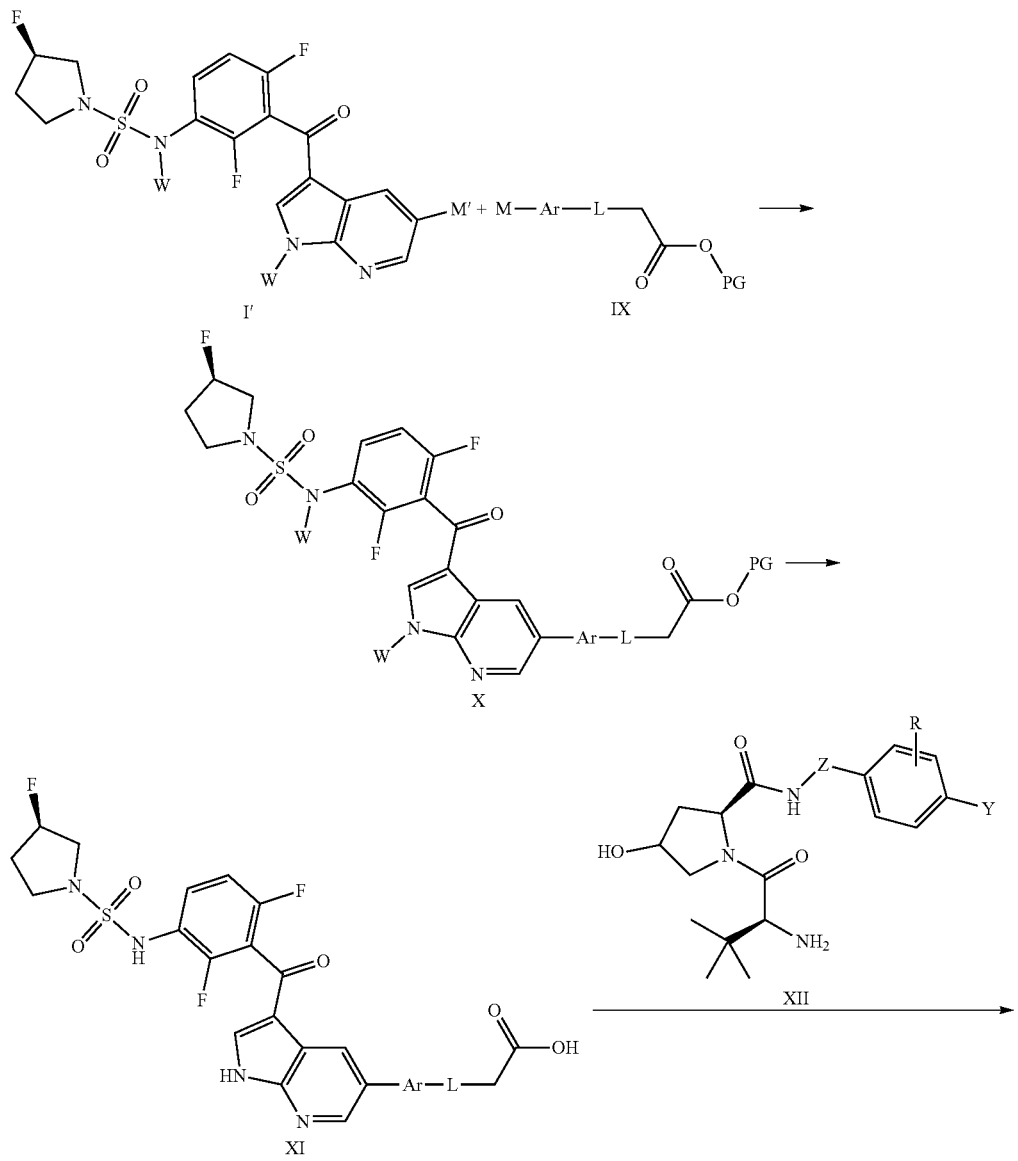

-continued

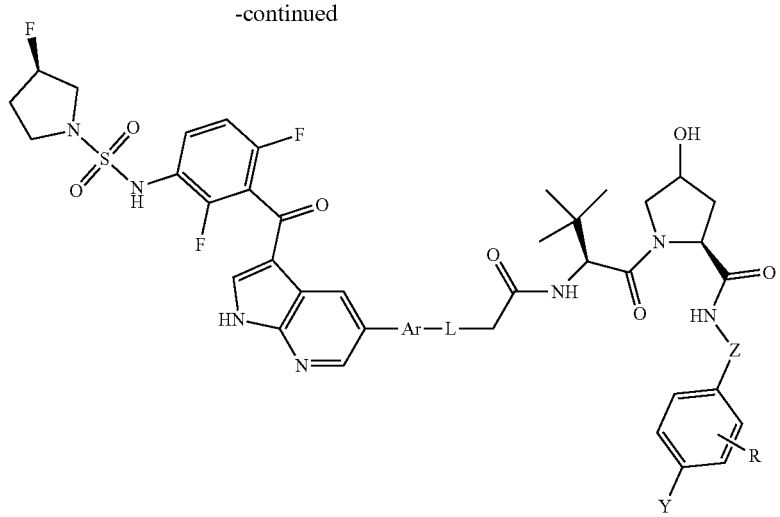

XIII

A compound of formula I' may be reacted with a reagent IX (commercially available or readily prepared using standard reaction techniques known to one skilled in the art) under palladium-catalyzed cross-coupling conditions, e.g. as shown in Scheme 1, to produce a compound of formula X. One of M or M' represents a functional group capable of undergoing palladium-catalyzed transmetallation, e.g. a boronic acid, boronic ester, or trialkylstannane; the other of M or M' represents a functional group capable of undergoing palladium-catalyzed oxidative addition, e.g. an iodide, bromide, chloride, or trifluoromethanesulfonate; Ar represents an aromatic or heteroaromatic ring system; L represents an optional linker or portion of a linker; PG represents a suitable ester protecting group, e.g. methyl, ethyl, or t-butyl; and W represents an optional protecting group, e.g. 2-(trimethylsilyl)ethoxymethyl. Where necessary, e.g. when L contains a primary or secondary amine or an alcohol, such functional groups may be optionally protected with a suitable protecting group, e.g. t-butoxycarbonyl when the functional group is an amine or t-butyldimethylsilyl when the functional group is an alcohol. Compounds of formula X may be converted to a compound of formula XI by treatment with a reagent suitable for the removal of the optional W, e.g. hydrogen chloride in 1,4-dioxane and methanol or ethylenediamine and tetra-n-butylammonium fluoride when W is 2-(trimethylsilyl)ethoxymethyl; followed by treatment with a reagent suitable for the removal of PG, e.g. hydrogen chloride in 1,4-dioxane when PG is t-butyl. Compound XI may then be reacted with compound XII, wherein Z is an optionally substituted carbon, e.g. $CH_2$, $CD_2$, CH(Me), CH($CH_2$OH), C($CH_3$)$_2$, R is an optional substituent, e.g. F or $CH_2$OH, and Y is an optional substituent, e.g. halogen, CN, or optionally substituted aryl or heterocyclyl, to produce compounds of formula XIII under amide formation conditions, e.g. (benzotriazol-1-yloxy)tripyrrolidinophosphonium hexafluorophosphate, diisopropylethylamine, DMF, room temperature. It will be apparent to one skilled in the art that when L contains a protected amine or alcohol, such protecting group may be removed as needed at the stage of compound X, XI, or XIII, e g by treatment with trifluoroacetic acid when said protecting group is t-butoxycarbonyl or hydrochloric acid in methanol when said protecting group is t-butyldimethylsilyl.

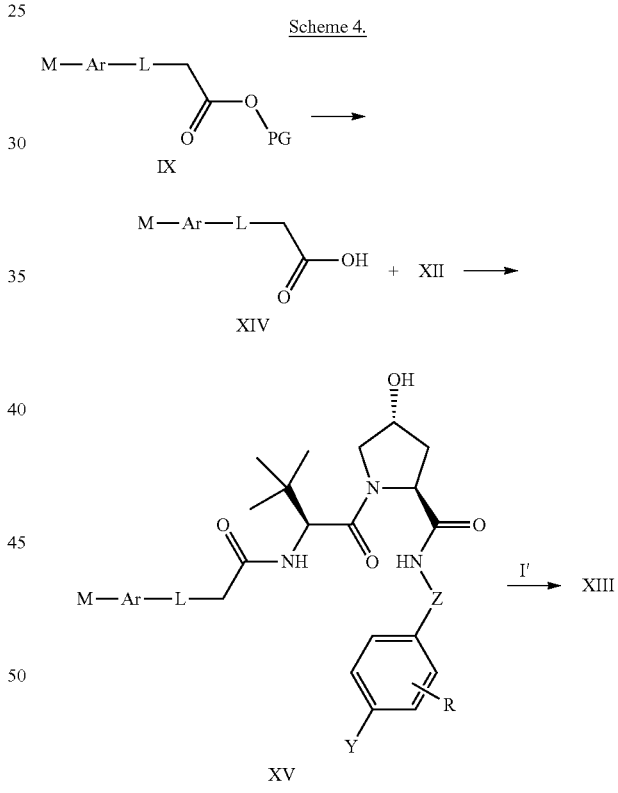

Scheme 4.

Alternatively, a compound of formula IX may be converted to a compound of formula XIV by using conditions analogous to those for the conversion of X to XI in Scheme 3. A compound of formula XIV may be converted to a compound of formula XV by using conditions analogous to those for the conversion of XI to XIII in Scheme 3. A compound of formula XV may then be converted to a compound of formula XIII by reaction with a compound of formula I' using conditions analogous to those for the conversion of I' and IX to X, followed by optional deprotection of W, in Scheme 3.

Scheme 5.

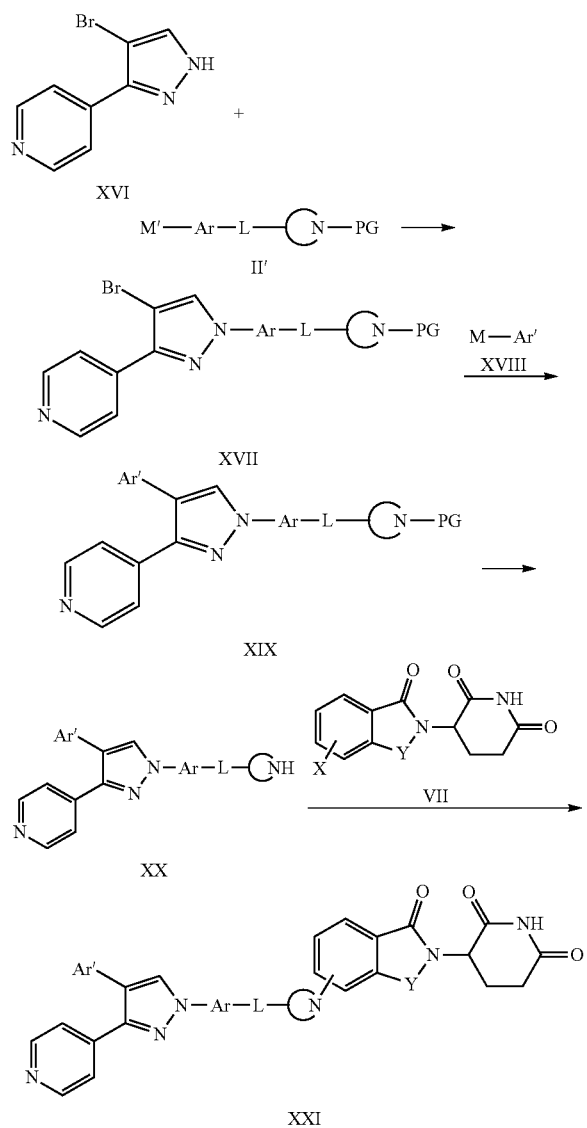

1,4-dioxane, 90° C., to produce a compound of formula XIX. M represents a functional group capable of undergoing palladium-catalyzed transmetallation, e.g. a boronic acid, boronic ester, or trialkylstannane and Ar' represents an aromatic or heteroaromatic ring system with optional substituents. A compound of formula XIX may then be converted to a compound of formula XX by treatment with a reagent suitable for the removal of PG, e.g. hydrogen chloride in 1,4-dioxane or methanol when PG is t-butyl. A compound of formula XX may also be reacted with a compound of formula VII to provide compounds of formula XXI, wherein X is a suitable leaving group such as fluorine or chlorine, Y is C=O, the aromatic ring of VII may have further optional substituents, and reaction conditions are those for a nucleophilic aromatic substitution, e.g. triethylamine, DMSO, 80° C. In cases where the group Ar' contains optional substituents, e.g. a ketone, these may undergo further functionalization, e.g. by treatment with hydroxylamine hydrochloride and pyridine at room temperature, to provide further compounds of formula XXI.

Scheme 6.

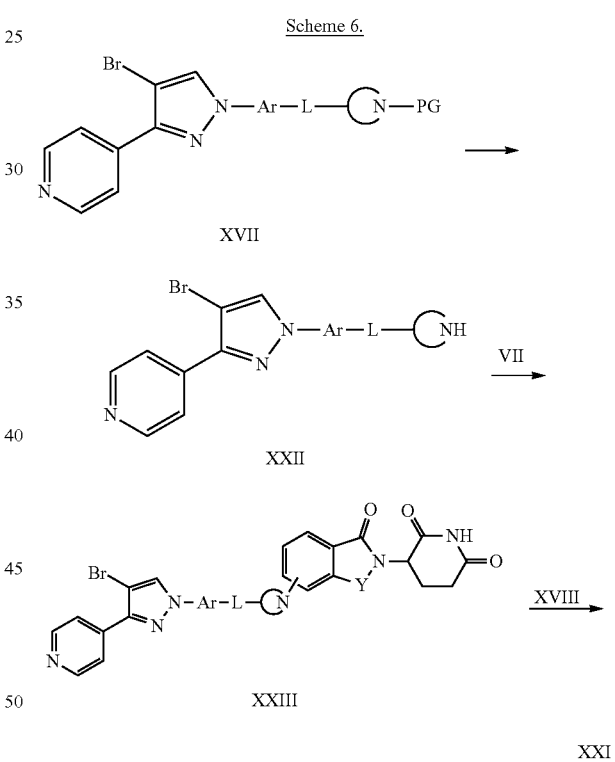

A compound of formula XVI may be reacted with a reagent II' (commercially available or readily prepared using standard reaction techniques known to one skilled in the art) under Chan-Lam cross-coupling conditions, e.g. copper (II) acetate, pyridine or diethylamine or triethylamine, 100° C., to produce a compound of formula XVII. M' represents a boronic acid or boronic ester; Ar represents an aromatic or heteroaromatic ring system; L represents an optional linker,

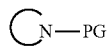

represents a primary or secondary amine, optionally cyclized into a 4 to 8 membered heterocyclic ring, wherein PG represents a suitable protecting group, including but not limited to t-butoxycarbonyl or benzyl. Compounds of formula XVII may be reacted with a reagent XVIII under palladium-catalyzed cross-coupling conditions, e.g. [1,1'-bis(diphenylphosphino)ferrocene]dichloropalladium, tri-tert-butylphosphine tetrafluoroborate, cesium fluoride, Alternatively, a compound of formula XVII may be converted to a compound of formula XXII by using conditions analogous to those for the conversion of XIX to XX in Scheme 5. A compound of formula XXII may then be treated with a compound of formula VII as defined in Scheme 5 to produce a compound of formula XXIII The compound of formula XXIII may then be treated with a reagent XVIII as defined in Scheme 5 to produce a compound of formula XXI. In cases where the group Ar' contains optional substituents, e.g. a ketone, these may undergo further functionalization, e.g. by treatment with hydroxylamine hydrochloride and pyridine at room temperature, to provide further compounds of formula XXI.

Scheme 7.

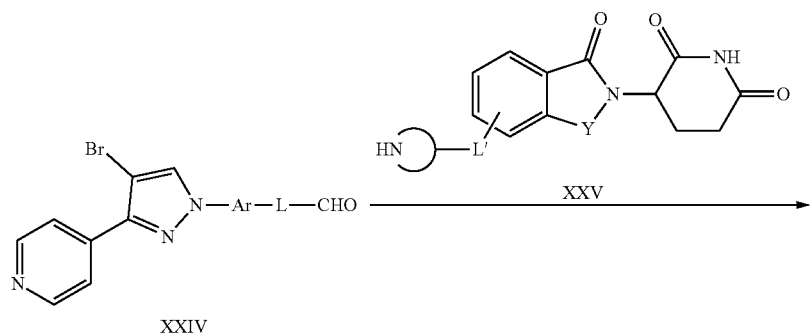

XXIV

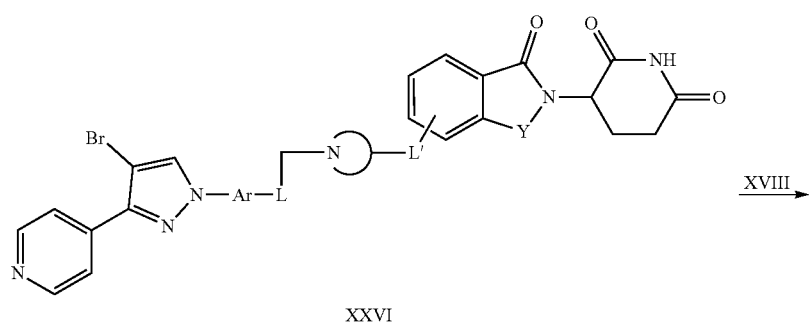

XXVI

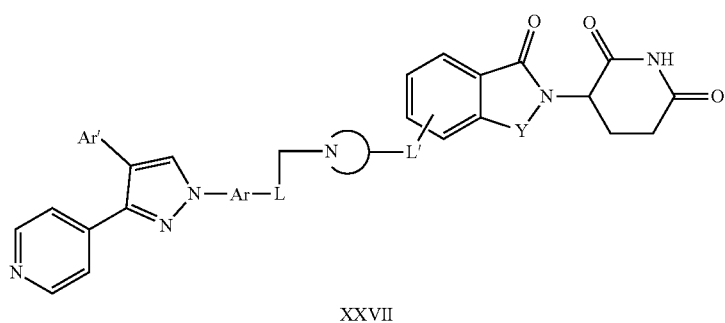

XXVII

A compound of formula XXIV (prepared in an analogous manner to the preparation of XVII from XVI and II' in Scheme 5, with additional functional group transformations as necessary, which are well known to one skilled in the art) may be reacted with a compound of formula XXV to prepare a compound of formula XXVI under reductive amination conditions, e.g. sodium cyanoborohydride, acetic acid, methanol, room temperature. Herein Ar represents an aromatic or heteroaromatic ring system; L and L' represent an optional linker or portion of a linker,

HN⟨ ⟩ represents a primary or secondary amine, optionally cyclized into a 4 to 8 membered heterocyclic ring, and Y is $CH_2$ or C=O. A compound of formula XXVI may then be treated with a reagent XVIII as defined in Scheme 5 to produce a compound of formula XXVII. In cases where the group Ar' contains optional substituents, e.g. a ketone, these may undergo further functionalization, e.g. by treatment with hydroxylamine hydrochloride and pyridine at room temperature, to provide further compounds of formula XVII.

Scheme 8.

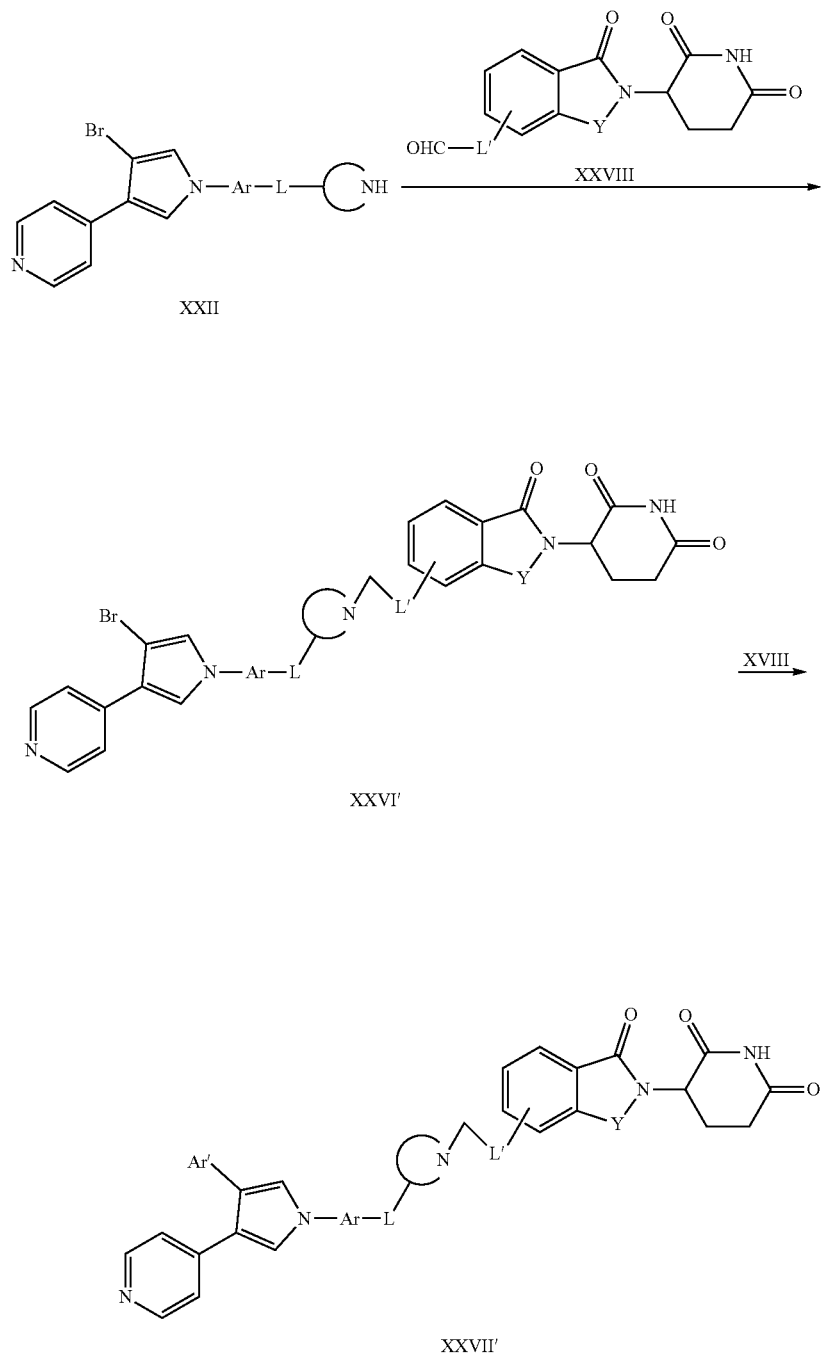

Alternatively, a compound of formula XXII may be treated with a compound of formula XXVIII under reductive amination conditions, e.g. as in Scheme 7, to provide a compound of formula XXVI'. Herein Ar, L, L', and Y are defined as in Scheme 7. A compound of formula XXVI' may then be treated with a reagent XVIII as defined in Scheme 5 to produce a compound of formula XXVII'. In cases where the group Ar' contains optional substituents, e.g. a ketone, these may undergo further functionalization, e.g. by treatment with hydroxylamine hydrochloride and pyridine at room temperature, to provide further compounds of formula XVII'.

Scheme 9.

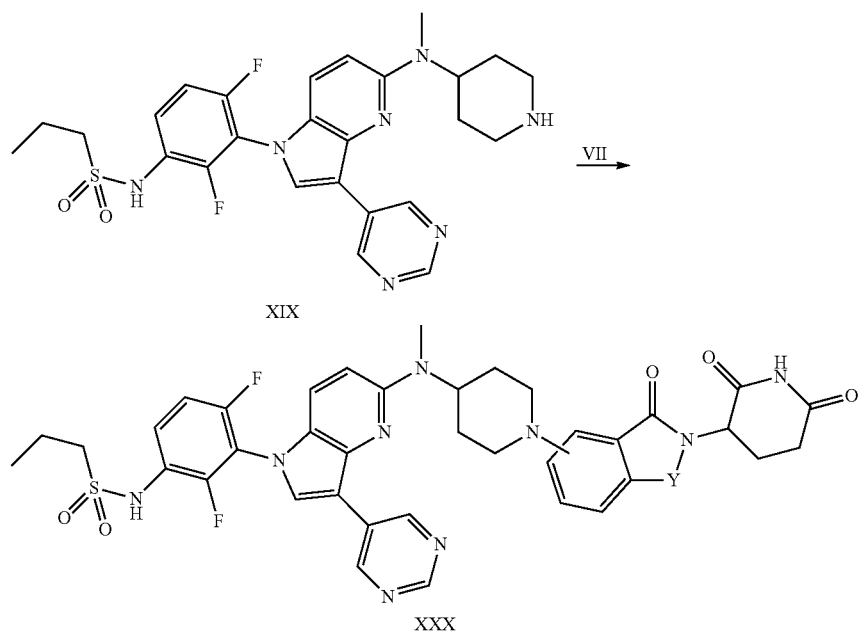

A compound of formula XIX may be reacted with a compound of formula VII to provide compounds of formula XXX, wherein X is a suitable leaving group such as fluorine or chlorine, Y is C=O, the aromatic ring of VII may have further optional substituents, and reaction conditions are those for a nucleophilic aromatic substitution, e.g. diisopropylethylamine, NMP, 130° C., with or without microwave irradiation.

Scheme 10.

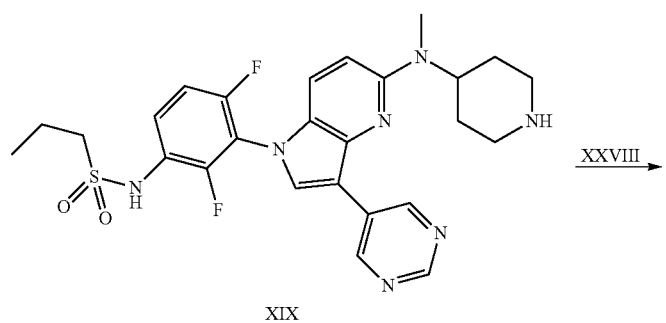

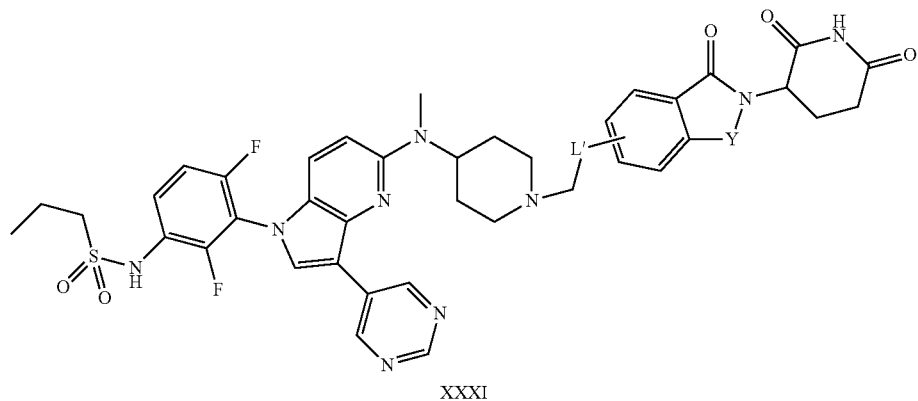

Alternatively, a compound of formula XIX may be treated with a compound of formula XXVIII to provide a compound of formula XXXI under reductive amination conditions, e.g. sodium triacetoxyborohydride, ethanol, dichloromethane, room temperature.

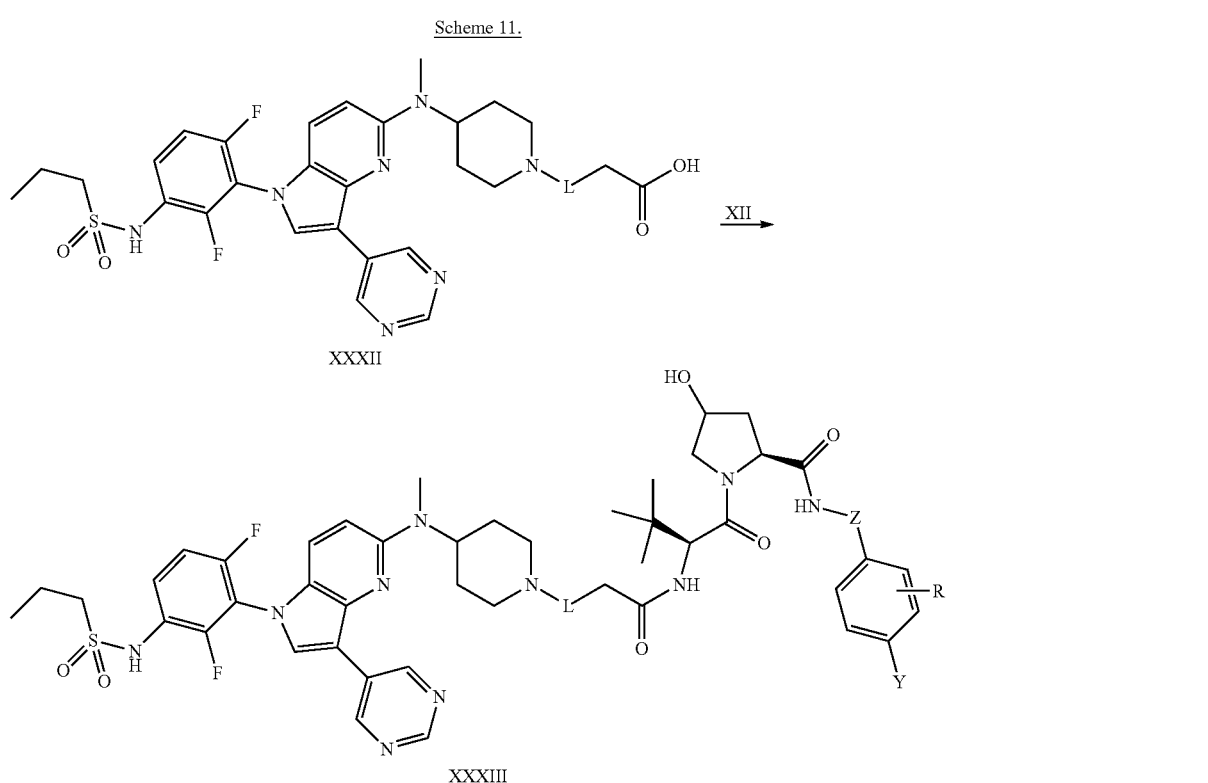

Alternatively, a compound of formula XXXII, prepared from a compound of formula XIX through simple transformations well-known by one skilled in the art, e.g. alkylation or reductive amination, may be reacted with a compound of formula XII to provide a compound of formula XXXIII under amide formation conditions, e.g. (benzotriazol-1-yloxy)tripyrrolidinophosphonium hexafluorophosphate, diisopropylethylamine, DMF, room temperature.

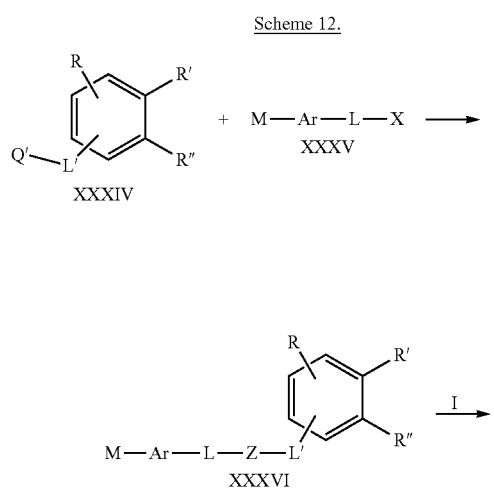

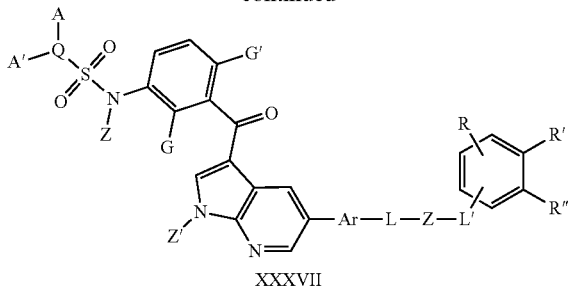

A compound of formula XXXIV may be reacted with a reagent XXXV (commercially available or readily prepared using standard reaction techniques known to one skilled in the art) to prepare a compound of formula XXXVI. In all cases, M represents a functional group capable of undergoing palladium-catalyzed transmetallation, e.g. a boronic acid, boronic ester, or trialkylstannane; or alternatively M represents a functional group capable of undergoing palladium-catalyzed oxidative addition, e.g. an iodide, bromide, chloride, or trifluoromethanesulfonate; Ar represents an aromatic or heteroaromatic ring system with one or more optional substitutions; L represents a linker; R represents one or more optional substituents; and R' and R" are either both carboxylic esters, e.g. $CO_2CH_2CH_3$, R is a carboxylic ester e.g. $CO_2CH_3$ and R' is CN or C(O)H, or together R and R' form either:

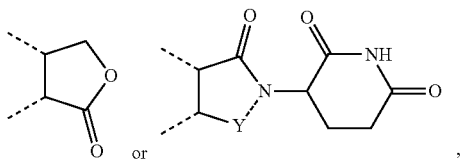

wherein Y is either CH$_2$ or C=O.

In some cases, X is a primary or secondary amine, optionally cyclized into a 4 to 8 membered heterocyclic ring, Q' is a suitable leaving group such as fluorine or chlorine, L' is null, and reaction conditions are those for a nucleophilic aromatic substitution, e.g. triethylamine, DMSO, 70° C. In these cases, Z becomes the corresponding secondary or tertiary amine derived from X.

In other cases, X is a suitable leaving group, e.g. p-toluenesulfonate, methanesulfonate, iodide, bromide, or chloride, Q is OH, L' is null or an optional linker, and reaction conditions are those for a nucleophilic substitution, e.g. potassium carbonate, potassium iodide, DMSO, 60° C. In these cases, Z is O.

In other cases, X is OH, Q is OH, L' is null, and reaction conditions may be those for a Mitsunobu reaction, e.g. triphenylphosphine, diethylazodicarboxylate, THF. In these cases, Z is O.

In other cases, X is a primary or secondary amine, optionally cyclized into a 4 to 8 membered heterocyclic ring; Q is C(O)R''', wherein R''' is H or alkyl, which may be optionally tied back into L' to form a ring; L' is null or an optional linker, and reaction conditions may be those for a reductive amination reaction, e.g. borane-picoline in dichloroethane at 40° C.; or sodium triacetoxyborohydride, diisopropylethylamine, and acetic acid in dichloromethane at 35° C. In these cases, Z is the primary or secondary amine plus a CR''' unit. It will be apparent to one skilled in the art that the positions of the primary or secondary amine in X and CR' in Q may be reversed as needed.

A compound of formula XXXVI may be further transformed into a different compound of formula XXXVI. When R' is a carboxylic ester and R'' is CN, reduction of R'' to CHO may be accomplished, e.g. by treatment with sodium hypophosphite and Raney nickel in a mixture of pyridine, acetic acid, and water. When R' and R'' together form

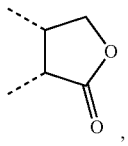

solvolysis e.g. with sodium hydroxide in an alcoholic solvent and tetrahydrofuran may afford a compound where R' is a carboxylic ester and R'' is CH$_2$OH. This compound may be further oxidized, e.g. with manganese dioxide, to afford an equivalent compound XXXVI where R' is a carboxylic ester and R'' is CHO. Such compounds where R' is a carboxylic ester and R'' is CHO may then be reacted with 3-aminoglutarimide in the presence of e.g. sodium triacetoxyborohydride, diisopropylethylamine, and acetic acid in methanol and dichloromethane to afford a new compound of formula XXXVI wherein R' and R'' together are

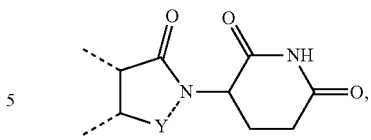

wherein Y is CH$_2$. As needed, the composition of L or L' in XXXVI may be adjusted in oxidation state e.g. by treatment with reagents including but not limited to chloro{[(1R,2R)-(−)-2-amino-1,2-diphenylethyl](4-toluenesulfonyl)amido}(mesitylene)ruthenium(II), formic acid, and triethylamine in dichloromethane at 40° C.; or (−)-B-chlorodiisopinocampheylborane in tetrahydrofuran at 50° C.

A compound of formula XXXVI may then be further transformed by reaction with a compound I under palladium-catalyzed cross-coupling conditions, e.g. with a suitable palladium catalyst such as bis(di-tert-butyl(4-dimethylaminophenyl)phosphine)dichloropalladium(II), suitable base such as cesium fluoride, suitable solvent such as mixtures of 1,4-dioxane and water, at a suitable temperature such as 100° C., with or without microwave irradiation to produce a compound of formula XXXVII. Herein Q, A, A', G, G', M', Z, and Z' are as defined in Scheme 1.

In cases where one or both of Z or Z' are a protecting group, such protecting group may be removed from a compound XXXVII, e.g. by treatment with trifluoroacetic acid when Z and/or Z' are t-butoxycarbonyl, to afford a different compound of formula XXXVII wherein Z and Z' are H.

In cases where in R' and R'' are both carboxylic esters in a compound XXXVII, hydrolysis e.g. with sodium hydroxide in methanol and water may afford a different compound XXXVII where R' and R'' are CO$_2$H. Such a compound may subsequently be reacted with e.g. 3-aminoglutarimide, (benzotriazol-1-yloxy)tris(dimethylamino)phosphonium hexafluorophosphate, and diisopropylamine in N,N-dimethylformamide to afford a new compound of formula XXXVII wherein R' and R'' together are

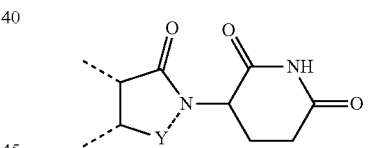

wherein Y is C=O.

A compound of formula XXXVII may be further transformed into a different compound of formula XXXVII. When R' is a carboxylic ester and R'' is CN, reduction of R'' to CHO may be accomplished, e.g. by treatment with sodium hypophosphite and Raney nickel in a mixture of pyridine, acetic acid, and water. Such compounds where R' is a carboxylic ester and R'' is CHO may then be reacted with 3-aminoglutarimide in the presence of e.g. sodium triacetoxyborohydride, diisopropylethylamine, and acetic acid in methanol and dichloromethane to afford a new compound of formula XXXVII wherein R' and R'' together are

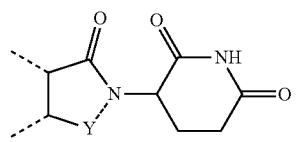

wherein Y is CH$_2$.

As needed, mixtures of enantiomers or diastereomers of any compounds XXXVI or XXXVII may be resolved into their constituent enantiomers or diastereomers using techniques known to one skilled in the art, including but not limited to preparative high performance liquid chromatography or preparative supercritical fluid chromatography.
Scheme 13.
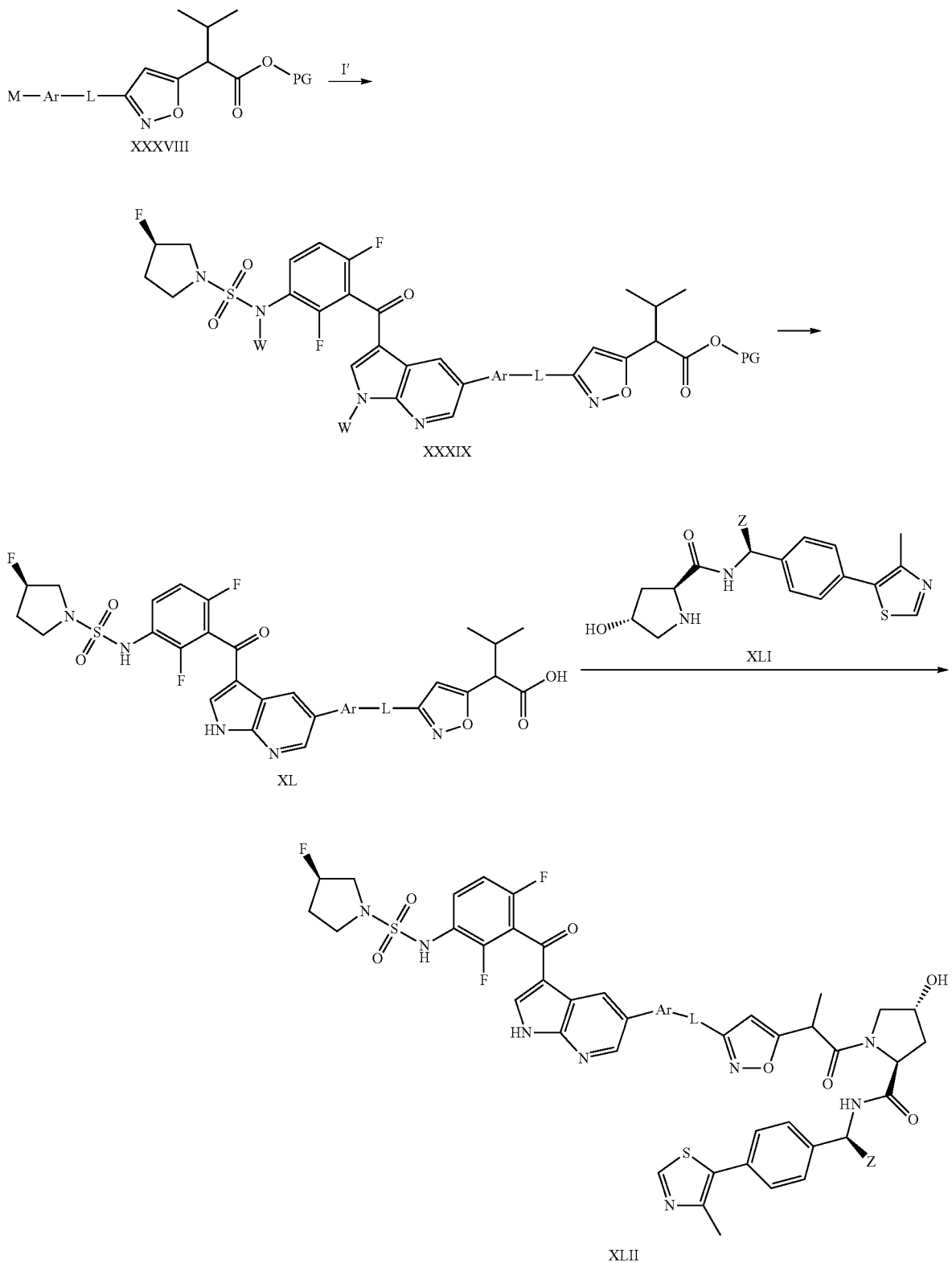

A compound of formula I' may be reacted with a reagent XXXVIII (readily prepared using standard reaction techniques known to one skilled in the art) under palladium-catalyzed cross-coupling conditions, e.g. [1,1'-bis(diphenylphosphino)ferrocene]dichloropalladium(II), sodium carbonate, in a suitable solvent such as 1,4-dioxane/water mixture, at a suitable temperature such as 100° C., with or without microwave heating, to produce a compound of formula XXXIX. One of M or M' represents a functional group capable of undergoing palladium-catalyzed transmetallation, e.g. a boronic acid, boronic ester, or trialkylstannane; the other of M or M' represents a functional group capable of undergoing palladium-catalyzed oxidative addition, e.g. an iodide, bromide, chloride, or trifluoromethanesulfonate; Ar represents an aromatic or heteroaromatic ring system; L represents an optional linker or portion of a linker; PG represents a suitable ester protecting group, e.g. methyl, ethyl, or t-butyl; W represents an optional protecting group, e.g. 2-(trimethylsilyl)ethoxymethyl; and the isoxazole of compound XXXVIII and following structures may have an optional substituent. Compounds of formula XXXIX may be converted to a compound of formula XL by treatment with a reagent suitable for the removal of the optional W, e.g. hydrogen chloride in 1,4-dioxane and methanol or ethylenediamine and tetra-n-butylammonium fluoride when W is 2-(trimethylsilyl)ethoxymethyl; followed by treatment with a reagent suitable for the removal of PG, e.g. sodium hydroxide in methanol and water at 40° C. when PG is methyl or ethyl. Compound XL may then be reacted with compound XLI, wherein Z is an optional substituent, e.g. H, methyl, or hydroxymethyl, to produce compounds of formula XLII under amide formation conditions, e.g. N-[(dimethylamino)-1H-1,2,3-triazolo-[4,5-b]pyridin-1-ylmethylene]-N-methylmethanaminium hexafluorophosphate N-oxide, diisopropylethylamine, DMF, room temperature. Optionally, as will be apparent to one skilled in the art, the order of the amide coupling and palladium-catalyzed cross-coupling steps may be reversed in the reaction sequence via suitable manipulations of M, M', and PG.

Scheme 14.

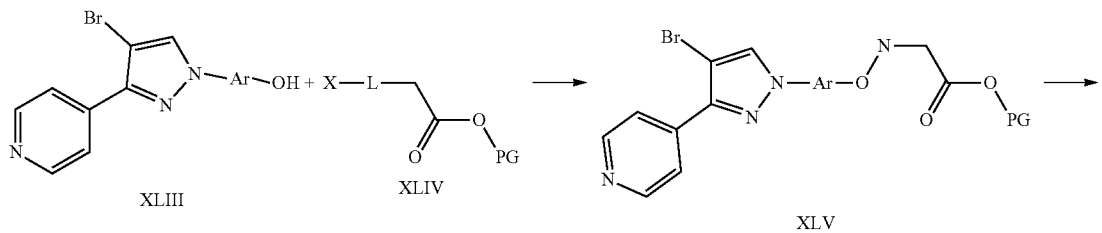

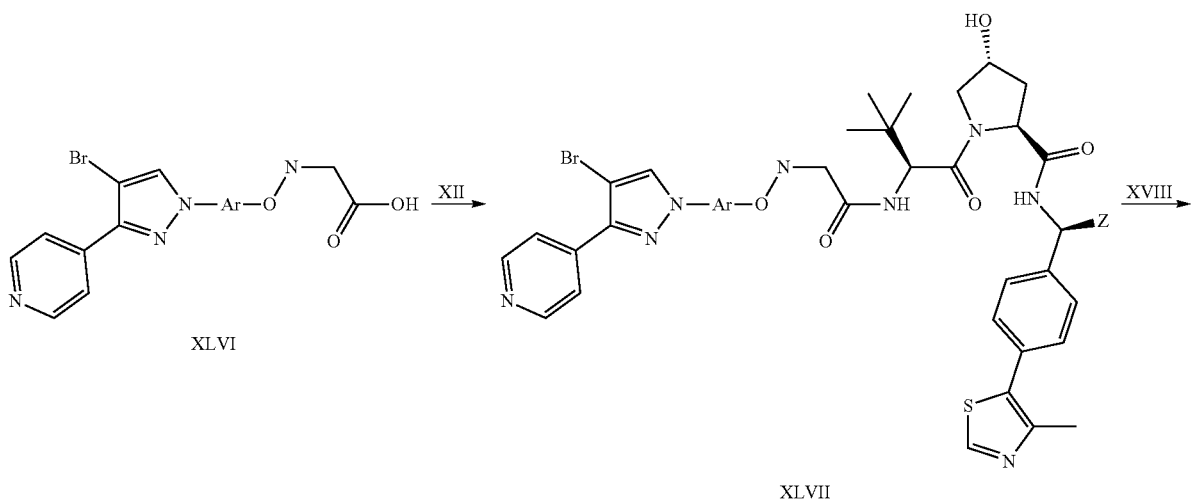

-continued

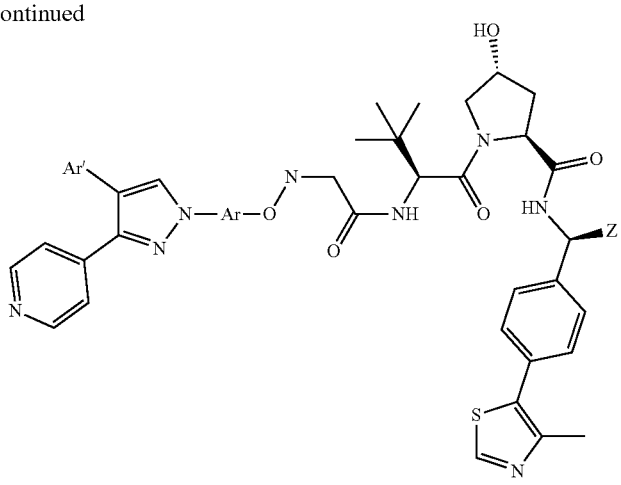

XLVIII

A compound of formula XLIII may be reacted with a reagent XLIV (commercially available or readily prepared using standard reaction techniques known to one skilled in the art) under nucleophilic substitution conditions, e.g. cesium carbonate, DMF, 75° C., to produce a compound of formula XLV. Ar represents an aromatic or heteroaromatic ring system; X represents a suitable leaving group, e.g. p-toluenesulfonate, methanesulfonate, iodide, bromide, or chloride; L represents an optional linker; and PG represents a suitable ester protecting group, e.g. methyl, ethyl, or t-butyl. Compounds of formula XLV may be converted to a compound of formula XLVI by treatment with a reagent suitable for the removal of PG, e.g. 3 N hydrochloric acid in 1,4-dioxane at room temperature when PG is t-butyl. Compound XLVI may then be reacted with compounds XII as defined in Scheme 3 to produce compounds of formula XLVII under amide formation conditions, e.g. (benzotriazol-1-yloxy)tripyrrolidinophosphonium hexafluorophosphate, diisopropylethylamine, DMF, room temperature. The compound of formula XLVII may then be treated with a reagent XVIII as defined in Scheme 5 to produce a compound of formula XLVIII. In cases where the group Ar' contains optional substituents, e.g. a ketone, these may undergo further functionalization, e.g. by treatment with hydroxylamine hydrochloride and pyridine at room temperature, to provide further compounds of formula XLVIII.

Scheme 15.

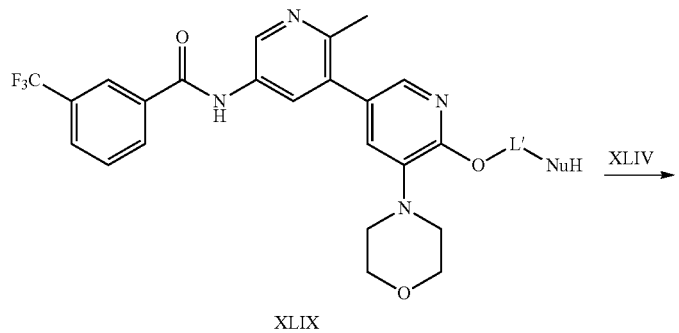

XLIX

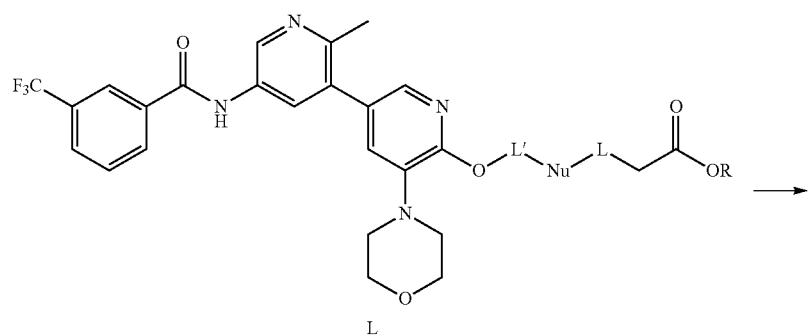

L

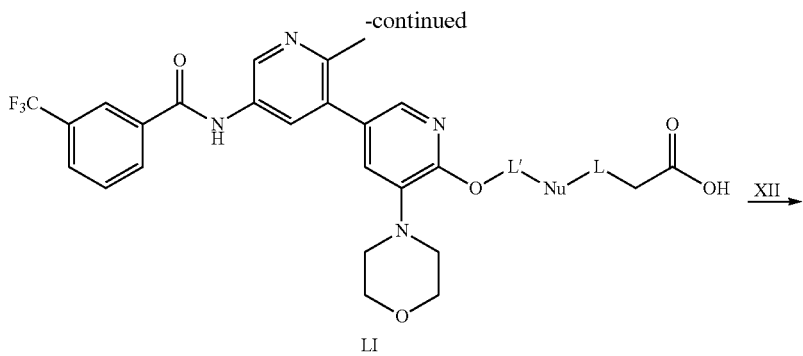

LI

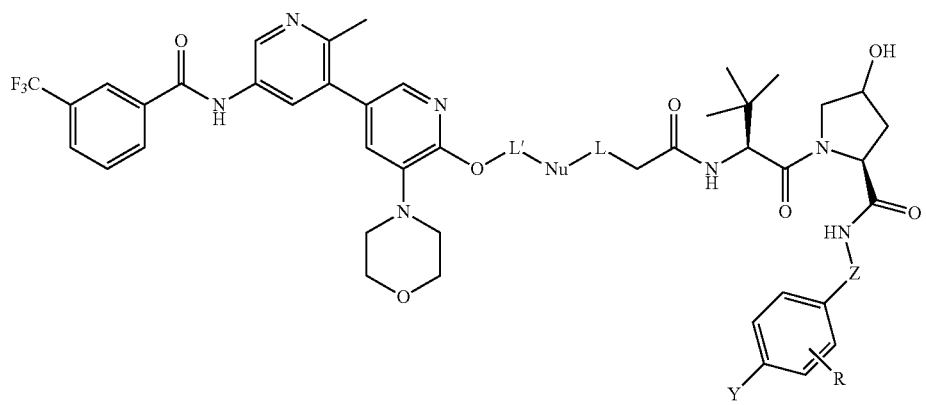

LII

A compound of formula XLIX (readily prepared using standard reaction techniques known to one skilled in the art) may be reacted with a compound of formula A compound of formula XLIX may be reacted with a reagent XLIV under nucleophilic substitution conditions, e.g. diisopropylethylamine, potassium iodide, acetonitrile, 100° C., to produce a compound of formula L. L' represents an optional linker or portion of a linker; Nu-H represents a suitable nucleophile such as an alcohol or secondary amine; X represents a suitable leaving group, e.g. p-toluenesulfonate, methanesulfonate, iodide, bromide, or chloride; L represents an optional linker; and PG represents a suitable ester protecting group, e.g. methyl, ethyl, or t-butyl. Compounds of formula L may be converted to a compound of formula LI by treatment with a reagent suitable for the removal of PG, e.g. trifluoroacetic acid, dichloromethane, 30° C. when PG is t-butyl. Compound LI may then be reacted with compounds XII as defined in Scheme 3 to produce compounds of formula LII under amide formation conditions, e.g. 1-ethyl-3-(3-dimethylaminopropyl)carbodiimide, 1-hydroxybenzotriazole, triethylamine, DMF, 30° C.

Scheme 16.

XLIX + 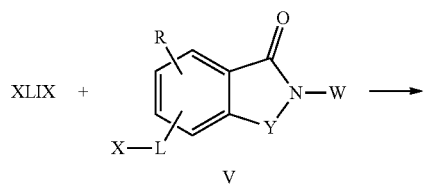

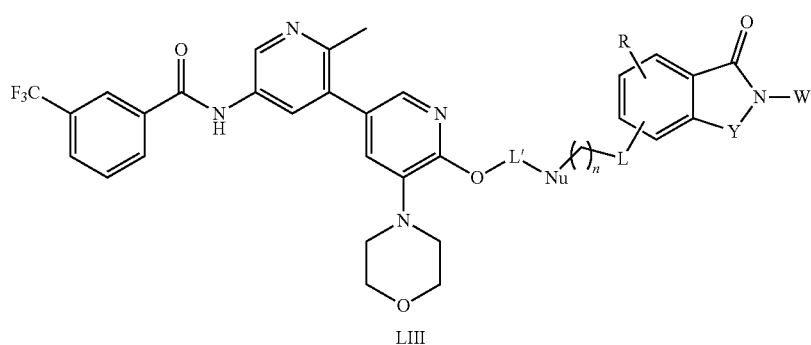

LIII

A compound of formula XLIX as defined in Scheme 15 may be reacted with compound V to produce compound LIII, wherein L represents an optional linker or portion of a linker, Y is CH$_2$ or C=O, X is either a suitable leaving group (e.g. OMs, OTs, Cl, etc.) or an aldehyde (CHO); R is an optional substituent (e.g. F or OCH$_3$); and W is:

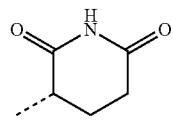

when Y is C=O; or

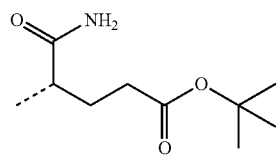

when Y is CH$_2$.

When X is a leaving group, n is 0, Nu-H is a primary or secondary amine or alcohol, and suitable reaction conditions are those for an alkylation reaction, e.g. potassium carbonate, DMF, 70° C. When X is an aldehyde, n is 1, Nu-H is a primary or secondary amine, and suitable reaction conditions are those for a reductive amination reaction, e.g. sodium cyanoborohydride, methanol, dichloromethane, acetic acid, room temperature. It will be apparent to one skilled in the art that the positions of Nu-H in XLIX and X in V' may also be reversed, such that the positions of Nu and (CH$_2$)$_n$ are reversed in compound LIII. A compound of formula LIII where W is in an open chain form may be further transformed to another compound of formula LIII where W is a glutarimide by cyclization under appropriate conditions, e.g. benzenesulfonic acid, acetonitrile, 100° C.

Scheme 17.

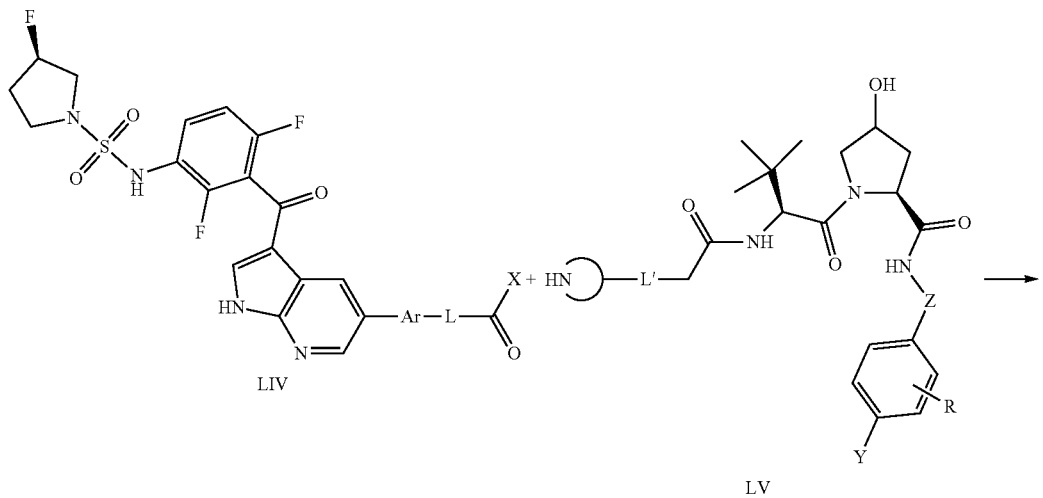

LIV

LV

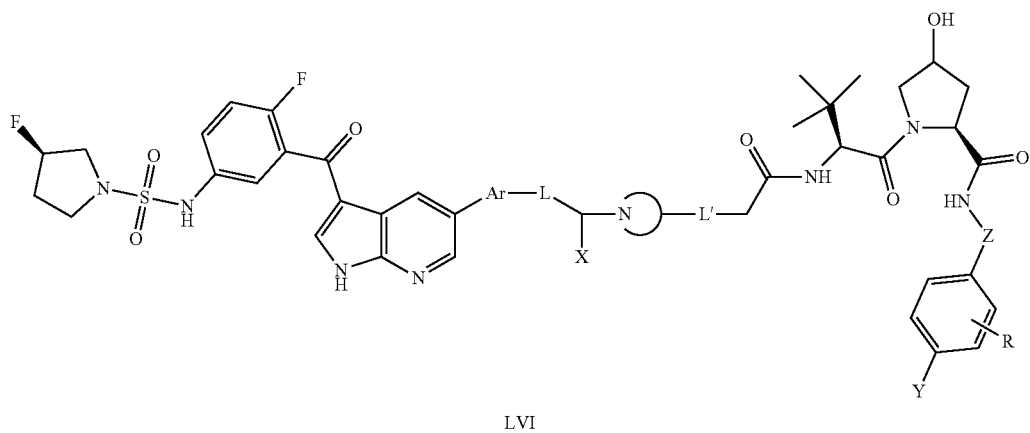

LVI

A compound of formula LIV (prepared using standard conditions known to one skilled in the art, analogous to the synthesis of compounds III in Scheme 1) may be reacted with a compound of formula LV (prepared using standard conditions known to one skilled in the art, analogous to the synthesis of compounds XV in Scheme 2) under reductive amination conditions, e.g. sodium triacetoxyborohydride, triethylamine, dichloroethane, 30° C., to produce a compound of formula LVI. Herein, Ar is an aromatic or heteroaromatic ring system; L and L' are an optional linker or portion of a linker; X is H or an optional substituent, which may be optionally cyclized into L to form a ring;

represents a primary or secondary amine, optionally cyclized into a 4 to 8 membered heterocyclic ring; and R, Z, and Y are as defined for compound XII in Scheme 3. It will be apparent to one skilled in the art that the positions of C(O)X in LIV and

in LV may be reversed, with X optionally cyclized into L' to form a ring, such that the positions of CHX and

are reversed in compound LVI.

Scheme 18.

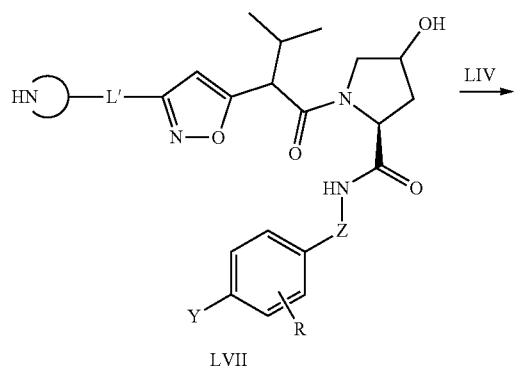

LVII

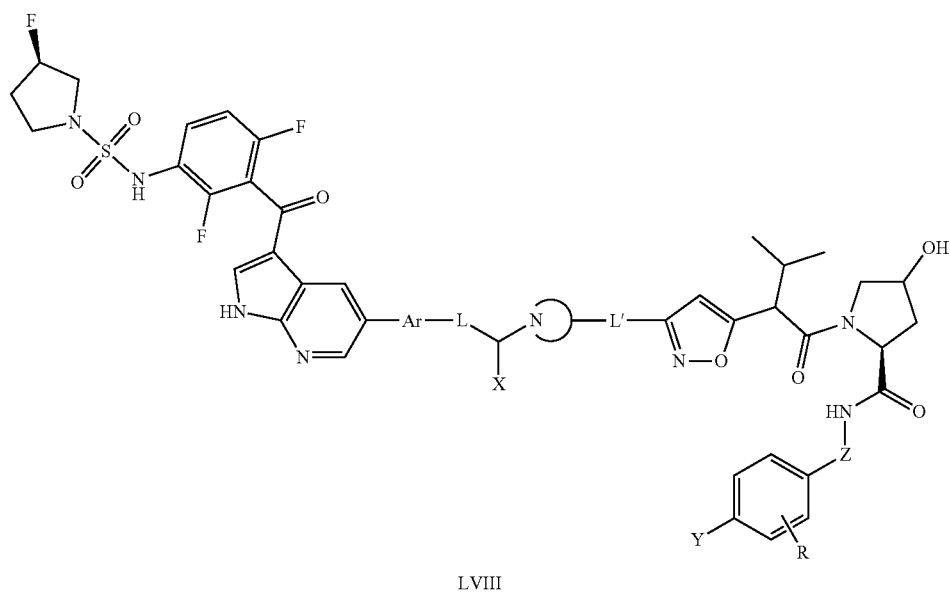

LVIII

A compound of formula LIV (prepared using standard conditions known to one skilled in the art, analogous to the synthesis of compounds III in Scheme 1) may be reacted with a compound of formula LVII (prepared using standard conditions known to one skilled in the art) under reductive amination conditions, e.g. sodium triacetoxyborohydride, acetic acid, dichloromethane, methanol, 30° C., to produce a compound of formula LVIII. Herein, Ar is an aromatic or heteroaromatic ring system; L and L' are an optional linker or portion of a linker; X is H or an optional substituent, which may be optionally cyclized into L to form a ring;

represents a primary or secondary amine, optionally cyclized into a 4 to 8 membered heterocyclic ring; R, Z, and Y are as defined for compound XII in Scheme 3; and the isoxazole of compound LVII and following structures may have an optional substituent. It will be apparent to one skilled in the art that the positions of C(O)X in LIV and

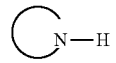

in LVII may be reversed, with X optionally cyclized into L' to form a ring, such that the positions of CHX and

are reversed in compound LVIII.

Exemplary Synthesis of Exemplary Compound 160: (3R)—N-[3-[5-[4-[4-[[4-[2-[(3S)-2,6-dioxo-3-piperidyl]-1-oxo-isoindolin-5-yl]-1-piperidyl]methyl]-1-piperidyl]phenyl]-1H-pyrrolo[2,3-b]pyridine-3-carbonyl]-2,4-difluoro-phenyl]-3-fluoro-pyrrolidine-1-sulfonamide

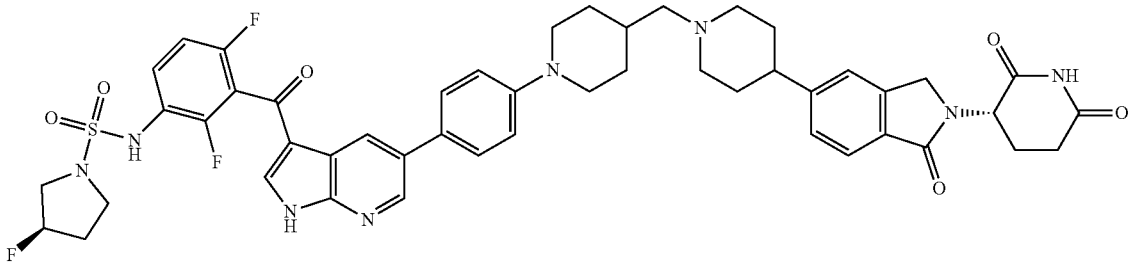 [SMILES: O=C1CC[C@H](N2Cc3cc(C4CCN(CC5CCN(c6ccc(-c7cnc8[nH]cc(C(=O)c9c(F)ccc(NS(=O)(=O)N%10CC[C@@H](F)C%10)c9F)c8c7)cc6)CC5)CC4)ccc3C2=O)C(=O)N1]

Step A: tert-butyl (4S)-5-amino-4-(5-bromo-1-oxo-isoindolin-2-yl)-5-oxo-pentanoate

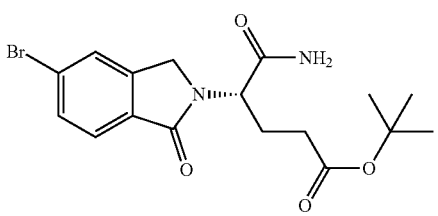 [SMILES: CC(C)(C)OC(=O)CC[C@@H](C(N)=O)N1Cc2cc(Br)ccc2C1=O]

To a solution of methyl 4-bromo-2-(bromomethyl)benzoate (25.0 g, 81.1 mmol) in N,N-dimethylformamide (300 mL) was added N,N-diisopropylethylamine (52.46 g, 405.8 mmol, 70.70 mL) and tert-butyl (4S)-4,5-diamino-5-oxo-pentanoate (18.06 g, 89.30 mmol). The mixture was stirred at 50° C. for 2 hours. Then the mixture was stirred at 100° C. for 12 hours. The reaction mixture was diluted with water (400 mL) and extracted with ethyl acetate (4×150 mL). The combined organic layers were washed with brine (3×200 mL), dried over anhydrous sodium sulfate, filtered and concentrated under reduced pressure to give a residue. The residue was purified by flash silica gel chromatography (0 to 50% ethyl acetate:petroleum ether). Then the product was triturated with 1:1 petroleum ether:ethyl acetate at 25° C. for 20 minutes to give tert-butyl (4S)-5-amino-4-(5-bromo-1-oxo-isoindolin-2-yl)-5-oxo-pentanoate (16 g, 49%) as a white solid. MS (ESI): m/z 341.2 [M−57+H]⁺.

Step B: benzyl 4-[2-[(1S)-4-tert-butoxy-1-carbamoyl-4-oxo-butyl]-1-oxo-isoindolin-5-yl]-3,6-dihydro-2H-pyridine-1-carboxylate

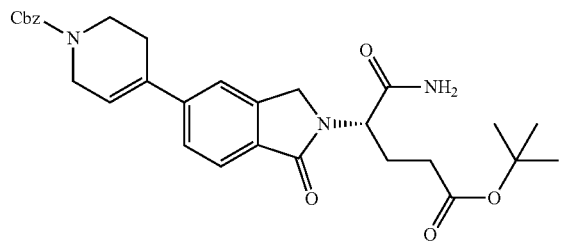 [SMILES: CC(C)(C)OC(=O)CC[C@@H](C(N)=O)N1Cc2cc(C3=CCN(C(=O)OCc4ccccc4)CC3)ccc2C1=O]

To a solution of tert-butyl (4S)-5-amino-4-(5-bromo-1-oxo-isoindolin-2-yl)-5-oxo-pentanoate (2.0 g, 5.0 mmol) and benzyl 4-(4,4,5,5-tetramethyl-1,3,2-dioxaborolan-2-yl)-3,6-dihydro-2H-pyridine-1-carboxylate (1.90 g, 5.54 mmol) in water (4 mL) and 1,4-dioxane (20 mL) was added cesium fluoride (2.29 g, 15.10 mmol) and dichloro[1,1'-bis(di-t-butylphosphino)ferrocene]palladium(II) (328 mg, 0.50 mmol). The mixture was stirred at 90° C. for 12 hours. The mixture was diluted with water (50 mL) and extracted with ethyl acetate (3×35 mL). The combined organic layers were washed with brine (2×80 mL), dried over anhydrous sodium sulfate, filtered, and concentrated. The crude product was purified by column chromatography (0 to 1% methanol:dichloromethane) to give benzyl 4-[2-[(1S)-4-tert-butoxy-1-carbamoyl-4-oxo-butyl]-1-oxo-isoindolin-5-yl]-3,6-dihydro-2H-pyridine-1-carboxylate (2.4 g, 84%) as a brown solid. MS (ESI): m/z 534.3 [M+H]⁺; ¹H NMR (400 MHz, CDCl₃) δ 7.75 (d, J=8.0 Hz, 1H), 7.48-7.41 (m, 2H), 7.40-7.31 (m, 5H), 6.60 (s, 1H), 6.21-6.03 (m, 1H), 5.71 (s, 1H), 5.18 (s, 2H), 4.92 (dd, J=6.4, 8.8 Hz, 1H), 4.59-4.38 (m, 2H), 4.23-4.15 (m, 2H), 3.74 (t, J=5.6 Hz, 2H), 2.56 (s, 2H), 2.42-2.31 (m, 2H), 2.30-2.21 (m, 1H), 2.20-2.11 (m, 1H), 1.40 (s, 9H).

Step C: benzyl 4-[2-[(3S)-2,6-dioxo-3-piperidyl]-1-oxo-isoindolin-5-yl]-3,6-dihydro-2H-pyridine-1-carboxylate

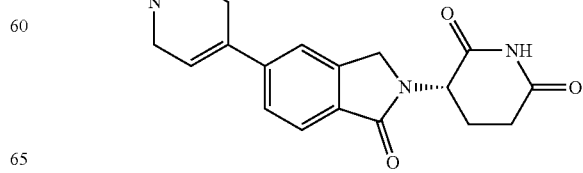

To a solution of benzyl 4-[2-[(1S)-4-tert-butoxy-1-carbamoyl-4-oxo-butyl]-1-oxo-isoindolin-5-yl]-3,6-dihydro-2H-pyridine-1-carboxylate (2.40 g, 4.50 mmol) in acetonitrile (20 mL) was added benzenesulfonic acid (2.13 g, 13.4 mmol). The mixture was stirred at 80° C. for 12 hours. The mixture was concentrated. The crude product was purified by preparative HPLC (Phenomenex Luna C18, 30-60% acetonitrile:(0.225% formic acid in water)) to give benzyl 4-[2-[(3S)-2,6-dioxo-3-piperidyl]-1-oxo-isoindolin-5-yl]-3,6-dihydro-2H-pyridine-1-carboxylate (1.1 g, 53%) as a brown solid.

MS (ESI): m/z 460.2 [M+H]$^+$; $^1$H NMR (400 MHz, DMSO-d$_6$) δ 10.98 (s, 1H), 7.69 (d, J=8.0 Hz, 1H), 7.65 (s, 1H), 7.59 (d, J=7.6 Hz, 1H), 7.43-7.30 (m, 5H), 6.38-6.25 (m, 1H), 5.17-5.07 (m, 3H), 4.50-4.40 (m, 1H), 4.36-4.28 (m, 1H), 4.20-4.06 (m, 2H), 3.65 (s, 2H), 2.97-2.84 (m, 1H), 2.65-2.53 (m, 3H), 2.45-2.34 (m, 1H), 2.05-1.95 (m, 1H).

Step D: benzyl 4-[2-[(3S)-2,6-dioxo-3-piperidyl]-1-oxo-isoindolin-5-yl]-3,6-dihydro-2H-pyridine-1-carboxylate

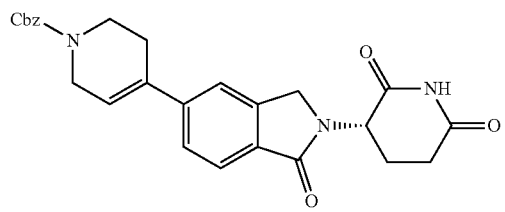 [SMILES: O=C1CC[C@H](N2Cc3cc(C4=CCN(C(=O)OCc5ccccc5)CC4)ccc3C2=O)C(=O)N1]

Benzyl 4-[2-[(3S)-2,6-dioxo-3-piperidyl]-1-oxo-isoindolin-5-yl]-3,6-dihydro-2H-pyridine-1-carboxylate (1 g, 2.18 mmol) was separated by SFC (REGIS (R,R)WHELK-O1, 70% IPA:(0.1% ammonia in water) to give benzyl 4-[2-[(3S)-2,6-dioxo-3-piperidyl]-1-oxo-isoindolin-5-yl]-3,6-dihydro-2H-pyridine-1-carboxylate (900 mg, 90%) as a brown solid.

Step E: (3S)-3-[1-oxo-5-(4-piperidyl)isoindolin-2-yl] piperidine-2,6-dione

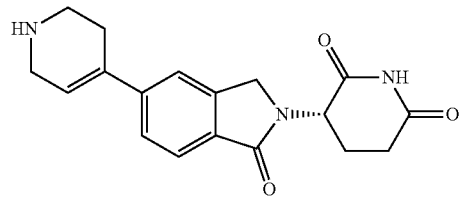 [SMILES: O=C1CC[C@H](N2Cc3cc(C4=CCNCC4)ccc3C2=O)C(=O)N1]

To a solution of benzyl 4-[2-[(3S)-2,6-dioxo-3-piperidyl]-1-oxo-isoindolin-5-yl]-3,6-dihydro-2H-pyridine-1-carboxylate (800 mg, 1.74 mmol) in tetrahydrofuran (16 mL) was added 10% palladium on activated carbon (100 mg) and aqueous 1 M hydrochloric acid (3.48 mL) under nitrogen. The suspension was degassed under vacuum and purged with hydrogen several times. The mixture was stirred under hydrogen (15 psi) at 20° C. for 12 hours. The mixture was filtered and concentrated to afford (3S)-3-[1-oxo-5-(4-piperidyl)isoindolin-2-yl]piperidine-2,6-dione hydrochloride (570 mg, 89%) as a pink oil.

Step F: (3R)—N-[3-[5-[4-[4-[[4-[2-[(3S)-2,6-dioxo-3-piperidyl]-1-oxo-isoindolin-5-yl]-1-piperidyl]methyl]-1-piperidyl]phenyl]-1H-pyrrolo[2,3-b]pyridine-3-carbonyl]-2,4-difluoro-phenyl]-3-fluoro-pyrrolidine-1-sulfonamide

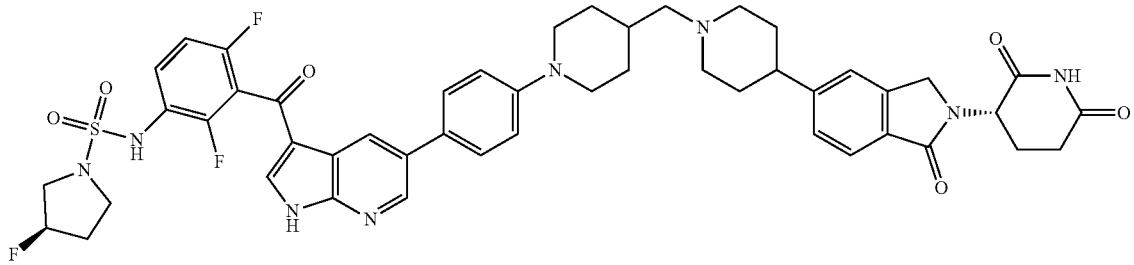 [SMILES: O=C1CC[C@H](N2Cc3cc(C4CCN(CC5CCN(c6ccc(-c7cnc8[nH]cc(C(=O)c9c(F)ccc(NS(=O)(=O)N%10CC[C@@H](F)C%10)c9F)c8c7)cc6)CC5)CC4)ccc3C2=O)C(=O)N1]

To a solution of (3S)-3-[1-oxo-5-(4-piperidyl)isoindolin-2-yl]piperidine-2,6-dione hydrochloride (570 mg, 1.57 mmol) in methanol (5 mL) and dichloroethane (5 mL) was added sodium acetate (128 mg, 1.57 mmol). The mixture was stirred at 20° C. for 30 minutes. Then (3R)—N-[2,4-difluoro-3-[5-[4-(4-formyl-1-piperidyl)phenyl]-1H-pyrrolo[2,3-b]pyridine-3-carbonyl]phenyl]-3-fluoro-pyrrolidine-1-sulfonamide (862 mg, 1.41 mmol) was added to the mixture. The mixture was stirred at 20° C. for 30 minutes. Then sodium cyanoborohydride (147 mg, 2.35 mmol) was added to the mixture. The mixture was stirred at 20° C. for 1 hour. The mixture was diluted with brine (30 mL) and extracted with tetrahydrofuran (3×30 mL). The combined organic layers were washed with brine (50 mL), dried with anhydrous sodium sulfate, filtered, and concentrated. The crude product was purified by silica column chromatography (0 to 6.7% methanol:dichloromethane). Then the product was diluted with tetrahydrofuran (50 mL) and washed with sodium bicarbonate (3×30 mL), brine (2×30 mL), dried with anhydrous sodium sulfate, filtered, and concentrated. The product was purified by column chromatography (0 to 6.7% methanol:dichloromethane) to afford (3R)—N-[3-[5-[4-[4-[[4-[2-[(3S)-2,6-dioxo-3-piperidyl]-1-oxo-isoindolin-5-yl]-1-piperidyl]methyl]-1-piperidyl]phenyl]-1H-pyrrolo[2,3-b]pyridine-3-carbonyl]-2,4-difluoro-phenyl]-3-fluoro-pyrrolidine-1-sulfonamide (552 mg, 36%) as a yellow solid. MS (ESI): m/z 923.2 [M]$^+$; $^1$H NMR (400 MHz, DMSO-d$_6$) δ 13.01-12.80 (m, 1H), 10.98 (s, 1H), 9.98-9.66 (m, 1H), 8.65 (d, J=2.0 Hz, 1H), 8.53 (s, 1H), 8.07 (s, 1H), 7.69-7.55 (m, 4H), 7.51 (s, 1H), 7.41 (d, J=7.6 Hz, 1H), 7.27 (t, J=8.8 Hz, 1H), 7.07 (d, J=8.8 Hz, 2H), 5.39-5.19 (m, 1H), 5.11 (dd, J=5.2, 13.2 Hz, 1H), 4.47-4.38 (m, 1H), 4.35-4.26 (m, 1H), 3.80 (d, J=12.0 Hz, 2H), 3.48 (s, 1H), 3.43-3.36 (m, 2H), 3.30 (s, 2H), 3.03 (d, J=10.0 Hz, 2H), 2.97-2.85 (m, 1H), 2.74 (t, J=11.6 Hz, 2H), 2.60 (d, J=17.2 Hz, 1H), 2.46-2.37 (m, 1H), 2.32-2.21 (m, 2H), 2.18-2.08 (m, 3H), 2.06-1.94 (m, 2H), 1.89-1.69 (m, 7H), 1.25 (q, J=10.8 Hz, 2H).

The following exemplary compounds may be prepared by a procedure analogous to that described for Exemplary Compound 160: 161, 2, 3, 6, 8, 11, 12, 13, 14, 18, 20, 21, 22, 24, 25, 38, 39, 40, 41, 44, 45, 46, 47, 49, 51, 52, 54, 55, 56, 59, 62, 63, 64, 65, 70, 80, 81, 83, 84, 89, 92, 93, 99, 100, 102, 110, 111, 118, 131, 132, 133, 134, 137, 144, 148, 149, 150, 151, 155, 167, 169, 175, 177, 181, 183, 185, 190, 191, 195, 198, 126, 127, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, and 292.

Exemplary Synthesis of Exemplary Compound 142: (3R)—N-[3-[5-[4-[6-[[1-[2-(2,6-dioxo-3-piperidyl)-1-oxo-isoindolin-5-yl]-4-hydroxy-4-piperidyl]methyl]-2,6-diazaspiro[3.3]heptan-2-yl]phenyl]-1H-pyrrolo[2,3-b]pyridine-3-carbonyl]-2,4-difluoro-phenyl]-3-fluoro-pyrrolidine-1-sulfonamide Step A: tert-butyl 4-[[2-(4-bromophenyl)-2,6-diazaspiro[3.3]heptan-6-yl]methyl]-4-hydroxy-piperidine-1-carboxylate

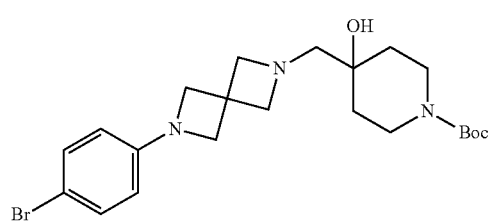

To a solution of 2-(4-bromophenyl)-2,6-diazaspiro[3.3]heptane (1.2 g, 4.7 mmol) and tert-butyl 1-oxa-6-azaspiro[2.5]octane-6-carboxylate (1.21 g, 5.69 mmol) in isopropanol (30 mL) was added triethylamine (1.44 g, 14.2 mmol, 1.98 mL). The mixture was stirred at 80° C. for 12 hours. The reaction mixture concentrated. The residue was purified by column chromatography (1:200 to 1:25 methanol:dichloromethane) to afford tert-butyl 4-[[2-(4-bromophenyl)-2,6-diazaspiro[3.3]heptan-6-yl]methyl]-4-hydroxy-piperidine-1-carboxylate (1.7 g, 76%) as a yellow solid. MS (ESI): m/z 466.2 [M+H]$^+$.

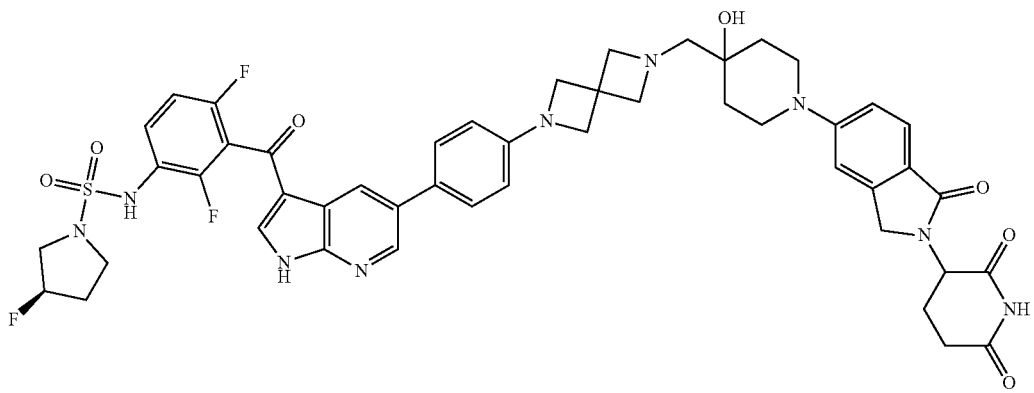 [SMILES: O=C1CCC(N2Cc3cc(N4CCC(O)(CN5CC6(C5)CN(c5ccc(-c7cnc8[nH]cc(C(=O)c9c(F)ccc(NS(=O)(=O)N%10CC[C@@H](F)C%10)c9F)c8c7)cc5)C6)CC4)ccc3C2=O)C(=O)N1]

Step B: tert-butyl 4-[[2-[4-[3-[3-[tert-butoxycarbonyl-[(3R)-3-fluoropyrrolidin-1-yl]sulfonyl-amino]-2,6-difluoro-benzoyl]-1H-pyrrolo[2,3-b]pyridin-5-yl]phenyl]-2,6-diazaspiro[3.3]heptan-6-yl]methyl]-4-hydroxy-piperidine-1-carboxylate

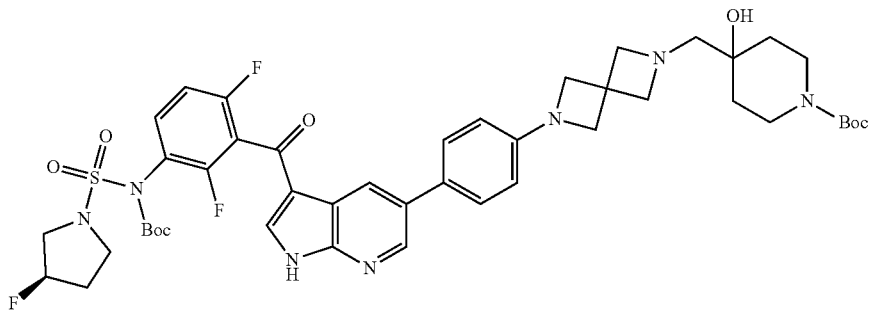 [SMILES: CC(C)(C)OC(=O)N1CCC(O)(CN2CC3(C2)CN(c2ccc(-c4cnc5[nH]cc(C(=O)c6c(F)ccc(N(C(=O)OC(C)(C)C)S(=O)(=O)N7CC[C@@H](F)C7)c6F)c5c4)cc2)C3)CC1]

To a solution of tert-butyl 3-[3-[tert-butoxycarbonyl-[(3R)-3-fluoropyrrolidin-1-yl]sulfonyl-amino]-2,6-difluoro-benzoyl]-5-(4,4,5,5-tetramethyl-1,3,2-dioxaborolan-2-yl)pyrrolo[2,3-b]pyridine-1-carboxylate (1.13 g, 1.50 mmol) and tert-butyl 4-[[2-(4-bromophenyl)-2,6-diazaspiro[3.3]heptan-6-yl]methyl]-4-hydroxy-piperidine-1-carboxylate (700 mg, 1.50 mmol) in N,N-dimethylformamide (20 mL) and water (2 mL) was added dichloro[1,1'-bis(di-t-butylphosphino)ferrocene]palladium(II) (97 mg, 0.15 mmol) and sodium carbonate (238 mg, 2.25 mmol). The mixture was stirred at 90° C. for 12 hours. Water (100 mL) was poured into the mixture and stirred for 1 minute. The aqueous phase was extracted with ethyl acetate (3×50 mL). The combined organic phase was washed with brine (2×50 mL), dried with anhydrous sodium sulfate, filtered, and concentrated. The residue was purified by column chromatography (1:100 to 1:10 methanol:dichloromethane) to afford tert-butyl 4-[[2-[4-[3-[3-[tert-butoxycarbonyl-[(3R)-3-fluoropyrrolidin-1-yl]sulfonyl-amino]-2,6-difluoro-benzoyl]-1H-pyrrolo[2,3-b]pyridin-5-yl]phenyl]-2,6-diazaspiro[3.3]heptan-6-yl]methyl]-4-hydroxy-piperidine-1-carboxylate (1 g, 73%) as a brown oil. MS (ESI): m/z 810.4 [M−100+1]$^+$.

Step C: (3R)—N-[2,4-difluoro-3-[5-[4-[6-[(4-hydroxy-4-piperidyl)methyl]-2,6-diazaspiro[3.3]heptan-2-yl]phenyl]-1H-pyrrolo[2,3-b]pyridine-3-carbonyl]phenyl]-3-fluoro-pyrrolidine-1-sulfonamide

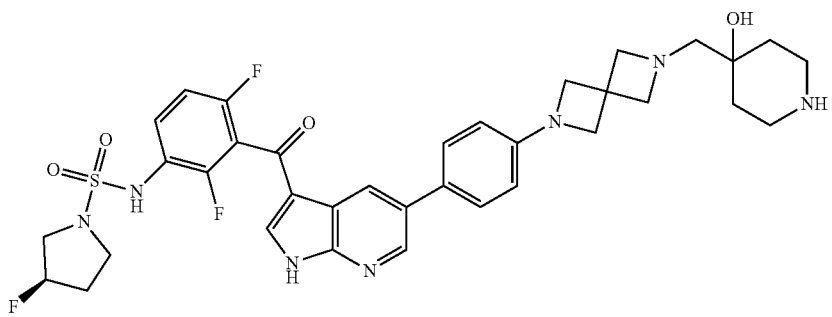 [SMILES: O=C(c1c(F)ccc(NS(=O)(=O)N2CC[C@@H](F)C2)c1F)c1c[nH]c2ncc(-c3ccc(N4CC5(CN(CC6(O)CCNCC6)C5)C4)cc3)cc12]

To a solution of tert-butyl 4-[[2-[4-[3-[3-[tert-butoxycarbonyl-[(3R)-3-fluoropyrrolidin-1-yl] sulfonyl-amino]-2,6-difluoro-benzoyl]-1H-pyrrolo[2,3-b]pyridin-5-yl]phenyl]-2,6-diazaspiro[3.3]heptan-6-yl]methyl]-4-hydroxy-piperidine-1-carboxylate (1.0 g, 1.1 mmol) in dichloromethane (15 mL) was added trifluoroacetic acid (4.62 g, 40.5 mmol, 3 mL). The mixture was stirred at 20° C. for 1 hour. The reaction mixture concentrated. The residue was purified by preparative HPLC (Phenomenex Luna C18, 5 to 35% acetonitrile:(0.225% formic acid in water)) to afford (3R)—N-[2,4-difluoro-3-[5-[(4-hydroxy-4-piperidyl)methyl]-2,6-diazaspiro[3.3]heptan-2-yl]phenyl]-1H-pyrrolo[2,3-b]pyridine-3-carbonyl]phenyl]-3-fluoro-pyrrolidine-1-sulfonamide formic acid salt (500 mg, 60%) as a yellow solid. MS (ESI): m/z 710.5 [M+H]+.

Step D: methyl 2-cyano-4-[4-[[2-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-2,6-diazaspiro[3.3]heptan-6-yl]methyl]-4-hydroxy-1-piperidyl]benzoate

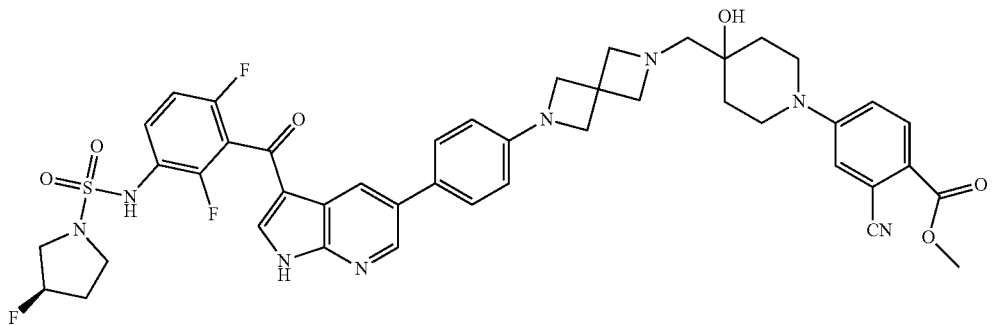 [SMILES: COC(=O)c1ccc(N2CCC(O)(CN3CC4(C3)CN(c3ccc(-c5cnc6[nH]cc(C(=O)c7c(F)ccc(NS(=O)(=O)N8CC[C@@H](F)C8)c7F)c6c5)cc3)C4)CC2)cc1C#N]

To a solution of (3R)—N-[2,4-difluoro-3-[5-[4-[6-[(4-hydroxy-4-piperidyl)methyl]-2,6-diazaspiro[3.3]heptan-2-yl]phenyl]-1H-pyrrolo[2,3-b]pyridine-3-carbonyl]phenyl]-3-fluoro-pyrrolidine-1-sulfonamide formic acid salt (450 mg, 0.59 mmol) and methyl 2-cyano-4-fluoro-benzoate (159 mg, 0.89 mmol) in dimethylsulfoxide (10 mL) was added diisopropylethylamine (230 mg, 1.79 mmol, 0.311 uL). The mixture was stirred at 90° C. for 2 hours. Water (50 mL) was poured into the mixture and stirred for 1 minute. The aqueous phase was extracted with ethyl acetate (3×20 mL). The combined organic phase was washed with brine (2×20 mL), dried with anhydrous sodium sulfate, filtered, and concentrated. The residue was purified by preparative HPLC (Phenomenex Luna C18, 24 to 44% acetonitrile:(0.225% formic acid in water)). The mixture was adjusted pH to 7 with saturated aqueous sodium bicarbonate, and then water (50 mL) was poured into the mixture and stirred for 1 minute. The aqueous phase was extracted with ethyl acetate (3×20 mL). The combined organic phase was washed with brine (2×20 mL), dried with anhydrous sodium sulfate, filtered, and concentrated to afford methyl 2-cyano-4-[4-[[2-[4-[3-[2,6-difluoro-3-[[(3R)-3-fluoropyrrolidin-1-yl]sulfonylamino] benzoyl]-1H-pyrrolo[2,3-b]pyridin-5-yl]phenyl]-2,6-diazaspiro[3.3]heptan-6-yl]methyl]-4-hydroxy-1-piperidyl]benzoate (160 mg, 30%) as a yellow solid. MS (ESI): m/z 869.1 [M+H]+.

Step E: methyl 4-[4-[[2-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-2,6-diazaspiro[3.3]heptan-6-yl]methyl]-4-hydroxy-1-piperidyl]-2-formyl-benzoate

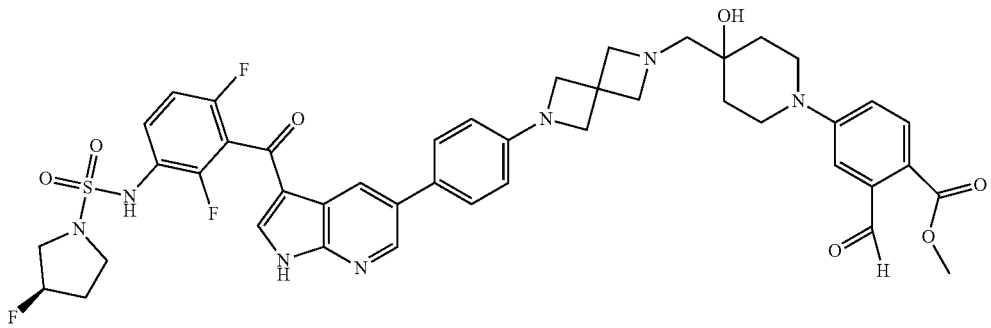 [SMILES: COC(=O)c1ccc(N2CCC(O)(CN3CC4(C3)CN(c3ccc(-c5cnc6[nH]cc(C(=O)c7c(F)ccc(NS(=O)(=O)N8CC[C@@H](F)C8)c7F)c6c5)cc3)C4)CC2)cc1C=O]

To a solution of methyl 2-cyano-4-[4-[[2-[4-[3-[2,6-difluoro-3-[[(3R)-3-fluoropyrrolidin-1-yl] sulfonylamino]benzoyl]-1H-pyrrolo[2,3-b]pyridin-5-yl]phenyl]-2,6-diazaspiro[3.3]heptan-6-yl]methyl]-4-hydroxy-1-piperidyl]benzoate (110 mg, 0.12 mmol) in pyridine (2 mL) was added Raney nickel (44 mg, 0.51 mmol). Then sodium dihydrogen phosphate hydrate (87 mg, 0.63 mmol) in water (1 mL) and acetic acid (1 mL) were added to the mixture. The mixture was stirred at 50° C. for 2 hours. The mixture was poured into water (50 mL). The aqueous phase was extracted with dichloromethane (3×20 mL). The combined organic phase was washed with aqueous 2 M sulfuric acid (2×20 mL), dried with anhydrous sodium sulfate, filtered, and concentrated to afford methyl 4-[4-[[2-[4-[3-[2,6-difluoro-3-[[(3R)-3-fluoropyrrolidin-1-yl] sulfonylamino]benzoyl]-1H-pyrrolo[2,3-b]pyridin-5-yl]phenyl]-2,6-diazaspiro[3.3]heptan-6-yl]methyl]-4-hydroxy-1-piperidyl]-2-formyl-benzoate (100 mg) as a yellow oil. MS (ESI): m/z 872.3 [M+H]⁺.

Step F: (3R)—N-[3-[5-[4-[6-[[1-[2-(2,6-dioxo-3-piperidyl)-1-oxo-isoindolin-5-yl]-4-hydroxy-4-piperidyl]methyl]-2,6-diazaspiro[3.3]heptan-2-yl]phenyl]-1H-pyrrolo[2,3-b]pyridine-3-carbonyl]-2,4-difluoro-phenyl]-3-fluoro-pyrrolidine-1-sulfonamide

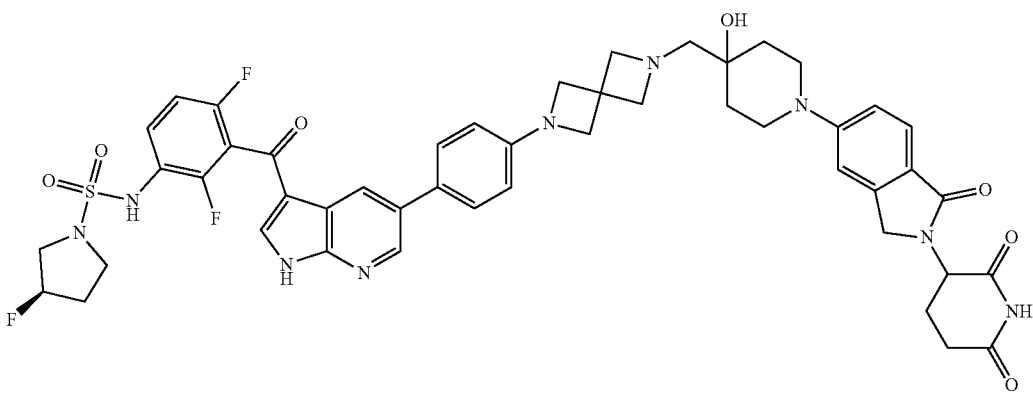 [SMILES: O=C1CCC(N2Cc3cc(N4CCC(O)(CN5CC6(C5)CN(c5ccc(-c7cnc8[nH]cc(C(=O)c9c(F)ccc(NS(=O)(=O)N%10CC[C@@H](F)C%10)c9F)c8c7)cc5)C6)CC4)ccc3C2=O)C(=O)N1]

To a solution of 3-aminopiperidine-2,6-dione (22 mg, 0.13 mmol) in methanol (2 mL) was added sodium acetate (18 mg, 0.22 mmol), the mixture was stirred at 35° C. for 30 minutes. methyl 4-[4-[[2-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-2,6-diazaspiro[3.3]heptan-6-yl]methyl]-4-hydroxy-1-piperidyl]-2-formyl-benzoate (100 mg, 0.11 mmol) in dichloromethane (1 mL) and acetic acid (20 mg, 0.34 mmol, 19.6 uL) was added to the mixture, and the mixture was stirred at 35° C. for 30 minutes. Sodium cyanoborohydride (14 mg, 0.22 mmol) was added to the mixture, the mixture was stirred at 35° C. for 11 hours. The reaction mixture concentrated. The residue was purified by preparative HPLC (Unisil 3-100 C18 Ultra, 20 to 40% acetonitrile:(0.225% formic acid in water)) to afford (3R)—N-[3-[5-[4-[6-[[1-[2-(2,6-dioxo-3-piperidyl)-1-oxo-isoindolin-5-yl]-4-hydroxy-4-piperidyl]methyl]-2,6-diazaspiro[3.3]heptan-2-yl]phenyl]-1H-pyrrolo[2,3-b]pyridine-3-carbonyl]-2,4-difluoro-phenyl]-3-fluoro-pyrrolidine-1-sulfonamide formic acid salt (21.8 mg, 18%) as a yellow solid. MS (ESI): m/z 952.5 [M+H]+; ¹H NMR (400 MHz, DMSO-d₆) δ 11.16-10.79 (m, 1H), 8.66-8.55 (m, 1H), 8.53-8.41 (m, 1H), 8.36-8.21 (m, 2H), 8.09-7.96 (m, 1H), 7.67-7.42 (m, 4H), 7.38-7.10 (m, 2H), 7.10-6.96 (m, 2H), 6.61-6.49 (m, 2H), 5.39-5.16 (m, 2H), 5.09-5.00 (m, 1H), 4.37-4.26 (m, 2H), 4.25-4.16 (m, 2H), 3.92 (s, 6H), 3.28-3.23 (m, 4H), 3.02-2.83 (m, 3H), 2.67 (s, 4H), 2.43-2.29 (m, 3H), 2.11-1.94 (m, 2H), 1.60-1.48 (m, 3H).

The following exemplary compounds may be prepared by a procedure analogous to that described for Exemplary Compound 142: 26, 60, 97, 145, 159, 182, and 293.

Exemplary Synthesis of Exemplary Compound 9: (3R)—N-(3-[5-[—4-(1-[1-[2-(2,6-dioxopiperidin-3-yl)-1-oxo-3H-isoindol-5-yl]piperidin-4-yl]-1,6-diazaspiro[3.3]heptan-6-yl)phenyl]-1H-pyrrolo[2,3-b]pyridine-3-carbonyl]-2,4-difluorophenyl)-3-fluoropyrrolidine-1-sulfonamide

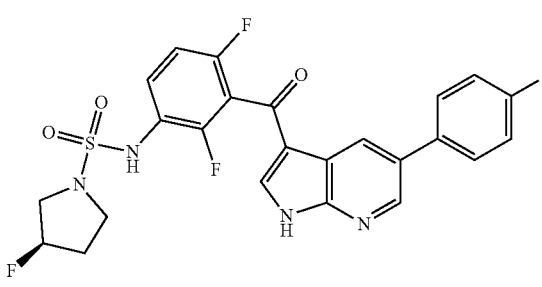

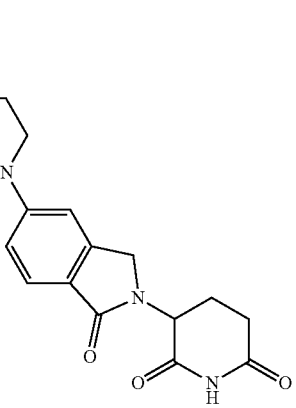

Step A: tert-butyl 6-(4-iodophenyl)-1,6-diazaspiro[3.3]heptane-1-carboxylate

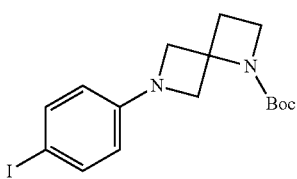 [SMILES: CC(C)(C)OC(=O)N1CCC12CN(c1ccc(I)cc1)C2]

A mixture of 4-iodophenylboronic acid (4.40 g, 17.7 mmol), dichloromethane (120 mL), tert-butyl 1,6-diazaspiro[3.3]heptane-1-carboxylate oxalic acid salt (3.50 g, 12.1 mmol), copper (II) acetate (3.50 g, 19.2 mmol), and triethylamine (3.00 mL, 21.5 mmol) was stirred for 16 hours at room temperature. The solids were filtered out. The residue purified by silica gel column chromatography (1:20 ethyl acetate:petroleum ether) to afford 3.23 g (45%) of tert-butyl 6-(4-iodophenyl)-1,6-diazaspiro[3.3]heptane-1-carboxylate as a white solid. MS (ESI): m/z 401.05 [M+H]$^+$.

Step B: 6-(4-iodophenyl)-1,6-diazaspiro[3.3]heptane

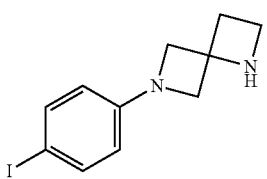 [SMILES: Ic1ccc(N2CC3(CCN3)C2)cc1]

A mixture of tert-butyl 6-(4-iodophenyl)-1,6-diazaspiro[3.3]heptane-1-carboxylate (3.23 g, 8.07 mmol), dichloromethane (25 mL), and trifluoroacetic acid (5 mL) was stirred for 1 hour at room temperature. The resulting mixture was concentrated. The crude product was purified by flash reverse phase chromatography (C18, 69 to 70% acetonitrile:(0.05% ammonium bicarbonate in water)) to afford 1.33 g (41%) of 6-(4-iodophenyl)-1,6-diazaspiro[3.3]heptane trifluoroacetic acid salt as a white solid. MS (ESI): m/z 300.95 [M+H]$^+$.

Step C: 3-[1-oxo-5-(4-oxopiperidin-1-yl)-3H-isoindol-2-yl]piperidine-2,6-dione

A mixture of 3-[5-(4-hydroxypiperidin-1-yl)-1-oxo-3H-isoindol-2-yl]piperidine-2,6-dione (2.20 g, 6.40 mmol), dimethylsulfoxide (30 mL), and IBX (5.00 g, 17.8 mmol) was stirred for 4 hours at 30° C. The resulting solution was extracted with dichloromethane (2×100 mL). The resulting mixture was washed with brine (2×100 mL). Purification by silica gel column chromatography (1:20 methanol:dichloromethane) to afford 1.44 g (66%) of 3-[1-oxo-5-(4-oxopiperidin-1-yl)-3H-isoindol-2-yl]piperidine-2,6-dione as a light yellow solid. MS (ESI): m/z 342.10 [M+H]$^+$.

Step D: 3-(5-[4-[6-(4-iodophenyl)-1,6-diazaspiro[3.3]heptan-1-yl]piperidin-1-yl]-1-oxo-3H-isoindol-2-yl)piperidine-2,6-dione

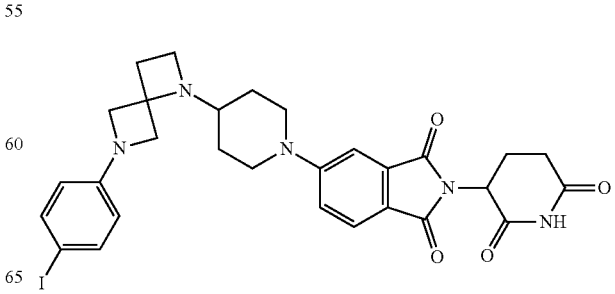

To a mixture of 6-(4-iodophenyl)-1,6-diazaspiro[3.3]heptane trifluoroacetic acid salt (230 mg, 0.578 mmol), 1,2-dichloroethane (150 mL), and 3-[1-oxo-5-(4-oxopiperidin-1-yl)-3H-isoindol-2-yl]piperidine-2,6-dione (210 mg, 0.615 mmol) was added acetic acid (0.10 mL). The resulting solution was stirred for 16 hours at 60° C. To this mixture was added borane-pyridine complex (361 mg, 3.37 mmol). The resulting solution was stirred for 5 hours at 60° C. The resulting solution was extracted with ethyl acetate (2×50 mL). Purification by silica gel column chromatography (1:20 methanol:dichloromethane) afforded 297 mg (82%) of 3-(5-[4-[6-(4-iodophenyl)-1,6-diazaspiro[3.3]heptan-1-yl]piperidin-1-yl]-1-oxo-3H-isoindol-2-yl)piperidine-2,6-dione as a white solid. MS (ESI): m/z 626.15 [M+H]⁺.

Step E: (3R)—N-(3-[5-[4-(1-[1-[2-(2,6-dioxopiperidin-3-yl)-1-oxo-3H-isoindol-5-yl]piperidin-4-yl]-1,6-diazaspiro[3.3]heptan-6-yl)phenyl]-1H-pyrrolo[2,3-b]pyridine-3-carbonyl]-2,4-difluorophenyl)-3-fluoropyrrolidine-1-sulfonamide

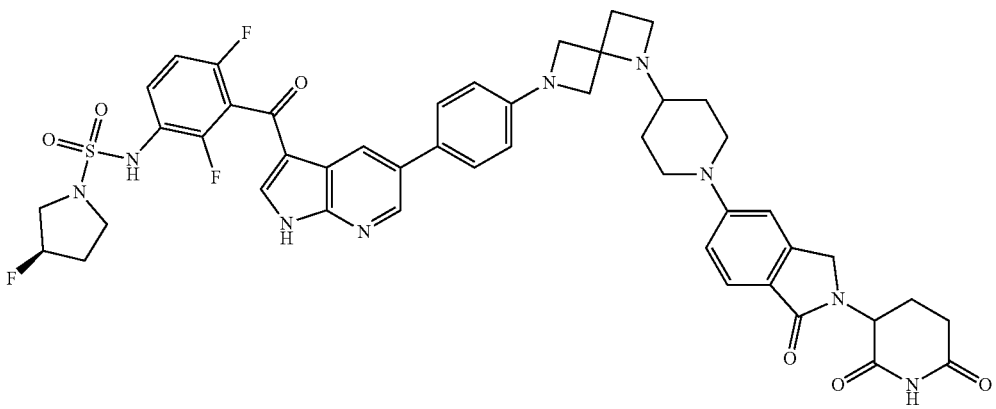 [SMILES: O=C1CCC(N2Cc3cc(N4CCC(N5CCC56CN(c5ccc(-c7cnc8[nH]cc(C(=O)c9c(F)ccc(NS(=O)(=O)N%10CC[C@@H](F)C%10)c9F)c8c7)cc5)C6)CC4)ccc3C2=O)C(=O)N1]

A mixture of 3-(5-[4-[6-(4-iodophenyl)-1,6-diazaspiro[3.3]heptan-1-yl]piperidin-1-yl]-1-oxo-3H-isoindol-2-yl)piperidine-2,6-dione (250 mg, 0.400 mmol), tert-butyl 3-(2,6-difluoro-3-[[(3R)-3-fluoropyrrolidin-1-ylsulfonyl]amino]benzoyl)-5-(4,4,5,5-tetramethyl-1,3,2-dioxaborolan-2-yl)pyrrolo[2,3-b]pyridine-1-carboxylate (390 mg, 0.600 mmol), dichloro[1,1'-bis(di-t-butylphosphino)ferrocene]palladium(II) (32 mg, 0.049 mmol), cesium fluoride (304 mg, 2.00 mmol), 1,4-dioxane (10 mL), water (1.4 mL) was stirred for 2 hours at 95° C. The resulting solution was extracted with dichloromethane (2×50 mL). Purification by silica gel column chromatography (1:20 methanol:dichloromethane), followed by flash reverse phase chromatography (C18, 66.5% to 68.3% acetonitrile:(0.05% ammonium bicarbonate in water)) resulted in 62.8 mg (17%) of (3R)—N-(3-[5-[4-(1-[1-[2-(2,6-dioxopiperidin-3-yl)-1-oxo-3H-isoindol-5-yl]piperidin-4-yl]-1,6-diazaspiro[3.3]heptan-6-yl)phenyl]-1H-pyrrolo[2,3-b]pyridine-3-carbonyl]-2,4-difluorophenyl)-3-fluoropyrrolidine-1-sulfonamide as a light yellow solid. MS (ESI): m/z 922.35 [M+H]⁺; ¹H NMR (400 MHz, DMSO-$d_6$) δ 12.90 (s, 1H), 10.94 (s, 1H), 9.86 (s, 1H), 8.64 (m, 1H), 8.51 (s, 1H), 8.07 (s, 1H), 7.63-7.58 (m, 3H), 7.49 (m, 1H), 7.28 (m, 1H), 7.05-7.03 (m, 2H), 6.59 (m, 2H), 5.37-5.23 (s, 1H), 5.04 (m, 1H), 4.31 (m, 1H), 4.23-4.14 (m, 3H), 3.92 (m, 2H), 3.75 (m, 2H), 3.49 (m, 1H), 3.40 (s, 3H), 3.29 (s, 1H), 3.09 (s, 2H), 3.05-2.98 (m, 3H), 2.95-2.83 (m, 1H), 2.78 (s, 1H), 2.58 (m, 1H), 2.39 (m, 1H), 2.37-2.30 (m, 1H), 2.26-2.11 (s, 2H), 2.06-1.96 (m, 2H), 1.82 (m, 2H), 1.40 (m, 2H).

The following exemplary compounds may be prepared by a procedure analogous to that described for Exemplary Compound 9: 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, and 336.

Exemplary Synthesis of Exemplary Compound 36: (3R)—N-[3-(5-[4-[4-([4-[2-(2,6-dioxopiperidin-3-yl)-1-oxo-3H-isoindol-5-yl]piperidin-1-yl]methyl)piperidin-1-yl]-3-fluorophenyl]-1H-pyrrolo[2,3-b]pyridine-3-carbonyl)-2,4-difluorophenyl]-3-fluoropyrrolidine-1-sulfonamide

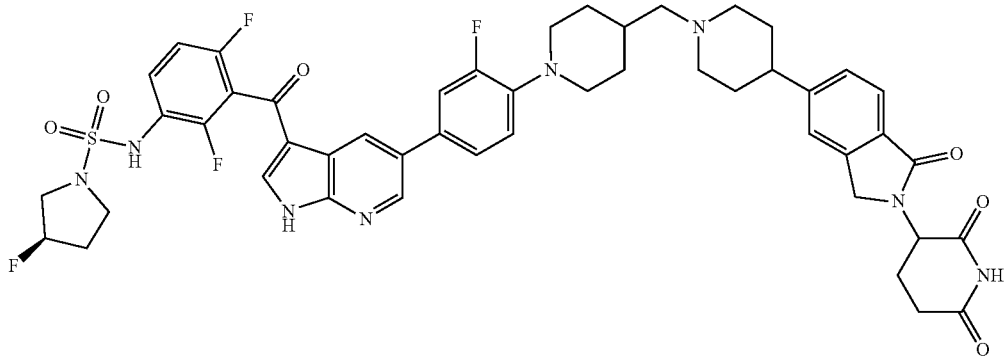 [SMILES: O=C1CCC(N2Cc3cc(C4CCN(CC5CCN(c6ccc(-c7cnc8[nH]cc(C(=O)c9c(F)ccc(NS(=O)(=O)N%10CC[C@@H](F)C%10)c9F)c8c7)cc6F)CC5)CC4)ccc3C2=O)C(=O)N1]

Step A: 1-(4-bromo-2-fluorophenyl)-4-(dimethoxymethyl)piperidine

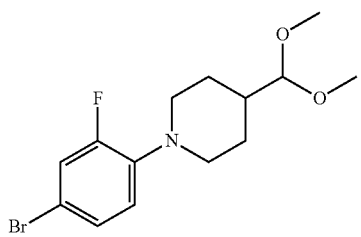 [SMILES: COC(OC)C1CCN(c2ccc(Br)cc2F)CC1]

Under an atmosphere of nitrogen, was placed 4-bromo-2-fluoro-1-iodobenzene (11.00 g, 36.79 mmol), DMSO (150 mL), 4-(dimethoxymethyl)piperidine (5.85 g, 36.7 mmol), K₂CO₃ (10.12 g, 73.33 mmol), L-proline (421 mg, 3.66 mmol), copper (I) iodide (700 mg, 3.66 mmol). The resulting solution was stirred for 3 hours at 90° C. The reaction mixture was cooled. The resulting solution was diluted with water (300 mL). The resulting solution was extracted with ethyl acetate (3×100 mL). The resulting mixture was washed with brine (2×50 mL). The mixture was dried over anhydrous sodium sulfate and concentrated. Purification by silica gel column chromatography (1:5 ethyl acetate:petroleum ether) afforded 1.03 g (9%) of 1-(4-bromo-2-fluorophenyl)-4-(dimethoxymethyl)piperidine as a light yellow solid. MS (ESI): m/z 286.10 [M+H]⁺.

Step B: 1-(4-bromo-2-fluorophenyl)piperidine-4-carbaldehyde

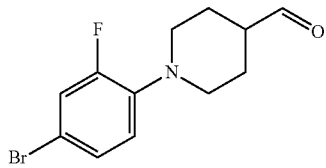 [SMILES: O=CC1CCN(c2ccc(Br)cc2F)CC1]

A mixture of 1-(4-bromo-2-fluorophenyl)-4-(dimethoxymethyl)piperidine (490.0 mg, 1.475 mmol), dichloromethane (12 mL), trifluoroacetic acid (6.00 mL), and water (3 mL) was stirred for 2 hours at 40° C. The resulting mixture was concentrated. Purification by silica gel column chromatography (1:20 methanol:dichloromethane) resulted in 449 mg of 1-(4-bromo-2-fluorophenyl)piperidine-4-carbaldehyde as a white solid. MS (ESI): m/z 286.10 [M+H]⁺.

Step C: 3-[5-(1-[[1-(4-bromo-2-fluorophenyl)piperidin-4-yl]methyl]piperidin-4-yl)-1-oxo-3H-isoindol-2-yl]piperidine-2,6-dione

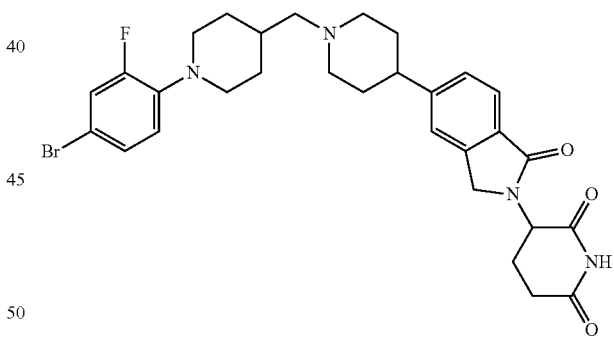

To a mixture of 3-[1-oxo-5-(piperidin-4-yl)-3H-isoindol-2-yl]piperidine-2,6-dione hydrochloride (570 mg, 1.56 mmol), dichloromethane (150 mL), diisopropylethylamine (1.00 mL, 5.74 mmol), and 1-(4-bromo-2-fluorophenyl)piperidine-4-carbaldehyde (449 mg, 1.56 mmol) was added acetic acid (0.50 mL, 8.7 mmol). The resulting solution was stirred for 4 hours at 35° C. To this was added sodium cyanoborohydride (300 mg, 4.77 mmol). The resulting solution was stirred for 16 hours at 35° C. The resulting solution was extracted with dichloromethane (2×50 mL). Purification by silica gel column chromatography (1:10 methanol:dichloromethane) resulted in 655 mg (70%) of 3-[5-(1-[[1-(4-bromo-2-fluorophenyl)piperidin-4-yl]methyl]piperidin-4-yl)-1-oxo-3H-isoindol-2-yl]piperidine-2,6-dione as a light brown solid. MS (ESI): m/z 599.25 [M+H]⁺.

Step D: (3R)—N-[3-(5-[4-[4-([4-[2-(2,6-dioxopiperidin-3-yl)-1-oxo-3H-isoindol-5-yl]piperidin-1-yl]methyl)piperidin-1-yl]-3-fluorophenyl]-1H-pyrrolo[2,3-b]pyridine-3-carbonyl)-2,4-difluorophenyl]-3-fluoropyrrolidine-1-sulfonamide

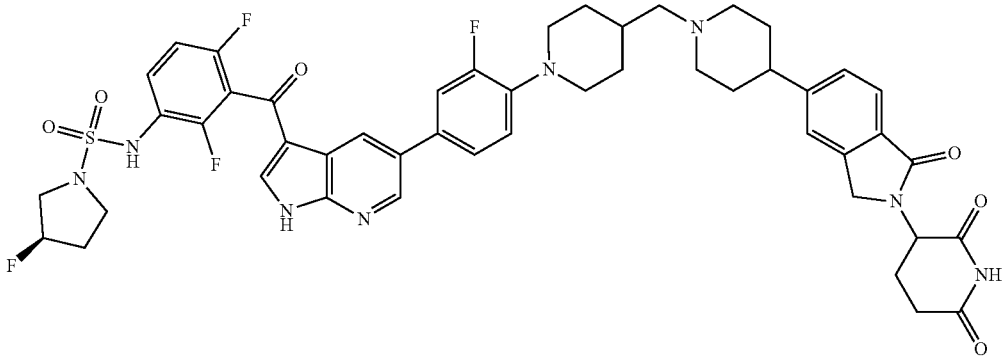 [SMILES: O=C1CCC(N2Cc3cc(C4CCN(CC5CCN(c6ccc(-c7cnc8[nH]cc(C(=O)c9c(F)ccc(NS(=O)(=O)N%10CC[C@@H](F)C%10)c9F)c8c7)cc6F)CC5)CC4)ccc3C2=O)C(=O)N1]

A mixture of 3-[5-(1-[[1-(4-bromo-2-fluorophenyl)piperidin-4-yl]methyl]piperidin-4-yl)-1-oxo-3H-isoindol-2-yl]piperidine-2,6-dione (290 mg, 0.485 mmol), (3R)—N-[2,4-difluoro-3-[5-(4,4,5,5-tetramethyl-1,3,2-dioxaborolan-2-yl)-1H-pyrrolo[2,3-b]pyridine-3-carbonyl]phenyl]-3-fluoropyrrolidine-1-sulfonamide (300 mg, 0.545 mmol), dichloro[1,1'-bis(di-t-butylphosphino)ferrocene]palladium (II) (65 mg, 0.10 mmol), cesium fluoride (370.0 mg, 2.436 mmol), 1,4-dioxane (14 mL), and water (2 mL) was stirred for 1.5 hours at 100° C. and then cooled and extracted with dichloromethane (50 mL). Purification by silica gel column chromatography (1:10 methanol:dichloromethane) and then flash reverse phase chromatography (C18, 53.4% acetonitrile:(0.05% ammonium bicarbonate in water)) afforded 97.7 mg (21%) of (3R)—N-[3-(5-[4-[4-([4-[2-(2,6-dioxopiperidin-3-yl)-1-oxo-3H-isoindol-5-yl]piperidin-1-yl]methyl)piperidin-1-yl]-3-fluorophenyl]-1H-pyrrolo[2,3-b]pyridine-3-carbonyl)-2,4-difluorophenyl]-3-fluoropyrrolidine-1-sulfonamide as a white solid. MS (ESI): m/z 964.35 [M+H]$^+$; $^1$H NMR (400 MHz, DMSO-$d_6$) δ 12.97 (s, 1H), 10.99 (s, 1H), 9.82 (s, 1H), 8.70 (s, 1H), 8.59 (s, 1H), 8.11 (s, 1H), 7.69-7.46 (m, 5H), 7.42-7.40 (m, 1H), 7.32-7.23 (m, 1H), 7.17-7.14 (m, 1H), 5.24 (d, J=32.0 Hz, 1H), 5.12-5.09 (m, 1H), 4.43-4.30 (m, 2H), 3.54-3.35 (m, 5H), 3.34-3.24 (m, 1H), 3.03-3.00 (m, 2H), 2.99-2.85 (m, 1H), 2.79-2.69 (m, 4H), 2.69-2.56 (m, 3H), 2.18-1.98 (m, 5H), 1.82-1.71 (m, 7H), 1.33-1.31 (m, 2H).

The following exemplary compounds may be prepared by a procedure analogous to that described for Exemplary Compounds 9 and 142: 1, 4, 5, 7, 10, 15, 16, 17, 19, 23, 34, 35, 42, 43, 50, 53, 57, 58, 66, 69, 76, 77, 78, 85, 86, 87, 88, 91, 94, 95, 96, 101, 103, 104, 112, 113, 114, 117, 120, 121, 135, 139, 141, 146, 147, 152, 153, 154, 157, 158, 162, 163, 164, 174, 179, 180, 188, 192, 193, 194, 200, and 125.

Exemplary Synthesis of Exemplary Compounds 67 and 68: (3R)—N-[3-[5-(4-[1-[(3R)-3-[2-[(3S)-2,6-dioxopiperidin-3-yl]-1-oxo-3H-isoindol-5-yl]-3-hydroxypropyl]piperidin-4-yl]phenyl)-1H-pyrrolo[2,3-b]pyridine-3-carbonyl]-2,4-difluorophenyl]-3-fluoropyrrolidine-1-sulfonamide and (3R)—N-[3-[5-(4-[1-[(3R)-3-[2-[(3R)-2,6-dioxopiperidin-3-yl]-1-oxo-3H-isoindol-5-yl]-3-hydroxypropyl]piperidin-4-yl]phenyl)-1H-pyrrolo[2,3-b]pyridine-3-carbonyl]-2,4-difluorophenyl]-3-fluoropyrrolidine-1-sulfonamide

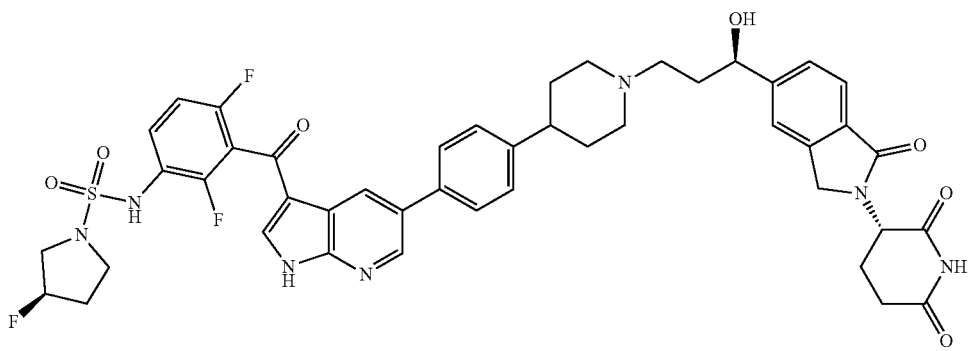

-continued

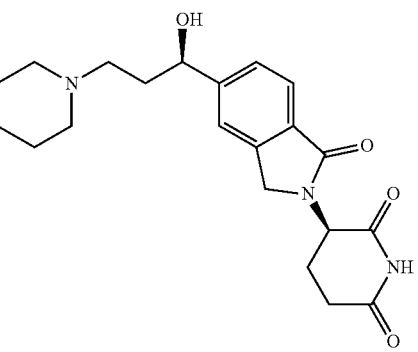

Step A: 3-(5-iodo-1-oxo-3H-isoindol-2-yl)piperidine-2,6-dione

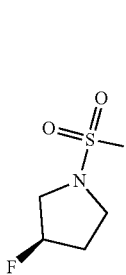

A mixture of 3-(5-bromo-1-oxo-3H-isoindol-2-yl)piperidine-2,6-dione (500 mg, 1.54 mmol), sodium iodide (465 mg, 3.10 mmol), copper (I) iodide (58.9 mg, 0.309 mmol), 1,4-dioxane (15 mL), and (1R,2R)—N1,N2-dimethylcyclohexane-1,2-diamine (88.2 mg, 0.620 mmol) was stirred for 2.5 hours at 125° C. The reaction mixture was cooled to 35° C. The resulting mixture was concentrated. The resulting solution was diluted with water (100 mL). The solids were collected by filtration. The resulting mixture was washed with 10:1 petroleum ether:ethyl acetate (2×100 mL). The solids were collected by filtration to afford 425.3 mg (74%) of 3-(5-iodo-1-oxo-3H-isoindol-2-yl)piperidine-2,6-dione as an off-white solid. MS (ESI): m/z 370.95 [M+H]⁺.

Step B: 3-[1-oxo-5-(prop-2-enoyl)-3H-isoindol-2-yl]piperidine-2,6-dione

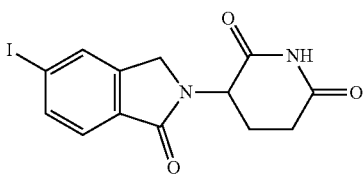 [SMILES: O=C1CCC(N2Cc3cc(I)ccc3C2=O)C(=O)N1]

A mixture of 3-(5-iodo-1-oxo-3H-isoindol-2-yl)piperidine-2,6-dione (2.00 g, 5.403 mmol), ethenyltrifluoro-λ4-borane potassium (942 mg, 7.03 mmol), sodium carbonate (744 mg, 6.95 mmol), palladium (II) acetate (121 mg, 0.539 mmol), triphenylphosphine (424.00 mg, 1.617 mmol), and THF (180 mL) was flushed with carbon monoxide three times. Keeping carbon monoxide under 5 atm, the resulting solution was stirred vigorously overnight at 80° C. The reaction was then cooled and quenched by the addition of water (200 mL). The resulting solution was extracted with ethyl acetate (3×100 mL). The resulting mixture was washed with brine (100 mL). The mixture was dried over anhydrous sodium sulfate and concentrated. Purification by silica gel column chromatography (10 to 70% ethyl acetate:petroleum ether) resulted in 1.04 g (80% pure) (52%) of 3-[1-oxo-5-(prop-2-enoyl)-3H-isoindol-2-yl]piperidine-2,6-dione as a yellow-brown solid. MS (ESI): m/z 298.95 [M+H]⁺.

Step C: 3-(5-[3-[4-(4-bromophenyl)piperidin-1-yl]propanoyl]-1-oxo-3H-isoindol-2-yl)piperidine-2,6-dione

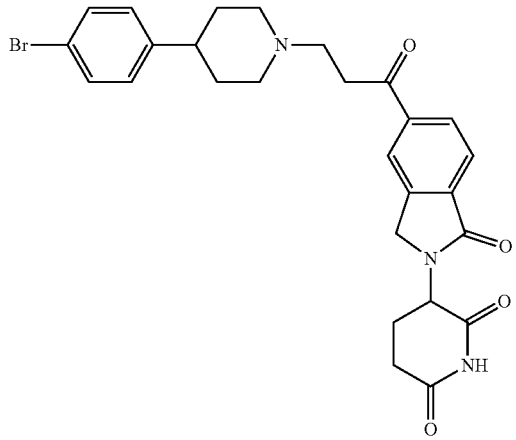 [SMILES: O=C1CCC(N2Cc3cc(C(=O)CCN4CCC(c5ccc(Br)cc5)CC4)ccc3C2=O)C(=O)N1]

To a mixture of 4-(4-bromophenyl)piperidine (513 mg, 2.13 mmol), dichloromethane (30 mL), 3-[1-oxo-5-(prop-2-enoyl)-3H-isoindol-2-yl]piperidine-2,6-dione (649 mg, 2.17 mmol) was added triethylamine (652 mg, 6.45 mmol) dropwise with stirring at 0° C. N,N-dimethylaminopyridine (52.2 mg, 0.427 mmol) was added at 0° C. The resulting solution was stirred for 3 hours at room temperature. The reaction was then quenched by the addition of water (30 mL). The resulting solution was extracted with dichloromethane (3×40 mL). The resulting mixture was washed with brine (30 mL). The mixture was dried over anhydrous sodium sulfate and concentrated. Purification by silica gel chromatography (1:10 methanol:dichloromethane with 5% triethylamine) resulted in 810 mg (70%) of 3-(5-[3-[4-(4-bromophenyl)piperidin-1-yl]propanoyl]-1-oxo-3H-isoindol-2-yl)piperidine-2,6-dione as a yellow solid. MS (ESI): m/z 538.05, 540.05 [M+H]⁺.

Step D: 3-[5-[(1R)-3-[4-(4-bromophenyl)piperidin-1-yl]-1-hydroxypropyl]-1-oxo-3H-isoindol-2-yl]piperidine-2,6-dione

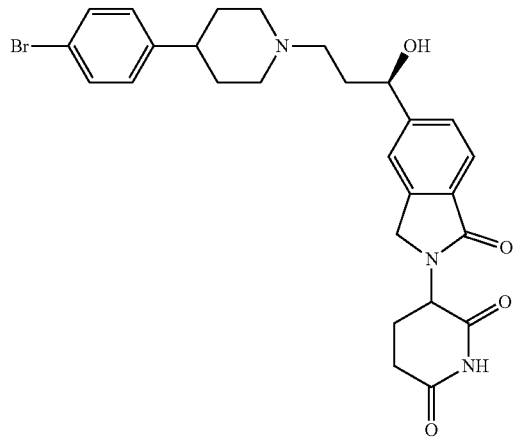 [SMILES: O=C1CCC(N2Cc3cc([C@H](O)CCN4CCC(c5ccc(Br)cc5)CC4)ccc3C2=O)C(=O)N1]

To a mixture of 3-(5-[3-[4-(4-bromophenyl)piperidin-1-yl]propanoyl]-1-oxo-3H-isoindol-2-yl)piperidine-2,6-dione (810 mg, 1.50 mmol), and THF (10 mL) was added (+)-DIP-Cl (1.7 M in heptane, 8.80 mL, 14.9 mmol) dropwise with stirring at −60° C. over 5 minutes. The resulting solution was stirred for 16 hours at 50° C. and then quenched with methanol (10 mL) and concentrated. Purification by silica gel column chromatography (1:10 methanol:dichloromethane) afforded 530 mg (65%) of 3-[5-[(1R)-3-[4-(4-bromophenyl)piperidin-1-yl]-1-hydroxypropyl]-1-oxo-3H-isoindol-2-yl]piperidine-2,6-dione as a white solid. MS (ESI): m/z 540.05/542.05 [M+H]$^+$.

Step E: (3R)—N-[3-[5-(4-[1-[(3R)-3-[2-(2,6-dioxopiperidin-3-yl)-1-oxo-3H-isoindol-5-yl]-3-hydroxypropyl]piperidin-4-yl]phenyl)-1H-pyrrolo[2,3-b]pyridine-3-carbonyl]-2,4-difluorophenyl]-3-fluoropyrrolidine-1-sulfonamide

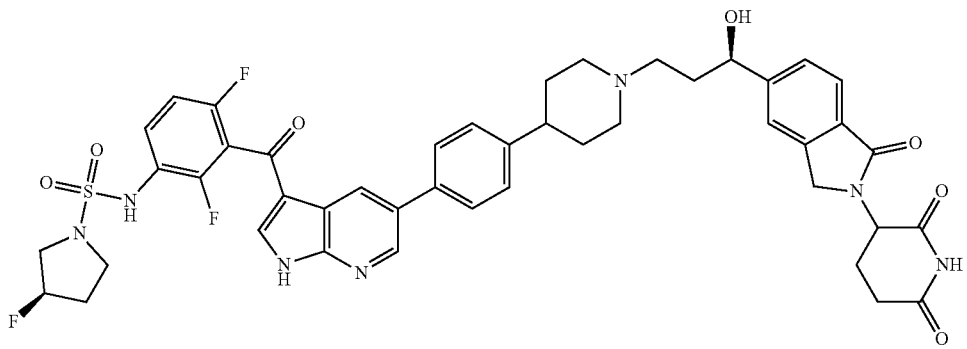

A mixture of 3-[5-[(1R)-3-[4-(4-bromophenyl)piperidin-1-yl]-1-hydroxypropyl]-1-oxo-3H-isoindol-2-yl]piperidine-2,6-dione (530 mg), (3R)—N-[2,4-difluoro-3-[5-(4,4,5,5-tetramethyl-1,3,2-dioxaborolan-2-yl)-1H-pyrrolo[2,3-b]pyridine-3-carbonyl]phenyl]-3-fluoropyrrolidine-1-sulfonamide (1.08 g), cesium fluoride (746 mg), dichloro[1,1'-bis(di-t-butylphosphino)ferrocene]palladium(II) (96 mg), 1,4-dioxane (14 mL), and water (2 mL) was stirred for 2 hours at 100° C. The reaction mixture was cooled and concentrated. Purification by reverse phase silica gel column chromatography (C18, 10 to 85% acetonitrile:water) afforded 280 mg (32%) of (3R)—N-[3-[5-(4-[1-[(3R)-3-[2-(2,6-dioxopiperidin-3-yl)-1-oxo-3H-isoindol-5-yl]-3-hydroxypropyl]piperidin-4-yl]phenyl)-1H-pyrrolo[2,3-b]pyridine-3-carbonyl]-2,4-difluorophenyl]-3-fluoropyrrolidine-1-sulfonamide as a white solid. MS (ESI): m/z 884.20 [M+H]$^+$.

Step F: (3R)—N-[3-[5-(4-[1-[(3R)-3-[2-[(3S)-2,6-dioxopiperidin-3-yl]-1-oxo-3H-isoindol-5-yl]-3-hydroxypropyl]piperidin-4-yl]phenyl)-1H-pyrrolo[2,3-b]pyridine-3-carbonyl]-2,4-difluorophenyl]-3-fluoropyrrolidine-1-sulfonamide and (3R)—N-[3-[5-(4-[1-[(3R)-3-[2-[(3R)-2,6-dioxopiperidin-3-yl]-1-oxo-3H-isoindol-5-yl]-3-hydroxypropyl]piperidin-4-yl]phenyl)-1H-pyrrolo[2,3-b]pyridine-3-carbonyl]-2,4-difluorophenyl]-3-fluoropyrrolidine-1-sulfonamide

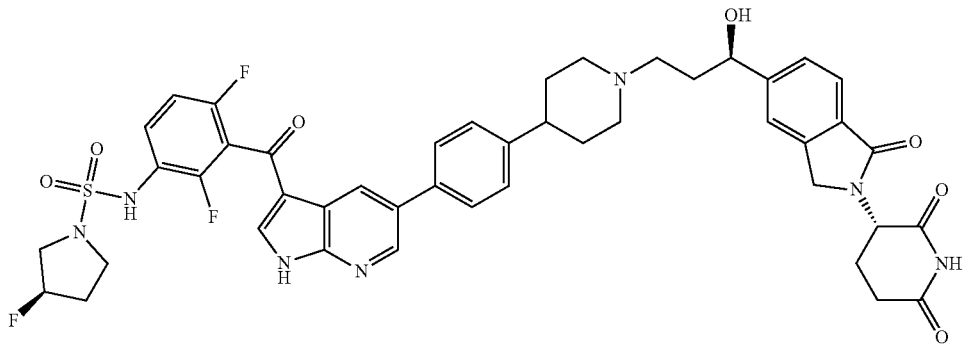 [SMILES: O=C1CCC(N2Cc3cc([C@H](O)CCN4CCC(c5ccc(-c6cnc7[nH]cc(C(=O)c8c(F)ccc(NS(=O)(=O)N9CC[C@@H](F)C9)c8F)c7c6)cc5)CC4)ccc3C2=O)C(=O)N1]

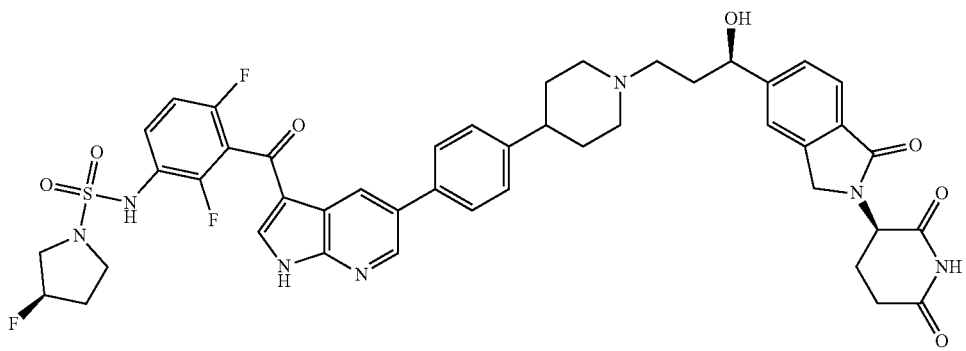

(3R)—N-[3-[5-(4-[1-[(3R)-3-[2-(2,6-dioxopiperidin-3-yl)-1-oxo-3H-isoindol-5-yl]-3-hydroxypropyl]piperidin-4-yl]phenyl)-1H-pyrrolo[2,3-b]pyridine-3-carbonyl]-2,4-difluorophenyl]-3-fluoropyrrolidine-1-sulfonamide (280.00 mg, 0.317 mmol) was purified by preparative HPLC (CHIRALPAK IC-3, 1:1 dichloromethane:ethano) to afford 54.2 mg (19%) of (3R)—N-[3-[5-(4-[1-[(3R)-3-[2-[(3S)-2,6-dioxopiperidin-3-yl]-1-oxo-3H-isoindol-5-yl]-3-hydroxypropyl]piperidin-4-yl]phenyl)-1H-pyrrolo[2,3-b]pyridine-3-carbonyl]-2,4-difluorophenyl]-3-fluoropyrrolidine-1-sulfonamide (absolute stereochemistry tentatively assigned) as a white solid. MS (ESI): m/z 884.30 [M+H]+; $^1$H NMR (400 MHz, DMSO-$d_6$) δ 12.91 (s, 1H), 11.00 (s, 1H), 8.70 (s, 1H), 8.67 (s, 1H), 8.12 (s, 1H), 7.71-7.64 (m, 5H), 7.60 (d, J=6.0 Hz, 1H), 7.40 (d, J=8.4 Hz, 2H), 7.29-7.27 (m, 1H), 5.32 (d, J=56 Hz, 1H), 5.05-5.03 (m, 1H), 4.81 (s, 1H), 4.44-4.31 (m, 2H), 3.51-3.31 (m, 6H), 3.16-3.10 (m, 2H), 2.99-2.96 (m, 1H), 2.51-2.40 (m, 3H), 2.37-2.35 (m, 1H), 2.20-2.01 (m, 5H), 1.87-1.84 (m, 4H), 1.74-1.71 (m, 2H).

Also obtained was 70.6 mg (25%) of (3R)—N-[3-[5-(4-[1-[(3R)-3-[2-[(3R)-2,6-dioxopiperidin-3-yl]-1-oxo-3H-isoindol-5-yl]-3-hydroxypropyl]piperidin-4-yl]phenyl)-1H-pyrrolo[2,3-b]pyridine-3-carbonyl]-2,4-difluorophenyl]-3-fluoropyrrolidine-1-sulfonamide (absolute stereochemistry tentatively assigned) as a white solid. MS (ESI): m/z 884.15 [M+H]+; $^1$H NMR (400 MHz, DMSO-$d_6$) δ 12.91 (s, 1H), 11.00 (s, 1H), 8.70 (s, 1H), 8.67 (s, 1H), 8.12 (s, 1H), 7.71-7.64 (m, 5H), 7.60 (d, J=6.0 Hz, 1H), 7.40 (d, J=8.4 Hz, 2H), 7.29-7.27 (m, 1H), 5.32 (d, J=56 Hz, 1H), 5.05-5.03 (m, 1H), 4.81 (s, 1H), 4.44-4.31 (m, 2H), 3.53-3.32 (m, 6H), 3.10-3.01 (m, 1H), 2.96-2.94 (m, 2H), 2.51-2.40 (m, 1H), 2.20-1.96 (m, 5H), 1.86-1.83 (m, 4H), 1.72-1.70 (m, 2H).

The following exemplary compounds may be prepared by a procedure analogous to that described for Exemplary Compounds 67 and 68: 77 and 72.

Exemplary Synthesis of Exemplary Compounds 123 and 124: (3R)—N-[3-[5-[4-[6-[(2R)-3-[2-[(3S)-2,6-dioxo-3-piperidyl]-1-oxo-isoindolin-5-yl]oxy-2-hydroxy-propyl]-2,6-diazaspiro[3.3]heptan-2-yl]phenyl]-1H-pyrrolo[2,3-b]pyridine-3-carbonyl]-2,4-difluoro-phenyl]-3-fluoro-pyrrolidine-1-sulfonamide and (3R)—N-[3-[5-[4-[6-[(2R)-3-[2-[(3R)-2,6-dioxo-3-piperidyl]-1-oxo-isoindolin-5-yl]oxy-2-hydroxy-propyl]-2,6-diazaspiro[3.3]heptan-2-yl]phenyl]-1H-pyrrolo[2,3-b]pyridine-3-carbonyl]-2,4-difluoro-phenyl]-3-fluoro-pyrrolidine-1-sulfonamide

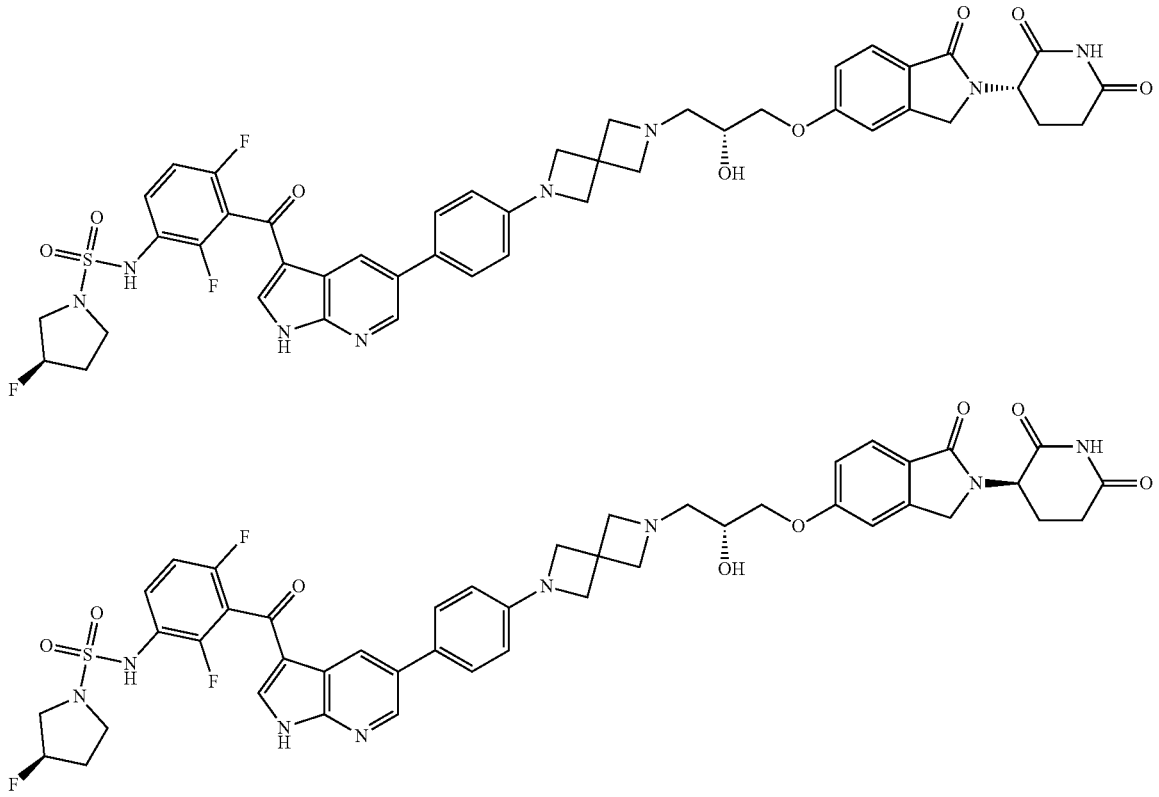

Step A: methyl 2-cyano-4-[[(2R)-oxiran-2-yl]methoxy] benzoate

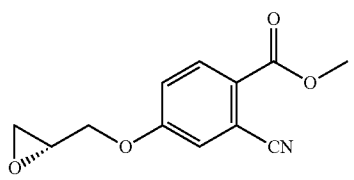 [SMILES: COC(=O)c1ccc(OC[C@H]2CO2)cc1C#N]

To a solution of methyl 2-cyano-4-hydroxy-benzoate (1.5 g, 8.4 mmol) in tetrahydrofuran (25 mL) was added [(2S)-oxiran-2-yl]methanol (815 mg, 11.0 mmol), triphenylphosphine (2.89 g, 11.0 mmol) and disopropylazodiformate (2.23 g, 11.0 mmol) at 0° C. The mixture was stirred at 25° C. for 12 hours. The mixture was concentrated and the residue purified by flash silica gel chromatography (0 to 25% ethyl acetate:petroleum ether) to afford methyl 2-cyano-4-[[(2R)-oxiran-2-yl]methoxy] benzoate (1.9 g, 92%) as a white solid. MS (ESI): m/z 234.2 [M+H]+.

Step B: methyl 4-[(2R)-3-[2-(4-bromophenyl)-2,6-diazaspiro[3.3]heptan-6-yl]-2-hydroxy-propoxy]-2-cyano-benzoate


To a solution of methyl 2-cyano-4-[[(2R)-oxiran-2-yl]methoxy]benzoate (1.9 g, 7.8 mmol) in isopropanol (30 mL) was added triethylamine (3.40 mL, 24.4 mmol) and 2-(4-bromophenyl)-2,6-diazaspiro[3.3]heptane (2.06 g, 8.15 mmol). The mixture was stirred at 80° C. for 12 hours. The reaction mixture was concentrated. The residue was purified by flash silica gel chromatography (0 to 5% methanol:dichloromethane) and then by preparative HPLC (Phenomenex Luna C18, 25 to 50% acetonitrile:(0.225% formic acid in water)) to afford methyl 4-[(2R)-3-[2-(4-bromophenyl)-2,6-diazaspiro[3.3]heptan-6-yl]-2-hydroxy-propoxy]-2-cyano-benzoate (1.6 g, 39%) as a white solid. MS (ESI): m/z 486.2 [M+H]⁺.

Step C: methyl 4-[(2R)-3-[2-(4-bromophenyl)-2,6-diazaspiro[3.3]heptan-6-yl]-2-hydroxy-propoxy]-2-formyl-benzoate

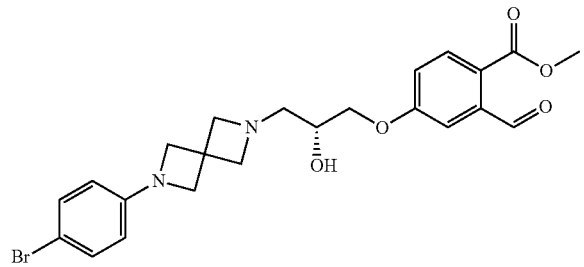 [SMILES: COC(=O)c1ccc(OC[C@H](O)CN2CC3(C2)CN(c2ccc(Br)cc2)C3)cc1C=O]

To a solution of methyl 4-[(2R)-3-[2-(4-bromophenyl)-2,6-diazaspiro[3.3]heptan-6-yl]-2-hydroxy-propoxy]-2-cyano-benzoate (1.6 g, 3.2 mmol) in pyridine (8 mL), acetic acid (4 mL), and water (3 mL) was added Raney nickel (1.0 g, 11 mmol) and sodium hypophosphite monohydrate (1.71 g, 16.4 mmol). The mixture was stirred at 50° C. for 2 hours. The reaction mixture was diluted with water (30 mL) and extracted with ethyl acetate:tetrahydrofuran (3×50 mL). The combined organic layers were washed with brine (3×50 mL), dried over anhydrous sodium sulfate, filtered, and concentrated. The residue was purified by flash silica gel chromatography (0 to 10% methanol:dichloromethane) to afford methyl 4-[(2R)-3-[2-(4-bromophenyl)-2,6-diazaspiro[3.3]heptan-6-yl]-2-hydroxy-propoxy]-2-formyl-benzoate (800 mg, 49%) as a light yellow gum. MS (ESI): m/z 491.3 [M+H]⁺.

Step D: 3-[5-[(2R)-3-[2-(4-bromophenyl)-2,6-diazaspiro[3.3]heptan-6-yl]-2-hydroxy-propoxy]-1-oxo-isoindolin-2-yl]piperidine-2,6-dione

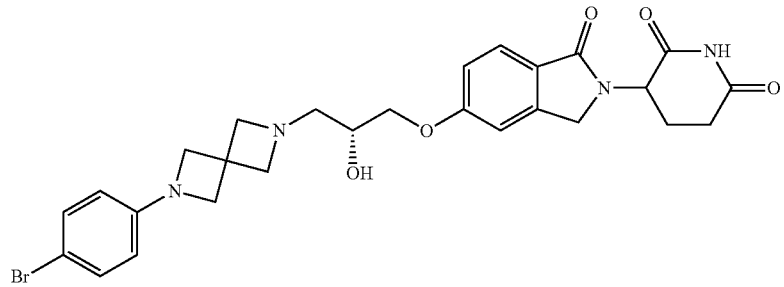 [SMILES: O=C1CCC(N2Cc3cc(OC[C@H](O)CN4CC5(C4)CN(c4ccc(Br)cc4)C5)ccc3C2=O)C(=O)N1]

To a mixture of 3-aminopiperidine-2,6-dione hydrochloride (251 mg, 1.96 mmol) in methanol (5 mL) and 1,2-dichloroethane (5 mL) was added sodium acetate (268 mg, 3.27 mmol) and methyl 4-[(2R)-3-[2-(4-bromophenyl)-2,6-diazaspiro[3.3]heptan-6-yl]-2-hydroxy-propoxy]-2-formyl-benzoate (800 mg, 1.63 mmol) in one portion. The mixture was stirred at 30° C. for 1 hour, then acetic acid (1.0 mL, 17 mmol) and sodium cyanoborohydride (205 mg, 3.27 mmol) were added and stirred at 30° C. for 11 hours. Water (10 mL) was added to the mixture and saturated aqueous sodium bicarbonate solution was added to adjust pH to ~8. Then the mixture was extracted with methanol:dichloromethane (2×20 mL). The combined organic layers were dried over sodium sulfate, filtered, and concentrated. The residue was purified by preparative HPLC (Phenomenex Luna C18, 8 to 43% acetonitrile:(0.225% formic acid in water)) to afford 3-[5-[(2R)-3-[2-(4-bromophenyl)-2,6-diazaspiro[3.3]heptan-6-yl]-2-hydroxy-propoxy]-1-oxo-isoindolin-2-yl]piperidine-2,6-dione formic acid salt (400 mg, 38%) as a white solid. MS (ESI): m/z 571.1 [M+H]⁺.

Step E: tert-butyl N-[3-[5-[4-[6-[(2R)-3-[2-(2,6-dioxo-3-piperidyl)-1-oxo-isoindolin-5-yl]oxy-2-hydroxy-propyl]-2,6-diazaspiro[3.3]heptan-2-yl]phenyl]-1H-pyrrolo[2,3-b]pyridine-3-carbonyl]-2,4-difluoro-phenyl]-N-[(3R)-3-fluoropyrrolidin-1-yl]sulfonyl-carbamate

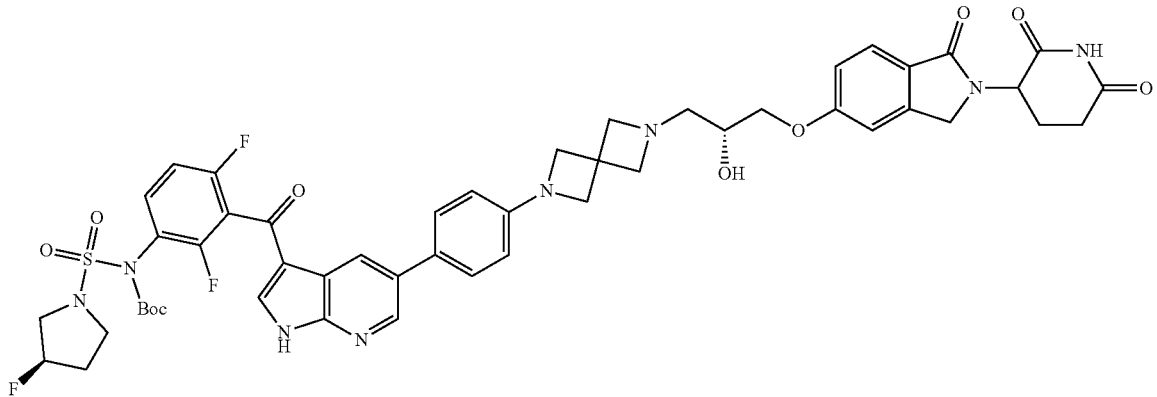 [SMILES: CC(C)(C)OC(=O)N(c1ccc(F)c(C(=O)c2c[nH]c3ncc(-c4ccc(N5CC6(CN(C[C@@H](O)COc7ccc8c(c7)CN(C7CCC(=O)NC7=O)C8=O)C6)C5)cc4)cc23)c1F)S(=O)(=O)N1CC[C@@H](F)C1]

A mixture of 3-[5-[(2R)-3-[2-(4-bromophenyl)-2,6-diazaspiro[3.3]heptan-6-yl]-2-hydroxy-propoxy]-1-oxo-isoindolin-2-yl]piperidine-2,6-dione formic acid salt (350 mg, 0.56 mmol), tert-butyl 3-[3-[tert-butoxycarbonyl-[(3R)-3-fluoropyrrolidin-1-yl]sulfonyl-amino]-2,6-difluoro-benzoyl]-5-(4,4,5,5-tetramethyl-1,3,2-dioxaborolan-2-yl)pyrrolo[2,3-b]pyridine-1-carboxylate (512 mg, 0.68 mmol), sodium carbonate (151 mg, 1.42 mmol) and dichloro[1,1'-bis(di-t-butylphosphino)ferrocene]palladium(II) (38 mg, 0.056 mmol) in N,N-dimethylformamide (20 mL) and water (2 mL) was degassed and purged with nitrogen 3×, and then the mixture was stirred at 90° C. for 3 hours. The reaction mixture was diluted with water (100 mL) and extracted with ethyl acetate:tetrahydrofuran (3×50 mL). The combined organic layers were washed with brine (3×100 mL), dried over anhydrous sodium sulfate, filtered, and concentrated. The residue was purified by flash silica gel chromatography (0 to 10% methanol:dichloromethane) to afford tert-butyl N-[3-[5-[4-[6-[(2R)-3-[2-(2,6-dioxo-3-piperidyl)-1-oxo-isoindolin-5-yl]oxy-2-hydroxy-propyl]-2,6-diazaspiro[3.3]heptan-2-yl]phenyl]-1H-pyrrolo[2,3-b]pyridine-3-carbonyl]-2,4-difluoro-phenyl]-N-[(3R)-3-fluoropyrrolidin-1-yl]sulfonyl-carbamate (340 mg, 50%) as a yellow solid. MS (ESI): m/z 913.3 [M−100+H]+.

Step F: (3R)—N-[3-[5-[4-[6-[(2R)-3-[2-(2,6-dioxo-3-piperidyl)-1-oxo-isoindolin-5-yl]oxy-2-hydroxy-propyl]-2,6-diazaspiro[3.3]heptan-2-yl]phenyl]-1H-pyrrolo[2,3-b]pyridine-3-carbonyl]-2,4-difluoro-phenyl]-3-fluoro-pyrrolidine-1-sulfonamide

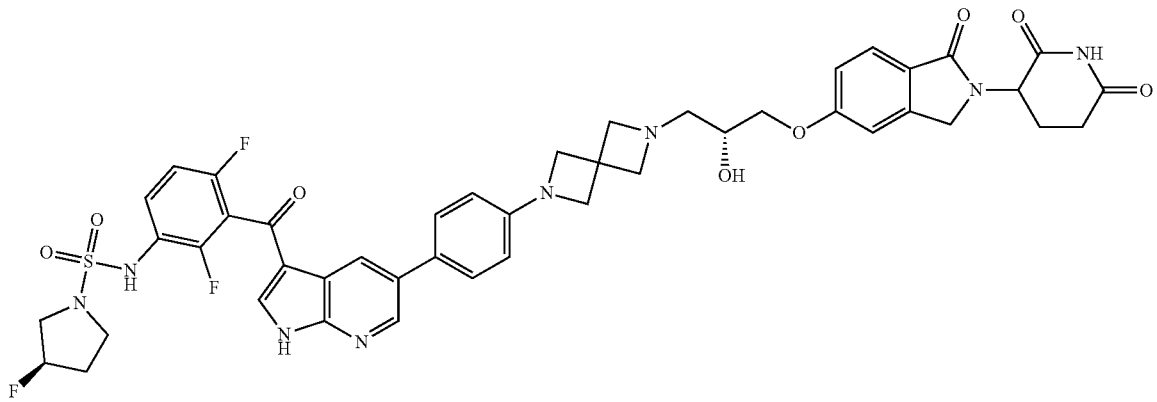 [SMILES: O=C1CCC(N2Cc3cc(OC[C@H](O)CN4CC5(C4)CN(c4ccc(-c6cnc7[nH]cc(C(=O)c8c(F)ccc(NS(=O)(=O)N9CC[C@@H](F)C9)c8F)c7c6)cc4)C5)ccc3C2=O)C(=O)N1]

To a solution of tert-butyl N-[3-[5-[4-[6-[(2R)-3-[2-(2,6-dioxo-3-piperidyl)-1-oxo-isoindolin-5-yl]oxy-2-hydroxy-propyl]-2,6-diazaspiro[3.3]heptan-2-yl]phenyl]-1H-pyrrolo[2,3-b]pyridine-3-carbonyl]-2,4-difluoro-phenyl]-N-[(3R)-3-fluoropyrrolidin-1-yl]sulfonyl-carbamate (340 mg, 0.28 mmol) in dichloromethane (5 mL) was added trifluoroacetic acid (2.0 mL, 27 mmol). The mixture was stirred at 20° C. for 2 hours. Water (10 mL) was added to the mixture and saturated aqueous sodium bicarbonate solution was added to adjust pH to ~8. Then the mixture was extracted with ethyl acetate:tetrahydrofuran (2×20 mL). The combined organic layers were dried over sodium sulfate, filtered, and concentrated. The residue was purified by flash silica gel chromatography (0 to 8% methanol:dichloromethane) to afford (3R)—N-[3-[5-[4-[6-[(2R)-3-[2-(2,6-dioxo-3-piperidyl)-1-oxo-isoindolin-5-yl]oxy-2-hydroxy-propyl]-2,6-diazaspiro[3.3]heptan-2-yl]phenyl]-1H-pyrrolo[2,3-b]pyridine-3-carbonyl]-2,4-difluoro-phenyl]-3-fluoro-pyrrolidine-1-sulfonamide (250 mg, 94%) as a yellow solid. MS (ESI): m/z 913.6 [M+H]$^+$.

Step G: (3R)—N-[3-[5-[4-[6-[(2R)-3-[2-[(3S)-2,6-dioxo-3-piperidyl]-1-oxo-isoindolin-5-yl]oxy-2-hydroxy-propyl]-2,6-diazaspiro[3.3]heptan-2-yl]phenyl]-1H-pyrrolo[2,3-b]pyridine-3-carbonyl]-2,4-difluoro-phenyl]-3-fluoro-pyrrolidine-1-sulfonamide and (3R)—N-[3-[5-[4-[6-[(2R)-3-[2-[(3R)-2,6-dioxo-3-piperidyl]-1-oxo-isoindolin-5-yl]oxy-2-hydroxy-propyl]-2,6-diazaspiro[3.3]heptan-2-yl]phenyl]-1H-pyrrolo[2,3-b]pyridine-3-carbonyl]-2,4-difluoro-phenyl]-3-fluoro-pyrrolidine-1-sulfonamide (3R)—N-[3-[5-[4-[6-[(2R)-3-[2-(2,6-dioxo-3-piperidyl)-1-oxo-isoindolin-5-yl]oxy-2-hydroxy-propyl]-2,6-diazaspiro[3.3]heptan-2-yl]phenyl]-1H-pyrrolo[2,3-b]pyridine-3-carbonyl]-2,4-difluoro-phenyl]-3-fluoro-pyrrolidine-1-sulfonamide (250 mg, 0.26 mmol) was separated by SFC (REGIS (S,S) WHELK-O1, 70% isopropanol:(0.1% ammonia in water)). The residue was basified with saturated aqueous sodium bicarbonate to pH 8. Then the mixture was diluted with water (20 mL) and extracted with tetrahydrofuran/ethyl acetate (2×30 mL). The combined organic layers were washed with brine (2×35 mL), dried over anhydrous sodium sulfate, filtered, and concentrated. The residue was further purified by preparative HPLC (Shim-pack C18, 18 to 42% acetonitrile:(0.225% formic acid in water)) and then SFC (REGIS (S,S) WHELK-O1, 70% isopropanol:(0.1% ammonia in water)). The residue was basified with saturated aqueous sodium bicarbonate to pH=8. Then the mixture was diluted with water (20 mL) and extracted with tetrahydrofuran/ethyl acetate (2×30 mL). The combined organic layers were washed with brine (2×35 mL), dried over anhydrous sodium sulfate, filtered, and concentrated. The residue was further purified by preparative HPLC (Phenomenex Synergi C18, 15 to 45% acetonitrile:(0.225% formic acid in water)) to afford (3R)—N-[3-[5-[4-[6-[(2R)-3-[2-[(3S)-2,6-dioxo-3-piperidyl]-1-oxo-isoindolin-5-yl]oxy-2-hydroxy-propyl]-2,6-diazaspiro[3.3]heptan-2-yl]phenyl]-1H-pyrrolo[2,3-b]pyridine-3-carbonyl]-2,4-difluoro-phenyl]-3-fluoro-pyrrolidine-1-sulfonamide formic acid salt (43.6 mg, 31%) as a yellow solid. MS (ESI): m/z 457.1 [M/2+H]$^+$; $^1$H NMR (400 MHz, DMSO-d$_6$) δ 13.06-12.69 (m, 1H), 10.97 (s, 1H), 8.61 (d, J=2.0 Hz, 1H), 8.49 (dd, J=2.8, 6.8 Hz, 1H), 8.19 (s, 1H), 8.04 (s, 1H), 7.66-7.51 (m, 4H), 7.27-7.15 (m, 2H), 7.09-7.03 (m, 1H), 6.56 (d, J=8.4 Hz, 2H), 5.42-5.18 (m, 1H),

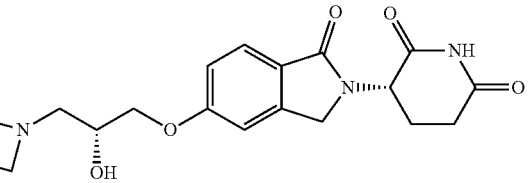

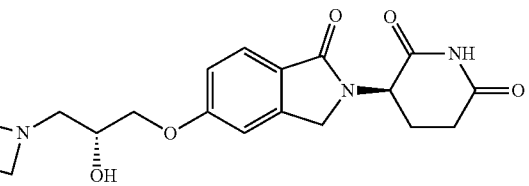

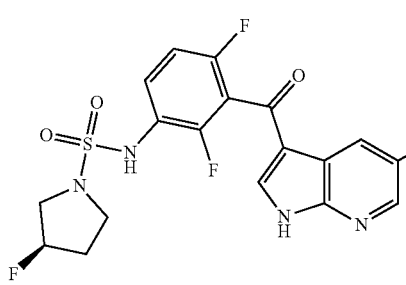

5.07 (dd, J=5.2, 13.2 Hz, 1H), 4.45-4.35 (m, 1H), 4.33-4.23 (m, 1H), 4.04 (dd, J=4.4, 10.0 Hz, 1H), 3.97-3.90 (m, 5H), 3.82-3.77 (m, 1H), 3.46 (s, 2H), 3.42 (s, 5H), 2.98-2.84 (m, 2H), 2.65-2.56 (m, 2H), 2.42-2.35 (m, 2H), 2.13-2.03 (m, 2H), 2.03-1.94 (m, 2H).

Also obtained was (3R)—N-[3-[5-[4-[6-[(2R)-3-[2-[(3R)-2,6-dioxo-3-piperidyl]-1-oxo-isoindolin-5-yl]oxy-2-hydroxy-propyl]-2,6-diazaspiro[3.3]heptan-2-yl]phenyl]-1H-pyrrolo[2,3-b]pyridine-3-carbonyl]-2,4-difluoro-phenyl]-3-fluoro-pyrrolidine-1-sulfonamide formic acid salt (38.0 mg, 27%) as a yellow solid. MS (ESI): m/z 913.3 [M+H]+; 1H NMR (400 MHz, DMSO-$d_6$) δ 12.90 (s, 1H), 10.97 (s, 1H), 8.61 (d, J=2.0 Hz, 1H), 8.56-8.41 (m, 1H), 8.20 (s, 1H), 8.04 (s, 1H), 7.65-7.51 (m, 4H), 7.26-7.15 (m, 2H), 7.06 (dd, J=2.0, 8.4 Hz, 1H), 6.56 (d, J=8.8 Hz, 2H), 5.42-5.18 (m, 1H), 5.07 (dd, J=5.2, 13.2 Hz, 1H), 4.44-4.35 (m, 1H), 4.32-4.24 (m, 1H), 4.06-4.01 (m, 1H), 3.96-3.91 (m, 5H), 3.83-3.78 (m, 1H), 3.45 (s, 2H), 3.42 (s, 5H), 2.98-2.85 (m, 2H), 2.66-2.55 (m, 2H), 2.40 (d, J=3.6 Hz, 1H), 2.37 (d, J=4.4 Hz, 1H), 2.13-2.03 (m, 2H), 2.03-1.93 (m, 2H).

The following exemplary compounds may be prepared by a procedure analogous to that described for Exemplary Compounds 123 and 124: 165 and 166.

Exemplary Synthesis of Exemplary Compound 27: 4-[4-[2-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]ethyl] piperazin-1-yl]-N-[(3S)-2,6-dioxo-3-piperidyl]-2-fluoro-benzamide

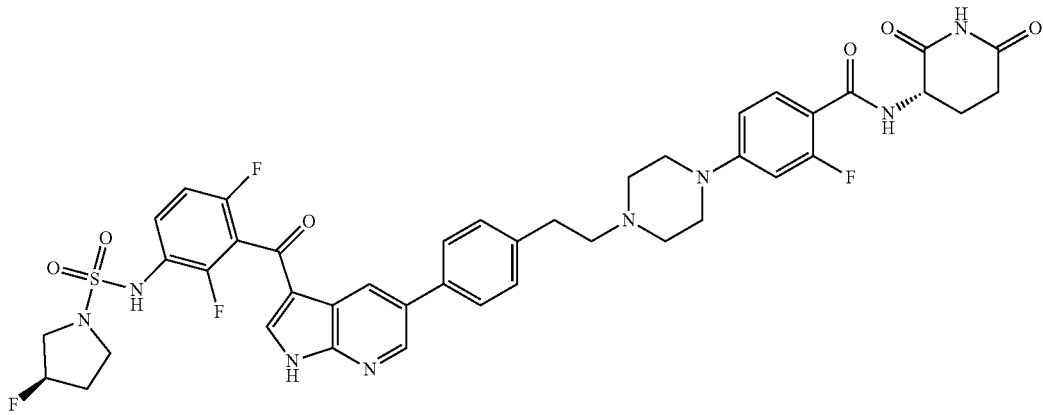 [SMILES: O=C1CC[C@H](NC(=O)c2ccc(N3CCN(CCc4ccc(-c5cnc6[nH]cc(C(=O)c7c(F)ccc(NS(=O)(=O)N8CC[C@@H](F)C8)c7F)c6c5)cc4)CC3)cc2F)C(=O)N1]

Step A: methyl 4-[4-(dimethoxymethyl)-1-piperidyl]-2-fluoro-benzoate

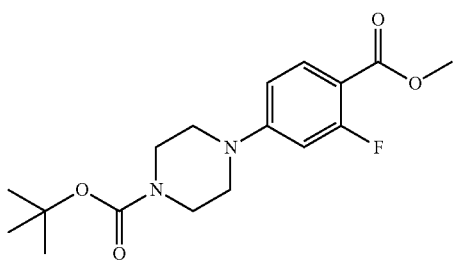 [SMILES: COC(=O)c1ccc(N2CCN(C(=O)OC(C)(C)C)CC2)cc1F]

To a solution of methyl 2,4-difluorobenzoate (1.70 g, 9.88 mmol) in N-methylpyrrolidinone (25 mL) was added diisopropylethylamine (3.48 g, 26.9 mmol, 4.69 mL) and tert-butyl piperazine-1-carboxylate hydrochloride (2.0 g, 8.9 mmol). The mixture was stirred at 100° C. for 5 hours. The reaction mixture was diluted with water (50 mL) and extracted with ethyl acetate (2×50 mL). The combined organic layers were washed with brine (2×50 mL), dried over anhydrous sodium sulfate, filtered, and concentrated. The residue was purified by column chromatography (petroleum ether:ethyl acetate 30:1 to 5:1) to afford tert-butyl 4-(3-fluoro-4-methoxycarbonyl-phenyl) piperazine-1-carboxylate (0.84 g, 27%) as a white solid. MS (ESI): m/z 312.2 [M+H]+.

Step B: methyl 2-fluoro-4-piperazin-1-yl-benzoate

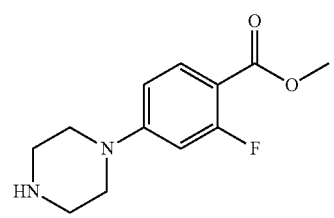 [SMILES: COC(=O)c1ccc(N2CCNCC2)cc1F]

To a solution of tert-butyl 4-(3-fluoro-4-methoxycarbonyl-phenyl)piperazine-1-carboxylate (0.84 g, 2.4 mmol) in dichloromethane (10 mL) was added 4 M hydrochloric acid in 1,4-dioxane (20 mL). The mixture was stirred at 30° C. for 1 hour. The reaction mixture was concentrated and the residue was purified by trituration with ethyl acetate (20 mL) to afford methyl 2-fluoro-4-piperazin-1-yl-benzoate hydrochloride (630 mg) as a white solid.

Step C: methyl 4-[4-[2-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]ethyl]piperazin-1-yl]-2-fluoro-benzoate

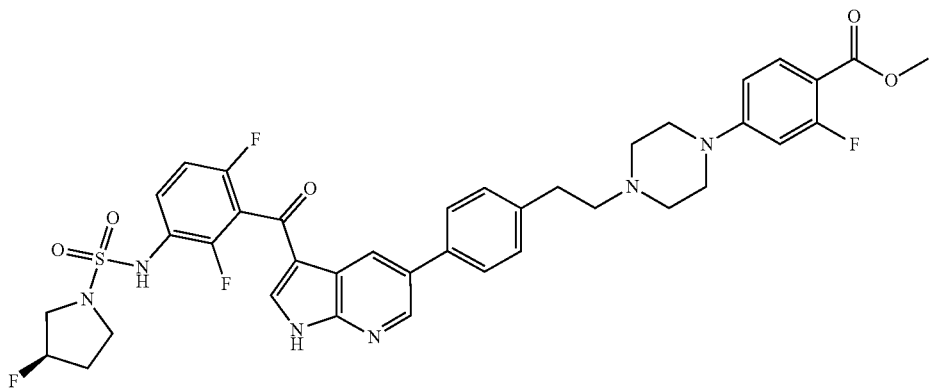 [SMILES: COC(=O)c1ccc(N2CCN(CCc3ccc(-c4cnc5[nH]cc(C(=O)c6c(F)ccc(NS(=O)(=O)N7CC[C@@H](F)C7)c6F)c5c4)cc3)CC2)cc1F]

To a solution of methyl 2-fluoro-4-piperazin-1-yl-benzoate hydrochloride (146 mg, 0.53 mmol) in methanol (5 mL) was added sodium acetate (87 mg, 1.06 mmol) to adjust the pH to ~8. The mixture was stirred at 25° C. for 10 minutes, then (3R)—N-[2,4-difluoro-3-[5-[4-(2-oxoethyl)phenyl]-1H-pyrrolo[2,3-b]pyridine-3-carbonyl]phenyl]-3-fluoro-pyrrolidine-1-sulfonamide (260 mg, 0.48 mmol) in dichloromethane (3 mL) was added, the mixture was stirred at 25° C. for 5 minutes. Acetic acid (64 mg, 1.0 mmol) was added to adjust the pH ~5.0. The mixture was stirred at 25° C. for 15 minutes. Then sodium cyanoborohydride (67 mg, 1.06 mmol) was added in portions. The reaction mixture was stirred at 25° C. for 30 minutes. The reaction mixture was diluted with water (40 mL), extracted with ethyl acetate (2×25 mL) and tetrahydrofuran (2×30 mL). The combined organic layers were washed with brine (2×40 mL), dried over anhydrous sodium sulfate, filtered, and concentrated. The residue was purified by preparative HPLC (Phenomenex Luna C18, 27% to 47% acetonitrile:(0.1% trifluoroacetic acid in water)) to afford methyl 4-[4-[2-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]ethyl]piperazin-1-yl]-2-fluoro-benzoate trifluoroacetic acid salt (260 mg, 55%) as a white solid.

Step D: 4, 4-[4-[2-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]ethyl]piperazin-1-yl]-2-fluoro-benzoic acid

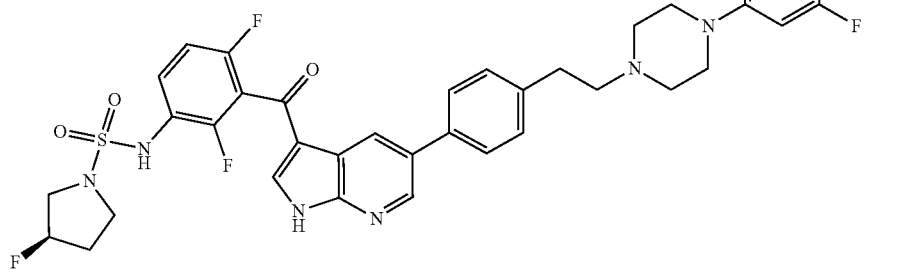

To a solution of methyl 4-[4-[2-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]ethyl]piperazin-1-yl]-2-fluoro-benzoate trifluoroacetic acid salt (260 mg, 0.29 mmol) in tetrahydrofuran (4 mL) and water (2 mL) was added sodium hydroxide (47 mg, 1.1 mmol) and methanol (3 mL). The mixture was stirred at 45° C. for 12 hours. The reaction mixture was concentrated and the residue was diluted with water (10 mL), then acidified with aqueous hydrochloric acid (2 M) to pH 5-6. Then the mixture was extracted with ethyl acetate (2×25 mL) and tetrahydrofuran (30 mL). The combined organic layers were washed with brine (2×25 mL), dried over anhydrous sodium sulfate, filtered and concentrated to afford 4-[4-[2-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]ethyl]piperazin-1-yl]-2-fluoro-benzoic acid (260 mg) as a light red solid. MS (ESI): m/z 750.8 [M+H]+.

Step E: 4-[4-[2-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]ethyl] piperazin-1-yl]-N-[(3S)-2,6-dioxo-3-piperidyl]-2-fluoro-benzamide

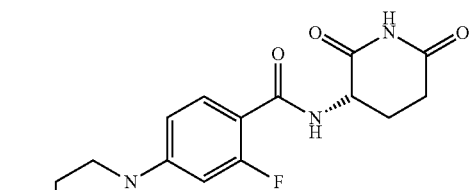

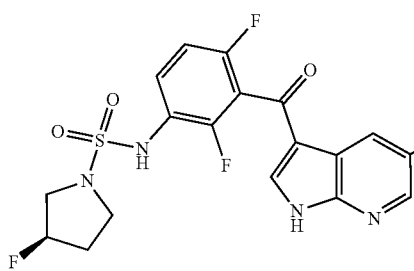

To a solution of 4-[4-[2-[4-[3-[2,6-difluoro-3-[[(3R)-3-fluoropyrrolidin-1-yl]sulfonylamino] benzoyl]-1H-pyrrolo[2,3-b]pyridin-5-yl]phenyl]ethyl]piperazin-1-yl]-2-fluoro-benzoic acid (130 mg, 0.17 mmol) in N,N-dimethylformamide (2 mL) was added hydroxybenzotriazole (35 mg, 0.26 mmol) and 4-methylmorpholine (53 mg, 0.52 mmol) to pH ~8, and then 1-(3-dimethylaminopropyl)-3-ethylcarbodiimide hydrochloride (50 mg, 0.26 mmol) and (3S)-3-aminopiperidine-2,6-dione hydrochloride (42 mg, 0.26 mmol) was added. The mixture was stirred at 25° C. for 12 hours. The reaction mixture was filtered and concentrated. The residue was purified by preparative HPLC (Phenomenex Luna C18, 18% to 48% acetonitrile:(0.1% trifluoroacetic acid in water) to afford 4-[4-[2-[4-[3-[2,6-difluoro-3-[[(3R)-3-fluoropyrrolidin-1-yl]sulfonylamino]-1H-pyrrolo[2,3-b]pyridin-5-yl]phenyl]ethyl]piperazin-1-yl]-N-[(3S)-2,6-dioxo-3-piperidyl]-2-fluoro-benzamide trifluoroacetic acid salt (82.5 mg, 47%) as an off-white solid. MS (ESI): m/z 862.3 [M+H]+; 1H NMR (400 MHz, DMSO-d6) δ 13.00 (d, J=2.8 Hz, 1H), 10.85 (s, 1H), 9.85 (s, 2H), 8.79-8.54 (m, 2H), 8.13 (d, J=4.0 Hz, 2H), 7.77 (d, J=8.0 Hz, 2H), 7.73-7.68 (m, 1H), 7.67-7.59 (m, 1H), 7.46 (d, J=8.4 Hz, 2H), 7.28 (t, J=8.8 Hz, 1H), 7.00-6.91 (m, 2H), 5.39-5.22 (m, 1H), 4.78-4.69 (m, 1H), 4.14-4.07 (m, 2H), 3.54-3.45 (m, 4H), 3.44-3.34 (m, 3H), 3.34-3.24 (m, 2H), 3.23-3.16 (m, 3H), 3.14-3.09 (m, 2H), 2.84-2.72 (m, 1H), 2.15-1.98 (m, 4H).

The following exemplary compounds may be prepared by a procedure analogous to that described for Exemplary Compound 27: 28, 29, 30, 31, 33, 37, 48, 194, 196, 197, 339, 340, 341, 342, 343, 344, 345, 346, 347, 348, 349, 350, 351, 352, 353, 354, 355, 356, 357, 358, 359, 360, 361, 362, and 363.

Exemplary Synthesis of Exemplary Compound 90: (3R)—N-[3-[5-[4-[(2R)-3-[4-[2-(2,6-dioxo-3-piperidyl)-1-oxo-isoindolin-5-yl]piperazin-1-yl]-2-hydroxy-propyl]phenyl]-1H-pyrrolo[2,3-b]pyridine-3-carbonyl]-2,4-difluoro-phenyl]-3-fluoro-pyrrolidine-1-sulfonamide

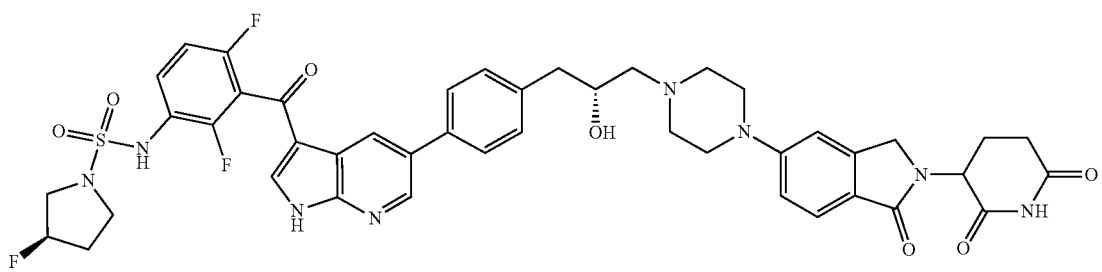 [SMILES: O=C1CCC(N2Cc3cc(N4CCN(C[C@H](O)Cc5ccc(-c6cnc7[nH]cc(C(=O)c8c(F)ccc(NS(=O)(=O)N9CC[C@@H](F)C9)c8F)c7c6)cc5)CC4)ccc3C2=O)C(=O)N1]

Step A:
(2R)-3-(4-bromophenyl)-2-hydroxy-propanal

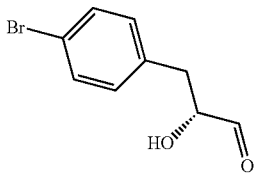 [SMILES: O=C[C@H](O)Cc1ccc(Br)cc1]

To a solution of (2R)-3-(4-bromophenyl)propane-1,2-diol (500 mg, 2.16 mmol) in dichloromethane (20 mL) and saturated aqueous sodium bicarbonate (10 mL) was added potassium bromide (257 mg, 2.16 mmol), 2,2,6,6-tetramethyl-1-piperidinyloxyl (17 mg, 0.10 mmol) and sodium hypochlorite (161 mg, 2.16 mmol) at 0° C. The mixture was stirred at 0° C. for 30 minutes. The reaction mixture was quenched by addition saturated aqueous sodium thiosulfate solution 5 mL at 0° C., and then diluted with water (50 mL) and extracted with tetrahydrofuran (2×30 mL). The combined organic layers were washed with brine (2×50 mL), dried over anhydrous sodium sulfate, filtered and concentrated under reduced pressure to give (2R)-3-(4-bromophenyl)-2-hydroxy-propanal (420 mg) as a yellow solid.

Step B: 3-[5-[4-[(2R)-3-(4-bromophenyl)-2-hydroxy-propyl]piperazin-1-yl]-1-oxo-isoindolin-2-yl]piperidine-2,6-dione

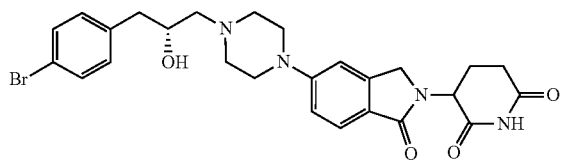 [SMILES: O=C1CCC(N2Cc3cc(N4CCN(C[C@H](O)Cc5ccc(Br)cc5)CC4)ccc3C2=O)C(=O)N1]

To a solution of 3-(1-oxo-5-piperazin-1-yl-isoindolin-2-yl)piperidine-2,6-dione hydrochloride (668 mg, 1.83 mmol) in methanol (5 mL) and dichloromethane (5 mL) was added sodium acetate (300 mg, 3.67 mmol), the mixture was stirred at 30° C. for 15 minutes, then (2R)-3-(4-bromophenyl)-2-hydroxy-propanal (420 mg, 1.83 mmol) was added and stirred at 30° C. for another 15 minutes, then sodium cyanoborohydride (230 mg, 3.67 mmol) was added. The mixture was stirred at 30° C. for 30 minutes. The reaction mixture was diluted with water (20 mL) and extracted with tetrahydrofuran (3×20 mL). The combined organic layers were washed with brine (2×30 mL), dried over anhydrous sodium sulfate, filtered, and concentrated. The residue was purified by flash silica gel chromatography (0 to 5% ethyl acetate:petroleum ether) to give 3-[5-[4-[(2R)-3-(4-bromophenyl)-2-hydroxy-propyl]piperazin-1-yl]-1-oxo-isoindolin-2-yl]piperidine-2,6-dione (589 mg, 56%) as a white solid. MS (ESI): m/z 541.1 [M+H]$^+$.

Step C: tert-butyl 3-[3-[tert-butoxycarbonyl-[(3R)-3-fluoropyrrolidin-1-yl]sulfonyl-amino]-2,6-difluoro-benzoyl]-5-[4-[(2R)-3-[4-[2-(2,6-dioxo-3-piperidyl)-1-oxo-isoindolin-5-yl]piperazin-1-yl]-2-hydroxy-propyl]phenyl]pyrrolo[2,3-b]pyridine-1-carboxylate

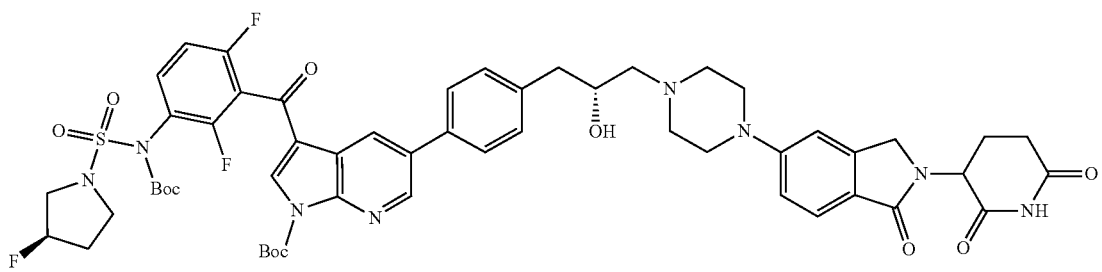 [SMILES: CC(C)(C)OC(=O)N(c1ccc(F)c(C(=O)c2cn(C(=O)OC(C)(C)C)c3ncc(-c4ccc(C[C@@H](O)CN5CCN(c6ccc7c(c6)CN(C6CCC(=O)NC6=O)C7=O)CC5)cc4)cc23)c1F)S(=O)(=O)N1CC[C@@H](F)C1]

To a solution of 3-[5-[4-[(2R)-3-(4-bromophenyl)-2-hydroxy-propyl]piperazin-1-yl]-1-oxo-isoindolin-2-yl]piperidine-2,6-dione (200 mg, 0.36 mmol) and tert-butyl 3-[3-[tert-butoxycarbonyl-[(3R)-3-fluoropyrrolidin-1-yl]sulfonyl-amino]-2,6-difluoro-benzoyl]-5-(4,4,5,5-tetramethyl-1,3,2-dioxaborolan-2-yl)pyrrolo[2,3-b]pyridine-1-carboxylate (277 mg, 0.36 mmol) in water (0.5 mL) and 1,4-dioxane (5 mL) was added dichloro[1,1'-bis(di-t-butylphosphino)ferrocene]palladium(II) (24 mg, 0.03 mmol) and potassium carbonate (102 mg, 0.73 mmol). The mixture was stirred at 100° C. for 1 hour. The reaction mixture was diluted with water (50 mL) and extracted with tetrahydrofuran (3×20 mL). The combined organic layers were washed with brine (2×50 mL), dried over anhydrous sodium sulfate, filtered and concentrated to give tert-butyl 3-[3-[tert-butoxycarbonyl-[(3R)-3-fluoropyrrolidin-1-yl]sulfonyl-amino]-2,6-difluoro-benzoyl]-5-[4-[(2R)-3-[4-[2-(2,6-dioxo-3-piperidyl)-1-oxo-isoindolin-5-yl]piperazin-1-yl]-2-hydroxy-propyl]phenyl]pyrrolo[2,3-b]pyridine-1-carboxylate (490 mg) as a yellow solid. MS (ESI): m/z 984.9 [M−100+H]$^+$.

Step D: (3R)—N-[3-[5-[4-[(2R)-3-[4-[2-(2,6-dioxo-3-piperidyl)-1-oxo-isoindolin-5-yl]piperazin-1-yl]-2-hydroxy-propyl]phenyl]-1H-pyrrolo[2,3-b]pyridine-3-carbonyl]-2,4-difluoro-phenyl]-3-fluoro-pyrrolidine-1-sulfonamide

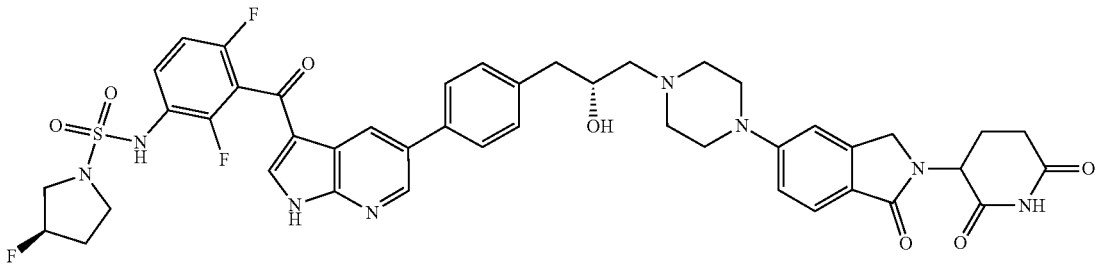 [SMILES: O=C1CCC(N2Cc3cc(N4CCN(C[C@H](O)Cc5ccc(-c6cnc7[nH]cc(C(=O)c8c(F)ccc(NS(=O)(=O)N9CC[C@@H](F)C9)c8F)c7c6)cc5)CC4)ccc3C2=O)C(=O)N1]

To a solution of tert-butyl 3-[3-[tert-butoxycarbonyl-[(3R)-3-fluoropyrrolidin-1-yl]sulfonyl-amino]-2,6-difluoro-benzoyl]-5-[4-[(2R)-3-[4-[2-(2,6-dioxo-3-piperidyl)-1-oxo-isoindolin-5-yl]piperazin-1-yl]-2-hydroxy-propyl]phenyl]pyrrolo[2,3-b]pyridine-1-carboxylate (490 mg, 0.45 mmol) in dichloromethane (8 mL) was added trifluoroacetic acid (2.31 g, 20.26 mmol, 1.5 mL). The mixture was stirred at 25° C. for 2 hours. The reaction mixture was diluted with water (50 mL) and extracted with tetrahydrofuran (3×20 mL). The combined organic layers were washed with brine (2×50 mL), dried over anhydrous sodium sulfate, filtered, and concentrated. The residue was purified by preparative HPLC (Phenomenex Synergi C18, 16 to 46% acetonitrile:(0.225% formic acid in water)) to give (3R)—N-[3-[5-[4-[(2R)-3-[4-[2-(2,6-dioxo-3-piperidyl)-1-oxo-isoindolin-5-yl]piperazin-1-yl]-2-hydroxy-propyl]phenyl]-1H-pyrrolo[2,3-b]pyridine-3-carbonyl]-2,4-difluoro-phenyl]-3-fluoro-pyrrolidine-1-sulfonamide formic acid salt (81.3 mg, 18%) as a white solid. MS (ESI): m/z 443.1 [M/2+H]+; $^1$H NMR (400 MHz, DMSO-$d_6$) δ 13.01-12.91 (m, 1H), 10.94 (s, 1H), 8.69 (d, J=2.0 Hz, 1H), 8.62-8.56 (m, 1H), 8.13 (d, J=12.8 Hz, 1H), 7.68-7.58 (m, 3H), 7.52 (d, J=8.8 Hz, 1H), 7.40 (d, J=8.4 Hz, 2H), 7.27 (t, J=8.0 Hz, 1H), 7.09-7.04 (m, 2H), 5.38-5.21 (m, 1H), 5.04 (dd, J=5.2, 13.6 Hz, 1H), 4.63-4.52 (m, 1H), 4.36-4.28 (m, 1H), 4.24-4.16 (m, 1H), 3.95 (td, J=4.8, 5.6 Hz, 1H), 3.48 (s, 1H), 3.40 (d, J=2.4 Hz, 2H), 3.26 (s, 5H), 2.95-2.83 (m, 2H), 2.63-2.56 (m, 5H), 2.37 (d, J=6.0 Hz, 2H), 2.15-2.04 (m, 2H), 2.02-1.90 (m, 2H).

The following exemplary compound may be prepared by a procedure analogous to that described for Exemplary Compound 90: 98.

Exemplary Synthesis of Exemplary Compound 105: (3R)—N-[3-[5-[4-[6-[(3R)-3-[2-[(3S)-2,6-dioxo-3-piperidyl]-1-oxo-isoindolin-5-yl]-3-hydroxy-propyl]-2,6-diazaspiro[3.3]heptan-2-yl]phenyl]-1H-pyrrolo[2,3-b]pyridine-3-carbonyl]-2,4-difluoro-phenyl]-3-fluoro-pyrrolidine-1-sulfonamide

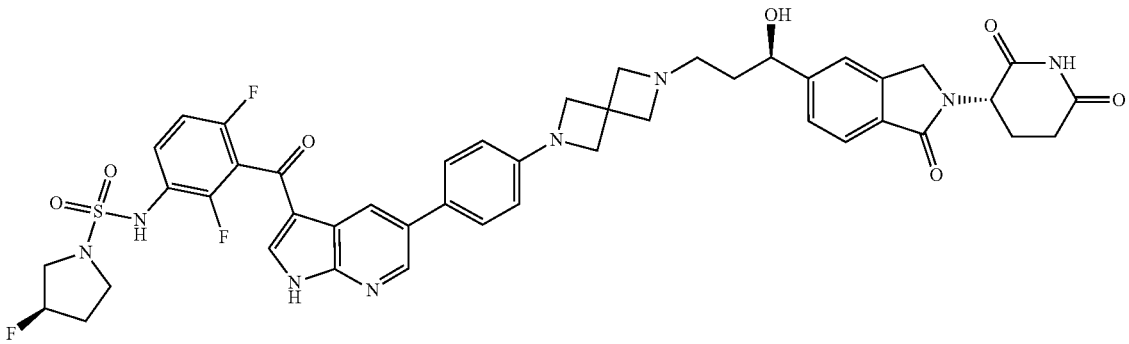 [SMILES: O=C1CC[C@H](N2Cc3cc([C@H](O)CCN4CC5(C4)CN(c4ccc(-c6cnc7[nH]cc(C(=O)c8c(F)ccc(NS(=O)(=O)N9CC[C@@H](F)C9)c8F)c7c6)cc4)C5)ccc3C2=O)C(=O)N1]

Step A: tert-butyl (4S)-5-amino-4-(5-bromo-1-oxo-isoindolin-2-yl)-5-oxo-pentanoate

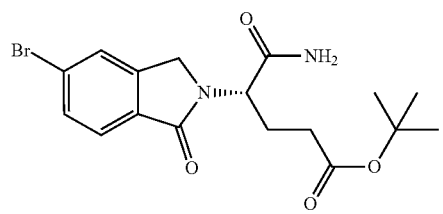 [SMILES: CC(C)(C)OC(=O)CC[C@@H](C(N)=O)N1Cc2cc(Br)ccc2C1=O]

To a solution of methyl 4-bromo-2-(bromomethyl)benzoate (12.79 g, 41.53 mmol) in dimethylformamide (200 mL) was added diisopropylethylamine (26.84 g, 207.65 mmol, 36.17 mL) and tert-butyl (4S)-4,5-diamino-5-oxo-pentanoate (9.24 g, 45.68 mmol). The mixture was stirred at 50° C. for 2 hours. Then the mixture was stirred at 100° C. for 12 hours. The reaction mixture was diluted with water (400 mL) and extracted with ethyl acetate (150 mL×4). The combined organic layers were washed with brine (3×200 mL), dried over anhydrous sodium sulfate, filtered, and concentrated. The residue was purified by flash silica gel chromatography (0 to 50% ethyl acetate:petroleum ether) and the product was triturated with 1:1 petroleum ether:ethyl acetate at 25° C. for 20 minutes to give tert-butyl (4S)-5-amino-4-(5-bromo-1-oxo-isoindolin-2-yl)-5-oxo-pentanoate (12.47 g, 75%) as a white solid. MS (ESI): m/z 343.2 [M−57+H]⁺; ¹H NMR (400 MHz, DMSO-d₆) δ 7.88 (d, J=0.8 Hz, 1H), 7.70-7.66 (m, 1H), 7.65-7.61 (m, 1H), 7.59 (s, 1H), 7.21 (s, 1H), 4.76-4.68 (m, 1H), 4.65-4.55 (m, 1H), 4.51-4.42 (m, 1H), 2.20-2.08 (m, 3H), 2.03-1.91 (m, 1H), 1.32 (s, 9H).

Step B: tert-butyl (4S)-5-amino-5-oxo-4-(1-oxo-5-vinyl-isoindolin-2-yl)pentanoate

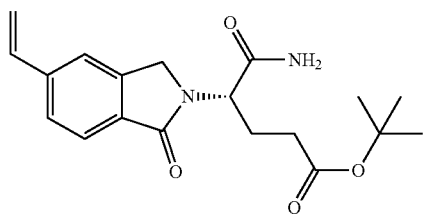 [SMILES: C=Cc1ccc2c(c1)CN([C@@H](CCC(=O)OC(C)(C)C)C(N)=O)C2=O]

To a solution of tert-butyl (4S)-5-amino-4-(5-bromo-1-oxo-isoindolin-2-yl)-5-oxo-pentanoate (8 g, 20.14 mmol) in 1,4-dioxane (120 mL) and water (15 mL) was added [1,1'-bis(diphenylphosphino)ferrocene]dichloropalladium(II) (1.47 g, 2.01 mmol), potassium carbonate (8.35 g, 60.41 mmol) and potassium vinyltrifluoroborate (5.39 g, 40.2 mmol). The mixture was stirred at 70° C. for 12 hours. The reaction mixture was diluted with water (300 mL) and extracted with ethyl acetate (2×100 mL). The combined organic phase was washed with brine (2×100 mL), dried with anhydrous sodium sulfate, filtered, and concentrated. The residue was purified by column chromatography (10:1 to 3:1 petroleum ether:ethyl acetate) to give tert-butyl (4S)-5-amino-5-oxo-4-(1-oxo-5-vinyl-isoindolin-2-yl)pentanoate (5.5 g, 79%) as a yellow solid. MS (ESI): m/z 289.1 [M+−57+H]⁺.

Step C: tert-butyl (4S)-5-amino-4-[5-(1,2-dihydroxyethyl)-1-oxo-isoindolin-2-yl]-5-oxo-pentanoate

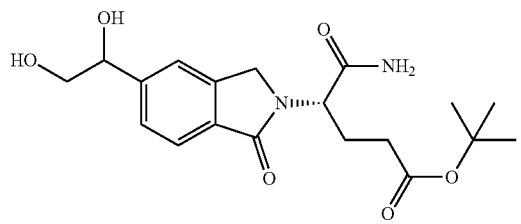 [SMILES: CC(C)(C)OC(=O)CC[C@@H](C(N)=O)N1Cc2cc(C(O)CO)ccc2C1=O]

To a solution of 4-methyl-4-oxido-morpholin-4-ium (5.10 g, 43.5 mmol, 4.60 mL) and osmium tetroxide (184 mg, 0.72 mmol) in water (30 mL), acetone (12 mL) and t-butanol (6 mL) was added tert-butyl (4S)-5-amino-5-oxo-4-(1-oxo-5-vinyl-isoindolin-2-yl)pentanoate (5.0 g, 14 mmol) in acetone (30 mL) and dichloromethane (100 mL) at 0° C. The mixture was stirred at 0° C. for 2 hours. The reaction was quenched by addition of saturated aqueous sodium thiosulfate solution (100 mL), extracted with dichloromethane (3×150 mL) and the organic phases were combined and washed sequentially with water (3×200 mL), saturated aqueous sodium chloride solution (3×100 mL), anhydrous sodium sulfate dried and filtered, and the filtrate was concentrated. The residue was purified by flash silica gel chromatography (0 to 5% methanol:dichloromethane) to give tert-butyl (4S)-5-amino-4-[5-(1,2-dihydroxyethyl)-1-oxo-isoindolin-2-yl]-5-oxo-pentanoate (4.6 g, 83%) as a white solid.

Step D: tert-butyl (4S)-5-amino-4-(5-formyl-1-oxo-isoindolin-2-yl)-5-oxo-pentanoate

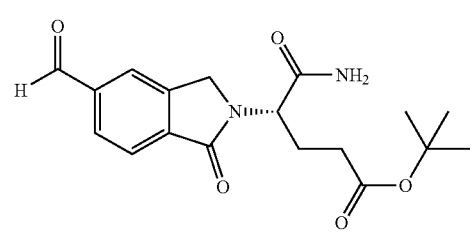 [SMILES: CC(C)(C)OC(=O)CC[C@@H](C(N)=O)N1Cc2cc(C=O)ccc2C1=O]

To a solution of tert-butyl (4S)-5-amino-4-[5-(1,2-dihydroxyethyl)-1-oxo-isoindolin-2-yl]-5-oxo-pentanoate (4.6 g, 12.16 mmol) in tetrahydrofuran (100 mL) was added dropwise sodium periodate (3.90 g, 18.2 mmol) in water (50 mL). The mixture was stirred at 25° C. for 5 minutes. The reaction mixture was diluted with water (150 mL) and extracted with ethyl acetate (3×100 mL). The combined organic phase was washed with saturated aqueous sodium thiosulfate (80 mL) and brine (12×50 mL), dried with anhydrous sodium sulfate, filtered, and concentrated. The residue was purified by flash silica gel chromatography (0 to 3% methanol:dichloromethane) to give tert-butyl (4S)-5-amino-4-(5-formyl-1-oxo-isoindolin-2-yl)-5-oxo-pentanoate (4.1 g, 97%) as a white solid.

Step E: tert-butyl (4S)-5-amino-4-[5-(1-hydroxybut-3-enyl)-1-oxo-isoindolin-2-yl]-5-oxo-pentanoate

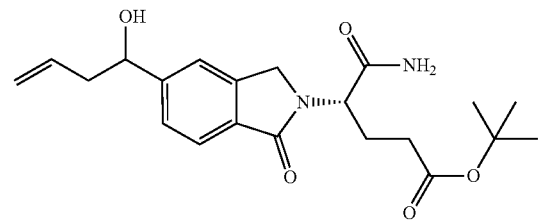 [SMILES: C=CCC(O)c1ccc2c(c1)CN([C@@H](CCC(=O)OC(C)(C)C)C(N)=O)C2=O]

To a solution of tert-butyl (4 S)-5-amino-4-(5-formyl-1-oxo-isoindolin-2-yl)-5-oxo-pentanoate (4.1 g, 11.84 mmol) and potassium allyltrifluoroborate (5.25 g, 35.5 mmol) in dichloromethane (200 mL) was dropwise added boron trifluoride ether solution (5.04 g, 35.5 mmol, 4.38 mL) at −70° C. The mixture was stirred at −70° C. for 45 minutes. The mixture was quenched by addition saturated aqueous sodium bicarbonate (100 mL) at −70° C. The reaction mixture was diluted with water (300 mL) and extracted with dichloromethane (3×150 mL). The combined organic phase was washed with brine (2×100 mL), dried with anhydrous sodium sulfate, filtered, and concentrated. The residue was purified by flash silica gel chromatography (0 to 5% methanol:dichloromethane) to give tert-butyl (4S)-5-amino-4-[5-(1-hydroxybut-3-enyl)-1-oxo-isoindolin-2-yl]-5-oxo-pentanoate (4.1 g, 85%) as a white solid. MS (ESI): m/z 333.1 [M−57+H]⁺.

249

Step F: (3S)-3-[5-(1-hydroxybut-3-enyl)-1-oxo-isoindolin-2-yl]piperidine-2,6-dione

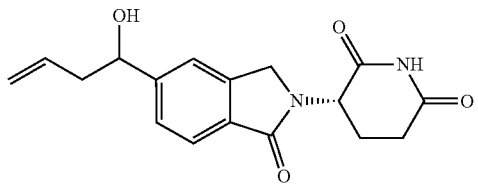 [SMILES: C=CCC(O)c1ccc2c(c1)CN([C@H]1CCC(=O)NC1=O)C2=O]

To a solution of tert-butyl (4S)-5-amino-4-[5-(1-hydroxy-but-3-enyl)-1-oxo-isoindolin-2-yl]-5-oxo-pentanoate (4.1 g, 10.55 mmol) in acetonitrile (80 mL) was added benzene-sulfonic acid (3.34 g, 21.1 mmol). The mixture was stirred at 80° C. for 12 hours. The mixture was quenched by addition saturated aqueous sodium bicarbonate (50 mL) at 20° C. The reaction mixture was diluted with water (150 mL) and extracted with 3:1 ethyl acetate:tetrahydrofuran (3×80 mL). The combined organic phase was washed with brine (2×210 mL), dried with anhydrous sodium sulfate, filtered, and concentrated. The residue was purified by flash silica gel chromatography (0 to 5% methanol:dichloromethane) to give (3S)-3-[5-(1-hydroxybut-3-enyl)-1-oxo-isoindolin-2-yl]piperidine-2,6-dione (2.6 g, 78%) as a white solid. MS (ESI): m/z 315.2 [M+H]+.

Step G: (3S)-3-[5-[1-[tert-butyl(dimethyl)silyl]oxy-but-3-enyl]-1-oxo-isoindolin-2-yl]piperidine-2,6-dione

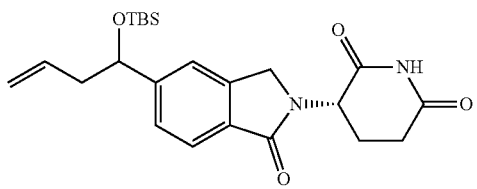 [SMILES: C=CCC(O[Si](C)(C)C(C)(C)C)c1ccc2c(c1)CN([C@H]1CCC(=O)NC1=O)C2=O]

To a solution of (3S)-3-[5-(1-hydroxybut-3-enyl)-1-oxo-isoindolin-2-yl]piperidine-2,6-dione (1.6 g, 5.0 mmol) in dichloromethane (80 mL) was added imidazole (1.73 g, 25.4 mmol) and tert-butyldimethylsilyl chloride (3.45 g, 22.9 mmol). The mixture was stirred at 30° C. for 4 hours. The reaction mixture was diluted with water (120 mL) and extracted with dichloromethane (2×80 mL). The combined organic phase was washed with brine (2×100 mL), dried with anhydrous sodium sulfate, filtered, and concentrated. The residue was purified by flash silica gel chromatography (0 to 3% methanol:dichloromethane) to give (3S)-3-[5-[1-[tert-butyl(dimethyl)silyl]oxybut-3-enyl]-1-oxo-isoindolin-2-yl]piperidine-2,6-dione (1.8 g, 4.12 mmol, 80%, 98% purity) as a white solid. MS (ESI): m/z 429.4 [M+H]+.

250

Step H: (3S)-3-[5-[(1S)-1-[tert-butyl(dimethyl)silyl]oxybut-3-enyl]-1-oxo-isoindolin-2-yl]piperidine-2,6-dione and (3S)-3-[5-[(1R)-1-[tert-butyl(dimethyl)silyl]oxybut-3-enyl]-1-oxo-isoindolin-2-yl]piperidine-2,6-dione

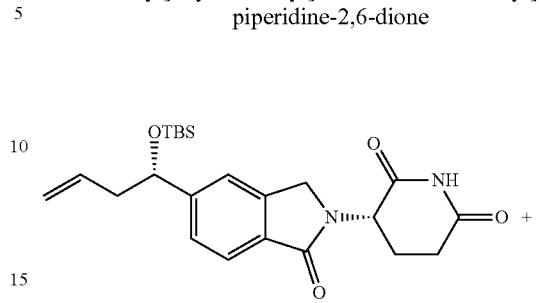

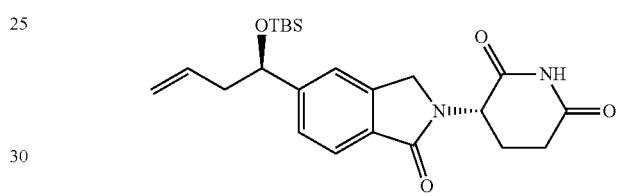

(3S)-3-[5-[1-[tert-butyl(dimethyl)silyl]oxybut-3-enyl]-1-oxo-isoindolin-2-yl]piperidine-2,6-dione (1 g, 2.33 mmol) was separated by SFC (DAICEL CHIRALPAK AS-H, 25% (0.1% ammonia in water:methanol)) and further separated by SFC (DAICEL CHIRALPAK AD-H, 20% (0.1% ammonia in water:isopropanol)) to give (3S)-3-[5-[(1S)-1-[tert-butyl(dimethyl)silyl]oxybut-3-enyl]-1-oxo-isoindolin-2-yl]piperidine-2,6-dione (500 mg, 97%) as a white solid and (3S)-3-[5-[(1R)-1-[tert-butyl(dimethyl)silyl]oxybut-3-enyl]-1-oxo-isoindolin-2-yl]piperidine-2,6-dione (500 mg, 97%) as a white solid.

Step I: (3S)-3-[5-[(1R)-1-[tert-butyl(dimethyl)silyl]oxy-3,4-dihydroxy-butyl]-1-oxo-isoindolin-2-yl]piperidine-2,6-dione

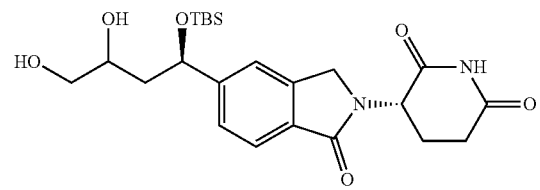 [SMILES: CC(C)(C)[Si](C)(C)O[C@H](CC(O)CO)c1ccc2c(c1)CN([C@H]1CCC(=O)NC1=O)C2=O]

To a solution of 4-methyl-4-oxido-morpholin-4-ium (410 mg, 3.50 mmol) and osmium tetroxide (15 mg, 0.05 mmol) in water (10 mL), acetone (8 mL), and t-butanol (4 mL) was added (3S)-3-[5-[(1R)-1-[tert-butyl(dimethyl)silyl]oxybut-3-enyl]-1-oxo-isoindolin-2-yl]piperidine-2,6-di one (500 mg, 1.17 mmol) in dichloromethane (30 mL) and acetone (9 mL). The mixture was stirred at 25° C. for 2 hours. The reaction was quenched by addition of (50 mL) of saturated aqueous sodium thiosulfate solution, extracted with dichloromethane (3×30 mL) and the organic phases were combined and washed sequentially with water (3×30 mL), saturated aqueous sodium chloride solution (3×30 mL), anhydrous sodium sulfate dried and filtered, and the filtrate was concentrated. The residue was purified by flash silica gel chromatography (0 to 5% methanol:dichloromethane) to give (3S)-3-[5-[(1R)-1-[tert-butyl(dimethyl)silyl]oxy-3,4-dihydroxy-butyl]-1-oxo-isoindolin-2-yl]piperidine-2,6-difor 10 minutes. The reaction mixture was diluted with water (30 mL) and extracted with ethyl acetate (2×15 mL). The combined organic phase was washed with saturated aqueous sodium thiosulfate (10 mL), brine (2×10 mL), dried with anhydrous sodium sulfate, filtered, and concentrated. The residue was purified by flash silica gel chromatography (0 to 3% methanol:dichloromethane) to give (3R)-3-[tert-butyl (dimethyl)silyl]oxy-3-[2-[(3S)-2,6-dioxo-3-piperidyl]-1-oxo-isoindolin-5-yl]propanal (390 mg, 89%) as a white solid. MS (ESI): m/z 431.1 [M+H]$^+$.

Step K: (3R)—N-[3-[5-[4-[6-[(3R)-3-[tert-butyl (dimethyl)silyl]oxy-3-[2-[(3S)-2,6-dioxo-3-piperidyl]-1-oxo-isoindolin-5-yl]propyl]-2,6-diazaspiro [3.3]heptan-2-yl]phenyl]-1H-pyrrolo[2,3-b]pyridine-3-carbonyl]-2,4-difluoro-phenyl]-3-fluoro-pyrrolidine-1-sulfonamide

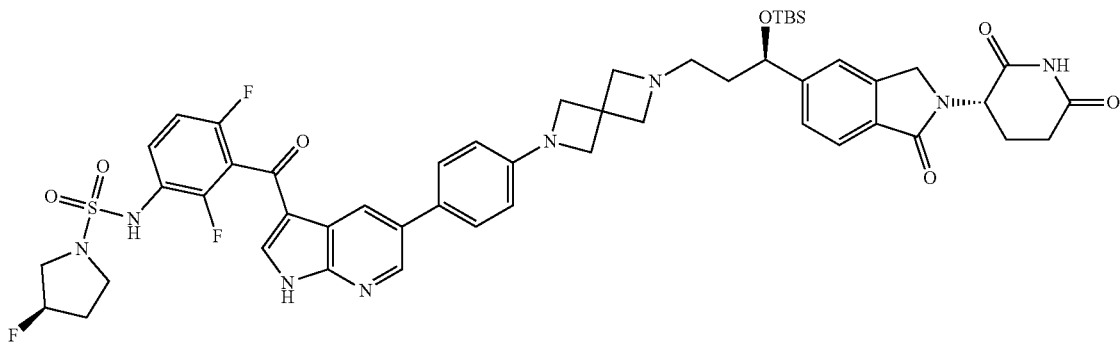

one (450 mg, 83%) as a white solid. MS (ESI): m/z 463.1 [M+H]$^+$; $^1$H NMR (400 MHz, CDCl$_3$) δ 8.27 (s, 1H), 7.85 (d, J=8.0 Hz, 1H), 7.52-7.41 (m, 2H), 5.26 (t, J=4.4 Hz, 1H), 5.24-5.19 (m, 1H), 5.04 (dd, J=5.2, 8.4 Hz, 1H), 4.54-4.46 (m, 1H), 4.40-4.32 (m, 1H), 3.88-3.78 (m, 1H), 3.76-3.70 (m, 2H), 3.64-3.54 (m, 1H), 3.51-3.38 (m, 1H), 2.98-2.79 (m, 2H), 2.47-2.31 (m, 3H), 2.30 (s, 1H), 2.26-2.18 (m, 1H), 2.02-1.89 (m, 1H), 1.77-1.69 (m, 1H), 0.10 (d, J=10.4 Hz, 3H), −0.06-−0.18 (m, 3H).

Step J: (3R)-3-[tert-butyl(dimethyl)silyl]oxy-3-[2-[(3S)-2,6-dioxo-3-piperidyl]-1-oxo-isoindolin-5-yl] propanal

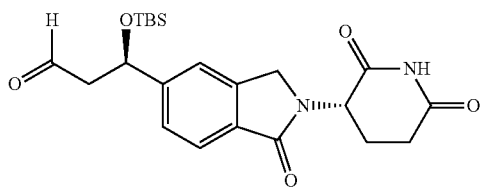 [SMILES: CC(C)(C)[Si](C)(C)O[C@H](CC=O)c1ccc2c(c1)CN([C@H]1CCC(=O)NC1=O)C2=O]

To a solution of (3S)-3-[5-[(1R)-1-[tert-butyl(dimethyl) silyl]oxy-3,4-dihydroxy-butyl]-1-oxo-isoindolin-2-yl]piperidine-2,6-dione (450 mg, 0.97 mmol) in tetrahydrofuran (5 mL) was added dropwise sodium periodate (312 mg, 1.46 mmol) in water (2.5 mL). The mixture was stirred at 25° C.

To a solution of (3R)—N-[3-[5-[4-(2,6-diazaspiro[3.3] heptan-2-yl)phenyl]-1H-pyrrolo[2,3-b]pyridine-3-carbonyl]-2,4-difluoro-phenyl]-3-fluoro-pyrrolidine-1-sulfonamide formic acid salt (300 mg, 0.46 mmol) in methanol (6 mL) and dichloromethane (2 mL) was added sodium acetate (76 mg, 0.94 mmol). The mixture was stirred at 30° C. for 10 minutes. (3R)-3-[tert-butyl(dimethyl)silyl]oxy-3-[2-[(3S)-2,6-dioxo-3-piperidyl]-1-oxo-isoindolin-5-yl]propanal (201 mg, 0.46 mmol) and acetic acid (56 mg, 0.93 mmol) was added, then the mixture was stirred at 30° C. for 20 minutes. Sodium cyanoborohydride (58 mg, 0.93 mmol) was added to the mixture and stirred at 30° C. for 1 hour. The reaction was diluted with water (15 mL) and extracted with 3:1 ethyl acetate:tetrahydrofuran (3×15 mL). The combined organic phase was washed with brine (2×15 mL), dried with anhydrous sodium sulfate, filtered, and concentrated. The residue was purified by flash silica gel chromatography (0 to 10% methanol:dichloromethane) to give (3R)—N-[3-[5-[4-[6-[(3R)-3-[tert-butyl(dimethyl)silyl]oxy-3-[2-[(3S)-2,6-dioxo-3-piperidyl]-1-oxo-isoindolin-5-yl]propyl]-2,6-diazaspiro[3.3]heptan-2-yl]phenyl]-1H-pyrrolo[2,3-b]pyridine-3-carbonyl]-2,4-difluoro-phenyl]-3-fluoro-pyrrolidine-1-sulfonamide (300 mg, 63%) as a yellow solid. MS (ESI): m/z 1011.1 [M+H]$^+$.

Step L: (3R)—N-[3-[5-[4-[6-[(3R)-3-[2-[(3S)-2,6-dioxo-3-piperidyl]-1-oxo-isoindolin-5-yl]-3-hydroxy-propyl]-2,6-diazaspiro[3.3]heptan-2-yl]phenyl]-1H-pyrrolo[2,3-b]pyridine-3-carbonyl]-2,4-difluoro-phenyl]-3-fluoro-pyrrolidine-1-sulfonamide

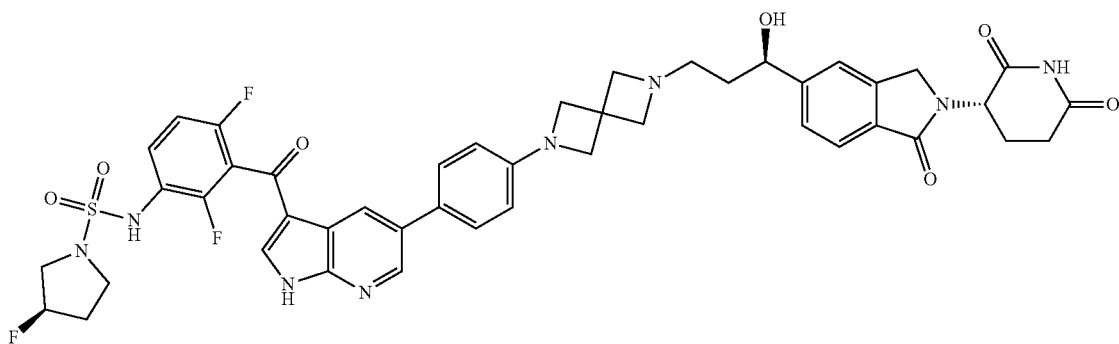 [SMILES: O=C1CC[C@H](N2Cc3cc([C@H](O)CCN4CC5(C4)CN(c4ccc(-c6cnc7[nH]cc(C(=O)c8c(F)ccc(NS(=O)(=O)N9CC[C@@H](F)C9)c8F)c7c6)cc4)C5)ccc3C2=O)C(=O)N1]

To a solution of (3R)—N-[3-[5-[4-[6-[(3R)-3-[tert-butyl(dimethyl)silyl]oxy-3-[2-[(3S)-2,6-dioxo-3-piperidyl]-1-oxo-isoindolin-5-yl]propyl]-2,6-diazaspiro[3.3]heptan-2-yl]phenyl]-1H-pyrrolo[2,3-b]pyridine-3-carbonyl]-2,4-difluoro-phenyl]-3-fluoro-pyrrolidine-1-sulfonamide (300 mg, 0.29 mmol) in dichloromethane (3 mL) was added trifluoroacetic acid (4 mL). The mixture was stirred at 30° C. for 20 hours. The mixture was dried and the residue was diluted with water (5 mL) and adjusted to pH 7-8 with saturated aqueous sodium bicarbonate. The mixture was extracted with dichloromethane (2×5 mL). The combined organic phase was washed with brine (2×5 mL), dried with anhydrous sodium sulfate, filtered, and concentrated. The residue was purified by preparative HPLC (Unisil 3-100 C18 Ultra, 15 to 45% acetonitrile:(0.225% formic acid in water)) to give (3R)—N-[3-[5-[4-[6-[(3R)-3-[2-[(3S)-2,6-dioxo-3-piperidyl]-1-oxo-isoindolin-5-yl]-3-hydroxy-propyl]-2,6-diazaspiro[3.3]heptan-2-yl]phenyl]-1H-pyrrolo[2,3-b]pyridine-3-carbonyl]-2,4-difluoro-phenyl]-3-fluoro-pyrrolidine-1-sulfonamide formic acid salt (111.8 mg, 38%) as a yellow solid. MS (ESI): m/z 897.3 [M+H]$^+$; 1H NMR (400 MHz, DMSO-$d_6$) δ 12.91 (s, 1H), 11.01 (s, 1H), 8.62 (d, J=2.0 Hz, 1H), 8.50 (s, 1H), 8.15 (s, 1H), 8.07 (s, 1H), 7.69 (d, J=8.0 Hz, 1H), 7.66-7.53 (m, 4H), 7.48 (d, J=8.4 Hz, 1H), 7.27 (t, J=8.8 Hz, 1H), 6.57 (d, J=8.8 Hz, 2H), 5.39-5.21 (m, 1H), 5.12 (dd, J=5.2, 13.2 Hz, 1H), 4.76 (t, J=6.0 Hz, 1H), 4.49-4.42 (m, 1H), 4.35-4.28 (m, 1H), 3.96 (s, 4H), 3.66 (s, 3H), 3.50-3.45 (m, 2H), 3.41-3.38 (m, 4H), 2.99-2.85 (m, 1H), 2.79-2.69 (m, 2H), 2.64-2.57 (m, 1H), 2.45-2.37 (m, 1H), 2.18-1.91 (m, 3H), 1.76-1.61 (m, 2H).

The following exemplary compounds may be prepared by a procedure analogous to that described for Exemplary Compound 105: 61 and 106.

Exemplary Synthesis of Exemplary Compound 74: (3R)—N-[3-[5-[4-[4-1(2S)-3-[2-[(3S)-2,6-dioxo-3-piperidyl]-1-oxo-isoindolin-5-yl]-2-hydroxy-propyl]piperazin-1-yl]phenyl]-1H-pyrrolo[2,3-b]pyridine-3-carbonyl]-2,4-difluoro-phenyl]-3-fluoro-pyrrolidine-1-sulfonamide

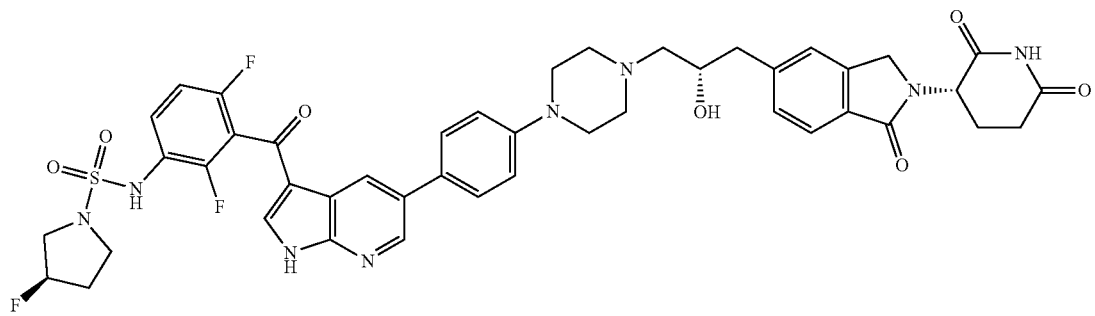 [SMILES: O=C1CC[C@H](N2Cc3cc(C[C@H](O)CN4CCN(c5ccc(-c6cnc7[nH]cc(C(=O)c8c(F)ccc(NS(=O)(=O)N9CC[C@@H](F)C9)c8F)c7c6)cc5)CC4)ccc3C2=O)C(=O)N1]

Step A: methyl 4-bromo-2-iodo-benzoate

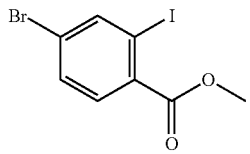

To 4-bromo-2-iodo-benzoic acid (24.55 g, 75.10 mmol) in methanol (151 mL) was added concentrated sulfuric acid (44.19 g, 450.58 mmol, 24 mL) and the reaction mixture was stirred for 90 minutes at 80° C. The reaction mixture was poured onto ice water (200 mL), sodium hydrogen carbonate was added until a pH value of 8 was reached and the reaction mixture was extracted with ethyl acetate (2×200 mL). The organic layer was washed with brine (2×200 mL), dried over sodium sulfate, filtered and concentrated to afford methyl 4-bromo-2-iodo-benzoate (25 g, 97%) as a black-brown oil.

Step B: methyl 4-bromo-2-cyano-benzoate

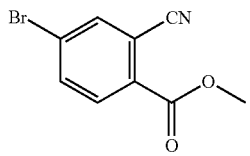

To a mixture of methyl 4-bromo-2-iodo-benzoate (25 g, 73 mmol) and copper(I) cyanide (6.57 g, 73.3 mmol) was added 1-methyl-2-pyrrolidinone (250 mL), and the mixture was stirred at 60° C. for 1 hour. The reaction mixture was cooled, a solution of saturated aqueous ammonium chloride and aqueous ammonia (1:1, 400 mL) was added, and the mixture was extracted with ethyl acetate (3×200 mL). The organic layer was washed with a solution of saturated aqueous ammonium chloride solution and aqueous ammonia (v:v=1:1, 200 mL), saturated aqueous ammonium chloride solution (2×100 mL), and brine (2×200 mL). The organic layer was dried over sodium sulfate, and the solvent was evaporated. The solid was triturated with 50:1 petroleum ether:ethyl acetate and the solid filtered to afford methyl 4-bromo-2-cyano-benzoate (12.9 g, 73%) as a brown solid. $^1$H NMR (400 MHz, CDCl$_3$) δ 8.02 (d, J=8.4 Hz, 1H), 7.95 (d, J=2.0 Hz, 1H), 7.83 (dd, J=2.0, 8.4 Hz, 1H), 4.01 (s, 3H).

Step C: methyl 4-allyl-2-cyano-benzoate

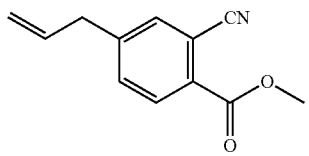

Allyl(tributyl)stannane (13.05 g, 39.41 mmol, 12 mL), methyl 4-bromo-2-cyano-benzoate (8.6 g, 35 mmol), cesium fluoride (11.97 g, 78.82 mmol), 2-(dicyclohexylphosphino)-2',4',6'-tri-i-propyl-1,1'-biphenyl (1.88 g, 3.94 mmol) and pre-milled palladium acetate (804 mg, 3.58 mmol) in 1,2-dimethoxyethane (36 mL) was degassed and then heated to 80° C. for 4 hours. The reaction mixture was cooled to room temperature, diluted with ethyl acetate (100 mL), filtered through a pad of silica gel eluting with ethyl acetate (200 mL), and concentrated. The residue was purified by flash chromatography (0 to 6% ethyl acetate:petroleum ether) to afford methyl 4-allyl-2-cyano-benzoate (6.2 g, 86%) as a red oil. MS (ESI): m/z 202.5 [M+H]$^+$.

Step D: methyl 2-cyano-4-(oxiran-2-ylmethyl)benzoate

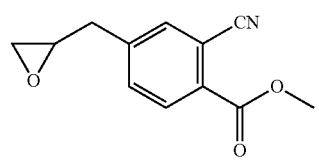 [SMILES: COC(=O)c1ccc(CC2CO2)cc1C#N]

To a mixture of methyl 4-allyl-2-cyano-benzoate (6.2 g, 30 mmol) in dichloromethane (150 mL) was added 3-chloroperbenzoic acid (7.51 g, 36.9 mmol) in one portion at 0° C. The mixture was stirred at 25° C. for 12 hours. Saturated aqueous sodium sulfite (100 mL) was poured into the mixture and stirred for 1 minute. The aqueous phase was extracted with dichloromethane (3×70 mL). The combined organic phase was washed with brine (2×70 mL), dried with anhydrous sodium sulfate, filtered and. The residue was purified by flash silica gel column chromatography (15 to 30% ethyl acetate:petroleum ether) to afford methyl 2-cyano-4-(oxiran-2-ylmethyl)benzoate (3.2 g, 47%) as a colorless oil. MS (ESI): m/z 218.6 [M+H]$^+$; $^1$H NMR (400 MHz, CDCl$_3$) δ 8.10 (d, J=8.0 Hz, 1H), 7.71 (d, J=1.6 Hz, 1H), 7.59 (dd, J=1.6, 8.0 Hz, 1H), 4.00 (s, 3H), 3.18 (dtd, J=2.4, 4.0, 6.4 Hz, 1H), 3.11-3.03 (m, 1H), 2.92-2.81 (m, 2H), 2.57-2.49 (m, 1H).

Step E: methyl 4-[3-[4-(4-bromophenyl)piperazin-1-yl]-2-hydroxy-propyl]-2-cyano-benzoate

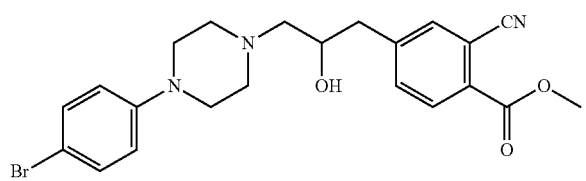 [SMILES: COC(=O)c1ccc(CC(O)CN2CCN(c3ccc(Br)cc3)CC2)cc1C#N]

Methyl 2-cyano-4-(oxiran-2-ylmethyl)benzoate (3.0 g, 13 mmol), 1-(4-bromophenyl) piperazine (3.33 g, 13.8 mmol) and diisopropylethylamine (3.93 g, 30.3 mmol, 5.3 mL) in dimethylacetamide (14 mL) was heated at 130° C. for 1 hour under microwave. Water (100 mL) was poured into the mixture and stirred for 1 minute. The aqueous phase was extracted with ethyl acetate (3×50 mL). The combined organic phase was washed with brine (3×50 mL), dried with anhydrous sodium sulfate, filtered, and concentrated. The oil was purified by flash silica gel column chromatography (10 to 70% ethyl acetate:petroleum ether) to afford methyl 4-[3-[4-(4-bromophenyl)piperazin-1-yl]-2-hydroxy-propyl]-2-cyano-benzoate (3.5 g, 47%) as a light yellow solid. MS (ESI): m/z 458.3 [M+H]$^+$.

Step F: methyl 4-[3-[4-(4-bromophenyl)piperazin-1-yl]-2-hydroxy-propyl]-2-formyl-benzoate

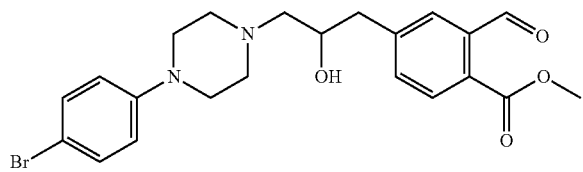 [SMILES: COC(=O)c1ccc(CC(O)CN2CCN(c3ccc(Br)cc3)CC2)cc1C=O]

To a mixture of methyl 4-[3-[4-(4-bromophenyl)piperazin-1-yl]-2-hydroxy-propyl]-2-cyano-benzoate (3.5 g, 6.5 mmol) in pyridine (20 mL) was added Raney nickel (558 mg, 6.52 mmol) in one portion at 25° C. Then sodium dihydrogen phosphate hydrate (3.60 g, 26.0 mmol) in water (5 mL) and acetic acid (10 mL) was added. The mixture was stirred at 50° C. for 1 hour. Dichloromethane (50 mL) was added into the solution. The organic phase was washed with saturated aqueous sodium bicarbonate (2×100 mL), brine (2×100 mL), dried with anhydrous sodium sulfate, filtered, and concentrated. The residue was purified by flash silica gel column chromatography (10 to 60% ethyl acetate:petroleum ether) and then preparative thin layer chromatography (1:20 methanol:dichloromethane) to afford methyl 4-[3-[4-(4-bromophenyl)piperazin-1-yl]-2-hydroxy-propyl]-2-formyl-benzoate (1.6 g, 51%) as a light yellow oil. MS (ESI): m/z 463.3 [M+H]$^+$.

Step G: 3-[5-[3-[4-(4-bromophenyl)piperazin-1-yl]-2-hydroxy-propyl]-1-oxo-isoindolin-2-yl]piperidine-2,6-dione

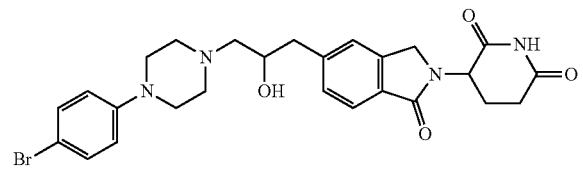 [SMILES: O=C1CCC(N2Cc3cc(CC(O)CN4CCN(c5ccc(Br)cc5)CC4)ccc3C2=O)C(=O)N1]

To a suspension of 3-aminopiperidine-2,6-dione hydrochloride (571 mg, 3.47 mmol) in methanol (10 mL) was added sodium acetate (569 mg, 6.94 mmol), the mixture was stirred at 25° C. for 10 minutes, then a solution of methyl 4-[3-[4-(4-bromophenyl)piperazin-1-yl]-2-hydroxy-propyl]-2-formyl-benzoate (1.6 g, 3.47 mmol) in dichloroethane (10 mL) was added, followed by acetic acid (416 mg, 6.94 mmol). The mixture was stirred at 25° C. for another 20 minutes, and then sodium cyanoborohydride (654 mg, 10.4 mmol) was added. Then resulting mixture was stirred at 35° C. for 14.5 hours. Saturated aqueous sodium bicarbonate (50 mL) was added into the mixture. The aqueous phase and the solid were extracted with dichloromethane (2×100 mL). The combined organic phase and white solid were concentrated. The residue was triturated with ethyl acetate (30 mL). The solid was collected by filtration and concentrated to afford 3-[5-[3-[4-(4-bromophenyl)piperazin-1-yl]-2-hydroxy-propyl]-1-oxo-isoindolin-2-yl]piperidine-2,6-dione (1.4 g, 74%) as a white solid. MS (ESI): m/z 543.3 [M+H]$^+$; $^1$H NMR (400 MHz, DMSO-d$_6$) δ 10.98 (s, 1H), 7.63 (d, J=8.0 Hz, 1H), 7.46 (s, 1H), 7.38 (d, J=8.0 Hz, 1H), 7.33 (d, J=9.2 Hz, 2H), 6.88 (d, J=9.2 Hz, 2H), 5.10 (dd, J=5.2, 13.2 Hz, 1H), 4.58 (s, 1H), 4.48-4.20 (m, 2H), 3.91 (d, J=8.4 Hz, 1H), 3.20-3.03 (m, 4H), 3.01-2.83 (m, 2H), 2.77-2.67 (m, 1H), 2.60-2.52 (m, 5H), 2.39 (dd, J=4.4, 13.2 Hz, 1H), 2.32 (d, J=6.4 Hz, 2H), 1.99 (dd, J=5.2, 7.2 Hz, 1H).

Step H: tert-butyl 3-[3-[tert-butoxycarbonyl-[(3R)-3-fluoropyrrolidin-1-yl]sulfonyl-amino]-2,6-difluoro-benzoyl]-5-[4-[4-[3-[2-(2,6-dioxo-3-piperidyl)-1-oxo-isoindolin-5-yl]-2-hydroxy-propyl]piperazin-1-yl]phenyl]pyrrolo[2,3-b]pyridine-1-carboxylate

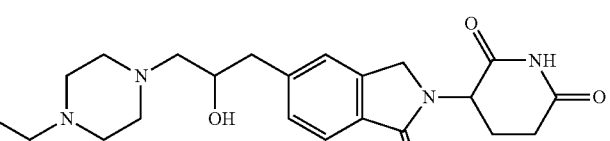

A mixture of 3-[5-[3-[4-(4-bromophenyl)piperazin-1-yl]-2-hydroxy-propyl]-1-oxo-isoindolin-2-yl]piperidine-2,6-dione (680 mg, 1.26 mmol), tert-butyl 3-[3-[tert-butoxycarbonyl-[(3R)-3-fluoropyrrolidin-1-yl]sulfonyl-amino]-2,6-difluoro-benzoyl]-5-(4,4,5,5-tetramethyl-1,3,2-dioxaborolan-2-yl)pyrrolo[2,3-b]pyridine-1-carboxylate (1.04 g, 1.38 mmol), sodium carbonate (200 mg, 1.88 mmol), dichloro[1,1'-bis(di-t-butylphosphino)ferrocene]palladium (II) (82 mg, 0.12 mmol) in N,N-dimethylformamide (15 mL) and water (2 mL) was degassed and purged with nitrogen 3x, and then the mixture was stirred at 90° C. for 3 hours. Water (50 mL) was poured into the mixture and stirred for 1 minute. The aqueous phase was extracted with ethyl acetate (3×30 mL). The combined organic phase was washed with brine (3×30 mL), dried with anhydrous sodium sulfate, filtered and concentrated to afford tert-butyl 3-[3-[tert-butoxycarbonyl-[(3R)-3-fluoropyrrolidin-1-yl]sulfonyl-amino]-2,6-difluoro-benzoyl]-5-[4-[4-[3-[2-(2,6-dioxo-3-piperidyl)-1-oxo-isoindolin-5-yl]-2-hydroxy-propyl]piperazin-1-yl]phenyl]pyrrolo[2,3-b]pyridine-1-carboxylate (1.3 g) as a brown oil. MS (ESI): m/z 984.8 [M−100+H]$^+$.

Step I: (3R)—N-[3-[5-[4-[4-[3-[2-(2,6-dioxo-3-piperidyl)-1-oxo-isoindolin-5-yl]-2-hydroxy-propyl]piperazin-1-yl]phenyl]-1H-pyrrolo[2,3-b]pyridine-3-carbonyl]-2,4-difluoro-phenyl]-3-fluoro-pyrrolidine-1-sulfonamide

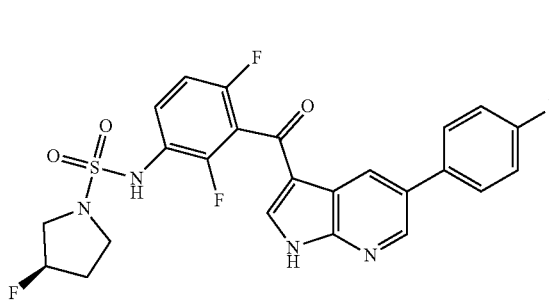

To a mixture of tert-butyl 3-[3-[tert-butoxycarbonyl-[(3R)-3-fluoropyrrolidin-1-yl]sulfonyl-amino]-2,6-difluoro-benzoyl]-5-[4-[4-[3-[2-(2,6-dioxo-3-piperidyl)-1-oxo-isoindolin-5-yl]-2-hydroxy-propyl]piperazin-1-yl]phenyl]pyrrolo[2,3-b]pyridine-1-carboxylate (1.3 g, 1.2 mmol) in dichloromethane (25 mL) was added trifluoroethane acid (5.46 g, 47.9 mmol) in one portion at 25° C. under nitrogen atmosphere. The mixture was stirred at 25° C. for 2 hours. Saturated aqueous sodium bicarbonate was added to adjust the pH to 8-9. Water (50 mL) was poured into the mixture and stirred for 1 minute. The aqueous phase was extracted with 1:1 tetrahydrofuran:ethyl acetate (2×30 mL). The combined organic phase was washed with brine (2×30 mL), dried with anhydrous sodium sulfate, filtered, and concentrated. The residue was purified by flash silica gel chromatography (0 to 13% methanol:dichloromethane) to afford (3R)—N-[3-[5-[4-[4-[3-[2-(2,6-dioxo-3-piperidyl)-1-oxo-isoindolin-5-yl]-2-hydroxy-propyl]piperazin-1-yl]phenyl]-1H-pyrrolo[2,3-b]pyridine-3-carbonyl]-2,4-difluoro-phenyl]-3-fluoro-pyrrolidine-1-sulfonamide (500 mg, 46%) as a brown solid. MS (ESI): m/z 884.9 [M+H]$^+$.

Step J (3R)—N-[3-[5-[4-[4-[(2S)-3-[2-[(3S)-2,6-dioxo-3-piperidyl]-1-oxo-isoindolin-5-yl]-2-hydroxy-propyl]piperazin-1-yl]phenyl]-1H-pyrrolo[2,3-b]pyridine-3-carbonyl]-2,4-difluoro-phenyl]-3-fluoro-pyrrolidine-1-sulfonamide O1, 60 to 70% 0.1% ammonia in water:isopropanol). The solution was acidified with formic acid and concentrated. Saturated aqueous sodium bicarbonate was added to adjust the pH to 9. The aqueous phase was extracted with 1:1 ethyl acetate:tetrahydrofuran (2×40 mL). The combined organic phase was washed with brine (2×40 mL), dried with anhydrous sodium sulfate, filtered, and concentrated. The residue was further purified by successive preparative HPLC (UniSil 3-100 C18 Ultra, 15 to 45% acetonitrile:(0.225% formic acid in water)) and chiral SFC (REGIS (S,S) WHELK-O1, 60% 0.1% ammonia in water:isopropanol). The resultant solution was acidified with formic acid and concentrated. Saturated aqueous sodium bicarbonate was added to adjust the pH to 9. The aqueous phase was extracted with 1:1 ethyl acetate:tetrahydrofuran (2×40 mL). The combined organic phase was washed with brine (2×40 mL), dried with anhydrous sodium sulfate, filtered, and concentrated. The residue was further purified by preparative HPLC (Shim-pack C18, 15 to 45% acetonitrile:(0.225% formic acid in water)) to afford (3R)—N-[3-[5-[4-[4-[(2S)-3-[2-[(3S)-2,6-dioxo-3-piperidyl]-1-oxo-isoindolin-5-yl]-2-hydroxy-propyl]piperazin-1-yl]phenyl]-1H-pyrrolo[2,3-b]pyridine-3-carbonyl]-2,4-difluoro-phenyl]-3-fluoro-pyrrolidine-1-sulfonamide (36.2 mg, 20%). MS (ESI): m/z 885.2 [M+H]$^+$; $^1$H NMR (400 MHz, DMSO-d$_6$) δ 12.91 (s, 1H), 10.99 (s, 1H), 10.32-9.44 (m, 1H), 8.66 (d, J=2.4 Hz, 1H), 8.55 (d, J=1.2 Hz, 1H), 8.14 (s, 1H), 8.08 (s, 1H), 7.63 (dd, J=8.4, 16.4 Hz, 4H), 7.49 (s, 1H), 7.41 (d, J=7.5 Hz, 1H), 7.33-7.24 (m, 1H), 7.08 (d, J=8.8 Hz, 2H), 5.39-5.19 (m, 1H), 5.11 (dd, J=5.2, 13.2 Hz, 1H), 4.78-4.58 (m, 1H), 4.50-4.26 (m, 2H), 3.99 (d, J=5.6 Hz, 1H), 3.26 (d, J=4.8 Hz, 5H), 3.08-2.82 (m, 3H), 2.75 (dd, J=7.6, 13.6 Hz, 1H), 2.70-2.61 (m, 5H), 2.55 (s, 2H), 2.43 (s, 1H), 2.42-2.35 (m, 2H), 2.12 (d, J=1.6 Hz, 1H), 2.08-1.95 (m, 2H).

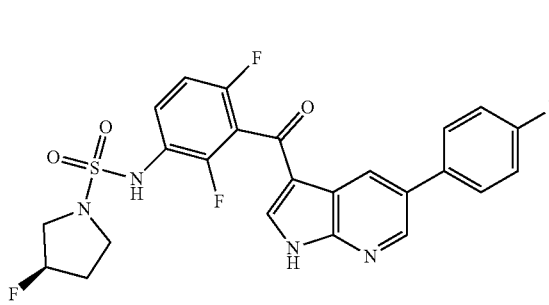

(3R)—N-[3-[5-[4-[4-[3-[2-(2,6-dioxo-3-piperidyl)-1-oxo-isoindolin-5-yl]-2-hydroxy-propyl]piperazin-1-yl]phenyl]-1H-pyrrolo[2,3-b]pyridine-3-carbonyl]-2,4-difluoro-phenyl]-3-fluoro-pyrrolidine-1-sulfonamide (700 mg, 0.79 mmol) was purified by chiral SFC (REGIS (R,R)WHELK- The following exemplary compounds may be prepared by a procedure analogous to that described for Exemplary Compound 74: 73, 75, 82, 107, 108, 109, 116, 128, 129, 130, 170, 171, and 32.

Exemplary Synthesis of Exemplary Compound 79: (3R)—N-[3-[5-[4-[4-[1-[2-(2,6-dioxo-3-piperidyl)-7-methoxy-1-oxo-isoindolin-5-yl]azetidin-3-yl]piperazin-1-yl]phenyl]-1H-pyrrolo[2,3-b]pyridine-3-carbonyl]-2,4-difluoro-phenyl]-3-fluoro-pyrrolidine-1-sulfonamide

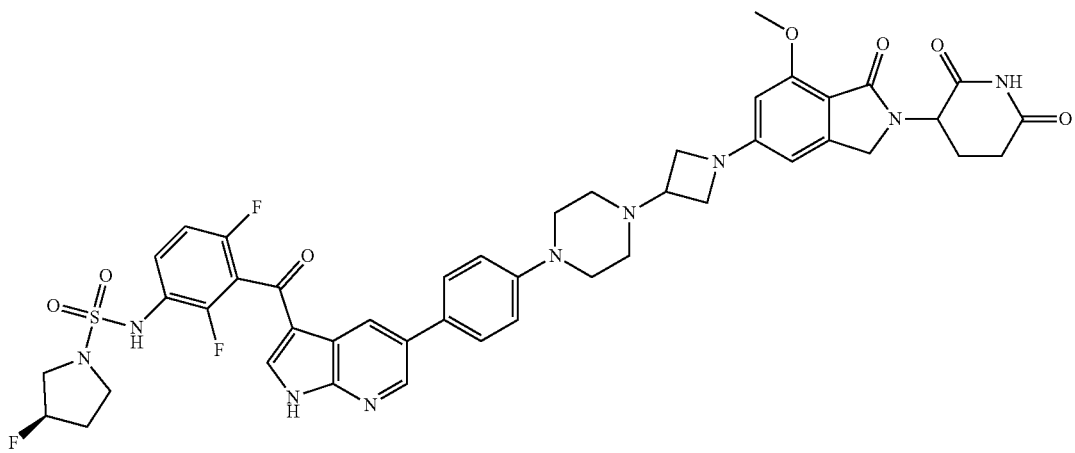 [SMILES: COc1cc(N2CC(N3CCN(c4ccc(-c5cnc6[nH]cc(C(=O)c7c(F)ccc(NS(=O)(=O)N8CC[C@@H](F)C8)c7F)c6c5)cc4)CC3)C2)cc2c1C(=O)N(C1CCC(=O)NC1=O)C2]

Step A: tert-butyl 4-(1-benzyloxycarbonylazetidin-3-yl)piperazine-1-carboxylate

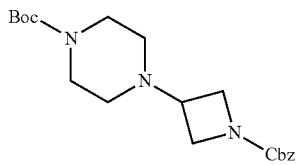

To a solution of tert-butyl piperazine-1-carboxylate (2.0 g, 10 mmol) and benzyl 3-oxoazetidine-1-carboxylate (2.20 g, 10.7 mmol) in dichloromethane (40 mL) was added triethylamine (2.17 g, 21.4 mmol). The mixture was stirred at 20° C. for 30 minutes. Then sodium triacetoxyborohydride (4.55 g, 21.4 mmol) was added to the mixture. The mixture was stirred at 20° C. for 2 h. The mixture was diluted with water (50 mL) and extracted with dichloromethane (3×50 mL). The combined organic layers were washed with brine (2×100 mL), dried with anhydrous sodium sulfate, filtered, and concentrated. The crude product was purified by preparative HPLC (Phenomenex Synergi Max-RP, 20 to 50% acetonitrile:(0.225% formic acid in water)) to afford tert-butyl 4-(1-benzyloxycarbonylazetidin-3-yl)piperazine-1-carboxylate (2.7 g, 66%) as a white solid. MS (ESI): m/z 376.2 [M+H]$^+$; $^1$H NMR (400 MHz, CDCl$_3$) δ 7.41-7.30 (m, 5H), 5.09 (s, 2H), 4.05-3.98 (m, 2H), 3.94-3.86 (m, 2H), 3.45 (t, J=4.8 Hz, 4H), 3.16-3.06 (m, 1H), 2.29 (t, J=4.8 Hz, 4H), 1.46 (s, 9H).

Step B: tert-butyl 4-(azetidin-3-yl)piperazine-1-carboxylate

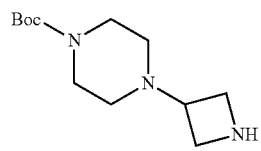 [SMILES: CC(C)(C)OC(=O)N1CCN(C2CNC2)CC1]

To a solution of tert-butyl 4-(1-benzyloxycarbonylazetidin-3-yl)piperazine-1-carboxylate (2.7 g, 7.1 mmol) in methanol (30 mL) and tetrahydrofuran (10 mL) was added 10% palladium on activated carbon (270 mg, 7.19 mmol) under nitrogen. The suspension was degassed under vacuum and purged with hydrogen several times. The mixture was stirred under hydrogen (50 psi) at 30° C. for 12 hours. The mixture was filtered and the filtrate was concentrated to afford tert-butyl 4-(azetidin-3-yl)piperazine-1-carboxylate (1.6 g, 92%) as a brown oil.

Step C: tert-butyl 4-[1-(3-cyano-5-methoxy-4-methoxycarbonyl-phenyl)azetidin-3-yl]piperazine-1-carboxylate

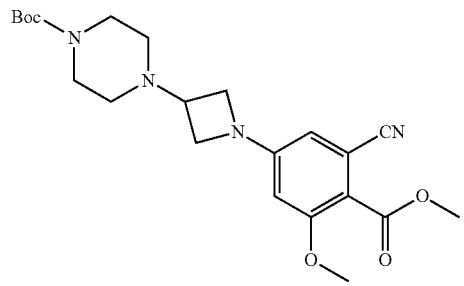 [SMILES: COC(=O)c1c(C#N)cc(N2CC(N3CCN(C(=O)OC(C)(C)C)CC3)C2)cc1OC]

To a solution of methyl 2-cyano-6-methoxy-4-(1,1,2,2,3,3,4,4,4-nonafluorobutylsulfonyloxy) benzoate (3.24 g, 6.63 mmol) and tert-butyl 4-(azetidin-3-yl)piperazine-1-carboxylate (1.6 g, 6.6 mmol) in 1,4-dioxane (20 mL) was added methanesulfonato(2-dicyclohexylphosphino-2,4,6-tri-i-propyl-1,1-biphenyl)(2-amino-1,1-biphenyl-2-yl)palladium(II) (561 mg, 0.66 mmol) and cesium carbonate (4.32 g, 13.2 mmol) under nitrogen atmosphere. The mixture was stirred at 90° C. for 12 hours. The mixture was diluted with water (50 mL) and extracted with ethyl acetate (3×30 mL). The combined organic layers were washed with brine (3×50 mL), dried with anhydrous sodium sulfate, filtered, and concentrated. The crude product was purified by column chromatography (1:0 to 5:1 petroleum ether:ethyl acetate) to afford tert-butyl 4-[1-(3-cyano-5-methoxy-4-methoxycarbonyl-phenyl)azetidin-3-yl]piperazine-1-carboxylate (2.2 g, 72%) as a yellow solid. MS (ESI): m/z 375.1 [M−56+1]$^+$; $^1$H NMR (400 MHz, CDCl$_3$) δ 6.29 (s, 1H), 6.01 (s, 1H), 4.05 (t, J=7.2 Hz, 2H), 3.92 (s, 3H), 3.86 (s, 3H), 3.84-3.79 (m, 2H), 3.48 (t, J=4.4 Hz, 4H), 3.40-3.31 (m, 1H), 2.37 (t, J=4.0 Hz, 4H), 1.47 (s, 9H).

Step D: methyl 4-[4-(dimethoxymethyl)-1-piperidyl]-2-formyl-6-methoxy-benzoate

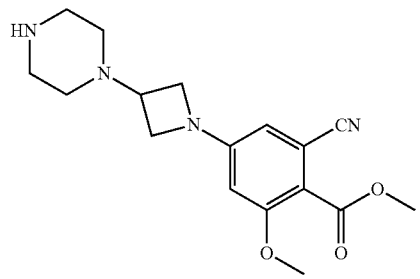 [SMILES: COC(=O)c1c(C#N)cc(N2CC(N3CCNCC3)C2)cc1OC]

To a solution of tert-butyl 4-[1-(3-cyano-5-methoxy-4-methoxycarbonyl-phenyl)azetidin-3-yl] piperazine-1-carboxylate (2.2 g, 5.11 mmol) in dichloromethane (20 mL) was added trifluoroacetic acid (15.40 g, 135.0 mmol). The mixture was stirred at 25° C. for 1 hour. The mixture was concentrated. The crude product was purified by preparative HPLC (Phenomenex Synergi Max-RP, 10 to 40% acetonitrile:(0.225% formic acid in water)) to afford methyl 2-cyano-6-methoxy-4-(3-piperazin-1-ylazetidin-1-yl)benzoate formic acid salt (1.5 g, 77%) as a white solid. MS (ESI): m/z 331.2 [M+H]$^+$; $^1$H NMR (400 MHz, DMSO-d$_6$) δ 8.59-8.43 (m, 2H), 6.48 (d, J=2.0 Hz, 1H), 6.29 (d, J=2.0 Hz, 1H), 4.12-4.05 (m, 2H), 3.84-3.79 (m, 5H), 3.78 (s, 3H), 3.59 (s, 2H), 3.15 (s, 4H), 2.69-2.59 (m, 4H).

Step E: methyl 4-[3-[4-(4-bromophenyl)piperazin-1-yl]azetidin-1-yl]-2-cyano-6-methoxy-benzoate

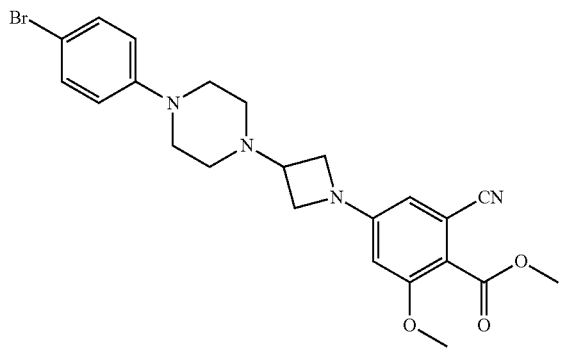 [SMILES: COC(=O)c1c(C#N)cc(N2CC(N3CCN(c4ccc(Br)cc4)CC3)C2)cc1OC]

To a solution of methyl 2-cyano-6-methoxy-4-(3-piperazin-1-ylazetidin-1-yl)benzoate formic acid salt (600 mg, 1.59 mmol) in dimethyl sulfoxide (20 mL) was added potassium carbonate (881 mg, 6.38 mmol). The mixture was stirred at 30° C. for 30 minutes. Then 1,4-dibromobenzene (1.13 g, 4.78 mmol), cuprous iodide (60 mg, 0.32 mmol) and 2-(2,6-dimethylanilino)-2-oxo-acetic acid (123 mg, 0.64 mmol) was added to the mixture. The mixture was stirred at 90° C. for 12 hours. The mixture was diluted with water (60 mL) and extracted with ethyl acetate (3×50 mL). The combined organic layers were washed with brine (3×150 mL), dried with anhydrous sodium sulfate, filtered, and concentrated. The crude product was purified by column chromatography (1:0 to 1:1 petroleum ether:ethyl acetate) to afford methyl 4-[3-[4-(4-bromophenyl)piperazin-1-yl]azetidin-1-yl]-2-cyano-6-methoxy-benzoate (550 mg, 71%) as a white solid. MS (ESI): m/z 487.1 [M+H]$^+$.

Step F: methyl 4-[3-[4-(4-bromophenyl)piperazin-1-yl] azetidin-1-yl]-2-formyl-6-methoxy-benzoate Step G: 3-[5-[3-[4-(4-bromophenyl)piperazin-1-yl] azetidin-1-yl]-7-methoxy-1-oxo-isoindolin-2-yl] piperidine-2,6-dione

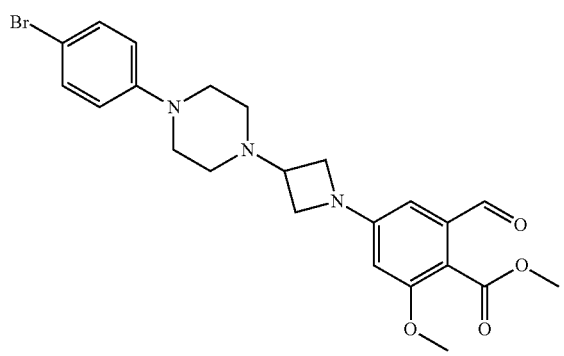 [SMILES: COC(=O)c1c(C=O)cc(N2CC(N3CCN(c4ccc(Br)cc4)CC3)C2)cc1OC]

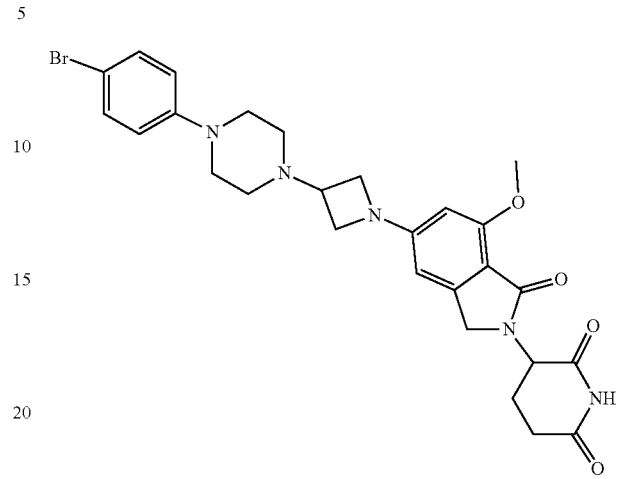

To a solution of methyl 4-[3-[4-(4-bromophenyl)piperazin-1-yl]azetidin-1-yl]-2-cyano-6-methoxy-benzoate (500 mg, 1.03 mmol) in pyridine was added Raney nickel (44 mg, 0.51 mmol). Then acetic acid (10 mL) and sodium dihydrogen phosphate hydrate (710 mg, 5.15 mmol) in water (5 mL) was added to the mixture. The mixture was stirred at 50° C. for 2 hours. The mixture was washed with ethyl acetate (3×30 mL). The combined organic layers were washed with brine (2×50 mL), 0.5 M aqueous sulfuric acid (50 mL), brine (50 mL), saturated aqueous sodium bicarbonate (50 mL) and brine (50 mL), dried with anhydrous sodium sulfate, filtered, and concentrated. Purification of the residue by column chromatography (10:1 to 2:1 petroleum ether:ethyl acetate) afforded methyl 4-[3-[4-(4-bromophenyl)piperazin-1-yl] azetidin-1-yl]-2-formyl-6-methoxy-benzoate (270 mg, 53%) as a yellow oil. MS (ESI): m/z 488.1 [M+H]$^+$.

To a solution of 3-aminopiperidine-2,6-dione hydrochloride (109 mg, 0.66 mmol) in dichloromethane (3 mL) and methanol (1 mL) was added sodium acetate (90 mg, 1.1 mmol). The mixture was stirred at 25° C. for 0.5 h. Then methyl 4-[3-[4-(4-bromophenyl) piperazin-1-yl]azetidin-1-yl]-2-formyl-6-methoxy-benzoate (270 mg, 0.55 mmol) and acetic acid (66 mg, 1.11 mmol) were added to the mixture. The mixture was stirred at 25° C. for 30 minutes. Then sodium cyanoborohydride (69 mg, 1.11 mmol) was added to the mixture. The mixture was stirred at 35° C. for 1 hour. The mixture was diluted with water (20 mL) and extracted with dichloromethane (3×15 mL). The combined organic layers were dried with anhydrous sodium sulfate, filtered, and concentrated. The residue was purified by column chromatography (1:0 to 30:1 methanol:dichloromethane) to afford 3-[5-[3-[4-(4-bromophenyl)piperazin-1-yl]azetidin-1-yl]-7-methoxy-1-oxo-isoindolin-2-yl]piperidine-2,6-dione (130 mg, 41%) as a white solid. MS (ESI): m/z 568.4 [M+H]$^+$.

Step H: tert-butyl 3-[3-[tert-butoxycarbonyl-[(3R)-3-fluoropyrrolidin-1-yl]sulfonyl-amino]-2,6-difluoro-benzoyl]-5-[4-[4-[1-[2-(2,6-dioxo-3-piperidyl)-7-methoxy-1-oxo-isoindolin-5-yl]azetidin-3-yl]piperazin-1-yl]phenyl]pyrrolo[2,3-b]pyridine-1-carboxylate

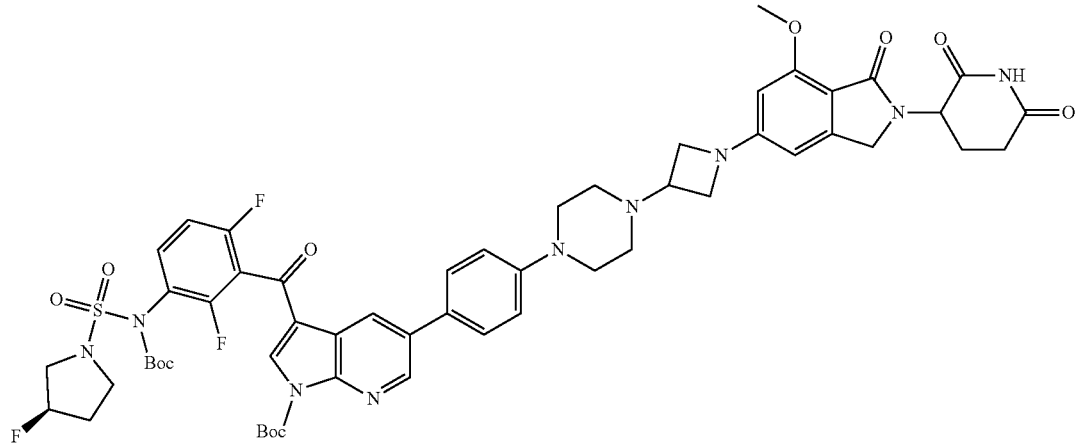 [SMILES: COc1cc(N2CC(N3CCN(c4ccc(-c5cnc6c(c5)c(C(=O)c5c(F)ccc(N(C(=O)OC(C)(C)C)S(=O)(=O)N7CC[C@@H](F)C7)c5F)cn6C(=O)OC(C)(C)C)cc4)CC3)C2)cc2c1C(=O)N(C1CCC(=O)NC1=O)C2]

To a solution of 3-[5-[3-[4-(4-bromophenyl)piperazin-1-yl]azetidin-1-yl]-7-methoxy-1-oxo-isoindolin-2-yl]piperidine-2,6-di one (100 mg, 0.17 mmol) and tert-butyl 3-[3-[tert-butoxycarbonyl-[(3R)-3-fluoropyrrolidin-1-yl]sulfonyl-amino]-2,6-difluoro-benzoyl]-5-(4,4,5,5-tetramethyl-1,3,2-dioxaborolan-2-yl)pyrrolo[2,3-b]pyridine-1-carboxylate (138 mg, 0.18 mmol) in N,N-dimethylformamide (6 mL) and water (1.5 mL) was added sodium carbonate (37 mg, 0.35 mmol) and dichloro[1,1'-bis(di-t-butylphosphino)ferrocene]palladium(II) (11 mg, 0.02 mmol). The mixture was stirred at 90° C. for 3 hours. The mixture was diluted with water (20 mL) and extracted with tetrahydrofuran (4×20 mL). The combined organic layers were dried with anhydrous sodium sulfate, filtered, and concentrated. The crude product was purified by column chromatography (0:1 to 1:20 methanol:dichloromethane) to afford tert-butyl 3-[3-[tert-butoxycarbonyl-[(3R)-3-fluoropyrrolidin-1-yl]sulfonyl-amino]-2,6-difluoro-benzoyl]-5-[4-[4-[1-[2-(2,6-dioxo-3-piperidyl)-7-methoxy-1-oxo-isoindolin-5-yl]azetidin-3-yl]piperazin-1-yl]phenyl]pyrrolo[2,3-b]pyridine-1-carboxylate (75 mg, 38%) as a brown solid. MS (ESI): m/z 506.9 [(M−100)/2+H]⁺.

Step I: (3R)—N-[3-[5-[4-[4-[1-[2-(2,6-dioxo-3-piperidyl)-7-methoxy-1-oxo-isoindolin-5-yl]azetidin-3-yl]piperazin-1-yl]phenyl]-1H-pyrrolo[2,3-b]pyridine-3-carbonyl]-2,4-difluoro-phenyl]-3-fluoro-pyrrolidine-1-sulfonamide

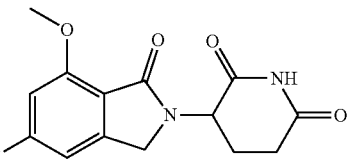
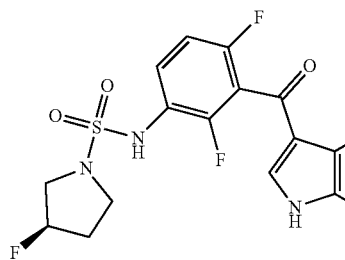

To a solution of tert-butyl 3-[3-[tert-butoxycarbonyl-[(3R)-3-fluoropyrrolidin-1-yl]sulfonyl-amino]-2,6-difluoro-benzoyl]-5-[4-[4-[1-[2-(2,6-dioxo-3-piperidyl)-7-methoxy-1-oxo-isoindolin-5-yl]azetidin-3-yl]piperazin-1-yl]phenyl] pyrrolo[2,3-b]pyridine-1-carboxylate (100 mg, 0.09 mmol) in dichloromethane (2 mL) was added trifluoroacetic acid (770 mg, 6.75 mmol). The mixture was stirred at 25° C. for 30 minutes. The mixture was concentrated. Purification of the residue by preparative HPLC (Phenomenex Synergi C18, 15 to 45% acetonitrile:(0.225% formic acid in water)) afforded (3R)—N-[3-[5-[4-[4-[1-[2-(2,6-dioxo-3-piperidyl)-7-methoxy-1-oxo-isoindolin-5-yl]azetidin-3-yl]piperazin-1-yl]phenyl]-1H-pyrrolo[2,3-b]pyridine-3-carbonyl]-2,4-difluoro-phenyl]-3-fluoro-pyrrolidine-1-sulfonamide formic acid salt (21.9 mg, 23%) as an off-white solid. MS (ESI): m/z 912.3 [M+H]⁺; ¹H NMR (400 MHz, DMSO-d₆) δ 13.19-12.63 (m, 1H), 10.91 (s, 1H), 8.70-8.62 (m, 1H), 8.60-8.46 (m, 1H), 8.27-8.19 (m, 1H), 8.06 (s, 1H), 7.68-7.52 (m, 3H), 7.25-7.16 (m, 1H), 7.09 (d, J=9.2 Hz, 2H), 6.14-6.08 (m, 1H), 6.02-5.92 (m, 1H), 5.40-5.18 (m, 1H), 5.02-4.88 (m, 1H), 4.26-4.17 (m, 1H), 4.09 (d, J=12.8 Hz, 1H), 4.07-4.02 (m, 2H), 3.82 (s, 3H), 3.81-3.76 (m, 2H), 3.44 (s, 2H), 3.38-3.37 (m, 2H), 3.27 (s, 4H), 2.96-2.83 (m, 1H), 2.59-2.55 (m, 2H), 2.54 (d, J=2.0 Hz, 4H), 2.30-2.24 (m, 1H), 2.15-2.02 (m, 2H), 2.01-1.86 (m, 2H).

Exemplary Synthesis of Exemplary Compound 115: (3R)—N-[3-[5-[4-[4-[6-[4-[2-(2,6-dioxo-3-piperidyl)-1-oxoisoindolin-5-yl]piperazin-1-yl]pyrimidin-4-yl]piperazin-1-yl]phenyl]-1H-pyrrolo[2,3-b]pyridine-3-carbonyl]-2,4-difluoro-phenyl]-3-fluoro-pyrrolidine-1-sulfonamide

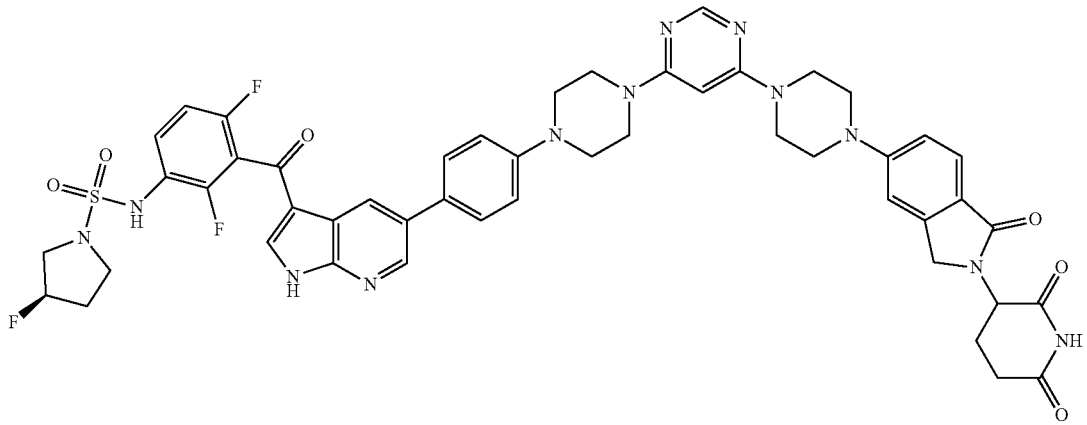 [SMILES: O=C1CCC(N2Cc3cc(N4CCN(c5cc(N6CCN(c7ccc(-c8cnc9[nH]cc(C(=O)c%10c(F)ccc(NS(=O)(=O)N%11CC[C@@H](F)C%11)c%10F)c9c8)cc7)CC6)ncn5)CC4)ccc3C2=O)C(=O)N1]

Step A: 3-[5-[4-(6-chloropyrimidin-4-yl)piperazin-1-yl]-1-oxo-isoindolin-2-yl]piperidine-2,6-dione

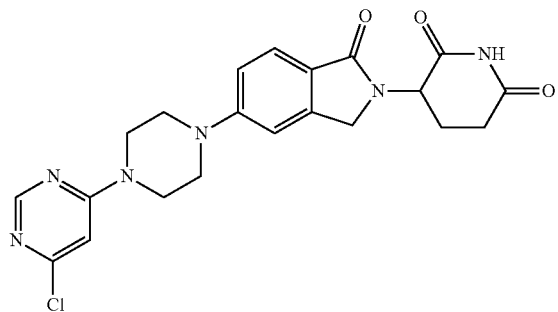 [SMILES: O=C1CCC(N2Cc3cc(N4CCN(c5cc(Cl)ncn5)CC4)ccc3C2=O)C(=O)N1]

To a solution of 3-(1-oxo-5-piperazin-1-yl-isoindolin-2-yl)piperidine-2,6-dione hydrochloride (0.20 g, 0.55 mmol) in dimethylsulfoxide (4 mL) was added N,N-diisopropylethylamine (212 mg, 1.64 mmol, 0.3 mL) and 4,6-dichloropyrimidine (90 mg, 0.60 mmol). The mixture was stirred at 110° C. for 3 hours. The reaction mixture was diluted with water (50 mL), extracted with ethyl acetate (2×30 mL) and tetrahydrofuran (30 mL). The combined organic layers were washed with brine (2×35 mL), dried over anhydrous sodium sulfate, filtered, and concentrated. The residue was purified by flash silica gel chromatography (0 to 8% methanol: dichloromethane) to afford 3-[5-[4-(6-chloropyrimidin-4-yl)piperazin-1-yl]-1-oxo-isoindolin-2-yl] piperidine-2,6-dione (226 mg, 92%) as a white solid. MS (ESI): m/z 441.2 [M+H]$^+$.

Step B: (3R)—N-[3-[5-[4-[4-[6-[4-[2-(2,6-dioxo-3-piperidyl)-1-oxo-isoindolin-5-yl]piperazin-1-yl]pyrimidin-4-yl]piperazin-1-yl]phenyl]-1H-pyrrolo[2,3-b]pyridine-3-carbonyl]-2,4-difluoro-phenyl]-3-fluoro-pyrrolidine-1-sulfonamide

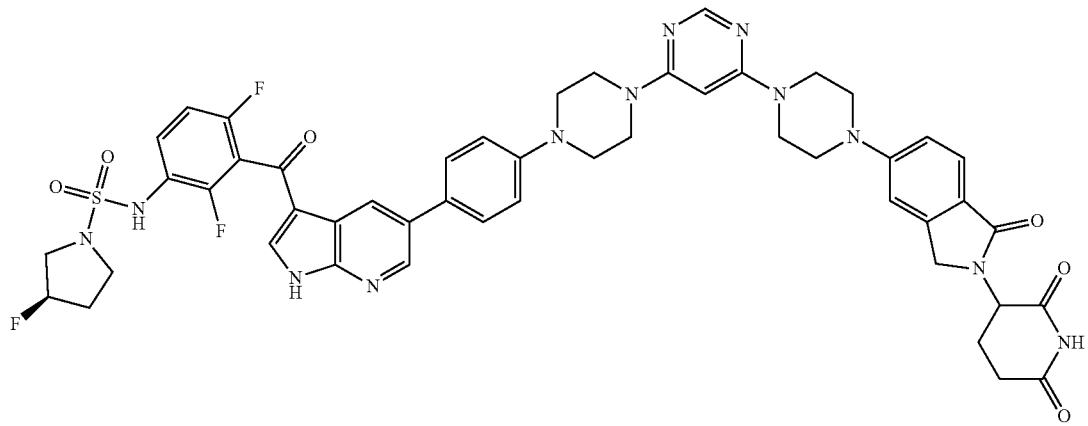 [SMILES: O=C1CCC(N2Cc3cc(N4CCN(c5cc(N6CCN(c7ccc(-c8cnc9[nH]cc(C(=O)c%10c(F)ccc(NS(=O)(=O)N%11CC[C@@H](F)C%11)c%10F)c9c8)cc7)CC6)ncn5)CC4)ccc3C2=O)C(=O)N1]

To a solution of 3-[5-[4-(6-chloropyrimidin-4-yl)piperazin-1-yl]-1-oxo-isoindolin-2-yl] piperidine-2,6-dione (0.15 g, 0.34 mmol) in dimethylsulfoxide (4 mL) was added N,N-diisopropylethylamine (132 mg, 1.02 mmol, 0.2 mL) and (3R)—N-[2,4-difluoro-3-[5-(4-piperazin-1-ylphenyl)-1H-pyrrolo[2,3-b]pyridine-3-carbonyl]phenyl]-3-fluoro-pyrrolidine-1-sulfonamide (199 mg, 0.34 mmol). The mixture was stirred at 90° C. for 16 hours. The reaction mixture was cooled to room temperature. Tetrahydrofuran (30 mL) and water were added. The aqueous phase was extracted with ethyl acetate (25 mL) and tetrahydrofuran (25 mL). The combined organic extracts were washed with brine (2×30 mL), dried over anhydrous sodium sulfate, filtered, and concentrated. The residue was purified by preparative HPLC (Phenomenex Luna C18, 17 to 47% acetonitrile:(0.225% formic acid in water)). The mixture was basified with saturated aqueous sodium bicarbonate to pH 8 and extracted with dichloromethane (2×40 mL). The combined organic layers were washed with brine (2×30 mL), dried over anhydrous sodium sulfate, filtered, and concentrated. The residue was further purified by preparative TLC (10:1 dichloromethane:methanol) to afford (3R)—N-[3-[5-[4-[4-[6-[4-[2-(2,6-dioxo-3-piperidyl)-1-oxo-isoindolin-5-yl]piperazin-1-yl]pyrimidin-4-yl]piperazin-1-yl]phenyl]-1H-pyrrolo[2,3-b]pyridine-3-carbonyl]-2,4-difluoro-phenyl]-3-fluoro-pyrrolidine-1-sulfonamide (60.1 mg, 17%) as a yellow solid. MS (ESI): m/z 989.3 [M+H]$^+$; $^1$H NMR (400 MHz, DMSO-d$_6$) δ 13.23-12.45 (m, 1H), 10.95 (s, 1H), 8.66 (d, J=2.0 Hz, 1H), 8.55 (s, 1H), 8.15 (s, 1H), 8.06 (s, 1H), 7.67-7.52 (m, 4H), 7.25 (t, J=8.8 Hz, 1H), 7.18-7.08 (m, 4H), 6.07 (s, 1H), 5.38-5.20 (m, 1H), 5.05 (dd, J=5.2, 13.2 Hz, 1H), 4.39-4.31 (m, 1H), 4.27-4.19 (m, 1H), 3.76 (s, 8H), 3.47 (s, 2H), 3.30 (d, J=5.2 Hz, 8H), 2.96-2.84 (m, 1H), 2.61 (s, 1H), 2.57 (s, 1H), 2.47-2.41 (m, 1H), 2.37 (dd, J=4.4, 13.2 Hz, 1H), 2.11 (s, 1H), 2.05-1.89 (m, 2H).

Exemplary Synthesis of Exemplary Compound 119: 144S (3R)—N-[3-[5-[4-[4-[[4-[2-(2,6-dioxo-3-piperidyl)-1-oxo-isoindolin-5-yl]-1-piperidyl]methyl]-4-hydroxy-1-piperidyl]phenyl]-1H-pyrrolo[2,3-b]pyridine-3-carbonyl]-2,4-difluoro-phenyl]-3-fluoro-pyrrolidine-1-sulfonamide mixture was filtered and concentrated to afford 4-methylenepiperidine trifluoracetic acid salt (5.35 g, 100%) as a colorless oil.

Step B: 1-(4-bromophenyl)-4-methylene-piperidine

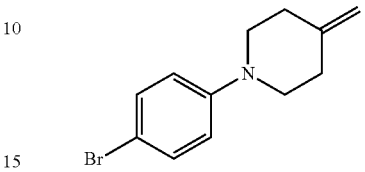

A mixture of 1,4-dibromobenzene (5.98 g, 25.3 mmol, 3.25 mL), 4-methylenepiperidine trifluoroacetic acid salt (5.35 g, 25.3 mmol), potassium carbonate (10.50 g, 75.99 mmol), L-proline (1.17 g, 10.1 mmol) and cuprous iodide (964 mg, 5.07 mmol) in dimethylsulfoxide (100 mL) was degassed and purged with nitrogen for 3 times, and then the mixture was stirred at 90° C. for 12 hours under nitrogen atmosphere. MS showed desired mass was detected. The reaction mixture was quenched by ammonium chloride 100 mL at 25° C., and then diluted extracted with ethyl acetate (3×30 mL). The combined organic layers were washed with brine (3×30 mL), dried over anhydrous sodium sulfate, filtered, and concentrated. The residue was purified by column chromatography (petroleum ether) to afford 1-(4-bromophenyl)-4-methylene-piperidine (2.8 g, 43%) as a yellow solid. MS (ESI): m/z 252.1 [M+H]$^+$.

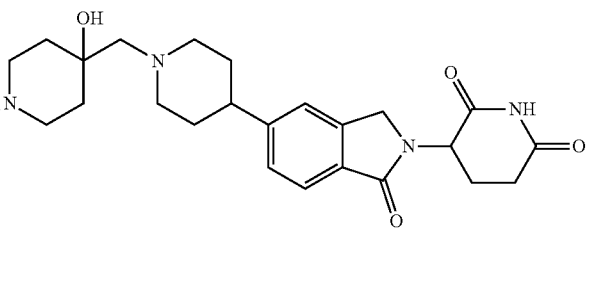

Step A: 4-methylenepiperidine

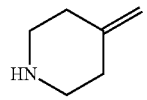

To a solution of tert-butyl 4-methylenepiperidine-1-carboxylate (5 g, 25.35 mmol) in dichloromethane (50 mL) was added trifluoroacetic acid (15.40 g, 135.0 mmol, 10 mL). The mixture was stirred at 25° C. for 12 hours. The reaction Step C: 1-(4-bromophenyl)-4-(hydroxymethyl)piperidin-4-ol

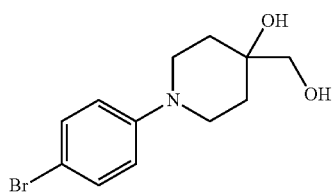 [SMILES: OCC1(O)CCN(c2ccc(Br)cc2)CC1]

To a solution of osmium tetroxide (141 mg, 0.55 mmol) and 4-methyl-4-oxido-morpholin-4-ium (3.90 g, 33 mmol) in water (54 mL), acetone (27 mL) and t-butanol (10.8 mL) was added 1-(4-bromophenyl)-4-methylene-piperidine (2.8 g, 11 mmol) in acetone (54 mL) and dichloromethane (162 mL). The mixture was stirred at 0° C. for 1 hour. The reaction mixture was quenched by addition of sodium thiosulfate (200 mL) at 25° C., and then extracted with dichloromethane (3×80 mL). The combined organic layers were washed with brine (3×30 mL), dried over anhydrous sodium sulfate, filtered, and concentrated to afford 1-(4-bromophenyl)-4-(hydroxymethyl)piperidin-4-ol (2 g, 6.99 mmol, 62%) as an off-white solid.

Step D: 6-(4-bromophenyl)-1-oxa-6-azaspiro[2.5]octane

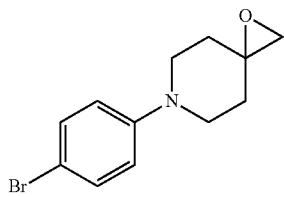 [SMILES: Brc1ccc(N2CCC3(CC2)CO3)cc1]

To a solution of 1-(4-bromophenyl)-4-(hydroxymethyl)piperidin-4-ol (1.2 g, 4.19 mmol) in tetrahydrofuran (10 mL) was added potassium hydroxide (705 mg, 12.58 mmol) and paratoluensulfonyl chloride (3.20 g, 16.77 mmol). The mixture was stirred at 25° C. for 1 hour. The reaction mixture was quenched by water 80 mL and extracted with ethyl acetate (3×30 mL). The combined organic layers were washed with brine (3×30 mL), dried over anhydrous sodium sulfate, filtered, and concentrated. The residue was purified by column chromatography (300:1 to 100:1 petroleum ether:ethyl acetate) to afford 6-(4-bromophenyl)-1-oxa-6-azaspiro[2.5]octane (1 g, 3.73 mmol, 89%) as a white solid. MS (ESI): m/z 268.1 [M+H]⁺.

Step E: 3-[5-[1-[[1-(4-bromophenyl)-4-hydroxy-4-piperidyl]methyl]-4-piperidyl]-1-oxo-isoindolin-2-yl]piperidine-2,6-dione

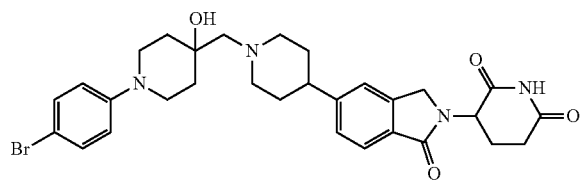 [SMILES: O=C1CCC(N2Cc3cc(C4CCN(CC5(O)CCN(c6ccc(Br)cc6)CC5)CC4)ccc3C2=O)C(=O)N1]

To a solution of 6-(4-bromophenyl)-1-oxa-6-azaspiro[2.5]octane (670 mg, 2.50 mmol) and 3-[1-oxo-5-(4-piperidyl)isoindolin-2-yl]piperidine-2,6-dione hydrochloride (1.0 g, 2.7 mmol) in N,N-dimethylformamide (10 mL) was added diisopropylethylamine (968 mg, 7.50 mmol) and potassium iodide (41 mg, 2.50 mmol). The mixture was stirred at 120° C. for 1 hour. The reaction mixture was filtered and concentrated. The residue was purified by preparative HPLC (Phenomenex Luna C18, 15 to 45% acetonitrile:(0.225% formic acid in water)) to afford 3-[5-[1-[[1-(4-bromophenyl)-4-hydroxy-4-piperidyl]methyl]-4-piperidyl]-1-oxo-isoindolin-2-yl]piperidine-2,6-dione (200 mg, 13%) as a yellow solid. MS (ESI): m/z 596.1 [M+H]⁺.

Step F: tert-butyl 3-[3-[tert-butoxycarbonyl-[(3R)-3-fluoropyrrolidin-1-yl]sulfonyl-amino]-2,6-difluoro-benzoyl]-5-[4-[4-[[4-[2-(2,6-dioxo-3-piperidyl)-1-oxo-isoindolin-5-yl]-1-piperidyl]methyl]-4-hydroxy-1-piperidyl]phenyl]pyrrolo[2,3-b]pyridine-1-carboxylate

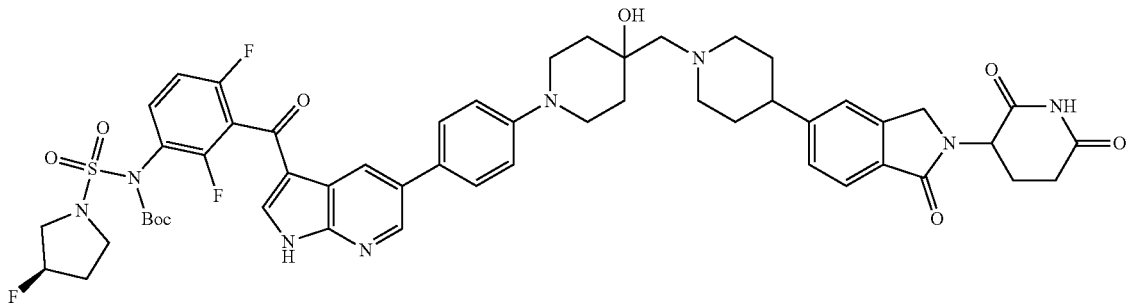 [SMILES: CC(C)(C)OC(=O)N(c1ccc(F)c(C(=O)c2c[nH]c3ncc(-c4ccc(N5CCC(O)(CN6CCC(c7ccc8c(c7)CN(C7CCC(=O)NC7=O)C8=O)CC6)CC5)cc4)cc23)c1F)S(=O)(=O)N1CC[C@@H](F)C1]

A mixture of 3-[5-[1-[[1-(4-bromophenyl)-4-hydroxy-4-piperidyl]methyl]-4-piperidyl]-1-oxo-isoindolin-2-yl]piperidine-2,6-dione (200 mg, 0.33 mmol), tert-butyl 3-[3-[tert-butoxycarbonyl-[(3R)-3-fluoropyrrolidin-1-yl]sulfonyl-amino]-2,6-difluoro-benzoyl]-5-(4,4,5,5-tetramethyl-1,3,2-dioxaborolan-2-yl)pyrrolo[2,3-b]pyridine-1-carboxylate (277 mg, 0.36 mmol), dichloro[1,1'-bis(di-t-butylphosphino)ferrocene]palladium(II) (11 mg, 0.02 mmol), sodium carbonate (71 mg, 0.67 mmol) and water (0.3 mL) in dimethyl formamide (3 mL) was degassed and purged with nitrogen for three times, and then the mixture was stirred at 90° C. for 3 hour. The reaction mixture was quenched with water (50 mL) at 25° C., and then extracted with 1:1 ethyl acetate:tetrahydrofuran (3×30 mL). The combined organic layers were dried over anhydrous sodium sulfate, filtered, and concentrated. The residue was purified by column chromatography (100:1 to 30:1 dichloromethane:methanol) to afford tert-butyl 3-[3-[tert-butoxycarbonyl-[(3R)-3-fluoropyrrolidin-1-yl]sulfonyl-amino]-2,6-difluoro-benzoyl]-5-[4-[4-[[4-[2-(2,6-dioxo-3-piperidyl)-1-oxo-isoindolin-5-yl]-1-piperidyl]methyl]-4-hydroxy-1-piperidyl]phenyl]pyrrolo[2,3-b]pyridine-1-carboxylate (200 mg, 0.17 mmol, 52%) as a yellow solid. MS (ESI): m/z 1039.1 [M+H]⁺.

Step G: (3R)—N-[3-[5-[4-[4-[[4-[2-(2,6-dioxo-3-piperidyl)-1-oxo-isoindolin-5-yl]-1-piperidyl]methyl]-4-hydroxy-1-piperidyl]phenyl]-1H-pyrrolo[2,3-b]pyridine-3-carbonyl]-2,4-difluoro-phenyl]-3-fluoro-pyrrolidine-1-sulfonamide

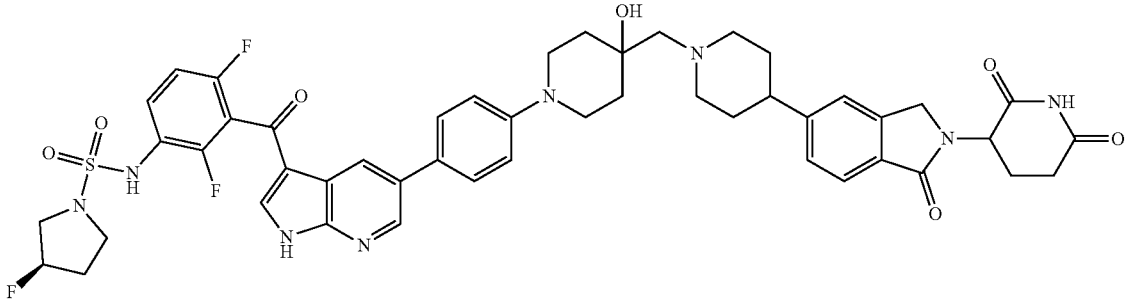 [SMILES: O=C1CCC(N2Cc3cc(C4CCN(CC5(O)CCN(c6ccc(-c7cnc8[nH]cc(C(=O)c9c(F)ccc(NS(=O)(=O)N%10CC[C@@H](F)C%10)c9F)c8c7)cc6)CC5)CC4)ccc3C2=O)C(=O)N1]

To a solution of tert-butyl N-[3-[5-[4-[4-[[4-[2-(2,6-dioxo-3-piperidyl)-1-oxo-isoindolin-5-yl]-1-piperidyl]methyl]-4-hydroxy-1-piperidyl]phenyl]-1H-pyrrolo[2,3-b]pyridine-3-carbonyl]-2,4-difluoro-phenyl]-N-[(3R)-3-fluoropyrrolidin-1-yl]sulfonyl-carbamate (200 mg, 0.19 mmol) in dichloromethane (5 mL) was added trifluoroacetic acid (1.54 g, 13.5 mmol). The mixture was stirred at 25° C. for 0.5 h. The reaction mixture was filtered and concentrated. The residue was purified by preparative HPLC (Unisil 3-100 C18 Ultra, 12 to 42% acetonitrile:(0.225% formic acid in water)) to afford (3R)—N-[3-[5-[4-[4-[[4-[2-(2,6-dioxo-3-piperidyl)-1-oxo-isoindolin-5-yl]-1-piperidyl]methyl]-4-hydroxy-1-piperidyl]phenyl]-1H-pyrrolo[2,3-b]pyridine-3-carbonyl]-2,4-difluoro-phenyl]-3-fluoro-pyrrolidine-1-sulfonamide formic acid salt (27.5 mg, 14%) as a yellow solid. MS (ESI): m/z 939.3 [M+H]$^+$; $^1$H NMR (400 MHz, DMSO-$d_6$) δ 12.90 (s, 1H), 10.98 (s, 1H), 8.66 (d, J=2.4 Hz, 1H), 8.53 (s, 1H), 8.17 (s, 1H), 8.07 (s, 1H), 7.68-7.57 (m, 4H), 7.51 (s, 1H), 7.41 (d, J=7.2 Hz, 1H), 7.26 (t, J=9.2 Hz, 1H), 7.09 (d, J=8.8 Hz, 2H), 5.39-5.20 (m, 1H), 5.10 (dd, J=5.2, 13.2 Hz, 1H), 4.45-4.39 (m, 1H), 4.32-4.26 (m, 1H), 3.51-3.42 (m, 2H), 3.21-3.08 (m, 3H), 2.96-2.85 (m, 2H), 2.62 (s, 3H), 2.60-2.56 (m, 3H), 2.38 (s, 2H), 2.31 (s, 2H), 2.10 (d, J=13.6 Hz, 2H), 1.99 (d, J=5.4 Hz, 2H), 1.83-1.68 (m, 7H), 1.64-1.54 (m, 2H).

Exemplary Synthesis of Exemplary Compound 138: (3R)—N-[3-[5-(4-[6-[(2R)-2-[2-(2,6-dioxopiperidin-3-yl)-1-oxo-3H-isoindol-5-yl]-2-hydroxyethyl]-2,6-diazaspiro[3.3]heptan-2-yl]phenyl)-1H-pyrrolo[2,3-b]pyridine-3-carbonyl]-2,4-difluorophenyl]-3-fluoropyrrolidine-1-sulfonamide

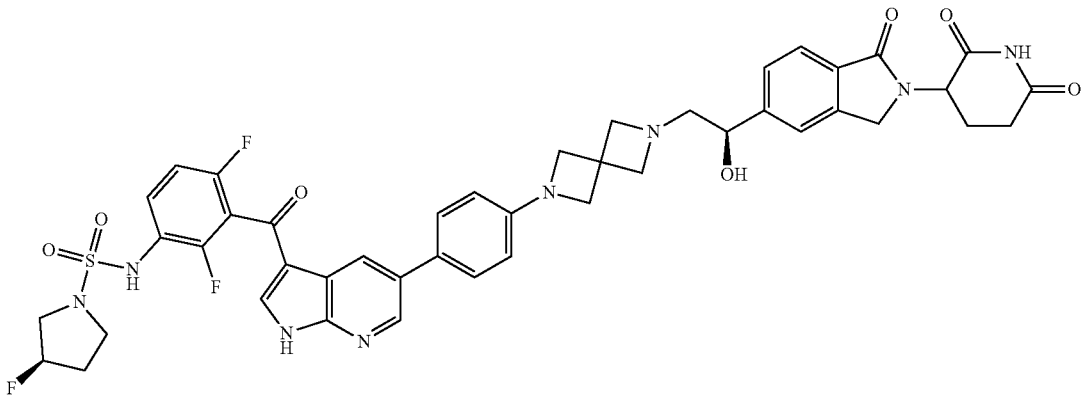 [SMILES: O=C1CCC(N2Cc3cc([C@@H](O)CN4CC5(C4)CN(c4ccc(-c6cnc7[nH]cc(C(=O)c8c(F)ccc(NS(=O)(=O)N9CC[C@@H](F)C9)c8F)c7c6)cc4)C5)ccc3C2=O)C(=O)N1]

Step A: tert-butyl 6-(4-bromophenyl)-2,6-diazaspiro[3.3]heptane-2-carboxylate

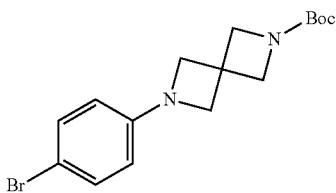 [SMILES: CC(C)(C)OC(=O)N1CC2(C1)CN(c1ccc(Br)cc1)C2]

A mixture of tert-butyl 2,6-diazaspiro[3.3]heptane-2-carboxylate oxalic acid salt (3.80 g, 13.1 mmol), 4-bromophenylboric acid (5.30 g, 26.3 mmol), copper (II) acetate (4.80 g, 26.4 mmol), dichloromethane (150 mL), and triethylamine (8.0 mL, 57 mmol) was stirred for 16 hours at room temperature. The solids were filtered out. Purification by silica gel column chromatography (1:10 ethyl acetate:petroleum ether) afforded 5.02 g (97%) of tert-butyl 6-(4-bromophenyl)-2,6-diazaspiro[3.3]heptane-2-carboxylate as a white solid. MS (ESI): m/z 354.95 [M+H]$^+$.

Step B: 2-(4-bromophenyl)-2,6-diazaspiro[3.3]heptane

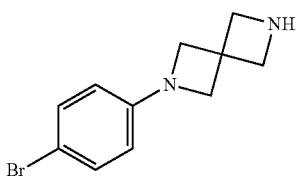 [SMILES: Brc1ccc(N2CC3(CNC3)C2)cc1]

A solution of tert-butyl 6-(4-bromophenyl)-2,6-diazaspiro[3.3]heptane-2-carboxylate (4.20 g, 11.8 mmol), dichloromethane (20 mL), and trifluoroacetic acid (6 mL) was stirred for 2 hours at room temperature. The resulting mixture was concentrated. The crude product was purified by flash reverse phase chromatography (C18, 10% acetonitrile:(0.05% trifluoroacetic acid in water)) to afford 3.82 g (91%) of 2-(4-bromophenyl)-2,6-diazaspiro[3.3]heptane as a white solid. MS (ESI): m/z 254.85 [M+H]$^+$.

Step C: 3-[5-(1-ethoxyethenyl)-1-oxo-3H-isoindol-2-yl]piperidine-2,6-dione

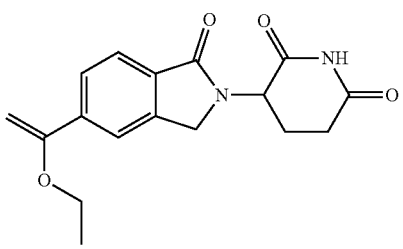 [SMILES: C=C(OCC)c1ccc2c(c1)CN(C1CCC(=O)NC1=O)C2=O]

A solution of 3-(5-bromo-1-oxo-3H-isoindol-2-yl)piperidine-2,6-dione (3.50 g, 10.831 mmol), tributyl(1-ethoxyethenyl)stannane (8.00 g, 22.1 mmol), and tetrakis(triphenylphosphine)palladium(0) (2.50 g, 2.16 mmol) in toluene (150 mL) was stirred for 16 hours at 100° C. The resulting mixture was concentrated. Purification by flash reverse phase chromatography (C18, 15 to 45% acetonitrile:water) afforded 1.52 g (45%) of 3-[5-(1-ethoxyethenyl)-1-oxo-3H-isoindol-2-yl]piperidine-2,6-dione as a white solid. MS (ESI): m/z 314.95 [M+H]$^+$.

Step D: 3-[5-(2-bromoacetyl)-1-oxo-3H-isoindol-2-yl]piperidine-2,6-dione

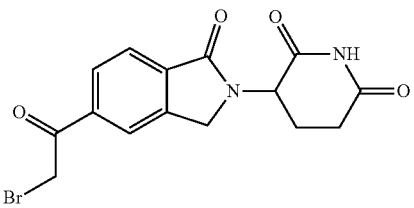 [SMILES: O=C1CCC(N2Cc3cc(C(=O)CBr)ccc3C2=O)C(=O)N1]

A mixture of 3-[5-(1-ethoxyethenyl)-1-oxo-3H-isoindol-2-yl]piperidine-2,6-dione (5.50 g, 17.4 mmol), THF (100 mL), water (20 mL), N-bromosuccinimide (3.70 g, 20.7 mmol) was stirred for 1 hour at 0° C. The solids were collected by filtration. The crude product was purified by flash reverse phase chromatography (C18, 10% acetonitrile:water) to afford 2.89 g (45%) of 3-[5-(2-bromoacetyl)-1-oxo-3H-isoindol-2-yl]piperidine-2,6-dione as a white solid. MS (ESI): m/z 367.10 [M+H]$^+$.

Step E: 3-(5-[2-[6-(4-bromophenyl)-2,6-diazaspiro[3.3]heptan-2-yl]acetyl]-1-oxo-3H-isoindol-2-yl)piperidine-2,6-dione

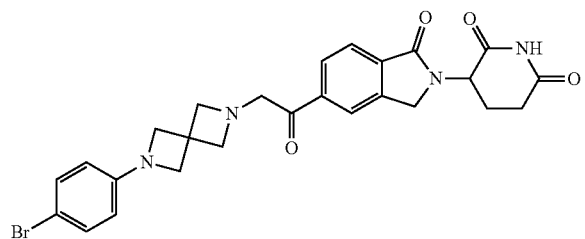 [SMILES: O=C1CCC(N2Cc3cc(C(=O)CN4CC5(C4)CN(c4ccc(Br)cc4)C5)ccc3C2=O)C(=O)N1]

A mixture of 3-[5-(2-bromoacetyl)-1-oxo-3H-isoindol-2-yl]piperidine-2,6-dione (1.35 g, 3.697 mmol), dichloromethane (150 mL), 2-(4-bromophenyl)-2,6-diazaspiro[3.3]heptane trifluoroacetic acid salt (930.0 mg, 2.648 mmol), and diisopropylethylamine (0.25 mL, 1.4 mmol) was stirred for 2 hour at 40° C. Purification by flash reverse phase chromatography (C18, 55% acetonitrile:water) afforded 515 mg (26%) of 3-(5-[2-[6-(4-bromophenyl)-2,6-diazaspiro[3.3]heptan-2-yl]acetyl]-1-oxo-3H-isoindol-2-yl)piperidine-2,6-dione as a yellow solid. MS (ESI): m/z 538.90 [M+H]$^+$.

Step F: 3-[5-[(1R)-2-[6-(4-bromophenyl)-2,6-diazaspiro[3.3]heptan-2-yl]-1-hydroxyethyl]-1-oxo-3H-isoindol-2-yl]piperidine-2,6-dione

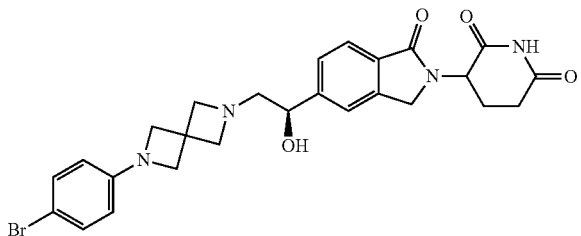 [SMILES: O=C1CCC(N2Cc3cc([C@@H](O)CN4CC5(C4)CN(c4ccc(Br)cc4)C5)ccc3C2=O)C(=O)N1]

A mixture of 3-(5-[2-[6-(4-bromophenyl)-2,6-diazaspiro[3.3]heptan-2-yl]acetyl]-1-oxo-3H-isoindol-2-yl)piperidine-2,6-dione (760.0 mg, 1.414 mmol), dichloromethane (70 mL), [N-[(1R,2R)-2-(amino-κN)-1,2-diphenylethyl]-4-methylbenzenesulfonamidato-κN]chloro [(1,2,3,4,5,6-η)-1,3,5-trimethylbenzene]-ruthenium (350 mg, 0.563 mmol), formic acid (10 mL), and triethylamine (4.00 mL, 28.7 mmol). The resulting solution was stirred for 16 hours at 40° C. The resulting solution was extracted with dichloromethane (2×50 mL). Purification by flash reverse phase chromatography (C18, 44 to 54% acetonitrile:water) afforded 420 mg (55%) of 3-[5-[(1R)-2-[6-(4-bromophenyl)-2,6-diazaspiro[3.3]heptan-2-yl]-1-hydroxyethyl]-1-oxo-3H-isoindol-2-yl]piperidine-2,6-dione as a white solid. MS (ESI): m/z 539.15 [M+H]+.

Step G: (3R)—N-[3-[5-(4-[6-[(2R)-2[2-(2,6-dioxopiperidin-3-yl)-1-oxo-3H-isoindol-5-yl]-2-hydroxyethyl]-2,6-diazaspiro[3.3]heptan-2-yl]phenyl)-1H-pyrrolo[2,3-b]pyridine-3-carbonyl]-2,4-difluorophenyl]-3-fluoropyrrolidine-1-sulfonamide

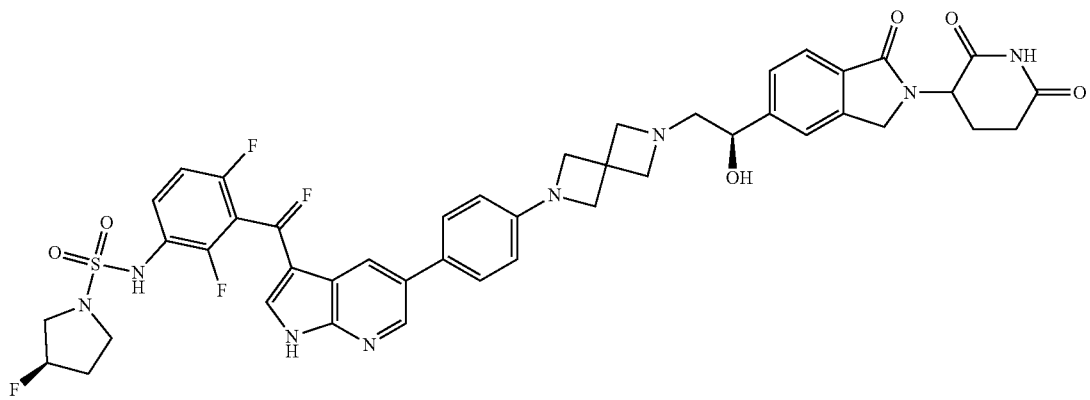

A mixture of 3-[5-[(1R)-2-[6-(4-bromophenyl)-2,6-diazaspiro[3.3]heptan-2-yl]-1-hydroxyethyl]-1-oxo-3H-isoindol-2-yl]piperidine-2,6-dione (256 mg, 0.475 mmol), (3R)—N-[2,4-difluoro-3-[5-(4,4,5,5-tetramethyl-1,3,2-dioxaborolan-2-yl)-1H-pyrrolo[2,3-b]pyridine-3-carbonyl]phenyl]-3-fluoropyrrolidine-1-sulfonamide (400 mg, 0.727 mmol), dichloro[1,1'-bis(di-t-butylphosphino)ferrocene]palladium (II) (124 mg, 0.190 mmol), cesium fluoride (370 mg, 2.43 mmol), 1,4-dioxane (7 mL), and water (1 mL) was stirred for 2 hours at 100° C. The resulting solution was extracted with dichloromethane (2×50 mL). Purification by flash reverse phase chromatography (C18, 40% acetonitrile:(0.05 ammonium bicarbonate in water)) afforded 50.8 mg (12%) of (3R)—N-[3-[5-(4-[6-[(2R)-2[2-(2,6-dioxopiperidin-3-yl)-1-oxo-3H-isoindol-5-yl]-2-hydroxyethyl]-2,6-diazaspiro[3.3]heptan-2-yl]phenyl)-1H-pyrrolo[2,3-b]pyridine-3-carbonyl]-2,4-difluorophenyl]-3-fluoropyrrolidine-1-sulfonamide as a yellow solid. MS (ESI): m/z 883.40 [M+H]+; $^1$H NMR (400 MHz, DMSO-$d_6$) δ 12.89 (s, 1H), 10.99 (s, 1H), 9.90 (s, 1H), 8.62 (m, 1H), 8.50 (s, 1H), 8.06 (s, 1H), 7.69-7.50 (m, 6H), 7.26 (m, 1H), 6.56 (m, 2H), 5.51 (s, 1H), 5.37-5.12 (m, 2H), 4.69 (s, 1H), 4.46 (m, 1H), 4.33 (m, 1H), 3.94 (s, 4H), 3.52 (s, 5H), 3.49-3.39 (m, 3H), 2.99-2.86 (m, 1H), 2.74-2.57 (m, 3H), 2.39 (m, 4.6 Hz, 1H), 2.10-1.93 (m, 3H).

Exemplary Synthesis of Exemplary Compound 143: (3R)—N-[3-[5-[4-[4-[[1-[2-(2,6-dioxo-3-piperidyl)-1-oxo-isoindolin-5-yl]-4-piperidyl]methoxymethyl]-1-piperidyl]phenyl]-1H-pyrrolo[2,3-b]pyridine-3-carbonyl]-2,4-difluoro-phenyl]-3-fluoro-pyrrolidine-1-sulfonamide

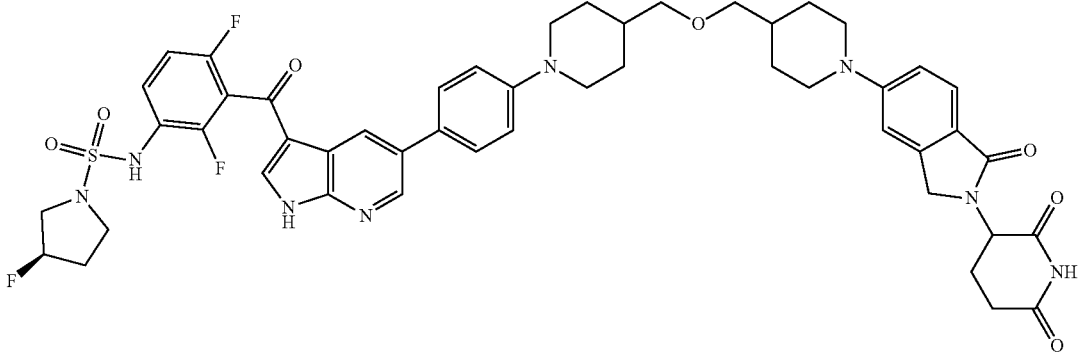 [SMILES: O=C1CCC(N2Cc3cc(N4CCC(COCC5CCN(c6ccc(-c7cnc8[nH]cc(C(=O)c9c(F)ccc(NS(=O)(=O)N%10CC[C@@H](F)C%10)c9F)c8c7)cc6)CC5)CC4)ccc3C2=O)C(=O)N1]

Step A: [1-(4-bromophenyl)-4-piperidyl]methanol

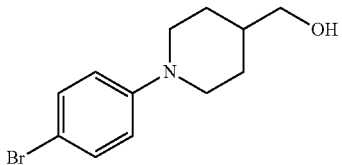 [SMILES: OCC1CCN(c2ccc(Br)cc2)CC1]

To a solution of 1,4-dibromobenzene (10.0 g, 42.3 mmol) and 4-piperidylmethanol (5.13 g, 44.5 mmol) in dimethylsulfoxide (150 mL) was added potassium carbonate (17.58 g, 127.1 mmol), cuprous iodide (1.61 g, 8.48 mmol) and L-proline (1.95 g, 16.9 mmol). The mixture was stirred at 90° C. for 12 hours. The mixture was diluted with water (450 mL) and extracted with ethyl acetate (3×300 mL). The combined organic layers were washed with brine (3×1000 mL), dried with anhydrous sodium sulfate, filtered, and concentrated. Purification of the residue by column chromatography (1:0 to 4:1 petroleum ether:ethyl acetate) afforded [1-(4-bromophenyl)-4-piperidyl]methanol (4.6 g, 40%) as a white solid. $^1$H NMR (400 MHz, DMSO-$d_6$) δ 7.33-7.27 (m, 2H), 6.90-6.84 (m, 2H), 4.46 (t, J=5.2 Hz, 1H), 3.68 (d, J=12.4 Hz, 2H), 3.27 (t, J=5.6 Hz, 2H), 2.69-2.58 (m, 2H), 1.75-1.67 (m, 2H), 1.57-1.45 (m, 1H), 1.19 (dq, J=4.0, 12.4 Hz, 2H).

Step B: [1-(4-bromophenyl)-4-piperidyl]methyl 4-methylbenzenesulfonate

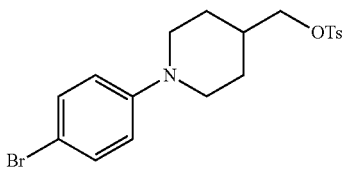 [SMILES: Cc1ccc(S(=O)(=O)OCC2CCN(c3ccc(Br)cc3)CC2)cc1]

To a solution of [1-(4-bromophenyl)-4-piperidyl]methanol (1.35 g, 5.00 mmol), 4-dimethylaminopyridine (61 mg, 0.50 mmol) and triethylamine (1.52 g, 14.9 mmol) in dichloromethane (30 mL) was added 4-methylbenzenesulfonyl chloride (1.43 g, 7.50 mmol) in portions. The mixture was stirred at 25° C. for 15 hours. The mixture was poured into brine (100 mL) and extracted with dichloromethane (2×50 mL). The combined organic layers were washed with brine (100 mL), dried over anhydrous sodium sulfate, filtered, and concentrated. The residue was purified by column chromatography (10:1 to 3:1 petroleum ether:ethyl acetate) to afford [1-(4-bromophenyl)-4-piperidyl]methyl 4-methylbenzenesulfonate (1.5 g, 65%) as an off-white solid. MS (ESI): m/z 426.2 [M+H]$^+$.

Step C: tert-butyl 4-[[1-(4-bromophenyl)-4-piperidyl] methoxymethyl]piperidine-1-carboxylate

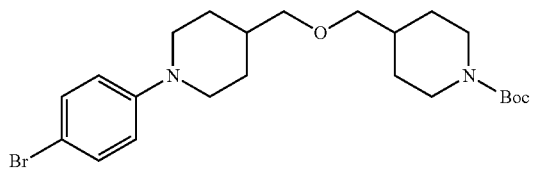 [SMILES: CC(C)(C)OC(=O)N1CCC(COCC2CCN(c3ccc(Br)cc3)CC2)CC1]

To a solution of tert-butyl 4-(hydroxymethyl)piperidine-1-carboxylate (913 mg, 4.24 mmol) in N,N-dimethylformamide (10 mL) was added 60% sodium hydride (226 mg, 5.66 mmol). The mixture was stirred at 25° C. for 30 min, then [1-(4-bromophenyl)-4-piperidyl]methyl 4-methylbenzenesulfonate (1.2 g, 2.8 mmol) was added. The resulting mixture was heated to 80° C. for 1 hour. The mixture was cooled to room temperature, and then poured inter brine (50 mL) and extracted with ethyl acetate (2×50 mL). The combined organic layers were washed with brine (3×100 mL), dried, and concentrated. The residue was purified by column chromatography (10:1 to 5:1 petroleum ether:ethyl acetate) to give tert-butyl 4-[[1-(4-bromophenyl)-4-piperidyl] methoxymethyl]piperidine-1-carboxylate (890 mg, 45%) as a colorless oil. MS (ESI): m/z 467.2 [M+H]$^+$.

Step D: 1-(4-bromophenyl)-4-(4-piperidyl-methoxymethyl)piperidine

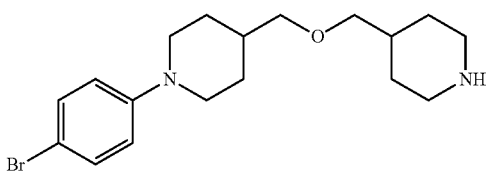 [SMILES: Brc1ccc(N2CCC(COCC3CCNCC3)CC2)cc1]

To a solution of tert-butyl 4-[[1-(4-bromophenyl)-4-piperidyl]methoxymethyl]piperidine-1-carboxylate (1 g, 2.14 mmol) in dichloromethane (10 mL) was added 4 N hydrochloric acid in 1,4-dioxane (5.0 mL). The mixture was stirred at 20° C. for 30 minutes. The mixture was concentrated to afford 1-(4-bromophenyl)-4-(4-piperidylmethoxymethyl)piperidine hydrochloride (830 mg, 96%) as a white solid.

Step E: methyl 4-[4-[[1-(4-bromophenyl)-4-piperidyl] methoxymethyl]-1-piperidyl]-2-cyano-benzoate

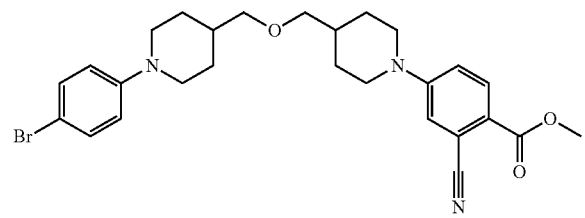 [SMILES: COC(=O)c1ccc(N2CCC(COCC3CCN(c4ccc(Br)cc4)CC3)CC2)cc1C#N]

To a solution of 1-(4-bromophenyl)-4-(4-piperidylmethoxymethyl)piperidine hydrochloride (830 mg, 2.06 mmol) and methyl 2-cyano-4-fluoro-benzoate (368 mg, 2.06 mmol) in dimethylsulfoxide (10 mL) was added N,N-diisopropylethylamine (797 mg, 6.17 mmol). The mixture was stirred at 120° C. for 2 hours. The mixture was diluted with water (30 mL) and extracted with ethyl acetate (3×20 mL). The combined organic layers were washed with brine (3×50 mL), dried with anhydrous sodium sulfate, filtered, and concentrated. The reside was purified by preparative HPLC (Phenomenex Luna C18, 70 to 100% acetonitrile:(0.225% formic acid in water)). Then the mixture was adjusted pH 8 with saturated aqueous sodium bicarbonate and extracted with ethyl acetate (2×20 mL). The combined organic layers were washed with brine (2×30 mL), dried with anhydrous sodium sulfate, filtered, and concentrated to afford methyl 4-[4-[[1-(4-bromophenyl)-4-piperidyl]methoxymethyl]-1-piperidyl]-2-cyano-benzoate (400 mg, 36%) as a brown oil. MS (ESI): m/z 526.2 [M+H]$^+$; $^1$H NMR (400 MHz, CDCl$_3$) δ 7.97 (d, J=9.0 Hz, 1H), 7.35-7.30 (m, 2H), 7.16 (d, J=2.7 Hz, 1H), 7.00 (dd, J=2.8, 9.2 Hz, 1H), 6.83-6.78 (m, 2H), 3.94 (s, 3H), 3.89 (d, J=12.8 Hz, 2H), 3.65 (d, J=12.4 Hz, 2H), 3.31 (d, J=6.2 Hz, 4H), 2.94 (dt, J=2.0, 12.8 Hz, 2H), 2.70 (dt, J=2.4, 12.4 Hz, 2H), 1.91-1.80 (m, 5H), 1.79-1.70 (m, 1H), 1.45-1.31 (m, 4H).

Step F: methyl 2-cyano-4-[4-[[1-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-4-piperidyl]methoxymethyl]-1-piperidyl]benzoate

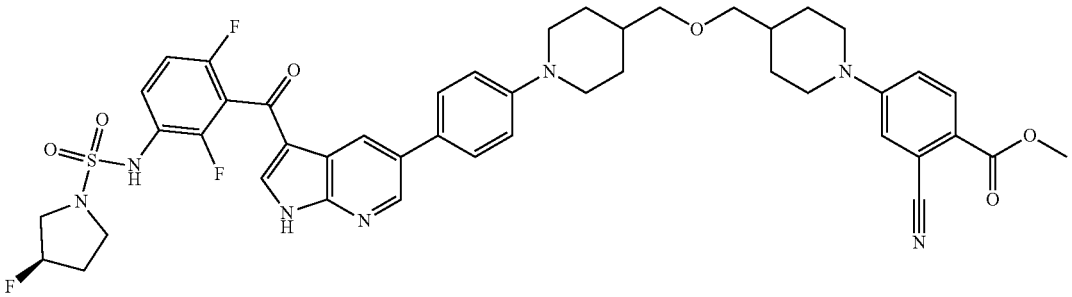 [SMILES: COC(=O)c1ccc(N2CCC(COCC3CCN(c4ccc(-c5cnc6[nH]cc(C(=O)c7c(F)ccc(NS(=O)(=O)N8CC[C@@H](F)C8)c7F)c6c5)cc4)CC3)CC2)cc1C#N]

To a solution of methyl 4-[4-[[1-(4-bromophenyl)-4-piperidyl]methoxymethyl]-1-piperidyl]-2-cyano-benzoate (350 mg, 0.66 mmol) and tert-butyl 3-[3-[tert-butoxycarbonyl-[(3R)-3-fluoropyrrolidin-1-yl]sulfonyl-amino]-2,6-difluoro-benzoyl]-5-(4,4,5,5-tetramethyl-1,3,2-dioxaborolan-2-yl)pyrrolo[2,3-b]pyridine-1-carboxylate (499 mg, 0.66 mmol) in N,N-dimethylformamide (5 mL) and water (1 mL) was added sodium carbonate (140 mg, 1.33 mmol) and dichloro[1,1'-bis(di-t-butylphosphino)ferrocene]palladium(II) (43 mg, 0.07 mmol). The mixture was stirred at 100° C. for 12 hours. The mixture was diluted with water (20 mL) and extracted with ethyl acetate (3×15 mL). The combined organic layers were washed with brine (3×30 mL), dried with anhydrous sodium sulfate, filtered, and concentrated. The crude product was purified by preparative HPLC (Phenomenex Luna C18, 50 to 80% acetonitrile:(0.225% formic acid in water)). Then the mixture was adjusted pH 7 with saturated aqueous sodium bicarbonate and concentrated. Then the mixture was extracted with ethyl acetate (2×30 mL). The combined organic layers were washed with brine (50 mL), dried with anhydrous sodium sulfate, filtered, and concentrated to afford methyl 2-cyano-4-[4-[[1-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-4-piperidyl]methoxymethyl]-1-piperidyl]benzoate (140 mg, 0.16 mmol, 24.21%) as a brown oil. MS (ESI): m/z 870.5 [M+H]$^+$.

Step G: methyl 4-[4-[[1-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-4-piperidyl]methoxymethyl]-1-piperidyl]-2-formyl-benzoate To a solution of 3-aminopiperidine-2,6-dione hydrochloride (12 mg, 0.07 mmol) in methanol (1 mL) and dichloromethane (0.5 mL) was added sodium acetate (10 mg, 0.12 mmol). The mixture was stirred at 20° C. for 10 minutes. Then methyl 4-[4-[[1-[4-[3-[2,6-difluoro-3-[[(3R)-3-fluoro-

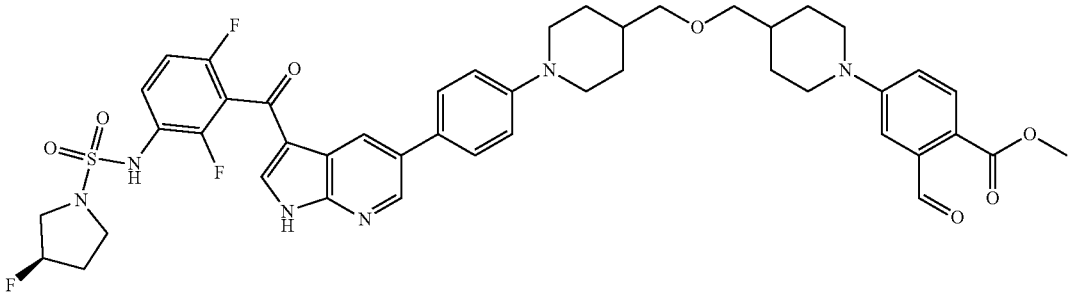 [SMILES: COC(=O)c1ccc(N2CCC(COCC3CCN(c4ccc(-c5cnc6[nH]cc(C(=O)c7c(F)ccc(NS(=O)(=O)N8CC[C@@H](F)C8)c7F)c6c5)cc4)CC3)CC2)cc1C=O]

To a solution of methyl 2-cyano-4-[4-[[1-[4-[3-[2,6-difluoro-3-[[(3R)-3-fluoropyrrolidin-1-yl] sulfonylamino]benzoyl]-1H-pyrrolo[2,3-b]pyridin-5-yl]phenyl]-4-piperidyl]methoxymethyl]-1-piperidyl]benzoate (140 mg, 0.16 mmol) in pyridine (4 mL) was added Raney nickel (6 mg, 0.08 mmol). Then acetic acid (2 mL) was added to the mixture. Then sodium dihydrogen phosphate hydrate (111 mg, 0.80 mmol) in water (1 mL) was added to the mixture. The mixture was stirred at 50° C. for 12 hours. The mixture was washed with ethyl acetate (3×20 mL). The combined organic layers were washed with brine (50 mL), aqueous 1 M hydrochloric acid (30 mL), brine (50 mL), saturated aqueous sodium bicarbonate (30 mL) and brine (50 mL), dried with anhydrous sodium sulfate, filtered, and concentrated to afford methyl 4-[4-[[1-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-4-piperidyl]methoxymethyl]-1-piperidyl]-2-formyl-benzoate (55 mg, 39%) as a brown oil. MS (ESI): m/z 873.4 [M+H]$^+$.

Step H: (3R)—N-[3-[5-[4-[4-[[1-[2-(2,6-dioxo-3-piperidyl)-1-oxo-isoindolin-5-yl]-4-piperidyl]methoxymethyl]-1-piperidyl]phenyl]-1H-pyrrolo[2,3-b]pyridine-3-carbonyl]-2,4-difluoro-phenyl]-3-fluoro-pyrrolidine-1-sulfonamide pyrrolidin-1-yl]sulfonylamino]benzoyl]-1H-pyrrolo[2,3-b]pyridin-5-yl]phenyl]-4-piperidyl]methoxymethyl]-1-piperidyl]-2-formyl-benzoate (55 mg, 0.06 mmol) and acetic acid (6 mg, 0.09 mmol) was added to the mixture. The mixture was stirred at 20° C. for 20 minutes. Then sodium cyanoborohydride (6 mg, 0.09 mmol) was added to the mixture. The mixture was stirred at 30° C. for 1 hours. The mixture was diluted with water (10 mL) and extracted with 2:1 tetrahydrofuran:ethyl acetate (3×10 mL). The combined organic layers were dried with anhydrous sodium sulfate, filtered, and concentrated. The crude product was purified by preparative HPLC (Unisil 3-100 C18 Ultra, 40 to 60% acetonitrile:(0.225% formic acid in water)) to afford (3R)—N-[3-[5-[4-[4-[[1-[2-(2,6-dioxo-3-piperidyl)-1-oxo-isoindolin-5-yl]-4-piperidyl]methoxymethyl]-1-piperidyl]phenyl]-1H-pyrrolo[2,3-b]pyridine-3-carbonyl]-2,4-difluoro-phenyl]-3-fluoro-pyrrolidine-1-sulfonamide formic acid salt (19.3 mg, 28%) as a yellow solid. MS (ESI): m/z 953.3 [M+H]$^+$; $^1$H NMR (400 MHz, DMSO-d$_6$) δ 13.26-12.52 (m, 1H), 11.06-10.84 (m, 1H), 8.64 (s, 1H), 8.51 (s, 1H), 8.26 (s, 1H), 8.03 (s, 1H), 7.63-7.53 (m, 3H), 7.52-7.45 (m, 1H), 7.21-7.12 (m, 1H), 7.10-7.00 (m, 4H), 5.38-5.17 (m, 1H), 5.10-4.98 (m, 1H), 4.38-4.27 (m, 1H), 4.23-4.13 (m, 1H), 3.93-3.86 (m, 2H), 3.83-3.76 (m, 2H), 3.29-3.28 (m, 2H), 3.27-3.26 (m, 3H), 2.91-2.78 (m, 4H), 2.77-2.64 (m, 4H), 2.42-2.35 (m, 2H), 2.13-2.04 (m, 2H), 2.01-1.91 (m, 2H), 1.81-1.76 (m, 3H), 1.76-1.70 (m, 3H), 1.37-1.29 (m, 2H), 1.28-1.19 (m, 2H).

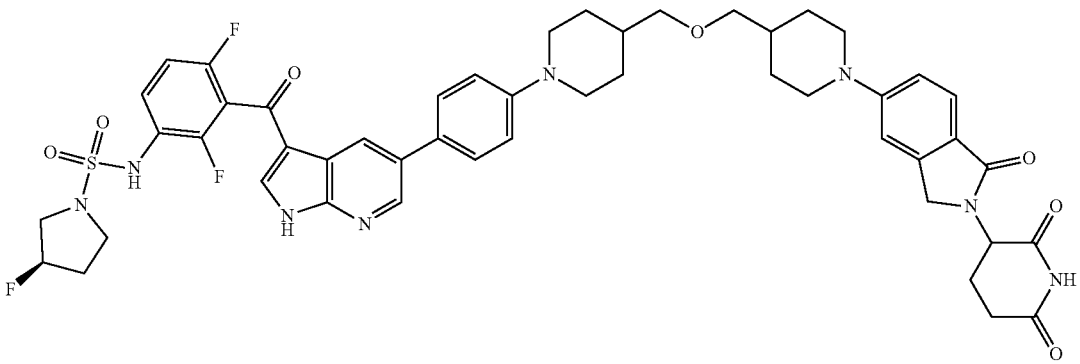 [SMILES: O=C1CCC(N2Cc3cc(N4CCC(COCC5CCN(c6ccc(-c7cnc8[nH]cc(C(=O)c9c(F)ccc(NS(=O)(=O)N%10CC[C@@H](F)C%10)c9F)c8c7)cc6)CC5)CC4)ccc3C2=O)C(=O)N1]

Exemplary Synthesis of Exemplary Compounds 172 or 173: (3R)—N-[3-[5-[4-[6-[(2S)-4-[2-[(3S)-2,6-dioxo-3-piperidyl]-1-oxo-isoindolin-5-yl]-2-hydroxy-butyl]-2,6-diazaspiro[3.3]heptan-2-yl]phenyl]-1H-pyrrolo[2,3-b]pyridine-3-carbonyl]-2,4-difluoro-phenyl]-3-fluoro-pyrrolidine-1-sulfonamide and (3R)—N-[3-[5-[4-[6-[(2S)-4-[2-[(3R)-2,6-dioxo-3-piperidyl]-1-oxo-isoindolin-5-yl]-2-hydroxy-butyl]-2,6-diazaspiro[3.3]heptan-2-yl]phenyl]-1H-pyrrolo[2,3-b]pyridine-3-carbonyl]-2,4-difluoro-phenyl]-3-fluoro-pyrrolidine-1-sulfonamide

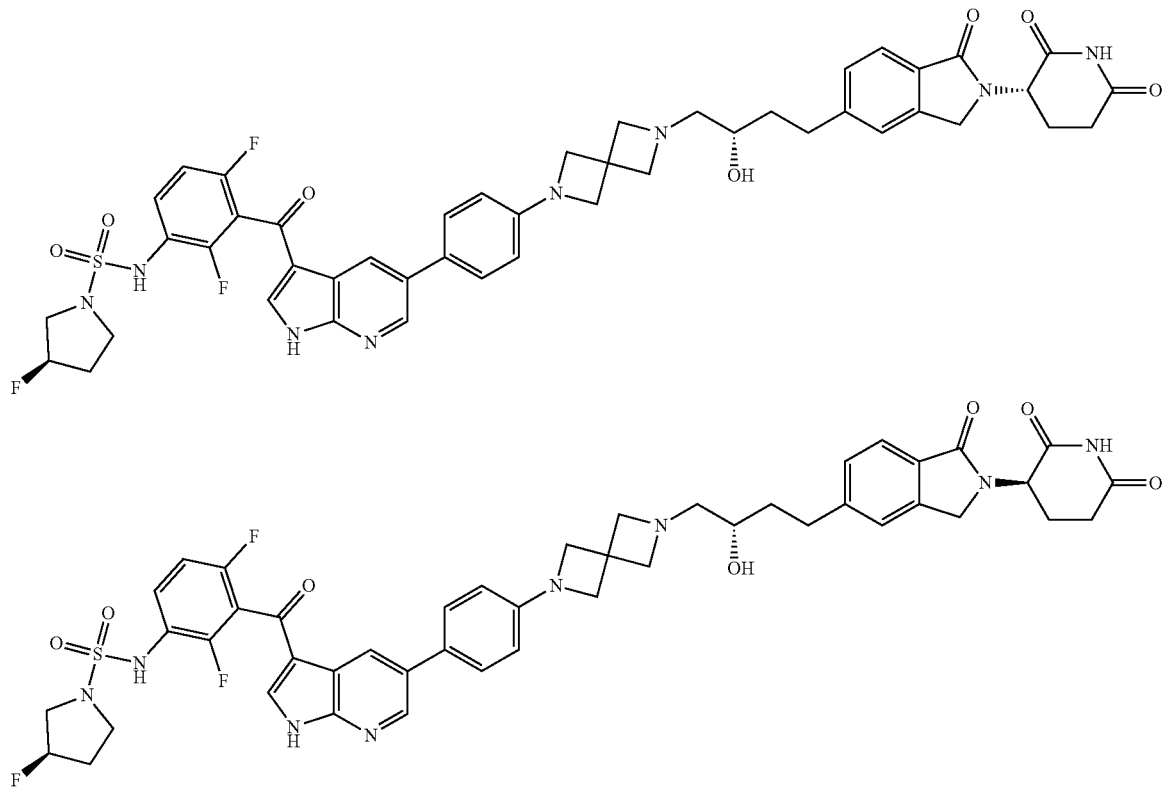

Step A: (4S)-4-ethynyl-2,2-dimethyl-1,3-dioxolane

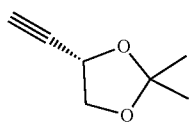

To a mixture of (4R)-2,2-dimethyl-1,3-dioxolane-4-carbaldehyde (15 g, 115.26 mmol) and 1-diazo-1-dimethoxyphosphoryl-propan-2-one (22.14 g, 115.26 mmol) in methanol (600 mL) was added potassium carbonate (31.86 g, 230.52 mmol) batchwise at 5° C. The mixture was stirred at 25° C. for 12 hours. Water (500 mL) was poured into the mixture and stirred for 1 minute. The aqueous phase was extracted with dichloromethane (2×400 mL). The combined organic phase was washed with brine (2×500 mL), dried with anhydrous sodium sulfate, filtered and concentrated. The oil was purified by silica gel column charomatography (1:0 to 0:1 pentane:dichloromethane) to afford (4S)-4-ethynyl-2,2-dimethyl-1,3-dioxolane (14 g, 96%) as a colorless oil.

Step B: methyl 2-cyano-4-[2-[(4S)-2,2-dimethyl-1,3-dioxolan-4-yl]ethynyl]benzoate

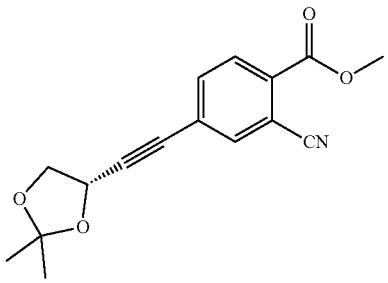

A mixture of methyl 4-bromo-2-cyano-benzoate (1.90 g, 7.93 mmol), (4S)-4-ethynyl-2,2-dimethyl-1,3-dioxolane (3 g, 23.78 mmol), cuprous iodide (151 mg, 0.79 mmol), N,N-diisopropylethylamine (10.24 g, 79.27 mmol, 13.81 mL) and bis(triphenylphosphine)palladium(II) dichloride (556 mg, 0.79 mmol) in tetrahydrofuran (30 mL) was degassed and purged with nitrogen for 3 times, and then the mixture was stirred at 60° C. for 12 hours under nitrogen atmosphere. Ethyl acetate (50 mL) and water (40 mL) were added and the layers were separated. The aqueous phase was extracted with tetrahydrofuran (2×40 mL). The combined organic extracts were washed with (2×50 mL), concentrated. The residue was purified by column chromatography (20:1 to 5:1 petroleum ether:ethyl acetate). Trituration of the residue with 6:1 petroleum ether:ethyl acetate afforded methyl 2-cyano-4-[2-[(4S)-2,2-dimethyl-1,3-dioxolan-4-yl]ethynyl]benzoate (1.76 g, 77%) as a yellow solid. MS (ESI): m/z 308.4 [M+23]$^+$; $^1$H NMR (400 MHz, CDCl$_3$) δ 8.10 (d, J=8.4 Hz, 1H), 7.84 (s, 1H), 7.70 (d, J=8.4 Hz, 1H), 4.96 (t, J=6.0 Hz, 1H), 4.26 (t, J=7.2 Hz, 1H), 4.05 (t, J=7.2 Hz, 1H), 4.01 (s, 3H), 1.57-1.40 (m, 6H).

Step C: 2-cyano-4-[2-[(4S)-2,2-dimethyl-1,3-dioxolan-4-yl]ethyl]benzoate

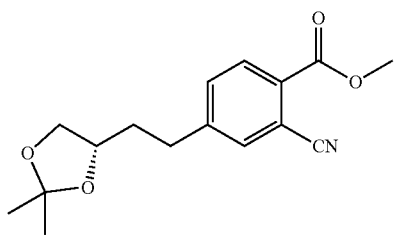

To a solution of methyl 2-cyano-4-[2-[(4S)-2,2-dimethyl-1,3-dioxolan-4-yl]ethynyl]benzoate (1.76 g, 6.17 mmol) in tetrahydrofuran (12 mL) and methanol (12 mL) was added 10% palladium on activated carbon (0.3 g). The suspension was degassed under vacuum and purged with hydrogen several times. The mixture was stirred under hydrogen (15 psi) at 40° C. for 12 hours. The reaction mixture was filtered and concentrated to afford methyl 2-cyano-4-[2-[(4S)-2,2-dimethyl-1,3-dioxolan-4-yl]ethyl] benzoate (1.78 g) as a colorless oil.

Step D: methyl 2-cyano-4-[(3S)-3,4-dihydroxybutyl] benzoate

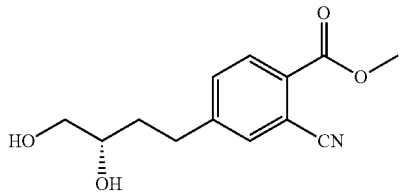 [SMILES: COC(=O)c1ccc(CC[C@H](O)CO)cc1C#N]

To a solution of methyl 2-cyano-4-[2-[(4S)-2,2-dimethyl-1,3-dioxolan-4-yl]ethyl]benzoate (1.78 g, 6.15 mmol) in acetonitrile (15 mL) and water (3 mL) was added p-toluenesulfonic acid (1.17 g, 6.77 mmol). The mixture was stirred at 30° C. for 20 hours. The reaction mixture was poured into saturated aqueous sodium bicarbonate (8 mL) to bring the pH to ~7. The mixture was purified by preparative HPLC (Phenomenex Luna C18, 10 to 30% acetonitrile:(0.225% formic acid in water)) to afford methyl 2-cyano-4-[(3S)-3,4-dihydroxybutyl]benzoate (1.35 g, 88%) as a white solid. MS (ESI): m/z 250.1 [M+H]$^+$.

Step E: methyl 2-cyano-4-[(3S)-3-hydroxy-4-oxobutyl] benzoate

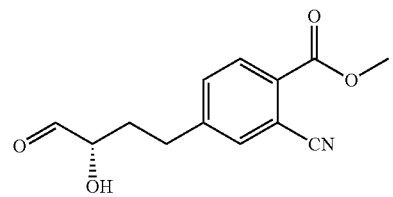 [SMILES: COC(=O)c1ccc(CC[C@H](O)C=O)cc1C#N]

To a solution of methyl 2-cyano-4-[(3S)-3,4-dihydroxybutyl]benzoate (1.1 g, 4.4 mmol) in dichloromethane (46 mL) and aqueous sodium bicarbonate (23 mL) was added potassium bromide (525 mg, 4.41 mmol) and (2,2,6,6-tetramethylpiperidin-1-yl)oxyl (69 mg, 0.44 mmol) at 0° C., followed by 5% aqueous sodium hypochlorite (6.57 g, 4.41 mmol, 5.4 mL) dropwise. The resulting mixture was stirred at 0° C. for 1 hour. The reaction mixture quenched by addition saturated aqueous sodium thiosulfate (30 mL) and then diluted with water (60 mL) and extracted with dichloromethane (2×50 mL). The combined organic layers were washed with brine (2×40 mL), dried over anhydrous sodium sulfate, filtered, and concentrated to afford methyl 2-cyano-4-[(3S)-3-hydroxy-4-oxo-butyl]benzoate (1.09 g) as a yellow oil.

Step F: methyl 4-[(3S)-4-[2-(4-bromophenyl)-2,6-diazaspiro[3.3]heptan-6-yl]-3-hydroxy-butyl]-2-cyano-benzoate

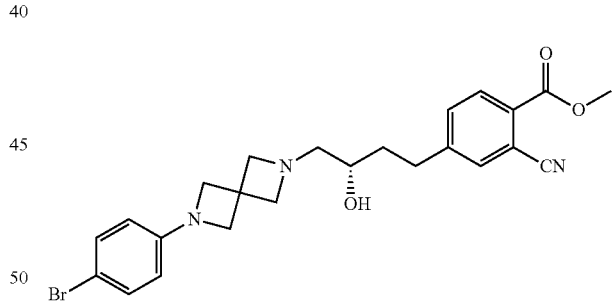

To a solution of 2-(4-bromophenyl)-2,6-diazaspiro[3.3]heptane (781 mg, 3.09 mmol) in dichloromethane (20 mL) was added triethylamine (1.78 g, 17.6 mmol, 2.5 mL), and then methyl 2-cyano-4-[(3S)-3-hydroxy-4-oxo-butyl]benzoate (1.09 g, 4.41 mmol) was added at 25° C. After 20 minutes, and sodium triacetoxyborohydride (1.87 g, 8.82 mmol) was added. The mixture was stirred at 25° C. for 40 minutes. Dichloromethane (30 mL) and water (50 mL) were added and layers were separated. The aqueous phase was extracted with dichloromethane (40 mL). The combined organic extracts were washed with brine (40 mL), dried over anhydrous sodium sulfate, filtered, and concentrated. The residue was purified by column chromatography (50:1 to 20:1 dichloromethane:methanol) and then preparative HPLC (Welch Ultimate XB-NH$_2$, 20 to 60% (0.1% ammonium hydroxide in ethanol):heptane) to afford methyl 4-[(3S)-4-[2-(4-bromophenyl)-2,6-diazaspiro[3.3]heptan-6-yl]-3-hydroxy-butyl]-2-cyano-benzoate (825 mg, 38%) as a yellow solid. MS (ESI): m/z 484.4 [M+H]⁺.

Step G: methyl 4-[(3S)-4-[2-(4-bromophenyl)-2,6-diazaspiro[3.3]heptan-6-yl]-3-hydroxy-butyl]-2-formyl-benzoate

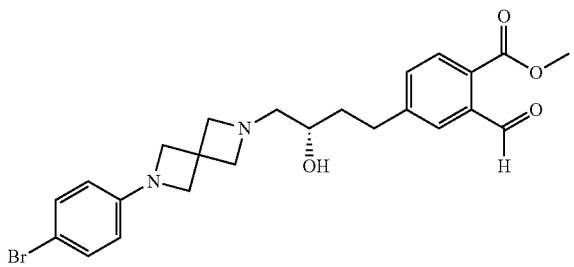 [SMILES: COC(=O)c1ccc(CC[C@H](O)CN2CC3(C2)CN(c2ccc(Br)cc2)C3)cc1C=O]

To a solution of methyl 4-[(3S)-4-[2-(4-bromophenyl)-2,6-diazaspiro[3.3]heptan-6-yl]-3-hydroxy-butyl]-2-cyano-benzoate (810 mg, 1.67 mmol) in pyridine (12 mL) was added Raney nickel (286 mg, 3.34 mmol) and acetic acid (4 mL). Then sodium dihydrogen phosphate hydrate (1.15 g, 8.36 mmol) in water (4 mL) was added at 30° C. The mixture was stirred at 30° C. for 2 hours. The reaction mixture was poured into saturated aqueous sodium bicarbonate (30 mL). Ethyl acetate (40 mL) and water (40 mL) were added and layers were separated. The aqueous phase was extracted with ethyl acetate (30 mL). The combined organic extracts were washed with brine (2×40 mL), dried over anhydrous sodium sulfate, filtered, and concentrated. The residue was purified by flash silica gel chromatography (0 to 7% methanol:dichloromethane) to afford methyl 4-[(3S)-4-[2-(4-bromophenyl)-2,6-diazaspiro[3.3]heptan-6-yl]-3-hydroxy-butyl]-2-formyl-benzoate (545 mg, 66%) as a yellow solid. MS (ESI): m/z 489.2 [M+2H]⁺.

Step H: 3-[5-[(3S)-4-[2-(4-bromophenyl)-2,6-diazaspiro[3.3]heptan-6-yl]-3-hydroxy-butyl]-1-oxo-isoindolin-2-yl]piperidine-2,6-dione

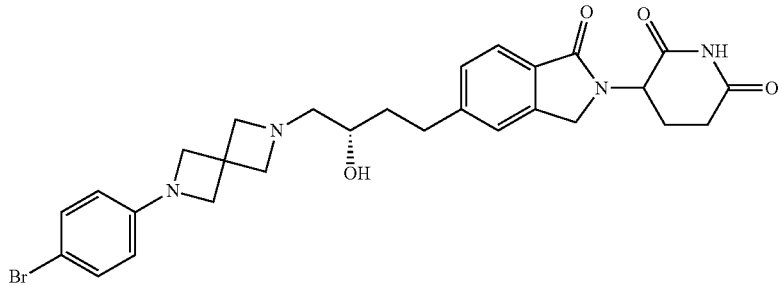 [SMILES: O=C1CCC(N2Cc3cc(CC[C@H](O)CN4CC5(C4)CN(c4ccc(Br)cc4)C5)ccc3C2=O)C(=O)N1]

To a suspension of 3-aminopiperidine-2,6-dione hydrochloride (202 mg, 1.23 mmol) in methanol (5 mL) was added sodium acetate (183 mg, 2.24 mmol). The mixture was stirred at 35° C. for 10 min, then a solution of methyl 4-[(3S)-4-[2-(4-bromophenyl)-2,6-diazaspiro[3.3]heptan-6-yl]-3-hydroxy-butyl]-2-formyl-benzoate (545 mg, 1.12 mmol) in dichloromethane (5 mL) was added, followed by acetic acid (335 mg, 5.59 mmol). The mixture was stirred at 35° C. for another 50 minutes. Then sodium cyanoborohydride (210 mg, 3.35 mmol) was added. Then resulting mixture was stirred at 35° C. for another 17 hours. The reaction mixture was diluted with water (60 mL), extracted with ethyl acetate (2×40 mL) and tetrahydrofuran (40 mL). The combined organic layers were washed with brine (2×50 mL), dried over anhydrous sodium sulfate, filtered, and concentrated. The residue triturated with 1:1 petroleum ether:ethyl acetate and then further purified by preparative HPLC (Phenomenex Luna C18, 13 to 43% acetonitrile: (0.225% formic acid in water)) to afford 3-[5-[(3S)-4-[2-(4-bromophenyl)-2,6-diazaspiro[3.3]heptan-6-yl]-3-hydroxy-butyl]-1-oxo-isoindolin-2-yl]piperidine-2,6-dione formic acid salt (350 mg, 50%) as a white solid. MS (ESI): m/z 567.2 [M+H]⁺.

Step I: tert-butyl N-[3-[5-[4-[6-[(2S)-4-[2-(2,6-di-oxo-3-piperidyl)-1-oxo-isoindolin-5-yl]-2-hydroxy-butyl]-2,6-diazaspiro[3.3]heptan-2-yl]phenyl]-1H-pyrrolo[2,3-b]pyridine-3-carbonyl]-2,4-difluoro-phenyl]-N-[(3R)-3-fluoropyrrolidin-1-yl]sulfonyl-carbamate

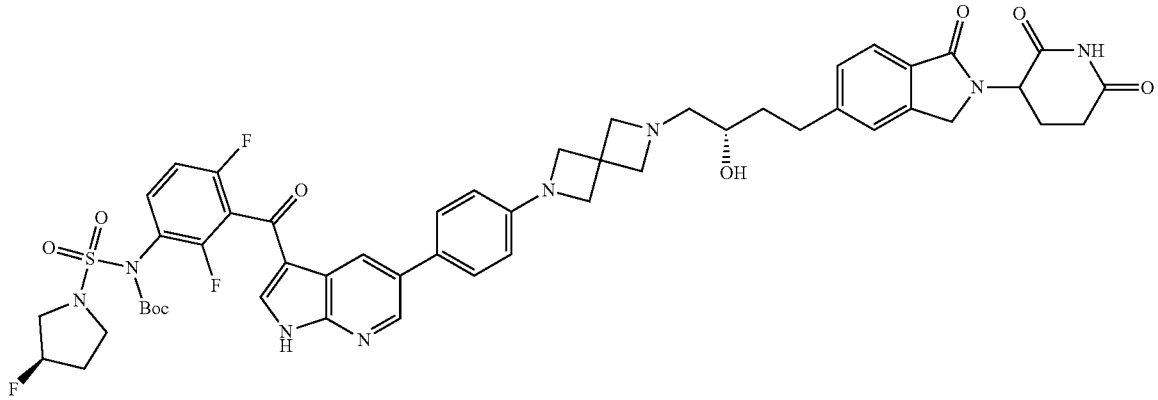 [SMILES: CC(C)(C)OC(=O)N(c1ccc(F)c(C(=O)c2c[nH]c3ncc(-c4ccc(N5CC6(CN(C[C@@H](O)CCc7ccc8c(c7)CN(C7CCC(=O)NC7=O)C8=O)C6)C5)cc4)cc23)c1F)S(=O)(=O)N1CC[C@@H](F)C1]

A mixture of 3-[5-[(3S)-4-[2-(4-bromophenyl)-2,6-diaz-aspiro[3.3]heptan-6-yl]-3-hydroxy-butyl]-1-oxo-isoindolin-2-yl]piperidine-2,6-dione formic acid salt (230 mg, 0.37 mmol), tert-butyl 3-[3-[tert-butoxycarbonyl-[(3R)-3-fluoro-pyrrolidin-1-yl]sulfonyl-amino]-2,6-difluoro-benzoyl]-5-(4,4,5,5-tetramethyl-1,3,2-dioxaborolan-2-yl)pyrrolo[2,3-b]pyridine-1-carboxylate (295 mg, 0.39 mmol), dichloro[1,1'-bis(di-t-butylphosphino)ferrocene]palladium(II) (36 mg, 0.056 mmol), and cesium fluoride (227 mg, 1.50 mmol) in N,N-dimethylformamide (5 mL) and water (1 mL) was degassed and purged with nitrogen for 3 times, and then the mixture was stirred at 80° C. for 2 hours. Ethyl acetate (20 mL), tetrahydrofuran (30 mL) and water (40 mL) were added and layers were separated. The aqueous phase was extracted with tetrahydrofuran (30 mL). The combined organic extracts were washed with brine (2×30 mL), dried over anhydrous sodium sulfate, filtered and concentrated to afford tert-butyl N-[3-[5-[4-[6-[(2S)-4-[2-(2,6-dioxo-3-piperidyl)-1-oxo-isoindolin-5-yl]-2-hydroxy-butyl]-2,6-diaz-aspiro[3.3]heptan-2-yl]phenyl]-1H-pyrrolo[2,3-b]pyridine-3-carbonyl]-2,4-difluoro-phenyl]-N-[(3R)-3-fluoropyrrol-idin-1-yl]sulfonyl-carbamate (250 mg) as a yellow solid. MS (ESI): m/z 1011.9 [M+H]⁺.

Step J: (3R)—N-[3-[5-[4-[6-[(2S)-4-[2-(2,6-dioxo-3-piperidyl)-1-oxo-isoindolin-5-yl]-2-hydroxy-butyl]-2,6-diazaspiro[3.3]heptan-2-yl]phenyl]-1H-pyrrolo[2,3-b]pyridine-3-carbonyl]-2,4-difluoro-phenyl]-3-fluoro-pyrrolidine-1-sulfonamide

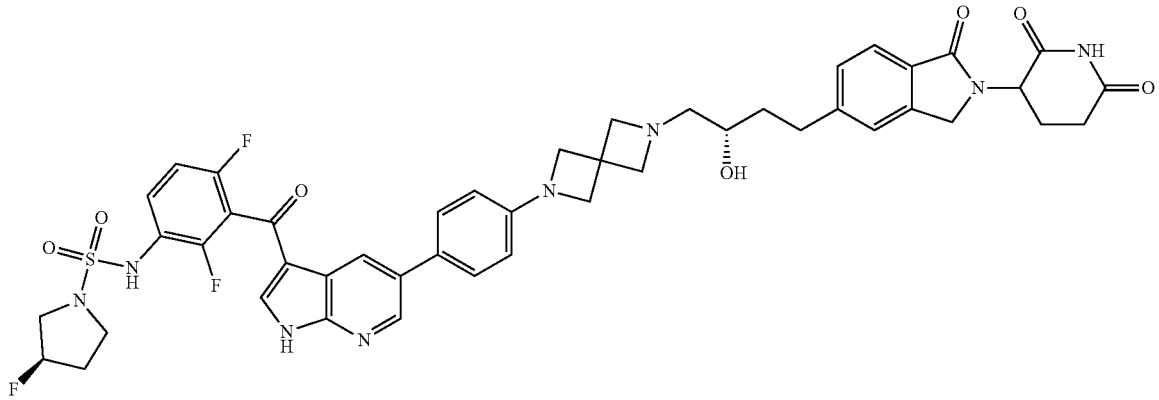 [SMILES: O=C1CCC(N2Cc3cc(CC[C@H](O)CN4CC5(C4)CN(c4ccc(-c6cnc7[nH]cc(C(=O)c8c(F)ccc(NS(=O)(=O)N9CC[C@@H](F)C9)c8F)c7c6)cc4)C5)ccc3C2=O)C(=O)N1]

To a solution of tert-butyl N-[3-[5-[4-[6-[(2S)-4-[2-(2,6-dioxo-3-piperidyl)-1-oxo-isoindolin-5-yl]-2-hydroxy-butyl]-2,6-diazaspiro[3.3]heptan-2-yl]phenyl]-1H-pyrrolo[2,3-b]pyridine-3-carbonyl]-2,4-difluoro-phenyl]-N-[(3R)-3-fluoropyrrolidin-1-yl]sulfonyl-carbamate (250 mg, 0.25 mmol) in dichloromethane (10 mL) was added trifluoroacetic acid (2.00 mL). The mixture was stirred at 25° C. for 1.5 hours. The reaction mixture was basified with saturated aqueous sodium bicarbonate to pH 8. Then the reaction mixture was diluted with water (30 mL) and extracted with tetrahydrofuran (2×40 mL). The combined organic layers were washed with brine (2×30 mL), dried over anhydrous sodium sulfate, filtered, and concentrated. The residue was purified by flash silica gel chromatography (0 to 10% methanol:dichloromethane) to afford (3R)—N-[3-[5-[4-[6-[(2S)-4-[2-(2,6-dioxo-3-piperidyl)-1-oxo-isoindolin-5-yl]-2-hydroxy-butyl]-2,6-diazaspiro[3.3]heptan-2-yl]phenyl]-1H-pyrrolo[2,3-b]pyridine-3-carbonyl]-2,4-difluoro-phenyl]-3-fluoro-pyrrolidine-1-sulfonamide (0.12 g, 53%) as a yellow solid. MS (ESI): m/z 911.4 [M+H]$^+$.

Step K: (3R)—N-[3-[5-[4-[6-[(2S)-4-[2-[(3S)-2,6-dioxo-3-piperidyl]-1-oxo-isoindolin-5-yl]-2-hydroxy-butyl]-2,6-diazaspiro[3.3]heptan-2-yl]phenyl]-1H-pyrrolo[2,3-b]pyridine-3-carbonyl]-2,4-difluoro-phenyl]-3-fluoro-pyrrolidine-1-sulfonamide and (3R)—N-[3-[5-[4-[6-[(2S)-4-[2-[(3R)-2,6-dioxo-3-piperidyl]-1-oxo-isoindolin-5-yl]-2-hydroxy-butyl]-2,6-diazaspiro[3.3]heptan-2-yl]phenyl]-1H-pyrrolo[2,3-b]pyridine-3-carbonyl]-2,4-difluoro-phenyl]-3-fluoro-pyrrolidine-1-sulfonamide (3R)—N-[3-[5-[4-[6-[(2S)-4-[2-(2,6-dioxo-3-piperidyl)-1-oxo-isoindolin-5-yl]-2-hydroxy-butyl]-2,6-diazaspiro[3.3]heptan-2-yl]phenyl]-1H-pyrrolo[2,3-b]pyridine-3-carbonyl]-2,4-difluoro-phenyl]-3-fluoro-pyrrolidine-1-sulfonamide (120 mg, 0.13 mmol) was separated by SFC (REGIS (R,R) WHELK-O1, 60% (0.1% ammonia in water:isopropanol)), then further purified by successive preparative HPLC (Unisil 3-100 C18 Ultra, 25 to 55% acetonitrile:(0.225% formic acid in water)), then SFC (REGIS (R,R) WHELK-O1, 60% (0.1% ammonia in water:isopropanol)), then preparative HPLC (Unisil 3-100 C18 Ultra, 20 to 40% acetonitrile:(0.225% formic acid in water)) to afford (3R)—N-[3-[5-[4-[6-[(2S)-4-[2-[(3S)-2,6-dioxo-3-piperidyl]-1-oxo-isoindolin-5-yl]-2-hydroxy-butyl]-2,6-diazaspiro[3.3]heptan-2-yl]phenyl]-1H-pyrrolo[2,3-b]pyridine-3-carbonyl]-2,4-difluoro-phenyl]-3-fluoro-pyrrolidine-1-sulfonamide formic acid salt (15.4 mg, 23%) as a yellow solid. MS (ESI): m/z 911.3 [M+H]$^+$; $^1$H NMR (400 MHz, DMSO-d$_6$) δ 10.98 (s, 1H), 8.60 (d, J=1.6 Hz, 1H), 8.48 (s, 1H), 8.26 (s, 1H), 8.03 (s, 1H), 7.67-7.51 (m, 4H), 7.44 (s, 1H), 7.35 (d, J=8.0 Hz, 1H), 7.18 (t, J=8.8 Hz, 1H), 6.55 (d, J=8.4 Hz, 2H), 5.38-5.18 (m, 1H), 5.10 (dd, J=4.8, 13.2 Hz, 1H), 4.45 (s, 1H), 4.32-4.26 (m, 1H), 3.92 (s, 4H), 3.36 (s, 6H), 3.29-3.22 (m, 4H), 2.97-2.80 (m, 3H), 2.71 (d, J=6.8 Hz, 1H), 2.62 (s, 1H), 2.57 (s, 1H), 2.39 (dd, J=4.4, 13.2 Hz, 2H), 2.10 (s, 1H), 2.00 (d, J=10.8 Hz, 2H), 1.73 (dd, J=2.4, 6.4 Hz, 1H), 1.63-1.52 (m, 1H).

Also obtained was (3R)—N-[3-[5-[4-[6-[(2S)-4-[2-[(3R)-2,6-dioxo-3-piperidyl]-1-oxo-isoindolin-5-yl]-2-hydroxy-butyl]-2,6-diazaspiro[3.3]heptan-2-yl]phenyl]-1H-pyrrolo

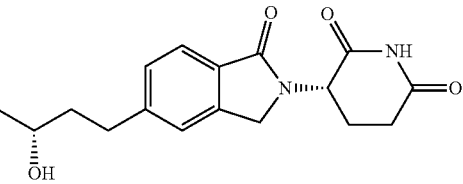

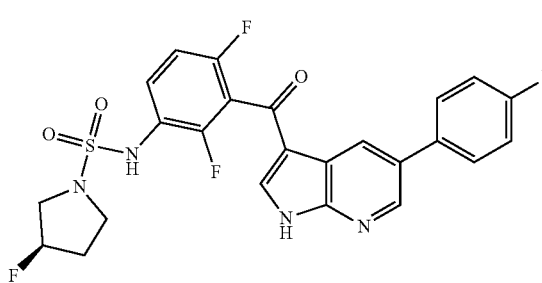

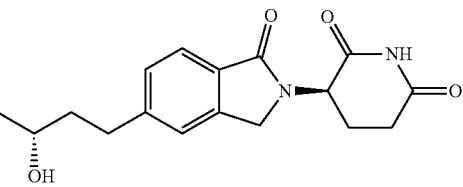

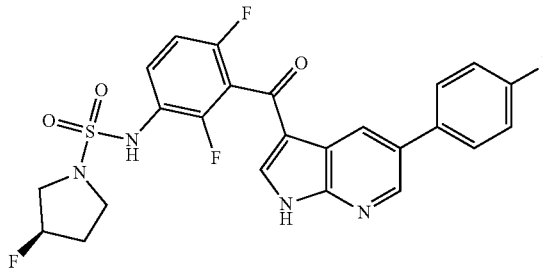

[2,3-b]pyridine-3-carbonyl]-2,4-difluoro-phenyl]-3-fluoro-pyrrolidine-1-sulfonamide formic acid salt (16.8 mg, 25%) as a yellow solid. MS (ESI): m/z 911.3 [M+H]⁺; ¹H NMR (400 MHz, DMSO-d₆) δ 13.31-12.43 (m, 1H), 10.98 (s, 1H), 8.61 (s, 1H), 8.49 (s, 1H), 8.20 (s, 1H), 8.04 (s, 1H), 7.64 (d, J=7.6 Hz, 2H), 7.55 (d, J=8.0 Hz, 2H), 7.44 (s, 1H), 7.35 (d, J=8.0 Hz, 1H), 7.23 (t, J=8.8 Hz, 1H), 6.56 (d, J=8.4 Hz, 2H), 5.37-5.20 (m, 1H), 5.10 (dd, J=4.8, 13.2 Hz, 1H), 4.47-4.38 (m, 1H), 4.35-4.24 (m, 1H), 3.93 (s, 4H), 3.35 (s, 6H), 3.29-3.23 (m, 4H), 2.97-2.79 (m, 3H), 2.75-2.69 (m, 1H), 2.62 (s, 1H), 2.57 (d, J=1.2 Hz, 1H), 2.45 (s, 1H), 2.39 (dd, J=4.4, 13.0 Hz, 1H), 2.13-1.97 (m, 3H), 1.78-1.66 (m, 1H), 1.59 (dd, J=4.4, 8.8 Hz, 1H).

Exemplary Synthesis of Exemplary Compound 178: (3R)—N-[3-(5-[4-[4-(2-[4-[4-(2,6-dioxopiperidin-3-yl)-3-fluorophenyl]piperidin-1-yl]ethyl)piperidin-1-yl]phenyl]-1H-pyrrolo[2,3-b]pyridine-3-carbonyl)-2,4-difluorophenyl]-3-fluoropyrrolidine-1-sulfonamide

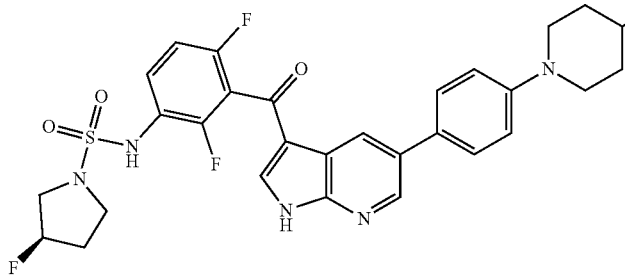

Step A: tert-butyl 4-[4-(2-ethoxy-2-oxoethyl)-3-fluorophenyl]-3,6-dihydro-2H-pyridine-1-carboxylate

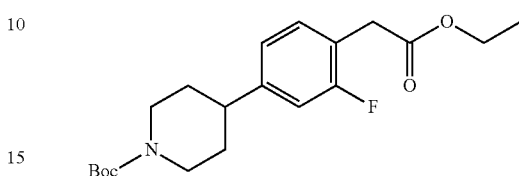

A mixture of ethyl 2-(4-bromo-2-fluorophenyl)acetate (4.00 g, 15.3 mmol), tert-butyl 4-(4,4,5,5-tetramethyl-1,3,2-dioxaborolan-2-yl)-3,6-dihydro-2H-pyridine-1-carboxylate (5.21 g, 16.8 mmol), cesium fluoride (9.31 g, 61.2 mmol), dichloro[1,1'-bis(di-t-butylphosphino)ferrocene]palladium (II) (2.00 g, 3.06 mmol), 1,4-dioxane (50 mL), and water (8 mL) was stirred for 2 hours at 100° C. After cooling to room temperature, the resulting solution was extracted with dichloromethane (3×200 mL) and the organic layers concentrated. The residue was triturated with 10% ethyl acetate:petroleum ether to afford 5.33 g (96%) of tert-butyl 4-[4-(2-ethoxy-2-oxoethyl)-3-fluorophenyl]-3,6-dihydro-2H-pyridine-1-carboxylate as brown oil. MS (ESI): m/z 363.18 [M+H]⁺.

Step B: tert-butyl 4-[4-(2-ethoxy-2-oxoethyl)-3-fluorophenyl]piperidine-1-carboxylate

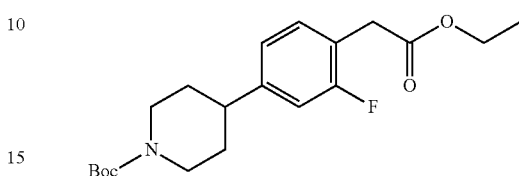

A mixture of tert-butyl 4-[4-(2-ethoxy-2-oxoethyl)-3-fluorophenyl]-3,6-dihydro-2H-pyridine-1-carboxylate (5.33 g, 14.6 mmol), ethanol (150 mL), palladium on carbon (4.50 g, 42.2 mmol) was evacuated and flushed with hydrogen. The reaction mixture was hydrogenated at room temperature for 6 hours at room temperature under a balloon of hydrogen, then filtered through a Celite pad and concentrated. Purification by silica gel column chromatography (11.7% ethyl acetate:petroleum ether) afforded 3.69 g (69%) of tert-butyl 4-[4-(2-ethoxy-2-oxoethyl)-3-fluorophenyl]piperidine-1-carboxylate as white oil. MS (ESI): m/z 365.2 [M+H]⁺.

Step C: tert-butyl 4-[4-(2,6-dioxopiperidin-3-yl)-3-fluorophenyl]piperidine-1-carboxylate

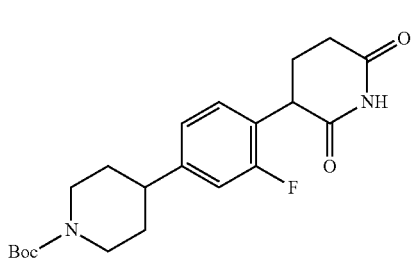 [SMILES: CC(C)(C)OC(=O)N1CCC(c2ccc(C3CCC(=O)NC3=O)c(F)c2)CC1]

To a mixture of tert-butyl 4-[4-(2-ethoxy-2-oxoethyl)-3-fluorophenyl]piperidine-1-carboxylate (3.45 g), polyacrylamide (570 mg), THF (120 mL) was added 1 M t-BuOK in THF (16 mL) dropwise at 0° C. The resulting mixture was stirred for 2 hours at 0° C., and then 2 hours at room temperature. The reaction was then quenched by the addition of ice water (200 mL) and extracted with ethyl acetate (3×200 mL). The combined organic layers were washed with brine (500 mL) and concentrated. The residue was triturated with ethyl acetate:petroleum to afford 1.37 g (44%) of tert-butyl 4-[4-(2,6-dioxopiperidin-3-yl)-3-fluorophenyl]piperidine-1-carboxylate as a white solid. MS (ESI): m/z 390.2 [M+H]$^+$.

Step D: 3-[2-fluoro-4-(piperidin-4-yl)phenyl]piperidine-2,6-dione

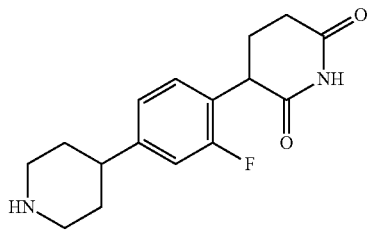 [SMILES: O=C1CCC(c2ccc(C3CCNCC3)cc2F)C(=O)N1]

A mixture of tert-butyl 4-[4-(2,6-dioxopiperidin-3-yl)-3-fluorophenyl]piperidine-1-carboxylate (700 mg, 1.79 mmol), dichloromethane (20 mL), and trifluoroacetic acid (4 mL) was stirred for 1 hour at room temperature. The resulting mixture was concentrated to afford 820 mg of 3-[2-fluoro-4-(piperidin-4-yl)phenyl]piperidine-2,6-dione trifluoroacetic acid salt as a yellow solid. MS (ESI): m/z 388.14 [M+H]$^+$.

Step E: 2-[1-(4-bromophenyl)piperidin-4-yl]ethanol

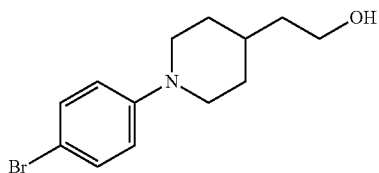 [SMILES: OCCC1CCN(c2ccc(Br)cc2)CC1]

A solution of 4-piperidineethanol (5.00 g, 38.6 mmol), 4-bromophenylboric acid (9.33 g, 46.4 mmol), and copper (II) acetate (9.14 g, 50.3 mmol) in dichloromethane (300 mL) and triethylamine (30 mL) was stirred for 16 hours at room temperature. The residue was triturated with 37.3% ethyl acetate:petroleum ether) to afford 3.8 g (35%) of 2-[1-(4-bromophenyl)piperidin-4-yl]ethanol as a light yellow solid. MS (ESI): m/z 283.06 [M+H]$^+$.

Step F: 2-[1-(4-bromophenyl)piperidin-4-yl]acetaldehyde

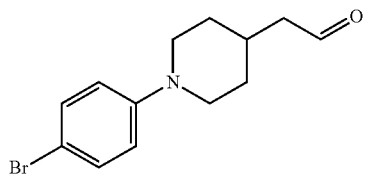 [SMILES: O=CCC1CCN(c2ccc(Br)cc2)CC1]

A mixture of 2-[1-(4-bromophenyl)piperidin-4-yl]ethanol (450 mg, 1.58 mmol), acetonitrile (40 mL), and IBX (670 mg, 2.39 mmol) was stirred for 2 hours at 80° C. After cooling to room temperature, the solids were filtered out. Purification by silica gel column chromatography (2:1 ethyl acetate:petroleum ether) afforded 320 mg (72%) of 2-[1-(4-bromophenyl)piperidin-4-yl]acetaldehyde as a yellow solid. MS (ESI): m/z 281.04 [M+H]$^+$.

Step G: 3-[4-(1-[2-[1-(4-bromophenyl)piperidin-4-yl]ethyl]piperidin-4-yl)-2-fluorophenyl]piperidine-2,6-dione

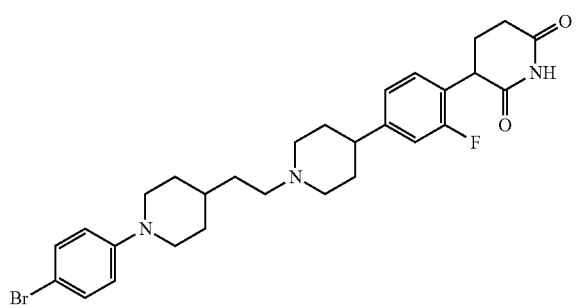

A mixture of 3-[2-fluoro-4-(piperidin-4-yl)cyclohexyl]piperidine-2,6-diol trifluoroacetic acid salt (820 mg), dichloromethane (50 mL), methanol (4 mL), and diisopropylethylamine (0.4 mL) was stirred for 1 hour and then 2-[1-(4-bromophenyl)piperidin-4-yl]acetaldehyde (320 mg) was added. Acetic acid (0.1 mL) was added after a further 30 minutes. The resulting mixture was stirred for 4 hours at 30° C. in an oil bath before the addition of sodium cyanoborohydride (210 mg), the resulting solution was stirred for another 14 hours at 30° C. The resulting solution was extracted with dichloromethane (3×200 mL) and the organic layers combined. The crude product was purified by flash reverse phase chromatography (C18, 0 to 100% acetonitrile: (0.05% ammonium bicarbonate in water)) to afford 450 mg (71%) of 3-[4-(1-[2-[1-(4-bromophenyl)piperidin-4-yl]ethyl]piperidin-4-yl)-2-fluorophenyl]piperidine-2,6-dione as a yellow solid. MS (ESI): m/z 555.19 [M+H]$^+$.

Step H: (3R)—N-[3-(5-[4-[4-(2-[4-[4-(2,6-dioxopiperidin-3-yl)-3-fluorophenyl]piperidin-1-yl]ethyl)piperidin-1-yl]phenyl]-1H-pyrrolo[2,3-b]pyridine-3-carbonyl)-2,4-difluorophenyl]-3-fluoropyrrolidine-1-sulfonamide

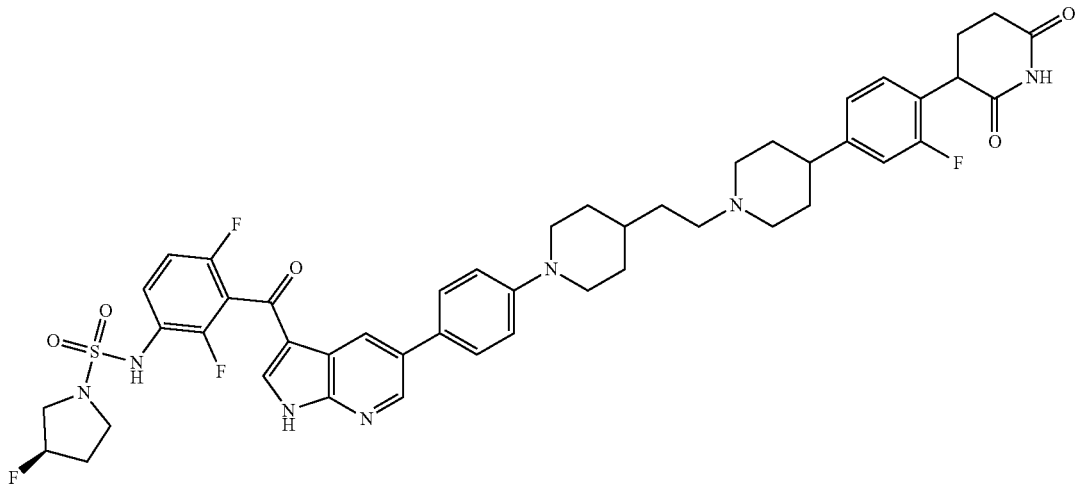 [SMILES: O=C1CCC(c2ccc(C3CCN(CCC4CCN(c5ccc(-c6cnc7[nH]cc(C(=O)c8c(F)ccc(NS(=O)(=O)N9CC[C@@H](F)C9)c8F)c7c6)cc5)CC4)CC3)cc2F)C(=O)N1]

A mixture of 3-[4-(1-[2-[1-(4-bromophenyl)piperidin-4-yl]ethyl]piperidin-4-yl)-2-fluorophenyl]piperidine-2,6-dione (300 mg, 0.539 mmol), (3R)—N-[2,4-difluoro-3-[5-(4,4,5,5-tetramethyl-1,3,2-dioxaborolan-2-yl)-1H-pyrrolo[2,3-b]pyridine-3-carbonyl]phenyl]-3-fluoropyrrolidine-1-sulfonamide (445 mg, 0.809 mmol), dichloro[1,1'-bis(di-t-butylphosphino)ferrocene]palladium(II) (70 mg, 0.107 mmol), cesium fluoride (410 mg, 2.69 mmol), 1,4-dioxane (10 mL), and water (1.4 mL) was stirred for 2 hours at 100° C. After cooling to room temperature, the resulting solution was extracted dichloromethane (3×100 mL) and the organic layers combined. Purification by silica gel column chromatography (1:17 methanol:dichloromethane) and then by flash reverse phase chromatography (C18, 0 to 100% acetonitrile:(0.05% ammonium bicarbonate in water)) afforded 54.5 mg (11%) of (3R)—N-[3-(5-[4-[4-(2-[4-[4-(2,6-dioxopiperidin-3-yl)-3-fluorophenyl]piperidin-1-yl]ethyl)piperidin-1-yl]phenyl]-1H-pyrrolo[2,3-b]pyridine-3-carbonyl)-2,4-difluorophenyl]-3-fluoropyrrolidine-1-sulfonamide as a yellow solid. MS (ESI): m/z 899.35 [M+H]$^+$; $^1$H NMR (400 MHz, DMSO-d$_6$) δ 12.87 (b, 1H), 10.85 (s, 1H), 8.65 (s, 1H), 8.53 (s, 1H), 8.06 (s, 1H), 7.67-7.57 (m, 3H), 7.25-7.20 (m, 2H), 7.11-7.04 (m, 4H), 5.30 (d, J=13.1 Hz, 1H), 4.02-3.99 (m, 1H), 3.80-3.76 (m, 2H), 3.42-3.37 (m, 2H), 3.06-3.04 (m, 2H), 2.75-2.70 (m, 3H), 2.45 (s, 1H), 2.22-2.14 (m, 3H), 2.14-1.94 (m, 2H), 1.82-1.79 (m, 4H), 1.73-1.59 (m, 2H), 1.51-1.41 (m, 3H), 1.39-1.21 (m, 6H), 1.16-1.11 (m, 1H), 0.84-0.82 (m, 1H).

Exemplary Synthesis of Exemplary Compound 186 and 187: (3R)—N-[3-[5-(4-[4-[(3R)-3-[2-[(3S)-2,6-dioxopiperidin-3-yl]-7-methoxy-1-oxo-3H-isoindol-5-yl]-3-hydroxypropyl]piperazin-1-yl]phenyl)-1H-pyrrolo[2,3-b]pyridine-3-carbonyl]-2,4-difluorophenyl]-3-fluoropyrrolidine-1-sulfonamide and (3R)—N-[3-[5-(4-[4-[(3R)-3-[2-[(3R)-2,6-dioxopiperidin-3-yl]-7-methoxy-1-oxo-3H-isoindol-5-yl]-3-hydroxypropyl]piperazin-1-yl]phenyl)-1H-pyrrolo[2,3-b]pyridine-3-carbonyl]-2,4-difluorophenyl]-3-fluoropyrrolidine-1-sulfonamide

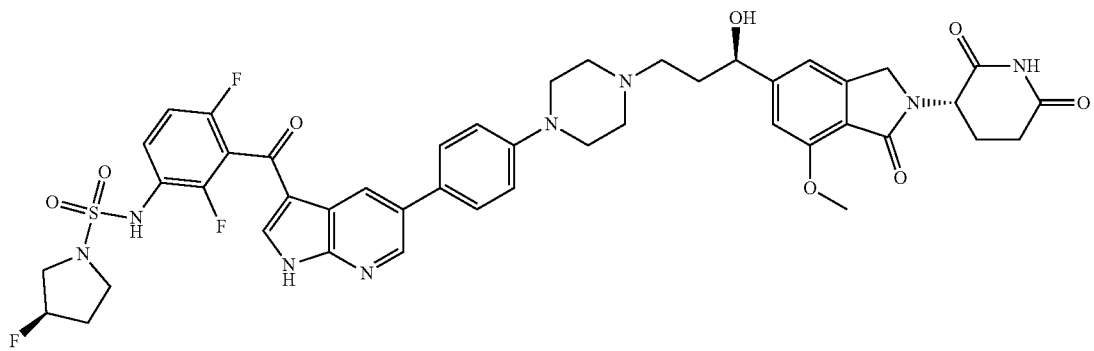

-continued

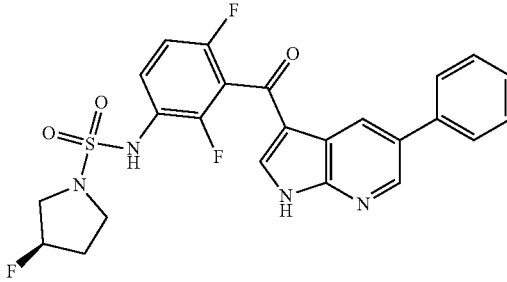

Step A: 3-(5-iodo-1-oxo-3H-isoindol-2-yl)piperidine-2,6-dione

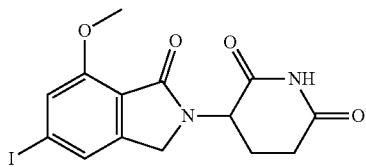 [SMILES: COc1cc(I)cc2c1C(=O)N(C1CCC(=O)NC1=O)C2]

A solution of 3-(5-bromo-1-oxo-3H-isoindol-2-yl)piperidine-2,6-dione (500 mg, 1.42 mmol), sodium iodide (466 mg, 3.1 mmol), copper (I) iodide (58.9 mg, 0.31 mmol), and (1R,2R)—N1,N2-dimethylcyclohexane-1,2-diamine (88 mg, 0.62 mmol) in 1,4-dioxane (15 mL) was stirred for 2.5 hours at 125° C. The reaction mixture was cooled to 25° C. and then concentrated. The resulting mixture was diluted with water (100 mL). The solid was collected by filtration and washed with 1:1 petroleum ether:ethyl acetate (2×30 mL) to afford 421.6 mg (62%) of 3-(5-iodo-1-oxo-3H-isoindol-2-yl)piperidine-2,6-dione as an off-white solid. MS (ESI): m/z 401.00 [M+H]$^+$.

Step B: 3-[7-methoxy-1-oxo-5-(prop-2-enoyl)-3H-isoindol-2-yl]piperidine-2,6-dione

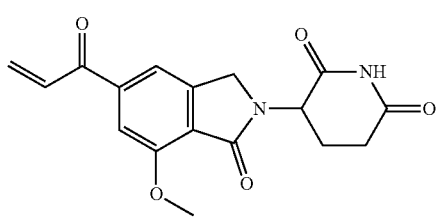 [SMILES: C=CC(=O)c1cc2c(c(OC)c1)C(=O)N(C1CCC(=O)NC1=O)C2]

A mixture of 3-(5-iodo-7-methoxy-1-oxo-3H-isoindol-2-yl)piperidine-2,6-dione (2.20 g, 5.49 mmol), ethenyltrifluoro-λ4-borane potassium (960 mg, 7.16 mmol), sodium carbonate (759 mg, 7.09 mmol), palladium (II) acetate (123 mg, 0.548 mmol), triphenylphosphine (432 mg, 1.64 mmol), and THF (120 mL) was stirred for overnight at 80° C. under a carbon monoxide atmosphere (5 atm). The solids were filtered out and the resulting mixture was concentrated to afford 2.7 g (41%) of 3-[7-methoxy-1-oxo-5-(prop-2-enoyl)-3H-isoindol-2-yl]piperidine-2,6-dione as a brown solid. MS (ESI): m/z 328.95 [M+H]$^+$.

Step C: 3-(5-[3-[4-(4-bromophenyl)piperazin-1-yl]propanoyl]-7-methoxy-1-oxo-3H-isoindol-2-yl)piperidine-2,6-dione

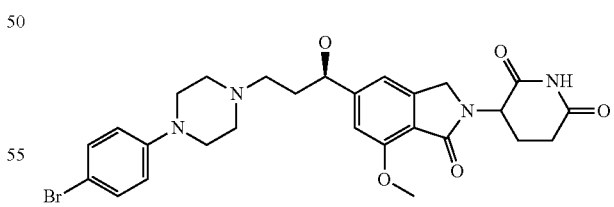

A mixture of 3-[7-methoxy-1-oxo-5-(prop-2-enoyl)-3H-isoindol-2-yl]piperidine-2,6-dione (1.22 g, 2.60 mmol), dichloromethane (80 mL), 1-(4-bromophenyl)piperazine (627 mg, 2.60 mmol), triethylamine (789 mg, 7.80 mmol), N,N-dimethylaminopyridine (64 mg, 0.52 mmol) was stirred for 3 hours at room temperature and then resulting mixture was concentrated. Purification by silica gel column chromatography (1:10 methanol:dichloromethane) afforded 586 mg (40%) of 3-(5-[3-[4-(4-bromophenyl)piperazin-1-yl]propanoyl]-7-methoxy-1-oxo-3H-isoindol-2-yl)piperidine-2,6-dione as a brown solid. MS (ESI): m/z 569.15/571.15 [M+H]$^+$.

Step D: 3-[5-[(1R)-3-[4-(4-bromophenyl)piperazin-1-yl]-1-hydroxypropyl]-7-methoxy-1-oxo-3H-isoindol-2-yl]piperidine-2,6-dione To a mixture of 3-(5-[3-[4-(4-bromophenyl)piperazin-1-yl]propanoyl]-7-methoxy-1-oxo-3H-isoindol-2-yl)piperidine-2,6-dione (330 mg, 0.579 mmol), and THF (10 mL) was added (+)-DIP-Cl (3.4 mL, 1.7 M in THF, 5.79 mmol) at −60° C. The reaction mixture stirred 30 minutes at −60° C., was allowed to warm to 20° C., and then stirred overnight at 50° C. The reaction was then quenched by the addition methanol (10 mL) and the resulting mixture was concentrated. Purification by silica gel column chromatography (1:10 methanol:dichloromethane) followed by flash reverse phase column chromatography (C18, 10 to 70% acetonitrile:water) afforded in 131 mg (40%) of 3-[5-[(1R)-3-[4-(4-bromophenyl)piperazin-1-yl]-1-hydroxypropyl]-7-methoxy-1-oxo-3H-isoindol-2-yl]piperidine-2,6-dione as a white solid. MS (ESI): m/z 571.20, 573.20 [M+H]⁺.

Step E: (3R)—N-[3-[5-(4-[4-[(3R)-3-[2-(2,6-dioxopiperidin-3-yl)-7-methoxy-1-oxo-3H-isoindol-5-yl]-3-hydroxypropyl]piperazin-1-yl]phenyl)-1H-pyrrolo[2,3-b]pyridine-3-carbonyl]-2,4-difluorophenyl]-3-fluoropyrrolidine-1-sulfonamide then quenched by the addition of water (100 mL). The resulting solution was extracted with dichloromethane (3×100 mL), washed with brine (20 mL), and concentrated. Purification by silica gel column chromatography (1:10 methanol:dichloromethane) afforded 71 mg (26%) of (3R)—N-[3-[5-(4-[4-[(3R)-3-[2-(2,6-dioxopiperidin-3-yl)-7-methoxy-1-oxo-3H-isoindol-5-yl]-3-hydroxypropyl]piperazin-1-yl]phenyl)-1H-pyrrolo[2,3-b]pyridine-3-carbonyl]-2,4-difluorophenyl]-3-fluoropyrrolidine-1-sulfonamide as a solid. MS (ESI): m/z 915.35 [M+H]⁺.

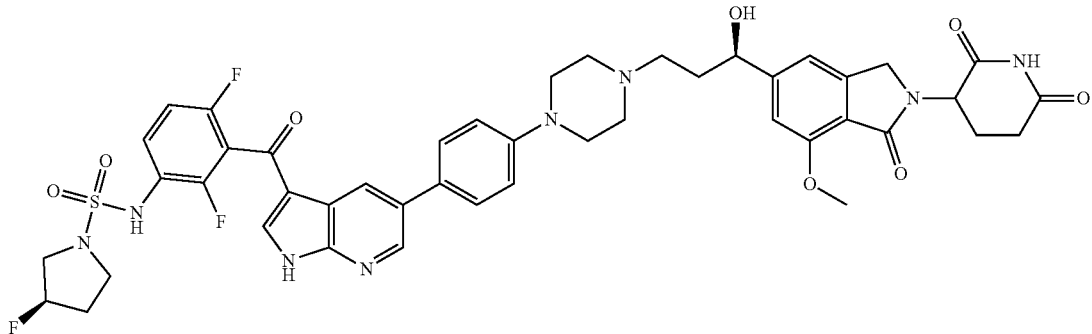 [SMILES: COc1cc([C@H](O)CCN2CCN(c3ccc(-c4cnc5[nH]cc(C(=O)c6c(F)ccc(NS(=O)(=O)N7CC[C@@H](F)C7)c6F)c5c4)cc3)CC2)cc2c1C(=O)N(C1CCC(=O)NC1=O)C2]

A mixture of 3-[5-[(1R)-3-[4-(4-bromophenyl)piperazin-1-yl]-1-hydroxypropyl]-7-methoxy-1-oxo-3H-isoindol-2-yl]piperidine-2,6-dione (170 mg, 0.297 mmol), (3R)—N-[2,4-difluoro-3-[5-(4,4,5,5-tetramethyl-1,3,2-dioxaborolan-2-yl)-1H-pyrrolo[2,3-b]pyridine-3-carbonyl]phenyl]-3-fluoropyrrolidine-1-sulfonamide (245.5 mg, 0.446 mmol), cesium fluoride (226 mg, 1.48 mmol), dichloro[1,1'-bis(di-t-butylphosphino)ferrocene]palladium(II) (38.7 mg, 0.060 mmol), 1,4-dioxane (14 mL), and water (2 mL) was stirred for 2 hours at 100° C. The reaction mixture was cooled and Step F: (3R)—N-[3-[5-(4-[4-[(3R)-3-[2-[(3S)-2,6-dioxopiperidin-3-yl]-7-methoxy-1-oxo-3H-isoindol-5-yl]-3-hydroxypropyl]piperazin-1-yl]phenyl)-1H-pyrrolo[2,3-b]pyridine-3-carbonyl]-2,4-difluorophenyl]-3-fluoropyrrolidine-1-sulfonamide (3R)—N-[3-[5-(4-[4-[(3R)-3-[2-[(3R)-2,6-dioxopiperidin-3-yl]-7-methoxy-1-oxo-3H-isoindol-5-yl]-3-hydroxypropyl]piperazin-1-yl]phenyl)-1H-pyrrolo[2,3-b]pyridine-3-carbonyl]-2,4-difluorophenyl]-3-fluoropyrrolidine-1-sulfonamide

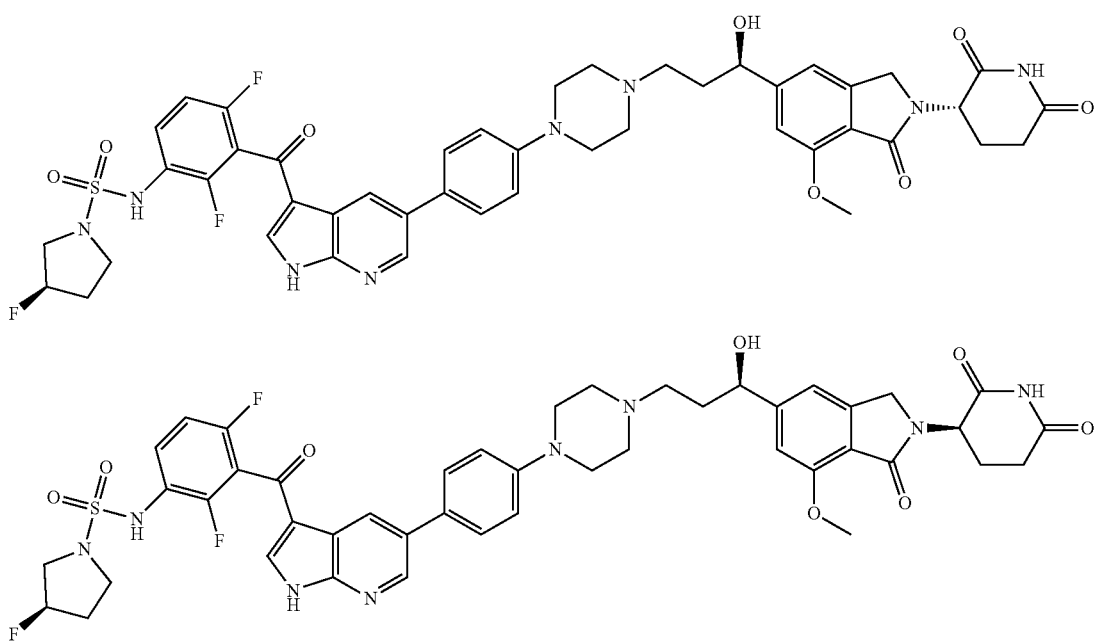

(3R)—N-[3-[5-(4-[4-[(3R)-3-[2-(2,6-dioxopiperidin-3-yl)-7-methoxy-1-oxo-3H-isoindol-5-yl]-3-hydroxypropyl]piperazin-1-yl]phenyl)-1H-pyrrolo[2,3-b]pyridine-3-carbonyl]-2,4-difluorophenyl]-3-fluoropyrrolidine-1-sulfonamide (71 mg) was separated by chiral preparative HPLC (CHIRALPAK IA, 70% dichloromethane) to afford 17.9 mg (25%) of (3R)—N-[3-[5-(4-[4-[(3R)-3-[2-[(3S)-2,6-dioxopiperidin-3-yl]-7-methoxy-1-oxo-3H-isoindol-5-yl]-3-hydroxypropyl]piperazin-1-yl]phenyl)-1H-pyrrolo[2,3-b]pyridine-3-carbonyl]-2,4-difluorophenyl]-3-fluoropyrrolidine-1-sulfonamide (absolute stereochemistry tentatively assigned) as a light yellow solid. MS (ESI): m/z 915.30 [M+H]+; 1H NMR (400 MHz, DMSO-d6+CDCl3) δ 12.54 (s, 1H), 10.86 (s, 1H), 9.61 (s, 1H), 8.59 (s, 1H), 8.53 (s, 1H), 7.66 (s, 1H), 7.59-7.53 (m, 3H), 7.03-6.96 (m, 5H), 5.20 (d, J=13.2 Hz, 1H), 5.12-5.01 (m, 1H), 4.28 (s, 2H), 3.90 (s, 3H), 3.51-3.45 (m, 4H), 3.67-3.33 (m, 2H), 2.79-2.67 (m, 4H), 2.30-2.19 (m, 1H), 2.17-2.03 (m, 3H), 2.02-1.95 (m, 2H), 1.35-1.34 (m, 1H), 1.33-1.31 (m, 3H), 1.01-0.99 (m, 1H), 0.81-0.79 (m, 3H).

Also obtained was 15.6 mg (22%) of (3R)—N-[3-[5-(4-[4-[(3R)-3-[2-[(3R)-2,6-dioxopiperidin-3-yl]-7-methoxy-1-oxo-3H-isoindol-5-yl]-3-hydroxypropyl]piperazin-1-yl]phenyl)-1H-pyrrolo[2,3-b]pyridine-3-carbonyl]-2,4-difluorophenyl]-3-fluoropyrrolidine-1-sulfonamide (absolute stereochemistry tentatively assigned) as a light yellow solid. MS (ESI): m/z 915.30 [M+H]+; 1H NMR (400 MHz, DMSO-d6+CDCl3, ppm) δ 12.54 (s, 1H), 10.90 (s, 1H), 9.61 (s, 1H), 8.57-8.534 (m, 2H), 7.66 (s, 1H), 7.59-7.53 (m, 3H), 7.03-6.96 (m, 5H), 5.20 (d, J=13.2 Hz, 1H), 5.12-5.01 (m, 1H), 4.28 (s, 2H), 3.90 (s, 3H), 3.51-3.45 (m, 4H), 3.67-3.33 (m, 2H), 2.81-2.67 (m, 6H), 2.30-1.95 (m, 6H) 1.35-1.34 (m, 1H), 1.53-1.41 (m, 1H), 1.33-1.31 (m, 1H), 1.01-0.99 (m, 1H), 0.81-0.79 (m, 2H).

Exemplary Synthesis of Exemplary Compound 199: (3R)—N-[3-(5-[4-[4-(2-[4-[4-(2,4-dioxo-1,3-diazinan-1-yl)-3-fluorophenyl]piperidin-1-yl]ethyl)piperidin-1-yl]phenyl]-1H-pyrrolo[2,3-b]pyridine-3-carbonyl)-2,4-difluorophenyl]-3-fluoropyrrolidine-1-sulfonamide

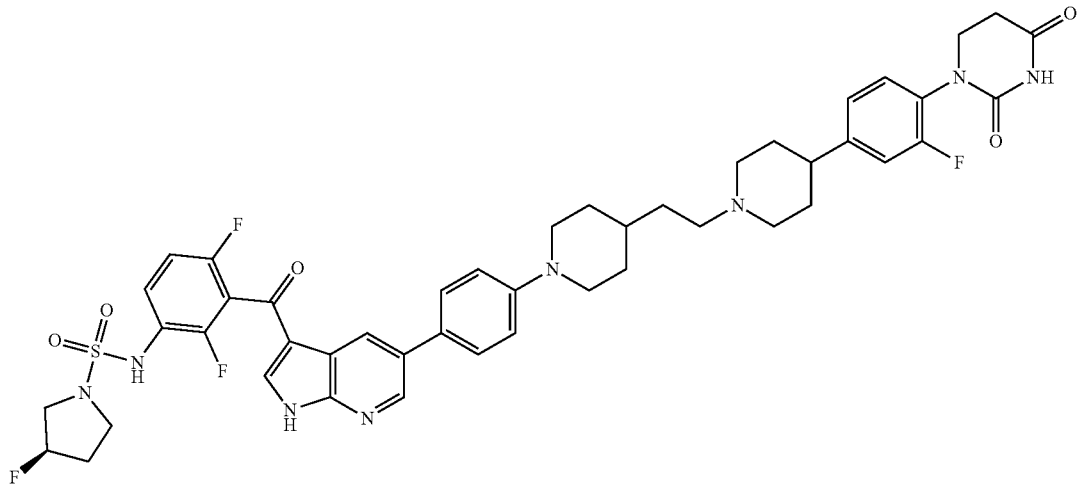 [SMILES: O=C1CCN(c2ccc(C3CCN(CCC4CCN(c5ccc(-c6cnc7[nH]cc(C(=O)c8c(F)ccc(NS(=O)(=O)N9CC[C@@H](F)C9)c8F)c7c6)cc5)CC4)CC3)cc2F)C(=O)N1]

Step A: 3-[(4-bromo-2-fluorophenyl)amino]propanoic acid

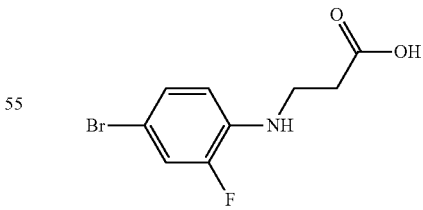

A mixture of 4-bromo-2-fluoroaniline (1 g, 5.263 mmol), acrylic acid (0.4 mL), acetic acid (2 mL) and water (8 mL) was stirred for 6 hours at 100° C. The resulting mixture was concentrated. The reaction was then quenched by the addition of water (100 mL). The mixture was extracted with dichloromethane (3×50 mL) and the aqueous layers combined. The pH of the solution was adjusted to 1 with 12 M aqueous hydrochloric acid. The resulting solution was extracted with dichloromethane (3×50 mL) and the organic layers combined and concentrated to afford 0.536 g (39%) of 3-[(4-bromo-2-fluorophenyl)amino]propanoic acid as a solid. MS (ESI): m/z 262.05 [M+H]+.

Step B:
1-(4-bromo-2-fluorophenyl)-1,3-diazinane-2,4-dione

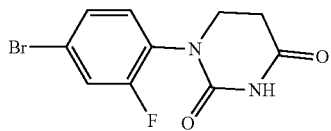 [SMILES: O=C1CCN(c2ccc(Br)cc2F)C(=O)N1]

A mixture of 3-[(4-bromo-2-fluorophenyl) amino]propanoic acid (3.60 g, 13.7 mmol), urea (2.07 g, 34.4 mmol), and acetic acid (36 mL) was stirred overnight at 100° C. The resulting solution was extracted with ethyl acetate (3×50 mL) and the organic layers combined. Purification by silica gel column chromatography (100% ethyl acetate) afforded 1.74 g (44%) of 1-(4-bromo-2-fluorophenyl)-1,3-diazinane-2,4-dione as a white solid. MS (ESI): m/z 286.95 [M+H]+.

Step C: tert-butyl 4-[4-(2,4-dioxo-1,3-diazinan-1-yl)-3-fluorophenyl]-3,6-dihydro-2H-pyridine-1-carboxylate

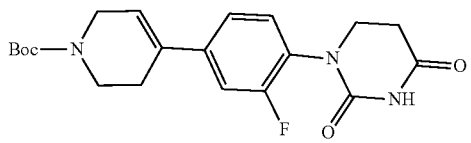 [SMILES: CC(C)(C)OC(=O)N1CC=C(c2ccc(N3CCC(=O)NC3=O)c(F)c2)CC1]

A mixture of 1-(4-bromo-2-fluorophenyl)-1,3-diazinane-2,4-dione (514 mg, 1.79 mmol), tert-butyl 4-(4,4,5,5-tetramethyl-1,3,2-dioxaborolan-2-yl)-3,6-dihydro-2H-pyridine-1-carboxylate (830 mg, 2.68 mmol), dichloro[1,1'-bis(di-t-butylphosphino)ferrocene]palladium(II) (233 mg, 0.358 mmol), cesium fluoride (816 mg, 5.37 mmol), 1,4-dioxane (9 mL), and water (1 mL) was stirred for 1.5 hours at 95° C. The mixture was concentrated. Purification by silica gel column chromatography (5:95 methanol:dichloromethane) afforded 550 mg (79%) of tert-butyl 4-[4-(2,4-dioxo-1,3-diazinan-1-yl)-3-fluorophenyl]-3,6-dihydro-2H-pyridine-1-carboxylate as a yellow solid. MS (ESI): m/z 334.05 [M+H]+.

Step D: tert-butyl 4-[4-(2,4-dioxo-1,3-diazinan-1-yl)-3-fluorophenyl]piperidine-1-carboxylate

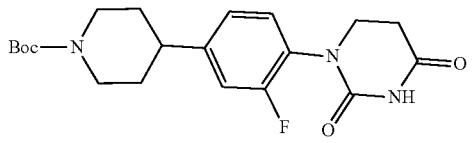 [SMILES: CC(C)(C)OC(=O)N1CCC(c2ccc(N3CCC(=O)NC3=O)c(F)c2)CC1]

A mixture of tert-butyl 4-[4-(2,4-dioxo-1,3-diazinan-1-yl)-3-fluorophenyl]-3,6-dihydro-2H-pyridine-1-carboxylate (1.08 g, 2.77 mmol), ethyl acetate (150 mL), methanol (30 mL), palladium on carbon (0.30 g, 2.8 mmol) was evacuated, flushed with hydrogen, and then hydrogenated at room temperature for 16 hours under a balloon of hydrogen. The mixture was then filtered through a Celite pad and concentrated to afford 1 g (92%) of tert-butyl 4-[4-(2,4-dioxo-1,3-diazinan-1-yl)-3-fluorophenyl]piperidine-1-carboxylate as a yellow solid. MS (ESI): m/z 336.20 [M+H]+.

Step E: 1-[2-fluoro-4-(piperidin-4-yl)phenyl]-1,3-diazinane-2,4-dione hydrochloride

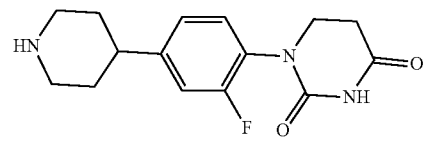 [SMILES: O=C1CCN(c2ccc(C3CCNCC3)cc2F)C(=O)N1]

A solution of tert-butyl 4-[4-(2,4-dioxo-1,3-diazinan-1-yl)-3-fluorophenyl]piperidine-1-carboxylate (1.00 g, 2.555 mmol) and trifluoroacetic acid (5 mL) in dichloromethane (15 mL) was stirred for 2 hours at room temperature. The resulting mixture was concentrated to afford 0.836 g (99%) of 1-[2-fluoro-4-(piperidin-4-yl)phenyl]-1,3-diazinane-2,4-dione hydrochloride as yellow oil.

Step F: 1-[4-(1-[2-[1-(4-bromophenyl)piperidin-4-yl]ethyl]piperidin-4-yl)-2-fluorophenyl]-1,3-diazinane-2,4-dione

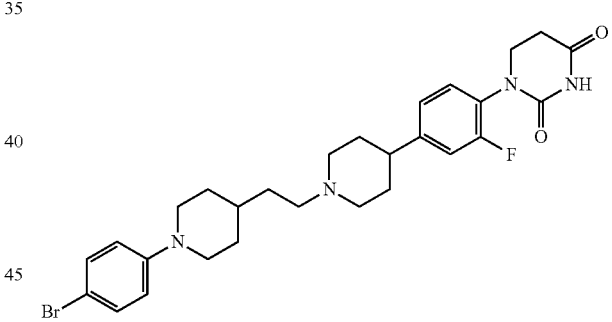

To a solution of 1-[2-fluoro-4-(piperidin-4-yl)phenyl]-1,3-diazinane-2,4-dione hydrochloride (609 mg, 0.128 mmol), 2-[1-(4-bromophenyl)piperidin-4-yl]acetaldehyde (552 mg, 0.106 mmol), diisopropylethylamine (4 mL), and methanol (6 mL) in dichloromethane (200 mL) was added acetic acid (3 mL) to bring the pH to 6. Then sodium cyanoborohydride (271 mg) was added in batches. The resulting solution was stirred overnight at 35° C. The mixture was washed with water (3×50 mL) and then concentrated. Purification by flash reverse phase chromatography (0 to 30% acetonitrile:(ammonium bicarbonate in water)) afforded 300 mg (27%) of 1-[4-(1-[2-[1-(4-bromophenyl)piperidin-4-yl]ethyl]piperidin-4-yl)-2-fluorophenyl]-1,3-diazinane-2,4-dione as a yellow solid. MS (ESI): m/z 557.15, 559.15 [M+H]+.

Step G: (3R)—N-[3-(5-[4-[4-(2-[4-[4-(2,4-dioxo-1,3-diazinan-1-yl)-3-fluorophenyl]piperidin-1-yl]ethyl)piperidin-1-yl]phenyl]-1H-pyrrolo[2,3-b]pyridine-3-carbonyl)-2,4-difluorophenyl]-3-fluoropyrrolidine-1-sulfonamide

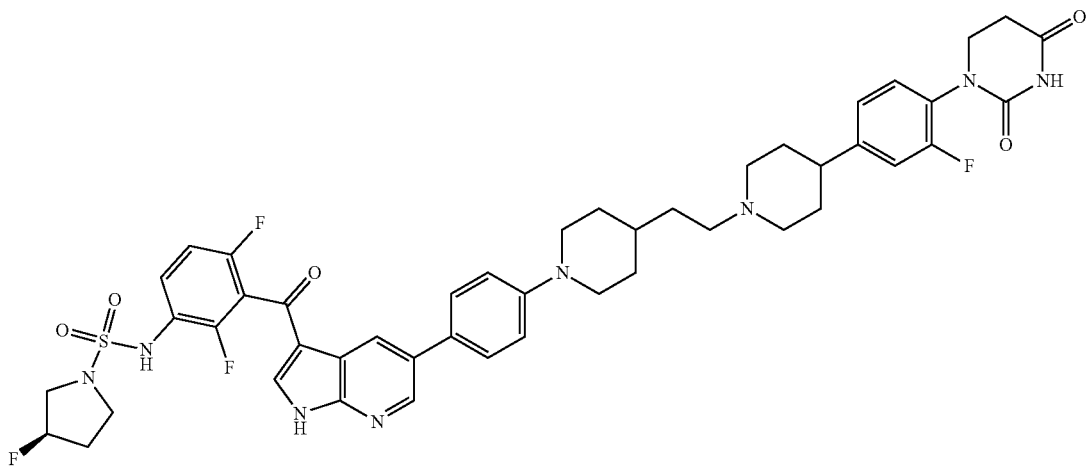 [SMILES: O=C1CCN(c2ccc(C3CCN(CCC4CCN(c5ccc(-c6cnc7[nH]cc(C(=O)c8c(F)ccc(NS(=O)(=O)N9CC[C@@H](F)C9)c8F)c7c6)cc5)CC4)CC3)cc2F)C(=O)N1]

A mixture of 1-[4-(1-[2-[1-(4-bromophenyl)piperidin-4-yl]ethyl]piperidin-4-yl)-2-fluorophenyl]-1,3-diazinane-2,4-dione (200 mg, 0.359 mmol), (3R)—N-[2,4-difluoro-3-[5-(4,4,5,5-tetramethyl-1,3,2-dioxaborolan-2-yl)-1H-pyrrolo[2,3-b]pyridine-3-carbonyl]phenyl]-3-fluoropyrrolidine-1-sulfonamide (296 mg, 0.538 mmol), dichloro[1,1′-bis(di-t-butylphosphino)ferrocene]palladium(II) (46.7 mg, 0.072 mmol), cesium fluoride (163 mg, 1.07 mmol), 1,4-dioxane (15 mL), and water (2 mL) was stirred for 1.5 hours at 95° C. The resulting mixture was concentrated. Purification by flash reverse phase chromatography (C18, 0 to 40% acetonitrile:(10 mM ammonium carbonate in water)) afforded 62.6 mg (19%) of (3R)—N-[3-(5-[4-[4-(2-[4-[4-(2,4-dioxo-1,3-diazinan-1-yl)-3-fluorophenyl]piperidin-1-yl]ethyl)piperidin-1-yl]phenyl]-1H-pyrrolo[2,3-b]pyridine-3-carbonyl)-2, 4-difluorophenyl]-3-fluoropyrrolidine-1-sulfonamide as a yellow solid. MS (ESI): m/z 901.55 [M+H]$^+$; $^1$H NMR (400 MHz, DMSO-d$_6$): δ 12.91 (b, 1H), 10.47 (s, 1H), 8.66 (d, J=2.2 Hz, 1H), 8.54 (s, 1H), 8.08 (s, 1H), 7.72-7.53 (m, 3H), 7.42-7.00 (m, 7H), 5.31 (d, J=13.2 Hz, 1H), 3.80-3.77 (m, 2H), 3.71-3.70 (m, 2H), 3.49-3.78 (m, 1H), 3.29-3.26 (m, 1H), 3.11 (d, J=11.0 Hz, 2H), 2.79-2.65 (m, 4H), 2.58-2.55 (m, 1H), 2.28-2.05 (m, 4H), 1.99-1.98 (m, 1H), 1.88-1.76 (m, 4H), 1.76-1.62 (m, 3H), 1.50-1.49 (m, 3H), 1.38-1.10 (m, 4H).

Exemplary Synthesis of Exemplary Compound 201: (3R)—N-(3-{5-[2-(1-{4-[(1-{2-[(3S)-2,6-dioxopiperidin-3-yl]-1-oxo-2,3-dihydro-1H-isoindol-5-yl}piperidin-4-yl)methyl]piperazin-1-yl}cyclopropyl)pyrimidin-5-yl]-1H-pyrrolo[2,3-b]pyridine-3-carbonyl}-2,4-difluorophenyl)-3-fluoropyrrolidine-1-sulfonamide (Compound 201)

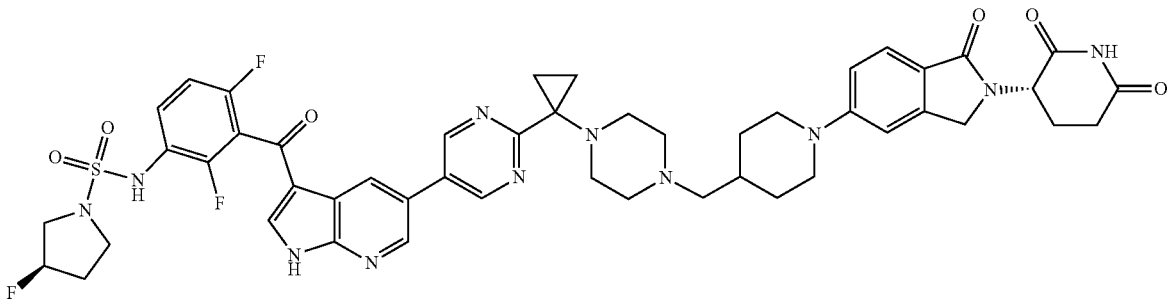 [SMILES: O=C1CC[C@H](N2Cc3cc(N4CCC(CN5CCN(C6(c7ncc(-c8cnc9[nH]cc(C(=O)c%10c(F)ccc(NS(=O)(=O)N%11CC[C@@H](F)C%11)c%10F)c9c8)cn7)CC6)CC5)CC4)ccc3C2=O)C(=O)N1]

Step A: methyl 2-bromo-4-[4-(dimethoxymethyl)-1-piperidyl]benzoate

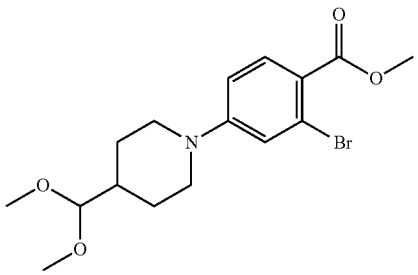

To a solution of 4-(dimethoxymethyl)piperidine (44.41 g, 278.9 mmol) and methyl 2-bromo-4-fluoro-benzoate (50.0 g, 214.6 mmol) in dimethyl sulfoxide (500 mL) was added N,N-diisopropylethylamine (55.46 g, 429.1 mmol). The reaction was stirred at 120° C. for 2 h. The mixture was diluted with water (1500 mL) and extracted with ethyl acetate (3×500 mL). The combined organic fractions were washed with saturated aqueous sodium chloride (3×1000 mL), dried over sodium sulfate, filtered, and concentrated. The crude product was triturated with 1:20 ethyl acetate:petroleum ether (200 mL) to afford methyl 2-bromo-4-[4-(dimethoxymethyl)-1-piperidyl]benzoate (64 g, 79%) as a light yellow solid.

Step B: methyl 4-[4-(dimethoxymethyl)-1-piperidyl]-2-formyl-benzoate

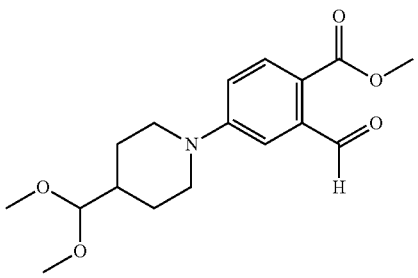

To a solution of methyl 2-bromo-4-[4-(dimethoxymethyl)-1-piperidyl]benzoate (52 g, 140 mmol) in N,N-dimethylformamide (500 mL) was added 2-isocyano-2-methylpropane (23.23 g, 279.4 mmol), palladium acetate (3.14 g, 14.0 mmol), tricyclohexylphosphine (3.92 g, 14.0 mmol), sodium carbonate (14.81 g, 139.7 mmol) and triethylsilane (48.73 g, 419.1 mmol). The reaction was stirred at 65° C. for 12 h. The mixture was diluted with water (500 mL) and extracted with ethyl acetate (3×300 mL). The combined organic fractions were washed with saturated aqueous sodium chloride (3×500 mL), dried over sodium sulfate, filtered, and concentrated. Purification of the residue by silica gel column chromatography (0% to 15% ethyl acetate:petroleum ether) followed by trituration with 1:10 ethyl acetate:petroleum ether (300 mL) afforded methyl 4-[4-(dimethoxymethyl)-1-piperidyl]-2-formyl-benzoate (22 g, 49%) as a light yellow solid. $^1$H NMR (400 MHz, CDCl$_3$) δ 10.74 (s, 1H), 7.90 (d, J=8.8 Hz, 1H), 7.33 (d, J=2.8 Hz, 1H), 7.00 (dd, J=2.8, 8.8 Hz, 1H), 4.06 (d, J=6.4 Hz, 1H), 3.96 (d, J=12.8 Hz, 2H), 3.91 (s, 3H), 3.38 (s, 6H), 2.93-2.82 (m, 2H), 1.86 (d, J=10.0 Hz, 3H), 1.46-1.35 (m, 2H).

Step C: 3-[5-[4-(dimethoxymethyl)-1-piperidyl]-1-oxo-isoindolin-2-yl]piperidine-2,6-dione

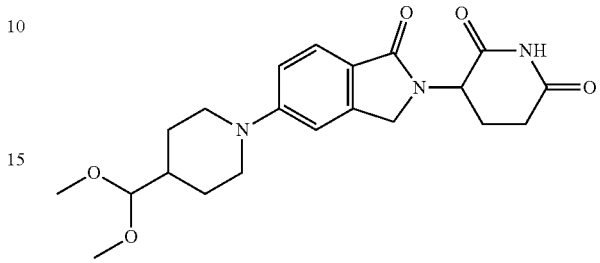

To a solution of 3-aminopiperidine-2,6-dione hydrochloride (12.11 g, 73.59 mmol) in methanol (400 mL) was added sodium acetate (10.98 g, 133.8 mmol). The mixture was stirred at 15° C. for 10 min. Then acetic acid (40.18 g, 669.0 mmol) and methyl 4-[4-(dimethoxymethyl)-1-piperidyl]-2-formyl-benzoate (21.5 g, 66.9 mmol) was added. The mixture was stirred at 15° C. for 20 min. Then sodium cyanoborohydride (8.41 g, 134 mmol) was added to the mixture. The reaction was stirred at 35° C. for 11.5 h. The mixture was poured into ice water (1000 mL) and adjusted pH 8 by addition of saturated aqueous sodium bicarbonate. The mixture was stirred at 15° C. for 10 min. The mixture was filtered and the filter cake was washed with water (200 mL) and acetonitrile (2×200 mL). The filter cake was triturated with ethyl acetate (100 mL) to afford 3-[5-[4-(dimethoxymethyl)-1-piperidyl]-1-oxo-isoindolin-2-yl]piperidine-2,6-dione (20 g, 73%) as a light yellow solid. MS (ESI): m/z 402.2 [M+H]$^+$; $^1$H NMR (400 MHz, DMSO-d$_6$) δ 10.93 (s, 1H), 7.49 (d, J=8.4 Hz, 1H), 7.07-7.00 (m, 2H), 5.04 (dd, J=5.2, 13.2 Hz, 1H), 4.35-4.25 (m, 1H), 4.24-4.14 (m, 1H), 4.07 (d, J=6.8 Hz, 1H), 3.89 (d, J=12.8 Hz, 2H), 3.27 (s, 6H), 2.94-2.85 (m, 1H), 2.83-2.72 (m, 2H), 2.63-2.54 (m, 1H), 2.36 (dq, J=4.4, 13.2 Hz, 1H), 2.00-1.91 (m, 1H), 1.80 (dtd, J=3.6, 7.6, 15.2 Hz, 1H), 1.70 (d, J=12.8 Hz, 2H), 1.30 (dq, J=3.6, 12.4 Hz, 2H).

Step D: (3R)-3-[5-[4-(dimethoxymethyl)-1-piperidyl]-1-oxo-isoindolin-2-yl]piperidine-2,6-dione and (3S)-3-[5-[4-(dimethoxymethyl)-1-piperidyl]-1-oxo-isoindolin-2-yl]piperidine-2,6-dione

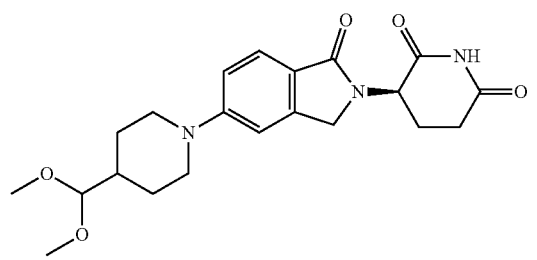 [SMILES: COC(OC)C1CCN(c2ccc3c(c2)CN(C2CCC(=O)NC2=O)C3=O)CC1]

and

-continued

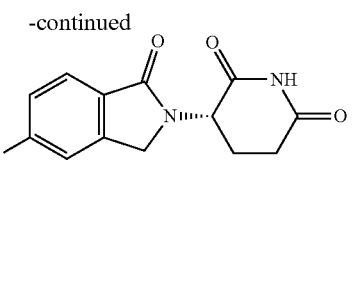

3-[5-[4-(dimethoxymethyl)-1-piperidyl]-1-oxo-isoindolin-2-yl]piperidine-2,6-dione (13 g, 32.38 mmol) was separated by preparative supercritical fluid chromatography (REGIS (s,$) WHELK-O1, 55% isopropanol:$CO_2$) to afford (3R)-3-[5-[4-(dimethoxymethyl)-1-piperidyl]-1-oxo-isoindolin-2-yl]piperidine-2,6-dione (6 g, 92%) as a light yellow solid and (3S)-3-[5-[4-(dimethoxymethyl)-1-piperidyl]-1-oxo-isoindolin-2-yl]piperidine-2,6-dione (6.2 g, 94%) as a light yellow solid.

Step E: 3-[5-[4-(dimethoxymethyl)-1-piperidyl]-1-oxo-isoindolin-2-yl]piperidine-2,6-dione

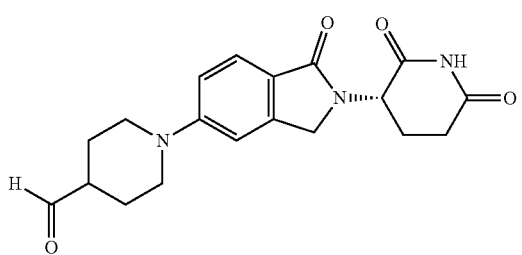 [SMILES: O=CC1CCN(c2ccc3c(c2)CN([C@H]2CCC(=O)NC2=O)C3=O)CC1]

To a solution of (3S)-3-[5-[4-(dimethoxymethyl)-1-piperidyl]-1-oxo-isoindolin-2-yl] piperidine-2,6-dione (6.1 g, 15.2 mmol) in dichloromethane (60 mL) was added trifluoroacetic acid (27.72 g, 243.1 mmol). The reaction was stirred at 30° C. for 1 h and concentrated to afford 1-[2-[(3S)-2,6-dioxo-3-piperidyl]-1-oxo-isoindolin-5-yl]piperidine-4-carbaldehyde (5.3 g, 98%), which was used into the next step without further purification.

Step F: (3R)—N-[3-[5-[2-[1-[4-[[1-[2-[(3S)-2,6-dioxo-3-piperidyl]-1-oxo-isoindolin-5-yl]-4-piperidyl]methyl]piperazin-1-yl]cyclopropyl]pyrimidin-5-yl]-1H-pyrrolo[2,3-b]pyridine-3-carbonyl]-2,4-difluoro-phenyl]-3-fluoro-pyrrolidine-1-sulfonamide To a solution of (3R)—N-[2,4-difluoro-3-[5-[2-(1-piperazin-1-ylcyclopropyl)pyrimidin-5-yl]-1H-pyrrolo[2,3-b]pyridine-3-carbonyl]phenyl]-3-fluoro-pyrrolidine-1-sulfonamide hydrochloride (7.91 g, 11.9 mmol) in dichloromethane (50 mL) and isopropanol (50 mL) was added 4-methylmorpholine (45.25 g, 447.4 mmol). The mixture was stirred at 15° C. for 10 min. Then 1-[2-[(3S)-2,6-dioxo-3-piperidyl]-1-oxo-isoindolin-5-yl]piperidine-4-carbaldehyde (5.3 g, 14.9 mmol) was added to the mixture. The mixture was stirred at 15° C. for 20 min. Then sodium cyanoborohydride (1.87 g, 29.8 mmol) was added to the mixture. The reaction was stirred at 15° C. for 0.5 h. The mixture was diluted with saturated aqueous sodium chloride (300 mL) and adjusted to pH 8 by addition of saturated aqueous sodium bicarbonate. The mixture was extracted with tetrahydrofuran (4×100 mL). The combined organic fractions were washed with saturated aqueous sodium chloride (3×200 mL), dried over sodium sulfate, filtered, and concentrated. Purification of the residue by preparative HPLC (Phenomenex Luna C18, 25% to 50% acetonitrile:(0.225% formic acid in water)) and then silica gel column chromatography (0% to 8% methanol:dichloromethane) afforded (3R)—N-[3-[5-[2-[1-[4-[[1-[2-[(3S)-2,6-dioxo-3-piperidyl]-1-oxo-isoindolin-5-yl]-4-piperidyl]methyl]piperazin-1-yl]cyclopropyl]pyrimidin-5-yl]-1H-pyrrolo[2,3-b]pyridine-3-carbonyl]-2,4-difluoro-phenyl]-3-fluoro-pyrrolidine-1-sulfonamide (4.5 g, 30%) as a light yellow solid.

Further purification by preparative supercritical fluid chromatography (REGIS(S,S)WHELK-O1, 60% (0.1% $NH_4OH$ in isopropanol):$CO_2$) afforded (3R)—N-[3-[5-[2-[1-[4-[[1-[2-[(3S)-2,6-dioxo-3-piperidyl]-1-oxo-isoindolin-5-yl]-4-piperidyl]methyl]piperazin-1-yl]cyclopropyl]pyrimidin-5-yl]-1H-pyrrolo[2,3-b]pyridine-3-carbonyl]-2,4-difluoro-phenyl]-3-fluoro-pyrrolidine-1-sulfonamide (3.9 g, 85%) as an off-white solid. MS (ESI): m/z 966.3 [M]$^+$; $^1$H NMR (400 MHz, DMSO-$d_6$) δ 13.08 (s, 1H), 10.93 (s, 1H), 9.81 (s, 1H), 9.09 (s, 2H), 8.76 (d, J=2.2 Hz, 1H), 8.69 (s, 1H), 8.17 (s, 1H), 7.63 (dt, J=6.0, 9.2 Hz, 1H), 7.50 (d, J=9.2 Hz, 1H), 7.33-7.23 (m, 1H), 7.09-6.99 (m, 2H), 5.40-5.21 (m, 1H), 5.04 (dd, J=5.2, 13.2 Hz, 1H), 4.36-4.28 (m, 1H), 4.23-4.15 (m, 1H), 3.88 (d, J=12.8 Hz, 2H), 3.51-3.47 (m, 1H), 3.44-3.36 (m, 2H), 3.31-3.26 (m, 2H), 3.25-3.14 (m, 3H), 2.97-2.86 (m, 1H), 2.86-2.78 (m, 2H), 2.63-2.51 (m, 2H), 2.43-2.29 (m, 4H), 2.24-2.09 (m, 3H), 2.06-1.91 (m, 2H), 1.86-1.72 (m, 3H), 1.44-1.34 (m, 2H), 1.27-1.14 (m, 2H), 1.14-1.06 (m, 2H).

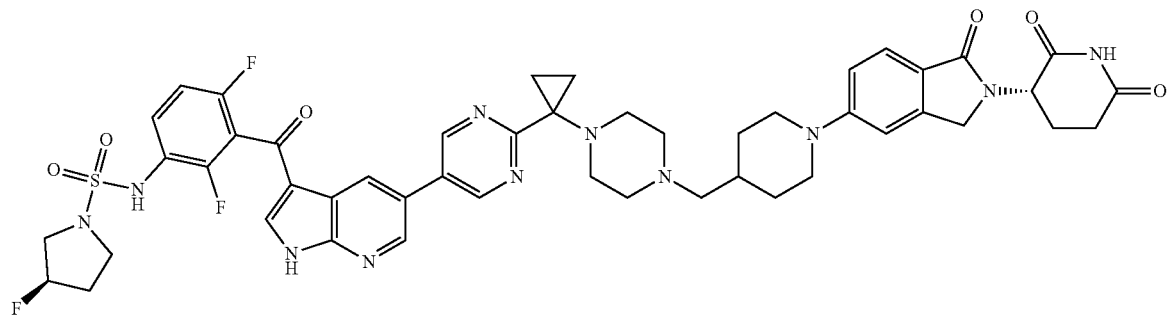 [SMILES: O=C1CC[C@H](N2Cc3cc(N4CCC(CN5CCN(C6(c7ncc(-c8cnc9[nH]cc(C(=O)c%10c(F)ccc(NS(=O)(=O)N%11CC[C@@H](F)C%11)c%10F)c9c8)cn7)CC6)CC5)CC4)ccc3C2=O)C(=O)N1]

Exemplary Synthesis of Exemplary Compound 202: (3R)—N-(3-{5-[2-(1-{4-[(1-{2-[(3S)-2,6-dioxopiperidin-3-yl]-1-oxo-2,3-dihydro-1H-isoindol-5-yl}azetidin-3-yl)methyl]piperazin-1-yl}cyclopropyl)pyrimidin-5-yl]-1H-pyrrolo[2,3-b]pyridine-3-carbonyl}-2,4-difluorophenyl)-3-fluoropyrrolidine-1-sulfonamide (Compound 202)

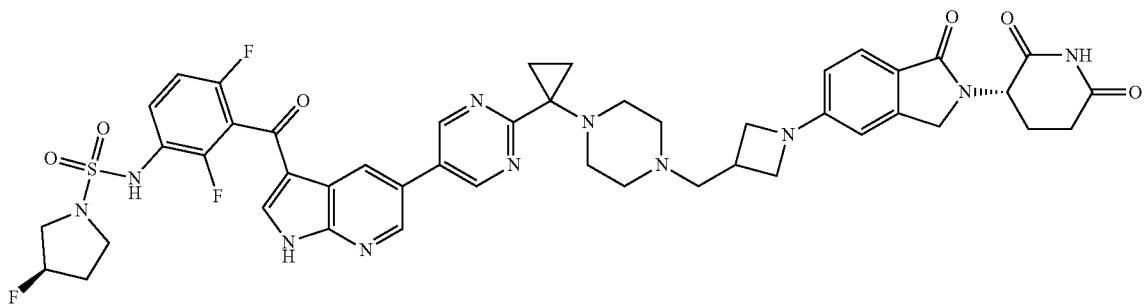 [SMILES: O=C1CC[C@H](N2Cc3cc(N4CC(CN5CCN(C6(c7ncc(-c8cnc9[nH]cc(C(=O)c%10c(F)ccc(NS(=O)(=O)N%11CC[C@@H](F)C%11)c%10F)c9c8)cn7)CC6)CC5)C4)ccc3C2=O)C(=O)N1]

Step A: benzyl N-(1-cyanocyclopropyl)carbamate

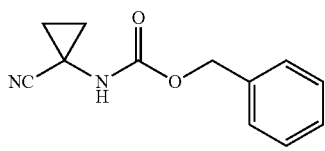 [SMILES: N#CC1(NC(=O)OCc2ccccc2)CC1]

To a solution of 1-aminocyclopropanecarbonitrile hydrochloride (205 g, 1.73 mol) and sodium bicarbonate (290 g, 3.46 mol) in tetrahydrofuran (1.5 L) and water (1 L) was added benzyl chloroformate (334 g, 1.90 mol). The reaction stirred at 25° C. for 12 h. The mixture was diluted with water (1.5 L) and extracted with ethyl acetate (3×1 L). The combined organic fractions were washed with saturated aqueous sodium chloride (3×1 L), dried over sodium sulfate, filtered, and concentrated. Trituration of the residue with 1:5 ethyl acetate:petroleum ether afforded benzyl N-(1-cyanocyclopropyl)carbamate (360 g, 96%) as a white solid. $^1$H NMR (400 MHz, DMSO-$d_6$) δ 8.50-8.27 (m, 1H), 7.54-7.15 (m, 5H), 5.26-4.89 (m, 2H), 1.51-1.42 (m, 2H), 1.22-1.12 (m, 2H).

Step B: methyl 1-(benzyloxycarbonylamino)cyclopropanecarboximidate

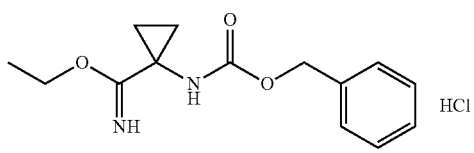 [SMILES: CCOC(=N)C1(NC(=O)OCc2ccccc2)CC1 ; Cl]

A solution of benzyl N-(1-cyanocyclopropyl)carbamate (5.0 g, 23.1 mmol) in 4 M hydrochloric acid in methanol (50 mL) was stirred at 25° C. for 12 h. The reaction mixture was concentrated to afford methyl 1-(benzyloxycarbonylamino)cyclopropanecarboximidate hydrochloride (6.4 g, 97%) as a white solid, which was used in the next step without further purification. $^1$H NMR (400 MHz, DMSO-$d_6$) δ 11.83-10.85 (m, 2H), 8.36 (s, 1H), 7.41-7.34 (m, 5H), 5.13-5.01 (m, 2H), 4.19-3.96 (m, 3H), 1.74-1.64 (m, 2H), 1.45-1.36 (m, 2H).

Step C: benzyl N-(1-carbamimidoylcyclopropyl)carbamate

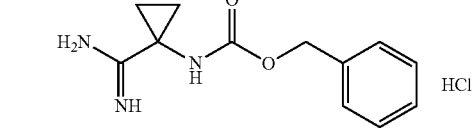

Ammonia gas (3.43 g, 201 mmol) was bubbled into a solution of methyl 1-(benzyloxycarbonylamino)cyclopropanecarboximidate (5.0 g, 20.1 mmol) in ethyl alcohol (50 mL) at −70° C. for 30 min. The reaction stirred at 25° C. for 12 h and was then concentrated to afford benzyl N-(1-carbamimidoylcyclopropyl)carbamate hydrochloride (4.8 g, 88%) as a white solid, which was used in the next step without further purification. $^1$H NMR (400 MHz, DMSO-$d_6$) δ: 9.21-8.90 (m, 1H), 8.79-8.44 (m, 2H), 8.23-8.12 (m, 1H), 7.41-7.35 (m, 5H), 5.07-5.02 (m, 2H), 1.70-1.57 (m, 2H), 1.37-1.30 (m, 2H).

Step D: benzyl N-[1-(5-chloropyrimidin-2-yl)cyclopropyl] carbamate

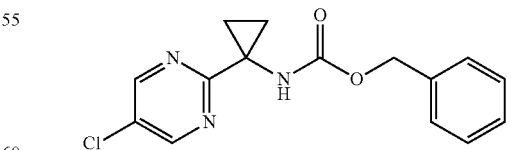

To a solution of benzyl N-(1-carbamimidoylcyclopropyl)carbamate hydrochloride (1.0 g, 3.71 mmol) and N-methylmorpholine (1.02 mL, 9.27 mmol) in N,N-dimethylacetamide (5 mL) was added [(E)-2-chloro-3-(dimethylamino)prop-2-enylidene]-dimethylammonium hexafluorophosphate (1.36 g, 4.45 mmol). The reaction was stirred at 75°

C. for 3 h. The mixture was diluted with water (50 mL) and extracted with ethyl acetate (3×50 mL). The combined organic fractions were washed with saturated aqueous sodium chloride (3×100 mL), dried over sodium sulfate, filtered, and concentrated. Purification of the residue by silica gel column chromatography (1:100 to 1:3 ethyl acetate:petroleum ether) afforded benzyl N-[1-(5-chloropyrimidin-2-yl)cyclopropyl]carbamate (710 mg, 63%) as a yellow oil. MS (ESI): m/z 304.3 [M+H]⁺.

Step E: 1-(5-chloropyrimidin-2-yl)cyclopropanamine

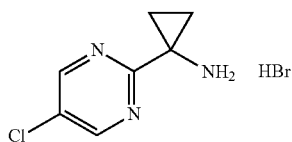 [SMILES: NC1(c2ncc(Cl)cn2)CC1 ; Br]

To a solution of benzyl N-[1-(5-chloropyrimidin-2-yl)cyclopropyl]carbamate (2.0 g, 6.58 mmol) in acetic acid (10 mL) was added 33% hydrogen bromide (1.08 mL, 6.58 mmol). The reaction stirred at 25° C. for 2 h and was then concentrated. The residue was triturated with tetrahydrofuran (50 mL) to afford 1-(5-chloropyrimidin-2-yl)cyclopropanamine hydrobromide (1.45 g, 87%) as a yellow solid. MS (ESI): m/z 260.4 [M+H]⁺; ¹H NMR (400 MHz, DMSO-d₆) δ 10.12-9.58 (m, 1H), 9.04 (s, 1H), 8.99 (s, 1H), 7.63-7.53 (m, 1H), 7.49-7.38 (m, 1H), 4.38 (s, 1H), 1.84-1.76 (m, 1H), 1.57 (d, J=2.4 Hz, 2H), 1.55-1.52 (m, 1H).

Step F: benzyl N-[1-(5-chloropyrimidin-2-yl)cyclopropyl] carbamate

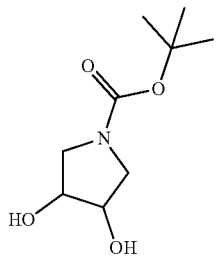

To a solution of tert-butyl 2,5-dihydropyrrole-1-carboxylate (75.0 g, 443 mmol), potassium carbonate (153 g, 1.11 mol), methanesulfonamide (42 g, 443.21 mmol) and osmium tetroxide dihydrate (16.0 g, 44.3 mmol) in tert-butanol (900 mL) and water (750 mL) was added potassium hexacyanoferrate (364 g, 1.11 mol). The reaction stirred at 25° C. for 12 h. The mixture was diluted with water (1.5 L) and extracted with ethyl acetate (3×1 L). The combined organic fractions were washed with saturated aqueous sodium chloride (3×1 L), dried over sodium sulfate, filtered, and concentrated. Purification of the residue by silica gel column chromatography (1:100 to 1:10 methanol:dichloromethane) afforded tert-butyl 3,4-dihydroxypyrrolidine-1-carboxylate (65 g, 72%) as a white solid.

Step G: tert-butyl N,N-bis(2-oxoethyl)carbamate

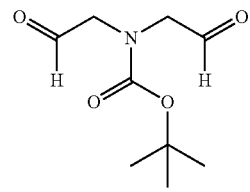

To a solution of tert-butyl 3,4-dihydroxypyrrolidine-1-carboxylate (45.0 g, 221 mmol) in tetrahydrofuran (400 mL) and water (80 mL) was added sodium periodate (71.04 g, 332.1 mmol). The reaction stirred at 25° C. for 12 h. The reaction mixture was quenched by addition of saturated aqueous sodium sulfite (1000 mL) at 20° C., and then extracted with ethyl acetate (3×1000 mL). The combined organic fractions were washed with saturated aqueous sodium chloride (3×1000 mL), dried over sodium sulfate, filtered, and concentrated to afford tert-butyl N,N-bis(2-oxoethyl)carbamate (32 g, 71%) as a colorless oil which was used in the next step without further purification.

Step H: tert-butyl 4-[1-(5-chloropyrimidin-2-yl)cyclopropyl]piperazine-1-carboxylate

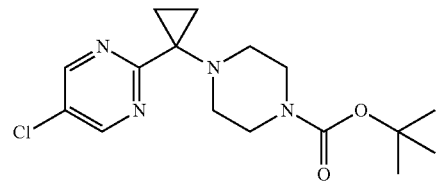 [SMILES: CC(C)(C)OC(=O)N1CCN(C2(c3ncc(Cl)cn3)CC2)CC1]

To a solution of 1-(5-chloropyrimidin-2-yl)cyclopropanamine hydrobromide (32.0 g, 127 mmol), sodium acetate (31.44 g, 383.2 mmol) and tert-butyl N,N-bis(2-oxoethyl)carbamate (28.27 g, 140.5 mmol) in methanol (300 mL) was added sodium cyanoborohydride (16.05 g, 255.5 mmol). The reaction stirred at 25° C. for 2 h. The reaction mixture was diluted with water (1 L) and extracted with ethyl acetate (3×500 mL). The combined organic fractions were washed with saturated aqueous sodium chloride (3×800 mL), dried over sodium sulfate, filtered, and concentrated. Purification of the residue by silica gel column chromatography (1:100 to 1:2 ethyl acetate:petroleum ether) afforded tert-butyl 4-[1-(5-chloropyrimidin-2-yl)cyclopropyl]piperazine-1-carboxylate (25 g, 57%) as a white solid. MS (ESI): m/z 339.3 [M+H]⁺; ¹H NMR (400 MHz, DMSO-d₆) δ 8.79 (s, 2H), 3.24 (s, 4H), 3.03 (s, 4H), 1.40 (s, 9H), 1.34-1.30 (m, 2H), 1.16-1.12 (m, 2H).

Step I: (3-amino-2,6-difluoro-phenyl)-(5-bromo-1H-pyrrolo[2,3-b]pyridin-3-yl)methanone

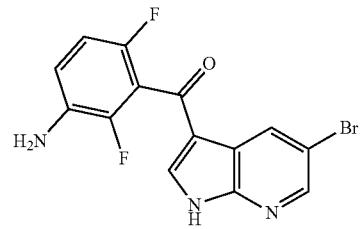 [SMILES: Nc1ccc(F)c(C(=O)c2c[nH]c3ncc(Br)cc23)c1F]

321

To a solution of (5-bromo-1H-pyrrolo[2,3-b]pyridin-3-yl)-(2,6-difluoro-3-nitro-phenyl) methanone (37 g, 96.83 mmol), 12 M aqueous hydrochloric acid (8.07 mL), and ammonium chloride (15.54 g, 290.5 mmol) in ethanol (1 L) and tetrahydrofuran (1 L) was added iron powder (27.04 g, 484.2 mmol). The reaction stirred at 40° C. for 12 h. The reaction mixture was concentrated, diluted with saturated aqueous sodium bicarbonate (500 mL) and extracted with ethyl acetate (3×500 mL). The combined organic fractions were washed with saturated aqueous sodium chloride (3×800 mL), dried over sodium sulfate, filtered, and concentrated to afford (3-amino-2,6-difluoro-phenyl)-(5-bromo-1H-pyrrolo[2,3-b]pyridin-3-yl)methanone (28 g, 82%) as a yellow solid, which was used in the next step without further purification. MS (ESI): m/z 382.1 [M+H]⁺.

Step J: (3-amino-2,6-difluoro-phenyl)-[5-bromo-1-(2,6-dichlorobenzoyl)pyrrolo[2,3-b]pyridin-3-yl]methanone

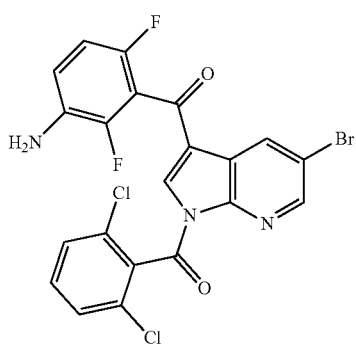 [SMILES: Nc1ccc(F)c(C(=O)c2cn(C(=O)c3c(Cl)cccc3Cl)c3ncc(Br)cc23)c1F]

To a cooled (0° C.) solution of (3-amino-2,6-difluoro-phenyl)-(5-bromo-1H-pyrrolo[2,3-b]pyridin-3-yl)methanone (26.0 g, 73.8 mmol), dimethylaminopyridine (9.0 g, 73.8 mmol), and triethylamine (30.83 mL, 221.5 mmol) in tetrahydrofuran (500 mL) was added 2,6-dichlorobenzoyl chloride (10.6 mL, 73.8 mmol). The reaction stirred at 25° C. for 1 h. The reaction mixture was diluted with water (500 mL) and extracted with ethyl acetate (3×500 mL). The combined organic fractions were washed with saturated aqueous sodium chloride (3×800 mL), dried over sodium sulfate, filtered, and concentrated. Purification of the residue by silica gel column chromatography (1:100 to 1:1 ethyl acetate:petroleum ether) afforded (3-amino-2,6-difluoro-phenyl)-[5-bromo-1-(2,6-dichlorobenzoyl)pyrrolo[2,3-b]pyridin-3-yl]methanone (30 g, 77%) as a yellow solid. MS (ESI): m/z 525.8 [M+H]⁺.

322

Step K: (3R)—N-[3-[5-bromo-1-(2,6-dichlorobenzoyl)pyrrolo[2,3-b]pyridine-3-carbonyl]-2,4-difluoro-phenyl]-3-fluoro-pyrrolidine-1-sulfonamide

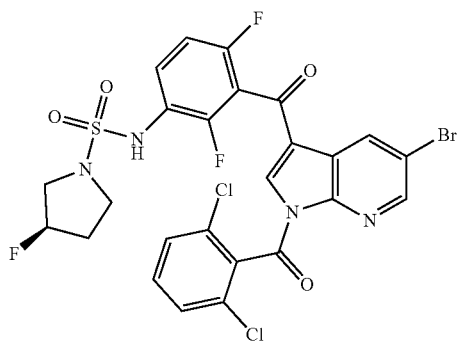 [SMILES: O=C(c1c(F)ccc(NS(=O)(=O)N2CC[C@@H](F)C2)c1F)c1cn(C(=O)c2c(Cl)cccc2Cl)c2ncc(Br)cc12]

To a cooled (−50° C.) solution of (3-amino-2,6-difluoro-phenyl)-[5-bromo-1-(2,6-dichlorobenzoyl)pyrrolo[2,3-b]pyridin-3-yl]methanone (10.0 g, 19.0 mmol) and triethylamine (15.90 mL, 114.3 mmol) in dichloromethane (10 mL) was added sulfuryl chloride (4.57 mL, 45.7 mmol) and the reaction stirred for 0.5 h. (3R)-3-fluoropyrrolidine hydrochloride (4.78 g, 38.1 mmol) and triethylamine (26.51 mL, 190.4 mmol) was added at −50° C. and the reaction stirred for 0.5 h. The reaction mixture was diluted with water (100 mL) and extracted with dichloromethane (3×100 mL). The combined organic fractions were washed with saturated aqueous sodium chloride (3×100 mL), dried over sodium sulfate, filtered, and concentrated. Purification of the residue by silica gel column chromatography (1:100 to 1:0 ethyl acetate:petroleum ether afforded (3R)—N-[3-[5-bromo-1-(2,6-dichlorobenzoyl)pyrrolo[2,3-b]pyridine-3-carbonyl]-2,4-difluoro-phenyl]-3-fluoro-pyrrolidine-1-sulfonamide (10 g, 77%) as a yellow solid. MS (ESI): m/z 677.0 [M+H]⁺.

Step L: (3R)—N-[3-(5-bromo-1H-pyrrolo[2,3-b]pyridine-3-carbonyl)-2,4-difluoro-phenyl]-3-fluoro-pyrrolidine-1-sulfonamide

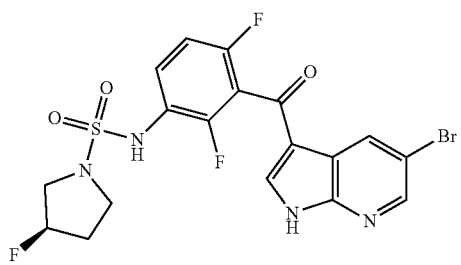 [SMILES: O=C(c1c(F)ccc(NS(=O)(=O)N2CC[C@@H](F)C2)c1F)c1c[nH]c2ncc(Br)cc12]

To a solution of (3R)—N-[3-[5-bromo-1-(2,6-dichlorobenzoyl)pyrrolo[2,3-b]pyridine-3-carbonyl]-2,4-difluoro-phenyl]-3-fluoropyrrolidine-1-sulfonamide (80.0 g, 118 mmol) in methanol (250 mL) was added 25% aqueous ammonium hydroxide (250 mL, 1.62 mol). The reaction stirred at 25° C. for 1 h. The pH was adjusted to 7 with 1 M hydrochloric acid, and the mixture was extracted with ethyl acetate (3×1500 mL). The combined organic fractions were washed with saturated aqueous sodium chloride (3×1500 mL), dried over sodium sulfate, filtered, and concentrated. The residue was triturated with ethyl acetate (50 mL) to afford (3R)—N-[3-(5-bromo-1H-pyrrolo[2,3-b]pyridine-3-carbonyl)-2,4-difluoro-phenyl]-3-fluoro-pyrrolidine-1-sulfonamide (48 g, 80%) as a yellow solid. MS (ESI): m/z 505.1 [M+H]+.

Step M: tert-butyl 5-bromo-3-[3-[tert-butoxycarbonyl-[(3R)-3-fluoropyrrolidin-1-yl]sulfonyl-amino]-2,6-difluoro-benzoyl]pyrrolo[2,3-b]pyridine-1-carboxylate

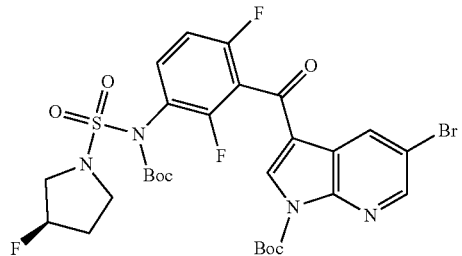 [SMILES: CC(C)(C)OC(=O)N(c1ccc(F)c(C(=O)c2cn(C(=O)OC(C)(C)C)c3ncc(Br)cc23)c1F)S(=O)(=O)N1CC[C@@H](F)C1]

To a solution of (3R)—N-[3-(5-bromo-1H-pyrrolo[2,3-b]pyridine-3-carbonyl)-2,4-difluoro-phenyl]-3-fluoro-pyrrolidine-1-sulfonamide (38.0 g, 75.5 mmol) in tetrahydrofuran (500 mL) was added 4-dimethylaminopyridine (1.84 g, 15.1 mmol), triethylamine (63.05 mL, 453.0 mmol) and di-tert-butyl dicarbonate (65.91 g, 302.0 mmol). The reaction stirred at 40° C. for 12 h. The reaction mixture was diluted with water (1 L) and extracted with ethyl acetate (3×1 L). The combined organic fractions were washed with saturated aqueous sodium chloride (3×2 L), dried over sodium sulfate, filtered, and concentrated. The crude product was triturated with petroleum ether (500 mL) to afford tert-butyl 5-bromo-3-[3-[tert-butoxycarbonyl-[(3R)-3-fluoropyrrolidin-1-yl]sulfonyl-amino]-2,6-difluoro-benzoyl]pyrrolo[2,3-b]pyridine-1-carboxylate (43 g, 80%) as a yellow solid. MS (ESI): m/z 705.1 [M+H]+.

Step N: tert-butyl 3-[3-[tert-butoxycarbonyl-[(3R)-3-fluoropyrrolidin-1-yl]sulfonyl-amino]-2,6-difluoro-benzoyl]-5-(4,4,5,5-tetramethyl-1,3,2-dioxaborolan-2-yl)pyrrolo[2,3-b]pyridine-1-carboxylate

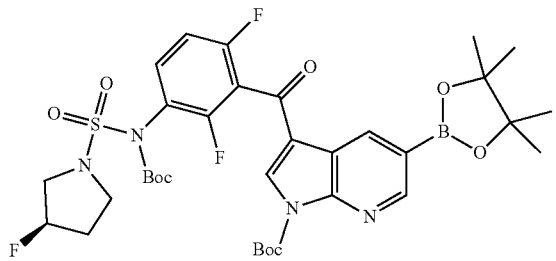 [SMILES: CC(C)(C)OC(=O)N(c1ccc(F)c(C(=O)c2cn(C(=O)OC(C)(C)C)c3ncc(B4OC(C)(C)C(C)(C)O4)cc23)c1F)S(=O)(=O)N1CC[C@@H](F)C1]

tert-butyl 5-bromo-3-[3-[tert-butoxycarbonyl-[(3R)-3-fluoropyrrolidin-1-yl]sulfonyl-amino]-2,6-difluoro-benzoyl]pyrrolo[2,3-b]pyridine-1-carboxylate (10.0 g, 14.2 mmol), bis(pinacolato)diboron (3.79 g, 14.9 mmol), potassium acetate (2.79 g, 28.4 mmol), and [1,1'-bis(diphenylphosphino)ferrocene]dichloropalladium(II) (1.04 g, 1.42 mmol) in 1,4-dioxane (150 mL) was de-gassed and then heated to 85° C. for 2 h. The reaction mixture was filtered and concentrated to afford tert-butyl 3-[3-[tert-butoxycarbonyl-[(3R)-3-fluoropyrrolidin-1-yl]sulfonyl-amino]-2,6-difluoro-benzoyl]-5-(4,4,5,5-tetramethyl-1,3,2-dioxaborolan-2-yl)pyrrolo[2,3-b]pyridine-1-carboxylate (10 g, 93%) as a brown oil which was used in the next step without further purification. MS (ESI): m/z 751.1 [M+H]+.

Step O: tert-butyl 3-[3-[tert-butoxycarbonyl-[(3R)-3-fluoropyrrolidin-1-yl]sulfonyl-amino]-2,6-difluoro-benzoyl]-5-[2-[1-(4-tertbutoxycarbonylpiperazin-1-yl)cyclopropyl]pyrimidin-5-yl]pyrrolo[2,3-b]pyridine-1-carboxylate

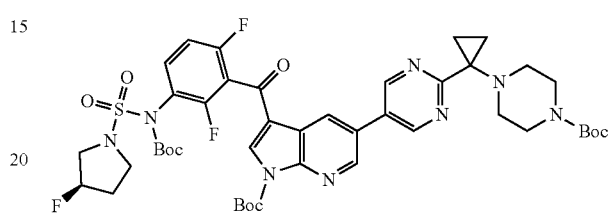

To a solution of tert-butyl 3-[3-[tert-butoxycarbonyl-[(3R)-3-fluoropyrrolidin-1-yl]sulfonyl-amino]-2,6-difluoro-benzoyl]-5-(4,4,5,5-tetramethyl-1,3,2-dioxaborolan-2-yl)pyrrolo[2,3-b]pyridine-1-carboxylate (10 g, 13.32 mmol), tert-butyl 4-[1-(5-chloropyrimidin-2-yl)cyclopropyl]piperazine-1-carboxylate (4.51 g, 13.32 mmol) and sodium carbonate (2.82 g, 26.65 mmol) in 1,4-dioxane (30 mL) and water (3 mL) was added [1,1'-bis(di-tert-butylphosphino)ferrocene]dichloropalladium(II) (868 mg, 1.33 mmol). The reaction stirred at 90° C. for 12 h and was then concentrated. Purification of the residue by column chromatography (1:100 to 1:1 ethyl acetate:petroleum ether) afforded tert-butyl 3-[3-[tert-butoxycarbonyl-[(3R)-3-fluoropyrrolidin-1-yl]sulfonyl-amino]-2,6-difluoro-benzoyl]-5-[2-[1-(4-tertbutoxycarbonylpiperazin-1-yl)cyclopropyl]pyrimidin-5-yl]pyrrolo[2,3-b]pyridine-1-carboxylate (7.0 g, 56%) as a yellow solid. MS (ESI): m/z 827.1 [M−100]+.

Step P: (3R)—N-[2,4-difluoro-3-[5-[2-(1-piperazin-1-ylcyclopropyl)pyrimidin-5-yl]-1H-pyrrolo[2,3-b]pyridine-3-carbonyl]phenyl]-3-fluoro-pyrrolidine-1-sulfonamide

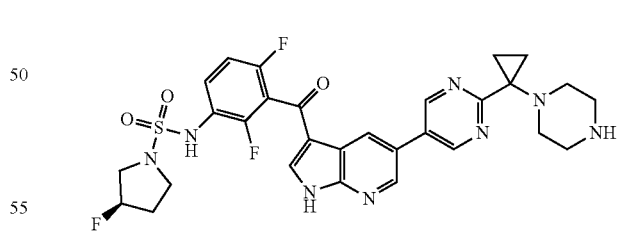

To a solution of tert-butyl 3-[3-[tert-butoxycarbonyl-[(3R)-3-fluoropyrrolidin-1-yl]sulfonyl-amino]-2,6-difluoro-benzoyl]-5-[2-[1-(4-tert-butoxycarbonylpiperazin-1-yl)cyclopropyl]pyrimidin-5-yl]pyrrolo[2,3-b]pyridine-1-carboxylate (15 g, 16.18 mmol) in dichloromethane (100 mL) was added 4.0 M hydrochloric acid in 1,4-dioxane (150 mL). The reaction stirred at 25° C. for 1 h. The reaction mixture was concentrated to afford (3R)—N-[2,4-difluoro-3-[5-[2-(1-piperazin-1-ylcyclopropyl)pyrimidin-5-yl]-1H-pyrrolo[2,3-b]pyridine-3-carbonyl]phenyl]-3-fluoro-pyrrolidine-1-sulfonamide hydrochloride (10 g, 93%) as a yellow solid which was used in the next step without further purification. MS (ESI): m/z 627.2 [M+H]+.

Step Q: azetidin-3-ylmethanol

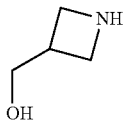

To a solution of tert-butyl 3-(hydroxymethyl)azetidine-1-carboxylate (28.0 g, 149.5 mmol) in dichloromethane (300 mL) was added 4 M hydrochloric acid in 1,4-dioxane (250 mL). The reaction was stirred at 15° C. for 1 h. The mixture was concentrated to afford azetidin-3-ylmethanol hydrochloride (54 g, 97%) as a white oil which was used in the next step without further purification.

Step R: methyl 2-cyano-4-[3-(hydroxymethyl) azetidin-1-yl]benzoate

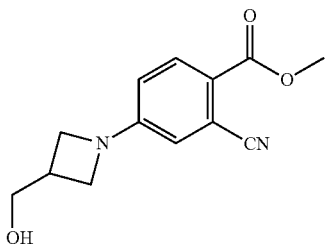 [SMILES: COC(=O)c1ccc(N2CC(CO)C2)cc1C#N]

To a solution of azetidin-3-ylmethanol hydrochloride (18.0 g, 145.7 mmol) in dimethylsulfoxide (300 mL) was added diisopropylethylamine (126.85 mL, 728.27 mmo). The mixture was stirred at 15° C. for 0.5 h. Then methyl 2-cyano-4-fluoro-benzoate (20.87 g, 116.5 mmol) was added and the reaction stirred at 120° C. for 11.5 h. The mixture was diluted with water (2000 mL) and extracted with ethyl acetate (5×1000 mL). The combined organic fractions were washed with saturated aqueous sodium chloride (3×2000 mL), dried over sodium sulfate, filtered, and concentrated. The residue was triturated with 1:2 ethyl acetate:petroleum ether (300 mL) to afford methyl 2-cyano-4-[3-(hydroxymethyl)azetidin-1-yl]benzoate (60 g, 55%) as a light yellow solid. MS (ESI): m/z 247.2 [M+H]+.

Step S: methyl 2-cyano-4-(3-formylazetidin-1-yl) benzoate

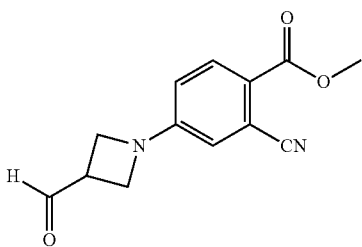 [SMILES: COC(=O)c1ccc(N2CC(C=O)C2)cc1C#N]

To a solution of oxalyl chloride (53.32 mL, 609.1 mmol) in dichloromethane (400 mL) was added dropwise dimethylsulfoxide (63.46 mL, 812.2 mmol) in dichloromethane (100 mL) at −70° C. The mixture was stirred at −70° C. for 1 h. Then methyl 2-cyano-4-[3-(hydroxymethyl)azetidin-1-yl]benzoate (50.0 g, 203.0 mmol) in dichloromethane (500 mL) was added dropwise. The reaction was stirred at −70° C. for 2 h. Then triethylamine (226 mL, 1.62 mol) was added dropwise. The reaction was warmed to 20° C. and stirred for 1 h. The mixture was diluted with water (1500 mL) and extracted with dichloromethane (2×500 mL). The combined organic fractions were washed with saturated aqueous sodium chloride (3×1000 mL), dried over sodium sulfate, filtered, and concentrated to afford methyl 2-cyano-4-(3-formylazetidin-1-yl)benzoate (45 g, 91%) as a yellow oil which was used in the next step without further purification. MS (ESI): m/z 245.5 [M+H]+.

Step T: methyl 2-cyano-4-[3-(dimethoxymethyl) azetidin-1-yl]benzoate

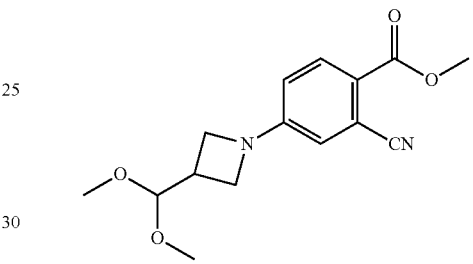

To a solution of methyl 2-cyano-4-(3-formylazetidin-1-yl)benzoate (45.0 g, 184 mmol) in methanol (200 mL) was added p-toluenesulfonic acid (3.17 g, 18.4 mmol) and trimethoxymethane (101 mL, 921 mmol). The reaction stirred at 15° C. for 12 h. The mixture was diluted with water (500 mL) and extracted with ethyl acetate (4×300 mL). The combined organic fractions were washed with saturated aqueous sodium chloride (2×1000 mL), dried over sodium sulfate, filtered, and concentrated. The residue was triturated with 1:5 ethyl acetate:petroleum ether (200 mL) and then purified by preparative HPLC (Phenomenex Luna C18, 30% to 60% acetonitrile:(0.225% formic acid in water)) to afford methyl 2-cyano-4-[3-(dimethoxymethyl)azetidin-1-yl]benzoate (40 g, 74%) as a light yellow solid. MS (ESI): m/z 291.2 [M+H]+; 1H NMR (400 MHz, DMSO-$d_6$) δ 7.87 (d, J=8.8 Hz, 1H), 6.86 (d, J=2.4 Hz, 1H), 6.65 (dd, J=2.4, 8.8 Hz, 1H), 4.64-4.60 (m, 1H), 4.04-3.98 (m, 2H), 3.82-3.77 (m, 5H), 3.30 (s, 6H), 3.08-2.98 (m, 1H).

Step U: methyl 4-[3-(dimethoxymethyl)azetidin-1-yl]-2-formyl-benzoate

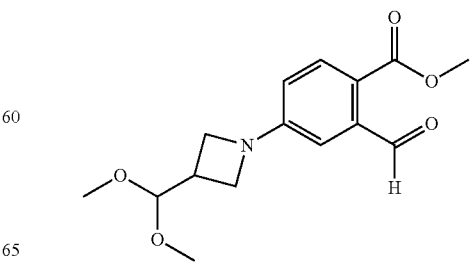

To a solution of methyl 2-cyano-4-[3-(dimethoxymethyl) azetidin-1-yl]benzoate (3.0 g, 10.3 mmol) in pyridine (60 mL) was added Raney nickel (2.0 g, 23.3 mmol), acetic acid (30 mL), and sodium dihydrogen phosphate hydrate (14.26 g, 103.3 mmol) in water (15 mL). The reaction was stirred at 50° C. for 2 h. The mixture was washed with ethyl acetate (2×100 mL). The mixture was diluted with water (200 mL) and extracted with ethyl acetate (2×100 mL). The combined organic fractions were washed with saturated aqueous sodium chloride (2×100 mL), 2 M aqueous sulfuric acid (2×100 mL), saturated aqueous sodium chloride (100 mL), saturated sodium bicarbonate (100 mL) and saturated aqueous sodium chloride (100 mL), dried over sodium sulfate, filtered, and concentrated. Purification of the residue by silica gel column chromatography (0% to 10% ethyl acetate: petroleum ether) afforded methyl 4-[3-(dimethoxymethyl) azetidin-1-yl]-2-formyl-benzoate (5.2 g, 57%) as a yellow oil. MS (ESI): m/z 294.2 [M+H]$^+$.

Step V: 3-[5-[3-(dimethoxymethyl)azetidin-1-yl]-1-oxo-isoindolin-2-yl]piperidine-2,6-dione

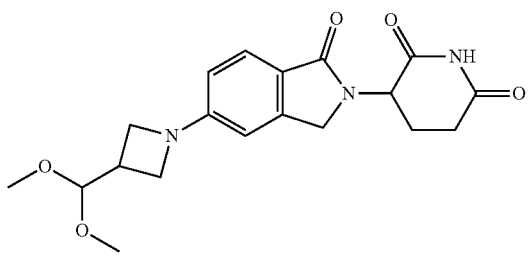 [SMILES: COC(OC)C1CN(c2ccc3c(c2)CN(C2CCC(=O)NC2=O)C3=O)C1]

To a solution of 3-aminopiperidine-2,6-dione hydrochloride (3.21 g, 19.5 mmol) in methanol (100 mL) was added sodium acetate (2.91 g, 35.5 mmol). The mixture was stirred at 15° C. for 10 min. Then acetic acid (10.14 mL, 177.3 mmol) and methyl 4-[3-(dimethoxymethyl)azetidin-1-yl]-2-formyl-benzoate (5.2 g, 17.7 mmol) were added to the mixture. The mixture was stirred at 15° C. for 20 min. Then sodium cyanoborohydride (2.23 g, 35.5 mmol) was added and the reaction stirred at 35° C. for 11 h. The mixture was poured into ice water (100 mL) and adjusted to pH 8 by addition of saturated aqueous sodium bicarbonate. The mixture was stirred at 15° C. for 10 min. The mixture was filtered and the filter cake was washed with water (20 mL) and acetonitrile (2×20 mL). Trituration of the filter cake with ethyl acetate (20 mL) afforded 3-[5-[3-(dimethoxymethyl) azetidin-1-yl]-1-oxo-isoindolin-2-yl]piperidine-2,6-dione (5.4 g, 79%) as a white solid. MS (ESI): m/z 374.1 [M+H]$^+$; $^1$H NMR (400 MHz, DMSO-d$_6$) δ 10.93 (s, 1H), 7.48 (d, J=8.4 Hz, 1H), 6.51 (s, 1H), 6.47 (dd, J=1.6, 8.4 Hz, 1H), 5.02 (dd, J=5.2, 13.2 Hz, 1H), 4.61 (d, J=6.8 Hz, 1H), 4.34-4.26 (m, 1H), 4.21-4.13 (m, 1H), 3.98-3.90 (m, 2H), 3.75-3.66 (m, 2H), 3.29 (s, 6H), 3.07-2.98 (m, 1H), 2.95-2.83 (m, 1H), 2.61-2.55 (m, 1H), 2.35 (dq, J=4.4, 13.2 Hz, 1H), 2.02-1.89 (m, 1H).

Step W: 1-[2-[(3S)-2,6-dioxo-3-piperidyl]-1-oxo-isoindolin-5-yl]azetidine-3-carbaldehyde and 1-[2-[(3R)-2,6-dioxo-3-piperidyl]-1-oxo-isoindolin-5-yl] azetidine-3-carbaldehyde

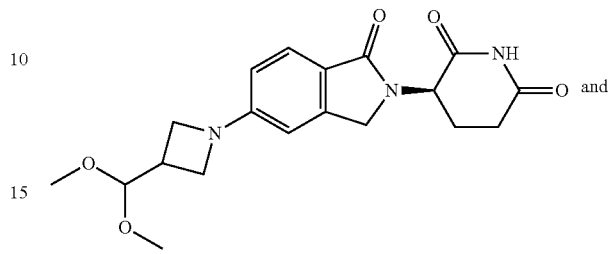

and

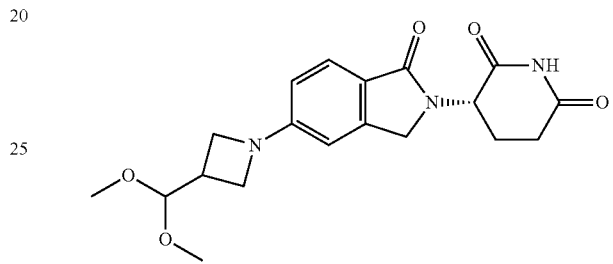

3-[5-[3-(dimethoxymethyl)azetidin-1-yl]-1-oxo-isoindolin-2-yl]piperidine-2,6-dione (5.6 g, 15.00 mmol) was separated by supercritical fluid chromatography (Chiralcel OJ-3, 5 to 40% (0.05% diethylamine in isopropanol):CO$_2$, 100 bar) to afford (3R)-3-[5-[3-(dimethoxymethyl)azetidin-1-yl]-1-oxo-isoindolin-2-yl]piperidine-2,6-dione (2.3 g, 82%) as a white solid and (3S)-3-[5-[3-(dimethoxymethyl)azetidin-1-yl]-1-oxo-isoindolin-2-yl]piperidine-2,6-dione (2.2 g, 78%) as a white solid.

Step X: 1-[2-[(3R)-2,6-dioxo-3-piperidyl]-1-oxo-isoindolin-5-yl]azetidine-3-carbaldehyde

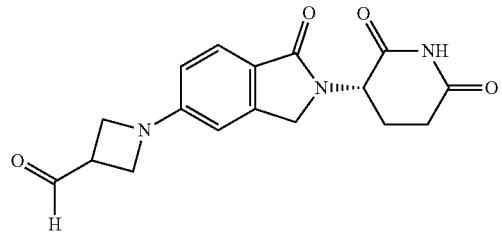 [SMILES: O=CC1CN(c2ccc3c(c2)CN([C@H]2CCC(=O)NC2=O)C3=O)C1]

To a solution of (3S)-3-[5-[3-(dimethoxymethyl)azetidin-1-yl]-1-oxo-isoindolin-2-yl]piperidine-2,6-dione (2.70 g, 7.23 mmol) in dichloromethane (40 mL) was added trifluoroacetic acid (20.00 mL, 270.1 mmol). The reaction stirred at 40° C. for 2 h. The pH was adjusted to 7 with N-methylmorpholine. 1-[2-[(3R)-2,6-dioxo-3-piperidyl]-1-oxo-isoindolin-5-yl]azetidine-3-carbaldehyde (2.3 g, 97%) was obtained as a yellow oil which was used in the next step without further purification.

Step Y: (3R)—N-(3-{5-[2-(1-{4-[(1-{2-[(3S)-2,6-dioxopiperidin-3-yl]-1-oxo-2,3-dihydro-1H-isoindol-5-yl}azetidin-3-yl)methyl]piperazin-1-yl}cyclopropyl)pyrimidin-5-yl]-1H-pyrrolo[2,3-b]pyridine-3-carbonyl}-2,4-difluorophenyl)-3-fluoropyrrolidine-1-sulfonamide

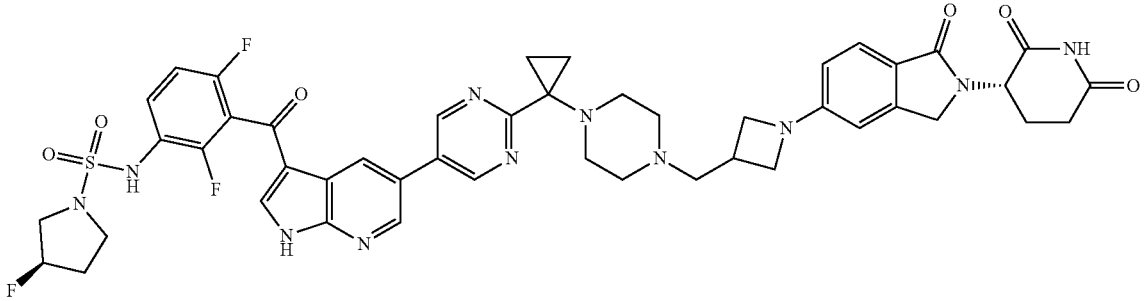 [SMILES: O=C1CC[C@H](N2Cc3cc(N4CC(CN5CCN(C6(c7ncc(-c8cnc9[nH]cc(C(=O)c%10c(F)ccc(NS(=O)(=O)N%11CC[C@@H](F)C%11)c%10F)c9c8)cn7)CC6)CC5)C4)ccc3C2=O)C(=O)N1]

To a solution of (3R)—N-[2,4-difluoro-3-[5-[2-(1-piperazin-1-ylcyclopropyl) pyrimidin-5-yl]-1H-pyrrolo[2,3-b]pyridine-3-carbonyl]phenyl]-3-fluoro-pyrrolidine-1-sulfonamide hydrochloride (3.96 g, 5.97 mmol) and N-methylmorpholine (710 mg, 7.03 mmol) in dichloromethane (40 mL) was added 1-[2-[(3R)-2,6-dioxo-3-piperidyl]-1-oxo-isoindolin-5-yl]azetidine-3-carbaldehyde (2.30 g, 7.03 mmol). The reaction stirred at 25° C. for 0.5 h. Sodium triacetoxyborohydride (2.98 g, 14.1 mmol) was added. The reaction stirred at 25° C. for 12 h. The reaction mixture was diluted with water (200 mL) and extracted with ethyl acetate (100 mL) and tetrahydrofuran (3×100 mL). The combined organic fractions were washed with saturated aqueous sodium chloride (1×200 mL), dried over sodium sulfate, filtered, and concentrated. Purification of the residue by preparative HPLC (Phenomenex Luna C18, 10% to 40% acetonitrile:(0.225% formic acid in water)) afforded (3R)—N-[3-[5-[2-[1-[4-[[1-[2-[(3S)-2,6-dioxo-3-piperidyl]-1-oxo-isoindolin-5-yl]azetidin-3-yl]methyl]piperazin-1-yl]cyclopropyl]pyrimidin-5-yl]-1H-pyrrolo[2,3-b]pyridine-3-carbonyl]-2,4-difluoro-phenyl]-3-fluoro-pyrrolidine-1-sulfonamide (2.56 g, 38%) as an off-white solid. MS (ESI): m/z 937.9 [M+H]$^+$; $^1$H NMR (400 MHz, DMSO-d$_6$) δ 13.42-12.72 (m, 1H), 10.93 (s, 1H), 10.21-9.51 (m, 1H), 9.08 (s, 2H), 8.76 (d, J=1.6 Hz, 1H), 8.69 (s, 1H), 8.17 (s, 1H), 7.69-7.57 (m, 1H), 7.48 (d, J=8.4 Hz, 1H), 7.27 (t, J=8.8 Hz, 1H), 6.51 (s, 1H), 6.47 (d, J=8.4 Hz, 1H), 5.43-5.19 (m, 1H), 5.11-4.92 (m, 1H), 4.38-4.10 (m, 2H), 4.03 (t, J=7.6 Hz, 2H), 3.57 (s, 2H), 3.49 (s, 1H), 3.43-3.37 (m, 2H), 3.29 (s, 2H), 3.27-3.09 (m, 4H), 3.01-2.94 (m, 1H), 2.92-2.82 (m, 1H), 2.64-2.53 (m, 3H), 2.47-2.27 (m, 5H), 2.18-2.10 (m, 1H), 2.16-2.04 (m, 1H), 1.98-1.92 (m, 1H), 1.38 (s, 2H), 1.10 (s, 2H).

Exemplary Synthesis of Exemplary Compound 203: (3R)—N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2-ethyl-4-fluorophenyl}-3-fluoropyrrolidine-1-sulfonamide (Compound 203)

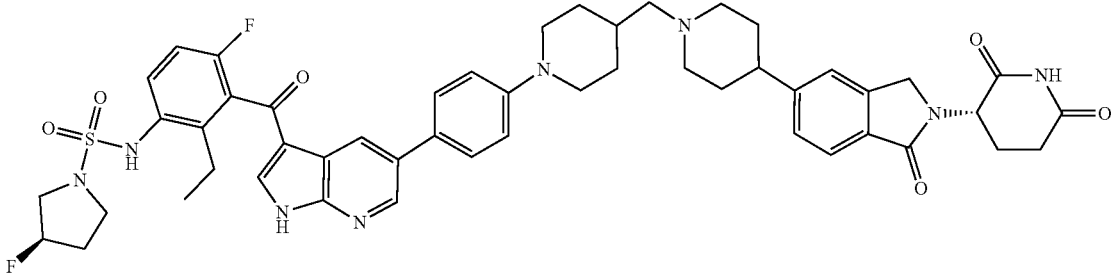 [SMILES: CCc1c(NS(=O)(=O)N2CC[C@@H](F)C2)ccc(F)c1C(=O)c1c[nH]c2ncc(-c3ccc(N4CCC(CN5CCC(c6ccc7c(c6)CN([C@H]6CCC(=O)NC6=O)C7=O)CC5)CC4)cc3)cc12]

Step A: 2-bromo-6-fluoro-3-nitrobenzoic acid

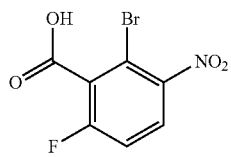 [SMILES: O=C(O)c1c(F)ccc([N+](=O)[O-])c1Br]

To a mixture of 2-bromo-6-fluorobenzoic acid (10 g, 45.7 mmol) in sulfuric acid (20 mL) was added 70% nitric acid (3.45 g, 54.8 mmol) dropwise at 0° C. The resulting mixture was stirred for 3 h at 0° C., then diluted with water (200 mL) and extracted with ethyl acetate (3×100 mL). The combined organic fractions were washed with saturated aqueous sodium chloride (100 mL), dried over sodium sulfate, filtered, and concentrated to afford 2-bromo-6-fluoro-3-nitrobenzoic acid (9.8 g, 81%) as a yellow oil. MS (ESI): m/z 261.98 [M−H]$^−$.

Step B: 2-ethenyl-6-fluoro-3-nitrobenzoic acid

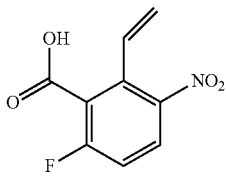

To a solution of 2-bromo-6-fluoro-3-nitrobenzoic acid (9.7 g, 36.7 mmol) and potassium vinyltrifluoroborate (6.74 g, 44.1 mmol) in 1,4-dioxane (30 mL) and water (5 mL) was added potassium carbonate (10.16 g, 73.48 mmol) and [1,1'-bis(diphenylphosphino)ferrocene]dichloropalladium (II) (2.69 g, 3.67 mmol). After stirring for 2 h at 80° C. under a nitrogen atmosphere, the resulting mixture was concentrated. Purification by preparative TLC (50% ethyl acetate:petroleum ether) afforded 2-ethenyl-6-fluoro-3-nitrobenzoic acid (5.8 g, 75%) as a yellow solid. MS (ESI): m/z 210.01 [M–H]⁻.

Step C: 2-ethyl-6-fluoro-3-nitrobenzoic acid

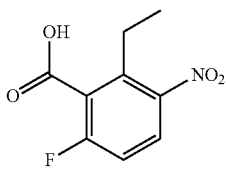

A mixture of 2-ethenyl-6-fluoro-3-nitrobenzoic acid (5.7 g, 27.0 mmol) and tris(triphenylphosphine)rhodium(I) chloride (0.95 g) in tetrahydrofuran (50 mL) and t-butanol (50 mL) was stirred at 50° C. under hydrogen atmosphere. The resulting mixture was filtered and the filter cake was washed with tetrahydrofuran (2×10 mL). The filtrate was concentrated to afford 2-ethyl-6-fluoro-3-nitrobenzoic acid (4.7 g, 82%) as a yellow solid. MS (ESI): m/z 212.01 [M–H]⁻.

Step D: 2-ethyl-6-fluoro-3-nitrobenzoyl chloride

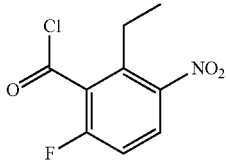

To a mixture of 2-ethyl-6-fluoro-3-nitrobenzoic acid (4.7 g, 22.07 mmol) in toluene (160 mL) was added thionyl chloride (160 mL) and N,N-dimethylformamide (0.3 mL) dropwise. The reaction was stirred overnight at 80° C. The mixture was cooled to room temperature and concentrated to afford 2-ethyl-6-fluoro-3-nitrobenzoyl chloride (4.38 g, 86%) as a light yellow oil.

Step D: (5-bromo-1H-pyrrolo[2,3-b]pyridin-3-yl)(2-ethyl-6-fluoro-3-nitrophenyl)methanone

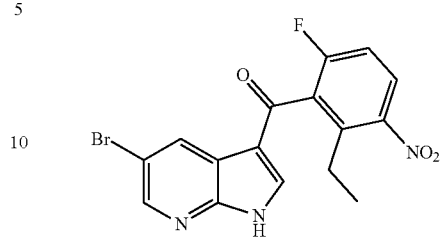

A mixture of 2-ethyl-6-fluoro-3-nitrobenzoyl chloride (3.9 g, 16.9 mmol) in 1,2-dichloroethane (500 mL) was treated with aluminum chloride (8.1 g, 211.240 mmol) under nitrogen atmosphere followed by the dropwise addition of 6-ethyl-2-fluoro-3-nitrobenzoyl chloride (6.2 g, 84.5 mmol) at 0° C. The resulting mixture was stirred overnight at 50° C. under a nitrogen atmosphere. The mixture was cooled to room temperature and diluted with water (200 mL). The precipitated solids were collected by filtration and washed with water (2×500 mL). The resulting mixture was concentrated to afford (5-bromo-1H-pyrrolo[2,3-b]pyridin-3-yl)(2-ethyl-6-fluoro-3-nitrophenyl)methanone (8.6 g, 93%) as a light yellow solid. MS (ESI): m/z 391.75, 393.75 [M+H]⁺; ¹H NMR (300 MHz, DMSO-d₆) δ 12.99 (s, 1H), 8.48-8.54 (m, 1H), 8.40 (d, J=2.3 Hz, 1H), 8.02-8.14 (m, 2H), 7.39 (dd, J=9.1, 8.1 Hz, 1H), 2.55 (s, 3H), 0.98 (t, J=7.4, 7.4 Hz, 3H).

Step E: (3-amino-2-ethyl-6-fluorophenyl)(5-bromo-1H-pyrrolo[2,3-b]pyridin-3-yl)methanone

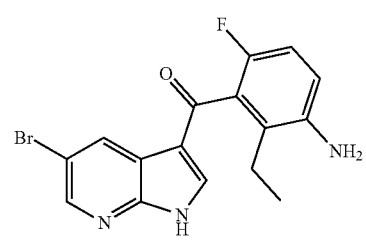 [SMILES: CCc1c([N+](=O)[O-])ccc(F)c1C(=O)c1c[nH]c2ncc(Br)cc12]

To a solution of (5-bromo-1H-pyrrolo[2,3-b]pyridin-3-yl)(2-ethyl-6-fluoro-3-nitrophenyl)methanone (8.6 g, 48.2 mmol) in ethanol (150 mL), tetrahydrofuran (150 mL), and aqueous 12 M hydrochloric acid (40 mL) was added iron powder (11.2 g, 465.574 mmol). The resulting mixture was stirred for 2 h at 50° C., then cooled to room temperature and concentrated, followed by addition of ice water (1 L) to the residue. The precipitated solids were collected by filtration and washed with water (2×500 mL) and then oven dried under reduced pressure to afford (3-amino-2-ethyl-6-fluorophenyl)(5-bromo-1H-pyrrolo[2,3-b]pyridin-3-yl)methanone (9.1 g, 91%) as a light yellow solid. MS (ESI): m/z 362.10, 364.10 [M+H]⁺.

Step F: (3-(3-amino-2-ethyl-6-fluorobenzoyl)-5-bromo-1H-pyrrolo[2,3-b]pyridin-1-yl)(2,6-dichlorophenyl)methanone

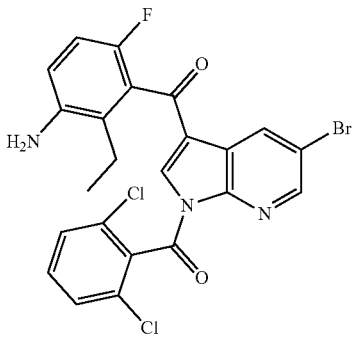 [SMILES: CCc1c(N)ccc(F)c1C(=O)c1cn(C(=O)c2c(Cl)cccc2Cl)c2ncc(Br)cc12]

To a cooled (10° C.) solution of (3-amino-2-ethyl-6-fluorophenyl)(5-bromo-1H-pyrrolo[2,3-b]pyridin-3-yl)methanone (3.83 g, 10.5 mmol) in tetrahydrofuran (100 mL) was added with triethylamine (1.30 g, 12.9 mmol), 2,6-dichlorobenzoyl chloride (2.10 g, 10.1 mmol) and 4-dimethylaminopyridine (121.5 mg, 1.00 mmol). The resulting mixture was stirred for 1 h at 25° C. and then water (100 mL) was added. The aqueous layer was extracted with ethyl acetate (3×100 mL). The resulting mixture was washed with saturated aqueous sodium chloride (50 mL), dried over sodium sulfate, filtered, and concentrated. Purification of the residue by trituration with 1:10 petroleum ether:ethyl acetate (30 mL) afforded (3-(3-amino-2-ethyl-6-fluorobenzoyl)-5-bromo-1H-pyrrolo[2,3-b]pyridin-1-yl)(2,6-dichlorophenyl)methanone (4.24 g, 76%) as a light yellow solid. MS (ESI): m/z 534.05, 536.05 [M+H]+.

Step G: N-(3-(5-bromo-1-(2,6-dichlorobenzoyl)-1H-pyrrolo[2,3-b]pyridine-3-carbonyl)-2-ethyl-4-fluorophenyl)-2-oxooxazolidine-3-sulfonamide

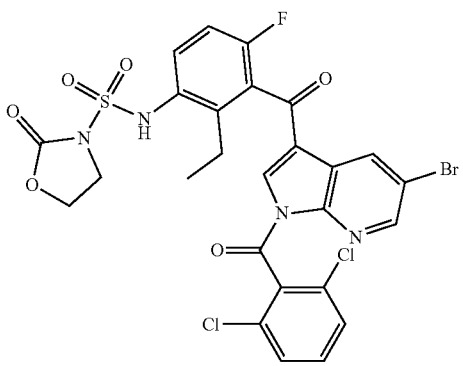 [SMILES: CCc1c(NS(=O)(=O)N2CCOC2=O)ccc(F)c1C(=O)c1cn(C(=O)c2c(Cl)cccc2Cl)c2ncc(Br)cc12]

To a cooled (0° C.) solution of chlorosulfonyl isocyanate (690 mg, 4.88 mmol) in dichloromethane (30 mL) was added 2-bromoethanol (598 mg, 4.79 mmol). The resulting mixture was stirred for 1 h at 10° C., and then (3-(3-amino-2-ethyl-6-fluorobenzoyl)-5-bromo-1H-pyrrolo[2,3-b]pyridin-1-yl)(2,6-dichlorophenyl)methanone (3.0 g, 5.38 mmol) and triethylamine (3.00 mL, 21.6 mmol) in dichloromethane (100 mL) were added at 0° C. The mixture was stirred overnight at 35° C. and then concentrated. Purification of the residue silica gel column chromatography (25% ethyl acetate:petroleum ether followed by 5% methanol:dichloromethane) afforded N-(3-(5-bromo-1-(2,6-dichlorobenzoyl)-1H-pyrrolo[2,3-b]pyridine-3-carbonyl)-2-ethyl-4-fluorophenyl)-2-oxooxazolidine-3-sulfonamide (3.34 g, 88%) as a light yellow solid. MS (ESI): m/z 682.85, 684.85 [M+H]+.

Step H: (R)—N-(3-(5-bromo-1-(2,6-dichlorobenzoyl)-1H-pyrrolo[2,3-b]pyridine-3-carbonyl)-2-ethyl-4-fluorophenyl)-3-fluoropyrrolidine-1-sulfonamide

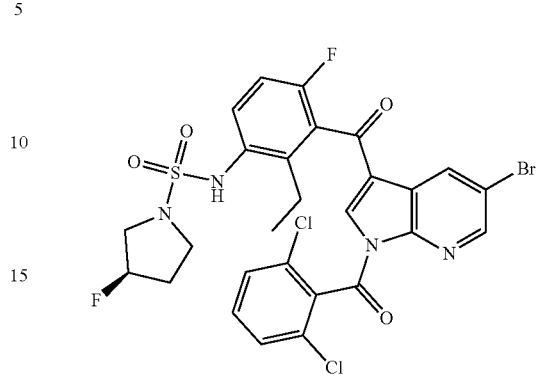

To a mixture of (3R)-3-fluoropyrrolidine hydrochloride (4.34 g, 34.6 mmol) in N,N-dimethylformamide (30 mL), diisopropylethylamine (3.0 mL, 17.2 mmol) was added in portions at room temperature. The resulting mixture was stirred for 1 h at room temperature. N-(3-(5-bromo-1-(2,6-dichlorobenzoyl)-1H-pyrrolo[2,3-b]pyridine-3-carbonyl)-2-ethyl-4-fluorophenyl)-2-oxooxazolidine-3-sulfonamide (3.34 g, 4.723 mmol) was added and the mixture was stirred overnight at 80° C. in a sealed tube. The mixture was cooled to room temperature diluted with water, extracted with ethyl acetate (3×100 mL), and concentrated. Purification by preparative HPLC (C18 column, 35-65% tetrahydrofuran:water over 35 min) afforded (R)—N-(3-(5-bromo-1-(2,6-dichlorobenzoyl)-1H-pyrrolo[2,3-b]pyridine-3-carbonyl)-2-ethyl-4-fluorophenyl)-3-fluoropyrrolidine-1-sulfonamide (660 mg, 26%) as a light yellow solid. MS (ESI): m/z 685.05, 687.05 [M+H]+; 1H NMR (400 MHz, CDCl3) δ 8.88 (d, J=2.3 Hz, 1H), 8.28 (s, 1H), 8.19 (s, 1H), 7.69 (dd, J=9.0, 5.1 Hz, 1H), 7.38-7.49 (m, 3H), 7.11 (t, J=8.6, 8.6 Hz, 1H), 6.24 (s, 1H), 5.37-5.24 (m, 1H), 4.14 (q, J=7.2, 7.2, 7.2 Hz, 1H), 3.76-3.61 (m, 4H), 2.67 (q, J=7.6, 7.6, 7.6 Hz, 2H), 2.28-2.41 (m, 1H), 2.06-2.07 (s, 2H), 1.20 (t, J=7.6, 7.6 Hz, 5H).

Step I: (R)—N-(3-(5-bromo-1H-pyrrolo[2,3-b]pyridine-3-carbonyl)-2-ethyl-4-fluorophenyl)-3-fluoropyrrolidine-1-sulfonamide

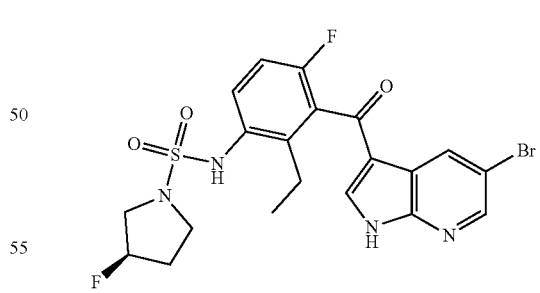

To a mixture of (3R)—N-{3-[5-bromo-1-(2,6-dichlorobenzoyl)pyrrolo[2,3-b]pyridine-3-carbonyl]-2-ethyl-4-fluorophenyl}-3-fluoropyrrolidine-1-sulfonamide (600 mg, 0.874 mmol) in methanol (5 mL) was added hydroxylamine hydrate (5 mL) at room temperature. The resulting mixture was stirred for 2 h at 30° C. and then concentrated to afford (R)—N-(3-(5-bromo-1H-pyrrolo[2,3-b]pyridine-3-carbonyl)-2-ethyl-4-fluorophenyl)-3-fluoropyrrolidine-1-sulfonamide (386 mg, 86%) as a white solid. MS (ESI): m/z 513.15, 515.15 [M+H]+.

Step J: (R)—N-(3-(5-(4-(4-(dimethoxymethyl)piperidin-1-yl)phenyl)-1H-pyrrolo[2,3-b]pyridine-3-carbonyl)-2-ethyl-4-fluorophenyl)-3-fluoropyrrolidine-1-sulfonamide

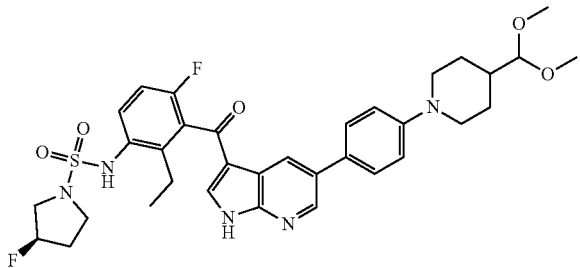 [SMILES: CCc1c(NS(=O)(=O)N2CC[C@@H](F)C2)ccc(F)c1C(=O)c1c[nH]c2ncc(-c3ccc(N4CCC(C(OC)OC)CC4)cc3)cc12]

To a solution of (R)—N-(3-(5-bromo-1H-pyrrolo[2,3-b]pyridine-3-carbonyl)-2-ethyl-4-fluorophenyl)-3-fluoropyrrolidine-1-sulfonamide (360 mg, 0.70 mmol) and 4-(dimethoxymethyl)-1-[4-(4,4,5,5-tetramethyl-1,3,2-dioxaborolan-2-yl)phenyl]piperidine (303 mg, 0.84 mmol) in 1,4-dioxane (18 mL) and water (3 mL) was added cesium fluoride (319 mg, 2.10 mmol) and [1,1'-bis(di-tert-butylphosphino)ferrocene]dichloropalladium(II) (45.6 mg, 0.07 mmol) in portions at room temperature. The mixture was stirred for 2 h at 100° C. Purification of the residue by silica gel column chromatography (1:12 methanol:dichloromethane) afforded (R)—N-(3-(5-(4-(4-(dimethoxymethyl)piperidin-1-yl)phenyl)-1H-pyrrolo[2,3-b]pyridine-3-carbonyl)-2-ethyl-4-fluorophenyl)-3-fluoropyrrolidine-1-sulfonamide (315 mg, 67%) as a yellow solid. MS (ESI): m/z 668.35 [M+H]$^+$.

Step K: (R)—N-(2-ethyl-4-fluoro-3-(5-(4-(4-formylpiperidin-1-yl)phenyl)-1H-pyrrolo[2,3-b]pyridine-3-carbonyl)phenyl)-3-fluoropyrrolidine-1-sulfonamide

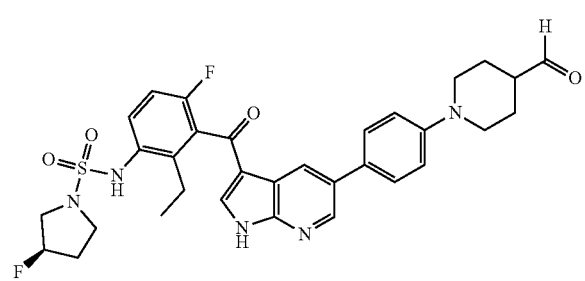 [SMILES: CCc1c(NS(=O)(=O)N2CC[C@@H](F)C2)ccc(F)c1C(=O)c1c[nH]c2ncc(-c3ccc(N4CCC(C=O)CC4)cc3)cc12]

To a mixture of (R)—N-(3-(5-(4-(4-(dimethoxymethyl)piperidin-1-yl)phenyl)-1H-pyrrolo[2,3-b]pyridine-3-carbonyl)-2-ethyl-4-fluorophenyl)-3-fluoropyrrolidine-1-sulfonamide (200 mg, 0.299 mmol) in tetrahydrofuran (20 mL) was added 2 M aqueous sulfuric acid (10 mL) in portions. The resulting mixture was stirred for 1 h at 70° C. The mixture was basified to pH 8 with saturated aqueous sodium bicarbonate. The resulting mixture was extracted with ethyl acetate (3×100 mL). The combined organic fractions were washed with saturated aqueous sodium chloride (2×50 mL), dried over sodium sulfate, filtered, and concentrated to afford (R)—N-(2-ethyl-4-fluoro-3-(5-(4-(4-formylpiperidin-1-yl)phenyl)-1H-pyrrolo[2,3-b]pyridine-3-carbonyl)phenyl)-3-fluoropyrrolidine-1-sulfonamide (183 mg, 97%) as a yellow oil. MS (ESI): m/z 622.30 [M+H]$^+$.

Step L: (3R)—N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2-ethyl-4-fluorophenyl}-3-fluoropyrrolidine-1-sulfonamide

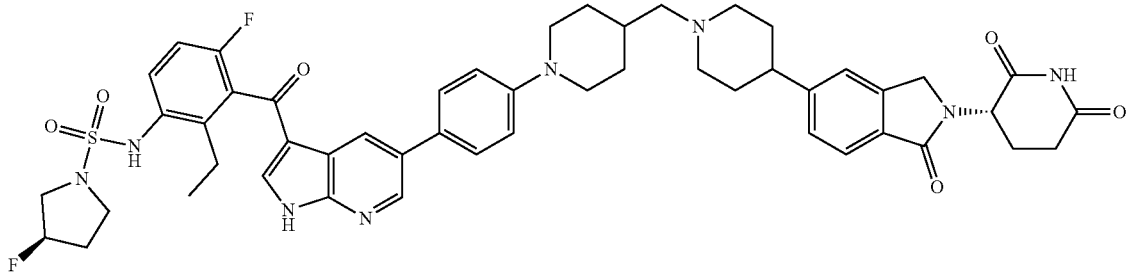 [SMILES: CCc1c(NS(=O)(=O)N2CC[C@@H](F)C2)ccc(F)c1C(=O)c1c[nH]c2ncc(-c3ccc(N4CCC(CN5CCC(c6ccc7c(c6)CN([C@H]6CCC(=O)NC6=O)C7=O)CC5)CC4)cc3)cc12]

A mixture of 3-[1-oxo-5-(piperidin-4-yl)-3H-isoindol-2-yl]piperidine-2,6-dione; [(1R)-7,7-dimethyl-2-oxobicyclo[2.2.1]heptan-1-yl]methanesulfonic acid (150 mg, 0.268 mmol) and sodium acetate (16.5 mg, 0.201 mmol) in dichloromethane (10 mL) and isopropanol (10 mL) at room temperature was stirred 10 min at room temperature. (3R)—N-(2-ethyl-4-fluoro-3-{5-[4-(4-formylpiperidin-1-yl)phenyl]-1H-pyrrolo[2,3-b]pyridine-3-carbonyl}phenyl)-3-fluoropyrrolidine-1-sulfonamide (183 mg, 0.295 mmol) was added and the mixture was stirred for additional 1 h at room temperature. Sodium triacetoxyborohydride (114 mg, 0.536 mmol) was then added and the mixture was stirred for additional 2 h at room temperature. The mixture was acidified to pH 8 with saturated aqueous sodium bicarbonate and then extracted with tetrahydrofuran (3×30 mL). The combined organic fractions were washed with saturated aqueous sodium chloride (50 mL), dried over sodium sulfate, filtered, and concentrated. Purification of the residue by preparative thin layer chromatography (1:8 methanol:dichloromethane) afforded (3R)—N-{3-[5-(4-{4-[(4-{2-[(3S)-2,6-dioxopiperidin-3-yl]-1-oxo-3H-isoindol-5-yl}piperidin-1-yl)methyl]piperidin-1-yl}phenyl)-1H-pyrrolo[2,3-b]pyridine-3-carbonyl]-2-ethyl-4-fluorophenyl}-3-fluoropyrrolidine-1-sulfonamide (143.3 mg, 56%) as a yellow solid. LC-MS (ES+): m/z 933.45 [M+H]$^+$; $^1$H NMR (400 MHz, DMSO-d$_6$) δ 12.90 (s, 1H), 10.98 (s, 1H), 9.58 (s, 1H), 8.65 (d, J=2.3 Hz, 1H), 8.52 (s, 1H), 7.91 (s, 1H), 7.66 (d, J=7.8 Hz, 1H), 7.59 (dd, J=8.8, 6.2 Hz, 3H), 7.51 (s, 1H), 7.41 (d, J=7.9 Hz, 1H), 7.32-7.23 (m, 1H), 7.07 (d, J=8.6 Hz, 1H), 5.11 (dd, J=13.3, 5.1 Hz, 1H), 4.43 (d, J=17.2 Hz, 1H), 4.30 (d, J=17.2 Hz, 1H), 3.90-3.77 (m, 3H), 3.64-3.56 (m, 2H), 3.00 (s, 1H), 2.91 (ddd, J=17.8, 13.6, 5.4 Hz, 1H), 2.75 (t, J=12.0 Hz, 2H), 2.60 (d, J=17.1 Hz, 1H), 2.40 (dd, J=12.9, 4.5 Hz, 1H), 2.10-1.97 (m, 4H), 1.88-1.70 (m, 7H), 1.25 (d, J=10.7 Hz, 3H), 1.01 (t, J=7.4 Hz, 3H).

Exemplary Synthesis of Exemplary Compound 204:
N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2,4-difluorophenyl}-2-methylpropane-1-sulfonamide (Compound 204)

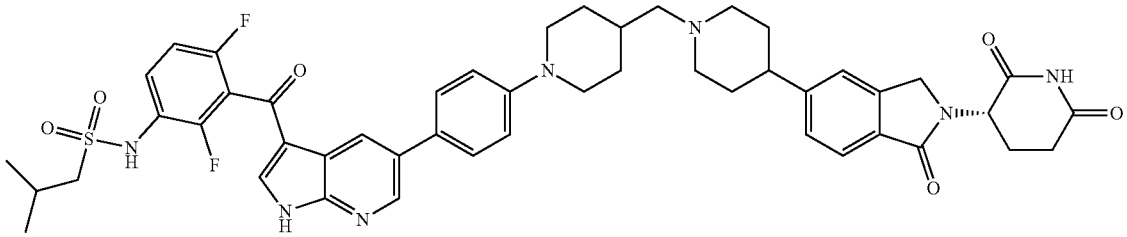 [SMILES: CC(C)CS(=O)(=O)Nc1ccc(F)c(C(=O)c2c[nH]c3ncc(-c4ccc(N5CCC(CN6CCC(c7ccc8c(c7)CN([C@H]7CCC(=O)NC7=O)C8=O)CC6)CC5)cc4)cc23)c1F]

Step A: N-(3-(5-bromo-1H-pyrrolo[2,3-b]pyridine-3-carbonyl)-2,4-difluorophenyl)-2-methylpropane-1-sulfonamide

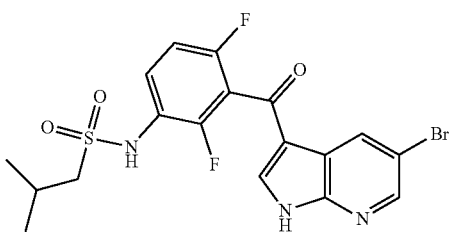 [SMILES: CC(C)CS(=O)(=O)Nc1ccc(F)c(C(=O)c2c[nH]c3ncc(Br)cc23)c1F]

To a solution of (3-amino-2,6-difluoro-phenyl)-(5-bromo-1H-pyrrolo[2,3-b]pyridin-3-yl) methanone hydrochloride (500 mg, 1.29 mmol) in pyridine (5 mL) was added 2-methylpropane-1-sulfonyl chloride (403 mg, 2.57 mmol) and dimethylaminopyridine (31 mg, 0.25 mmol) at 25° C. The mixture was stirred at 50° C. for 12 h. The reaction mixture was diluted with water (50 mL) and extracted with ethyl acetate (3×50 mL). The combined organic fractions were washed with saturated aqueous sodium chloride (3×50 mL), dried over sodium sulfate anhydrous, filtered, and concentrated. Purification of the residue by preparative HPLC (Phenomenex Luna C18, 40-70% acetonitrile:(0.225% formic acid in water)) afforded N-[3-(5-bromo-1H-pyrrolo[2,3-b]pyridine-3-carbonyl)-2,4-difluoro-phenyl]-2-methylpropane-1-sulfonamide (310 mg, 0.65 mmol, 51%) as a white solid. MS (ESI): m/z 415.1 [M+H]$^+$; $^1$H NMR (400 MHz, DMSO-d$_6$) δ 13.53-12.40 (m, 1H), 10.55-9.16 (m, 1H), 8.59 (s, 1H), 8.51 (d, J=2.3 Hz, 1H), 8.29 (s, 1H), 7.59 (dt, J=6.0, 8.8 Hz, 1H), 7.28 (t, J=8.8 Hz, 1H), 3.05 (d, J=6.4 Hz, 2H), 2.17 (quind, J=6.4, 13.2 Hz, 1H), 1.02 (d, J=6.8 Hz, 6H).

Step B: N-(2,4-difluoro-3-(5-(4-(4-formylpiperidin-1-yl)phenyl)-1H-pyrrolo[2,3-b]pyridine-3-carbonyl)phenyl)-2-methylpropane-1-sulfonamide

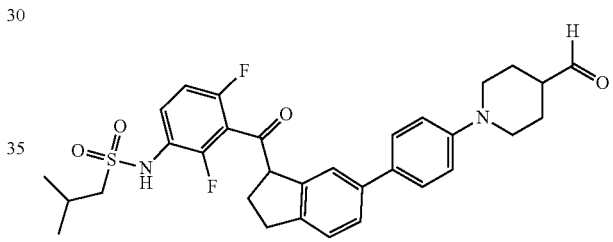

A mixture of N-[3-(5-bromo-1H-pyrrolo[2,3-b]pyridine-3-carbonyl)-2,4-difluoro-phenyl]-2-methyl-propane-1-sulfonamide (300 mg, 0.63 mmol), 4-(dimethoxymethyl)-1-[4-(4,4,5,5-tetramethyl-1,3,2-dioxaborolan-2-yl)phenyl]piperidine (275 mg, 0.76 mmol), bis(di-tert-butyl(4-dimethylaminophenyl)phosphine)dichloropalladium(II) (67 mg, 0.095 mmol), and cesium fluoride (385 mg, 2.54 mmol) in 1,4-dioxane (5 mL) and water (1 mL) was degassed and purged with nitrogen 3 times, and then the mixture was stirred at 95° C. for 12 h. The reaction mixture was filtered and concentrated. Purification of the residue by silica gel chromatography (1:50 to 1:20 methanol:dichloromethane) afforded N-[2,4-difluoro-3-[5-[4-(4-formyl-1-piperidyl)phenyl]-1H-pyrrolo[2,3-b]pyridine-3-carbonyl]phenyl]-2-methyl-propane-1-sulfonamide (200 mg, 54%) as a yellow solid. MS (ESI): m/z 599.3 [M+H$_2$O]$^+$.

Step C: N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2,4-difluorophenyl}-2-methylpropane-1-sulfonamide

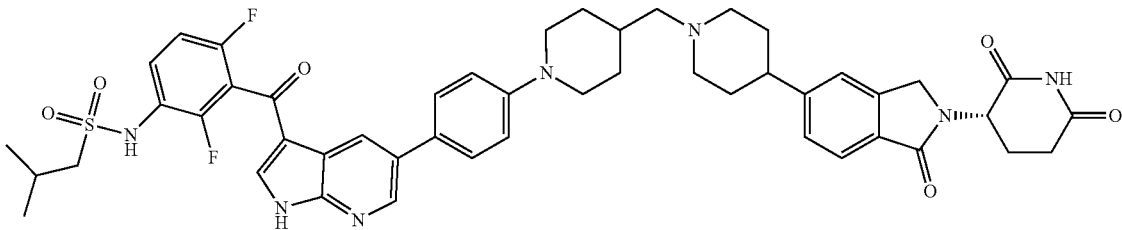 [SMILES: CC(C)CS(=O)(=O)Nc1ccc(F)c(C(=O)c2c[nH]c3ncc(-c4ccc(N5CCC(CN6CCC(c7ccc8c(c7)CN([C@H]7CCC(=O)NC7=O)C8=O)CC6)CC5)cc4)cc23)c1F]

To a solution of (3S)-3-[1-oxo-5-(4-piperidyl)isoindolin-2-yl]piperidine-2,6-dione hydrochloride (93 mg, 0.25 mmol) in dichloromethane (2 mL) and isopropanol (2 mL) was added sodium acetate (19 mg, 0.23 mmol). The mixture was stirred at 25° C. for 10 min, and then N-[2,4-difluoro-3-[5-[4-(4-formyl-1-piperidyl)phenyl]-1H-pyrrolo[2,3-b]pyridine-3-carbonyl]phenyl]-2-methyl-propane-1-sulfonamide (150 mg, 0.25 mmol) was added. The mixture was stirred at 25° C. for 20 min, and then sodium triacetoxyborohydride (109 mg, 0.51 mmol) was added. The mixture was stirred at 25° C. for 60 min. The reaction mixture was concentrated. Purification of the residue by preparative HPLC (Phenomenex Luna C18, 18 to 48% acetonitrile:(0.225% formic acid in water)) afforded N-[3-[5-[4-[4-[[4-[2-[(3S)-2,6-dioxo-3-piperidyl]-1-oxo-isoindolin-5-yl]-1-piperidyl]methyl]-1-piperidyl]phenyl]-1H-pyrrolo[2,3-b]pyridine-3-carbonyl]-2,4-difluoro-phenyl]-2-methyl-propane-1-sulfonamide formic acid salt (71.9 mg, 29%) as a yellow solid. MS (ESI): m/z 892.3 [M+H]$^+$; $^1$H NMR (400 MHz, DMSO-d$_6$) δ 13.61-12.13 (m, 1H), 10.99 (s, 1H), 8.65 (d, J=2.4 Hz, 1H), 8.60-8.44 (m, 1H), 8.19 (d, J=9.6 Hz, 2H), 7.65 (d, J=7.6 Hz, 1H), 7.61-7.53 (m, 3H), 7.51 (s, 1H), 7.41 (d, J=7.6 Hz, 1H), 7.26 (t, J=8.8 Hz, 1H), 7.07 (d, J=8.8 Hz, 2H), 5.10 (dd, J=5.2, 13.2 Hz, 1H), 4.47-4.24 (m, 2H), 3.83-3.76 (m, 2H), 3.02 (d, J=6.4 Hz, 3H), 2.98 (s, 1H), 2.95-2.86 (m, 1H), 2.79-2.69 (m, 2H), 2.65-2.52 (m, 2H), 2.44-2.35 (m, 2H), 2.24-2.19 (m, 2H), 2.19-2.12 (m, 1H), 2.05-1.97 (m, 3H), 1.86-1.81 (m, 2H), 1.78-1.69 (m, 4H), 1.29-1.19 (m, 2H), 1.01 (d, J=6.7 Hz, 6H).

Exemplary Synthesis of Exemplary Compound 205: (3R)—N-{3-[5-(3-cyano-4-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2,4-difluorophenyl}-3-fluoropyrrolidine-1-sulfonamide (Compound 205)

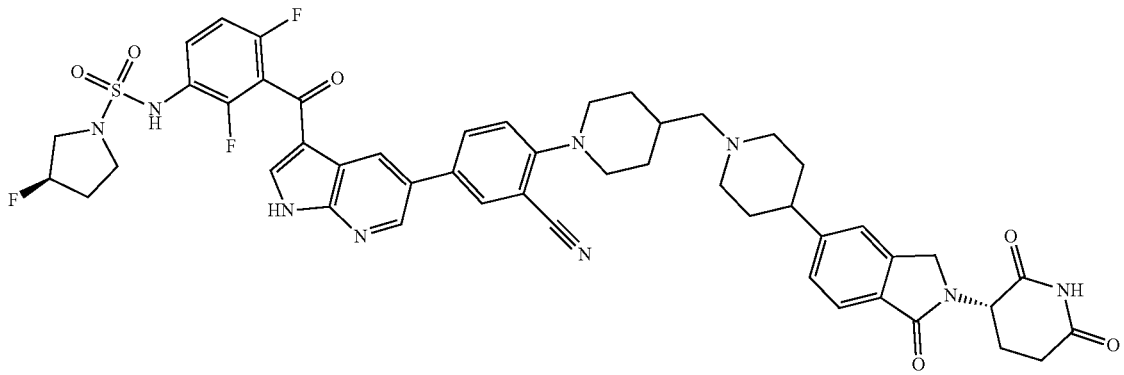 [SMILES: N#Cc1cc(-c2cnc3[nH]cc(C(=O)c4c(F)ccc(NS(=O)(=O)N5CC[C@@H](F)C5)c4F)c3c2)ccc1N1CCC(CN2CCC(c3ccc4c(c3)CN([C@H]3CCC(=O)NC3=O)C4=O)CC2)CC1]

Step A: 5-bromo-2-[4-(dimethoxymethyl)piperidin-1-yl]benzonitrile

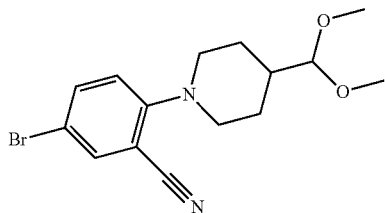 [SMILES: COC(OC)C1CCN(c2ccc(Br)cc2C#N)CC1]

A solution of 5-bromo-2-fluorobenzonitrile (3.00 g, 15.0 mmol), dimethylsulfoxide (60 mL), diisopropylethylamine (3.88 g, 30.0 mmol), and 4-(dimethoxymethyl)piperidine (2.50 g, 15.7 mmol) was stirred for 4 h 110° C. The reaction mixture was cooled and water (300 mL) was added. The resulting mixture was extracted with 3×100 mL of ethyl acetate (3×100 mL). The combined organic fractions were washed with water (100 mL) and saturated aqueous sodium chloride (100 mL) and concentrated. Purification of the residue by silica gel column chromatography (1:1 ethyl acetate:petroleum/ether) afforded 5-bromo-2-[4-(dimethoxymethyl)piperidin-1-yl]benzonitrile (4.7 g, 92%) as a yellow solid. MS (ESI): m/z 339.15 [M+H]+.

Step B: 2-[4-(dimethoxymethyl)piperidin-1-yl]-5-(4,4,5,5-tetramethyl-1,3,2-dioxaborolan-2-yl)benzonitrile

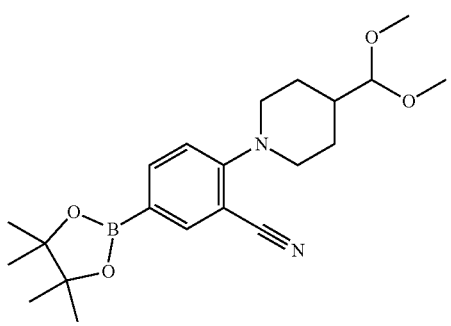

A mixture of 5-bromo-2-[4-(dimethoxymethyl)piperidin-1-yl]benzonitrile (4.7 g, 13.9 mmol), bis(pinacolato)diboron (5.28 g, 20.8 mmol), [1,1'-bis(diphenylphosphino)ferrocene]dichloropalladium(II) (1.01 g, 1.38 mmol), and potassium acetate (2.72 g, 27.7 mmol) in 1,4-dioxane (100 mL) was stirred for 5 h at 90° C. The reaction mixture was concentrated. Purification by silica gel column chromatography (1:3 ethyl acetate:petroleum ether) afforded 2-[4-(dimethoxymethyl)piperidin-1-yl]-5-(4,4,5,5-tetramethyl-1,3,2-dioxaborolan-2-yl)benzonitrile (4.8 g, 89%) as a light yellow solid. MS (ESI): m/z 387.35 [M+H]+.

Step C: (3R)—N-[3-(5-[3-cyano-4-[4-(dimethoxymethyl)piperidin-1-yl]phenyl]-1H-pyrrolo[2,3-b]pyridine-3-carbonyl)-2,4-difluorophenyl]-3-fluoropyrrolidine-1-sulfonamide

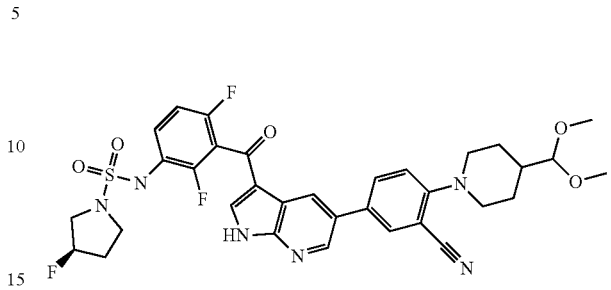

A solution of 2-[4-(dimethoxymethyl)piperidin-1-yl]-5-(4,4,5,5-tetramethyl-1,3,2-dioxaborolan-2-yl)benzonitrile (1 g), (3R)—N-(3-[5-bromo-1H-pyrrolo[2,3-b]pyridine-3-carbonyl]-2,4-difluorophenyl)-3-fluoropyrrolidine-1-sulfonamide (923 mg), [1,1'-bis(diphenylphosphino)ferrocene]dichloropalladium(II) (163 mg) and potassium carbonate (825 mg) in 1,4-dioxane (15 mL) and water (2 mL) was heated in a sealed tube at 95° C. overnight. The resulting mixture was concentrated. Purification of the residue by silica gel column chromatography (1:1 tetrahydrofuran:petroleum ether) afforded (3R)—N-[3-(5-[3-cyano-4-[4-(dimethoxymethyl)piperidin-1-yl]phenyl]-1H-pyrrolo[2,3-b]pyridine-3-carbonyl)-2,4-difluorophenyl]-3-fluoropyrrolidine-1-sulfonamide (869 mg, 69%) as a yellow solid. MS (ESI): m/z 683.20 [M+H]+.

Step D: (3R)—N-(3-[5-[3-cyano-4-(4-formylpiperidin-1-yl)phenyl]-1H-pyrrolo[2,3-b]pyridine-3-carbonyl]-2,4-difluorophenyl)-3-fluoropyrrolidine-1-sulfonamide

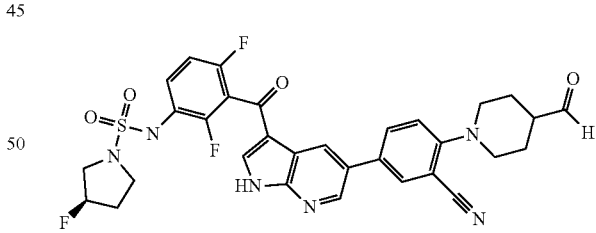

A solution of (3R)—N-[3-(5-[3-cyano-4-[4-(dimethoxymethyl)piperidin-1-yl]phenyl]-1H-pyrrolo[2,3-b]pyridine-3-carbonyl)-2,4-difluorophenyl]-3-fluoropyrrolidine-1-sulfonamide (564 mg, 0.146 mmol), dichloromethane (6 mL), trifluoroacetic acid (6 mL), and water (1.50 mL) was stirred for 2 h at 40° C. The resulting mixture was concentrated to afford (3R)—N-(3-[5-[3-cyano-4-(4-formylpiperidin-1-yl)phenyl]-1H-pyrrolo[2,3-b]pyridine-3-carbonyl]-2,4-difluorophenyl)-3-fluoropyrrolidine-1-sulfonamide (421 mg, 80.4%) as yellow oil. MS (ESI): m/z 637.15 [M+H]+.

Step E: (3R)—N-{3-[5-(3-cyano-4-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2,4-difluorophenyl}-3-fluoropyrrolidine-1-sulfonamide

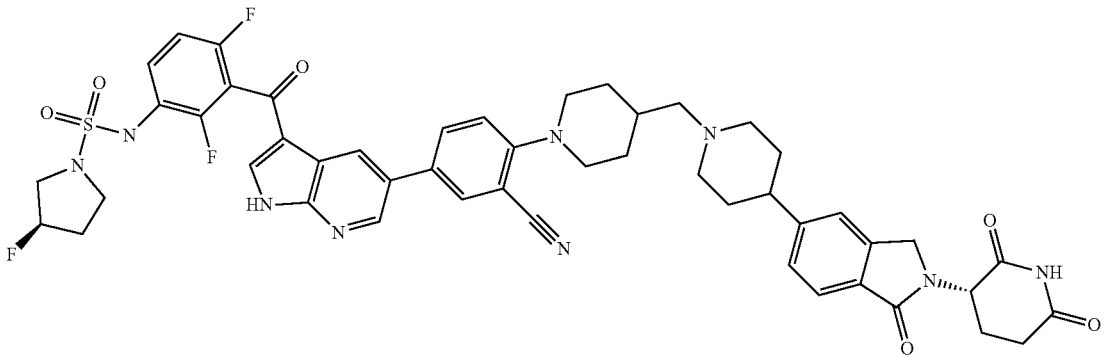 [SMILES: N#Cc1cc(-c2cnc3[nH]cc(C(=O)c4c(F)ccc(NS(=O)(=O)N5CC[C@@H](F)C5)c4F)c3c2)ccc1N1CCC(CN2CCC(c3ccc4c(c3)CN([C@H]3CCC(=O)NC3=O)C4=O)CC2)CC1]

To a solution of (3R)—N-(3-[5-[3-cyano-4-(4-formylpiperidin-1-yl)phenyl]-1H-pyrrolo[2,3-b]pyridine-3-carbonyl]-2,4-difluorophenyl)-3-fluoropyrrolidine-1-sulfonamide (445 mg, 0.699 mmol), 3-[1-oxo-5-(piperidin-4-yl)-3H-isoindol-2-yl]piperidine-2,6-dione hydrochloride (254 mg, 0.699 mmol), dichloromethane (3 mL), methanol (200 mg), and diisopropylethylamine (2 mL) was added acetic acid until the pH was ~6, followed by addition of sodium cyanoborohydride (84 mg, 1.337 mmol) in batches. The resulting solution was stirred for overnight at 35° C. and then 3 h at room temperature. Water (100 mL) was added, and the mixture was extracted with dichloromethane (3×100 mL). The organic fractions were combined and concentrated. Purification of the residue by silica gel column chromatography (1:10 methanol:dichloromethane) and then preparative HPLC (C18, 0 to 65% acetonitrile:water with ammonium bicarbonate afforded (3R)—N-[3-[5-(3-cyano-4-[4-[(4-{2-[(3S)-2,6-dioxopiperidin-3-yl]-1-oxo-3H-isoindol-5-yl]piperidin-1-yl)methyl]piperidin-1-yl}phenyl)-1H-pyrrolo[2,3-b]pyridine-3-carbonyl]-2,4-difluorophenyl]-3-fluoropyrrolidine-1-sulfonamide (69.8 mg, 11%) as a white solid. $^1$H NMR (400 MHz, DMSO-$d_6$): δ 12.98 (s, 1H), 10.99 (s, 1H), 9.81 (s, 1H), 8.80-8.59 (m, 2H), 8.12 (d, J=2.0 Hz, 2H), 7.97 (dd, J=8.6, 2.4 Hz, 1H), 7.74-7.34 (m, 4H), 7.27 (td, J=8.9, 1.9 Hz, 2H), 5.31 (dt, J=53.0, 3.1 Hz, 1H), 5.11 (dd, J=13.3, 5.1 Hz, 1H), 4.44 (d, J=17.2 Hz, 1H), 4.30 (d, J=17.2 Hz, 1H), 3.62 (d, J=11.3 Hz, 2H), 3.49 (d, J=2.5 Hz, 1H), 3.46-3.37 (m, 2H), 3.04 (d, J=10.8 Hz, 2H), 2.99-2.79 (m, 3H), 2.73-2.54 (m, 2H), 2.42 (td, J=13.2, 4.5 Hz, 1H), 2.31 (d, J=7.0 Hz, 2H), 2.20-2.05 (m, 4H), 2.00 (tt, J=7.6, 3.0 Hz, 2H), 1.96-1.86 (m, 2H), 1.86-1.66 (m, 5H), 1.44-1.20 (m, 2H); MS (ESI): m/z 948.30 [M+H]$^+$.

Exemplary Synthesis of Exemplary Compound 206:
1-cyclopropyl-N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2,4-difluorophenyl}methanesulfonamide
(Compound 206)

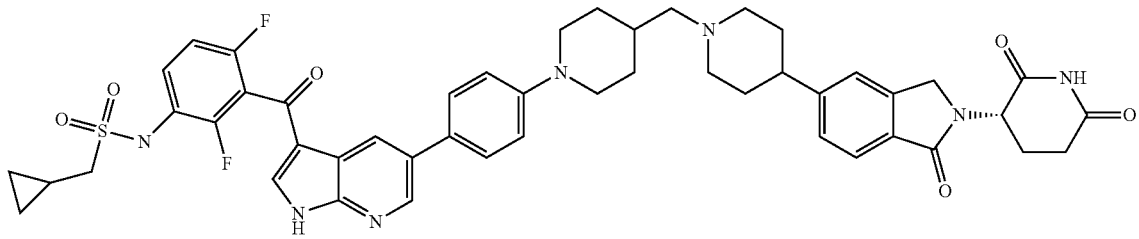 [SMILES: O=C1CC[C@H](N2Cc3cc(C4CCN(CC5CCN(c6ccc(-c7cnc8[nH]cc(C(=O)c9c(F)ccc(NS(=O)(=O)CC%10CC%10)c9F)c8c7)cc6)CC5)CC4)ccc3C2=O)C(=O)N1]

Step A: (3-amino-2,6-difluoro-phenyl)-[5-bromo-1-(2,6-dichlorobenzoyl)pyrrolo[2,3-b]pyridin-3-yl]methanone To a solution of (3-amino-2,6-difluoro-phenyl)-(5-bromo-1H-pyrrolo[2,3-b]pyridin-3-yl)methanone (5.0 g, 14.2 mmol), 4-dimethylaminopyridine (1.73 g, 14.2 mmol) and triethylamine (5.93 mL, 42.6 mmol) in tetrahydrofuran (50 mL) was added 2,6-dichlorobenzoyl chloride (2.04 mL, 14.2 mmol) at 0° C. The reaction stirred at 25° C. for 12 h. The reaction mixture was diluted with water (100 mL) and extracted with ethyl acetate (3×100 mL). The combined organic fractions were washed with saturated aqueous sodium chloride (3×100 mL), dried over sodium sulfate, filtered, and concentrated. Purification of the residue by silica gel column chromatography (1:100 to 1:3 ethyl acetate:petroleum ether) afforded (3-amino-2,6-difluoro-phenyl)-[5-bromo-1-(2,6-dichlorobenzoyl)pyrrolo[2,3-b]pyridin-3-yl]methanone (5.2 g, 69%) as a yellow solid.

Step B: N-[3-[5-bromo-1-(2,6-dichlorobenzoyl)pyrrolo[2,3-b]pyridine-3-carbonyl]-2,4-difluoro-phenyl]-1-cyclopropyl-methanesulfonamide

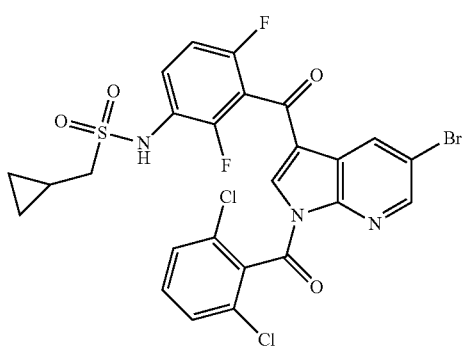 [SMILES: O=C(c1c(F)ccc(NS(=O)(=O)CC2CC2)c1F)c1cn(C(=O)c2c(Cl)cccc2Cl)c2ncc(Br)cc12]

General Procedure:
To a solution of (3-amino-2,6-difluoro-phenyl)-[5-bromo-1-(2,6-dichlorobenzoyl)pyrrolo[2,3-b]pyridin-3-yl]methanone (400 mg, 0.76 mmol) in pyridine (2 mL) was added 4-dimethylaminopyridine (9.0 mg, 0.076 mmol) and cyclopropylmethanesulfonyl chloride (235 mg, 1.52 mmol). The mixture was stirred at 50° C. for 12 h. Water (80 mL) was poured into the mixture and stirred for 1 min. The aqueous fraction was extracted with ethyl acetate (3×30 mL). The combined organic fractions were washed with saturated aqueous sodium chloride (2×30 mL), dried over sodium sulfate, filtered, and concentrated. Purification of the residue by column chromatography (1:50 to 1:3 ethyl acetate:petroleum ether) afforded N-[3-[5-bromo-1-(2,6-dichlorobenzoyl)pyrrolo[2,3-b]pyridine-3-carbonyl]-2,4-di fluoro-phenyl]-1-cyclopropyl-methanesulfonamide (300 mg, 61%) as a yellow solid. MS (ESI): m/z 644.1 [M+H]$^+$.

Step C: 1-cyclopropyl-N-[3-[1-(2,6-dichlorobenzoyl)-5-[4-[4-(dimethoxymethyl)-1-piperidyl]phenyl]pyrrolo[2,3-b]pyridine-3-carbonyl]-2,4-difluoro-phenyl]methanesulfonamide

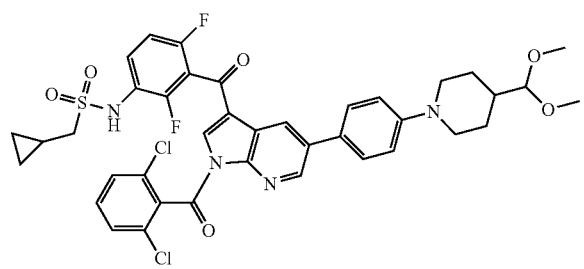 [SMILES: COC(OC)C1CCN(c2ccc(-c3cnc4c(c3)c(C(=O)c3c(F)ccc(NS(=O)(=O)CC5CC5)c3F)cn4C(=O)c3c(Cl)cccc3Cl)cc2)CC1]

To a solution of N-[3-[5-bromo-1-(2,6-dichlorobenzoyl)pyrrolo[2,3-b]pyridine-3-carbonyl]-2,4-difluoro-phenyl]-1-cyclopropyl-methanesulfonamide (250 mg, 0.38 mmol) and 4-(dimethoxymethyl)-1-[4-(4,4,5,5-tetramethyl-1,3,2-dioxaborolan-2-yl)phenyl]piperidine (140 mg, 0.38 mmol) in 1,4-dioxane (8 mL) and water (0.8 mL) was added cesium fluoride (236 mg, 1.55 mmol) and bis(di-tert-butyl(4-dimethylaminophenyl)phosphine)dichloropalladium(II) (27 mg, 0.38 mmol). The mixture was stirred at 90° C. for 12 h. Water (80 mL) was poured into the mixture and stirred for 1 min. The aqueous fraction was extracted with tetrahydrofuran (3×20 mL). The combined organic fractions were washed with saturated aqueous sodium chloride (2×20 mL), dried over sodium sulfate, filtered, and concentrated. Purification of the residue by column chromatography (1:0 to 1:30 methanol:dichloromethane) afforded 1-cyclopropyl-N-[3-[1-(2,6-dichlorobenzoyl)-5-[4-[4-(dimethoxymethyl)-1-piperidyl]phenyl]pyrrolo[2,3-b]pyridine-3-carbonyl]-2,4-difluoro-phenyl]methanesulfonamide (250 mg, 80%) as a yellow solid. MS (ESI): m/z 797.2 [M+H]$^+$.

Step D: 1-cyclopropyl-N-[3-[5-[4-[4-(dimethoxymethyl)-1-piperidyl]phenyl]-1H-pyrrolo[2,3-b]pyridine-3-carbonyl]-2,4-difluoro-phenyl]methanesulfonamide

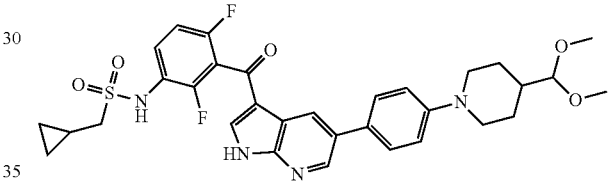

To a solution of 1-cyclopropyl-N-[3-[1-(2,6-dichlorobenzoyl)-5-[4-[4-(dimethoxymethyl)-1-piperidyl]phenyl]pyrrolo[2,3-b]pyridine-3-carbonyl]-2,4-difluoro-phenyl]methanesulfonamide (250 mg, 0.31 mmol) in methanol (5 mL) was added 25% aqueous ammonium hydroxide (5.0 mL, 32.5 mmol). The mixture was stirred at 20° C. for 11 h. The reaction mixture concentrated. Purification of the residue by silica gel column chromatography (0:1 to 1:20 methanol:dichloromethane) afforded 1-cyclopropyl-N-[3-[5-[4-[4-(dimethoxymethyl)-1-piperidyl]phenyl]-1H-pyrrolo[2,3-b]pyridine-3-carbonyl]-2,4-difluoro-phenyl]methanesulfonamide (180 mg, 91%) as a yellow solid. MS (ESI): m/z 625.3 [M+H]$^+$.

Step E: 3-[2,6-difluoro-3-[[cyclopropyl(methyl)sulfamoyl]amino]benzoyl]-5-[4-(4-formyl-1-piperidyl)phenyl]-1H-pyrrolo[2,3-b]pyridine

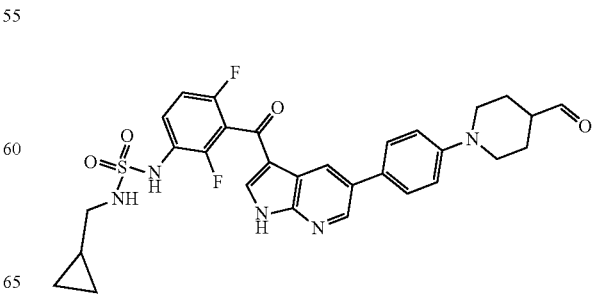

To a solution of 1-cyclopropyl-N-[3-[5-[4-[4-(dimethoxymethyl)-1-piperidyl]phenyl]-1H-pyrrolo[2,3-b]pyridine-3-carbonyl]-2,4-difluoro-phenyl]methanesulfonamide (180 mg, 0.28 mmol) in tetrahydrofuran (5 mL) was added aqueous 2 M sulfuric acid (5 mL). The mixture was stirred at 70° C. for 0.5 h. The reaction pH was adjusted to 8 with saturated aqueous sodium bicarbonate. The aqueous fraction was extracted with tetrahydrofuran (3×20 mL). The combined organic fractions were washed with saturated aqueous sodium chloride (1×20 mL), dried over sodium sulfate, filtered, and concentrated to afford crude 1-cyclopropyl-N-[2,4-difluoro-3-[5-[4-(4-formyl-1-piperidyl)phenyl]-1H-pyrrolo[2,3-b]pyridine-3-carbonyl]phenyl]methanesulfonamide (160 mg) as a yellow solid. MS (ESI): m/z 597.3 [M+H$_2$O]$^+$.

Step F: 1-cyclopropyl-N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2,4-difluorophenyl}methanesulfonamide

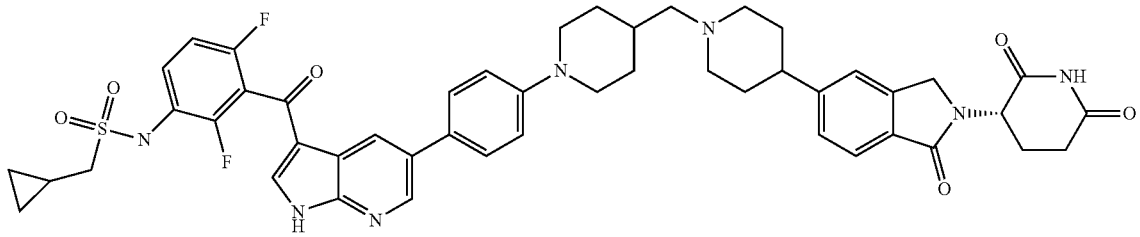 [SMILES: O=C1CC[C@H](N2Cc3cc(C4CCN(CC5CCN(c6ccc(-c7cnc8[nH]cc(C(=O)c9c(F)ccc(NS(=O)(=O)CC%10CC%10)c9F)c8c7)cc6)CC5)CC4)ccc3C2=O)C(=O)N1]

To a solution of (3S)-3-[1-oxo-5-(4-piperidyl)isoindolin-2-yl]piperidine-2,6-dione [(1R,4S)-7,7-dimethyl-2-oxo-norbornan-1-yl]methanesulfonic acid salt (80 mg, 0.14 mmol) in dichloromethane (2 mL) and isopropanol (2 mL) was added sodium acetate (8 mg, 0.10 mmol), the mixture was stirred at 30° C. for 15 min. 1-cyclopropyl-N-[2,4-difluoro-3-[5-[4-(4-formyl-1-piperidyl)phenyl]-1H-pyrrolo[2,3-b]pyridine-3-carbonyl]phenyl]methanesulfonamide (82 mg, 0.14 mmol) was added to the mixture and stirred at 30° C. for 15 min. Sodium triacetoxyborohydride (90 mg, 0.42 mmol) was added to the mixture, and the mixture was stirred at 30° C. for 0.5 h and then concentrated. Purification of the residue by preparative HPLC (Phenomenex Synergi C18, 16 to 36% acetonitrile:(0.225% formic acid in water)) afforded 1-cyclopropyl-N-[3-[5-[4-[4-[[4-[2-[(3S)-2,6-dioxo-3-piperidyl]-1-oxo-isoindolin-5-yl]-1-piperidyl]methyl]-1-piperidyl]phenyl]-1H-pyrrolo[2,3-b]pyridine-3-carbonyl]-2,4-difluoro-phenyl]methanesulfonamide formic acid salt (55.3 mg, 41%) as a yellow solid. MS (ESI): m/z 890.3 [M+H]$^+$; $^1$H NMR (400 MHz, DMSO-d$_6$) δ 12.98-12.84 (m, 1H), 10.97 (s, 1H), 8.65 (s, 1H), 8.60-8.50 (m, 1H), 8.16 (s, 1H), 8.14 (s, 1H), 7.68-7.55 (m, 4H), 7.51 (s, 1H), 7.41 (d, J=7.6 Hz, 1H), 7.26 (t, J=8.8 Hz, 1H), 7.07 (d, J=8.8 Hz, 2H), 5.10 (dd, J=5.2, 13.2 Hz, 1H), 4.48-4.38 (m, 1H), 4.36-4.26 (m, 1H), 3.80 (d, J=12.4 Hz, 2H), 3.13 (d, J=7.2 Hz, 2H), 3.05 (d, J=9.6 Hz, 2H), 2.97-2.70 (m, 4H), 2.68-2.57 (m, 2H), 2.39 (dd, J=4.8, 13.2 Hz, 1H), 2.31 (d, J=6.0 Hz, 2H), 2.19-2.08 (m, 2H), 2.04-1.95 (m, 1H), 1.88-1.73 (m, 7H), 1.30-1.22 (m, 2H), 1.08-1.03 (m, 1H), 0.61-0.51 (m, 2H), 0.39-0.29 (m, 2H).

Exemplary Synthesis of Exemplary Compound 207: (3R)—N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-4-fluoro-2-methoxyphenyl}-3-fluoropyrrolidine-1-sulfonamide (Compound 207)

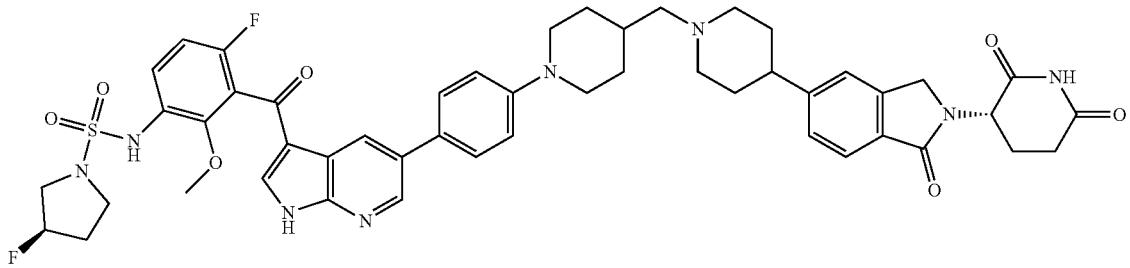 [SMILES: COc1c(NS(=O)(=O)N2CC[C@@H](F)C2)ccc(F)c1C(=O)c1c[nH]c2ncc(-c3ccc(N4CCC(CN5CCC(c6ccc7c(c6)CN([C@H]6CCC(=O)NC6=O)C7=O)CC5)CC4)cc3)cc12]

Step A: 5-bromo-3-(6-fluoro-2-methoxy-3-nitrobenzoyl)-1H-pyrrolo[2,3-b]pyridine

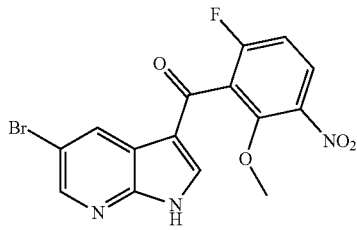 [SMILES: COc1c([N+](=O)[O-])ccc(F)c1C(=O)c1c[nH]c2ncc(Br)cc12]

To a mixture of 5-bromo-3-(2,6-difluoro-3-nitrobenzoyl)-1H-pyrrolo[2,3-b]pyridine (10 g, 26.2 mmol) in methanol (100 mL) was added sodium methoxide (8.48 g, 157 mmol) in portions at 0° C. The resulting mixture was stirred overnight at 30° C. The mixture was acidified to pH 8 with concentrated hydrochloric acid and then extracted with tetrahydrofuran (3×100 mL). The combined organic fractions were washed with saturated aqueous sodium chloride (100 mL), dried over sodium sulfate, filtered, and concentrated. Purification of the residue by silica gel column chromatography, (3:7 ethyl acetate:petroleum ether) afforded 5-bromo-3-(6-fluoro-2-methoxy-3-nitrobenzoyl)-1H-pyrrolo[2,3-b]pyridine (1.95 g, 19%) as a yellow solid. MS (ESI): m/z 393.90, 395.90 [M−H]−; $^1$H NMR (300 MHz, DMSO-$d_6$) δ 13.11 (s, 1H), 8.64 (d, J=2.3 Hz, 1H), 8.51 (d, J=2.3 Hz, 1H), 8.33 (s, 1H), 8.23 (dd, J=9.2, 6.0 Hz, 1H), 7.39 (dd, J=9.2, 8.1 Hz, 1H), 3.76 (s, 3H).

Step B: (3-amino-6-fluoro-2-methoxyphenyl)(5-bromo-1H-pyrrolo[2,3-b]pyridin-3-yl)methanone

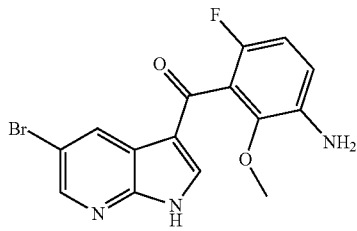 [SMILES: COc1c(N)ccc(F)c1C(=O)c1c[nH]c2ncc(Br)cc12]

To a solution of 5-bromo-3-(6-fluoro-2-methoxy-3-nitrobenzoyl)-1H-pyrrolo[2,3-b]pyridine (1.95 g, 4.95 mmol) in ethanol (20 mL), tetrahydrofuran (20 mL), and 12 M aqueous hydrochloric acid (1 mL) was added iron powder (1.66 g, 29.7 mmol). The resulting mixture was stirred for 2 h at 50° C., cooled to room temperature, and then concentrated. Ice water (200 mL) was added to the residue. The precipitated solids were collected by filtration, washed with water (2×100 mL), and dried in a vacuum oven to afford (3-amino-6-fluoro-2-methoxyphenyl)(5-bromo-1H-pyrrolo[2,3-b]pyridin-3-yl)methanone (1.55 g, 86%) as a light yellow solid. MS (ESI): m/z 364.05, 366.05 [M+H]+.

Step C: 3-[5-bromo-1-(2,6-dichlorobenzoyl)pyrrolo[2,3-b]pyridine-3-carbonyl]-4-fluoro-2-methoxyaniline

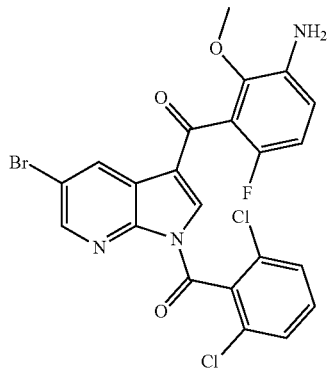 [SMILES: COc1c(N)ccc(F)c1C(=O)c1cn(C(=O)c2c(Cl)cccc2Cl)c2ncc(Br)cc12]

To a mixture of 3-{5-bromo-1H-pyrrolo[2,3-b]pyridine-3-carbonyl}-4-fluoro-2-methoxyaniline (1.5 g, 4.12 mmol) and 2,6-dichlorobenzoyl chloride (0.86 g, 4.12 mmol) in tetrahydrofuran (50 mL) was added 4-dimethylaminopyridine (0.050 g, 0.41 mmol) and triethylamine (0.83 g, 8.2 mmol) at 0° C. The resulting mixture was stirred for 0.5 h at room temperature. The mixture was extracted with ethyl acetate (3×100 mL). The combined organic fractions were washed with saturated aqueous sodium chloride (100 mL), dried over sodium sulfate, filtered, and concentrated. Purification of the residue by silica gel column chromatography, (1:4 tetrahydrofuran:petroleum ether) afforded 3-[5-bromo-1-(2,6-dichlorobenzoyl)pyrrolo[2,3-b]pyridine-3-carbonyl]-4-fluoro-2-methoxyaniline (1.2 g, 54%) as an off-white solid. MS (ESI): m/z 536.05, 538.05 [M+H]+.

Step D: N-{3-[5-bromo-1-(2,6-dichlorobenzoyl)pyrrolo[2,3-b]pyridine-3-carbonyl]-4-fluoro-2-methoxyphenyl}-2-oxo-1,3-oxazolidine-3-sulfonamide

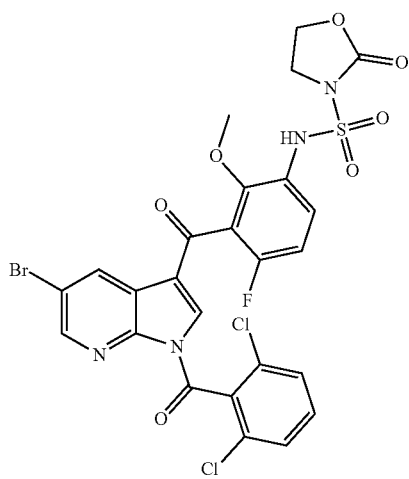 [SMILES: COc1c(NS(=O)(=O)N2CCOC2=O)ccc(F)c1C(=O)c1cn(C(=O)c2c(Cl)cccc2Cl)c2ncc(Br)cc12]

To a mixture of 2-bromoethanol (0.33 g, 2.68 mmol) in dichloromethane (100 mL) was added chlorosulfonyl isocyanate (0.38 g, 2.68 mmol) dropwise at 0° C. The resulting mixture was stirred for 30 min at 0° C. Then 3-[5-bromo-1-(2,6-dichlorobenzoyl)pyrrolo[2,3-b]pyridine-3-carbonyl]-4-fluoro-2-methoxyaniline (1.2 g, 2.234 mmol) and triethylamine (0.68 g, 6.702 mmol) were added dropwise over 15 min at 0° C. The resulting mixture was stirred overnight at 35° C. and was then extracted with dichloromethane (3×100 mL). The combined organic fractions were washed with saturated aqueous sodium chloride (100 mL), dried over sodium sulfate, filtered, and concentrated. Purification of the residue by silica gel column chromatography, (2:1 ethyl acetate:petroleum ether) afforded N-{3-[5-bromo-1-(2,6-dichlorobenzoyl)pyrrolo[2,3-b]pyridine-3-carbonyl]-4-fluoro-2-methoxyphenyl}-2-oxo-1,3-oxazolidine-3-sulfonamide (675 mg, 44%) as a white solid. MS (ESI): m/z 685.00, 687.00 [M+H]$^+$.

Step E: (R)—N-(3-(5-bromo-1-(2,6-dichlorobenzoyl)-1H-pyrrolo[2,3-b]pyridine-3-carbonyl)-4-fluoro-2-methoxyphenyl)-3-fluoropyrrolidine-1-sulfonamide

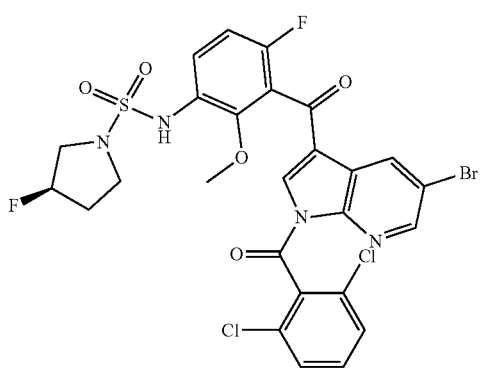 [SMILES: COc1c(NS(=O)(=O)N2CC[C@@H](F)C2)ccc(F)c1C(=O)c1cn(C(=O)c2c(Cl)cccc2Cl)c2ncc(Br)cc12]

To a mixture of (3R)-3-fluoropyrrolidine hydrochloride (356 mg, 2.83 mmol) in 1,4-dioxane (30 mL) was added diisopropylethylamine (606 mg, 4.70 mmol). The resulting mixture was stirred for 1 h at room temperature. Then N-{3-[5-bromo-1-(2,6-dichlorobenzoyl)pyrrolo[2,3-b]pyridine-3-carbonyl]-4-fluoro-2-methoxyphenyl}-2-oxo-1,3-oxazolidine-3-sulfonamide (650 mg, 0.94 mmol) was added. The resulting mixture stirred for 2 h at 85° C. in a sealed tube. The mixture then cooled to room temperature, diluted with water, and extracted with ethyl acetate (3×100 mL). The combined organic fractions were concentrated. Purification of the residue by preparative HPLC (C18 column, 35 to 65% tetrahydrofuran:water) afforded (R)—N-(3-(5-bromo-1-(2,6-dichlorobenzoyl)-1H-pyrrolo[2,3-b]pyridine-3-carbonyl)-4-fluoro-2-methoxyphenyl)-3-fluoropyrrolidine-1-sulfonamide (543 mg, 83%) as a light yellow solid. MS (ESI): m/z 687.05, 689.05 [M+H]$^+$.

Step F: (R)—N-(3-(5-bromo-1H-pyrrolo[2,3-b]pyridine-3-carbonyl)-4-fluoro-2-methoxyphenyl)-3-fluoropyrrolidine-1-sulfonamide

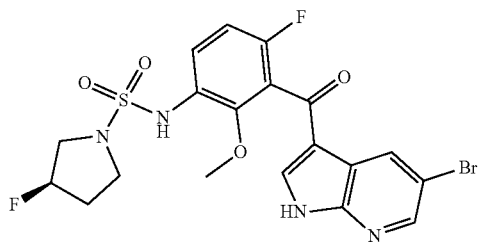 [SMILES: COc1c(NS(=O)(=O)N2CC[C@@H](F)C2)ccc(F)c1C(=O)c1c[nH]c2ncc(Br)cc12]

To a mixture of (R)—N-(3-(5-bromo-1-(2,6-dichlorobenzoyl)-1H-pyrrolo[2,3-b]pyridine-3-carbonyl)-4-fluoro-2-methoxyphenyl)-3-fluoropyrrolidine-1-sulfonamide (540 mg, 0.785 mmol) in methanol (5 mL) was added ammonium hydroxide (5 mL). The resulting mixture was stirred for 2 h at 30° C. and then concentrated to afford (R)—N-(3-(5-bromo-1H-pyrrolo[2,3-b]pyridine-3-carbonyl)-4-fluoro-2-methoxyphenyl)-3-fluoropyrrolidine-1-sulfonamide (359 mg, 89%) as a white solid. MS (ESI): m/z 515.05, 517.05 [M+H]$^+$; $^1$H NMR (300 MHz, DMSO-d$_6$) δ 13.02 (s, 1H), 9.38 (s, 1H), 8.27-8.46 (m, 2H), 8.1-8.0 (m, 2H), 7.80 (s, 1H), 7.59-7.34 (m, 3H), 7.12 (t, J=8.8 Hz, 1H), 5.41-5.23 (m, 1H), 4.03 (q, J=7.1 Hz, 1H), 3.66 (s, 3H), 3.53 (d, J=2.2 Hz, 1H), 3.46-3.31 (m, 2H), 2.19-2.03 (m, 2H), 1.17 (t, J=7.1 Hz, 1H).

Step G: (R)—N-(3-(5-(4-(4-(dimethoxymethyl)piperidin-1-yl)phenyl)-1H-pyrrolo[2,3-b]pyridine-3-carbonyl)-4-fluoro-2-methoxyphenyl)-3-fluoropyrrolidine-1-sulfonamide

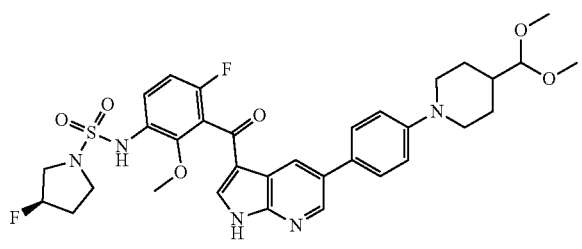 [SMILES: COc1c(NS(=O)(=O)N2CC[C@@H](F)C2)ccc(F)c1C(=O)c1c[nH]c2ncc(-c3ccc(N4CCC(C(OC)OC)CC4)cc3)cc12]

To solution of (R)—N-(3-(5-bromo-1H-pyrrolo[2,3-b]pyridine-3-carbonyl)-4-fluoro-2-methoxyphenyl)-3-fluoropyrrolidine-1-sulfonamide (280 mg, 0.54 mmol) and 4-(dimethoxymethyl)-1-[4-(4,4,5,5-tetramethyl-1,3,2-dioxaborolan-2-yl)phenyl]piperidine (236 mg, 0.65 mmol) in 1,4-dioxane (6 mL) and water (1 mL) was added cesium fluoride (246 mg, 1.6 mmol) and [1,1'-bis(di-tert-butylphosphino)ferrocene]dichloropalladium(II) (33 mg, 0.05 mmol) in portions at room temperature. The resulting mixture was stirred for 2 h at 100° C. Purification of the residue by silica gel column chromatography (1:12 methanol:dichloromethane) afforded (R)—N-(3-(5-(4-(4-(dimethoxymethyl)piperidin-1-yl)phenyl)-1H-pyrrolo[2,3-b]pyridine-3-carbonyl)-4-fluoro-2-methoxyphenyl)-3-fluoropyrrolidine-1-sulfonamide (212 mg, 67%) as a yellow solid. MS (ESI): m/z 670.03 [M+H]$^+$.

Step H: (R)-3-fluoro-N-(4-fluoro-3-(5-(4-(4-formylpiperidin-1-yl)phenyl)-1H-pyrrolo[2,3-b]pyridine-3-carbonyl)-2-methoxyphenyl)pyrrolidine-1-sulfonamide

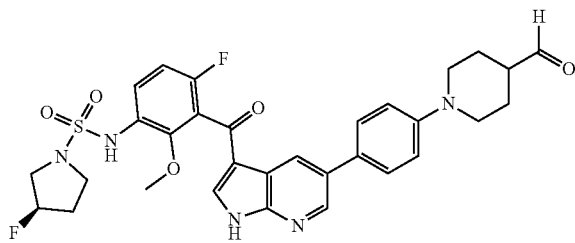 [SMILES: COc1c(NS(=O)(=O)N2CC[C@@H](F)C2)ccc(F)c1C(=O)c1c[nH]c2ncc(-c3ccc(N4CCC(C=O)CC4)cc3)cc12]

To a mixture of (R)—N-(3-(5-(4-(4-(dimethoxymethyl)piperidin-1-yl)phenyl)-1H-pyrrolo[2,3-b]pyridine-3-carbo-nyl)-4-fluoro-2-methoxyphenyl)-3-fluoropyrrolidine-1-sulfonamide (212 mg, 0.32 mmol) in tetrahydrofuran (10 mL) was added 2 M aqueous sulfuric acid (5 mL) in portions. The reaction was stirred for 1 h at 70° C. The mixture was basified to pH 8 with saturated aqueous sodium bicarbonate and extracted with ethyl acetate (3×100 mL). The combined organic fractions were washed with saturated aqueous sodium chloride (2×50 mL), dried over sodium sulfate, filtered, and concentrated to afford (R)-3-fluoro-N-(4-fluoro-3-(5-(4-(4-formylpiperidin-1-yl)phenyl)-1H-pyrrolo[2,3-b]pyridine-3-carbonyl)-2-methoxyphenyl)pyrrolidine-1-sulfonamide (183 mg, 93%) as a yellow oil. MS (ESI): m/z 624.25 [M+H]⁺.

Step I: (3R)—N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-4-fluoro-2-methoxyphenyl}-3-fluoropyrrolidine-1-sulfonamide

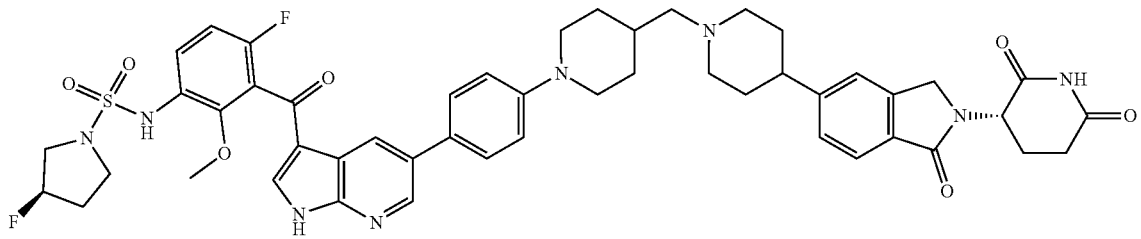 [SMILES: COc1c(NS(=O)(=O)N2CC[C@@H](F)C2)ccc(F)c1C(=O)c1c[nH]c2ncc(-c3ccc(N4CCC(CN5CCC(c6ccc7c(c6)CN([C@H]6CCC(=O)NC6=O)C7=O)CC5)CC4)cc3)cc12]

To a mixture of (3S)-3-[1-oxo-5-(piperidin-4-yl)-3H-isoindol-2-yl]piperidine-2,6-dione [(1R)-7,7-dimethyl-2-oxobicyclo[2.2.1]heptan-1-yl]methanesulfonic acid salt (100 mg, 0.179 mmol) in isopropanol (10 mL) and dichloromethane (10 mL) was added sodium acetate (11.0 mg, 0.134 mmol). The mixture was stirred for 30 min at room temperature. Then (3R)-3-fluoro-N-(4-fluoro-3-{5-[4-(4-formylpiperidin-1-yl)phenyl]-1H-pyrrolo[2,3-b]pyridine-3-carbonyl}-2-methoxyphenyl)pyrrolidine-1-sulfonamide (133.72 mg, 0.215 mmol) was added, and the mixture stirred for 1 h at room temperature. Then sodium triacetoxyborohydride (75.7 mg, 0.358 mmol) was added and the reaction stirred for 2 h at room temperature. The mixture was acidified to pH 8 with saturated aqueous sodium bicarbonate and extracted with tetrahydrofuran (3×100 mL). The combined organic fractions were washed with saturated aqueous sodium chloride (2×100 mL), dried over sodium sulfate, filtered, and concentrated. Purification of the residue by preparative TLC (1:8 methanol:dichloromethane) afforded (3R)—N-{3-[5-(4-{4-[(4-{2-[(3S)-2,6-dioxopiperidin-3-yl]-1-oxo-3H-isoindol-5-yl}piperidin-1-yl)methyl]piperidin-1-yl}phenyl)-1H-pyrrolo[2,3-b]pyridine-3-carbonyl]-4-fluoro-2-methoxyphenyl}-3-fluoropyrrolidine-1-sulfonamide (50.1 mg, 30%) as a yellow solid. MS (ESI): m/z 935.10 [M+H]⁺; ¹H NMR (400 MHz, DMSO-$d_6$) δ 12.81 (s, 1H), 10.98 (s, 1H), 9.32 (s, 1H), 8.65 (d, J=2.3 Hz, 1H), 8.52 (s, 1H), 7.91 (s, 1H), 7.66 (d, J=7.8 Hz, 1H), 7.59 (dd, J=8.8, 6.2 Hz, 4H), 7.51 (s, 1H), 7.41 (d, J=7.9 Hz, 1H), 7.18-7.01 (m, 3H), 5.39-5.24 (m, 1H), 5.11 (dd, J=13.3, 5.1 Hz, 1H), 4.43 (d, J=17.2 Hz, 1H), 4.30 (d, J=17.2 Hz, 1H), 3.90-3.77 (m, 2H), 3.64-3.56 (m, 3H), 3.00 (s, 1H), 2.91-2.75 (m, 3H), 2.60 (d, J=17.1 Hz, 2H), 2.40 (dd, J=12.9, 4.5 Hz, 1H), 2.10-1.97 (m, 7H), 1.21-0.89 (m, 5H).

Exemplary Synthesis of Exemplary Compound 208: (3S)-3-(5-{1-[(1-{4-[3-(2,6-difluoro-3-{[methyl(propan-2-yl)sulfamoyl]amino}benzoyl)-1H-pyrrolo[2,3-b]pyridin-5-yl]phenyl}piperidin-4-yl)methyl]piperidin-4-yl}-1-oxo-2,3-dihydro-1H-isoindol-2-yl)piperidine-2,6-dione (Compound 208)

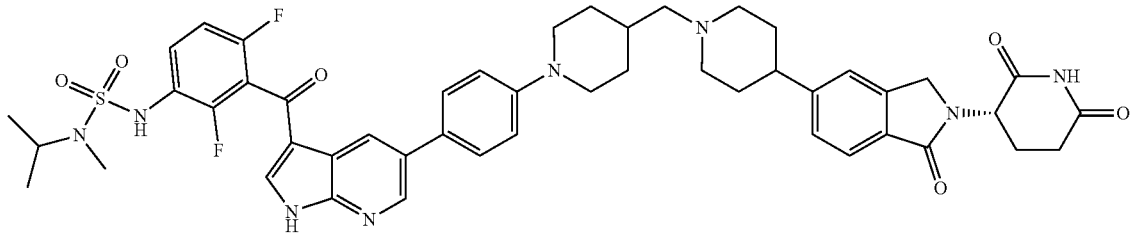 [SMILES: CC(C)N(C)S(=O)(=O)Nc1ccc(F)c(C(=O)c2c[nH]c3ncc(-c4ccc(N5CCC(CN6CCC(c7ccc8c(c7)CN([C@H]7CCC(=O)NC7=O)C8=O)CC6)CC5)cc4)cc23)c1F]

Step A: 5-bromo-1-(2,6-dichlorobenzoyl)-3-[2,6-difluoro-3-[[isopropyl(methyl)sulfamoyl]amino]benzoyl]pyrrolo[2,3-b]pyridine

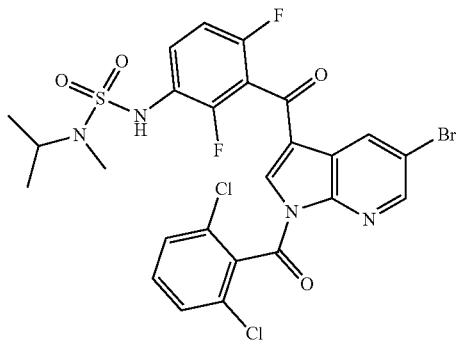 [SMILES: CC(C)N(C)S(=O)(=O)Nc1ccc(F)c(C(=O)c2cn(C(=O)c3c(Cl)cccc3Cl)c3ncc(Br)cc23)c1F]

To a cooled (−50° C.) solution of (3-amino-2,6-difluorophenyl)-[5-bromo-1-(2,6-dichlorobenzoyl)pyrrolo[2,3-b]pyridin-3-yl]methanone (500 mg, 0.95 mmol) and triethylamine (1.19 mL, 8.52 mmol) in dichloromethane (15 mL) was added sulfuryl chloride (308 mg, 2.29 mmol) and the reaction stirred at −50° C. for 0.5 h. Then triethylamine (1.33 mL, 9.52 mmol) and N-methylpropan-2-amine (208 mg, 2.86 mmol) in dichloromethane (3 mL) was added and the reaction stirred a further 0.5 h at −50° C. Water (80 mL) was added and the mixture stirred for 1 min. The aqueous fraction was extracted with dichloromethane (3×30 mL). The combined organic fractions were washed with saturated aqueous sodium chloride (2×30 mL), dried over sodium sulfate, filtered, and concentrated to afford crude 5-bromo-1-(2,6-dichlorobenzoyl)-3-[2,6-difluoro-3-[[isopropyl(methyl)sulfamoyl]amino]benzoyl]pyrrolo[2,3-b]pyridine (500 mg) as a yellow solid. MS (ESI): m/z 660.9 [M]+.

Step B: 5-bromo-3-[2,6-difluoro-3-[[isopropyl(methyl)sulfamoyl]amino]benzoyl]-1H-pyrrolo[2,3-b]pyridine

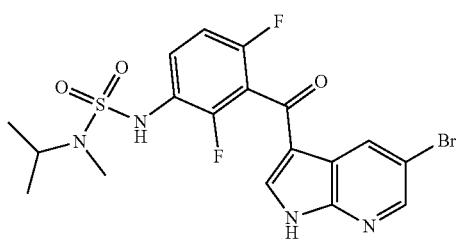 [SMILES: CC(C)N(C)S(=O)(=O)Nc1ccc(F)c(C(=O)c2c[nH]c3ncc(Br)cc23)c1F]

To a solution of 5-bromo-1-(2,6-dichlorobenzoyl)-3-[2,6-difluoro-3-[[isopropyl(methyl) sulfamoyl]amino]benzoyl]pyrrolo[2,3-b]pyridine (500 mg, 0.75 mmol) in methanol (15 mL) was added 25% aqueous ammonium hydroxide (14.68 mL, 95.30 mmol). The mixture was stirred at 15° C. for 2 h and then concentrated. Purification of the residue by silical gel column chromatography (1:50 to 1:1 petroleum ether:ethyl acetate) afforded 5-bromo-3-[2,6-difluoro-3-[[isopropyl(methyl)sulfamoyl]amino]benzoyl]-1H-pyrrolo[2,3-b]pyridine (350 mg, 94%) as a yellow solid. MS (ESI): m/z 487.1 [M]+.

Step C: 3-[2,6-difluoro-3-[[isopropyl(methyl)sulfamoyl]amino]benzoyl]-5-[4-[4-(dimethoxymethyl)-1-piperidyl]phenyl]-1H-pyrrolo[2,3-b]pyridine

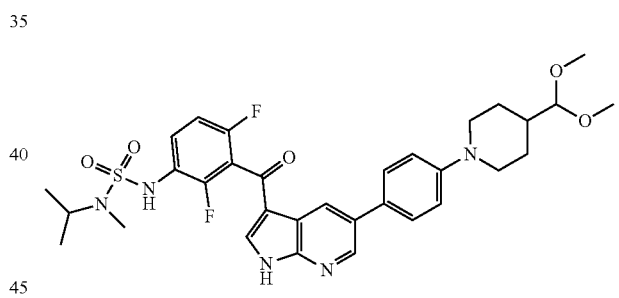

To a solution of 5-bromo-3-[2,6-difluoro-3-[[isopropyl(methyl)sulfamoyl]amino]benzoyl]-1H-pyrrolo[2,3-b]pyridine (250 mg, 0.51 mmol) and 4-(dimethoxymethyl)-1-[4-(4,4,5,5-tetramethyl-1,3,2-dioxaborolan-2-yl)phenyl]piperidine (185 mg, 0.51 mmol) in 1,4-dioxane (10 mL) and water (1 mL) was added cesium fluoride (311 mg, 2.05 mmol, 75.66 uL) and bis(di-tert-butyl(4-dimethylaminophenyl)phosphine)dichloropalladium(II) (36 mg, 0.051 mmol). The mixture was stirred at 90° C. for 12 h. Water (50 mL) was poured into the mixture and stirred for 1 min. The aqueous fraction was extracted with ethyl acetate (3×10 mL). The combined organic fractions were washed with saturated aqueous sodium chloride (2×10 mL), dried over sodium sulfate, filtered, and concentrated. Purification of the residue by silica gel column chromatography (0:1 to 1:30 methanol:dichloromethane) afforded 3-[2,6-difluoro-3-[[isopropyl(methyl)sulfamoyl]amino]benzoyl]-5-[4-[4-(dimethoxymethyl)-1-piperidyl]phenyl]-1H-pyrrolo[2,3-b]pyridine (170 mg, 51%) as a yellow solid. MS (ESI): m/z 642.2 [M+H]+.

Step D: 3-[2,6-difluoro-3-[[isopropyl(methyl)sulfa-moyl]amino]benzoyl]-5-[4-(4-formyl-1-piperidyl)phenyl]-1H-pyrrolo[2,3-b]pyridine

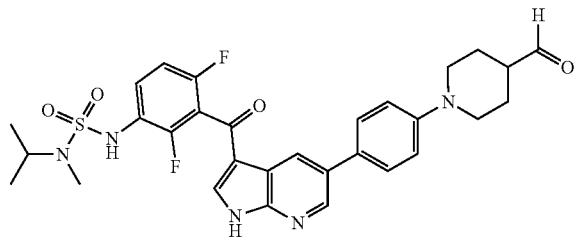 [SMILES: CC(C)N(C)S(=O)(=O)Nc1ccc(F)c(C(=O)c2c[nH]c3ncc(-c4ccc(N5CCC(C=O)CC5)cc4)cc23)c1F]

To a solution of 3-[2,6-difluoro-3-[[isopropyl(methyl)sulfamoyl]amino]benzoyl]-5-[4-[4-(dimethoxymethyl)-1-piperidyl]phenyl]-1H-pyrrolo[2,3-b]pyridine (170 mg, 0.26 mmol) in tetrahydrofuran (5 mL) was added aqueous 2 M sulfuric acid (5 mL). The mixture was stirred at 70° C. for 0.5 h. The reaction mixture was adjusted pH to 9 with saturated aqueous sodium bicarbonate. Water (80 mL) was poured into the mixture and stirred for 1 min. The aqueous fraction was extracted with sulfuric acid (3×20 mL). The combined organic fractions were washed with saturated aqueous sodium chloride (2×20 mL), dried over sodium sulfate, filtered, and concentrated. Purification of the residue by silica gel column chromatography (0:1 to 1:20 methanol:dichloromethane) afforded 3-[2,6-difluoro-3-[[isopropyl(methyl)sulfamoyl]amino]benzoyl]-5-[4-(4-formyl-1-piperidyl)phenyl]-1H-pyrrolo[2,3-b]pyridine (100 mg, 63%) as a yellow solid. MS (ESI): m/z 596.3 [M+H]$^+$.

Step E: (3S)-3-(5-{1-[(1-{4-[3-(2,6-difluoro-3-{[methyl(propan-2-yl)sulfamoyl]amino}benzoyl)-1H-pyrrolo[2,3-b]pyridin-5-yl]phenyl}piperidin-4-yl)methyl]piperidin-4-yl}-1-oxo-2,3-dihydro-1H-isoindol-2-yl)piperidine-2,6-dione

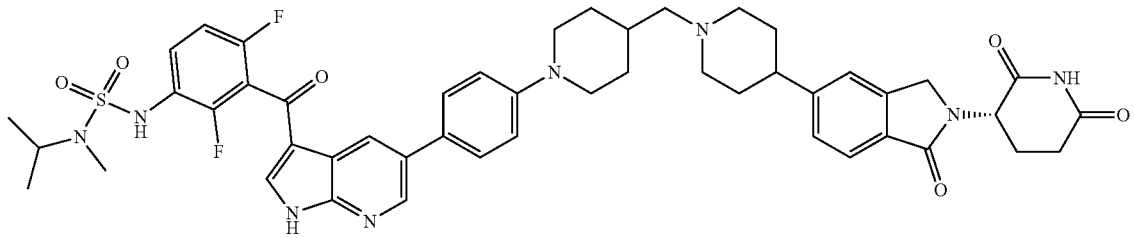 [SMILES: CC(C)N(C)S(=O)(=O)Nc1ccc(F)c(C(=O)c2c[nH]c3ncc(-c4ccc(N5CCC(CN6CCC(c7ccc8c(c7)CN([C@H]7CCC(=O)NC7=O)C8=O)CC6)CC5)cc4)cc23)c1F]

To a solution of (3S)-3-[1-oxo-5-(4-piperidyl)isoindolin-2-yl]piperidine-2,6-dione [(1R,4S)-7,7-dimethyl-2-oxo-norbornan-1-yl]methanesulfonic acid salt (60 mg, 0.10 mmol) in dichloromethane (2 mL) and isopropanol (2 mL) was added sodium acetate (6.0 mg, 0.075 mmol). The mixture was stirred at 30° C. for 15 min. 3-[2,6-difluoro-3-[[isopropyl (methyl)sulfamoyl]amino]benzoyl]-5-[4-(4-formyl-1-piperidyl)phenyl]-1H-pyrrolo[2,3-b]pyridine (63 mg, 0.10 mmol) was added and the mixture stirred at 30° C. for 15 min. Sodium triacetoxyborohydride (68 mg, 0.32 mmol) was added, and the mixture was stirred at 30° C. for 0.5 h and then concentrated. Purification of the residue by preparative HPLC (Phenomenex Synergi C18, 14% to 43% acetonitrile:(0.225% formic acid in water)) afforded 3-[2,6-difluoro-3-[[isopropyl(methyl)sulfamoyl]amino]benzoyl]-5-[4-[4-[[4-2-[(3S)-2,6-dioxo-3-piperidyl]-1-oxo-isoindolin-5-yl]-1-piperidyl]methyl]-1-piperidyl]phenyl]-1H-pyrrolo[2,3-b]pyridine formic acid salt (83.7 mg, 79%) as a yellow solid. MS (ESI): m/z 907.2 [M+H]$^+$; $^1$H NMR (400 MHz, DMSO-d$_6$) δ 13.06-12.84 (m, 1H), 11.00 (s, 1H), 8.65 (d, J=2.0 Hz, 1H), 8.58-8.49 (m, 1H), 8.15 (s, 1H), 8.07 (s, 1H), 7.65 (d, J=7.6 Hz, 1H), 7.62-7.49 (m, 4H), 7.41 (d, J=7.6 Hz, 1H), 7.27 (t, J=8.0 Hz, 1H), 7.07 (d, J=8.8 Hz, 2H), 5.11 (dd, J=5.2, 13.2 Hz, 1H), 4.46-4.39 (m, 1H), 4.34-4.24 (m, 1H), 3.95 (td, J=6.8, 13.2 Hz, 1H), 3.80 (d, J=12.0 Hz, 2H), 3.02 (d, J=11.2 Hz, 3H), 2.93-2.85 (m, 1H), 2.74 (t, J=11.6 Hz, 2H), 2.68-2.64 (m, 1H), 2.57 (s, 2H), 2.55-2.52 (m, 1H), 2.47-2.39 (m, 1H), 2.39-2.31 (m, 1H), 2.26 (d, J=7.2 Hz, 2H), 2.11-1.95 (m, 3H), 1.87-1.71 (m, 7H), 1.31-1.19 (m, 2H), 1.01 (d, J=6.8 Hz, 6H).

Exemplary Synthesis of Exemplary Compound 209: (3R)—N-{3-[5-(4-{4-[4-({1-[2-(2,6-dioxopiperidin-3-yl)-1-oxo-2,3-dihydro-1H-isoindol-5-yl]azetidin-3-yl}methyl)piperazin-1-yl]piperidin-1-yl}phenyl)-1H-pyrrolo[2,3-b]pyridine-3-carbonyl]-2,4-difluorophenyl}-3-fluoropyrrolidine-1-sulfonamide (Compound 209)

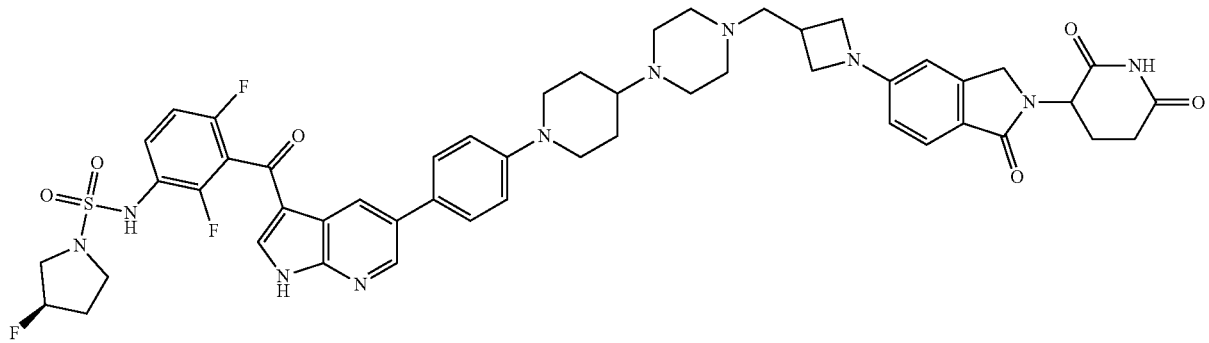 [SMILES: O=C1CCC(N2Cc3cc(N4CC(CN5CCN(C6CCN(c7ccc(-c8cnc9[nH]cc(C(=O)c%10c(F)ccc(NS(=O)(=O)N%11CC[C@@H](F)C%11)c%10F)c9c8)cc7)CC6)CC5)C4)ccc3C2=O)C(=O)N1]

Step A: azetidin-3-ylmethanol

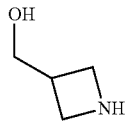

To a solution of tert-butyl 3-(hydroxymethyl)azetidine-1-carboxylate (4.7 g, 25.1 mmol) in dichloromethane (75 mL) was added trifluoroacetic acid (14 mL). The reaction was stirred at 15° C. for 12 h and then concentrated to afford crude azetidin-3-ylmethanol trifluoroacetic acid salt (10.1 g) as a colorless oil.

Step B: benzyl 3-(hydroxymethyl) azetidine-1-carboxylate

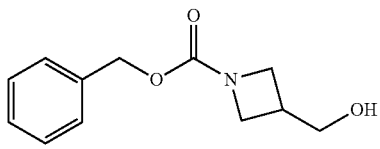 [SMILES: O=C(OCc1ccccc1)N1CC(CO)C1]

To a solution of azetidin-3-ylmethanol trifluoroacetic acid salt (10.1 g, 50.2) in N,N-dimethylformamide (120 mL) and water (30 mL) was added sodium carbonate (15.97 g, 150.6 mmol) at 0° C. Then benzyl chloroformate (21.41 g, 125.5 mmol) was added to the mixture at 0° C. The mixture was stirred at 15° C. for 12 h. Ethyl acetate (200 mL) and water (300 mL) were added and layers were separated. The aqueous fraction was extracted with ethyl acetate (200 mL). The combined organic fractions were washed with saturated aqueous sodium chloride (2×200 mL), dried over sodium sulfate, filtered, and concentrated. Purification of the residue by silica gel column chromatography (10% to 100% ethyl acetate:petroleum ether) afforded benzyl 3-(hydroxymethyl) azetidine-1-carboxylate (7.0 g, 58%) as a yellow oil. MS (ESI): m/z 308.4 [M+Na]+.

Step C: benzyl 3-formylazetidine-1-carboxylate

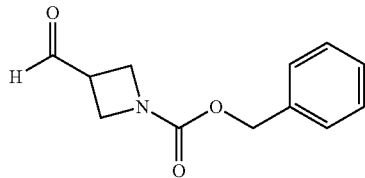 [SMILES: O=CC1CN(C(=O)OCc2ccccc2)C1]

To a cooled (−70° C.) solution of oxalyl chloride (24.3 mL, 278 mmol) in dichloromethane (160 mL) was added a solution of dimethylsulfoxide (21.7 mL, 278 mmol) in dichloromethane (100 mL). The mixture was stirred at −70° C. for 30 min, and then benzyl 3-(hydroxymethyl)azetidine-1-carboxylate (15.4 g, 69.6 mmol) in dichloromethane (80 mL) was added. The mixture was stirred at −70° C. for 60 min, and then triethylamine (77.5 mL, 557) was added. The reaction was stirred at 15° C. for 30 min. Dichloromethane (80 mL) and water (300 mL) were added and the layers were separated. The aqueous fraction was extracted with dichloromethane (150 mL). The combined organic extracts were washed with saturated aqueous sodium chloride (2×150 mL), dried over sodium sulfate, filtered, and concentrated. Purification of the residue by silica gel column chromatography (1:10 to 1:0 ethyl acetate:petroleum ether) afforded benzyl 3-formylazetidine-1-carboxylate (11.51 g, 75%) as a yellow oil. $^1$H NMR (400 MHz, DMSO-$d_6$) δ 9.74 (s, 1H), 7.45-7.24 (m, 5H), 5.09-4.96 (m, 2H), 4.11-3.97 (m, 2H), 3.96-3.68 (m, 2H), 3.56-3.46 (m, 1H).

Step D: benzyl 3-(dimethoxymethyl)azetidine-1-carboxylate

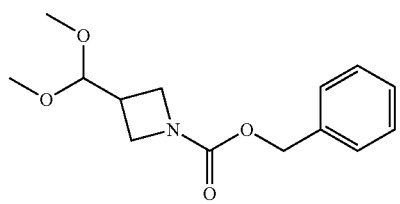 [SMILES: COC(OC)C1CN(C(=O)OCc2ccccc2)C1]

To a mixture of trimethoxymethane (32.50 mL, 296.5 mmol) and benzyl 3-formylazetidine-1-carboxylate (13 g, 59.3 mmol) in methanol (180 mL) was added p-toluenesulfonic acid monohydrate (564 mg, 2.96 mmol) in one portion at 15° C. under nitrogen. The mixture was stirred at 15° C. for 16 h. The reaction mixture was concentrated and then saturated aqueous sodium bicarbonate was added to adjust the pH to 8-9. The mixture was poured into water (200 mL) and stirred for 1 min. The aqueous fraction was extracted with ethyl acetate (2×200 mL). The combined organic fractions were washed with saturated aqueous sodium chloride (2×200 mL), dried over sodium sulfate, filtered, and concentrated. Purification of the residue by column chromatography (1:10 to 1:1 ethyl acetate:petroleum ether) afforded benzyl 3-(dimethoxymethyl)azetidine-1-carboxylate (7.8 g, 49%) as a colorless oil. $^1$H NMR (400 MHz, CDCl$_3$) δ 7.47-7.28 (m, 5H), 5.10 (s, 2H), 4.53 (d, J=6.8 Hz, 1H), 4.09-4.01 (m, 2H), 3.87 (dd, J=5.6, 8.8 Hz, 2H), 3.36 (s, 6H), 2.85 (dt, J=5.6, 6.8, 8.4 Hz, 1H)

Step E: 3-(dimethoxymethyl)azetidine

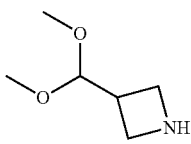

To a solution of benzyl 3-(dimethoxymethyl)azetidine-1-carboxylate (7.7 g, 29.0 mmol) in 2,2,2-trifluoroethanol (100 mL) was added 10% palladium on carbon (1.0 g, 3.5 mmol). The suspension was degassed under vacuum and purged with hydrogen (15 psi) several times. The mixture was stirred under hydrogen (15 psi) at 45° C. for 20 h. The reaction mixture was filtered and concentrated to afford crude 3-(dimethoxymethyl)azetidine (4.96 g) as a colorless oil. $^1$H NMR (400 MHz, CDCl$_3$) δ 4.59 (d, J=6.8 Hz, 1H), 3.93-3.87 (m, 1H), 3.70-3.63 (m, 2H), 3.61-3.54 (m, 2H), 3.34 (s, 6H), 3.09-2.95 (m, 1H).

Step F: methyl 2-bromo-4-[3-(dimethoxymethyl) azetidin-1-yl] benzoate

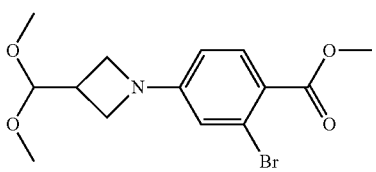 [SMILES: COC(=O)c1ccc(N2CC(C(OC)OC)C2)cc1Br]

To a solution of 3-(dimethoxymethyl)azetidine (0.50 g, 3.8 mmol) in dimethylsulfoxide (12 mL) was added N,N-diisopropylethylamine (1.33 mL, 7.62 mmol) and methyl 2-bromo-4-fluoro-benzoate (844 mg, 3.62 mmol). The mixture was stirred at 110° C. for 3 h. Ethyl acetate (40 mL) and water (40 mL) were added and layers were separated. The aqueous fraction was extracted with ethyl acetate (40 mL). The combined organic fractions were washed with saturated aqueous sodium chloride (2×40 mL), dried over sodium sulfate, filtered, and concentrated. Purification of the residue by silica gel chromatography (3 to 15% ethyl acetate:petroleum ether) afforded methyl 2-bromo-4-[3-(dimethoxymethyl)azetidin-1-yl]benzoate (668 mg, 46%) as a yellow oil. MS (ESI): m/z 344.2 [M+H]$^+$.

Step G: methyl 4-[3-(dimethoxymethyl) azetidin-1-yl]-2-formyl-benzoate

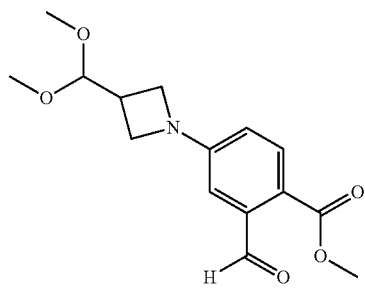

To a solution of methyl 2-bromo-4-[3-(dimethoxymethyl)azetidin-1-yl]benzoate (500 mg, 1.45 mmol) in N,N-dimethylformamide (5 mL) was added tert-butylisocyanide (241 mg, 2.91 mmol), palladium acetate (16 mg, 0.07 mmol), tricyclohexylphosphine (20 mg, 0.07 mmol), sodium carbonate (154 mg, 1.45 mmol) and triethylsilane (507 mg, 4.36 mmol). The mixture was stirred at 65° C. for 18 h in a Teflon vessel. Ethyl acetate (40 mL) and water (40 mL) were added and layers were separated. The aqueous fraction was extracted with ethyl acetate (40 mL). The combined organic fractions were washed with saturated aqueous sodium chloride (2×30 mL), dried over sodium sulfate, filtered, and concentrated. Purification of the residue by silica gel column chromatography (1:15 to 1:2 ethyl acetate:petroleum ether) afforded methyl 4-[3-(dimethoxymethyl)azetidin-1-yl]-2-formyl-benzoate (340 mg, 79%) as a yellow oil. MS (ESI): m/z 294.1 [M+2H]$^+$; $^1$H NMR (400 MHz, DMSO-d$_6$) δ 10.48 (s, 1H), 7.80 (d, J=8.4 Hz, 1H), 6.66-6.59 (m, 2H), 4.62 (d, J=6.8 Hz, 1H), 4.04-3.99 (m, 2H), 3.82 (s, 3H), 3.77 (dd, J=5.6, 8.0 Hz, 2H), 3.29 (s, 6H), 3.08-2.98 (m, 1H).

Step H: 3-[5[3-(dimethoxymethyl)azetidin-1-yl]-1-oxo-isoindolin-2-yl]piperidine-2,6-dione

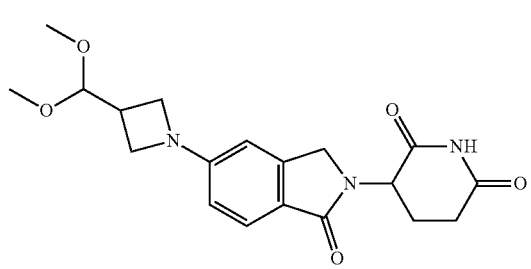 [SMILES: COC(OC)C1CN(c2ccc3c(c2)CN(C2CCC(=O)NC2=O)C3=O)C1]

To a suspension of 3-aminopiperidine-2,6-dione hydrochloride (432 mg, 2.63 mmol) in methanol (7 mL) was added sodium acetate (391 mg, 4.77 mmol). The mixture was stirred at 35° C. for 10 min, then a solution of methyl 4-[3-(dimethoxymethyl) azetidin-1-yl]-2-formyl-benzoate (0.70 g, 2.39 mmol) in dichloromethane (7 mL) was added, followed by acetic acid (0.68 mL, 11.9 mmol) was added. The mixture was stirred at 35° C. for 20 min, then sodium cyanoborohydride (450 mg, 7.16 mmol) was added. Then resulting mixture was stirred at 35° C. for 17.5 h. The reaction mixture was diluted with water (40 mL) and then extracted with ethyl acetate (2×30 mL) and tetrahydrofuran (40 mL). The combined organic fractions were washed with saturated aqueous sodium chloride (2×40 mL), dried over sodium sulfate, filtered, and concentrated. Purification of the residue by trituration with 1:1 petroleum ether:ethyl acetate (16 mL) afforded 3-[5-[3-(dimethoxymethyl)azetidin-1-yl]-1-oxo-isoindolin-2-yl]piperidine-2,6-dione (0.64 g, 71%) as a purple solid. MS (ESI): m/z 374.3 [M]⁺.

Step I: 1-[2-(2,6-dioxo-3-piperidyl)-1-oxo-isoindolin-5-yl]azetidine-3-carbaldehyde

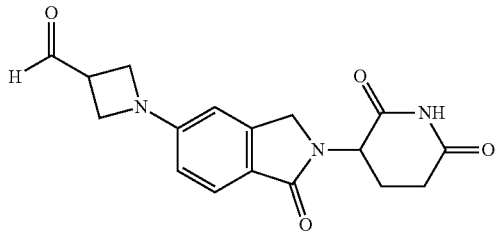 [SMILES: O=CC1CN(c2ccc3c(c2)CN(C2CCC(=O)NC2=O)C3=O)C1]

To a solution of 3-[5-[3-(dimethoxymethyl)azetidin-1-yl]-1-oxo-isoindolin-2-yl]piperidine-2,6-dione (0.10 g, 0.27 mmol) in dichloromethane (4 mL) was added trifluoroacetic acid (0.80 mL, 10.8 mmol). The mixture was stirred at 30° C. for 6 h. The reaction mixture was concentrated to afford crude 1-[2-(2,6-dioxo-3-piperidyl)-1-oxo-isoindolin-5-yl]azetidine-3-carb aldehyde (87 mg) as a yellow liquid. MS (ESI): m/z 328.2 [M+H]⁺.

Step J: tert-butyl 4-[1-(4-bromophenyl)-4-piperidyl]piperazine-1-carboxylate

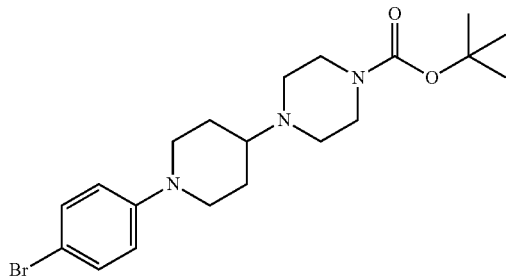 [SMILES: CC(C)(C)OC(=O)N1CCN(C2CCN(c3ccc(Br)cc3)CC2)CC1]

A mixture of tert-butyl 4-(4-piperidyl)piperazine-1-carboxylate (6.0 g, 22.3 mmol), 1,4-dibromobenzene (6.30 g, 26.7 mmol), copper (I) iodide (848 mg, 4.45 mmol), L-proline (1.03 g, 8.91 mmol) and potassium carbonate (6.16 g, 44.54 mmol) in dimethylsulfoxide (90 mL) was degassed and purged with nitrogen for 3 times, and then the mixture was stirred at 95° C. for 12 h. Ethyl acetate (150 mL), water (200 mL) and saturated ammonium chloride (50 mL) were added and layers were separated. The aqueous fraction was extracted with ethyl acetate (150 mL). The organic extracts were washed with saturated aqueous sodium chloride (2×200 mL), dried over sodium sulfate, filtered, and concentrated. Purification of the residue by silica gel column chromatography (1:10 to 1:1 ethyl acetate:petroleum ether) and then preparative HPLC (Welch Ultimate XB-NH2, 10% to 50% heptane:(0.1% ammonia in ethanol)) afforded tert-butyl 4-[1-(4-bromophenyl)-4-piperidyl] piperazine-1-carboxylate (1.37 g, 14%) as a pink solid. MS (ESI): m/z 426.2 [M+2H]⁺.

Step K: tert-butyl 4-[1-[4-[3-[2, 6-difluoro-3-[[(3R)-3-fluoropyrrolidin-1-yl]sulfonylamino]benzoyl]-1H-pyrrolo[2,3-b]pyridin-5-yl]phenyl]-4-piperidyl]piperazine-1-carboxylate

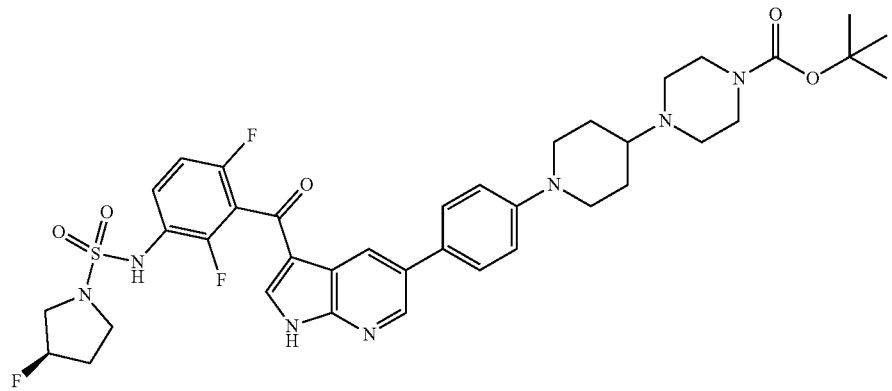 [SMILES: CC(C)(C)OC(=O)N1CCN(C2CCN(c3ccc(-c4cnc5[nH]cc(C(=O)c6c(F)ccc(NS(=O)(=O)N7CC[C@@H](F)C7)c6F)c5c4)cc3)CC2)CC1]

A mixture of tert-butyl 4-[1-(4-bromophenyl)-4-piperidyl]piperazine-1-carboxylate (0.20 g, 0.47 mmol), (3R)—N-[2,4-difluoro-3-[5-(4,4,5,5-tetramethyl-1,3,2-dioxaborolan-2-yl)-1H-pyrrolo[2,3-b]pyridine-3-carbonyl]phenyl]-3-fluoro-pyrrolidine-1-sulfonamide (285 mg, 0.51 mmol), cesium fluoride (286 mg, 1.89 mmol, 4 eq) and bis(di-tert-butyl(4-dimethylaminophenyl)phosphine)dichloropalladium(II) (66 mg, 0.09 mmol) in water (0.8 mL) and 1,4-dioxane (7 mL) was degassed and purged with nitrogen 3

(4-piperazin-1-yl-1-piperidyl)phenyl]-1H-pyrrolo[2,3-b]pyridine-3-carbonyl]phenyl]-3-fluoro-pyrrolidine-1-sulfonamide trifluoroacetic acid salt (142 mg) as a yellow liquid.

Step M: (3R)—N-{3-[5-(4-{4-[4-({1-[2-(2,6-dioxopiperidin-3-yl)-1-oxo-2,3-dihydro-1H-isoindol-5-yl]azetidin-3-yl}methyl)piperazin-1-yl]piperidin-1-yl}phenyl)-1H-pyrrolo[2,3-b]pyridine-3-carbonyl]-2,4-difluorophenyl}-3-fluoropyrrolidine-1-sulfonamide

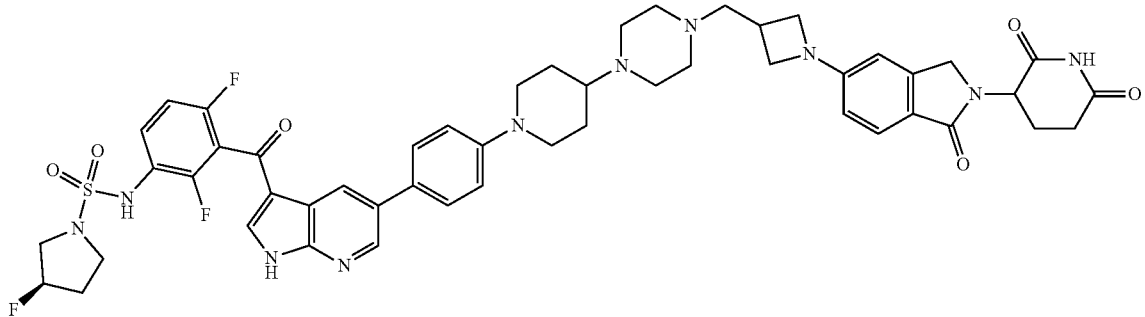

times, and then the mixture was stirred at 90° C. for 5 h. Tetrahydrofuran (20 mL), ethyl acetate (20 mL) and water (40 mL) were added and layers were separated. The aqueous fraction was extracted with ethyl acetate (30 mL). The combined organic fractions were washed with saturated aqueous sodium chloride (2×40 mL), dried over sodium sulfate, filtered, and concentrated. Purification of the residue by silica gel column chromatography (1% to 7% methanol:dichloromethane) and then preparative HPLC (Phenomenex Luna C18, 21% to 51% acetonitrile:0.225% formic acid in water) afforded tert-butyl 4-[1-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]-4-piperidyl]piperazine-1-carboxylate (250 mg, 69%) as a yellow solid. MS (ESI): m/z 768.4 [M+H]⁺.

Step L: (3R)—N-[2,4-difluoro-3-[5-[4-(4-piperazin-1-yl-1-piperidyl)phenyl]-1H-pyrrolo[2,3-b]pyridine-3-carbonyl]phenyl]-3-fluoro-pyrrolidine-1-sulfonamide

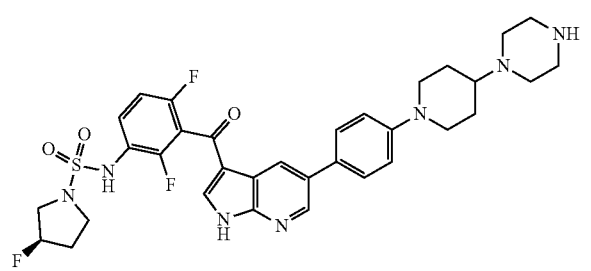 [SMILES: O=C(c1c(F)ccc(NS(=O)(=O)N2CC[C@@H](F)C2)c1F)c1c[nH]c2ncc(-c3ccc(N4CCC(N5CCNCC5)CC4)cc3)cc12]

To a solution of tert-butyl 4-[1-[4-[3[2,6-difluoro-3-[[(3R)-3-fluoropyrrolidin-1-yl] sulfonylamino]benzoyl]-1H-pyrrolo[2,3-b]pyridin-5-yl]phenyl]-4-piperidyl]piperazine-1-carboxylate (140 mg, 0.18 mmol) in dichloromethane (5 mL) was added trifluoroacetic acid (1.56 mL, 21.0 mmol). The mixture was stirred at 30° C. for 0.5 h and then concentrated to afford crude (3R)—N-[2,4-difluoro-3-[5-[4-

To a solution of (3R)—N-[2,4-difluoro-3-[5-[4-(4-piperazin-1-yl-1-piperidyl)phenyl]-1H-pyrrolo[2,3-b]pyridine-3-carbonyl]phenyl]-3-fluoro-pyrrolidine-1-sulfonamide trifluoroacetic acid salt (142 mg, 0.18 mmol) and 1-[2-(2,6-dioxo-3-piperidyl)-1-oxo-isoindolin-5-yl]azetidine-3-carbaldehyde (65 mg, 0.20 mmol) in dichloromethane (8 mL) was added triethylamine (4.2 mL). The mixture was stirred for 5 min at 30° C., and then sodium triacetoxyborohydride (77 mg, 0.36 mmol) was added. The mixture was stirred at 30° C. for 10 min. Tetrahydrofuran (30 mL), ethyl acetate (20 mL) and water (40 mL) were added and layers were separated. The aqueous fraction was extracted with tetrahydrofuran (30 mL). The combined organic fractions were washed with saturated aqueous sodium chloride (40 mL), dried over sodium sulfate, filtered, and concentrated. Purification of the residue by preparative HPLC (Shim-pack C18, 21% to 41% acetonitrile:0.225% formic acid in water) afforded (3R)—N-[3-[5-[4-[4-[4-[[1-[2-(2,6-dioxo-3-piperidyl)-1-oxo-isoindolin-5-yl]azetidin-3-yl]methyl]piperazin-1-yl]-1-piperidyl]phenyl]-1H-pyrrolo[2,3-b]pyridine-3-carbonyl]-2,4-difluoro-phenyl]-3-fluoro-pyrrolidine-1-sulfonamide formic acid salt (134 mg, 71%) as a yellow solid. MS (ESI): m/z 980.3 [M+H]⁺; ¹H NMR (400 MHz, DMSO-$d_6$) δ 12.99-12.81 (m, 1H), 10.93 (s, 1H), 8.65 (d, J=2.0 Hz, 1H), 8.58-8.49 (m, 1H), 8.15 (s, 1H), 8.07 (s, 1H), 7.67-7.55 (m, 3H), 7.48 (d, J=8.4 Hz, 1H), 7.27 (t, J=8.8 Hz, 1H), 7.07 (d, J=8.8 Hz, 2H), 6.54-6.42 (m, 2H), 5.38-5.21 (m, 1H), 5.03 (dd, J=5.2, 13.2 Hz, 1H), 4.33-4.25 (m, 1H), 4.21-4.13 (m, 1H), 4.01 (t, J=7.2 Hz, 2H), 3.83 (d, J=12.0 Hz, 2H), 3.55 (t, J=5.2 Hz, 2H), 3.48 (s, 1H), 3.37 (d, J=2.0 Hz, 1H), 3.29 (dt, J=6.8, 10.0 Hz, 3H), 3.00-2.84 (m, 3H), 2.74 (t, J=11.2 Hz, 2H), 2.63-2.55 (m, 6H), 2.45 (d, J=5.6 Hz, 4H), 2.37-2.32 (m, 1H), 2.15-2.04 (m, 2H), 2.01-1.84 (m, 4H), 1.59-1.43 (m, 2H).

Exemplary Synthesis of Exemplary Compound 210: (3R)—N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}-3-(methylamino)phenyl)-1H-pyrrolo[2,3-b]pyridine-3-carbonyl]-2,4-difluorophenyl}-3-fluoropyrrolidine-1-sulfonamide (Compound 210)

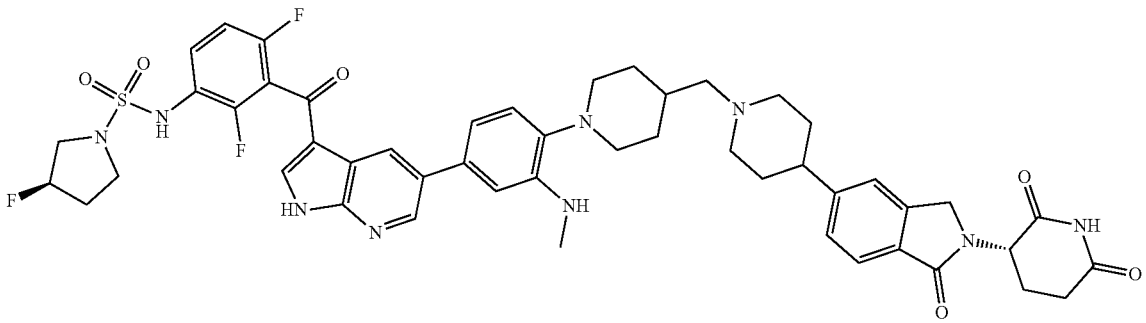 [SMILES: CNc1cc(-c2cnc3[nH]cc(C(=O)c4c(F)ccc(NS(=O)(=O)N5CC[C@@H](F)C5)c4F)c3c2)ccc1N1CCC(CN2CCC(c3ccc4c(c3)CN([C@H]3CCC(=O)NC3=O)C4=O)CC2)CC1]

Step A: 1-(4-bromo-2-nitrophenyl)-4-(dimethoxymethyl)piperidine

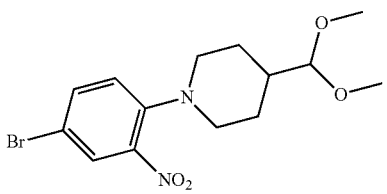 [SMILES: COC(OC)C1CCN(c2ccc(Br)cc2[N+](=O)[O-])CC1]

To a solution of 4-bromo-1-fluoro-2-nitrobenzene (3.0 g, 13.0 mmol) and 4-(dimethoxymethyl)piperidine (2.27 g, 14.3) in dimethylsulfoxide (30 mL) was added diisopropylethylamine (5.02 g, 36.9 mmol). The reaction was stirred for 3 h at 100° C. and then concentrated. Purification of the residue by silica gel column chromatography (1:1 ethyl acetate:petroleum ether) afforded 1-(4-bromo-2-nitrophenyl)-4-(dimethoxymethyl)piperidine (3.2 g, 62%) as a yellow solid. MS (ESI): m/z 444.1 [M+H]⁺.

Step B: 5-bromo-2-[4-(dimethoxymethyl)piperidin-1-yl]aniline

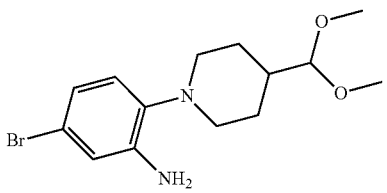

To a solution of 1-(4-bromo-2-nitrophenyl)-4-(dimethoxymethyl)piperidine (3.0 g, 7.93 mmol) and iron powder (3.73 g, 63.5 mmol) in ethanol (60 mL) and water (20 mL) was added ammonium chloride (1.79 g, 31.7 mmol). The reaction was stirred for 4 h at room temperature. The mixture was then filtered and the filter cake washed with ethanol (3×100 mL). The filtrate was concentrated. The aqueous layer was extracted with dichloromethane (3×100 mL) and concentrated to afford 5-bromo-2-[4-(dimethoxymethyl)piperidin-1-yl]aniline (2.1 g, 76%) as a yellow solid. MS (ESI): m/z 329.0 [M+H]⁺.

Step C: bis(5-bromo-2-[4-(dimethoxymethyl)piperidin-1-yl]-N-methylaniline)

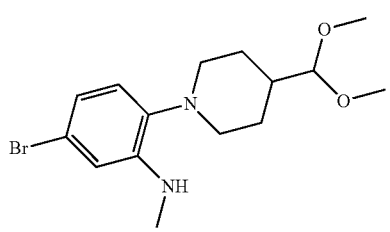 [SMILES: CNc1cc(Br)ccc1N1CCC(C(OC)OC)CC1]

To a solution of bis(5-bromo-2-[4-(dimethoxymethyl)piperidin-1-yl]aniline) (2.0 g, 2.89 mmol) and methoxymethanol amine (0.40 g, 8.63 mmol) in methanol (10 mL) was added sodium methoxide (0.49 g, 8.66 mmol) and sodium borohydride (0.34 g, 8.54 mmol). The resulting mixture was stirred for overnight at 65° C. The resulting mixture was concentrated. Purification of the residue by silica gel column chromatography (1:1 ethyl acetate:petroleum ether) afforded bis(5-bromo-2-[4-(dimethoxymethyl)piperidin-1-yl]-N-methylaniline) (1.2 g, 56%) as a yellow solid. MS (ESI): m/z 343.0 [M+H]⁺.

Step D: 2-[4-(dimethoxymethyl)piperidin-1-yl]-N-methyl-5-(4,4,5,5-tetramethyl-1,3,2-dioxaborolan-2-yl)aniline

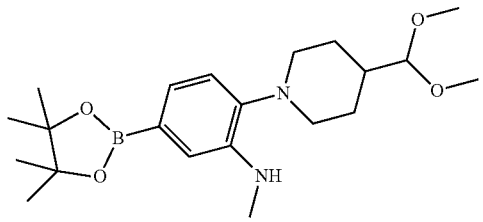

To a solution of 5-bromo-2-[4-(dimethoxymethyl)piperidin-1-yl]-N-methylaniline (1.0 g, 2.77 mmol) and bis(pinacolato)diboron (0.81 g, 3.05 mmol) in 1,4-dioxane (6 mL) was added [1,1'-bis(diphenylphosphino)ferrocene]dichloropalladium(II) dichloromethane (0.24 g, 0.28 mmol) and potassium acetate (0.86 g, 8.33 mmol). The resulting mixture was stirred for 3 h at 90° C. and then concentrated. Purification of the residue by silica gel column chromatography (1:10 methanol:dichloromethane) afforded 2-[4-(dimethoxymethyl)piperidin-1-yl]-N-methyl-5-(4,4,5,5-tetramethyl-1,3,2-dioxaborolan-2-yl)aniline (680 mg, 63%) as a yellow solid. MS (ESI): m/z 391.2 [M+H]$^+$.

Step E: (3R)—N-[3-(5-{4-[4-(dimethoxymethyl)piperidin-1-yl]-3-(methylamino)phenyl}-1H-pyrrolo[2,3-b]pyridine-3-carbonyl)-2,4-difluorophenyl]-3-fluoropyrrolidine-1-sulfonamide

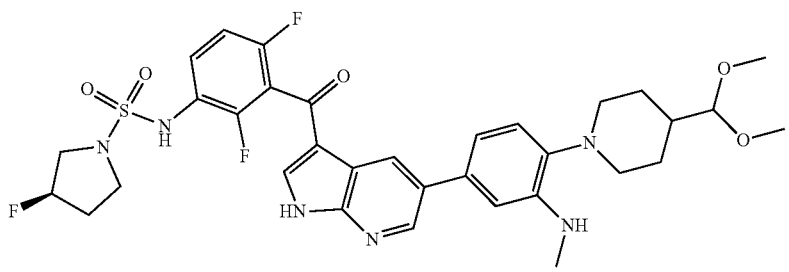 [SMILES: CNc1cc(-c2cnc3[nH]cc(C(=O)c4c(F)ccc(NS(=O)(=O)N5CC[C@@H](F)C5)c4F)c3c2)ccc1N1CCC(C(OC)OC)CC1]

To a solution of 2-[4-(dimethoxymethyl)piperidin-1-yl]-N-methyl-5-(4,4,5,5-tetramethyl-1,3,2-dioxaborolan-2-yl)aniline (600 mg, 1.460 mmol) and (3R)—N-(3-{5-bromo-1H-pyrrolo[2,3-b]pyridine-3-carbonyl}-2,4-difluorophenyl)-3-fluoropyrrolidine-1-sulfonamide (928.37 mg, 1.752 mmol) in 1,4-dioxane (6 mL) and water (1 mL) was added [1,1'-bis(diphenylphosphino)ferrocene]dichloropalladium (II) dichloromethane (125 mg, 0.146 mmol) and potassium carbonate (637 mg, 4.38 mmol). The resulting mixture was stirred for 3 h at 100° C. and then concentrated. Purification of the residue by silica gel column chromatography, (1:10 methanol:dichloromethane) afforded (3R)—N-[3-(5-{4-[4-(dimethoxymethyl)piperidin-1-yl]-3-(methyl amino)phenyl}-1H-pyrrolo[2,3-b]pyridine-3-carbonyl)-2,4-difluorophenyl]-3-fluoropyrrolidine-1-sulfonamide (510 mg, 47%) as a yellow solid. MS (ESI): m/z 687.2 [M+H]+.

Step F: (3R)—N-(2,4-difluoro-3-{5-[4-(4-formylpiperidin-1-yl)-3-(methylamino)phenyl]-1H-pyrrolo[2,3-b]pyridine-3-carbonyl}phenyl)-3-fluoropyrrolidine-1-sulfonamide

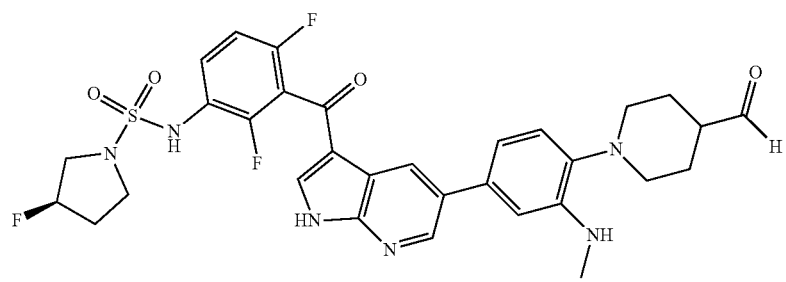 [SMILES: CNc1cc(-c2cnc3[nH]cc(C(=O)c4c(F)ccc(NS(=O)(=O)N5CC[C@@H](F)C5)c4F)c3c2)ccc1N1CCC(C=O)CC1]

To a solution of (3R)—N-[3-(5-{4-[4-(dimethoxymethyl)piperidin-1-yl]-3-(methylamino)phenyl}-1H-pyrrolo[2,3-b]pyridine-3-carbonyl)-2,4-difluorophenyl]-3-fluoropyrrolidine-1-sulfonamide (400 mg, 0.553 mmol) and trifluoroacetic acid (4 mL) in dichloromethane (2 mL) was added water (1 mL). The reaction was stirred for 3 h at 40° C. The mixture was basified to pH 8 with saturated aqueous sodium bicarbonate and the concentrated to afford (3R)—N-(2,4-difluoro-3-{5-[4-(4-formylpiperidin-1-yl)-3-(methylamino)phenyl]-1H-pyrrolo[2,3-b]pyridine-3-carbonyl} phenyl)-3-fluoropyrrolidine-1-sulfonamide (310 mg, 87%) as a yellow solid. MS (ESI): m/z 641.2 [M+H]$^+$.

Step G: (3R)—N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}-3-(methylamino)phenyl)-1H-pyrrolo[2,3-b]pyridine-3-carbonyl]-2,4-difluorophenyl}-3-fluoropyrrolidine-1-sulfonamide

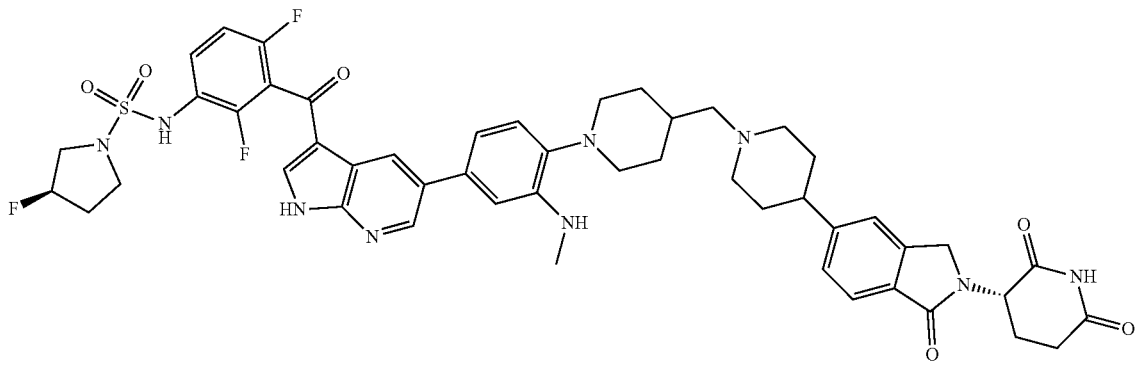 [SMILES: CNc1cc(-c2cnc3[nH]cc(C(=O)c4c(F)ccc(NS(=O)(=O)N5CC[C@@H](F)C5)c4F)c3c2)ccc1N1CCC(CN2CCC(c3ccc4c(c3)CN([C@H]3CCC(=O)NC3=O)C4=O)CC2)CC1]

To a solution of (3R)—N-(2,4-difluoro-3-{5-[4-(4-formylpiperidin-1-yl)-3-(methylamino)phenyl]-1H-pyrrolo[2,3-b]pyridine-3-carbonyl}phenyl)-3-fluoropyrrolidine-1-sulfonamide (150 mg, 0.222 mmol) and 3-[1-oxo-5-(piperidin-4-yl)-3H-isoindol-2-yl]piperidine-2,6-dione hydrochloride (102 mg, 0.266 mmol) in dichloromethane (10 mL) and isopropanol (10 mL) was added diisopropylethylamine (91 mg, 0.67 mmol) and acetic acid (42 mg, 0.67 mmol). The resulting mixture was stirred overnight at room temperature and then sodium triacetoxyborohydride (149 mg, 0.666 mmol) was added. The reaction stirred for additional 3 h. The aqueous layer was extracted with dichloromethane (3×100 mL). Purification of combined and concentrated organic fractions by silica gel column chromatography, (1:10 methanol:dichloromethane) afforded (3R)—N-{3-[5-(4-{4-[(4-{2-[(3S)-2,6-dioxopiperidin-3-yl]-1-oxo-3H-isoindol-5-yl}piperidin-1-yl)methyl]piperidin-1-yl}-3-(methylamino)phenyl)-1H-pyrrolo[2,3-b]pyridine-3-carbonyl]-2,4-difluorophenyl}-3-fluoropyrrolidine-1-sulfonamide (66.8 mg, 32%) as a yellow solid. $^1$H NMR (300 MHz, DMSO-d$_6$) δ 12.98 (s, 1H), 11.00 (s, 1H), 9.90 (s, 1H), 8.67 (s, 1H), 8.63 (s, 1H), 8.11 (s, 1H), 7.68-7.63 (m, 2H), 7.52 (s, 1H), 7.33-7.27 (m, 1H), 7.05 (d, J=8.1 Hz, 1H), 6.90 (d, J=8.1 Hz, 1H), 6.77 (s, 1H), 5.41-5.01 (m, 3H), 4.41-4.27 (q, 2H), 3.40 (s, 1H), 3.22 (s, 1H), 3.10 (s, 1H), 3.05-3.00 (m, 4H), 2.93-2.88 (m, 4H), 2.74-2.71 (m, 4H), 2.28-2.22 (m, 1H), 2.12-2.08 (m, 5H), 1.97-1.75 (m, 7H), 1.43-1.40 (m, 2H), 1.24-1.16 (m, 4H); MS (ESI): m/z 952.45 [M+H]$^+$.

Exemplary Synthesis of Exemplary Compound 211: (2S)—N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2,4-difluorophenyl}-2-methylpyrrolidine-1-sulfonamide (Compound 211)

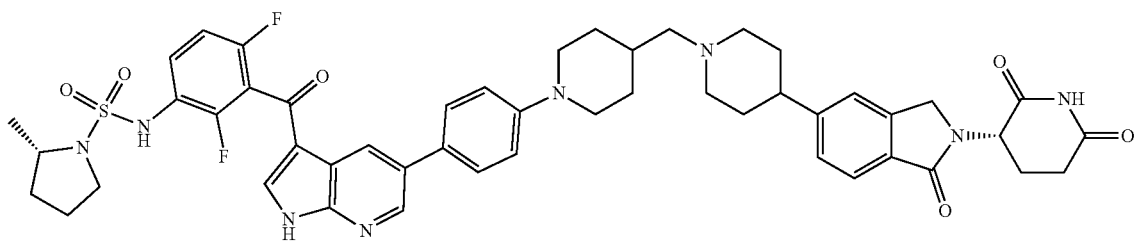 [SMILES: C[C@H]1CCCN1S(=O)(=O)Nc1ccc(F)c(C(=O)c2c[nH]c3ncc(-c4ccc(N5CCC(CN6CCC(c7ccc8c(c7)CN([C@H]7CCC(=O)NC7=O)C8=O)CC6)CC5)cc4)cc23)c1F]

Step A: (S)—N-(3-(5-bromo-1H-pyrrolo[2,3-b]pyridine-3-carbonyl)-2,4-difluorophenyl)-2-methylpyrrolidine-1-sulfonamide

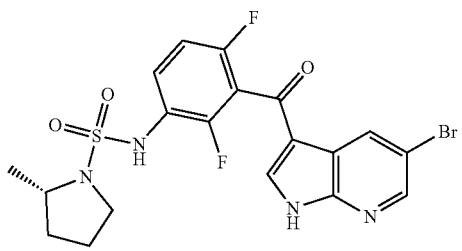 [SMILES: C[C@H]1CCCN1S(=O)(=O)Nc1ccc(F)c(C(=O)c2c[nH]c3ncc(Br)cc23)c1F]

To a mixture of N-(3-{5-bromo-1H-pyrrolo[2,3-b]pyridine-3-carbonyl}-2,4-difluorophenyl)-2-oxo-1,3-oxazolidine-3-sulfonamide (1.0 g, 2.0 mmol) in N,N-dimethylformamide was added (S)-2-methylpyrrolidine hydrochloride (0.73 g, 5.99 mmol) and diisopropylethylamine (1.29 g, 9.98 mmol) at room temperature. The reaction stirred for 2 h at 85° C. Purification of the concentrated residue by reverse flash chromatography (C18 silica gel, 10% to 70% tetrahydrofuran:water) afforded (S)—N-(3-(5-bromo-1H-pyrrolo[2,3-b]pyridine-3-carbonyl)-2,4-difluorophenyl)-2-methylpyrrolidine-1-sulfonamide (520 mg, 52%) as a white solid. MS (ESI): m/z 499.00, 501.00 [M+H]$^+$; $^1$H NMR (300 MHz, DMSO-d$_6$) δ 10.10 (s, 2H), 8.51 (d, J=2.3 Hz, 1H), 8.13 (s, 1H), 7.62 (td, J=9.1, 6.0 Hz, 1H), 7.23 (td, J=8.9, 1.6 Hz, 1H), 3.77-3.55 (m, 1H), 3.22 (dd, J=7.1, 5.8 Hz, 2H), 1.97-1.63 (m, 3H), 1.48 (ddd, J=9.6, 5.9, 4.3 Hz, 1H), 1.07 (d, J=6.3 Hz, 3H).

Step B: (S)—N-(3-(5-(4-(4-(dimethoxymethyl)piperidin-1-yl)phenyl)-1H-pyrrolo[2,3-b]pyridine-3-carbonyl)-2,4-difluorophenyl)-2-methylpyrrolidine-1-sulfonamide

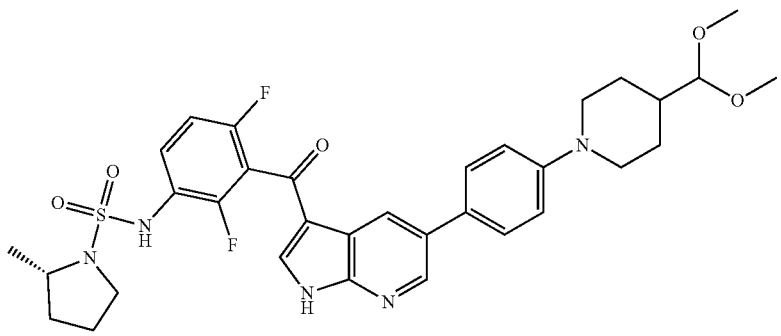

To a solution of (S)—N-(3-(5-bromo-1H-pyrrolo[2,3-b]pyridine-3-carbonyl)-2,4-difluorophenyl)-2-methylpyrrolidine-1-sulfonamide (500 mg, 0.974 mmol) and 4-(dimethoxymethyl)-1-[4-(4,4,5,5-tetramethyl-1,3,2-dioxaborolan-2-yl)phenyl]piperidine (422.3 mg, 1.169 mmol) in 1,4-dioxane (6 mL) and water (1 mL) was added cesium fluoride (443.9 mg, 2.922 mmol) and [1,1'-bis(di-tert-butylphosphino)ferrocene]dichloropalladium(II) (63.5 mg, 0.097 mmol). After stirring for 2 h at 100° C., the mixture was concentrated. Purification of the residue by preparative TLC/silica gel column chromatography (1:20 methanol:dichloromethane) afforded (S)—N-(3-(5-(4-(4-(dimethoxymethyl)piperidin-1-yl)phenyl)-1H-pyrrolo[2,3-b]pyridine-3-carbonyl)-2,4-difluorophenyl)-2-methylpyrrolidine-1-sulfonamide (501 mg, 77%) as a yellow solid. MS (ESI): m/z 654.20 [M+H]$^+$.

Step C: (S)—N-(2,4-difluoro-3-(5-(4-(4-formylpiperidin-1-yl)phenyl)-1H-pyrrolo[2,3-b]pyridine-3-carbonyl)phenyl)-2-methylpyrrolidine-1-sulfonamide

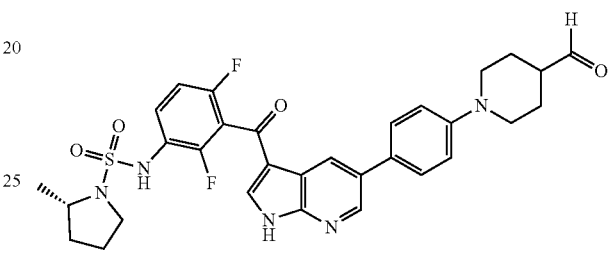

To a mixture of (2S,5S)—N-[3-(5-{4-[4-(dimethoxymethyl)piperidin-1-yl]phenyl}-1H-pyrrolo[2,3-b]pyridine-3-carbonyl)-2,4-difluorophenyl]-2,5-dimethylpyrrolidine-1-sulfonamide (500 mg, 0.765 mmol) in tetrahydrofuran (20 mL) was added 2 M aqueous sulfuric acid (10 mL). The reaction was stirred for 1 h at 70° C. The mixture was acidified to pH 9 with saturated aqueous sodium bicarbonate and then extracted with tetrahydrofuran (3×50 mL). The combined organic fractions were washed with saturated aqueous sodium chloride (50 mL), dried over sodium sulfate, filtered, and concentrated to afford (S)—N-(2,4-difluoro-3-(5-(4-(4-formylpiperidin-1-yl)phenyl)-1H-pyrrolo[2,3-b]pyridine-3-carbonyl)phenyl)-2-methylpyrrolidine-1-sulfonamide (425 mg, 91%), which was directly for next step without further purification. MS (ESI): m/z 608.20 [M+H]$^+$.

Step D: (2 S)—N-{3-[5-(4-{4-[(4-{2-[(3S)-2,6-di-oxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2,4-difluorophenyl}-2-methylpyrrolidine-1-sulfonamide

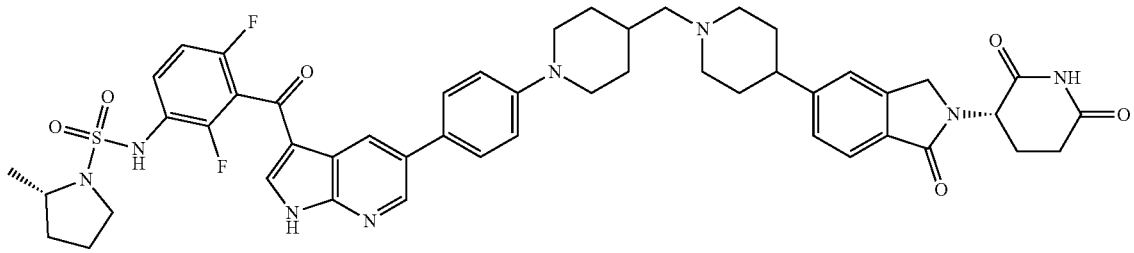 [SMILES: C[C@H]1CCCN1S(=O)(=O)Nc1ccc(F)c(C(=O)c2c[nH]c3ncc(-c4ccc(N5CCC(CN6CCC(c7ccc8c(c7)CN([C@H]7CCC(=O)NC7=O)C8=O)CC6)CC5)cc4)cc23)c1F]

A mixture of (3S)-3-[1-oxo-5-(piperidin-4-yl)-3H-isoindol-2-yl]piperidine-2,6-dione [(1R)-7,7-dimethyl-2-oxobicyclo[2.2.1]heptan-1-yl]methanesulfonic acid salt (100 mg, 0.179 mmol) and sodium acetate (11.0 mg, 0.134 mmol) in dichloromethane (10 mL) and isopropanol (10 mL) was stirred for 10 min at room temperature. Then (S)—N-(2,4-difluoro-3-(5-(4-(4-formylpiperidin-1-yl)phenyl)-1H-pyrrolo[2,3-b]pyridine-3-carbonyl)phenyl)-2-methylpyrrolidine-1-sulfonamide (122 mg, 0.197 mmol) was added and the mixture stirred 1 h at room temperature. Then sodium triacetoxyborohydride (75.7 mg, 0.358 mmol) was added and the reaction stirred 2 h at room temperature. The mixture was acidified to pH 8 with saturated aqueous sodium bicarbonate and then extracted with tetrahydrofuran (3×30 mL). The combined organic fractions were washed with saturated aqueous sodium chloride (50 mL), dried over sodium sulfate, filtered, and concentrated. Purification of the residue by preparative TLC (1:8 methanol:dichloromethane) afforded (S)—N-(3-(5-(4-(4-((4-(2-((S)-2,6-dioxopiperidin-3-yl)-1-oxoisoindolin-5-yl)piperidin-1-yl)methyl)piperidin-1-yl)phenyl)-1H-pyrrolo[2,3-b]pyridine-3-carbonyl)-2,4-difluorophenyl)-2-methylpyrrolidine-1-sulfonamide (74.6 mg, 45%) as a yellow solid. MS (ESI): m/z=919.20 [M+H]$^+$; $^1$H NMR (400 MHz, DMSO-$d_6$) δ 12.91 (s, 1H), 10.97 (s, 1H), 9.66 (s, 1H), 8.65 (d, J=2.2 Hz, 1H), 8.52 (s, 1H), 8.08 (s, 1H), 7.69-7.57 (m, 4H), 7.57 (s, 1H), 7.51 (s, 1H), 7.41 (dd, J=8.1, 1.4 Hz, 1H), 7.28 (td, J=8.8, 1.6 Hz, 1H), 7.11-7.04 (m, 2H), 5.10 (dd, J=13.3, 5.1 Hz, 1H), 4.43 (d, J=17.3 Hz, 1H), 4.29 (d, J=17.2 Hz, 1H), 3.80 (d, J=12.2 Hz, 2H), 3.71 (td, J=6.8, 3.9 Hz, 1H), 3.64-3.56 (m, 1H), 3.23 (t, J=6.7 Hz, 2H), 3.12-2.94 (m, 3H), 2.74 (t, J=12.0 Hz, 2H), 2.63 (s, 2H), 2.25-1.95 (m, 3H), 1.95-1.67 (m, 11H), 1.47 (dd, J=9.2, 4.8 Hz, 1H), 1.26 (s, 1H), 1.23 (s, 5H), 1.06 (d, J=6.3 Hz, 3H).

Exemplary Synthesis of Exemplary Compound 212:
(3R)—N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2-fluoro-4-methoxyphenyl}-3-fluoropyrrolidine-1-sulfonamide
(Compound 212)

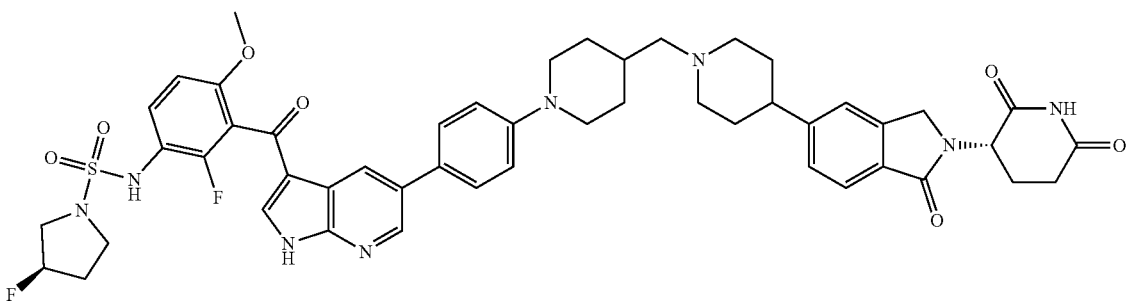 [SMILES: COc1ccc(NS(=O)(=O)N2CC[C@@H](F)C2)c(F)c1C(=O)c1c[nH]c2ncc(-c3ccc(N4CCC(CN5CCC(c6ccc7c(c6)CN([C@H]6CCC(=O)NC6=O)C7=O)CC5)CC4)cc3)cc12]

Step A: tert-butyl 2,6-difluoro-3-nitrobenzoate

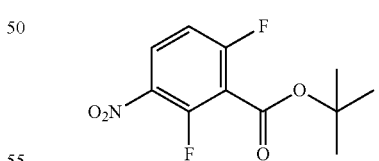

To a solution of 2,6-difluoro-3-nitrobenzoic acid (50 g, 246 mmol) in t-butanol (600 mL) was added 4-dimethylaminopyridine (6.02 g, 49.2 mmol) and di-tert-butyldicarbonate (80.59 g, 369.3 mmol) in portions at room temperature. The reaction stirred for 48 h at 40° C. The resulting mixture was extracted with ethyl acetate (3×300 mL). The combined organic fractions were washed with saturated aqueous sodium chloride (2×100 mL), dried over sodium sulfate, filtered, and concentrated. Purification of the residue by silica gel column chromatography, (1:10 ethyl acetate:

Step B: tert-butyl 2-fluoro-6-methoxy-3-nitrobenzoate

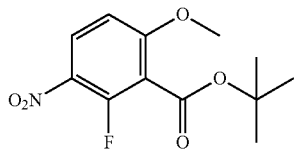 [SMILES: COc1ccc([N+](=O)[O-])c(F)c1C(=O)OC(C)(C)C]

To a solution of tert-butyl 2,6-difluoro-3-nitrobenzoate (23.8 g, 91.8 mmol) in methanol (300 mL) was added sodium methoxide (6.45 g, 119 mmol) in portions at 0° C. The reaction was stirred for 48 h at 25° C. The resulting mixture was concentrated and the residue extracted with ethyl acetate (3×100 mL). The combined organic fractions were washed with saturated aqueous sodium chloride (2×50 mL), dried over sodium sulfate, filtered, and concentrated. Purification of the residue by silica gel column chromatography (1:5 ethyl acetate:petroleum ether) afforded tert-butyl 2-fluoro-6-methoxy-3-nitrobenzoate (9.2 g, 45%) as a white solid.

Step C: 2-fluoro-6-methoxy-3-nitrobenzoic acid

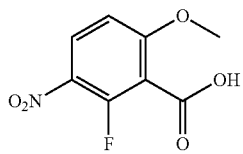

To a solution of tert-butyl 2-fluoro-6-methoxy-3-nitrobenzoate (9.0 g, 33.2 mmol) in tetrahydrofuran (100 mL) was added 4 M hydrochloric acid in 1,4-dioxane (300 mL) in portions at room temperature. The reaction stirred for 20 h at room temperature. The resulting mixture was concentrated to afford 2-fluoro-6-methoxy-3-nitrobenzoic acid (8.2 g) as a white solid.

Step D: 2-fluoro-6-methoxy-3-nitrobenzoyl chloride

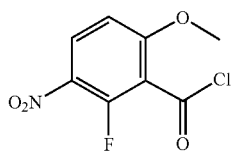

To a solution of 2-fluoro-6-methoxy-3-nitrobenzoic acid (6.5 g, 30.2 mmol) in thionyl chloride (65.01 mL) and toluene (65.00 mL) was added N,N-dimethylformamide (0.04 g, 0.55 mmol) in portions at room temperature under nitrogen atmosphere. The reaction stirred for additional 12 h at 80° C. and was then concentrated. The crude product was used in the next step directly without further purification.

Step E: 5-bromo-3-(2-fluoro-6-methoxy-3-nitrobenzoyl)-1H-pyrrolo[2,3-b]pyridine

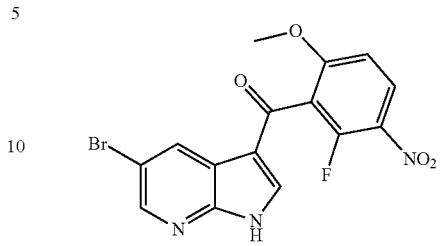

To a solution of 5-bromo-1H-pyrrolo[2,3-b]pyridine (3.6 g, 18.3 mmol) and aluminum chloride (8.53 g, 63.9 mmol) in dichloromethane (200 mL) was added 2-fluoro-6-methoxy-3-nitrobenzoyl chloride (5.55 g, 23.8 mmol) in portions at 0° C. The reaction stirred for 12 h at 25° C. The mixture was extracted with dichloromethane (3×100 mL). The combined organic fractions were washed with saturated aqueous sodium chloride (2×100 mL), dried over sodium sulfate, filtered, and concentrated. Purification of the residue by silica gel column chromatography (1:1 ethyl acetate:petroleum ether) afforded 5-bromo-3-(2-fluoro-6-methoxy-3-nitrobenzoyl)-1H-pyrrolo[2,3-b]pyridine (3.5 g, 40%) as a white solid. MS (ESI): m/z 393.95 [M+H]$^+$.

Step F: 3-{5-bromo-1H-pyrrolo[2,3-b]pyridine-3-carbonyl}-2-fluoro-4-methoxyaniline

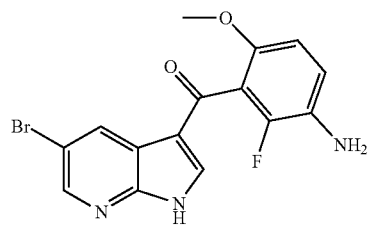 [SMILES: COc1ccc(N)c(F)c1C(=O)c1c[nH]c2ncc(Br)cc12]

To a solution of 5-bromo-3-(2-fluoro-6-methoxy-3-nitrobenzoyl)-1H-pyrrolo[2,3-b]pyridine (3.5 g, 8.88 mmol) in ethanol (300 mL) and tetrahydrofuran (300 mL) was added hydrochloric acid (1.94 g, 53.3 mmol) and iron powder (2.98 g, 53.3 mmol) in portions at room temperature. The reaction stirred for 1 h at 50° C. The resulting mixture was filtered, the filter cake was washed with tetrahydrofuran (2×50 mL). The filtrate was concentrated. The mixture was basified to pH 8 with saturated aqueous sodium bicarbonate. The resulting mixture was extracted with ethyl acetate (3×100 mL). The combined organic fractions were washed with saturated aqueous sodium chloride (2×100 mL), dried over sodium sulfate, filtered, and concentrated to afford 3-{5-bromo-1H-pyrrolo[2,3-b]pyridine-3-carbonyl}-2-fluoro-4-methoxyaniline (3 g, 93%) as a yellow solid. MS (ESI): m/z 364.00 [M+H]$^+$.

Step G: 3-[5-bromo-1-(2,6-dichlorobenzoyl)pyrrolo[2,3-b]pyridine-3-carbonyl]-2-fluoro-4-methoxyaniline

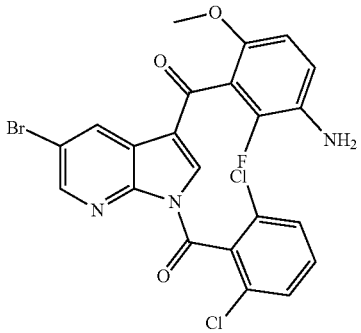

To a solution of 3-{5-bromo-1H-pyrrolo[2,3-b]pyridine-3-carbonyl}-2-fluoro-4-methoxyaniline (3.0 g, 8.24 mmol) in tetrahydrofuran (100 mL) was added triethylamine (1.08 g, 10.7 mmol) and 2,6-dichlorobenzoyl chloride (1.74 g, 8.32 mmol) in portions at 0° C. The reaction stirred for 1 h at room temperature. The resulting mixture was extracted with ethyl acetate (3×100 mL). The combined organic fractions were washed with saturated aqueous sodium chloride (2×50 mL), dried over sodium sulfate, filtered, and concentrated. Purification of the residue by silica gel column chromatography (1:3 ethyl acetate:petroleum ether) afforded 3-[5-bromo-1-(2,6-dichlorobenzoyl)pyrrolo[2,3-b]pyridine-3-carbonyl]-2-fluoro-4-methoxyaniline (3.02 g, 68%) as a yellow solid. MS (ESI): m/z 538.00 [M+H]$^+$.

Step H: N-{3-[5-bromo-1-(2,6-dichlorobenzoyl)pyrrolo[2,3-b]pyridine-3-carbonyl]-2-fluoro-4-methoxyphenyl}-2-oxo-1,3-oxazolidine-3-sulfonamide

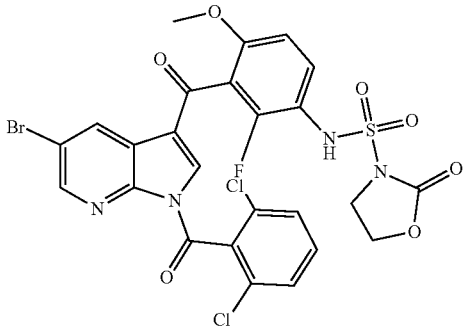

A solution of 2-bromoethanol (651 mg, 5.21 mmol) and chlorosulfonyl isocyanate (737 mg, 5.21 mmol) in dichloromethane (300 mL) was stirred for 2 h at 0° C. Then 3-[5-bromo-1-(2,6-dichlorobenzoyl)pyrrolo[2,3-b]pyridine-3-carbonyl]-2-fluoro-4-methoxyaniline (2.8 g, 5.21 mmol) was added in portions at 0° C. The reaction stirred 12 h at 36° C. and was then concentrated. Purification of the residue by silica gel column chromatography, (1:10 methanol:dichloromethane) afforded N-{3-[5-bromo-1-(2,6-dichlorobenzoyl)pyrrolo[2,3-b]pyridine-3-carbonyl]-2-fluoro-4-methoxyphenyl}-2-oxo-1,3-oxazolidine-3-sulfonamide (2.5 g, 70%) as a yellow oil. MS (ESI): m/z 686.90 [M+H]$^+$.

Step I: (3R)—N-{3-[5-bromo-1-(2,6-dichlorobenzoyl)pyrrolo[2,3-b]pyridine-3-carbonyl]-2-fluoro-4-methoxyphenyl}-3-fluoropyrrolidine-1-sulfonamide

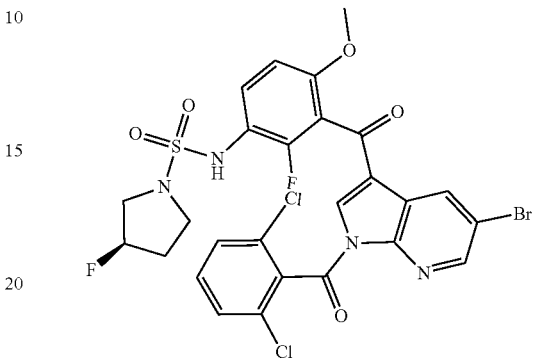

To a mixture of (3R)-3-fluoropyrrolidine (1298 mg, 14.570 mmol) and diisopropylethylamine (564 mg, 4.37 mmol) in 1,4-dioxane (20 mL) was added N-{3-[5-bromo-1-(2,6-dichlorobenzoyl)pyrrolo[2,3-b]pyridine-3-carbonyl]-2-fluoro-4-methoxyphenyl}-2-oxo-1,3-oxazolidine-3-sulfonamide (1.0 g, 1.46 mmol) in portions at room temperature. The reaction was stirred for 1 h at 100° C. and then concentrated. Purification of the residue by silica gel column chromatography (1:1 ethyl acetate:petroleum ether) to afford (3R)—N-{3-[5-bromo-1-(2,6-dichlorobenzoyl)pyrrolo[2,3-b]pyridine-3-carbonyl]-2-fluoro-4-methoxyphenyl}-3-fluoropyrrolidine-1-sulfonamide (700 mg, 70%) as a yellow solid. MS (ESI): m/z 688.95 [M+H]$^+$.

Step J: (3R)—N-(3-{5-bromo-1H-pyrrolo[2,3-b]pyridine-3-carbonyl}-2-fluoro-4-methoxyphenyl)-3-fluoropyrrolidine-1-sulfonamide

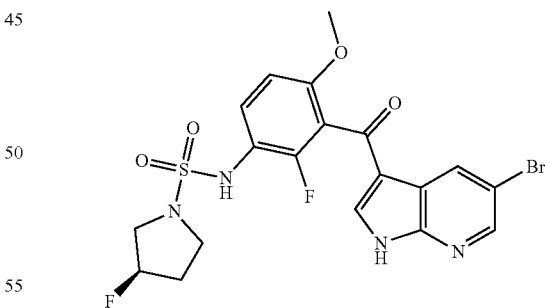

To a solution of (3R)—N-{3-[5-bromo-1-(2,6-dichlorobenzoyl)pyrrolo[2,3-b]pyridine-3-carbonyl]-2-fluoro-4-methoxyphenyl}-3-fluoropyrrolidine-1-sulfonamide (700 mg) in methanol (10 mL) was added ammonium hydroxide (10 mL) in portions at room temperature. The reaction stirred for 1 h at 30° C. The resulting mixture was concentrated to afford (3R)—N-(3-{5-bromo-1H-pyrrolo[2,3-b]pyridine-3-carbonyl}-2-fluoro-4-methoxyphenyl)-3-fluoropyrrolidine-1-sulfonamide (630 mg) as a off-white solid. MS (ESI): m/z 517.00 [M+H]$^+$.

Step K: (3R)—N-[3-(5-{4-[4-(dimethoxymethyl)piperidin-1-yl]phenyl}-1H-pyrrolo[2,3-b]pyridine-3-carbonyl)-2-fluoro-4-methoxyphenyl]-3-fluoropyrrolidine-1-sulfonamide

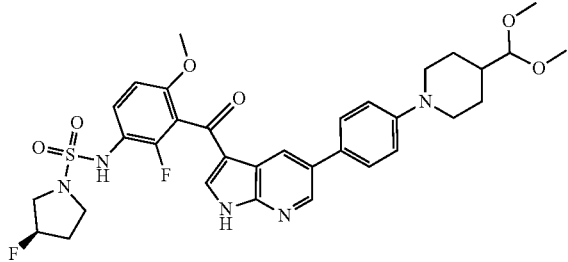 [SMILES: COc1ccc(NS(=O)(=O)N2CC[C@@H](F)C2)c(F)c1C(=O)c1c[nH]c2ncc(-c3ccc(N4CCC(C(OC)OC)CC4)cc3)cc12]

To a solution/mixture of (3R)—N-(3-{5-bromo-1H-pyrrolo[2,3-b]pyridine-3-carbonyl}-2-fluoro-4-methoxyphenyl)-3-fluoropyrrolidine-1-sulfonamide (600 mg, 1.16 mmol) and 4-(dimethoxymethyl)-1-[4-(4,4,5,5-tetramethyl-1,3,2-dioxaborolan-2-yl)phenyl]piperidine (505 mg, 1.40 mmol) in 1,4-dioxane (18 mL) and water (3 mL) was added cesium fluoride (531 mg, 3.49 mmol) and [1,1'-bis(di-tert-butylphosphino)ferrocene]dichloropalladium(II) (75.9 mg, 0.116 mmol) in portions at room temperature under nitrogen atmosphere. The reaction was stirred for 1 h at 100° C. Purification of the residue by silica gel column chromatography (1:12 methanol:dichloromethane) afforded (3R)—N-[3-(5-{4-[4-(dimethoxymethyl)piperidin-1-yl]phenyl}-1H-pyrrolo[2,3-b]pyridine-3-carbonyl)-2-fluoro-4-methoxyphenyl]-3-fluoropyrrolidine-1-sulfonamide (450 mg, 58%) as a yellow solid. MS (ESI): m/z 670.20 [M+H]$^+$.

Step L: (3R)-3-fluoro-N-(2-fluoro-3-{5-[4-(4-formylpiperidin-1-yl)phenyl]-1H-pyrrolo[2,3-b]pyridine-3-carbonyl}-4-methoxyphenyl)pyrrolidine-1-sulfonamide

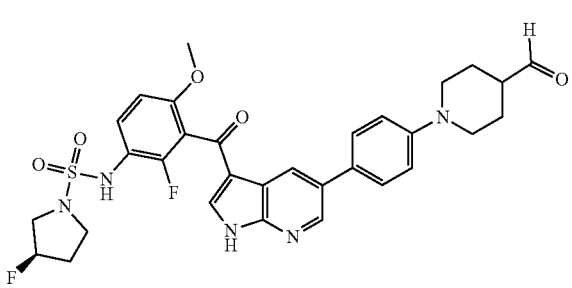 [SMILES: COc1ccc(NS(=O)(=O)N2CC[C@@H](F)C2)c(F)c1C(=O)c1c[nH]c2ncc(-c3ccc(N4CCC(C=O)CC4)cc3)cc12]

To a mixture of (3R)—N-[3-(5-{4-[4-(dimethoxymethyl)piperidin-1-yl]phenyl}-1H-pyrrolo[2,3-b]pyridine-3-carbonyl)-2-fluoro-4-methoxyphenyl]-3-fluoropyrrolidine-1-sulfonamide (200 mg, 0.299 mmol) in tetrahydrofuran (20 mL) was added sulfuric acid (10 mL) in portions at room temperature under an air atmosphere. The mixture was basified to pH 8 with saturated aqueous sodium bicarbonate. The resulting mixture was extracted with ethyl acetate (3×100 mL). The combined organic fractions were washed with saturated aqueous sodium chloride (2×50 mL), dried over sodium sulfate, filtered, and concentrated to afford (3R)-3-fluoro-N-(2-fluoro-3-{5-[4-(4-formylpiperidin-1-yl)phenyl]-1H-pyrrolo[2,3-b]pyridine-3-carbonyl}-4-methoxyphenyl)pyrrolidine-1-sulfonamide (180 mg, 97%) as a yellow oil. MS (ESI): m/z 624.10 [M+H]$^+$.

Step M: (3R)—N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2-fluoro-4-methoxyphenyl}-3-fluoropyrrolidine-1-sulfonamide

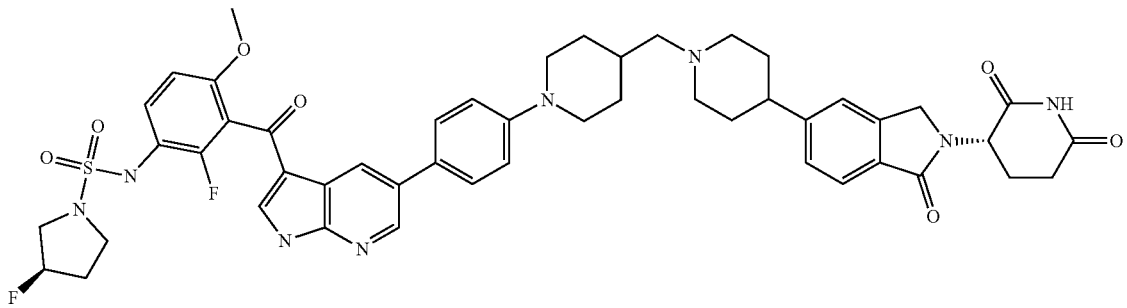

To a solution of (3S)-3-[1-oxo-5-(piperidin-4-yl)-3H-isoindol-2-yl]piperidine-2,6-dione (75.6 mg, 0.231 mmol) in dichloromethane (20 mL) and isopropanol (20 mL) was added diisopropylethylamine in portions at room temperature. Then the mixture was acidified to pH 7 with acetic acid. Then (3R)-3-fluoro-N-(2-fluoro-3-{5-[4-(4-formylpiperidin-1-yl)phenyl]-1H-pyrrolo[2,3-b]pyridine-3-carbonyl}-4-methoxyphenyl)pyrrolidine-1-sulfonamide (180 mg, 0.289 mmol) was added in portions. The reaction stirred for 2 h at room temperature, and then sodium triacetoxyborohydride (184 mg, 0.867 mmol) was added. The reaction stirred for 1 h at room temperature and was then basified to pH 8 with saturated aqueous sodium bicarbonate. The resulting mixture was extracted with ethyl acetate (3×100 mL). The combined organic fractions were washed with saturated aqueous sodium chloride (3×50 mL), dried over sodium sulfate, filtered, and concentrated. Purification of the residue by silica gel column chromatography (1:8 methanol:dichloromethane) afforded (3R)—N-{3-[5-(4-{4-[(4-{2-[(3S)-2,6-dioxopiperidin-3-yl]-1-oxo-3H-isoindol-5-yl}piperidin-1-yl)methyl]piperidin-1-yl}phenyl)-1H-pyrrolo[2,3-b]pyridine-3-carbonyl]-2-fluoro-4-methoxyphenyl}-3-fluoropyrrolidine-1-sulfonamide (38.7 mg, 14%). 1H NMR (400 MHz, DMSO-d$_6$) δ 12.71 (s, 1H), 10.98 (s, 1H), 9.52 (s, 1H), 8.62 (d, J=2.2 Hz, 1H), 8.45 (s, 1H), 7.84 (s, 1H), 7.66 (d, J=7.9 Hz, 1H), 7.57-7.46 (m, 4H), 7.42 (d, J=8.0 Hz, 1H), 7.02-7.07 (m, 3H), 5.35 (s, 1H), 5.11 (dd, J=13.3, 5.1 Hz, 1H), 4.43 (d, J=17.2 Hz, 1H), 4.30 (d, J=17.2 Hz, 1H), 3.80 (d, J=12.0 Hz, 2H), 3.74 (s, 3H), 3.45 (d, J=2.0 Hz, 2H), 3.32 (d, 2H), 3.00 (s, 3H), 2.97-2.85 (m, 2H), 2.75 (t, J=12.1 Hz, 2H), 2.48 (s, 2H), 2.11-1.99 (m, 6H), 1.85 (d, J=13.0 Hz, 7H), 1.45 (s, 1H), 1.23 (s, 7H), 0.91-0.81 (m, 1H); MS (ESI): m/z 935.40 [M+H]$^+$.

Exemplary Synthesis of Exemplary Compound 373:
4-[6-(2-[4-[3-(2,6-difluoro-3-[[(3R)-3-fluoropyrrolidin-1-ylsulfonyl]amino]benzoyl)-1H-pyrrolo[2,3-b]pyridin-5-yl]phenyl]ethyl)-2,6-diazaspiro[3.3]heptan-2-yl]-N-[(3S)-2,6-dioxopiperidin-3-yl]-2-fluorobenzamide (Compound 373)

Step A: tert-butyl 6-[3-fluoro-4-(methoxycarbonyl)phenyl]-2,6-diazaspiro[3.3]heptane-2-carboxylate

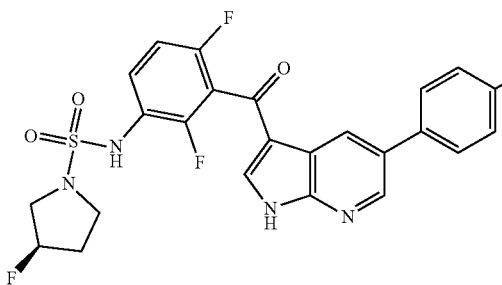

A mixture of methyl 4-bromo-2-fluorobenzoate (750 mg, 3.22 mmol), tert-butyl 2,6-diazaspiro[3.3]heptane-2-carboxylate oxalic acid salt (782 mg, 3.22 mmol), cesium carbonate (2.10 g, 6.44 mmol), toluene (60 mL), palladium (II) acetate (36 mg, 0.16 mmol), and 4,5-bis(diphenylphosphino)-9,9-dimethylxanthene (150 mg, 0.256 mmol) was stirred for 3 h at 90° C. The reaction mixture was cooled and diluted with ethyl acetate (100 mL). The solids were filtered out and the resulting mixture was concentrated. Purification of the residue by silica gel column chromatography (1:3 ethyl acetate:petroleum ether) afforded 804 mg (71%) of tert-butyl 6-[3-fluoro-4-(methoxycarbonyl)phenyl]-2,6-diazaspiro[3.3]heptane-2-carboxylate as a white solid.

Step B: methyl 4-[2,6-diazaspiro[3.3]heptan-2-yl]-2-fluorobenzoate

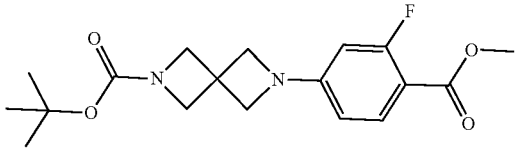 [SMILES: COC(=O)c1ccc(N2CC3(CN(C(=O)OC(C)(C)C)C3)C2)cc1F]

A mixture of tert-butyl 6-[3-fluoro-4-(methoxycarbonyl)phenyl]-2,6-diazaspiro[3.3]heptane-2-carboxylate (300 mg, 0.856 mmol), dichloromethane (15 mL), and trifluoroacetic acid (3 mL) was stirred for 2 h at 25° C. The resulting mixture was concentrated to afford crude methyl 4-[2,6-diazaspiro[3.3]heptan-2-yl]-2-fluorobenzoate (300 mg) as a solid. MS (ESI): m/z 250.90 [M+H]$^+$.

Step C: methyl 4-[6-[2-(4-bromophenyl)ethyl]-2,6-diazaspiro[3.3]heptan-2-yl]-2-fluorobenzoate

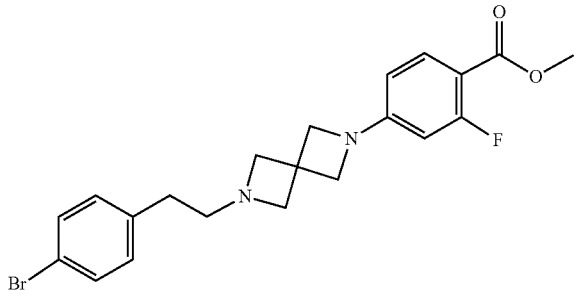 [SMILES: COC(=O)c1ccc(N2CC3(CN(CCc4ccc(Br)cc4)C3)C2)cc1F]

A mixture of methyl 4-[2,6-diazaspiro[3.3]heptan-2-yl]-2-fluorobenzoate (200 mg, 0.799 mmol), acetonitrile (10 mL), potassium carbonate (221 mg, 1.60 mmol), and 2-(4-bromophenyl)acetaldehyde (175 mg, 0.879 mmol) was stirred for 12 h at 70° C. Purification of the concentrated residue by silica gel column chromatography (1:1 petroleum ether:ethyl acetate) afforded methyl 4-[6-[2-(4-bromophenyl)ethyl]-2,6-diazaspiro[3.3]heptan-2-yl]-2-fluorobenzoate (180 mg, 52%) as a solid. MS (ESI): m/z 433.00 [M+H]$^+$.

Step D: methyl 4-[6-(2-[4-[3-(2,6-difluoro-3-[[(3R)-3-fluoropyrrolidin-1-ylsulfonyl]amino]benzoyl)-1H-pyrrolo[2,3-b]pyridin-5-yl]phenyl]ethyl)-2,6-diazaspiro[3.3]heptan-2-yl]-2-fluorobenzoate

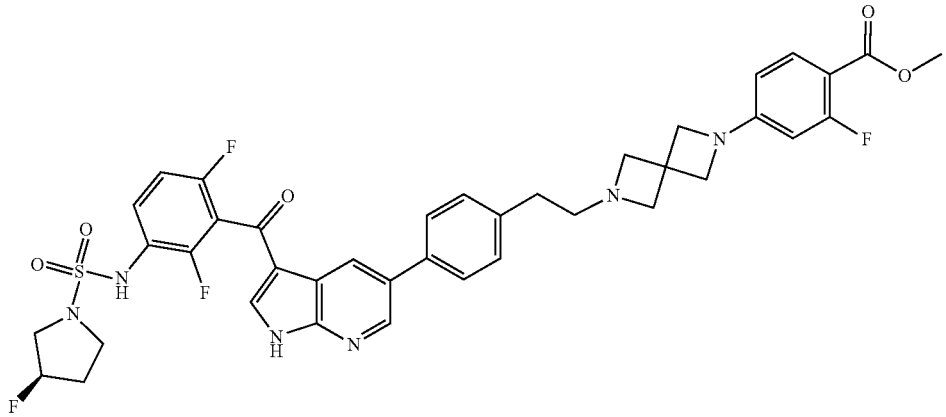 [SMILES: COC(=O)c1ccc(N2CC3(CN(CCc4ccc(-c5cnc6[nH]cc(C(=O)c7c(F)ccc(NS(=O)(=O)N8CC[C@@H](F)C8)c7F)c6c5)cc4)C3)C2)cc1F]

A mixture of methyl 4-[6-[2-(4-bromophenyl)ethyl]-2,6-diazaspiro[3.3]heptan-2-yl]-2-fluorobenzoate (150 mg, 0.346 mmol), 1,4-dioxane (12 mL), water (2 mL), cesium fluoride (105 mg, 0.692 mmol), [1,1'-bis(di-tert-butylphosphino)ferrocene]dichloropalladium(II) (45 mg, 0.069 mmol), and (3R)—N-[2,4-difluoro-3-[5-(4,4,5,5-tetramethyl-1,3,2-dioxaborolan-2-yl)-1H-pyrrolo[2,3-b]pyridine-3-carbonyl]phenyl]-3-fluoropyrrolidine-1-sulfonamide (191 mg, 0.346 mmol) was stirred for 3 h at 90° C. Purification of the concentrated residue by silica gel column chromatography (12:1 dichloromethane:methanol) afforded methyl 4-[6-(2-[4-[3-(2,6-difluoro-3-[[(3R)-3-fluoropyrrolidin-1-ylsulfonyl]amino]benzoyl)-1H-pyrrolo[2,3-b]pyridin-5-yl]phenyl]ethyl)-2,6-diazaspiro[3.3]heptan-2-yl]-2-fluorobenzoate (200 mg, 74%) as a solid. MS (ESI): m/z 777.35 [M+H]$^+$.

Step E: 4-[6-(2-[4-[3-(2,6-difluoro-3-[[(3R)-3-fluoropyrrolidin-1-ylsulfonyl]amino]benzoyl)-1H-pyrrolo[2,3-b]pyridin-5-yl]phenyl]ethyl)-2,6-diazaspiro[3.3]heptan-2-yl]-2-fluorobenzoic acid

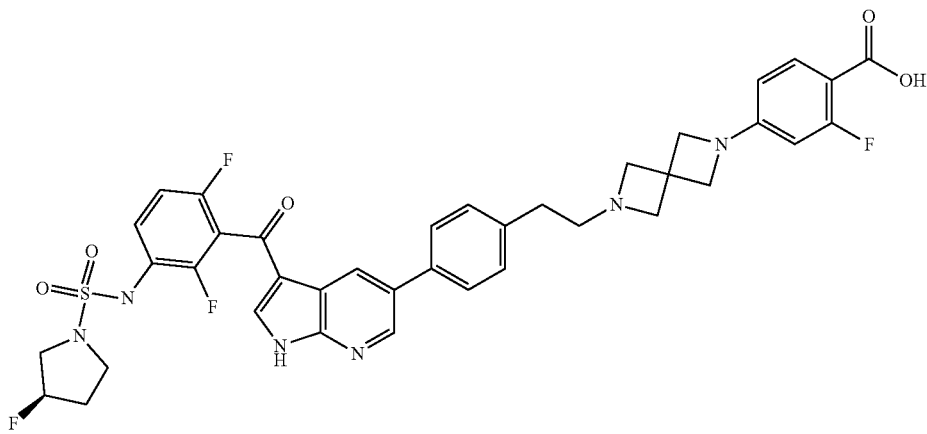 [SMILES: O=C(O)c1ccc(N2CC3(CN(CCc4ccc(-c5cnc6[nH]cc(C(=O)c7c(F)ccc(NS(=O)(=O)N8CC[C@@H](F)C8)c7F)c6c5)cc4)C3)C2)cc1F]

A mixture of methyl 4-[6-(2-[4-[3-(2,6-difluoro-3-[[(3R)-3-fluoropyrrolidin-1-ylsulfonyl]amino]benzoyl)-1H-pyrrolo[2,3-b]pyridin-5-yl]phenyl]ethyl)-2,6-diazaspiro[3.3]heptan-2-yl]-2-fluorobenzoate (200 mg, 0.257 mmol), tetrahydrofuran (10 mL), methanol (10 mL), sodium hydroxide (31 mg, 0.77 mmol), and water (5 mL) was stirred for 3 h at 25° C. The mixture was then concentrated and acidified to pH 6 with concentrated hydrochloric acid. The precipitated solids were collected by filtration and washed with water (3×10 mL) to afford 180 mg (92%) of 4-[6-(2-[4-[3-(2,6-difluoro-3-[[(3R)-3-fluoropyrrolidin-1-ylsulfonyl]amino]benzoyl)-1H-pyrrolo[2,3-b]pyridin-5-yl]phenyl]ethyl)-2,6-diazaspiro[3.3]heptan-2-yl]-2-fluorobenzoic acid as a solid. MS (ESI): m/z 763.15 [M+H]$^+$.

Step F: 4-[6-(2-[4-[3-(2,6-difluoro-3-[[(3R)-3-fluoropyrrolidin-1-ylsulfonyl]amino]benzoyl)-1H-pyrrolo[2,3-b]pyridin-5-yl]phenyl]ethyl)-2,6-diazaspiro[3.3]heptan-2-yl]-N-[(3S)-2,6-dioxopiperidin-3-yl]-2-fluorobenzamide

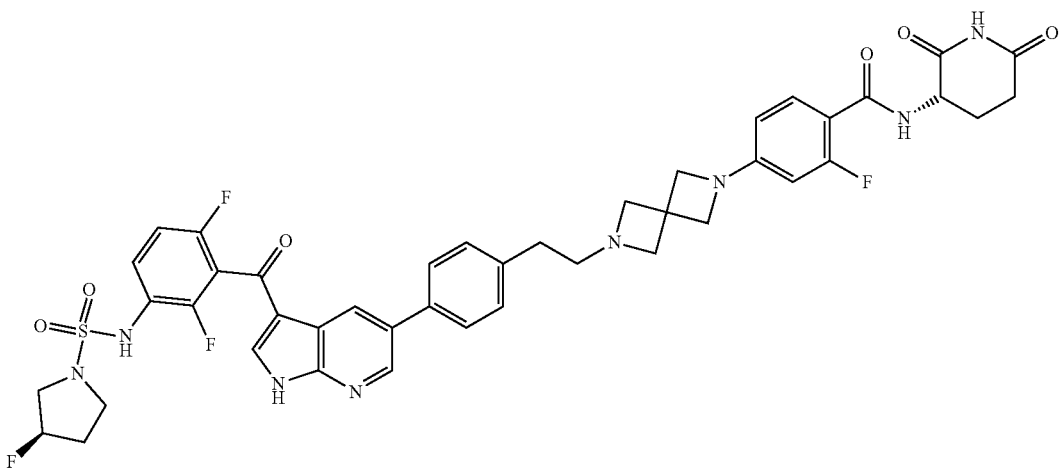

A cooled (0° C.) mixture of 4-[6-(2-[4-[3-(2,6-difluoro-3-[[(3R)-3-fluoropyrrolidin-1-ylsulfonyl]amino]benzoyl)-1H-pyrrolo[2,3-b]pyridin-5-yl]phenyl]ethyl)-2,6-diazaspiro[3.3]heptan-2-yl]-2-fluorobenzoic acid (100 mg, 0.131 mmol), N,N-dimethylformamide (5 mL), hydroxybenzotriazole (44.29 mg, 0.328 mmol), 1-ethyl-3-(3'-dimethylaminopropyl)carbodiimide (101 mg, 0.524 mmol), N-methylmorpholine (66 mg, 0.66 mmol), (3S)-3-aminopiperidine-2,6-dione (17 mg, 0.131 mmol) was stirred for 2 h at 25° C. The concentrated residue was purified by reverse phase flash chromatography (C18 silica, 10 to 60% tetrahydrofuran:water) to afford 4-[6-(2-[4-[3-(2,6-difluoro-3-[[(3R)-3-fluoropyrrolidin-1-ylsulfonyl]amino]benzoyl)-1H-pyrrolo[2,3-b]pyridin-5-yl]phenyl]ethyl)-2,6-diazaspiro[3.3]heptan-2-yl]-N-[(3S)-2,6-dioxopiperidin-3-yl]-2-fluorobenzamide (47 mg, 41%) as a white solid. $^1$H NMR (300 MHz, DMSO-d6) δ 12.97 (s, 1H), 10.84 (s, 1H), 8.69 (s, 1H), 8.59 (s, 1H), 8.01 (s, 1H), 7.98-7.96 (m, 1H), 7.67-7.65 (m, 4H), 7.45-7.43 (m, 2H), 7.29-7.25 (m, 1H), 6.31-6.23 (m, 2H), 5.42-5.13 (m, 1H), 4.77-4.68 (m, 1H), 4.00 (s, 4H), 3.61-3.60 (m, 3H), 2.77-2.54 (m, 4H), 2.22-1.95 (m, 5H), 1.26-1.24 (m, 5H); MS (ESI): m/z 873.35 [M+H]$^+$.

The following exemplary compounds may be prepared by a procedure analogous to that described for Exemplary Compounds 373: 274, 375, 376, 377, 378, 379, and 380.

Exemplary Synthesis of Exemplary Compound 337: (3R)—N-(3-(5-(4-(4-((4-(1-(2,6-dioxopiperidin-3-yl)-3-methyl-2-oxo-2,3-dihydro-1H-benzo[d]imidazol-4-yl)piperidin-1-yl)methyl)piperidin-1-yl)phenyl)-1H-pyrrolo[2,3-b]pyridine-3-carbonyl)-2,4-difluorophenyl)-3-fluoropyrrolidine-1-sulfonamide (Compound 337)

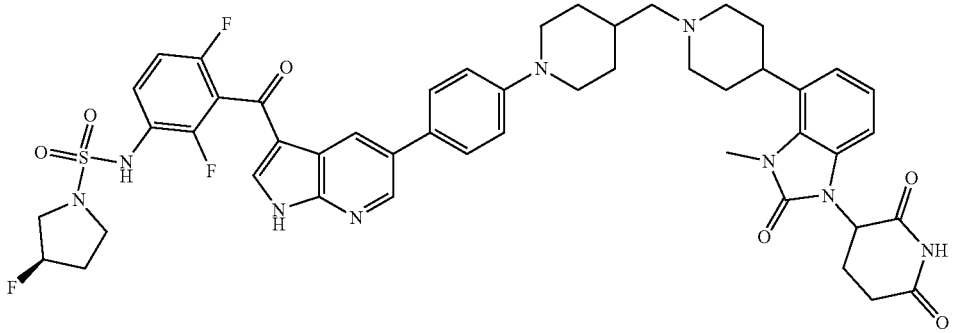 [SMILES: Cn1c(=O)n(C2CCC(=O)NC2=O)c2cccc(C3CCN(CC4CCN(c5ccc(-c6cnc7[nH]cc(C(=O)c8c(F)ccc(NS(=O)(=O)N9CC[C@@H](F)C9)c8F)c7c6)cc5)CC4)CC3)c21]

Step A: N-(4-methoxybenzyl)-5-oxotetrahydrofuran-2-carboxamide

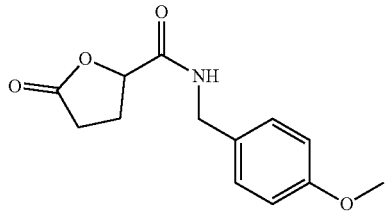 [SMILES: COc1ccc(CNC(=O)C2CCC(=O)O2)cc1]

To 5-oxotetrahydrofuran-2-carboxylic acid (10 g, 77 mmol) was added thionyl chloride (21 g, 173 mmol) at 0° C. slowly. The mixture was stirred at 85° C. for 3 h and then at 15° C. for 6 h, and then concentrated. The residue was dissolved in dry dichloromethane (1 L) at 0° C., then a solution of triethylamine (15.5 g, 153 mmol) and 4-methoxybenzylamine (8.4 g, 62 mmol) in dichloromethane (400 mL) was added, and then the mixture stirred at 15° C. for 3 h. Water (600 mL) was added and the mixture was extracted with dichloromethane (3×300 mL). The combined organic fractions were washed with 0.5 M aqueous hydrochloric acid (500 mL), saturated aqueous sodium chloride (500 mL), dried over sodium sulfate, filtered, and concentrated. Purification of the residue by flash silica gel chromatography (1:1 petroleum ether:ethyl acetate) afforded N-(4-methoxybenzyl)-5-oxotetrahydrofuran-2-carboxamide (2.4 g, 65%) as a yellow solid. MS (ESI): m/z 250.10 [M+H]$^+$.

Step B: 3-hydroxy-1-(4-methoxybenzyl)piperidine-2,6-dione

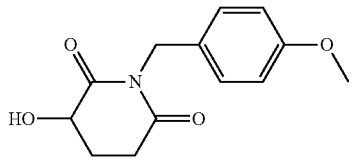 [SMILES: COc1ccc(CN2C(=O)CCC(O)C2=O)cc1]

To a cooled (−78° C.) solution of N-[(4-methoxyphenyl)methyl]-5-oxo-tetrahydrofuran-2-carboxamide (12.0 g, 48 mmol) in tetrahydrofuran (150 mL) was added dropwise a solution of potassium tert-butoxide (6.45 g, 57.6 mmol) in tetrahydrofuran (100 mL). The reaction mixture stirred at −40° C. for 1 h and was then quenched with saturated aqueous ammonium chloride (100 mL). The mixture was extracted with ethyl acetate (3×150 mL). The combined organic fractions were washed with saturated aqueous sodium chloride (30 mL), dried over sodium sulfate, filtered and concentrated. Purification of the residue by silica gel column chromatography (1:1 petroleum ether:ethyl acetate) afforded 3-hydroxy-1-(4-methoxybenzyl)piperidine-2,6-dione (11.0 g, 92%) as a white solid.

Step C: 1-(4-methoxybenzyl)-2,6-dioxopiperidin-3-yl trifluoromethanesulfonate

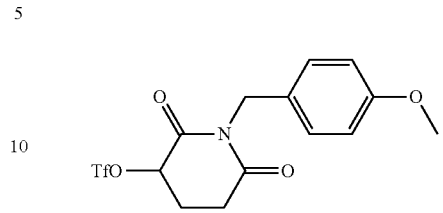

To a solution of 3-hydroxy-1-[(4-methoxyphenyl)methyl] piperidine-2, 6-dione (11.0 g, 44.0 mmol) and pyridine (6.86 g, 88.0 mmol) in dichloromethane (500 mL) was added trifluoromethylsulfonyl trifluoromethanesulfonate (13.6 g, 48.4 mmol) dropwise at 0° C. The mixture was stirred at −10° C. for 1.5 h and was then concentrated. Purification of the residue by silica gel column chromatography on silica gel (20:1 petroleum ether:ethyl acetate) afforded 1-(4-methoxybenzyl)-2,6-dioxopiperidin-3-yl trifluoromethanesulfonate (11.4 g, 68%) as a light yellow gum.

Step D: 2-bromo-N-methyl-6-nitroaniline

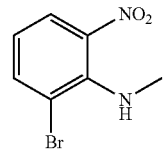

To a solution of 1-bromo-2-fluoro-3-nitro-benzene (40.0 g, 181 mmol) in tetrahydrofuran (40 mL) was added 2.0 M methylamine (400 mL). The reaction mixture was stirred at 60° C. for 12 h and was then poured into saturated aqueous sodium bicarbonate (30 mL) and extracted with ethyl acetate (3×200 mL). The combined organic fractions were washed with saturated aqueous sodium chloride (2×200 mL), dried with sodium sulfate, filtered and concentrated to afford 2-bromo-N-methyl-6-nitroaniline (40.0 g, 95%) as a red oil. MS (ESI): m/z 230.80 [M+H]$^+$.

Step E: 6-bromo-N1-methylbenzene-1,2-diamine

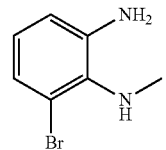

To a mixture of 2-bromo-N-methyl-6-nitro-aniline (23.0 g, 99.5 mmol) in ethyl acetate (300 mL) and water (10 mL) was added acetic acid (100 mL). The mixture was warmed to 50° C. Then iron powder (22.2 g, 398 mmol) was added and the mixture was heated to 80° C. for 4 h. The mixture was filtered and concentrated. The residue was diluted with water (100 mL) and extracted with ethyl acetate (3×200 mL). The combined organic fractions were dried over sodium sulfate, filtered and concentrated to afford 6-bromo- N1-methylbenzene-1,2-diamine (20.0 g, 99%) as a red oil. MS (ESI): m/z 201.05 [M+H]⁺.

Step F: 7-bromo-1-methyl-1,3-dihydro-2H-benzo[d]imidazol-2-one

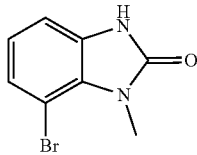

To a mixture of 3-bromo-N2-methyl-benzene-1,2-diamine (20.0 g, 99.4 mmol) in acetonitrile (300 mL) was added carbonyldiimidazole (32.2 g, 198 mmol). The reaction mixture was stirred at 85° C. for 12 h and then concentrated. The residue was diluted with water (200 mL). The resulting precipitate was filtered, washed with water (1 L) and dried to afford 7-bromo-1-methyl-1,3-dihydro-2H-benzo[d]imidazol-2-one (20 g, 88%) as white solid. MS (ESI): m/z 226.85 [M+H]⁺.

Step G: 4-bromo-3-methyl-2-oxo-2,3-dihydro-1H-benzo[d]imidazol-1-yl)-1-(4-methoxybenzyl)piperidine-2,6-dione

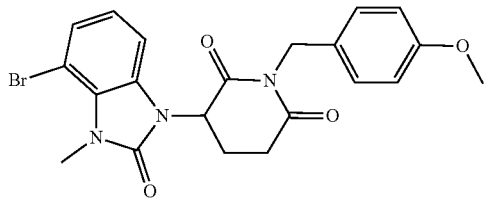 [SMILES: COc1ccc(CN2C(=O)CCC(n3c(=O)n(C)c4c(Br)cccc43)C2=O)cc1]

To a solution of 5-bromo-3-methyl-1H-benzimidazol-2-one (4.90 g, 21.6 mmol) in tetrahydrofuran (300 mL) was added potassium tert-butoxide (3.63 g, 32.3 mmol) at 0° C. The mixture was stirred at 0 to 10° C. for 1 h. Then a solution of [1-[(4-methoxyphenyl)methyl]-2,6-dioxo-3-piperidyl] trifluoromethanesulfonate (9.87 g, 25.9 mmol) in tetrahydrofuran (100 mL) was added to the reaction mixture at 0 to 10° C. over 30 min. The mixture was stirred at 0 to 10° C. for 30 min, and then an additional solution of [1-[(4 methoxyphenyl) methyl]-2,6-dioxo-3-piperidyl] trifluoromethanesulfonate (2.47 g, 6.47 mmol) in tetrahydrofuran (20 mL) was added at 0 to 10° C. dropwise. The mixture was then stirred at 0 to 10° C. for another 30 min. The reaction was quenched water (400 mL) and extracted with ethyl acetate (3×200 mL). The combined organic fractions were concentrated. The residue was triturated with ethyl acetate (80 mL) and filtered. The filter cake was collected dried to afford 4-bromo-3-methyl-2-oxo-2,3-dihydro-1H-benzo[d]imidazol-1-yl)-1-(4-methoxybenzyl)piperidine-2,6-dione (6.70 g, 67%) as light yellow solid. MS (ESI): m/z 460.10 [M+H]⁺.

Step H: 3-(4-bromo-3-methyl-2-oxo-2,3-dihydro-1H-benzo[d]imidazol-1-yl)piperidine-2,6-dione

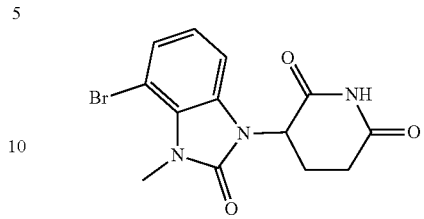

To a mixture of 3-(5-bromo-3-methyl-2-oxo-benzimidazol-1-yl)-1-[(4-methoxyphenyl)methyl] piperidine-2,6-dione (4.3 g, 9.3 mmol) in toluene (50 mL) was added methanesulfonic acid (25.0 mL, 176 mmol) at 15° C. The mixture was stirred at 120° C. for 2 h, then cooled to room temperature and concentrated. The residue was poured into ice water (200 mL) and extracted with ethyl acetate (3×100 mL). The combined organic fractions were washed with saturated aqueous sodium chloride (50 mL), dried over sodium sulfate, filtered, and concentrated. The residue was triturated with ethyl acetate (80 mL) and filtered and dried to afford 3-(4-bromo-3-methyl-2-oxo-2,3-dihydro-1H-benzo[d]imidazol-1-yl)piperidine-2,6-dione (2.13 g, 67%) as light yellow solid. MS (ESI): m/z 338.05 [M+H]⁺.

Step I: tert-butyl 4-(1-(2,6-dioxopiperidin-3-yl)-3-methyl-2-oxo-2,3-dihydro-1H-benzo[d]imidazol-4-yl)-3,6-dihydropyridine-1(2H)-carboxylate

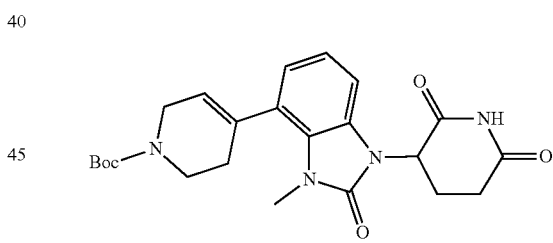

A mixture of 3-(4-bromo-3-methyl-2-oxo-benzimidazol-1-yl)piperidine-2,6-dione (1.00 g, 2.96 mmol), tert-butyl 4-(4,4,5,5-tetramethyl-1,3,2-dioxaborolan-2-yl)-3,6-dihydro-2H-pyridine-1-carboxylate (1.19 g, 3.84 mmol), (2-dicyclohexylphosphino-2',4',6'-triisopropyl-1,1'-biphenyl)[2-(2'-amino-1,1'-biphenyl)]palladium(II) methanesulfonate (376 mg, 0.444 mmol), and potassium phosphate (1.88 g, 8.87 mmol) in 1,4-dioxane (20 mL) and water (2 mL) was stirred at 60° C. for 3 h. The mixture was filtered and concentrated. Purification of the residue by reverse phase chromatography afforded tert-butyl 4-(1-(2,6-dioxopiperidin-3-yl)-3-methyl-2-oxo-2,3-dihydro-1H-benzo[d]imidazol-4-yl)-3,6-dihydropyridine-1(2H)-carboxylate (1.00 g, 75%) as white solid. MS (ESI): m/z 441.30 [M+H]⁺.

Step J: tert-butyl 4-(1-(2,6-dioxopiperidin-3-yl)-3-methyl-2-oxo-2,3-dihydro-1H-benzo[d]imidazol-4-yl)piperidine-1-carboxylate

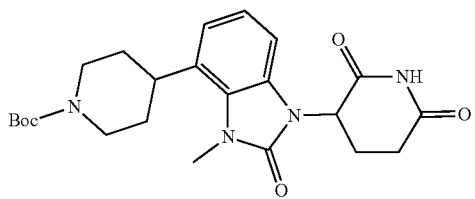 [SMILES: Cn1c(=O)n(C2CCC(=O)NC2=O)c2cccc(C3CCN(C(=O)OC(C)(C)C)CC3)c21]

To a solution of tert-butyl 4-[1-(2,6-dioxo-3-piperidyl)-3-methyl-2-oxo-benzimidazol-4-yl]-3,6-dihydro-2H-pyridine-1-carboxylate (900 mg, 2.04 mmol) in tetrahydrofuran (270 mL) was added 10 wt % palladium on carbon (180 mg). The suspension was degassed and purged with hydrogen three times. The mixture was stirred at 30° C. for 48 h under 50 psi of hydrogen. The reaction mixture was filtered and concentrated to afford tert-butyl 4-(1-(2,6-dioxopiperidin-3-yl)-3-methyl-2-oxo-2,3-dihydro-1H-benzo[d]imidazol-4-yl)piperidine-1-carboxylate as white solid. Step K: 3-(3-methyl-2-oxo-4-(piperidin-4-yl)-2,3-dihydro-1H-benzo[d]imidazol-1-yl)piperidine-2,6-dione

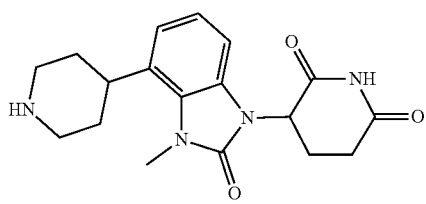 [SMILES: Cn1c(=O)n(C2CCC(=O)NC2=O)c2cccc(C3CCNCC3)c21]

To a solution of tert-butyl 4-(1-(2,6-dioxopiperidin-3-yl)-3-methyl-2-oxo-2,3-dihydro-1H-benzo[d]imidazol-4-yl)piperidine-1-carboxylate (1.00 g, 2.26 mmol) in dichloromethane (10 mL) was added 4 N hydrochloric acid in 1,4-dioxane (5 mL). The reaction mixture was stirred at 25° C. for 1 h and then concentrated to afford 3-(3-methyl-2-oxo-4-(piperidin-4-yl)-2,3-dihydro-1H-benzo[d]imidazol-1-yl)piperidine-2,6-dione (900 mg, 88%) as white solid. MS (ESI): m/z 343.15 [M+H]$^+$.

Step L: (3R)—N-(3-(5-(4-(4-((4-(1-(2,6-dioxopiperidin-3-yl)-3-methyl-2-oxo-2,3-dihydro-1H-benzo[d]imidazol-4-yl)piperidin-1-yl)methyl)piperidin-1-yl)phenyl)-1H-pyrrolo[2,3-b]pyridine-3-carbonyl)-2,4-difluorophenyl)-3-fluoropyrrolidine-1-sulfonamide

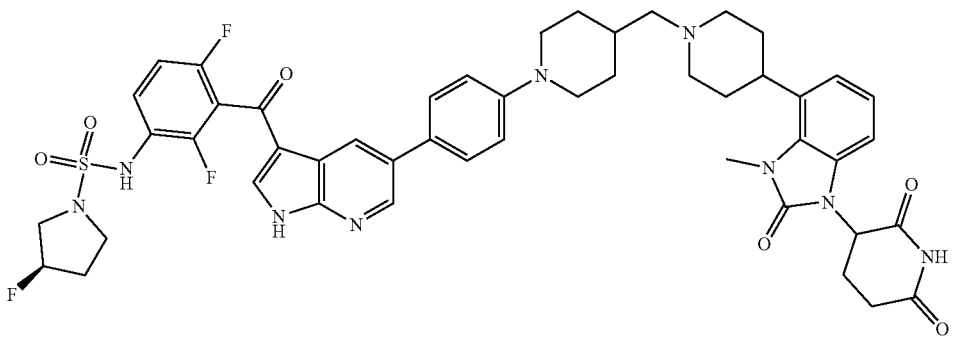 [SMILES: Cn1c(=O)n(C2CCC(=O)NC2=O)c2cccc(C3CCN(CC4CCN(c5ccc(-c6cnc7[nH]cc(C(=O)c8c(F)ccc(NS(=O)(=O)N9CC[C@@H](F)C9)c8F)c7c6)cc5)CC4)CC3)c21]

A solution of 3-(3-methyl-2-oxo-4-(piperidin-4-yl)-2,3-dihydro-1H-benzo[d]imidazol-1-yl)piperidine-2,6-dione (100 mg, 0.26 mmol) in dichloromethane (5 mL) and methanol (0.5 mL) at room temperature was adjusted to pH 9 with diisopropylethylamine, then acidified to pH 5 with acetic acid. Then (R)—N-(2,4-difluoro-3-(5-(4-(4-formylpiperidin-1-yl)phenyl)-1H-pyrrolo[2,3-b]pyridine-3-carbonyl)phenyl)-3-fluoropyrrolidine-1-sulfonamide (177 mg, 0.29 mmol) was added and the mixture was stirred for 2 h at room temperature. Then sodium triacetoxyborohydride (110.0 mg, 0.52 mmol) was added and the mixture stirred 2 h at room temperature. The mixture was acidified to pH 8 by addition of saturated aqueous sodium bicarbonate and extracted with tetrahydrofuran (3×20 mL). The combined organic factions were washed with saturated aqueous sodium chloride (30 mL), dried over sodium sulfate, filtered, and concentrated. Purification of the residue by preparative thin layer chromatography (8:1 dichloromethane:methanol) afforded (3R)—N-(3-(5-(4-(4-((4-(1-(2,6-dioxopiperidin-3-yl)-3-methyl-2-oxo-2,3-dihydro-1H-benzo[d]imidazol-4-yl)piperidin-1-yl)methyl)piperidin-1-yl)phenyl)-1H-pyrrolo[2,3-b]pyridine-3-carbonyl)-2,4-difluorophenyl)-3-fluoropyrrolidine-1-sulfonamide (80.1 mg, 33%) as a yellow solid. MS (ESI): m/z 939.40 [M+H]$^+$; $^1$H NMR (400 MHz, DMSO-d6) δ 12.91 (s, 1H), 11.10 (s, 1H), 9.85 (s, 1H), 8.65 (d, J=2.2 Hz, 1H), 8.53 (s, 1H), 8.07 (s, 1H), 7.67-7.55 (m, 3H), 7.26 (t, J=9.1 Hz, 1H), 7.08 (s, 1H), 7.06 (s, 1H), 7.06-6.94 (m, 3H), 5.38 (dd, J=12.7, 5.0 Hz, 2H), 5.23 (d, J=3.5 Hz, OH), 3.80 (d, J=12.0 Hz, 2H), 3.59 (s, 3H), 3.48 (d, J=2.3 Hz, 1H), 3.38 (dd, J=12.2, 3.4 Hz, 3H), 3.32-3.25 (m, 1H), 3.02 (d, J=10.8 Hz, 2H), 2.92-2.82 (m, 1H), 2.76 (d, J=11.9 Hz, 2H), 2.70 (d, J=12.8 Hz, 1H), 2.62 (d, J=17.9 Hz, 1H), 2.52 (s, 1H), 2.26 (d, J=6.9 Hz, 2H), 2.11 (s, 4H), 1.99 (dd, J=10.6, 5.8 Hz, 2H), 1.88-1.74 (m, 8H), 1.25 (d, J=13.8 Hz, 5H).

Exemplary Synthesis of Exemplary Example 9:
N-[4-[4-[2-[4-[1-[2,6-difluoro-3-[[(3R)-3-fluoropyrrolidin-1-yl]sulfonylamino]benzoyl]-1H-pyrrolo[2,3-b]pyridin-5-yl]phenyl]ethyl]piperazin-1-yl]-2-fluorophenyl]-2-(2,4-dioxopyrimidin-1-yl)acetamide (Example 9)

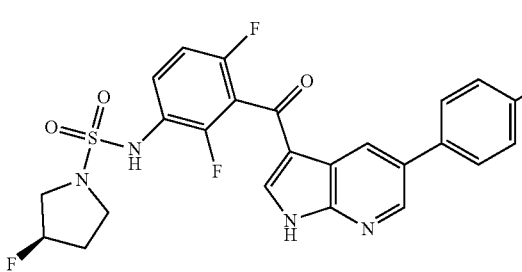

Step A: 1, 2-(2,4-dioxo-3,4-dihydropyrimidin-1(2H)-yl)acetic acid

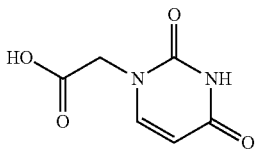

To a stirred solution of 1H-pyrimidine-2,4-dione (2.00 g, 17.84 mmol) and potassium hydroxide (4.00 g, 71.37 mmol) in water (10 mL) was added dropwise 2-bromoacetic acid (3.72 g, 26.7 mmol, 1.9 mL) over 30 min. The solution was then stirred at 25° C. for 2 h. The mixture was adjusted to pH 5 with aqueous 4 N hydrochloric acid solution. The solution was cooled to 0° C. and the resulting precipitate was collected by filtration, which was then discarded. The pH of the filtrate was adjusted to 2 with aqueous 4 N hydrochloric acid solution and cooled to 0° C. The resulting white precipitate was collected by filtration and dried under reduced pressure to give 2-(2,4-dioxopyrimidin-1-yl)acetic acid (870 mg, 29%) as a white solid. $^1$H NMR (400 MHz, DMSO-d$_6$) δ 11.35 (s, 1H), 7.61 (d, J=8.0 Hz, 1H), 5.59 (dd, J=2.0, 8.0 Hz, 1H), 4.41 (s, 2H).

Step B: benzyl 4-(4-(2-(2,4-dioxo-3,4-dihydropyrimidin-1(2H)-yl)acetamido)-3-fluorophenyl)piperazine-1-carboxylate

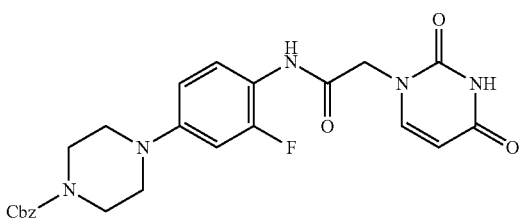 [SMILES: O=C(Cn1ccc(=O)[nH]c1=O)Nc1ccc(N2CCN(C(=O)OCc3ccccc3)CC2)cc1F]

To a solution of 2-(2,4-dioxopyrimidin-1-yl)acetic acid (200 mg, 1.18 mmol) in N,N-dimethylformamide (4 mL) was added diisopropylethyllamine (608 mg, 4.70 mmol), hydroxybenzotriazole (238 mg, 1.76 mmol), 1-(3-dimethylaminopropyl)-3-ethylcarbodiimide hydrochloride (338 mg, 1.76 mmol) and benzyl 4-(4-amino-3-fluoro-phenyl)piperazine-1-carboxylate (465 mg, 1.41 mmol). The mixture was stirred at 25° C. for 10 h. The mixture was poured into water (20 mL) and a gray precipitate was formed. The mixture was filtered. The precipitate was recrystallized from 1:1 petroleum ether:ethyl acetate to give benzyl 4-[4[[2-(2,4-dioxopyrimidin-1-yl)acetyl]amino]-3-fluoro-phenyl] piperazine-1-carboxylate (400 mg, 70%) as a gray solid, which was used into the next step without further purification. MS (ESI): m/z 482.2 [M+H]$^+$; $^1$H NMR (400 MHz, DMSO-d$_6$) δ 11.31 (br s, 1H), 9.87 (s, 1H), 7.72-7.50 (m, 2H), 7.47-7.23 (m, 5H), 6.87 (br d, J=14.0 Hz, 1H), 6.75 (br d, J=8.8 Hz, 1H), 5.59 (br d, J=8.0 Hz, 1H), 5.11 (s, 2H), 4.57 (s, 2H), 3.53 (br s, 4H), 3.15 (br s, 4H).

Step C: 2-(2,4-dioxo-3,4-dihydropyrimidin-1(2H)-yl)-N-(2-fluoro-4-(piperazin-1-yl)phenyl)acetamide

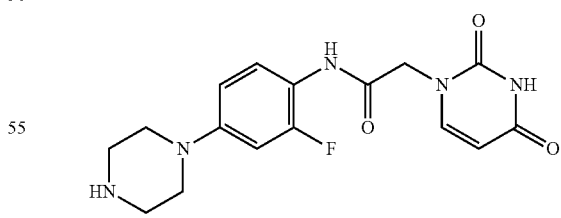

To a solution of benzyl 4-[4-[2-(2,4-dioxopyrimidin-1-yl)acetyl]amino]-3-fluoro-phenyl]piperazine-1-carboxylate (180 mg, 0.37 mmol) in acetonitrile (5 mL) was added iodotrimethylsilane (224 mg, 1.12 mmol, 152.66 uL). The mixture was stirred at 60° C. for 2 h. The mixture was concentrated to give 2-(2,4-dioxopyrimidin-1-yl)-N-(2-fluoro-4-piperazin-1-yl-phenyl)acetamide (120 mg, 92%).

Step D: N-[4-[4-[2-[4-[3-[2, 6-difluoro-3-[[(3R)-3-fluoropyrrolidin-1-yl]sulfonylamino]benzoyl]-1H-pyrrolo[2,3-b]pyridin-5-yl]phenyl]ethyl]piperazin-1-yl]-2-fluoro-phenyl]-2-(2,4-dioxopyrimidin-1-yl)acetamide

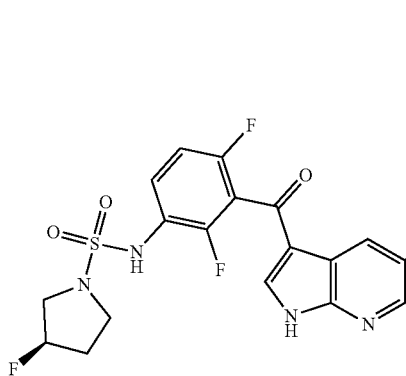
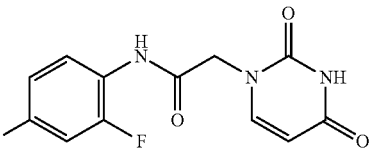

To a solution of 2-(2,4-dioxopyrimidin-1-yl)-N-(2-fluoro-4-piperazin-1-yl-phenyl)acetamide (96 mg, 0.28 mmol) in N,N-dimethylformamide (5 mL) was added sodium acetate (68 mg, 0.83 mmol) to pH ~8. The mixture was stirred at 30° C. for 20 min, and (3R)—N-[2,4-difluoro-3-[5-[4-(2-oxoethyl)phenyl]-1H-pyrrolo[2,3-b]pyridine-3-carbonyl]phenyl]-3-fluoro-pyrrolidine-1-sulfonamide (120 mg, 0.22 mmol) was added, and acetic acid (33 mg, 0.55 mmol) was added to pH ~5, the mixture was stirred at 30° C. for 2 h, then sodium cyanoborohydride (35 mg, 0.55 mmol) was added. The mixture was stirred at 30° C. for 40 min. Ethyl acetate (20 mL), tetrahydrofuran (30 mL) and water (40 mL) were added and layers were separated. The aqueous phase was extracted with tetrahydrofuran (20 mL). The combined organic extracts were washed with brine (40 mL), dried over anhydrous sodium sulfate, filtered, and concentrated. The residue was purified by preparative HPLC (Phenomenex Synergi C18, 11 to 41% acetonitrile:(0.225% formic acid in water)) to afford N-[4-[4-[2-[4-[3-[2,6-difluoro-3-[[(3R)-3-fluoropyrrolidin-1-yl]sulfonylamino] benzoyl]-1H-pyrrolo[2,3-b]pyridin-5-yl]phenyl]ethyl]piperazin-1-yl]-2-fluoro-phenyl]-2-(2,4-dioxopyrimidin-1-yl)acetamide formic acid salt (62.6 mg, 24%) as a white solid. MS (ESI): m/z 874.3 [M+H]$^+$; $^1$H NMR (400 MHz, DMSO-d$_6$) δ 13.10-12.82 (m, 1H), 11.32 (s, 1H), 9.85 (s, 1H), 8.69 (d, J=2.4 Hz, 1H), 8.59 (s, 1H), 8.15 (s, 1H), 8.11 (s, 1H), 7.70-7.52 (m, 5H), 7.40 (d, J=8.0 Hz, 2H), 7.31-7.23 (m, 1H), 6.85 (dd, J=2.4, 14.4 Hz, 1H), 6.74 (dd, J=2.0, 8.8 Hz, 1H), 5.58 (d, J=8.0 Hz, 1H), 5.39-5.20 (m, 1H), 4.56 (s, 2H), 3.48 (s, 2H), 3.29 (dt, J=6.8, 10.0 Hz, 3H), 3.17 (s, 4H), 2.88-2.82 (m, 2H), 2.66-2.58 (m, 6H), 2.16-1.94 (m, 2H).

The following exemplary compounds may be prepared by a procedure analogous to that described for Exemplary Compounds 381: 364, 365, 366, 367, 368, 369, 370, 371, and 372.

Protein Level Control

This description also provides methods for the control of protein levels within a cell. The method is based on the use of compounds as described herein such that degradation of the target protein RAF (such as B-Raf) in vivo will result in the reducing the amount of the target protein in a biological system, preferably to provide a particular therapeutic benefit.

The following examples are used to assist in describing the present disclosure, but should not be seen as limiting the present disclosure in any way.

In certain embodiments, the description provides the following exemplary Raf-degrading bifunctional molecules (compounds of Table 1 or exemplary compounds 1-200), including salts, polymorphs, analogs, derivatives, and deuterated forms thereof.

In any aspect or embodiment described herein, such as a method of that includes the degradation of BRaf or mutant form thereof (such as BRaf V600E), the description provides exemplary compounds: 6, 12, 13, 18, 24, 26, 27, 28, 33, 41, 57, 58, 62, 75, 78, 80, 83, 85, 87, 88, 89, 90, 92, 93, 102, 104, 111, 118, 119, 127, 138, 144, 153, 160, 177, 190, 203 and 204.

In aspect or embodiment described herein, such as a method of that includes the degradation of BRaf or mutant form thereof (such as BRaf G466V), the description provides exemplary compounds: 3, 4, 6, 7, 9, 10, 11, 12, 16, 18, 19, 20, 21, 22, 24, 25, 26, 28, 31, 32, 34, 35, 36, 37, 38, 39, 40, 41, 42, 44, 45, 46, 48, 49, 50, 51, 52, 53, 54, 55, 56, 57, 58, 59, 60, 61, 62, 63, 64, 65, 66, 67, 68, 69, 70, 71, 72, 73, 74, 75, 80, 81, 83, 84, 85, 86, 87, 88, 89, 90, 91, 92, 93, 94, 95, 97, 98, 99, 100, 101, 103, 104, 105, 106, 107, 108, 109, 110, 111, 113, 114, 115, 116, 117, 118, 119, 120, 121, 122, 123, 124, 125, 126, 127, 128, 129, 130, 131, 132, 133, 134, 135, 137, 138, 139, 140, 141, 142, 144, 145, 146, 147, 148, 149, 150, 151, 152, 153, 154, 155, 156, 157, 158, 160, 161, 163, 164, 165, 166, 167, 168, 170, 171, 172, 173, 174, 175, 176, 177, 178, 179, 180, 182, 184, 185, 186, 187, 188, 189, 190, 191, 192, 193, 194, 195, 196, 198, 199, 201, 202, 203, 204, 205, 206, 207, 208, 209, 210, 211, and 212.

Protocol for a cellular assay of target protein degradation (T-Rex 293 cells). T-Rex 293 cells were purchased from Invitrogen (#R71007), and stably transfected with a pcDNA4/TO_HA-BRAF_V600E construct, using 400 ug Zeocin for selection. V600e cells are plated in Dulbecco's Modified Eagle Medium (DMEM; Gibco #11965118) containing 10% fetal bovine serum (FBS; Gibco #16000044) and 1 ng/mL doxycycline (Selleckchem #4163) at a density of 5,000 cells/well in 50 µl on poly-D-lysine (PDL) coated, black clear bottom 96-well plates (Corning #354640) and incubated for 24 hours at 37° C. with 5% C$_0$2. The following day 50 ul of tested compound was added at 2x concentration in DMEM with a final concentration ranging from 1 µM to 0.1 nM in 0.1% dimethylsulfoxide (DMSO), and incubated for 24 hours at 37° C. with 5% CO$_2$. At the end of the experimental treatment, the media was flicked off and cells washed once with phosphate-buffered saline (PBS)++ (PBS with CaCl and MgCl) and gently replacing with 200 µl PBS++ per well. The PBS++ was removed and 50 uL 4% paraformaldehyde (PFA; EMS #15710) in PBS++ was added, and incubate at room temperature for 15 minutes. Cells were washed once with PBS++ and 50 uL 0.1% Triton X-100 (Fisher #BP151-500) in PBS++ was added. Plate was incubate for 5 minutes at room temperature. Cells were was once with PBS++. Cells were blocked with 100 uL Licor blocking buffer (Licor #927-50000) for 1 hour at room temperature. Next, 50 uL of HA antibody (CST #3724) at 1:1000 in Licor blocking buffer was added, and the plate incubate overnight at 4° C. The plates were parafilmed to prevent evaporation. Plate was washed three times with 200 uL PBS++. Fifty microliters of HCS secondary antibody solution [1:1000 Hoechst (Invitrogen #H3570), 1:1000 phalloidin (Invitrogen #A22287) and 1:5000 Alexa fluor (Invitrogen #A11008)] was added and incubated for 1 hour. Plate was wash three times with 200 uL PBS++, and imaged on a high content reader (ImageXpress Micro XLS, Molecular Devices).

Protocol for a cellular assay of target protein degradation (T-Rex 293 cells). T-Rex 293 cells were purchased from Invitrogen (#R71007), and stably transfected with a pcDNA4/TO_HA-BRAF G466V construct, using 400 ug Zeocin for selection. G466V cells are plated in Dulbecco's Modified Eagle Medium (DMEM; Gibco #11965118) containing 10% fetal bovine serum (FBS; Gibco #16000044) and 0.75 ng/mL doxycycline (Selleckchem #4163) at a density of 5,000 cells/well in 50 µl on poly-D-lysine (PDL) coated, black clear bottom 96-well plates (Corning #354640) and incubated for 24 hours at 37° C. with 5% $CO_2$.

The following day 50 ul of tested compound was added at 2x concentration in DMEM with a final concentration ranging from 30 nM to 3 pM in 0.1% dimethylsulfoxide (DMSO), and incubated for 24 hours at 37° C. with 5% $CO_2$. At the end of the experimental treatment, the media was flicked off and cells washed once with phosphate-buffered saline (PBS)++ (PBS with CaCl and MgCl) and gently replacing with 200 µl PBS++ per well. The PBS++ was removed and 50 uL 4% paraformaldehyde (PFA; EMS #15710) in PBS++ was added, and incubate at room temperature for 15 minutes. Cells were washed once with PBS++ and 50 uL 0.1% Triton X-100 (Fisher #BP151-500) in PBS++ was added. Plate was incubate for 5 minutes at room temperature. Cells were was once with PBS++. Cells were blocked with 100 uL Licor blocking buffer (Licor #927-50000) for 1 hour at room temperature. Next, 50 uL of HA antibody (CST #3724) at 1:1000 in Licor blocking buffer was added, and the plate incubate overnight at 4° C. The plates were parafilmed to prevent evaporation. Plate was washed three times with 200 uL PBS++. Fifty microliters of HCS secondary antibody solution [1:1000 Hoechst (Invitrogen #H3570), 1:1000 phalloidin (Invitrogen #A22287) and 1:5000 Alexa fluor (Invitrogen #A11008)] was added and incubated for 1 hour. Plate was wash three times with 200 uL PBS++, and imaged on a high content reader (ImageXpress Micro XLS, Molecular Devices).

The concentration of exemplary compound that leads to half maximal degradation ($DC_{50}$) as well as the maximum degradation observed ($D_{max}$, conventionally expressed as a percentage of control), which are below in Table 2 for the exemplary compounds of Table 1. Table 3 shows $^1$H NMR data for some exemplary bifunctional compounds of the present disclosure.

TABLE 1

Exemplary bifunctional compounds of the present disclosure

| Ex. No. | Parent Mol Structure | Synthetic Scheme | IUPAC Name |
|---|---|---|---|
| 1 | | 1 | (3R)-N-(3-{5-[4-({2-[2-(2,6-dioxopiperidin-3-yl)-1-oxo-2,3-dihydro-1H-isoindol-5-yl]-2-azaspiro[3.3]heptan-6-yl}oxy)phenyl]-1H-pyrrolo[2,3-b]pyridine-3-carbonyl}-2,4-difluorophenyl)-3-fluoropyrrolidine-1-sulfonamide. |
| 2 | | 1 | (3R)-N-[3-(5-{4-[(3aR,6aS)-5-({1-[2-(2,6-dioxopiperidin-3-yl)-1-oxo-2,3-dihydro-1H-isoindol-5-yl]piperidin-4-yl}methyl)-3a,6a-dimethyl-octahydropyrrolo[3,4-c]pyrrol-2-yl]phenyl}-1H-pyrrolo[2,3-b]pyridine-3-carbonyl)-2,4-difluorophenyl]-3-fluoropyrrolidine-1-sulfonamide |
| 3 | | 1 | (3R)-N-[3-(5-{4-[(3aR,7aS)-2-({1-[2-(2,6-dioxopiperidin-3-yl)-1-oxo-2,3-dihydro-1H-isoindol-5-yl)piperidin-4-yl]methyl)-octahydro-1H-pyrrolo[3,4-c]pyridin-5-yl]phenyl}-1H-pyrrolo[2,3-b]pyridine-3-carbonyl)-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 4 | | 1 | (3R)-N-(3-{5-[4-(3-{2-[2-(2,6-dioxopiperidin-3-yl)-1-oxo-2,3-dihydro-1H-isoindol-5-yl]-2,6-diazaspiro[3.4]octan-6-yl}prop-1-yn-1-yl)phenyl]-1H-pyrrolo[2,3-b]pyridine-3-carbonyl}-2,4-difluorophenyl)-3-fluoropyrrolidine-1-sulfonamide |
| 5 | | 1 | (3R)-N-[3-(5-{4-[(1R,4R)-5-{1-[2-(2,6-dioxopiperidin-3-yl)-1-oxo-2,3-dihydro-1H-isoindol-5-yl]azetidin-3-yl}-2,5-diazabicyclo[2.2.1]heptan-2-yl]phenyl}-1H-pyrrolo[2,3-b]pyridine-3-carbonyl)-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 6 | | 1 | (3R)-N-[3-(5-{4-[9-({1-[2-(2,6-dioxopiperidin-3-yl)-7-methoxy-1-oxo-2,3-dihydro-1H-isoindol-5-yl]piperidin-4-yl}methyl)-3,9-diazaspiro[5.5]undecan-3-yl]phenyl}-1H-pyrrolo[2,3-b]pyridine-3-carbonyl)-2,4-difluorophenyl]-3-fluoropyrrolidine-1-sulfonamide |
| 7 | | 1 | (3R)-N-[3-(5-{4-[1-({1-[2-(2,6-dioxopiperidin-3-yl)-1-oxo-2,3-dihydro-1H-isoindol-5-yl]azetidin-3-yl}methyl)piperidin-4-yl]phenyl}-1H-pyrrolo[2,3-b]pyridine-3-carbonyl)-2,4-difluorophenyl]-3-fluoropyrrolidine-1-sulfonamide |
| 8 | | 1 | (3R)-N-(3-{5-[2-({2-[2-(2,6-dioxopiperidin-3-yl)-1-oxo-2,3-dihydro-1H-isoindol-5-yl]-2-azaspiro[3.3]heptan-6-yl}methyl)-1,2,3,4-tetrahydroisoquinolin-6-yl]-1H-pyrrolo[2,3-b]pyridine-3-carbonyl}-2,4-difluorophenyl)-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 9 | | 1 | (3R)-N-(3-{5-[4-(1-{1-[2-(2,6-dioxopiperidin-3-yl)-1-oxo-2,3-dihydro-1H-isoindol-5-yl]piperidin-4-yl}-1,6-diazaspiro[3.3]heptan-6-yl)phenyl]-1H-pyrrolo[2,3-b]pyridine-3-carbonyl}-2,4-difluorophenyl)-3-fluoropyrrolidine-1-sulfonamide |
| 10 | | 1 | (3R)-N-(3-{5-[4-(2-{2-[2-(2,6-dioxopiperidin-3-yl)-1-oxo-2,3-dihydro-1H-isoindol-5-yl]-2,8-diazaspiro[4.5]decan-8-yl}ethyl)phenyl]-1H-pyrrolo[2,3-b]pyridine-3-carbonyl}-2,4-difluorophenyl)-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 11 | | 1 | (3R)-N-[3-(5-{4-[4-({1-[2-(2,6-dioxopiperidin-3-yl)-1-oxo-2,3-dihydro-1H-isoindol-5-yl]piperidin-4-yl}methyl)piperazin-1-yl]-3-fluorophenyl}-1H-pyrrolo[2,3-b]pyridine-3-carbonyl)-2,4-difluorophenyl]-3-fluoropyrrolidine-1-sulfonamide |
| 12 | | 1 | (3R)-N-(3-{5-[4-(4-{[(1S)-6-[2-(2,6-dioxopiperidin-3-yl)-7-methoxy-1-oxo-2,3-dihydro-1H-isoindol-5-yl]-1-methyl-2,6-diazaspiro[3.3]heptan-2-yl]methyl}piperidin-1-yl)phenyl]-1H-pyrrolo[2,3-b]pyridine-3-carbonyl}-2,4-difluorophenyl)-3-fluoropyrrolidine-1-sulfonamide |
| 13 | | 1 | (3R)-N-(2,4-difluoro-3-{5-[4-(4-{[(2r,4r)-2-{[2-(2,6-dioxopiperidin-3-yl)-1-oxo-2,3-dihydro-1H-isoindol-5-yl]oxy}-8-oxa-5-azaspiro[3.5]nonan-5-yl]methyl}piperidin-1-yl)phenyl]-1H-pyrrolo[2,3-b]pyridine-3-carbonyl}phenyl)-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 14 | | 12 | (3R)-N-(2,4-difluoro-3-{5-[4-(4-{[(2s,4s)-2-[2-(2,6-dioxopiperidin-3-yl)-1-oxo-2,3-dihydro-1H-isoindol-5-yl]oxy}-8-oxa-5-azaspiro[3.5]nonan-5-yl]methyl}piperidin-1-yl)phenyl]-1H-pyrrolo[2,3-b]pyridine-3-carbonyl}phenyl)-3-fluoropyrrolidine-1-sulfonamide |
| 15 | | 1 | (3R)-N-{3-[5-(4-{[(2R)-1-[2-(2,6-dioxopiperidin-3-yl)-1-oxo-2,3-dihydro-1H-isoindol-5-yl]azetidin-2-yl]methoxy}phenyl)-1H-pyrrolo[2,3-b]pyridine-3-carbonyl]-2,4-difluorophenyl}-3-fluoropyrrolidine-1-sulfonamide |
| 16 | | 1 | (3R)-N-{3-(5-{4-[(1S,5S)-6-{1-[2-(2,6-dioxopiperidin-3-yl)-1-oxo-2,3-dihydro-1H-isoindol-5-yl]piperidin-4-yl}-3,6-diazabicyclo[3.2.1]octan-3-yl]phenyl}-1H-pyrrolo[2,3-b]pyridine-3-carbonyl)-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 17 | | 12 | (3R)-N-[3-(5-{4-[(2S)-2-({[2-(2,6-dioxopiperidin-3-yl)-1-oxo-2,3-dihydro-1H-isoindol-5-yl]oxy}methyl)azetidin-1-yl]phenyl}-1H-pyrrolo[2,3-b]pyridine-3-carbonyl)-2,4-difluorophenyl]-3-fluoropyrrolidine-1-sulfonamide |
| 18 | | 1 | (3R)-N-[3-(5-{2-[4-({1-[2-(2,6-dioxopiperidin-3-yl)-1-oxo-2,3-dihydro-1H-isoindol-5-yl]methyl}piperazin-1-yl)pyrimidin-5-yl]-1H-pyrrolo[2,3-b]pyridine-3-carbonyl)-2,4-difluorophenyl]-3-fluoropyrrolidine-1-sulfonamide |
| 19 | | 1 | (3R)-N-[3-(5-{4-[6-({1-[2-(2,6-dioxopiperidin-3-yl)-1-oxo-2,3-dihydro-1H-isoindol-5-yl]methyl}-2,6-diazaspiro[3.3]heptan-2-yl]phenyl}-1H-pyrrolo[2,3-b]pyridine-3-carbonyl)-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 20 | | 1 | (3R)-N-(3-{5-[4-(4-{[(1R)-6-[2-(2,6-dioxopiperidin-3-yl)-7-methoxy-1-oxo-2,3-dihydro-1H-isoindol-5-yl]-1-methyl-2,6-diazaspiro[3.3]heptan-2-yl]methyl}piperidin-1-yl)phenyl]-1H-pyrrolo[2,3-b]pyridine-3-carbonyl}-2,4-difluorophenyl)-3-fluoropyrrolidine-1-sulfonamide |
| 21 | | 1 | (3R)-N-(3-{5-[4-(2-{6-[2-(2,6-dioxopiperidin-3-yl)-7-methoxy-1-oxo-2,3-dihydro-1H-isoindol-5-yl]-2,6-diazaspiro[3.3]heptan-2-yl}ethyl)phenyl]-1H-pyrrolo[2,3-b]pyridine-3-carbonyl}-2,4-difluorophenyl)-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 22 | | 12 | (3R)-N-(3-{5-[4-(6-{3-[2-(2,6-dioxopiperidin-3-yl)-7-methoxy-1-oxo-2,3-dihydro-1H-isoindol-5-yl]propyl}-2,6-diazaspiro[3.3]heptan-2-yl)phenyl]-1H-pyrrolo[2,3-b]pyridine-3-carbonyl}-2,4-difluorophenyl)-3-fluoropyrrolidine-1-sulfonamide |
| 23 | | 1 | (3R)-N-{3-[5-(4-{[(2S)-1-[2-(2,6-dioxopiperidin-3-yl)-1-oxo-2,3-dihydro-1H-isoindol-5-yl]azetidin-2-yl]methoxy}phenyl)-1H-pyrrolo[2,3-b]pyridine-3-carbonyl]-2,4-difluorophenyl}-3-fluoropyrrolidine-1-sulfonamide |
| 24 | | 1 | (3R)-N-[3-(5-{6-[4-({4-[2-(2,6-dioxopiperidin-3-yl)-1-oxo-2,3-dihydro-1H-isoindol-5-yl]piperidin-1-yl}methyl)piperidin-1-yl]pyridin-3-yl}-1H-pyrrolo[2,3-b]pyridine-3-carbonyl)-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 25 | | 1 | (3R)-N-[3-(5-{6-[4-({1-[2-(2,6-dioxopiperidin-3-yl)-1-oxo-2,3-dihydro-1H-isoindol-5-yl]piperidin-4-yl}methyl)piperazin-1-yl]pyridin-3-yl}-1H-pyrrolo[2,3-b]pyridine-3-carbonyl)-2,4-difluorophenyl]-3-fluoropyrrolidine-1-sulfonamide |
| 26 | | 1 | (3R)-N-{3-[5-(4-{6-[2-(2,6-dioxopiperidin-3-yl)-1-oxo-2,3-dihydro-1H-isoindol-5-yl]-2,6-diazaspiro[3.3]heptan-2-yl}phenyl)-1H-pyrrolo[2,3-b]pyridine-3-carbonyl]-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 27 | | 3 | 4-{4-[2-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)ethyl]piperazin-1-yl}-N-[(3S)-2,6-dioxopiperidin-3-yl]-2-fluorobenzamide |
| 28 | | 3 | 4-{4-[2-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)ethyl]piperazin-1-yl}-N-[(3R)-2,6-dioxopiperidin-3-yl]-2-fluorobenzamide |

TABLE 1-continued

Exemplary bifunctional compounds of the present disclosure

| Ex. No. | Parent Mol Structure | Synthetic Scheme | IUPAC Name |
|---|---|---|---|
| 29 | | 3 | 4-(4-{[6-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)-2,6-diazaspiro[3.3]heptan-2-yl]methyl}piperidin-1-yl)-N-[(3S)-2,6-dioxopiperidin-3-yl]-2-fluorobenzamide |
| 30 | | 3 | 4-(4-{[6-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)-2,6-diazaspiro[3.3]heptan-2-yl]methyl}piperidin-1-yl)-N-[(3R)-2,6-dioxopiperidin-3-yl]-2-fluorobenzamide |
| 31 | | 3 | 4-(6-{[1-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperidin-4-yl]methyl}-2,6-diazaspiro[3.3]heptan-2-yl)-N-[(3S)-2,6-dioxopiperidin-3-yl]-2-fluorobenzamide |

TABLE 1-continued

Exemplary bifunctional compounds of the present disclosure

| Ex. No. | Parent Mol Structure | Synthetic Scheme | IUPAC Name |
|---|---|---|---|
| 32 | | 12 | (3R)-N-(3-{5-[4-(4-{2-[2-(2,6-dioxopiperidin-3-yl)-1-oxo-2,3-dihydro-1H-isoindol-5-yl]-2-hydroxyethyl}piperazin-1-yl)phenyl]-1H-pyrrolo[2,3-b]pyridin-3-carbonyl}-2,4-difluorophenyl)-3-fluoropyrrolidine-1-sulfonamide |
| 33 | | 3 | 4-(1-{[1-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperidin-4-yl]methyl}piperidin-4-yl)-N-[(3S)-2,6-dioxopiperidin-3-yl]-2-fluorobenzamide |

TABLE 1-continued

Exemplary bifunctional compounds of the present disclosure

| Ex. No. | Parent Mol Structure | Synthetic Scheme | IUPAC Name |
|---|---|---|---|
| 34 | | 1 | (3R)-N-{3-[5-(4-{4-[(1-{2-[(3S)-2,6-dioxopiperidin-3-yl]-1-oxo-2,3-dihydro-1H-isoindol-5-yl]piperidin-4-yl}oxy]piperidin-1-yl}phenyl)-1H-pyrrolo[2,3-b]pyridine-3-carbonyl]-2,4-difluorophenyl}-3-fluoropyrrolidine-1-sulfonamide |
| 35 | | 1 | (3R)-N-{3-[5-(4-{4-[(1-{2-[(3R)-2,6-dioxopiperidin-3-yl]-1-oxo-2,3-dihydro-1H-isoindol-5-yl]piperidin-4-yl}oxy]piperidin-1-yl}phenyl)-1H-pyrrolo[2,3-b]pyridine-3-carbonyl]-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 36 | | 1 | (3R)-N-[3-(5-{4-[2-(2,6-dioxopiperidin-3-yl)-1-oxo-2,3-dihydro-1H-isoindol-5-yl]piperidin-1-yl]methyl}piperidin-1-yl]-3-fluorophenyl]-1H-pyrrolo[2,3-b]pyridine-3-carbonyl)-2,4-difluorophenyl]-3-fluoropyrrolidine-1-sulfonamide |
| 37 | | 3 | 4-(6-{[1-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperidin-4-yl]methyl}-2,6-diazaspiro[3.3]heptan-2-yl)-N-[(3R)-2,6-dioxopiperidin-3-yl]-2-fluorobenzamide |
| 38 | | 12 | (3R)-N-{3-[5-(4-{6-[(2E)-3-{2-[(3S)-2,6-dioxopiperidin-3-yl]-1-oxo-2,3-dihdyro-1H-isoindol-5-yl}prop-2-en-1-yl]-2,6-diazaspiro[3.3]heptan-2-yl}phenyl)-1H-pyrrolo[2,3-b]pyridine-3-carbonyl]-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 39 | | 12 | (3R)-N-{3-[5-(4-{6-[(2E)-3-{2-[(3R)-2,6-dioxopiperidin-3-yl]-1-oxo-2,3-dihydro-1H-isoindol-5-yl}prop-2-en-1-yl]-2,6-diazaspiro[3.3]heptan-2-yl}phenyl)-1H-pyrrolo[2,3-b]pyridine-3-carbonyl]-2,4-difluorophenyl}-3-fluoropyrrolidine-1-sulfonamide |
| 40 | | 1 | (3R)-N-{3-[5-(4-{4-[(1-{2-[(3S)-2,6-dioxopiperidin-3-yl]-6-fluoro-1-oxo-2,3-dihydro-1H-isoindol-5-yl}piperidin-4-yl)methyl]piperazin-1-yl}phenyl)-1H-pyrrolo[2,3-b]pyridine-3-carbonyl]-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 41 | | 1 | (3R)-N-{3-[5-(4-{4-[(1-{2-[(3R)-2,6-dioxopiperidin-3-yl]-6-fluoro-1-oxo-2,3-dihydro-1H-isoindol-5-yl}piperidin-4-yl)methyl]piperazin-1-yl}phenyl)-1H-pyrrolo[2,3-b]pyridine-3-carbonyl]-2,4-difluorophenyl}-3-fluoropyrrolidine-1-sulfonamide |
| 42 | | 1 | (3R)-N-(3-{5-[4-(3-{6-[2-(2,6-dioxopiperidin-3-yl)-1-oxo-2,3-dihydro-1H-isoindol-5-yl]-2,6-diazaspiro[3.3]heptan-2-yl}prop-1-yn-1-yl)phenyl]-1H-pyrrolo[2,3-b]pyridin-3-carbonyl}-2,4-difluorophenyl)-3-fluoropyrrolidine-1-sulfonamide |
| 43 | | 12 | (3R)-N-(3-{5-[4-(6-{[2-(2,6-dioxopiperidin-3-yl)-1-oxo-2,3-dihydro-1H-isoindol-5-yl]oxy}-2-azaspiro[3.3]heptan-2-yl)phenyl]-1H-pyrrolo[2,3-b]pyridine-3-carbonyl}-2,4-difluorophenyl)-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 44 | | 12 | (3R)-N-(3-{5-[4-(2-{4-[2-({2-[(3S)-2,6-dioxopiperidin-3-yl]-7-methoxy-1-oxo-2,3-dihydro-1H-isoindol-5-yl}oxy)ethyl]piperazin-1-yl}ethoxy)phenyl]-1H-pyrrolo[2,3-b]pyridine-3-carbonyl}-2,4-difluorophenyl)-3-fluoropyrrolidine-1-sulfonamide |
| 45 | | 12 | (3R)-N-(3-{5-[4-(2-{4-[2-({2-[(3R)-2,6-dioxopiperidin-3-yl]-7-methoxy-1-oxo-2,3-dihydro-1H-isoindol-5-yl}oxy)ethyl]piperazin-1-yl}ethoxy)phenyl]-1H-pyrrolo[2,3-b]pyridine-3-carbonyl}-2,4-difluorophenyl)-3-fluoropyrrolidine-1-sulfonamide |
| 46 | | 1 | (3R)-N-[3-(5-{2-[4-({4-[2-(2,6-dioxopiperidin-3-yl)-1-oxo-2,3-dihydro-1H-isoindol-5-yl]piperidin-1-yl}methyl)piperidin-1-yl]pyrimidin-5-yl}-1H-pyrrolo[2,3-b]pyridine-3-carbonyl)-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 47 | | 1 | (3R)-N-(3-{5-[1-({2-[2-(2,6-dioxopiperidin-3-yl)-1-oxo-2,3-dihydro-1H-isoindol-5-yl]-2-azaspiro[3.3]heptan-6-yl}methyl)-1,2,3,4-tetrahydroquinolin-6-yl]-1H-pyrrolo[2,3-b]pyridine-3-carbonyl]-2,4-difluorophenyl)-3-fluoropyrrolidine-1-sulfonamide |
| 48 | | 3 | 4-(1-{[1-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperidin-4-yl]methyl}piperidin-4-yl)-N-[(3R)-2,6-dioxopiperidin-3-yl]-2-fluorobenzamide |

TABLE 1-continued

Exemplary bifunctional compounds of the present disclosure

| Ex. No. | Parent Mol Structure | Synthetic Scheme | IUPAC Name |
|---|---|---|---|
| 49 | | 1 | (3R)-N-(3-{5-[4-(3-{4-[2-(2,6-dioxopiperidin-3-yl)-1-oxo-2,3-dihydro-1H-isoindol-5-yl]piperidin-1-yl}propyl)phenyl]-1H-pyrrolo[2,3-b]pyridine-3-carbonyl}-2,4-difluorophenyl)-3-fluoropyrrolidine-1-sulfonamide |
| 50 | | 1 | (3R)-N-(3-{5-[4-(2-{6-[2-(2,6-dioxopiperidin-3-yl)-1-oxo-2,3-dihydro-1H-isoindol-5-yl]-2,6-diazaspiro[3.3]heptan-2-yl}ethoxy)phenyl]-1H-pyrrolo[2,3-b]pyridine-3-carbonyl}-2,4-difluorophenyl)-3-fluoropyrrolidine-1-sulfonamide |
| 51 | | 1 | (3R)-N-[3-(5-{4-[(3aS,6aR)-5-[(1-{2-[(3S)-2,6-dioxopiperidin-3-yl]-1-oxo-2,3-dihydro-1H-isoindol-5-yl}piperidin-4-yl)methyl]-3a-methyl-octahydropyrrolo[3,4-c]pyrrol-2-yl]phenyl}-1H-pyrrolo[2,3-b]pyridine-3-carbonyl)-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 52 | | 1 | (3R)-N-[3-(5-{4-[(3aS,6aR)-5-[(1-{2-[(3R)-2,6-dioxopiperidin-3-yl]-1-oxo-2,3-dihydro-1H-isoindol-5-yl}piperidin-4-yl)methyl]-3a-methyl-octahydropyrrolo[3,4-c]pyrrol-2-yl]phenyl}-1H-pyrrolo[2,3-b]pyridine-3-carbonyl)-2,4-difluorophenyl]-3-fluoropyrrolidine-1-sulfonamide |
| 53 | | 1 | (3R)-N-[3-(5-{4-[(3R,5S)-4-({1-[2-(2,6-dioxopiperidin-3-yl)-1-oxo-2,3-dihydro-1H-isoindol-5-yl]azetidin-3-yl}methyl)-3,5-dimethylpiperazin-1-yl]phenyl}-1H-pyrrolo[2,3-b]pyridine-3-carbonyl)-2,4-difluorophenyl]-3-fluoropyrrolidine-1-sulfonamide |
| 54 | | 1 | (3R)-N-[3-(5-{4-[6-({4-[2-(2,6-dioxopiperidin-3-yl)-7-methoxy-1-oxo-2,3-dihydro-1H-isoindol-5-yl]piperidin-1-yl}methyl)-2-azaspiro[3.3]heptan-2-yl]phenyl}-1H-pyrrolo[2,3-b]pyridine-3-carbonyl)-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 55 | | 1 | (3R)-N-{3-[5-(4-{6-[(1-{2-[(3S)-2,6-dioxopiperidin-3-yl]-6-fluoro-1-oxo-2,3-dihydro-1H-isoindol-5-yl}piperidin-4-yl]methyl]-2,6-diazaspiro[3.3]heptan-2-yl}phenyl)-1H-pyrrolo[2,3-b]pyridine-3-carbonyl]-2,4-difluorophenyl}-3-fluoropyrrolidine-1-sulfonamide |
| 56 | | 1 | (3R)-N-{3-[5-(4-{6-[(1-{2-[(3R)-2,6-dioxopiperidin-3-yl]-6-fluoro-1-oxo-2,3-dihydro-1H-isoindol-5-yl}piperidin-4-yl]methyl]-2,6-diazaspiro[3.3]heptan-2-yl}phenyl)-1H-pyrrolo[2,3-b]pyridine-3-carbonyl]-2,4-difluorophenyl}-3-fluoropyrrolidine-1-sulfonamide |
| 57 | | 1 | (3R)-N-(3-{5-[4-(4-{[(3aR,6aS)-5-{2-[(3S)-2,6-dioxopiperidin-3-yl]-1-oxo-2,3-dihydro-1H-isoindol-5-yl}-octahydropyrrolo[3,4-c]pyrrol-2-yl]methyl}piperidin-1-yl)phenyl]-1H-pyrrolo[2,3-b]pyridine-3-carbonyl}-2,4-difluorophenyl)-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 58 | | 1 | (3R)-N-(3-{5-[4-(4-{[(3aR,6aS)-5-{2-[(3R)-2,6-dioxopiperidin-3-yl]-1-oxo-2,3-dihydro-1H-isoindol-5-yl}-octahydropyrrolo[3,4-c]pyrrol-2-yl]methyl}piperidin-1-yl)phenyl]-1H-pyrrolo[2,3-b]pyridine-3-carbonyl}-2,4-difluorophenyl)-3-fluoropyrrolidine-1-sulfonamide |
| 59 | | 1 | (3R)-N-[3-(5-{4-[4-({2-[2-(2,6-dioxopiperidin-3-yl)-7-methoxy-1-oxo-2,3-dihydro-1H-isoindol-5-yl]-2-azaspiro[3.3]heptan-6-yl}methyl)piperazin-1-yl]phenyl}-1H-pyrrolo[2,3-b]pyridine-3-carbonyl)-2,4-difluorophenyl]-3-fluoropyrrolidine-1-sulfonamide |
| 60 | | 1 | (3R)-N-[3-(5-{4-[4-(2-{6-[2-(2,6-dioxopiperidin-3-yl)-1-oxo-2,3-dihydro-1H-isoindol-5-yl]-2,6-diazaspiro[3.3]heptan-2-yl}propan-2-yl)piperidin-1-yl]phenyl}-1H-pyrrolo[2,3-b]pyridine-3-carbonyl)-2,4-difluorophenyl]-3-fluoropyrrolidine-1-sulfonamide |

| Ex. No. | Parent Mol Structure | Synthetic Scheme | IUPAC Name |
|---|---|---|---|
| 61 | | 12 | (3R)-N-(3-{5-[4-(6-{3-[2-(2,6-dioxopiperidin-3-yl)-1-oxo-2,3-dihydro-1H-isoindol-5-yl]-3-hydroxypropyl}-2,6-diazaspiro[3.3]heptan-2-yl]phenyl}-1H-pyrrolo[2,3-b]pyridine-3-carbonyl)-2,4-difluorophenyl)-3-fluoropyrrolidine-1-sulfonamide |
| 62 | | 12 | (3R)-N-{3-(5-{4-[6-(4-{2-[(3S)-2,6-dioxopiperidin-3-yl]-1-oxo-2,3-dihydro-1H-isoindol-5-yl}butyl)-2,6-diazaspiro[3.3]heptan-2-yl]phenyl}-1H-pyrrolo[2,3-b]pyridine-3-carbonyl)-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 63 | | 12 | (3R)-N-[3-(5-{4-[6-(4-{2-[(3R)-2,6-dioxopiperidin-3-yl]-1-oxo-2,3-dihydro-1H-isoindol-5-yl}butyl)-2,6-diazaspiro[3.3]heptan-2-yl]phenyl}-1H-pyrrolo[2,3-b]pyridine-3-carbonyl)-2,4-difluorophenyl]-3-fluoropyrrolidine-1-sulfonamide |
| 64 | | 12 | (3R)-N-(3-{5-[4-(4-{5-[2-(2,6-dioxopiperidin-3-yl)-1-oxo-2,3-dihydro-1H-isoindol-5-yl]pentyl}piperazin-1-yl)phenyl]-1H-pyrrolo[2,3-b]pyridine-3-carbonyl}-2,4-difluorophenyl)-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 65 | | 12 | (3R)-N-(3-{5-[4-(1-{5-[2-(2,6-dioxopiperidin-3-yl)-1-oxo-2,3-dihydro-1H-isoindol-5-yl]pentyl]piperidin-4-yl}phenyl)-1H-pyrrolo[2,3-b]pyridine-3-carbonyl]-2,4-difluorophenyl)-3-fluoropyrrolidine-1-sulfonamide |
| 66 | | 1 | (3R)-N-(3-{5-[4-(5-{1-[2-(2,6-dioxopiperidin-3-yl)-1-oxo-2,3-dihydro-1H-isoindol-5-yl]piperidin-4-yl}-2,5-diazaspiro[3.4]octan-2-yl)phenyl]-1H-pyrrolo[2,3-b]pyridine-3-carbonyl}-2,4-difluorophenyl)-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 67 | | 12 | (3R)-N-{3-[5-(4-{1-[(3R)-3-{2-[(3S)-2,6-dioxopiperidin-3-yl]-1-oxo-2,3-dihydro-1H-isoindol-5-yl}-3-hydroxypropyl]piperidin-4-yl}phenyl)-1H-pyrrolo[2,3-b]pyridine-3-carbonyl]-2,4-difluorophenyl}-3-fluoropyrrolidine-1-sulfonamide |
| 68 | | 12 | (3R)-N-{3-[5-(4-{1-[(3R)-3-{2-[(3R)-2,6-dioxopiperidin-3-yl]-1-oxo-2,3-dihydro-1H-isoindol-5-yl}-3-hydroxypropyl]piperidin-4-yl}phenyl)-1H-pyrrolo[2,3-b]pyridine-3-carbonyl]-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 69 | | 1 | (3R)-N-(3-{5-[4-(2-{4-[2-(2,6-dioxopiperidin-3-yl)-1-oxo-2,3-dihydro-1H-isoindol-5-yl]piperidin-1-yl}ethoxy)phenyl]-1H-pyrrolo[2,3-b]pyridine-3-carbonyl}-2,4-difluorophenyl)-3-fluoropyrrolidine-1-sulfonamide |
| 70 | | 1 | (3R)-N-[3-(5-{4-[4-({1-[2-(2,6-dioxopiperidin-3-yl)-7-methoxy-1-oxo-2,3-dihydro-1H-isoindol-5-yl]azetidin-3-yl}methyl)piperazin-1-yl]phenyl}-1H-pyrrolo[2,3-b]pyridine-3-carbonyl)-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 71 | | 12 | (3R)-N-{3-[5-(4-{1-[(3S)-3-{2-[(3S)-2,6-dioxopiperidin-3-yl]-1-oxo-2,3-dihydro-1H-isoindol-5-yl}-3-hydroxypropyl]piperidin-4-yl}phenyl)-1H-pyrrolo[2,3-b]pyridine-3-carbonyl]-2,4-difluorophenyl}-3-fluoropyrrolidine-1-sulfonamide |
| 72 | | 12 | (3R)-N-{3-[5-(4-{1-[(3S)-3-{2-[(3R)-2,6-dioxopiperidin-3-yl]-1-oxo-2,3-dihydro-1H-isoindol-5-yl}-3-hydroxypropyl]piperidin-4-yl}phenyl)-1H-pyrrolo[2,3-b]pyridine-3-carbonyl]-2,4-difluorophenyl}-3-fluoropyrrolidine-1-sulfonamide |
| 73 | | 12 | (3R)-N-{3-[5-(4-{4-[(2R)-3-{2-[(3R)-2,6-dioxopiperidin-3-yl]-1-oxo-2,3-dihydro-1H-isoindol-5-yl}-2-hydroxypropyl]piperazin-1-yl}phenyl)-1H-pyrrolo[2,3-b]pyridine-3-carbonyl]-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 74 | | 12 | (3R)-N-{3-[5-(4-{4-[(2S)-3-{2-[(3S)-2,6-dioxopiperidin-3-yl]-1-oxo-2,3-dihydro-1H-isoindol-5-yl}-2-hydroxypropyl]piperazin-1-yl]phenyl]-1H-pyrrolo[2,3-b]pyridine-3-carbonyl]-2,4-difluorophenyl}-3-fluoropyrrolidine-1-sulfonamide |
| 75 | | 12 | (3R)-N-{3-[5-(4-{4-[(2S)-3-{2-[(3R)-2,6-dioxopiperidin-3-yl]-1-oxo-2,3-dihydro-1H-isoindol-5-yl}-2-hydroxypropyl]piperazin-1-yl]phenyl]-1H-pyrrolo[2,3-b]pyridine-3-carbonyl]-2,4-difluorophenyl}-3-fluoropyrrolidine-1-sulfonamide |
| 76 | | 1 | (3R)-N-[3-(5-{4-[(3aR,6aS)-5-({2-[(3S)-2,6-dioxopiperidin-3-yl]-1-oxo-2,3-dihydro-1H-isoindol-5-yl}methyl)-octahydropyrrolo[3,4-c]pyrrol-2-yl]phenyl}-1H-pyrrolo[2,3-b]pyridine-3-carbonyl)-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 77 | | 1 | (3R)-N-[3-(5-{4-[(3aR,6aS)-5-({2-[(3R)-2,6-dioxopiperidin-3-yl]-1-oxo-2,3-dihydro-1H-isoindol-5-yl}methyl)octahydropyrrolo[3,4-c]pyrrol-2-yl]phenyl}-1H-pyrrolo[2,3-b]pyridine-3-carbonyl)-2,4-difluorophenyl]-3-fluoropyrrolidine-1-sulfonamide |
| 78 | | 1 | (3R)-N-[3-(5-{4-[(3R)-4-{[2-(2,6-dioxopiperidin-3-yl)-1-oxo-2,3-dihydro-1H-isoindol-5-yl]methyl}-3-(hydroxymethyl)piperazin-1-yl]phenyl}-1H-pyrrolo[2,3-b]pyridine-3-carbonyl)-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 79 | | 1 | (3R)-N-(3-{5-[4-(4-{1-[2-(2,6-dioxopiperidin-3-yl)-7-methoxy-1-oxo-2,3-dihydro-1H-isoindol-5-yl]azetidin-3-yl}piperazin-1-yl)phenyl]-1H-pyrrolo[2,3-b]pyridine-3-carbonyl}-2,4-difluorophenyl)-3-fluoropyrrolidine-1-sulfonamide |
| 80 | | 12 | (3R)-N-{3-[5-(4-{6-[3-({2-[(3S)-2,6-dioxopiperidin-3-yl]-1-oxo-2,3-dihydro-1H-isoindol-5-yl}oxy)propyl]-2,6-diazaspiro[3.3]heptan-2-yl}phenyl)-1H-pyrrolo[2,3-b]pyridine-3-carbonyl]-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 81 | | 12 | (3R)-N-{3-[5-(4-{6-[3-({2-[(3R)-2,6-dioxopiperidin-3-yl]-1-oxo-2,3-dihydro-1H-isoindol-5-yl}oxy)propyl]-2,6-diazaspiro[3.3]heptan-2-yl}phenyl)-1H-pyrrolo[2,3-b]pyridine-3-carbonyl]-2,4-difluorophenyl}-3-fluoropyrrolidine-1-sulfonamide |
| 82 | | 12 | (3R)-N-{3-[5-(4-{4-[(2R)-3-{2-[(3S)-2,6-dioxopiperidin-3-yl]-1-oxo-2,3-dihydro-1H-isoindol-5-yl]-2-hydroxypropyl]piperazin-1-yl}phenyl)-1H-pyrrolo[2,3-b]pyridine-3-carbonyl]-2,4-difluorophenyl}-3-fluoropyrrolidine-1-sulfonamide |
| 83 | | 1 | (3R)-N-{3-[5-(4-{4-[(3-{2-[(3S)-2,6-dioxopiperidin-3-yl]-1-oxo-2,3-dihydro-1H-isoindol-5-yl}azetidin-1-yl)methyl]piperidin-1-yl}phenyl)-1H-pyrrolo[2,3-b]pyridine-3-carbonyl]-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 84 | | 1 | (3R)-N-{3-[5-(4-{4-[(3-{2-[(3R)-2,6-dioxopiperidin-3-yl]-1-oxo-2,3-dihydro-1H-isoindol-5-yl}azetidin-1-yl)methyl]piperidin-1-yl}phenyl)-1H-pyrrolo[2,3-b]pyridine-3-carbonyl]-2,4-difluorophenyl}-3-fluoropyrrolidine-1-sulfonamide |
| 85 | | 1 | (3R)-N-[3-(5-{4-[(3aR,6aS)-5-[(1-{2-[(3S)-2,6-dioxopiperidin-3-yl]-1-oxo-2,3-dihydro-1H-isoindol-5-yl}azetidin-3-yl)methyl]-octahydropyrrolo[3,4-c]pyrrol-2-yl]phenyl}-1H-pyrrolo[2,3-b]pyridine-3-carbonyl)-2,4-difluorophenyl]-3-fluoropyrrolidine-1-sulfonamide |
| 86 | | 1 | (3R)-N-[3-(5-{4-[(3aR,6aS)-5-[(1-{2-[(3R)-2,6-dioxopiperidin-3-yl]-1-oxo-2,3-dihydro-1H-isoindol-5-yl}azetidin-3-yl)methyl]-octahydropyrrolo[3,4-c]pyrrol-2-yl]phenyl}-1H-pyrrolo[2,3-b]pyridine-3-carbonyl)-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 87 | | 1 | (3R)-N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}-3-fluorophenyl)-1H-pyrrolo[2,3-b]pyridine-3-carbonyl]-2,4-difluorophenyl}-3-fluoropyrrolidine-1-sulfonamide |
| 88 | | 1 | (3R)-N-{3-[5-(4-{4-[(4-{2-[(3R)-2,6-dioxopiperidin-3-yl]-1-oxo-2,3-dihydro-1H-isoindol-5-yl}piperidin-1-yl)methyl]piperidin-1-yl}-3-fluorophenyl)-1H-pyrrolo[2,3-b]pyridine-3-carbonyl]-2,4-difluorophenyl}-3-fluoropyrrolidine-1-sulfonamide |
| 89 | | 12 | (3R)-N-[3-(5-{4-[6-(2-{[2-(2,6-dioxopiperidin-3-yl)-1-oxo-2,3-dihydro-1H-isoindol-5-yl]oxy}ethyl)-2,6-diazaspiro[3.3]heptan-2-yl]phenyl}-1H-pyrrolo[2,3-b]pyridine-3-carbonyl)-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 90 | | 1 | (3R)-N-[3-(5-{4-[(2R)-3-{4-[2-(2,6-dioxopiperidin-3-yl)-1-oxo-2,3-dihydro-1H-isoindol-5-yl]piperazin-1-yl}-2-hydroxypropyl]phenyl}-1H-pyrrolo[2,3-b]pyridine-3-carbonyl)-2,4-difluorophenyl]-3-fluoropyrrolidine-1-sulfonamide |
| 91 | | 1 | (3R)-N-[3-(5-{2-[3-({4-[2-(2,6-dioxopiperidin-3-yl)-1-oxo-2,3-dihydro-1H-isoindol-5-yl]piperazin-1-yl}methyl)azetidin-1-yl]pyrimidin-5-yl}-1H-pyrrolo[2,3-b]pyridine-3-carbonyl)-2,4-difluorophenyl]-3-fluoropyrrolidine-1-sulfonamide |
| 92 | | 1 | (3R)-N-[3-(5-{6-[2-({1-[2-(2,6-dioxopiperidin-3-yl)-1-oxo-2,3-dihydro-1H-isoindol-5-yl]piperidin-4-yl}methyl)-2,6-diazaspiro[3.4]octan-6-yl]pyridin-3-yl}-1H-pyrrolo[2,3-b]pyridine-3-carbonyl)-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 93 | | 1 | (3R)-N-[3-(5-{2-[2-({1-[2-(2,6-dioxopiperidin-3-yl)-1-oxo-2,3-dihydro-1H-isoindol-5-yl]piperidin-4-yl}methyl)-2,6-diazaspiro[3.4]octan-6-yl]pyrimidin-5-yl}-1H-pyrrolo[2,3-b]pyridine-3-carbonyl)-2,4-difluorophenyl]-3-fluoropyrrolidine-1-sulfonamide |
| 94 | | 1 | (3R)-N-[3-(5-{4-[4-({4-[2-(2,6-dioxopiperidin-3-yl)-1-oxo-2,3-dihydro-1H-isoindol-5-yl]piperidin-1-yl}methyl)piperidin-1-yl]-3,5-difluorophenyl}-1H-pyrrolo[2,3-b]pyridine-3-carbonyl)-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 95 | | 1 | (3R)-N-[3-(5-{6-[2-({1-[2-(2,6-dioxopiperidin-3-yl)-1-oxo-2,3-dihydro-1H-isoindol-5-yl]piperidin-4-yl}methyl)-2,8-diazaspiro[4.5]decan-8-yl]pyridin-3-yl}-1H-pyrrolo[2,3-b]pyridine-3-carbonyl)-2,4-difluorophenyl]-3-fluoropyrrolidine-1-sulfonamide |
| 96 | | 1 | (3R)-N-[3-(5-{2-[2-({1-[2-(2,6-dioxopiperidin-3-yl)-1-oxo-2,3-dihydro-1H-isoindol-5-yl]piperidin-4-yl}methyl)-2,8-diazaspiro[4.5]decan-8-yl]pyrimidin-5-yl}-1H-pyrrolo[2,3-b]pyridine-3-carbonyl)-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 97 | | 1 | (3R)-N-[3-(5-{4-[4-(2-{4-[2-(2,6-dioxopiperidin-3-yl)-1-oxo-2,3-dihydro-1H-isoindol-5-yl]piperazin-1-yl}propan-2-yl)piperidin-1-yl]phenyl}-1H-pyrrolo[2,3-b]pyridine-3-carbonyl)-2,4-difluorophenyl]-3-fluoropyrrolidine-1-sulfonamide |
| 98 | | 1 | (3R)-N-[3-(5-{4-[(2S)-3-{4-[2-(2,6-dioxopiperidin-3-yl)-1-oxo-2,3-dihydro-1H-isoindol-5-yl]piperazin-1-yl}-2-hydroxypropyl]phenyl}-1H-pyrrolo[2,3-b]pyridine-3-carbonyl)-2,4-difluorophenyl]-3-fluoropyrrolidine-1-sulfonamide |
| 99 | | 1 | (3R)-N-{3-[5-(4-{6-[(3-{2-[(3S)-2,6-dioxopiperidin-3-yl]-1-oxo-2,3-dihydro-1H-isoindol-5-yl}azetidin-1-yl)methyl]-2-azaspiro[3.3]heptan-2-yl}phenyl)-1H-pyrrolo[2,3-b]pyridine-3-carbonyl]-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 100 | | 1 | (3R)-N-{3-[5-(4-{6-[(3-{2-[(3R)-2,6-dioxopiperidin-3-yl]-1-oxo-2,3-dihydro-1H-isoindol-5-yl}azetidin-1-yl)methyl]-2-azaspiro[3.3]heptan-2-yl}phenyl)-1H-pyrrolo[2,3-b]pyridine-3-carbonyl]-2,4-difluorophenyl}-3-fluoropyrrolidine-1-sulfonamide |
| 101 | | 1 | (3R)-N-[3-(5-{6-[3-({4-[2-(2,6-dioxopiperidin-3-yl)-1-oxo-2,3-dihydro-1H-isoindol-5-yl]piperazin-1-yl}methyl)azetidin-1-yl]pyridin-3-yl}-1H-pyrrolo[2,3-b]pyridine-3-carbonyl)-2,4-difluorophenyl]-3-fluoropyrrolidine-1-sulfonamide |
| 102 | | 1 | (3R)-N-(3-{5-[4-(4-{[2-(2,6-dioxopiperidin-3-yl)-7-methoxy-1-oxo-2,3-dihydro-1H-isoindol-5-yl]methyl}piperazin-1-yl)phenyl]-1H-pyrrolo[2,3-b]pyridine-3-carbonyl}-2,4-difluorophenyl)-3-fluoropyrrolidine-1-sulfonamide |

| Ex. No. | Parent Mol Structure | Synthetic Scheme | IUPAC Name |
|---|---|---|---|
| 103 | | 1 | (3R)-N-[3-(5-{6-[(4-[2-(2,6-dioxopiperidin-3-yl)-1-oxo-2,3-dihydro-1H-isoindol-5-yl]piperidin-1-yl]methyl)-2-azaspiro[3.3]heptan-2-yl]pyridin-3-yl}-1H-pyrrolo[2,3-b]pyridine-3-carbonyl)-2,4-difluorophenyl]-3-fluoropyrrolidine-1-sulfonamide |
| 104 | | 1 | (3R)-N-[3-(5-{4-[2-({1-[2-(2,6-dioxopiperidin-3-yl)-1-oxo-2,3-dihydro-1H-isoindol-5-yl]piperidin-4-yl}methyl)-2,8-diazaspiro[4.5]decan-8-yl]-3-fluorophenyl]-1H-pyrrolo[2,3-b]pyridine-3-carbonyl)-2,4-difluorophenyl]-3-fluoropyrrolidine-1-sulfonamide |
| 105 | | 12 | (3R)-N-{3-[5-(4-{6-[(3R)-3-{2-[(3S)-2,6-dioxopiperidin-3-yl]-1-oxo-2,3-dihydro-1H-isoindol-5-yl}-3-hydroxypropyl]-2,6-diazaspiro[3.3]heptan-2-yl]phenyl)-1H-pyrrolo[2,3-b]pyridine-3-carbonyl]-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 106 | | 12 | (3R)-N-{3-[5-(4-{6-[(3S)-3-{2-[(3S)-2,6-dioxopiperidin-3-yl]-1-oxo-2,3-dihydro-1H-isoindol-5-yl}-3-hydroxypropyl]-2,6-diazaspiro[3.3]heptan-2-yl}phenyl)-1H-pyrrolo[2,3-b]pyridine-3-carbonyl]-2,4-difluorophenyl}-3-fluoropyrrolidine-1-sulfonamide |
| 107 | | 12 | (3R)-N-{3-[5-(4-{1-[(2R)-3-{2-[(3S)-2,6-dioxopiperidin-3-yl]-1-oxo-2,3-dihydro-1H-isoindol-5-yl}-1-hydroxypropyl]piperidin-4-yl}phenyl)-1H-pyrrolo[2,3-b]pyridine-3-carbonyl]-2,4-difluorophenyl}-3-fluoropyrrolidine-1-sulfonamide |
| 108 | | 12 | (3R)-N-{3-[5-(4-{1-[(2R)-3-{2-[(3R)-2,6-dioxopiperidin-3-yl]-1-oxo-2,3-dihydro-1H-isoindol-5-yl}-2-hydroxypropyl]piperidin-4-yl}phenyl)-1H-pyrrolo[2,3-b]pyridine-3-carbonyl]-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 109 | | 12 | (3R)-N-{3-[5-(4-{1-[(2S)-3-{2-[(3S)-2,6-dioxopiperidin-3-yl]-1-oxo-2,3-dihydro-1H-isoindol-5-yl}-2-hydroxypropyl]piperidin-4-yl}phenyl)-1H-pyrrolo[2,3-b]pyridine-3-carbonyl]-2,4-difluorophenyl}-3-fluoropyrrolidine-1-sulfonamide |
| 110 | | 1 | (3R)-N-[3-(5-{4-[(2R)-3-{4-[2-(2,6-dioxopiperidin-3-yl)-1-oxo-2,3-dihydro-1H-isoindol-5-yl]piperidin-1-yl}-2-hydroxypropyl]phenyl}-1H-pyrrolo[2,3-b]pyridine-3-carbonyl)-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 111 | | 1 | (3R)-N-[3-(5-{4-[2-({1-[2-(2,6-dioxopiperidin-3-yl)-1-oxo-2,3-dihydro-1H-isoindol-5-yl]piperidin-4-yl}methyl)-2,6-diazaspiro[3.4]octan-6-yl]-3-fluorophenyl}-1H-pyrrolo[2,3-b]pyridine-3-carbonyl)-2,4-difluorophenyl]-3-fluoropyrrolidine-1-sulfonamide |
| 112 | | 1 | (3R)-N-[3-(5-{4-[(3S)-4-{[2-(2,6-dioxopiperidin-3-yl)-1-oxo-2,3-dihydro-1H-isoindol-5-yl]methyl}-3-(hydroxymethyl)piperazin-1-yl]phenyl}-1H-pyrrolo[2,3-b]pyridine-3-carbonyl)-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 113 | | 12 | (3R)-N-[3-(5-{4-[4-(4-{[2-(2,6-dioxopiperidin-3-yl)-1-oxo-2,3-dihydro-1H-isoindol-5-yl]oxy}butyl)piperazin-1-yl]-3-fluorophenyl}-1H-pyrrolo[2,3-b]pyridine-3-carbonyl)-2,4-difluorophenyl]-3-fluoropyrrolidine-1-sulfonamide |
| 114 | | 1 | (3R)-N-(3-{5-[4-(2-{6-[2-(2,6-dioxopiperidin-3-yl)-1-oxo-2,3-dihydro-1H-isoindol-5-yl]-2,6-diazaspiro[3.3]heptan-2-yl}ethoxy)-3-fluorophenyl]-1H-pyrrolo[2,3-b]pyridine-3-carbonyl}-2,4-difluorophenyl)-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 115 | | 1 | (3R)-N-[3-(5-{4-[4-(6-{4-[2-(2,6-dioxopiperidin-3-yl)-1-oxo-2,3-dihydro-1H-isoindol-5-yl]piperazin-1-yl}pyrimidin-4-yl)piperazin-1-yl]phenyl}-1H-pyrrolo[2,3-b]pyridine-3-carbonyl)-2,4-difluorophenyl]-3-fluoropyrrolidine-1-sulfonamide |
| 116 | | 12 | (3R)-N-{3-[5-(4-{1-[(2S)-3-{2-[(3R)-2,6-dioxopiperidin-3-yl]-1-oxo-2,3-dihydro-1H-isoindol-5-yl]-2-hydroxypropyl]piperidin-4-yl}phenyl)-1H-pyrrolo[2,3-b]pyridine-3-carbonyl]-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 117 | | 1 | (3R)-N-(3-{5-[2-(2-{6-[2-(2,6-dioxopiperidin-3-yl)-1-oxo-2,3-dihydro-1H-isoindol-5-yl]-2,6-diazaspiro[3.3]heptan-2-yl}ethoxy)pyrimidin-5-yl]-1H-pyrrolo[2,3-b]pyridine-3-carbonyl}-2,4-difluorophenyl)-3-fluoropyrrolidine-1-sulfonamide |
| 118 | | 1 | (3R)-N-[3-(5-{4-[(2S)-3-{4-[2-(2,6-dioxopiperidin-3-yl)-1-oxo-2,3-dihydro-1H-isoindol-5-yl]piperidin-1-yl}-2-hydroxypropyl]phenyl}-1H-pyrrolo[2,3-b]pyridine-3-carbonyl)-2,4-difluorophenyl]-3-fluoropyrrolidine-1-sulfonamide |
| 119 | | 1 | (3R)-N-[3-(5-{4-[4-((4-[2-(2,6-dioxopiperidin-3-yl)-1-oxo-2,3-dihydro-1H-isoindol-5-yl]piperidin-1-yl}methyl)-4-hydroxypiperidin-1-yl]phenyl}-1H-pyrrolo[2,3-b]pyridine-3-carbonyl)-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 120 | | 12 | (3R)-N-[3-(5-{6-[4-(4-{[2-(2,6-dioxopiperidin-3-yl)-1-oxo-2,3-dihydro-1H-isoindol-5-yl]oxy}butyl)piperazin-1-yl]pyridin-3-yl}-1H-pyrrolo[2,3-b]pyridine-3-carbonyl)-2,4-difluorophenyl]-3-fluoropyrrolidine-1-sulfonamide |
| 121 | | 12 | (3R)-N-[3-(5-{2-[4-(4-{[2-(2,6-dioxopiperidin-3-yl)-1-oxo-2,3-dihydro-1H-isoindol-5-yl]oxy}butyl)piperazin-1-yl]pyrimidin-5-yl}-1H-pyrrolo[2,3-b]pyridine-3-carbonyl)-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 122 | | 12 | (3R)-N-{3-[5-(4-{6-[(2S)-3-{[2-(2,6-dioxopiperidin-3-yl)-1-oxo-2,3-dihydro-1H-isoindol-5-yl]oxy}-2-hydroxypropyl]-2,6-diazaspiro[3.3]heptan-2-yl}phenyl)-1H-pyrrolo[2,3-b]pyridine-3-carbonyl]-2,4-difluorophenyl}-3-fluoropyrrolidine-1-sulfonamide |
| 123 | | 12 | (3R)-N-{3-[5-(4-{6-[(2R)-3-({2-[(3S)-2,6-dioxopiperidin-3-yl]-1-oxo-2,3-dihydro-1H-isoindol-5-yl}oxy)-2-hydroxypropyl]-2,6-diazaspiro[3.3]heptan-2-yl}phenyl)-1H-pyrrolo[2,3-b]pyridine-3-carbonyl]-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 124 | | 12 | (3R)-N-{3-[5-(4-{6-[(2R)-3-(4-{2-[(3R)-2,6-dioxopiperidin-3-yl]-1-oxo-2,3-dihydro-1H-isoindol-5-yl}oxy)-2-hydroxypropyl]-2,6-diazaspiro[3.3]heptan-2-yl}phenyl)-1H-pyrrolo[2,3-b]pyridine-3-carbonyl]-2,4-difluorophenyl}-3-fluoropyrrolidine-1-sulfonamide |
| 125 | | 1 | (3R)-N-[3-(5-{4-[(3R,4S)-4-({4-[2-(2,6-dioxopiperidin-3-yl)-1-oxo-2,3-dihydro-1H-isoindol-5-yl]piperidin-1-yl}methyl)-3-fluoropiperidin-1-yl]phenyl}-1H-pyrrolo[2,3-b]pyridine-3-carbonyl)-2,4-difluorophenyl]-3-fluoropyrrolidine-1-sulfonamide |
| 126 | | 12 | (3R)-N-[2,4-difluoro-3-(5-{4-[4-(2-{methyl[(1s,3s)-3-{[2-(2,6-dioxopiperidin-3-yl)-1-oxo-2,3-dihydro-1H-isoindol-5-yl]oxy}cyclobutyl]amino}ethyl)piperazin-1-yl]phenyl}-1H-pyrrolo[2,3-b]pyridine-3-carbonyl)phenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 127 | | 1 | (3R)-N-[3-(5-{4-[4-(2-{4-[2-(2,6-dioxopiperidin-3-yl)-1-oxo-2,3-dihydro-1H-isoindol-5-yl]piperidin-1-yl}ethyl)piperidin-1-yl]phenyl}-1H-pyrrolo[2,3-b]pyridine-3-carbonyl)-2,4-difluorophenyl]-3-fluoropyrrolidine-1-sulfonamide |
| 128 | | 12 | (3R)-N-{3-[5-(4-{6-[(2R)-3-{2-[(3S)-2,6-dioxopiperidin-3-yl]-1-oxo-2,3-dihydro-1H-isoindol-5-yl}-2-hydroxypropyl]-2,6-diazaspiro[3.3]heptan-2-yl}phenyl)-1H-pyrrolo[2,3-b]pyridine-3-carbonyl]-2,4-difluorophenyl}-3-fluoropyrrolidine-1-sulfonamide |
| 129 | | 12 | (3R)-N-{3-[5-(4-{6-[(2R)-3-{2-[(3R)-2,6-dioxopiperidin-3-yl]-1-oxo-2,3-dihydro-1H-isoindol-5-yl}-2-hydroxypropyl]-2,6-diazaspiro[3.3]heptan-2-yl}phenyl)-1H-pyrrolo[2,3-b]pyridine-3-carbonyl]-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 130 | | 12 | (3R)-N-{3-[5-(4-{6-[(2S)-3-[2-(2,6-dioxopiperidin-3-yl)-1-oxo-2,3-dihydro-1H-isoindol-5-yl]-2-hydroxypropyl]-2,6-diazaspiro[3.3]heptan-2-yl}phenyl)-1H-pyrrolo[2,3-b]pyridine-3-carbonyl]-2,4-difluorophenyl]-3-fluoropyrrolidine-1-sulfonamide |
| 131 | | 1 | (3R)-N-[3-(5-{4-[3-({4-[2-(2,6-dioxopiperidin-3-yl)-1-oxo-2,3-dihydro-1H-isoindol-5-yl]piperazin-1-yl}methyl)azetidin-1-yl]-3-fluorophenyl}-1H-pyrrolo[2,3-b]pyridine-3-carbonyl)-2,4-difluorophenyl]-3-fluoropyrrolidine-1-sulfonamide |
| 132 | | 1 | (3R)-N-{3-(5-{4-[4-({6-[2-(2,6-dioxopiperidin-3-yl)-7-methoxy-1-oxo-2,3-dihydro-1H-isoindol-5-yl]-2,6-diazaspiro[3.3]heptan-2-yl}methyl)piperidin-1-yl]-3-fluorophenyl}-1H-pyrrolo[2,3-b]pyridine-3-carbonyl)-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 133 | | 1 | (3R)-N-[3-(5-{6-[4-({6-[2-(2,6-dioxopiperidin-3-yl)-7-methoxy-1-oxo-2,3-dihydro-1H-isoindol-5-yl]-2,6-diazaspiro[3.3]heptan-2-yl}methyl)piperidin-1-yl]pyridin-3-yl}-1H-pyrrolo[2,3-b]pyridine-3-carbonyl)-2,4-difluorophenyl]-3-fluoropyrrolidine-1-sulfonamide |
| 134 | | 1 | (3R)-N-[3-(5-{2-[4-({6-[2-(2,6-dioxopiperidin-3-yl)-7-methoxy-1-oxo-2,3-dihydro-1H-isoindol-5-yl]-2,6-diazaspiro[3.3]heptan-2-yl}methyl)piperidin-1-yl]pyrimidn-5-yl}-1H-pyrrolo[2,3-b]pyridine-3-carbonyl)-2,4-difluorophenyl]-3-fluoropyrrolidine-1-sulfonamide |
| 135 | | 1 | (3R)-N-[3-(5-{4-[4-(3-{4-[2-(2,6-dioxopiperidin-3-yl)-1-oxo-2,3-dihydro-1H-isoindol-5-yl]piperazin-1-yl}propyl)piperidin-1-yl]phenyl}-1H-pyrrolo[2,3-b]pyridine-3-carbonyl)-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 136 | | 3 | (3R)-N-(3-{5-[4-(2-{4-[4-(2,4-dioxo-1,3-diazinan-1-yl)-3-fluorophenyl]piperazin-1-yl}ethyl)phenyl]-1H-pyrrolo[2,3-b]pyridine-3-carbonyl}-2,4-difluorophenyl)-3-fluoropyrrolidine-1-sulfonamide |
| 137 | | 1 | (3R)-N-[3-(5-{4-[4-(3-{1-[2-(2,6-dioxopiperidin-3-yl)-1-oxo-2,3-dihydro-1H-isoindol-5-yl]piperidin-4-yl}propyl)piperazin-1-yl]phenyl}-1H-pyrrolo[2,3-b]pyridine-3-carbonyl)-2,4-difluorophenyl]-3-fluoropyrrolidine-1-sulfonamide |
| 138 | | 12 | (3R)-N-{3-[5-(4-{6-[(2R)-2-[2-(2,6-dioxopiperidin-3-yl)-1-oxo-2,3-dihydro-1H-isoindol-5-yl]-2-hydroxyethyl]-2,6-diazaspiro[3.3]heptan-2-yl}phenyl)-1H-pyrrolo[2,3-b]pyridine-3-carbonyl]-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 139 | | 12 | (3R)-N-[3-(5-{4-[4-(3-{[2-(2,6-dioxopiperidin-3-yl)-1-oxo-2,3-dihydro-1H-isoindol-5-yl]oxy}propoxy)piperidin-1-yl]phenyl}-1H-pyrrolo[2,3-b]pyridine-3-carbonyl)-2,4-difluorophenyl]-3-fluoropyrrolidine-1-sulfonamide |
| 140 | | 3 | (3R)-N-[3-(5-{4-[4-({4-[4-(2,4-dioxo-1,3-diazinan-1-yl)-3-fluorophenyl]piperidin-1-yl}methyl)piperidin-1-yl]phenyl}-1H-pyrrolo[2,3-b]pyridine-3-carbonyl)-2,4-difluorophenyl]-3-fluoropyrrolidine-1-sulfonamide |
| 141 | | 12 | (3R)-N-(3-{5-[6-(6-{3-[2-(2,6-dioxopiperidin-3-yl)-1-oxo-2,3-dihydro-1H-isoindol-5-yl]propyl}-2,6-diazaspiro[3.3]heptan-2-yl)pyridin-3-yl]-1H-pyrrolo[2,3-b]pyridine-3-carbonyl}-2,4-difluorophenyl)-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 142 | | 1 | (3R)-N-[3-(5-{4-[6-({1-[2-(2,6-dioxopiperidin-3-yl)-1-oxo-2,3-dihydro-1H-isoindol-5-yl]-4-hydroxypiperidin-4-yl}methyl)-2,6-diazaspiro[3.3]heptan-2-yl]phenyl}-1H-pyrrolo[2,3-b]pyridine-3-carbonyl)-2,4-difluorophenyl]-3-fluoropyrrolidine-1-sulfonamide |
| 143 | | 1 | (3R)-N-{3-[5-(4-{4-[({1-[2-(2,6-dioxopiperidin-3-yl)-1-oxo-2,3-dihydro-1H-isoindol-5-yl]piperidin-4-yl}methoxy)methyl]piperidin-1-yl}phenyl)-1H-pyrrolo[2,3-b]pyridine-3-carbonyl]-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 144 | | 1 | (3R)-N-{3-[5-(4-{3-[(4-{1-[2-(2,6-dioxopiperidin-3-yl)-1-oxo-2,3-dihydro-1H-isoindol-5-yl]piperidin-4-yl}piperazin-1-yl)methyl]azetidin-1-yl}phenyl)-1H-pyrrolo[2,3-b]pyridine-3-carbonyl]-2,4-difluorophenyl}-3-fluoropyrrolidine-1-sulfonamide |
| 145 | | 1 | (3R)-N-{2,4-difluoro-3-[5-(4-{[(1,4r)-4-[(2-{4-[2-(2,6-dioxopiperidin-3-yl)-1-oxo-2,3-dihydro-1H-isoindol-5-yl]piperazin-1-yl}ethyl)(methyl)amino]cyclohexyl]oxy}phenyl)-1H-pyrrolo[2,3-b]pyridine-3-carbonyl]phenyl}-3-fluoropyrrolidine-1-sulfonamide |
| 146 | | 1 | (3R)-N-{3-[5-(4-{[4-({1-[2-(2,6-dioxopiperidin-3-yl)-1-oxo-2,3-dihydro-1H-isoindol-5-yl]piperidin-4-yl}methyl)piperazin-1-yl]methyl}phenyl)-1H-pyrrolo[2,3-b]pyridine-3-carbonyl]-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 147 | | 1 | (3R)-N-(3-{5-[2-(6-{3-[2-(2,6-dioxopiperidin-3-yl)-1-oxo-2,3-dihydro-1H-isoindol-5-yl]propyl]-2,6-diazaspiro[3.3]heptan-2-yl)pyrimidin-5-yl]-1H-pyrrolo[2,3-b]pyridine-3-carbonyl}-2,4-difluorophenyl)-3-fluoropyrrolidine-1-sulfonamide |
| 148 | | 12 | (3R)-N-[3-(5-{4-[4-(2-{2-[2-(2,6-dioxopiperidin-3-yl)-1-oxo-2,3-dihydro-1H-isoindol-5-yl]ethoxy}ethyl)piperazin-1-yl]phenyl}-1H-pyrrolo[2,3-b]pyridine-3-carbonyl)-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 149 | 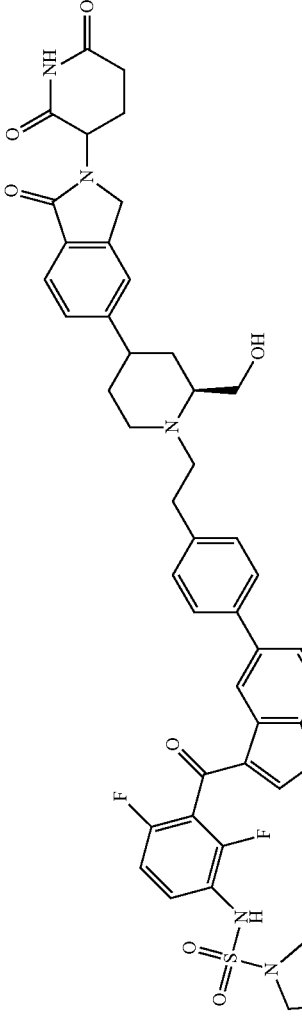 | 1 | (3R)-N-{3-[5-(4-{2-[(2S)-4-[2-(2,6-dioxopiperidin-3-yl)-1-oxo-2,3-dihydro-1H-isoindol-5-yl]-2-(hydroxymethyl)piperidin-1-yl]ethyl}phenyl)-1H-pyrrolo[2,3-b]pyridine-3-carbonyl]-2,4-difluorophenyl}-3-fluoropyrrolidine-1-sulfonamide |
| 150 | 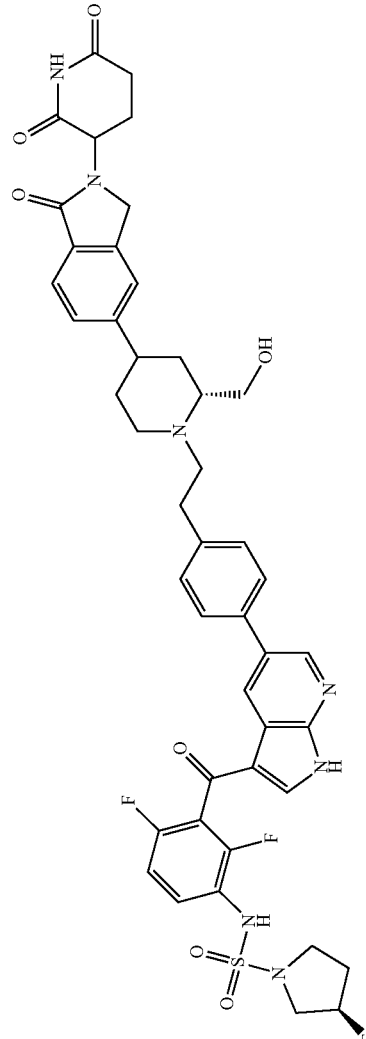 | 1 | (3R)-N-{3-[5-(4-{2-[(2R)-4-[2-(2,6-dioxopiperidin-3-yl)-1-oxo-2,3-dihydro-1H-isoindol-5-yl]-2-(hydroxymethyl)piperidin-1-yl]ethyl}phenyl)-1H-pyrrolo[2,3-b]pyridine-3-carbonyl]-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 151 | | 12 | (3R)-N-[3-(5-{4-[1-(2-{2-(2,6-dioxopiperidin-3-yl)-1-oxo-2,3-dihydro-1H-isoindol-5-yl]ethoxy}ethyl)piperidin-4-yl]phenyl}-1H-pyrrolo[2,3-b]pyridine-3-carbonyl)-2,4-difluorophenyl]-3-fluoropyrrolidine-1-sulfonamide |
| 152 | | 1 | (3R)-N-(3-{5-[4-(2-{4-[2-(2,6-dioxopiperidin-3-yl)-6-fluoro-1-oxo-2,3-dihydro-1H-isoindol-5-yl]piperazin-1-yl}ethyl)phenyl]-1H-pyrrolo[2,3-b]pyridine-3-carbonyl}-2,4-difluorophenyl)-3-fluoropyrrolidine-1-sulfonamide |
| 153 | | 1 | (3R)-N-{3-[5-(2-{[4-({1-[2-(2,6-dioxopiperidin-3-yl)-1-oxo-2,3-dihydro-1H-isoindol-5-yl]piperidin-4-yl}methyl)piperazin-1-yl]methyl}pyrimidin-5-yl)-1H-pyrrolo[2,3-b]pyridine-3-carbonyl]-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 154 | | 1 | (3R)-N-{3-[5-(4-{[1-({1-[2-(2,6-dioxopiperidin-3-yl)-1-oxo-2,3-dihydro-1H-isoindol-5-yl]piperidin-4-yl}methyl)piperidin-4-yl]methyl}phenyl)-1H-pyrrolo[2,3-b]pyridine-3-carbonyl]-2,4-difluorophenyl}-3-fluoropyrrolidine-1-sulfonamide |
| 155 | | 12 | (3R)-N-[2,4-difluoro-3-(5-{4-[4-({methyl[(1s,3s)-3-{[2-(2,6-dioxopiperidin-3-yl)-1-oxo-2,3-dihydro-1H-isoindol-5-yl]oxy}cyclobutyl]amino}methyl)piperidin-1-yl]phenyl}-1H-pyrrolo[2,3-b]pyridine-3-carbonyl)phenyl]-3-fluoropyrrolidine-1-sulfonamide |
| 156 | | 3 | (3R)-N-[3-(5-{4-[6-({1-[4-(2,4-dioxo-1,3-diazinan-1-yl)-3-fluorophenyl]piperidin-4-yl}methyl)-2,6-diazaspiro[3.3]heptan-2-yl]phenyl}-1H-pyrrolo[2,3-b]pyridine-3-carbonyl)-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 157 | | 1 | (3R)-N-[3-(5-{4-[4-({4-[2-(2,6-dioxopiperidin-3-yl)-6-fluoro-1-oxo-2,3-dihydro-1H-isoindol-5-yl]piperidin-1-yl}methyl)piperidin-1-yl]phenyl}-1H-pyrrolo[2,3-b]pyridine-3-carbonyl)-2,4-difluorophenyl]-3-fluoropyrrolidine-1-sulfonamide |
| 158 | | 1 | (3R)-N-(3-{5-[6-(2-{6-[2-(2,6-dioxopiperidin-3-yl)-1-oxo-2,3-dihydro-1H-isoindol-5-yl]-2,6-diazaspiro[3.3]heptan-2-yl}ethoxy)pyridin-3-yl]-1H-pyrrolo[2,3-b]pyridine-3-carbonyl}-2,4-difluorophenyl)-3-fluoropyrrolidine-1-sulfonamide |
| 159 | | 1 | (3R)-N-{3-[5-(4-{1'-[2-(2,6-dioxopiperidin-3-yl)-1-oxo-2,3-dihydro-1H-isoindol-5-yl]-[3,3'-biazetidin]-1-yl}phenyl)-1H-pyrrolo[2,3-b]pyridine-3-carbonyl]-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 160 | | 1 | (3R)-N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2,4-difluorophenyl]-3-fluoropyrrolidine-1-sulfonamide |
| 161 | | 1 | (3R)-N-{3-[5-(4-{4-[(4-{2-[(3R)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2,4-difluorophenyl]-3-fluoropyrrolidine-1-sulfonamide |
| 162 | | 1 | (3R)-N-{3-[5-(4-{1-[4-({1-[2-(2,6-dioxopiperidin-3-yl)-1-oxo-2,3-dihydro-1H-isoindol-5-yl]piperidin-4-yl}methyl)piperazin-1-yl]cyclopropyl}phenyl)-1H-pyrrolo[2,3-b]pyridine-3-carbonyl]-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 163 | | 1 | (3R)-N-[3-(5-{4-[4-({4-[2-(2,6-dioxopiperidin-3-yl)-7-methoxy-1-oxo-2,3-dihydro-1H-isoindol-5-yl]piperidin-1-yl}methyl)piperidin-1-yl]-3-fluorophenyl}-1H-pyrrolo[2,3-b]pyridine-3-carbonyl)-2,4-difluorophenyl]-3-fluoropyrrolidine-1-sulfonamide |
| 164 | | 1 | (3R)-N-[3-(5-{6-[4-({4-[2-(2,6-dioxopiperidin-3-yl)-7-methoxy-1-oxo-2,3-dihydro-1H-isoindol-5-yl]piperidin-1-yl}methyl)piperidin-1-yl]pyridin-3-yl}-1H-pyrrolo[2,3-b]pyridine-3-carbonyl)-2,4-difluorophenyl]-3-fluoropyrrolidine-1-sulfonamide |
| 165 | | 12 | (3R)-N-{3-[5-(4-{6-[(2S)-3-(4-{6-[(3S)-2,6-dioxopiperidin-3-yl]-1-oxo-2,3-dihydro-1H-isoindol-5-yl}oxy)-2-hydroxypropyl]-2,6-diazaspiro[3.3]heptan-2-yl}phenyl)-1H-pyrrolo[2,3-b]pyridine-3-carbonyl]-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 166 | | 12 | (3R)-N-{3-{4-[6-[(2)S-3-({2-[(3R)-2,6-dioxopiperidin-3-yl]-1-oxo-2,3-dihydro-1H-isoindol-5-yl}oxy)-2-hydroxypropyl]-2,6-diazaspiro[3.3]heptan-2-yl]phenyl}-1H-pyrrolo[2,3-b]pyridine-3-carbonyl]-2,4-difluorophenyl]-3-fluoropyrrolidine-1-sulfonamide |
| 167 | | 1 | (3R)-N-[2,4-difluoro-3-(5-{4-[(1s,3s)-3-[({1-[2-(2,6-dioxopiperidin-3-yl)-1-oxo-2,3-dihydro-1H-isoindol-5-yl]piperidin-4-yl}methyl)(methyl)amino]cyclobutoxy)phenyl]-1H-pyrrolo[2,3-b]pyridine-3-carbonyl)phenyl]-3-fluoropyrrolidine-1-sulfonamide |
| 168 | | 3 | (3R)-N-[3-(5-{4-[4-({4-[4-(2,6-dioxopiperidin-3-yl)-3-fluorophenyl]piperidin-1-yl}methyl)piperidin-1-yl]phenyl}-1H-pyrrolo[2,3-b]pyridine-3-carbonyl)-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 169 | | 1 | (3R)-N-[2,4-difluoro-3-(5-{4-[4-({4-[2-(1-methyl-2,6-dioxopiperidin-3-yl)-1-oxo-2,3-dihydro-1H-isoindol-5-yl]piperidin-1-yl}methyl)piperidin-1-yl]phenyl}-1H-pyrrolo[2,3-b]pyridine-3-carbonyl)phenyl]-3-fluoropyrrolidine-1-sulfonamide |
| 170 | | 12 | (3R)-N-{3-[5-(4-{6-[(2S)-3-{2-[(3S)-2,6-dioxopiperidin-3-yl]-1-oxo-2,3-dihydro-1H-isoindol-5-yl}-2-hydroxypropyl]-2,6-diazaspiro[3.3]heptan-2-yl}phenyl)-1H-pyrrolo[2,3-b]pyridine-3-carbonyl]-2,4-difluorophenyl}-3-fluoropyrrolidine-1-sulfonamide |
| 171 | | 12 | (3R)-N-{3-[5-(4-{6-[(2S)-4-{2-[(3R)-2,6-dioxopiperidin-3-yl]-1-oxo-2,3-dihydro-1H-isoindol-5-yl}-2-hydroxybutyl]-2,6-diazaspiro[3.3]heptan-2-yl}phenyl)-1H-pyrrolo[2,3-b]pyridine-3-carbonyl]-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 172 | | 12 | (3R)-N-{3-[5-(4-{6-[(2S)-4-{6-[(2S)-2,6-dioxopiperidin-3-yl]-1-oxo-2,3-dihydro-1H-isoindol-5-yl}-2-hydroxybutyl]-2,6-diazaspiro[3.3]heptan-2-yl}phenyl)-1H-pyrrolo[2,3-b]pyridine-3-carbonyl]-2,4-difluorophenyl}-3-fluoropyrrolidine-1-sulfonamide |
| 173 | | 12 | (3R)-N-{3-[5-(4-{6-[(2S)-4-{2-[(3R)-2,6-dioxopiperidin-3-yl]-1-oxo-2,3-dihydro-1H-isoindol-5-yl}-2-hydroxybutyl]-2,6-diazaspiro[3.3]heptan-2-yl}phenyl)-1H-pyrrolo[2,3-b]pyridine-3-carbonyl]-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 174 | | 1 | (3R)-N-{3-[5-(4-{1-[1-{1-[2-(2,6-dioxopiperidin-3-yl)-1-oxo-2,3-dihydro-1H-isoindol-5-yl]piperidin-4-yl}methyl)piperidin-4-yl]cyclopropyl]phenyl}-1H-pyrrolo[2,3-b]pyridine-3-carbonyl]-2,4-difluorophenyl}-3-fluoropyrrolidine-1-sulfonamide |
| 175 | | 1 | (3R)-N-[3-(5-{2-[4-({4-[2-(2,6-dioxopiperidin-3-yl)-7-methoxy-1-oxo-2,3-dihydro-1H-isoindol-5-yl]piperidin-1-yl}methyl)piperidin-1-yl]pyrimidin-5-yl}-1H-pyrrolo[2,3-b]pyridine-3-carbonyl)-2,4-difluorophenyl]-3-fluoropyrrolidine-1-sulfonamide |
| 176 | | 3 | (3R)-N-[2,4-difluoro-3-(5-{4-[4-({4-[3-fluoro-4-(3-methyl-2,6-dioxopiperidin-3-yl)phenyl]piperidin-1-yl}methyl)piperidin-1-yl]phenyl}-1H-pyrrolo[2,3-b]pyridine-3-carbonyl)phenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 177 | | 3 | N-[3-(5-{4-[4-({4-[2-(2,6-dioxopiperidin-3-yl)-1-oxo-2,3-dihydro-1H-isoindol-5-yl]piperidin-1-yl}methyl)piperidin-1-yl]phenyl}-1H-pyrrolo[2,3-b]pyridine-3-carbonyl)-2,4-difluorophenyl]pyrrolidine-1-sulfonamide |
| 178 | | 3 | (3R)-N-[3-(5-{4-[4-(2-{4-[4-(2,6-dioxopiperidin-3-yl)-3-fluorophenyl]piperidin-3-yl}ethyl)piperidin-1-yl]phenyl}-1H-pyrrolo[2,3-b]pyridine-3-carbonyl)-2,4-difluorophenyl]-3-fluoropyrrolidine-1-sulfonamide |
| 179 | | 1 | (3R)-N-[3-(5-{4-[(1R,5S,6S)-6-({4-[2-(2,6-dioxopiperidin-3-yl)-1-oxo-2,3-dihydro-1H-isoindol-5-yl]piperidin-1-yl}methyl)-3-azabicyclo[3.1.0]hexan-3-yl]phenyl}-1H-pyrrolo[2,3-b]pyridine-3-carbonyl)-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 180 | | 1 | (3R)-N-[3-(5-{4-[((1R,3S,5S)-3-{[4-[2-(2,6-dioxopiperidin-3-yl)-1-oxo-2,3-dihydro-1H-isoindol-5-yl]piperidin-1-yl]methyl}-8-azabicyclo[3.2.1]octan-8-yl]phenyl)-1H-pyrrolo[2,3-b]pyridine-3-carbonyl)-2,4-difluorophenyl]-3-fluoropyrrolidine-1-sulfonamide |
| 181 | | 1 | (3R)-N-[3-(5-{4-[4-({1-[2-(2,6-dioxopiperidin-3-yl)-1-oxo-2,3-dihydro-1H-isoindol-5-yl]piperidin-4-yl}methyl)piperidin-1-yl]phenyl}-1H-pyrrolo[2,3-b]pyridine-3-carbonyl)-2,4-difluorophenyl]-3-fluoropyrrolidine-1-sulfonamide |
| 182 | | 1 | (3R)-N-[2,4-difluoro-3-(5-{4-[(1s,3s)-3-[(2-{4-[2-(2,6-dioxopiperidin-3-yl)-1-oxo-2,3-dihydro-1H-isoindol-5-yl]piperazin-1-yl}ethyl)(methyl)amino]cyclobutoxy}phenyl)-1H-pyrrolo[2,3-b]pyridine-3-carbonyl)phenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 183 | | 3 | (3R)-N-[2,4-difluoro-3-(5-{4-[4-({4-[2-(3-methyl-2,6-dioxopiperidin-3-yl)-1-oxo-2,3-dihydro-1H-isoindol-5-yl]piperidin-1-yl}methyl)piperidin-1-yl]phenyl}-1H-pyrrolo[2,3-b]pyridine-3-carbonyl)phenyl]-3-fluoropyrrolidine-1-sulfonamide |
| 184 | | 3 | 4-(1-{[1-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperidin-4-yl]methyl}piperidin-4-yl)-N-(2,6-dioxopiperidin-3-yl)-2-methoxybenzamide |
| 185 | | 1 | (3R)-N-[3-(5-{4-[4-({4-[2-(2,6-dioxopiperidin-3-yl)-3-oxo-2,3-dihydro-1H-isoindol-5-yl]piperidin-1-yl}methyl)piperidin-1-yl]phenyl}-1H-pyrrolo[2,3-b]pyridine-3-carbonyl)-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 186 | | 1 | (3R)-N-{3-[5-(4-{4-[(3R)-3-{2-[(3S)-2,6-dioxopiperidin-3-yl]-7-methoxy-1-oxo-2,3-dihydro-1H-isoindol-5-yl}-3-hydroxypropyl]piperazin-1-yl}phenyl)-1H-pyrrolo[2,3-b]pyridine-3-carbonyl]-2,4-difluorophenyl}-3-fluoropyrrolidine-1-sulfonamide |
| 187 | | 1 | (3R)-N-{3-[5-(4-{4-[(3R)-3-{2-[(3R)-2,6-dioxopiperidin-3-yl]-7-methoxy-1-oxo-2,3-dihydro-1H-isoindol-5-yl}-3-hydroxypropyl]piperazin-1-yl}phenyl)-1H-pyrrolo[2,3-b]pyridine-3-carbonyl]-2,4-difluorophenyl}-3-fluoropyrrolidine-1-sulfonamide |
| 188 | | 1 | (3R)-N-[3-(5-{4-[(1R,3R,5S)-3-({4-[2-(2,6-dioxopiperidin-3-yl)-1-oxo-2,3-dihydro-1H-isoindol-5-yl]piperidin-1-yl}methyl)-8-azabicyclo[3.2.1]octan-8-yl]phenyl}-1H-pyrrolo[2,3-b]pyridine-3-carbonyl)-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 189 | | 3 | (3R)-N-[3-(5-{4-[4-({4-[4-(2,6-dioxopiperidin-3-yl)phenyl]piperidin-1-yl}methyl)piperidin-1-yl]phenyl}-1H-pyrrolo[2,3-b]pyridine-3-carbonyl)-2,4-difluorophenyl]-3-fluoropyrrolidine-1-sulfonamide |
| 190 | | 1 | N-[3-(5-{4-[4-({4-[2-(2,6-dioxopiperidin-3-yl)-1-oxo-2,3-dihydro-1H-isoindol-5-yl]piperidin-1-yl}methyl)piperidin-1-yl]phenyl}-1H-pyrrolo[2,3-b]pyridine-3-carbonyl)-2,4-difluorophenyl]-3,3-difluoropyrrolidine-1-sulfonamide |
| 191 | | 1 | 3-(5-{1-{(1-{4-[3-{[ethyl(methyl)sulfamoyl]amino}-2,6-difluorobenzoyl)-1H-pyrrolo[2,3-b]pyridin-5-yl]phenyl}piperidin-4-yl}methyl)piperidin-4-yl]-1-oxo-2,3-dihydro-1H-isoindol-2-yl)piperidine-2,6-dione |

TABLE 1-continued

Exemplary bifunctional compounds of the present disclosure

| Ex. No. | Parent Mol Structure | Synthetic Scheme | IUPAC Name |
|---|---|---|---|
| 192 | | 1 | (3R)-N-{3-[5-(4-{[4-({1-[2-(2,6-dioxopiperidin-3-yl)-1-oxo-2,3-dihydro-1H-isoindol-5-yl]azetidin-3-yl}methyl)piperazin-1-yl]methyl}phenyl)-1H-pyrrolo[2,3-b]pyridine-3-carbonyl]-2,4-difluorophenyl}-3-fluoropyrrolidine-1-sulfonamide |
| 193 | | 1 | (3R)-N-{3-[5-(2-{[4-({1-[2-(2,6-dioxopiperidin-3-yl)-1-oxo-2,3-dihydro-1H-isoindol-5-yl]azetidin-3-yl}methyl)piperazin-1-yl]methyl}pyrimidin-5-yl)-1H-pyrrolo[2,3-b]pyridine-3-carbonyl]-2,4-difluorophenyl}-3-fluoropyrrolidine-1-sulfonamide |
| 194 | | 1 | (3R)-N-{3-[5-(2-{[1-({1-[2-(2,6-dioxopiperidin-3-yl)-1-oxo-2,3-dihydro-1H-isoindol-5-yl]azetidin-3-yl}methyl)piperidin-4-yl]methyl}pyrimidin-5-yl)-1H-pyrrolo[2,3-b]pyridine-3-carbonyl]-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 195 | | 1 | (3R)-N-[2,4-difluoro-3-(5-{4-[4-(2-{methyl[(1r,4r)-4-{[2-(2,6-dioxopiperidin-3-yl)-1-oxo-2,3-dihydro-1H-isoindol-5-yl]oxy}cyclohexyl]amino}ethyl)piperazin-1-yl]phenyl}-1H-pyrrolo[2,3-b]pyridine-3-carbonyl)phenyl]-3-fluoropyrrolidine-1-sulfonamide |
| 196 | | 3 | 5-(1-{[1-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperidin-4-yl]methyl}piperidin-4-yl)-N-[(3S)-2,6-dioxopiperidin-3-yl]-2-fluorobenzamide |
| 197 | | 3 | 5-(1-{[1-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperidin-4-yl]methyl}piperidin-4-yl)-N-[(3R)-2,6-dioxopiperidin-3-yl]-2-fluorobenzamide |

TABLE 1-continued

Exemplary bifunctional compounds of the present disclosure

| Ex. No. | Parent Mol Structure | Synthetic Scheme | IUPAC Name |
|---|---|---|---|
| 198 | | 1 | (3R)-N-[3-(5-{4-[3-({4-[2-(2,6-dioxopiperidin-3-yl)-1-oxo-2,3-dihydro-1H-isoindol-5-yl]piperidin-1-yl}methyl)azetidin-1-yl]phenyl}-1H-pyrrolo[2,3-b]pyridine-3-carbonyl)-2,4-difluorophenyl]-3-fluoropyrrolidine-1-sulfonamide |
| 199 | | 3 | (3R)-N-[3-(5-{4-[4-(2-{4-[4-(2,4-dioxo-1,3-diazinan-1-yl)-3-fluorophenyl]piperidin-1-yl}ethyl)piperidin-1-yl]phenyl}-1H-pyrrolo[2,3-b]pyridine-3-carbonyl)-2,4-difluorophenyl]-3-fluoropyrrolidine-1-sulfonamide |
| 200 | | 1 | (3R)-N-{3-[5-(4-{1-[4-({1-[2-(2,6-dioxopiperidin-3-yl)-1-oxo-2,3-dihydro-1H-isoindol-5-yl]azetidin-3-yl}methyl)piperazin-1-yl]cyclopropyl}phenyl)-1H-pyrrolo[2,3-b]pyridine-3-carbonyl]-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 201 | 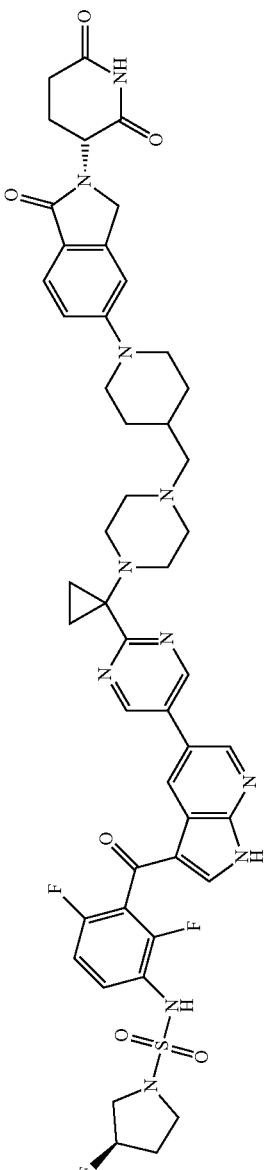 | 1 | (3R)-N-(3-{5-[2-(1-{4-[(1-{2-[(3S)-2,6-dioxopiperidin-3-yl]-1-oxo-2,3-dihydro-1H-isoindol-5-yl}piperidin-4-yl]methyl}piperazin-1-yl}cyclopropyl)pyrimidin-5-yl]-1H-pyrrolo[2,3-b]pyridine-3-carbonyl}-2,4-difluorophenyl)-3-fluoropyrrolidine-1-sulfonamide |
| 202 | 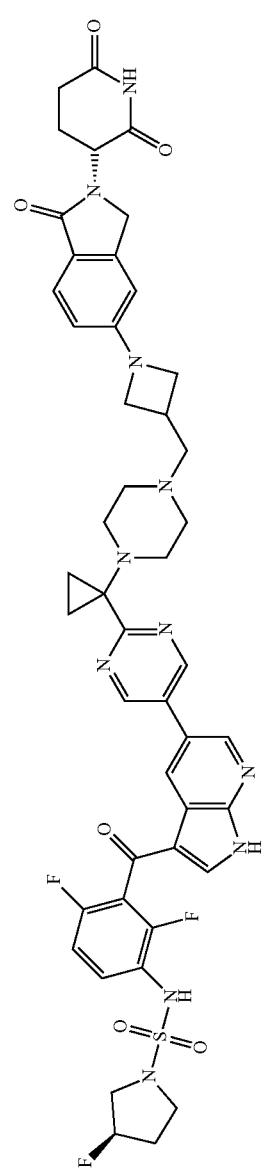 | 1 | (3R)-N-(3-{5-[2-(1-{4-[(1-{2-[(3S)-2,6-dioxopiperidin-3-yl]-1-oxo-2,3-dihydro-1H-isoindol-5-yl}azetidin-3-yl)methyl]piperazin-1-yl}cyclopropyl)pyrimidin-5-yl]-1H-pyrrolo[2,3-b]pyridine-3-carbonyl}-2,4-difluorophenyl)-3-fluoropyrrolidine-1-sulfonamide |
| 203 | 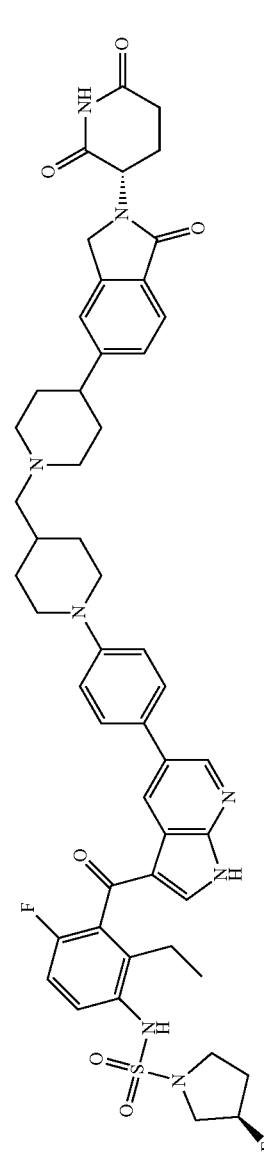 | 1 | (3R)-N-{3-[5-(4-{4-[2-(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2-ethyl-4-fluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 204 | | 1 | N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2,4-difluorophenyl}-2-methylpropane-1-sulfonamide |
| 205 | | 1 | (3R)-N-{3-[5-(3-cyano-4-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2,4-difluorophenyl}-3-fluoropyrrolidine-1-sulfonamide |
| 206 | | 1 | 1-cyclopropyl-N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2,4-difluorophenyl}methanesulfonamide |

TABLE 1-continued

Exemplary bifunctional compounds of the present disclosure

| Ex. No. | Parent Mol Structure | Synthetic Scheme | IUPAC Name |
|---|---|---|---|
| 207 | | 1 | (3R)-N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-4-fluoro-2-methoxyphenyl}-3-fluoropyrrolidine-1-sulfonamide |
| 208 | | 1 | (3S)-3-(5-{1-[(1-{4-[3-(2,6-difluoro-3-{[methyl(propan-2-yl)sulfamoyl]amino}benzoyl)-1H-pyrrolo[2,3-b]pyridin-5-yl]phenyl}piperidin-4-yl)methyl]piperidin-4-yl}-1-oxo-2,3-dihydro-1H-isoindol-2-yl)piperidine-2,6-dione |
| 209 | | 1 | (3R)-N-{3-[5-(4-{4-[(1-[2-(2,6-dioxopiperidin-3-yl)-1-oxo-2,3-dihydro-1H-isoindol-5-yl]methyl}piperazin-1-yl]phenyl)-1H-pyrrolo[2,3-b]pyridine-3-carbonyl]-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 210 | | 1 | (3R)-N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}-3-(methylamino)phenyl)-1H-pyrrolo[2,3-b]pyridine-3-carbonyl]-2,4-difluorophenyl}-3-fluoropyrrolidine-1-sulfonamide |
| 211 | | 1 | (2S)-N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2,4-difluorophenyl}-2-methylpyrrolidine-1-sulfonamide |
| 212 | | 1 | (3R)-N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2-fluoro-4-methoxyphenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 213 | | 1 | 3-(5-{1-((1-{4-[3-(3-{[(2,2-difluoroethyl)(methyl)sulfamoyl]amino}-2,6-difluorobenzoyl)-1H-pyrrolo[2,3-b]pyridin-5-yl]phenyl}piperidin-4-yl)methyl]piperidin-4-yl)-1-oxo-2,3-dihydro-1H-isoindol-2-yl)piperidine-2,6-dione |
| 214 | | 1 | (3R)-N-{3-[5-(4-{1'-[2-(2,6-dioxopiperidin-3-yl)-1-oxo-2,3-dihydro-1H-isoindol-5-yl]-[4,4'-bipiperidin]-1-yl}phenyl)-1H-pyrrolo[2,3-b]pyridine-3-carbonyl]-2,4-difluorophenyl}-3-fluoropyrrolidine-1-sulfonamide |
| 215 | | 1 | (3R)-N-[3-(5-{4-[(4-[2-(2,6-dioxopiperidin-3-yl)-1-oxo-2,3-dihydro-1H-isoindol-5-yl]piperidin-1-yl}methyl)piperidin-1-yl]pyrimidin-2-yl}-1H-pyrrolo[2,3-b]pyridine-3-carbonyl)-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 216 | | 1 | (3R)-N-[3-(5-{4-[(3R)-3-(2-{4-[2-(2,6-dioxopiperidin-3-yl)-1-oxo-2,3-dihydro-1H-isoindol-5-yl]piperidin-1-yl}ethyl)pyrrolidin-1-yl]phenyl}-1H-pyrrolo[2,3-b]pyridine-3-carbonyl)-2,4-difluorophenyl]-3-fluoropyrrolidine-1-sulfonamide |
| 217 | | 1 | (3R)-N-[3-(5-{4-[(3S)-3-(2-{4-[2-(2,6-dioxopiperidin-3-yl)-1-oxo-2,3-dihydro-1H-isoindol-5-yl]piperidin-1-yl}ethyl)pyrrolidin-1-yl]phenyl}-1H-pyrrolo[2,3-b]pyridine-3-carbonyl)-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 218 | | 1 | (3R)-N-[3-(5-{4-[3-(2-{4-[2-(2,6-dioxopiperidin-3-yl)-1-oxo-2,3-dihydro-1H-isoindol-5-yl]piperidin-1-yl}ethyl)azetidin-1-yl]phenyl}-1H-pyrrolo[2,3-b]pyridine-3-carbonyl]-2,4-difluorophenyl]-3-fluoropyrrolidine-1-sulfonamide |
| 219 | | 1 | (3R)-N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2,4-difluorophenyl}-3-fluoropyrrolidine-1-sulfonamide |
| 220 | | 1 | (3R)-N-{3-[5-(4-{4-[(4-{2-[(3R)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 221 | | 1 | (3R)-N-{3-[5-(4-{4-[(6-{2-[(3S)-2,6-dioxopiperidin-3-yl]-1-oxo-2,3-dihydro-1H-isoindol-5-yl}-2,6-diazaspiro[3.3]heptan-2-yl)methyl]piperidin-1-yl}phenyl)-1H-pyrrolo[2,3-b]pyridine-3-carbonyl]-2,4-difluorophenyl}-3-fluoropyrrolidine-1-sulfonamide |
| 222 | | 1 | (3R)-N-{3-[5-(4-{4-[(6-{2-[(3R)-2,6-dioxopiperidin-3-yl]-1-oxo-2,3-dihydro-1H-isoindol-5-yl}-2,6-diazaspiro[3.3]heptan-2-yl)methyl]piperidin-1-yl}phenyl)-1H-pyrrolo[2,3-b]pyridine-3-carbonyl]-2,4-difluorophenyl}-3-fluoropyrrolidine-1-sulfonamide |
| 223 | | 1 | (3R)-N-{3-[5-(4-{4-[(1-{2-[(3S)-2,6-dioxopiperidin-3-yl]-1-oxo-2,3-dihydro-1H-isoindol-5-yl}piperidin-4-yl)methyl]piperazin-1-yl}phenyl)-1H-pyrrolo[2,3-b]pyridine-3-carbonyl]-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 224 | | 1 | (3R)-N-{3-[5-(4-{4-[(1-[2-[(3R)-2,6-dioxopiperidin-3-yl]-1-oxo-2,3-dihydro-1H-isoindol-5-yl]piperidin-4-yl)methyl]piperazin-1-yl}phenyl)-1H-pyrrolo[2,3-b]pyridine-3-carbonyl]-2,4-difluorophenyl]-3-fluoropyrrolidine-1-sulfonamide |
| 225 | | 1 | (3R)-N-{3-[5-(4-{6-[(1-{2-[(3R)-2,6-dioxopiperidin-3-yl]-7-methoxy-1-oxo-2,3-dihydro-1H-isoindol-5-yl}piperidin-4-yl)methyl]-2,6-diazaspiro[3.3]heptan-2-yl}phenyl)-1H-pyrrolo[2,3-b]pyridine-3-carbonyl]-2,4-difluorophenyl}-3-fluoropyrrolidine-1-sulfonamide |
| 226 | | 1 | (3R)-N-{3-[5-(4-{6-[(1-{2-[(3S)-2,6-dioxopiperidin-3-yl]-7-methoxy-1-oxo-2,3-dihydro-1H-isoindol-5-yl}piperidin-4-yl)methyl]-2,6-diazaspiro[3.3]heptan-2-yl}phenyl)-1H-pyrrolo[2,3-b]pyridine-3-carbonyl]-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 227 | | 1 | (3R)-N-[3-(5-{4-[4-({1'-[2-(2,6-dioxopiperidin-3-yl)-1-oxo-2,3-dihydro-1H-isoindol-5-yl]-[3,3'-biazetidin]-1-yl}methyl)piperidin-1-yl]phenyl}-1H-pyrrolo[2,3-b]pyridine-3-carbonyl)-2,4-difluorophenyl]-3-fluoropyrrolidine-1-sulfonamide |
| 228 | | 1 | N-{3-[5-(4-{4-[(6-{2-[(3S)-2,6-dioxopiperidin-3-yl]-1-oxo-2,3-dihydro-1H-isoindol-5-yl]-2,6-diazaspiro[3.3]heptan-2-yl}methyl)piperidin-1-yl]phenyl}-1H-pyrrolo[2,3-b]pyridine-3-carbonyl)-2,4-difluorophenyl]propane-1-sulfonamide |
| 229 | | 1 | N-{3-[5-(4-{4-[(6-{2-[(3R)-2,6-dioxopiperidin-3-yl]-1-oxo-2,3-dihydro-1H-isoindol-5-yl]-2,6-diazaspiro[3.3]heptan-2-yl}methyl)piperidin-1-yl]phenyl}-1H-pyrrolo[2,3-b]pyridine-3-carbonyl)-2,4-difluorophenyl]propane-1-sulfonamide |
| 230 | | 1 | N-{3-[5-(4-{4-[(4-{2-[(3S)-2,6-dioxopiperidin-3-yl]-1-oxo-2,3-dihydro-1H-isoindol-5-yl]piperidin-1-yl}methyl)piperidin-1-yl]phenyl}-1H-pyrrolo[2,3-b]pyridine-3-carbonyl)-2,4-difluorophenyl]pyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 231 | | 1 | N-{3-[5-(4-{4-[(4-{2-[(3R)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2,4-difluorophenyl}pyrrolidine-1-sulfonamide |
| 232 | | 1 | N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2,4-difluorophenyl}-3,3-difluoropyrrolidine-1-sulfonamide |
| 233 | | 1 | N-{3-[5-(4-{4-[(4-{2-[(3R)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2,4-difluorophenyl}-3,3-difluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 234 | | 1 | N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2,4-difluorophenyl}propane-1-sulfonamide |
| 235 | | 1 | N-{3-[5-(4-{4-[(4-{2-[(3R)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2,4-difluorophenyl}propane-1-sulfonamide |
| 236 | | 1 | N-[3-(5-{4-[4-({4-[2-(2,6-dioxopiperidin-3-yl)-1-oxo-2,3-dihydro-1H-isoindol-5-yl]piperidin-1-yl}methyl)piperidin-1-yl]phenyl})-1H-pyrrolo[2,3-b]pyridine-3-carbonyl)-2,4-difluorophenyl]propane-1-sulfonamide |
| 237 | | 1 | N-{3-[5-(4-{6-[(1-{2-[(3S)-2,6-dioxopiperidin-3-yl]-7-methoxy-1-oxo-2,3-dihydro-1H-isoindol-5-yl}piperidin-4-yl)methyl]-2,6-diazaspiro[3.3]heptan-2-yl}phenyl)-1H-pyrrolo[2,3-b]pyridine-3-carbonyl]-2,4-difluorophenyl}propane-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 238 | | 1 | N-{3-[5-(4-{6-[(1-{2-[(3R)-2,6-dioxopiperidin-3-yl]-7-methoxy-1-oxo-2,3-dihydro-1H-isoindol-5-yl}piperidin-4-yl)methyl]-2,6-diazaspiro[3.3]heptan-2-yl}phenyl)-1H-pyrrolo[2,3-b]pyridine-3-carbonyl]-2,4-difluorophenyl}propane-1-sulfonamide |
| 239 | | 1 | (3R)-N-[3-(5-{4-[(2S,4S)-4-[(2-[(3S)-2,6-dioxopiperidin-3-yl]-1-oxo-2,3-dihydro-1H-isoindol-5-yl}piperidin-1-yl)methyl]-2-methylpiperidin-1-yl]phenyl)-1H-pyrrolo[2,3-b]pyridine-3-carbonyl]-2,4-difluorophenyl]-3-fluoropyrrolidine-1-sulfonamide |
| 240 | | 1 | (3R)-N-[3-(5-{4-[(2S,4S)-4-[(4-{2-[(3R)-2,6-dioxopiperidin-3-yl]-1-oxo-2,3-dihydro-1H-isoindol-5-yl}piperidin-1-yl)methyl]-2-methylpiperidin-1-yl]phenyl)-1H-pyrrolo[2,3-b]pyridine-3-carbonyl]-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 241 | | 1 | (3R)-N-[3-(5-{4-[(2R,4R)-4-[(4-{2-[(3S)-2,6-dioxopiperidin-3-yl]-1-oxo-2,3-dihydro-1H-isoindol-5-yl}piperidin-1-yl)methyl]-2-methylpiperidin-1-yl]phenyl}-1H-pyrrolo[2,3-b]pyridine-3-carbonyl)-2,4-difluorophenyl]-3-fluoropyrrolidine-1-sulfonamide |
| 242 | | 1 | (3R)-N-[3-(5-{4-[(2R,4R)-4-[(4-{2-[(3R)-2,6-dioxopiperidin-3-yl]-1-oxo-2,3-dihydro-1H-isoindol-5-yl}piperidin-1-yl)methyl]-2-methylpiperidin-1-yl]phenyl}-1H-pyrrolo[2,3-b]pyridine-3-carbonyl)-2,4-difluorophenyl]-3-fluoropyrrolidine-1-sulfonamide |
| 243 | | 1 | N-{3-[5-(4-{[4-((1-{2-[(3S)-2,6-dioxopiperidin-3-yl]-1-oxo-2,3-dihydro-1H-isoindol-5-yl}piperidin-4-yl)methyl]piperazin-1-yl}phenyl)-1H-pyrrolo[2,3-b]pyridine-3-carbonyl]-2,4-difluorophenyl}propane-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 244 | | 1 | N-[3-(5-{4-[4-({1-[2-(2,6-dioxopiperidin-3-yl)-1-oxo-2,3-dihydro-1H-isoindol-5-yl]piperidin-4-yl}methyl)piperazin-1-yl]phenyl}-1H-pyrrolo[2,3-b]pyridine-3-carbonyl)-2,4-difluorophenyl]propane-1-sulfonamide |
| 245 | | 1 | N-{3-[5-(4-{4-[(4-{2-[(3S)-2,6-dioxopiperidin-3-yl]-1-oxo-2,3-dihydro-1H-isoindol-5-yl}methyl)piperidin-1-yl]phenyl)-1H-pyrrolo[2,3-b]pyridine-3-carbonyl]-2,4-difluorophenyl}propane-1-sulfonamide |
| 246 | | 1 | N-[3-(5-{4-[4-({6-[2-(2,6-dioxopiperidin-3-yl)-1-oxo-2,3-dihydro-1H-isoindol-5-yl]-2,6-dioxaspiro[3.3]heptan-2-yl}methyl)piperidin-1-yl]phenyl}-1H-pyrrolo[2,3-b]pyridine-3-carbonyl)-2,4-difluorophenyl]-3,3-difluoropyrrolidine-1-sulfonamide |
| 247 | | 1 | N-[3-(5-{4-[6-({1-[2-(2,6-dioxopiperidin-3-yl)-7-methoxy-1-oxo-2,3-dihydro-1H-isoindol-5-yl]piperidin-4-yl}methyl)-2,6-diazaspiro[3.3]heptan-2-yl]phenyl}-1H-pyrrolo[2,3-b]pyridine-3-carbonyl)-2,4-difluorophenyl]-3,3-difluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 248 | | 1 | N-(3-{5-[4-(6-{3-[2-(2,6-dioxopiperidin-3-yl)-1-oxo-2,3-dihydro-1H-isoindol-5-yl]propyl}-2,6-diazaspiro[3.3]heptan-2-yl)phenyl]-1H-pyrrolo[2,3-b]pyridine-3-carbonyl}-2,4-difluorophenyl)-3,3-difluoropyrrolidine-1-sulfonamide |
| 249 | | 1 | (3R)-N-{3-[5-(4-{4-[(6-{2-[(3S)-2,6-dioxopiperidin-3-yl]-7-methoxy-1-oxo-2,3-dihydro-1H-isoindol-5-yl]-2,6-diazaspiro[3.3]heptan-2-yl}methyl)piperidin-1-yl]phenyl}-1H-pyrrolo[2,3-b]pyridine-3-carbonyl]-2,4-difluorophenyl}-3-fluoropyrrolidine-1-sulfonamide |
| 250 | | 1 | (3R)-N-{3-[5-(4-{4-[(6-{2-[(3R)-2,6-dioxopiperidin-3-yl]-7-methoxy-1-oxo-2,3-dihydro-1H-isoindol-5-yl]-2,6-diazaspiro[3.3]heptan-2-yl}methyl)piperidin-1-yl]phenyl}-1H-pyrrolo[2,3-b]pyridine-3-carbonyl]-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 251 | | 1 | N-[3-(5-{4-[4-(4-{[2-(2,6-dioxopiperidin-3-yl)-1-oxo-2,3-dihydro-1H-isoindol-5-yl]oxy}butyl)piperazin-1-yl]phenyl}-1H-pyrrolo[2,3-b]pyridine-3-carobnyl)-2,4-difluorophenyl]-3,3-difluoropyrrolidine-1-sulfonamide |
| 252 | | 1 | (3R)-N-{2-chloro-3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-4-fluorophenyl}-3-fluoropyrrolidine-1-sulfonamide |
| 253 | | 1 | (3R)-N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-4-fluoro-2-methylphenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 254 | | 1 | (3S)-3-(5-{1-[(1-{4-[3-(3-amino-2,6-difluorobenzoyl)-1H-pyrrolo[2,3-b]pyridin-5-yl]phenyl}piperidin-4-yl)methyl]piperidin-4-yl}-1-oxo-2,3-dihydro-1H-isoindol-2-yl)piperidine-2,6-dione |
| 255 | | 1 | (3R)-N-[3-(5-{3-cyano-4-[(4-{[2-(2,6-dioxopiperidin-3-yl)-1-oxo-2,3-dihydro-1H-isoindol-5-yl]piperidin-1-yl}methyl)piperidin-1-yl]phenyl}-1H-pyrrolo[2,3-b]pyridine-3-carbonyl)-2,4-difluorophenyl]-3-fluoropyrrolidine-1-sulfonamide |
| 256 | | 1 | (3R)-N-{3-[5-(4-{[4-{2-[(3S)-2,6-dioxopiperidin-3-yl]-1-oxo-2,3-dihydro-1H-isoindol-5-yl}piperidin-1-yl]methyl}piperidin-1-yl)-3-methoxyphenyl]-1H-pyrrolo[2,3-b]pyridine-3-carbonyl]-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 257 | | 1 | (3R)-N-[3-(5-{4-[4-({4-[2-(2,6-dioxopiperidin-3-yl)-1-oxo-2,3-dihydro-1H-isoindol-5-yl]piperidin-1-yl}methyl)piperidin-1-yl]-3-(methylamino)phenyl}-1H-pyrrolo[2,3-b]pyridine-3-carbonyl)-2,4-difluorophenyl]-3-fluoropyrrolidine-1-sulfonamide |
| 258 | | 1 | (3R)-N-{3-[5-(4-{2-[(1-{2-[(3S)-2,6-dioxopiperidin-3-yl]-1-oxo-2,3-dihydro-1H-isoindol-5-yl}piperidin-4-yl)methyl]-2,8-diazaspiro[4.5]decan-8-yl}-3-fluorophenyl)-1H-pyrrolo[2,3-b]pyridine-3-carbonyl]-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 259 | | 1 | (3R)-N-{3-[5-(4-{2-[(1-{2-[(3R)-2,6-dioxopiperidin-3-yl]-1-oxo-2,3-dihydro-1H-isoindol-5-yl}piperidin-4-yl)methyl]-2,8-diazaspiro[4.5]decan-8-yl}-3-fluorophenyl)-1H-pyrrolo[2,3-b]pyridine-3-carbonyl]-2,4-difluorophenyl}-3-fluoropyrrolidine-1-sulfonamide |
| 260 | | 1 | (3R)-N-{3-[5-(3,5-dicyano-4-{4-[(3S)-2,6-dioxopiperidin-3-yl]-1-oxo-2,3-dihydro-1H-isoindol-5-yl}piperidin-1-yl]methyl]piperidin-1-yl}phenyl)-1H-pyrrolo[2,3-b]pyridine-3-carbonyl]-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 261 | | 1 | (3R)-N-[3-(5-{3,5-dicyano-4-[4-({4-[2-(2,6-dioxopiperidin-3-yl)-1-oxo-2,3-dihydro-1H-isoindol-5-yl]piperidin-1-yl}methyl)piperidin-1-yl]phenyl}-1H-pyrrolo[2,3-b]pyridine-3-carbonyl)-2,4-difluorophenyl]-3-fluoropyrrolidine-1-sulfonamide |
| 262 | | 1 | (2S,5S)-N-{3-[5-(4-{4-[2-[(3S)-2,6-dioxopiperidin-3-yl]-1-oxo-2,3-dihydro-1H-isoindol-5-yl}piperidin-1-yl)methyl)piperidin-1-yl]phenyl}-1H-pyrrolo[2,3-b]pyridine-3-carbonyl]-2,4-difluorophenyl]-2,5-dimethylpyrrolidine-1-sulfonamide |
| 263 | | 1 | (2S,5S)-N-[3-(5-{4-[4-({4-[2-(2,6-dioxopiperidin-3-yl)-1-oxo-2,3-dihydro-1H-isoindol-5-yl]piperidin-1-yl}methyl)piperidin-1-yl]phenyl}-1H-pyrrolo[2,3-b]pyridine-3-carbonyl)-2,4-difluorophenyl]-2,5-dimethylpyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 264 | | 1 | (2S)-N-[3-(5-{4-[4-({4-[2-(2,6-dioxopiperidin-3-yl)-1-oxo-2,3-dihydro-1H-isoindol-5-yl]piperidin-1-yl}methyl)piperidin-1-yl]phenyl}-1H-pyrrolo[2,3-b]pyridine-3-carbonyl)-2,4-difluorophenyl]-2-methylpyrrolidine-1-sulfonamide |
| 265 | | 1 | (3R)-N-{3-[5-(4-{4-[4-({4-[2-[(3S)-2,6-dioxopiperidin-3-yl]-1-oxo-2,3-dihydro-1H-isoindol-5-yl]piperidin-1-yl}methyl)piperidin-1-yl]phenyl}-1H-pyrrolo[2,3-b]pyridine-3-carbonyl)-4-ethyl-2-fluorophenyl]-3-fluoropyrrolidine-1-sulfonamide |
| 266 | | 1 | (3R)-N-{3-[5-(4-{4-[4-({4-[2-(2,6-dioxopiperidin-3-yl)-1-oxo-2,3-dihydro-1H-isoindol-5-yl]piperidin-1-yl}methyl)piperidin-1-yl]phenyl}-1H-pyrrolo[2,3-b]pyridine-3-carbonyl)-4-ethyl-2-fluorophenyl]-3-fluoropyrrolidine-1-sulfonamide |
| 267 | | 1 | (3R)-N-{2,4-dichloro-3-[5-(4-{4-[4-({4-[2-[(3S)-2,6-dioxopiperidin-3-yl]-1-oxo-2,3-dihydro-1H-isoindol-5-yl]piperidin-1-yl}methyl)piperidin-1-yl]phenyl}-1H-pyrrolo[2,3-b]pyridine-3-carbonyl)phenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 268 | | 1 | (3R)-N-[2,4-dichloro-3-(5-{4-[4-({4-[2-(2,6-dioxopiperidin-3-yl)-1-oxo-2,3-dihydro-1H-isoindol-5-yl]piperidin-1-yl}methyl)piperidin-1-yl]phenyl}-1H-pyrrolo[2,3-b]pyridine-3-carbonyl)phenyl]-3-fluoropyrrolidine-1-sulfonamide |
| 269 | | 1 | (3R)-N-[3-(5-{4-[4-({4-[2-(2,6-dioxopiperidin-3-yl)-1-oxo-2,3-dihydro-1H-isoindol-5-yl]piperidin-1-yl}methyl)piperidin-1-yl]phenyl}-1H-pyrrolo[2,3-b]pyridine-3-carbonyl)-2-fluoro-4-methoxyphenyl]-3-fluoropyrrolidine-1-sulfonamide |
| 270 | | 1 | (2S,3R)-N-{3-[5-(4-{4-[({4-[2-[(3S)-2,6-dioxopiperidin-3-yl)-1-oxo-2,3-dihydro-1H-isoindol-5-yl]piperidin-1-yl}methyl)piperidin-1-yl]phenyl}-1H-pyrrolo[2,3-b]pyridine-3-carbonyl]-2,4-difluorophenyl}-3-fluoro-2-methylpyrrolidine-1-sulfonamide |
| 271 | | 1 | (2S,3R)-N-[3-(5-{4-[4-({4-[2-(2,6-dioxopiperidin-3-yl)-1-oxo-2,3-dihydro-1H-isoindol-5-yl]piperidin-1-yl}methyl)piperidin-1-yl]phenyl}-1H-pyrrolo[2,3-b]pyridine-3-carbonyl]-3-fluoro-2-difluorophenyl]-3-fluoro-2-methylpyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 272 | | 1 | (3R)-N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-4-fluoro-2-(trifluoromethyl)phenyl}-3-fluoropyrrolidine-1-sulfonamide |
| 273 | | 1 | (3R)-N-[3-(5-{4-[4-({4-[2-(2,6-dioxopiperidin-3-yl)-1-oxo-2,3-dihydro-1H-isoindol-5-yl]piperidin-1-yl}methyl)piperidin-1-yl]phenyl}-1H-pyrrolo[2,3-b]pyridine-3-carbonyl)-4-fluoro-2-(trifluoromethyl)phenyl]-3-fluoropyrrolidine-1-sulfonamide |
| 274 | | Method for Cmp. 373 | (3R)-N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2,4-dimethoxyphenyl}-3-fluoropyrrolidine-1-sulfonamide |
| 275 | | 1 | (3R)-N-[3-(5-{4-[4-({4-[2-(2,6-dioxopiperidin-3-yl)-1-oxo-2,3-dihydro-1H-isoindol-5-yl]piperidin-1-yl}methyl)piperidin-1-yl]phenyl}-1H-pyrrolo[2,3-b]pyridine-3-carbonyl)-2,4-dimethoxyphenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 276 | | 1 | (3R)-N-[3-(5-{4-[4-({4-[2-(2,6-dioxopiperidin-3-yl)-1-oxo-2,3-dihydro-1H-isoindol-5-yl]piperidin-1-yl}methyl)piperidin-1-yl]phenyl}-1H-pyrrolo[2,3-b]pyridine-3-carbonyl)-2-ethyl-4-fluorophenyl]-3-fluoropyrrolidine-1-sulfonamide |
| 277 | | 1 | (2R,5R)-N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2,4-difluorophenyl}-2,5-dimethylpyrrolidine-1-sulfonamide |
| 278 | | 1 | (3R)-N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2,4-difluorophenyl}-3-hydroxypyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 279 | | 1 | N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2,4-difluorophenyl}-3-hydroxyazetidine-1-sulfonamide |
| 280 | | 1 | (3S)-3-(5-{1-[(1-{4-[3-(2,6-difluoro-3-{[(2-hydroxyethyl)(methyl)sulfamoyl]amino}benzoyl)-1H-pyrrolo[2,3-b]pyridin-5-yl]phenyl}piperidin-4-yl)methyl]piperidin-4-yl}-1-oxo-2,3-dihydro-1H-isoindol-2-yl)piperidine-2,6-dione |
| 281 | | 1 | (3S)-3-(5-{1-[(1-{4-[3-(3-{[cyclopropyl(methyl)sulfamoyl]amino}-2,6-difluorobenzoyl)-1H-pyrrolo[2,3-b]pyridin-5-yl]phenyl}piperidin-4-yl)methyl]piperidin-4-yl}-1-oxo-2,3-dihydro-1H-isoindol-2-yl)piperidine-2,6-dione |

TABLE 1-continued

Exemplary bifunctional compounds of the present disclosure

| Ex. No. | Parent Mol Structure | Synthetic Scheme | IUPAC Name |
|---|---|---|---|
| 282 | | 1 | N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2,4-difluorophenyl}-2-hydroxyethane-1-sulfonamide |
| 283 | | 1 | (3R)-N-[3-(5-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-4-fluoro-2-methoxyphenyl]-3-fluoropyrrolidine-1-sulfonamide |
| 284 | | 1 | (3R)-N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}-3,5-bis(methylamino)phenyl)-1H-pyrrolo[2,3-b]pyridine-3-carbonyl]-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 285 | | 1 | (3R)-N-[3-(5-{4-[4-({4-[2-(2,6-dioxopiperidin-3-yl)-1-oxo-2,3-dihydro-1H-isoindol-5-yl]piperidin-1-yl}methyl)piperidin-1-yl]-3,5-bis(methylamino)phenyl}-1H-pyrrolo[2,3-b]pyridine-3-carbonyl)-2,4-difluorophenyl]-3-fluoropyrrolidine-1-sulfonamide |
| 286 | | 1 | (3R)-N-(3-{5-[2-(1-{4-8 (1-{2-[(3R)-2,6-dioxopiperidin-3-yl]-1-oxo-2,3-dihydro-1H-isoindol-5-yl}azetidin-3-yl}methyl)piperazin-1-yl]cyclopropyl)pyrimidin-5-l]-1H-pyrrolo[2,3-b]pyridine-3-carbonyl}-2,4-difluorophenyl)-3-fluoropyrrolidine-1-sulfonamide |
| 287 | | 1 | (3R)-N-(3-{5-[2-({1-[(1-{2-[(3S)-2,6-dioxopiperidin-3-yl]-1-oxo-2,3-dihydro-1H-isoindol-5-yl}piperidin-4-yl)methyl]piperidin-4-yl}(methyl)amino)pyrimidin-5-yl]-1H-pyrrolo[2,3-b]pyridine-3-carbonyl}-2,4-difluorophenyl)-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 288 | 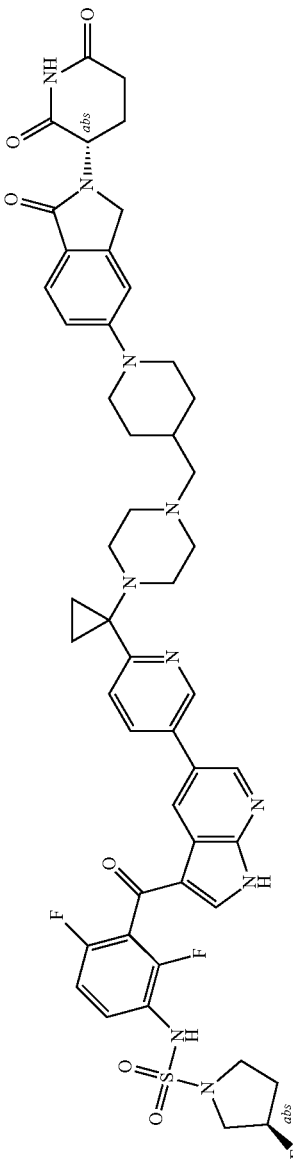 | 1 | (3R)-N-(3-{5-[6-(1-{4-[(1-{2-[(3S)-2,6-dioxopiperidin-3-yl]-1-oxo-2,3-dihydro-1H-isoindol-5-yl}piperidin-4-yl]methyl]piperazin-1-yl}cyclopropyl)pyridin-3-yl]-1H-pyrrolo[2,3-b]pyridine-3-carbonyl}-2,4-difluorophenyl)-3-fluoropyrrolidine-1-sulfonamide |
| 289 | 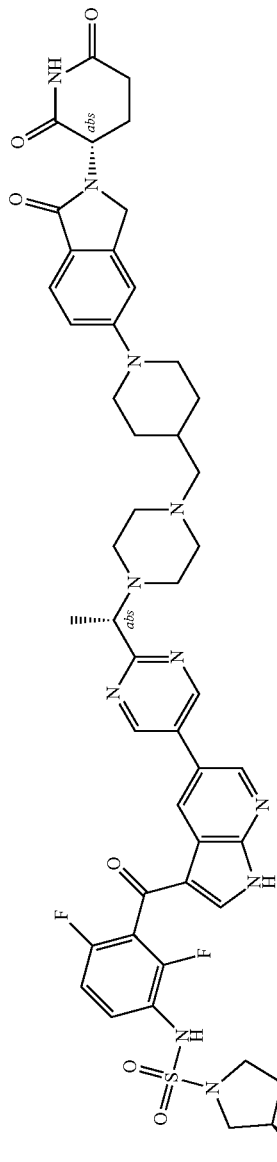 | 1 | (3R)-N-[3-(5-{2-[(1S)-1-{4-[(1-{2-[(3S)-2,6-dioxopiperidin-3-yl]-1-oxo-2,3-dihydro-1H-isoindol-5-yl}piperidin-4-yl]methyl]piperazin-1-yl}ethyl]pyrimidin-5-yl}-1H-pyrrolo[2,3-b]pyridine-3-carbonyl)-2,4-difluorophenyl]-3-fluoropyrrolidine-1-sulfonamide |
| 290 | 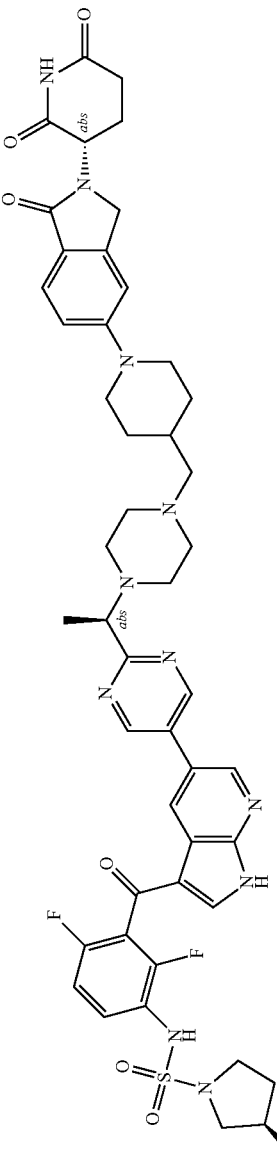 | 1 | (3R)-N-[3-(5-{2-[(1R)-1-{4-[(1-{2-[(3S)-2,6-dioxopiperidin-3-yl]-1-oxo-2,3-dihydro-1H-isoindol-5-yl}piperidin-4-yl]methyl]piperazin-1-yl}ethyl]pyrimidin-5-yl}-1H-pyrrolo[2,3-b]pyridine-3-carbonyl)-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 291 | | 1 | (3R)-N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-4-fluoro-2-propylphenyl}-3-fluoropyrrolidine-1-sulfonamide |
| 292 | | 1 | (3R)-N-3-{5-[2-(1-{4-[(1-{2-[(3R)-2,6-dioxopiperidin-3-yl]-1-oxo-2,3-dihydro-1H-isoindol-5-yl}piperidin-4-yl)methyl]piperazin-1-yl}cyclopropyl)pyrimidin-5-yl]-1H-pyrrolo[2,3-b]pyridine-3-carbonyl}-2,4-difluorophenyl}-3-fluoropyrrolidine-1-sulfonamide |
| 293 | | 2 | (3R)-N-(3-{5-[4-(3-{1-[2-(2,6-dioxopiperidin-3-yl)-1-oxo-2,3-dihydro-1H-isoindol-5-yl]piperidin-4-yl}azetidin-1-yl)phenyl]-1H-pyrrolo[2,3-b]pyridine-3-carbonyl}-2,4-difluorophenyl)-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 294 | | 12 | (3R)-N-[3-(5-{3-[4-({3-[2-(2,6-dioxopiperidin-3-yl)-1-oxo-2,3-dihydro-1H-isoindol-5-yl]propoxy}methyl)piperidin-1-yl]phenyl}-1H-pyrrolo[2,3-b]pyridine-3-carbonyl)-2,4-difluorophenyl]-3-fluoropyrrolidine-1-sulfonamide |
| 295 | | 12 | (3R)-N-{3-[5-(4-{4-[(3S)-3-{2-[(3S)-2,6-dioxopiperidin-3-yl]-7-methoxy-1-oxo-2,3-dihydro-1H-isoindol-5-yl}-3-hydroxypropyl]piperazin-1-yl}phenyl)-1H-pyrrolo[2,3-b]pyridine-3-carbonyl]-2,4-difluorophenyl}-3-fluoropyrrolidine-1-sulfonamide |
| 296 | | 12 | (3R)-N-{3-[5-(4-{4-[(3S)-3-{2-[(3R)-2,6-dioxopiperidin-3-yl]-7-methoxy-1-oxo-2,3-dihydro-1H-isoindol-5-yl}-3-hydroxypropyl]piperazin-1-yl}phenyl)-1H-pyrrolo[2,3-b]pyridine-3-carbonyl]-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 297 | | 12 | (3R)-N-[3-(5-{4-[(3S,4R)-4-({4-[2-(2,6-dioxopiperidin-3-yl)-1-oxo-2,3-dihydro-1H-isoindol-5-yl]piperidin-1-yl}methyl)-3-fluoropiperidin-1-yl]phenyl}-1H-pyrrolo[2,3-b]pyridine-3-carbonyl)-2,4-difluorophenyl]-3-fluoropyrrolidine-1-sulfonamide |
| 298 | | 12 | (3R)-N-{3-[5-(2-{1-[4-({1-[2-(2,6-dioxopiperidin-3-yl)-1-oxo-2,3-dihydro-1H-isoindol-5-yl]piperidin-4-yl}methyl)piperazin-1-yl]cyclopropyl}pyrimidin-5-yl)-1H-pyrrolo[2,3-b]pyridine-3-carbonyl]-2,4-difluorophenyl}-3-fluoropyrrolidine-1-sulfonamide |
| 299 | | 12 | (3R)-N-{3-[5-(4-{6-[(2S)-2-[2-(2,6-dioxopiperidin-3-yl)-1-oxo-2,3-dihydro-1H-isoindol-5-yl]-2-hydroxyethyl]-2,6-diazaspiro[3.3]heptan-2-yl}phenyl)-1H-pyrrolo[2,3-b]pyridine-3-carbonyl]-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 300 | | 12 | (3R)-N-{3-[5-(4-{4-[(3S)-3-{2-[(3S)-2,6-dioxopiperidin-3-yl]-6-fluoro-1-oxo-2,3-dihydro-1H-isoindol-5-yl}-3-hydroxypropyl]piperazin-1-yl}phenyl)-1H-pyrrolo[2,3-b]pyridine-3-carbonyl]-2,4-difluorophenyl}-3-fluoropyrrolidine-1-sulfonamide |
| 301 | | 12 | (3R)-N-{3-[5-(4-{4-[(3S)-3-{2-[(3R)-2,6-dioxopiperidin-3-yl]-6-fluoro-1-oxo-2,3-dihydro-1H-isoindol-5-yl}-3-hydroxypropyl]piperazin-1-yl}phenyl)-1H-pyrrolo[2,3-b]pyridine-3-carbonyl]-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 302 | | 12 | (3R)-N-[3-(5-{4-[3-({1-[2-(2,6-dioxopiperidin-3-yl)-1-oxo-2,3-dihydro-1H-isoindol-5-yl]piperidin-4-yl}methyl)azetidin-1-yl]phenyl}-1H-pyrrolo[2,3-b]pyridine-3-carbonyl)-2,4-difluorophenyl]-3-fluoropyrrolidine-1-sulfonamide |
| 303 | | 12 | (3R)-N-{3-[5-(4-{[1-({1-[2-(2,6-dioxopiperidin-3-yl)-1-oxo-2,3-dihydro-1H-isoindol-5-yl]piperidin-4-yl}methyl)azetidin-3-yl]methyl}piperidin-4-yl]phenyl}-1H-pyrrolo[2,3-b]pyridine-3-carbonyl)-2,4-difluorophenyl]-3-fluoropyrrolidine-1-sulfonamide |
| 304 | | 12 | (3R)-N-{3-[5-(4-{1-[1-({1-[2-(2,6-dioxopiperidin-3-yl)-1-oxo-2,3-dihydro-1H-isoindol-5-yl]piperidin-4-yl]azetidin-3-yl}methyl)piperidin-4-yl]cyclopropyl]phenyl)-1H-pyrrolo[2,3-b]pyridine-3-carbonyl]-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 305 | | 12 | (3R)-N-{3-[5-(4-{[1-({1-[2-(2,6-dioxopiperidin-3-yl)-1-oxo-2,3-dihydro-1H-isoindol-5-yl]piperidin-4-yl}methyl)azetidin-3-yl]methyl}phenyl)-1H-pyrrolo[2,3-b]pyridine-3-carbonyl]-2,4-difluorophenyl]-3-fluoropyrrolidine-1-sulfonamide |
| 306 | | 12 | (3R)-N-[3-(5-{4-[4-({1-[2-(2,6-dioxopiperidin-3-yl)-1-oxo-2,3-dihydro-1H-isoindol-5-yl]azetidin-3-yl}methyl)piperidin-1-yl]phenyl}-1H-pyrrolo[2,3-b]pyridine-3-carbonyl)-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 307 | | 12 | (3R)-N-{3-[5-(2-{[1-({1-[2-(2,6-dioxopiperidin-3-yl)-1-oxo-2,3-dihydro-1H-isoindol-5-yl]piperidin-4-yl}methyl)azetidin-3-yl]methyl}pyrimidin-5-yl)-1H-pyrrolo[2,3-b]pyridine-3-carbonyl]-2,4-difluorophenyl}-3-fluoropyrrolidine-1-sulfonamide |
| 308 | | 12 | (3R)-N-[3-(5-{4-[4-(2-{1-[2-(2,6-dioxopiperidin-3-yl)-1-oxo-2,3-dihydro-1H-isoindol-5-yl]piperidin-4-yl}ethyl)piperidin-1-yl]phenyl}-1H-pyrrolo[2,3-b]pyridine-3-carbonyl)-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 309 | | 12 | (3R)-N-[3-(5-{4-[(3aS,7aS)-5-({1-[2-(2,6-dioxopiperidin-3-yl)-1-oxo-2,3-dihydro-1H-isoindol-5-yl]piperidin-4-yl}methyl)octahydro-1H-pyrrolo[2,3-c]pyridin-2-yl]phenyl}-1H-pyrrolo[2,3-b]pyridine-3-carbonyl)-2,4-difluorophenyl]-3-fluoropyrrolidine-1-sulfonamide |
| 310 | | 12 | (3R)-N-(3-{5-[4-(6-{3-[2-(2,6-dioxopiperidin-3-yl)-1-oxo-2,3-dihydro-1H-isoindol-5-yl]propyl}-2,6-diazaspiro[3.3]heptan-2-yl)-3-fluorophenyl]-1H-pyrrolo[2,3-b]pyridine-3-carbonyl}-2,4-difluorophenyl)-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 311 | | 12 | (3R)-N-[3-(5-{4-[(1R,6R)-3-({1-[2-(2,6-dioxopiperidin-3-yl)-1-oxo-2,3-dihydro-1H-isoindol-5-yl]piperidin-4-yl}methyl)-3,7-diazabicyclo[4.2.0]octan-7-yl]phenyl)-1H-pyrrolo[2,3-b]pyridine-3-carbonyl]-2,4-difluorophenyl]-3-fluoropyrrolidine-1-sulfonamide |
| 312 | | 12 | (3R)-N-[3-(5-{4-[(4R)-4-({4-[2-(2,6-dioxopiperidin-3-yl)-1-oxo-2,3-dihydro-1H-isoindol-5-yl]piperidin-1-yl}methyl)-2-oxopiperidin-1-yl]phenyl}-1H-pyrrolo[2,3-b]pyridine-3-carbonyl)-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 313 | 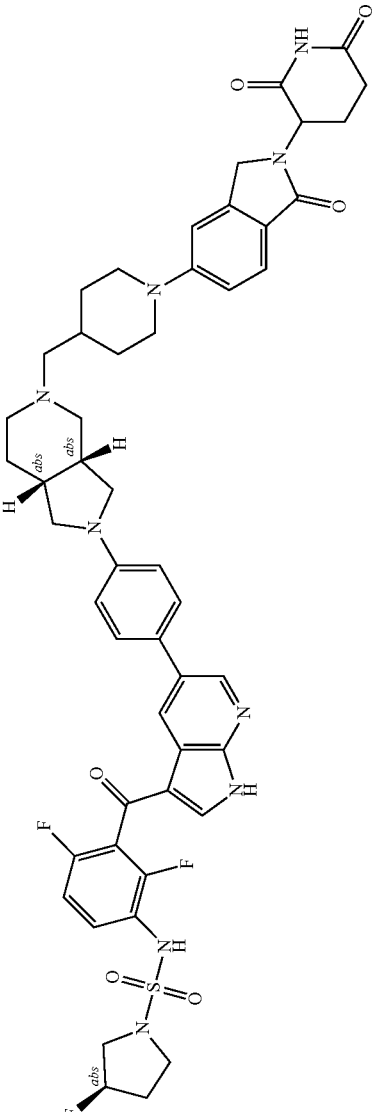 | 12 | (3R)-N-[3-(5-{4-[(3aR,7aR)-5-({1-[2-(2,6-dioxopiperidin-3-yl)-1-oxo-2,3-dihydro-1H-isoindol-5-yl]piperidin-4-yl}methyl)-octahydro-1H-pyrrolo[3,4-c]pyridin-2-yl]phenyl}-1H-pyrrolo[2,3-b]pyridine-3-carbonyl)-2,4-difluorophenyl]-3-fluoropyrrolidine-1-sulfonamide |
| 314 | 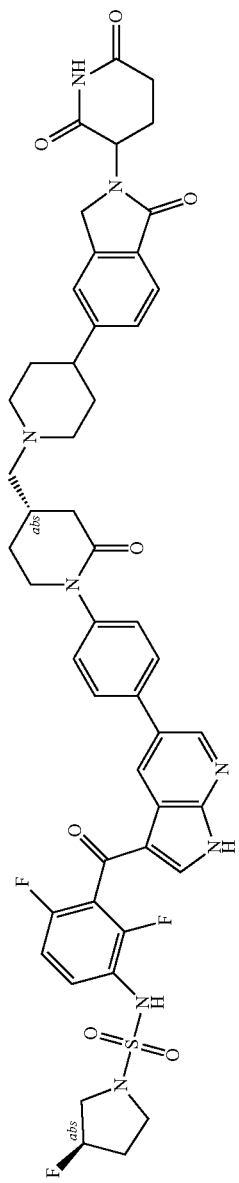 | 12 | (3R)-N-[3-(5-{4-[(4S)-4-({4-[2-(2,6-dioxopiperidin-3-yl)-1-oxo-2,3-dihydro-1H-isoindol-5-yl]piperidin-1-yl}methyl)-2-oxopiperidin-1-yl]phenyl}-1H-pyrrolo[2,3-b]pyridine-3-carbonyl)-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 315 | | 12 | (3R)-N-{3-(5-{4-[4-({1-[2-(2,6-dioxopiperidin-3-yl)-1-oxo-2,3-dihydro-1H-isoindol-5-yl]piperidin-4-yl}methyl)-6,6-difluoro-1,4-diazepan-1-yl]phenyl}-1H-pyrrolo[2,3-b]pyridine-3-carbonyl)-2,4-difluorophenyl][-3-fluoropyrrolidine-1-sulfonamide |
| 316 | | 12 | (3R)-N-{3-[5-(4-{1-[1-({1-[2-(2,6-dioxopiperidin-3-yl)-1-oxo-2,3-dihydro-1H-isoindol-5-yl]piperidin-4-yl}methyl)azetidin-3-yl]cyclopropyl}phenyl)-1H-pyrrolo[2,3-b]pyridine-3-carbonyl]-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 317 | | 12 | (3R)-N-(3-{5-[4-(4-{4-[2-(2,6-dioxopiperidin-3-yl)-1-oxo-2,3-dihydro-1H-isoindol-5-yl]piperazin-1-yl}butyl)phenyl]-1H-pyrrolo[2,3-b]pyridine-3-carbonyl}-2,4-difluorophenyl)-3-fluoropyrrolidine-1-sulfonamide |
| 318 | | 12 | (3R)-N-(3-{5-[4-(5-{4-[2-(2,6-dioxopiperidin-3-yl)-1-oxo-2,3-dihydro-1H-isoindol-5-yl]piperazin-1-yl}penyl)phenyl]-1H-pyrrolo[2,3-b]pyridine-3-carbonyl}-2,4-difluorophenyl)-3-fluoropyrrolidine-1-sulfonamide |

| Ex. No. | Parent Mol Structure | Synthetic Scheme | IUPAC Name |
|---|---|---|---|
| 319 | | 12 | (3R)-N-[3-(5-{4-[6-({4-[2-(2,6-dioxopiperidin-3-yl)-1-oxo-2,3-dihydro-1H-isoindol-5-yl]piperidin-1-yl}methyl)-2-azaspiro[3.3]heptan-2-yl]-3-fluorophenyl}-1H-pyrrolo[2,3-b]pyridine-3-carbonyl)-2,4-difluorophenyl]-3-fluoropyrrolidine-1-sulfonamide |
| 320 | | 12 | (3R)-N-{3-[5-(2-{1-[4-({1-[2-(2,6-dioxopiperidin-3-yl)-1-oxo-2,3-dihydro-1H-isoindol-5-yl]azetidin-3-yl}methyl)piperazin-1-yl]cyclopropyl}pyrimidin-5-yl)-1H-pyrrolo[2,3-b]pyridine-3-carbonyl]-2,4-difluorophenyl}-3-fluoropyrrolidine-1-sulfonamide |
| 321 | | 12 | (3R)-N-(3-{5-[4-(6-{4-[2-(2,6-dioxopiperidin-3-yl)-1-oxo-2,3-dihydro-1H-isoindol-5-yl]-2,6-diazaspiro[3.3]heptan-2-yl}phenyl]-1H-pyrrolo[2,3-b]pyridine-3-carbonyl}-2,4-difluorophenyl)-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 322 | | 12 | (3R)-N-[3-(5-{4-[4-({1-[2-(2,6-dioxopiperidin-3-yl)-1-oxo-2,3-dihydro-1H-isoindol-5-yl]piperidin-4-yl}methyl)-1,4-diazepan-1-yl]phenyl}-1H-pyrrolo[2,3-b]pyridine-3-carbonyl)-2,4-difluorophenyl]-3-fluoropyrrolidine-1-sulfonamide |
| 323 | | 12 | (3R)-N-[3-(5-{4-[4-({4-[2-(2,6-dioxopiperidin-3-yl)-1,3-dioxo-2,3-dihydro-1H-isoindol-5-yl]piperidin-1-yl}methyl)piperidin-1-yl]phenyl}-1H-pyrrolo[2,3-b]pyridine-3-carbonyl)-2,4-difluorophenyl]-3-fluoropyrrolidine-1-sulfonamide |
| 324 | | 12 | (3R)-N-[3-(5-{4-[4-({4-[2-(2,6-dioxopiperidin-3-yl)-1-oxo-2,3-dihydro-1H-isoindol-5-yl]-1,4-diazepan-1-yl}methyl)piperidin-1-yl]phenyl}-1H-pyrrolo[2,3-b]pyridine-3-carbonyl)-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 325 | | 12 | (3R)-N-(3-{5-[4-(4-{4-[2-(2,6-dioxopiperidin-3-yl)-1-oxo-2,3-dihydro-1H-isoindol-5-yl]butyl]piperazin-1-yl}phenyl)-1H-pyrrolo[2,3-b]pyridine-3-carbonyl]-2,4-difluorophenyl}-3-fluoropyrrolidine-1-sulfonamide |
| 326 | | 12 | (3R)-N-{3-[5-(4-{4-[2-(2,6-dioxopiperidin-3-yl)-1-oxo-2,3-dihydro-1H-isoindol-5-yl]-[1,4'-bipiperidin]-1'-yl}phenyl)-1H-pyrrolo[2,3-b]pyridine-3-carbonyl]-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 327 | | 12 | (3R)-N-{3-[5-(4-{6-[(2R)-4-{6-[(2R)-4-{2-[(3)S-2,6-dioxopiperidin-3-yl]-1-oxo-2,3-dihydro-1H-isoindol-5-yl}-2-hydroxybutyl]-2,6-diazaspiro[3.3]heptan-2-yl}phenyl)-1H-pyrrolo[2,3-b]pyridine-3-carbonyl]-2,4-difluorophenyl}-3-fluoropyrrolidine-1-sulfonamide |
| 328 | | 12 | (3R)-N-{3-[5-(4-{6-[(2R)-4-{2-[(3R)-2,6-dioxopiperidin-3-yl]-1-oxo-2,3-dihydro-1H-isoindol-5-yl}-2-hydroxybutyl]-2,6-diazaspiro[3.3]heptan-2-yl}phenyl)-1H-pyrrolo[2,3-b]pyridine-3-carbonyl]-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 329 | | 12 | (3R)-N-[3-(5-{4-[(1S,6S)-3-({1-[2-(2,6-dioxopiperidin-3-yl)-1-oxo-2,3-dihydro-1H-isoindol-5-yl]piperidin-4-yl}methyl)-3,7-diazabicyclo[4.2.0]octan-7-yl]phenyl}-1H-pyrrolo[2,3-b]pyridine-3-carbonyl)-2,4-difluorophenyl]-3-fluoropyrrolidine-1-sulfonamide |
| 330 | | 12 | (3R)-N-[3-(5-{4-[1'-({1-[2-(2,6-dioxopiperidin-3-yl)-1-oxo-2,3-dihydro-1H-isoindol-5-yl]piperidin-4-yl}methyl)-[3,3'-biazetidin]-1-yl]phenyl}-1H-pyrrolo[2,3-b]pyridine-3-carbonyl)-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 331 | | 12 | (3R)-N-[3-(5-{4-[4-(4-{[2-(2,6-dioxopiperidin-3-yl)-7-methoxy-1-oxo-2,3-dihydro-1H-isoindol-5-yl]oxy}butyl)piperazin-1-yl]phenyl}-1H-pyrrolo[2,3-b]pyridine-3-carbonyl)-2,4-difluorophenyl]-3-fluoropyrrolidine-1-sulfonamide |
| 332 | | 12 | (3R)-N-(3-{5-[4-(1-{4-[2-(2,6-dioxopiperidin-3-yl)-1-oxo-2,3-dihydro-1H-isoindol-5-yl]butyl}piperidin-4-yl)phenyl]-1H-pyrrolo[2,3-b]pyridine-3-carbonyl}-2,4-difluorophenyl)-3-fluoropyrrolidine-1-sulfonamide |
| 333 | | 12 | (3R)-N-[3-(5-{4-[4-({4-[2-(2,6-dioxopiperidin-3-yl)-1-oxo-2,3-dihydro-1H-isoindol-5-yl]-6,6-difluoro-1,4-diazepan-1-yl}methyl)piperidin-1-yl]phenyl}-1H-pyrrolo[2,3-b]pyridine-3-carbonyl)-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 334 | | 12 | (3R)-N-{3-[5-(2-{1-[2-({1-[2-(2,6-dioxopiperidin-3-yl)-1-oxo-2,3-dihydro-1H-isoindol-5-yl]azetidin-3-yl}methyl)piperidin-4-yl]cyclopropyl}pyrimidin-5-yl)-1H-pyrrolo[2,3-b]pyridine-3-carbonyl]-2,4-difluorophenyl}-3-fluoropyrrolidine-1-sulfonamide |
| 335 | | 12 | (3R)-N-{3-[5-(4-{[(3R)-1-{2-[(3S)-2,6-dioxopiperidin-3-yl]-1-oxo-2,3-dihydro-1H-isoindol-5-yl]pyrrolidin-3-yl]methoxy}phenyl)-1H-pyrrolo[2,3-b]pyridine-3-carbonyl]-2,4-difluorophenyl}-3-fluoropyrrolidine-1-sulfonamide |
| 336 | | 12 | (3R)-N-{3-[5-(4-{[(3R)-1-{2-[(3R)-2,6-dioxopiperidin-3-yl]-1-oxo-2,3-dihydro-1H-isoindol-5-yl]pyrrolidin-3-yl]methoxy}phenyl)-1H-pyrrolo[2,3-b]pyridine-3-carbonyl]-2,4-difluorophenyl}-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 337 | | 1 | (3R)-N-[3-(5-{4-[4-({4-[1-(2,6-dioxopiperidin-3-yl)-3-methyl-2-oxo-2,3-dihydro-1H-1,3-benzodiazol-4-yl]piperidin-1-yl}methyl)piperidin-1-yl]phenyl}-1H-pyrrolo[2,3-b]pyridine-3-carbonyl)-2,4-difluorophenyl]-3-fluoropyrrolidine-1-sulfonamide |
| 338 | | 10 | N-[3-(5-{[1-(2-{[2-(2,6-dioxopiperidin-3-yl)-1,3-dioxo-2,3-dihydro-1H-isoindol-4-yl]amino}-3,6,9,12-tetraoxapentadecanoyl)piperidin-4-yl](methyl)amino]-3-(pyrimidin-5-yl)-1H-pyrrolo[3,2-b]pyridin-1-yl)-2,4-difluorophenyl]propane-1-sulfonamide |
| 339 | | 3 | 4-(4-{[4-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperazin-1-yl]methyl}piperidin-1-yl)-N-[(3S)-2,6-dioxopiperidin-3-yl]-2-fluorobenzamide |

TABLE 1-continued

Exemplary bifunctional compounds of the present disclosure

| Ex. No. | Parent Mol Structure | Synthetic Scheme | IUPAC Name |
|---|---|---|---|
| 340 | | 3 | 4-(4-{[4-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperazin-1-yl]methyl}piperidin-1-yl)-N-[(3R)-2,6-dioxopiperidin-3-yl]-2-fluorobenzamide |
| 341 | | 3 | 4-(4-{[1-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperazin-1-yl]methyl}piperidin-1-yl)-N-[(3S)-2,6-dioxopiperidin-3-yl]-2-fluorobenzamide |
| 342 | | 3 | 4-(4-{[1-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperidin-4-yl]methyl}piperazin-1-yl)-N-[(3R)-2,6-dioxopiperidin-3-yl]-2-fluorobenzamide |

TABLE 1-continued

Exemplary bifunctional compounds of the present disclosure

| Ex. No. | Parent Mol Structure | Synthetic Scheme | IUPAC Name |
|---|---|---|---|
| 343 | | 3 | 4-(6-{[1-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperidin-4-yl]methyl}-2,6-diazaspiro[3.3]heptan-2-yl)-N-[(3S)-2,6-dioxopiperidin-3-yl]-2-methoxybenzamide |
| 344 | | 3 | 4-(6-{[1-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperidin-4-yl]methyl}-2,6-diazaspiro[3.3]heptan-2-yl)-N-[(3R)-2,6-dioxopiperidin-3-yl]-2-methoxybenzamide |
| 345 | | 3 | 5-(6-{[1-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperidin-4-yl]methyl}-2,6-diazaspiro[3.3]heptan-2-yl)-N-[(3S)-2,6-dioxopiperidin-3-yl]pyridine-2-carboxamide |

TABLE 1-continued

Exemplary bifunctional compounds of the present disclosure

| Ex. No. | Parent Mol Structure | Synthetic Scheme | IUPAC Name |
|---|---|---|---|
| 346 | | 3 | 5-(6-{[1-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperidin-4-yl]methyl}-2,6-diazaspiro[3.3]heptan-2-yl)-N-[(3R)-2,6-dioxopiperidin-3-yl]pyridine-2-carboxamide |
| 347 | | 3 | 4-(6-{[1-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperidin-4-yl]methyl}-2,6-diazaspiro[3.3]heptan-2-yl)-N-[(3S)-2,6-dioxopiperidin-3-yl]-2-fluoro-6-methoxybenzamide |
| 348 | | 3 | 4-(6-{[1-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperidin-4-yl]methyl}-2,6-diazaspiro[3.3]heptan-2-yl)-N-(2,6-dioxopiperidin-3-yl)-2-fluoro-6-methoxybenzamide |

TABLE 1-continued

Exemplary bifunctional compounds of the present disclosure

| Ex. No. | Parent Mol Structure | Synthetic Scheme | IUPAC Name |
|---|---|---|---|
| 349 | | 3 | 4-{4-(4-{3-[2,6-difluoro-3-{[(3R)-fluoropyrrolidin-1-yl]sulfonyl}amino)benzoyl]-1H-pyrrolo[2,3-b]pyridin-5-yl}phenyl)piperazin-1-yl]butoxy}-N-[(3S)-2,6-dioxopiperidin-3-yl]-2-fluorobenzamide |
| 350 | | 3 | 4-{4-(4-{3-[2,6-difluoro-3-{[(3R)-3-fluoropyrrolidin-1-yl]sulfonyl}amino)benzoyl]-1H-pyrrolo[2,3-b]pyridin-5-yl}phenyl)piperazin-1-yl]butoxy}-N-(2,6-dioxopiperidin-3-yl)-2-fluorobenzamide |
| 351 | | 3 | 4-{6-[(1-{4-[3-(3-{[(3,3-difluoropyrrolidin-1-yl)sulfonyl]amino}-2,6-difluorobenzoyl)-1H-pyrrolo[2,3-b]pyridin-5-yl]phenyl}piperidin-4-yl)methyl]-2,6-diazaspiro[3.3]heptan-2-yl}-N-[(3S)-2,6-dioxopiperidin-3-yl]-2-fluorobenzamide |

TABLE 1-continued

Exemplary bifunctional compounds of the present disclosure

| Ex. No. | Parent Mol Structure | Synthetic Scheme | IUPAC Name |
|---|---|---|---|
| 352 | | 3 | 4-(4-{[6-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)-2,6-diazaspiro[3.3]heptan-2-yl]methyl}piperidin-1-yl)-N-[(3S)-2,6-dioxopiperidin-3-yl]-2-methoxybenzamide |
| 353 | | 3 | 5-(4-{[6-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)-2,6-diazaspiro[3.3]heptan-2-yl]methyl}piperidin-1-yl)-N-[(3S)-2,6-dioxopiperidin-3-yl]pyridine-2-carboxamide |
| 354 | | 3 | 5-(4-{[6-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)-2,6-diazaspiro[3.3]heptan-2-yl]methyl}piperidin-1-yl)-N-(2,6-dioxopiperidin-3-yl)pyridine-2-carboxamide |

TABLE 1-continued

Exemplary bifunctional compounds of the present disclosure

| Ex. No. | Parent Mol Structure | Synthetic Scheme | IUPAC Name |
|---|---|---|---|
| 355 | | 3 | 4-{3-[6-(4-{3-[2,6-difluoro-1-yl]sulfonyl}aminobenzoyl]-1H-pyrrolo[2,3-b]pyridin-5-yl}phenyl)-2,6-diazaspiro[3.3]heptan-2-yl]propyl}-N-[(3S)-2,6-dioxopiperidin-3-yl]-2-fluorobenzamide |
| 356 | | 3 | 4-{3-[6-(4-{3-[2,6-difluoro-1-yl]sulfonyl}aminobenzoyl]-1H-pyrrolo[2,3-b]pyridin-5-yl}phenyl)-2,6-diazaspiro[3.3]heptan-2-yl]propyl}-N-(2,6-dioxopiperidin-3-yl)-2-fluorobenzamide |
| 357 | | 3 | 4-(4-{[4-(4-{3-[2,6-difluoro-1-yl]sulfonyl}aminobenzoyl]-1H-pyrrolo[2,3-b]pyridin-5-yl}phenyl)piperazin-1-yl]phenyl}piperidin-1-yl]methyl}piperidin-1-yl)-N-[(3S)-2,6-dioxopiperidin-3-yl]-2-methoxybenzamide |

TABLE 1-continued

Exemplary bifunctional compounds of the present disclosure

| Ex. No. | Parent Mol Structure | Synthetic Scheme | IUPAC Name |
|---|---|---|---|
| 358 | | 3 | 4-(4-{[4-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperazin-1-yl]methyl}piperidin-1-yl)-N-(2,6-dioxopiperidin-3-yl)-2-methoxybenzamide |
| 359 | | 3 | 4-(4-{[1-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperidin-4-yl]methyl}piperazin-1-yl)-N-[(3S)-2,6-dioxopiperidin-3-yl]-2-methoxybenzamide |
| 360 | | 3 | 4-(4-{[1-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperidin-4-yl]methyl}piperazin-1-yl)-N-(2,6-dioxopiperidin-3-yl)-2-methoxybenzamide |

TABLE 1-continued

Exemplary bifunctional compounds of the present disclosure

| Ex. No. | Parent Mol Structure | Synthetic Scheme | IUPAC Name |
|---|---|---|---|
| 361 | | 3 | 4-{6-[2-(4-{3-[2,6-difluoro-3-{[(3R)-3-fluoropyrrolidin-1-yl]sulfonyl}amino)benzoyl]-1H-pyrrolo[2,3-b]pyridin-5-yl}phenyl)ethyl]-2,6-diazaspiro[3.3]heptan-2-yl}-N-[(3S)-2,6-dioxopiperidin-3-yl]-2-methoxybenzamide |
| 362 | | 3 | 4-{6-[2-(4-{3-[2,6-difluoro-3-{[(3R)-3-fluoropyrrolidin-1-yl]sulfonyl}amino)benzoyl]-1H-pyrrolo[2,3-b]pyridin-5-yl}phenyl)ethyl]-2,6-diazaspiro[3.3]heptan-2-yl}-N-(2,6-dioxopiperidin-3-yl)-2-methoxybenzamide |

TABLE 1-continued

Exemplary bifunctional compounds of the present disclosure

| Ex. No. | Parent Mol Structure | Synthetic Scheme | IUPAC Name |
|---|---|---|---|
| 363 | | 3 | 4-{6-[(1-{4-[3-(3-amino-2,6-difluorobenzoyl)-1H-pyrrolo[2,3-b]pyridin-5-yl]phenyl}piperidin-4-yl)methyl]-2,6-diazaspiro[3.3]heptan-2-yl}-N-[(3S)-2,6-dioxopiperidin-3-yl]-2-fluorobenzamide |
| 364 | | 5 | 5-(1-{[1-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperidin-4-yl]methyl}piperidin-4-yl)-N-(2,6-dioxopiperidin-3-yl)-1,2,3,4-tetrahydro-1,8-naphthyridine-1-carboxamide |
| 365 | | 5 | (3R)-N-[3-(5-{4-[4-({4-[6-(2,6-dioxopiperidin-3-yl)pyridin-3-yl]piperidin-1-yl}methyl)piperidin-1-yl]phenyl}-1H-pyrrolo[2,3-b]pyridine-3-carbonyl)-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 366 | | 5 | 5-(1-{[1-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperidin-4-yl]methyl}piperidin-4-yl)-N-[(3S)-2,6-dioxopiperidin-3-yl]-1,2,3,4-tetrahydro-1,8-naphthyridine-1-carboxamide |
| 367 | | 5 | 5-(1-{[1-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperidin-4-yl]methyl}piperidin-4-yl)-N-[(3R)-2,6-dioxopiperidin-3-yl]-1,2,3,4-tetrahydro-1,8-naphthyridine-1-carboxamide |
| 368 | | 5 | (3R)-N-[3-(5-{4-[4-({6-[4-(2,6-dioxopiperidin-3-yl)phenyl]-2,6-diazaspiro[3.3]heptan-2-yl}methyl)piperidin-1-yl]phenyl}-1H-pyrrolo[2,3-b]pyridine-3-carbonyl)-2,4-difluorophenyl]-3-fluoropyrrolidine-1-sulfonamide |

TABLE 1-continued

Exemplary bifunctional compounds of the present disclosure

| Ex. No. | Parent Mol Structure | Synthetic Scheme | IUPAC Name |
|---|---|---|---|
| 369 | | 5 | 5-(4-{[1-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperidin-4-yl]methyl}piperazin-1-yl)-N-[(3S)-2,6-dioxopiperidin-3-yl]-1,2,3,4-tetrahydro-1,8-naphthyridine-1-carboxamide |
| 370 | | 5 | 5-(4-{[1-(4-{3-[2,6-difluoro-3-({[(3R)-3-fluoropyrrolidin-1-yl]sulfonyl}amino)benzoyl]-1H-pyrrolo[2,3-b]pyridin-4-yl}phenyl)piperidin-4-yl]methyl}piperazin-1-yl)-N-(2,6-dioxopiperidin-3-yl)-1,2,3,4-tetrahydro-1,8-naphthyridine-1-carboxamide |
| 371 | | 5 | 5-(4-{[4-(4-{3-[2,6-difluoro-3-({[(3R)-3-fluoropyrrolidin-1-yl]sulfonyl}amino)benzoyl]-1H-pyrrolo[2,3-b]pyridin-1-yl}phenyl)piperazin-1-yl]methyl}piperidin-1-yl)-N-[(3S)-2,6-dioxopiperidin-3-yl]-1,2,3,4-tetrahydro-1,8-naphthyridine-1-carboxamide |
| 372 | | 5 | 5-(4-{[4-(4-{3-[2,6-difluoro-3-({[(3R)-3-fluoropyrrolidin-1-yl]sulfonyl}amino)benzoyl]-1H-pyrrolo[2,3-b]pyridin-1-yl}phenyl)piperazin-1-yl]methyl}piperidin-1-yl)-N-[(3R)-2,6-dioxopiperidin-3-yl]-1,2,3,4-tetrahydro-1,8-naphthyridine-1-carboxamide |

TABLE 1-continued

Exemplary bifunctional compounds of the present disclosure

| Ex. No. | Parent Mol Structure | Synthetic Scheme | IUPAC Name |
|---|---|---|---|
| 373 | 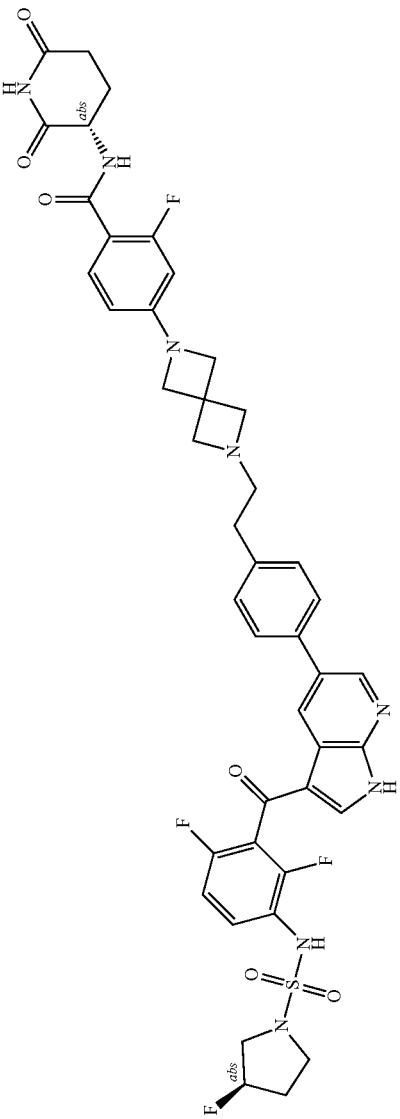 | 9 | 4-{6-[2-(4-{3-[2,6-difluoro-3-{[(3R)-3-fluoropyrrolidin-1-yl]sulfonyl}amino]benzoyl]-1H-pyrrolo[2,3-b]pyridin-5-yl}phenyl)ethyl]-2,6-diazaspiro[3.3]heptan-2-yl}-N-[(3S)-2,6-dioxopiperidin-3-yl]-2-fluorobenzamide |
| 374 | 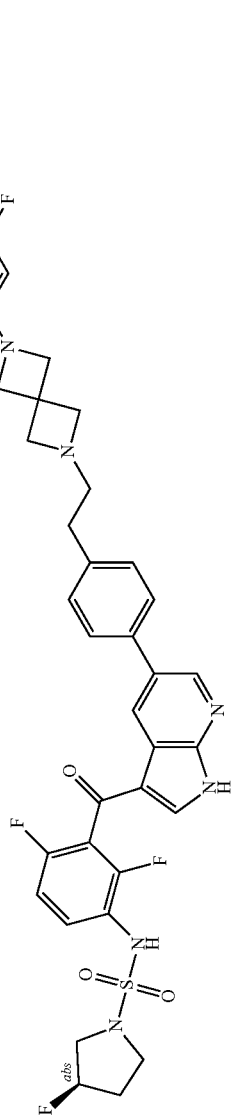 | 9 | 4-{6-[2-(4-{3-[2,6-difluoro-3-{[(3R)-3-fluoropyrrolidin-1-yl]sulfonyl}amino]benzoyl]-1H-pyrrolo[2,3-b]pyridin-5-yl}phenyl)ethyl]-2,6-diazaspiro[3.3]heptan-2-yl}-N-(2,6-dioxopiperidin-3-yl)-2-fluorobenzamide |

TABLE 1-continued

Exemplary bifunctional compounds of the present disclosure

| Ex. No. | Parent Mol Structure | Synthetic Scheme | IUPAC Name |
|---|---|---|---|
| 375 | 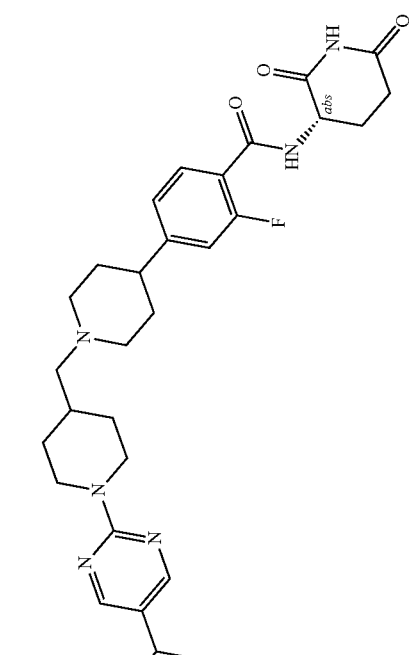 | Method for Cmp. 373 | 4-(1-{[1-(5-{3-[2,6-difluoro-3-({[(3R)-3-fluoropyrrolidin-1-yl]sulfonyl}amino)benzoyl]-1H-pyrrolo[2,3-b]pyridin-5-yl}pyrimidin-2-yl)piperidin-4-yl]methyl}piperidin-4-yl)-N-[(3S)-2,6-dioxopiperidin-3-yl]-2-fluorobenzamide |
| 376 | 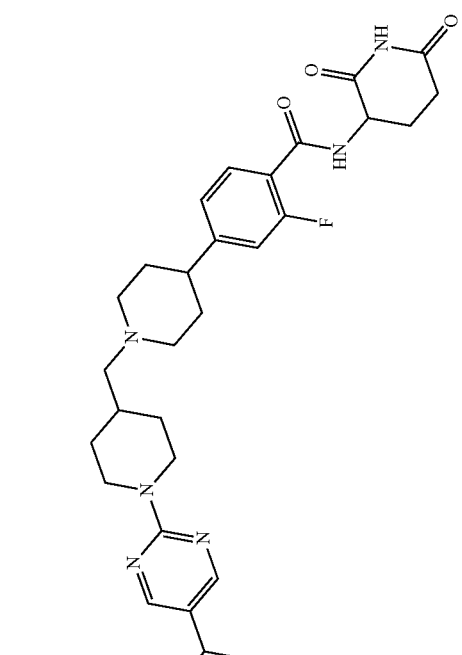 | Method for Cmp. 373 | 4-(1-{[1-(5-{3-[2,6-difluoro-3-({[(3R)-3-fluoropyrrolidin-1-yl]sulfonyl}amino)benzoyl]-1H-pyrrolo[2,3-b]pyridin-5-yl}pyrimidin-2-yl)piperidin-4-yl]methyl}piperidin-4-yl)-N-(2,6-dioxopiperidin-3-yl)-2-fluorobenzamide |

TABLE 1-continued

Exemplary bifunctional compounds of the present disclosure

| Ex. No. | Parent Mol Structure | Synthetic Scheme | IUPAC Name |
|---|---|---|---|
| 377 | | Method for Cmp. 373 | 4-(4-{2-[4-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperazin-1-yl]ethyl}piperazin-1-yl)-N-[(3S)-2,6-dioxopiperidin-3-yl]-2-fluorobenzamide |
| 378 | | Method for Cmp. 373 | 4-(4-{4-[4-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperazin-1-yl]ethyl}piperazin-1-yl)-N-(2,6-dioxopiperidin-3-yl)-2-fluorobenzamide |
| 379 | | Method for Cmp. 373 | 5-{6-[2-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)ethyl]-2,6-diazaspiro[3.3]heptan-2-yl}-N-[(3S)-2,6-dioxopiperidin-3-yl]-1,2,3,4-tetrahydro-1,8-naphthyridine-1-carboxamide |

TABLE 1-continued
Exemplary bifunctional compounds of the present disclosure
| Ex. No. | Parent Mol Structure | Synthetic Scheme | IUPAC Name |
|---|---|---|---|
| 380 | 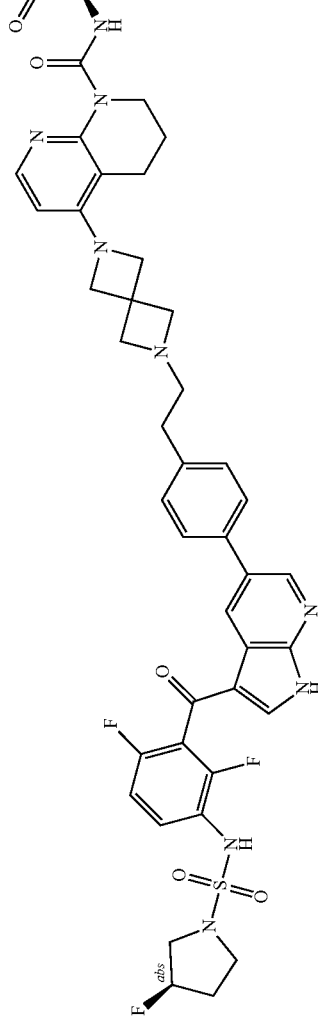 | Method for Cmp. 373 | 5-{6-[2-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)ethyl]-2,6-diazaspiro[3.3]heptan-2-yl}-N-[(3R)-2,6-dioxopiperidin-3-yl]-1,2,3,4-tetrahydro-1,8-naphthyridine-1-carboxamide |

In any aspect or embodiment described herein, the disclosure provides a compound selected from the group consisting of compounds 1-212 or compound 3, 4, 6, 7, 9, 10, 11, 12, 16, 18, 19, 20, 21, 22, 24, 25, 26, 28, 31, 32, 34, 35, 36, 37, 38, 39, 40, 41, 42, 44, 45, 46, 48, 49, 50, 51, 52, 53, 54, 55, 56, 57, 58, 59, 60, 61, 62, 63, 64, 65, 66, 67, 68, 69, 70, 71, 72, 73, 74, 75, 80, 81, 83, 84, 85, 86, 87, 88, 89, 90, 91, 92, 93, 94, 95, 97, 98, 99, 100, 101, 103, 104, 105, 106, 107, 108, 109, 110, 111, 113, 114, 115, 116, 117, 118, 119, 120, 121, 122, 123, 124, 125, 126, 127, 128, 129, 130, 131, 132, 133, 134, 135, 137, 138, 139, 140, 141, 142, 144, 145, 146, 147, 148, 149, 150, 151, 152, 153, 154, 155, 156, 157, 158, 160, 161, 163, 164, 165, 166, 167, 168, 170, 171, 172, 173, 174, 175, 176, 177, 178, 179, 180, 182, 184, 185, 186, 187, 188, 189, 190, 191, 192, 193, 194, 195, 196, 198, 199, 201, 202, 203, 204, 205, 206, and 207 of Table 1. In any aspect or embodiment described herein, the disclosure provides a compound selected from the group consisting of compounds 6, 12, 13, 18, 24, 26, 27, 28, 33, 41, 57, 58, 62, 75, 78, 80, 83, 85, 87, 88, 89, 90, 92, 93, 102, 104, 111, 118, 119, 127, 138, 144, 153, 160, 177, 190, 201, 202, 203, and 204 of Table 1. In any aspect or embodiment described herein, the disclosure provides a pharmaceutical dosage form comprising an effective amount of a compound selected from the group consisting of compounds 1-212 of Table I or salt thereof, and a pharmaceutically acceptable carrier. In any aspect or embodiment described herein, the disclosure provides a pharmaceutical dosage form comprising an effective amount of a compound selected from the group consisting of compounds 6, 12, 13, 18, 24, 26, 27, 28, 33, 41, 57, 58, 62, 75, 78, 80, 83, 85, 87, 88, 89, 90, 92, 93, 102, 104, 111, 118, 119, 127, 138, 144, 153, 160, 177, 190, 201, 202, 203, and 204 of Table 1 or salt thereof, and a pharmaceutically acceptable carrier.

In any aspect or embodiment described herein, the disclosure provides a pharmaceutical dosage form as described above, further comprising at least one of additional bioactive agent or a second bifunctional compound selected from the group consisting of compounds 1-381 of Table I. In any aspect or embodiment described herein, the additional bioactive agent is an anti-cancer agent.

In any aspect or embodiment described herein, the disclosure provides a compound selected from the group consisting of compounds 213-381 of Table I. In any aspect or embodiment described herein, the disclosure provides a compound selected from the group consisting of 213, 219-221, 223-225, 227, 228-245, 247-264, 268-271, 276, 278, 280, 281, 283-287, 295-301, 303, 305, 307, 310-312, 319, 320, 325, 326, 328, 329,331, 334, 339, 340, 342, 343, 345-347, 351, 352, 354, 357-359, 361, 362, 364-370, and 373-380 of Table I.

In any aspect or embodiment described herein, the disclosure provides a pharmaceutical dosage form comprising an effective amount of a compound selected from the group consisting of compounds 213-381 of Table I or salt thereof, and a pharmaceutically acceptable carrier. In any aspect or embodiment described herein, the disclosure provides a pharmaceutical dosage form comprising an effective amount of a compound selected from the group consisting of compounds 213, 219-221, 223-225, 227, 228-245, 247-264, 268-271, 276, 278, 280, 281, 283-287, 295-301, 303, 305, 307, 310-312, 319, 320, 325, 326, 328, 329,331, 334, 339, 340, 342, 343, 345-347, 351, 352, 354, 357-359, 361, 362, 364-370, and 373-380 of Table I or salt thereof, and a pharmaceutically acceptable carrier.

TABLE 2

Degradation and characterization of exemplary bifunctional compounds of the present disclosure

| Ex. No. | BRaf V600E $DC_{50}$ (nM) | BRaf V600E $D_{Max}$ (%) | BRaf G466V $DC_{50}$ (nM) | BRaf G466V $D_{Max}$ (%) | MH+ (1) | Mol Weight |
|---|---|---|---|---|---|---|
| 1 | B | B | B | B | 854.24 | 853.86 |
| 2 | B | B | C | B | 978.37 | 978.09 |
| 3 | B | B | B | A | 964.36 | 964.06 |
| 4 | C | C | B | B | 891.27 | 890.93 |
| 5 | D | ND | B | B | 894.28 | 893.93 |
| 6 | A | B | B | B | 1022.40 | 1022.14 |
| 7 | B | B | B | A | 895.30 | 894.96 |
| 8 | B | B | C | B | 907.30 | 906.97 |
| 9 | C | B | B | B | 922.30 | 921.99 |
| 10 | B | B | A | B | 909.31 | 908.99 |
| 11 | B | B | A | B | 942.31 | 941.99 |
| 12 | B | A | B | B | 980.30 | 980.06 |
| 13 | D | A | C | B | 981.20 | 981.05 |
| 14 | D | B | | C | 981.20 | 981.05 |
| 15 | D | ND | D | ND | 828.10 | 827.83 |
| 16 | C | B | B | B | 936.20 | 936.01 |
| 17 | D | ND | D | ND | 828.10 | 827.83 |
| 18 | C | A | A | B | 926.20 | 925.98 |
| 19 | B | B | B | B | 954.20 | 954.00 |
| 20 | B | B | A | B | 980.20 | 980.06 |
| 21 | B | B | B | B | 897.20 | 896.93 |
| 22 | B | B | A | B | 911.20 | 910.96 |
| 23 | D | ND | D | ND | 828.10 | 827.83 |
| 24 | A | B | A | B | 924.20 | 924.00 |
| 25 | B | B | A | A | 925.10 | 924.99 |
| 26 | D | A | A | B | 839.20 | 838.85 |
| 27 | B | A | B | B | 861.10 | 860.88 |
| 28 | C | A | A | B | 861.10 | 860.88 |
| 29 | B | B | B | B | 942.20 | 941.99 |
| 30 | D | ND | C | C | 942.20 | 941.99 |
| 31 | B | B | A | B | 942.20 | 941.99 |
| 32 | A | B | B | B | 871.20 | 870.90 |
| 33 | B | A | B | B | 929.20 | 928.99 |
| 34 | C | B | B | B | 925.10 | 924.99 |
| 35 | B | B | B | A | 925.20 | 924.99 |
| 36 | B | B | A | B | 941.20 | 941.00 |
| 37 | B | C | B | B | 942.10 | 941.99 |
| 38 | B | B | A | B | 879.20 | 878.92 |
| 39 | B | B | A | B | 879.20 | 878.92 |
| 40 | B | B | B | B | 942.20 | 941.99 |
| 41 | D | A | B | B | 942.10 | 941.99 |
| 42 | B | B | B | B | 877.20 | 876.90 |
| 43 | C | B | C | B | 854.20 | 853.86 |
| 44 | B | B | A | B | 945.10 | 944.97 |
| 45 | B | B | A | B | 945.10 | 944.97 |
| 46 | B | B | A | A | 925.20 | 924.99 |
| 47 | D | ND | C | B | 907.10 | 906.97 |
| 48 | C | C | B | C | 929.30 | 928.99 |
| 49 | B | B | A | B | 868.20 | 867.93 |
| 50 | B | B | A | A | 883.60 | 882.91 |
| 51 | C | B | B | B | 964.70 | 964.06 |
| 52 | C | C | B | B | 964.20 | 964.06 |
| 53 | B | B | A | A | 924.20 | 924.00 |
| 54 | B | B | A | B | 965.30 | 965.05 |
| 55 | B | B | A | A | 954.20 | 954.00 |
| 56 | B | B | A | A | 954.20 | 954.00 |
| 57 | A | B | A | A | 950.20 | 950.04 |
| 58 | A | C | A | B | 950.20 | 950.04 |
| 59 | B | B | B | A | 966.20 | 966.04 |
| 60 | B | B | B | A | 964.20 | 964.06 |
| 61 | B | B | B | B | 897.20 | 896.93 |
| 62 | A | B | A | B | 895.20 | 894.96 |
| 63 | D | ND | B | A | 895.20 | 894.96 |
| 64 | B | B | A | B | 897.20 | 896.98 |
| 65 | B | B | A | B | 896.20 | 895.99 |
| 66 | D | ND | C | A | 936.20 | 936.01 |
| 67 | B | B | B | A | 884.10 | 883.93 |
| 68 | D | ND | B | A | 884.20 | 883.93 |
| 69 | B | B | B | A | 870.10 | 869.91 |
| 70 | B | B | A | B | 926.20 | 925.97 |
| 71 | B | B | B | A | 884.20 | 883.93 |
| 72 | B | C | B | B | 884.20 | 883.93 |

TABLE 2-continued

Degradation and characterization of exemplary bifunctional compounds of the present disclosure

| Ex. No. | BRaf V600E DC$_{50}$ (nM) | BRaf V600E D$_{Max}$ (%) | BRaf G466V DC$_{50}$ (nM) | BRaf G466V D$_{Max}$ (%) | MH+ (1) | Mol Weight |
|---|---|---|---|---|---|---|
| 73 | B | B | B | A | 885.20 | 884.92 |
| 74 | B | B | B | A | 885.20 | 884.92 |
| 75 | A | B | B | A | 885.20 | 884.92 |
| 76 | B | B | D | ND | 867.10 | 866.91 |
| 77 | B | B | D | ND | 867.20 | 866.91 |
| 78 | D | A | D | ND | 871.10 | 870.90 |
| 79 | B | B | D | ND | 912.20 | 911.95 |
| 80 | A | B | B | A | 897.20 | 896.93 |
| 81 | B | B | B | A | 897.20 | 896.93 |
| 82 | B | B | D | ND | 885.20 | 884.92 |
| 83 | C | A | A | B | 895.20 | 894.96 |
| 84 | B | B | A | A | 895.10 | 894.96 |
| 85 | A | B | B | A | 922.20 | 921.99 |
| 86 | B | B | B | A | 922.20 | 921.99 |
| 87 | A | B | A | A | 941.10 | 941.00 |
| 88 | A | B | A | A | 941.10 | 941.00 |
| 89 | A | B | A | B | 883.60 | 882.91 |
| 90 | B | B | B | B | 885.20 | 884.92 |
| 91 | B | B | B | A | 898.10 | 897.92 |
| 92 | A | B | B | A | 951.20 | 951.03 |
| 93 | A | B | B | A | 952.20 | 952.01 |
| 94 | B | B | B | A | 959.10 | 958.99 |
| 95 | D | ND | A | B | 979.20 | 979.08 |
| 96 | A | C | ND | ND | 980.20 | 980.07 |
| 97 | B | B | B | A | 952.20 | 952.05 |
| 98 | B | B | B | A | 885.20 | 884.92 |
| 99 | B | B | B | A | 907.20 | 906.97 |
| 100 | B | B | B | A | 907.20 | 906.97 |
| 101 | B | B | B | A |  | 896.94 |
| 102 | D | A | B | B | 871.20 | 870.90 |
| 103 | B | B | B | A | 936.20 | 936.01 |
| 104 | A | C | B | A | 996.20 | 996.08 |
| 105 | B | B | B | B |  | 896.93 |
| 106 | B | B | B | A |  | 896.93 |
| 107 | B | B | B | B |  | 883.93 |
| 108 | B | B | B | A |  | 883.93 |
| 109 | B | B | B | A |  | 883.93 |
| 110 | C | B | B | A |  | 883.93 |
| 111 | A | B | B | B |  | 968.03 |
| 112 | C | C | C | B | 871.20 | 870.90 |
| 113 | B | B | B | A | 917.20 | 916.94 |
| 114 | B | B | B | A | 901.20 | 900.90 |
| 115 | B | C | B | B | 989.20 | 989.03 |
| 116 | B | B | A | B | 884.10 | 883.93 |
| 117 | C | B | B | A | 885.20 | 884.88 |
| 118 | D | A | B | A | 884.20 | 883.93 |
| 119 | A | B | A | B | 939.20 | 939.01 |
| 120 | B | B | B | A | 900.20 | 899.94 |
| 121 | B | B | B | A | 901.10 | 900.92 |
| 122 | B | B | B | A | 913.20 | 912.93 |
| 123 | B | B | B | A | 913.20 | 912.93 |
| 124 | B | B | B | A | 913.20 | 912.93 |
| 125 | B | B | B | A | 941.40 | 941.00 |
| 126 | B | B | B | B | 954.50 | 954.03 |
| 127 | A | C | B | A | 937.50 | 937.04 |
| 128 | B | B | B | A | 897.20 | 896.93 |
| 129 | B | B | B | A | 897.20 | 896.93 |
| 130 | B | B | B | B | 897.20 | 896.93 |
| 131 | B | B | B | B | 914.20 | 913.94 |
| 132 | B | B | A | A | 984.20 | 984.03 |
| 133 | B | B | A | A | 967.20 | 967.03 |
| 134 | B | B | A | A | 968.20 | 968.01 |
| 135 | B | B | B | A | 952.20 | 952.05 |
| 136 | C | C | D | ND | 819.10 | 818.84 |
| 137 | B | B | B | A | 952.20 | 952.05 |
| 138 | B | A | A | A | 883.20 | 882.91 |
| 139 | C | B | B | A | 900.10 | 899.93 |
| 140 | B | B | B | B | 887.30 | 886.96 |
| 141 | B | B | B | A | 882.20 | 881.92 |
| 142 | B | B | B | A | 952.20 | 952.01 |
| 143 | B | C | C | B | 953.20 | 953.04 |
| 144 | A | B | B | A | 979.20 | 979.08 |
| 145 | B | B | B | A | 982.20 | 982.08 |
| 146 | B | B | B | A | 938.20 | 938.03 |
| 147 | C | B | B | B | 883.20 | 882.91 |
| 148 | B | B | B | A | 899.10 | 898.95 |
| 149 | C | B | B | A | 884.20 | 883.93 |
| 150 | C | B | B | A | 884.10 | 883.93 |
| 151 | C | B | B | A | 898.10 | 897.96 |
| 152 | B | B | B | A | 873.20 | 872.89 |
| 153 | C | A | B | A | 940.35 | 940.00 |
| 154 | B | B | A | A | 937.30 | 937.04 |
| 155 | B | B | B | A | 939.30 | 939.01 |
| 156 | B | B | B | A | 900.30 | 899.95 |
| 157 | B | B | B | A | 941.20 | 941.00 |
| 158 | B | B | B | A | 884.10 | 883.89 |
| 159 | D | ND | D | ND | 853.10 | 852.88 |
| 160 | A | B | A | A | 923.40 | 923.01 |
| 161 | B | B | A | A | 923.20 (923.50)$^{\#}$ | 923.01 |
| 162 | C | C | B | B | 964.30 | 964.06 |
| 163 | B | B | B | A | 971.20 | 971.03 |
| 164 | B | B | A | A | 954.20 | 954.03 |
| 165 | B | B | B | A | 913.20 | 912.93 |
| 166 | B | B | B | A | 913.20 | 912.93 |
| 167 | B | B | B | B | 939.20 | 939.01 |
| 168 | B | C | B | A | 886.10 | 885.97 |
| 169 | D | ND | D | ND | 937.20 | 937.04 |
| 170 | C | B | B | A | 897.20 | 896.93 |
| 171 | C | B | B | A | 897.20 | 896.93 |
| 172 | B | B | B | A | 911.10 | 910.96 |
| 173 | B | B | B | A | 911.20 | 910.96 |
| 174 | B | C | B | A | 963.30 | 963.08 |
| 175 | B | B | A | A | 955.30 | 955.01 |
| 176 | B | C | B | B | 900.30 | 899.99 |
| 177 | A | B | A | A | 905.30 | 905.02 |
| 178 | B | C | B | A | 900.49 | 899.99 |
| 179 | B | B | B | A | 921.47 | 921.00 |
| 180 | B | B | B | A | 949.51 | 949.05 |
| 181 | C | C | C | B | 923.49 | 923.01 |
| 182 | C | B | B | A | 954.50 | 954.03 |
| 183 | C | C | D | ND | 937.51 | 937.04 |
| 184 | B | C | B | B | 941.50 | 941.03 |
| 185 | B | C | B | A | 923.49 | 923.01 |
| 186 | C | B | B | A | 915.40 | 914.95 |
| 187 | C | B | B | A | 915.40 | 914.95 |
| 188 | B | B | B | A | 949.50 | 949.05 |
| 189 | B | B | A | B | 868.40 | 867.98 |
| 190 | A | B | B | A | 941.40 | 941.00 |
| 191 | B | B | A | A | 893.40 | 893.01 |
| 192 | B | B | B | A | 910.40 | 909.97 |
| 193 | C | B | B | B | 912.40 | 911.95 |
| 194 | C | B | B | A | 911.40 | 910.96 |
| 195 | B | B | B | B | 982.50 | 982.08 |
| 196 | B | B | B | B | 929.40 | 928.99 |
| 197 | B | C | B | B | 929.40 | 928.99 |
| 198 | B | C | B | A | 895.40 | 894.96 |
| 199 | B | B | B | A | 901.40 | 900.98 |
| 200 | C | B | B | B | 936.40 | 936.01 |
| 201 | B | C | B | B | 966.21 | 966.04 |
| 202 | C | B | B | B | 938.18 | 937.99 |
| 203 | A | B | A | A | 933.33 | 933.08 |
| 204 | A | B | A | A | 892.52 | 892.02 |
| 205 | B | B | A | B |  | 948.02 |
| 206 | B | B | A | B | 890.49 | 890.01 |
| 207 | B | B | A | B | 935.38 | 935.05 |
| 208 | B | B | A | B | 907.46 | 907.04 |
| 209 | B | C | B | B | 979.50 | 979.08 |
| 210 | B | B | B | A | 952.18 | 952.05 |
| 211 | B | B | B | B | 919.32 | 919.05 |
| 212 | B | B | B | A | 935.18 | 935.05 |
| 213 | B | B | B | A | 929.40 | 928.99 |
| 214 | B | C | B | B | 909.40 | 908.99 |
| 215 | B | B | B | A | 925.40 | 924.99 |
| 216 | B | C | B | A | 923.08 | 923.01 |

TABLE 2-continued

Degradation and characterization of exemplary bifunctional compounds of the present disclosure

| Ex. No. | BRaf V600E DC$_{50}$ (nM) | BRaf V600E D$_{Max}$ (%) | BRaf G466V DC$_{50}$ (nM) | BRaf G466V D$_{Max}$ (%) | MH+ (1) | Mol Weight |
|---|---|---|---|---|---|---|
| 217 | B | B | C | A | 923.08 | 923.01 |
| 218 | D | ND | D | ND | 909.16 | 908.99 |
| 219 | B | B | B | A | 924.08 | 924.00 |
| 220 | B | B | B | A | 924.07 | 924.00 |
| 221 | B | B | B | A | 936.07 | 936.01 |
| 222 | B | B | B | A | 936.08 | 936.01 |
| 223 | B | B | B | A | 924.08 | 924.00 |
| 224 | B | B | B | A | 924.08 | 924.00 |
| 225 | B | B | B | A | 966.08 | 966.04 |
| 226 | B | C | B | A | 966.08 | 966.04 |
| 227 | B | C | B | A | 950.09 | 950.04 |
| 228 | B | B | A | A | 891.08 | 891.00 |
| 229 | B | B | A | A | 891.08 | 891.00 |
| 230 | B | B | A | A | 905.18 | 905.02 |
| 231 | B | B | B | A | 905.09 | 905.02 |
| 232 | B | B | B | A | 941.07 | 941.00 |
| 233 | B | B | A | A | 941.07 | 941.00 |
| 234 | B | B | A | A | 878.09 / 878.09 | 878.00 |
| 235 | B | B | B | A | 878.09 | 878.00 |
| 236 | B | B | A | A | 878.09 | 878.00 |
| 237 | B | B | A | A | 921.09 | 921.02 |
| 238 | B | B | B | A | 921.09 | 921.02 |
| 239 | B | B | B | A | 937.10 | 937.04 |
| 240 | B | B | B | A | 937.09 | 937.04 |
| 241 | B | B | B | A | 937.10 | 937.04 |
| 242 | B | B | B | A | 937.10 | 937.04 |
| 243 | B | B | B | A | 879.09 | 878.99 |
| 244 | B | B | B | A | 879.08 | 878.99 |
| 245 | B | B | B | A | 879.09 | 878.99 |
| 246 | B | B | B | A | 954.06 | 954.00 |
| 247 | B | C | B | A | 984.07 | 984.03 |
| 248 | B | B | B | A | 899.03 | 898.92 |
| 249 | B | B | B | A | 966.08 | 966.04 |
| 250 | B | C | B | A | 966.08 | 966.04 |
| 251 | B | B | B | B | 917.04 | 916.94 |
| 252 | B | B | A | B | 939.41 | 939.47 |
| 253 | B | B | B | B | 919.46 | 919.05 |
| 254 | D | ND | A | C | 772.42 | 771.85 |
| 255 | B | B | A | A | 948.42 | 948.02 |
| 256 | B | B | A | A | 953.42 | 953.04 |
| 257 | B | B | B | A | 952.18 | 952.05 |
| 258 | A | B | A | B | 996.36 | 996.08 |
| 259 | A | B | A | B | 996.36 | 996.08 |
| 260 | B | B | B | B | 973.06 | 973.03 |
| 261 | B | B | B | A | 973.07 | 973.03 |
| 262 | B | C | B | B | 933.20 / 933.19 | 933.08 |
| 263 | C | C | B | B | 933.21 | 933.08 |
| 264 | B | B | B | B | 919.32 | 919.05 |
| 265 | D | ND | D | ND | 933.20 | 933.08 |
| 266 | D | ND | D | ND | 933.20 | 933.08 |
| 267 | B | B | B | B | 955.09 | 955.92 |
| 268 | C | B | B | C | 955.09 | 955.92 |
| 269 | B | B | B | B | 935.18 | 935.05 |
| 270 | B | B | B | A | 937.18 | 937.04 |
| 271 | B | B | B | A | 937.17 | 937.04 |
| 272 | C | B | B | B | 973.14 / 973.07 | 973.02 |
| 273 | D | B | C | B | 973.27 | 973.02 |
| 274 | D | ND | D | ND | 947.19 | 947.08 |
| 275 | D | ND | D | ND | 947.19 | 947.08 |
| 276 | A | B | A | B | 933.33 | 933.08 |
| 277 | B | C | C | A | 933.11 | 933.08 |
| 278 | B | B | B | B | 921.44 | 921.02 |
| 279 | B | C | C | A | 907.43 | 907.00 |
| 280 | B | B | B | B | 909.44 | 909.01 |
| 281 | B | B | B | B | 905.44 | 905.02 |
| 282 | C | B | B | A | 880.47 | 879.97 |
| 283 | B | B | B | A | 935.38 | 935.05 |
| 284 | B | B | B | A | 981.33 | 981.10 |
| 285 | B | C | B | B | 981.33 | 981.10 |
| 286 | C | B | B | B | 938.18 | 937.99 |
| 287 | B | B | B | B | 954.28 | 954.03 |
| 288 | C | B | D | A | 965.23 | 965.05 |
| 289 | C | B | C | B | 954.10 | 954.03 |
| 290 | C | B | B | B | 954.10 | 954.03 |
| 291 | ND | ND |  | ND | 947.14 | 947.10 |
| 292 | ND | ND |  | ND | 966.10 | 966.04 |
| 293 | C | B | B | B | 881.40 | 880.93 |
| 294 | C | B | B | B | 898.20 | 897.96 |
| 295 | C | B | B | B | 915.40 | 914.95 |
| 296 | C | B | B | B | 915.40 | 914.95 |
| 297 | B | B | A | A | 941.40 | 941.00 |
| 298 | C | C | A | B | 966.50 / 966.50 | 966.04 / 966.17 |
| 299 | B | B | B | A | 883.40 | 882.91 |
| 300 | C | B | A | B | 903.40 | 902.91 |
| 301 | C | B | A | A | 903.40 | 902.91 |
| 302 | C | B | B | B | 895.40 | 894.96 |
| 303 | B | B | B | A | 909.40 | 908.99 |
| 304 | C | B | B | A | 935.40 | 935.02 |
| 305 | C | B | B | A | 909.40 | 908.99 |
| 306 | C | B | B | B | 895.40 | 894.96 |
| 307 | D | A | B | B | 911.46 | 910.96 |
| 308 | C | C | D | ND | 937.50 | 937.04 |
| 309 | B | B | B | A | 964.51 | 964.06 |
| 310 | B | B | B | A | 899.42 | 898.92 |
| 311 | B | B | B | A | 950.09 | 950.04 |
| 312 | C | A | B | A | 937.06 | 937.00 |
| 313 | ND | ND |  | ND | 964.09 | 964.06 |
| 314 | ND | ND |  | ND | 937.05 | 937.00 |
| 315 | D | ND | D | ND | 974.06 | 974.01 |
| 316 | C | C | B | A | 935.08 | 935.02 |
| 317 | C | B | B | A | 883.06 | 882.95 |
| 318 | C | B | C | B | 897.07 | 896.98 |
| 319 | B | B | B | A | 953.07 | 953.01 |
| 320 | C | B | B | B | 938.14 | 937.99 |
| 321 | B | B | B | A | 895.05 | 894.96 |
| 322 | C | C | B | B | 938.09 | 938.03 |
| 323 | C | C | C | B | 937.05 / 937.06 | 937.00 |
| 324 | B | C | B | A | 938.09 | 938.03 |
| 325 | B | B | B | A | 883.06 | 882.95 |
| 326 | B | B | A | A | 909.07 | 908.99 |
| 327 | B | B | B | A | 911.13 | 910.96 |
| 328 | B | B | B | A | 911.13 | 910.96 |
| 329 | B | B | B | A | 950.10 | 950.04 |
| 330 | B | B | B | A | 950.09 | 950.04 |
| 331 | B | B | B | B | 929.14 | 928.97 |
| 332 | B | B | B | A | 882.06 | 881.96 |
| 333 | D | ND | B | C | 974.06 | 974.01 |
| 334 | C | B | B | A | 937.07 | 937.00 |
| 335 | D | ND | D | ND | 842.01 | 841.85 |
| 336 | D | B | D | ND | 842.01 | 841.85 |
| 337 | B | B | B | A | 938.28 | 938.03 |
| 338 | C | B | C | B | 1045.39 | 1045.12 |
| 339 | B | B | B | A | 930.07 | 929.98 |
| 340 | C | C | B | B | 930.07 | 929.98 |
| 341 | B | B | B | A | 930.07 | 929.98 |
| 342 | C | B | B | A | 930.07 | 929.98 |
| 343 | B | B | B | A | 954.08 | 954.03 |
| 344 | C | C | C | A | 654.08 | 954.03 |
| 345 | B | B | B | A | 925.08 | 924.99 |
| 346 | C | C | B | C | 925.08 | 924.99 |
| 347 | B | B | B | A | 972.07 | 972.02 |
| 348 | B | B | B | A | 972.07 | 972.02 |
| 349 | D | A | D | ND | 905.04 | 904.93 |
| 350 | C | C | D | ND | 905.04 | 904.93 |
| 351 | B | B | B | B | 960.05 | 959.98 |
| 352 | B | B | B | A | 954.08 | 954.03 |
| 353 | B | B | B | B | 925.07 | 924.99 |
| 354 | B | C | B | C | 925.07 | 924.99 |

TABLE 2-continued

Degradation and characterization of exemplary bifunctional compounds of the present disclosure

| Ex. No. | BRaf V600E DC$_{50}$ (nM) | BRaf V600E D$_{Max}$ (%) | BRaf G466V DC$_{50}$ (nM) | BRaf G466V D$_{Max}$ (%) | MH+ (1) | Mol Weight |
|---|---|---|---|---|---|---|
| 355 | C | B | D | ND | 887.38 | 886.91 |
| 356 | D | ND | D | ND | 887.38 | 886.91 |
| 357 | B | B | B | A | 942.44 | 942.02 |
| 358 | B | B | B | A | 942.44 | 942.02 |
| 359 | B | B | B | A | 942.44 | 942.02 |
| 360 | A | C | B | A | 942.44 | 942.02 |
| 361 | B | B | B | A | 885.38 | 884.92 |
| 362 | B | B | B | A | 885.38 | 884.92 |
| 363 | D | ND | D | ND | 791.40 | 790.83 |
| 364 | B | B | B | A | 967.50 | 967.07 |
| 365 | B | A | B | A | 869.40 | 868.97 |
| 366 | B | B | B | A | 967.11 | 967.07 |
| 367 | D | ND | B | C | 967.11 | 967.07 |
| 368 | B | B | B | B | 881.43 | 880.98 |
| 369 | B | B | B | A | 968.46 | 968.06 |
| 370 | B | B | B | A | 968.47 | 968.06 |
| 371 | C | A | B | A | 968.11 | 968.06 |
| 372 | D | ND | D | ND | 968.11 | 968.06 |
| 373 | B | B | B | A | 873.37 | 872.89 |
| 374 | B | B | A | B | 873.36 | 872.89 |
| 375 | C | B | B | B | 931.39 | 930.97 |
| 376 | C | B | B | B | 931.39 | 930.97 |
| 377 | B | B | B | B | 945.53 | 945.00 |
| 378 | B | C | A | C | 945.53 | 945.00 |
| 379 | C | B | B | B | 911.06 | 910.96 |
| 380 | D | ND | B | C | 911.06 | 910.96 |

*DC$_{50}$ V600E (nM) D > 500; 50 < C ≤ 500; 5 < B ≤ 50; A ≤ 5
*DC$_{50}$ G446V (nM) A ≤ 1; 1 < B ≤ 10; 10 < C < 30; D > 30
**D$_{Max}$ (%): C ≤ 35; 35 < B < 70; A ≥ 70
MH+ (2)
ND—not determined

TABLE 3

¹H NMR data of exemplary bifunctional compounds of the present disclosure

| Parent Mol Structure | Ex. No. | IUPAC Name | ¹H NMR tabulation |
|---|---|---|---|
| 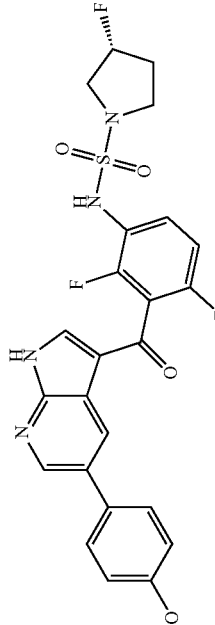 | 1 | (3R)-N-(3-{5-[4-({2-[2-(2,6-dioxopiperidin-3-yl)-1-oxo-2,3-dihydro-1H-isoindol-5-yl]-2-azaspiro[3.3]heptan-6-yl}oxy)phenyl]-1H-pyrrolo[2,3-b]pyridine-3-carbonyl]-2,4-difluorophenyl)-3-fluoropyrrolidine-1-sulfonamide | 1H NMR (400 MHz, DMSO-d6) δ 12.93 (s, 1H), 10.93 (s, 1H), 9.87 (s, 1H), 8.66 (d, J = 2.2 Hz, 1H), 8.55 (s, 1H), 8.08 (s, 1H), 7.66-7.57 (m, 3H), 7.50 (d, J = 8.3 Hz, 1H), 7.26 (t, J = 8.7 Hz, 1H), 7.04-6.98 (m, 2H), 6.55-6.45 (m, 2H), 5.36-5.23 (m, 1H), 5.03 (dd, J = 13.3, 5.1 Hz, 1H), 4.77 (q, J = 6.7 Hz, 1H), 4.31 (d, J = 17.0 Hz, 1H), 4.19 (d, J = 16.9 Hz, 1H), 4.02-3.95 (m, 4H), 3.48-3.40 (m, 3H), 2.95-2.84 (m, 3H), 2.58 (d, J = 16.5 Hz, 1H), 2.35-2.30(m, 3H), 2.09-1.92 (m, 3H), 1.34-1.06(m, 1H) |
| 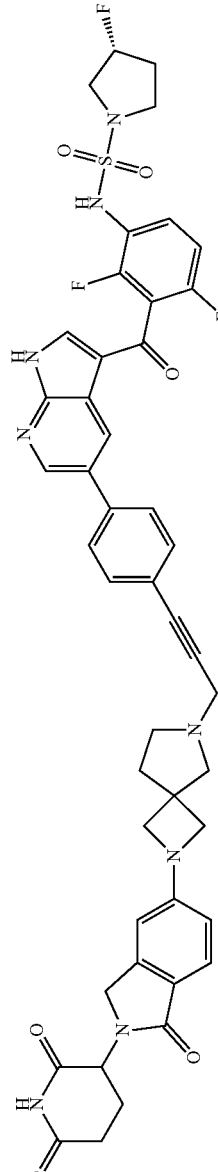 | 4 | (3R)-N-(3-{5-[4-(3-{2-[2-(2,6-dioxopiperidin-3-yl)-1-oxo-2,3-dihydro-1H-isoindol-5-yl]-2,6-diazaspiro[3.4]octan-6-yl}prop-1-yn-1-yl)phenyl]-1H-pyrrolo[2,3-b]pyridine-3-carbonyl]-2,4-difluorophenyl)-3-fluoropyrrolidine-1-sulfonamide | 1H NMR (400 MHz, DMSO-d6, ppm) δ 13.05 (s, 1H), 10.95 (s, 1H), 9.88 (s, 1H), 8.76 (s, 1H), 8.68 (s, 1H), 8.16 (s, 1H), 7.82 (d, J = 8.0 Hz, 2H), 7.68-7.60 (m, 3H), 7.52 (d, J = 8.4 Hz, 1H), 7.29-7.26 (m, 1H), 6.61-6.46 (m, 2H), 5.32 (d, J = 53.2 Hz, 1H), 5.05 (dd, J = 13.3, 5.1 Hz, 1H), 4.32 (d, J = 17.0 Hz, 1H), 4.19 (d, J = 17.0 Hz, 1H), 4.04-3.79 (m, 5H), 3.54-3.38 (m, 4H), 3.34-3.25 (m, 1H), 3.10 (s, 1H), 2.99-2.83 (m, 2H), 2.60-2.54 (m, 2H), 2.42-2.30 (m, 1H), 2.22-2.21 (m, 2H), 2.17-2.05 (m, 2H), 2.05-1.91 (m, 2H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| | 5 | (3R)-N-[3-(5-{4-[(1R,4R)-5-{1-[2-(2,6-dioxopiperidin-3-yl)-1-oxo-2,3-dihydro-1H-isoindol-5-yl]azetidin-3-yl}-2,5-diazabicyclo[2.2.1]heptan-2-yl]phenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ: 1.80-2.00 (m, 4H) 2.00-2.18 (m, 2H) 2.22-2.31 (m, 1H) 2.53-2.60 (m, 1H) 2.67-2.77 (m, 1H) 2.83-2.94 (m, 2H) 3.15 (d, J = 8.8 Hz, 1H) 3.25-3.29 (m, 2H) 3.44 (s, 1H) 3.48 (s, 1H) 3.54-3.61 (m, 1H) 3.62-3.69 (m, 2H) 3.70-3.78 (m, 1H) 3.94-4.05 (m, 2H) 4.08-4.19 (m, 1H) 4.20-4.33 (m, 1H) 4.45 (s, 1H) 5.01 (dd, J = 13.2, 5.2 Hz, 1H) 5.20-5.40 (m, 1H) 6.38-6.49 (m, 2H) 6.73 (d, J = 8.8 Hz, 2H) 7.23-7.32 (m, 1H) 7.46 (d, J = 8.2 Hz, 1H) 7.55 (d, J = 8.4 Hz, 2H) 7.62 (td, J = 8.8, 6.0 Hz, 1H) 8.02-8.10 (m, 1H) 8.12-8.15 (m, 1H) 8.45-8.57 (m, 1H) 8.63 (t, J = 1.83 Hz, 1H) 9.76-9.97 (m, 1H) 10.91 (s, 1H) 12.84-12.96 (m, 1H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| 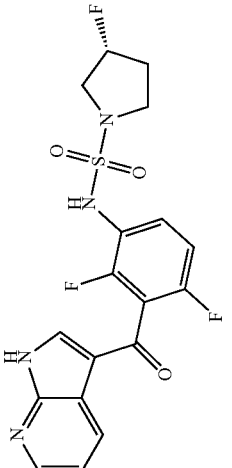 | 7 | (3R)-N-[3-(5-{4-[1-({1-[2-(2,6-dioxopiperidin-3-yl)-1-oxo-2,3-dihydro-1H-isoindol-5-yl]azetidin-3-yl}methyl)piperidin-4-yl]phenyl}-1H-pyrrolo[2,3-b]pyridine-3-carbonyl)-2,4-difluorophenyl]-3-fluoropyrrolidine-1-sulfonamide | HNMR (400 MHz, DMSO-d6) δ 13.01 (d, J = 2.8 Hz, 1H), 10.95 (s, 1H), 9.86 (s, 1H), 9.48 (s, 1H), 8.72 (d, J = 2.0 Hz, 1H), 8.63 (s, 1H), 8.13 (d, J = 2.8 Hz, 1H), 7.76 (d, J = 8.0 Hz, 2H), 7.64 (t, J = 6.0, 9.2 Hz, 1H), 7.54 (d, J = 8.4 Hz, 1H), 7.42 (d, J = 8.4 Hz, 2H), 7.29 (t, J = 8.4 Hz, 1H), 6.63-6.45 (m, 2H), 5.44-5.18 (m, 1H), 5.05 (d, J = 5.2, 13.2 Hz, 1H), 4.40-4.28 (m, 1H), 4.26-4.09 (m, 3H), 3.76 (d, J = 5.6 Hz, 2H), 3.66-3.58 (m, 3H), 3.46-3.22 (m, 8H), 3.14 (d, J = 11.6 Hz, 2H), 3.00-2.85 (m, 2H), 2.60 (d, J = 16.8 Hz, 1H), 2.44-2.35 (m, 1H), 2.22-2.02 (m, 4H), 1.97 (t, J = 11.6 Hz, 3H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 9 | 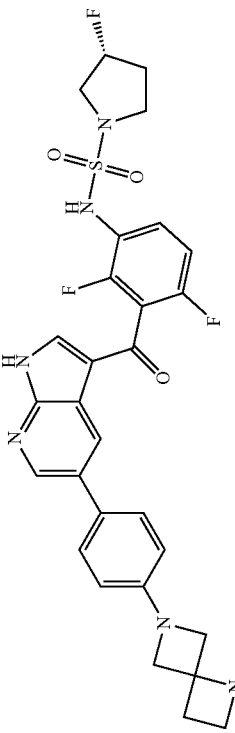 | (3R)-N-(3-{5-[4-(1-{1-[2-(2,6-dioxopiperidin-3-yl)-1-oxo-2,3-dihydro-1H-isoindol-5-yl]piperidin-4-yl}-1,6-diazaspiro[3.3]heptan-6-yl)phenyl]-1H-pyrrolo[2,3-b]pyridine-3-carbonyl}-2,4-difluorophenyl)-3-fluoropyrrolidine-1-sulfonamide | 1H NMR (400 MHz, DMSO-d6) δ 12.90 (s, 1H), 10.94 (s, 1H), 9.86 (s, 1H), 8.64 (m, 1H), 8.51 (s, 1H), 8.07 (s, 1H), 7.63-7.58 (m, 3H), 7.49 (m, 1H), 7.28 (m, 1H), 7.05-7.03 (m, 2H), 6.59 (m, 2H), 5.37-5.23 (s, 1H), 5.04 (m, 1H), 4.31 (m, 1H), 4.23-4.14 (m, 3H), 3.92 (m, 2H), 3.75 (m, 2H), 3.49 (m, 1H), 3.40 (s, 3H), 3.29 (s, 1H), 3.09 (s, 2H), 3.05-2.98 (m, 3H), 2.95-2.83 (m, 1H), 2.78 (s, 1H), 2.58 (m, 1H), 2.39 (m, 1H), 2.37-2.30 (m, 1H), 2.26-2.11 (s, 2H), 2.06-1.96 (m, 2H), 1.82 (m, 2H), 1.40 (m, 2H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 10 | | (3R)-N-(3-{5-[4-(2-{2-[2-(2,6-dioxopiperidin-3-yl)-1-oxo-2,3-dihydro-1H-isoindol-5-yl]-2,8-diazaspiro[4.5]decan-8-yl}ethyl)phenyl]-1H-pyrrolo[2,3-b]pyridine-3-carbonyl]-2,4-difluorophenyl)-3-fluoropyrrolidine-1-sulfonamide | 1H NMR (400 MHz, DMSO-d6) δ 12.96 (s, 1H), 10.92 (s, 1H), 9.84 (s, 1H), 8.69 (d, J = 2.3 Hz, 1H), 8.59 (s, 1H), 8.11 (s, 1H), 7.69-7.57 (m, 3H), 7.48 (d, J = 8.4 Hz, 1H), 7.39 (d, J = 7.9 Hz, 2H), 7.25 (t, J = 8.7 Hz, 1H), 6.64 (s, 1H), 6.62 (d, J = 2.1 Hz, 1H), 5.36 (s, 1H), 5.22 (s, 0H), 5.03 (dd, J = 13.3, 5.1 Hz, 1H), 4.30 (d, J = 16.7 Hz, 1H), 4.18 (d, J = 16.7 Hz, 1H), 3.43-3.34 (m, 5H), 3.27 (dd, J = 9.8, 7.0 Hz, 1H), 3.20 (s, 2H), 2.97-2.79 (m, 3H), 2.61 (dd, J = 28.0, 10.9 Hz, 2H), 2.60 (s, 3H), 2.35 (dt, J = 13.5, 6.5 Hz, 1H), 2.10 (s, 2H), 2.00-1.92 (m, 1H), 1.88 (t, J = 6.9 Hz, 2H), 1.61 (d, J = 6.5 Hz, 4H) |
| 15 | | (3R)-N-{3-[5-(4-{[(2R)-1-[2-(2,6-dioxopiperidin-3-yl)-1-oxo-2,3-dihydro-1H-isoindol-5-yl]azetidin-2-yl]methoxy}phenyl)-1H-pyrrolo[2,3-b]pyridine-3-carbonyl]-2,4-difluorophenyl}-3-fluoropyrrolidine-1-sulfonamide | 1H NMR (400 MHz, DMSO-d6, ppm) δ 12.95 (s, 1H), 10.95 (s, 1H), 9.87 (s, 1H), 8.67 (s, 1H), 8.58 (s, 1H), 8.11 (s, 1H), 7.70-7.63 (m, 3H), 7.53 (d, J = 8.0 Hz, 1H), 7.28 (d, J = 7.6 Hz, 1H), 7.17 (d, J = 7.6 Hz, 2H), 6.82-6.75 (m, 2H), 5.32 (d, J = 12.9 Hz, 1H), 5.05-5.01 (m, 1H), 4.56 (s, 1H), 4.43-4.29 (m, 4H), 4.22-4.20 (m, 1H), 4.08 (s, 1H), 3.75 (s, 1H), 3.51-3.38 (m, 3H), 3.00-2.84 (m, 1H), 2.70-2.56 (m, 1H), 2.43-2.31 (m, 2H), 2.22-2.05 (m, 2H), 2.03-1.87 (m, 2H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 16 | | (3R)-N-[3-(5-{4-[(1S,5S)-6-{1-[2-(2,6-dioxopiperidin-3-yl)-1-oxo-2,3-dihydro-1H-isoindol-5-yl]piperidin-4-yl}-3,6-diazabicyclo[3.2.1]octan-3-yl]phenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 12.88 (s, 1H), 10.94 (s, 1H), 9.82 (s, 1H), 8.63 (s, 1H), 8.52 (s, 1H), 8.05 (s, 1H), 7.60-7.58 (m, 3H), 7.50 (d, J = 8.7 Hz, 1H), 7.22-7.06 (m, 1H), 7.07 (s, 2H), 6.98 (d, J = 8.6 Hz, 2H), 5.32 (d, J = 13.3, 5.1 Hz, 1H), 4.32-4.20 (m, 2H), 3.87-3.76 (m, 3H), 3.60-3.46 (m, 3H), 3.39 (s, 2H), 3.14 (s, 1H), 3.03-2.83 (m, 4H), 2.72-2.52 (m, 4H), 2.37-2.06 (m, 4H), 2.05-1.87 (m, 5H), 1.67-1.53 (m, 2H), 1.26-1.21 (m, 2H) |
| 17 | | (3R)-N-[3-(5-{4-[(2S)-2-({[2-(2,6-dioxopiperidin-3-yl)-1-oxo-2,3-dihydro-1H-isoindol-5-yl]oxy}methyl)azetidin-1-yl]phenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ (ppm): 12.89 (s, 1H), 10.97 (s, 1H), 9.86 (s, 1H), 8.64 (s, 1H), 8.52 (s, 1H), 8.06 (s, 1H), 7.68-7.63 (m, 4H), 7.24-7.17 (m, 3H), 6.82 (d, J = 8.4 Hz, 2H), 5.34 (d, J = 12.4 Hz, 1H), 5.14-5.11 (m, 1H), 4.47-4.39 (m, 5H), 4.04-4.02 (m, 1H), 3.72-3.71 (m, 1H), 3.51 (s, 1H), 3.49-3.26 (m, 2H), 2.96-2.85 (m, 1H), 2.61-2.60 (m, 1H), 2.58-2.46 (m, 7H), 2.37-2.35 (m, 1H), 2.16-1.96 (m, 2H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 19 | | (3R)-N-[3-(5-{4-[6-({1-[2-(2,6-dioxopiperidin-3-yl)-1-oxo-2,3-dihydro-1H-isoindol-5-yl]-4-fluoropiperidin-4-yl}methyl)-2,6-diazaspiro[3.3]heptan-2-yl]phenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ: 1.63-1.80 (m, 2H) 1.81-1.90 (m, 2H) 1.91-2.01 (m, 2H) 2.02-2.18 (m, 2H) 2.34-2.44 (m, 1H) 2.52 (s, 1H) 2.54-2.58 (m, 1H) 2.58-2.66 (m, 2H) 2.68-2.74 (m, 1H) 2.82-2.98 (m, 2H) 3.12 (t, J = 11.2 Hz, 3H) 3.46 (s, 4H) 3.48 (s, 2H) 3.60-3.77 (m, 3H) 4.15-4.25 (m, 1H) 4.26-4.38 (m, 1H) 5.04 (dd, J = 13.2, 5.2 Hz, 1H) 5.20-5.41 (m, 1H) 6.56 (d, J = 8.8 Hz, 2H) 7.04-7.15 (m, 2H) 7.22-7.32 (m, 1H) 7.44-7.67 (m, 4H) 8.06 (s, 1H) 8.13 (s, 1H) 8.42-8.55 (m, 1H) 8.61 (d, J = 2.4 Hz, 1H) 10.81-11.14 (m, 1H) 12.72-13.06 (m, 1H) |
| 23 | | (3R)-N-{3-[5-(4-{[(2S)-1-[2-(2,6-dioxopiperidin-3-yl)-1-oxo-2,3-dihydro-1H-isoindol-5-yl]azetidin-2-yl]methoxy}phenyl)-1H-pyrrolo[2,3-b]pyridine-3-carbonyl]-2,4-difluorophenyl}-3-fluoropyrrolidine-1-sulfonamide | 1H NMR (400 MHz, DMSO-d6, ppm) δ 12.96 (s, 1H), 10.95 (s, 1H), 9.87 (s, 1H), 8.67 (s, 1H), 8.58 (s, 1H), 8.10 (s, 1H), 7.70 (d, J = 8.2 Hz, 2H), 7.67-7.59 (m, 1H), 7.53 (d, J = 8.2 Hz, 1H), 7.28 (t, J = 8.7 Hz, 1H), 7.17 (d, J = 8.3 Hz, 2H), 6.82 (d, J = 5.2 Hz, 1H), 6.74 (t, J = 7.1 Hz, 1H), 5.30 (d, J = 53.2 Hz, 1H), 5.05 (dd, J = 13.4, 5.2 Hz, 1H), 4.55 (s, 1H), 4.43-4.29 (m, 3H), 4.22 (d, J = 17.2 Hz, 1H), 4.14-4.01 (m, 1H), 3.81-3.70 (m, 1H), 3.53-3.41 (m, 3H), 3.33-3.25 (m, 1H), 2.98-2.80 (m, 1H), 2.59 (d, J = 18.6 Hz, 2H), 2.37 (d, J = 12.7 Hz, 2H), 2.21-1.87 (m, 3H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 34 | | (3R)-N-{3-[5-(4-{4-[(1-{2-[(3S)-2,6-dioxopiperidin-3-yl]-1-oxo-2,3-dihydro-1H-isoindol-5-yl}piperidin-4-yl)oxy]piperidin-1-yl}phenyl)-1H-pyrrolo[2,3-b]pyridine-3-carbonyl]-2,4-difluorophenyl}-3-fluoropyrrolidine-1-sulfonamide | 1H NMR (400 MHz, DMSO-d6) δ 12.91 (s, 1H), 10.96 (s, 1H), 9.88 (s, 1H), 8.65 (m, 2H), 8.07 (s, 1H), 7.68-7.45 (m, 4H), 7.27 (m, 1H), 7.08 (m, 4H), 5.32 (d, J = 56 Hz, 1H), 5.05 (m, 1H), 4.33 (m, 1H), 4.20 (m, 1H), 3.70 (m, 7H), 3.61 (m, 3H), 3.10 (m, 1H), 2.99 (m, 5H), 2.59 (m, 1H), 2.37 (m, 1H), 2.07 (m, 1H), 1.95 (s, 5H), 1.59-1.50 (m, 4H) |
| 35 | | (3R)-N-{3-[5-(4-{4-[(1-{2-[(3R)-2,6-dioxopiperidin-3-yl]-1-oxo-2,3-dihydro-1H-isoindol-5-yl}piperidin-4-yl)oxy]piperidin-1-yl}phenyl)-1H-pyrrolo[2,3-b]pyridine-3-carbonyl]-2,4-difluorophenyl}-3-fluoropyrrolidine-1-sulfonamide | 1H NMR (400 MHz, DMSO-d6) δ 12.91 (s, 1H), 10.96 (s, 1H), 9.88 (s, 1H), 8.65 (m, 2H), 8.07 (s, 1H), 7.68-7.45 (m, 4H), 7.27 (m, 1H), 7.08 (s, 4H), 5.32 (d, J = 56.0 1H), 5.05 (m, 1H), 4.33-4.20(m, 2H), 3.70 (m, 9H), 3.10 (m, 8H), 2.59 (m, 1H), 2.37 (m, 1H), 2.07-1.95 (s, 8H), 1.5 (s, 4H) |
| 36 | | (3R)-N-[3-(5-{4-[4-({4-[2-(2,6-dioxopiperidin-3-yl)-1-oxo-2,3-dihydro-1H-isoindol-5-yl]piperidin-1-yl}methyl)piperidin-1-yl]-3-fluorophenyl})-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 12.97 (s, 1H), 10.99 (s, 1H), 9.82 (s, 1H), 8.70 (s, 1H), 8.59 (s, 1H), 8.11 (s, 1H), 7.69-7.46 (m, 5H), 7.42-7.40 (m, 1H), 7.32-7.23 (m, 1H), 7.17-7.14 (m, 1H), 5.24 (d, J = 32.0 Hz, 1H), 5.12-5.09 (m, 1H), 4.43-4.30 (m, 2H), 3.54-3.35 (m, 5H), 3.34-3.24 (m, 1H), 3.03-3.00 (m, 2H), 2.99-2.85 (m, 1H), 2.79-2.69 (m, 4H), 2.69-2.56 (m, 3H), 2.18-1.98 (m, 5H), 1.82-1.71 (m, 7H), 1.33-1.31 (m, 2H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| | 42 | (3R)-N-(3-{5-[4-(3-{6-[2-(2,6-dioxopiperidin-3-yl)-1-oxo-2,3-dihydro-1H-isoindol-5-yl]-2,6-diazaspiro[3.3]heptan-2-yl}prop-1-yn-1-yl)phenyl]-1H-pyrrolo[2,3-b]pyridine-3-carbonyl}-2,4-difluorophenyl)-3-fluoropyrrolidine-1-sulfonamide | 1H NMR (400 MHz, DMSO-d6) δ 13.03 (s, 1H), 10.94 (s, 1H), 9.88 (s, 1H), 8.75 (m, 1H), 8.67 (s, 1H), 8.15 (s, 1H), 7.84-7.77 (m, 2H), 7.69-7.58 (m, 3H), 7.50 (m, 1H), 7.29 (m, 1H), 6.55-6.50 (m, 2H), 5.37-5.24 (s, 2H), 5.04 (m, 1H), 4.31 (m, 1H), 4.18 (m, 1H), 4.03 (s, 4H), 3.51 (m, 8H), 3.41 (m, 2H), 3.29 (m, 1H), 2.90 (m, 1H), 2.75-2.58 (m, 1H), 2.43-2.34 (m, 1H), 2.15-2.05 (m, 2H), 1.96 (m, 2H) |
| | 43 | (3R)-N-(3-{5-[4-(6-{[2-(2,6-dioxopiperidin-3-yl)-1-oxo-2,3-dihydro-1H-isoindol-5-yl]oxy}-2-azaspiro[3.3]heptan-2-yl)phenyl]-1H-pyrrolo[2,3-b]pyridine-3-carbonyl}-2,4-difluorophenyl)-3-fluoropyrrolidine-1-sulfonamide | 1H NMR (300 MHz, DMSO-d6, ppm) δ 12.91 (s, 1H), 10.99 (s, 1H), 9.87 (s, 1H), 8.63 (s, 1H), 8.52 (s, 1H), 8.07 (s, 1H), 7.72-7.51 (m, 4H), 7.28 (t, J = 8.6 Hz, 1H), 7.10 (s, 1H), 7.00 (d, J = 8.6 Hz, 1H), 6.64-6.49 (m, 2H), 5.30 (d, J = 53.1 Hz, 1H), 5.08 (d, J = 13.3, 5.0 Hz, 1H), 4.82 (d, J = 6.4 Hz, 1H), 4.41 (d, J = 17.1, 3.9 Hz, 1H), 4.27 (d, J = 16.0 Hz, 1H), 3.93 (d, J = 31.6, 4.1 Hz, 4H), 3.49 (s, 2H), 3.32-3.24 (m, 1H), 2.99-2.77 (m, 3H), 2.70-2.56 (m, 2H), 2.46-2.27 (m, 3H), 2.22-1.87 (m, 3H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 50 | | (3R)-N-(3-{5-[4-(2-{6-[2-(2,6-dioxopiperidin-3-yl)-1-oxo-2,3-dihydro-1H-isoindol-5-yl]-2,6-diazaspiro[3.3]heptan-2-yl}ethoxy)phenyl]-1H-pyrrolo[2,3-b]pyridine-3-carbonyl}-2,4-difluorophenyl)-3-fluoropyrrolidine-1-sulfonamide | 1H NMR (400 MHz, DMSO-d6) δ 12.95 (s, 1H), 10.95 (s, 1H), 9.89 (s, 1H), 8.67 (m, 1H), 8.57 (s, 1H), 8.10 (s, 1H), 7.71-7.61 (m, 3H), 7.64-7.58 (m, 1H), 7.49 (m, 1H), 7.27 (m, 1H), 7.08 (m, 2H), 6.53-6.49 (m, 2H), 5.37-5.24 (s, 1H), 5.04 (m, 1H), 4.31-4.18 (m, 2H), 4.01 (s, 6H), 3.54 (m, 5H), 3.41 (s, 2H), 3.32 (s, 1H), 2.91 (m, 1H), 2.83 (s, 2H), 2.58 (m, 1H), 2.42-2.28 (m, 1H), 2.11-2.07 (m, 1H), 1.95 (m, 1H) |
| 53 | | (3R)-N-[3-(5-{4-[(3R,5S)-4-({1-[2-(2,6-dioxopiperidin-3-yl)-1-oxo-2,3-dihydro-1H-isoindol-5-yl]azetidin-3-yl}methyl)-3,5-dimethylpiperazin-1-yl]phenyl}-1H-pyrrolo[2,3-b]pyridine-3-carbonyl)-2,4-difluorophenyl]-3-fluoropyrrolidine-1-sulfonamide | HNMR (400 MHz, DMSO-d6) δ = 12.91 (s, 1H), 11.02-10.84 (m, 1H), 8.65 (s, 1H), 8.53 (s, 1H), 8.07 (s, 1H), 7.60 (d, J = 8.4 Hz, 3H), 7.50 (d, J = 8.0 Hz, 1H), 7.26 (t, J = 8.8 Hz, 1H), 7.07 (d, J = 7.6 Hz, 2H), 6.58-6.42 (m, 2H), 5.42-5.19 (m, 1H), 5.03 (d, J = 8.8 Hz, 1H), 4.38-4.13 (m, 2H), 4.04 (s, 3H), 3.59 (s, 2H), 3.04 (s, 2H), 2.95 (s, 2H), 2.68 (s, 6H), 2.40-2.36 (m, 2H), 2.09 (d, J = 15.2 Hz, 3H), 1.97 (s, 3H), 1.24 (s, 1H), 1.15 (d, J = 5.6 Hz, 6H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| | 57 | (3R)-N-(3-{5-[4-(4-{[(3aR,6aS)-5-{2-[(3S)-2,6-dioxopiperidin-3-yl]-1-oxo-2,3-dihydro-1H-isoindol-5-yl}-octahydropyrrolo[3,4-c]pyrrol-2-yl]methyl}piperidin-1-yl]phenyl]-1H-pyrrolo[2,3-b]pyridine-3-carbonyl}-2,4-difluorophenyl)-3-fluoropyrrolidine-1-sulfonamide | 1H NMR (400 MHz, DMSO-d6) δ 12.90 (s, 1H), 10.95 (s, 1H), 9.86 (s, 1H), 8.64 (d, J = 2.2 Hz, 1H), 8.52 (s, 1H), 8.07 (s, 1H), 7.68-7.54 (m, 3H), 7.51 (d, J = 9.1 Hz, 1H), 7.32-7.23 (m, 1H), 7.05 (d, J = 8.8 Hz, 2H), 6.73 (d, J = 6.9 Hz, 2H), 5.30 (d, J = 53.0 Hz, 1H), 5.05 (dd, J = 13.3, 5.1 Hz, 1H), 4.33 (d, J = 16.8 Hz, 1H), 4.20 (d, J = 16.8 Hz, 1H), 3.77 (d, J = 12.0 Hz, 2H), 3.62-3.55 (m, 2H), 3.48 (d, J = 2.3 Hz, 1H), 3.21-3.12 (m, 2H), 3.01-2.84 (m, 3H), 2.77-2.66 (m, 2H), 2.59-2.56 (m, 4H), 2.40-2.27 (m, 3H), 2.09-2.06 (m, 2H), 2.03-1.90 (m, 2H), 1.81 (d, J = 12.5 Hz, 2H), 1.64 (s, 1H), 1.32-1.11 (m, 5H) |
| | 58 | (3R)-N-(3-{5-[4-(4-{[(3aR,6aS)-5-{2-[(3R)-2,6-dioxopiperidin-3-yl]-1-oxo-2,3-dihydro-1H-isoindol-5-yl}-octahydropyrrolo[3,4-c]pyrrol-2-yl]methyl}piperidin-1-yl]phenyl]-1H-pyrrolo[2,3-b]pyridine-3-carbonyl}-2,4-difluorophenyl)-3-fluoropyrrolidine-1-sulfonamide | 1H NMR (400 MHz, DMSO-d6) δ 12.90 (s, 1H), 10.95 (s, 1H), 9.86 (s, 1H), 8.64 (d, J = 2.2 Hz, 1H), 8.52 (s, 1H), 8.07 (s, 1H), 7.68-7.54 (m, 3H), 7.51 (d, J = 9.1 Hz, 1H), 7.32-7.23 (m, 1H), 7.05 (d, J = 8.8 Hz, 2H), 6.73 (d, J = 6.9 Hz, 2H), 5.30 (d, J = 53.0 Hz, 1H), 5.05 (dd, J = 13.3, 5.1 Hz, 1H), 4.33 (d, J = 16.8 Hz, 1H), 4.20 (d, J = 16.8 Hz, 1H), 3.77 (d, J = 12.0 Hz, 2H), 3.62-3.55 (m, 2H), 3.48 (s, 1H), 3.21-3.12 (m, 2H), 3.01-2.84 (m, 3H), 2.77-2.66 (m, 2H), 2.59-2.57 (m, 4H), 2.40-2.27 (m, 3H), 2.09-2.06 (m, 2H), 2.03-1.90 (m, 2H), 1.81-1.78 (m, 2H), 1.64 (s, 1H), 1.32-1.11 (m, 5H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 66 | | (3R)-N-(3-{5-[4-(5-{1-[2-(2,6-dioxopiperidin-3-yl)-1-oxo-2,3-dihydro-1H-isoindol-5-yl]piperidin-4-yl}-2,5-diazaspiro[3.4]octan-2-yl)phenyl]-1H-pyrrolo[2,3-b]pyridine-3-carbonyl}-2,4-difluorophenyl)-3-fluoropyrrolidine-1-sulfonamide | 1H NMR (400 MHz, DMSO-d6) δ 12.90 (s, 1H), 10.95 (s, 1H), 9.86 (s, 1H), 8.63-8.51 (m, 2H), 8.07 (s, 1H), 7.64-7.48 (m, 4H), 7.27 (m, 1H), 7.05 (m, 2H), 6.63 (m, 2H), 5.36-5.23 (m, 1H), 5.03 (m, 1H), 4.33-4.16 (m, 2H), 3.90-3.79 (m, 5H), 3.48 (m, 1H), 3.29 (m, 1H), 3.15-3.10 (m, 1H), 2.90-2.80 (m, 4H), 2.60-2.50 (m, 7H), 2.38-2.25 (m, 1H), 2.18-1.96 (m, 4H), 1.69 (m, 5H) |
| 69 | | (3R)-N-(3-{5-[4-(2-{4-[2-(2,6-dioxopiperidin-3-yl)-1-oxo-2,3-dihydro-1H-isoindol-5-yl]piperidin-1-yl}ethoxy)phenyl]-1H-pyrrolo[2,3-b]pyridine-3-carbonyl}-2,4-difluorophenyl)-3-fluoropyrrolidine-1-sulfonamide | 1H NMR (400 MHz, DMSO-d6) δ 12.95 (s, 1H), 10.99 (s, 1H), 9.86 (s, 1H), 8.68-8.58 (s, 2H), 8.11 (s, 1H), 7.70-7.58 (m, 4H), 7.51 (s, 1H), 7.42 (m, 1H), 7.32-7.23 (m, 1H), 7.16-7.09 (m, 2H), 5.37-5.24 (s, 1H), 5.11 (m, 1H), 4.43 (m, 1H), 4.29-4.21 (m, 3H), 3.49-3.35 (m, 3H), 3.14 (m, 2H), 2.92-2.83 (m, 3H), 2.72-2.61 (m, 2H), 2.40 (m, 1H), 2.25 (s, 2H), 2.14-2.05 (m, 2H), 2.04-1.91 (m, 2H), 1.82-1.69 (m, 4H) |

TABLE 3-continued

¹H NMR data of exemplary bifunctional compounds of the present disclosure

| Ex. No. | IUPAC Name | ¹H NMR tabulation |
|---|---|---|
| 76 | (3R)-N-[3-(5-{4-[(3aR,6aS)-5-({2-[(3S)-2,6-dioxopiperidin-3-yl]-1-oxo-2,3-dihydro-1H-isoindol-5-yl}methyl)octahydropyrrolo[3,4-c]pyrrol-2-yl]phenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ12.89 (s, 1H), 10.98 (s, 1H), 9.86 (s, 1H), 8.65-8.64 (m, 2H), 8.07 (s, 1H), 7.68-7.45 (m, 6H), 7.29-7.25 (m, 1H), 6.80-6.77 (d, J = 8.4 Hz, 2H), 5.36-5.23 (m, 1H), 5.13-5.08 (m, 1H), 4.46-4.28 (m, 2H), 3.71 (s, 2H), 3.48-3.37 (m, 5H), 3.31-3.28 (m, 2H), 3.15-3.13 (m, 2H), 2.94-2.80 (m, 3H), 2.69-2.51 (m, 3H), 2.38-2.21 (m, 1H), 2.12-1.91 (m, 4H) |
| 77 | (3R)-N-[3-(5-{4-[(3aR,6aS)-5-({2-[(3R)-2,6-dioxopiperidin-3-yl]-1-oxo-2,3-dihydro-1H-isoindol-5-yl}methyl)octahydropyrrolo[3,4-c]pyrrol-2-yl]phenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ12.89 (s, 1H), 10.98 (s, 1H), 9.86 (s, 1H), 8.65-8.64 (m, 2H), 8.07 (s, 1H), 7.68-7.45 (m, 6H), 7.30-7.25 (m, 1H), 6.80-6.78 (d, J = 8.0 Hz, 2H), 5.36-5.23 (m, 1H), 5.13-5.08 (m, 1H), 4.46-4.28 (m, 2H), 3.72 (s, 2H), 3.48-3.38 (m, 5H), 3.31-3.28 (m, 3H), 2.94-2.80 (m, 3H), 2.69-2.51 (m, 3H), 2.38-2.21 (m, 1H), 2.12-1.91 (m, 3H) |
| 78 | (3R)-N-[3-(5-{4-[(3R)-4-[[2-(2,6-dioxopiperidin-3-yl)-1-oxo-2,3-dihydro-1H-isoindol-5-yl]methyl]-3-(hydroxymethyl)piperazin-1-yl]phenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ12.89 (s, 1H), 10.98 (s, 1H), 9.86 (s, 1H), 8.65-8.64 (m, 2H), 8.07 (s, 1H), 7.68-7.45 (m, 6H), 7.30-7.25 (m, 1H), 6.80-6.78 (d, J = 8.0 Hz, 2H), 5.36-5.23 (m, 1H), 5.13-5.08 (m, 1H), 4.46-4.28 (m, 2H), 3.72 (s, 2H), 3.48-3.38 (m, 5H), 3.31-3.28 (m, 3H), 3.16-3.13 (m, 2H), 2.94-2.80 (m, 3H), 2.69-2.51 (m, 3H), 2.38-2.21 (m, 1H), 2.12-1.91 (m, 3H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 85 | | (3R)-N-[3-(5-{4-[(3aR,6aS)-5-[(1-{2-[(3S)-2,6-dioxopiperidin-3-yl]-1-oxo-2,3-dihydro-1H-isoindol-5-yl}azetidin-3-yl)methyl]-octahydropyrrolo[3,4-c]pyrrol-2-yl]phenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 12.89 (s, 1H), 10.93 (s, 1H), 9.85 (s, 1H), 8.64 (s, 1H), 8.52 (s, 1H), 8.06 (s, 1H), 7.68-7.55 (m, 3H), 7.47 (d, J = 8.4 Hz, 1H), 7.32-7.23 (m, 1H), 6.79 (d, J = 8.6 Hz, 2H), 6.53-6.41 (m, 2H), 5.30 (d, J = 52.0 Hz, 1H), 5.05-5.01 (m, 1H), 4.29 (d, J = 16.6 Hz, 1H), 4.16 (d, J = 16.6 Hz, 1H), 4.07-3.98 (m, 2H), 3.63-3.43 (m, 8H), 3.31-3.24 (m, 1H), 3.14-3.13 (m, 2H), 2.98-2.82 (m, 4H), 2.77-2.58 (m, 5H), 2.41-2.27 (m, 1H), 2.20-2.05 (m, 2H), 2.05-1.88 (m, 2H), 1.24 (s, 1H) |
| 86 | | (3R)-N-[3-(5-{4-[(3aR,6aS)-5-[(1-{2-[(3R)-2,6-dioxopiperidin-3-yl]-1-oxo-2,3-dihydro-1H-isoindol-5-yl}azetidin-3-yl)methyl]-octahydropyrrolo[3,4-c]pyrrol-2-yl]phenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 12.89 (s, 1H), 10.93 (s, 1H), 9.85 (s, 1H), 8.64 (d, J = 2.4 Hz, 1H), 8.52 (s, 1H), 8.06 (s, 1H), 7.68-7.55 (m, 3H), 7.47 (d, J = 8.4 Hz, 1H), 7.32-7.23 (m, 1H), 6.79 (d, J = 8.4 Hz, 2H), 6.53-6.41 (m, 2H), 5.30 (d, J = 52.0 Hz, 1H), 5.05-5.02 (m, 1H), 4.29 (d, J = 16.6 Hz, 1H), 4.16 (d, J = 16.6 Hz, 1H), 4.07-3.98 (m, 2H), 3.63-3.43 (m, 8H), 3.31-3.24 (m, 1H), 3.15-3.13 (m, 2H), 2.98-2.82 (m, 4H), 2.77-2.58 (m, 5H), 2.41-2.27 (m, 1H), 2.20-2.05 (m, 2H), 2.05-1.88 (m, 2H) |

TABLE 3-continued

1H NMR data of exemplary bifunctional compounds of the present disclosure

| Parent Mol Structure | Ex. No. | IUPAC Name | 1H NMR tabulation |
|---|---|---|---|
| | 87 | (3R)-N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}-3-fluorophenyl)-1H-pyrrolo[2,3-b]pyridine-3-carbonyl]-2,4-difluorophenyl}-3-fluoropyrrolidine-1-sulfonamide | 1HNMR (400 MHz, DMSO-d6) δ 12.98 (s, 1H), 11.00 (s, 1H), 9.82 (b, 1H), 8.71 (s, 1H), 8.60 (s, 1H), 8.12 (s, 1H), 7.70-7.51 (m, 6H), 7.44-7.42 (m, 1H), 7.21-7.19 (m, 1H), 5.24 (d, J = 32.0 Hz, 1H), 5.10-5.09 (m, 1H), 4.44-4.30 (m, 2H), 3.52-3.398 (m, 8H), 2.93-2.63 (m, 7H), 2.38-2.32 (m, 2H), 2.22-1.71 (m, 11H), 1.33-1.31 (m, 2H) |
| | 88 | (3R)-N-{3-[5-(4-{4-[(4-{2-[(3R)-2,6-dioxopiperidin-3-yl]-1-oxo-2,3-dihydro-1H-isoindol-5-yl}piperidin-1-yl)methyl]piperidin-1-yl}-3-fluorophenyl)-1H-pyrrolo[2,3-b]pyridine-3-carbonyl]-2,4-difluorophenyl}-3-fluoropyrrolidine-1-sulfonamide | 1HNMR (400 MHz, DMSO-d6) δ 12.98 (s, 1H), 11.00 (s, 1H), 9.82 (b, 1H), 8.70 (s, 1H), 8.60 (s, 1H), 8.12 (s, 1H), 7.70-7.51 (m, 6H), 7.44-7.42 (m, 1H), 7.21-7.19 (m, 1H), 5.24 (d, J = 32.0 Hz, 1H), 5.10-5.09 (m, 1H), 4.44-4.30 (m, 2H), 3.52-3.398 (m, 10H), 2.93-2.63 (m, 6H), 2.38-2.32 (m, 2H), 2.22-1.71 (m, 10H), 1.33-1.31 (m, 2H) |
| | 91 | (3R)-N-[3-(5-{2-[3-({4-[2-(2,6-dioxopiperidin-3-yl)-1-oxo-2,3-dihydro-1H-isoindol-5-yl]piperazin-1-yl}methyl)azetidin-1-yl]pyrimidin-5-yl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 12.99 (s, 1H), 10.95 (s, 1H), 8.74 (s, 2H), 8.65 (d, J = 2.0 Hz, 1H), 8.55 (s, 1H), 8.16 (s, 1H), 8.12 (s, 1H), 7.63 (dt, J = 6.0, 8.8 Hz, 1H), 7.53 (d, J = 8.8 Hz, 1H), 7.27 (t, J = 8.8 Hz, 1H), 7.11-7.05 (m, 2H), 5.48-5.20 (m, 1H), 5.06 (dd, J = 5.2, 13.2 Hz, 1H), 4.40-4.30 (m, 1H), 4.27-4.17 (m, 3H), 3.80 (dd, J = 5.6, 8.8 Hz, 2H), 3.49 (s, 2H), 3.39 (d, J = 11.2 Hz, 5H), 3.07-2.99 (m, 1H), 2.71-2.66 (m, 2H), 2.61 (s, 1H), 2.57 (s, 5H), 2.39 (dt, J = 4.4, 13.2 Hz, 2H), 2.29-2.02 (m, 2H), 2.01-1.95 (m, 1H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 94 | | (3R)-N-[3-(5-{4-[({4-[2-(2,6-dioxopiperidin-3-yl)-1-oxo-2,3-dihydro-1H-isoindol-5-yl]piperidin-1-yl}methyl)piperidin-1-yl]-3,5-difluorophenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 12.97 (s, 1H), 10.99 (s, 1H), 9.82 (s, 1H), 8.73 (s, 1H), 8.72 (s, 1H), 8.13 (s, 1H), 7.67-7.64(m, 2H), 7.22-7.47 (m, 4H), 7.43-7.41 (m, 1H), 5.24 (d, J = 32.0 Hz, 1H), 5.12-5.09 (m, 1H), 4.43-4.30 (m, 2H), 3.41-3.35 (m, 3H), 3.26-3.04 (m, 3H), 2.99-2.85 (m, 1H), 2.79-2.69 (m, 2H), 2.51-2.25 (m, 4H), 2.18-1.98 (m, 5H), 1.82-1.71 (m, 6H), 1.33-1.27(m, 6H) |
| 95 | | (3R)-N-[3-(5-{6-[2-({1-[2-(2,6-dioxopiperidin-3-yl)-1-oxo-2,3-dihydro-1H-isoindol-5-yl]piperidin-4-yl}methyl)-2,8-diazaspiro[4.5]decan-8-yl]pyridin-3-yl]-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 12.94 (s, 1H), 10.95 (s, 1H), 9.85 (s, 1H), 8.66 (s, 1H), 8.61-8.41 (m, 2H), 8.09 (s, 1H), 7.91 (dd, J = 8.8, 2.6 Hz, 1H), 7.71-7.60 (m, 1H), 7.50 (d, J = 8.9 Hz, 1H), 7.26 (td, J = 8.8, 1.6 Hz, 1H), 7.12-6.93 (m, 3H), 5.39-5.18 (m, 1H), 5.05 (dd, J = 13.3, 5.1 Hz, 1H), 4.32 (d, J = 16.8 Hz, 1H), 4.20 (d, J = 16.8 Hz, 1H), 3.88 (d, J = 12.9 Hz, 2H), 3.65 (dd, J = 13.3, 6.0 Hz, 2H), 3.58-3.46 (m, 4H), 3.43-3.38 (m, 2H), 3.29-3.24 (m, 2H), 2.97-2.76 (m, 3H), 2.70-2.55 (m, 3H), 2.45 (s, 2H), 2.40-2.27 (m, 3H), 2.17-2.05 (m, 1H), 2.03-1.93 (m, 1H), 1.82 (d, J = 12.0 Hz, 2H), 1.75-1.49 (m, 7H), 1.27-1.13 (m, 2H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| | 96 | (3R)-N-[3-(5-{2-[2-({1-[2-(2,6-dioxopiperidin-3-yl)-1-oxo-2,3-dihydro-1H-isoindol-5-yl]piperidin-4-yl}methyl)-2,8-diazaspiro[4.5]decan-8-yl]pyrimidin-5-yl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 12.98 (s, 1H), 10.95 (s, 1H), 9.84 (s, 1H), 8.79-8.63 (m, 3H), 8.55 (s, 1H), 8.11 (s, 1H), 7.63 (td, J = 9.0, 5.9 Hz, 1H), 7.57-7.46 (m, 1H), 7.26 (td, J = 8.8, 1.6 Hz, 1H), 7.05 (d, J = 7.8 Hz, 2H), 5.45-5.16 (m, 1H), 5.05 (dd, J = 13.2, 5.1 Hz, 1H), 4.32 (d, J = 16.9 Hz, 1H), 4.20 (d, J = 16.8 Hz, 1H), 3.89 (dd, J = 12.9, 5.8 Hz, 4H), 3.76 (q, J = 7.4, 6.2 Hz, 2H), 3.54-3.47 (m, 1H), 3.44-3.37 (m, 2H), 3.28 (d, J = 9.8 Hz, 1H), 2.99-2.74 (m, 3H), 2.71-2.56 (m, 3H), 2.47 (s, 1H), 2.44-2.35 (m, 1H), 2.35-2.29 (m, 2H), 2.18-2.05 (m, 2H), 1.97 (tt, J = 8.0, 3.7 Hz, 2H), 1.82 (d, J = 12.6 Hz, 2H), 1.68 (t, J = 6.8 Hz, 3H), 1.62-1.48 (m, 3H), 1.32-1.12 (m, 2H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 101 | | (3R)-N-[3-(5-{6-[3-({4-[2-(2,6-dioxopiperidin-3-yl)-1-oxo-2,3-dihydro-1H-isoindol-5-yl]piperazin-1-yl}methyl)azetidin-1-yl]pyridin-3-yl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 12.96 (s, 1H), 10.96 (s, 1H), 9.86 (s, 1H), 8.65 (d, J = 2.0 Hz, 1H), 8.52 (s, 1H), 8.45 (d, J = 2.0 Hz, 1H), 8.14 (s, 1H), 8.10 (s, 1H), 7.93 (dd, J = 2.4, 8.8 Hz, 1H), 7.63 (dt, J = 6.0, 9.2 Hz, 1H), 7.56 (d, J = 8.4 Hz, 1H), 7.28 (t, J = 8.0 Hz, 1H), 7.15-7.04 (m, 2H), 6.54 (d, J = 8.8 Hz, 1H), 5.48-5.17 (m, 1H), 5.06 (dd, J = 5.2, 13.2 Hz, 1H), 4.41-4.30 (m, 1H), 4.27-4.20 (m, 1H), 4.16 (t, J = 8.0 Hz, 2H), 3.74 (s, 2H), 3.49 (s, 2H), 3.41 (s, 4H), 3.30-3.24 (m, 4H), 3.09 (s, 2H), 2.98-2.86 (m, 1H), 2.85-2.71 (m, 2H), 2.60 (d, J = 16.4 Hz, 2H), 2.46-2.36 (m, 1H), 2.19-1.93 (m, 3H) |
| 103 | | (3R)-N-[3-(5-{6-[6-({4-[2-(2,6-dioxopiperidin-3-yl)-1-oxo-2,3-dihydro-1H-isoindol-5-yl]piperidin-1-yl}methyl)-2-azaspiro[3.3]heptan-2-yl]pyridin-3-yl}-1H-pyrrolo[2,3-b]pyridine-3-carbonyl)-2,4-difluorophenyl]-3-fluoropyrrolidine-1-sulfonamide | 1H NMR (300 MHz, DMSO-d6) δ 12.91 (s, 1H), 10.99 (s, 1H), 9.86 (s, 1H), 8.65 (s, 1H), 8.51 (s, 1H), 8.42 (s, 1H), 8.09 (s, 1H), 7.91 (d, J = 2.4 Hz, 1H), 7.68-7.58 (m, 2H), 7.49 (s, 1H), 7.40 (d, J = 8.8 Hz, 1H), 7.27-7.25 (m, 1H), 7.11 (d, J = 8.7 Hz, 2H), 6.49 (d, J = 12.4 Hz, 1H), 5.29 (s, 1H), 5.14-4.08 (m, 1H), 4.46-4.25 (m, 2H), 3.52 (s, 1H), 3.36 (s, 2H), 4.04 (s, 2H), 3.91 (s, 2H), 3.49-3.33 (m, 4H), 3.05-2.82 (m, 4H), 2.69-2.61 (m, 2H), 2.43-2.32 (m, 4H), 2.19-2.09 (m, 4H), 2.01-2.1.91 (m, 4H), 1.81-1.67 (m, 4H), 1.23(s. 1H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| | 104 | (3R)-N-[3-(5-{4-[2-({1-[2-(2,6-dioxopiperidin-3-yl)-1-oxo-2,3-dihydro-1H-isoindol-5-yl]piperidin-4-yl}methyl)-2,8-diazaspiro[4.5]decan-8-yl]-3-fluorophenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 12.98 (s, 1H), 10.95 (s, 1H), 9.63 (s, 1H), 8.70 (s, 1H), 8.59 (s, 1H), 8.10 (s, 1H), 7.67-7.53 (m, 2H), 7.53-7.46 (m, 2H), 7.32-7.12 (m, 2H), 7.05 (d, J = 7.8 Hz, 2H), 5.41-5.17 (m, 1H), 5.05-5.02 (m, 1H), 4.32 (d, J = 16.6 Hz, 1H), 4.20 (d, J = 16.6 Hz, 1H), 3.88-3.86 (m, 2H), 3.52-3.38 (m, 3H), 3.25-3.23 (m, 4H), 2.97-2.75 (m, 3H), 2.64-2.54 (m, 3H), 2.45-2.42 (m, 2H), 2.41-2.26 (m, 3H), 2.16-2.05 (m, 2H), 1.97-1.96 (m, 1H), 1.86-1.77 (m, 2H), 1.77-1.61 (m, 7H), 1.29-1.13 (m, 3H) |
| | 112 | (3R)-N-[3-(5-{4-[(3S)-4-{[2-(2,6-dioxopiperidin-3-yl)-1-oxo-2,3-dihydro-1H-isoindol-5-yl]methyl}-3-(hydroxymethyl)piperazin-1-yl]phenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ12.89 (s, 1H), 10.98 (s, 1H), 9.86 (s, 1H), 8.65-8.64 (m, 2H), 8.07 (s, 1H), 7.68-7.45 (m, 6H), 7.30-7.25 (m, 1H), 6.80-6.78 (d, J = 8.0 Hz, 2H), 5.36-5.23 (m, 1H), 5.13-5.08 (m, 1H), 4.46-4.28 (m, 2H), 3.72 (s, 2H), 3.48-3.38 (m, 5H), 3.31-3.28 (m, 3H), 3.16-3.13 (m, 2H), 2.94-2.80 (m, 3H), 2.69-2.51 (m, 3H), 2.38-2.21 (m, 1H), 2.12-1.91 (m, 3H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 113 | | (3R)-N-[3-{5-{4-[4-(4-{[2-(2,6-dioxopiperidin-3-yl)-1-oxo-2,3-dihydro-1H-isoindol-5-yl]oxy}butyl)piperazin-1-yl]-3-fluorophenyl}-1H-pyrrolo[2,3-b]pyridine-3-carbonyl]-2,4-difluorophenyl]-3-fluoropyrrolidine-1-sulfonamide | 1H NMR: (400 MHz, DMSO-d6, ppm) δ 12.98 (br, 1H), 10.97 (br, 1H), 8.70 (s, 1H), 8.59 (s, 1H), 8.11 (s, 1H), 7.64-7.49 (m, 4H), 7.29-7.27 (t, J = 8.4 Hz, 1H), 7.18-7.13 (m, 2H), 7.08-7.05 (d, J = 10.4 Hz, 1H), 5.36-5.23 (m, 1H), 5.10-5.05 (m, 1H), 4.41-4.37 (d, J = 17.2 Hz, 1H), 4.29-4.25 (d, J = 17.2 Hz, 1H), 4.13-4.09 (m, 2H), 3.48 (s, 1H), 3.40-3.39 (m, 2H), 3.28-3.26 (m, 1H), 3.10 (s, 4H), 2.94-2.87 (m, 1H), 2.61-2.56 (m, 5H), 2.46-2.33 (m, 3H), 2.11-2.07 (m, 2H), 1.99-1.96 (m, 2H), 1.82-1.78 (m, 2H), 1.66-1.65 (m, 2H) |
| 114 | | (3R)-N-(3-{5-{4-(2-{6-[2-(2,6-dioxopiperidin-3-yl)-1-oxo-2,3-dihydro-1H-isoindol-5-yl]-2,6-diazaspiro[3.3]heptan-2-yl}ethoxy)-1H-pyrrolo[2,3-b]pyridine-3-fluorophenyl]-1H-pyrrolo[2,3-b]pyridine-3-carbonyl]-2,4-difluorophenyl)-3-fluoropyrrolidine-1-sulfonamide | 1H NMR (400 MHz, DMSO-d6) δ 12.97 (s, 1H), 10.94 (s, 1H), 9.87 (s, 1H), 8.70-8.60 (s, 2H), 8.12 (s, 1H), 7.72-7.58 (m, 2H), 7.51 (m, 2H), 7.35-7.23 (m, 2H), 6.53-6.49 (m, 2H), 5.37-5.24 (s, 1H), 5.04 (m, 1H), 4.31-4.12 (m, 5H), 4.01 (s, 4H), 3.50 (m, 5H), 3.40 (m, 3H), 2.89 (m, 3H), 2.59 (m, 1H), 2.39 (m, 1H), 2.12 (s, 1H), 2.08-1.97 (m, 1H) |

TABLE 3-continued

1H NMR data of exemplary bifunctional compounds of the present disclosure

| Ex. No. | Parent Mol Structure | IUPAC Name | 1H NMR tabulation |
|---|---|---|---|
| 117 | | (3R)-N-(3-{5-[2-(2-{6-[2-(2,6-dioxopiperidin-3-yl)-1-oxo-2,3-dihydro-1H-isoindol-5-yl]-2,6-diazaspiro[3.3]heptan-5-yl}ethoxy)pyrimidin-5-yl]-1H-pyrrolo[2,3-b]pyridine-3-carbonyl}-2,4-difluorophenyl)-3-fluoropyrrolidine-1-sulfonamide | 1H NMR (400 MHz, DMSO-d6) δ 13.06 (s, 1H), 10.94 (s, 1H), 9.88 (s, 1H), 9.01 (m, 2H), 8.74-8.69 (s, 2H), 8.16 (s, 1H), 7.63 (m, 1H), 7.49 (m, 1H), 7.28 (m, 1H), 6.53-6.49 (m, 2H), 5.38-5.24 (m, 1H), 5.03 (m, 1H), 4.37-4.31 (m, 3H), 4.18 (m, 1H), 4.01 (s, 4H), 3.65-3.53 (m, 5H), 3.53-3.47 (m, 3H), 3.29 (m, 1H), 2.91 (m, 3H), 2.58 (m, 1H), 2.41-2.30 (m, 1H), 2.15-2.06 (m, 1H), 1.96 (m, 1H) |
| 120 | | (3R)-N-[3-(5-{6-[4-(4-{[2-(2,6-dioxopiperidin-3-yl)-1-oxo-2,3-dihydro-1H-isoindol-5-yl]oxy}butyl)piperazin-1-yl]pyridin-3-yl}-1H-pyrrolo[2,3-b]pyridine-3-carbonyl)-2,4-difluorophenyl]-3-fluoropyrrolidine-1-sulfonamide | 1H NMR: (400 MHz, DMSO-d6, ppm) δ 12.96 (br, 1H), 10.97 (br, 1H), 9.87 (br, 1H), 8.66 (s, 1H), 8.53-8.48 (m, 2H), 8.09 (s, 1H), 7.94-7.92 (d, J = 8.4 Hz, 1H), 7.64-7.62 (m, 2H), 7.29-7.25 (m, 1H), 7.18 (s, 1H), 7.07-7.05 (d, J = 8.4 Hz, 1H), 6.97-6.95 (d, J = 8.8 Hz, 1H), 5.36-5.23 (m, 1H), 5.10-5.05 (m, 1H), 4.41-4.37 (d, J = 17.2 Hz, 1H), 4.29-4.24 (d, J = 17.2 Hz, 1H), 4.12-4.09 (m, 2H), 3.56-3.53 (m, 4H), 3.50 (s, 2H), 3.48-3.40 (m, 4H), 2.91-2.88 (m, 1H), 2.61-2.56 (m, 1H), 2.43-2.36 (m, 4H), 2.11-2.07 (m, 2H), 1.99-1.96 (m, 2H), 1.82-1.78 (m, 2H), 1.66-1.63 (m, 2H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 121 | | (3R)-N-[3-(5-{2-[4-(4-{[2-(2,6-dioxopiperidin-3-yl)-1-oxo-2,3-dihydro-1H-isoindol-5-yl]oxy}butyl)piperazin-1-yl]pyrimidin-5-yl}-1H-pyrrolo[2,3-b]pyridine-3-carbonyl)-2,4-difluorophenyl]-3-fluoropyrrolidine-1-sulfonamide | 1H NMR: (400 MHz, DMSO-d6, ppm) δ 12.99 (br, 1H), 10.97 (br, 1H), 9.87 (br, 1H), 8.76 (s, 2H), 8.66 (s, 1H), 8.56 (s, 1H), 8.11 (s, 1H), 7.64-7.62 (m, 2H), 7.27-7.25 (m, 1H), 7.18 (s, 1H), 7.08-7.06 (d, J = 8 Hz, 1H), 5.36-5.24 (m, 1H), 5.10-5.05 (m, 1H), 4.41-4.37 (d, J = 17.2 Hz, 1H), 4.29-4.25 (d, J = 17.2 Hz, 1H), 4.13-4.10 (m, 2H), 3.81 (m, 4H), 3.48 (s, 1H), 3.42-3.40 (m, 2H), 3.29-3.28 (m, 3H), 2.95-2.86 (m, 1H), 2.61-2.58 (m, 1H), 2.43-2.33 (m, 4H), 2.12-2.08 (m, 2H), 2.00-1.97 (m, 2H), 1.84-1.80 (m, 2H), 1.68-1.64 (m, 2H) |
| 135 | | (3R)-N-[3-(5-{4-[4-(3-{4-[2-(2,6-dioxopiperidin-3-yl)-1-oxo-2,3-dihydro-1H-isoindol-5-yl]piperazin-1-yl}propyl)piperidin-1-yl]phenyl}-1H-pyrrolo[2,3-b]pyridine-3-carbonyl)-2,4-difluorophenyl]-3-fluoropyrrolidine-1-sulfonamide | 1H NMR: (400 MHz, DMSO-d6) δ 12.90 (s, 1H), 10.94 (s, 1H), 9.85 (s, 1H), 8.64 (s, 1H), 8.53 (s, 1H), 8.06 (s, 1H), 7.59-7.51 (m, 4H), 7.26 (s, 1H), 7.07 (s, 4H), 5.30 (d, J = 13.2 Hz, 1H), 5.096-5.03 (m, 1H), 4.35-4.18 (q, 2H), 3.77-3.76 (m, 2H), 3.77-3.39 (s, 4H), 2.89-2.86 (m, 1H), 2.73-2.70 (m, 2H), 2.68-2.60 (m, 4H), 2.59-2.50 (m, 4H), 2.33-2.20 (m, 3H), 2.11-1.96 (m, 4H), 1.79-1.76 (m, 2H), 1.52-1.43 (m, 3H), 1.26-1.24 (m, 4H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 139 | | (3R)-N-[3-(5-{4-[4-(3-{[2-(2,6-dioxopiperidin-3-yl)-1-oxo-2,3-dihydro-1H-isoindol-5-yl]oxy}propoxy)piperidin-1-yl]phenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 12.91 (s, 1H), 10.97 (s, 1H), 9.86 (s, 1H), 8.65 (s, 1H), 8.55 (s, 1H), 8.07 (s, 1H), 7.64-7.56 (m, 4H), 7.27-7.24 (m, 1H), 7.19 (s, 1H), 7.08-7.04 (m, 3H), 5.40-5.23 (d, J = 53.8 Hz, 1H), 5.19-5.03 (m, 1H), 4.36-4.29 (q, 2H), 4.17-4.14 (m, 2H), 3.65-3.62 (m, 6H), 3.34-3.31 (m, 2H), 3.08-2.97 (m, 3H), 2.51-2.50 (m, 1H), 2.33-2.30 (m, 1H), 2.20-2.02 (m, 2H), 2.01-1.98 (m, 6H), 1.66-1.62 (m, 2H) |
| 141 | | (3R)-N-(3-{5-[6-(6-{3-[2-(2,6-dioxopiperidin-3-yl)-1-oxo-2,3-dihydro-1H-isoindol-5-yl]propyl}-2,6-diazaspiro[3.3]heptan-2-yl]pyridin-3-yl]-1H-pyrrolo[2,3-b]pyridine-3-carbonyl)-2,4-difluorophenyl)-3-fluoropyrrolidine-1-sulfonamide | 1H NMR (400 MHz, DMSO-d6) δ 12.98 (s, 1H), 10.97 (s, 1H), 9.85 (b, 1H), 8.62 (s, 1H), 8.50 (s, 1H), 8.43 (s, 1H), 8.08 (s, 1H), 7.90 (d, J = 8.8 Hz, 1H), 7.65-7.63 (m, 2H), 7.44 (s, 1H), 7.26 (d, J = 7.6 Hz, 1H), 7.25-7.23 (m, 1H), 6.51 (d, J = 8.8 Hz, 1H), 5.30 (d, J = 13.2 Hz, 1H), 5.06-5.03 (m, 1H), 4.45-4.28 (q, 2H), 4.07 (s, 4H), 3.50 (s, 1H), 3.47-3.45 (m, 6H), 2.91-2.88 (m, 1H), 2.70-2.67 (m, 2H), 2.62-2.58 (m, 1H), 2.44-2.35 (m, 3H), 2.11-1.99 (m, 3H), 1.65-1.62 (m, 2H), 1.23 (s, 1H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 146 | | (3R)-N-{3-[5-(4-{[4-({1-[2-(2,6-dioxopiperidin-3-yl)-1-oxo-2,3-dihydro-1H-isoindol-5-yl]piperidin-4-yl}methyl)piperazin-1-yl]methyl}phenyl)-1H-pyrrolo[2,3-b]pyridine-3-carbonyl]-2,4-difluorophenyl}-3-fluoropyrrolidine-1-sulfonamide | 1H NMR (400 MHz, DMSO-d6, ppm): δ 12.97 (s, 1H), 10.93 (s, 1H), 9.84 (s, 1H), 8.72 (s, 1H), 8.61 (s, 1H), 8.12 (s, 1H), 7.75-7.58 (m, 3H), 7.47 (dd, J = 20.4, 8.3 Hz, 3H), 7.27 (td, J = 8.8, 1.6 Hz, 1H), 7.04 (d, J = 7.7 Hz, 2H), 5.44-5.18 (m, 1H), 5.04 (dd, J = 13.2, 5.1 Hz, 1H), 4.38-4.13 (m, 2H), 3.86 (d, J = 12.5 Hz, 2H), 3.62-3.45 (m, 3H), 3.43-3.35 (m, 3H), 3.02-2.75 (m, 3H), 2.72-2.53 (m, 2H), 2.48-2.29 (m, 7H), 2.17-2.05 (m, 3H), 1.97-1.96 (m, 2H), 1.79-1.76 (m, 3H), 1.30-1.05 (m, 3H) |
| 147 | | (3R)-N-(3-{5-[2-(6-{3-[2-(2,6-dioxopiperidin-3-yl)-1-oxo-2,3-dihydro-1H-isoindol-5-yl]propyl}-2,6-diazaspiro[3.3]heptan-2-yl]pyrimidin-5-yl}-1H-pyrrolo[2,3-b]pyridine-3-carbonyl)-2,4-difluorophenyl}-3-fluoropyrrolidine-1-sulfonamide | 1H NMR (400 MHz, DMSO-d6) δ 13.00 (s, 1H), 10.98 (s, 1H), 8.74 (s, 2H), 8.64 (s, 1H), 8.54 (s, 1H), 8.11 (s, 1H), 7.67-7.61 (m, 2H), 7.37 (s, 1H), 7.26 (d, J = 8.4 Hz, 1H), 7.25-7.23 (m, 1H), 5.30 (d, J = 13.2 Hz, 1H), 5.06-5.03 (m, 1H), 4.45-4.28 (q, 2H), 4.07 (s, 4H), 3.47-3.45 (m, 8H), 2.96-2.92 (m, 1H), 2.70-2.67 (m, 3H), 2.40-2.38 (m, 3H), 2.22-1.99 (m, 3H), 1.65-1.62 (m, 2H), 1.23-1.21 (m, 1H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 152 | | (3R)-N-(3-{5-[4-(2-{4-[2-(2,6-dioxopiperidin-3-yl)-6-fluoro-1-oxo-2,3-dihydro-1H-isoindol-5-yl]piperazin-1-yl}ethyl)phenyl]-1H-pyrrolo[2,3-b]pyridine-3-carbonyl}-2,4-difluorophenyl)-3-fluoropyrrolidine-1-sulfonamide | 1H NMR (400 MHz, DMSO-d6, ppm): δ 12.98 (s, 1H), 10.97 (s, 1H), 9.85 (s, 1H), 8.71 (s, 1H), 8.61 (s, 1H), 8.13 (s, 1H), 7.70-7.62 (m, 3H), 7.46-7.42 (m, 3H), 7.29-7.27 (m, 2H), 5.22 (d, J = 13.2 Hz, 1H), 5.09-5.06 (m, 1H), 4.40-4.24 (m, 2H), 3.49 (s, 1H), 3.42-3.41 (m, 2H), 3.17 (s, 4H), 2.95-2.91 (m, 4H), 2.68-2.61 (m, 5H), 2.38-2.34 (m, 1H), 2.12-1.98 (m, 4H), 1.20-1.18 (m, 1H) |
| 153 | | (3R)-N-{3-[5-(2-{4-[({1-[2-(2,6-dioxopiperidin-3-yl)-1-oxo-2,3-dihydro-1H-isoindol-5-yl]piperidin-4-yl}methyl)piperazin-1-yl]methyl}pyrimidin-5-yl)-1H-pyrrolo[2,3-b]pyridine-3-carbonyl]-2,4-difluorophenyl}-3-fluoropyrrolidine-1-sulfonamide | 1H NMR (400 MHz, DMSO-d6) δ 13.08 (s, 1H), 10.93 (s, 1H), 9.83 (s, 1H), 9.18 (s, 2H), 8.81 (s, 1H), 8.74 (s, 1H), 8.17 (s, 1H), 7.63 (d, J = 8.6 Hz, 1H), 7.49 (d, J = 8.4 Hz, 1H), 7.27 (t, J = 8.7 Hz, 1H), 7.03 (d, J = 8.5 Hz, 2H), 5.33 (d, J = 13.2 Hz, 1H), 5.03 (dd, J = 13.3, 5.1 Hz, 1H), 4.31 (d, J = 16.9 Hz, 1H), 4.19 (d, J = 16.7 Hz, 1H), 3.86-3.79 (m, 4H), 3.54 (s, 1H), 3.31 (s, 3H), 2.90-2.81 (m, 3H), 2.59-2.57 (m, 5H), 2.41-2.38 (m, 4H), 2.20-2.05 (m, 3H), 1.97-1.95 (m, 2H), 1.78-1.76 (m, 3H), 1.24-1.15 (m, 3H) |

| Ex. No. | IUPAC Name | ¹H NMR tabulation |
|---|---|---|
| 154 | (3R)-N-{3-[5-(4-{[1-({1-[2-(2,6-dioxopiperidin-3-yl)-1-oxo-2,3-dihydro-1H-isoindol-5-yl]piperidin-4-yl}methyl)piperidin-4-yl]methyl}phenyl)-1H-pyrrolo[2,3-b]pyridine-3-carbonyl]-2,4-difluorophenyl}-3-fluoropyrrolidine-1-sulfonamide | 1H NMR (400 MHz, DMSO-d6) δ 12.95 (s, 1H), 10.93 (s, 1H), 9.79 (s, 1H), 8.70-8.60 (s, 2H), 8.11 (s, 1H), 7.70-7.58 (m, 3H), 7.50 (m, 1H), 7.32-7.26 (m, 3H), 7.04 (m, 2H), 5.36-5.22 (m, 1H), 5.04 (m, 1H), 4.32-4.20 (m, 2H), 3.86 (m, 2H), 3.54-3.46 (m, 3H), 3.43-3.37 (m, 2H), 2.87 (m, 5H), 2.63-2.55 (m, 3H), 2.41-2.32 (m, 1H), 2.19-2.06 (m, 3H), 1.94 (s, 3H), 1.89-1.77 (m, 3H), 1.61 (m, 3H), 1.28-1.14 (m, 4H) |
| 157 | (3R)-N-[3-(5-{4-[4-({4-[2-(2,6-dioxopiperidin-3-yl)-6-fluoro-1-oxo-2,3-dihydro-1H-isoindol-5-yl]piperidin-1-yl]methyl)piperidin-1-yl]phenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ12.89 (s, 1H), 10.98 (s, 1H), 9.86 (s, 1H), 8.65-8.64 (m, 2H), 8.07 (s, 1H), 7.68-7.45 (m, 6H), 7.30-7.25 (m, 1H), 6.80-6.78 (d, J = 8.0 Hz, 2H), 5.36-5.23 (m, 1H), 5.13-5.08 (m, 1H), 4.46-4.28 (m, 2H), 3.72 (s, 2H), 3.48-3.38 (m, 5H), 3.31-3.28 (m, 3H), 3.16-3.13 (m, 2H), 2.94-2.80 (m, 3H), 2.69-2.51 (m, 3H), 2.38-2.21 (m, 1H), 2.12-1.91 (m, 3H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 158 | | (3R)-N-(3-{5-[6-(2-{6-[2-(2,6-dioxopiperidin-3-yl)-1-oxo-2,3-dihydro-1H-isoindol-5-yl]-2,6-diazaspiro[3.3]heptan-2-yl}ethoxy)pyridin-3-yl]-1H-pyrrolo[2,3-b]pyridine-3-carbonyl}-2,4-difluorophenyl)-3-fluoropyrrolidine-1-sulfonamide | 1H NMR (400 MHz, DMSO-d6) δ 8.64 (s, 1H), 8.52 (s, 1H), 8.47 (s, 1H), 8.06 (dd, J = 8.6, 2.6 Hz, 1H), 7.99 (s, 1H), 7.57-7.43 (m, 2H), 7.04-6.94 (m, 1H), 6.94 (d, J = 8.6 Hz, 1H), 6.54-6.44 (m, 2H), 5.16 (d, J = 13.2 Hz, 1H), 4.97 (dd, J = 13.3, 5.1 Hz, 1H), 4.35-4.24 (m, 3H), 4.17 (d, J = 17.1 Hz, 1H), 3.97 (s, 4H), 3.41 (s, 4H), 3.39-3.09 (m, 4H), 2.85-2.81 (m, 2H), 2.77-2.76 (m, 1H), 2.63-2.54 (m, 1H), 2.41-2.25 (m, 1H), 2.09-1.99 (m, 1H), 1.99-1.92 (m, 2H) |
| 162 | | (3R)-N-{3-[5-(4-{1-[4-({1-[2-(2,6-dioxopiperidin-3-yl)-1-oxo-2,3-dihydro-1H-isoindol-5-yl]piperidin-4-yl}methyl)piperazin-1-yl]cyclopropyl}phenyl)-1H-pyrrolo[2,3-b]pyridine-3-carbonyl]-2,4-difluorophenyl}-3-fluoropyrrolidine-1-sulfonamide | 1H NMR (300 MHz, DMSO-d6) δ 12.98 (s, 1H), 10.91 (s, 1H), 9.83 (s, 1H), 8.71 (m, 1H), 8.61 (s, 1H), 8.12 (s, 1H), 7.71-7.63 (m, 3H), 7.46-7.40 (m, 3H), 7.33-7.20 (m, 1H), 6.97 (m, 2H), 5.37-5.20 (s, 1H), 5.01 (m, 1H), 4.28-4.15 (m, 2H), 3.79 (m, 2H), 3.57-3.39 (m, 4H), 3.29 (m, 2H), 2.91-2.68 (m, 4H), 2.59 (s, 2H), 2.42-2.23 (m, 6H), 2.08-1.89 (m, 5H), 1.67 (m, 3H), 1.08 (m, 2H), 0.89-0.80 (s, 4H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 163 | | (3R)-N-[3-(5-{4-[4-({4-[2-(2,6-dioxopiperidin-3-yl)-7-methoxy-1-oxo-2,3-dihydro-1H-isoindol-5-yl]piperidin-1-yl}methyl)piperidin-1-yl]-3-fluorophenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 12.96 (s, 1H), 10.95 (s, 1H), 9.83 (s, 1H), 8.70 (d, J = 2.2 Hz, 1H), 8.59 (s, 1H), 8.11 (s, 1H), 7.72-7.46 (m, 3H), 7.22 (d, J = 41.3, 9.1 Hz, 2H), 7.02 (s, 1H), 6.93 (s, 1H), 5.44-5.17 (m, 1H), 5.02 (dd, J = 13.3, 5.1 Hz, 1H), 4.33 (d, J = 17.2 Hz, 1H), 4.19 (d, J = 17.2 Hz, 1H), 3.88 (s, 3H), 3.52-3.39 (m, 5H), 3.02 (d, J = 10.8 Hz, 2H), 2.97-2.86 (m, 1H), 2.73 (t, J = 11.5 Hz, 2H), 2.66-2.54 (m, 2H), 2.43-2.23 (m, 3H), 2.19-1.91 (m, 5H), 1.90-1.65 (m, 7H), 1.40-1.27 (m, 2H) |
| 164 | | (3R)-N-[3-(5-{6-[4-[2-(2,6-dioxopiperidin-3-yl)-7-methoxy-1-oxo-2,3-dihydro-1H-isoindol-5-yl]piperidin-1-yl}methyl)piperidin-1-yl]-1H-pyrrolo[2,3-b]pyridin-3-yl]-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 12.94 (s, 1H), 10.95 (s, 1H), 9.83 (s, 1H), 8.66 (d, J = 2.2 Hz, 1H), 8.56-8.45 (m, 2H), 7.63 (td, J = 9.0, 5.9 Hz, 1H), 7.33-7.22 (m, 1H), 7.08-6.83 (m, 3H), 5.30 (d, J = 51.9 Hz, 1H), 5.02 (dd, J = 13.3, 5.1 Hz, 1H), 4.54-4.29 (m, 3H), 4.19 (d, J = 17.4 Hz, 1H), 3.88 (s, 3H), 3.49 (d, J = 2.3 Hz, 1H), 3.43-3.37 (m, 2H), 3.30-3.24 (m, 1H), 3.01 (d, J = 10.7 Hz, 2H), 2.95-2.80 (m, 3H), 2.72-2.55 (m, 2H), 2.42-2.29 (m, 1H), 2.23 (d, J = 6.6 Hz, 2H), 2.18-1.92 (m, 5H), 1.90-1.68 (m, 7H), 1.26-1.07 (m, 2H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| 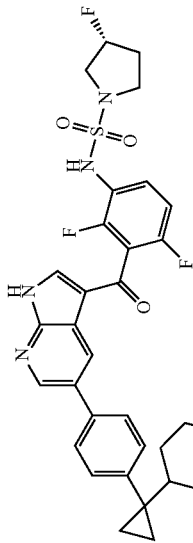 | 174 | (3R)-N-{3-[5-(4-{1-[1-({1-[2-(2,6-dioxopiperidin-3-yl)-1-oxo-2,3-dihydro-1H-isoindol-5-yl]piperidin-4-yl}methyl)piperidin-4-yl]cyclopropyl}phenyl)-1H-pyrrolo[2,3-b]pyridine-3-carbonyl]-2,4-difluorophenyl}-3-fluoropyrrolidine-1-sulfonamide | 1H NMR (400 MHz, DMSO-d6) δ 8.68 (s, 1H), 8.57 (s, 1H), 8.05 (s, 1H), 7.47 (s, 1H), 7.68-7.56 (m, 3H), 7.47 (d, J = 8.8 Hz, 1H), 7.38 (d, J = 7.8 Hz, 2H), 7.23 (t, J = 8.8 Hz, 1H), 6.99 (s, 2H), 5.19 (d, J = 13.2 Hz, 1H), 4.97 (dd, J = 13.3, 5.1 Hz, 1H), 4.29 (d, J = 16.8 Hz, 1H), 4.16 (d, J = 16.8 Hz, 1H), 3.79 (d, J = 12.6 Hz, 2H), 3.45 (d, J = 2.4 Hz, 1H), 3.41-3.31 (m, 2H), 3.25-3.23 (m, 1H), 2.93-2.91 (m, 2H), 2.80-2.78 (m, 3H), 2.63-2.54 (m, 1H), 2.40-2.25 (m, 1H), 2.19-2.07 (m, 3H), 2.00-1.89 (m, 3H), 1.73-1.67 (m, 4H), 1.21 (s, 4H), 1.15-1.04 (m, 2H), 0.92-0.91 (m, 1H), 0.90-0.79 (m, 1H), 0.70 (d, J = 12.0 Hz, 3H) |
| 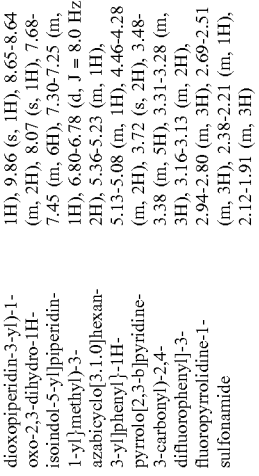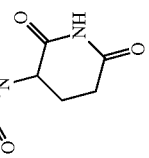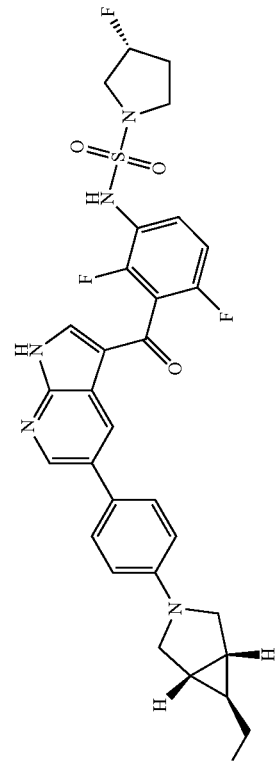 | 179 | (3R)-N-[3-(5-{4-[((1R,5S,6S)-6-({4-[2-(2,6-dioxopiperidin-3-yl)-1-oxo-2,3-dihydro-1H-isoindol-5-yl]piperidin-1-yl}methyl)-3-azabicyclo[3.1.0]hexan-3-yl]phenyl}-1H-pyrrolo[2,3-b]pyridine-3-carbonyl]-2,4-difluorophenyl]-3-fluoropyrrolidine-1-sulfonamide | 1H NMR (400 MHz, DMSO-d6) δ12.89 (s, 1H), 10.98 (s, 1H), 9.86 (s, 1H), 8.65-8.64 (m, 2H), 8.07 (s, 1H), 7.68-7.45 (m, 6H), 7.30-7.25 (m, 1H), 6.80-6.78 (d, J = 8.0 Hz, 2H), 5.36-5.23 (m, 1H), 5.13-5.08 (m, 2H), 4.46-4.28 (m, 2H), 3.72 (s, 2H), 3.48-3.38 (m, 5H), 3.31-3.28 (m, 3H), 3.16-3.13 (m, 2H), 2.94-2.80 (m, 3H), 2.69-2.51 (m, 3H), 2.38-2.21 (m, 1H), 2.12-1.91 (m, 3H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 180 | | (3R)-N-[3-(5-{4-[(1R,3S,5S)-3-({4-[2-(2,6-dioxopiperidin-3-yl)-1-oxo-2,3-dihydro-1H-isoindol-5-yl]piperidin-1-yl}methyl)-8-azabicyclo[3.2.1]octan-8-yl]phenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 12.86 (s, 1H), 10.96 (s, 1H), 9.79 (s, 1H), 8.65 (s, 1H), 8.50 (s, 1H), 8.05 (s, 1H), 7.67-7.56 (m, 2H), 7.56 (d, J = 8.4 Hz, 2H), 7.47 (s, 1H), 7.38 (dd, J = 8.0, 1.4 Hz, 1H), 7.30-7.21 (m, 1H), 6.91 (d, J = 8.4 Hz, 2H), 5.21 (d, J = 13.2 Hz, 1H), 5.09 (dd, J = 13.3, 5.1 Hz, 1H), 4.41-4.23 (m, 4H), 3.40-3.34 (m, 1H), 2.94 (s, 2H), 2.96-2.84 (m, 3H), 2.63-2.55 (m, 2H), 2.45-2.32 (m, 1H), 2.25-2.21 (m, 2H), 2.09-2.07 (m, 1H), 2.06-1.93 (m, 8H), 1.84-1.82 (m, 2H), 1.73-1.68 (m, 4H), 1.67-1.65 (m, 2H), 1.43-1.40 (m, 2H) |
| 188 | | (3R)-N-[3-(5-{4-[(1R,3R,5S)-3-({4-[2-(2,6-dioxopiperidin-3-yl)-1-oxo-2,3-dihydro-1H-isoindol-5-yl]piperidin-1-yl}methyl)-8-azabicyclo[3.2.1]octan-8-yl]phenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 12.87 (s, 1H), 10.97 (d, J = 2.4 Hz, 1H), 8.65 (d, J = 2.4 Hz, 1H), 8.50 (s, 1H), 8.05 (s, 1H), 7.67-7.56 (m, 2H), 7.56 (d, J = 8.4 Hz, 2H), 7.47 (s, 1H), 7.38 (dd, J = 8.0, 1.4 Hz, 1H), 7.30-7.21 (m, 1H), 6.91 (d, J = 8.4 Hz, 2H), 5.21 (d, J = 3.8 Hz, 1H), 5.09 (dd, J = 13.2, 5.1 Hz, 1H), 4.41 (d, J = 17.2 Hz, 1H), 4.34-4.23 (m, 3H), 3.40-3.34 (m, 3H), 2.94 (s, 2H), 2.96-2.84 (m, 1H), 2.63-2.55 (m, 2H), 2.45-2.32 (m, 1H), 2.25 (s, 1H), 2.10-2.09 (m, 1H), 2.06-1.93 (m, 7H), 1.85-1.83 (m, 2H), 1.73 (s, 4H), 1.76-1.75 (m, 2H), 1.49-1.41 (m, 2H), 1.41-1.40 (m, 1H) |

TABLE 3-continued

¹H NMR data of exemplary bifunctional compounds of the present disclosure

| Ex. No. | IUPAC Name | ¹H NMR tabulation |
|---|---|---|
| 192 | (3R)-N-{3-[5-(4-{[4-({1-[2-(2,6-dioxopiperidin-3-yl)-1-oxo-2,3-dihydro-1H-isoindol-5-yl]azetidin-3-yl}methyl)piperazin-1-yl]methyl}phenyl)-1H-pyrrolo[2,3-b]pyridine-3-carbonyl]-2,4-difluorophenyl}-3-fluoropyrrolidine-1-sulfonamide | 1H NMR (400 MHz, DMSO-d6) δ 12.98 (s, 1H), 10.94 (s, 1H), 9.85 (s, 1H), 8.72 (s, 1H), 8.62 (s, 1H), 8.13 (s, 1H), 7.72 (d, J = 7.7 Hz, 2H), 7.69-7.59 (m, 1H), 7.53-7.42 (m, 3H), 7.28 (t, J = 8.8 Hz, 1H), 6.55-6.43 (m, 2H), 5.31 (d, J = 53.2 Hz, 1H), 5.04 (dd, J = 13.2, 5.1 Hz, 1H), 4.30 (d, J = 16.8 Hz, 1H), 4.18 (d, J = 16.8 Hz, 1H), 4.02 (t, J = 7.8 Hz, 2H), 3.56 (d, J = 8.9 Hz, 4H), 3.49 (s, 1H), 3.44-3.37 (m, 2H), 3.30-3.25 (m, 1H), 3.08-2.82 (m, 2H), 2.65-2.55 (m, 4H), 2.45 (s, 5H), 2.38-2.28 (m, 2H), 2.19-2.06 (m, 2H), 2.03-1.87 (m, 2H) |
| 193 | (3R)-N-{3-[5-(2-{4-({1-[2-(2,6-dioxopiperidin-3-yl)-1-oxo-2,3-dihydro-1H-isoindol-5-yl]azetidin-3-yl}methyl)piperazin-1-yl]methyl}pyrimidin-5-yl)-1H-pyrrolo[2,3-b]pyridine-3-carbonyl]-2,4-difluorophenyl}-3-fluoropyrrolidine-1-sulfonamide | 1H NMR (400 MHz, DMSO-d6) δ 8.68 (s, 1H), 8.57 (s, 1H), 8.05 (s, 1H), 7.68-7.56 (m, 3H), 7.47 (d, J = 8.8 Hz, 1H), 7.38 (d, J = 7.8 Hz, 2H), 7.23 (t, J = 8.8 Hz, 1H), 6.99 (s, 2H), 5.19 (d, J = 13.2 Hz, 1H), 4.97 (dd, J = 13.3, 5.1 Hz, 1H), 4.29 (d, J = 16.8 Hz, 1H), 4.16 (d, J = 16.8 Hz, 1H), 3.79 (d, J = 12.6 Hz, 2H), 3.45 (d, J = 2.4 Hz, 1H), 3.41-3.31 (m, 2H), 3.25-3.23 (m, 1H), 2.93-2.91 (m, 2H), 2.80-2.78 (m, 3H), 2.63-2.54 (m, 1H), 2.40-2.25 (m, 1H), 2.19-2.07 (m, 3H), 2.00-1.89 (m, 3H), 1.73-1.67 (m, 4H), 1.21 (s, 4H), 1.15-1.04 (m, 2H), 0.92-0.91 (m, 1H), 0.90-0.79 (m, 1H), 0.70 (d, J = 12.0 Hz, 3H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 194 | | (3R)-N-{3-[5-(2-{[1-({1-[2-(2,6-dioxopiperidin-3-yl)-1-oxo-2,3-dihydro-1H-isoindol-5-yl]azetidin-3-yl}methyl)piperidin-4-yl]methyl}pyrimidin-5-yl)-1H-pyrrolo[2,3-b]pyridine-3-carbonyl]-2,4-difluorophenyl}-3-fluoropyrrolidine-1-sulfonamide | ¹H NMR (400 MHz, DMSO-d6) δ 8.68 (s, 1H), 8.57 (s, 1H), 8.05 (s, 1H), 7.68-7.56 (m, 3H), 7.47 (d, J = 8.8 Hz, 1H), 7.38 (d, J = 7.8 Hz, 2H), 7.23 (t, J = 8.8 Hz, 1H), 6.99 (s, 2H), 5.19 (d, J = 13.2 Hz, 1H), 4.97 (dd, J = 13.3, 5.1 Hz, 1H), 4.29 (d, J = 16.8 Hz, 1H), 4.16 (d, J = 16.8 Hz, 1H), 3.79 (d, J = 12.6 Hz, 2H), 3.45 (d, J = 2.4 Hz, 1H), 3.41-3.31 (m, 2H), 3.25-3.23 (m, 1H), 2.93-2.91 (m, 2H), 2.80-2.78 (m, 3H), 2.63-2.54 (m, 1H), 2.40-2.25 (m, 1H), 2.19-2.07 (m, 3H), 2.00-1.89 (m, 3H), 1.73-1.67 (m, 4H), 1.21 (s, 4H), 1.15-1.04 (m, 2H), 0.92-0.91 (m, 1H), 0.90-0.79 (m, 1H), 0.70 (d, J = 12.0 Hz, 3H) |
| 199 | | (3R)-N-[3-(5-{4-[4-(2-{4-[4-(2,4-dioxo-1,3-diazinan-1-yl)-3-fluorophenyl]piperidin-1-yl}ethyl)piperidin-1-yl]phenyl}-1H-pyrrolo[2,3-b]pyridine-3-carbonyl)-2,4-difluorophenyl]-3-fluoropyrrolidine-1-sulfonamide | ¹H NMR (400 MHz, DMSO-d6) δ 12.91 (b, 1H), 10.47 (s, 1H), 8.66 (d, J = 2.2 Hz, 1H), 8.54 (s, 1H), 8.08 (s, 1H), 7.72-7.53 (m, 3H), 7.42-7.00 (m, 7H), 5.31 (d, J = 13.2 Hz, 1H), 3.80-3.77 (m, 2H), 3.71-3.70 (m, 2H), 3.49-3.78 (m, 1H), 3.29-3.26 (m, 1H), 3.11 (d, J = 11.0 Hz, 2H), 2.79-2.65 (m, 4H), 2.58-2.55 (m, 1H), 2.28-2.05 (m, 4H), 1.99-1.98 (m, 4H), 1.88-1.76 (m, 4H), 1.76-1.62 (m, 3H), 1.50-1.49 (m, 3H), 1.38-1.10 (m, 4H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| 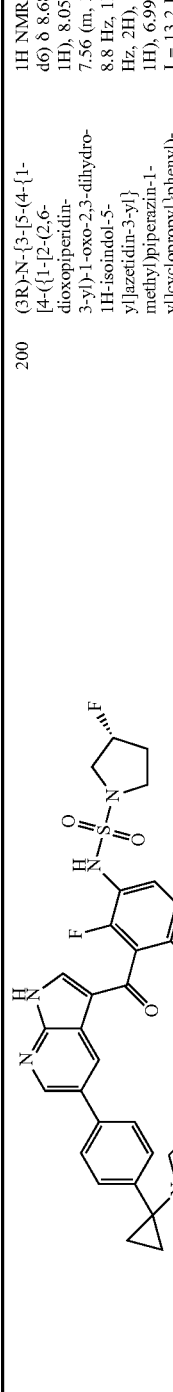 | 200 | (3R)-N-{3-[5-(4-{1-[4-({1-[2-(2,6-dioxopiperidin-3-yl)-1-oxo-2,3-dihydro-1H-isoindol-5-yl]azetidin-3-yl}methyl)piperazin-1-yl]cyclopropyl}phenyl)-1H-pyrrolo[2,3-b]pyridine-3-carbonyl]-2,4-difluorophenyl}-3-fluoropyrrolidine-1-sulfonamide | 1H NMR (400 MHz, DMSO-d6) δ 8.68 (s, 1H), 8.57 (s, 1H), 8.05 (s, 1H), 7.68-7.56 (m, 3H), 7.47 (d, J = 8.8 Hz, 1H), 7.38 (d, J = 7.8 Hz, 2H), 7.23 (t, J = 8.8 Hz, 1H), 6.99 (s, 2H), 5.19 (d, J = 13.2 Hz, 1H), 4.97 (dd, J = 13.3, 5.1 Hz, 1H), 4.29 (d, J = 16.8 Hz, 1H), 4.16 (d, J = 16.8 Hz, 1H), 3.79 (d, J = 12.6 Hz, 2H), 3.45 (d, J = 2.4 Hz, 1H), 3.41-3.31 (m, 2H), 3.25-3.23 (m, 1H), 2.93-2.91 (m, 2H), 2.80-2.78 (m, 3H), 2.63-2.54 (m, 1H), 2.40-2.25 (m, 1H), 2.19-2.07 (m, 3H), 2.00-1.89 (m, 3H), 1.73-1.67 (m, 4H), 1.21 (s, 4H), 1.15-1.04 (m, 2H), 0.92-0.91 (m, 1H), 0.90-0.79 (m, 1H), 0.70 (d, J = 12.0 Hz, 3H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| | 125 | (3R)-N-[3-(5-{4-[(3R,4S)-4-({4-[2-(2,6-dioxopiperidin-3-yl)-1-oxo-2,3-dihydro-1H-isoindol-5-yl]piperidin-1-yl}methyl)-3-fluoropiperidin-1-yl]phenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 12.92 (s, 1H), 11.00 (s, 1H), 9.86 (s, 1H), 8.66 (d, J = 2.2 Hz, 1H), 8.55 (s, 1H), 8.08 (s, 1H), 7.71-7.57 (m, 4H), 7.52 (s, 1H), 7.42 (d, J = 7.9 Hz, 1H), 7.33-7.22 (m, 1H), 7.08 (d, J = 8.6 Hz, 2H), 5.30 (d, J = 53.4 Hz, 1H), 5.12 (dd, J = 13.3, 5.1 Hz, 1H), 4.92 (d, J = 48.0 Hz, 1H), 4.44 (d, J = 17.3 Hz, 1H), 4.30 (d, J = 17.2 Hz, 1H), 4.08 (t, J = 12.5 Hz, 1H), 3.87 (d, J = 12.1 Hz, 1H), 3.49 (s, 1H), 3.44-3.38 (m, 2H), 3.31-3.25 (m, 1H), 3.09-2.75 (m, 5H), 2.73-2.57 (m, 2H), 2.40 (qd, J = 13.2, 12.8, 6.9 Hz, 2H), 2.27 (dd, J = 12.2, 6.8 Hz, 1H), 2.19-2.05 (m, 3H), 2.04-1.89 (m, 3H), 1.86-1.55 (m, 6H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| 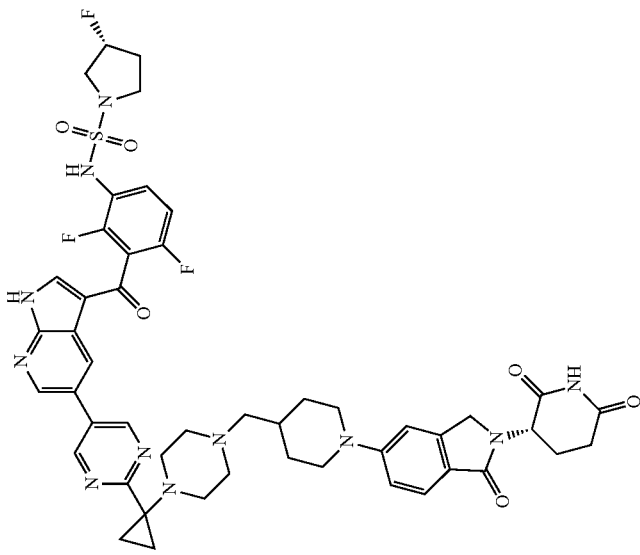 | 201 | (3R)-N-[3-[5-[2-[1-[4-[[1-[2-[(3S)-2,6-dioxo-3-piperidyl]-1-oxo-isoindolin-5-yl]-4-piperidyl]methyl]piperazin-1-yl]cyclopropyl]pyrimidin-5-yl]-1H-pyrrolo[2,3-b]pyridine-3-carbonyl]-2,4-difluoro-phenyl]-3-fluoro-pyrrolidine-1-sulfonamide | ¹H NMR (400 MHz, DMSO-$d_6$) δ 13.08(s, 1H), 10.93 (s, 1H), 9.81 (s, 1H), 9.09 (s, 2H), 8.76 (d, J = 2.2 Hz, 1H), 8.69 (s, 1H), 8.17 (s, 1H), 7.63 (dt, J = 6.0, 9.2 Hz, 1H), 7.50 (d, J = 9.2 Hz, 1H), 7.33-7.23 (m, 1H), 7.09-6.99 (m, 2H), 5.40-5.21 (m, 1H), 5.04 (dd, J = 5.2, 13.2 Hz, 1H), 4.36-4.28 (m, 1H), 4.23-4.15 (m, 1H), 3.88 (d, J = 12.8 Hz, 2H), 3.51-3.47 (m, 1H), 3.44-3.36 (m, 2H), 3.31-3.26 (m, 2H), 3.25-3.14 (m, 3H), 2.97-2.86 (m, 1H), 2.86-2.78 (m, 2H), 2.63-2.51 (m, 2H), 2.43-2.29 (m, 4H), 2.24-2.09 (m, 3H), 2.06-1.91 (m, 2H), 1.86-1.72 (m, 3H), 1.44-1.34 (m, 2H), 1.27-1.14 (m, 2H), 1.14-1.06 (m, 2H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| 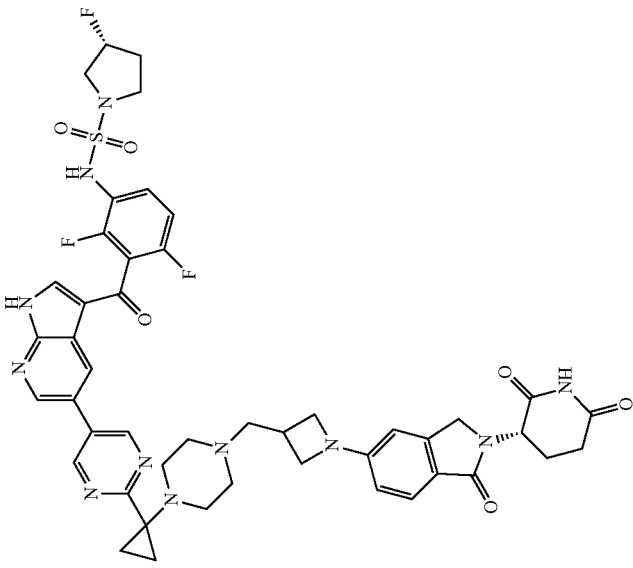 | 202 | (3R)-N-(3-{5-[2-(1-{4-[(1-{2-[(3S)-2,6-dioxopiperidin-3-yl]-1-oxo-2,3-dihydro-1H-isoindol-5-yl}azetidin-3-yl)methyl]piperazin-1-yl}cyclopropyl)pyrimidin-5-yl]-1H-pyrrolo[2,3-b]pyridine-3-carbonyl]-2,4-difluorophenyl)-3-fluoropyrrolidine-1-sulfonamide | ¹H NMR (400 MHz, DMSO-d₆) δ 13.42-12.72 (m, 1H), 10.93 (s, 1H), 10.21-9.51 (m, 1H), 9.08 (s, 2H), 8.76 (d, J = 1.6 Hz, 1H), 8.69 (s, 1H), 8.17 (s, 1H), 7.69-7.57 (m, 1H), 7.48 (d, J = 8.4 Hz, 1H), 7.27 (t, J = 8.8 Hz, 1H), 6.51 (s, 1H), 6.47 (d, J = 8.4 Hz, 1H), 5.43-5.19 (m, 1H), 5.11-4.92 (m, 1H), 4.38-4.10 (m, 2H), 4.03 (t, J = 7.6 Hz, 2H), 3.57 (s, 2H), 3.49 (s, 1H), 3.43-3.37 (m, 2H), 3.29 (s, 2H), 3.27-3.09 (m, 4H), 3.01-2.94 (m, 1H), 2.92-2.82 (m, 1H), 2.64-2.53 (m, 3H), 2.47-2.27 (m, 5H), 2.18-2.10 (m, 1H), 2.16-2.04 (m, 1H), 1.98-1.92 (m, 1H), 1.38 (s, 2H), 1.10 (s, 2H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 203 | | (3R)-N-{3-[5-(4-{2-[(3S)-2,6-dioxopiperidin-3-yl]-1-oxo-2,3-dihydro-1H-isoindol-5-yl}piperidin-1-yl)methyl]piperidin-1-yl]phenyl)-1H-pyrrolo[2,3-b]pyridine-3-carbonyl]-2-ethyl-4-fluorophenyl}-3-fluoropyrrolidine-1-sulfonamide | ¹H NMR (400 MHz, DMSO-d₆) δ 12.90 (s, 1H), 10.98 (s, 1H), 9.58 (s, 1H), 8.65 (d, J = 2.3 Hz, 1H), 8.52 (s, 1H), 7.91 (s, 1H), 7.66 (d, J = 7.8 Hz, 1H), 7.59 (dd, J = 8.8, 6.2 Hz, 3H), 7.51 (s, 1H), 7.41 (d, J = 7.9 Hz, 1H), 7.32–7.23 (m, 1H), 7.07 (d, J = 8.6 Hz, 1H), 5.11 (dd, J = 13.3, 5.1 Hz, 1H), 4.43 (d, J = 17.2 Hz, 1H), 4.30 (d, J = 17.2 Hz, 1H), 3.90–3.77 (m, 3H), 3.64-3.56 (m, 2H), 3.00 (s, 1H), 2.91 (ddd, J = 17.8, 13.6, 5.4 Hz, 1H), 2.75 (t, J = 12.0 Hz, 2H), 2.60 (d, J = 17.1 Hz, 1H), 2.40 (dd, J = 12.9, 4.5 Hz, 1H), 2.10-1.97 (m, 4H), 1.88-1.70 (m, 7H), 1.25 (d, J = 10.7 Hz, 3H), 1.01 (t, J = 7.4 Hz, 3H) |
| 204 | | N-{3-[5-(4-{2-[(3S)-2,6-dioxopiperidin-3-yl]-1-oxo-2,3-dihydro-1H-isoindol-5-yl}piperidin-1-yl)methyl]piperidin-1-yl]phenyl)-1H-pyrrolo[2,3-b]pyridine-3-carbonyl]-2,4-difluorophenyl}-2-methylpropane-1-sulfonamide | ¹H NMR (400 MHz, DMSO-d₆) δ 13.61-12.13 (m, 1H), 10.99 (s, 1H), 8.65 (d, J = 2.4 Hz, 1H), 8.60-8.44 (m, 1H), 8.19 (d, J = 9.6 Hz, 2H), 7.65 (d, J = 7.6 Hz, 1H), 7.61-7.53 (m, 3H), 7.51 (s, 1H), 7.41 (d, J = 7.6 Hz, 1H), 7.26 (t, J = 8.8 Hz, 1H), 7.07 (t, J = 8.8 Hz, 2H), 5.10 (dd, J = 5.2, 13.2 Hz, 1H), 4.47-4.24 (m, 2H), 3.83–3.76 (m, 2H), 3.02 (d, J = 6.4 Hz, 3H), 2.98 (s, 1H), 2.95-2.86 (m, 1H), 2.79-2.69 (m, 2H), 2.65-2.52 (m, 2H), 2.44-2.35 (m, 2H), 2.24-2.19 (m, 2H), 2.19-2.12 (m, 1H), 2.05-1.97 (m, 3H), 1.86-1.81 (m, 2H), 1.78-1.69 (m, 4H), 1.29-1.19 (m, 2H), 1.01 (d, J = 6.7 Hz, 6H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 205 | | (3R)-N-{3-[5-(3-cyano-4-{[(4-{[2-[(3S)-2,6-dioxopiperidin-3-yl]-1-oxo-2,3-dihydro-1H-isoindol-5-yl]piperidin-1-yl}methyl)piperidin-1-yl]phenyl)-1H-pyrrolo[2,3-b]pyridine-3-carbonyl]-2,4-difluorophenyl}-3-fluoropyrrolidine-1-sulfonamide | ¹H NMR (400 MHz, DMSO-d₆): δ 12.98 (s, 1H), 10.99 (s, 1H), 9.81 (s, 1H), 8.80-8.59 (m, 2H), 8.12 (d, J = 2.0 Hz, 2H), 7.97 (dd, J = 8.6, 2.4 Hz, 1H), 7.74-7.34 (m, 4H), 7.27 (td, J = 8.9, 1.9 Hz, 2H), 5.31 (dt, J = 53.0, 3.1 Hz, 1H), 5.11 (dd, J = 13.3, 5.1 Hz, 1H), 4.44 (d, J = 17.2 Hz, 1H), 4.30 (d, J = 17.2 Hz, 1H), 3.62 (d, J = 11.3 Hz, 2H), 3.49 (d, J = 2.5 Hz, 1H), 3.46-3.37 (m, 2H), 3.04 (d, J = 10.8 Hz, 2H), 2.99-2.79 (m, 3H), 2.73-2.54 (m, 2H), 2.42 (td, J = 13.2, 4.5 Hz, 1H), 2.31 (d, J = 7.0 Hz, 2H), 2.20-2.05 (m, 4H), 2.00 (tt, J = 7.6, 3.0 Hz, 2H), 1.96-1.86 (m, 2H), 1.86-1.66 (m, 5H), 1.44-1.20 (m, 2H) |
| 206 | | 1-cyclopropyl-N-{3-[5-(4-{[2-[(3S)-2,6-dioxopiperidin-3-yl]-1-oxo-2,3-dihydro-1H-isoindol-5-yl]piperidin-1-yl}methyl)piperidin-1-yl]phenyl)-1H-pyrrolo[2,3-b]pyridine-3-carbonyl]-2,4-difluorophenyl}methanesulfonamide | ¹H NMR (400 MHz, DMSO-d₆) δ 12.98-12.84 (m, 1H), 10.97 (s, 1H), 8.65 (s, 1H), 8.60-8.50 (m, 1H), 8.16 (s, 1H), 8.14 (s, 1H), 7.68-7.55 (m, 4H), 7.51 (s, 1H), 7.41 (d, J = 7.6 Hz, 1H), 7.26 (t, J = 8.8 Hz, 1H), 7.07 (d, J = 8.8 Hz, 2H), 5.10 (dd, J = 5.2, 13.2 Hz, 1H), 4.48-4.38 (m, 1H), 4.36-4.26 (m, 1H), 3.80 (d, J = 12.4 Hz, 2H), 3.13 (d, J = 7.2 Hz, 2H), 3.05 (d, J = 9.6 Hz, 2H), 2.97-2.70 (m, 4H), 2.68-2.57 (m, 2H), 2.39 (dd, J = 4.8, 13.2 Hz, 1H), 2.31 (d, J = 6.0 Hz, 2H), 2.19-2.08 (m, 2H), 2.04-1.95 (m, 1H), 1.88-1.73 (m, 7H), 1.30-1.22 (m, 2H), 1.08-1.03 (m, 1H), 0.61-0.51 (m, 2H), 0.39-0.29 (m, 2H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 207 | | (3R)-N-{3-[5-(4-{4-[(4-{2-[(3S)-2,6-dioxopiperidin-3-yl]-1-oxo-2,3-dihydro-1H-isoindol-5-yl]piperidin-1-yl}methyl)piperidin-1-yl]phenyl}-1H-pyrrolo[2,3-b]pyridine-3-carbonyl]-4-fluoro-2-methoxyphenyl]-3-fluoropyrrolidine-1-sulfonamide | ¹H NMR (400 MHz, DMSO-d₆) δ 12.81 (s, 1H), 10.98 (s, 1H), 9.32 (s, 1H), 8.65 (d, J = 2.3 Hz, 1H), 8.52 (s, 1H), 7.91 (s, 1H), 7.66 (d, J = 7.8 Hz, 1H), 7.59 (dd, J = 8.8, 6.2 Hz, 4H), 7.51 (s, 1H), 7.41 (d, J = 7.9 Hz, 1H), 7.18-7.01(m, 3H), 5.39-5.24(m, 1H), 5.11 (dd, J = 13.3, 5.1 Hz, 1H), 4.43 (d, J = 17.2 Hz, 1H), 4.30 (d, J = 17.2 Hz, 1H), 3.90-3.77 (m, 2H), 3.64-3.56 (m, 3H), 3.00 (s, 1H), 2.91-2.75 (m, 3H), 2.60 (d, J = 17.1 Hz, 2H), 2.40 (dd, J = 12.9, 4.5 Hz, 1H), 2.10-1.97 (m, 7H), 1.21-0.89 (m, 5H) |
| 208 | | (3S)-3-(5-{1-[(1-{4-[3-(2,6-difluoro-3-{[methyl(propan-2-yl)sulfamoyl]amino}benzoyl)-1H-pyrrolo[2,3-b]pyridin-5-yl]phenyl}piperidin-4-yl)methyl]piperidin-4-yl}-1-oxo-2,3-dihydro-1H-isoindol-2-yl)piperidine-2,6-dione | ¹H NMR (400 MHz, DMSO-d₆) δ 13.06-12.84 (m, 1H), 11.00 (s, 1H), 8.65 (d, J = 2.0 Hz, 1H), 8.58-8.49 (m, 1H), 8.15 (s, 1H), 8.07 (s, 1H), 7.65 (d, J = 7.6 Hz, 1H), 7.62-7.49 (m, 4H), 7.41 (d, J = 7.6 Hz, 1H), 7.27 (t, J = 8.0 Hz, 1H), 7.07 (d, J = 8.8 Hz, 2H), 5.11 (dd, J = 5.2, 13.2 Hz, 1H), 4.46-4.39 (m, 1H), 4.34-4.24 (m, 1H), 3.95 (td, J = 6.8, 13.2 Hz, 1H), 3.80 (d, J = 12.0 Hz, 2H), 3.02 (d, J = 11.2 Hz, 3H), 2.93-2.85 (m, 1H), 2.74 (t, J = 11.6 Hz, 2H), 2.68-2.64 (m, 1H), 2.57 (s, 2H), 2.55-2.52 (m, 1H), 2.47-2.39 (m, 1H), 2.39-2.31 (m, 1H), 2.26 (d, J = 7.2 Hz, 2H), 2.11-1.95 (m, 3H), 1.87-1.71 (m, 7H), 1.31-1.19 (m, 2H), 1.01 (d, J = 6.8 Hz, 6H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 209 | | (3R)-N-{3-[5-(4-{[4-({1-[2-(2,6-dioxopiperidin-3-yl)-1-oxo-2,3-dihydro-1H-isoindol-5-yl]azetidin-3-yl}methyl)piperazin-1-yl]piperidin-1-yl}phenyl)-1H-pyrrolo[2,3-b]pyridine-3-carbonyl]-2,4-difluorophenyl}-3-fluoropyrrolidine-1-sulfonamide | ¹H NMR (400 MHz, DMSO-d₆) δ 12.99-12.81 (m, 1H), 10.93 (s, 1H), 8.65 (d, J = 2.0 Hz, 1H), 8.58-8.49 (m, 1H), 8.15 (s, 1H), 8.07 (s, 1H), 7.67-7.55 (m, 3H), 7.48 (d, J = 8.4 Hz, 1H), 7.27 (t, J = 8.8 Hz, 1H), 7.07 (d, J = 8.8 Hz, 2H), 6.54-6.42 (m, 2H), 5.38-5.21 (m, 1H), 5.03 (dd, J = 5.2, 13.2 Hz, 1H), 4.33-4.25 (m, 1H), 4.21-4.13 (m, 1H), 4.01 (t, J = 7.2 Hz, 2H), 3.83 (d, J = 12.0 Hz, 2H), 3.55 (t, J = 5.2 Hz, 2H), 3.48 (s, 1H), 3.37 (d, J = 2.0 Hz, 1H), 3.29 (dt, J = 6.8, 10.0 Hz, 3H), 3.00-2.84 (m, 3H), 2.74 (t, J = 11.2 Hz, 2H), 2.63-2.55 (m, 6H), 2.45 (d, J = 5.6 Hz, 4H), 2.37-2.32 (m, 1H), 2.15-2.04 (m, 2H), 2.01-1.84 (m, 4H), 1.59-1.43 (m, 2H) |
| 210 | | (3R)-N-{3-[5-(4-{[4-[2-[(3S)-2,6-dioxopiperidin-3-yl]-1-oxo-2,3-dihydro-1H-isoindol-5-yl]piperidin-3-yl]methyl]piperidin-1-yl]-3-(methylamino)phenyl]-1H-pyrrolo[2,3-b]pyridine-3-carbonyl}-2,4-difluorophenyl}-3-fluoropyrrolidine-1-sulfonamide | ¹H NMR (300 MHz, DMSO-d₆) δ 12.98 (s, 1H), 11.00 (s, 1H), 9.90 (s, 1H), 8.67 (s, 1H), 8.63 (s, 1H), 8.11 (s, 1H), 7.68-7.63 (m, 2H), 7.52 (s, 1H), 7.33-7.27 (m, 1H), 7.05 (d, J = 8.1 Hz, 1H), 6.90 (d, J = 8.1 Hz, 1H), 6.77 (s, 1H), 5.41-5.01 (m, 3H), 4.41-4.27 (q, 2H), 3.40 (s, 1H), 3.22 (s, 1H), 3.10 (s, 1H), 3.05-3.00 (m, 4H), 2.93-2.88 (m, 4H), 2.74-2.71 (m, 4H), 2.28-2.22 (m, 1H), 2.12-2.08 (m, 5H), 1.97-1.75 (m, 7H), 1.43-1.40 (m, 2H), 1.24-1.16 (m, 4H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 211 | | (2S)-N-{3-[5-(4-{[(4-{2-[(3S)-2,6-dioxopiperidin-3-yl]-1-oxo-2,3-dihydro-1H-isoindol-5-yl]piperidin-1-yl}methyl)piperidin-1-yl]phenyl)-1H-pyrrolo[2,3-b]pyridine-3-carbonyl]-2,4-difluorophenyl}-2-methylpyrrolidine-1-sulfonamide | ¹H NMR (400 MHz, DMSO-d₆) δ 12.91 (s, 1H), 10.97 (s, 1H), 9.66 (s, 1H), 8.65 (d, J = 2.2 Hz, 1H), 8.52 (s, 1H), 8.08 (s, 1H), 7.69-7.57 (m, 4H), 7.57 (s, 1H), 7.51 (s, 1H), 7.41 (dd, J = 8.1, 1.4 Hz, 1H), 7.28 (td, J = 8.8, 1.6 Hz, 1H), 7.11-7.04 (m, 2H), 5.10 (dd, J = 13.3, 5.1 Hz, 1H), 4.43 (d, J = 17.3 Hz, 1H), 4.29 (d, J = 17.2 Hz, 1H), 3.80 (d, J = 12.2 Hz, 2H), 3.71 (td, J = 6.8, 3.9 Hz, 1H), 3.64-3.56 (m, 1H), 3.23 (t, J = 6.7 Hz, 2H), 3.12-2.94 (m, 3H), 2.74 (t, J = 12.0 Hz, 2H), 2.63 (s, 2H), 2.25-1.95 (m, 3H), 1.95-1.67 (m, 11H), 1.47 (dd, J = 9.2, 4.8 Hz, 1H), 1.26 (s, 1H), 1.23 (s, 5H), 1.06 (d, J = 6.3 Hz, 3H) |
| 212 | | (3R)-N-{3-[5-(4-{[(4-{2-[(3S)-2,6-dioxopiperidin-3-yl]-1-oxo-2,3-dihydro-1H-isoindol-5-yl]piperidin-1-yl}methyl)piperidin-1-yl]phenyl)-1H-pyrrolo[2,3-b]pyridine-3-carbonyl]-2-fluoro-4-methoxyphenyl}-3-fluoropyrrolidine-1-sulfonamide | 1H NMR (400 MHz, DMSO-d₆) δ 12.71 (s, 1H), 10.98 (s, 1H), 9.52 (s, 1H), 8.62 (d, J = 2.2 Hz, 1H), 8.45 (s, 1H), 7.84 (s, 1H), 7.66 (d, J = 7.9 Hz, 1H), 7.57-7.46 (m, 4H), 7.42 (d, J = 8.0 Hz, 1H), 7.02-7.07 (m, 3H), 5.35 (s, 1H), 5.11 (dd, J = 13.3, 5.1 Hz, 1H), 4.43 (d, J = 17.2 Hz, 1H), 4.30 (d, J = 17.2 Hz, 1H), 3.80 (d, J = 12.0 Hz, 2H), 3.74 (s, 3H), 3.45 (d, J = 2.0 Hz, 2H), 3.32 (d, 2H), 3.00 (s, 3H), 2.97-2.85 (m, 2H), 2.75 (t, J = 12.1 Hz, 2H), 2.48 (s, 2H), 2.11-1.99 (m, 6H), 1.85 (d, J = 13.0 Hz, 7H), 1.45 (s, 1H), 1.23 (s, 7H), 0.91-0.81 (m, 1H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 213 | | 3-(5-{1-[(1-{[4-[3-(3-{[(2,2-difluoroethyl)(methyl)sulfamoyl]amino}-2,6-difluorobenzoyl)-1H-pyrrolo[2,3-b]pyridin-5-yl]phenyl}piperidin-4-yl)methyl]piperidin-4-yl}methyl]piperidin-4-yl)-1-oxo-2,3-dihydro-1H-isoindol-2-yl)piperidine-2,6-dione | 1H NMR (400 MHz, DMSO-d6) δ 12.92 (s, 1H), 10.99 (s, 1H), 8.66 (d, J = 2.0 Hz, 1H), 8.56 (s, 1H), 8.16 (s, 1H), 8.10 (s, 1H), 7.66 (d, J = 7.6 Hz, 1H), 7.63-7.54 (m, 3H), 7.52 (s, 1H), 7.43 (d, J = 8.2 Hz, 1H), 7.26 (t, J = 8.8 Hz, 1H), 7.09 (d, J = 8.4 Hz, 2H), 6.40-5.76 (m, 1H), 5.12 (dd, J = 5.2, 13.2 Hz, 1H), 4.49-4.39 (m, 1H), 4.35-4.26 (m, 1H), 3.81 (br d, J = 11.9 Hz, 2H), 3.49 (dt, J = 3.5, 14.9 Hz, 2H), 3.05 (d, J = 10.8 Hz, 2H), 2.97-2.89 (m, 1H), 2.85 (s, 3H), 2.76 (t, J = 11.6 Hz, 2H), 2.71-2.60 (m, 2H), 2.41 (d, J = 12.4 Hz, 1H), 2.34-2.27 (m, 2H), 2.11 (t, J = 10.4 Hz, 2H), 2.05-1.95 (m, 1H), 1.93-1.67 (m, 7H), 1.37-1.20 (m, 2H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 214 | | (3R)-N-{3-[5-(4-{1'-[2-(2,6-dioxopiperidin-3-yl)-1-oxo-2,3-dihydro-1H-isoindol-5-yl]-[4,4'-bipiperidin]-1-yl}phenyl)-1H-pyrrolo[2,3-b]pyridine-3-carbonyl]-2,4-difluorophenyl}-3-fluoropyrrolidine-1-sulfonamide | 1H NMR (400 MHz, DMSO-d6) δ 12.95 (d, J = 1.8 Hz, 1H), 10.94 (s, 1H), 9.85 (s, 1H), 8.68 (d, J = 2.0 Hz, 1H), 8.58 (s, 1H), 8.09 (d, J = 2.0 Hz, 1H), 7.74-7.67 (m, 2H), 7.66-7.59 (m, 1H), 7.51 (d, J = 8.8 Hz, 1H), 7.34-7.22 (m, 3H), 7.10-7.04 (m, 2H), 5.38-5.21 (m, 1H), 5.04 (dd, J = 5.2, 13.2 Hz, 1H), 4.36-4.29 (m, 1H), 4.24-4.17 (m, 1H), 3.93 (d, J = 12.4 Hz, 2H), 3.79 (d, J = 11.6 Hz, 2H), 3.49-3.46 (m, 2H), 3.42-3.38 (m, 2H), 3.34-3.24 (m, 2H), 3.01-2.85 (m, 3H), 2.80 (t, J = 11.6 Hz, 2H), 2.63-2.5 (m, 1H), 2.43-2.34 (m, 1H), 2.16-2.08 (m, 1H), 2.06-1.92 (m, 2H), 1.91-1.75 (m, 4H), 1.47-1.22 (m, 6H) |
| 215 | | (3R)-N-[3-(5-{5-[4-({4-[2-(2,6-dioxopiperidin-3-yl)-1-oxo-2,3-dihydro-1H-isoindol-5-yl]piperidin-1-yl}methyl)piperidin-1-yl]pyrimidin-2-yl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 12.98 (s, 1H), 10.99 (s, 1H), 9.86 (s, 1H), 9.32 (m, 2H), 8.65 (s, 2H), 8.10 (s, 1H), 7.69-7.58 (m, 2H), 7.52 (s, 1H), 7.45-7.39 (m, 1H), 7.27 (m, 1H), 5.37-5.24 (m, 1H), 5.11 (m, 1H), 4.43 (m, 1H), 4.30 (m, 1H), 3.94 (m, 1H), 3.49-3.36 (m, 3H), 3.05-3.00 (m, 2H), 2.95-2.81 (m, 3H), 2.62 (m, 2H), 2.45-2.34 (m, 2H), 2.26 (m, 2H), 2.15-1.96 (m, 5H), 1.94-1.67 (m, 7H), 1.26 (m, 2H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| 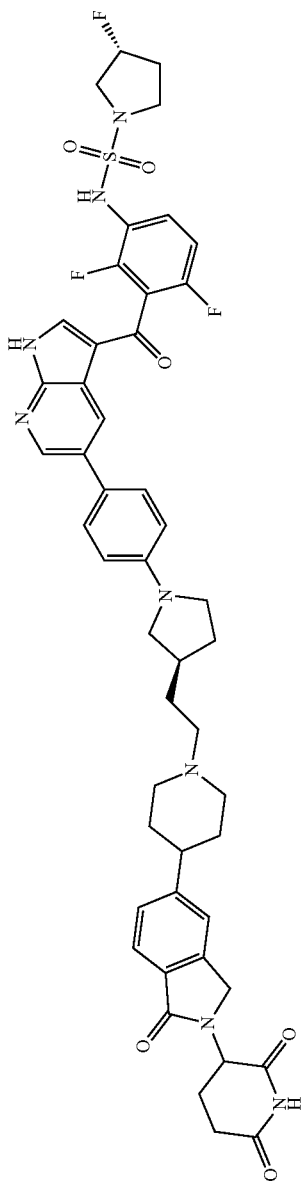 | 216 | (3R)-N-[3-(5-{4-[(3R)-3-(2-{4-[2-(2,6-dioxopiperidin-3-yl)-1-oxo-2,3-dihydro-1H-isoindol-5-yl]piperidin-1-yl}ethyl)pyrrolidin-1-yl]phenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 13.00-12.74 (m, 1H), 10.98 (s, 1H), 8.63 (d, J = 2.0 Hz, 1H), 8.56-8.42 (m, 1H), 8.16 (s, 1H), 8.04 (s, 1H), 7.68-7.60 (m, 2H), 7.56 (d, J = 8.8 Hz, 2H), 7.50 (s, 1H), 7.41 (d, J = 8.0 Hz, 1H), 7.26 (t, J = 8.4 Hz, 1H), 6.67 (d, J = 8.8 Hz, 2H), 5.38-5.21 (m, 1H), 5.10 (dd, J = 5.2, 13.2 Hz, 1H), 4.46-4.38 (m, 1H), 4.33-4.26 (m, 1H), 3.48 (s, 2H), 3.40 (s, 2H), 3.30 (s, 2H), 3.12 (d, J = 10.8 Hz, 2H), 2.96-2.86 (m, 3H), 2.75-2.70 (m, 1H), 2.64-2.57 (m, 3H), 2.39 (dd, J = 4.4, 13.2 Hz, 2H), 2.22-2.15 (m, 3H), 2.14-2.05 (m, 2H), 2.03-1.94 (m, 2H), 1.87-1.77 (m, 3H), 1.74-1.64 (m, 4H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 217 | 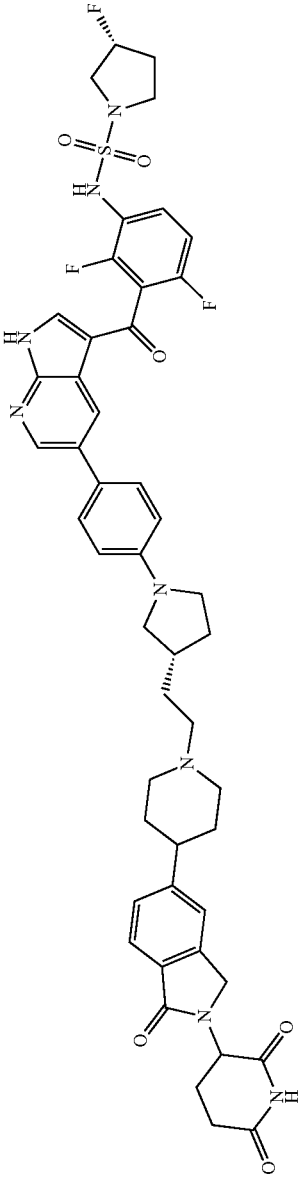 | (3R)-N-[3-(5-{4-[(3S)-3-(2-{4-[2-(2,6-dioxopiperidin-3-yl)-1-oxo-2,3-dihydro-1H-isoindol-5-yl]piperidin-1-yl}ethyl)pyrrolidin-1-yl]phenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 12.97-12.76 (m, 1H), 10.98 (s, 1H), 8.63 (d, J = 2.0 Hz, 1H), 8.59-8.45 (m, 1H), 8.15 (s, 1H), 8.05 (s, 1H), 7.66 (d, J = 8.0 Hz, 1H), 7.64-7.60 (m, 1H), 7.57 (d, J = 8.8 Hz, 2H), 7.50 (s, 1H), 7.41 (d, J = 8.0 Hz, 1H), 7.26 (t, J = 8.4 Hz, 1H), 6.67 (d, J = 8.8 Hz, 2H), 5.39-5.20 (m, 1H), 5.10 (dd, J = 5.2, 13.2 Hz, 1H), 4.45-4.27 (m, 2H), 3.54-3.46 (m, 4H), 3.39 (s, 4H), 3.19 (d, J = 10.0 Hz, 2H), 3.00-2.86 (m, 3H), 2.76-2.69 (m, 1H), 2.64-2.56 (m, 3H), 2.39 (dd, J = 4.4, 13.2 Hz, 2H), 2.15 (d, J = 18.8 Hz, 2H), 2.12-2.06 (m, 1H), 2.03-1.95 (m, 2H), 1.90-1.81 (m, 3H), 1.68 (s, 4H) |
| 218 | 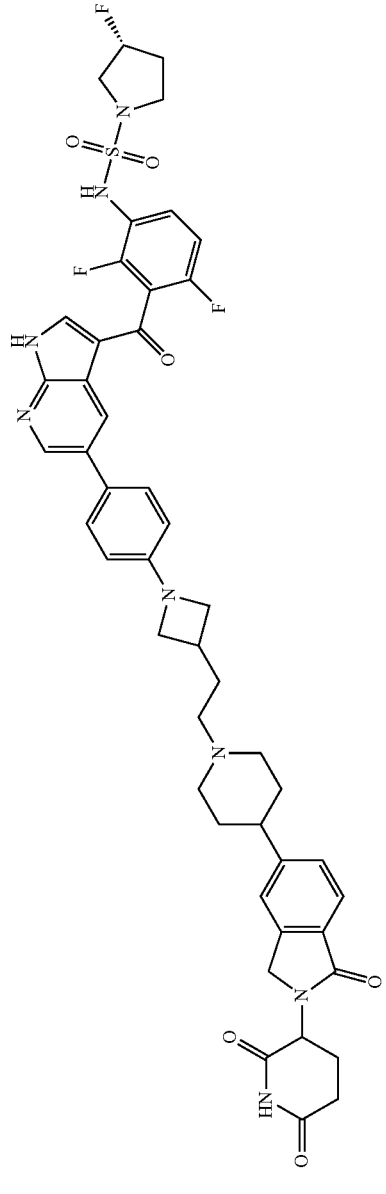 | (3R)-N-[3-(5-{4-[3-(2-{4-[2-(2,6-dioxopiperidin-3-yl)-1-oxo-2,3-dihydro-1H-isoindol-5-yl]piperidin-1-yl}ethyl)azetidin-1-yl]phenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 10.98 (s, 1H), 8.59 (d, J = 2.4 Hz, 1H), 8.50-8.38 (m, 1H), 8.33 (s, 1H), 7.97 (s, 1H), 7.75-7.69 (m, 1H), 7.61 (s, 1H), 7.53-7.48 (m, 4H), 7.02-6.93 (m, 1H), 6.79-6.74 (m, 2H), 6.09-5.99 (m, 1H), 5.34-5.05 (m, 1H), 4.48-4.41 (m, 1H), 4.36-4.28 (m, 1H), 4.21-4.14 (m, 1H), 3.76-3.66 (m, 4H), 3.23-3.10 (m, 8H), 2.97-2.84 (m, 3H), 2.69-2.59 (m, 1H), 2.40-2.29 (m, 2H), 2.13-1.89 (m, 9H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 219 | | (3R)-N-{3-[5-(4-{4-[(4-{2-[(3S)-2,6-dioxopiperidin-3-yl]-1-oxo-2,3-dihydro-1H-isoindol-5-yl}piperazin-1-yl)methyl]piperidin-1-yl}phenyl)-1H-pyrrolo[2,3-b]pyridine-3-carbonyl]-2,4-difluorophenyl}-3-fluoropyrrolidine-1-sulfonamide | 1H NMR (400 MHz, DMSO-d6) δ 12.93 (s, 1H), 10.95 (s, 1H), 10.15-9.58 (m, 1H), 8.65 (d, J = 2.0 Hz, 1H), 8.58-8.45 (m, 1H), 8.14 (s, 1H), 8.07 (s, 1H), 7.72-7.50 (m, 4H), 7.27 (t, J = 8.8 Hz, 1H), 7.18-7.02 (m, 4H), 5.40-5.18 (m, 1H), 5.05 (dd, J = 5.2, 13.2 Hz, 1H), 4.39-4.28 (m, 1H), 4.26-4.18 (m, 1H), 3.80 (d, J = 11.6 Hz, 2H), 3.48 (br s, 2H), 3.40 (br s, 2H), 3.34-3.25 (m, 8H), 2.96-2.87 (m, 1H), 2.76 (t, J = 11.6 Hz, 4H), 2.62-2.56 (m, 1H), 2.45-2.35 (m, 1H), 2.14-1.79 (m, 6H), 1.38-1.19 (m, 2H) |
| 220 | | (3R)-N-{3-[5-(4-{4-[(4-{2-[(3S)-2,6-dioxopiperidin-3-yl]-1-oxo-2,3-dihydro-1H-isoindol-5-yl}piperazin-1-yl)methyl]piperidin-1-yl}phenyl)-1H-pyrrolo[2,3-b]pyridine-3-carbonyl]-2,4-difluorophenyl}-3-fluoropyrrolidine-1-sulfonamide | 1H NMR (400 MHz, DMSO-d6) δ 12.90 (s, 1H), 10.95 (s, 1H), 9.85 (br s, 1H), 8.65 (d, J = 2.0 Hz, 1H), 8.53 (br s, 1H), 8.07 (s, 1H), 7.68-7.50 (m, 4H), 7.27 (t, J = 8.8 Hz, 1H), 7.13-7.01 (m, 4H), 5.39-5.20 (m, 1H), 5.05 (dd, J = 5.2, 13.2 Hz, 1H), 4.38-4.29 (m, 1H), 4.26-4.16 (m, 1H), 3.79 (d, J = 12.0 Hz, 2H), 3.51-3.36 (m, 4H), 3.33-3.25 (d, J = 2.8 Hz, 8H), 2.98-2.83 (m, 1H), 2.74 (br t, J = 11.5 Hz, 2H), 2.64-2.56 (s, 1H), 2.44-2.33 (m, 1H), 2.29-2.20 (m, 2H), 2.16-1.92 (m, 4H), 1.89-1.72 (m, 3H), 1.33-1.19 (m, 2H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 221 | | (3R)-N-{3-[5-(4-{4-[(6-{2-[(3S)-2,6-dioxopiperidin-3-yl]-1-oxo-2,3-dihydro-1H-isoindol-5-yl}-2,6-diazaspiro[3.3]heptan-2-yl)methyl]piperidin-1-yl}phenyl)-1H-pyrrolo[2,3-b]pyridine-3-carbonyl]-2,4-difluorophenyl}-3-fluoropyrrolidine-1-sulfonamide | 1H NMR (400 MHz, DMSO-d6) δ 13.17-12.62 (m, 1H), 10.94 (s, 1H), 8.65 (d, J = 2.0 Hz, 1H), 8.53 (br s, 1H), 8.06 (s, 1H), 7.68-7.55 (m, 3H), 7.49 (d, J = 8.4 Hz, 1H), 7.26 (t, J = 8.4 Hz, 1H), 7.06 (d, J = 8.8 Hz, 2H), 6.56-6.45 (m, 2H), 5.40-5.19 (m, 2H), 5.03 (dd, J = 5.2, 13.2 Hz, 1H), 4.36-4.26 (m, 1H), 4.22-4.13 (m, 1H), 4.00 (s, 4H), 3.76 (d, J = 12.0 Hz, 2H), 3.60-3.46 (m, 6H), 3.31-3.25 (m, 4H), 2.96-2.82 (m, 1H), 2.70 (t, J = 11.4 Hz, 2H), 2.63-2.54 (m, 1H), 2.35 (dq, J = 4.0, 13.2 Hz, 1H), 2.18-1.90 (m, 3H), 1.77 (d, J = 10.8 Hz, 2H), 1.61-1.45 (m, 1H), 1.33-1.17 (m, 2H) |
| 222 | | (3R)-N-{3-[5-(4-{4-[(6-{2-[(3R)-2,6-dioxopiperidin-3-yl]-1-oxo-2,3-dihydro-1H-isoindol-5-yl}-2,6-diazaspiro[3.3]heptan-2-yl)methyl]piperidin-1-yl}phenyl)-1H-pyrrolo[2,3-b]pyridine-3-carbonyl]-2,4-difluorophenyl}-3-fluoropyrrolidine-1-sulfonamide | 1H NMR (400 MHz, DMSO-d6) δ 13.11-12.63 (m, 1H), 10.94 (s, 1H), 8.65 (d, J = 2.0 Hz, 1H), 8.58-8.47 (m, 1H), 8.12 (s, 1H), 7.72-7.54 (m, 3H), 7.50 (d, J = 8.4 Hz, 1H), 7.27 (t, J = 8.4 Hz, 1H), 7.06 (br d, J = 8.8 Hz, 2H), 6.58-6.42 (m, 2H), 5.43-5.19 (m, 1H), 5.03 (dd, J = 5.2, 13.2 Hz, 1H), 4.35-4.26 (m, 1H), 4.23-4.14 (m, 1H), 4.01 (s, 4H), 3.77 (d, J = 12.4 Hz, 2H), 3.59-3.48 (m, 6H), 3.31-3.25 (m, 4H), 2.98-2.83 (m, 1H), 2.76-2.67 (m, 2H), 2.64-2.56 (m, 1H), 2.42-2.31 (m, 1H), 2.18-1.91 (m, 3H), 1.77 (d, J = 10.8 Hz, 2H), 1.58-1.43 (m, 1H), 1.32-1.17 (m, 2H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| | 223 | (3R)-N-{3-[5-(4-{4-[(1-{2-[(3S)-2,6-dioxopiperidin-3-yl]-1-oxo-2,3-dihydro-1H-isoindol-5-yl}piperidin-4-yl)methyl]piperazin-1-yl}phenyl)-1H-pyrrolo[2,3-b]pyridine-3-carbonyl]-2,4-difluorophenyl}-3-fluoropyrrolidine-1-sulfonamide | 1H NMR (400 MHz, DMSO-d6) δ 12.91 (s, 1H), 10.94 (s, 1H), 9.84 (s, 1H), 8.65 (s, 1H), 8.59-8.44 (m, 1H), 8.07 (s, 1H), 7.66-7.58 (m, 3H), 7.50 (d, J = 8.4 Hz, 1H), 7.27 (t, J = 8.4 Hz, 1H), 7.12-7.00 (m, 4H), 5.41-5.18 (m, 1H), 5.04 (dd, J = 5.2, 13.2 Hz, 1H), 4.37-4.26 (m, 1H), 4.23-4.16 (m, 1H), 3.89 (d, J = 12.0 Hz, 2H), 3.48 (s, 1H), 3.44-3.36 (m, 2H), 3.30-3.27 (m, 1H), 3.26-3.18 (m, 4H), 2.97-2.79 (m, 3H), 2.63-2.52 (m, 5H), 2.44-2.34 (m, 1H), 2.30-2.20 (m, 2H), 2.15-1.92 (m, 3H), 1.82 (d, J = 11.2 Hz, 3H), 1.26-1.16 (m, 2H) |
| | 224 | (3R)-N-{3-[5-(4-{4-[(1-{2-[(3R)-2,6-dioxopiperidin-3-yl]-1-oxo-2,3-dihydro-1H-isoindol-5-yl}piperidin-4-yl)methyl]piperazin-1-yl}phenyl)-1H-pyrrolo[2,3-b]pyridine-3-carbonyl]-2,4-difluorophenyl}-3-fluoropyrrolidine-1-sulfonamide | 1H NMR (400 MHz, DMSO-d6) δ 12.91 (s, 1H), 10.94 (s, 1H), 9.84 (s, 1H), 8.65 (s, 1H), 8.54 (s, 1H), 8.07 (s, 1H), 7.67-7.57 (m, 3H), 7.50 (d, J = 8.4 Hz, 1H), 7.27 (t, J = 8.4 Hz, 1H), 7.13-7.00 (m, 4H), 5.44-5.15 (m, 1H), 5.04 (dd, J = 5.2, 13.2 Hz, 1H), 4.37-4.27 (m, 1H), 4.24-4.16 (m, 1H), 3.89 (d, J = 12.4 Hz, 2H), 3.48 (s, 1H), 3.44-3.36 (m, 2H), 3.30-3.27 (m, 1H), 3.27-3.18 (m, 4H), 2.97-2.78 (m, 3H), 2.64-2.52 (m, 5H), 2.43-2.30 (m, 1H), 2.24 (d, J = 5.2 Hz, 2H), 2.15-1.92 (m, 3H), 1.82 (d, J = 10.8 Hz, 3H), 1.27-1.17 (m, 2H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 225 | | (3R)-N-{3-[5-(4-{6-[(1-{2-[(3R)-2,6-dioxopiperidin-3-yl]-7-methoxy-1-oxo-2,3-dihydro-1H-isoindol-5-yl}piperidin-4-yl)methyl]-2,6-diazaspiro[3.3]heptan-2-yl}phenyl)-1H-pyrrolo[2,3-b]pyridine-3-carbonyl]-2,4-difluorophenyl}-3-fluoropyrrolidine-1-sulfonamide | 1H NMR (400 MHz, DMSO-d6) δ 12.98-12.82 (m, 1H), 10.90 (s, 1H), 10.02-9.73 (m, 1H), 8.62 (d, J = 2.0 Hz, 1H), 8.50 (s, 1H), 8.06 (s, 1H), 7.66-7.52 (m, 3H), 7.26 (t, J = 8.8 Hz, 1H), 6.61-6.54 (m, 3H), 6.45 (s, 1H), 5.41-5.19 (m, 1H), 4.96 (dd, J = 5.2, 13.2 Hz, 1H), 4.26-4.18 (m, 1H), 4.14-4.06 (m, 1H), 3.95 (s, 4H), 3.88 (d, J = 12.6 Hz, 2H), 3.83 (s, 3H), 3.49-3.38 (m, 6H), 3.31-3.23 (m, 2H), 2.97-2.75 (m, 3H), 2.62-2.53 (m, 1H), 2.43-2.35 (m, 2H), 2.34-2.26 (m, 1H), 2.16-1.87 (m, 3H), 1.75 (d, J = 11.6 Hz, 2H), 1.60-1.46 (m, 1H), 1.28-1.12 (m, 2H) |
| 226 | | (3R)-N-{3-[5-(4-{6-[(1-{2-[(3S)-2,6-dioxopiperidin-3-yl]-7-methoxy-1-oxo-2,3-dihydro-1H-isoindol-5-yl}piperidin-4-yl)methyl]-2,6-diazaspiro[3.3]heptan-2-yl}phenyl)-1H-pyrrolo[2,3-b]pyridine-3-carbonyl]-2,4-difluorophenyl}-3-fluoropyrrolidine-1-sulfonamide | 1H NMR (400 MHz, DMSO-d6) δ 13.09-12.76 (m, 1H), 10.90 (s, 1H), 10.03-9.76 (m, 1H), 8.62 (d, J = 2.0 Hz, 1H), 8.50 (d, J = 2.0 Hz, 1H), 8.06 (s, 1H), 7.67-7.52 (m, 3H), 7.26 (t, J = 8.0 Hz, 1H), 6.62-6.54 (m, 3H), 6.45 (s, 1H), 5.39-5.19 (m, 1H), 4.96 (dd, J = 5.2, 13.2 Hz, 1H), 4.27-4.18 (m, 1H), 4.13-4.05 (m, 1H), 3.95 (s, 4H), 3.87 (d, J = 13.2 Hz, 2H), 3.83 (s, 3H), 3.55-3.45 (m, 4H), 3.42-3.36 (m, 2H), 3.31-3.25 (m, 2H), 2.97-2.74 (m, 3H), 2.60-2.53 (m, 1H), 2.48-2.40 (m, 2H), 2.37-2.28 (m, 1H), 2.17-1.86 (m, 3H), 1.75 (d, J = 10.8 Hz, 2H), 1.61-1.49 (m, 1H), 1.28-1.12 (m, 2H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 227 | | (3R)-N-[3-(5-{4-[4-({1'-[2-(2,6-dioxopiperidin-3-yl)-1-oxo-2,3-dihydro-1H-isoindol-5-yl]-[3,3'-biazetidin]-1-yl}methyl)piperidin-1-yl]phenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 12.84 (s, 1H), 10.94 (s, 1H), 8.65 (m, 1H), 8.53 (s, 1H), 8.07 (s, 1H), 7.64 (m, 1H), 7.59 (s, 1H), 7.57 (s, 1H), 7.50 (m, 1H), 7.31-7.22 (m, 1H), 7.06 (m, 2H), 6.54-6.44 (m, 2H), 5.37-5.23 (m, 1H), 5.04 (m, 1H), 4.31 (m, 1H), 4.19 (m, 1H), 4.05-3.97 (m, 2H), 3.77 (m, 2H), 3.64 (m, 2H), 3.48 (m, 1H), 3.41 (s, 1H), 3.39-3.24 (m, 2H), 3.07 (s, 2H), 3.04-2.84 (m, 2H), 2.74 (m, 2H), 2.63-2.54 (m, 1H), 2.46 (m, 2H), 2.43-2.28 (m, 1H), 2.19-2.04 (m, 2H), 2.00 (s, 1H), 1.97 (m, 1H), 1.92 (s, 1H), 1.76 (m, 2H), 1.51 (s, 1H), 1.32-1.13 (m, 3H) |
| 228 | | N-{3-[5-(4-{4-[(6-{2-[(3S)-2,6-dioxopiperidin-3-yl]-1-oxo-2,3-dihydro-1H-isoindol-5-yl}-2,6-diazaspiro[3.3]heptan-2-yl)methyl]piperidin-1-yl}phenyl)-1H-pyrrolo[2,3-b]pyridine-3-carbonyl]-2,4-difluorophenyl}propane-1-sulfonamide | 1H NMR (400 MHz, DMSO-d6) δ 12.91 (s, 1H), 10.93 (s, 1H), 9.76 (s, 1H), 8.65 (d, J = 2.2 Hz, 1H), 8.54 (s, 1H), 8.18 (s, 1H), 7.64-7.53 (m, 3H), 7.49 (d, J = 8.2 Hz, 1H), 7.28 (t, J = 8.7 Hz, 1H), 7.06 (d, J = 8.6 Hz, 2H), 6.56-6.46 (m, 2H), 5.03 (dd, J = 13.3, 5.1 Hz, 1H), 4.31 (d, J = 17.0 Hz, 1H), 4.18 (d, J = 17.0 Hz, 1H), 4.00 (s, 4H), 3.77 (d, J = 12.2 Hz, 2H), 3.16-3.08 (m, 3H), 2.95-2.84 (m, 1H), 2.73 (d, J = 11.9 Hz, 2H), 2.58 (d, J = 16.4 Hz, 3H), 1.99-1.91 (m, 1H), 1.74 (td, J = 15.1, 14.7, 7.6 Hz, 4H), 1.50 (s, 1H), 1.25 (d, J = 11.7 Hz, 2H), 0.96 (t, J = 7.5 Hz, 3H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 229 | | N-{3-[5-(4-{4-[(6-{2-[(3R)-2,6-dioxopiperidin-3-yl]-1-oxo-2,3-dihydro-1H-isoindol-5-yl}-2,6-diazaspiro[3.3]heptan-2-yl)methyl]piperidin-1-yl}phenyl)-1H-pyrrolo[2,3-b]pyridine-3-carbonyl]-2,4-difluorophenyl}propane-1-sulfonamide | 1H NMR (400 MHz, DMSO-d6) δ 12.91 (s, 1H), 10.93 (s, 1H), 9.76 (s, 1H), 8.65 (d, J = 2.2 Hz, 1H), 8.54 (s, 1H), 8.18 (s, 1H), 7.64-7.53 (m, 3H), 7.49 (d, J = 8.2 Hz, 1H), 7.28 (t, J = 8.7 Hz, 1H), 7.06 (d, J = 8.6 Hz, 2H), 6.56-6.46 (m, 2H), 5.03 (dd, J = 13.3, 5.1 Hz, 1H), 4.31 (d, J = 17.0 Hz, 1H), 4.18 (d, J = 17.0 Hz, 1H), 4.00 (s, 4H), 3.77 (d, J = 12.2 Hz, 2H), 3.16-3.08 (m, 3H), 2.95-2.84 (m, 1H), 2.73 (d, J = 11.9 Hz, 2H), 2.58 (d, J = 16.4 Hz, 3H), 1.99-1.91 (m, 1H), 1.74 (td, J = 15.1, 14.7, 7.6 Hz, 4H), 1.50 (s, 1H), 1.25 (d, J = 11.7 Hz, 3H), 0.96 (t, J = 7.5 Hz, 3H) |
| 230 | | N-{3-[5-(4-{4-[2-{(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2,4-difluorophenyl}pyrrolidine-1-sulfonamide | 1H NMR (400 MHz, DMSO-d6) δ 13.12-12.77 (m, 1H), 10.99 (s, 1H), 10.13-9.27 (m, 1H), 8.66 (d, J = 2.4 Hz, 1H), 8.60-8.45 (m, 1H), 8.13-8.03 (m, 1H), 7.69-7.62 (m, 2H), 7.60 (d, J = 8.8 Hz, 2H), 7.51 (s, 1H), 7.42 (d, J = 8.0 Hz, 1H), 7.28 (t, J = 8.8 Hz, 1H), 7.08 (dd, J = 5.2, 13.2 Hz, 1H), 5.11 (dd, J = 8.8 Hz, 2H), 4.48-4.39 (m, 1H), 4.36-4.26 (m, 1H), 3.81 (d, J = 12.0 Hz, 2H), 3.19 (t, J = 6.4 Hz, 5H), 3.11-3.02 (m, 2H), 2.96-2.88 (m, 1H), 2.75 (t, J = 11.6 Hz, 3H), 2.65-2.56 (m, 2H), 2.44-2.39 (m, 1H), 2.12 (s, 2H), 2.06-1.98 (m, 1H), 1.89-1.81 (m, 4H), 1.81-1.73 (m, 7H), 1.33-1.20 (m, 2H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| | 231 | N-{3-[5-(4-{4-[(4-{2-[(3R)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2,4-difluorophenyl}pyrrolidine-1-sulfonamide | 1H NMR (400 MHz, DMSO-d6) δ 13.03-12.78 (m, 1H), 11.00 (s, 1H), 9.53 (s, 1H), 8.65 (d, J = 2.0 Hz, 1H), 8.57-8.42 (m, 1H), 8.13-8.02 (m, 1H), 7.66-7.60 (m, 2H), 7.58 (d, J = 8.8 Hz, 2H), 7.51 (s, 1H), 7.41 (d, J = 8.4 Hz, 1H), 7.30-7.24 (m, 1H), 7.07 (d, J = 8.8 Hz, 2H), 5.10 (dd, J = 5.2, 13.2 Hz, 1H), 4.48-4.38 (m, 1H), 4.33-4.25 (m, 1H), 3.85-3.74 (m, 2H), 3.21-3.12 (m, 5H), 3.00 (d, J = 10.8 Hz, 2H), 2.93-2.86 (m, 1H), 2.74 (t, J = 11.2 Hz, 2H), 2.64-2.55 (m, 2H), 2.39 (dd, J = 4.4, 13.2 Hz, 1H), 2.24 (d, J = 5.2 Hz, 2H), 2.04-1.96 (m, 2H), 1.88-1.80 (m, 3H), 1.79-1.71 (m, 8H), 1.29-1.21 (m, 2H) |
| | 232 | N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2,4-difluorophenyl}-3,3-difluoropyrrolidine-1-sulfonamide | 1H NMR (400 MHz, DMSO-d6) δ 13.01-12.83 (m, 1H), 10.99 (s, 1H), 8.65 (d, J = 2.4 Hz, 1H), 8.55 (br s, 1H), 8.10 (s, 1H), 7.72-7.57 (m, 4H), 7.51 (s, 1H), 7.42 (d, J = 8.0 Hz, 1H), 7.32-7.24 (m, 1H), 7.08 (d, J = 8.8 Hz, 2H), 5.11 (dd, J = 5.2, 13.2 Hz, 1H), 4.48-4.40 (m, 1H), 4.36-4.27 (m, 1H), 3.81 (br d, J = 12.0 Hz, 2H), 3.61 (t, J = 13.2 Hz, 2H), 3.45-3.40 (m, 6H), 2.98-2.86 (m, 1H), 2.76 (t, J = 12.0 Hz, 3H), 2.65-2.55 (m, 3H), 2.47-2.37 (m, 3H), 2.05-1.82 (m, 8H), 1.39-1.20 (m, 2H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 233 | | N-{3-[5-(4-{4-[(4-{2-[(3R)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2,4-difluorophenyl}-3,3-difluoropyrrolidine-1-sulfonamide | 1H NMR (400 MHz, DMSO-d6) δ 12.91 (s, 1H), 10.99 (s, 1H), 8.65 (d, J = 2.4 Hz, 1H), 8.54 (br s, 1H), 8.10 (s, 1H), 7.69-7.56 (m, 4H), 7.51 (s, 1H), 7.42 (d, J = 8.4 Hz, 1H), 7.31-7.22 (m, 1H), 7.08 (d, J = 8.8 Hz, 2H), 5.10 (dd, J = 5.2, 13.2 Hz, 1H), 4.48-4.38 (m, 1H), 4.35-4.25 (m, 1H), 3.81 (d, J = 12.4 Hz, 2H), 3.60 (t, J = 13.2 Hz, 2H), 3.45-3.40 (m, 5H), 3.20-3.12 (m, 2H), 2.98-2.85 (m, 1H), 2.81-2.70 (m, 3H), 2.64-2.56 (m, 1H), 2.46-2.36 (m, 4H), 2.05-1.95 (m, 1H), 1.93-1.70 (m, 7H), 1.40-1.20 (m, 2H) |
| 234 | | N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2,4-difluorophenyl}propane-1-sulfonamide | 1H NMR (400 MHz, DMSO-d6) δ 12.92 (s, 1H), 10.99 (s, 1H), 9.77 (s, 1H), 8.66 (d, J = 2.3 Hz, 1H), 8.54 (s, 1H), 8.19 (s, 1H), 7.65 (d, J = 7.8 Hz, 1H), 7.60 (dd, J = 8.8, 4.8 Hz, 3H), 7.54 (d, J = 16.6 Hz, 1H), 7.42 (dd, J = 7.9, 1.3 Hz, 1H), 7.28 (td, J = 9.0, 1.5 Hz, 1H), 7.08 (d, J = 8.7 Hz, 2H), 5.11 (dd, J = 13.3, 5.1 Hz, 1H), 4.43 (d, J = 17.3 Hz, 1H), 4.30 (d, J = 17.2 Hz, 1H), 3.80 (d, J = 12.0 Hz, 2H), 3.16-3.08 (m, 2H), 3.01 (s, 2H), 2.92 (ddd, J = 17.8, 13.5, 5.3 Hz, 1H), 2.75 (t, J = 11.9 Hz, 2H), 2.62 (t, J = 17.1 Hz, 2H), 2.44-2.33 (m, 1H), 2.26 (s, 2H), 2.06 (s, 3H), 1.92-1.78 (m, 9H), 1.73 (p, J = 7.6 Hz, 3H), 1.25 (d, J = 12.6 Hz, 3H), 0.96 (t, J = 7.4 Hz, 3H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| | 235 | N-{3-[5-(4-{4-[(4-{2-[(3R)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2,4-difluorophenyl}propane-1-sulfonamide | 1H NMR (400 MHz, DMSO-d6) δ 12.92 (s, 1H), 10.99 (s, 1H), 9.77 (s, 1H), 8.66 (d, J = 2.3 Hz, 1H), 8.54 (s, 1H), 8.19 (s, 1H), 7.65 (d, J = 7.8 Hz, 1H), 7.60 (dd, J = 8.8, 4.8 Hz, 3H), 7.54 (d, J = 16.6 Hz, 1H), 7.42 (dd, J = 7.9, 1.3 Hz, 1H), 7.28 (td, J = 9.0, 1.5 Hz, 1H), 7.08 (d, J = 8.7 Hz, 2H), 5.11 (dd, J = 13.3, 5.1 Hz, 1H), 4.43 (d, J = 17.3 Hz, 1H), 4.30 (d, J = 17.2 Hz, 1H), 3.80 (d, J = 12.0 Hz, 2H), 3.16-3.08 (m, 2H), 3.01 (s, 2H), 2.92 (ddd, J = 17.8, 13.5, 5.3 Hz, 1H), 2.75 (t, J = 11.9 Hz, 2H), 2.62 (t, J = 17.1 Hz, 2H), 2.44-2.33 (m, 1H), 2.26 (s, 2H), 2.06 (s, 2H), 1.92-1.78 (m, 4H), 1.73 (p, J = 7.6 Hz, 3H), 1.35-1.23 (m, 4H), 0.96 (t, J = 7.4 Hz, 3H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 236 | | N-[3-(5-{4-[4-({4-[2-(2,6-dioxopiperidin-3-yl)-1-oxo-2,3-dihydro-1H-isoindol-5-yl]piperidin-1-yl}methyl)piperidin-1-yl]phenyl}-1H-pyrrolo[2,3-b]pyridine-3-carbonyl)-2,4-difluorophenyl]propane-1-sulfonamide | 1H NMR (400 MHz, DMSO-d6) δ 12.92 (s, 1H), 10.99 (s, 1H), 9.77 (s, 1H), 8.66 (d, J = 2.3 Hz, 1H), 8.54 (s, 1H), 8.19 (s, 1H), 7.65 (d, J = 7.8 Hz, 1H), 7.60 (dd, J = 8.8, 4.8 Hz, 3H), 7.54 (d, J = 16.6 Hz, 1H), 7.42 (dd, J = 7.9, 1.3 Hz, 1H), 7.28 (td, J = 9.0, 1.5 Hz, 1H), 7.08 (d, J = 8.7 Hz, 2H), 5.11 (dd, J = 13.3, 5.1 Hz, 1H), 4.43 (d, J = 17.3 Hz, 1H), 4.30 (d, J = 17.2 Hz, 1H), 3.80 (d, J = 12.0 Hz, 2H), 3.16-3.08 (m, 2H), 3.01 (s, 2H), 2.92 (ddd, J = 17.8, 13.5, 5.3 Hz, 1H), 2.75 (t, J = 11.9 Hz, 2H), 2.62 (t, J = 17.1 Hz, 2H), 2.44-2.33 (m, 1H), 2.26 (s, 2H), 2.06 (s, 3H), 1.92-1.78 (m, 7H), 1.73 (p, J = 7.6 Hz, 3H), 1.35-1.23 (m, 5H), 0.96 (t, J = 7.4 Hz, 3H) |
| 237 | | N-{3-[5-(4-{6-[(1-{2-[(3S)-2,6-dioxopiperidin-3-yl]-7-methoxy-1-oxo-2,3-dihydro-1H-isoindol-5-yl}piperidin-4-yl)methyl]-2,6-diazaspiro[3.3]heptan-2-yl}phenyl)-1H-pyrrolo[2,3-b]pyridine-3-carbonyl]-2,4-difluorophenyl}propane-1-sulfonamide | 1H NMR (400 MHz, DMSO-d6) δ 12.92 (s, 1H), 10.91 (s, 1H), 9.78 (s, 1H), 8.75-8.38 (m, 2H), 8.18 (s, 1H), 7.58 (dd, J = 8.7, 6.2 Hz, 3H), 7.29 (td, J = 8.8, 1.6 Hz, 1H), 6.66-6.54 (m, 3H), 6.46 (d, J = 1.8 Hz, 3H), 4.97 (dd, J = 13.3, 5.1 Hz, 1H), 4.23 (d, J = 16.9 Hz, 1H), 4.10 (d, J = 16.9 Hz, 1H), 3.96 (s, 4H), 3.84 (s, 5H), 3.52 (s, 4H), 3.16-3.07 (m, 2H), 2.98-2.75 (m, 3H), 2.57 (dd, J = 16.5, 3.3 Hz, 1H), 2.46 (s, 2H), 2.32 (qd, J = 13.2, 4.5 Hz, 1H), 1.91 (td, J = 6.9, 6.0, 3.2 Hz, 1H), 1.81-1.68 (m, 4H), 1.56 (s, 1H), 1.32-1.14 (m, 2H), 0.97 (t, J = 7.4 Hz, 3H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 238 | | N-{3-[5-(4-{6-[(1-{2-[(3R)-2,6-dioxopiperidin-3-yl]-7-methoxy-1-oxo-2,3-dihydro-1H-isoindol-5-yl]piperidin-4-yl}methyl)-2,6-diazaspiro[3.3]heptan-2-yl]phenyl)-1H-pyrrolo[2,3-b]pyridine-3-carbonyl]-2,4-difluorophenyl]propane-1-sulfonamide | 1H NMR (400 MHz, DMSO-d6) δ 12.93 (s, 1H), 10.92 (s, 1H), 9.80 (s, 1H), 8.73-8.40 (m, 2H), 8.18 (s, 1H), 7.71-7.49 (m, 3H), 7.29 (td, J = 8.7, 1.6 Hz, 1H), 6.69-6.51 (m, 3H), 6.47 (d, J = 1.8 Hz, 1H), 4.97 (dd, J = 13.3, 5.1 Hz, 1H), 4.23 (d, J = 16.9 Hz, 1H), 4.10 (d, J = 16.9 Hz, 1H), 3.99 (s, 4H), 3.89 (d, J = 12.6 Hz, 2H), 3.84 (s, 4H), 3.80-3.50 (m, 3H), 3.19-3.03 (m, 2H), 3.01-2.72 (m, 3H), 2.71-2.54 (m, 2H), 2.33 (tt, J = 13.3, 6.5 Hz, 1H), 2.00-1.83 (m, 1H), 1.75 (tq, J = 10.0, 7.5 Hz, 4H), 1.62 (s, 1H), 1.32-1.12 (m, 3H), 0.97 (t, J = 7.4 Hz, 3H) |
| 239 | | (3R)-N-[3-(5-{4-[(2S,4S)-4-{4-[2-[(3S)-2,6-dioxopiperidin-3-yl]-1-oxo-2,3-dihydro-1H-isoindol-5-yl]piperidin-1-yl]methyl}piperidin-1-yl]phenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 10.98 (s, 1H), 8.68 (d, J = 2.4 Hz, 1H), 8.57 (d, J = 1.2 Hz, 1H), 8.18 (s, 1H), 8.08 (s, 1H), 7.69-7.57 (m, 4H), 7.51 (s, 1H), 7.41 (d, J = 7.6 Hz, 1H), 7.29-7.18 (m, 3H), 5.38-5.20 (m, 1H), 5.10 (dd, J = 5.2, 13.2 Hz, 1H), 4.46-4.38 (m, 1H), 4.33-4.24 (m, 1H), 3.30-3.17 (m, 6H), 3.11-2.98 (m, 4H), 2.96-2.74 (m, 3H), 2.64-2.55 (m, 1H), 2.39 (dd, J = 4.8, 13.2 Hz, 1H), 2.27 (d, J = 6.4 Hz, 2H), 2.16-1.87 (m, 6H), 1.85-1.66 (m, 6H), 1.37-1.24 (m, 1H), 1.11-1.00 (m, 1H), 0.97 (d, J = 6.0 Hz, 3H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| | 240 | (3R)-N-[3-(5-{4-[(2S,4S)-4-[(4-{2-[(3R)-2,6-dioxopiperidin-3-yl]-1-oxo-2,3-dihydro-1H-isoindol-5-yl}piperidin-1-yl)methyl]-2-methylpiperidin-1-yl]phenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 13.01-12.74 (m, 1H), 10.98 (s, 1H), 8.64 (d, J = 2.4 Hz, 1H), 8.57-8.47 (m, 1H), 8.05 (s, 1H), 7.68-7.54 (m, 4H), 7.51 (s, 1H), 7.42 (d, J = 7.6 Hz, 1H), 7.30-7.22 (m, 1H), 7.02 (d, J = 8.8 Hz, 2H), 5.38-5.19 (m, 1H), 5.10 (dd, J = 5.2, 13.2 Hz, 1H), 4.47-4.38 (m, 1H), 4.35-4.26 (m, 2H), 3.57-3.46 (m, 4H), 3.33-3.18 (m, 4H), 3.11-2.84 (m, 4H), 2.60 (d, J = 16.4 Hz, 1H), 2.46-2.36 (m, 1H), 2.24 (d, J = 5.2 Hz, 2H), 2.15-1.95 (m, 6H), 1.90 (d, J = 12.4 Hz, 5H), 1.42 (dt, J = 4.8, 12.4 Hz, 1H), 1.24-1.12 (m, 1H), 1.03 (d, J = 6.4 Hz, 3H) |
| | 241 | (3R)-N-[3-(5-{4-[(2R,4R)-4-[(4-{2-[(3S)-2,6-dioxopiperidin-3-yl]-1-oxo-2,3-dihydro-1H-isoindol-5-yl}piperidin-1-yl)methyl]-2-methylpiperidin-1-yl]phenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 12.96 (d, J = 1.6 Hz, 1H), 10.99 (s, 1H), 8.69 (d, J = 2.4 Hz, 1H), 8.59 (s, 1H), 8.15-8.07 (m, 1H), 7.76-7.57 (m, 4H), 7.50 (s, 1H), 7.43 (d, J = 7.6 Hz, 1H), 7.32-7.19 (m, 3H), 5.38-5.21 (m, 1H), 5.11 (dd, J = 5.2, 13.2 Hz, 1H), 4.49-4.41 (m, 1H), 4.36-4.28 (m, 1H), 3.48 (s, 8H), 3.23-3.08 (m, 4H), 2.98-2.79 (m, 6H), 2.65-2.56 (m, 1H), 2.40 (dd, J = 4.4, 13.2 Hz, 1H), 2.15-1.82 (m, 9H), 1.47-1.33 (m, 1H), 1.20-1.09 (m, 1H), 0.99 (d, J = 6.0 Hz, 3H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 242 | 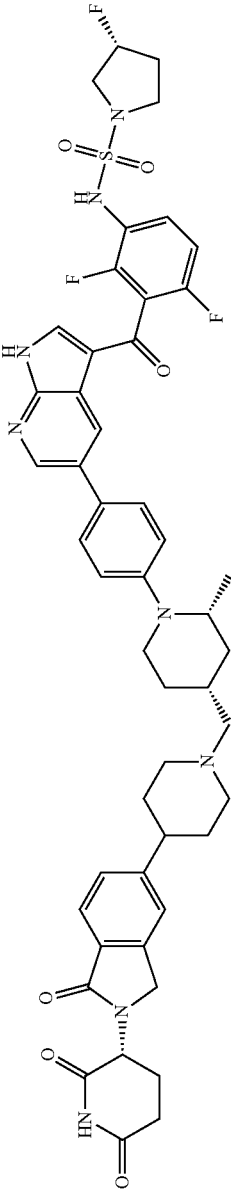 | (3R)-N-[3-(5-{4-[(2R,4R)-4-[(4-{2-[(3R)-2,6-dioxopiperidin-3-yl]-1-oxo-2,3-dihydro-1H-isoindol-5-yl}piperidin-1-yl)methyl]-2-methylpiperidin-1-yl]phenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 12.90 (t, J = 9.6 Hz, 1H), 10.99 (s, 1H), 8.65 (d, J = 2.4 Hz, 1H), 8.53 (d, J = 1.6 Hz, 1H), 8.15-8.03 (m, 1H), 7.72-7.55 (m, 4H), 7.51 (s, 1H), 7.42 (d, J = 7.6 Hz, 1H), 7.31-7.23 (m, 1H), 7.04 (d, J = 8.8 Hz, 2H), 5.38-5.20 (m, 1H), 5.11 (dd, J = 5.2, 13.2 Hz, 1H), 4.48-4.39 (m, 1H), 4.36-4.27 (m, 2H), 3.58-3.45 (m, 8H), 3.17 (s, 1H), 3.00-2.86 (m, 3H), 2.84-2.77 (m, 1H), 2.65-2.55 (m, 3H), 2.40 (dd, J = 4.4, 13.2 Hz, 1H), 2.21-1.70 (m, 11H), 1.53-1.41 (m, 1H), 1.28-1.13 (m, 1H), 1.09-0.96 (m, 3H) |
| 243 | 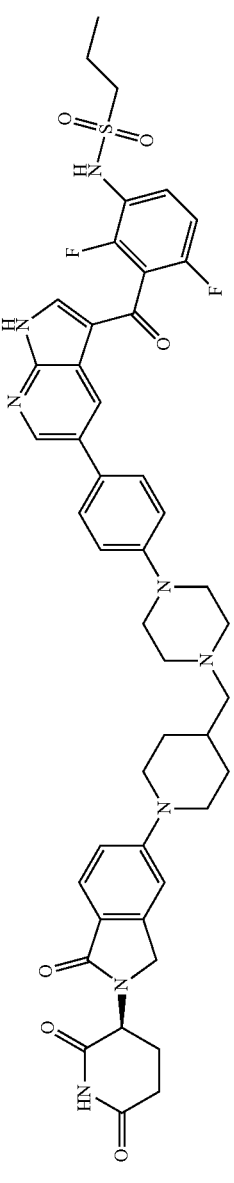 | N-{3-[5-(4-{4-[(1-{2-[(3S)-2,6-dioxopiperidin-3-yl]-1-oxo-2,3-dihydro-1H-isoindol-5-yl}piperidin-4-yl)methyl]piperazin-4-yl}phenyl)-1H-pyrrolo[2,3-b]pyridine-3-carbonyl]-2,4-difluorophenyl}propane-1-sulfonamide | 1H NMR (400 MHz, DMSO-d6) δ 12.90 (s, 1H), 10.95 (s, 1H), 9.85 (b, 1H), 8.67 (s, 1H), 8.55 (s, 1H), 8.19 (s, 1H), 7.62-7.60 (m, 3H), 7.50 (d, J = 8.4 Hz, 1H), 7.29-7.26 (m, 1H), 7.09-7.05 (m, 4H), 5.04 (dd, J = 13.2, 5.1 Hz, 1H), 4.31 (d, J = 17.0 Hz, 1H), 4.19 (d, J = 16.9 Hz, 1H), 3.89 (d, J = 12.4 Hz, 2H), 3.23 (s, 4H), 3.23-3.14 (m, 2H), 2.91-2.82 (m, 3H), 2.66-2.62 (m, 5H), 2.52-2.50 (m, 1H), 2.24-2.22 (m, 2H), 1.98-1.97 (m, 1H), 1.84-1.74 (m, 5H), 1.24-1.20 (m, 2H), 0.97-0.95 (m, 3H) |

TABLE 3-continued

¹H NMR data of exemplary bifunctional compounds of the present disclosure

| Ex. No. | IUPAC Name | ¹H NMR tabulation |
|---|---|---|
| 244 | N-[3-(5-{4-[4-({1-[2-(2,6-dioxopiperidin-3-yl)-1-oxo-2,3-dihydro-1H-isoindol-5-yl]piperidin-4-yl}methyl)piperazin-1-yl]phenyl}-1H-pyrrolo[2,3-b]pyridine-3-carbonyl)-2,4-difluorophenyl]propane-1-sulfonamide | 1H NMR (400 MHz, DMSO-d6) δ 12.90 (s, 1H), 10.95 (s, 1H), 9.85 (b, 1H), 8.67 (s, 1H), 8.55 (s, 1H), 8.19 (s, 1H), 7.62-7.60 (m, 3H), 7.50 (d, J = 8.4 Hz, 1H), 7.29-7.26 (m, 1H), 7.09-7.05 (m, 4H), 5.04 (dd, J = 13.2, 5.1 Hz, 1H), 4.31 (d, J = 17.0 Hz, 1H), 4.19 (d, J = 16.9 Hz, 1H), 3.89 (d, J = 12.4 Hz, 2H), 3.23 (s, 4H), 3.23-3.14 (m, 4H), 2.91-2.82 (m, 4H), 2.66-2.62 (m, 4H), 2.52-2.50 (m, 1H), 2.24-2.22 (m, 2H), 1.98-1.97 (m, 1H), 1.84-1.74 (m, 5H), 1.24-1.20 (m, 2H), 0.97-0.95 (m, 3H) |
| 245 | N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperazin-1-yl}phenyl)-1H-pyrrolo[2,3-b]pyridine-3-carbonyl]-2,4-difluorophenyl}propane-1-sulfonamide | 1H NMR (400 MHz, DMSO-d6) δ 12.92 (s, 1H), 10.96 (s, 1H), 9.78 (s, 1H), 8.66 (d, J = 2.2 Hz, 1H), 8.55 (s, 1H), 8.19 (s, 1H), 7.69-7.47 (m, 4H), 7.29 (td, J = 8.8, 1.6 Hz, 1H), 7.16-6.98 (m, 4H), 5.06 (dd, J = 13.2, 5.1 Hz, 1H), 4.34 (d, J = 16.9 Hz, 1H), 4.22 (d, J = 16.9 Hz, 1H), 3.80 (d, J = 12.0 Hz, 2H), 3.33-3.24 (m, 4H), 3.18-3.05 (m, 2H), 3.01-2.83 (m, 1H), 2.81-2.70 (m, 2H), 2.72-2.51 (m, 4H), 2.50 (s, 1H), 2.37 (qd, J = 13.2, 4.6 Hz, 1H), 2.24 (d, J = 7.0 Hz, 2H), 1.97 (dp, J = 11.4, 4.1, 3.7 Hz, 1H), 1.84 (d, J = 12.9 Hz, 2H), 1.79-1.63 (m, 3H), 1.33-1.16 (m, 2H), 0.97 (t, J = 7.4 Hz, 3H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 246 | | N-[3-(5-{4-[4-({6-[2-(2,6-dioxopiperidin-3-yl)-1-oxo-2,3-dihydro-1H-isoindol-5-yl]-2,6-diazaspiro[3.3]heptan-2-yl}methyl)piperidin-1-yl]phenyl}-1H-pyrrolo[2,3-b]pyridine-3-carbonyl)-2,4-difluorophenyl]-3,3-difluoropyrrolidine-1-sulfonamide | 1H NMR (400 MHz, DMSO-d6) δ 12.90 (s, 1H), 10.95 (s, 1H), 8.65 (d, J = 2.2 Hz, 1H), 8.54 (s, 1H), 8.08 (s, 1H), 7.60 (dd, J = 9.1, 5.3 Hz, 3H), 7.50 (d, J = 8.3 Hz, 1H), 7.22 (t, J = 8.8 Hz, 1H), 7.06 (d, J = 8.4 Hz, 2H), 6.55-6.46 (m, 2H), 5.04 (dd, J = 13.2, 5.1 Hz, 1H), 4.31 (d, J = 17.0 Hz, 1H), 4.19 (d, J = 16.9 Hz, 1H), 4.00 (s, 4H), 3.77 (d, J = 12.0 Hz, 2H), 3.57 (t, J = 13.3 Hz, 2H), 3.49 (t, 3H), 3.39 (t, J = 7.3 Hz, 3H), 2.97-2.84 (m, 1H), 2.76-2.66 (m, 2H), 2.59 (d, J = 17.4 Hz, 1H), 2.47-2.32 (m, 4H), 1.96 (d, J = 12.1 Hz, 2H), 1.81-1.73 (m, 2H), 1.49 (s, 1H), 1.25 (d, J = 9.6 Hz, 3H) |
| 247 | | N-[3-(5-{4-[6-({1-[2-(2,6-dioxopiperidin-3-yl)-7-methoxy-1-oxo-2,3-dihydro-1H-isoindol-5-yl]piperidin-4-yl}methyl)-2,6-diazaspiro[3.3]heptan-2-yl]phenyl}-1H-pyrrolo[2,3-b]pyridine-3-carbonyl)-2,4-difluorophenyl]-3,3-difluoropyrrolidine-1-sulfonamide | 1H NMR (400 MHz, DMSO-d6) δ 12.89 (s, 1H), 10.91 (s, 1H), 8.62 (d, J = 2.2 Hz, 1H), 8.58-8.41 (m, 1H), 8.08 (s, 1H), 7.68-7.50 (m, 3H), 7.22 (td, J = 8.8, 1.6 Hz, 1H), 6.72-6.49 (m, 3H), 6.46 (d, J = 1.7 Hz, 1H), 4.97 (dd, J = 13.3, 5.1 Hz, 1H), 4.33-4.04 (m, 2H), 3.90 (d, J = 48.3 Hz, 9H), 3.57 (t, J = 13.2 Hz, 2H), 3.49 (s, 4H), 3.41 (s, 2H), 3.00-2.73 (m, 3H), 2.64-2.54 (m, 1H), 2.37 (ddd, J = 29.2, 14.3, 7.7 Hz, 5H), 1.92 (ddd, J = 11.0, 5.5, 3.2 Hz, 1H), 1.81-1.68 (m, 2H), 1.55 (s, 1H), 1.19 (tt, J = 12.0, 6.9 Hz, 2H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 248 | | N-(3-{5-[4-(6-{3-[2-(2,6-dioxopiperidin-3-yl)-1-oxo-2,3-dihydro-1H-isoindol-5-yl]propyl]-2,6-diazaspiro[3.3]heptan-2-yl]phenyl}-1H-pyrrolo[2,3-b]pyridine-3-carbonyl]-2,4-difluorophenyl)-3,3-difluoropyrrolidine-1-sulfonamide | 1H NMR (400 MHz, DMSO-d6) δ 12.87 (s, 1H), 11.00 (s, 1H), 8.71-8.38 (m, 2H), 8.07 (s, 1H), 7.72-7.30 (m, 6H), 7.20 (td, J = 8.8, 1.5 Hz, 1H), 6.57 (d, J = 8.2 Hz, 2H), 5.11 (dd, J = 13.3, 5.1 Hz, 1H), 4.49-4.21 (m, 2H), 3.95 (s, 4H), 3.68-3.45 (m, 7H), 2.92 (ddd, J = 17.3, 13.6, 5.4 Hz, 1H), 2.78-2.58 (m, 6H), 2.47-2.29 (m, 3H), 2.01 (ddq, J = 10.4, 5.4, 3.2, 2.7 Hz, 1H), 1.66 (p, J = 7.4 Hz, 2H) |
| 249 | | (3R)-N-{3-[5-(4-{[(6-{2-[(3S)-2,6-dioxopiperidin-3-yl]-7-methoxy-1-oxo-2,3-dihydro-1H-isoindol-5-yl]-2,6-diazaspiro[3.3]heptan-1-yl}methyl)piperidin-1-yl]phenyl)-1H-pyrrolo[2,3-b]pyridine-3-carbonyl]-2,4-difluorophenyl}-3-fluoropyrrolidine-1-sulfonamide | 1H NMR (400 MHz, DMSO-d6) δ 13.27-12.68 (m, 1H), 10.89 (s, 1H), 10.53-9.66 (m, 1H), 8.65 (d, J = 2.0 Hz, 1H), 8.53 (s, 1H), 8.06 (s, 1H), 7.66-7.60 (m, 1H), 7.58 (d, J = 8.8 Hz, 2H), 7.31-7.23 (m, 1H), 7.06 (d, J = 8.8 Hz, 2H), 6.08 (s, 1H), 5.93 (s, 1H), 5.38-5.20 (m, 1H), 4.94 (dd, J = 5.2, 13.2 Hz, 1H), 4.24-4.17 (m, 1H), 4.11-4.04 (m, 1H), 4.02 (s, 4H), 3.81 (s, 3H), 3.80-3.73 (m, 2H), 3.72-3.52 (m, 4H), 3.48 (s, 1H), 3.43-3.38 (m, 2H), 3.31-3.25 (m, 2H), 2.96-2.83 (m, 1H), 2.79-2.65 (m, 2H), 2.60-2.53 (m, 2H), 2.37-2.23 (m, 1H), 2.17-2.07 (m, 1H), 2.06-1.85 (m, 2H), 1.78 (d, J = 11.6 Hz, 2H), 1.54 (s, 1H), 1.33-1.18 (m, 2H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 250 | | (3R)-N-{3-[5-(4-{[6-{2-[(3R)-2,6-dioxopiperidin-3-yl]-7-methoxy-1-oxo-2,3-dihydro-1H-isoindol-5-yl}-2,6-diazaspiro[3.3]heptan-2-yl]methyl]piperidin-1-yl]phenyl)-1H-pyrrolo[2,3-b]pyridine-3-carbonyl]-2,4-difluorophenyl]-3-fluoropyrrolidine-1-sulfonamide | 1H NMR (400 MHz, DMSO-d6) δ 13.13-12.76 (m, 1H), 10.89 (s, 1H), 10.30-9.72 (m, 1H), 8.65 (d, J = 2.4 Hz, 1H), 8.59-8.47 (m, 1H), 8.06 (s, 1H), 7.67-7.60 (m, 1H), 7.58 (d, J = 8.8 Hz, 2H), 7.30-7.22 (m, 1H), 7.06 (d, J = 8.8 Hz, 2H), 6.08 (s, 1H), 5.92 (s, 1H), 5.40-5.19 (m, 1H), 4.94 (dd, J = 5.2, 13.2 Hz, 1H), 4.26-4.16 (m, 1H), 4.11-4.04 (m, 1H), 4.00 (s, 4H), 3.81 (s, 3H), 3.77 (d, J = 12.4 Hz, 2H), 3.52-3.45 (m, 4H), 3.42-3.38 (m, 2H), 3.31-3.25 (m, 2H), 2.97-2.83 (m, 1H), 2.70 (t, J = 11.6 Hz, 2H), 2.60-2.53 (m, 1H), 2.48-2.40 (m, 2H), 2.36-2.23 (m, 1H), 2.16-2.08 (m, 1H), 2.06-1.85 (m, 2H), 1.77 (d, J = 10.8 Hz, 2H), 1.57-1.46 (m, 1H), 1.33-1.18 (m, 2H) |
| 251 | | N-[3-(5-{4-[4-(4-{[2-(2,6-dioxopiperidin-3-yl)-1-oxo-2,3-dihydro-1H-isoindol-5-yl]oxy}butyl)piperazin-1-yl]phenyl}-1H-pyrrolo[2,3-b]pyridine-3-carbonyl)-2,4-difluorophenyl]-3,3-difluoropyrrolidine-1-sulfonamide | 1H NMR (400 MHz, DMSO-d6) δ 12.92 (s, 1H), 10.97 (s, 1H), 8.73-8.43 (m, 2H), 8.10 (s, 1H), 7.75-7.52 (m, 4H), 7.40-7.16 (m, 2H), 7.16-6.95 (m, 3H), 5.08 (dd, J = 13.3, 5.1 Hz, 1H), 4.45-4.22 (m, 2H), 4.12 (t, J = 6.4 Hz, 2H), 3.61 (t, J = 13.1 Hz, 3H), 3.46 (s, 3H), 3.23 (t, J = 5.1 Hz, 3H), 2.91 (ddd, J = 18.1, 13.5, 5.4 Hz, 1H), 2.71-2.56 (m, 4H), 2.40 (th, J = 17.0, 4.1 Hz, 5H), 2.12-1.89 (m, 1H), 1.81 (p, J = 6.7 Hz, 2H), 1.66 (p, J = 7.2 Hz, 2H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| | 252 | (3R)-N-{2-chloro-3-[5-(4-{[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-4-fluorophenyl}-3-fluoropyrrolidine-1-sulfonamide | 1H NMR (400 MHz, DMSO-d6) δ 12.98-12.78 (m, 1H), 11.06-10.91 (m, 1H), 9.73-9.46 (m, 1H), 8.64 (d, J = 2.4 Hz, 1H), 8.10-7.91 (m, 1H), 7.72-7.64 (m, 2H), 7.62-7.53 (m, 2H), 7.51 (s, 1H), 7.45-7.38 (m, 2H), 7.07 (d, J = 8.8 Hz, 2H), 5.40-5.20 (m, 1H), 5.11 (dd, J = 5.2, 13.2 Hz, 1H), 4.48-4.39 (m, 1H), 4.33-4.26 (m, 1H), 3.86-3.74 (m, 2H), 3.50 (s, 1H), 3.44-3.39 (m, 2H), 3.15-3.04(m, 2H), 2.99-2.85 (m, 1H), 2.81-2.69 (m, 3H), 2.64-2.54 (m, 2H), 2.43-2.35 (m, 3H), 2.29-2.14 (m, 2H), 2.14-2.02 (m, 2H), 2.01-1.96 (m, 1H), 1.89-1.74 (m, 7H), 1.34-1.17 (m, 3H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| (structure) | 253 | (3R)-N-{3-[5-(4-{4-[(4-{2-[(3S)-2,6-dioxopiperidin-3-yl]-1-oxo-2,3-dihydro-1H-isoindol-5-yl}methyl)piperidin-1-yl]piperidin-1-yl}phenyl)-1H-pyrrolo[2,3-b]pyridine-3-carbonyl]-4-fluoro-2-methylphenyl}-3-fluoropyrrolidine-1-sulfonamide | 1H NMR (400 MHz, DMSO-d6) δ 12.79 (d, J = 2.8 Hz, 1H), 10.98 (s, 1H), 9.28 (d, J = 9.2 Hz, 1H), 8.62 (d, J = 2.0 Hz, 1H), 7.93-7.76 (m, 1H), 7.65 (d, J = 8.0 Hz, 1H), 7.55 (d, J = 5.2 Hz, 2H), 7.53-7.44 (m, 2H), 7.41 (d, J = 8.0 Hz, 1H), 7.21 (t, J = 8.8 Hz, 1H), 7.06 (d, J = 8.8 Hz, 2H), 5.42-5.23 (m, 1H), 5.10 (dd, J = 5.2, 13.2 Hz, 1H), 4.47-4.37 (m, 1H), 4.35-4.23 (m, 1H), 3.79 (d, J = 12.0 Hz, 2H), 3.50 (s, 1H), 3.44-3.36 (m, 2H), 3.32-3.25 (m, 2H), 3.05-2.94 (m, 2H), 2.93-2.86 (m, 1H), 2.73 (t, J = 11.2 Hz, 2H), 2.66-2.55 (m, 2H), 2.39 (dd, J = 4.4, 13.2 Hz, 1H), 2.23 (d, J = 6.0 Hz, 2H), 2.18 (s, 3H), 2.07 (s, 1H), 2.05-1.94 (m, 3H), 1.88-1.67 (m, 7H), 1.32-1.17 (m, 2H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 254 | | (3S)-3-(5-{1-[(1-{4-[3-(3-amino-2,6-difluorobenzoyl)-1H-pyrrolo[2,3-b]pyridin-5-yl]phenyl}piperidin-4-yl)methyl]piperidin-4-yl}methyl)piperidin-4-yl)-1-oxo-2,3-dihydro-1H-isoindol-2-yl)piperidine-2,6-dione | 1H NMR (400 MHz, DMSO-d6) δ 12.85-12.71 (m, 1H), 11.02-10.93 (m, 1H), 8.63 (d, J = 2.4 Hz, 1H), 8.57-8.48 (m, 1H), 8.04 (s, 1H), 7.65 (d, J = 7.6 Hz, 1H), 7.58 (d, J = 8.8 Hz, 2H), 7.51 (s, 1H), 7.41 (d, J = 8.0 Hz, 1H), 7.07 (d, J = 8.8 Hz, 2H), 6.97-6.86 (m, 2H), 5.20 (s, 2H), 5.10 (dd, J = 5.2, 13.2 Hz, 1H), 4.47-4.38 (m, 1H), 3.79 (d, J = 12.4 Hz, 2H), 3.28-3.18 (m, 1H), 3.03-2.94 (m, 2H), 2.93-2.85 (m, 1H), 2.79-2.69 (m, 2H), 2.65-2.55 (m, 2H), 2.39 (dd, J = 4.8, 13.2 Hz, 1H), 2.22 (d, J = 5.6 Hz, 2H), 2.05-1.96 (m, 3H), 1.88-1.81(m, 2H), 1.78-1.69 (m, 4H), 1.31-1.18 (m, 2H) |
| 255 | | (3R)-N-[3-(5-{3-cyano-4-[4-({4-[2-(2,6-dioxopiperidin-3-yl)-1-oxo-2,3-dihydro-1H-isoindol-5-yl]piperidin-1-yl}methyl)piperidin-1-yl]phenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 12.98 (s, 1H), 10.99 (s, 1H), 8.79-8.57 (m, 2H), 8.12 (d, J = 1.8 Hz, 2H), 7.97 (dd, J = 8.6, 2.4 Hz, 1H), 7.72-7.58 (m, 2H), 7.58-7.38 (m, 2H), 5.43-5.20 7.21 (m, 2H), 5.11 (dd, J = 13.3, 5.1 Hz, 1H), 4.44 (d, J = 17.2 Hz, 1H), 4.30 (d, J = 17.2 Hz, 1H), 3.62 (d, J = 11.4 Hz, 2H), 3.49 (d, J = 2.6 Hz, 1H), 3.44-3.38 (m, 2H), 3.28 (d, J = 11.1 Hz, 1H), 3.03 (d, J = 10.7 Hz, 1H), 2.99-2.80 (m, 3H), 2.74-2.55 (m, 2H), 2.42 (td, J = 13.1, 4.5 Hz, 1H), 2.37-2.23 (m, 2H), 2.19-1.96 (m, 5H), 1.96-1.85 (m, 2H), 1.85-1.66 (m, 5H), 1.44-1.27 (m, 2H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 256 | | (3R)-N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}-3-methoxyphenyl)-1H-pyrrolo[2,3-b]pyridine-3-carbonyl]-2,4-difluorophenyl}-3-fluoropyrrolidine-1-sulfonamide | 1H NMR (400 MHz, DMSO-d6) δ 13.14-12.74 (m, 1H), 11.02-10.94 (m, 1H), 8.69 (d, J = 2.4 Hz, 1H), 8.61-8.46 (m, 1H), 8.16 (s, 1H), 8.12-8.06 (m, 1H), 7.69-7.58 (m, 2H), 7.51 (s, 1H), 7.41 (d, J = 8.0 Hz, 1H), 7.30-7.19 (m, 3H), 7.07-6.96 (m, 1H), 5.39-5.17 (m, 1H), 5.16-5.05 (m, 1H), 4.49-4.37 (m, 1H), 4.34-4.24 (m, 1H), 3.91 (s, 3H), 3.52-3.44 (m, 4H), 3.01 (d, J = 11.2 Hz, 2H), 2.93-2.85 (m, 1H), 2.64-2.55 (m, 4H), 2.41-2.38 (m, 2H), 2.29-2.23 (m, 2H), 2.15-1.94 (m, 6H), 1.87-1.64 (m, 8H), 1.38-1.27 (m, 2H) |
| 257 | | (3R)-N-{3-(5-{4-[4-({4-[2-(2,6-dioxopiperidin-3-yl)-1-oxo-2,3-dihydro-1H-isoindol-5-yl]piperidin-1-yl}methyl)piperidin-1-yl]-3-(methylamino)phenyl}-1H-pyrrolo[2,3-b]pyridine-3-carbonyl)-2,4-difluorophenyl]-3-fluoropyrrolidine-1-sulfonamide | 1HNMR (400 MHz, DMSO-d6) δ 12.98 (s, 1H), 11.00 (s, 1H), 9.90 (s, 1H), 8.67 (s, 1H), 8.63 (s, 1H), 8.11 (s, 1H), 7.68-7.63 (m, 2H), 7.52 (s, 1H), 7.33-7.27 (m, 1H), 7.05 (d, J = 8.1 Hz, 1H), 6.90 (d, J = 8.1 Hz, 1H), 6.77 (s, 1H), 5.41-5.01 (m, 3H), 4.41-4.27 (q, 2H), 3.25-3.22 (m, 4H), 2.93-2.88 (m, 2H), 2.74-2.70 (m, 5H), 2.28-2.02 (m, 6H), 2.12-2.08 (m, 5H), 1.97-1.75 (m, 2H), 1.43-1.40 (m, 3H), 1.25-1.17 (m, 6H), 0.96-0.93 (m, 2H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| | 258 | (3R)-N-{3-[5-(4-{2-[(1-{2-[(3S)-2,6-dioxopiperidin-3-yl]-1-oxo-2,3-dihydro-1H-isoindol-5-yl}piperidin-4-yl)methyl]-2,8-diazaspiro[4.5]decan-8-yl}-3-fluorophenyl)-1H-pyrrolo[2,3-b]pyridine-3-carbonyl]-2,4-difluorophenyl}-3-fluoropyrrolidine-1-sulfonamide | 1HNMR (300 MHz, DMSO-d6) δ 12.96 (s, 1H), 10.94 (s, 1H), 9.80 (s, 1H), 8.70 (s, 1H), 8.59 (s, 1H), 8.11 (s, 1H), 7.62-7.50 (m, 5H), 7.27-7.21 (m, 2H), 7.07-7.05 (m, 2H), 5.22 (d, J = 17.2 Hz, 1H), 5.03-5.01 (m, 1H), 4.35-4.17 (q, 2H), 3.93-3.88 (m, 2H), 3.44-3.25 (m, 8H), 3.06-3.02 (m, 4H), 2.95-2.84 (m, 6H), 2.41-2.37 (m, 2H), 2.12-2.07 (m, 2H), 1.85-1.78 (m, 10H), 1.35-1.24 (m, 2H) |
| | 259 | (3R)-N-{3-[5-(4-{2-[(1-{2-[(3R)-2,6-dioxopiperidin-3-yl]-1-oxo-2,3-dihydro-1H-isoindol-5-yl}piperidin-4-yl)methyl]-2,8-diazaspiro[4.5]decan-8-yl}-3-fluorophenyl)-1H-pyrrolo[2,3-b]pyridine-3-carbonyl]-2,4-difluorophenyl}-3-fluoropyrrolidine-1-sulfonamide | 1HNMR (300 MHz, DMSO-d6) δ 12.96 (s, 1H), 10.94 (s, 1H), 9.80 (s, 1H), 8.70 (s, 1H), 8.59 (s, 1H), 8.11 (s, 1H), 7.62-7.50 (m, 5H), 7.27-7.21 (m, 2H), 7.07-7.05 (m, 2H), 5.22 (d, J = 17.2 Hz, 1H), 5.03-5.01 (m, 1H), 4.35-4.17 (q, 2H), 3.93-3.88 (m, 2H), 3.60 (s, 1H), 3.51 (s, 1H), 3.44-3.25 (m, 6H), 3.06-3.02 (m, 4H), 2.95-2.84 (m, 5H), 2.41-2.37 (m, 1H), 2.12-2.07 (m, 2H), 1.85-1.78 (m, 12H), 1.35-1.24 (m, 2H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 260 | | (3R)-N-{3-[5-(3,5-dicyano-4-{[(4-[2-[(3S)-2,6-dioxopiperidin-3-yl]-1-oxo-2,3-dihydro-1H-isoindol-5-yl]piperidin-1-yl)methyl]piperidin-1-yl]phenyl)-1H-pyrrolo[2,3-b]pyridine-3-carbonyl]-2,4-difluorophenyl}-3-fluoropyrrolidine-1-sulfonamide | 1H NMR (400 MHz, DMSO-d6) δ 13.02 (s, 1H), 10.99 (s, 1H), 9.83 (s, 1H), 8.79-8.73 (m, 2H), 8.45 (s, 2H), 8.13 (s, 1H), 7.65 (dd, J = 8.5, 4.0 Hz, 2H), 7.64-7.57 (m, 1H), 7.42 (s, 1H), 7.31-7.22 (m, 1H), 5.37-5.24 (s, 1H), 5.11 (dd, J = 13.3, 5.1 Hz, 1H), 4.43 (d, J = 17.3 Hz, 1H), 4.29 (d, J = 17.2 Hz, 1H), 3.73 (d, J = 12.1 Hz, 2H), 3.49 (d, J = 2.7 Hz, 4H), 3.28 (dd, J = 9.8, 6.9 Hz, 1H), 3.05 (d, J = 10.6 Hz, 1H), 2.92 (ddd, J = 17.7, 13.5, 5.5 Hz, 1H), 2.60 (d, J = 16.7 Hz, 2H), 2.40 (dd, J = 13.2, 4.6 Hz, 3H), 2.31 (s, 3H), 2.08 (s, 1H), 2.03-1.88 (m, 2H), 1.79 (s, 4H), 1.36 (d, J = 7.3 Hz, 4H), 0.82 (s, 1H) |
| 261 | | (3R)-N-[3-(5-{3,5-dicyano-4-[4-({4-[2-(2,6-dioxopiperidin-3-yl)-1-oxo-2,3-dihydro-1H-isoindol-5-yl]piperidin-1-yl}methyl)piperidin-1-yl]phenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 13.02 (s, 1H), 10.99 (s, 1H), 9.83 (s, 1H), 8.79-8.73 (s, 2H), 8.45 (s, 2H), 8.13 (s, 1H), 7.65 (dd, J = 8.5, 4.0 Hz, 2H), 7.64-7.57 (m, 1H), 7.42 (s, 1H), 7.31-7.22 (m, 1H), 5.40-5.22 (s, 1H), 5.13 (dd, J = 13.3, 5.1 Hz, 1H), 4.41 (d, 2H), 3.73 (d, J = 12.1 Hz, 2H), 3.49 (d, J = 2.7 Hz, 4H), 3.28 (dd, J = 9.8, 6.9 Hz, 1H), 3.05 (d, J = 10.6 Hz, 1H), 2.92 (ddd, J = 17.7, 13.5, 5.5 Hz, 1H), 2.60 (d, J = 16.7 Hz, 2H), 2.27 (dd, J = 13.2, 4.6 Hz, 3H), 2.08 (s, 5H), 2.03-1.88 (m, 4H), 1.79 (s, 4H), 1.36 (d, J = 7.3 Hz, 5H), 1.24 (s, 1H), 0.82 (s, 1H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| 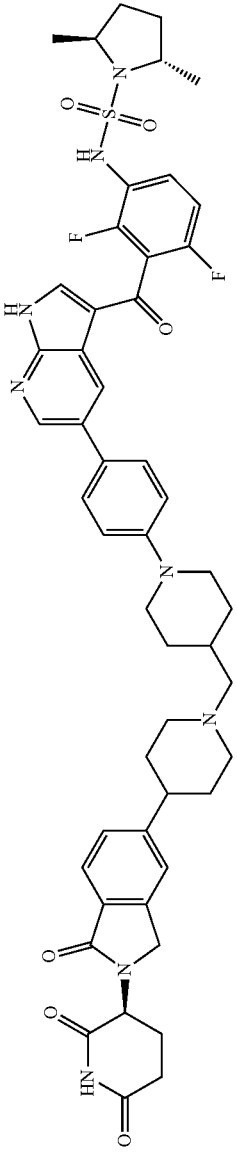 | 262 | (2S,5S)-N-{3-[5-(4-{[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2,4-difluorophenyl}-2,5-dimethylpyrrolidine-1-sulfonamide | 1H NMR (400 MHz, DMSO-d6) δ 12.90 (s, 1H), 10.98 (s, 1H), 9.58 (s, 1H), 8.65 (d, J = 2.3 Hz, 1H), 8.52 (s, 1H), 8.04 (s, 1H), 7.66 (d, J = 7.8 Hz, 1H), 7.59 (dd, J = 8.8, 6.2 Hz, 3H), 7.51 (s, 1H), 7.41 (d, J = 7.9 Hz, 1H), 7.32-7.23 (m, 1H), 7.07 (d, J = 8.6 Hz, 1H), 5.11 (dd, J = 13.3, 5.1 Hz, 1H), 4.43 (d, J = 17.2 Hz, 1H), 4.30 (d, J = 17.2 Hz, 1H), 3.90-3.77 (m, 3H), 3.64-3.56 (m, 2H), 3.00 (s, 1H), 2.91 (ddd, J = 17.8, 13.6, 5.4 Hz, 1H), 2.75 (t, J = 12.0 Hz, 2H), 2.60 (d, J = 17.1 Hz, 1H), 2.40 (dd, J = 12.9, 4.5 Hz, 1H), 2.10-1.97 (m, 4H), 1.88-1.70 (m, 8H), 1.53-1.40 (m, 2H), 1.35 (s, 1H), 1.25 (d, J = 11.4 Hz, 4H), 1.05 (d, J = 6.3 Hz, 6H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 263 | | (2S,5S)-N-[3-(5-{4-[4-({4-[2-(2,6-dioxopiperidin-3-yl)-1-oxo-2,3-dihydro-1H-isoindol-5-yl]piperidin-1-yl}methyl)piperidin-1-yl]phenyl}-1H-pyrrolo[2,3-b]pyridine-3-carbonyl)-2,4-difluorophenyl]-2,5-dimethylpyrrolidine-1-sulfonamide | 1H NMR (400 MHz, DMSO-d6) δ 12.90 (s, 1H), 10.98 (s, 1H), 9.58 (s, 1H), 8.65 (d, J = 2.3 Hz, 1H), 8.52 (s, 1H), 8.04 (s, 1H), 7.66 (d, J = 7.8 Hz, 1H), 7.59 (dd, J = 8.8, 6.2 Hz, 3H), 7.51 (s, 1H), 7.41 (d, J = 7.9 Hz, 1H), 7.32-7.23 (m, 1H), 7.07 (d, J = 8.6 Hz, 1H), 5.11 (dd, J = 13.3, 5.1 Hz, 1H), 4.43 (d, J = 17.2 Hz, 1H), 4.30 (d, J = 17.2 Hz, 1H), 3.90-3.77 (m, 3H), 3.64-3.56 (m, 2H), 3.00 (s, 1H), 2.91 (ddd, J = 17.8, 13.6, 5.4 Hz, 1H), 2.75 (t, J = 12.0 Hz, 2H), 2.60 (d, J = 17.1 Hz, 1H), 2.40 (dd, J = 12.9, 4.5 Hz, 1H), 2.10-1.97 (m, 4H), 1.88-1.70 (m, 8H), 1.53-1.40 (m, 2H), 1.35 (s, 1H), 1.25 (d, J = 11.4 Hz, 4H), 1.05 (d, J = 6.3 Hz, 6H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 264 | | (2S)-N-[3-(5-{4-[4-({4-[2-(2,6-dioxopiperidin-3-yl)-1-oxo-2,3-dihydro-1H-isoindol-5-yl]piperidin-1-yl}methyl)piperidin-1-yl]phenyl}-1H-pyrrolo[2,3-b]pyridine-3-carbonyl)-2,4-difluorophenyl]-2-methylpyrrolidine-1-sulfonamide | 1H NMR (400 MHz, DMSO-d6) δ 12.91 (s, 1H), 10.97 (s, 1H), 9.66 (s, 1H), 8.65 (d, J = 2.2 Hz, 1H), 8.52 (s, 1H), 8.08 (s, 1H), 7.69-7.57 (m, 4H), 7.57 (s, 1H), 7.51 (s, 1H), 7.41 (dd, J = 8.1, 1.4 Hz, 1H), 7.28 (td, J = 8.8, 1.6 Hz, 1H), 7.11-7.04 (m, 2H), 5.10 (dd, J = 13.3, 5.1 Hz, 1H), 4.43 (d, J = 17.3 Hz, 1H), 3.80 (d, J = 17.2 Hz, 1H), 3.71 (td, J = 12.2 Hz, 2H), 3.64-3.56 (m, 1H), 3.23 (t, J = 6.7 Hz, 2H), 3.12-2.94 (m, 3H), 2.74 (t, J = 12.0 Hz, 2H), 2.63 (s, 2H), 2.25-1.95 (m, 3H), 1.95-1.67 (m, 11H), 1.47 (dd, J = 9.2, 4.8 Hz, 1H), 1.26 (s, 1H), 1.23 (s, 5H), 1.06 (d, J = 6.3 Hz, 3H) |
| 265 | | (3R)-N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-4-ethyl-2-fluorophenyl}-3-fluoropyrrolidine-1-sulfonamide | 1H NMR (300 MHz, DMSO-d6) δ 12.65 (s, 1H), 10.85 (s, 1H), 10.32 (s, 1H), 9.57 (s, 1H), 8.51 (d, J = 2.2 Hz, 1H), 7.71 (s, 1H), 7.54 (d, J = 7.8 Hz, 1H), 7.48-7.34 (m, 4H), 7.30 (d, J = 8.3 Hz, 1H), 7.09 (d, J = 8.2 Hz, 1H), 6.95 (d, J = 8.5 Hz, 2H), 5.24 (s, 1H), 5.10-4.92 (s, 1H), 4.32 (d, J = 17.3 Hz, 1H), 4.18 (d, J = 17.2 Hz, 1H), 3.68 (d, J = 12.1 Hz, 2H), 3.42-3.33 (s, 1H), 2.91 (d, 2H), 2.87-2.71 (s, 1H), 2.51 (s, 1H), 2.41 (s, 1H), 1.91 (m, 3H), 1.70 (m, 9H), 1.12 (m, 6H), 0.96 (m, J = 7.5 Hz, 5H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 266 | | (3R)-N-[3-(5-{4-[4-({4-[2-(2,6-dioxopiperidin-3-yl)-1-oxo-2,3-dihydro-1H-isoindol-5-yl]piperidin-1-yl}methyl)piperidin-1-yl]phenyl}-1H-pyrrolo[2,3-b]pyridine-3-carbonyl)-4-ethyl-2-fluorophenyl]-3-fluoropyrrolidine-1-sulfonamide | 1H NMR (300 MHz, DMSO-d6) δ 12.65 (s, 1H), 10.85 (s, 1H), 10.32 (s, 1H), 9.57 (s, 1H), 8.51 (d, J = 2.2 Hz, 1H), 7.71 (s, 1H), 7.54 (d, J = 7.8 Hz, 1H), 7.48-7.34 (m, 4H), 7.30 (d, J = 8.3 Hz, 1H), 7.09 (d, J = 8.2 Hz, 1H), 6.95 (d, J = 8.5 Hz, 2H), 5.24 (s, 1H), 5.10-4.92 (s, 1H), 4.32 (d, J = 17.3 Hz, 1H), 4.18 (d, J = 17.2 Hz, 1H), 3.68 (d, J = 12.1 Hz, 2H), 3.42-3.33 (s, 1H), 2.91 (d, 2H), 2.87-2.71 (s, 1H), 2.51 (s, 1H), 2.41 (s, 1H), 1.91 (m, 3H), 1.70 (m, 9H), 1.12 (m, 6H), 0.96 (m, J = 7.5 Hz, 5H) |
| 267 | | (3R)-N-{2,4-dichloro-3-[5-(4-{4-[2-[(3S)-2,6-dioxopiperidin-3-yl]-1-oxo-2,3-dihydro-1H-isoindol-5-yl]piperidin-1-yl}methyl)piperidin-1-yl]phenyl}-1H-pyrrolo[2,3-b]pyridine-3-carbonyl]phenyl}-3-fluoropyrrolidine-1-sulfonamide | 1H NMR (400 MHz, DMSO-d6) δ 10.98 (s, 1H), 8.63 (s, 1H), 7.67 (s, 1H), 7.66-7.65 (m, 2H), 7.64 (s, 1H), 7.55-7.52 (m, 2H), 7.51-7.42 (m, 4H), 7.41 (s, 1H), 7.07-7.05 (m, 2H), 5.13-5.11 (s, 1H), 5.09-5.08 (s, 1H), 4.45-4.41 (s, 1H), 4.32-4.28 (s, 1H), 3.82-3.79 (m, 2H), 3.47 (s, 1H), 3.39-3.32 (m, 2H), 3.31-3.12 (m, 2H), 3.10 (s, 1H), 2.78-2.72 (m, 3H), 2.67 (s, 1H), 2.66-2.62 (m, 2H), 2.57-2.50 (m, 2H), 2.49-2.40 (s, 1H), 2.38-2.32 (m, 2H), 2.01-1.99 (m, 7H), 1.86-1.77 (m, 4H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 268 | | (3R)-N-[2,4-dichloro-3-(5-{4-[4-[2-(2,6-dioxopiperidin-3-yl)-1-oxo-2,3-dihydro-1H-isoindol-5-yl]piperidin-1-yl]methyl)piperidin-1-yl]phenyl}-1H-pyrrolo[2,3-b]pyridine-3-carbonyl)phenyl]-3-fluoropyrrolidine-1-sulfonamide | 1H NMR (400 MHz, DMSO-d6) δ 10.98 (s, 1H), 8.63 (s, 1H), 7.67 (s, 1H), 7.65 (s, 1H), 7.64-7.55 (m, 2H), 7.51 (s, 1H), 7.42-7.40 (m, 2H), 7.40 (s, 1H), 7.08-7.05 (m, 2H), 5.13 (s, 1H), 5.11 (s, 1H), 5.09 (s, 1H), 5.05 (s, 1H), 4.45-4.41 (m, 2H), 4.32-4.27 (m, 2H), 3.82-3.79 (m, 2H), 3.47-3.31 (m, 2H), 3.13 (s, 1H), 2.94-2.91 (m, 2H), 2.78-2.72 (m, 2H), 2.67-2.50 (m, 2H), 2.49 (s, 1H), 2.38-2.01 (m, 3H), 1.99-1.83 (m, 6H), 1.83 (s, 1H), 1.47-1.23 (m, 4H), 0.95-0.65 (m, 3H) |
| 269 | | (3R)-N-[3-(5-{4-[4-[2-(2,6-dioxopiperidin-3-yl)-1-oxo-2,3-dihydro-1H-isoindol-5-yl]piperidin-1-yl]methyl)piperidin-1-yl]phenyl}-1H-pyrrolo[2,3-b]pyridine-3-carbonyl)-2-fluoro-4-methoxyphenyl]-3-fluoropyrrolidine-1-sulfonamide | 1H NMR (400 MHz, DMSO-d6) δ 12.71 (s, 1H), 10.98 (s, 1H), 9.52 (s, 1H), 8.62 (d, J = 2.2 Hz, 1H), 8.45 (s, 1H), 7.84 (d, J = 7.9 Hz, 1H), 7.66 (d, J = 8.3 Hz, 2H), 7.57 (d, J = 7.54-7.46 (m, 2H), 7.42 (d, J = 8.0 Hz, 1H), 7.02-7.07 (m, 3H), 5.35 (s, 1H), 5.11 (dd, J = 13.3, 5.1 Hz, 1H), 4.43 (d, J = 17.2 Hz, 1H), 4.30 (d, J = 17.2 Hz, 1H), 3.80 (d, J = 12.0 Hz, 2H), 3.79 (s, 3H), 3.73 (s, 1H), 3.50 (s, 1H),3.45 (d, J = 2.0 Hz, 2H), 3.32 (d, 2H), 3.00 (s, 3H), 2.97-2.85 (m, 2H), 2.75 (t, J = 12.1 Hz, 2H), 2.48 (s, 1H), 2.11-1.99 (m, 5H), 1.85 (d, J = 13.0 Hz, 6H), 1.23 (s, 9H), 0.91-0.81 (m, 1H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| | 270 | (2S,3R)-N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2,4-difluorophenyl}-3-fluoro-2-methylpyrrolidine-1-sulfonamide | 1H NMR (400 MHz, DMSO-d6) δ 12.88 (s, 1H), 10.97 (s, 1H), 9.79 (s, 1H), 8.65 (d, J = 2.2 Hz, 1H), 8.53 (s, 1H), 8.01 (s, 1H), 7.64 (dd, J = 6.3, 8.6 Hz, 2H), 7.59 (d, J = 8.6 Hz, 2H), 7.51 (s, 1H), 7.41 (dd, J = 1.5, 7.9 Hz, 1H), 7.21-7.3 (m, 1H), 7.07 (d, J = 8.8 Hz, 2H), 5.10 (dd, J = 5.1, 13.2 Hz, 1H), 4.84 (d, J = 2.6 Hz, 1H), 4.43 (d, J = 17.2 Hz, 1H), 4.30 (d, J = 17.2 Hz, 1H), 3.81 (dd, J = 9.0, 15.4 Hz, 3H), 3.39 (dt, J = 9.1, 21.3 Hz, 2H), 3.03 (s, 2H), 2.94-2.88 (m, 1H), 2.75 (t, J = 12.0 Hz, 2H), 2.62 (s, 1H), 2.18-2.05 (m, 4H), 2.08 (s, 1H), 1.84-1.69 (m, 7H), 1.26 (d, J = 15.1 Hz, 4H), 1.04 (d, J = 6.8 Hz, 3H) |
| | 271 | (2S,3R)-N-{3-(5-{4-[4-({4-[2-(2,6-dioxopiperidin-3-yl)-1-oxo-2,3-dihydro-1H-isoindol-5-yl]piperidin-1-yl}methyl)piperidin-1-yl]phenyl}-1H-pyrrolo[2,3-b]pyridine-3-carbonyl)-2,4-difluorophenyl]-3-fluoro-2-methylpyrrolidine-1-sulfonamide | 1H NMR (400 MHz, DMSO-d6) δ 12.88 (s, 1H), 10.97 (s, 1H), 9.79 (s, 1H), 8.65 (d, J = 2.2 Hz, 1H), 8.53 (s, 1H), 8.01 (s, 1H), 7.64 (dd, J = 6.3, 8.6 Hz, 2H), 7.59 (d, J = 8.6 Hz, 2H), 7.51 (s, 1H), 7.41 (dd, J = 1.5, 7.9 Hz, 1H), 7.21-7.3 (m, 1H), 7.07 (d, J = 8.8 Hz, 2H), 5.10 (dd, J = 5.1, 13.2 Hz, 1H), 4.84 (d, J = 2.6 Hz, 1H), 4.43 (d, J = 17.2 Hz, 1H), 4.30 (d, J = 17.2 Hz, 1H), 3.81 (dd, J = 9.0, 15.4 Hz, 3H), 3.39 (dt, J = 9.1, 21.3 Hz, 2H), 3.03 (s, 2H), 2.94-2.88 (m, 1H), 2.75 (t, J = 12.0 Hz, 2H), 2.62 (s, 1H), 2.18-2.05 (m, 4H), 2.08 (s, 1H), 1.84-1.69 (m, 7H), 1.26 (d, J = 15.1 Hz, 4H), 1.04 (d, J = 6.8 Hz, 3H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 272 | | (3R)-N-{3-[5-{4-{4-[(3S)-2,6-dioxopiperidin-3-yl]-[(4-{2-[(3S)-2,6-dioxopiperidin-1-yl]methyl]piperidin-1-yl]phenyl}-1H-pyrrolo[2,3-b]pyridine-3-carbonyl]-4-fluoro-2-(trifluoromethyl)phenyl}-3-fluoropyrrolidine-1-sulfonamide | 1H NMR (300 MHz, DMSO-d6) δ 12.64 (s, 1H), 10.86 (s, 1H), 9.18 (s, 1H), 8.51 (d, J = 2.1 Hz, 1H), 7.81 (s, 1H), 7.56 (d, J = 7.7 Hz, 2H), 7.49-7.36 (m, 4H), 7.30 (d, J = 7.9 Hz, 1H), 6.95 (d, J = 8.5 Hz, 2H), 5.29 (s, 1H), 5.11 (s, 1H), 4.99 (m, 2H), 4.33 (d, J = 17.4 Hz, 2H), 4.19 (m, 4H), 3.70 (m, 4H), 3.26 (s, 3H), 2.87-2.71 (m, 3H), 2.67(m, 5H), 2.51 (m, 7H), 1.95-1.87 (m, 1H), 1.74 (d, J = 12.2 Hz, 8H), 1.36 (s, 1H), 1.12 (s, 2H) |
| 273 | | (3R)-N-[3-(5-{4-[4-[2-(2,6-dioxopiperidin-3-yl)-1-oxo-2,3-dihydro-1H-isoindol-5-yl]piperidin-1-yl]methyl)piperidin-1-yl]phenyl}-1H-pyrrolo[2,3-b]pyridine-3-carbonyl)-4-fluoro-2-(trifluoromethyl)phenyl]-3-fluoropyrrolidine-1-sulfonamide | 1H NMR (300 MHz, DMSO-d6) δ 12.64 (s, 1H), 10.86 (s, 1H), 9.18 (s, 1H), 8.51 (d, J = 2.1 Hz, 1H), 7.81 (s, 1H), 7.56 (d, J = 7.7 Hz, 2H), 7.49-7.36 (m, 4H), 7.30 (d, J = 7.9 Hz, 1H), 6.95 (d, J = 8.5 Hz, 2H), 5.29 (s, 1H), 5.11 (s, 1H), 4.99 (m, 2H), 4.33 (d, J = 17.4 Hz, 2H), 4.19 (m, 4H), 3.70 (m, 4H), 3.26 (s, 3H), 2.87-2.71 (m, 3H), 2.67(m, 5H), 2.51 (m, 7H), 1.95-1.87 (m, 1H), 1.74 (d, J = 12.2 Hz, 8H), 1.36 (s, 1H), 1.12 (s, 2H) |

TABLE 3-continued

¹H NMR data of exemplary bifunctional compounds of the present disclosure

| Ex. No. | IUPAC Name | Parent Mol Structure | ¹H NMR tabulation |
|---|---|---|---|
| 274 | (3R)-N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2,4-dimethoxyphenyl}-3-fluoropyrrolidine-1-sulfonamide | | 1H NMR (400 MHz, DMSO-d6) δ 12.58 (s, 1H), 10.98 (s, 1H), 9.12 (s, 1H), 8.59 (d, J = 2.2 Hz, 1H), 7.73-7.66 (m, 2H), 7.58-7.49 (m, 3H), 7.43 (dd, J = 11.6, 8.5 Hz, 2H), 7.07 (d, J = 8.5 Hz, 2H), 6.92 (d, J = 9.0 Hz, 1H), 5.35 (s, 1H), 5.11 (dd, J = 13.3, 5.1 Hz, 1H), 4.43 (d, J = 17.2 Hz, 1H), 4.30 (d, J = 17.2 Hz, 1H), 3.80 (d, J = 12.2 Hz, 2H), 3.66 (d, J = 9.5 Hz, 6H), 3.50 (s, 2H), 3.38 (s, 2H), 3.01 (s, 3H), 2.98-2.86 (m, 2H), 2.76 (d, J = 12.1 Hz, 1H), 2.50 (s, 1H), 2.49 (s, 1H), 2.09 (s, 2H), 1.85 (d, J = 12.6 Hz, 6H), 1.83-1.79 (m, 7H), 1.24 (s, 4H), 0.80 (s, 1H) |
| 275 | (3R)-N-[3-(5-{4-[4-({4-[2-(2,6-dioxopiperidin-3-yl)-1-oxo-2,3-dihydro-1H-isoindol-5-yl]piperidin-1-yl}methyl)piperidin-1-yl]phenyl}-1H-pyrrolo[2,3-b]pyridine-3-carbonyl)-2,4-dimethoxyphenyl]-3-fluoropyrrolidine-1-sulfonamide | | 1H NMR (300 MHz, DMSO-d6) δ 12.57 (s, 1H), 10.96 (s, 1H), 9.07 (s, 1H), 8.58 (d, J = 2.3 Hz, 1H), 8.56-8.32 (s, 1H), 7.74-7.60 (m, 2H), 7.47 (dt, J = 32.6, 8.2 Hz, 4H), 7.05 (d, J = 8.5 Hz, 2H), 6.90 (d, J = 9.0 Hz, 1H), 5.39-5.26 (m, 1H), 5.21-5.03 (m, 1H), 4.42-4.28 (d, J = 17.2 Hz, 3H), 3.78 (d, J = 11.7 Hz, 3H), 3.68-3.55 (m, 8H), 3.49 (s, 6H), 2.07-1.97 (s, 8H), 1.83 (d, J = 14.0 Hz, 9H), 1.78-1.69 (m, 4H), 1.22 (s, 35H), 0.82 (q, J = 7.3, 6.3 Hz, 10H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 276 | | (3R)-N-[3-(5-{4-[4-((4-[2-(2,6-dioxopiperidin-3-yl)-1-oxo-2,3-dihydro-1H-isoindol-5-yl]piperidin-1-yl)methyl)piperidin-1-yl]phenyl}-1H-pyrrolo[2,3-b]pyridine-3-carbonyl)-2-ethyl-4-fluorophenyl]-3-fluoropyrrolidine-1-sulfonamide | 1H NMR (400 MHz, DMSO-d6) δ 12.90 (s, 1H), 10.98 (s, 1H), 9.58 (s, 1H), 8.65 (d, J = 2.3 Hz, 1H), 8.52 (s, 1H), 7.91 (s, 1H), 7.66 (d, J = 7.8 Hz, 1H), 7.59 (dd, J = 8.8, 6.2 Hz, 3H), 7.51 (s, 1H), 7.41 (d, J = 7.9 Hz, 1H), 7.32-7.23 (m, 1H), 7.07 (d, J = 8.6 Hz, 1H), 5.11 (dd, J = 13.3, 5.1 Hz, 1H), 4.43 (d, J = 17.2 Hz, 1H), 4.30 (d, J = 17.2 Hz, 1H), 3.90-3.77 (m, 3H), 3.64-3.56 (m, 2H), 3.00 (s, 1H), 2.91 (ddd, J = 17.8, 13.6, 5.4 Hz, 1H), 2.75 (t, J = 12.0 Hz, 2H), 2.60 (d, J = 17.1 Hz, 1H), 2.40 (dd, J = 12.9, 4.5 Hz, 1H), 2.10-1.97 (m, 7H), 1.88-1.70 (m, 4H), 1.25 (d, J = 10.7 Hz, 3H), 1.01 (t, J = 7.4 Hz, 3H) |
| 277 | | (2R,5R)-N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2,4-difluorophenyl}-2,5-dimethylpyrrolidine-1-sulfonamide | 1H NMR (400 MHz, DMSO-d6) δ 13.05-12.83 (m, 1H), 10.98 (s, 1H), 9.81-9.37 (m, 1H), 8.65 (d, J = 2.4 Hz, 1H), 8.58-8.45 (m, 1H), 8.18-8.11 (m, 1H), 8.04 (s, 1H), 7.66 (d, J = 8.0 Hz, 1H), 7.62-7.54 (m, 3H), 7.51 (s, 1H), 7.41 (d, J = 8.0 Hz, 1H), 7.33-7.23 (m, 1H), 7.07 (d, J = 8.8 Hz, 2H), 5.16-5.05 (m, 1H), 4.48-4.38 (m, 1H), 4.35-4.26 (m, 1H), 3.88-3.77 (m, 4H), 3.07 (d, J = 9.6 Hz, 2H), 2.97-2.87 (m, 1H), 2.85-2.68 (m, 3H), 2.62 (s, 1H), 2.44-2.36 (m, 3H), 2.21-2.11 (m, 2H), 1.97 (s, 2H), 1.89-1.72 (m, 8H), 1.51-1.42 (m, 2H), 1.29-1.22 (m, 2H), 1.05 (d, J = 6.4 Hz, 6H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 278 | | (3R)-N-{3-[5-(4-{[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2,4-difluorophenyl}-3-hydroxypyrrolidine-1-sulfonamide | 1H NMR (400 MHz, DMSO-d6) δ 13.01-12.80 (m, 1H), 11.00 (s, 1H), 8.65 (d, J = 2.0 Hz, 1H), 8.60-8.48 (m, 1H), 8.14 (s, 1H), 8.10 (s, 1H), 7.68-7.62 (m, 2H), 7.61-7.57 (m, 2H), 7.51 (s, 1H), 7.41 (d, J = 8.0 Hz, 1H), 7.30-7.20 (m, 1H), 7.08 (d, J = 8.8 Hz, 2H), 5.18-4.93 (m, 2H), 4.46-4.27 (m, 2H), 4.27-4.22 (m, 1H), 3.86-3.76 (m, 2H), 3.10-3.02 (m, 3H), 2.94-2.85 (m, 1H), 2.78-2.66 (m, 4H), 2.63-2.56 (m, 1H), 2.41-2.30 (m, 4H), 2.22-2.10 (m, 2H), 2.02-1.95 (m, 1H), 1.88-1.71 (m, 10H), 1.34-1.15 (m, 3H) |
| 279 | | N-{3-[5-(4-{[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2,4-difluorophenyl}-3-hydroxyazetidine-1-sulfonamide | 1H NMR (400 MHz, DMSO-d6) δ 12.89 (s, 1H), 11.98 (s, 1H), 8.64 (d, J = 2.0 Hz 1H), 8.60 (s, 1H), 8.11 (s, 1H), 7.68-7.62 (m, 1H), 7.60-7.55 (m, 3H), 7.49-7.45 (m, 1H), 7.41-7.35 (m, 1H), 7.27-7.21 (m, 1H), 7.05 (d, J = 8.4 Hz 2H), 5.75 (d, J = 6.0 Hz 1H), 5.03 (s, 1H), 4.44-4.25 (m, 3H), 3.89-3.84 (m, 2H), 3.82-3.75 (m, 2H), 3.62 (d, J = 6.0 Hz, 2H), 3.27 (s, 2H), 2.82 (s, 2H), 2.76-2.70 (m, 2H), 2.58 (s, 3H), 2.36-2.32 (m, 1H), 2.24-2.16 (m, 1H), 2.04-1.90 (m, 2H), 1.89-1.77(s, 8H), 1.21 (s, 3H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 280 | | (3S)-3-(5-{1-[(1-{4-[3-(2,6-difluoro-3-{[(2-hydroxyethyl)(methyl)sulfamoyl]amino}benzoyl)-1H-pyrrolo[2,3-b]pyridin-5-yl]phenyl}piperidin-4-yl)methyl]piperidin-4-yl}-1-oxo-2,3-dihydro-1H-isoindol-2-yl)piperidine-2,6-dione | 1H NMR (400 MHz, DMSO-d6) δ 12.90 (s, 1H), 10.98 (s, 1H), 8.65 (d, J = 2.0 Hz, 1H), 8.61-8.46 (m, 1H), 8.14 (s, 1H), 8.10 (s, 1H), 7.70-7.55 (m, 4H), 7.51 (s, 1H), 7.41 (d, J = 8.0 Hz, 1H), 7.27 (t, J = 8.8 Hz, 1H), 7.08 (d, J = 8.8 Hz, 2H), 5.10 (dd, J = 5.2, 13.2 Hz, 1H), 4.46-4.27 (m, 2H), 3.80 (d, J = 11.8 Hz, 2H), 3.47 (t, J = 6.0 Hz, 4H), 3.12 (t, J = 6.0 Hz, 2H), 3.06 (d, J = 10.4 Hz, 2H), 3.01-2.84 (m, 2H), 2.80 (s, 3H), 2.79-2.69 (m, 3H), 2.62 (s, 2H), 2.33 (d, J = 2.0 Hz, 2H), 2.24-2.09 (m, 2H), 1.85-1.74 (m, 6H), 1.31-1.23 (m, 2H) |
| 281 | | (3S)-3-(5-{1-[(1-{4-[3-{[cyclopropyl(methyl)sulfamoyl]amino}-2,6-difluorobenzoyl)-1H-pyrrolo[2,3-b]pyridin-5-yl]phenyl}piperidin-4-yl)methyl]piperidin-4-yl}-1-oxo-2,3-dihydro-1H-isoindol-2-yl)piperidine-2,6-dione | 1H NMR (400 MHz, DMSO-d6) δ 12.98-12.87 (m, 1H), 11.00 (s, 1H), 8.65 (d, J = 2.0 Hz, 1H), 8.59-8.45 (m, 1H), 8.14 (s, 1H), 8.09 (s, 1H), 7.69-7.61 (m, 2H), 7.61-7.56 (m, 2H), 7.51 (s, 1H), 7.42 (d, J = 7.6 Hz, 1H), 7.31-7.23 (m, 1H), 7.11-7.06 (m, 2H), 5.19-5.01 (m, 1H), 4.50-4.23 (m, 2H), 3.88-3.76 (m, 2H), 3.19-3.08 (m, 2H), 2.98-2.89 (m, 1H), 2.81-2.77 (m, 1H), 2.72-2.65 (m, 2H), 2.65-2.55 (m, 2H), 2.42-2.31 (m, 4H), 2.30-2.11 (m, 2H), 2.04-1.96 (m, 1H), 1.90-1.74 (m, 8H), 1.35-1.19 (m, 3H), 0.67-0.61 (m, 2H), 0.60-0.54 (m, 2H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 282 | | N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}phenyl)-1H-pyrrolo[2,3-b]pyridine-3-carbonyl]-2,4-difluorophenyl]-2-hydroxyethane-1-sulfonamide | 1H NMR (400 MHz, DMSO-d6) δ 13.15-12.72 (m, 1H), 11.01-10.91 (m, 1H), 8.65 (s, 1H), 8.55 (s, 1H), 8.16 (s, 1H), 8.14 (s, 1H), 7.65 (d, J = 7.6 Hz, 1H), 7.63-7.56 (m, 3H), 7.51 (s, 1H), 7.41 (d, J = 7.6 Hz, 1H), 7.26 (t, J = 8.8 Hz, 1H), 7.07 (d, J = 8.4 Hz, 2H), 5.10 (dd, J = 5.2, 13.2 Hz, 1H), 4.47-4.37 (m, 1H), 4.35-4.26 (m, 1H), 3.80 (t, J = 6.4 Hz, 4H), 3.06 (s, 4H), 2.80-2.69 (m, 2H), 2.69-2.51 (m, 2H), 2.43-2.30 (m, 2H), 2.26 (d, J = 6.8 Hz, 2H), 2.12-1.96 (m, 3H), 1.88-1.67 (m, 7H), 1.29-1.19 (m, 2H) |
| 283 | | (3R)-N-[3-(5-{4-[4-({4-[2-(2,6-dioxopiperidin-3-yl)-1-oxo-2,3-dihydro-1H-isoindol-5-yl]piperidin-1-yl}methyl)piperidin-1-yl]phenyl}-1H-pyrrolo[2,3-b]pyridine-3-carbonyl)-4-fluoro-2-methoxyphenyl]-3-fluoropyrrolidine-1-sulfonamide | 1H NMR (400 MHz, DMSO-d6) δ 12.81 (s, 1H), 10.98 (s, 1H), 9.32 (s, 1H), 8.65 (d, J = 2.3 Hz, 1H), 8.52 (s, 1H), 7.91 (s, 1H), 7.66 (d, J = 7.8 Hz, 1H), 7.59 (dd, J = 8.8, 6.2 Hz, 4H), 7.51 (s, 1H), 7.41 (d, J = 7.9 Hz, 1H), 7.18-7.01(m, 3H), 5.39-5.24(m, 1H), 5.11 (dd, J = 13.3, 5.1 Hz, 1H), 4.43 (d, J = 17.2 Hz, 1H), 4.30 (d, J = 17.2 Hz, 1H), 3.90-3.77 (m, 2H), 3.64-3.56 (m, 3H), 3.00 (s, 1H), 2.91-2.75 (m, 3H), 2.60 (d, J = 17.1 Hz, 2H), 2.40 (dd, J = 12.9, 4.5 Hz, 1H), 2.10-1.97 (m, 7H), 1.21-0.89(m, 5H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| | 284 | (3R)-N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl}-3,5-bis(methylamino)phenyl)-1H-pyrrolo[2,3-b]pyridine-3-carbonyl]-2,4-difluorophenyl}-3-fluoropyrrolidine-1-sulfonamide | ¹H NMR (300 MHz, DMSO-d6) δ 12.98 (s, 1H), 11.00 (s, 1H), 9.90 (s, 1H), 8.67 (s, 1H), 8.63 (s, 1H), 8.11 (s, 1H), 7.68-7.63 (m, 2H), 7.52 (s, 1H), 7.33-7.27 (m, 1H), 7.21 (t, J = 8.8 Hz, 1H), 6.05 (d, J = 8.4 Hz, 2H), 5.41-5.01 (m, 3H), 4.41-4.27 (m, 2H), 3.40 (s, 1H), 3.22 (s, 1H), 3.10 (s, 1H), 3.05-3.00 (m, 4H), 2.93-2.88 (m, 6H), 2.74-2.71 (m, 5H), 2.28-2.22 (m, 1H), 2.12-2.08 (m, 6H), 1.97-1.75 (m, 7H), 1.43-1.40 (m, 2H) |
| | 285 | (3R)-N-[3-(5-{4-[4-({4-[2-(2,6-dioxopiperidin-3-yl)-1-oxo-2,3-dihydro-1H-isoindol-5-yl]piperidin-1-yl}methyl)piperidin-1-yl]-3,5-bis(methylamino)phenyl}-1H-pyrrolo[2,3-b]pyridine-3-carbonyl)-2,4-difluorophenyl]-3-fluoropyrrolidine-1-sulfonamide | ¹HNMR (400 MHz, DMSO-d6) δ 12.98 (s, 1H), 11.00 (s, 1H), 9.90 (s, 1H), 8.67 (s, 1H), 8.63 (s, 1H), 8.11 (s, 1H), 7.68-7.63 (m, 2H), 7.52 (s, 1H), 7.33-7.27 (m, 1H), 7.21 (t, J = 8.8 Hz, 1H), 6.05 (d, J = 8.4 Hz, 2H), 5.41-5.01 (m, 3H), 5.41-5.01 (m, 3H), 4.41-4.27 (q, 2H), 3.25-3.22 (m, 4H), 2.93-2.88 (m, 2H), 2.74-2.70 (m, 5H), 2.28-2.02 (m, 6H), 2.12-2.08 (m, 6H), 1.97-1.75 (m, 8H), 1.43-1.40 (m, 3H), 1.25-1.17 (m, 5H), 0.96-0.93 (m, 2H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| 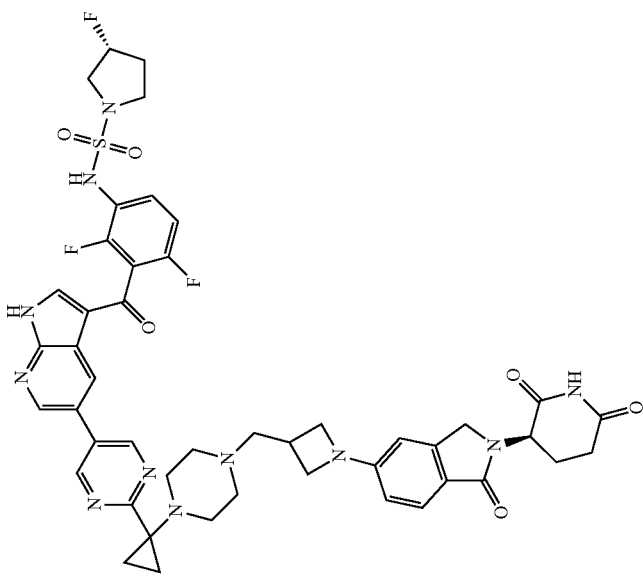 | 286 | (3R)-N-(3-{5-[2-(1-{[(1-{2-[(3R)-2,6-dioxopiperidin-3-yl]-1-oxo-2,3-dihydro-1H-isoindol-5-yl}azetidin-3-yl)methyl]piperazin-1-yl}cyclopropyl)pyrimidin-5-yl]-1H-pyrrolo[2,3-b]pyridine-3-carbonyl]-2,4-difluorophenyl)-3-fluoropyrrolidine-1-sulfonamide | 1H NMR (400 MHz, DMSO-d6) δ 13.13 (s, 1H), 10.95 (s, 1H), 10.27-9.65 (m, 1H), 9.08 (s, 2H), 8.77 (d, J = 2.0 Hz, 1H), 8.71 (s, 1H), 8.18 (s, 1H), 7.69-7.58 (m, 1H), 7.50 (d, J = 8.0 Hz, 1H), 7.28 (t, J = 8.8 Hz, 1H), 6.52 (s, 1H), 6.49 (d, J = 8.4 Hz, 1H), 5.41-5.20 (m, 1H), 5.09-4.98 (m, 1H), 4.34-4.15 (m, 2H), 4.08 (t, J = 7.2 Hz, 2H), 3.64 (s, 2H), 3.55-3.38 (m, 11H), 3.17-3.07 (m, 2H), 2.95-2.84 (m, 2H), 2.81-2.67 (m, 2H), 2.58 (d, J = 16.8 Hz, 1H), 2.41-2.28 (m, 1H), 2.16-2.09 (m, 1H), 1.98-1.91 (m, 1H), 1.42 (s, 2H), 1.21-1.09 (m, 2H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| 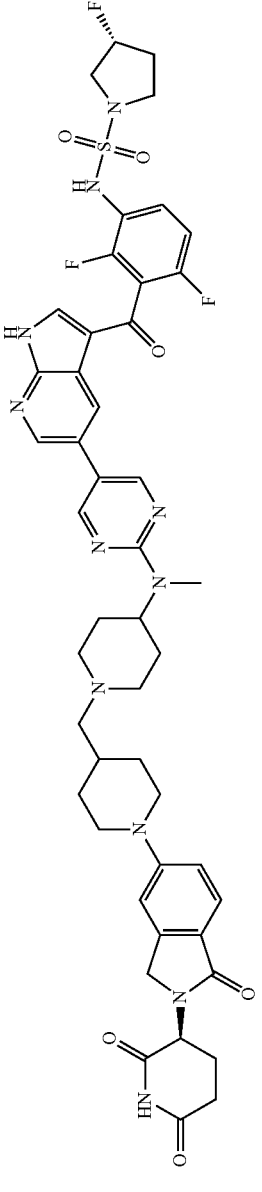 | 287 | (3R)-N-(3-{5-[2-({1-[(1-{2-[(3S)-2,6-dioxopiperidin-3-yl]-1-oxo-2,3-dihydro-1H-isoindol-5-yl}piperidin-4-yl)methyl]piperidin-4-yl}(methyl)amino)pyrimidin-5-yl]-1H-pyrrolo[2,3-b]pyridine-3-carbonyl}-2,4-difluorophenyl)-3-fluoropyrrolidine-1-sulfonamide | 1H NMR (400 MHz, DMSO-d6) δ 10.94 (s, 1H), 8.74 (s, 2H), 8.64 (d, J = 2.2 Hz, 1H), 8.59-8.48 (m, 1H), 8.20 (s, 1H), 8.09 (s, 1H), 7.66-7.55 (m, 1H), 7.50 (d, J = 8.8 Hz, 1H), 7.22 (t, J = 8.8 Hz, 1H), 7.11-6.99 (m, 2H), 5.43-5.19 (m, 1H), 5.12-4.97 (m, 1H), 4.74-4.57 (m, 1H), 4.39-4.14 (m, 2H), 4.00-3.82 (m, 2H), 3.49-3.44 (m, 2H), 3.40 (s, 2H), 3.06 (s, 3H), 3.01-2.93 (m, 2H), 2.89-2.76 (m, 3H), 2.58 (m, 2H), 2.42-2.29 (m, 2H), 2.19 (d, J = 6.4 Hz, 2H), 2.13-1.94 (m, 5H), 1.88-1.73 (m, 5H), 1.68-1.53 (m, 2H), 1.31-1.08 (m, 2H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| 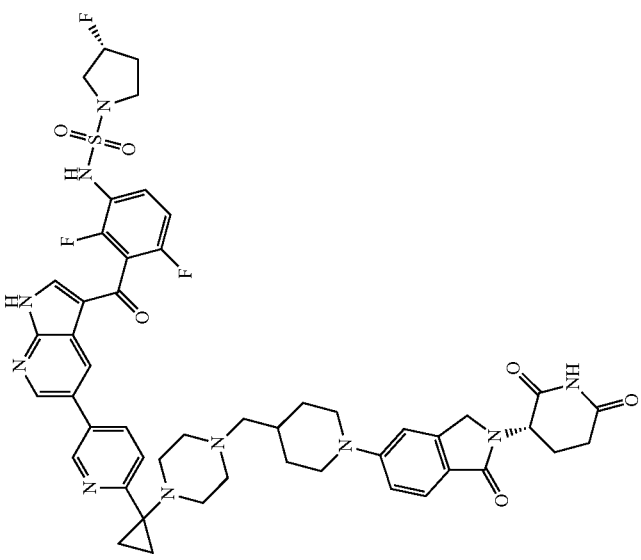 | 288 | (3R)-N-(3-{5-[6-(1-{4-[((1-{2-[(3S)-2,6-dioxopiperidin-3-yl]-1-oxo-2,3-dihydro-1H-isoindol-5-yl}piperidin-4-yl)methyl]piperazin-1-yl}cyclopropyl)pyridin-3-yl]-1H-pyrrolo[2,3-b]pyridine-3-carbonyl]-2,4-difluorophenyl)-3-fluoropyrrolidine-1-sulfonamide | 1H NMR (400 MHz, DMSO-d6) δ 13.05 (d, J = 3.6 Hz, 1H), 10.93 (s, 1H), 8.88 (d, J = 2.4 Hz, 1H), 8.74 (d, J = 2.4 Hz, 1H), 8.64 (d, J = 1.2 Hz, 1H), 8.21-8.05 (m, 3H), 7.70-7.55 (m, 2H), 7.48 (d, J = 8.8 Hz, 1H), 7.34-7.21 (m, 1H), 7.07-6.92 (m, 2H), 5.42-5.19 (m, 1H), 5.03 (dd, J = 4.8, 13.2 Hz, 1H), 4.33-4.27 (m, 1H), 4.21-4.15 (m, 1H), 3.84 (d, J = 12.4 Hz, 2H), 3.48 (s, 1H), 3.40 (s, 3H), 2.94-2.75 (m, 4H), 2.64-2.53 (m, 4H), 2.52 (d, J = 2.0 Hz, 4H), 2.39 (s, 1H), 2.26-2.20 (m, 1H), 2.16-2.05 (m, 2H), 2.00-1.89 (m, 2H), 1.74 (d, J = 10.4 Hz, 3H), 1.19-1.10 (m, 2H), 1.07 (s, 4H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| 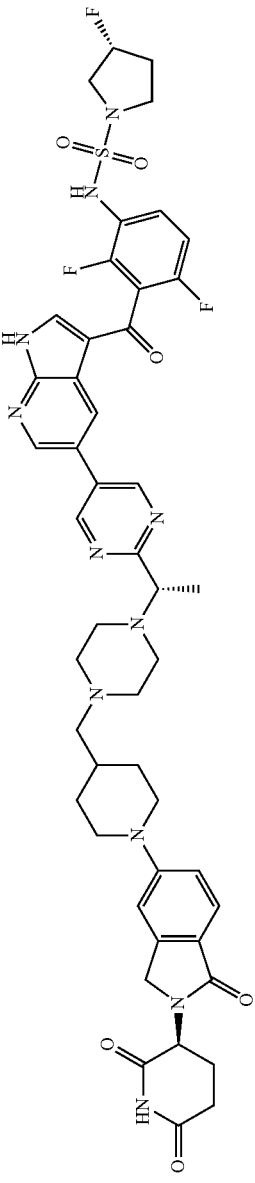 | 289 | (3R)-N-[3-(5-{2-[(1S)-1-{4-[(1-{2-[(3S)-2,6-dioxopiperidin-3-yl]-1-oxo-2,3-dihydro-1H-isoindol-5-yl}piperidin-4-yl)methyl]piperazin-1-yl}ethyl]pyrimidin-5-yl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 13.10 (d, J = 4.0 Hz, 1H), 10.93 (s, 1H), 10.71-9.36 (m, 1H), 9.21 (s, 2H), 8.81 (d, J = 2.4 Hz, 1H), 8.75 (s, 1H), 8.18 (s, 1H), 7.63 (dt, J = 6.0, 9.2 Hz, 1H), 7.48 (d, J = 8.8 Hz, 1H), 7.36-7.20 (m, 1H), 7.07-6.91 (m, 2H), 5.44-5.15 (m, 1H), 5.03 (dd, J = 5.2, 13.2 Hz, 1H), 4.40-4.10 (m, 2H), 3.99 (d, J = 4.0 Hz, 1H), 3.84 (d, J = 12.4 Hz, 2H), 3.49 (s, 1H), 3.46-3.36 (m, 4H), 3.31-3.25 (m, 4H), 2.94-2.84 (m, 1H), 2.79 (t, J = 11.6 Hz, 2H), 2.60 (s, 2H), 2.55 (s, 2H), 2.42-2.31 (m, 2H), 2.26 (s, 1H), 2.20-2.06 (m, 2H), 2.05-1.89 (m, 2H), 1.73 (d, J = 10.4 Hz, 2H), 1.46 (d, J = 6.8 Hz, 3H), 1.21-1.08 (m, 2H) |

| Parent Mol Structure | Ex. No. | IUPAC Name | ¹H NMR tabulation |
|---|---|---|---|
| (structure) | 290 | (3R)-N-[3-(5-{2-[(1R)-1-{4-[(1-{2-[(3S)-2,6-dioxopiperidin-3-yl]-1-oxo-2,3-dihydro-1H-isoindol-5-yl}piperidin-4-yl)methyl]piperazin-1-yl}ethyl]pyrimidin-5-yl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 13.10 (s, 1H), 10.93 (s, 1H), 10.71-9.36 (m, 1H), 9.21 (s, 2H), 8.81 (d, J = 2.4 Hz, 1H), 8.75 (s, 1H), 8.18 (s, 1H), 7.63 (d, J = 9.2 Hz, 1H), 7.48 (d, J = 8.8 Hz, 1H), 7.36-7.20 (m, 1H), 7.07-6.91 (m, 2H), 5.44-5.15 (m, 1H), 5.03 (J = 13.2 Hz, 1H), 4.40-4.10 (m, 2H), 3.99 (d, J = 4.0 Hz, 1H), 3.84 (d, J = 12.4 Hz, 2H), 3.49 (s, 1H), 3.46-3.36 (m, 4H), 3.31-3.25 (m, 4H), 2.94-2.84 (m, 1H), 2.79 (t, J = 11.6 Hz, 2H), 2.60 (s, 2H), 2.55 (s, 2H), 2.42-2.31 (m, 2H), 2.26 (s, 1H), 2.20-2.06 (m, 2H), 2.05-1.89 (m, 2H), 1.73 (d, J = 10.4 Hz, 2H), 1.46 (d, J = 6.8 Hz, 3H), 1.21-1.08 (m, 2H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| | 291 | (3R)-N-{3-[5-(4-{4-[(4-{2-[(3S)-2,6-dioxopiperidin-3-yl]-1-oxo-2,3-dihydro-1H-isoindol-5-yl}piperidin-1-yl)methyl]piperidin-1-yl]phenyl)-1H-pyrrolo[2,3-b]pyridine-3-carbonyl]-4-fluoro-2-propylphenyl]-3-fluoropyrrolidine-1-sulfonamide | 1H NMR (400 MHz, DMSO-d6) δ 12.77 (d, J = 0.8 Hz, 1H), 10.99 (s, 1H), 9.39-9.04 (m, 1H), 8.62 (s, 2H), 8.07-7.74 (m, 1H), 7.69 (d, J = 8.0 Hz, 1H), 7.61-7.54 (m, 1H), 7.51 (s, 1H), 7.49-7.40 (m, 2H), 7.21 (t, J = 8.8 Hz, 1H), 7.07 (d, J = 8.0 Hz, 2H), 5.48-5.26 (m, 1H), 5.11 (dd, J = 5.2, 13.2 Hz, 1H), 4.50-4.25 (m, 2H), 3.81 (d, J = 12.0 Hz, 2H), 3.54 (s, 1H), 3.48-3.41 (m, 4H), 2.97-2.90 (m, 1H), 2.89-2.82 (m, 2H), 2.81-2.72 (m, 4H), 2.71-2.65 (m, 2H), 2.64-2.57 (m, 2H), 2.41 (d, J = 4.8 Hz, 1H), 2.39-2.36 (m, 1H), 2.35-2.31 (m, 1H), 2.27-2.17 (m, 2H), 1.96-1.89 (m, 4H), 1.54-1.41 (m, 2H), 1.37-1.22 (m, 4H), 1.05 (s, 2H), 0.74 (s, 3H). |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| | 292 | (3R)-N-(3-{5-[2-(1-{[4-[(1-{2-[(3R)-2,6-dioxopiperidin-3-yl]-1-oxo-2,3-dihydro-1H-isoindol-5-yl]piperidin-4-yl}methyl)piperazin-1-yl]cyclopropyl)pyrimidin-5-yl]-1H-pyrrolo[2,3-b]pyridine-3-carbonyl]-2,4-difluorophenyl)-3-fluoropyrrolidine-1-sulfonamide | 1H NMR (400 MHz, DMSO-d6) δ 13.39-12.76 (m, 1H), 10.93 (s, 1H), 10.16-9.56 (m, 1H), 9.08 (s, 2H), 8.76 (d, J = 2.4 Hz, 1H), 8.69 (s, 1H), 8.16 (s, 1H), 7.69-7.57 (m, 1H), 7.50 (d, J = 9.2 Hz, 1H), 7.34-7.21 (m, 1H), 7.12-6.98 (m, 2H), 5.43-5.20 (m, 1H), 5.11-4.95 (m, 1H), 4.42-4.12 (m, 2H), 3.87 (d, J = 12.0 Hz, 2H), 3.49 (s, 1H), 3.40 (d, J = 2.0 Hz, 3H), 3.31 (d, J = 3.6 Hz, 2H), 3.19 (s, 3H), 2.91-2.76 (m, 3H), 2.58 (d, J = 16.8 Hz, 1H), 2.42-2.30 (m, 4H), 2.21-2.09 (m, 3H), 2.04-1.89 (m, 2H), 1.80 (d, J = 11.2 Hz, 3H), 1.38 (s, 2H), 1.24-1.16 (m, 2H), 1.10 (d, J = 2.4 Hz, 2H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 293 | | (3R)-N-(3-{5-[4-(3-{1-[2-(2,6-dioxopiperidin-3-yl)-1-oxo-2,3-dihydro-1H-isoindol-5-yl]piperidin-4-yl}azetidin-1-yl)phenyl]-1H-pyrrolo[2,3-b]pyridine-3-carbonyl}-2,4-difluorophenyl)-3-fluoropyrrolidine-1-sulfonamide | 1H NMR (400 MHz, DMSO-d6) δ 13.01-12.64 (m, 1H), 10.94 (s, 1H), 8.62 (d, J = 2.0 Hz, 1H), 8.55-8.42 (m, 1H), 8.03 (s, 1H), 7.67-7.46 (m, 4H), 7.19 (t, J = 8.8 Hz, 1H), 7.10-7.02 (m, 2H), 6.56 (d, J = 8.8 Hz, 2H), 5.38-5.16 (m, 1H), 5.04 (dd, J = 5.2, 13.2 Hz, 1H), 4.37-4.28 (m, 1H), 4.24-4.13 (m, 1H), 4.03-3.87 (m, 4H), 3.62 (t, J = 6.4 Hz, 2H), 3.44 (d, J = 4.0 Hz, 1H), 3.36 (s, 2H), 3.27-3.20 (m, 2H), 2.98-2.76 (m, 3H), 2.63-2.54 (m, 1H), 2.43-2.34 (m, 1H), 2.18-1.87 (m, 4H), 1.85-1.66 (m, 3H), 1.34-1.11 (m, 2H) |
| 294 | | (3R)-N-[3-(5-{4-[4-({3-[2-(2,6-dioxopiperidin-3-yl)-1-oxo-2,3-dihydro-1H-isoindol-5-yl]propoxy}methyl)piperidin-1-yl]phenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 12.95 (d, J = 1.6 Hz, 1H), 10.99 (s, 1H), 9.86 (s, 1H), 8.68 (d, J = 2.0 Hz, 1H), 8.63-8.53 (m, 1H), 8.10 (d, J = 2.4 Hz, 1H), 7.76-7.57 (m, 4H), 7.48-7.43 (m, 1H), 7.38-7.23 (m, 3H), 5.39-5.20 (m, 1H), 5.15-5.06 (m, 1H), 4.45-4.50 (m, 1H), 4.32-4.27 (m, 1H), 3.83-3.72 (m, 2H), 3.50-3.47 (m, 1H), 3.45-3.36 (m, 4H), 3.34-3.24 (m, 3H), 3.06-2.85 (m, 2H), 2.81-2.72 (m, 2H), 2.65-2.55 (m, 1H), 2.46-2.35 (m, 1H), 2.30-2.16 (m, 1H), 2.14-1.96 (m, 3H), 1.93-1.75 (m, 5H), 1.53-1.34 (m, 2H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 295 | | (3R)-N-{3-[5-(4-{[(3S)-3-{2-[(3S)-2,6-dioxopiperidin-3-yl]-7-methoxy-1-oxo-2,3-dihydro-1H-isoindol-5-yl}-3-hydroxypropyl]piperazin-1-yl}phenyl)-1H-pyrrolo[2,3-b]pyridine-3-carbonyl]-2,4-difluorophenyl}-3-fluoropyrrolidine-1-sulfonamide | 1H NMR (400 MHz, DMSO-d6 + D2O ppm) δ 8.64 (s, 1H), 8.63 (s, 1H), 8.03 (s, 1H), 7.60-7.58 (m, 3H), 7.25-7.21 (m, 1H), 7.11-7.02 (m, 4H), 5.20 (d, J = 13.2 Hz, 1H), 5.12-5.01 (m, 1H), 4.74-4.72 (m, 1H), 4.32-4.24 (q, 2H), 3.86 (s, 3H), 3.53 (s, 2H), 3.38-3.17 (m, 5H), 2.95-2.80 (m, 1H), 2.56-2.51 (m, 6H), 2.45-2.33 (m, 2H), 2.12-2.02 (m, 2H), 2.00-1.92 (m, 2H), 1.85-1.83 (m, 2H) |
| 296 | | (3R)-N-{3-[5-(4-{[(3S)-3-{2-[(3R)-2,6-dioxopiperidin-3-yl]-7-methoxy-1-oxo-2,3-dihydro-1H-isoindol-5-yl}-3-hydroxypropyl]piperazin-1-yl}phenyl)-1H-pyrrolo[2,3-b]pyridine-3-carbonyl]-2,4-difluorophenyl}-3-fluoropyrrolidine-1-sulfonamide | 1H NMR (400 MHz, DMSO-d6 + D2O ppm) δ 8.65 (s, 1H), 8.64 (s, 1H), 8.05 (s, 1H), 7.63-7.61 (m, 3H), 7.29-7.27 (m, 1H), 7.11-7.03 (m, 4H), 5.20 (d, J = 13.2 Hz, 1H), 5.12-5.01 (m, 1H), 4.76-4.74 (m, 1H), 4.38-4.23 (q, 2H), 3.87 (s, 3H), 3.53 (s, 2H), 3.39-3.23 (m, 5H), 2.95-2.82 (m, 1H), 2.66-2.55 (m, 6H), 2.45-2.33 (m, 1H), 2.20-2.01 (m, 2H), 1.98-1.95 (m, 2H), 1.87-1.85 (m, 2H), 1.22 (s, 1H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| | 297 | (3R)-N-[3-(5-{4-[(3S,4R)-4-{[2-(2,6-dioxopiperidin-3-yl)-1-oxo-2,3-dihydro-1H-isoindol-5-yl]piperidin-1-yl}methyl]-3-fluoropiperidin-1-yl]phenyl}-1H-pyrrolo[2,3-b]pyridine-3-carbonyl)-2,4-difluorophenyl]-3-fluoropyrrolidine-1-sulfonamide | 1H-NMR (400 MHz, DMSO-d6) δ 12.92 (s, 1H), 10.99 (s, 1H), 9.86 (s, 1H), 8.70-8.44 (m, 2H), 8.08 (s, 1H), 7.70-7.56 (m, 4H), 7.52 (s, 1H), 7.42 (d, J = 8.0 Hz, 1H), 7.28 (t, J = 8.7 Hz, 1H), 7.08 (d, J = 8.6 Hz, 2H), 5.30 (d, J = 53.2 Hz, 1H), 5.11 (dd, J = 13.3, 5.1 Hz, 1H), 4.93 (d, J = 48.0 Hz, 1H), 4.44 (d, J = 17.2 Hz, 1H), 4.30 (d, J = 17.2 Hz, 1H), 4.08 (t, J = 12.7 Hz, 1H), 3.87 (d, J = 12.1 Hz, 1H), 3.49 (d, J = 2.2 Hz, 2H), 3.15-2.77 (m, 6H), 2.72-2.57 (m, 2H), 2.44 (d, J = 8.6 Hz, 2H), 2.32-2.24 (m, 1H), 2.21-2.05 (m, 3H), 2.05-1.92 (m, 3H), 1.88-1.48 (m, 6H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 298 | | (3R)-N-{3-[5-(2-{1-[4-({1-[2-(2,6-dioxopiperidin-3-yl)-1-oxo-2,3-dihydro-1H-isoindol-5-yl]piperidin-4-yl}methyl)piperazin-1-yl]cyclopropyl}pyrimidin-5-yl)-1H-pyrrolo[2,3-b]pyridine-3-carbonyl]-2,4-difluorophenyl}-3-fluoropyrrolidine-1-sulfonamide | 1H NMR (300 MHz, DMSO-d6) δ 13.06 (s, 1H), 10.93 (s, 1H), 9.83 (s, 1H), 9.09 (s, 2H), 8.76-8.69 (m, 2H), 8.16 (s, 1H), 7.70-7.56 (m, 1H), 7.50 (m, 1H), 7.27 (m, 1H), 7.04 (m, 2H), 5.39-5.21 (m, 1H), 5.04 (m, 1H), 4.32-4.19 (m, 2H), 3.88 (m, 2H), 3.52-3.37 (m, 3H), 3.19 (s, 3H), 2.89-2.77 (m, 3H), 2.63-2.51 (m, 2H), 2.35 (s, 5H), 2.15-1.96 (m, 6H), 1.80-1.78 (m, 3H), 1.38 (s, 2H), 1.19-1.10 (m, 4H) |
| 299 | | (3R)-N-{3-[5-(4-{6-[(2S)-2-[2-(2,6-dioxopiperidin-3-yl)-1-oxo-2,3-dihydro-1H-isoindol-5-yl]-2-hydroxyethyl]-2,6-diazaspiro[3.3]heptan-2-yl}phenyl)-1H-pyrrolo[2,3-b]pyridine-3-carbonyl]-2,4-difluorophenyl}-3-fluoropyrrolidine-1-sulfonamide | 1H NMR (400 MHz, DMSO-d6) δ 12.87 (s, 1H), 10.99 (s, 1H), 8.62-8.49 (s, 2H), 8.05 (s, 1H), 7.68-7.49 (m, 6H), 7.26-7.17 (m, 1H), 6.56 (m, 2H), 5.40-5.12 (m, 3H), 4.66 (m, 1H), 4.46 (m, 1H), 4.32 (m, 1H), 3.91 (m, 4H), 3.38-3.37 (m, 5H), 3.31-3.22 (m, 3H), 2.99-2.86 (m, 1H), 2.66-2.53 (m, 3H), 2.43-2.40 (m, 1H), 2.14-1.93 (m, 3H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 300 | | (3R)-N-{3-[5-(4-{4-[(3S)-3-{2-[(3S)-2,6-dioxopiperidin-3-yl]-6-fluoro-1-oxo-2,3-dihydro-1H-isoindol-5-yl}-3-hydroxypropyl]piperazin-1-yl]phenyl)-1H-pyrrolo[2,3-b]pyridine-3-carbonyl]-2,4-difluorophenyl}-3-fluoropyrrolidine-1-sulfonamide | 1H NMR (400 MHz, DMSO-d6) δ 12.98 (s, 1H), 10.99 (s, 1H), 9.80 (b, 1H), 8.65 (s, 1H), 8.53 (s, 1H), 8.06 (s, 1H), 7.78 (s, 1H), 7.60 (s, 3H), 7.47-7.47 (m, 1H), 7.26 (s, 1H), 7.08 (s, 2H), 5.85 (b, 1H), 5.23 (d, J = 13.2 Hz, 1H), 5.09-5.06 (m, 2H), 4.47-4.31 (m, 2H), 3.48 (s, 1H), 3.32-3.31 (m, 5H), 2.92-2.91 (m, 1H), 2.49-2.46 (m, 10H), 2.12-1.81 (m, 5H) |
| 301 | | (3R)-N-{3-[5-(4-{4-[(3S)-3-{2-[(3R)-2,6-dioxopiperidin-3-yl]-6-fluoro-1-oxo-2,3-dihydro-1H-isoindol-5-yl}-3-hydroxypropyl]piperazin-1-yl]phenyl)-1H-pyrrolo[2,3-b]pyridine-3-carbonyl]-2,4-difluorophenyl}-3-fluoropyrrolidine-1-sulfonamide | 1H NMR (400 MHz, DMSO-d6) δ 12.98 (s, 1H), 10.99 (s, 1H), 9.80 (b, 1H), 8.65 (s, 1H), 8.53 (s, 1H), 8.06 (s, 1H), 7.77 (d, J = 6.0 Hz, 1H), 7.63-7.59 (m, 3H), 7.47 (d, J = 7.2 Hz, 1H), 7.26-7.25 (m, 1H), 7.08-7.06 (m, 2H), 5.85 (b, 1H), 5.23 (d, J = 13.2 Hz, 1H), 5.09-5.06 (m, 2H), 4.44-4.35 (m, 2H), 3.48-3.40 (m, 4H), 3.26-3.23 (m, 4H), 2.92-2.91 (m, 1H), 2.62-2.50 (m, 6H), 2.22-1.95 (m, 3H), 1.94-1.75 (m, 2H) |

TABLE 3-continued

1H NMR data of exemplary bifunctional compounds of the present disclosure

| Ex. No. | Parent Mol Structure | IUPAC Name | 1H NMR tabulation |
|---|---|---|---|
| 302 | | (3R)-N-[3-(5-{4-[3-({1-[2-(2,6-dioxopiperidin-3-yl)-1-oxo-2,3-dihydro-1H-isoindol-5-yl]piperidin-4-yl}methyl)azetidin-1-yl]phenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 13.02-12.76 (m, 1H), 11.02-10.88 (m, 1H), 10.26-9.80 (m, 1H), 8.67 (s, 1H), 8.57-8.44 (m, 1H), 8.05 (s, 1H), 7.66-7.57 (m, 1H), 7.55 (d, J = 8.4 Hz, 2H), 7.52-7.46 (m, 1H), 7.24 (t, J = 8.4 Hz, 1H), 7.09-7.01 (m, 2H), 6.54 (d, J = 8.4 Hz, 2H), 5.39-5.19 (m, 1H), 5.09-4.99 (m, 1H), 4.39-4.28 (m, 1H), 4.26-4.14 (m, 1H), 4.09-3.99 (m, 2H), 3.89 (d, J = 12.4 Hz, 2H), 3.50-3.45 (m, 3H), 3.28-3.23 (m, 1H), 2.91-2.76 (m, 4H), 2.65-2.58 (m, 1H), 2.55 (d, J = 8.8 Hz, 1H), 2.48-2.26 (m, 2H), 2.12-1.93 (m, 3H), 1.74 (dd, J = 1.6, 12.4 Hz, 2H), 1.65-1.48 (m, 3H), 1.31-1.21 (m, 2H) |
| 303 | | (3R)-N-{3-[5-(4-{[1-({1-[2-(2,6-dioxopiperidin-3-yl)-1-oxo-2,3-dihydro-1H-isoindol-5-yl]azetidin-3-yl}methyl)piperidin-4-yl]methyl}phenyl)-1H-pyrrolo[2,3-b]pyridine-3-carbonyl]-2,4-difluorophenyl}-3-fluoropyrrolidine-1-sulfonamide | 1H NMR (300 MHz, DMSO-d6) δ 12.94 (s, 1H), 10.91 (s, 1H), 8.69-8.59 (m, 2H), 8.10 (s, 1H), 7.70-7.55 (m, 3H), 7.48-7.45 (m, 1H), 7.29-7.22 (m, 3H), 6.52-6.41 (m, 2H), 5.37-5.20 (m, 1H), 5.05-5.01 (m, 1H), 4.29-4.16 (m, 2H), 4.02-3.99 (m, 2H), 3.56-3.45 (m, 3H), 3.45-3.36 (m, 3H), 2.93-2.84 (m, 4H), 2.57 (m, 5H), 2.40-2.28 (m, 1H), 2.08-1.93 (m, 5H), 1.61-1.57 (m, 3H), 1.25-1.22 (m, 2H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| 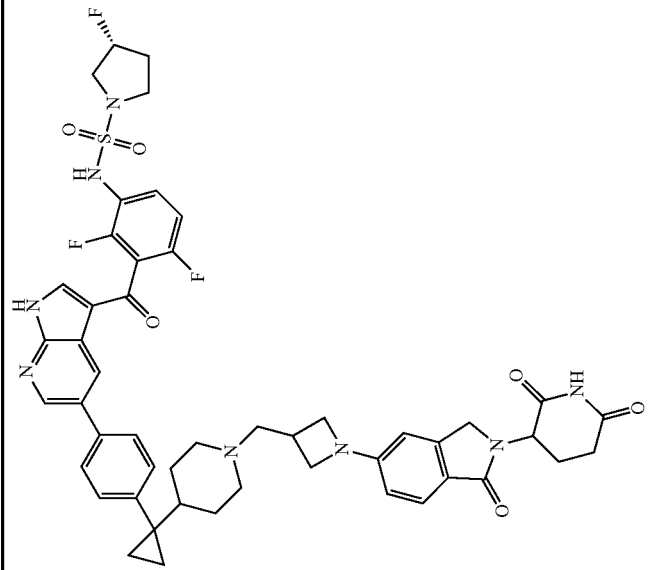 | 304 | (3R)-N-{3-[5-(4-{1-[1-({1-[2-(2,6-dioxopiperidin-3-yl)-1-oxo-2,3-dihydro-1H-isoindol-5-yl]azetidin-3-yl}methyl)piperidin-4-yl]cyclopropyl}phenyl)-1H-pyrrolo[2,3-b]pyridine-3-carbonyl]-2,4-difluorophenyl}-3-fluoropyrrolidine-1-sulfonamide | 1H NMR (400 MHz, DMSO-d6) δ 12.96 (s, 1H), 10.91 (s, 1H), 9.79 (s, 1H), 8.70 (d, J = 2.2 Hz, 1H), 8.60 (s, 1H), 8.11 (s, 1H), 7.68 (s, 1H), 7.68-7.57 (m, 2H), 7.44 (d, J = 8.3 Hz, 1H), 7.38 (d, J = 8.1 Hz, 2H), 7.26 (td, J = 8.7, 1.5 Hz, 1H), 6.48-6.38 (m, 2H), 5.22 (d, J = 3.8 Hz, 1H), 5.01 (dd, J = 13.3, 5.1 Hz, 1H), 4.26 (d, J = 16.9 Hz, 1H), 4.14 (d, J = 16.9 Hz, 1H), 3.94 (td, J = 7.8, 1.8 Hz, 2H), 3.52-3.43 (m, 3H), 3.39 (q, J = 2.8, 2.1 Hz, 4H), 2.95-2.81 (m, 4H), 2.61-2.52 (m, 1H), 2.41-2.25 (m, 1H), 2.07 (dt, J = 12.0, 6.8 Hz, 2H), 2.02-1.86 (m, 4H), 1.78-1.67 (m, 2H), 1.16 (q, J = 11.2 Hz, 2H), 0.89 (d, J = 12.4 Hz, 1H), 0.72 (d, J = 7.1 Hz, 4H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 305 | 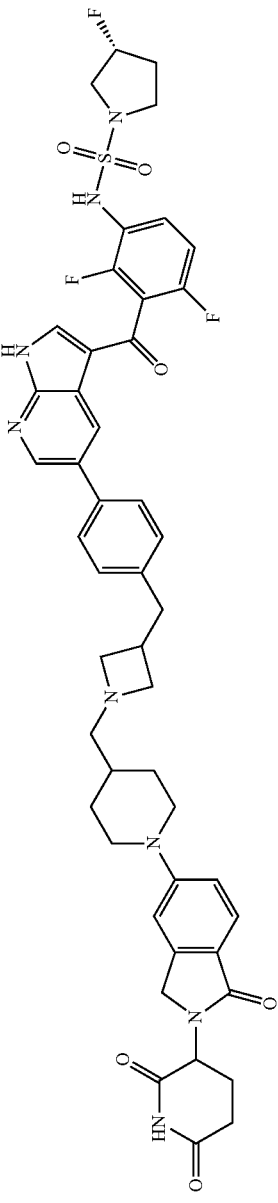 | (3R)-N-{3-[5-(4-{[1-({1-[2-(2,6-dioxopiperidin-3-yl)-1-oxo-2,3-dihydro-1H-isoindol-5-yl]piperidin-4-yl}methyl)azetidin-3-yl]methyl}phenyl)-1H-pyrrolo[2,3-b]pyridine-3-carbonyl]-2,4-difluorophenyl}-3-fluoropyrrolidine-1-sulfonamide | 1H NMR (400 MHz, DMSO-d6) δ 10.94 (s, 1H), 8.69 (d, J = 2.2 Hz, 1H), 8.59 (s, 1H), 8.11 (s, 1H), 7.71-7.58 (m, 3H), 7.50 (d, J = 8.5 Hz, 1H), 7.33 (d, J = 7.9 Hz, 2H), 7.24 (t, J = 8.7 Hz, 1H), 7.03 (d, J = 8.0 Hz, 2H), 5.29 (d, J = 53.5 Hz, 1H), 5.04 (dd, J = 13.3, 5.1 Hz, 1H), 4.42-4.08 (m, 2H), 3.85 (d, J = 12.4 Hz, 2H), 3.44 (dd, J = 19.7, 5.3 Hz, 4H), 3.28 (td, J = 9.8, 6.9 Hz, 2H), 3.04-2.85 (m, 5H), 2.86-2.65 (m, 3H), 2.58 (dd, J = 16.8, 3.7 Hz, 1H), 2.36 (dd, J = 11.5, 5.6 Hz, 3H), 2.16-2.02 (m, 1H), 1.96 (ddd, J = 13.9, 6.7, 4.4 Hz, 2H), 1.81-1.65 (m, 2H), 1.53 (d, J = 10.9 Hz, 1H), 1.19 (qd, J = 12.7, 3.8 Hz, 2H) |
| 306 | 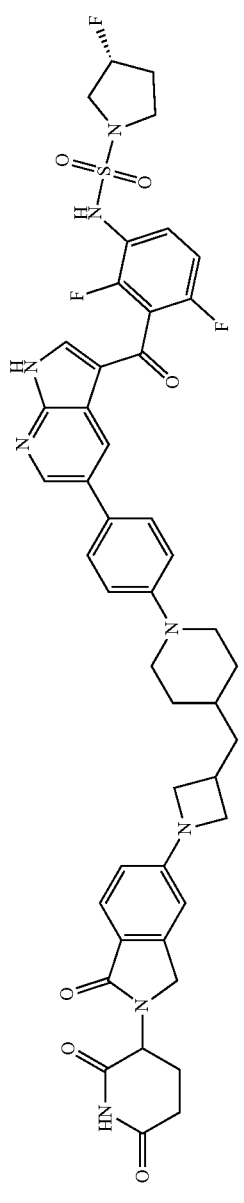 | (3R)-N-[3-(5-{4-[4-({1-[2-(2,6-dioxopiperidin-3-yl)-1-oxo-2,3-dihydro-1H-isoindol-5-yl]azetidin-3-yl}methyl)piperidin-1-yl]phenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 11.00-10.87 (m, 1H), 8.70-8.43 (m, 2H), 8.35-8.23 (m, 1H), 8.10-7.97 (m, 1H), 7.70-7.40 (m, 4H), 7.20-7.00 (m, 3H), 6.57-6.37 (m, 2H), 5.45-5.14 (m, 1H), 5.10-4.95 (m, 1H), 4.41-4.23 (m, 1H), 4.17 (d, J = 16.0 Hz, 1H), 4.13-4.03 (m, 2H), 3.83-3.72 (m, 3H), 3.00-2.81 (m, 4H), 2.65-2.57 (m, 2H), 2.39-2.26 (m, 2H), 2.14-1.86 (m, 4H), 1.75 (d, J = 8.0 Hz, 2H), 1.68 (s, 4H), 1.38-1.19 (m, 3H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 307 | | (3R)-N-{3-[5-(2-{[1-({1-[2-(2,6-dioxopiperidin-3-yl)-1-oxo-2,3-dihydro-1H-isoindol-5-yl]piperidin-4-yl}methyl)azetidin-3-yl]methyl}pyrimidin-5-yl)-1H-pyrrolo[2,3-b]pyridine-3-carbonyl]-2,4-difluorophenyl}-3-fluoropyrrolidine-1-sulfonamide | 1H NMR (300 MHz, DMSO-d6) δ 10.92 (s, 1H), 9.11 (s, 1H), 8.76 (d, J = 2.3 Hz, 1H), 8.70 (s, 1H), 8.12 (s, 1H), 7.59 (td, J = 9.1, 5.9 Hz, 1H), 7.48 (d, J = 9.0 Hz, 1H), 7.17 (td, J = 8.9, 1.6 Hz, 1H), 7.06-6.98 (m, 2H), 5.28 (d, J = 53.7 Hz, 1H), 5.03 (dd, J = 13.2, 5.1 Hz, 1H), 4.35-4.12 (m, 2H), 3.84 (d, J = 12.5 Hz, 2H), 3.43 (p, J = 7.1, 5.6 Hz, 3H), 3.24-3.19 (m, 3H), 3.06-2.87 (m, 4H), 2.86-2.71 (m, 3H), 2.57 (d, J = 16.8 Hz, 2H), 2.40-2.25 (m, 3H), 2.14-2.05 (m, 1H), 2.04-1.87 (m, 2H), 1.80-1.64 (m, 2H), 1.51 (s, 1H), 1.28-1.08 (m, 2H) |
| 308 | | (3R)-N-[3-(5-{4-[4-(2-{1-[2-(2,6-dioxopiperidin-3-yl)-1-oxo-2,3-dihydro-1H-isoindol-5-yl]piperidin-4-yl}ethyl)piperidin-1-yl]phenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 12.95 (s, 1H), 10.94 (s, 1H), 9.85 (s, 1H), 8.68 (s, 1H), 8.64-8.54 (m, 1H), 8.10 (d, J = 2.0 Hz, 1H), 7.79-7.67 (m, 2H), 7.62 (dt, J = 6.0, 8.8 Hz, 1H), 7.54-7.48 (m, 1H), 7.39-7.21 (m, 2H), 7.10-7.02 (m, 2H), 5.40-5.20 (m, 1H), 5.04-5.04 (m, 1H), 5.04 (dd, J = 5.2, 13.2 Hz, 1H), 4.30 (s, 1H), 4.22 (s, 1H), 3.88 (d, J = 12.0 Hz, 2H), 3.75 (d, J = 12.0 Hz, 2H), 3.48 (s, 1H), 3.43-3.36 (m, 2H), 3.34-3.25 (m, 1H), 2.96-2.78 (m, 3H), 2.63-2.55 (m, 1H), 2.52-2.51 (m, 2H), 2.42-2.35 (m, 1H), 2.20-1.81 (m, 5H), 1.80-1.73 (m, 2H), 1.58-1.11 (m, 10H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 309 | | (3R)-N-[3-(5-{4-[(3aS,7aS)-5-({1-[2-(2,6-dioxopiperidin-3-yl)-1-oxo-2,3-dihydro-1H-isoindol-5-yl]piperidin-4-yl}methyl)-octahydro-1H-pyrrolo[3,4-c]pyridin-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 12.88 (s, 1H), 10.96 (d, J = 3.6 Hz, 1H), 9.85 (s, 1H), 8.64 (q, J = 2.2 Hz, 1H), 8.59-8.45 (m, 1H), 8.06 (d, J = 3.7 Hz, 1H), 7.58 (dddd, J = 31.9, 23.3, 9.3, 4.5 Hz, 5H), 7.28 (td, J = 8.8, 3.5 Hz, 1H), 7.06 (d, J = 3.5 Hz, 1H), 6.64 (dd, J = 8.8, 3.6 Hz, 2H), 5.48-5.17 (m, 1H), 5.05 (dt, J = 13.5, 4.4 Hz, 1H), 4.33 (dd, J = 16.8, 3.6 Hz, 1H), 4.20 (dd, J = 16.8, 3.6 Hz, 1H), 3.89 (d, J = 12.4 Hz, 2H), 3.45 (d, J = 31.4 Hz, 4H), 3.28-3.14 (m, 1H), 3.03-2.74 (m, 4H), 2.64 (d, J = 28.0 Hz, 3H), 2.44-2.29 (m, 2H), 2.27-2.05 (m, 5H), 1.96 (ddd, J = 20.8, 10.1, 4.4 Hz, 2H), 1.80 (d, J = 12.4 Hz, 4H), 1.54 (s, 1H), 1.31-1.05 (m, 3H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
|  | 310 | (3R)-N-(3-{5-[4-(6-{3-[2-(2,6-dioxopiperidin-3-yl)-1-oxo-2,3-dihydro-1H-isoindol-5-yl]propyl}-2,6-diazaspiro[3.3]heptan-2-yl)-3-fluorophenyl]-1H-pyrrolo[2,3-b]pyridine-3-carbonyl}-2,4-difluorophenyl)-3-fluoropyrrolidine-1-sulfonamide | 1H-NMR (400 MHz, DMSO-d6) δ 12.93 (s, 1H), 11.00 (s, 1H), 9.88 (s, 1H), 8.65 (d, J = 2.3 Hz, 1H), 8.59-8.43 (m, 1H), 8.09 (d, J = 5.1 Hz, 1H), 7.71-7.57 (m, 2H), 7.53-7.39 (m, 3H), 7.38-7.32 (m, 1H), 7.25 (t, J = 8.8 Hz, 1H), 6.68 (t, J = 9.0 Hz, 1H), 6.44-6.35 (m, 1H), 5.30 (d, J = 53.2 Hz, 1H), 5.11 (dd, J = 13.3, 5.1 Hz, 1H), 4.44 (d, J = 17.3 Hz, 1H), 4.30 (d, J = 17.2 Hz, 1H), 4.04 (s, 3H), 3.96 (d, J = 5.0 Hz, 2H), 3.48 (d, J = 2.9 Hz, 1H), 3.39 (s, 3H), 3.01-2.85 (m, 1H), 2.73-2.72 (m, 3H), 2.65-2.56 (m, 1H), 2.46-2.30 (m, 4H), 2.19-2.05 (m, 2H), 2.04-1.90 (m, 2H), 1.65-1.61 (m, 2H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| 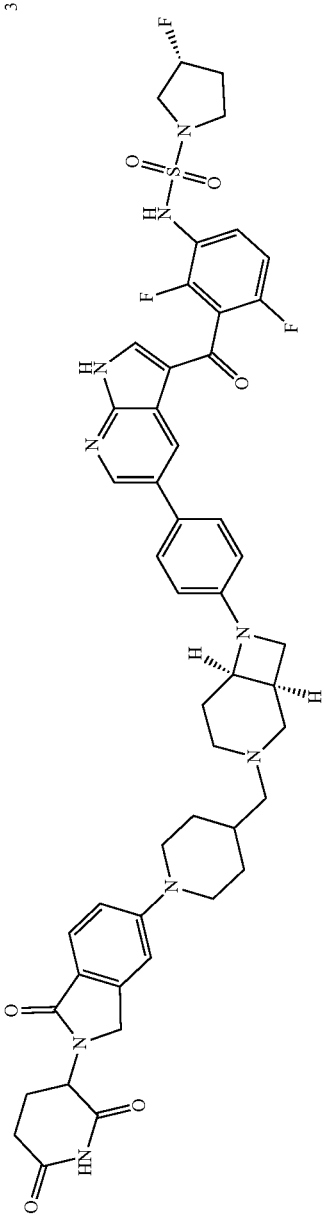 | 311 | (3R)-N-[3-(5-{4-[(1R,6R)-3-({1-[2-(2,6-dioxopiperidin-3-yl)-1-oxo-2,3-dihydro-1H-isoindol-5-yl]piperidin-4-yl}methyl)-3,7-diazabicyclo[4.2.0]octan-7-yl]phenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 12.91 (s, 1H), 10.96 (s, 1H), 9.85 (s, 1H), 8.63 (d, J = 2.2 Hz, 1H), 8.52 (s, 1H), 8.08 (s, 1H), 7.68-7.47 (m, 4H), 7.27 (td, J = 8.7, 1.6 Hz, 1H), 7.05 (d, J = 7.9 Hz, 2H), 6.67 (d, J = 8.4 Hz, 2H), 5.30 (d, J = 54.6 Hz, 1H), 5.05 (dd, J = 13.3, 5.1 Hz, 1H), 4.32 (d, J = 16.9 Hz, 1H), 4.20 (d, J = 16.9 Hz, 1H), 4.10 (dt, J = 7.1, 3.4 Hz, 1H), 3.89 (d, J = 12.3 Hz, 2H), 3.58 (d, J = 5.5 Hz, 2H), 3.49 (s, 1H), 3.44-3.39 (m, 2H), 3.28 (d, J = 9.8 Hz, 1H), 3.03 (t, J = 9.5 Hz, 1H), 2.98-2.77 (m, 3H), 2.72-2.55 (m, 3H), 2.46-2.29 (m, 3H), 2.23 (d, J = 6.5 Hz, 2H), 2.18-2.05 (m, 2H), 2.03-1.90 (m, 3H), 1.87-1.71 (m, 3H), 1.20 (q, J = 12.5, 11.3 Hz, 2H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| | 312 | (3R)-N-[3-(5-{4-[(4R)-4-[2-(2,6-dioxopiperidin-3-yl)-1-oxo-2,3-dihydro-1H-isoindol-5-yl]piperidin-1-yl}methyl)-2-oxopiperidin-1-yl]phenyl]-1H-pyrrolo[2,3-b]pyridine-3-carbonyl]-2,4-difluorophenyl]-3-fluoropyrrolidine-1-sulfonamide | 1H NMR (400 MHz, DMSO-d6) δ 12.97 (s, 1H), 10.97 (s, 1H), 9.83 (s, 1H), 8.72 (d, J = 2.2 Hz, 1H), 8.62 (s, 1H), 8.12 (s, 1H), 7.76 (d, J = 8.1 Hz, 2H), 7.64 (dd, J = 9.1, 6.7 Hz, 2H), 7.52 (s, 1H), 7.43 (t, J = 7.7 Hz, 3H), 7.26 (t, J = 8.7 Hz, 1H), 5.36-5.23 (s, 1H), 5.10 (dd, J = 13.3, 5.1 Hz, 1H), 4.43 (d, J = 17.2 Hz, 1H), 4.29 (d, J = 17.2 Hz, 1H), 3.76 (dt, J = 11.1, 5.9 Hz, 1H), 3.70-3.61 (m, 1H), 3.39 (s, 4H), 3.03 (d, J = 10.6 Hz, 2H), 2.91 (td, J = 14.8, 13.7, 5.3 Hz, 1H), 2.72-2.60 (m, 2H), 2.58 (d, J = 5.2 Hz, 1H), 2.44-2.29 (m, 1H), 2.33 (s, 2H), 2.30 (s, 1H), 2.21-2.10 (m, 2H), 2.09 (t, J = 11.0 Hz, 3H), 2.03-1.94 (m, 2H), 1.79 (s, 4H), 1.74 (d, J = 11.4 Hz, 1H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 313 | | (3R)-N-[3-(5-{4-[(3aR,7aR)-5-({1-[2-(2,6-dioxopiperidin-3-yl)-1-oxo-2,3-dihydro-1H-isoindol-5-yl]piperidin-4-yl}methyl)-octahydro-1H-pyrrolo[3,4-c]pyridin-2-yl]phenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 12.88 (s, 1H), 10.95 (s, 1H), 9.85 (s, 1H), 8.64 (d, J = 2.2 Hz, 1H), 8.51 (s, 1H), 8.06 (s, 1H), 7.77-7.44 (m, 5H), 7.28 (td, J = 8.8, 1.6 Hz, 1H), 7.05 (d, J = 7.9 Hz, 3H), 6.64 (d, J = 8.4 Hz, 2H), 5.45-5.16 (m, 1H), 5.05 (dd, J = 13.2, 5.1 Hz, 1H), 4.40-4.12 (m, 2H), 3.89 (d, J = 12.2 Hz, 2H), 3.55-3.44 (m, 1H), 3.42-3.38 (m, 2H), 3.29 (t, J = 8.2 Hz, 3H), 3.20 (dd, J = 9.8, 4.3 Hz, 1H), 3.00-2.79 (m, 3H), 2.68-2.56 (m, 1H), 2.40 (dd, J = 13.3, 4.5 Hz, 2H), 2.37-2.27 (m, 2H), 2.23-2.05 (m, 4H), 2.03-1.88 (m, 2H), 1.80 (d, J = 11.8 Hz, 4H), 1.53 (d, J = 9.2 Hz, 1H), 1.19 (dd, J = 23.5, 11.4 Hz, 3H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 314 | | (3R)-N-[3-(5-{4-[(4S)-4-[(4-[2-(2,6-dioxopiperidin-3-yl)-1-oxo-2,3-dihydro-1H-isoindol-5-yl]piperidin-1-yl}methyl)-2-oxopiperidin-1-yl]phenyl]-1H-pyrrolo[2,3-b]pyridine-3-carbonyl]-2,4-difluorophenyl]-3-fluoropyrrolidine-1-sulfonamide | 1H NMR (400 MHz, DMSO-d6) δ 12.98 (s, 1H), 10.97 (s, 1H), 9.85 (s, 1H), 8.72 (d, J = 2.2 Hz, 1H), 8.62 (s, 1H), 8.12 (s, 1H), 7.76 (d, J = 8.3 Hz, 2H), 7.64 (dd, J = 8.8, 6.7 Hz, 2H), 7.52 (s, 1H), 7.43 (dd, J = 8.7, 7.0 Hz, 3H), 7.27 (td, J = 8.8, 1.6 Hz, 1H), 5.23 (t, J = 3.3 Hz, 1H), 5.10 (dd, J = 13.3, 5.1 Hz, 1H), 4.43 (d, J = 17.3 Hz, 1H), 4.29 (d, J = 17.2 Hz, 1H), 3.77 (td, J = 11.4, 4.4 Hz, 1H), 3.65 (dt, J = 11.8, 4.6 Hz, 1H), 3.48 (d, J = 2.4 Hz, 1H), 3.42-3.37 (m, 1H), 3.29 (d, J = 7.2 Hz, 2H), 3.07-2.99 (m, 2H), 2.98-2.84 (m, 1H), 2.72-2.53 (m, 3H), 2.47-2.27 (m, 4H), 2.21-2.07 (m, 4H), 2.06 (s, 1H), 2.09-1.93 (m, 2H), 1.77 (q, J = 10.9 Hz, 4H), 1.67-1.59 (m, 1H) |

TABLE 3-continued

1H NMR data of exemplary bifunctional compounds of the present disclosure

| Ex. No. | Parent Mol Structure | IUPAC Name | 1H NMR tabulation |
|---|---|---|---|
| 315 | 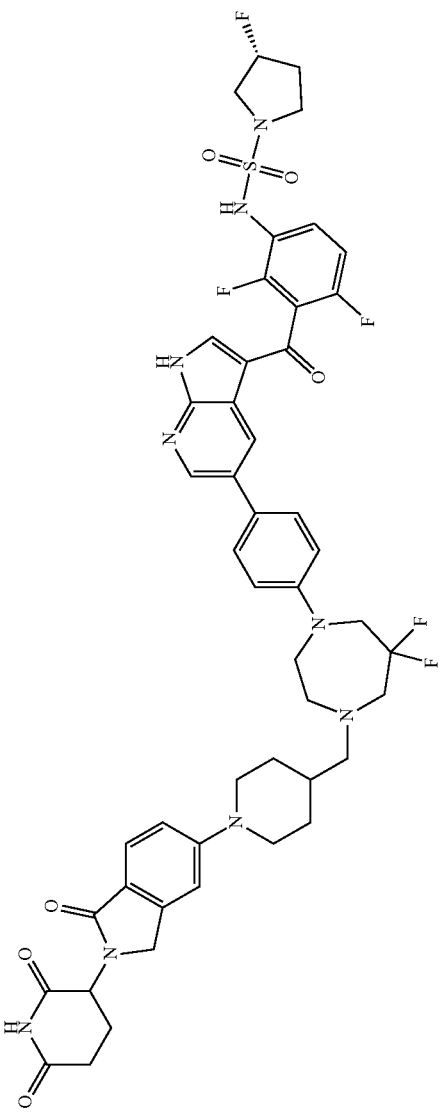 | (3R)-N-[3-(5-{4-[4-({1-[2-(2,6-dioxopiperidin-3-yl)-1-oxo-2,3-dihydro-1H-isoindol-5-yl]piperidin-4-yl}methyl)-6,6-difluoro-1,4-diazepan-1-yl]phenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 12.91 (s, 1H), 10.95 (s, 1H), 9.87 (s, 1H), 8.66 (d, J = 2.2 Hz, 1H), 8.54 (s, 1H), 8.07 (s, 1H), 7.72-7.43 (m, 4H), 7.35-7.18 (m, 1H), 7.02 (t, J = 5.5 Hz, 4H), 5.30 (d, J = 53.0 Hz, 1H), 5.04 (dd, J = 13.3, 5.1 Hz, 1H), 4.30 (d, J = 16.9 Hz, 1H), 4.18 (d, J = 16.8 Hz, 1H), 4.06 (t, J = 12.8 Hz, 2H), 3.87 (d, J = 12.5 Hz, 2H), 3.68 (s, 2H), 3.49 (s, 1H), 3.39 (d, J = 13.5 Hz, 2H), 3.30-3.24 (m, 0H), 3.03-2.86 (m, 4H), 2.81 (t, J = 12.1 Hz, 3H), 2.68-2.55 (m, 2H), 2.46 (s, 0H), 2.44-2.28 (m, 1H), 2.21-2.03 (m, 2H), 2.03-1.89 (m, 2H), 1.78 (d, J = 12.6 Hz, 3H), 1.29-1.06 (m, 3H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| 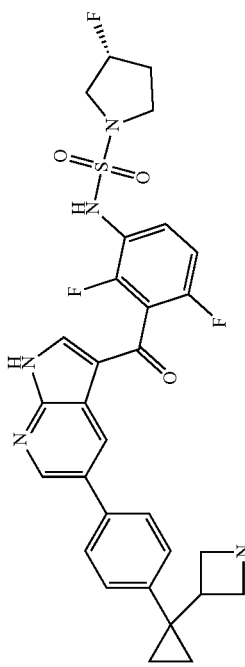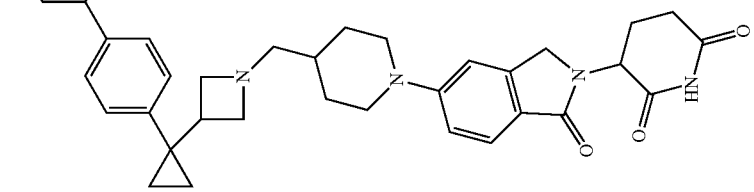 | 316 | (3R)-N-{3-(4-{5-(4-{1-[1-({1-[2-(2,6-dioxopiperidin-3-yl)-1-oxo-2,3-dihydro-1H-isoindol-5-yl]piperidin-4-yl}methyl)azetidin-3-yl]cyclopropyl}phenyl)-1H-pyrrolo[2,3-b]pyridine-3-carbonyl]-2,4-difluorophenyl}-3-fluoropyrrolidine-1-sulfonamide | 1H NMR (400 MHz, DMSO-d6) δ 12.96 (s, 1H), 10.94 (s, 1H), 9.86 (s, 1H), 8.69 (m, 1H), 8.60 (s, 1H), 8.11 (s, 1H), 7.67 (m, 2H), 7.62 (m, 1H), 7.49 (m, 1H), 7.37 (m, 2H), 7.29-7.20 (m, 1H), 7.03-7.01 (m, 2H), 5.36-5.23 (m, 1H), 5.04 (m, 1H), 4.31 (m, 1H), 4.19 (m, 1H), 3.84 (m, 2H), 3.47 (m, 1H), 3.43-3.34 (m, 2H), 3.28 (m, 1H), 3.06-2.83 (m, 1H), 2.81 (s, 1H), 2.79-2.72 (m, 7H), 2.63-2.54 (m, 1H), 2.44-2.29 (m, 1H), 2.27 (m, 2H), 2.10-2.06 (m, 2H), 2.03-1.89 (m, 2H), 1.79-1.68 (m, 2H), 1.49 (s, 1H), 1.18 (m, 2H), 0.95-0.95 (s, 2H), 0.86-0.83 (s, 2H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 317 | | (3R)-N-(3-{5-[4-(4-{4-[2-(2,6-dioxopiperidin-3-yl)-1-oxo-2,3-dihydro-1H-isoindol-5-yl]piperazin-1-yl}butyl)phenyl]-1H-pyrrolo[2,3-b]pyridine-3-carbonyl}-2,4-difluorophenyl)-3-fluoropyrrolidine-1-sulfonamide | 1H NMR (400 MHz, DMSO-d6) δ 8.70 (s, 1H), 8.55 (s, 1H), 8.01 (s, 1H), 7.66 (d, J = 7.9 Hz, 2H), 7.56-7.46 (m, 2H), 7.36 (d, J = 8.0 Hz, 2H), 7.07 (s, 1H), 7.05 (d, J = 2.2 Hz, 1H), 6.92 (t, J = 8.8 Hz, 1H), 6.09 (s, 1H), 5.34-5.27 (m, 1H), 5.05 (dd, J = 13.3, 5.1 Hz, 1H), 4.33 (d, J = 16.9 Hz, 1H), 4.20 (d, J = 16.9 Hz, 1H), 3.39-3.18 (m, 7H), 3.21-3.07 (m, 3H), 2.90-2.81 (m, 1H), 2.69-2.67 (m, 2H), 2.59-2.58 (m, 1H), 2.51-2.50 (m, 3H), 2.06-1.94 (m, 3H), 1.67-1.66 (m, 2H), 1.55-1.51 (m, 2H) |
| 318 | | (3R)-N-(3-{5-[4-(5-[4-[2-(2,6-dioxopiperidin-3-yl)-1-oxo-2,3-dihydro-1H-isoindol-5-yl]piperazin-1-yl}pentyl)phenyl]-1H-pyrrolo[2,3-b]pyridine-3-carbonyl}-2,4-difluorophenyl)-3-fluoropyrrolidine-1-sulfonamide | 1H NMR (400 MHz, DMSO-d6) δ 12.98 (s, 1H), 10.96 (s, 1H), 9.85 (s, 1H), 8.70 (d, J = 2.2 Hz, 1H), 8.61 (s, 1H), 8.13 (s, 1H), 7.74-7.58 (m, 3H), 7.52 (d, J = 9.0 Hz, 1H), 7.41-7.21 (m, 3H), 7.06 (d, J = 7.5 Hz, 2H), 5.42-5.19 (m, 1H), 5.05 (dd, J = 13.3, 5.1 Hz, 1H), 4.33 (d, J = 16.9 Hz, 1H), 4.20 (d, J = 16.9 Hz, 1H), 3.58-3.38 (m, 4H), 3.32-3.24 (m, 4H), 2.91 (ddd, J = 17.2, 13.6, 5.4 Hz, 1H), 2.67 (t, J = 7.5 Hz, 2H), 2.56 (s, 4H), 2.47-2.30 (m, 3H), 2.22-2.05 (m, 2H), 2.05-1.90 (m, 2H), 1.67 (p, J = 7.6 Hz, 2H), 1.54 (p, J = 7.5 Hz, 2H), 1.36 (dd, J = 10.6, 4.9 Hz, 2H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| 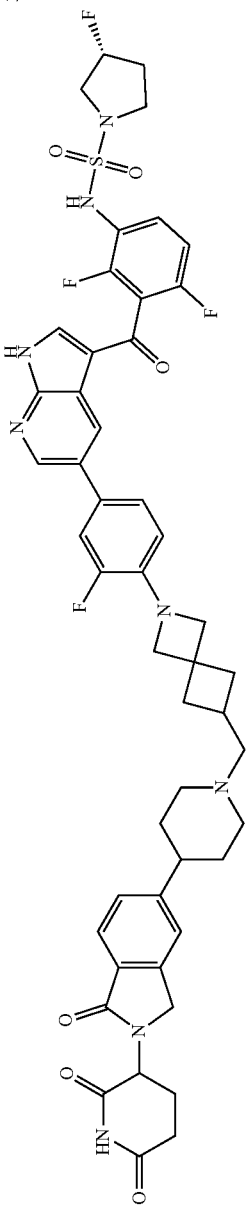 | 319 | (3R)-N-[3-(5-{4-[6-({4-[2-(2,6-dioxopiperidin-3-yl)-1-oxo-2,3-dihydro-1H-isoindol-5-yl]piperidin-1-yl}methyl)-2-azaspiro[3.3]heptan-2-yl]-3-fluorophenyl]-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 12.91 (s, 1H), 10.99 (s, 1H), 8.66 (m, 1H), 8.54 (s, 1H), 8.08 (s, 1H), 7.68-7.57 (m, 2H), 7.48 (m, 2H), 7.47-7.32 (m, 2H), 7.30-7.21 (m, 1H), 6.65 (m, 1H), 5.37-5.23 (m, 1H), 5.11 (m, 1H), 4.43 (m, 1H), 4.29 (m, 1H), 4.01 (m, 2H), 3.88 (m, 2H), 3.45-3.40 (m, 2H), 3.01-2.85 (m, 3H), 2.61 (m, 3H), 2.44 (m, 3H), 2.44-2.30 (m, 3H), 2.09 (m, 4H), 2.00 (m, 2H), 1.95-1.87 (m, 2H), 1.82-1.63 (m, 4H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| 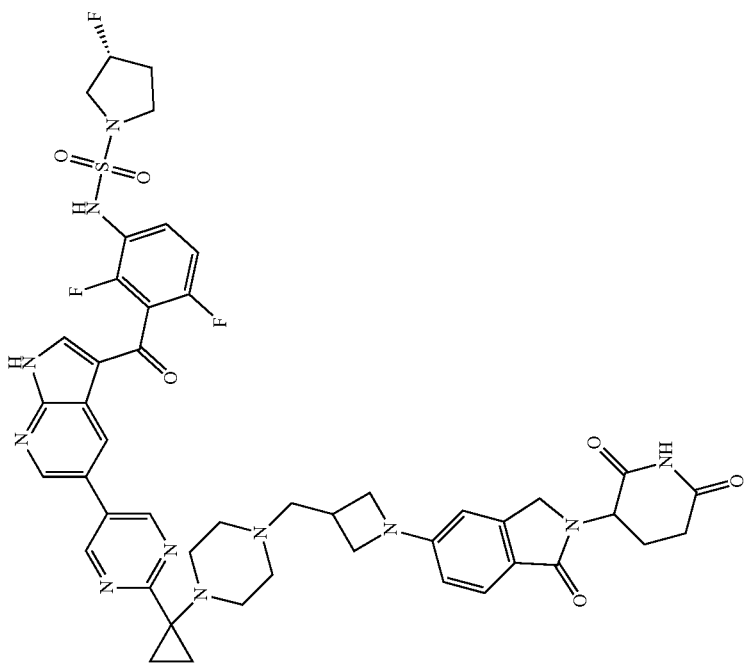 | 320 | (3R)-N-{3-[5-(2-{1-[4-({1-[2-(2,6-dioxopiperidin-3-yl)-1-oxo-2,3-dihydro-1H-isoindol-5-yl]azetidin-3-yl}methyl)piperazin-1-yl]cyclopropyl}pyrimidin-5-yl)-1H-pyrrolo[2,3-b]pyridine-3-carbonyl]-2,4-difluorophenyl}-3-fluoropyrrolidine-1-sulfonamide | 1H NMR (300 MHz, DMSO-d6) δ 13.12 (s, 1H), 10.92 (s, 1H), 9.85 (s, 1H), 9.08 (s, 2H), 8.76-8.69 (m, 2H), 8.16 (s, 1H), 7.62 (m, 1H), 7.47 (m, 1H), 7.26 (m, 1H), 6.54-6.42 (m, 2H), 5.39-5.21 (s, 1H), 5.02 (m, 1H), 4.30-4.16 (m, 2H), 4.03 (m, 2H), 3.57-3.39 (m, 5H), 3.18 (s, 4H), 2.98-2.87 (m, 2H), 2.60 (s, 3H), 2.38 (s, 5H), 2.19-1.89 (m, 3H), 1.38 (s, 2H), 1.10 (s, 3H) |

TABLE 3-continued

¹H NMR data of exemplary bifunctional compounds of the present disclosure

| Ex. No. | IUPAC Name | Parent Mol Structure | ¹H NMR tabulation |
|---|---|---|---|
| 321 | (3R)-N-(3-{5-[4-(6-{4-[2-(2,6-dioxopiperidin-3-yl)-1-oxo-2,3-dihydro-1H-isoindol-5-yl]butyl}-2,6-diazaspiro[3.3]heptan-2-yl)phenyl]-1H-pyrrolo[2,3-b]pyridine-3-carbonyl}-2,4-difluorophenyl)-3-fluoropyrrolidine-1-sulfonamide | | 1H NMR (300 MHz, DMSO-d6) δ 12.98 (s, 1H), 10.96 (s, 1H), 8.61 (s, 1H), 8.49 (s, 1H), 8.04 (s, 1H), 7.65-7.58 (m, 4H), 7.52 (s, 1H), 7.46-7.44 (m, 1H), 7.36-7.34 (m, 1H), 6.55 (d, J = 8.7 Hz, 2H), 5.42-5.19 (d, J = 36.0 Hz 1H), 5.05 (dd, J = 13.3, 5.1 Hz, 1H), 4.46-4.27 (q, 2H), 3.93 (s, 4H), 3.53-3.48 (m, 7H), 2.92-2.86 (m, 2H), 2.73-2.63 (m, 4H), 2.56-2.45 (m, 2H), 2.17-1.86 (m, 3H), 1.65-1.62 (m, 2H), 1.35-1.32 (m, 2H) |
| 322 | (3R)-N-[3-(5-{4-[4-({1-[2-(2,6-dioxopiperidin-3-yl)-1-oxo-2,3-dihydro-1H-isoindol-5-yl]piperidin-4-yl}methyl)-1,4-diazepan-1-yl]phenyl}-1H-pyrrolo[2,3-b]pyridine-3-carbonyl)-2,4-difluorophenyl]-3-fluoropyrrolidine-1-sulfonamide | | 1H NMR (300 MHz, DMSO-d6) δ 12.98 (s, 1H), 10.91(s, 1H), 9.85 (s, 1H), 8.64 (s, 1H), 8.51 (s, 1H), 8.13 (s, 1H), 7.63-7.54 (m, 4H), 7.29-7.26 (m, 1H), 7.02 (s, 2H), 6.86-6.81 (m, 2H), 5.42-5.19 (d, J = 62 Hz, 1H), 5.05 (dd, J = 13.3, 5.1 Hz, 1H), 4.33-4.20 (q, 2H), 3.87-3.83 (m, 2H), 3.61-3.50 (m, 5H), 2.89-2.85(m, 5H), 2.81-2.77 (m, 3H), 2.56-2.51 (m, 3H), 2.17-2.11 (m, 2H), 1.97-1.91 (m, 4H), 1.78-1.74 (m, 3H), 1.23-1.17 (m, 4H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 323 | | (3R)-N-[3-(5-{4-[4-({4-[2-(2,6-dioxopiperidin-3-yl)-1,3-dioxo-2,3-dihydro-1H-isoindol-5-yl]piperidin-1-yl]methyl)phenyl]-1H-pyrrolo[2,3-b]pyridine-3-carbonyl)-2,4-difluorophenyl]-3-fluoropyrrolidine-1-sulfonamide | 1H NMR (300 MHz, DMSO-d6) δ 12.88 (s, 1H), 11.10 (s, 1H), 9.81 (s, 1H), 8.64 (m, 1H), 8.52 (s, 1H), 8.05 (s, 1H), 7.93-7.74 (m, 3H), 7.69-7.54 (m, 3H), 7.25 (m, 1H), 7.07 (m, 2H), 5.39-5.07 (m, 2H), 3.79 (m, 2H), 3.49 (m, 1H), 3.41 (m, 2H), 3.01 (m, 2H), 2.90 (m, 1H), 2.75 (m, 3H), 2.66-2.55 (m, 3H), 2.52 (s, 2H), 2.29-1.92 (m, 5H), 1.90-1.68 (m, 7H), 1.23 (m, 2H) |
| 324 | | (3R)-N-[3-(5-{4-[4-({4-[2-(2,6-dioxopiperidin-3-yl)-1-oxo-2,3-dihydro-1H-isoindol-5-yl]-1,4-diazepan-1-yl]methyl)phenyl]piperidin-1-yl]methyl)phenyl]-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 12.88 (s, 1H), 10.92 (s, 1H), 9.83 (s, 1H), 8.64 (m, 1H), 8.52 (s, 1H), 8.06 (s, 1H), 7.68-7.56 (m, 2H), 7.56 (s, 1H), 7.48 (d, 1H), 7.27 (m, 1H), 7.05 (m, 2H), 6.83 (m, 2H), 5.36-5.23 (s, 1H), 5.03 (m, 1H), 4.31 (m, 1H), 4.19 (m, 1H), 3.76 (m, 3H), 3.64-3.54 (m, 5H), 3.48 (s, 1H), 2.92-2.83 (m, 1H), 2.83-2.73 (m, 5H), 2.73 (m, 2H), 2.60 (s, 1H), 2.30-2.11 (s, 2H), 1.93 (s, 4H), 1.77 (m, 2H), 1.64 (s, 1H), 1.24 (s, 2H), 1.17 (m, 2H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 325 | | (3R)-N-(3-{5-[4-(4-{[2-(2,6-dioxopiperidin-3-yl)-1-oxo-2,3-dihydro-1H-isoindol-5-yl]butyl}piperazin-1-yl)phenyl]-1H-pyrrolo[2,3-b]pyridine-3-carbonyl}-2,4-difluorophenyl)-3-fluoropyrrolidine-1-sulfonamide | 1H NMR (300 MHz, DMSO-d6) δ 12.89 (s, 1H), 10.97 (s, 1H), 9.84 (s, 1H), 8.63 (m, 1H), 8.52 (s, 1H), 8.05 (s, 1H), 7.61 (m, 4H), 7.44 (s, 1H), 7.35 (m, 1H), 7.31-7.18 (m, 1H), 7.05 (m, 2H), 5.37-5.19 (s, 1H), 5.09 (m, 1H), 4.42 (m, 1H), 4.28 (m, 1H), 3.48 (m, 1H), 3.45-3.39 (m, 3H), 3.39-3.30 (m, 4H), 3.28-3.10 (m, 5H), 2.90 (m, 1H), 2.74 (m, 1H), 2.61 (s, 1H), 2.52 (s, 3H), 2.35 (m, 4H), 2.15-1.94 (m, 1H), 1.64-1.50 (m, 2H) |
| 326 | | (3R)-N-{3-[5-(4-{[2-(2,6-dioxopiperidin-3-yl)-1-oxo-2,3-dihydro-1H-isoindol-5-yl]-[1,4-bipiperidin]-1'-yl}phenyl)-1H-pyrrolo[2,3-b]pyridine-3-carbonyl]-2,4-difluorophenyl}-3-fluoropyrrolidine-1-sulfonamide | 1H NMR (400 MHz, DMSO-d6) δ 12.89 (s, 1H), 10.98 (s, 1H), 8.66 (d, J = 2.0 Hz, 1H), 8.54 (s, 1H), 8.18 (s, 1H), 8.07 (s, 1H), 7.69-7.55 (m, 4H), 7.51 (s, 1H), 7.41 (d, J = 8.0 Hz, 1H), 7.26 (t, J = 8.4 Hz, 1H), 7.09 (d, J = 8.8 Hz, 2H), 5.40-5.20 (m, 1H), 5.11 (dd, J = 5.2, 13.2 Hz, 1H), 4.46-4.27 (m, 2H), 3.87 (d, J = 11.2 Hz, 2H), 3.48 (s, 2H), 3.26-3.24 (m, 1H), 3.07 (d, J = 11.2 Hz, 2H), 3.01-2.86 (m, 2H), 2.77 (t, J = 11.6 Hz, 2H), 2.60 (d, J = 17.6 Hz, 2H), 2.47-2.40 (m, 1H), 2.37 (d, J = 12.0 Hz, 2H), 2.19-1.55 (m, 12H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 327 | | (3R)-N-{3-[5-(4-{6-[(2R)-4-{2-[(3S)-2,6-dioxopiperidin-3-yl]-1-oxo-2,3-dihydro-1H-isoindol-5-yl}-2-hydroxybutyl]-2,6-diazaspiro[3.3]heptan-2-yl}phenyl)-1H-pyrrolo[2,3-b]pyridine-3-carbonyl]-2,4-difluorophenyl}-3-fluoropyrrolidine-1-sulfonamide | 1H NMR (400 MHz, DMSO-d6) δ 13.52-12.40 (m, 1H), 11.09-10.86 (m, 1H), 8.61 (d, J = 2.0 Hz, 1H), 8.54-8.41 (m, 1H), 8.31-8.18 (m, 1H), 8.03 (s, 1H), 7.64 (d, J = 8.0 Hz, 1H), 7.60 (dd, J = 2.8, 9.2 Hz, 1H), 7.55 (d, J = 8.4 Hz, 2H), 7.44 (s, 1H), 7.35 (d, J = 7.6 Hz, 1H), 7.30-7.15 (m, 1H), 6.55 (d, J = 8.4 Hz, 2H), 5.39-5.19 (m, 1H), 5.10 (dd, J = 5.2, 13.2 Hz, 1H), 4.73-4.55 (m, 1H), 4.47-4.25 (m, 3H), 3.92 (s, 4H), 2.97-2.78 (m, 5H), 2.76-2.69 (m, 2H), 2.61 (d, J = 2.8 Hz, 1H), 2.57 (s, 2H), 2.46-2.40 (m, 3H), 2.37 (d, J = 4.4 Hz, 1H), 2.12-1.96 (m, 3H), 1.81-1.49 (m, 3H) |
| 328 | | (3R)-N-{3-[5-(4-{6-[(2R)-4-{2-[(3R)-2,6-dioxopiperidin-3-yl]-1-oxo-2,3-dihydro-1H-isoindol-5-yl}-2-hydroxybutyl]-2,6-diazaspiro[3.3]heptan-2-yl}phenyl)-1H-pyrrolo[2,3-b]pyridine-3-carbonyl]-2,4-difluorophenyl}-3-fluoropyrrolidine-1-sulfonamide | 1H NMR (400 MHz, DMSO-d6) δ 13.27-12.46 (m, 1H), 10.98 (s, 1H), 8.60 (s, 1H), 8.54-8.40 (m, 1H), 8.23 (s, 1H), 8.03 (s, 1H), 7.66-7.52 (m, 4H), 7.44 (s, 1H), 7.35 (d, J = 8.0 Hz, 1H), 7.20 (t, J = 8.8 Hz, 1H), 6.55 (d, J = 8.4 Hz, 2H), 5.38-5.19 (m, 1H), 5.10 (dd, J = 4.8, 13.2 Hz, 1H), 4.74-4.51 (m, 1H), 4.48-4.25 (m, 3H), 3.92 (s, 4H), 2.96-2.78 (m, 5H), 2.76-2.69 (m, 2H), 2.62 (s, 1H), 2.57 (d, J = 1.6 Hz, 2H), 2.46-2.42 (m, 2H), 2.39 (dd, J = 5.2, 13.2 Hz, 2H), 2.13-2.06 (m, 1H), 2.05-1.95 (m, 2H), 1.79-1.50 (m, 3H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 329 | | (3R)-N-[3-(5-{4-[(1S,6S)-3-({1-[2-(2,6-dioxopiperidin-3-yl)-1-oxo-2,3-dihydro-1H-isoindol-5-yl]piperidin-4-yl}methyl)-3,7-diazabicyclo[4.2.0]octan-7-yl]phenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 12.98 (s, 1H), 10.95 (s, 1H), 9.86 (b, 1H), 8.63-8.61 (m, 1H), 8.51 (s, 1H), 8.07 (s, 1H), 7.63-7.61 (m, 1H), 7.56-7.54 (m, 2H), 7.51-7.48 (m, 1H), 7.32-7.23 (m, 1H), 7.05-7.03 (m, 2H), 6.68-6.67 (d, J = 8.4 Hz, 2H), 5.37-5.23 (d, J = 32.6 Hz, 1H), 5.05-5.01 (m, 1H), 4.33 (d, J = 17.9 Hz, 1H), 4.20 (d, J = 17.9 Hz, 1H), 4.11 (s, 1H), 3.91-3.89 (m, 3H), 3.89-3.59 (m, 2H), 3.58-3.57 (m, 2H), 3.54-3.34 (m, 3H), 3.19-3.02 (m, 1H), 2.86-2.84 (m, 4H), 2.61-2.58 (m, 3H), 2.26 (s, 1H), 2.14-2.04 (m, 2H), 1.98-1.96 (m, 4H), 1.82-1.80 (m, 3H), 1.26-1.13 (m, 2H) |
| 330 | | (3R)-N-[3-(5-{4-[1'-({1-[2-(2,6-dioxopiperidin-3-yl)-1-oxo-2,3-dihydro-1H-isoindol-5-yl]piperidin-4-yl}methyl)-[3,3'-biazetidin]-1-yl]phenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 12.90 (b, 1H), 10.94 (s, 1H), 8.62 (s, 1H), 8.61 (s, 1H), 8.05 (s, 1H), 7.56-7.48 (m, 4H), 7.31-7.29 (m, 1H), 7.03 (d, J = 6.0 Hz, 2H), 6.55 (d, J = 8.4 Hz, 2H), 5.23 (d, J = 36.2 Hz, 1H), 5.10-5.08 (m, 1H), 4.29 (d, J = 17.2 Hz, 1H), 4.21 (d, J = 17.2 Hz, 1H), 3.96-3.94 (m, 2H), 3.92-3.90 (m, 2H), 3.60-3.58 (m, 4H), 3.00-2.83 (m, 5H), 2.84-2.80 (m, 4H), 2.52-2.51 (m, 1H), 2.42-2.40 (m, 2H), 2.12-2.02 (m, 2H), 1.93-1.91 (m, 2H), 1.71-1.70 (m, 2H), 1.61-1.60 (m, 2H), 1.33-1.30 (m, 4H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| | 331 | (3R)-N-[3-(5-{4-[4-(4-{[2-(2,6-dioxopiperidin-3-yl)-7-methoxy-1-oxo-2,3-dihydro-1H-isoindol-5-yl]oxy}butyl)piperazin-1-yl]phenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 12.88 (s, 1H), 10.90 (s, 1H), 9.82 (s, 1H), 8.63 (d, J = 2.2 Hz, 1H), 8.52 (s, 1H), 8.05 (s, 1H), 7.66-7.55 (m, 3H), 7.29-7.20 (m, 1H), 7.06 (d, J = 8.6 Hz, 2H), 6.71 (d, J = 1.9 Hz, 1H), 6.54 (d, J = 1.8 Hz, 1H), 5.34-5.21 (s, 1H), 4.96 (dd, J = 13.3, 5.1 Hz, 1H), 4.28 (d, J = 17.3 Hz, 1H), 4.15 (d, J = 17.3 Hz, 1H), 4.09 (t, J = 6.4 Hz, 2H), 3.82 (s, 3H), 3.46 (d, J = 2.3 Hz, 1H), 3.39 (s, 2H), 3.21 (t, J = 5.0 Hz, 4H), 2.93-2.81 (m, 1H), 2.55 (t, J = 5.2 Hz, 5H), 2.41 (t, J = 7.1 Hz, 2H), 2.37-2.22 (m, 1H), 2.09 (s, 2H), 2.02-1.87 (m, 2H), 1.77 (q, J = 6.9 Hz, 2H), 1.64 (q, J = 7.5 Hz, 2H) |
| | 332 | (3R)-N-(3-{5-[4-(1-{4-[2-(2,6-dioxopiperidin-3-yl)-1-oxo-2,3-dihydro-1H-isoindol-5-yl]butyl}piperidin-4-yl)phenyl]-1H-pyrrolo[2,3-b]pyridine-3-carbonyl}-2,4-difluorophenyl)-3-fluoropyrrolidine-1-sulfonamide | 1H NMR (300 MHz, DMSO-d6) δ 12.95 (s, 1H), 10.99 (s, 1H), 8.69 (m, 1H), 8.59 (s, 1H), 8.11 (s, 1H), 7.65 (s, 1H), 7.47 (s, 1H), 7.39 (m, 4H), 7.32-7.19 (m, 3H), 5.38 (s, 1H), 5.21 (s, 1H), 5.11 (m, 1H), 4.45 (m, 1H), 4.31 (m, 1H), 3.49 (m, 1H), 3.39 (m, 2H), 3.04 (m, 2H), 3.00-2.83 (m, 1H), 2.77 (m, 2H), 2.63 (s, 1H), 2.49-2.48 (m, 1H), 2.43 (s, 1H), 2.12 (s, 4H), 2.03 (s, 1H), 1.98 (s, 1H), 1.83 (m, 2H), 1.69 (s, 3H), 1.64 (s, 2H), 1.53 (s, 2H), 1.27-1.13 (m, 1H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 333 | 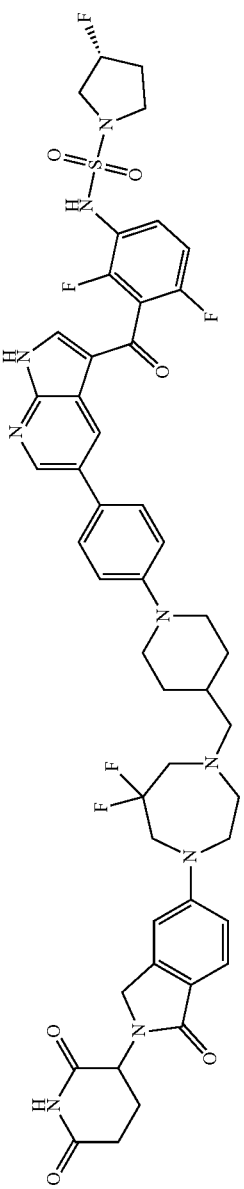 | (3R)-N-[3-(5-{4-[4-({4-[2-(2,6-dioxopiperidin-3-yl)-1-oxo-2,3-dihydro-1H-isoindol-5-yl]-6,6-difluoro-1,4-diazepan-1-yl}methyl)piperidin-1-yl]phenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 12.91 (d, J = 3.3 Hz, 1H), 10.95 (s, 1H), 9.86 (s, 1H), 8.65 (d, J = 2.3 Hz, 1H), 8.54 (s, 1H), 8.08 (d, J = 3.4 Hz, 1H), 7.72-7.55 (m, 3H), 7.52 (d, J = 8.5 Hz, 1H), 7.36-7.24 (m, 1H), 7.14-6.92 (m, 4H), 5.43-5.18 (m, 1H), 5.06 (dd, J = 13.3, 5.1 Hz, 1H), 4.43-4.22 (m, 2H), 4.14 (dd, J = 25.5, 13.1 Hz, 2H), 3.86-3.65 (m, 4H), 3.55-3.37 (m, 2H), 3.31-3.23 (m, 1H), 2.92 (q, J = 10.3, 6.8 Hz, 5H), 2.79-2.65 (m, 3H), 2.65-2.57 (m, 1H), 2.44-2.28 (m, 2H), 2.24-2.05 (m, 2H), 2.05-1.88 (m, 2H), 1.80 (d, J = 12.5 Hz, 2H), 1.64 (s, 1H), 1.27-1.10 (m, 2H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| | 334 | (3R)-N-{3-[5-(2-{1-[1-({1-[2-(2,6-dioxopiperidin-3-yl)-1-oxo-2,3-dihydro-1H-isoindol-5-yl]azetidin-3-yl}methyl)piperidin-4-yl]cyclopropyl}pyrimidin-5-yl)-1H-pyrrolo[2,3-b]pyridine-3-carbonyl]-2,4-difluorophenyl}-3-fluoropyrrolidine-1-sulfonamide | 1H NMR (400 MHz, DMSO-d6) δ 13.05 (s, 1H), 10.94 (d, J = 2.5 Hz, 1H), 9.08 (d, J = 2.6 Hz, 2H), 8.85-8.57 (m, 2H), 8.17 (d, J = 2.5 Hz, 1H), 7.63 (tdd, J = 8.9, 5.9, 2.5 Hz, 1H), 7.48 (dd, J = 8.3, 2.6 Hz, 1H), 7.26 (t, J = 8.9 Hz, 1H), 6.66-6.36 (m, 2H), 5.42-5.18 (m, 1H), 5.04 (ddd, J = 13.4, 5.2, 2.7 Hz, 1H), 4.39-4.09 (m, 2H), 4.03 (t, J = 7.8 Hz, 2H), 3.57 (dt, J = 7.8, 4.2 Hz, 2H), 3.45 (dt, J = 32.7, 2.8 Hz, 3H), 3.06-2.82 (m, 4H), 2.68-2.54 (m, 3H), 2.34 (t, J = 12.4 Hz, 2H), 2.19-1.87 (m, 6H), 1.67 (d, J = 12.1 Hz, 2H), 1.44 (t, J = 12.4 Hz, 2H), 1.29-1.14 (m, 2H), 1.03 (s, 2H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
|  | 335 | (3R)-N-{3-[5-(4-{[(3R)-1-{2-[(3S)-2,6-dioxopiperidin-3-yl]-1-oxo-2,3-dihydro-1H-isoindol-5-yl}pyrrolidin-3-yl]methoxy}phenyl)-1H-pyrrolo[2,3-b]pyridine-3-carbonyl]-2,4-difluorophenyl}-3-fluoropyrrolidine-1-sulfonamide | 1H NMR (400 MHz, DMSO-d6) δ 12.95 (s, 1H), 10.94 (s, 1H), 9.86 (s, 1H), 8.67 (s, 1H), 8.66 (s, 1H), 8.10 (s, 1H), 7.69-7.63 (m, 3H), 7.50 (d, J = 8.4 Hz, 1H), 7.27-7.11 (m, 1H), 7.12 (d, J = 8.8 Hz, 2H), 6.68 (s, 2H), 5.28 (d, J = 31.2 Hz, 1H), 5.03 (dd, J = 13.2, 5.0 Hz, 1H), 4.34-4.30 (m, 1H), 4.22-4.11 (m, 3H), 3.58-3.56 (m, 4H), 3.48-3.46 (m, 4H), 3.32-3.30 (m, 2H), 2.90-2.87 (m, 2H), 2.58-2.48 (m, 1H), 2.45-2.20 (m, 2H), 2.12-2.10 (m, 2H), 1.98-1.94 (m, 3H) |
|  | 336 | (3R)-N-{3-[5-(4-{[(3R)-1-{2-[(3R)-2,6-dioxopiperidin-3-yl]-1-oxo-2,3-dihydro-1H-isoindol-5-yl}pyrrolidin-3-yl]methoxy}phenyl)-1H-pyrrolo[2,3-b]pyridine-3-carbonyl]-2,4-difluorophenyl}-3-fluoropyrrolidine-1-sulfonamide | 1H NMR (400 MHz, DMSO-d6) δ 12.95 (s, 1H), 10.94 (s, 1H), 9.86 (s, 1H), 8.67 (s, 1H), 8.66 (s, 1H), 8.10 (s, 1H), 7.69-7.63 (m, 3H), 7.50 (d, J = 8.4 Hz, 1H), 7.27-7.11 (m, 1H), 7.12 (d, J = 8.8 Hz, 2H), 6.68 (s, 2H), 5.28 (d, J = 31.2 Hz, 1H), 5.03 (dd, J = 13.2, 5.0 Hz, 1H), 4.34-4.30 (m, 1H), 4.22-4.11 (m, 3H), 3.58-3.56 (m, 3H), 3.48-3.46 (m, 5H), 2.90-2.87 (m, 2H), 2.58-2.48 (m, 1H), 2.15-2.10 (m, 2H), 1.98-1.96 (m, 3H), 1.78-1.76 (m, 2H) |

TABLE 3-continued

<sup></sup>H NMR data of exemplary bifunctional compounds of the present disclosure

| Parent Mol Structure | Ex. No. | IUPAC Name | $^1$H NMR tabulation |
|---|---|---|---|
| 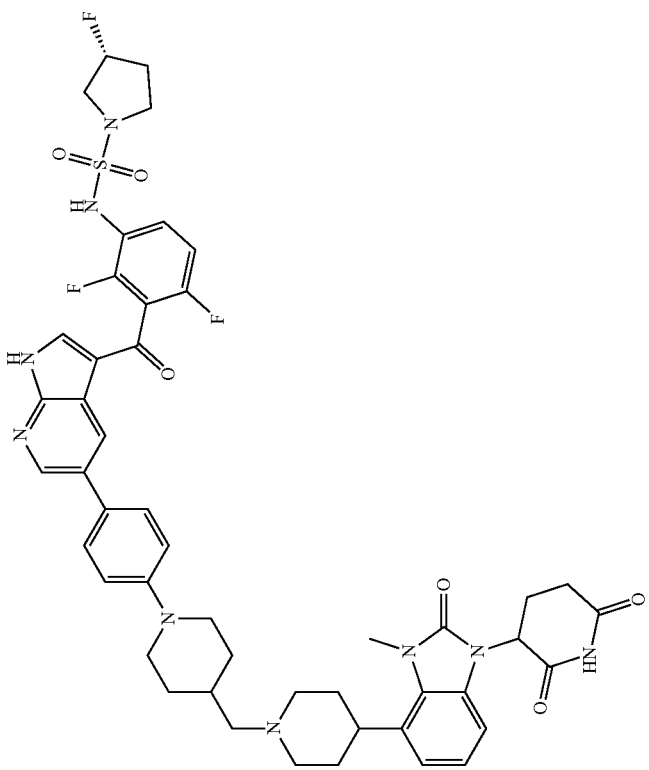 | 337 | (3R)-N-[3-(5-{4-[4-({4-[1-(2,6-dioxopiperidin-3-yl)-3-methyl-2-oxo-2,3-dihydro-1H-1,3-benzodiazol-4-yl]piperidin-1-yl}methyl)piperidin-1-yl]phenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 12.91 (s, 1H), 11.10 (s, 1H), 9.85 (s, 1H), 8.65 (d, J = 2.2 Hz, 1H), 8.53 (s, 1H), 8.07 (s, 1H), 7.67-7.55 (m, 3H), 7.26 (t, J = 9.1 Hz, 1H), 7.08 (s, 1H), 7.06 (s, 1H), 7.06-6.94 (m, 3H), 5.38 (dd, J = 12.7, 5.0 Hz, 2H), 5.23 (d, J = 3.5 Hz, 0H), 3.80 (d, J = 12.0 Hz, 2H), 3.59 (s, 3H), 3.48 (d, J = 2.3 Hz, 1H), 3.38 (dd, J = 12.2, 3.4 Hz, 3H), 3.32-3.25 (m, 1H), 3.02 (d, J = 10.8 Hz, 2H), 2.92-2.82 (m, 1H), 2.76 (d, J = 11.9 Hz, 2H), 2.70 (d, J = 12.8 Hz, 1H), 2.62 (d, J = 17.9 Hz, 1H), 2.52 (s, 1H), 2.26 (d, J = 6.9 Hz, 2H), 2.11 (s, 4H), 1.99 (dd, J = 10.6, 5.8 Hz, 2H), 1.88-1.74 (m, 8H), 1.25 (d, J = 13.8 Hz, 5H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 338 | 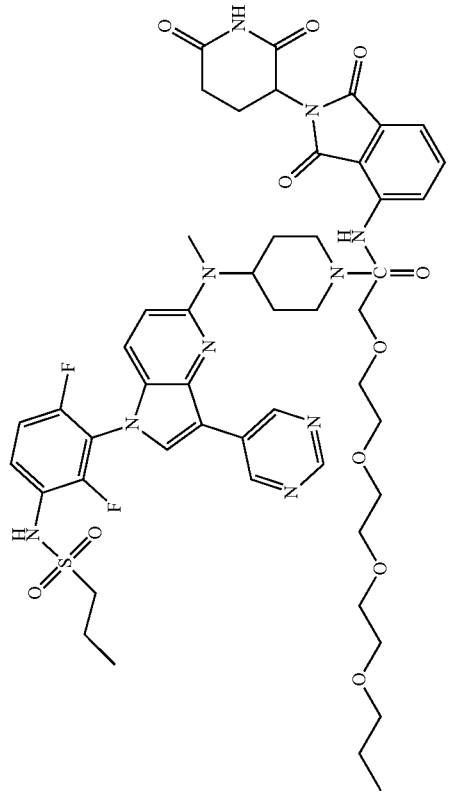 Caution: Valence appears to be exceeded | N-[3-(5-{[1-(1-{[2-(2,6-dioxopiperidin-3-yl)-1,3-dioxo-2,3-dihydro-1H-isoindol-4-yl]amino}-3,6,9,12-tetraoxapentadecanoyl)piperidin-4-yl](methyl)amino]-3-(pyrimidin-5-yl)-1H-pyrrolo[3,2-b]pyridin-1-yl)-2,4-difluorophenyl]propane-1-sulfonamide | 1H NMR (400 MHz, DMSO-d6) δ 11.10 (s, 1H), 9.90 (s, 1H), 9.65 (s, 2H), 9.03 (s, 1H), 8.42 (s, 1H), 7.58-7.56 (m, 2H), 7.55-7.54 (m, 2H), 7.12 (d, J = 8.8 Hz, 1H), 7.02 (d, J = 8.8 Hz, 1H), 6.81 (d, J = 9.2 Hz, 1H), 6.60 (t, 1H), 5.04-5.01 (m, 1H), 4.72-4.70 (m, 2H), 4.02-4.00 (m, 1H), 3.66-3.64 (m, 4H), 3.58-3.56 (m, 14H), 3.20-3.17 (m, 3H), 2.97 (s, 3H), 2.96-2.95 (m, 1H), 2.63-2.56 (m, 5H), 2.01-1.98 (m, 1H), 1.78-1.75 (m, 5H), 1.66-1.65 (m, 1H), 1.01-0.98 (m, 3H) |
| 339 | 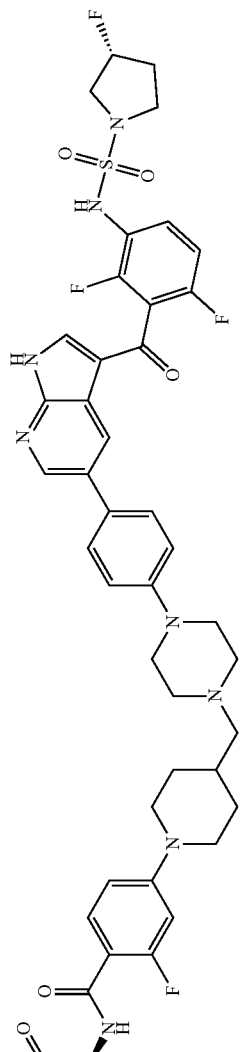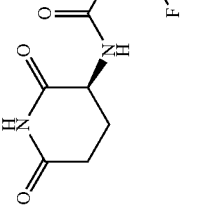 | 4-(4-{[4-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperazin-1-yl]methyl}piperidin-1-yl)-N-[(3S)-2,6-dioxopiperidin-3-yl]-2-fluorobenzamide | 1H NMR (300 MHz, DMSO-d6) δ 12.87 (s, 1H), 10.84 (s, 1H), 8.65 (s, 1H), 8.53 (s, 1H), 8.08-7.95 (m, 2H), 7.62 (t, J = 9.4 Hz, 4H), 7.22 (t, J = 8.7 Hz, 2H), 7.07 (d, J = 8.5 Hz, 2H), 6.78 (dd, J = 18.8, 12.6 Hz, 2H), 5.37 (s, 1H), 4.72 (dt, J = 12.7, 6.5 Hz, 1H), 3.89 (d, J = 12.7 Hz, 2H), 3.47 (s, 10H), 2.81 (dt, J = 23.9, 12.3 Hz, 3H), 2.54 (d, J = 3.8 Hz, 2H), 2.21 (d, J = 6.7 Hz, 2H), 2.18-1.94 (m, 4H), 1.80 (d, J = 12.0 Hz, 3H), 1.26-1.07 (m, 3H) |

TABLE 3-continued

¹H NMR data of exemplary bifunctional compounds of the present disclosure

| Ex. No. | IUPAC Name | ¹H NMR tabulation |
|---|---|---|
| 340 | 4-(4-{[4-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperazin-1-yl]methyl}piperidin-1-yl)-N-[(3R)-2,6-dioxopiperidin-3-yl]-2-fluorobenzamide | 1H NMR (300 MHz, DMSO-d6) δ 12.92 (s, 1H), 10.84 (s, 1H), 8.65 (s, 1H), 8.64 (s, 1H), 8.06-8.00 (m, 2H), 7.65-7.59 (m, 4H), 7.24-7.06 (m, 1H), 7.07 (d, J = 8.5 Hz, 2H), 6.83-6.78 (m, 2H), 5.37-5.20 (d, J = 52.2 Hz, 1H), 4.77-4.68 (m, 1H), 3.89 (d, J = 12.7 Hz, 2H), 3.47-3.45 (m, 11H), 2.89-2.81 (m, 3H), 2.27-2.21 (m, 2H), 2.13-1.92 (m, 4H), 1.94-1.92 (m, 3H), 1.23-1.15 (m, 4H) |
| 341 | 4-(4-{[1-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperidin-4-yl]methyl}piperazin-1-yl)-N-[(3S)-2,6-dioxopiperidin-3-yl]-2-fluorobenzamide | 1H NMR (300 MHz, DMSO-d6) δ 12.90 (s, 1H), 10.84 (s, 1H), 9.88 (s, 1H), 8.65 (d, J = 2.2 Hz, 1H), 8.53 (s, 1H), 8.04 (d, J = 10.5 Hz, 2H), 7.69-7.54 (m, 4H), 7.26 (t, J = 8.7 Hz, 1H), 7.07 (d, J = 8.4 Hz, 2H), 6.80 (t, J = 14.0 Hz, 2H), 5.38 (s, 1H), 4.76 (s, 1H), 3.79 (d, J = 12.0 Hz, 2H), 3.48 (s, 11H), 2.76 (d, J = 11.7 Hz, 4H), 2.23 (d, J = 6.5 Hz, 2H), 2.04 (s, 4H), 1.79 (d, J = 17.5 Hz, 3H), 1.25 (d, J = 11.0 Hz, 3H) |
| 342 | 4-(4-{[1-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperidin-4-yl]methyl}piperazin-1-yl)-N-[(3R)-2,6-dioxopiperidin-3-yl]-2-fluorobenzamide | 1H NMR (300 MHz, DMSO-d6) δ 12.91 (b, 1H), 10.84 (s, 1H), 9.85 (b, 1H), 8.64 (s, 1H), 8.53 (s, 1H), 8.06 (s, 2H), 7.69-7.57 (m, 4H), 7.29-7.23 (m, 1H), 7.08-7.02 (m, 2H), 6.84-6.75 (m, 2H), 5.38 (d, J = 35.2 Hz, 1H), 5.01 (s, 1H), 4.75-4.71 (m, 1H), 3.79-3.78 (m, 4H), 3.18-3.11 (m, 3H), 2.97 (s, 3H), 2.87-2.74 (m, 4H), 2.24-2.22 (m, 3H), 2.13-1.98 (m, 4H), 1.85-1.76 (m, 3H), 1.26-1.19 (m, 4H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| | 343 | 4-(6-{[1-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperidin-4-yl]methyl}-2,6-diazaspiro[3.3]heptan-2-yl)-N-[(3S)-2,6-dioxopiperidin-3-yl]-2-methoxybenzamide | 1H NMR (400 MHz, DMSO-d6) δ 12.91 (s, 1H), 10.87 (s, 1H), 8.65 (s, 1H), 8.64 (s, 1H), 8.40 (d, J = 6.8 Hz, 1H), 8.06 (s, 1H), 7.76 (d, J = 8.8 Hz, 1H), 7.63-7.57 (m, 3H), 7.27-7.25 (m, 1H), 7.06-7.04 (d, J = 8.8 Hz, 2H), 6.08-6.06 (m, 1H), 6.01 (s, 1H), 5.30 (d, J = 12.0 Hz, 1H), 4.69-4.67 (m, 1H), 4.05 (s, 4H), 3.99 (s, 3H), 3.78-3.74 (m, 2H), 3.46-3.46 (m, 2H), 2.73-2.70 (m, 3H), 2.23 (d, J = 6.4 Hz, 1H), 2.12-2.06 (m, 4H), 1.78-1.75 (m, 2H), 1.55-1.53 (m, 1H), 1.24-1.22 (m, 2H) |
| | 344 | 4-(6-{[1-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperidin-4-yl]methyl}-2,6-diazaspiro[3.3]heptan-2-yl)-N-[(3R)-2,6-dioxopiperidin-3-yl]-2-methoxybenzamide | 1H NMR (400 MHz, DMSO-d6) δ 12.90 (s, 1H), 10.87 (s, 1H), 8.64 (s, 1H), 8.53 (s, 1H), 8.40 (d, J = 6.8 Hz, 1H), 8.06 (s, 1H), 7.76 (d, J = 8.8 Hz, 1H), 7.63-7.57 (m, 3H), 7.27-7.25 (m, 1H), 7.06-7.04 (d, J = 8.8 Hz, 2H), 6.07 (d, J = 8.8 Hz, 1H), 6.01 (s, 1H), 5.30 (d, J = 12.0 Hz, 1H), 4.69-4.67 (m, 1H), 4.05 (s, 4H), 3.97 (s, 3H), 3.78-3.74 (m, 2H), 3.46-3.46 (m, 2H), 2.70-2.50 (m, 4H), 2.25-2.23 (m, 2H), 2.12-1.91 (m, 5H), 1.78-1.75 (m, 2H), 1.47-1.45 (m, 1H), 1.27-1.25 (m, 3H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 345 | | 5-(6-{[1-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperidin-4-yl]methyl}-2,6-diazaspiro[3.3]heptan-2-yl)-N-[(3S)-2,6-dioxopiperidin-3-yl]pyridine-2-carboxamide | 1H NMR (400 MHz, DMSO-d6) δ 12.90 (s, 1H), 10.84 (s, 1H), 8.69-8.67 (m, 2H), 8.53 (s, 1H), 8.06 (s, 1H), 7.85-7.79 (m, 2H), 7.61-7.57 (m, 3H), 7.27-7.25 (m, 1H), 7.05 (d, J = 8.8 Hz, 2H), 6.90 (d, J = 2.4 Hz, 1H), 5.30 (d, J = 12.4 Hz, 1H), 4.73-4.71 (m, 1H), 4.07 (s, 4H), 3.78-3.74 (m, 2H), 3.34-3.33 (m, 2H), 2.70-2.50 (m, 3H), 2.34-2.33 (m, 2H), 2.19-1.98 (m, 4H), 1.78-1.75 (m, 2H), 1.47-1.45 (m, 1H), 1.27-1.25 (m, 2H) |
| 346 | | 5-(6-{[1-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperidin-4-yl]methyl}-2,6-diazaspiro[3.3]heptan-2-yl)-N-[(3R)-2,6-dioxopiperidin-3-yl]pyridine-2-carboxamide | 1H NMR (400 MHz, DMSO-d6) δ 12.90 (s, 1H), 10.84 (s, 1H), 8.69-8.67 (m, 2H), 8.53 (s, 1H), 8.06 (s, 1H), 7.85-7.79 (m, 2H), 7.61-7.57 (m, 3H), 7.27-7.25 (m, 1H), 7.05 (d, J = 8.8 Hz, 2H), 6.90 (d, J = 2.4 Hz, 1H), 5.30 (d, J = 12.4 Hz, 1H), 4.73-4.71 (m, 1H), 4.07 (s, 4H), 3.78-3.74 (m, 2H), 3.34-3.33 (m, 2H), 2.70-2.50 (m, 3H), 2.34-2.33 (m, 2H), 2.19-1.98 (m, 4H), 1.78-1.75 (m, 2H), 1.47-1.45 (m, 1H), 1.27-1.25 (m, 2H) |
| 347 | | 4-(6-{[1-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperidin-4-yl]methyl}-2,6-diazaspiro[3.3]heptan-2-yl)-N-[(3S)-2,6-dioxopiperidin-3-yl]-2-fluoro-6-methoxybenzamide | 1H NMR (300 MHz, DMSO-d6) δ 12.90 (s, 1H), 10.86 (s, 1H), 8.66 (s, 1H), 8.65 (s, 1H), 8.53 (s, 1H), 8.07 (s, 1H), 7.64-7.57 (m, 3H), 7.28-7.25 (m, 1H), 7.06 (d, J = 9.0 Hz, 2H), 5.86-5.82 (m, 2H), 5.30 (d, J = 12.4 Hz, 1H), 4.69-4.65 (m, 1H), 3.94 (s, 4H), 3.79 (s, 6H), 3.54-3.53 (m, 2H), 3.34-3.33 (m, 4H), 2.73-2.71 (m, 4H), 2.18-2.14 (m, 2H), 2.11-1.93 (m, 5H), 1.52-1.50 (m, 2H), 1.29-1.24 (m, 1H), 1.22-1.10 (m, 3H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 348 | | 4-(6-{[1-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperidin-4-yl]methyl}-2,6-diazaspiro[3.3]heptan-2-yl)-N-(2,6-dioxopiperidin-3-yl)-2-fluoro-6-methoxybenzamide | 1H NMR (300 MHz, DMSO-d6) δ 12.90 (s, 1H), 10.86 (s, 1H), 8.66 (s, 1H), 8.65 (s, 1H), 8.53 (s, 1H), 8.07 (s, 1H), 7.64-7.57 (m, 3H), 7.28-7.25 (m, 1H), 7.06 (d, J = 9.0 Hz, 2H), 5.86-5.82 (m, 2H), 5.30 (d, J = 12.4 Hz, 2H), 4.69-4.65 (m, 1H), 3.94 (s, 4H), 3.79 (s, 6H), 3.54-3.53 (m, 2H), 3.34-3.33 (m, 3H), 2.73-2.71 (m, 3H), 2.18-2.14 (m, 2H), 2.11-1.93 (m, 5H), 1.79-1.76 (m, 4H), 1.52-1.50 (m, 1H), 1.32-1.12 (m, 3H) |
| 349 | | 4-{4-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperazin-1-yl]butoxy}-N-[(3S)-2,6-dioxopiperidin-3-yl]-2-fluorobenzamide | 1H NMR (400 MHz, DMSO-d6) δ 12.90 (s, 1H), 10.86 (s, 1H), 9.90 (b, 1H), 8.66 (s, 1H), 8.65 (s, 1H), 8.33 (d, J = 8.4 Hz, 1H), 8.07 (s, 1H), 7.69-7.60 (m, 4H), 7.27-7.25 (m, 1H), 7.08 (d, J = 8.4 Hz, 2H), 6.91-6.80 (m, 2H), 5.30 (d, J = 12.4 Hz, 1H), 4.73-4.71 (m, 1H), 4.11-4.09 (m, 2H), 3.49-3.40 (m, 4H), 3.34-3.33 (m, 5H), 2.80-2.70 (m, 1H), 2.56-2.51 (m, 4H), 2.50-2.42 (m, 2H), 2.22-1.90 (m, 4H), 1.78-1.76 (m, 2H), 1.65-1.63 (m, 2H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 350 | | 4-{4-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperazin-1-yl]butoxy}-N-(2,6-dioxopiperidin-3-yl)-2-fluorobenzamide | 1H NMR (400 MHz, DMSO-d6) δ 12.90 (s, 1H), 10.86 (s, 1H), 9.90 (b, 1H), 8.66 (s, 1H), 8.65 (s, 1H), 8.33 (d, J = 8.4 Hz, 1H), 8.07 (s, 1H), 7.69-7.60 (m, 4H), 7.27-7.25 (m, 1H), 7.08 (d, J = 8.4 Hz, 2H), 6.91-6.80 (m, 2H), 5.30 (d, J = 12.4 Hz, 1H), 4.73-4.71 (m, 1H), 4.11-4.09 (m, 2H), 3.49-3.40 (m, 4H), 3.34-3.33 (m, 7H), 2.80-2.70 (m, 1H), 2.56-2.51 (m, 4H), 2.50-2.42 (m, 2H), 2.22-1.90 (m, 4H), 1.78-1.76 (m, 2H), 1.65-1.63 (m, 2H) |
| 351 | | 4-{6-[(1-{4-[3-({[(3,3-difluoropyrrolidin-1-yl)sulfonyl]amino}-2,6-difluorobenzoyl)-1H-pyrrolo[2,3-b]pyridin-5-yl]phenyl}piperidin-4-yl)methyl]-2,6-diazaspiro[3.3]heptan-2-yl]-N-[(3S)-2,6-dioxopiperidin-3-yl]-2-fluorobenzamide | 1H NMR (400 MHz, DMSO-d6) δ 12.89 (s, 1H), 10.83 (s, 1H), 9.98 (b, 1H), 8.65 (s, 1H), 8.64 (s, 1H), 8.08 (s, 1H), 7.97 (d, J = 7.2 Hz, 1H), 7.64-7.57 (m, 4H), 7.25-7.25 (m, 1H), 7.05 (d, J = 8.8 Hz, 2H), 6.30-6.28 (m, 2H), 4.72-4.71 (m, 1H), 4.00 (s, 4H), 3.76 (d, J = 7.2 Hz, 2H), 3.61-3.57 (m, 2H), 3.54-3.53 (m, 3H), 3.37-3.33 (m, 3H), 2.77-2.74 (m, 3H), 2.54-2.46 (m, 4H), 2.11-1.95 (m, 2H), 1.78-1.75 (m, 2H), 1.52-1.50 (m, 1H) 1.26-1.24 (m, 2H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 352 | | 4-(4-{[6-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)-2,6-diazaspiro[3.3]heptan-2-yl]methyl}piperidin-1-yl)-N-[(3S)-2,6-dioxopiperidin-3-yl]-2-methoxybenzamide | 1H NMR (400 MHz, DMSO-d6) δ 12.98 (s, 2H), 10.99 (s, 4H), 9.81 (s, 2H), 8.81-8.56 (m, 2H), 8.12 (d, J = 2.0 Hz, 2H), 7.97 (dd, J = 8.6, 2.4 Hz, 1H), 7.75-7.38 (m, 4H), 7.27 (td, J = 8.9, 1.9 Hz, 2H), 5.31 (dt, J = 53.0, 3.1 Hz, 1H), 5.11 (dd, J = 13.3, 5.1 Hz, 1H), 4.44 (d, J = 17.2 Hz, 1H), 4.30 (d, J = 17.2 Hz, 1H), 3.62 (d, J = 11.3 Hz, 2H), 3.49 (d, J = 2.5 Hz, 1H), 3.45-3.39 (m, 2H), 3.04 (d, J = 10.8 Hz, 2H), 2.99-2.78 (m, 3H), 2.75-2.57 (m, 2H), 2.40 (dd, J = 13.2, 4.6 Hz, 1H), 2.33 (s, 2H), 2.23-2.05 (m, 4H), 2.00 (tt, J = 7.6, 3.0 Hz, 2H), 1.94-1.85 (m, 2H), 1.85-1.65 (m, 5H), 1.45-1.21 (m, 2H) |
| 353 | | 5-(4-{[6-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)-2,6-diazaspiro[3.3]heptan-2-yl]methyl}piperidin-1-yl)-N-[(3S)-2,6-dioxopiperidin-3-yl]pyridine-2-carboxamide | 1H NMR (400 MHz, DMSO-d6) δ 12.88 (s, 1H), 10.85 (s, 1H), 8.79-8.45 (m, 3H), 8.30 (d, J = 2.8 Hz, 1H), 8.06 (s, 1H), 7.85 (d, J = 8.8 Hz, 1H), 7.68-7.52 (m, 3H), 7.40 (dd, J = 9.0, 2.9 Hz, 1H), 7.26 (td, J = 8.8, 1.6 Hz, 1H), 6.57 (d, J = 8.4 Hz, 2H), 5.42-5.17 (m, 1H), 4.74 (ddd, J = 13.0, 8.2, 5.3 Hz, 1H), 3.94 (s, 6H), 3.48 (d, J = 2.5 Hz, 1H), 3.47-3.36 (m, 5H), 3.28 (dd, J = 9.9, 7.0 Hz, 2H), 2.93-2.73 (m, 3H), 2.54 (d, J = 3.9 Hz, 1H), 2.34 (d, J = 6.6 Hz, 2H), 2.28-1.90 (m, 4H), 1.77 (d, J = 12.7 Hz, 2H), 1.56 (d, J = 11.8 Hz, 1H), 1.29-1.10 (m, 2H) |

TABLE 3-continued

¹H NMR data of exemplary bifunctional compounds of the present disclosure

| Ex. No. | IUPAC Name | ¹H NMR tabulation |
|---|---|---|
| 354 | 5-(4-{[6-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)-2,6-diazaspiro[3.3]heptan-2-yl]methyl}piperidin-1-yl)-N-(2,6-dioxopiperidin-3-yl)pyridine-2-carboxamide | 1H NMR (400 MHz, DMSO-d6) δ 12.85 (s, 1H), 10.85 (s, 1H), 8.70 (d, J = 8.2 Hz, 1H), 8.62 (d, J = 2.2 Hz, 1H), 8.50 (s, 1H), 8.30 (d, J = 2.8 Hz, 1H), 8.05 (s, 1H), 7.84 (d, J = 8.8 Hz, 1H), 7.70-7.49 (m, 3H), 7.39 (dd, J = 9.0, 2.9 Hz, 1H), 7.25 (t, J = 8.7 Hz, 1H), 6.56 (d, J = 8.3 Hz, 2H), 5.41-5.17 (m, 1H), 4.74 (ddd, J = 13.0, 8.3, 5.3 Hz, 1H), 3.94 (s, 6H), 3.48 (d, J = 2.6 Hz, 2H), 3.30-3.16 (m, 5H), 2.92-2.71 (m, 3H), 2.55 (t, J = 3.7 Hz, 1H), 2.33 (d, J = 6.7 Hz, 2H), 2.26-1.90 (m, 4H), 1.77 (dd, J = 13.3, 3.6 Hz, 2H), 1.54 (ddq, J = 11.6, 8.1, 4.8, 4.4 Hz, 1H), 1.20 (ddd, J = 24.5, 12.4, 4.6 Hz, 3H) |
| 355 | 4-{3-[6-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)-2,6-diazaspiro[3.3]heptan-2-yl]propyl}-N-[(3S)-2,6-dioxopiperidin-3-yl]-2-fluorobenzamide | 1H NMR (400 MHz, DMSO-d6) δ 12.85 (s, 1H), 10.87 (s, 1H), 8.62 (d, J = 2.3 Hz, 1H), 8.56-8.41 (m, 2H), 8.06 (s, 1H), 7.73-7.51 (m, 4H), 7.26 (td, J = 8.8, 1.6 Hz, 1H), 7.21-7.09 (m, 2H), 6.66-6.45 (m, 2H), 5.42-5.16 (m, 1H), 4.77 (ddd, J = 12.8, 8.1, 5.4 Hz, 1H), 3.94 (s, 4H), 3.48 (d, J = 2.5 Hz, 1H), 3.40 (d, J = 4.3 Hz, 6H), 3.29 (td, J = 9.9, 6.8 Hz, 2H), 2.79 (ddd, J = 17.3, 13.2, 5.7 Hz, 1H), 2.66 (t, J = 7.6 Hz, 2H), 2.56 (t, J = 3.8 Hz, 1H), 2.44 (t, J = 7.2 Hz, 2H), 2.27-1.87 (m, 4H), 1.61 (t, J = 7.5 Hz, 2H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 356 | | 4-{3-[6-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)-2,6-diazaspiro[3.3]heptan-2-yl]propyl}-N-(2,6-dioxopiperidin-3-yl)-2-fluorobenzamide | 1H NMR (400 MHz, DMSO-d6) δ 12.89 (s, 1H), 10.87 (s, 1H), 8.62 (d, J = 2.2 Hz, 1H), 8.47 (dt, J = 8.1, 5.2 Hz, 2H), 8.05 (s, 1H), 7.71-7.47 (m, 4H), 7.25 (t, J = 8.7 Hz, 1H), 7.16 (t, J = 9.0 Hz, 2H), 6.56 (d, J = 8.3 Hz, 2H), 5.29 (d, J = 52.8 Hz, 1H), 4.76 (ddd, J = 12.8, 8.1, 5.4 Hz, 1H), 3.93 (s, 4H), 3.47 (d, J = 2.7 Hz, 2H), 3.39 (s, 6H), 3.31-3.24 (m, 2H), 2.79 (ddd, J = 18.0, 13.1, 5.7 Hz, 1H), 2.65 (t, J = 7.6 Hz, 2H), 2.55 (d, J = 4.0 Hz, 1H), 2.41 (t, J = 7.1 Hz, 2H), 2.19-1.88 (m, 4H), 1.61 (p, J = 7.5 Hz, 2H) |
| 357 | | 4-(4-{[4-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperazin-1-yl]methyl}piperidin-1-yl)-N-[(3S)-2,6-dioxopiperidin-3-yl]-2-methoxybenzamide | 1H NMR (300 MHz, DMSO-d6) δ 12.90 (s, 1H), 10.86 (s, 1H), 9.82 (s, 1H), 8.65 (d, J = 2.3 Hz, 1H), 8.54 (s, 1H), 8.42 (d, J = 6.9 Hz, 1H), 8.07 (s, 1H), 7.77 (d, J = 8.8 Hz, 1H), 7.69-7.56 (m, 3H), 7.26 (t, J = 8.7 Hz, 1H), 7.08 (d, J = 8.4 Hz, 2H), 6.60 (d, J = 8.7 Hz, 1H), 6.52 (s, 1H), 5.38 (s, 1H), 4.70 (dt, J = 12.5, 6.4 Hz, 1H), 3.93 (s, 5H), 3.89 (s, 1H), 3.49 (s, 2H) 3.39 (s, 4H), 2.91-2.67 (m, 4H), 2.54 (s, 4H), 2.23 (d, J = 6.5 Hz, 2H), 2.12 (s, 4H), 1.82 (d, J = 11.9 Hz, 3H), 1.21 (d, J = 15.6 Hz, 3H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 358 | | 4-(4-{[4-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperazin-1-yl]methyl}piperidin-1-yl)-N-(2,6-dioxopiperidin-3-yl)-2-methoxybenzamide | 1H NMR (300 MHz, DMSO-d6) δ 12.90 (s, 1H), 10.86 (s, 1H), 9.82 (s, 1H), 8.65 (d, J = 2.3 Hz, 1H), 8.54 (s, 1H), 8.42 (d, J = 6.9 Hz, 1H), 8.07 (s, 1H), 7.77 (d, J = 8.8 Hz, 1H), 7.69-7.56 (m, 3H), 7.26 (t, J = 8.7 Hz, 1H), 7.08 (d, J = 8.4 Hz, 2H), 6.60 (d, J = 8.7 Hz, 1H), 6.52 (s, 1H), 5.32 (d, J = 19.2 Hz, 1H), 4.70 (dt, J = 12.5, 6.4 Hz, 1H), 3.93 (s, 5H), 3.89-3.83 (m, 3H), 3.49-3.23 (m, 4H), 2.91-2.67 (m, 4H), 2.64-2.61 (m, 2H), 2.23 (d, J = 6.5 Hz, 2H), 2.12-1.92 (m, 5H), 1.82 (d, J = 11.9 Hz, 3H), 1.24-1.21 (m, 4H) |
| 359 | | 4-(4-{[1-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperidin-4-yl]methyl}piperazin-1-yl)-N-[(3S)-2,6-dioxopiperidin-3-yl]-2-methoxybenzamide | 1H NMR (300 MHz, DMSO-d6) δ 8.63 (d, J = 2.2 Hz, 1H), 8.52-8.41 (m, 2H), 7.97 (s, 1H), 7.79 (d, J = 8.8 Hz, 1H), 7.63-7.44 (m, 3H), 7.29 (s, 3H), 7.07 (d, J = 8.8 Hz, 2H), 6.99-6.85 (m, 2H), 6.67-6.53 (m, 1H), 5.33 (s, 1H), 5.15 (s, 1H), 4.71 (m, 1H), 3.94 (s, 2H), 3.80 (m, 2H), 3.26-3.17 (m, 3H), 3.20-3.05 (m, 4H), 2.76 (m, 3H), 2.54 (d, J = 3.6 Hz, 2H), 2.29-1.96 (m, 7H), 1.85 (d, J = 12.8 Hz, 7H), 1.36 (s, 1H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 360 | | 4-(4-{1-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperidin-4-yl]methyl}piperazin-1-yl)-N-(2,6-dioxopiperidin-3-yl)-2-methoxybenzamide | 1H NMR (300 MHz, DMSO-d6) δ 8.63 (d, J = 2.2 Hz, 1H), 8.52-8.41 (m, 2H), 7.97 (s, 1H), 7.79 (d, J = 8.8 Hz, 1H), 7.63-7.44 (m, 3H), 7.29 (s, 3H), 7.07 (d, J = 8.8 Hz, 2H), 6.99-6.85 (m, 2H), 6.67-6.53 (m, 1H), 5.33 (s, 1H), 5.15 (s, 1H), 4.71 (m, 1H), 3.94 (s, 2H), 3.80 (m, 2H), 3.26-3.17 (m, 3H), 3.20-3.05 (m, 4H), 2.76 (m, 3H), 2.54 (d, J = 3.6 Hz, 2H), 2.29-1.96 (m, 7H), 1.85 (d, J = 12.8 Hz, 7H), 1.36 (s, 1H) |
| 361 | | 4-{6-[2-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)ethyl]-2,6-diazaspiro[3.3]heptan-2-yl}-N-[(3S)-2,6-dioxopiperidin-3-yl]-2-methoxybenzamide | 1H NMR (300 MHz, DMSO-d6) δ 12.98 (s, 1H), 10.88 (s, 1H), 8.70 (d, J = 2.2 Hz, 1H), 8.59 (s, 1H), 8.40 (d, J = 7.0 Hz, 1H), 8.12 (s, 1H), 7.77 (d, J = 8.5 Hz, 1H), 7.71-7.56 (m, 3H), 7.37 (d, J = 8.1 Hz, 2H), 7.26 (m, 1H), 6.13-5.99 (m, 2H), 5.38 (s, 1H), 5.21 (s, 1H), 4.70 (m, 4H), 4.00 (s, 3H), 3.90 (s, 2H), 3.66-3.56 (m, 2H), 3.49 (d, J = 2.6 Hz, 2H), 3.39 (s, 6H), 3.27 (s, 4H), 2.86-2.68 (m, 1H), 1.24 (s, 1H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 362 | | 4-[6-[2-(4-[3-[2,6-difluoro-3-({[(3R)-3-fluoropyrrolidin-1-yl]sulfonyl}amino)benzoyl]-1H-pyrrolo[2,3-b]pyridin-5-yl]phenyl)ethyl]-2,6-diazaspiro[3.3]heptan-2-yl]-N-(2,6-dioxopiperidin-3-yl)-2-methoxybenzamide | 1H NMR (300 MHz, DMSO-d6) δ 12.98 (s, 1H), 10.88 (s, 1H), 8.70 (d, J = 2.2 Hz, 1H), 8.59 (s, 1H), 8.40 (d, J = 7.0 Hz, 1H), 8.12 (s, 1H), 7.77 (d, J = 8.5 Hz, 1H), 7.71-7.56 (m, 3H), 7.37 (d, J = 8.1 Hz, 2H), 7.26 (m, 1H), 6.13-5.99 (m, 2H), 5.38 (s, 1H), 5.21 (s, 1H), 4.70 (m, 4H), 4.00 (s, 3H), 3.90 (s, 2H), 3.66-3.56 (m, 2H), 3.49 (d, J = 2.6 Hz, 2H), 3.39 (s, 6H), 3.27 (s, 4H), 2.86-2.68 (m, 1H), 1.24 (s, 1H) |
| 363 | | 4-[6-[(1-{4-[3-(3-amino-2,6-difluorobenzoyl)-1H-pyrrolo[2,3-b]pyridin-5-yl]piperidin-4-yl}methyl)-2,6-diazaspiro[3.3]heptan-2-yl]-N-[(3S)-2,6-dioxopiperidin-3-yl]-2-fluorobenzamide | 1H NMR (400 MHz, DMSO-d6) δ 12.89-12.70 (m, 1H), 10.83 (s, 1H), 8.63 (d, J = 2.4 Hz, 1H), 8.52 (s, 1H), 8.08-7.93 (m, 2H), 7.65-7.51 (m, 3H), 7.05 (d, J = 8.8 Hz, 2H), 6.98-6.84 (m, 2H), 6.34-6.16 (m, 2H), 5.20 (s, 2H), 4.77-4.67 (m, 1H), 3.98 (s, 4H), 3.75 (d, J = 12.8 Hz, 2H), 3.28-3.20 (m, 2H), 2.77-2.63 (m, 3H), 2.56-2.51 (m, 2H), 2.38-2.22 (m, 2H), 2.11 (dd, J = 4.4, 12.8 Hz, 1H), 2.04-1.96 (m, 1H), 1.76 (d, J = 11.2 Hz, 2H), 1.44 (d, J = 8.0 Hz, 1H), 1.32-1.11 (m, 3H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 364 | | 5-(1-{[1-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperidin-4-yl]methyl}piperidin-4-yl)-N-(2,6-dioxopiperidin-3-yl)-1,2,3,4-tetrahydro-1,8-naphthyridine-1-carboxamide | 1H NMR (400 MHz, DMSO-d6) δ 13.16-12.64 (m, 1H), 10.90 (d, J = 6.8 Hz, 1H), 10.83 (s, 1H), 8.65 (d, J = 2.4 Hz, 1H), 8.53 (s, 1H), 8.17 (s, 1H), 8.11-8.02 (m, 2H), 7.66-7.55 (m, 3H), 7.30-7.22 (m, 1H), 7.07 (d, J = 8.8 Hz, 2H), 7.00 (d, J = 5.4 Hz, 1H), 5.38-5.19 (m, 1H), 4.60-4.51 (m, 1H), 3.90-3.76 (m, 4H), 3.43 (s, 2H), 3.38-3.25 (m, 2H), 3.00 (d, J = 11.2 Hz, 2H), 2.83-2.78 (m, 2H), 2.77-2.66 (m, 4H), 2.52 (d, J = 2.0 Hz, 2H), 2.24 (d, J = 6.8 Hz, 2H), 2.17-1.94 (m, 6H), 1.89-1.78 (m, 4H), 1.78-1.61 (m, 5H), 1.31-1.18 (m, 2H) |
| 365 | | (3R)-N-[3-(5-{4-[4-({4-[6-(2,6-dioxopiperidin-3-yl)pyridin-3-yl]piperidin-1-yl}methyl)piperidin-1-yl]phenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 12.91 (s, 1H), 10.84 (s, 1H), 9.98-9.62 (m, 1H), 8.65 (d, J = 2.0 Hz, 1H), 8.53 (s, 1H), 8.41 (d, J = 1.6 Hz, 1H), 8.07 (s, 1H), 7.71-7.55 (m, 4H), 7.32-7.22 (m, 2H), 7.07 (d, J = 8.8 Hz, 2H), 5.38-5.20 (m, 1H), 3.99 (dd, J = 5.2, 9.2 Hz, 1H), 3.79 (d, J = 12.4 Hz, 2H), 3.48 (s, 1H), 3.44-3.37 (m, 2H), 3.30-3.24 (m, 2H), 3.02 (d, J = 10.4 Hz, 2H), 2.74 (t, J = 11.2 Hz, 2H), 2.58-2.55 (m, 1H), 2.31-2.19 (m, 3H), 2.18-2.00 (m, 5H), 1.87-1.68 (m, 7H), 1.31-1.18 (m, 3H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| 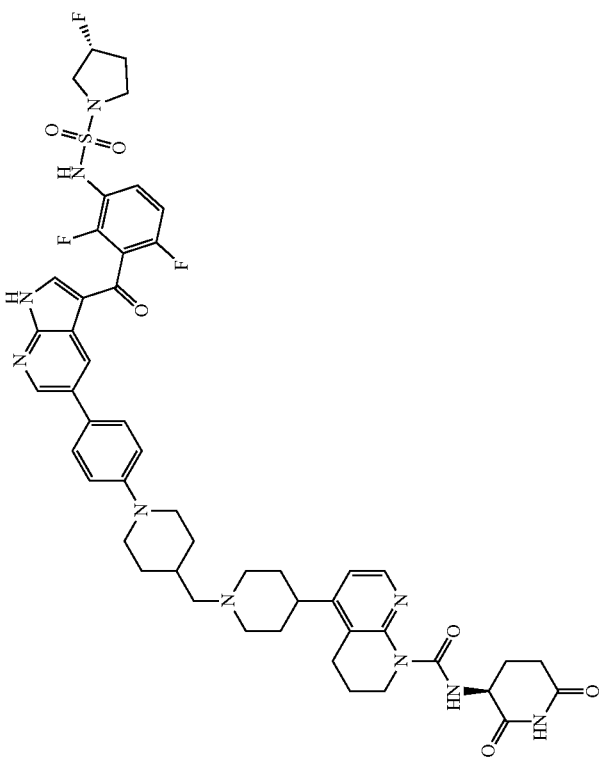 | 366 | 5-(1-{[1-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperidin-4-yl]methyl}piperidin-4-yl)-N-[(3S)-2,6-dioxopiperidin-3-yl]-1,2,3,4-tetrahydro-1,8-naphthyridine-1-carboxamide | 1H NMR (400 MHz, CDCl3) δ 13.09-12.76 (m, 1H), 10.90 (d, J = 6.8 Hz, 1H), 10.83 (s, 1H), 10.14-9.48 (m, 1H), 8.65 (d, J = 2.0 Hz, 1H), 8.59-8.45 (m, 1H), 8.11-8.02 (m, 2H), 7.67-7.55 (m, 3H), 7.30-7.23 (m, 1H), 7.07 (d, J = 8.8 Hz, 2H), 7.00 (d, J = 5.2 Hz, 1H), 5.38-5.18 (m, 1H), 3.89-4.62-4.48 (m, 1H), 3.89-3.75 (m, 4H), 3.48 (s, 2H), 3.40-3.40 (m, 2H), 3.28 (s, 2H), 3.02 (d, J = 9.2 Hz, 2H), 2.84-2.77 (m, 3H), 2.75-2.68 (m, 3H), 2.31-2.23 (m, 2H), 2.18-2.08 (m, 4H), 2.04-1.95 (m, 2H), 1.88-1.80 (m, 4H), 1.71-1.64 (m, 4H), 1.30-1.21 (m, 2H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 367 | | 5-(1-{[1-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperidin-4-yl]methyl}piperidin-4-yl)-N-[(3R)-2,6-dioxopiperidin-3-yl]-1,2,3,4-tetrahydro-1,8-naphthyridine-1-carboxamide | 1H NMR (400 MHz, DMSO-d6) δ 13.04-12.77 (m, 1H), 10.90 (d, J = 6.8 Hz, 1H), 10.83 (s, 1H), 10.09-9.56 (m, 1H), 8.65 (d, J = 2.0 Hz, 1H), 8.57-8.46 (m, 1H), 8.10-8.03 (m, 2H), 7.66-7.55 (m, 3H), 7.26 (t, J = 8.0 Hz, 1H), 7.11-7.03 (m, 2H), 7.03-6.98 (m, 1H), 5.41-5.18 (m, 1H), 4.61-4.50 (m, 1H), 3.88-3.75 (m, 4H), 3.48 (s, 2H), 3.41-3.40 (m, 2H), 3.28-3.27 (m, 2H), 3.00 (d, J = 9.6 Hz, 2H), 2.81 (t, J = 6.0 Hz, 3H), 2.75-2.70 (m, 3H), 2.25 (d, J = 6.0 Hz, 2H), 2.20-2.08 (m, 4H), 2.02-1.94 (m, 2H), 1.89-1.80 (m, 4H), 1.72-1.63 (m, 4H), 1.29-1.20 (m, 2H) |
| 368 | | (3R)-N-[3-(5-{4-[4-({6-[4-(2,6-dioxopiperidin-3-yl)phenyl]-2,6-diazaspiro[3.3]heptan-2-yl}methyl)piperidin-1-yl]phenyl}-1H-pyrrolo[2,3-b]pyridine-3-carbonyl)-2,4-difluorophenyl]-3-fluoropyrrolidine-1-sulfonamide | 1H NMR (400 MHz, DMSO-d6) δ 12.91 (s, 1H), 10.76 (s, 1H), 9.84 (s, 1H), 8.65 (d, J = 2.2 Hz, 1H), 8.54 (s, 1H), 8.07 (s, 1H), 7.61 (m, 3H), 7.27 (m, 1H), 7.07 (d, J = 8.7 Hz, 2H), 7.02 (d, J = 8.3 Hz, 2H), 6.42 (d, J = 8.1 Hz, 2H), 5.36 (s, 1H), 3.92 (s, 4H), 3.79 (d, J = 12.3 Hz, 2H), 3.70 (m, 4.9 Hz, 1H), 3.48 (s, 1H), 3.40 (s, 2H), 3.31 (s, 1H), 2.78-2.67 (m, 2H), 2.61 (m, 1H), 2.12 (s, 1H), 2.03-1.94 (m, 3H), 1.91 (s, 2H), 1.76 (m,3H), 1.63 (s, 3H), 1.63 (s, 1H), 1.25 (d, J = 9.2 Hz, 3H), 0.83 (s, 1H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| 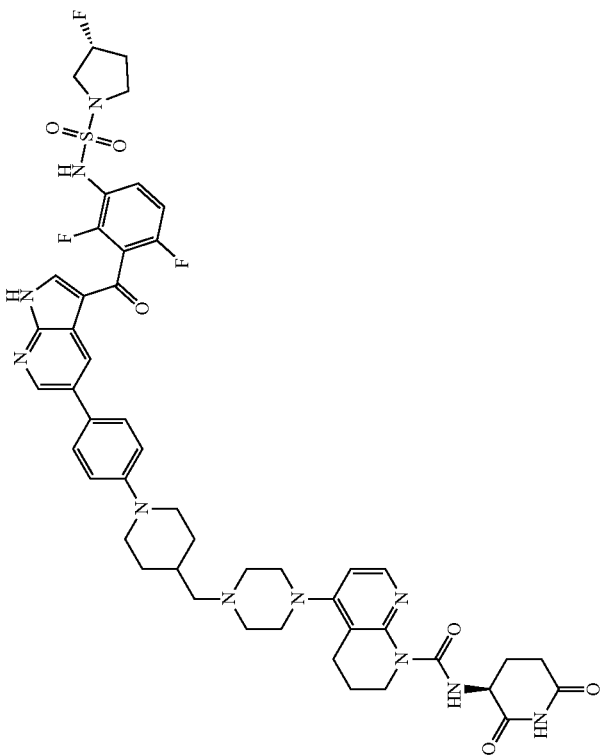 | 369 | 5-(4-{1-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperidin-4-yl]methyl}piperazin-1-yl)-N-[(3S)-2,6-dioxopiperidin-3-yl]-1,2,3,4-tetrahydro-1,8-naphthyridine-1-carboxamide | 1H NMR (400 MHz, DMSO-d6) δ 12.98 (s, 1H), 11.15 (s, 1H), 10.83 (s, 1H), 9.82 (s, 1H), 8.66 (s, 1H), 8.65 (s, 1H), 8.07 (s, 1H), 8.02 (s, 1H), 7.65-7.58 (m, 3H), 7.28-7.25 (m, 1H), 7.07 (d, J = 7.2 Hz, 2H), 6.70 (d, J = 7.2 Hz, 1H), 5.31 (d, J = 53.2 Hz, 1H), 4.56-4.55 (m, 1H), 3.80 (s, 4H), 3.49 (s, 1H), 3.46 (s, 2H), 3.33 (s, 1H), 3.04 (s, 4H), 2.99-2.81 (m, 5H), 2.54 (s, 3H), 2.24 (s, 2H), 2.23-2.01 (m, 4H), 1.85-1.76 (m, 5H), 1.26-1.24 (m, 4H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 370 | 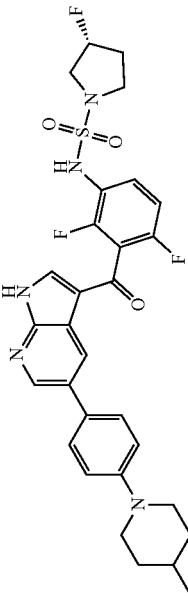 | 5-(4-{1-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperidin-4-yl]methyl}piperazin-1-yl)-N-(2,6-dioxopiperidin-3-yl)-1,2,3,4-tetrahydro-1,8-naphthyridine-1-carboxamide | 1H NMR (400 MHz, DMSO-d6) δ 12.98 (s, 1H), 11.15 (s, 1H), 10.83 (s, 1H), 9.82 (s, 1H), 8.66 (s, 1H), 8.65 (s, 1H), 8.07 (s, 1H), 8.02 (s, 1H), 7.65-7.58 (m, 3H), 7.28-7.25 (m, 1H), 7.07 (d, J = 7.2 Hz, 2H), 6.70 (d, J = 7.2 Hz, 1H), 5.31 (d, J = 53.2 Hz, 1H), 4.56-4.55 (m, 1H), 3.80 (s, 4H), 3.49 (s, 1H), 3.46 (s, 2H), 3.33 (s, 1H), 3.04 (s, 4H), 2.99-2.81 (m, 5H), 2.54 (s, 3H), 2.24 (s, 2H), 2.23-2.01 (m, 4H), 1.85-1.76 (m, 5H), 1.26-1.24 (m, 4H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| 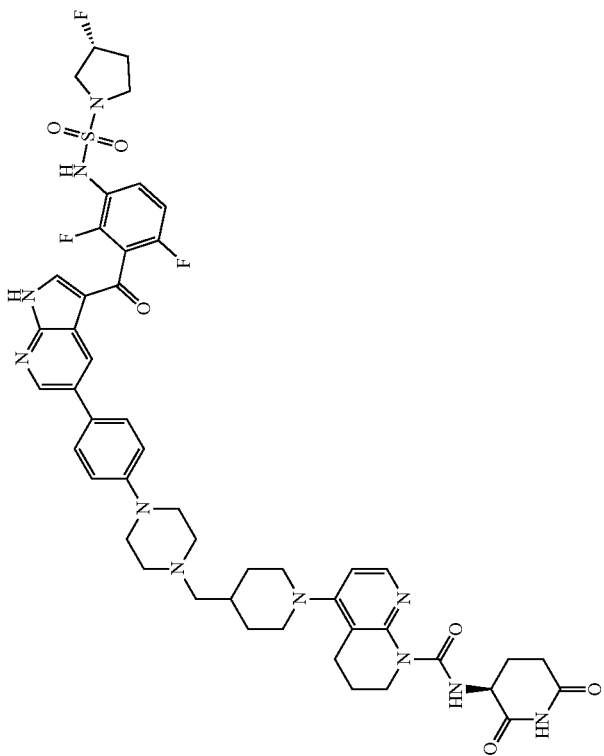 | 371 | 5-(4-{[4-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperazin-1-yl]methyl}piperidin-1-yl)-N-[(3S)-2,6-dioxopiperidin-3-yl]-1,2,3,4-tetrahydro-1,8-naphthyridine-1-carboxamide | 1H NMR (400 MHz, DMSO-d6) δ 12.91 (s, 1H), 11.15 (d, J = 6.7 Hz, 1H), 10.83 (s, 1H), 9.86 (s, 1H), 8.65 (d, J = 2.3 Hz, 1H), 8.54 (s, 1H), 8.08 (s, 1H), 7.99 (d, J = 5.6 Hz, 1H), 7.61 (dd, J = 8.9, 5.8 Hz, 3H), 7.27 (t, J = 8.6 Hz, 1H), 7.08 (d, J = 8.6 Hz, 2H), 6.69 (d, J = 5.7 Hz, 1H), 5.23 (s, 1H), 4.55 (dt, J = 12.2, 6.0 Hz, 1H), 3.79 (t, J = 5.9 Hz, 2H), 3.48 (d, J = 2.2 Hz, 1H), 3.38 (dd, J = 9.0, 1.9 Hz, 2H), 3.32-3.22 (m, 8H), 2.81-2.64 (m, 4H), 2.55 (s, 5H), 2.27 (d, J = 7.1 Hz, 2H), 2.09-1.94 (m, 4H), 1.85 (d, J = 12.4 Hz, 2H), 1.76 (s, 3H), 1.32 (d, J = 12.1 Hz, 2H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 372 | | 5-(4-{[4-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperazin-1-yl]methyl}piperidin-1-yl)-N-[(3R)-2,6-dioxopiperidin-3-yl]-1,2,3,4-tetrahydro-1,8-naphthyridine-1-carboxamide | 1H NMR (400 MHz, DMSO-d6) δ 12.91 (s, 1H), 11.15 (d, J = 6.7 Hz, 1H), 10.83 (s, 1H), 9.86 (s, 1H), 8.65 (d, J = 2.3 Hz, 1H), 8.54 (s, 1H), 8.08 (s, 1H), 7.99 (d, J = 5.6 Hz, 1H), 7.68-7.57 (m, 3H), 7.31-7.22 (m, 1H), 7.08 (d, J = 8.6 Hz, 2H), 6.69 (d, J = 5.7 Hz, 1H), 5.23 (s, 1H), 4.54 (dq, J = 12.7, 6.4 Hz, 1H), 3.83-3.75 (m, 2H), 3.48 (d, J = 2.2 Hz, 1H), 3.38 (dd, J = 9.0, 1.9 Hz, 2H), 3.32-3.22 (m, 7H), 2.81-2.64 (m, 3H), 2.55 (s, 5H), 2.27 (d, J = 7.0 Hz, 2H), 2.18-2.09 (m, 3H), 2.09-1.94 (m, 2H), 1.85 (d, J = 12.4 Hz, 2H), 1.76 (s, 3H), 1.32 (d, J = 11.7 Hz, 3H) |
| 373 | | 4-{6-[2-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)ethyl]-2,6-diazaspiro[3.3]heptan-2-yl}-N-[(3S)-2,6-dioxopiperidin-3-yl]-2-fluorobenzamide | 1H NMR (300 MHz, DMSO-d6) δ 12.97 (s, 1H), 10.84 (s, 1H), 8.69 (s, 1H), 8.59 (s, 1H), 8.01 (s, 1H), 7.98-7.96 (m, 1H), 7.67-7.65 (m, 4H), 7.45-7.43 (m, 2H), 7.29-7.25 (m, 1H), 6.31-6.23 (m, 2H), 5.42-5.13 (m, 1H), 4.77-4.68 (m, 1H), 4.00 (s, 4H), 3.61-3.60 (m, 3H), 2.77-2.54 (m, 4H), 2.22-1.95 (m, 5H), 1.26-1.24 (m, 5H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 374 | | 4-{6-[2-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)ethyl]-2,6-diazaspiro[3.3]heptan-2-yl}-N-(2,6-dioxopiperidin-3-yl)-2-fluorobenzamide | 1H NMR (300 MHz, DMSO-d6) δ 12.97 (s, 1H), 10.84 (s, 1H), 8.69 (s, 1H), 8.59 (s, 1H), 8.01 (s, 1H), 7.98-7.96 (m, 1H), 7.67-7.65 (m, 4H), 7.45-7.43 (m, 2H), 7.29-7.25 (m, 1H), 6.31-6.23 (m, 2H), 5.42-5.13 (m, 1H), 4.77-4.68 (m, 1H), 4.00 (s, 4H), 3.61-3.60 (m, 2H), 2.77-2.54 (m, 4H), 2.22-1.95 (m, 5H), 1.26-1.24 (m, 7H) |
| 375 | | 4-(1-{[1-(5-{3-[2,6-difluoro-3-({[(3R)-3-fluoropyrrolidin-1-yl]sulfonyl}amino)benzoyl]-1H-pyrrolo[2,3-b]pyridin-5-yl}pyrimidin-2-yl)piperidin-4-yl]methyl}piperidin-4-yl)-N-[(3S)-2,6-dioxopiperidin-3-yl]-2-fluorobenzamide | 1H NMR (300 MHz, DMSO-d6) δ 12.90 (s, 1H), 10.87 (s, 1H), 9.75 (s, 1H), 8.73 (s, 2H), 8.64 (s, 1H), 8.47 (dd, 2H), 8.10 (s, 1H), 7.65-7.59 (m, 2H), 7.19-7.28 (dd, J = 16.7, 9.2 Hz, 3H), 5.22-5.40 (d, 1H), 4.74 (d, J = 13.3 Hz, 3H), 3.49 (s, 1H), 3.31 (s, 2H), 2.97 (t, J = 12.7 Hz, 4H), 2.76 (s, 3H), 2.49 (s, 2H), 1.98-2.22 (d, 6H), 1.66-1.86 (s, 7H), 1.24 (s, 1H), 1.09 (d, J = 12.6 Hz, 2H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 376 | | 4-(1-{[1-(5-{3-[2,6-difluoro-3-({[(3R)-3-fluoropyrrolidin-1-yl]sulfonyl}amino)benzoyl]-1H-pyrrolo[2,3-b]pyridin-5-yl}pyrimidin-2-yl)piperidin-4-yl]methyl}piperidin-4-yl)-N-(2,6-dioxopiperidin-3-yl)-2-fluorobenzamide | 1H NMR (300 MHz, DMSO-d6) δ 12.90 (s, 1H), 10.87 (s, 1H), 9.75 (s, 1H) 8.74 (s, 2H), 8.66 (d, J = 2.2 Hz, 1H), 8.55 (dd, 2H), 8.12 (s, 1H), 7.70-7.56 (m, 2H), 7.25 (dd, J = 16.7, 9.2 Hz, 3H), 5.22-5.40 (d, 1H), 4.74 (d, J = 13.3 Hz, 3H), 3.50 (s, 3H), 2.97 (t, J = 12.7 Hz, 4H), 2.73 (s, 1H), 2.56 (s, 1H), 1.98-2.22 (d, 9H), 1.66-1.86 (s, 7H), 1.24 (s, 1H), 1.09 (d, J = 12.6 Hz, 2H) |
| 377 | | 4-(4-{2-[4-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperazin-1-yl]ethyl}piperazin-1-yl)-N-[(3S)-2,6-dioxopiperidin-3-yl]-2-fluorobenzamide | 1H NMR (300 MHz, DMSO-d6) δ 12.90 (s, 1H), 10.85 (s, 1H), 9.88 (s, 1H), 8.65(s, 1H), 8.64 (s, 1H), 8.04 (s, 2H), 7.65 (m, 4H), 7.25 (s, 2H), 7.08 (s, 2H), 6.80 (m, 2H), 5.35 (m, 1H), 4.73 (s, 1H), 3.47 (s, 1H), 3.39 (s, 2H), 3.33 (s, 6H), 3.24 (s, 4H), 2.77 (m, 1H), 2.67 (m, 3H), 2.60 (s, 3H), 2.49 (s, 3H), 2.13 (d, 3H), 1.97(s, 2H), 1.23 (s, 2H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| | 378 | 4-(4-{2-[4-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)piperazin-1-yl]ethyl}piperazin-1-yl)-N-(2,6-dioxopiperidin-3-yl)-2-fluorobenzamide | 1H NMR (300 MHz, DMSO-d6) δ 12.90 (s, 1H), 10.87 (s, 1H), 8.66(s, 1H), 8.54 (s, 1H), 8.04 (s, 2H), 7.63 (m, 4H), 7.25 (s, 1H), 7.09 (s, 2H), 6.85 (m, 2H), 5.32 (m, 1H), 4.75 (s, 1H), 3.50 (s, 1H), 3.48 (s, 2H), 3.38 (s, 3H), 3.22 (s, 3H), 2.77 (m, 6H), 2.27 (d, 5H), 1.24 (s, 9H), 0.88 (s, 1H) |

TABLE 3-continued

¹H NMR data of exemplary bifunctional compounds of the present disclosure

| Ex. No. | Parent Mol Structure | IUPAC Name | ¹H NMR tabulation |
|---|---|---|---|
| 379 | 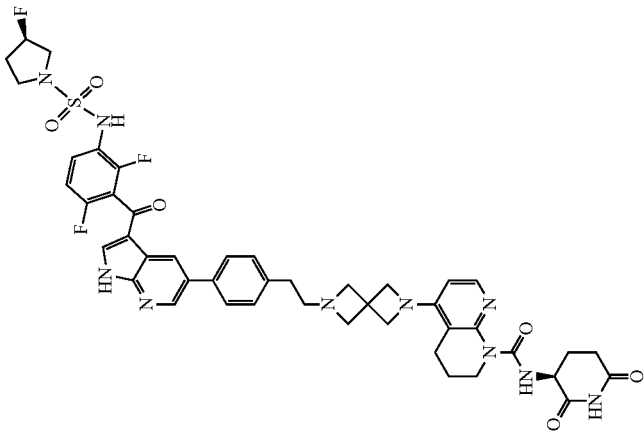 | 5-[6-[2-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)ethyl]-2,6-diazaspiro[3.3]heptan-2-yl]-N-[(3S)-2,6-dioxopiperidin-3-yl]-1,2,3,4-tetrahydro-1,8-naphthyridine-1-carboxamide | 1H NMR (400 MHz, DMSO-d6) δ 12.97 (s, 1H), 11.20 (d, J = 6.7 Hz, 1H), 10.80 (s, 1H), 9.78 (s, 1H), 8.69 (d, J = 2.3 Hz, 1H), 8.59 (s, 1H), 8.11 (s, 1H), 7.80 (d, J = 5.7 Hz, 1H), 7.70-7.57 (m, 3H), 7.37 (d, J = 7.9 Hz, 2H), 7.32-7.16 (m, 2H), 6.13 (d, J = 5.8 Hz, 1H), 5.23-5.36 (d, 1H), 4.52 (dt, J = 12.2, 5.9 Hz, 1H), 4.12 (d, J = 8.6 Hz, 4H), 3.77 (tq, J = 12.5, 6.6, 4.9 Hz, 2H), 3.48 (d, J = 2.3 Hz, 1H), 3.44-3.35 (m, 4H), 2.59 (s, 2H), 2.50 (s, 3H), 2.12 (s, 3H), 1.97 (tt, J = 12.4, 6.3 Hz, 2H), 1.78-1.70 (m, 2H), 1.24 (s, 3H), 0.853 (s, 1H) |

TABLE 3-continued

¹H NMR data of exemplary bifunctional compounds of the present disclosure

| Parent Mol Structure | Ex. No. | IUPAC Name | ¹H NMR tabulation |
|---|---|---|---|
| 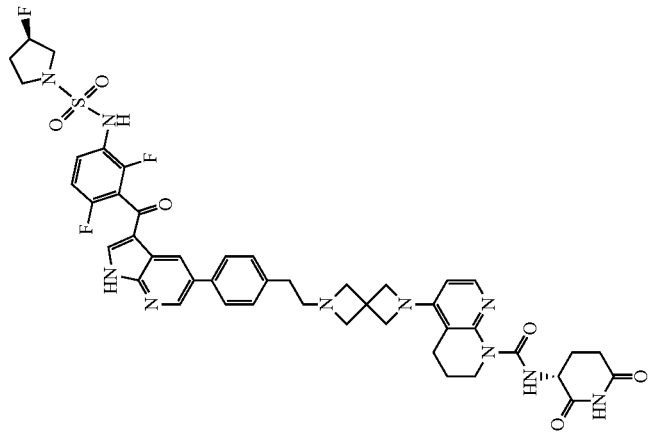 | 380 | 5-[6-[2-(4-{3-[2,6-difluoro-3-({[(3R)-3-fluoropyrrolidin-1-yl]sulfonyl}amino)benzoyl]-1H-pyrrolo[2,3-b]pyridin-5-yl}phenyl)ethyl]-2,6-diazaspiro[3.3]heptan-2-yl]-N-[(3R)-2,6-dioxopiperidin-3-yl]-1,2,3,4-tetrahydro-1,8-naphthyridine-1-carboxamide | 1H NMR (400 MHz, DMSO-d6) δ 12.97 (s, 1H), 11.20 (d, J = 6.7 Hz, 1H), 10.80 (s, 1H), 9.78 (s, 1H), 8.69 (d, J = 2.3 Hz, 1H), 8.59 (s, 1H), 8.11 (s, 1H), 7.80 (d, J = 5.7 Hz, 1H), 7.70-7.57 (m, 3H), 7.37 (d, J = 7.9 Hz, 2H), 7.32-7.16 (m, 1H), 6.13 (d, J = 5.8 Hz, 1H), 5.23-5.36 (d, 1H), 4.52 (dt, J = 12.2, 5.9 Hz, 1H), 4.12 (d, J = 8.6 Hz, 4H), 3.77 (tq, J = 12.5, 6.6, 4.9 Hz, 2H), 3.48 (d, J = 2.3 Hz, 1H), 3.44-3.35 (m, 4H), 2.59 (s, 2H), 2.50 (s, 3H), 2.12 (s, 3H), 1.97 (tt, J = 12.4, 6.3 Hz, 2H), 1.78-1.70 (m, 2H), 1.24 (s, 3H), 0.853 (s, 1H) |

A novel bifunctional molecule, which contains a RAF recruiting moiety and an E3 ubiquitin ligase recruiting moiety is described. The bifunctional molecules of the present disclosure actively degrades RAF, leading to robust cellular proliferation suppression and apoptosis induction. Protein degradation mediated by the bifunctional compounds of the present disclosure provides a promising strategy in targeting the "undruggable" pathological proteins by traditional approaches.

The preceding general areas of utility are given by way of example only and are not intended to be limiting on the scope of the present disclosure and appended claims. Additional objects and advantages associated with the compositions, methods, and processes of the present disclosure will be appreciated by one of ordinary skill in the art in light of the instant claims, description, and examples. For example, the various aspects and embodiments of the disclosure may be utilized in numerous combinations, all of which are expressly contemplated by the present description. These additional aspects and embodiments are expressly included within the scope of the present disclosure. The publications and other materials used herein to illuminate the background of the disclosure, and in particular cases, to provide additional details respecting the practice, are incorporated by reference.

Thus, those skilled in the art will recognize, or be able to ascertain using no more than routine experimentation, many equivalents to the specific embodiments of the disclosure described herein. Such equivalents are intended to be encompassed by the following claims. It is understood that the detailed examples and embodiments described herein are given by way of example for illustrative purposes only, and are in no way considered to be limiting to the disclosure. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

What is claimed is:

1. A compound, wherein the compound is selected from the group consisting of:

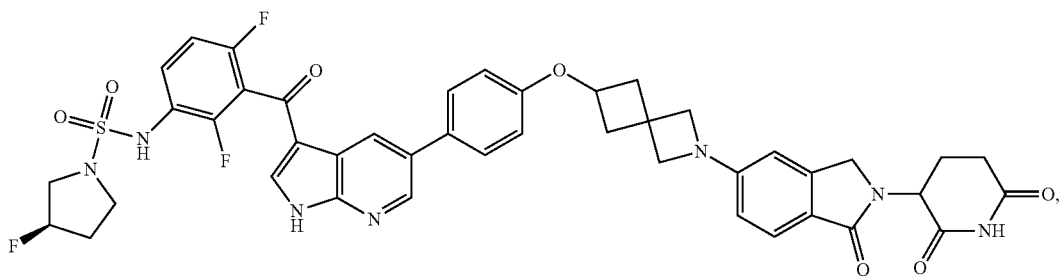

(1)

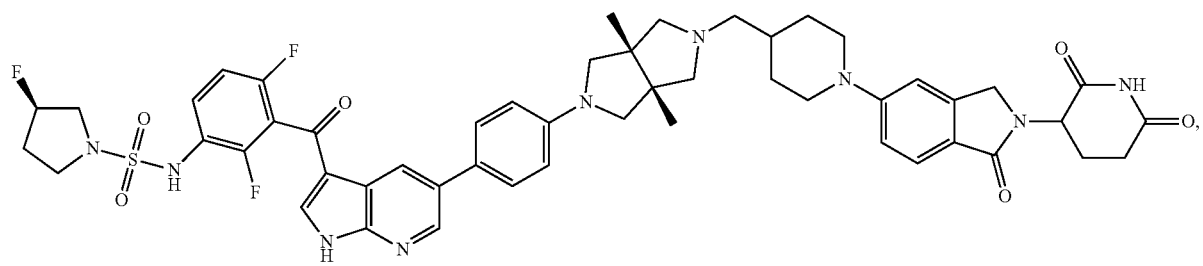

(2)

-continued
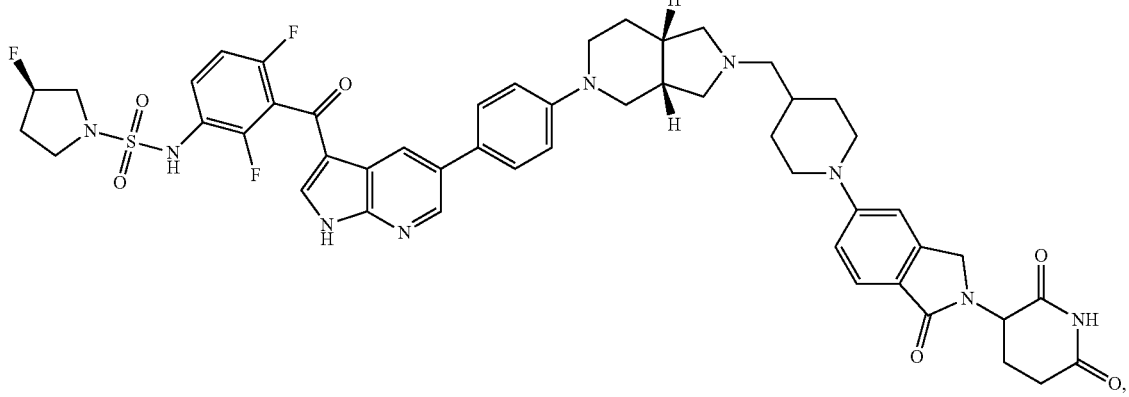
(3)
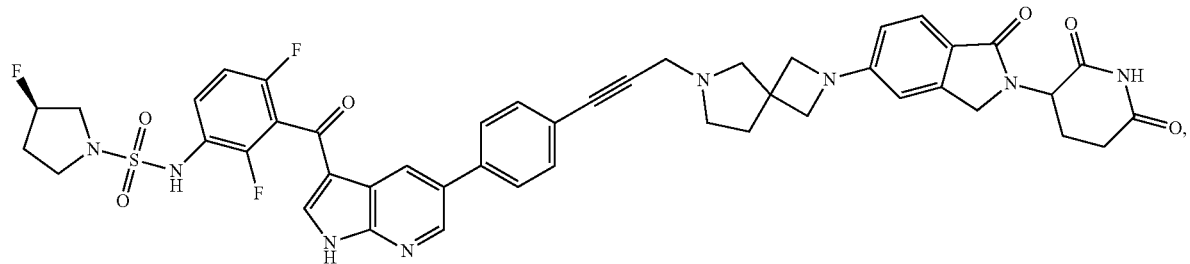
(4)
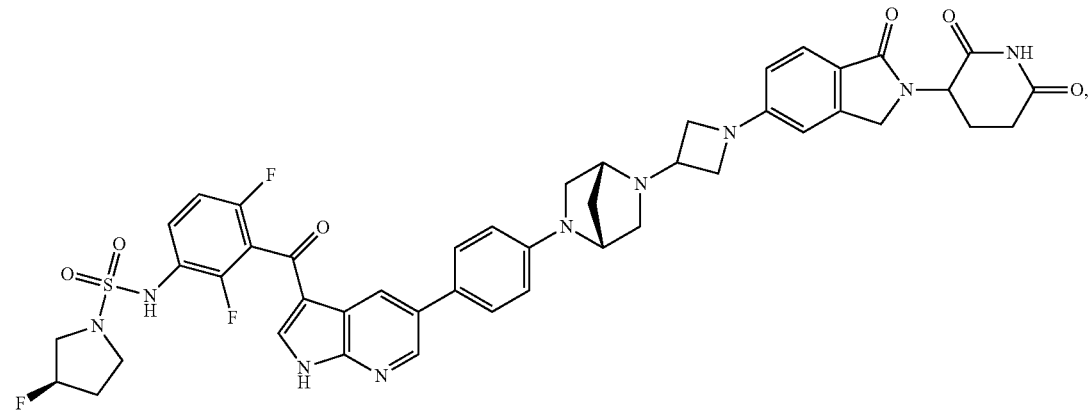
(5)
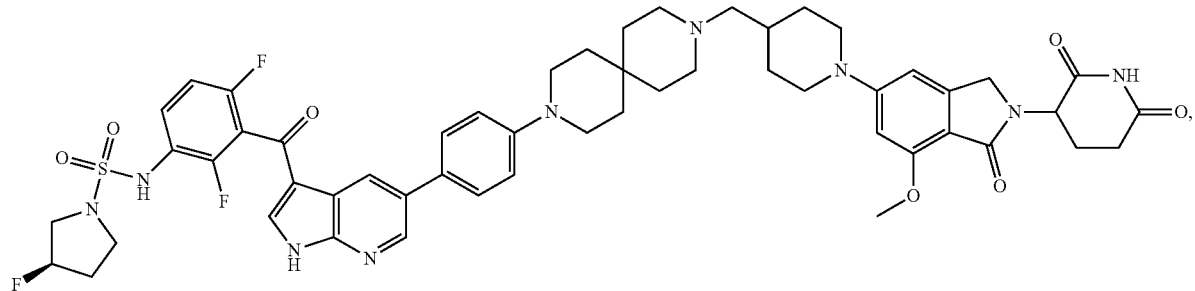
(6)

-continued
(7)
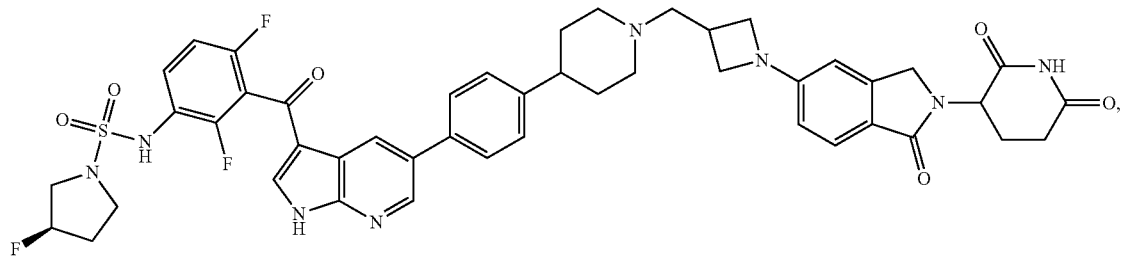
(8)
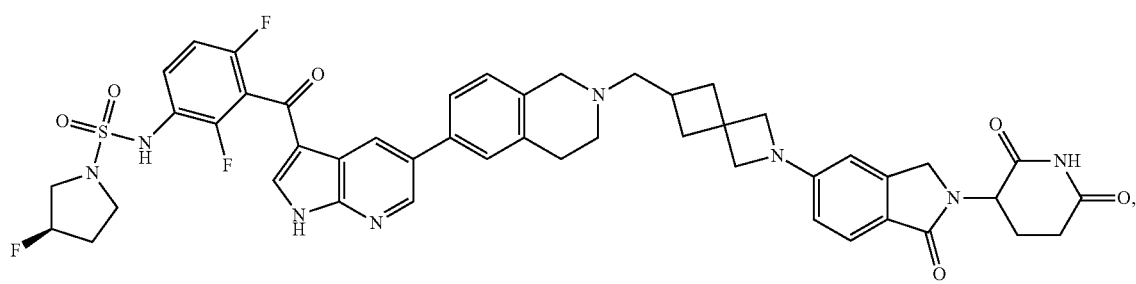
(9)
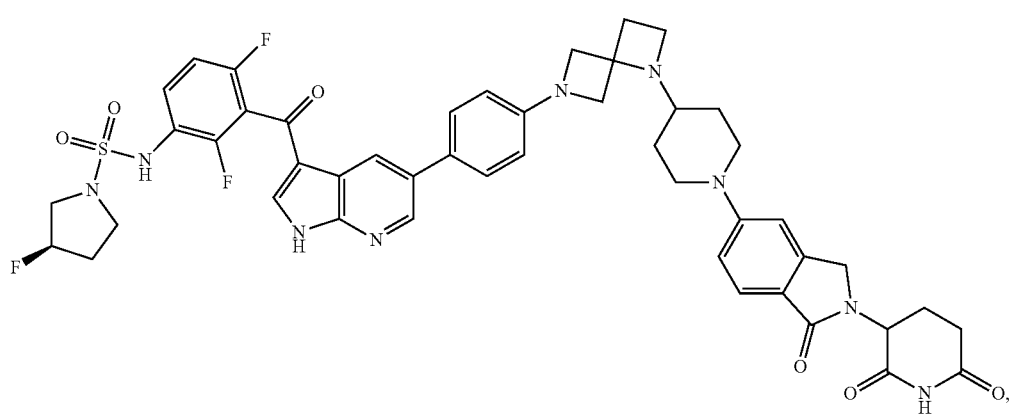
(10)
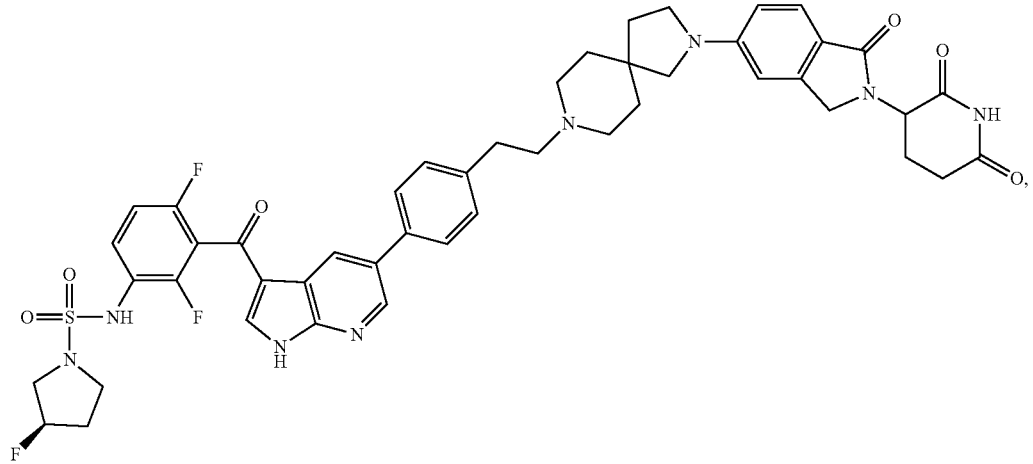

-continued
(11)
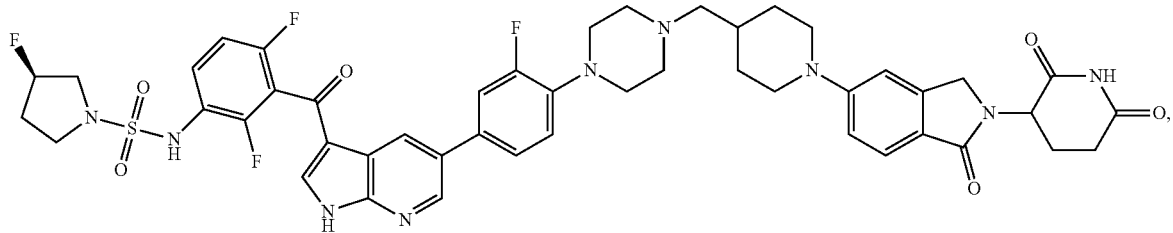
(12)
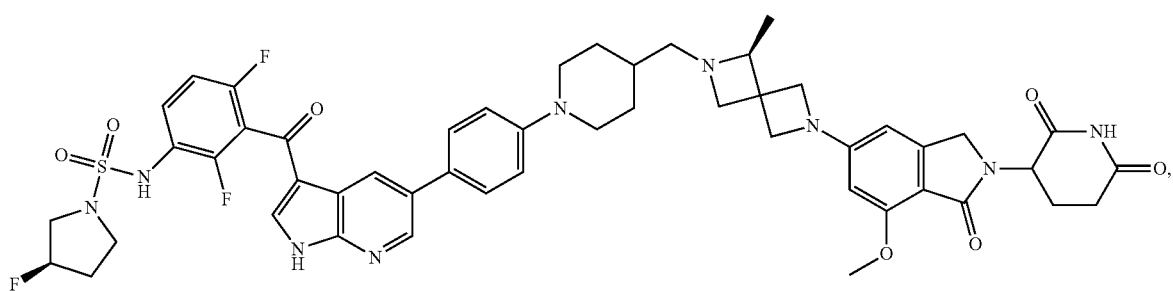
(13)
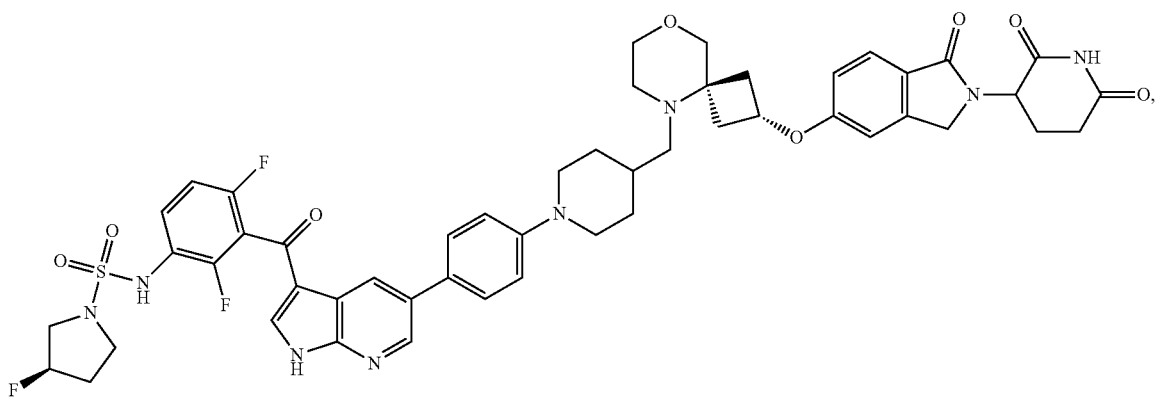
(14)
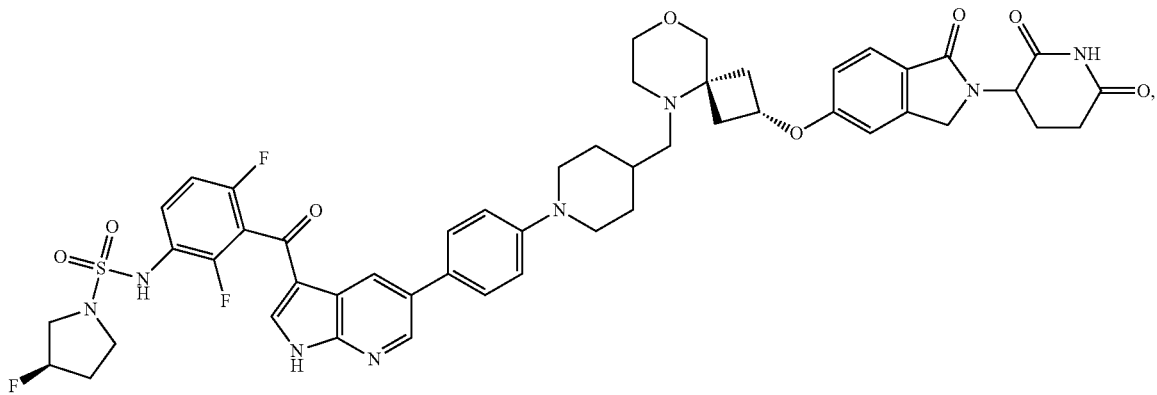

(15)
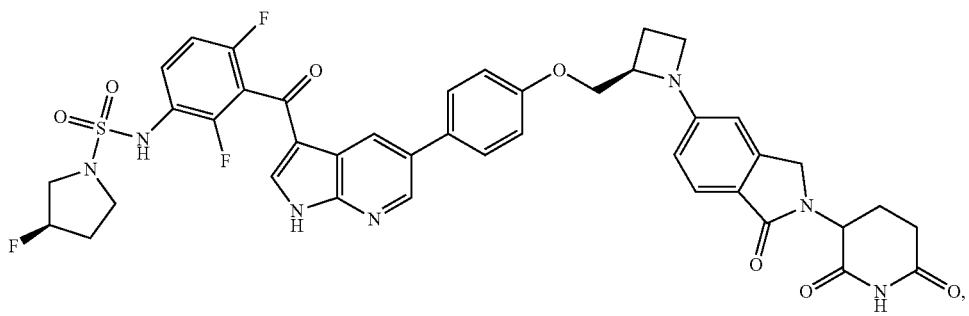
(16)
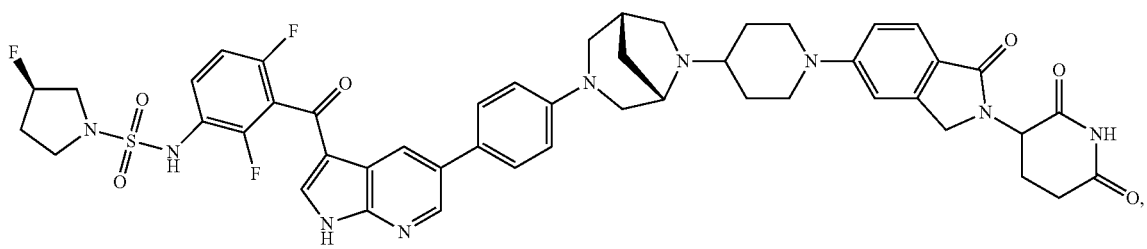
(17)
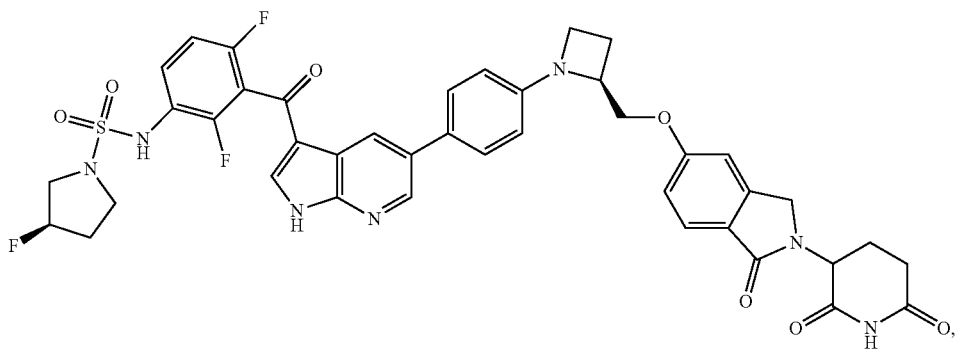 [SMILES: O=C1CCC(N2Cc3cc(OC[C@@H]4CCN4c4ccc(-c5cnc6[nH]cc(C(=O)c7c(F)ccc(NS(=O)(=O)N8CC[C@@H](F)C8)c7F)c6c5)cc4)ccc3C2=O)C(=O)N1]
(18)
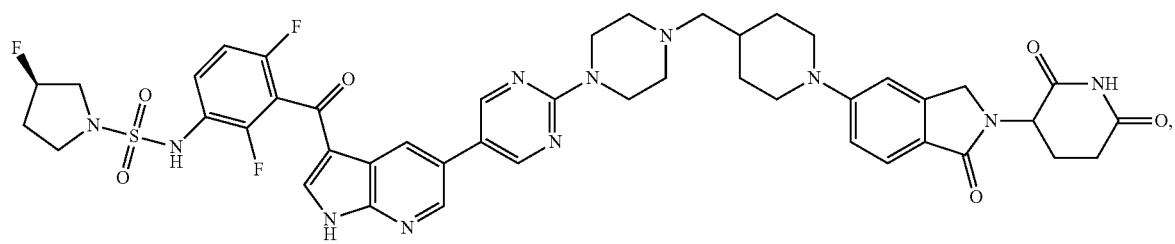
(19)
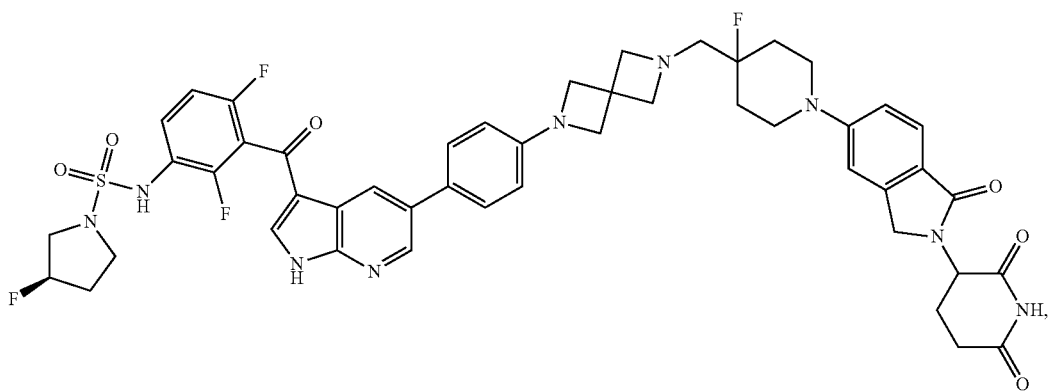

-continued
(20)
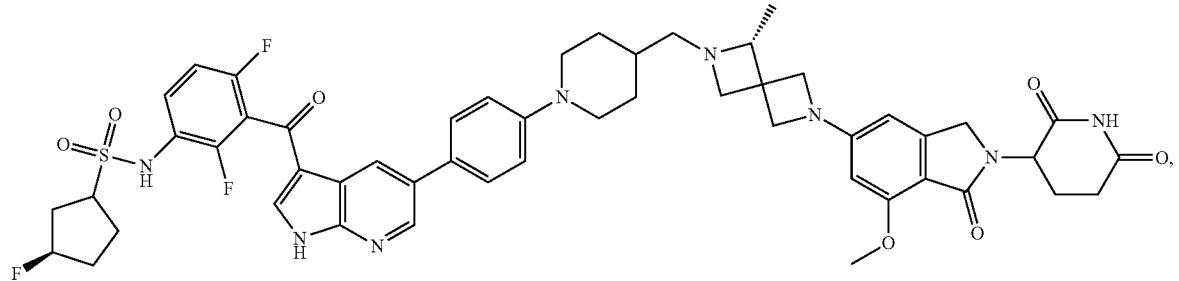
(21)
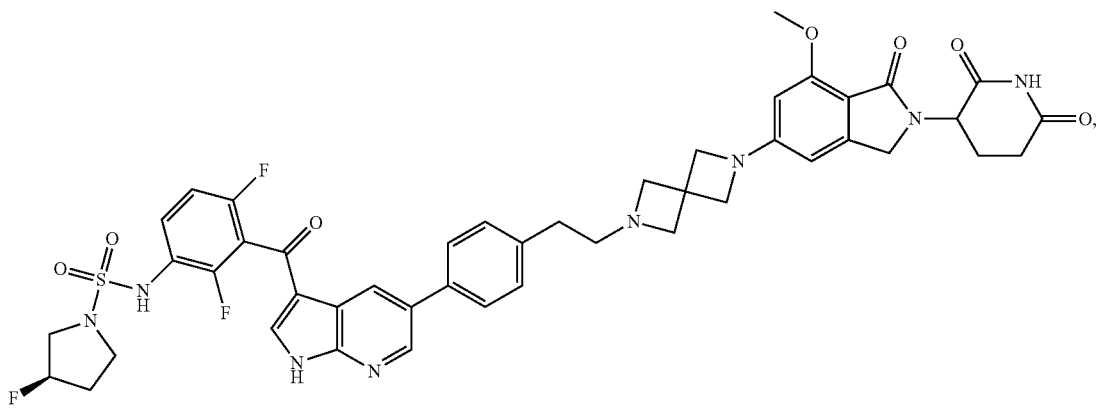
(22)
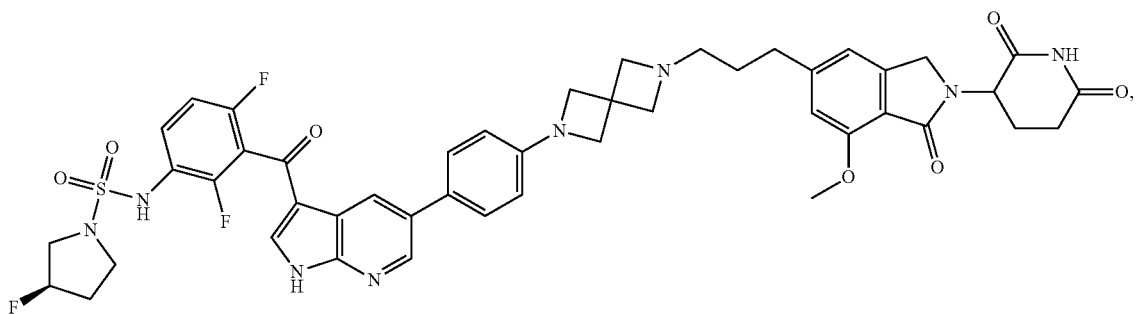
(23)
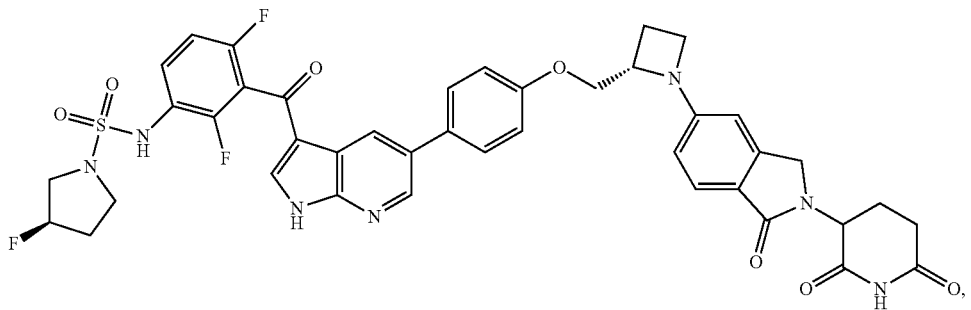 [SMILES: O=C1CCC(N2Cc3cc(N4CC[C@H]4COc4ccc(-c5cnc6[nH]cc(C(=O)c7c(F)ccc(NS(=O)(=O)N8CC[C@@H](F)C8)c7F)c6c5)cc4)ccc3C2=O)C(=O)N1]

-continued
(24)
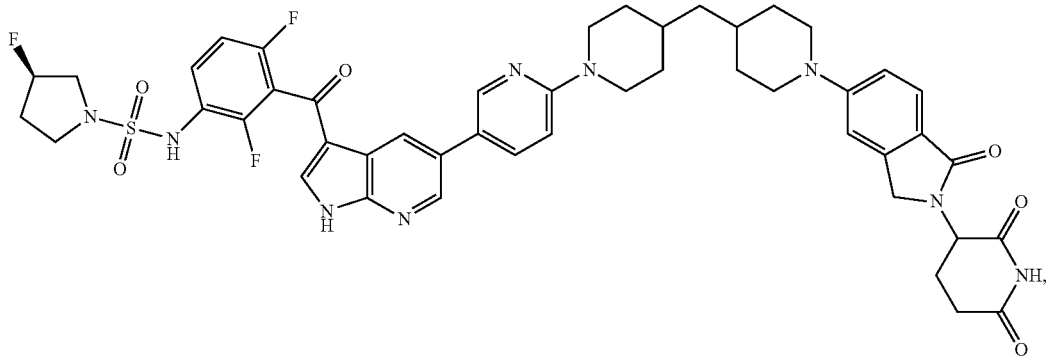
(25)
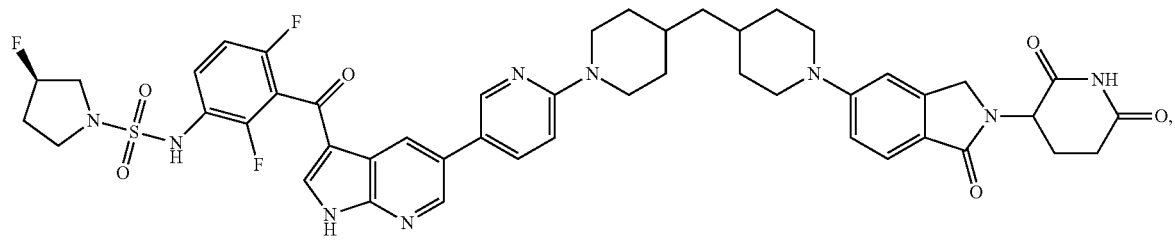
(26)
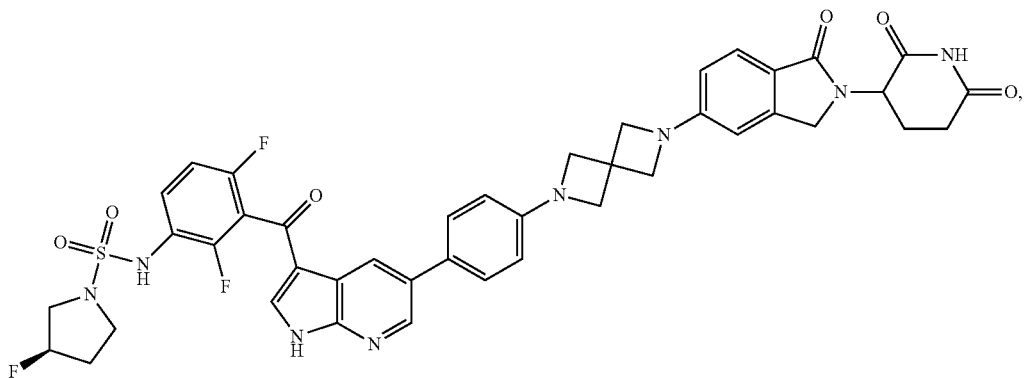
(27)
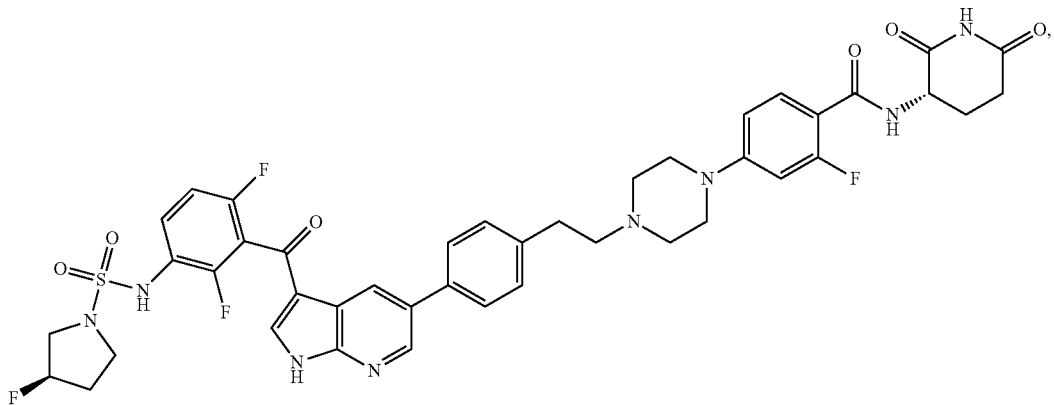

-continued
(28)
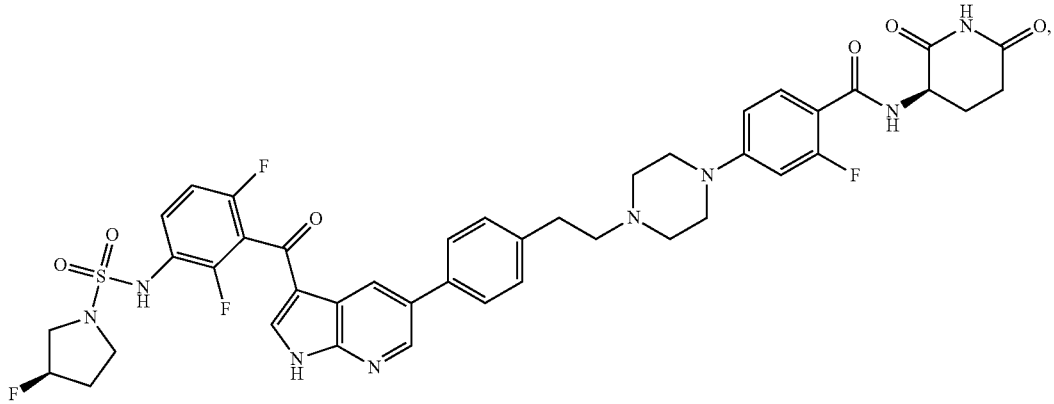
(29)
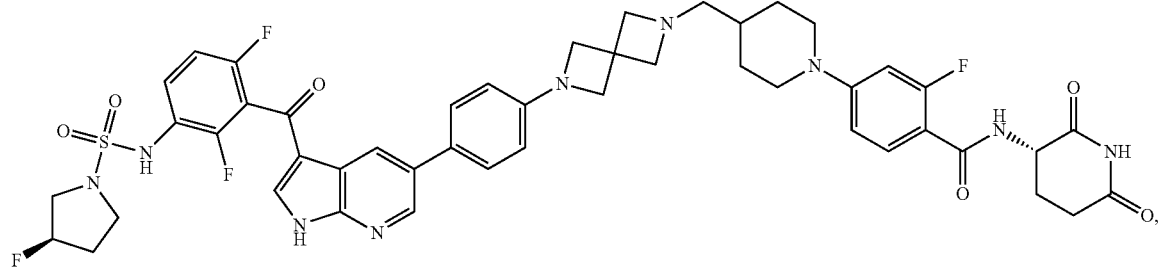
(30)
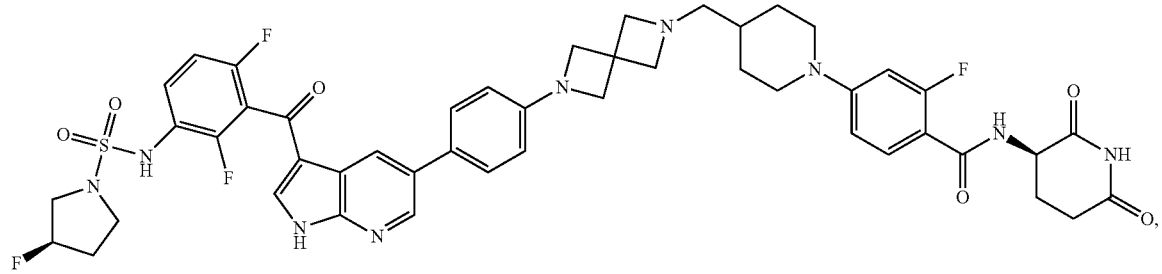
(31)
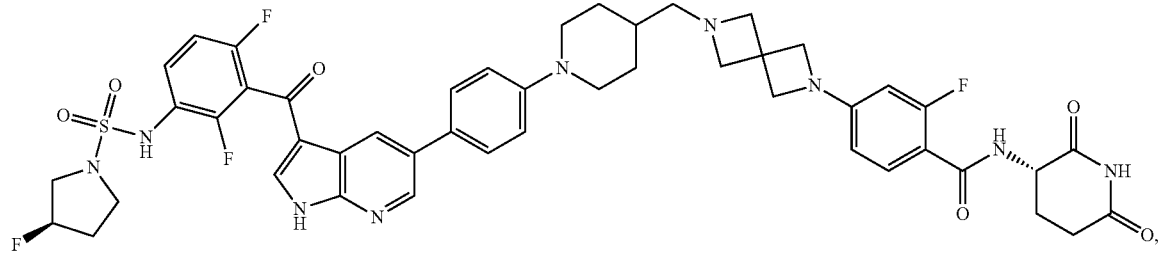
(32)
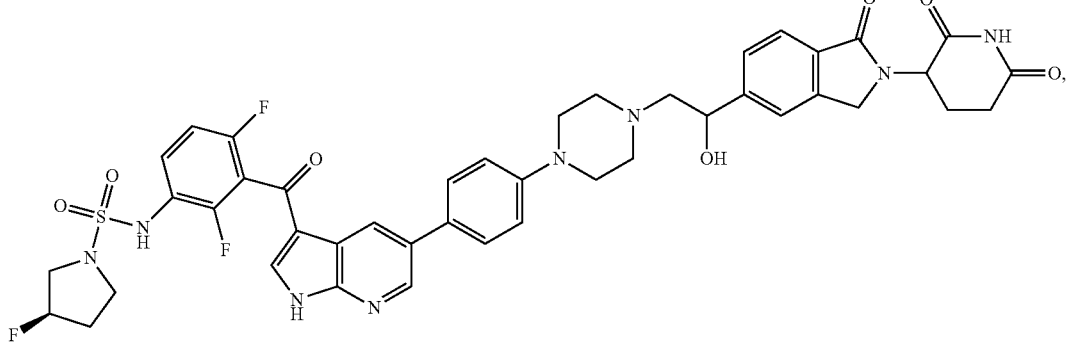

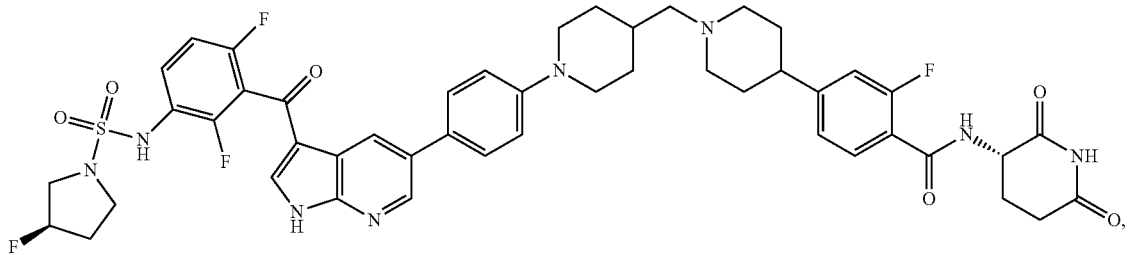
(33)
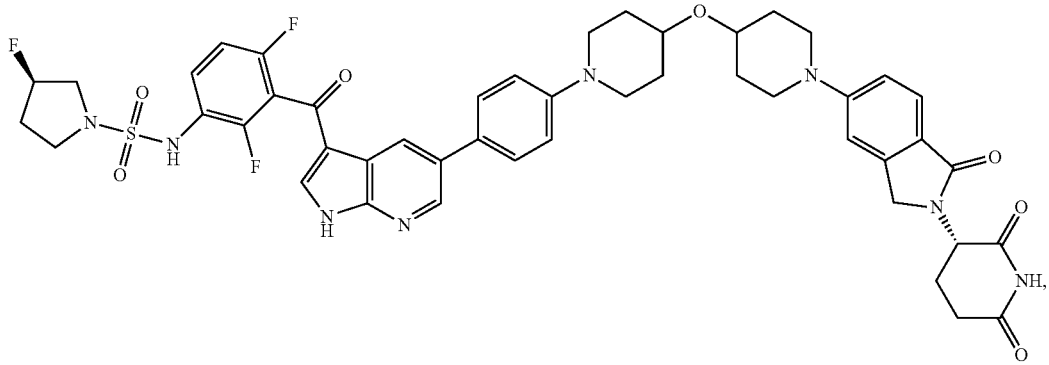 [SMILES: O=C1CC[C@H](N2Cc3cc(N4CCC(OC5CCN(c6ccc(-c7cnc8[nH]cc(C(=O)c9c(F)ccc(NS(=O)(=O)N%10CC[C@@H](F)C%10)c9F)c8c7)cc6)CC5)CC4)ccc3C2=O)C(=O)N1]
(34)
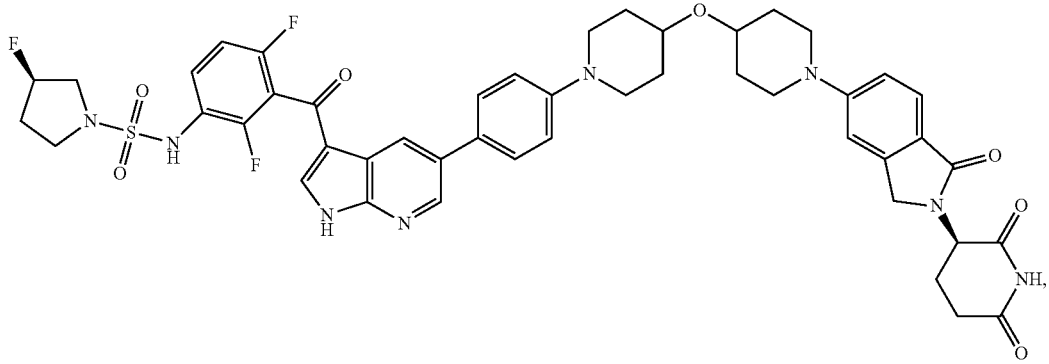 [SMILES: O=C1CC[C@@H](N2Cc3cc(N4CCC(OC5CCN(c6ccc(-c7cnc8[nH]cc(C(=O)c9c(F)ccc(NS(=O)(=O)N%10CC[C@@H](F)C%10)c9F)c8c7)cc6)CC5)CC4)ccc3C2=O)C(=O)N1]
(35)
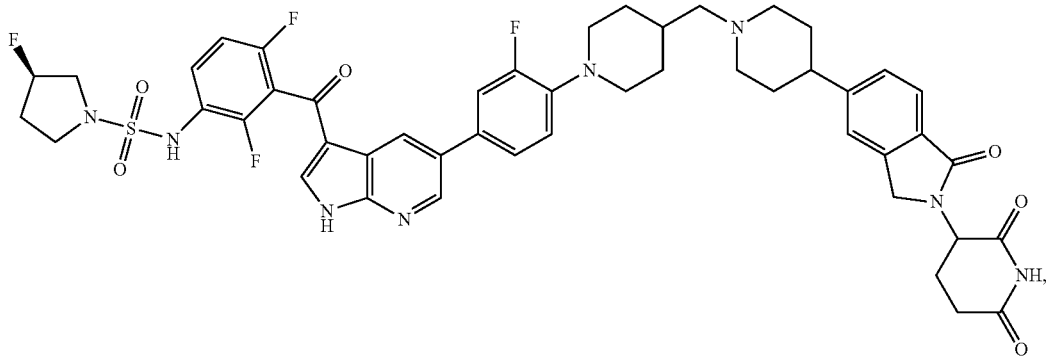 [SMILES: O=C1CCC(N2Cc3cc(N4CCC(CC5CCN(c6ccc(-c7cnc8[nH]cc(C(=O)c9c(F)ccc(NS(=O)(=O)N%10CC[C@@H](F)C%10)c9F)c8c7)cc6F)CC5)CC4)ccc3C2=O)C(=O)N1]
(36)
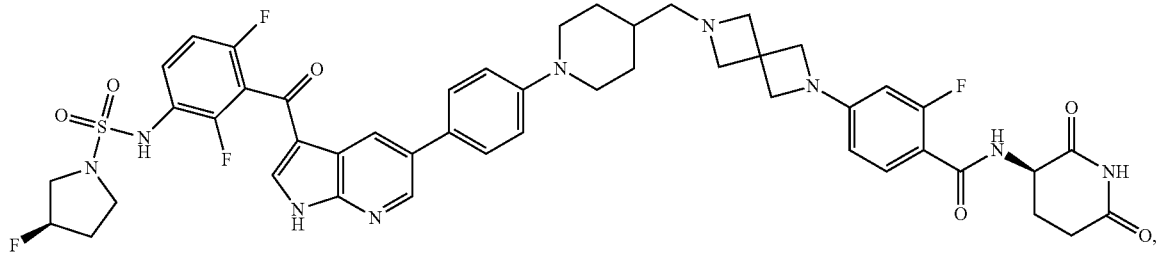
(37)

-continued
(38)
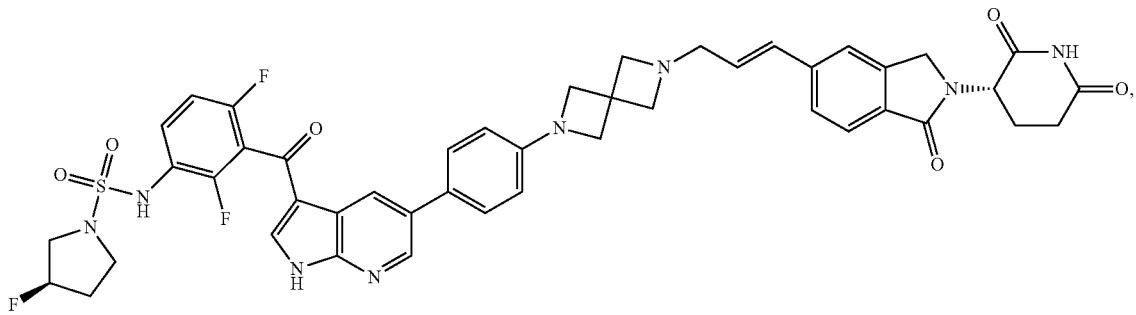
(39)
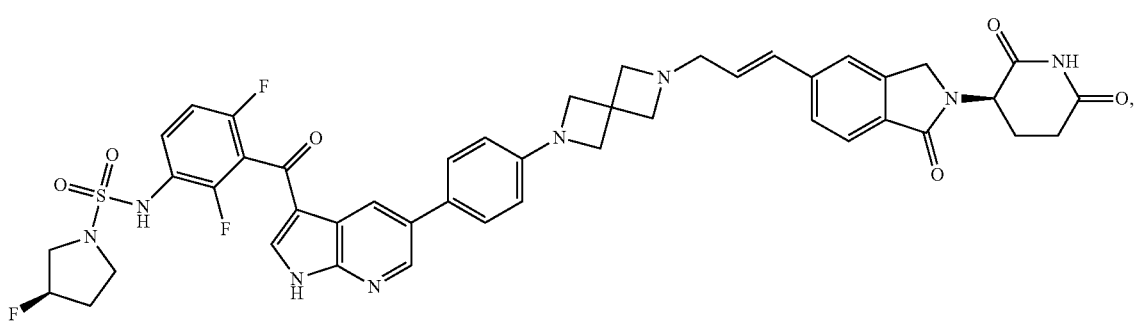
(40)
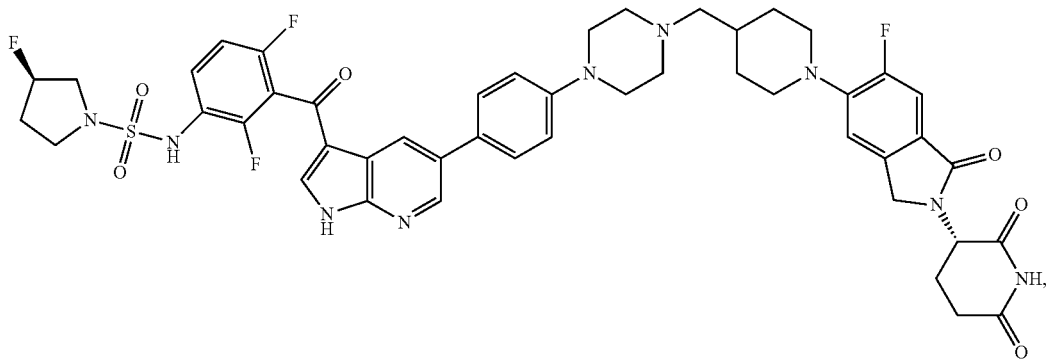 [SMILES: O=C1CC[C@H](N2Cc3cc(N4CCC(CN5CCN(c6ccc(-c7cnc8[nH]cc(C(=O)c9c(F)ccc(NS(=O)(=O)N%10CC[C@@H](F)C%10)c9F)c8c7)cc6)CC5)CC4)c(F)cc3C2=O)C(=O)N1]
(41)
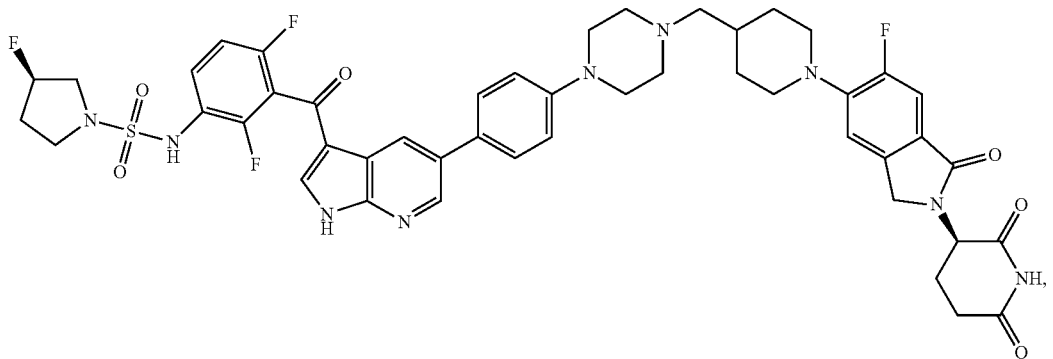 [SMILES: O=C1CC[C@@H](N2Cc3cc(N4CCC(CN5CCN(c6ccc(-c7cnc8[nH]cc(C(=O)c9c(F)ccc(NS(=O)(=O)N%10CC[C@@H](F)C%10)c9F)c8c7)cc6)CC5)CC4)c(F)cc3C2=O)C(=O)N1]

-continued
(42)
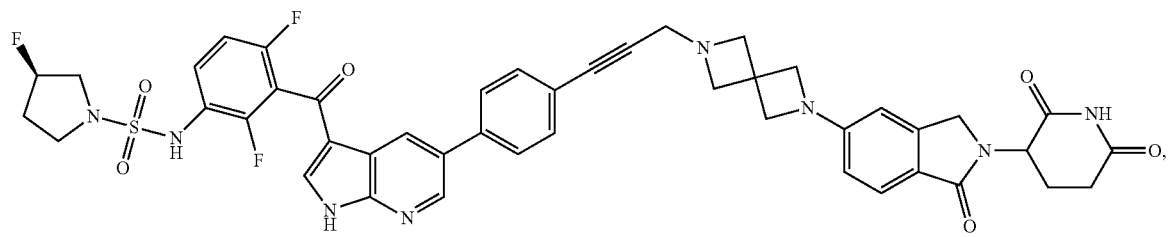
(43)
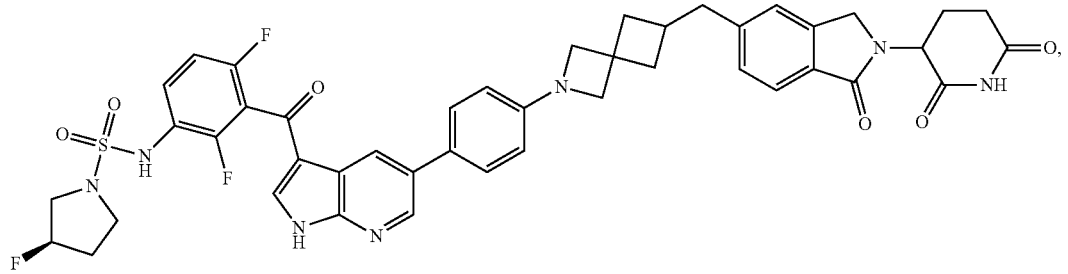
(44)
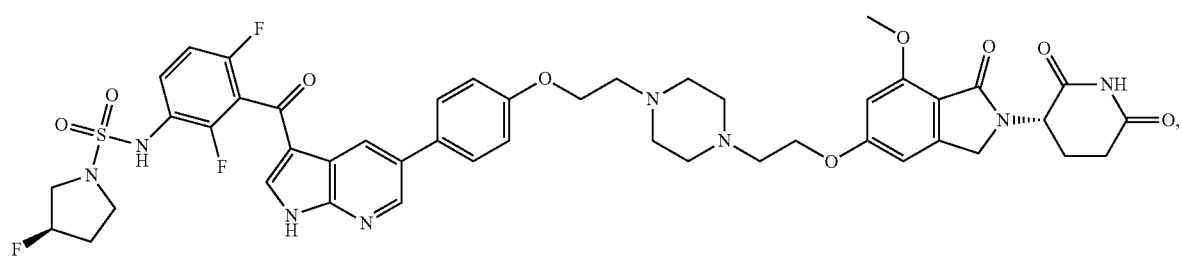
(45)
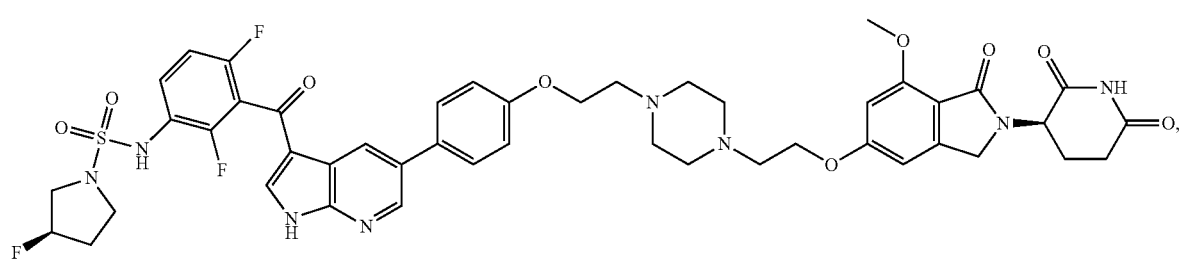
(46)
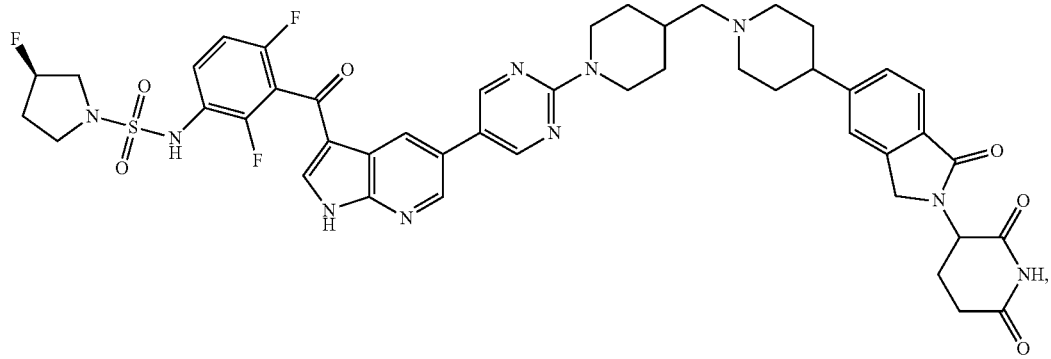 [SMILES: O=C1CCC(N2Cc3cc(C4CCN(CC5CCC(c6ncc(-c7cnc8[nH]cc(C(=O)c9c(F)ccc(NS(=O)(=O)N%10CC[C@@H](F)C%10)c9F)c8c7)cn6)CC5)CC4)ccc3C2=O)C(=O)N1]

(47)
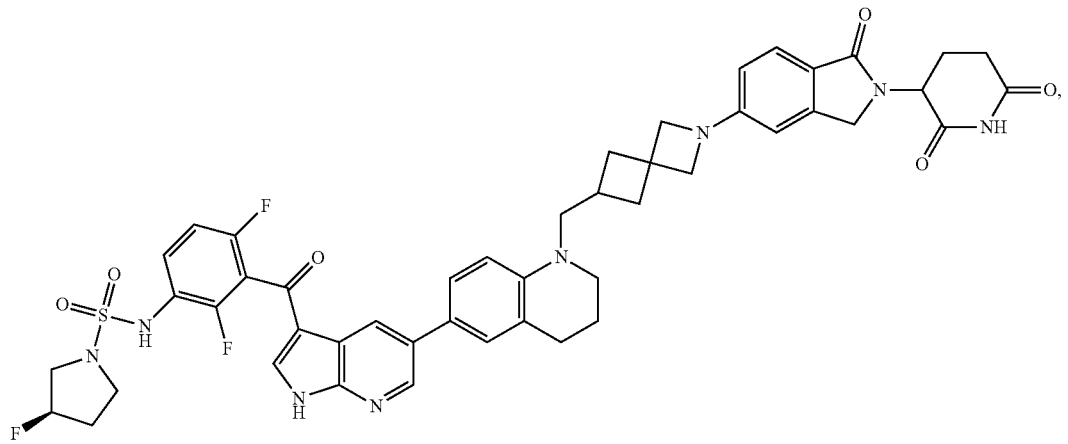
(48)
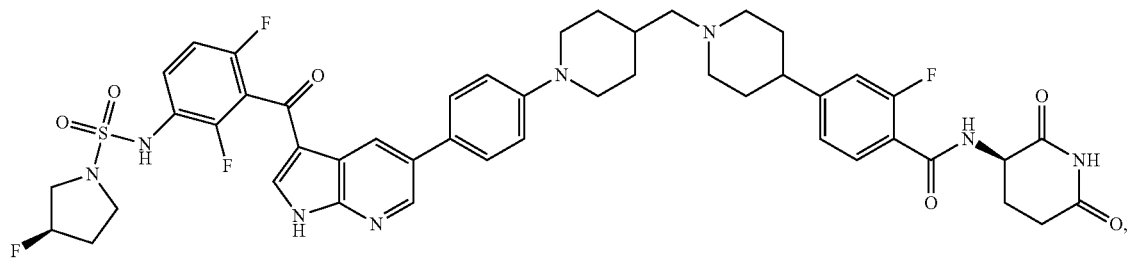
(49)
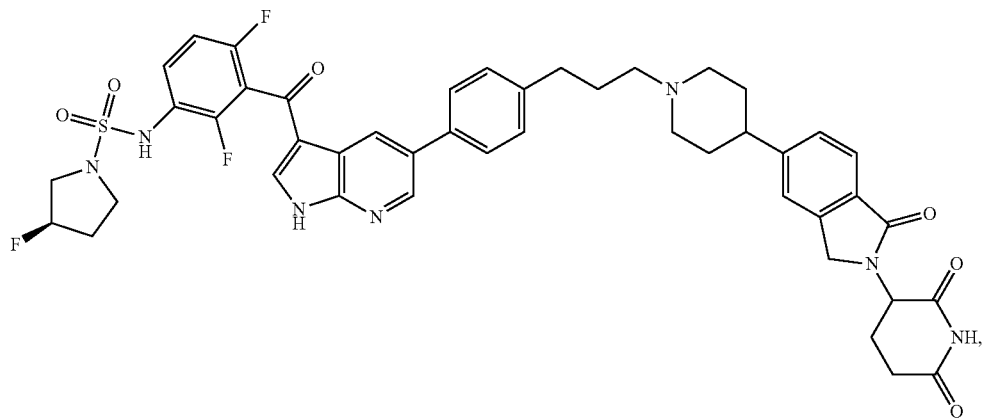 [SMILES: O=C1CCC(N2Cc3cc(C4CCN(CCCc5ccc(-c6cnc7[nH]cc(C(=O)c8c(F)ccc(NS(=O)(=O)N9CC[C@@H](F)C9)c8F)c7c6)cc5)CC4)ccc3C2=O)C(=O)N1]
(50)
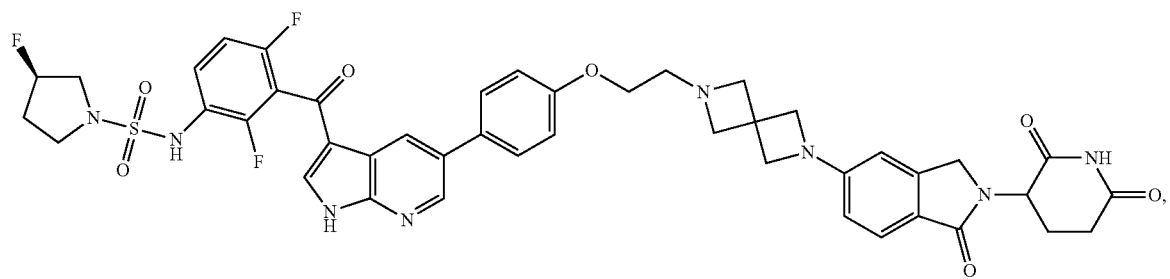

-continued
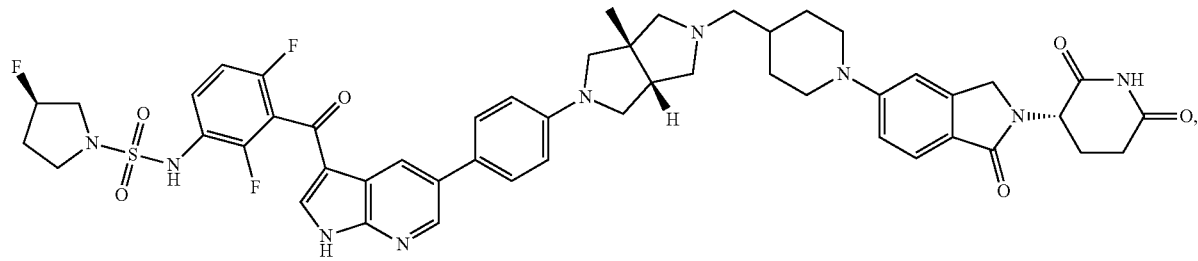
(51)
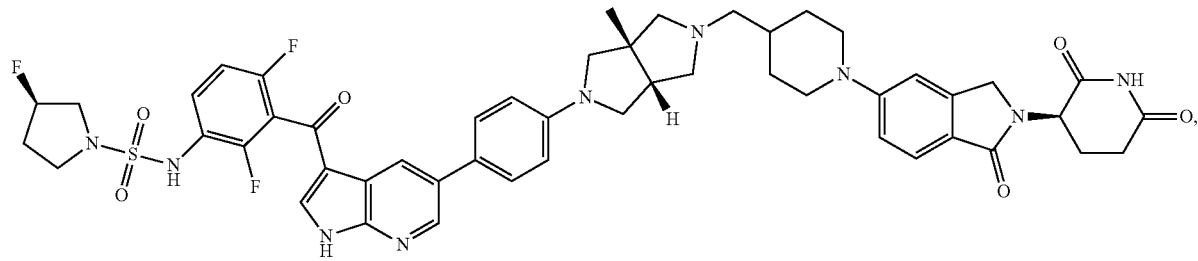
(52)
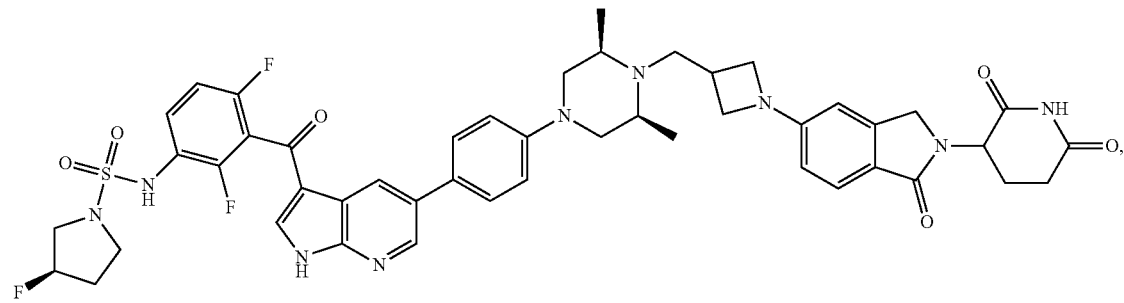
(53)
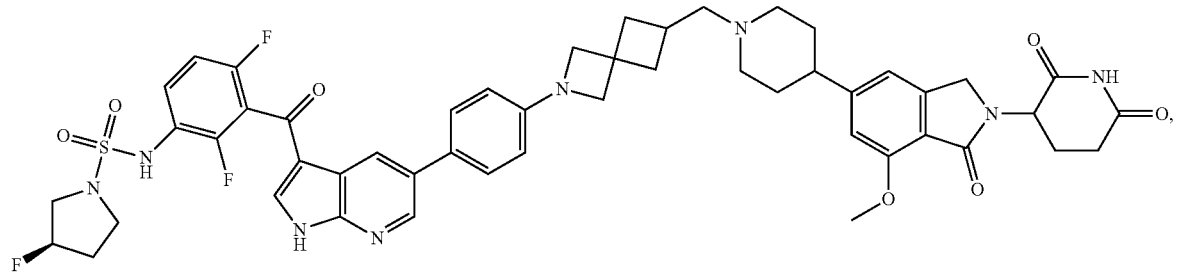
(54)
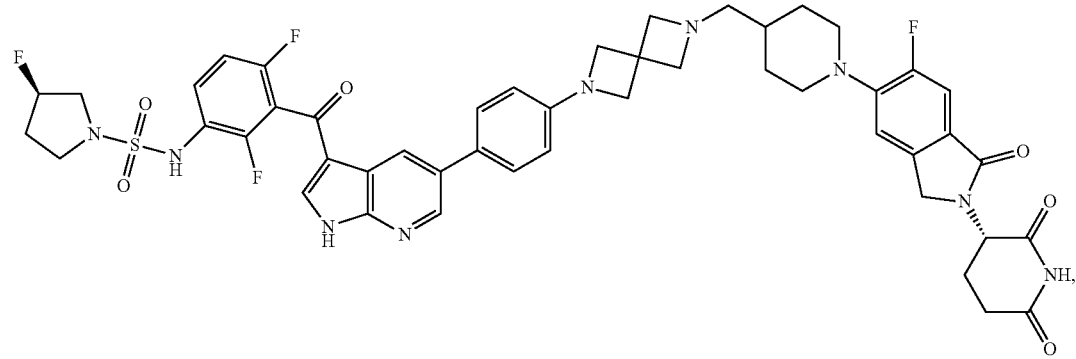 [SMILES: O=C1CC[C@H](N2Cc3cc(N4CCC(CN5CC6(C5)CN(c5ccc(-c7cnc8[nH]cc(C(=O)c9c(F)ccc(NS(=O)(=O)N%10CC[C@@H](F)C%10)c9F)c8c7)cc5)C6)CC4)c(F)cc3C2=O)C(=O)N1]
(55)

(56)
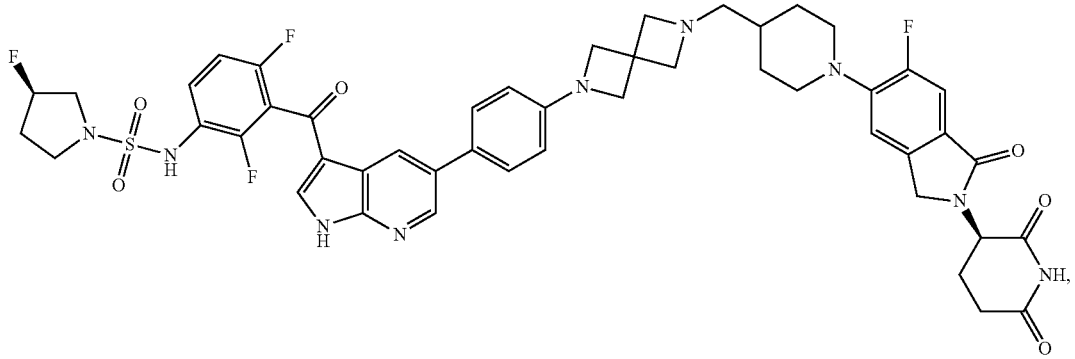 [SMILES: O=C1CC[C@@H](N2Cc3cc(N4CCC(CN5CC6(C5)CN(c5ccc(-c7cnc8[nH]cc(C(=O)c9c(F)ccc(NS(=O)(=O)N%10CC[C@@H](F)C%10)c9F)c8c7)cc5)C6)CC4)c(F)cc3C2=O)C(=O)N1]
(57)
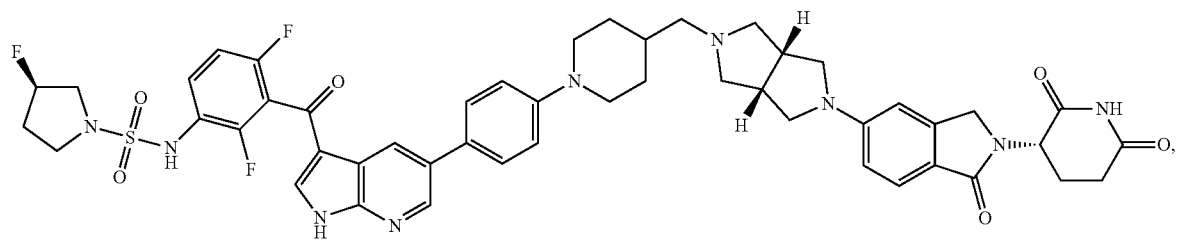
(58)
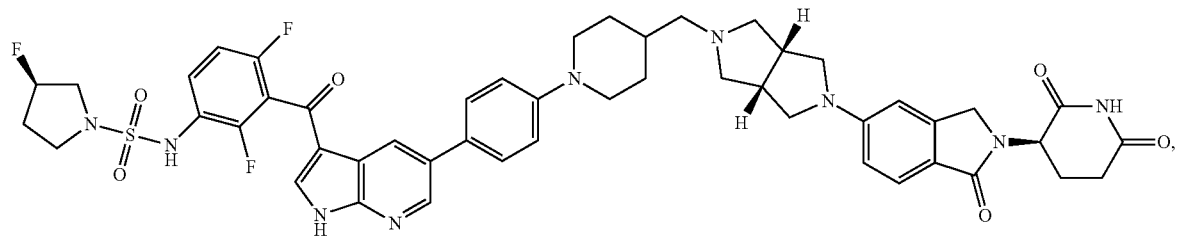
(59)
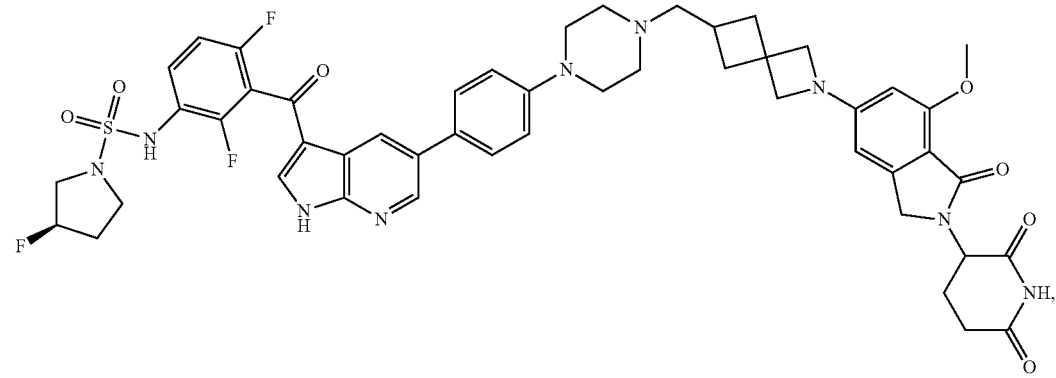
(60)
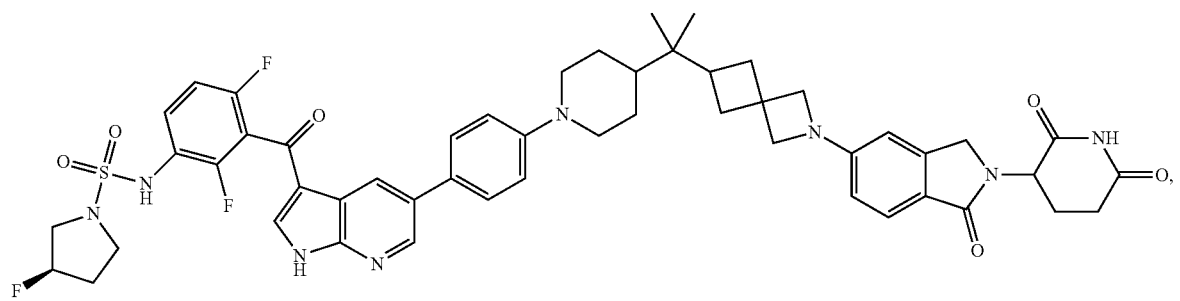

-continued
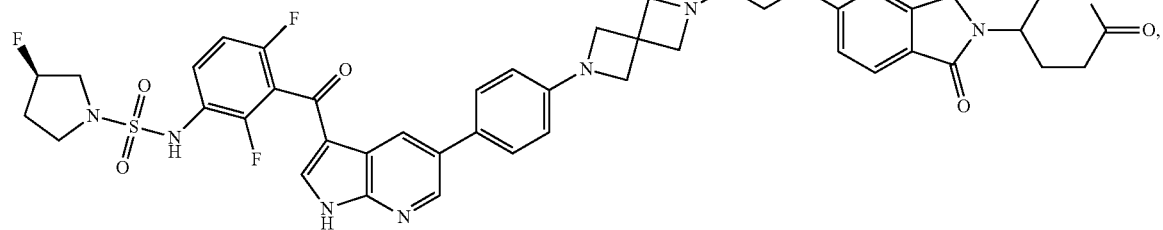
(61)
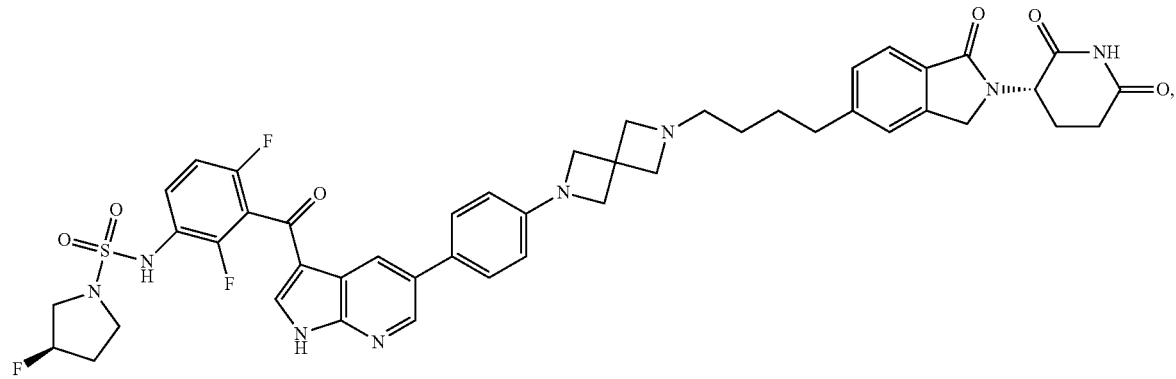
(62)
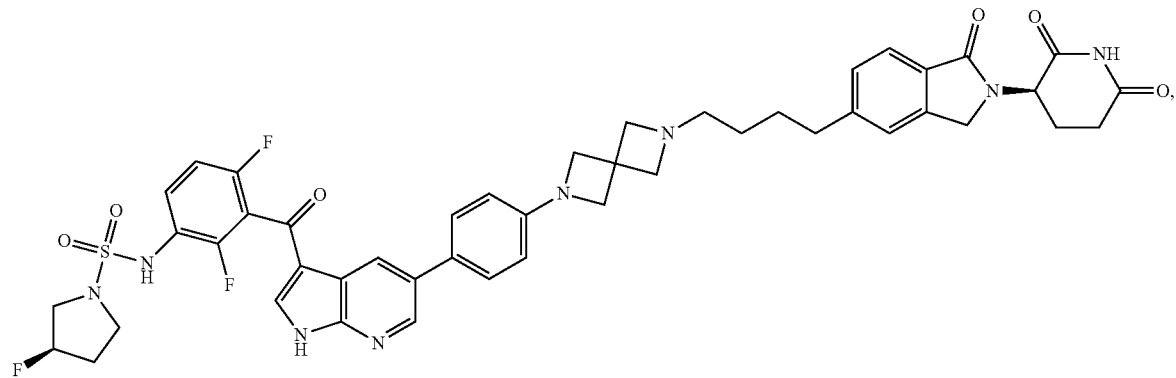
(63)
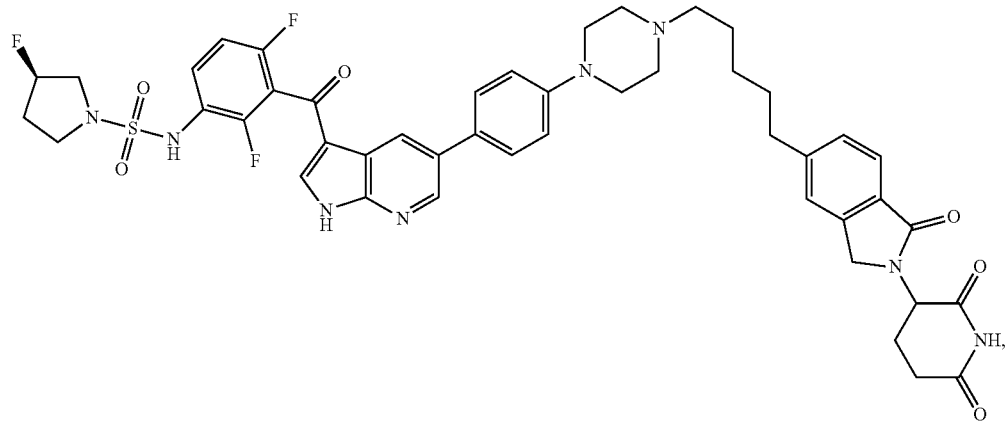
(64)

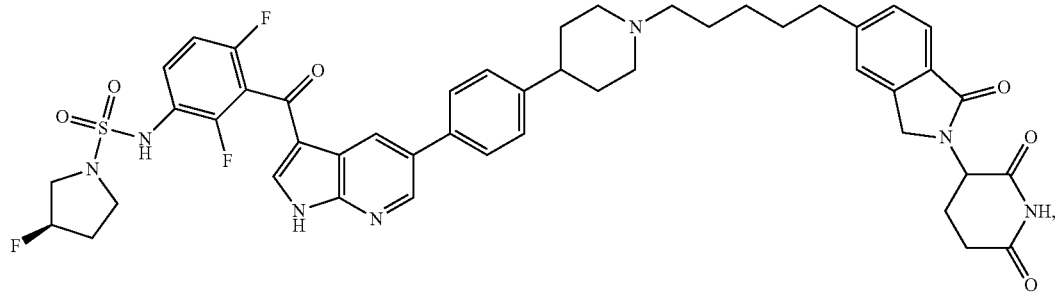
(65)
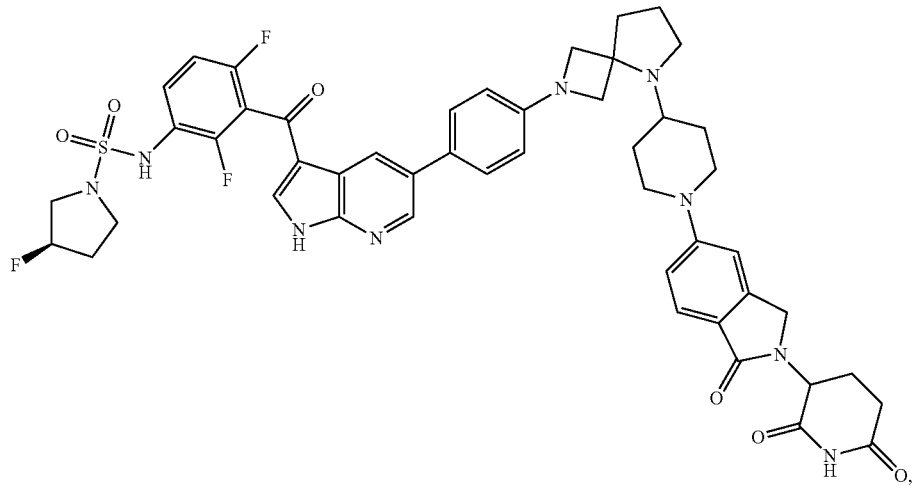
(66)
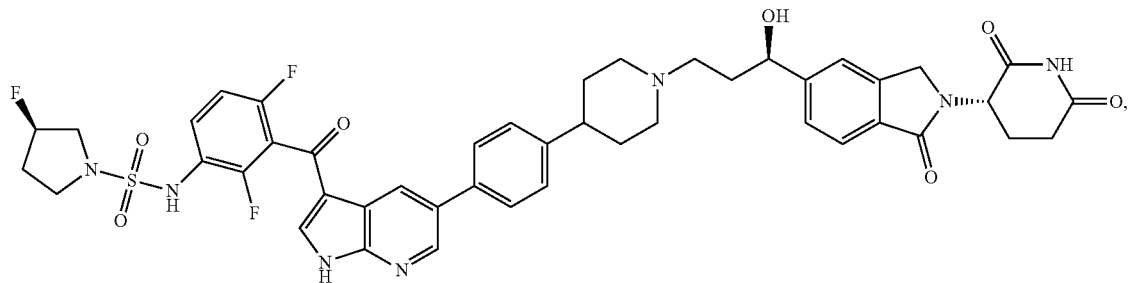
(67)
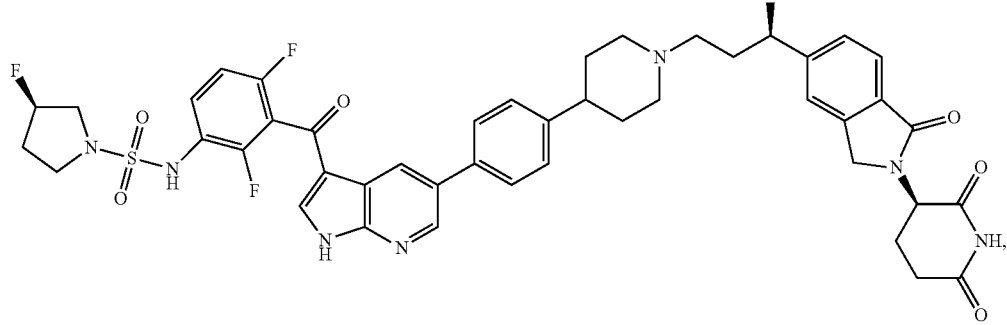
(68)

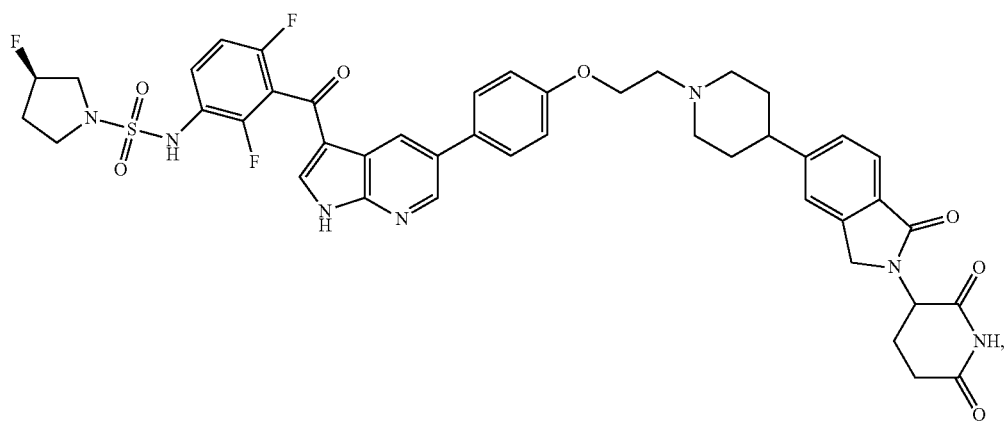
(69)
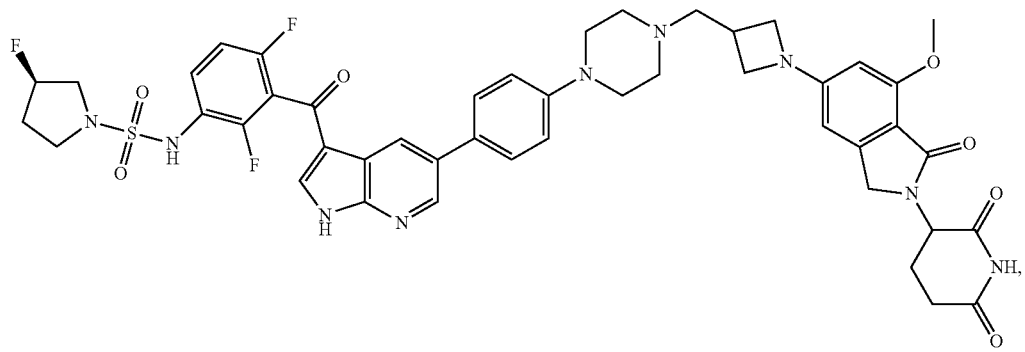
(70)
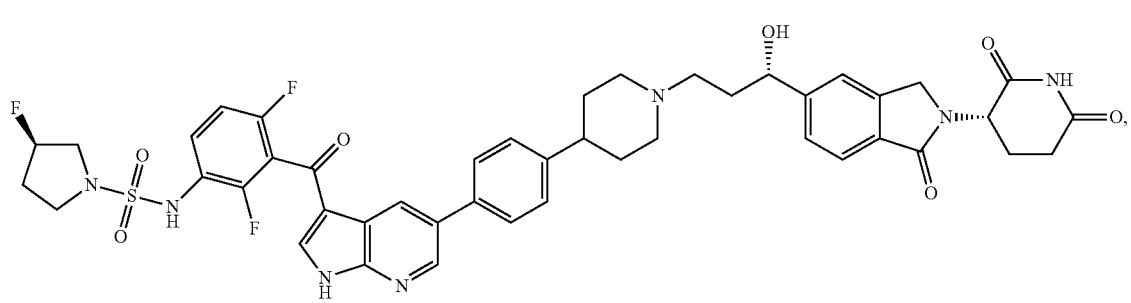
(71)
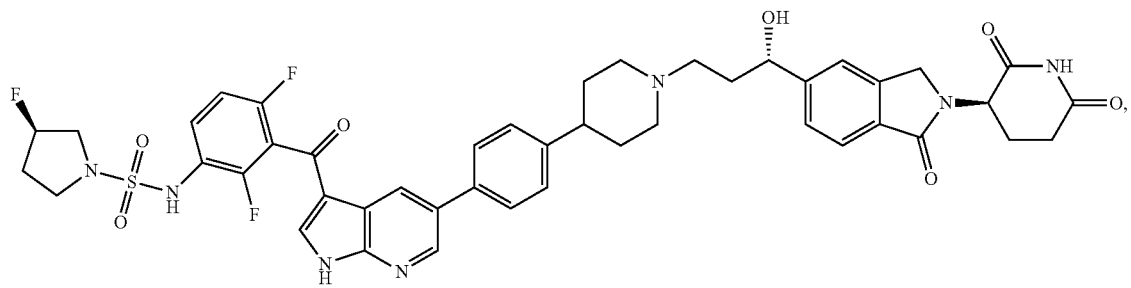
(72)

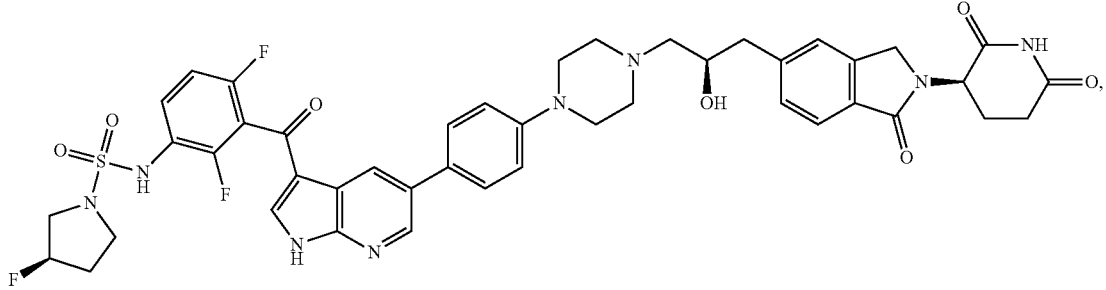
(73)
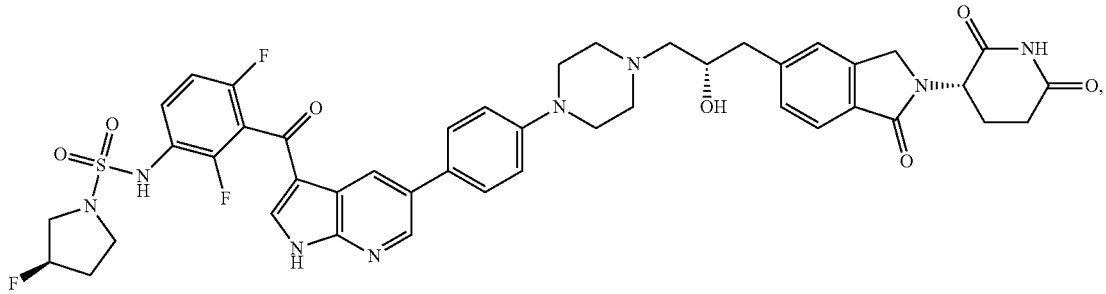
(74)
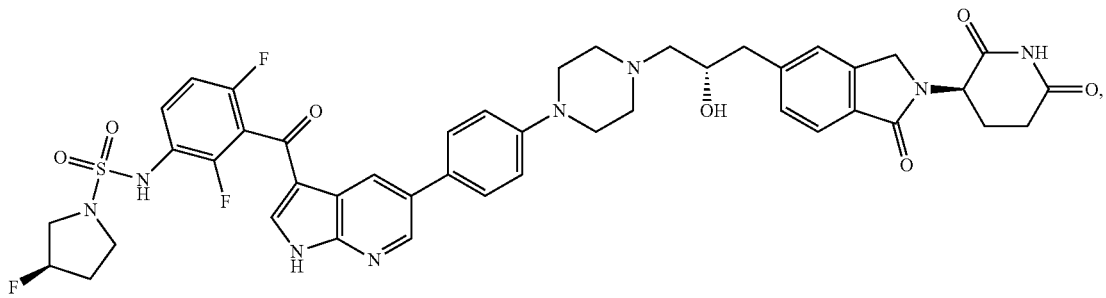
(75)
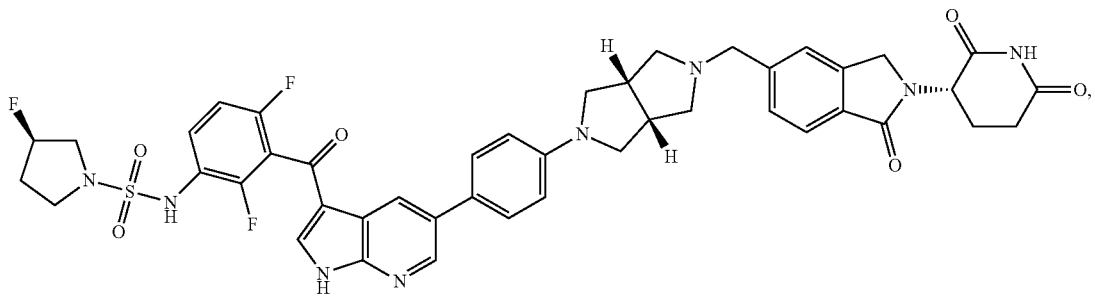
(76)
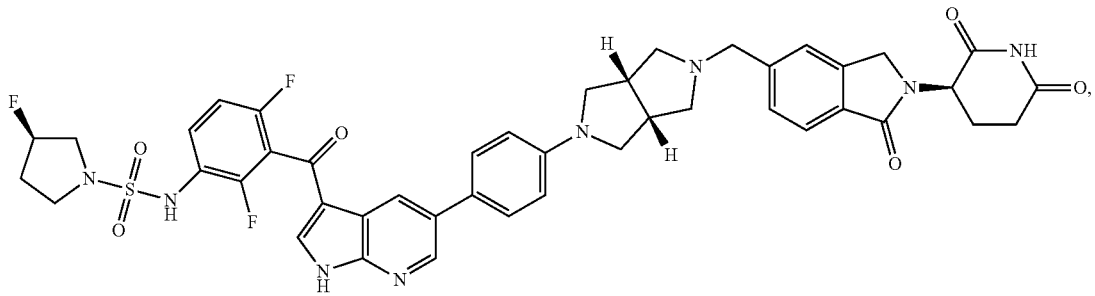
(77)

-continued
(78)
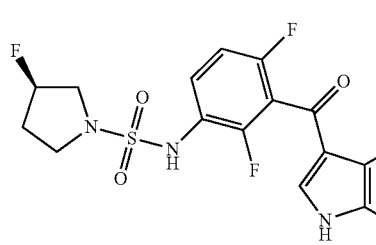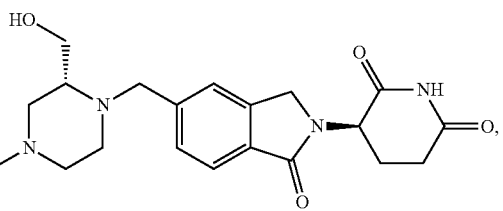
(79)
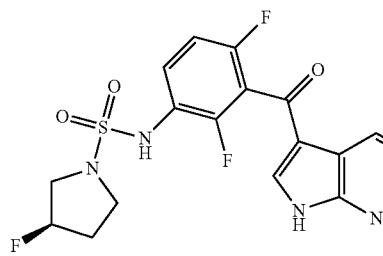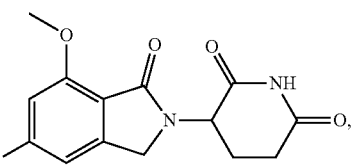
(80)
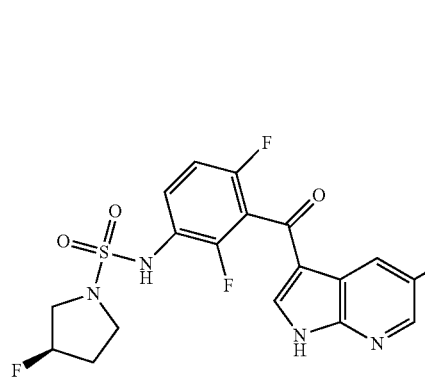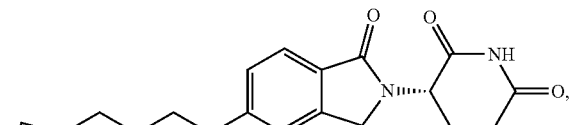
(81)
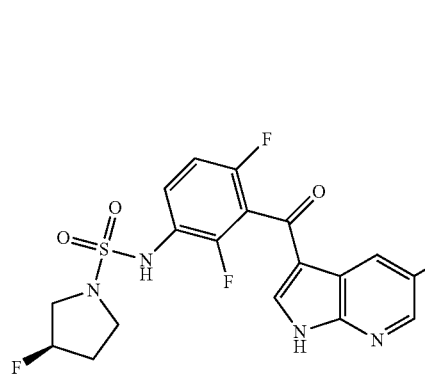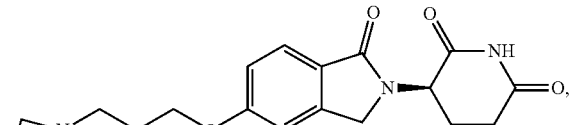

-continued
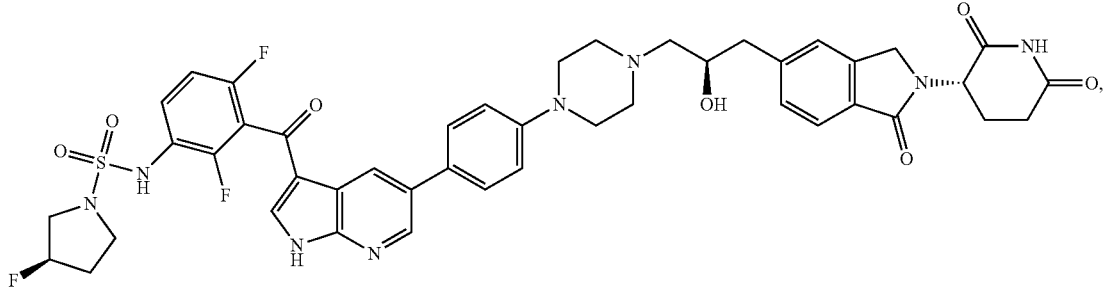
(82)
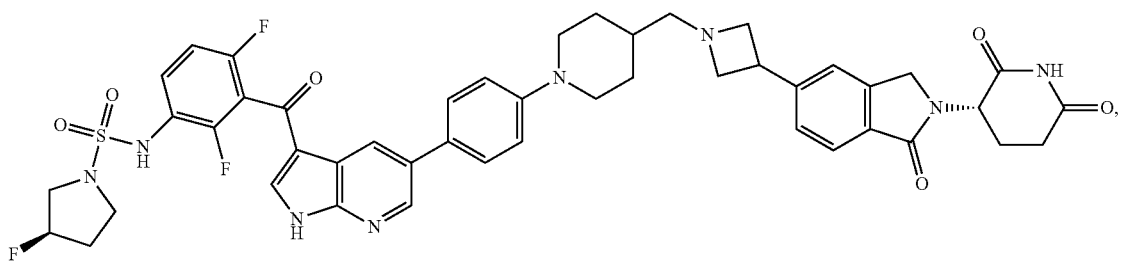
(83)
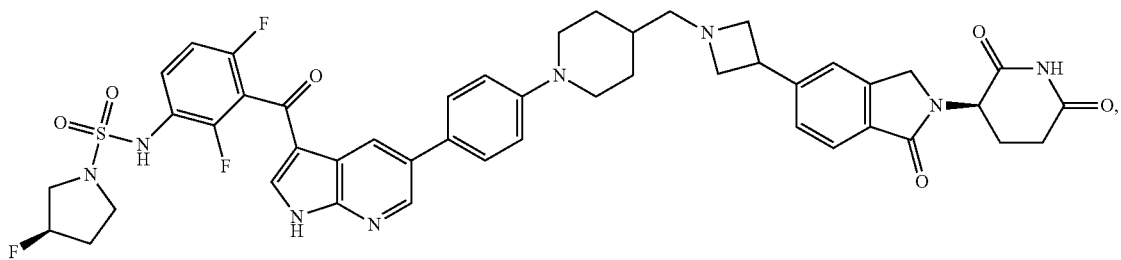
(84)
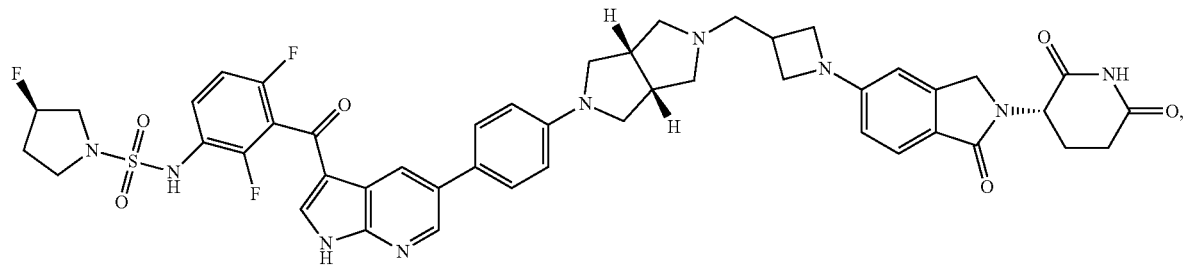
(85)
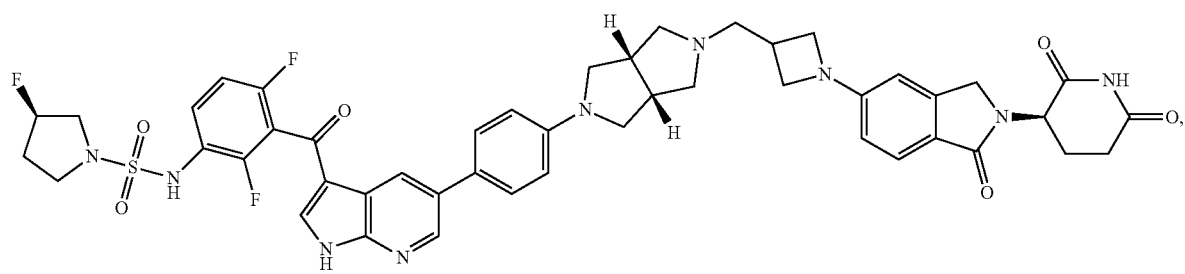
(86)

(87)
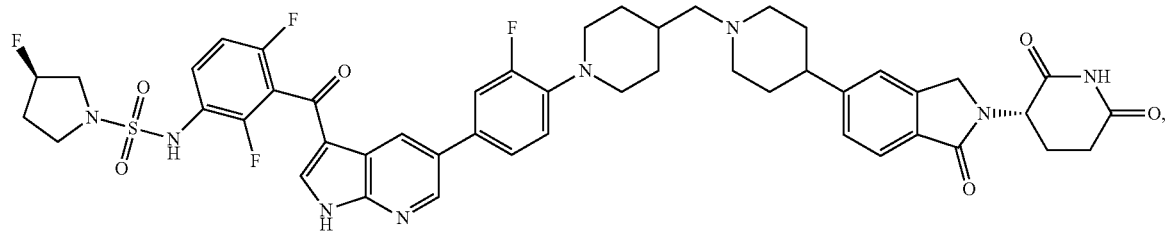
(88)
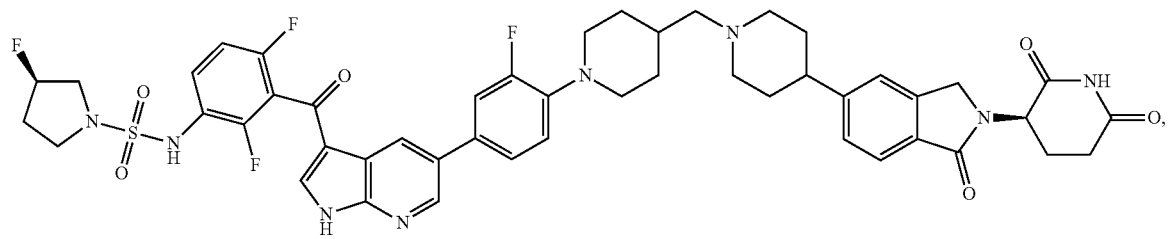
(89)
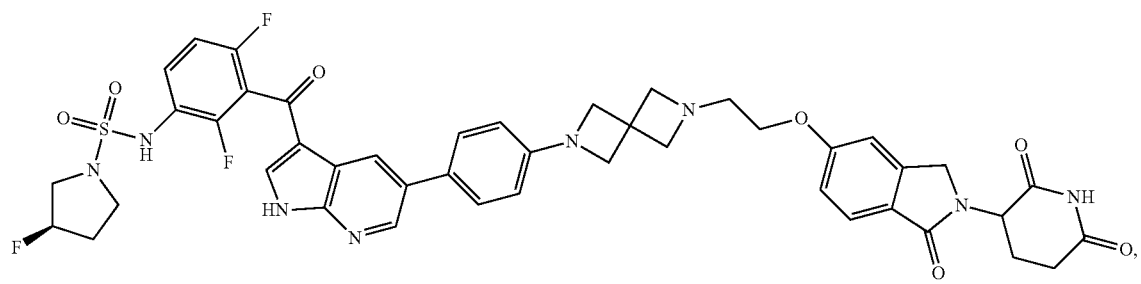
(90)
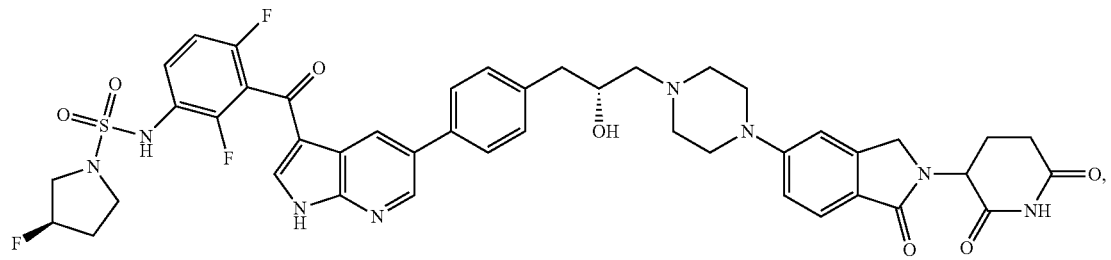
(91)
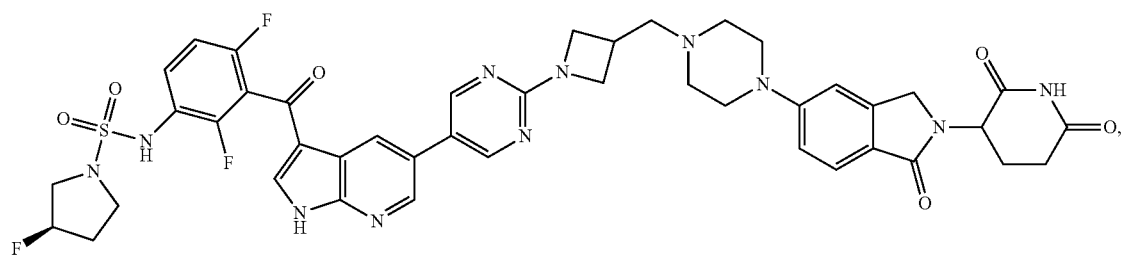

-continued
(92)
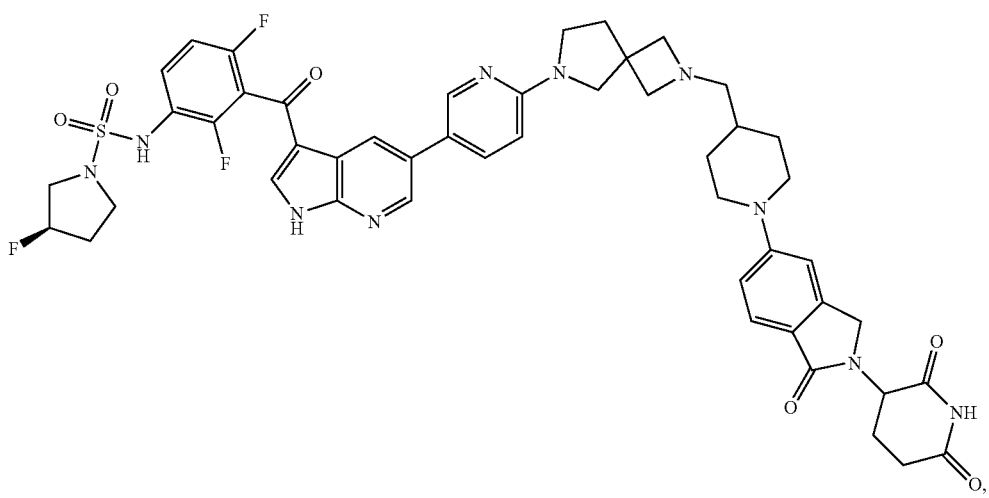
(93)
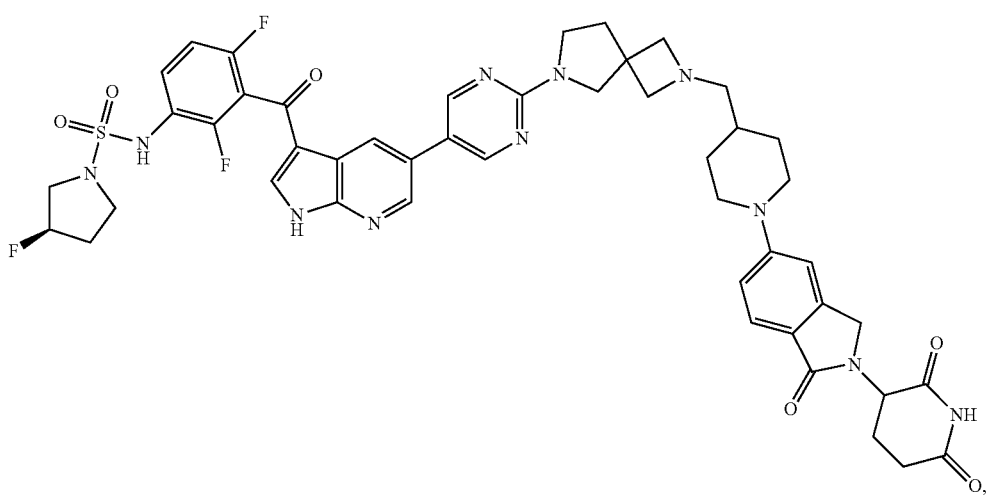
(94)
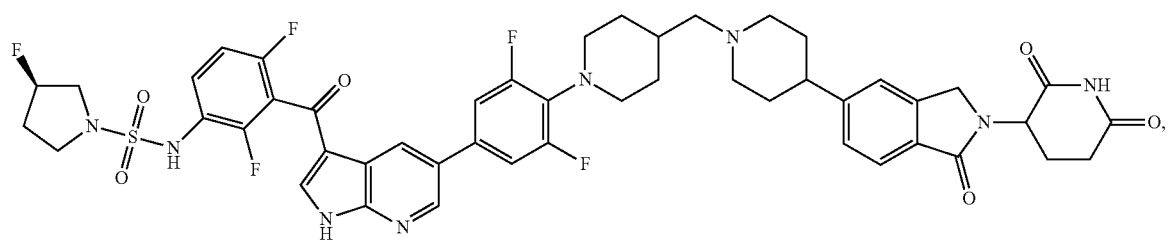
(95)
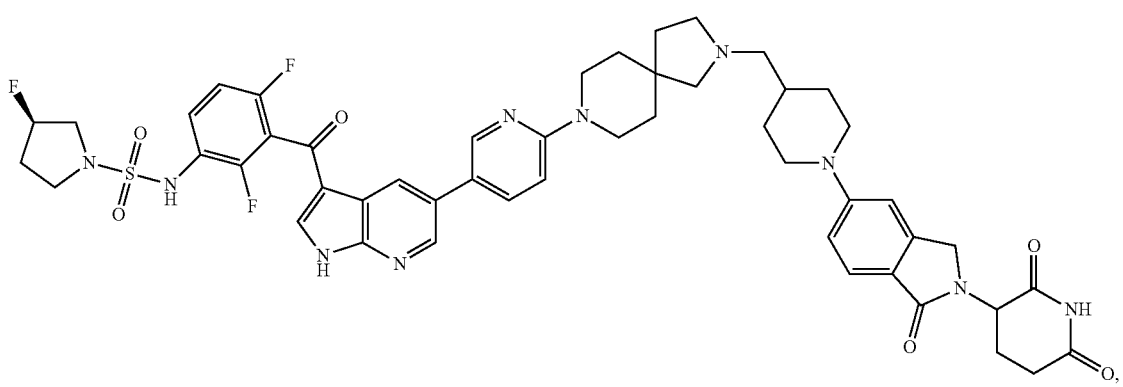

-continued
(96)
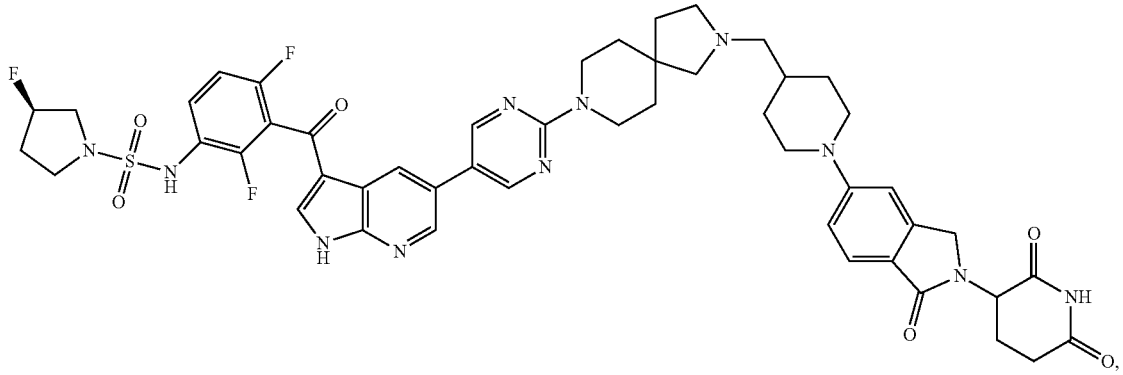
(97)
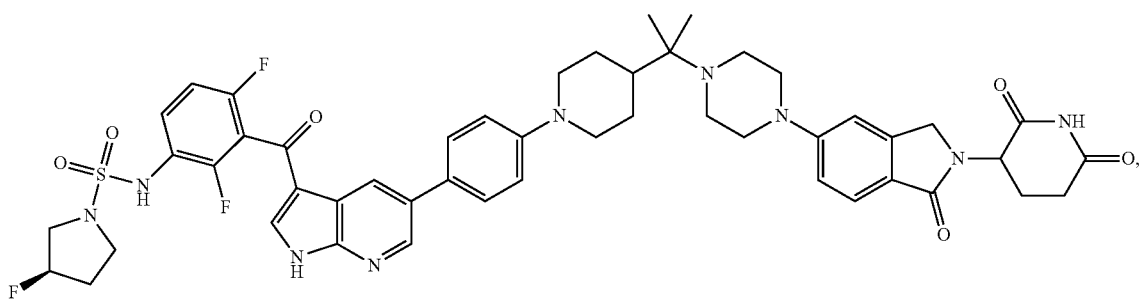
(98)
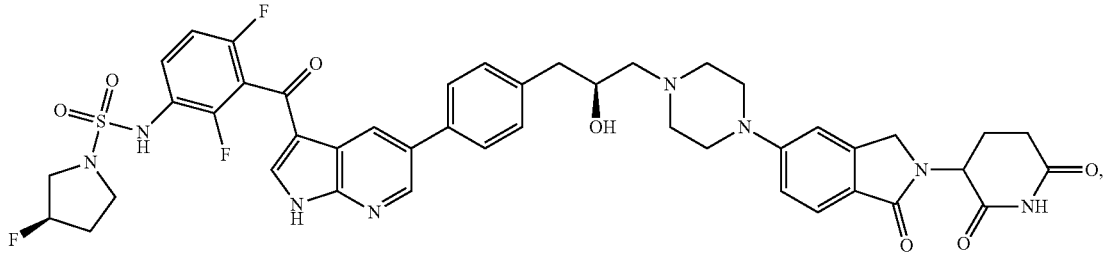
(99)
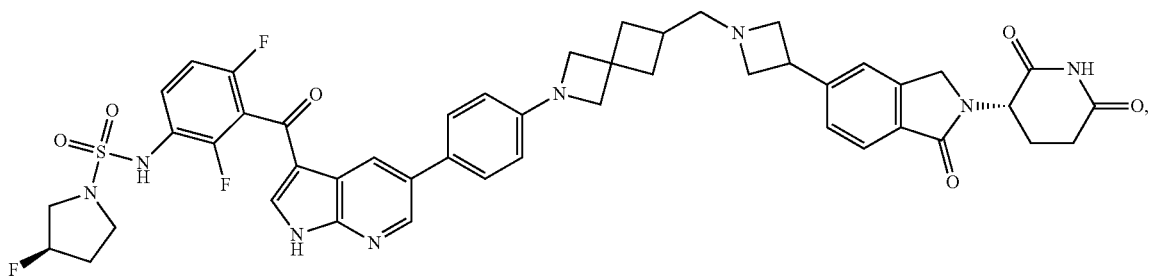
(100)
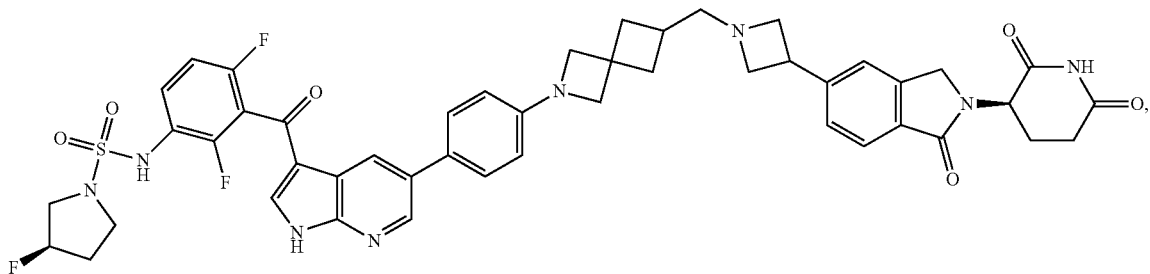

(101)
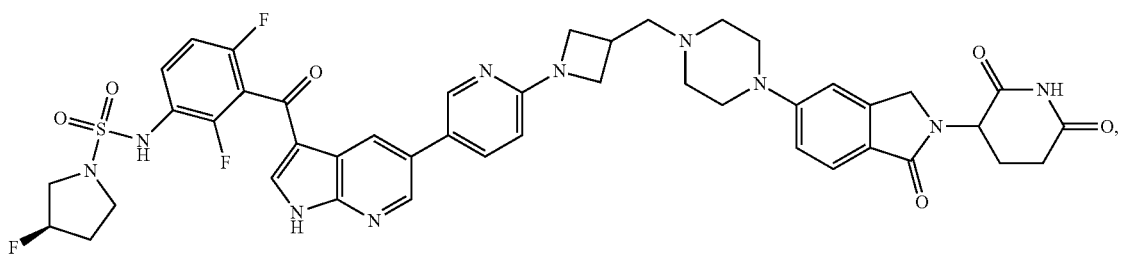
(102)
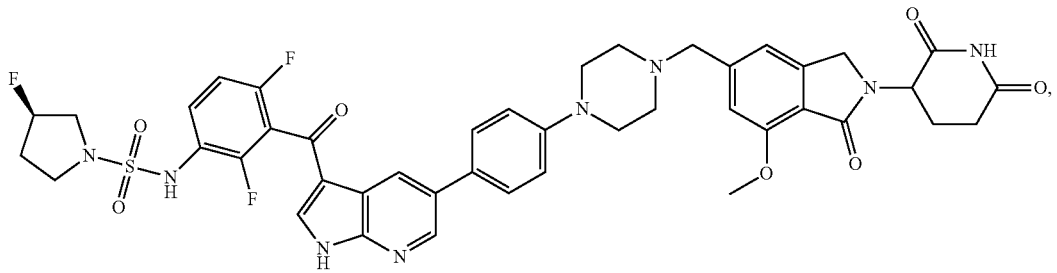
(103)
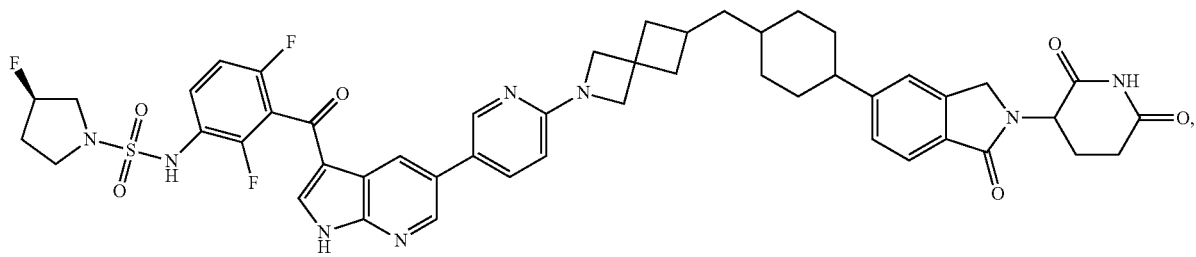
(104)
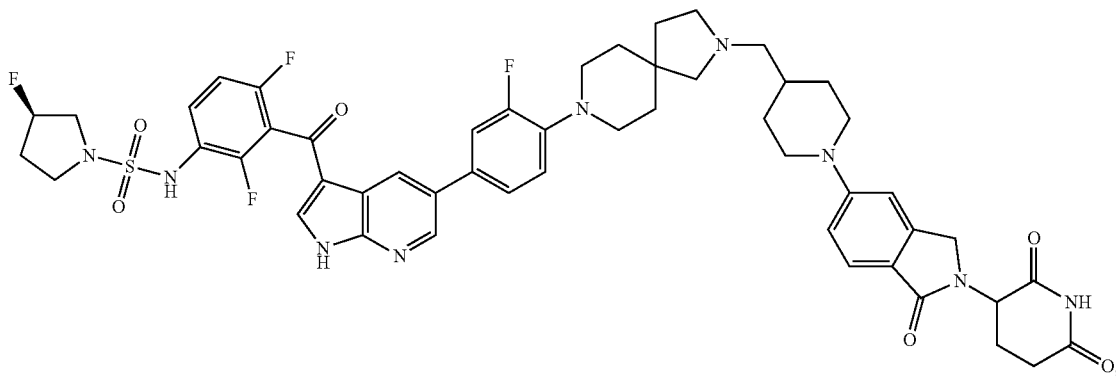
(105)
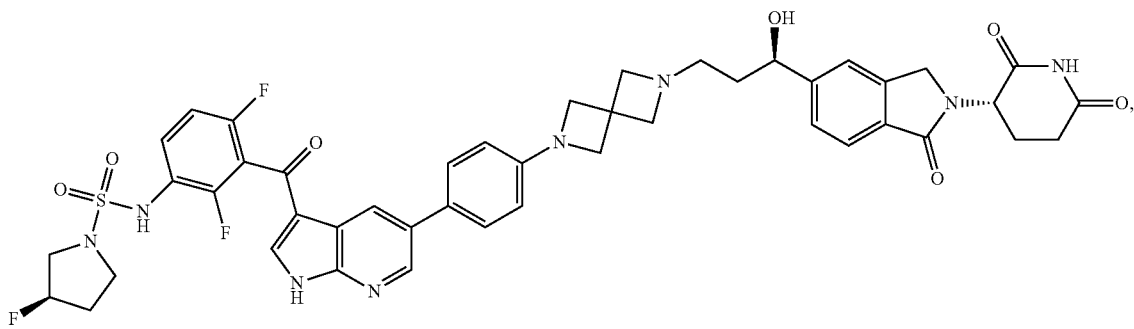

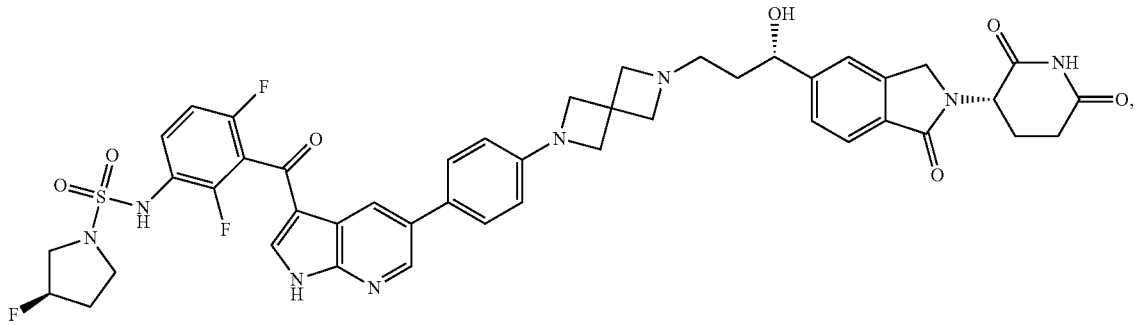
(106)
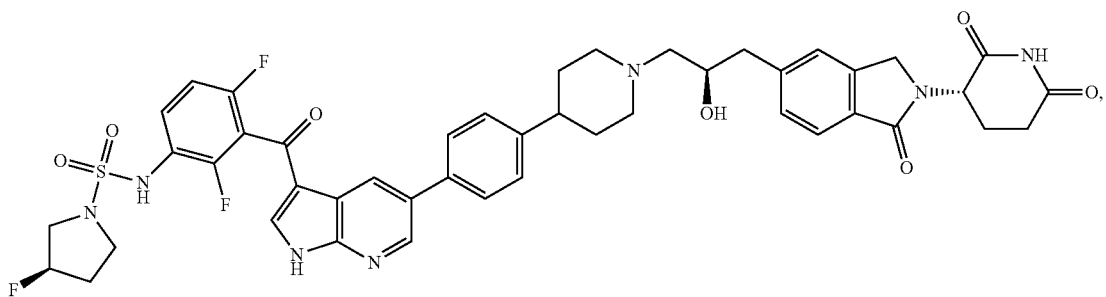
(107)
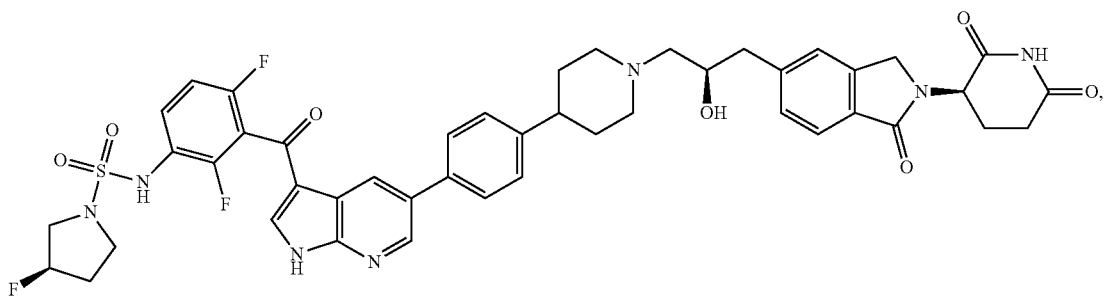
(108)
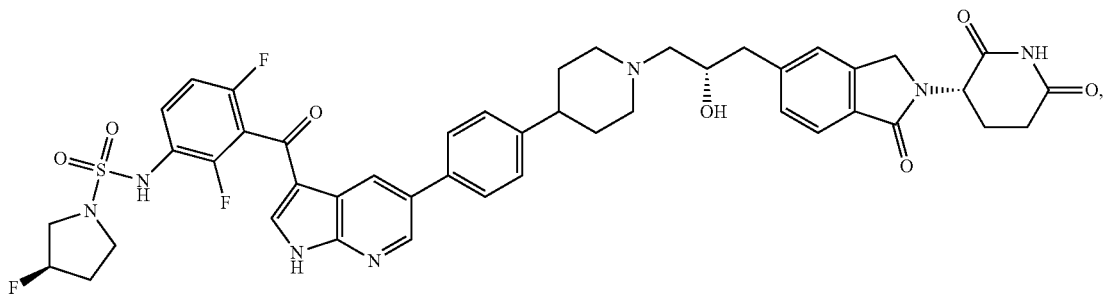
(109)

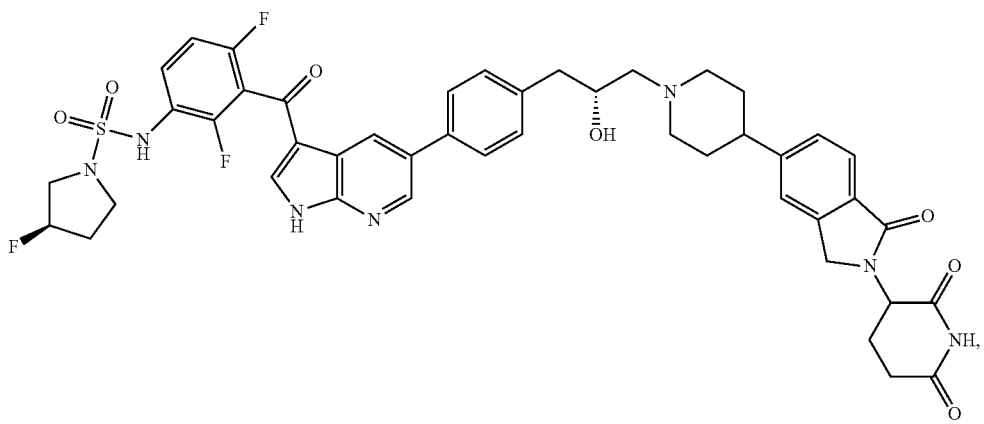 [SMILES: O=C1CCC(N2Cc3cc(C4CCN(C[C@H](O)Cc5ccc(-c6cnc7[nH]cc(C(=O)c8c(F)ccc(NS(=O)(=O)N9CC[C@@H](F)C9)c8F)c7c6)cc5)CC4)ccc3C2=O)C(=O)N1]
(110)
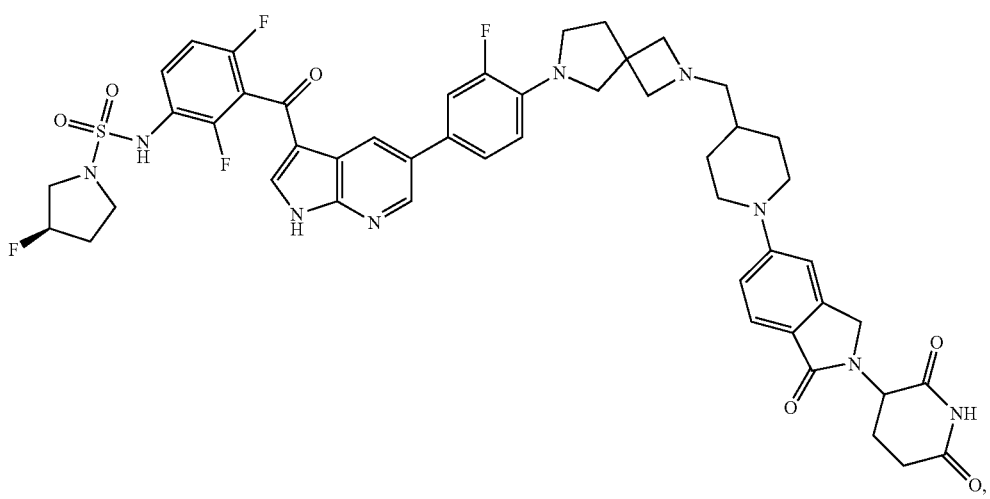
(111)
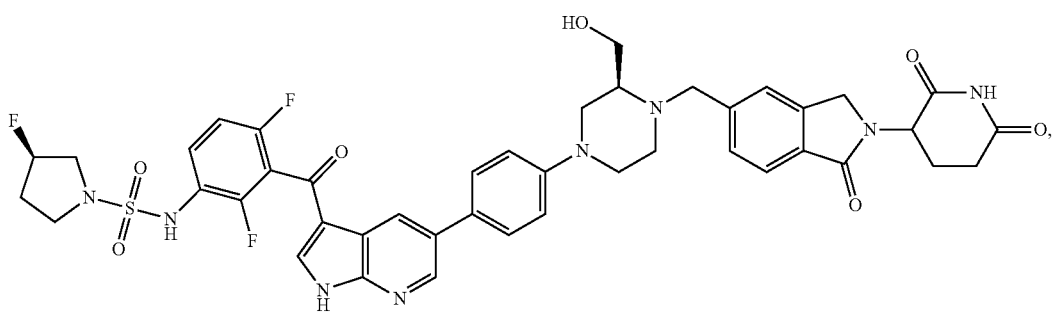
(112)
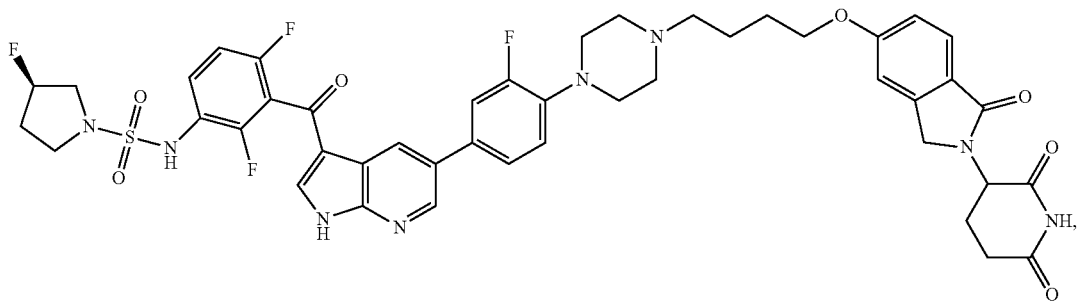
(113)

1025 1026
-continued
(114)
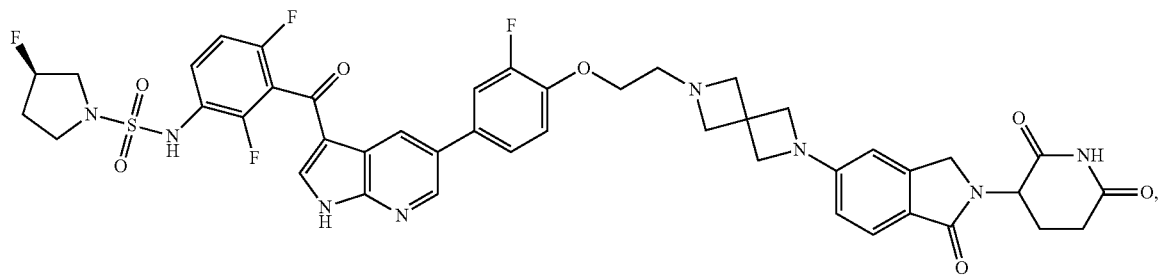
(115)
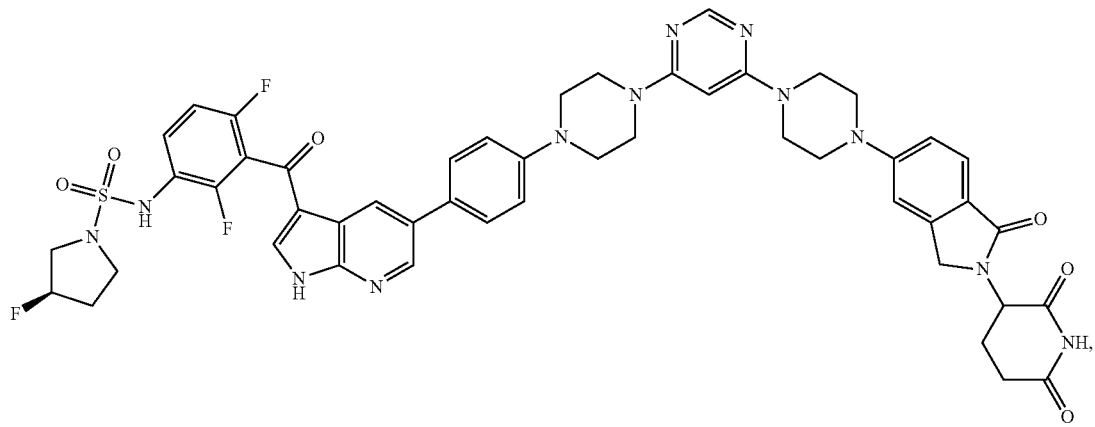
(116)
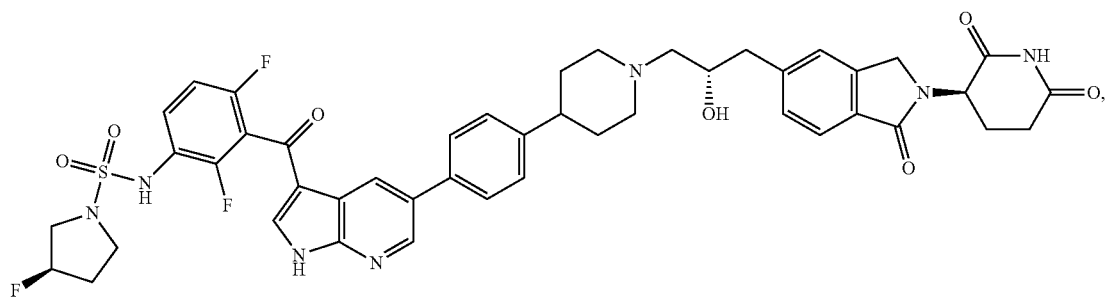
(117)
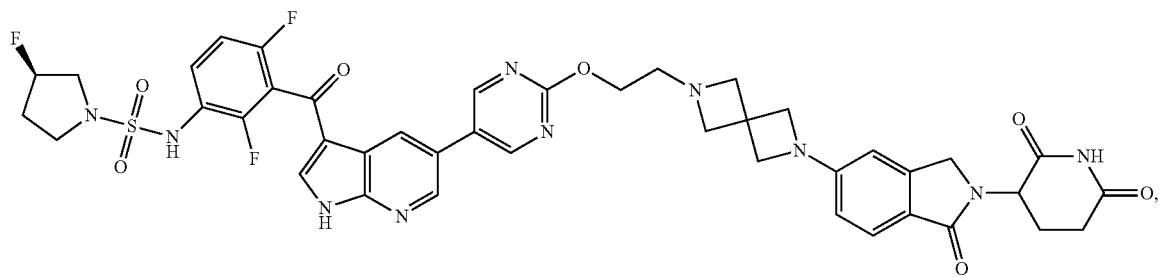

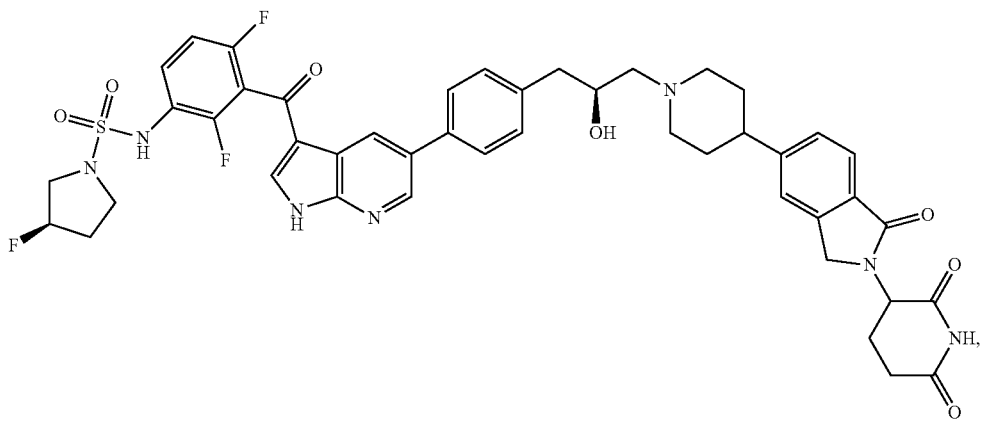 [SMILES: O=C1CCC(N2Cc3cc(C4CCN(C[C@@H](O)Cc5ccc(-c6cnc7[nH]cc(C(=O)c8c(F)ccc(NS(=O)(=O)N9CC[C@@H](F)C9)c8F)c7c6)cc5)CC4)ccc3C2=O)C(=O)N1]
(118)
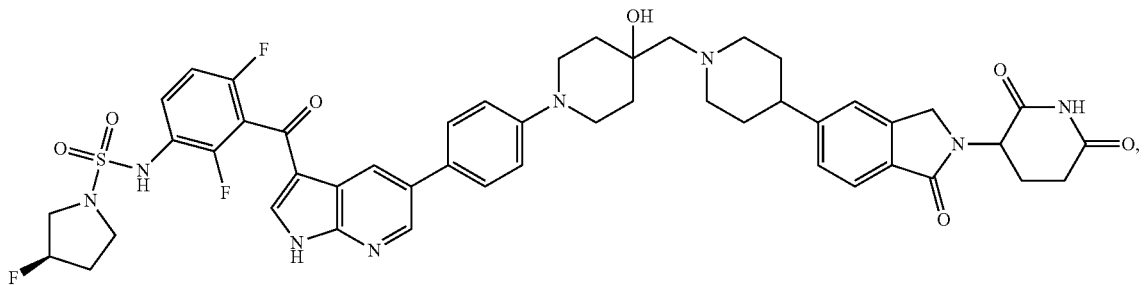
(119)
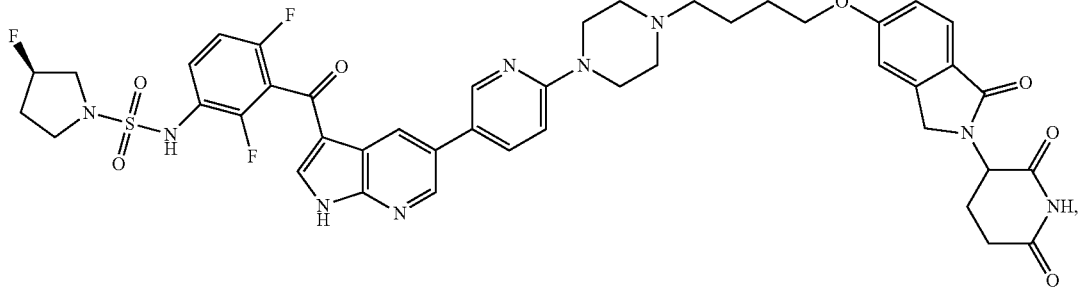
(120)
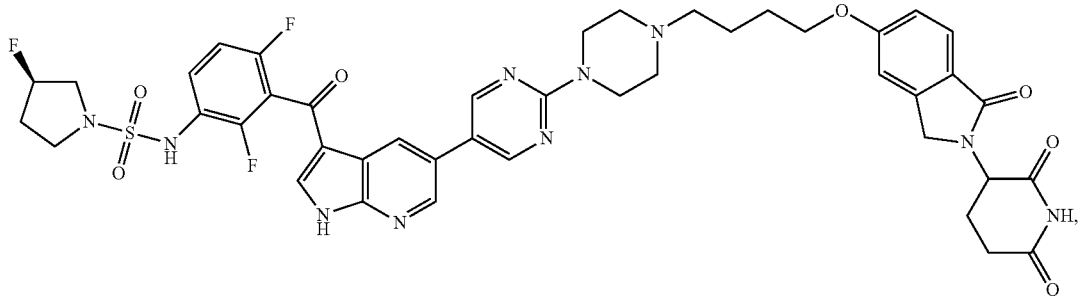
(121)

-continued
(122)
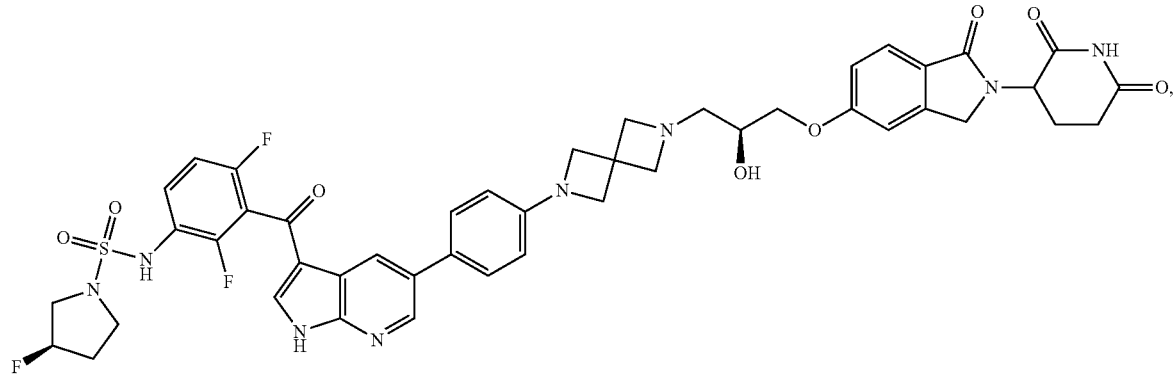
(123)
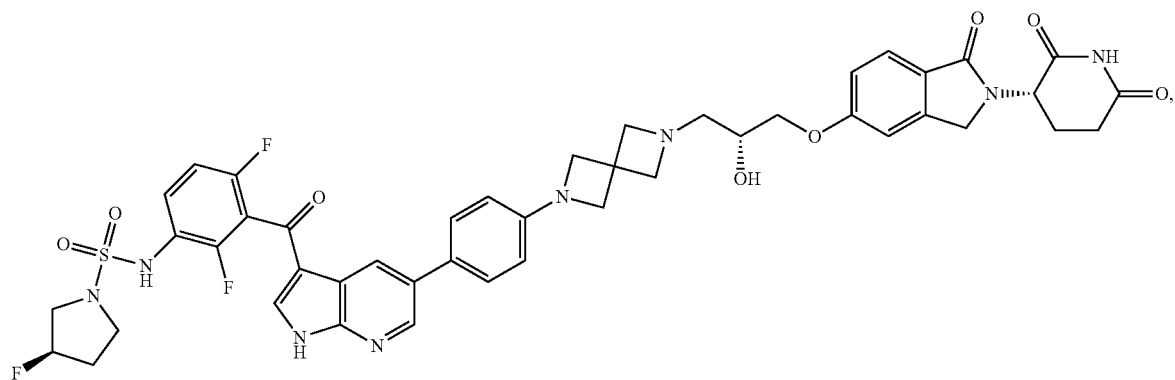
(124)
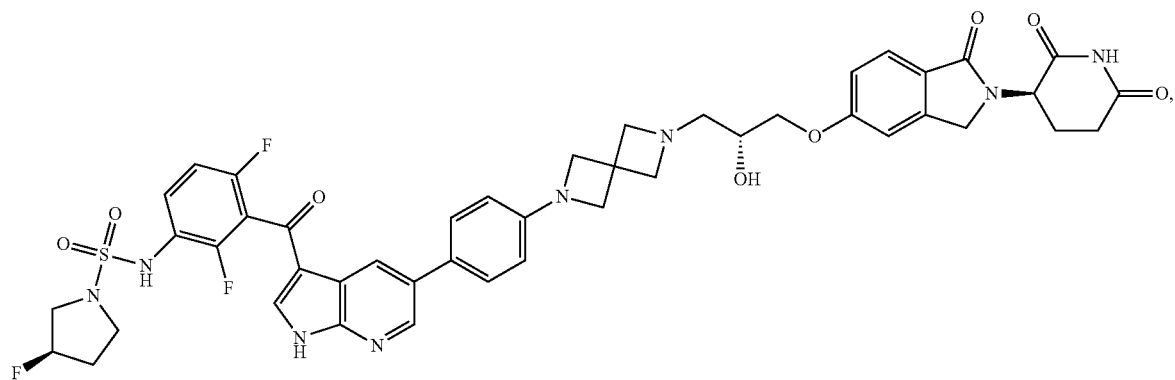
(125)
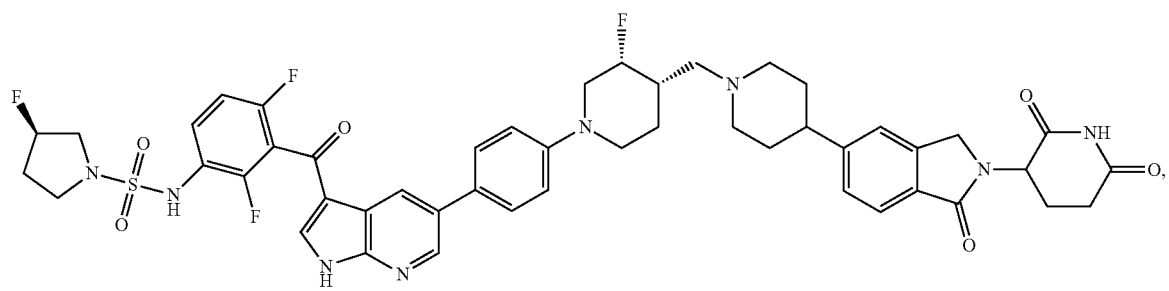

(126)
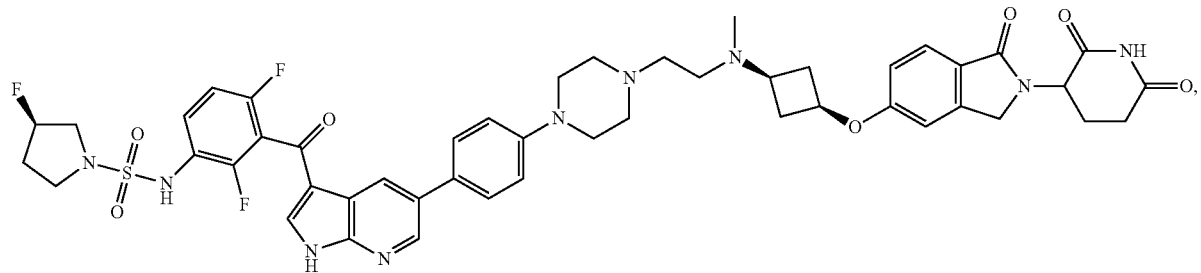
(127)
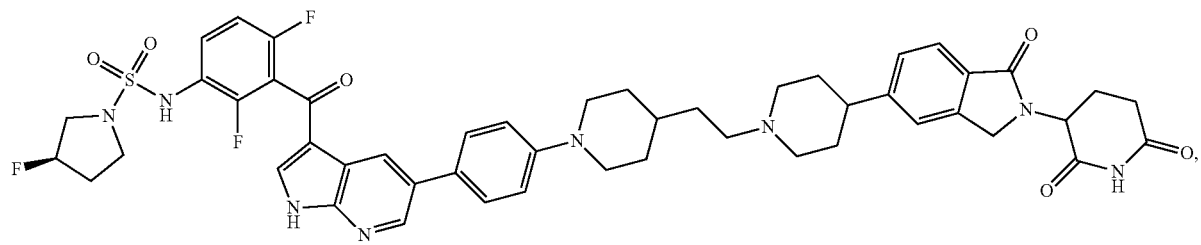
(128)
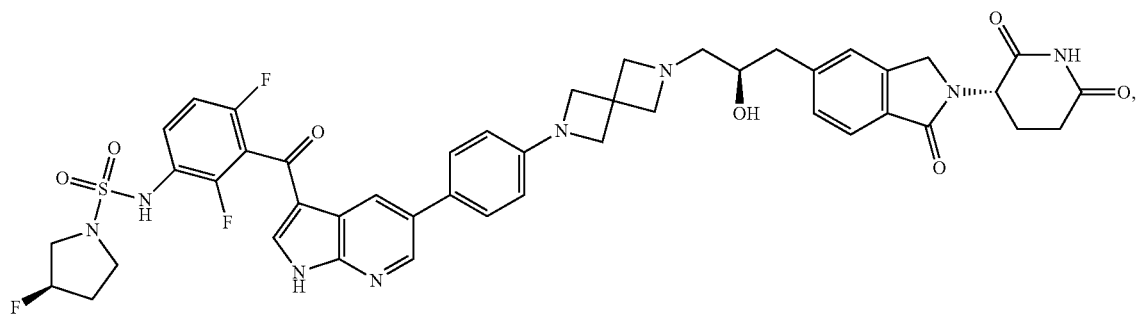
(129)
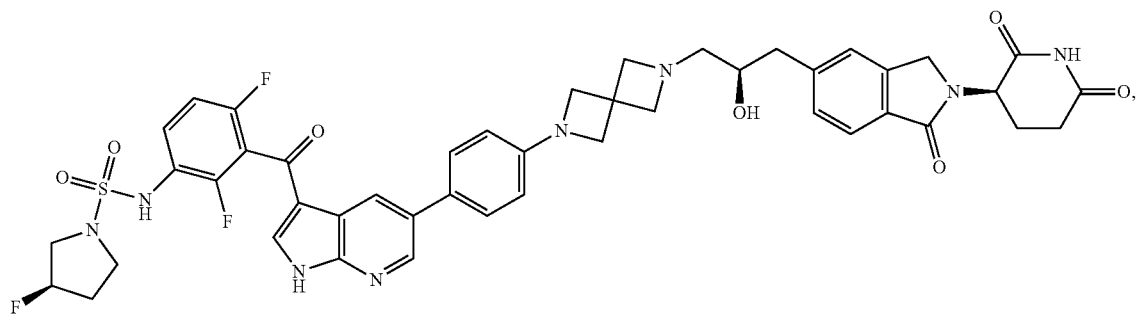
(130)
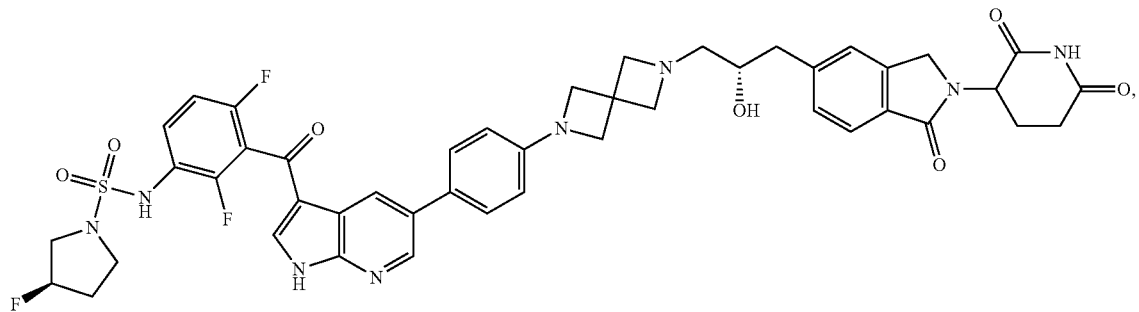

-continued
(131)
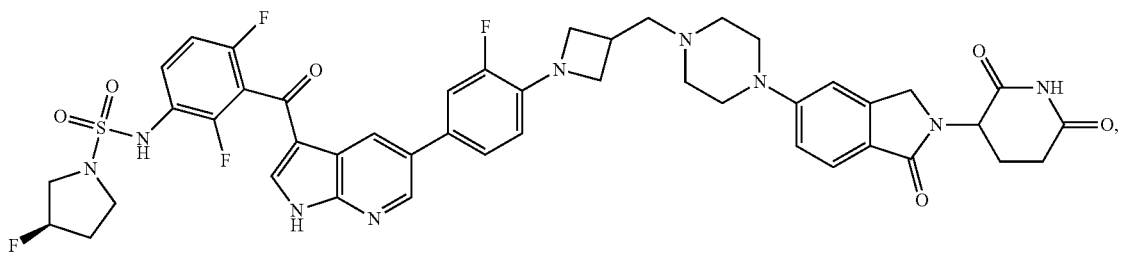
(132)
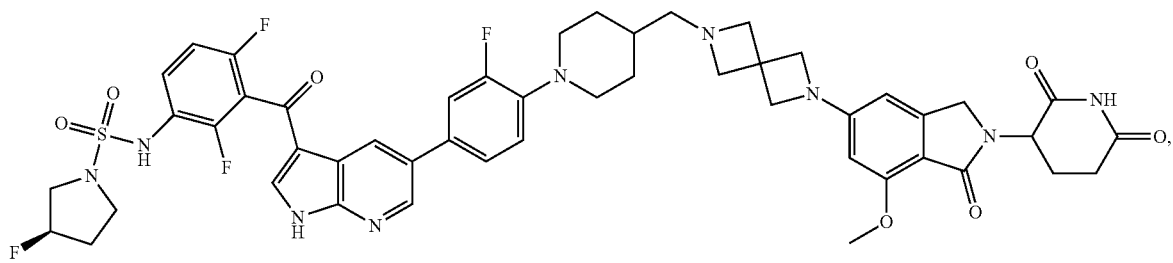
(133)
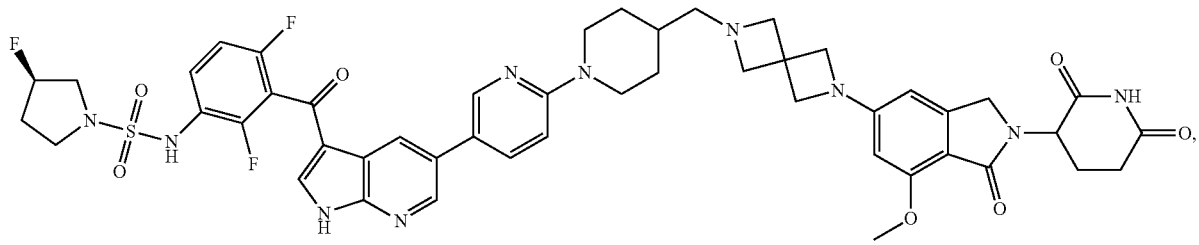
(134)
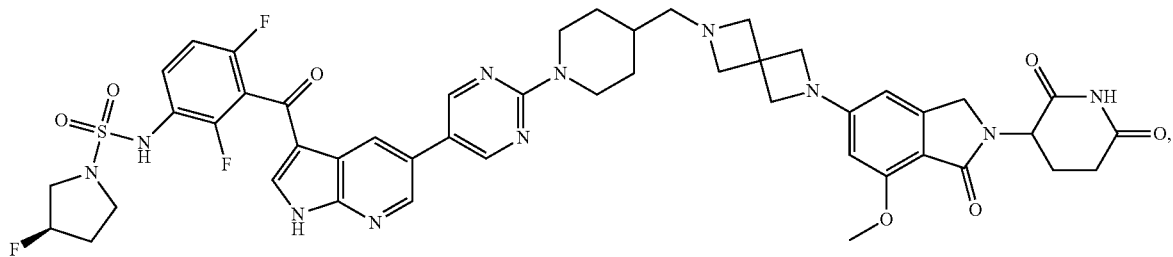
(135)
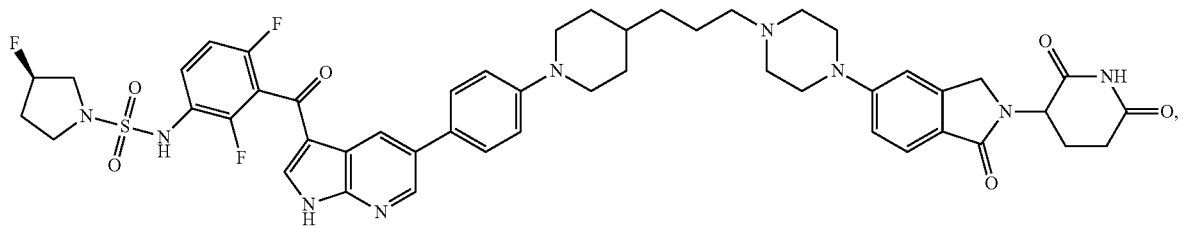

-continued
(136)
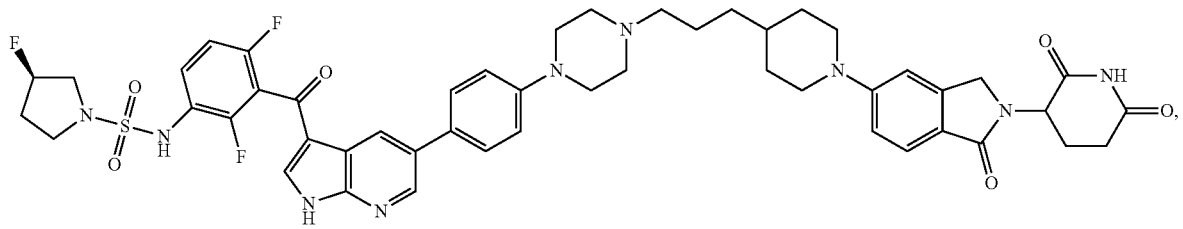
(137)
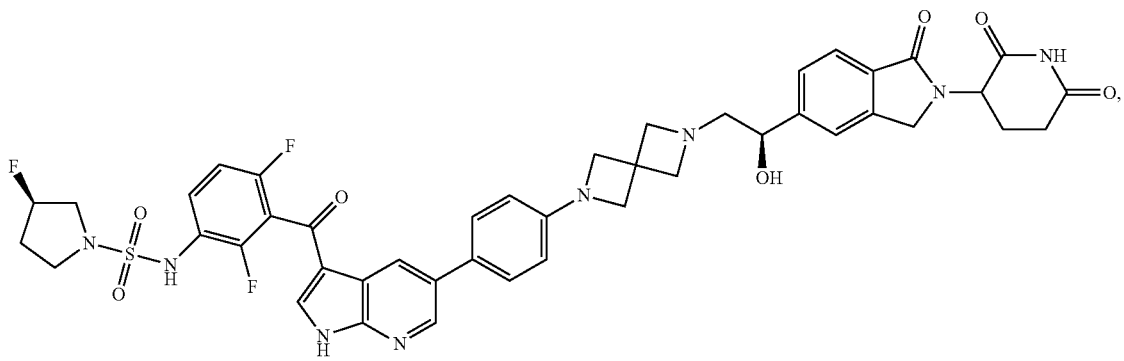
(138)
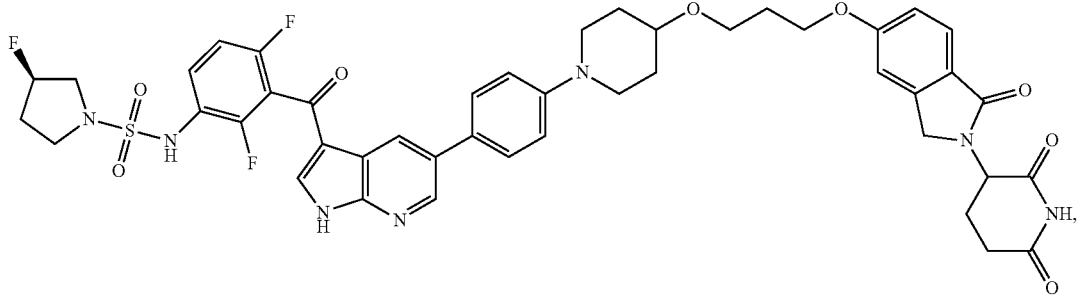
(139)
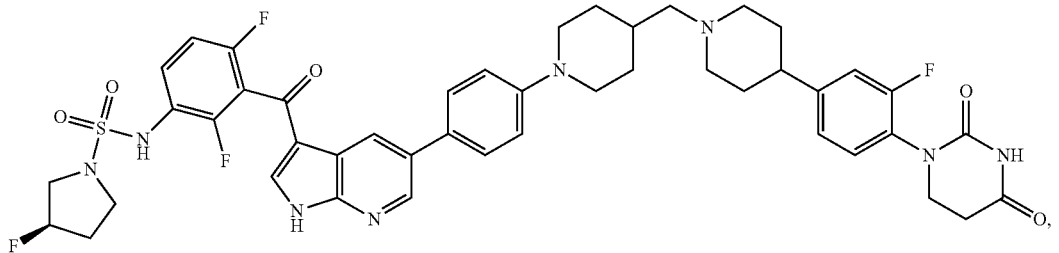
(140)

1037 1038
-continued
(141)
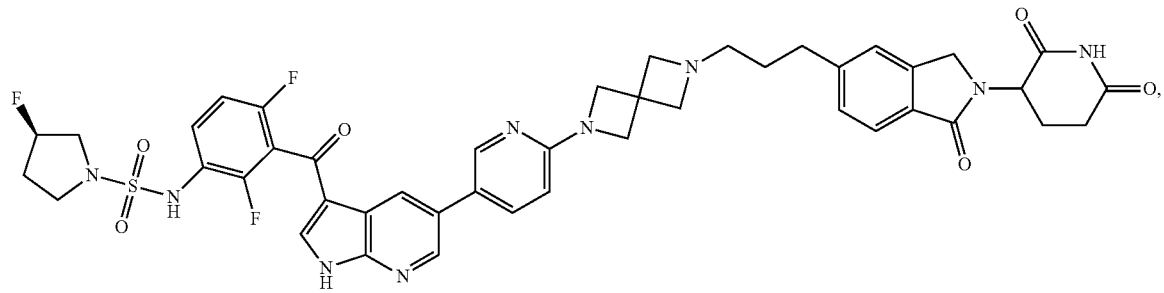
(142)
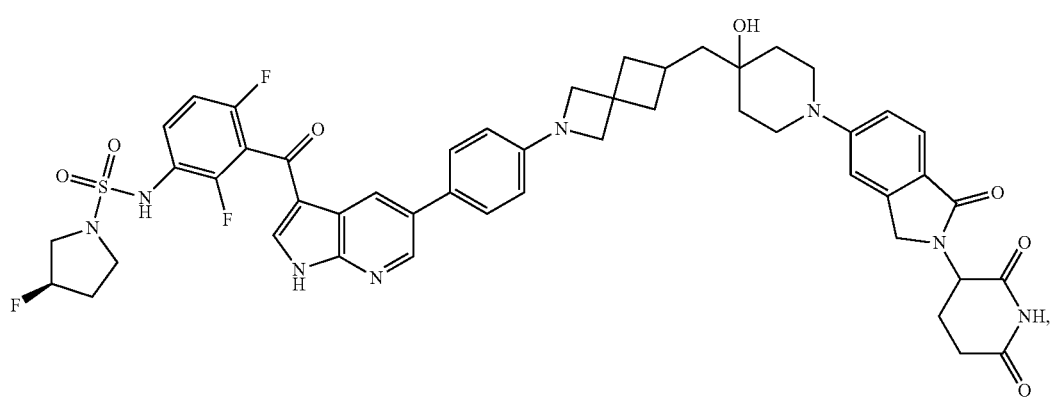
(143)
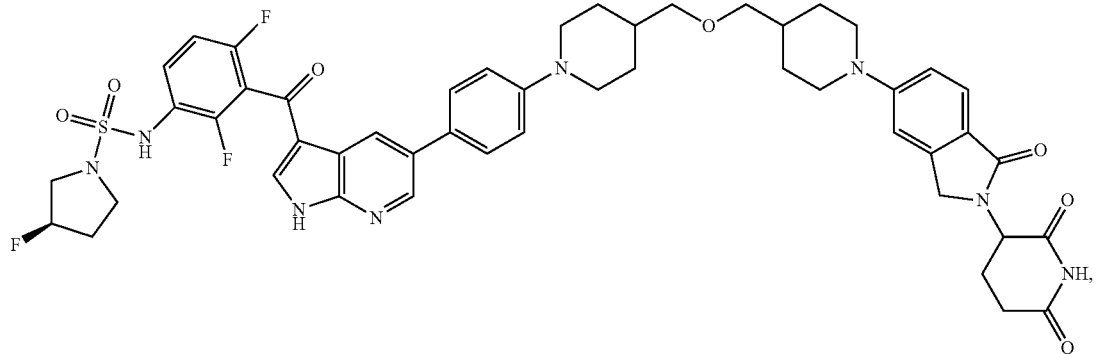 [SMILES: O=C1CCC(N2Cc3cc(N4CCC(COCC5CCN(c6ccc(-c7cnc8[nH]cc(C(=O)c9c(F)ccc(NS(=O)(=O)N%10CC[C@@H](F)C%10)c9F)c8c7)cc6)CC5)CC4)ccc3C2=O)C(=O)N1]
(144)
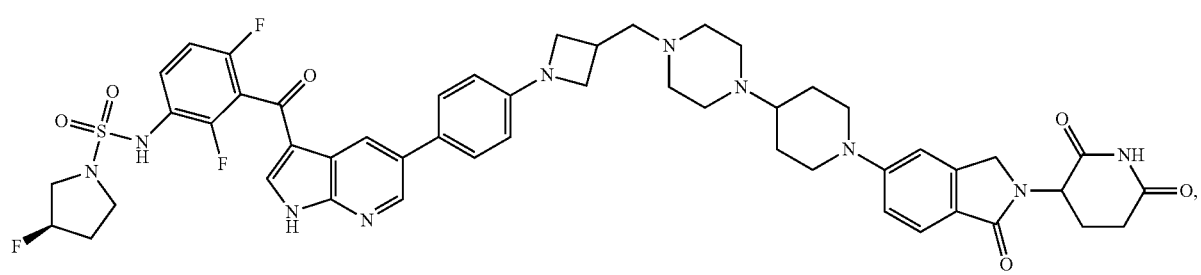 [SMILES: O=C1CCC(N2Cc3cc(N4CCC(N5CCN(CC6CN(c7ccc(-c8cnc9[nH]cc(C(=O)c%10c(F)ccc(NS(=O)(=O)N%11CC[C@@H](F)C%11)c%10F)c9c8)cc7)C6)CC5)CC4)ccc3C2=O)C(=O)N1]

-continued
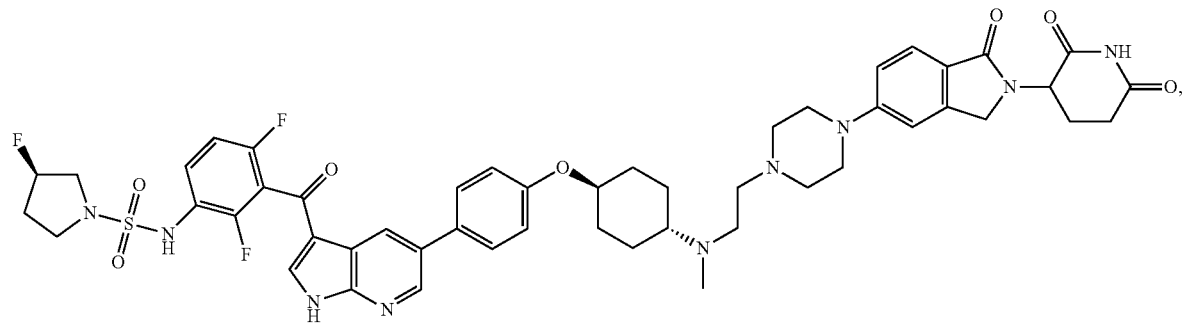
(145)
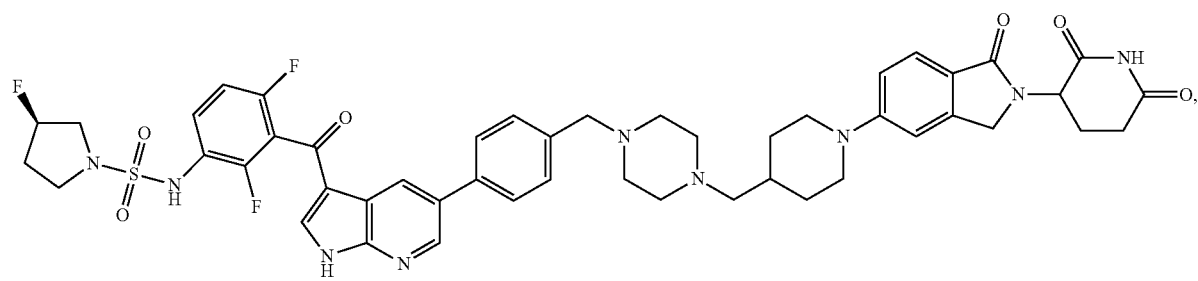
(146)
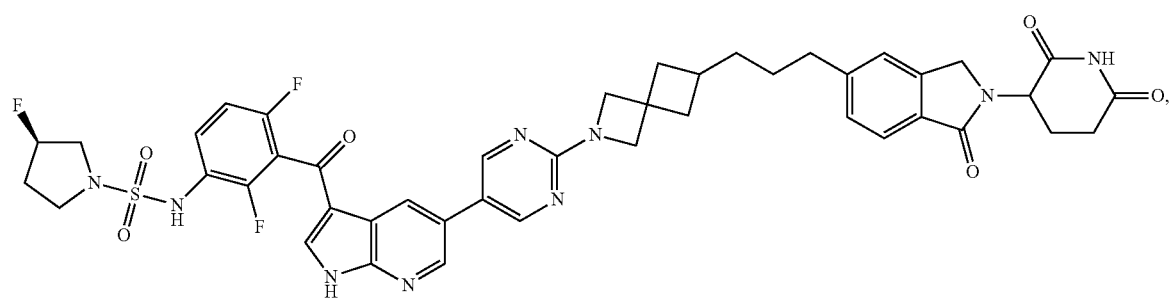
(147)
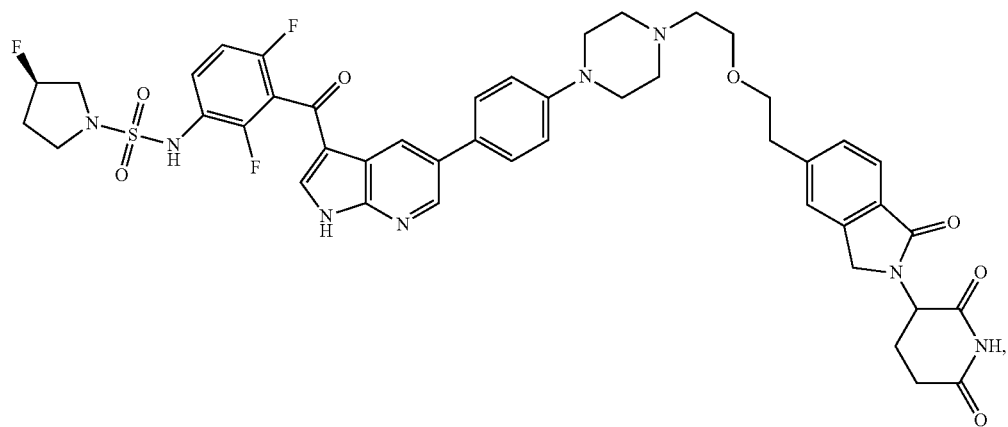
(148)

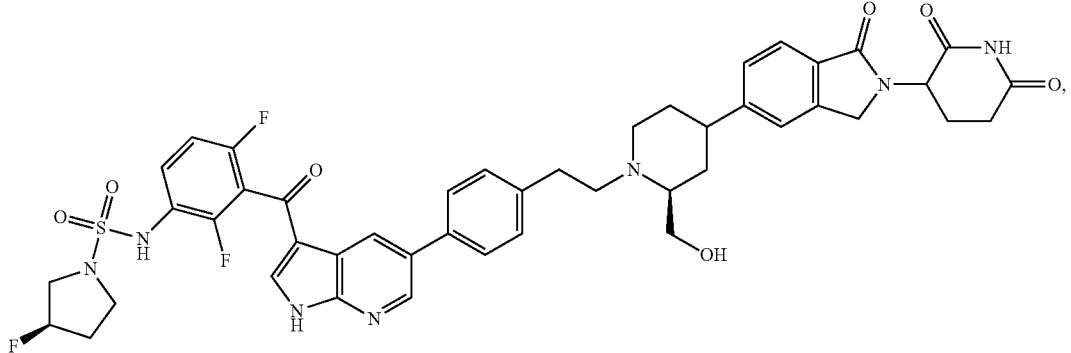
(149)
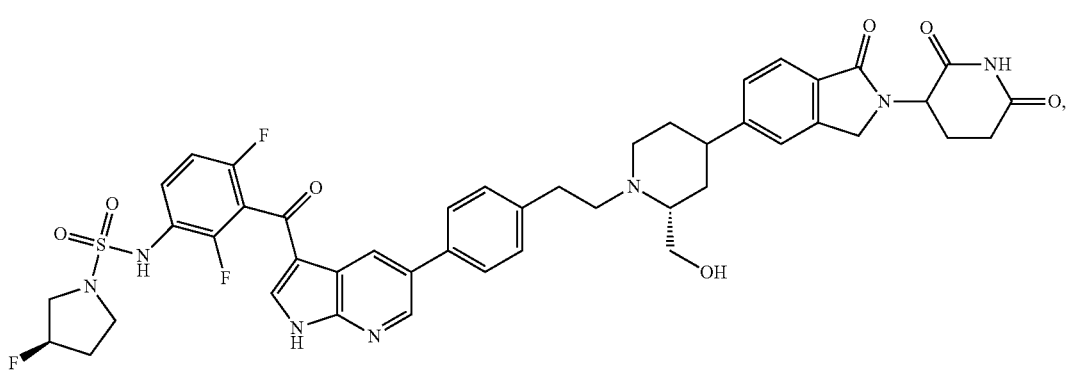
(150)
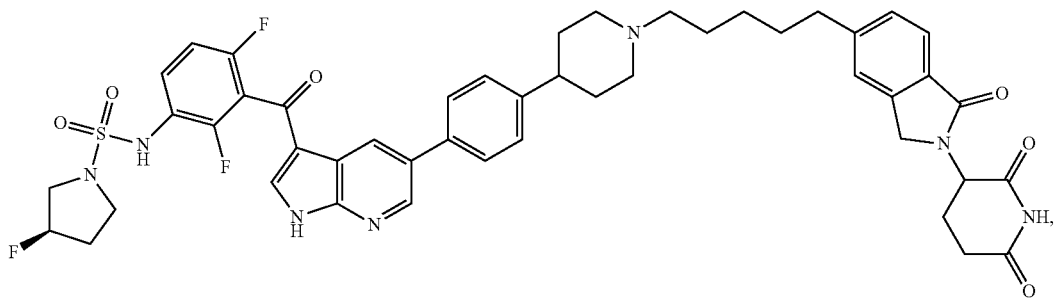
(151)
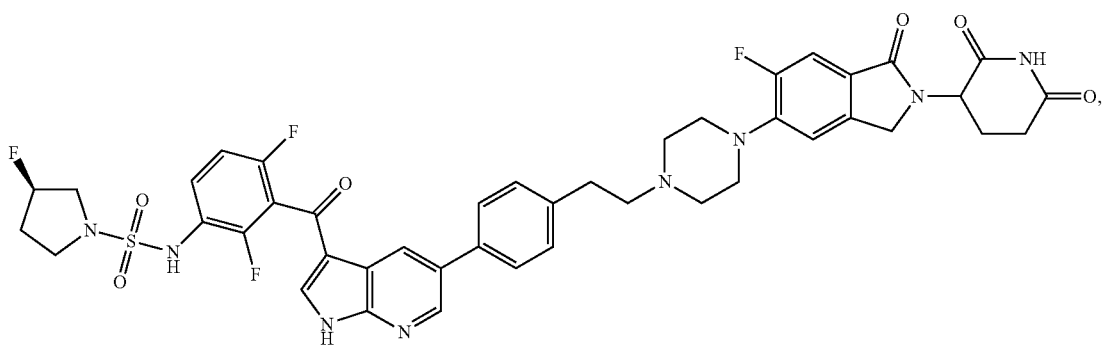
(152)

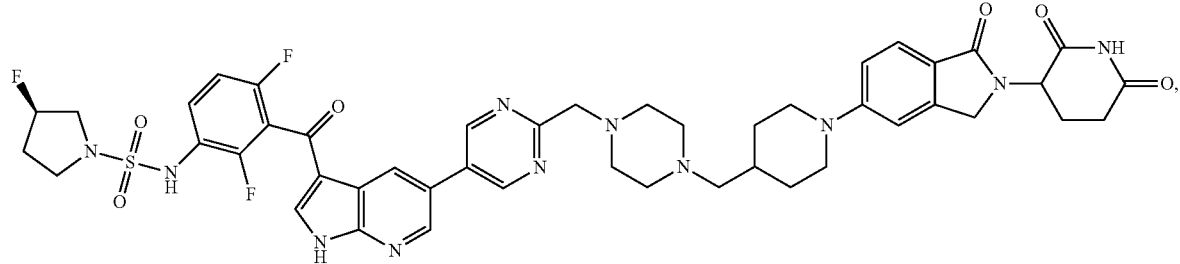
(153)
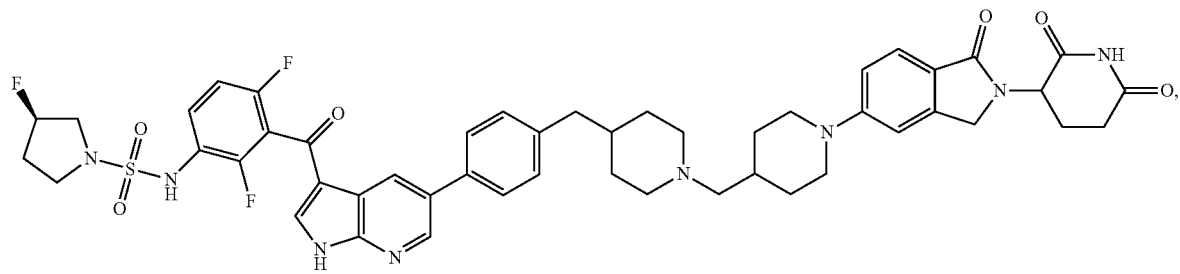
(154)
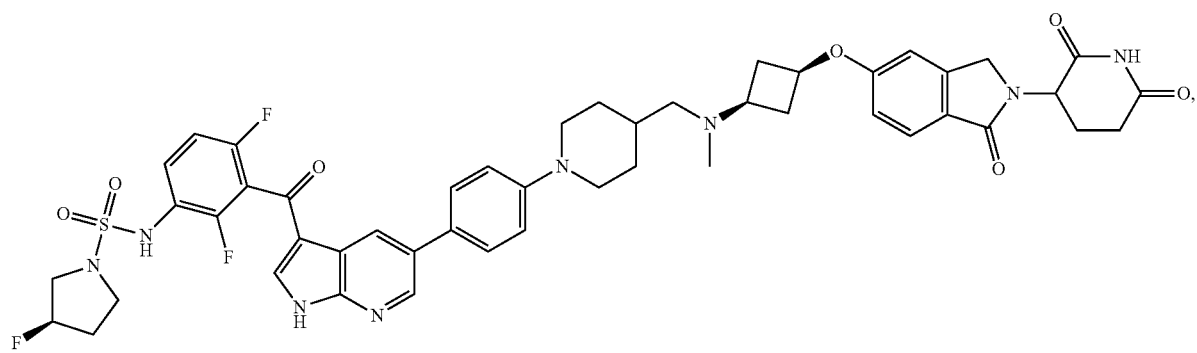
(155)
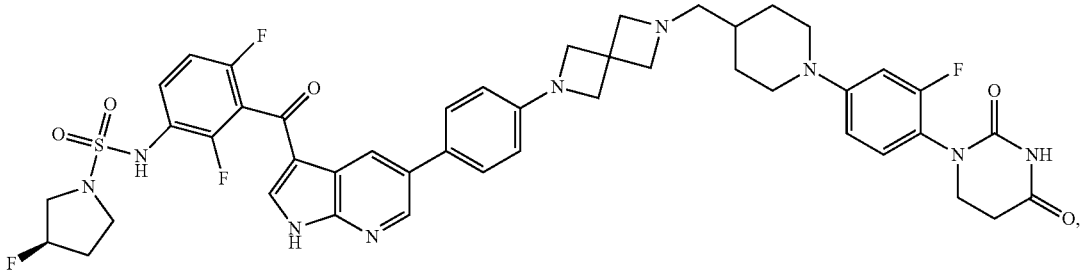
(156)
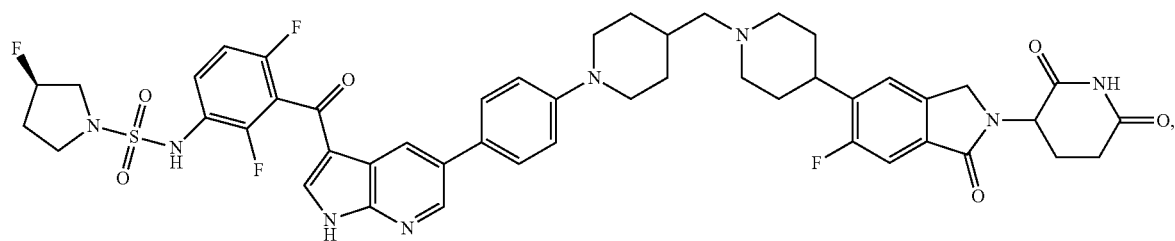
(157)

(158)
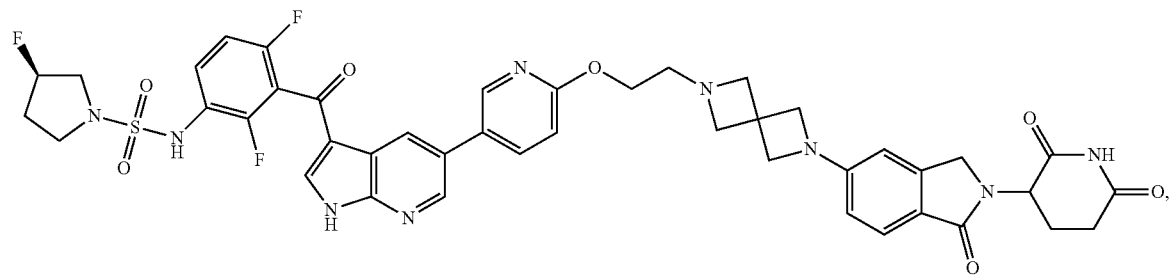
(159)
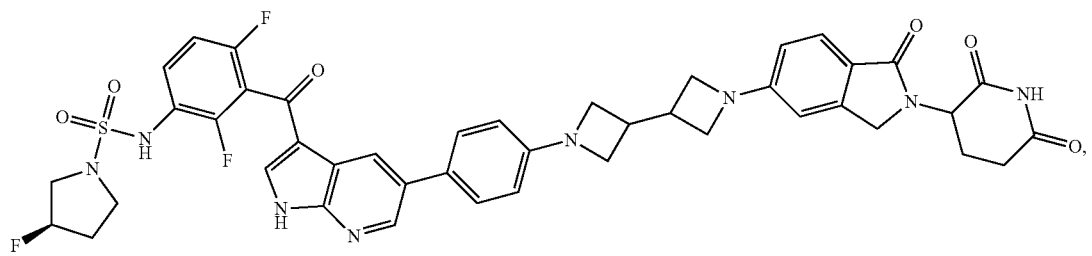
(160)
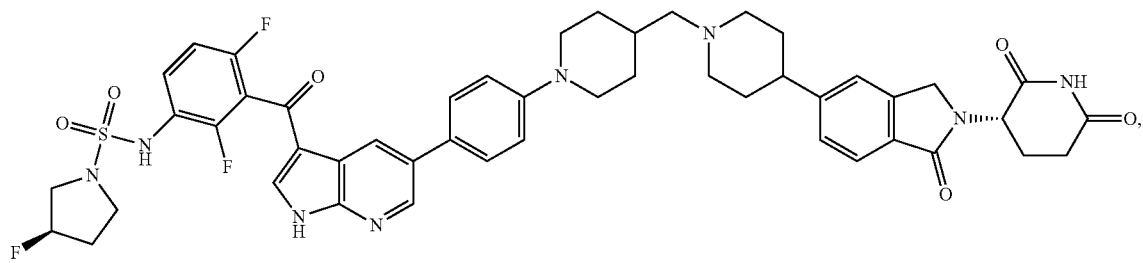
(161)
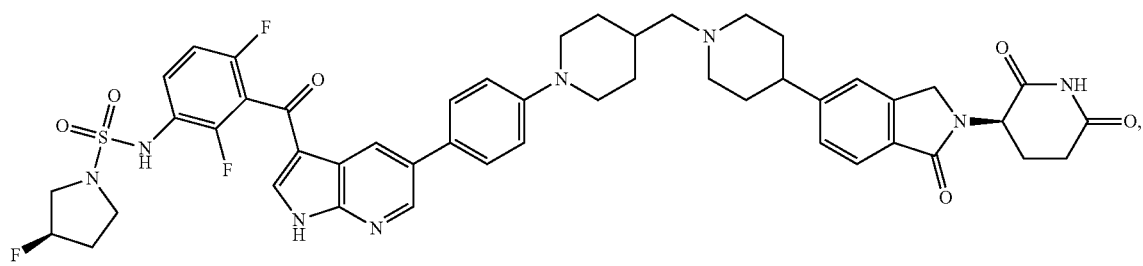
(162)
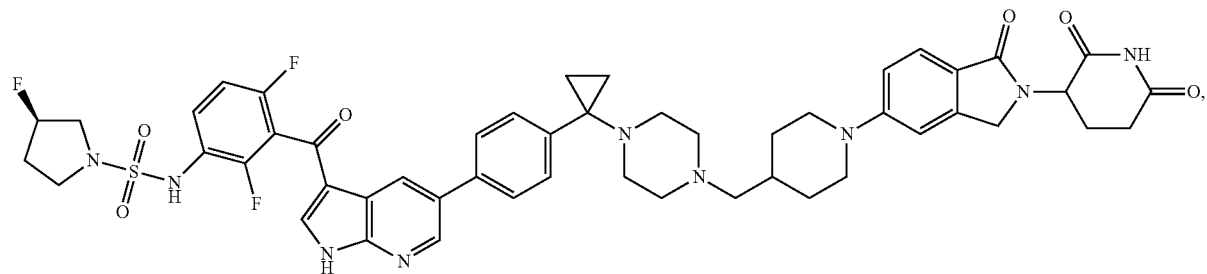

(163)
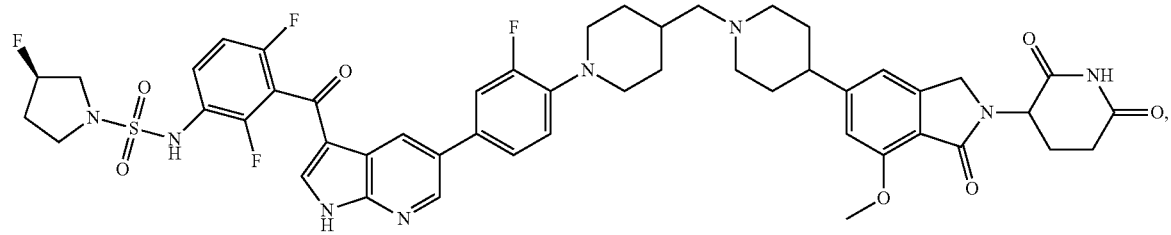
(164)
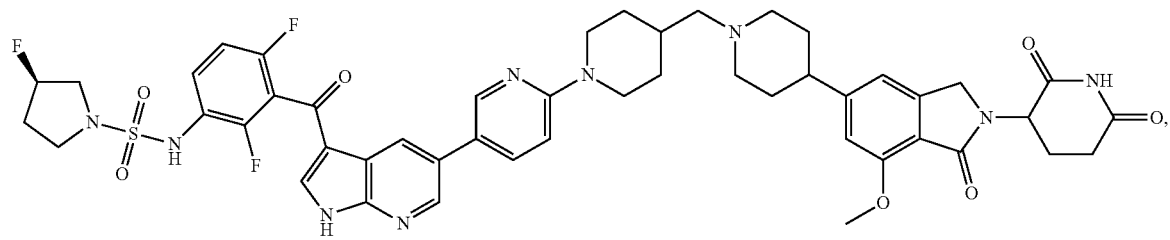
(165)
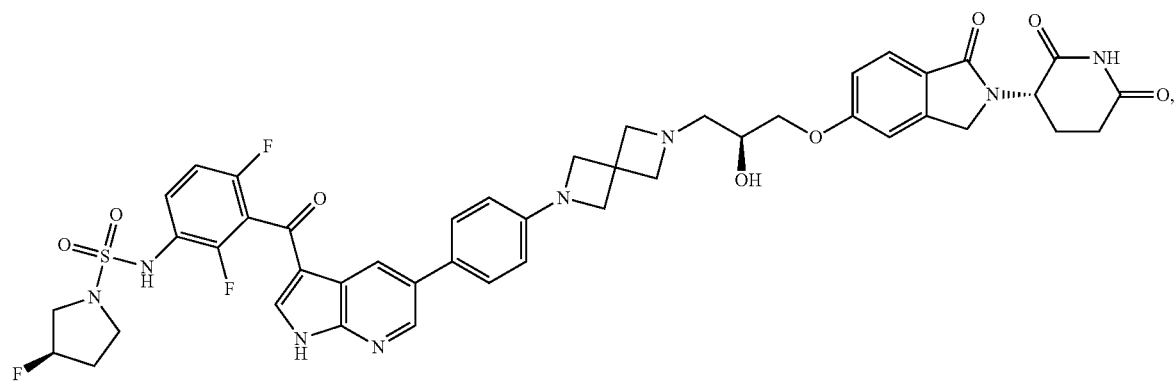
(166)
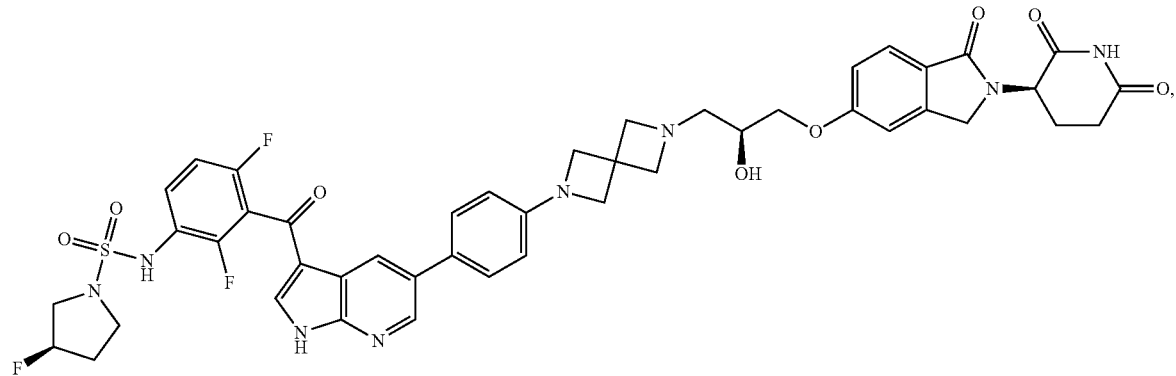

-continued
(167)
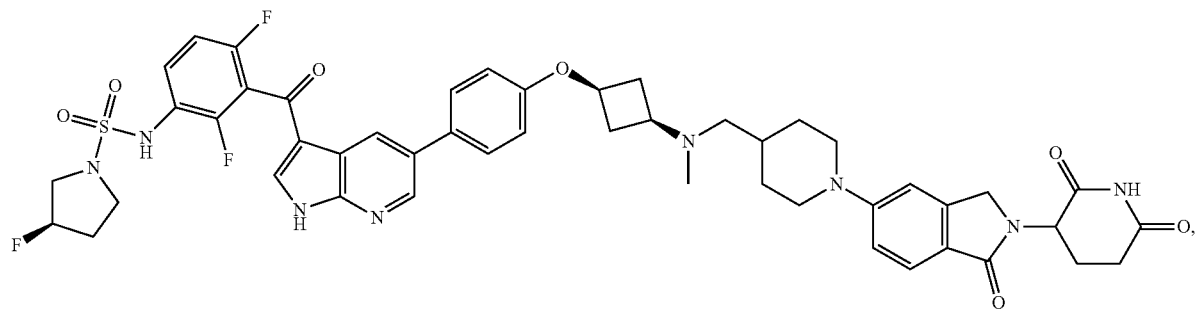 [SMILES: CN(CC1CCN(c2ccc3c(c2)CN(C2CCC(=O)NC2=O)C3=O)CC1)[C@H]1C[C@@H](Oc2ccc(-c3cnc4[nH]cc(C(=O)c5c(F)ccc(NS(=O)(=O)N6CC[C@@H](F)C6)c5F)c4c3)cc2)C1]
(168)
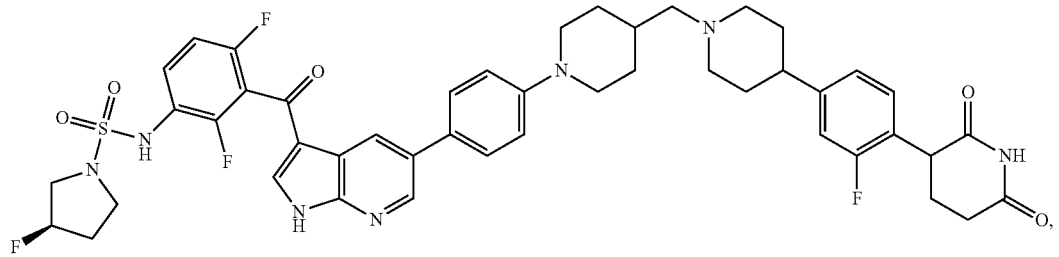
(170)
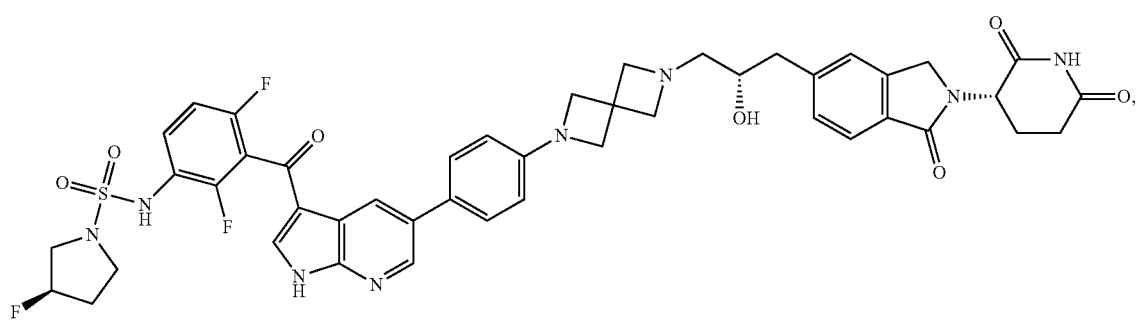
(171)
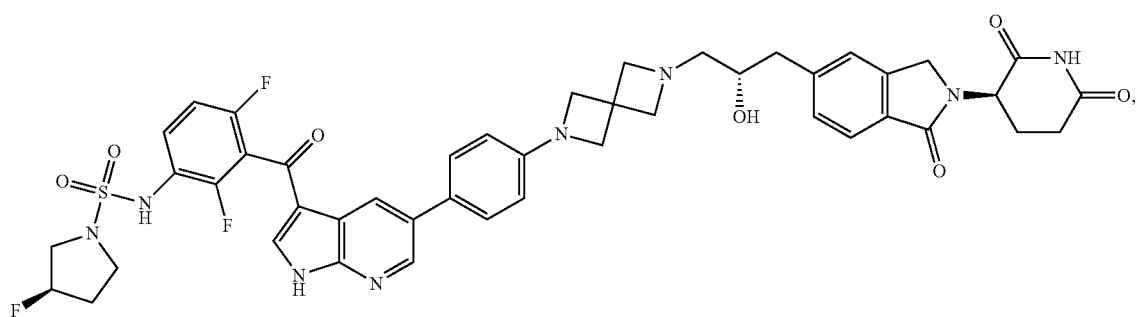

-continued
(172)
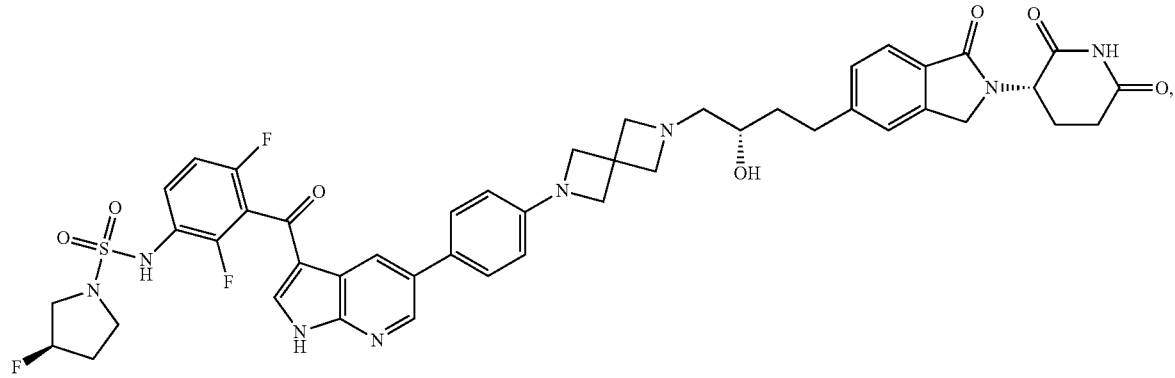
(173)
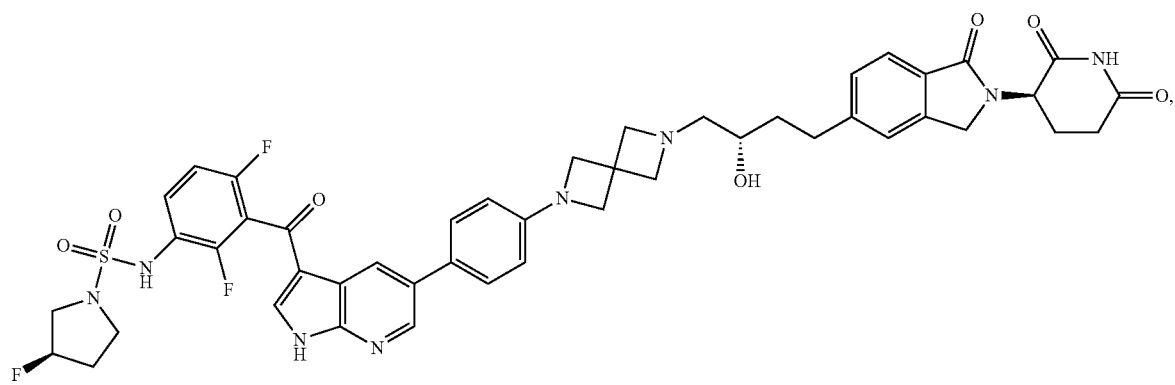
(174)
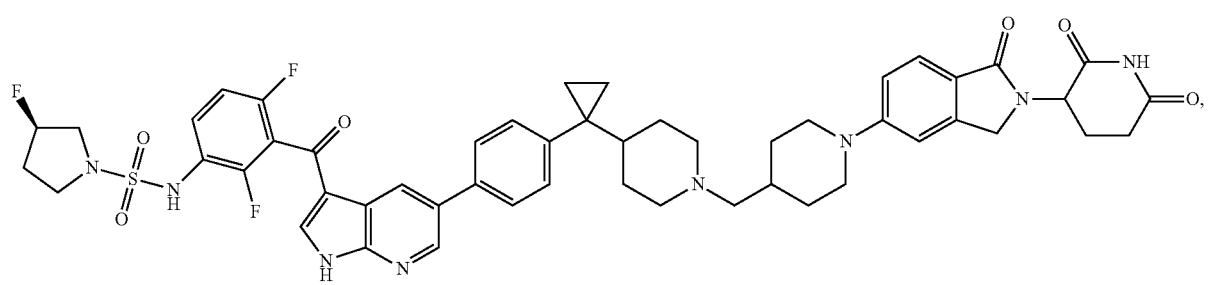
(175)
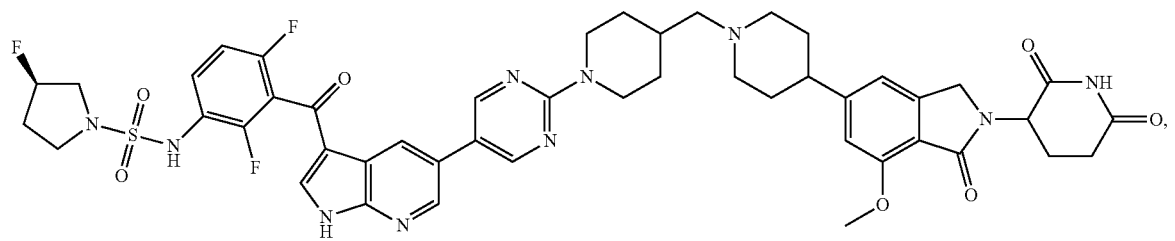
(176)
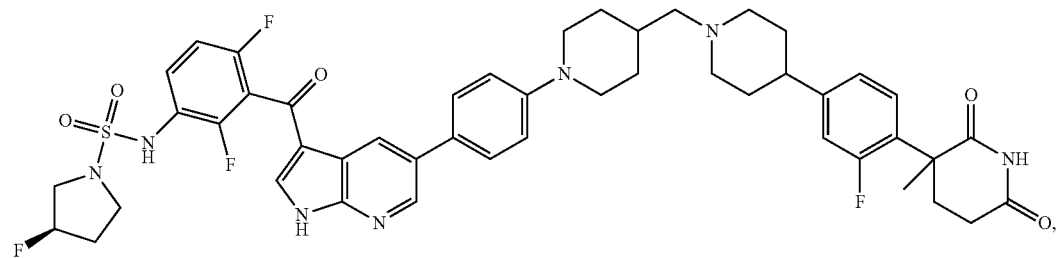

-continued
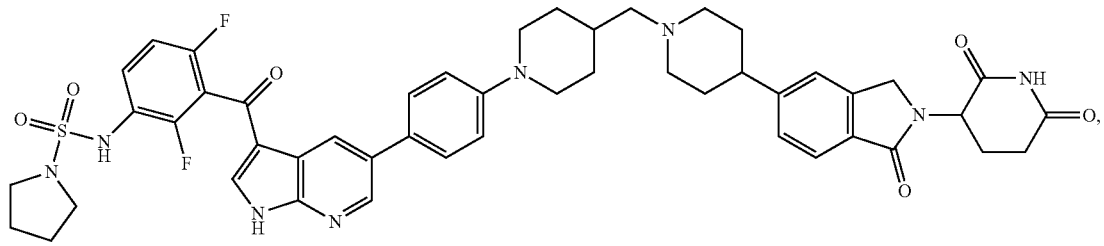 [SMILES: O=C1CCC(N2Cc3cc(C4CCN(CC5CCN(c6ccc(-c7cnc8[nH]cc(C(=O)c9c(F)ccc(NS(=O)(=O)N%10CCCC%10)c9F)c8c7)cc6)CC5)CC4)ccc3C2=O)C(=O)N1]
(177)
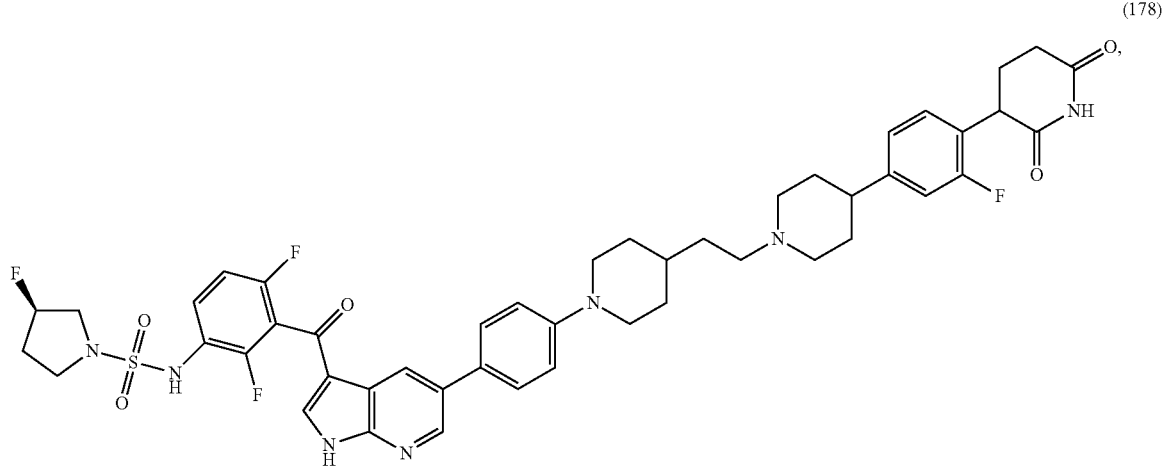
(178)
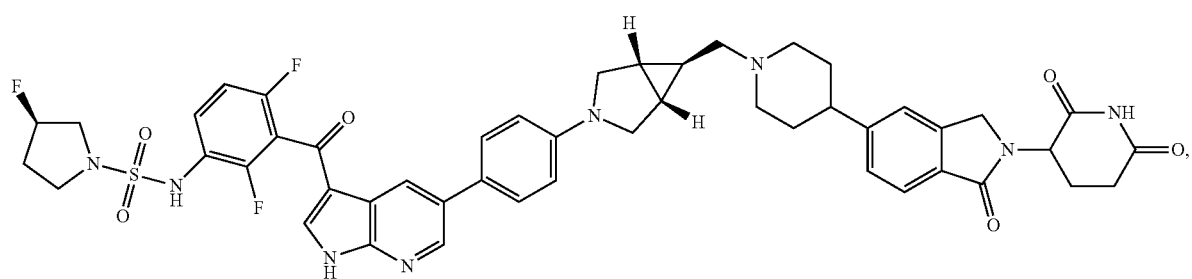
(179)
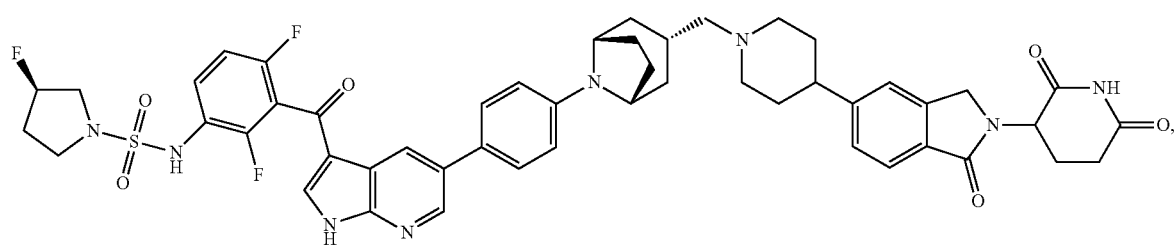
(180)

(181)
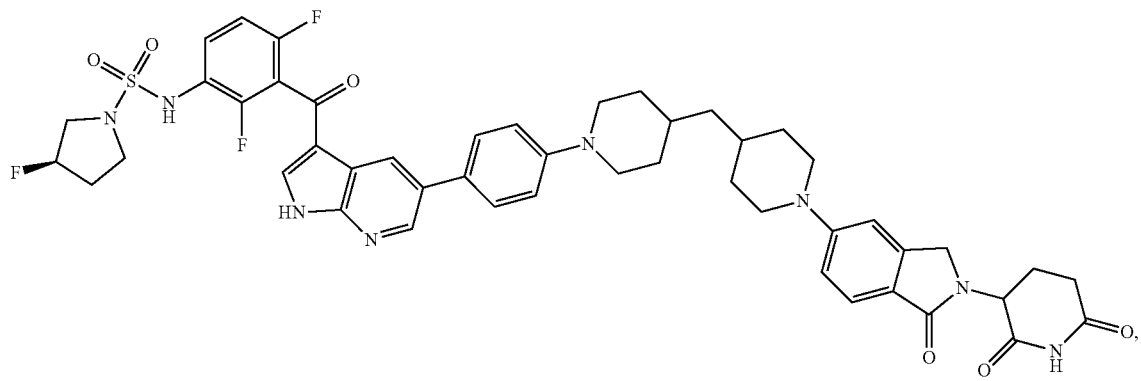
(182)
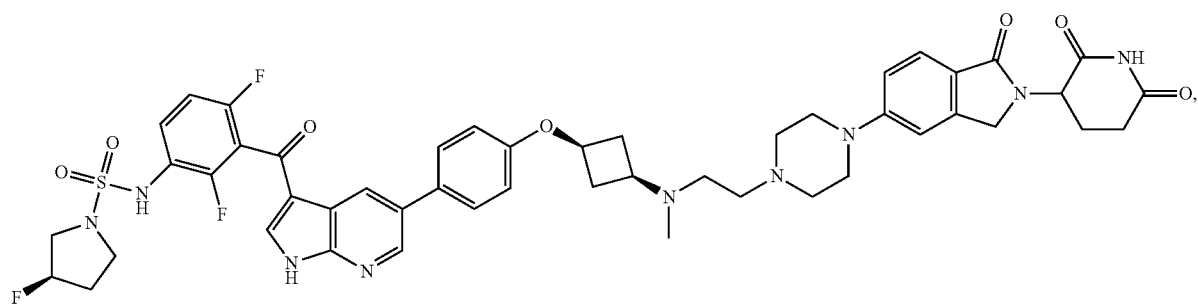
(184)
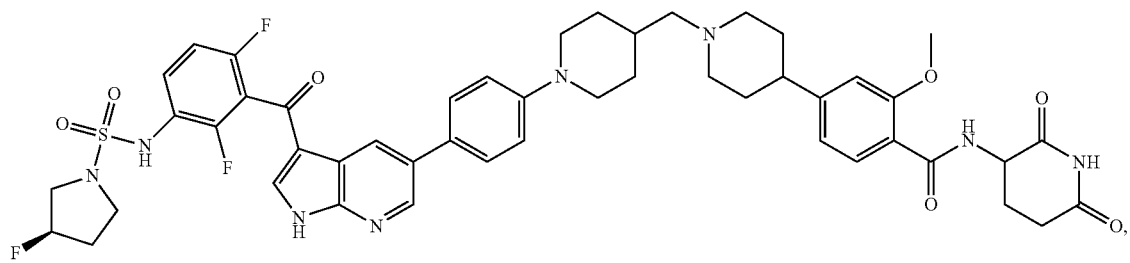
(185)
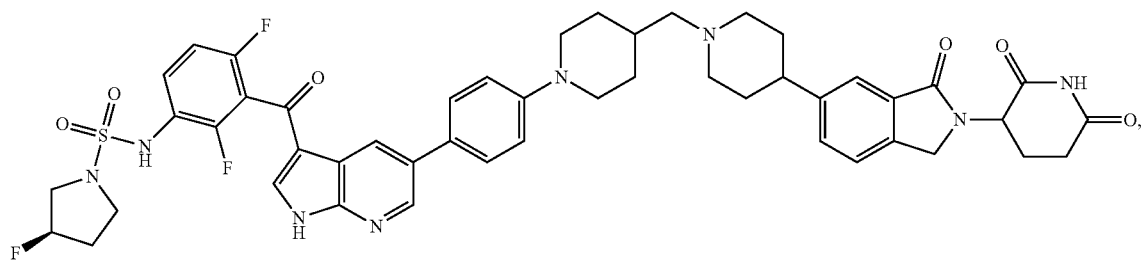
(186)
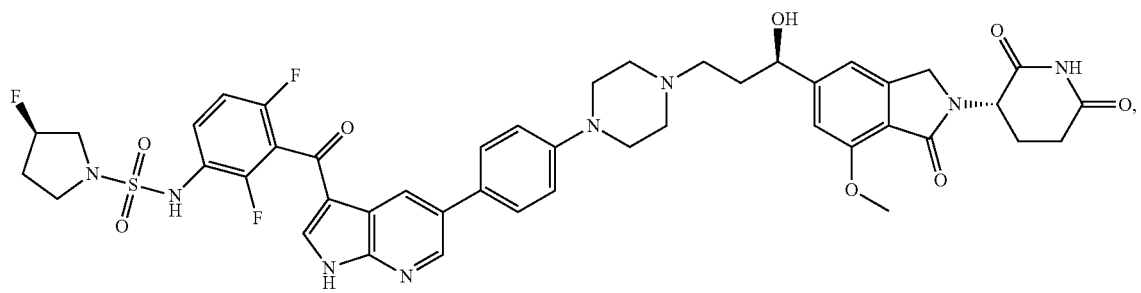

(187)
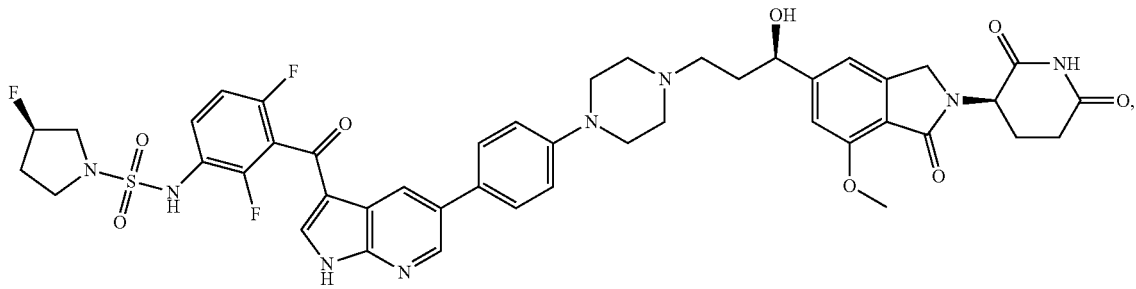
(188)
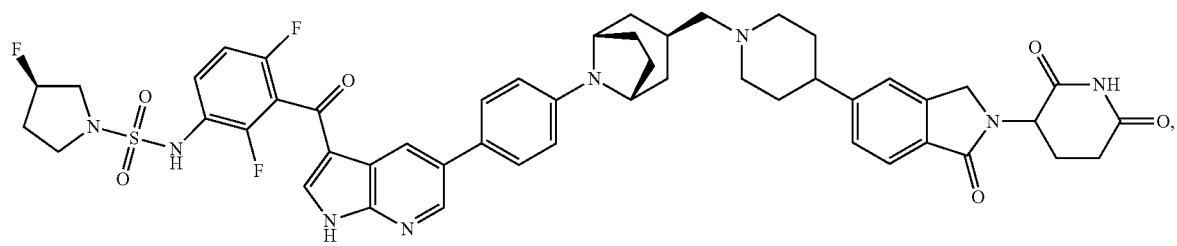
(189)
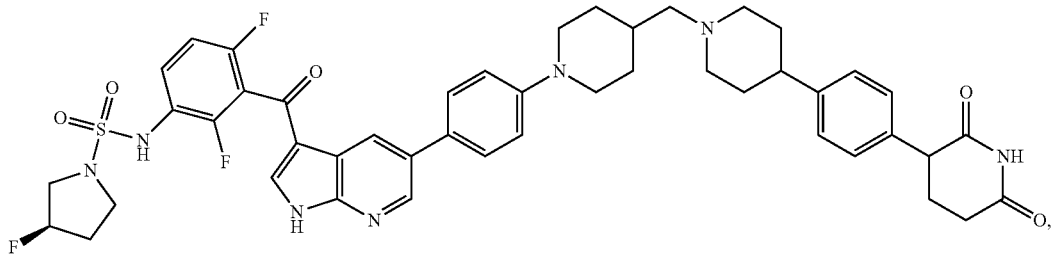
(190)
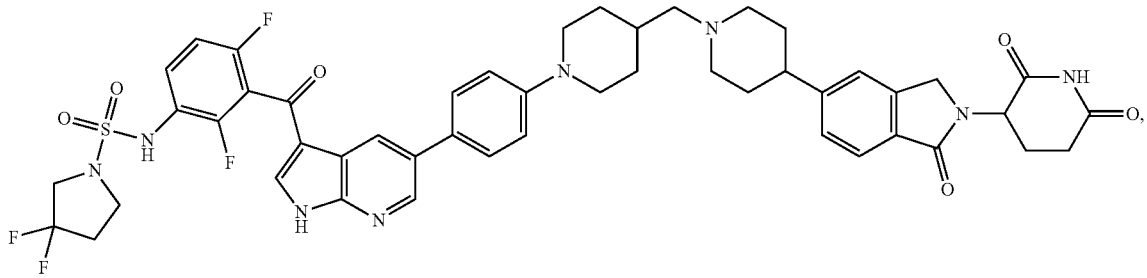 [SMILES: O=C1CCC(N2Cc3cc(C4CCN(CC5CCN(c6ccc(-c7cnc8[nH]cc(C(=O)c9c(F)ccc(NS(=O)(=O)N%10CCC(F)(F)C%10)c9F)c8c7)cc6)CC5)CC4)ccc3C2=O)C(=O)N1]
(191)
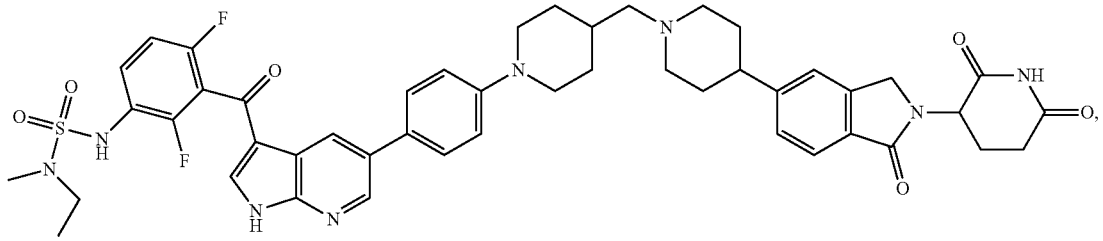

(192)
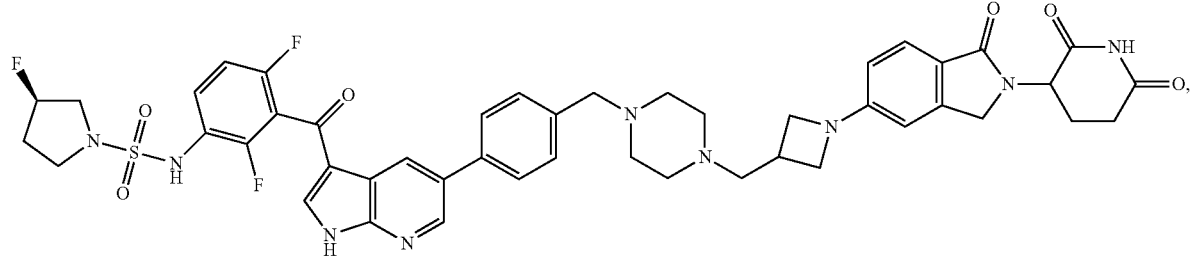
(193)
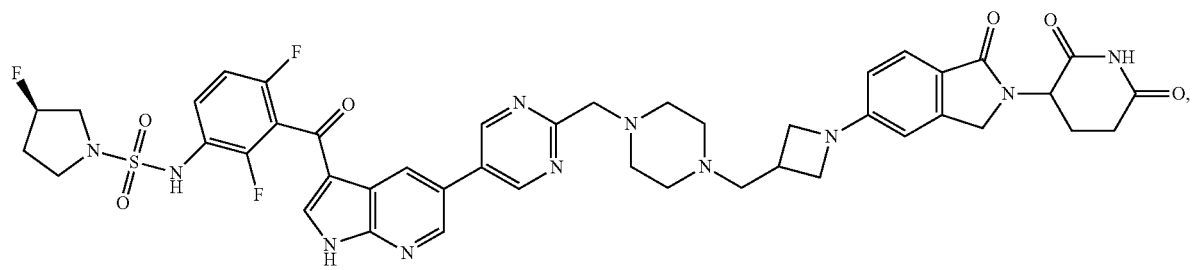
(194)
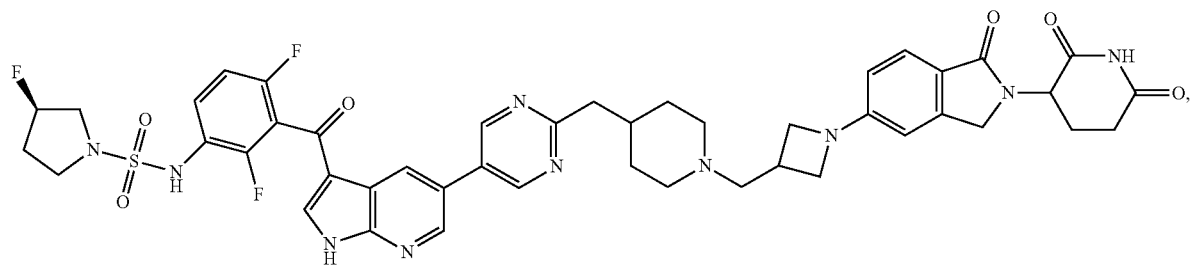
(195)
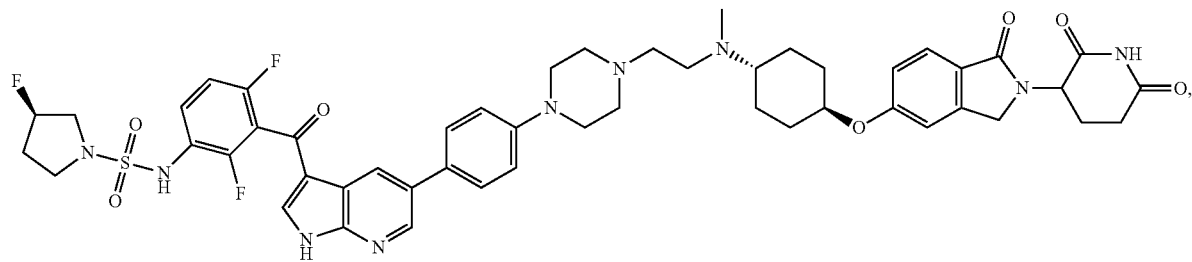
(196)
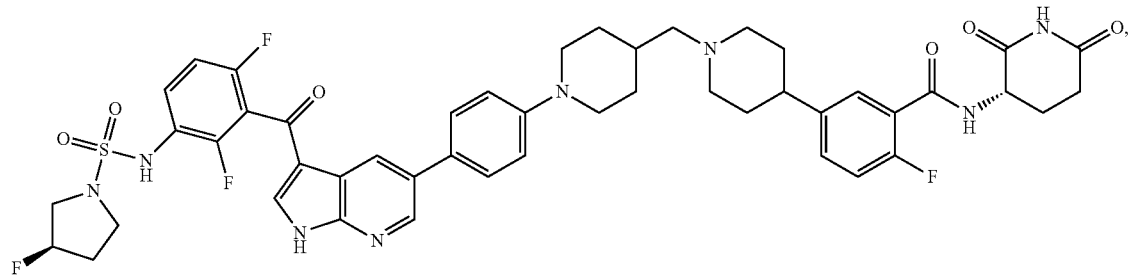

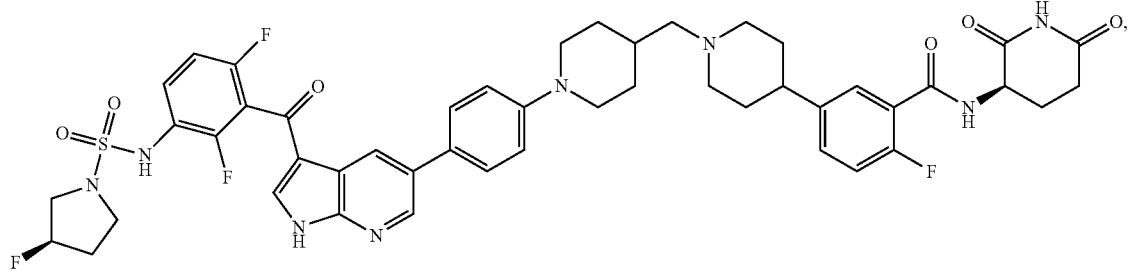
(197)
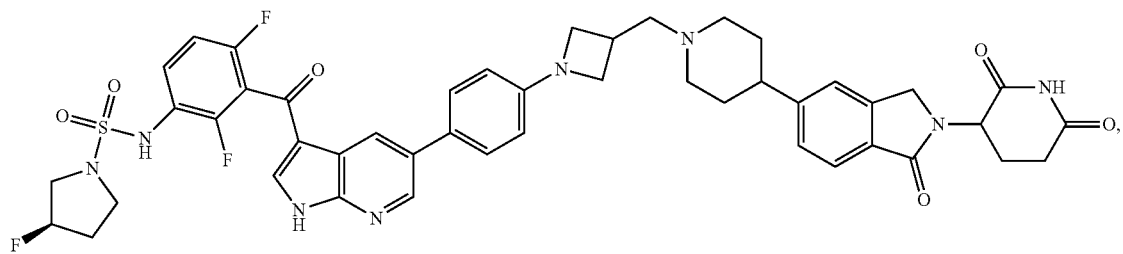
(198)
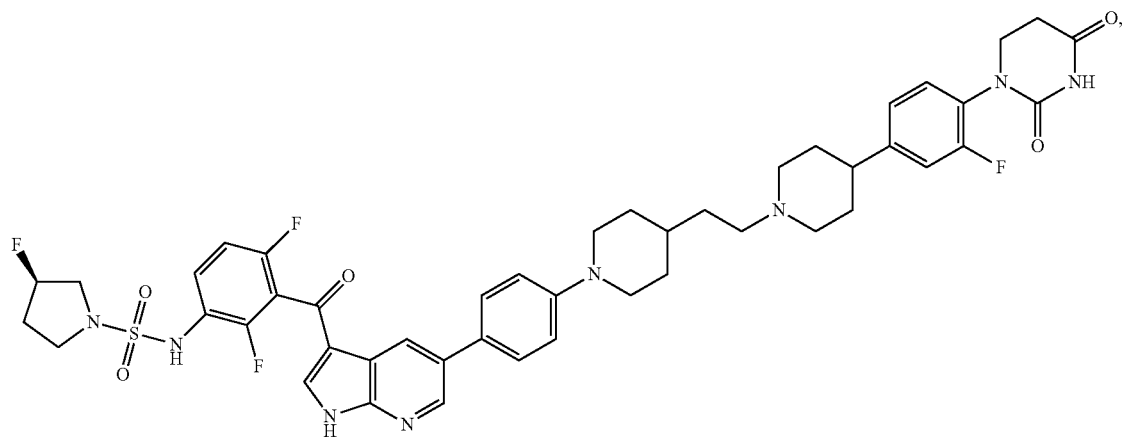
(199)
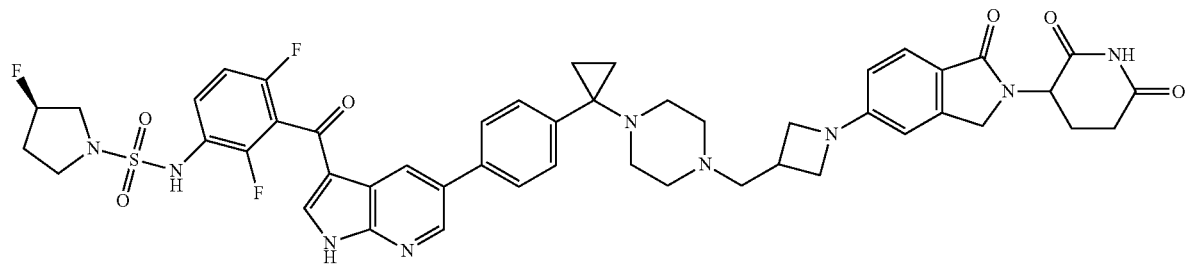
(200)

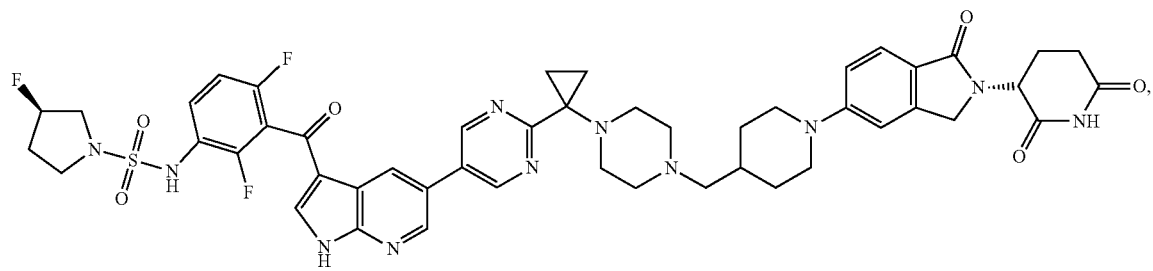
(201)
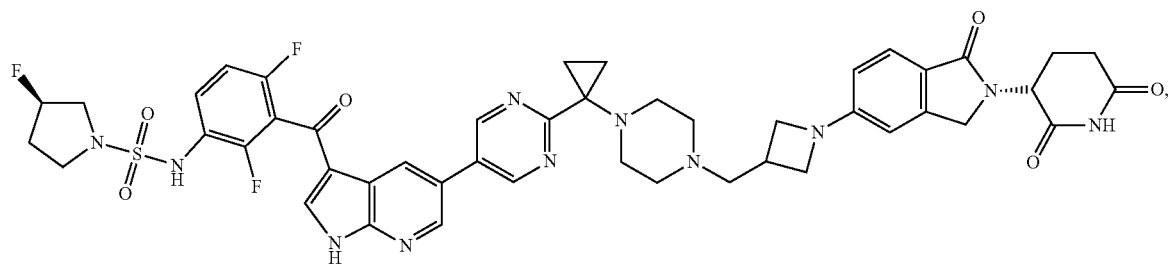
(202)
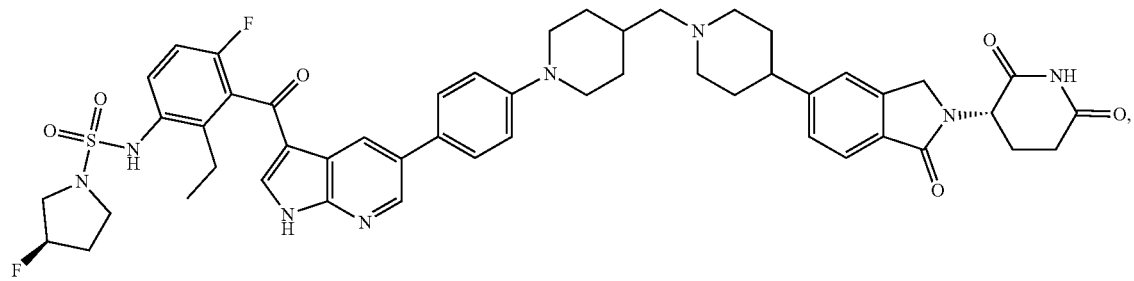
(203)
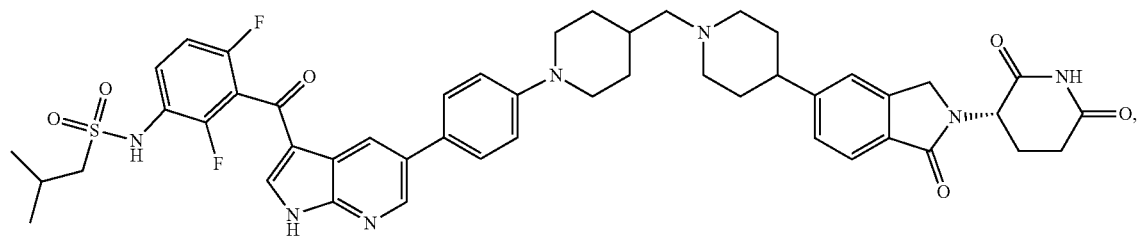
(204)
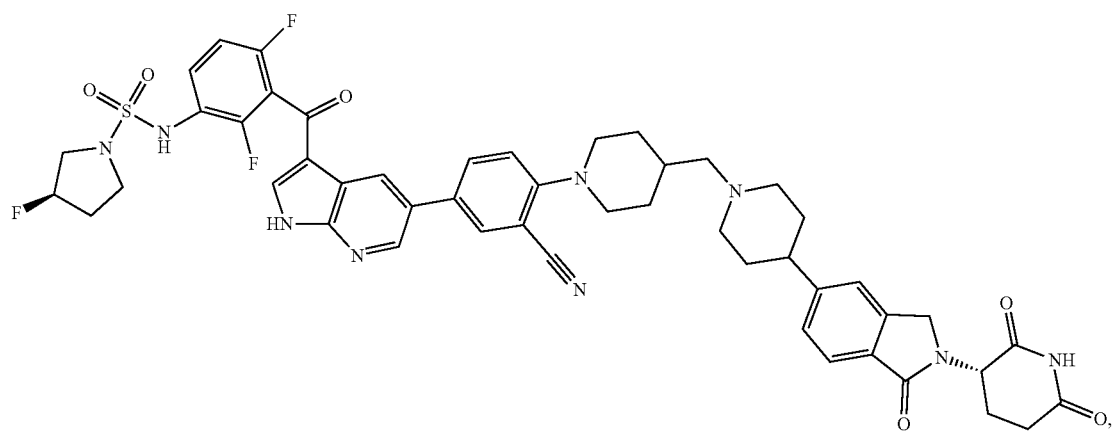
(205)

(206)
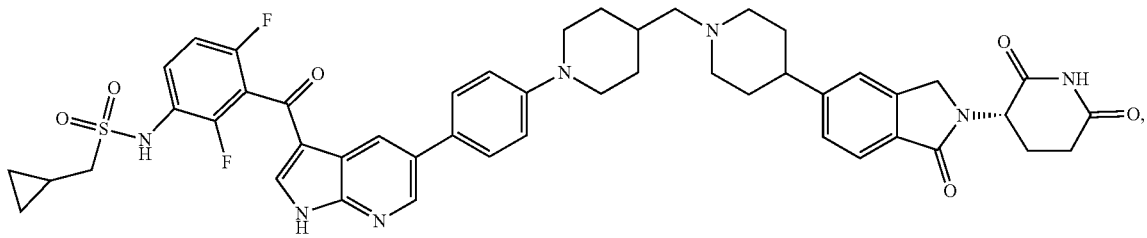
(207)
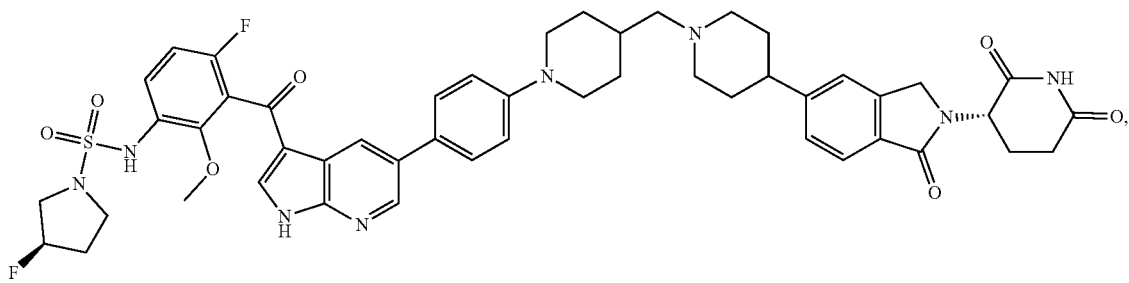
(208)
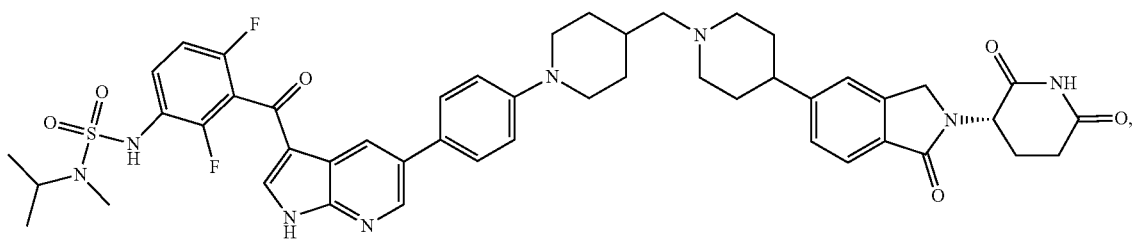 [SMILES: CC(C)N(C)S(=O)(=O)Nc1ccc(F)c(C(=O)c2c[nH]c3ncc(-c4ccc(N5CCC(CN6CCC(c7ccc8c(c7)CN([C@H]7CCC(=O)NC7=O)C8=O)CC6)CC5)cc4)cc23)c1F]
(209)
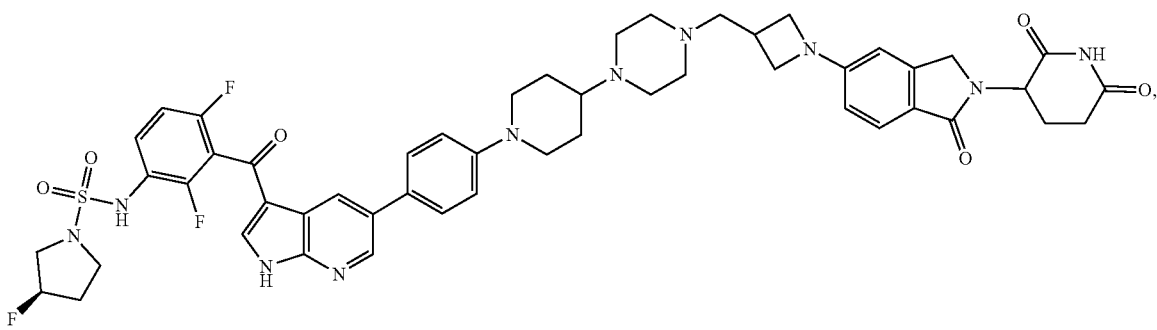
(210)
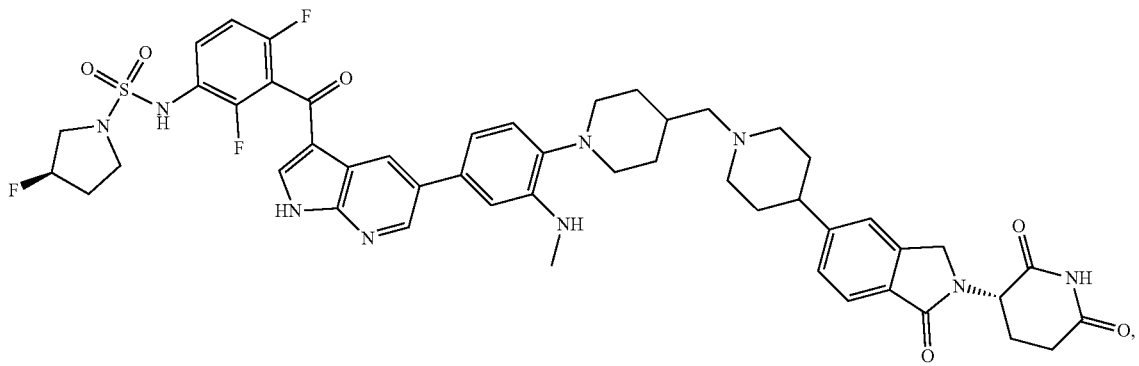

(211)
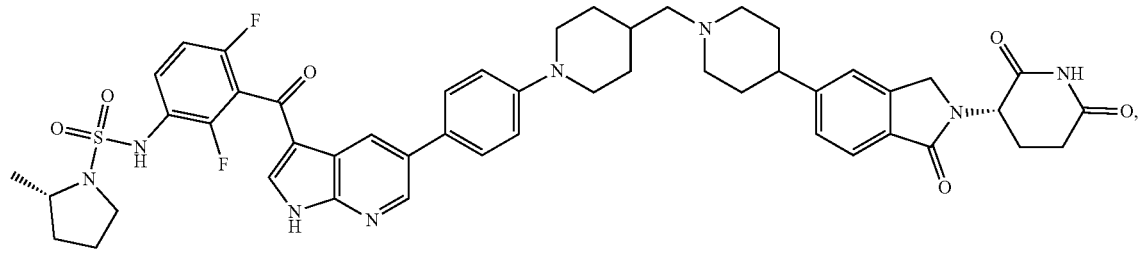
(212)
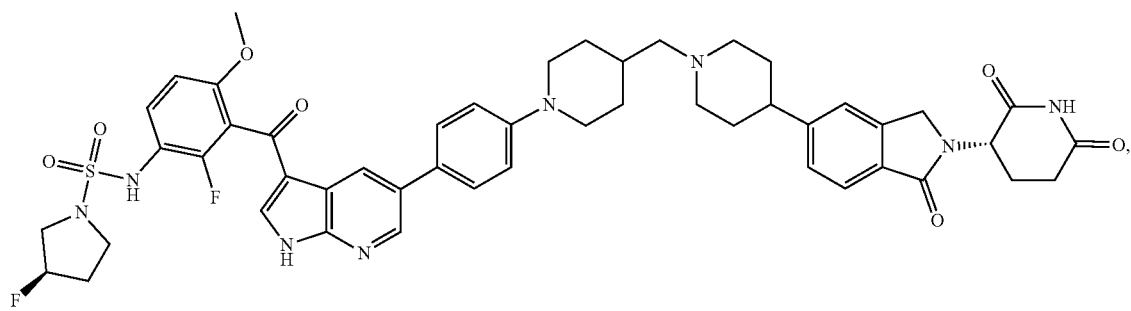
(213)
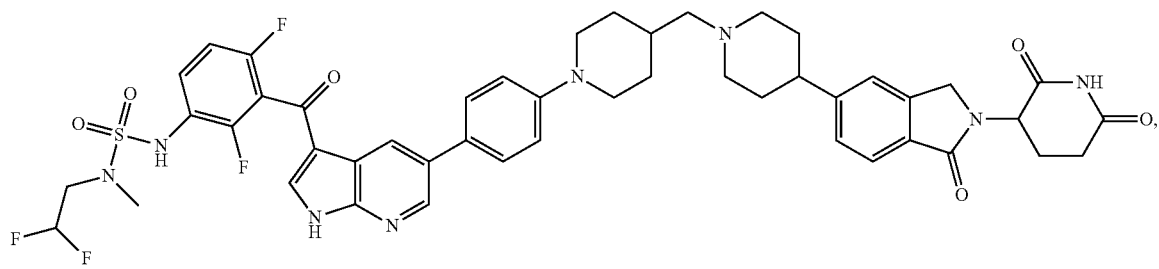 [SMILES: CN(CC(F)F)S(=O)(=O)Nc1ccc(F)c(C(=O)c2c[nH]c3ncc(-c4ccc(N5CCC(CN6CCC(c7ccc8c(c7)CN(C7CCC(=O)NC7=O)C8=O)CC6)CC5)cc4)cc23)c1F]
(214)
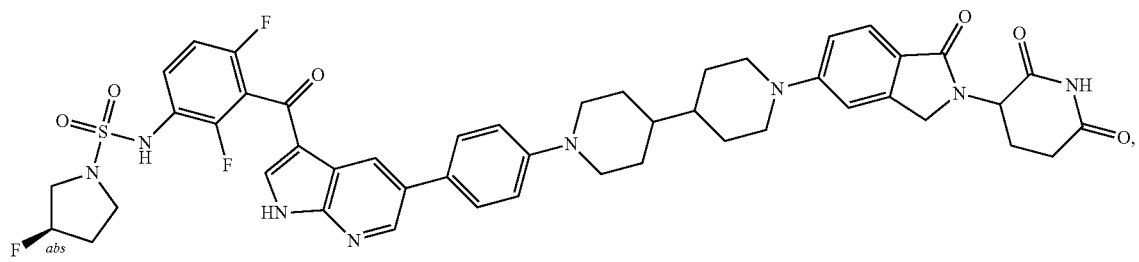
(215)
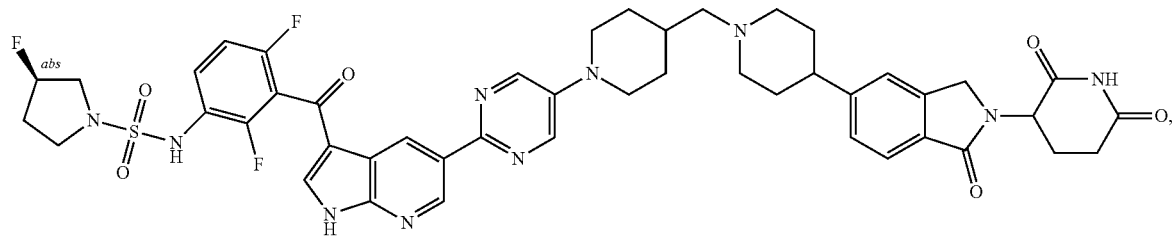

(216)
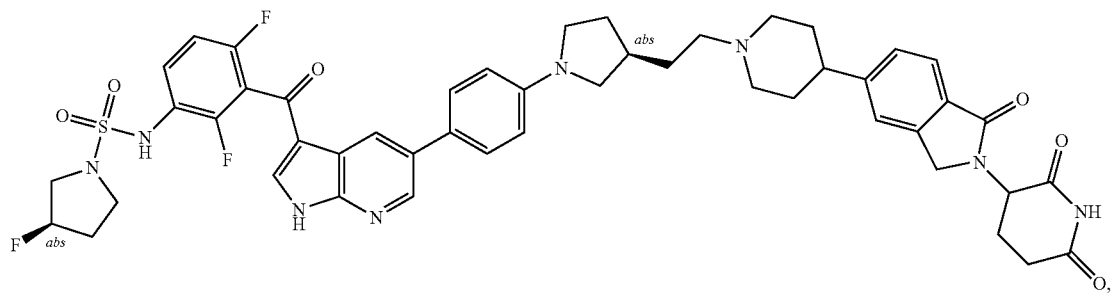
(217)
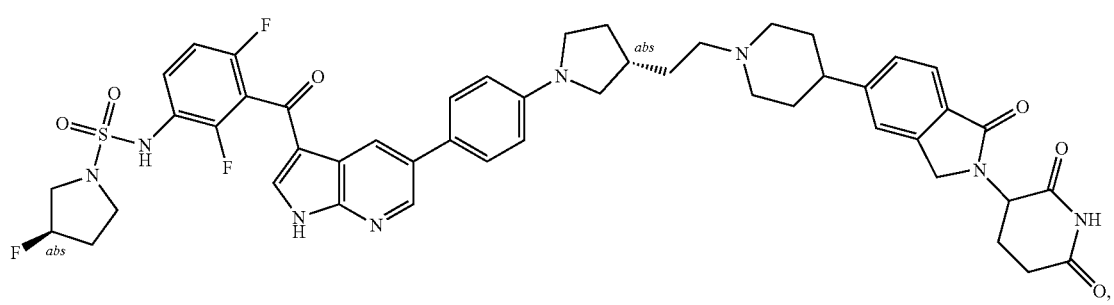
(218)
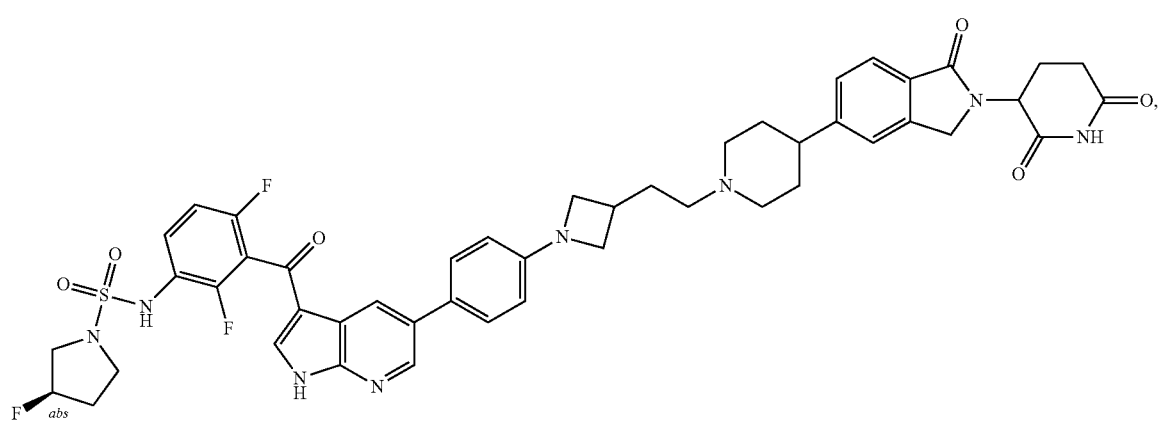
(225)
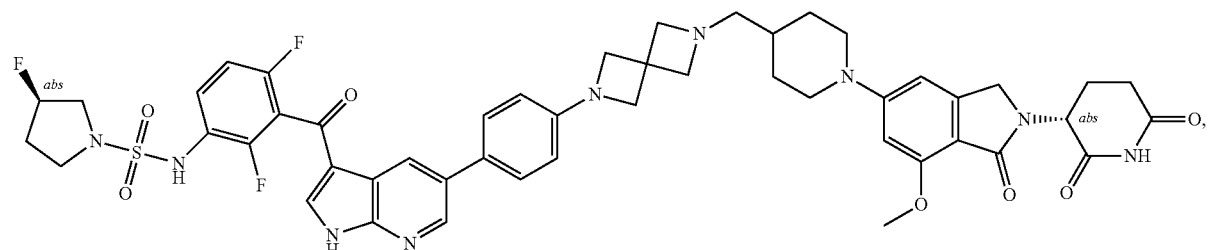
(226)
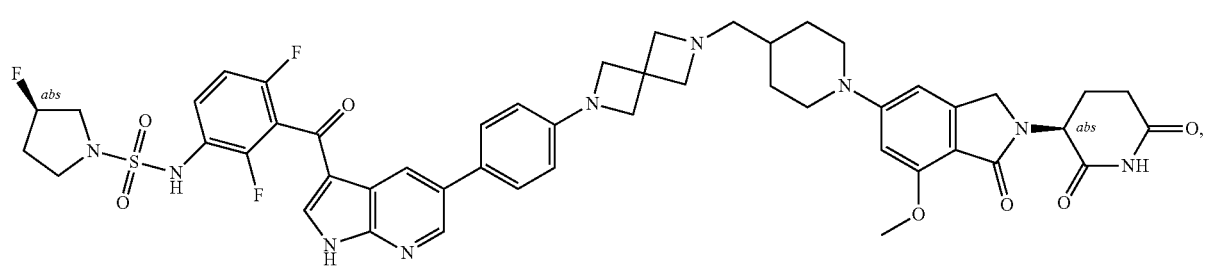

-continued
(227)
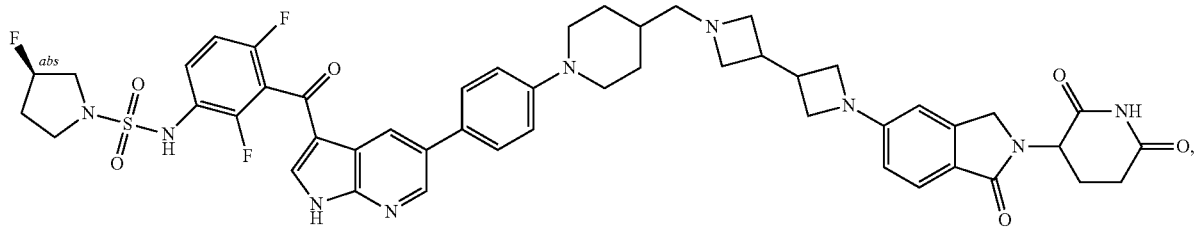
(228)
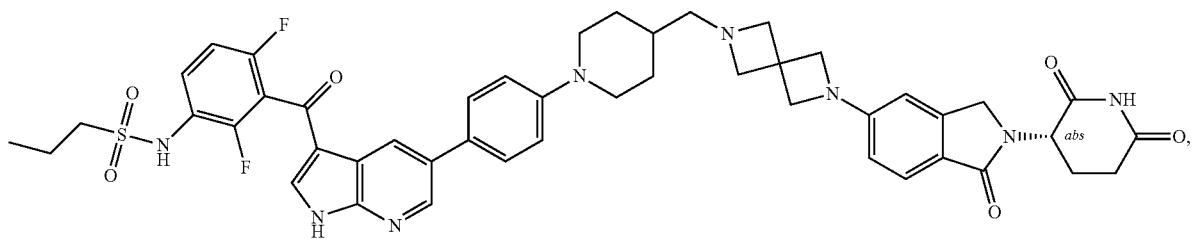 [SMILES: CCCS(=O)(=O)Nc1ccc(F)c(C(=O)c2c[nH]c3ncc(-c4ccc(N5CCC(CN6CC7(C6)CN(c6ccc8c(c6)CN([C@H]6CCC(=O)NC6=O)C8=O)C7)CC5)cc4)cc23)c1F]
(229)
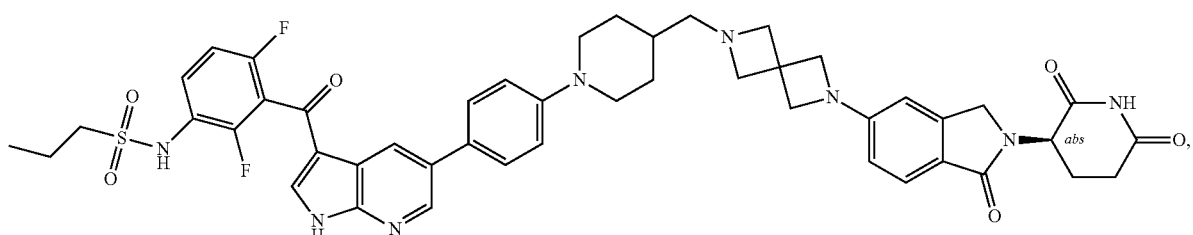
(230)
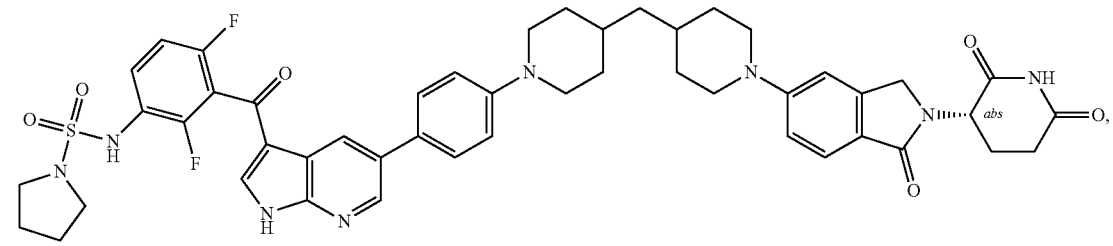
(231)
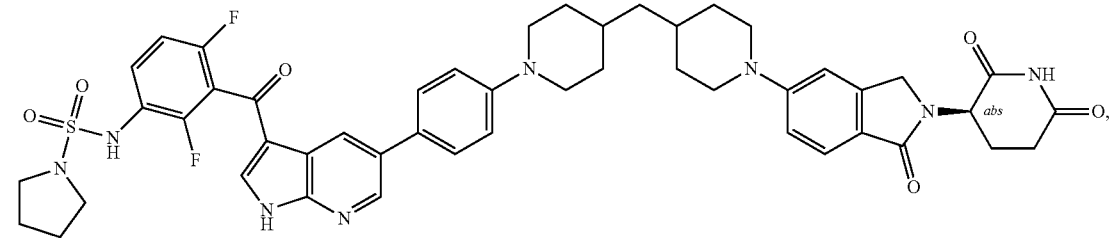 [SMILES: O=C1CC[C@@H](N2Cc3cc(C4CCN(CC5CCN(c6ccc(-c7cnc8[nH]cc(C(=O)c9c(F)ccc(NS(=O)(=O)N%10CCCC%10)c9F)c8c7)cc6)CC5)CC4)ccc3C2=O)C(=O)N1]
(232)
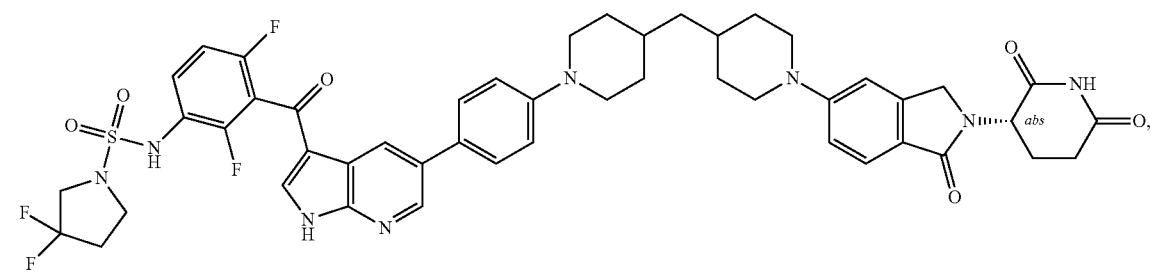

-continued
(233)
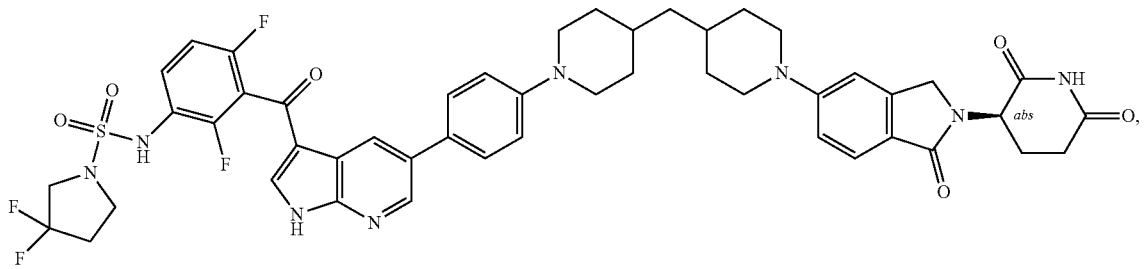
(234)
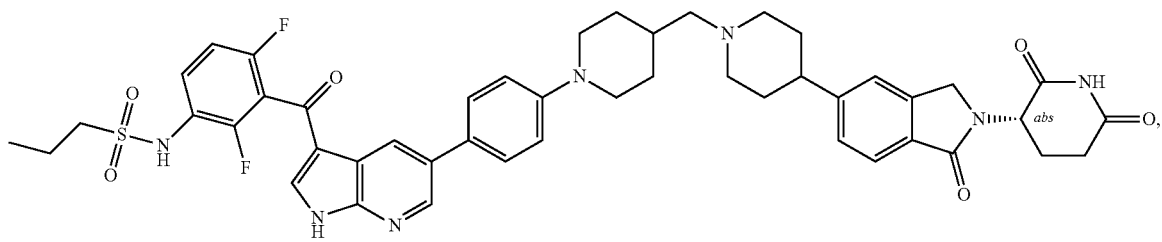 [SMILES: CCCS(=O)(=O)Nc1ccc(F)c(C(=O)c2c[nH]c3ncc(-c4ccc(N5CCC(CN6CCC(c7ccc8c(c7)CN([C@H]7CCC(=O)NC7=O)C8=O)CC6)CC5)cc4)cc23)c1F]
(235)
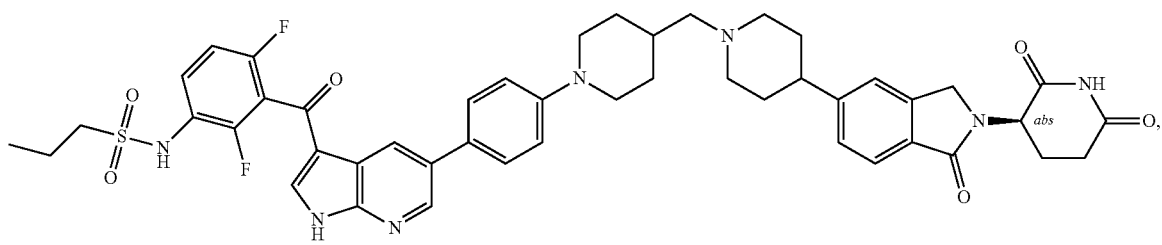 [SMILES: CCCS(=O)(=O)Nc1ccc(F)c(C(=O)c2c[nH]c3ncc(-c4ccc(N5CCC(CN6CCC(c7ccc8c(c7)CN([C@@H]7CCC(=O)NC7=O)C8=O)CC6)CC5)cc4)cc23)c1F]
(236)
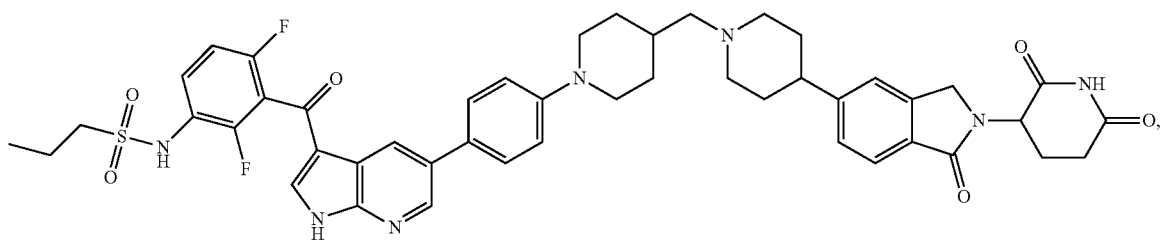 [SMILES: CCCS(=O)(=O)Nc1ccc(F)c(C(=O)c2c[nH]c3ncc(-c4ccc(N5CCC(CN6CCC(c7ccc8c(c7)CN(C7CCC(=O)NC7=O)C8=O)CC6)CC5)cc4)cc23)c1F]
(237)
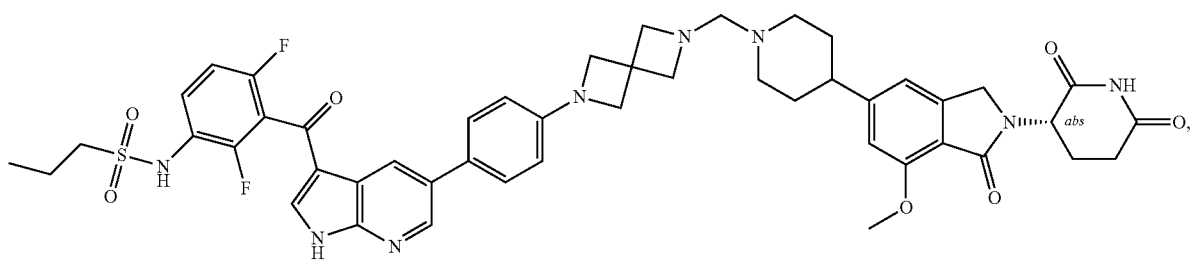 [SMILES: CCCS(=O)(=O)Nc1ccc(F)c(C(=O)c2c[nH]c3ncc(-c4ccc(N5CC6(CN(CC7CCN(c8cc9c(c(OC)c8)C(=O)N([C@H]8CCC(=O)NC8=O)C9)CC7)C6)C5)cc4)cc23)c1F]
(238)
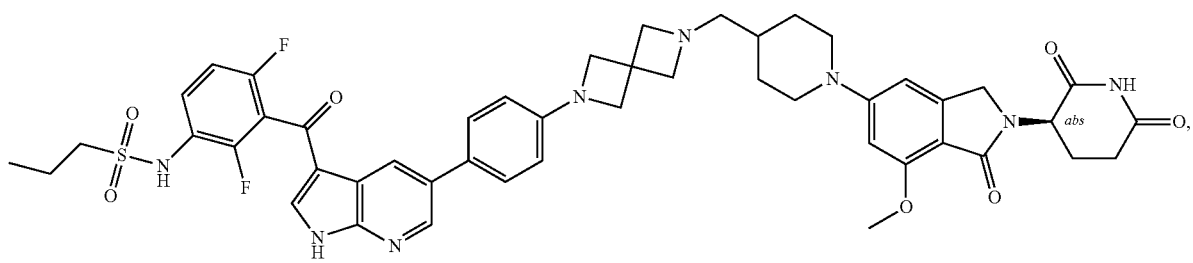 [SMILES: CCCS(=O)(=O)Nc1ccc(F)c(C(=O)c2c[nH]c3ncc(-c4ccc(N5CC6(CN(CC7CCN(c8cc9c(c(OC)c8)C(=O)N([C@@H]8CCC(=O)NC8=O)C9)CC7)C6)C5)cc4)cc23)c1F]

(239)
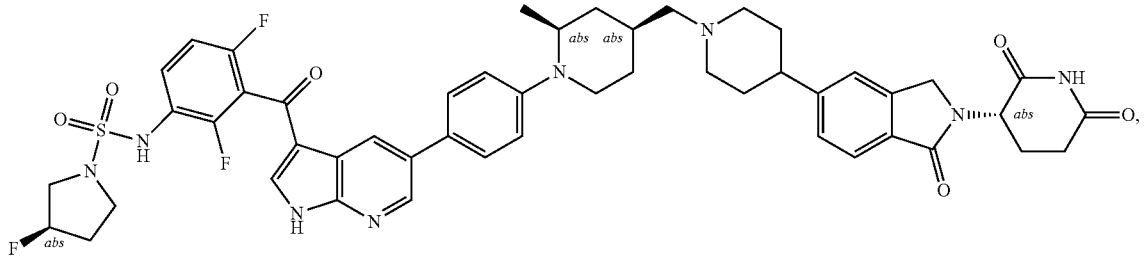
(240)
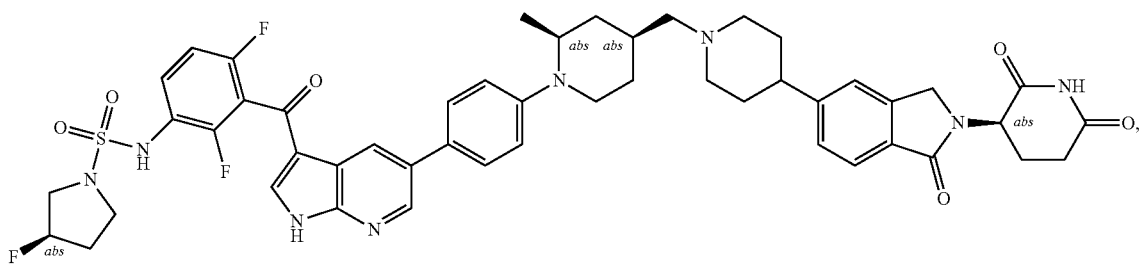
(241)
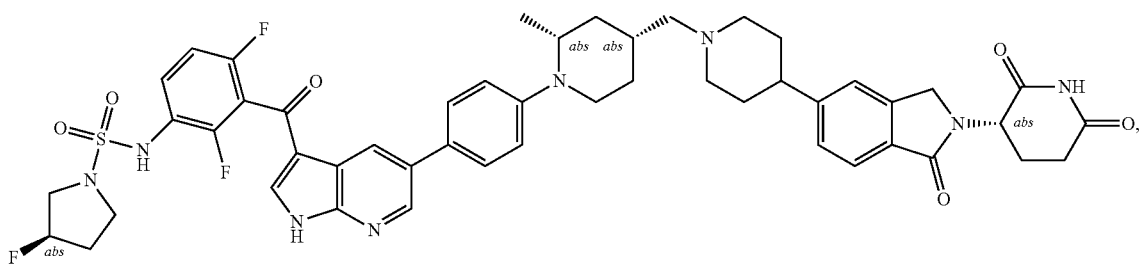
(242)
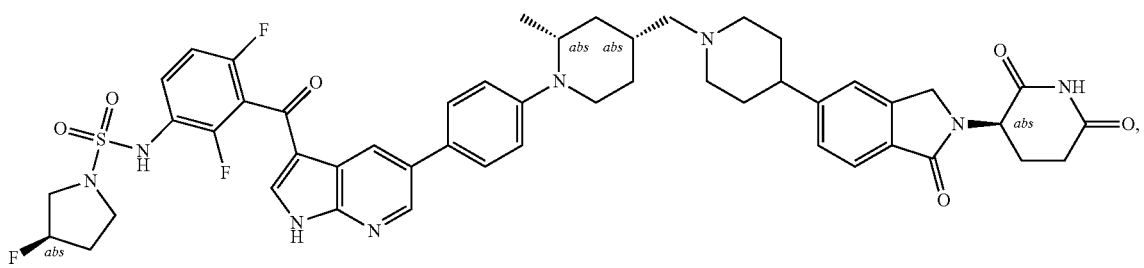
(243)
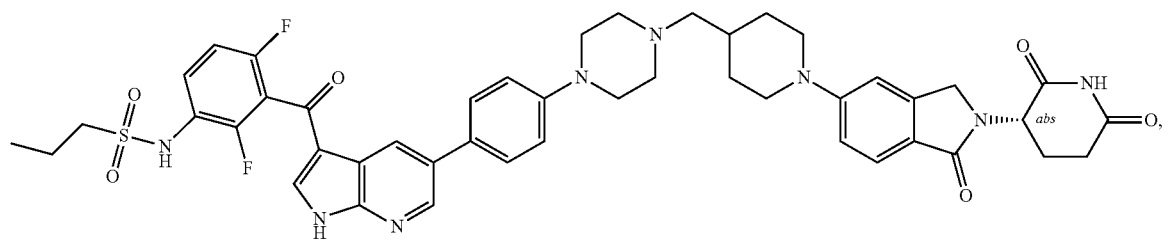 [SMILES: CCCS(=O)(=O)Nc1ccc(F)c(C(=O)c2c[nH]c3ncc(-c4ccc(N5CCN(CC6CCN(c7ccc8c(c7)CN([C@H]7CCC(=O)NC7=O)C8=O)CC6)CC5)cc4)cc23)c1F]

-continued
(244)
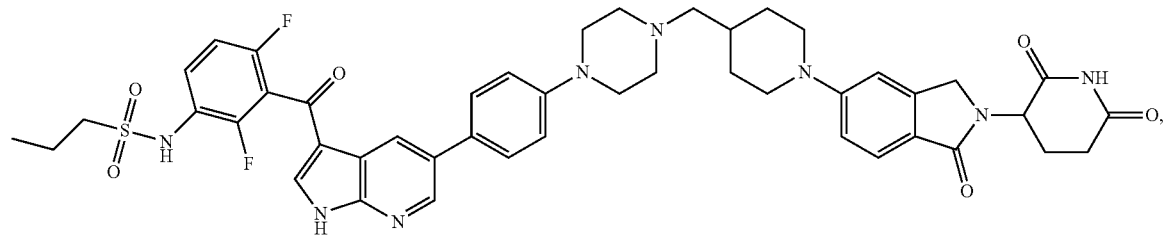 [SMILES: CCCS(=O)(=O)Nc1ccc(F)c(C(=O)c2c[nH]c3ncc(-c4ccc(N5CCN(CC6CCN(c7ccc8c(c7)CN(C7CCC(=O)NC7=O)C8=O)CC6)CC5)cc4)cc23)c1F]
(245)
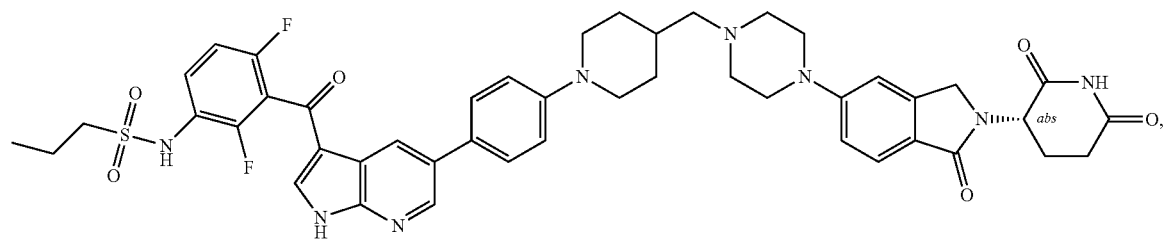 [SMILES: CCCS(=O)(=O)Nc1ccc(F)c(C(=O)c2c[nH]c3ncc(-c4ccc(N5CCC(CN6CCN(c7ccc8c(c7)CN([C@H]7CCC(=O)NC7=O)C8=O)CC6)CC5)cc4)cc23)c1F]
(246)
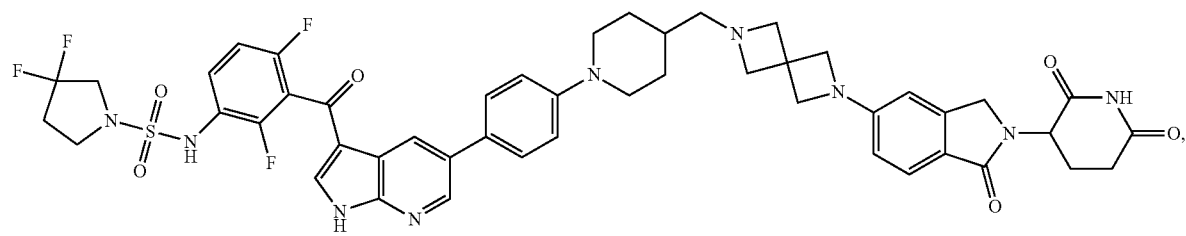
(247)
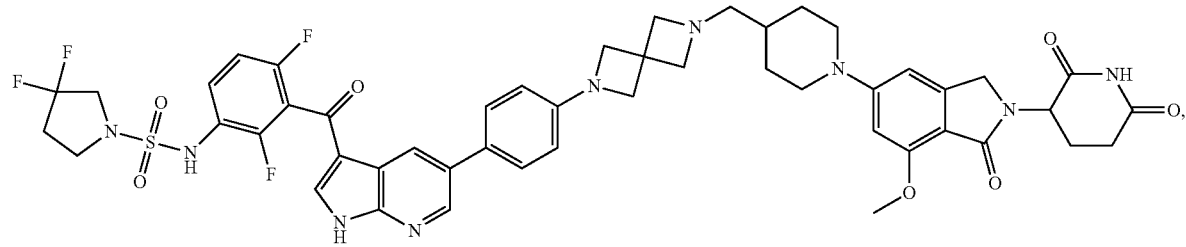
(248)
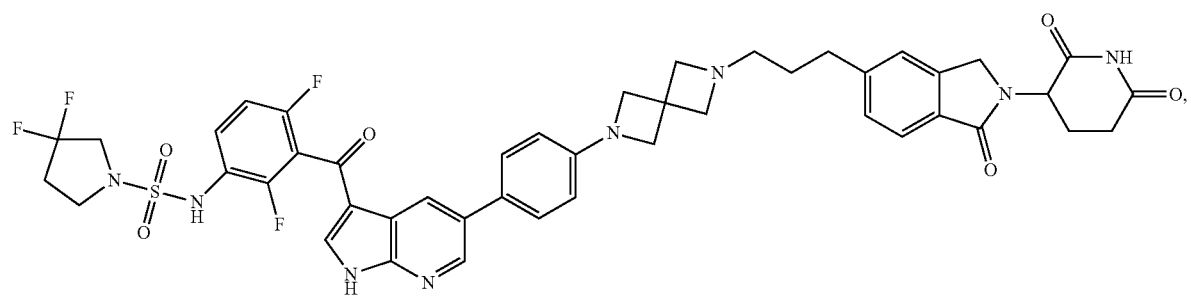 [SMILES: O=C1CCC(N2Cc3cc(CCCN4CC5(C4)CN(c4ccc(-c6cnc7[nH]cc(C(=O)c8c(F)ccc(NS(=O)(=O)N9CCC(F)(F)C9)c8F)c7c6)cc4)C5)ccc3C2=O)C(=O)N1]

-continued
(249)
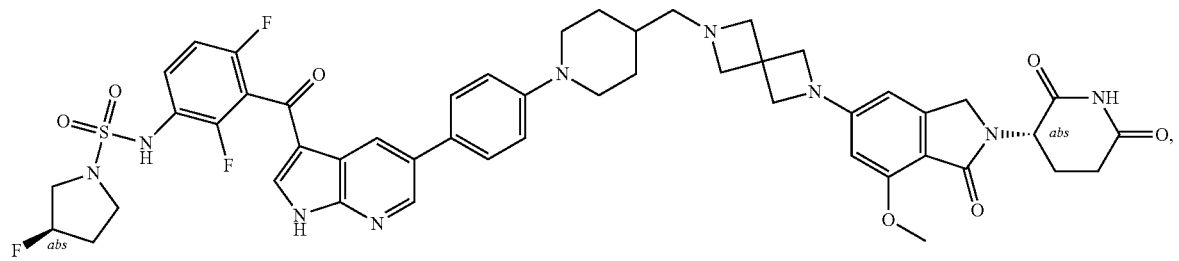
(250)
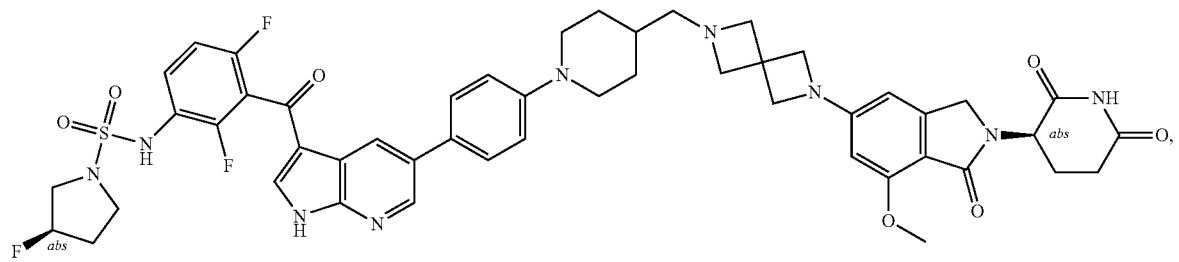
(251)
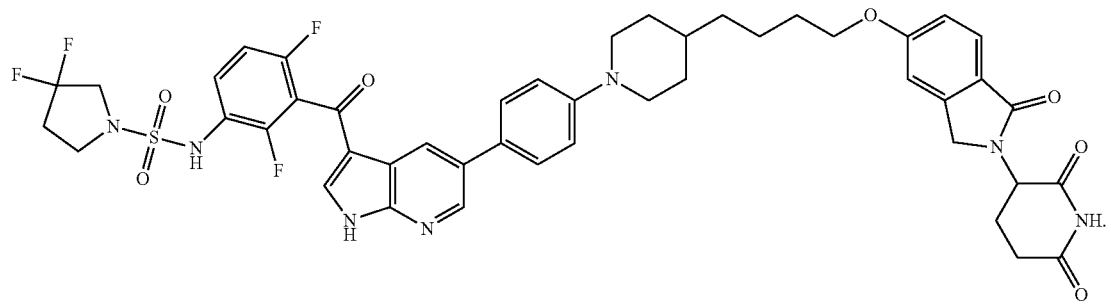
(252)
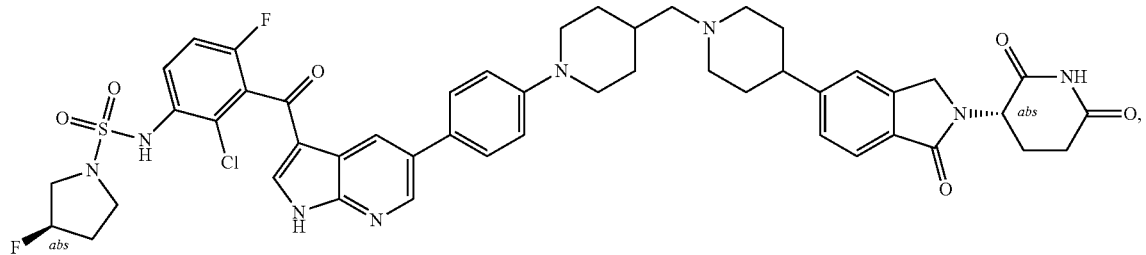
(253)
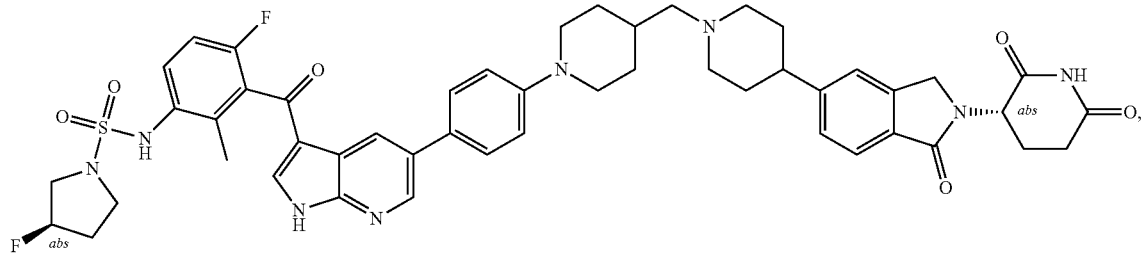

(254)
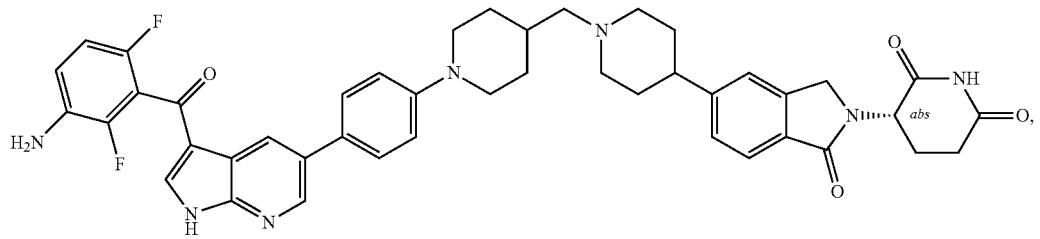 [SMILES: Nc1ccc(F)c(C(=O)c2c[nH]c3ncc(-c4ccc(N5CCC(CN6CCC(c7ccc8c(c7)CN([C@H]7CCC(=O)NC7=O)C8=O)CC6)CC5)cc4)cc23)c1F]
(255)
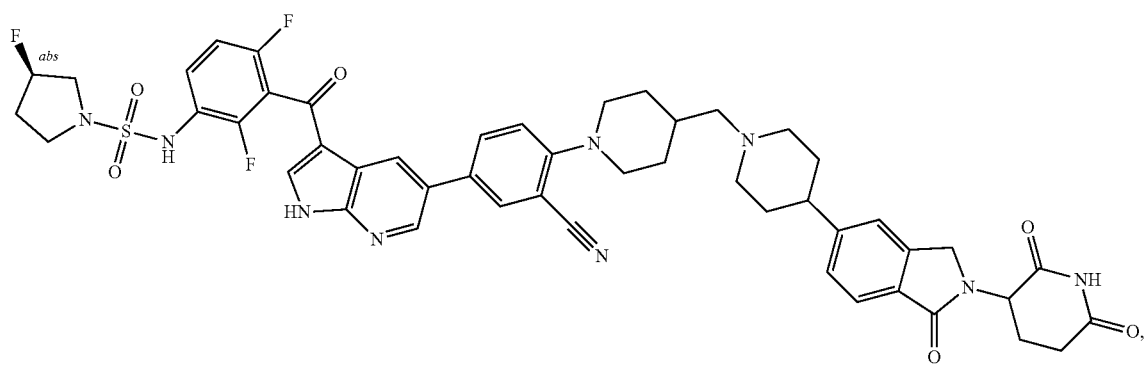
(256)
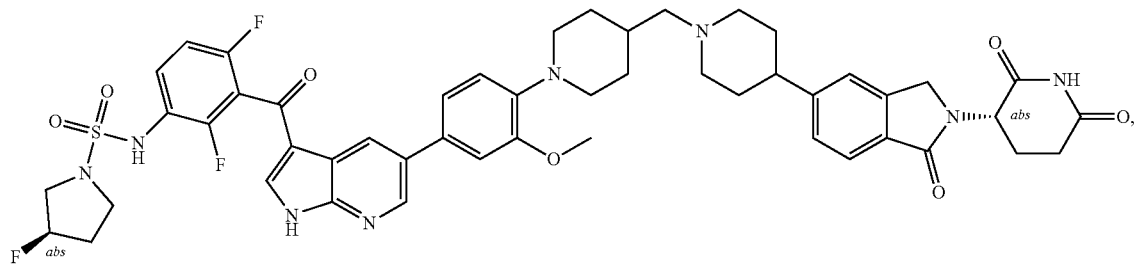
(257)
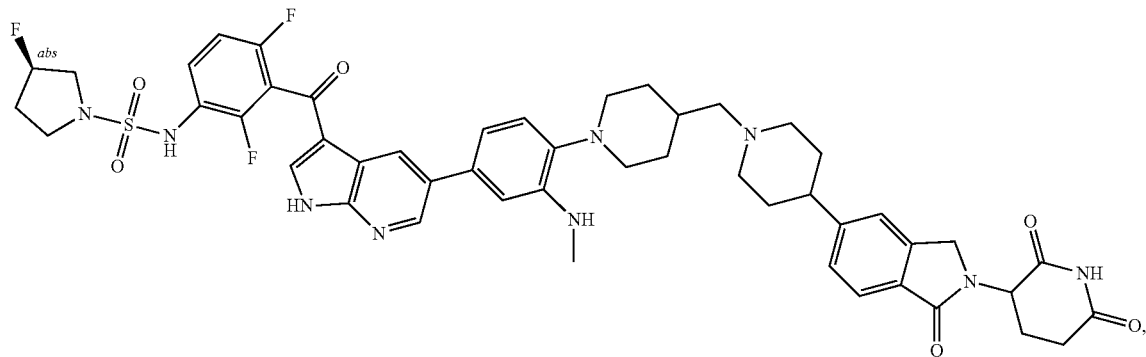

(258)
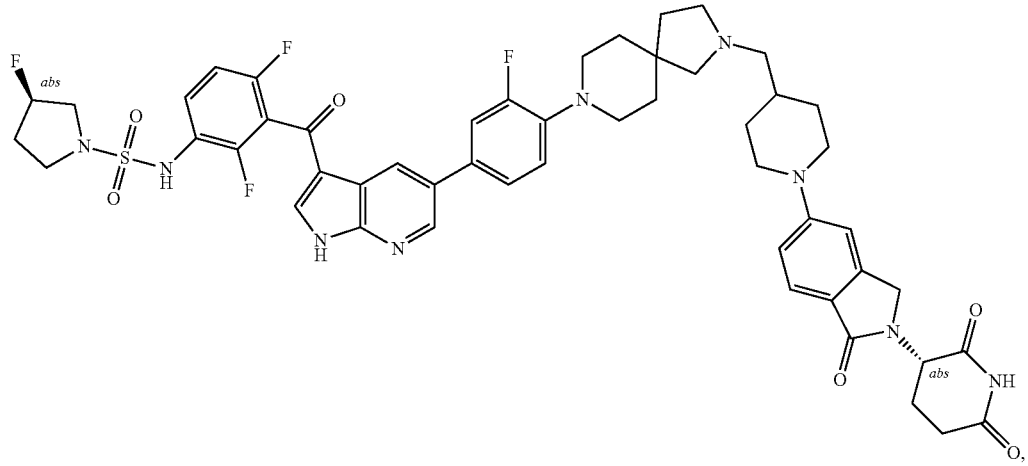
(259)
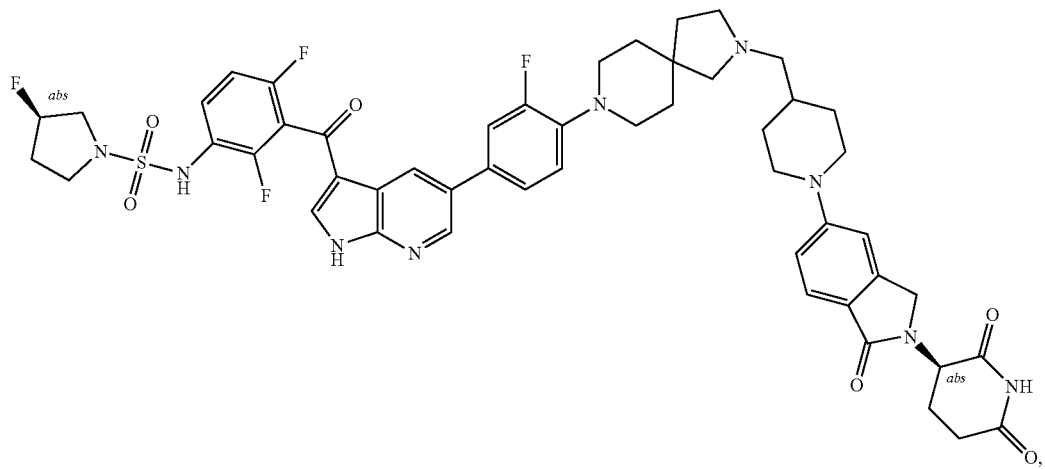
(260)
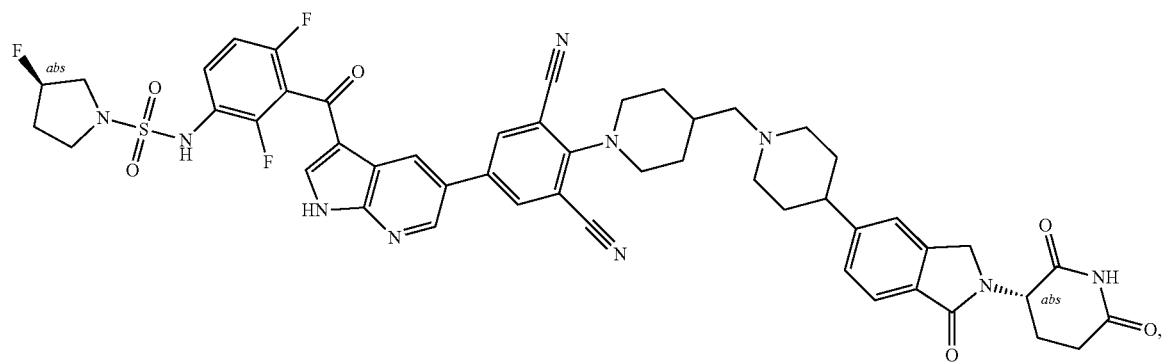

(261)
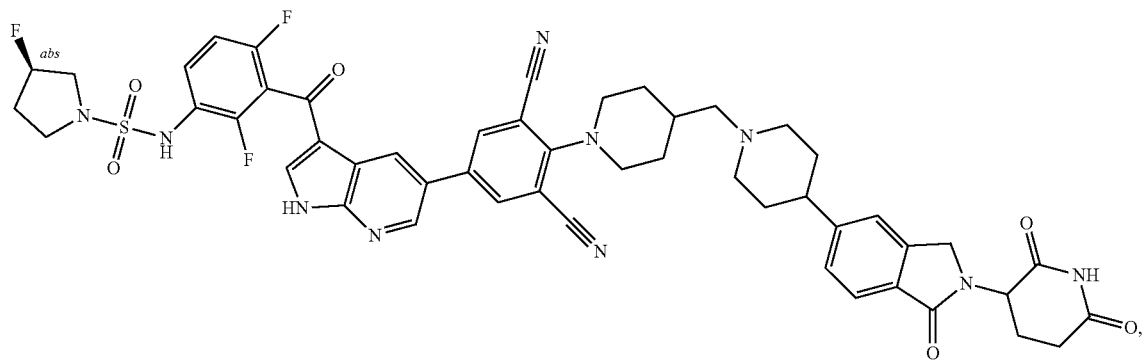
(262)
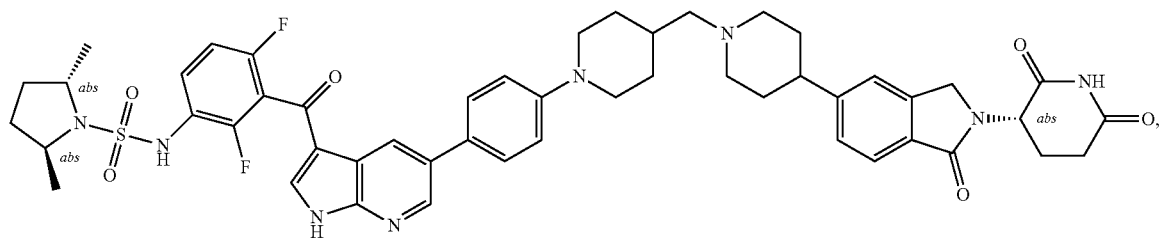 [SMILES: C[C@H]1CC[C@H](C)N1S(=O)(=O)Nc1ccc(F)c(C(=O)c2c[nH]c3ncc(-c4ccc(N5CCC(CN6CCC(c7ccc8c(c7)CN([C@H]7CCC(=O)NC7=O)C8=O)CC6)CC5)cc4)cc23)c1F]
(263)
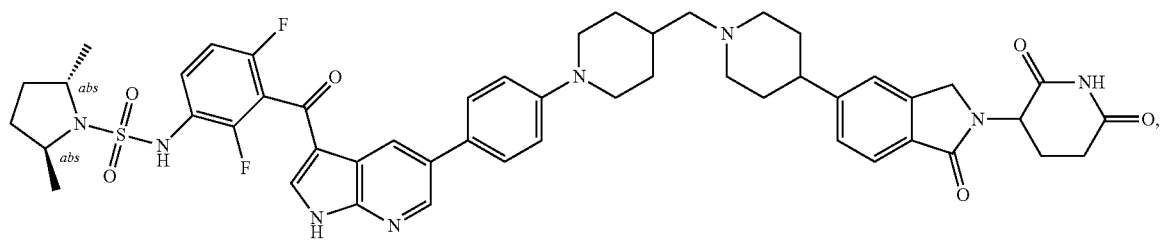 [SMILES: C[C@H]1CC[C@H](C)N1S(=O)(=O)Nc1ccc(F)c(C(=O)c2c[nH]c3ncc(-c4ccc(N5CCC(CN6CCC(c7ccc8c(c7)CN(C7CCC(=O)NC7=O)C8=O)CC6)CC5)cc4)cc23)c1F]
(264)
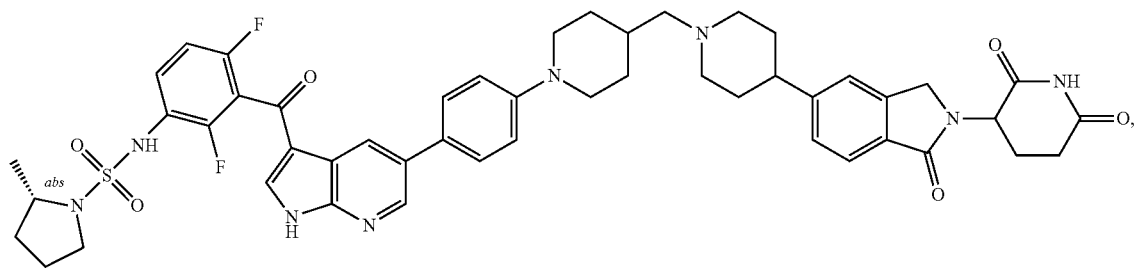
(265)
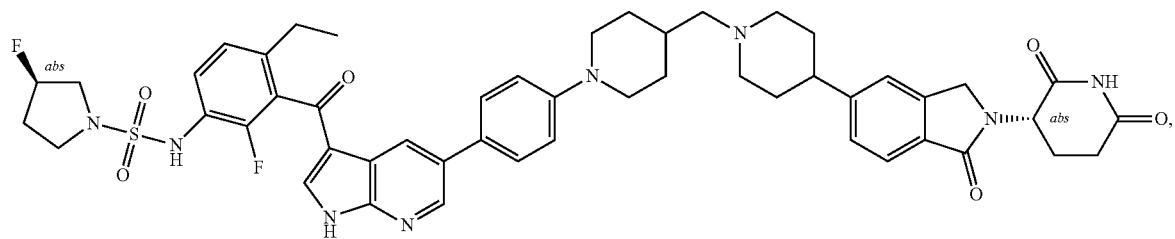

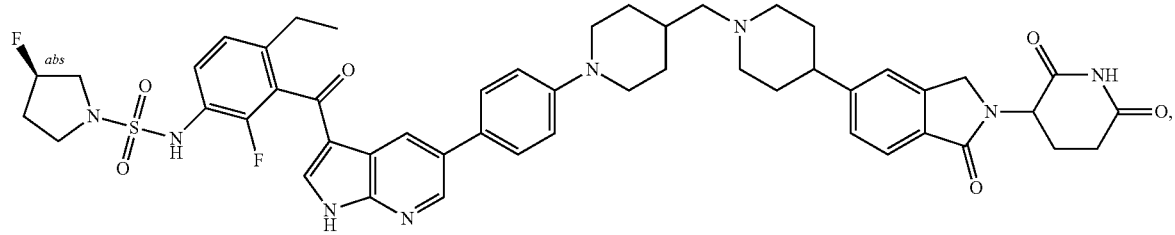
(266)
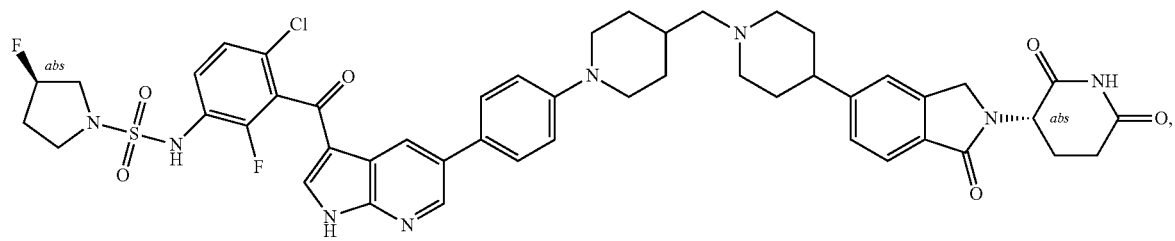
(267)
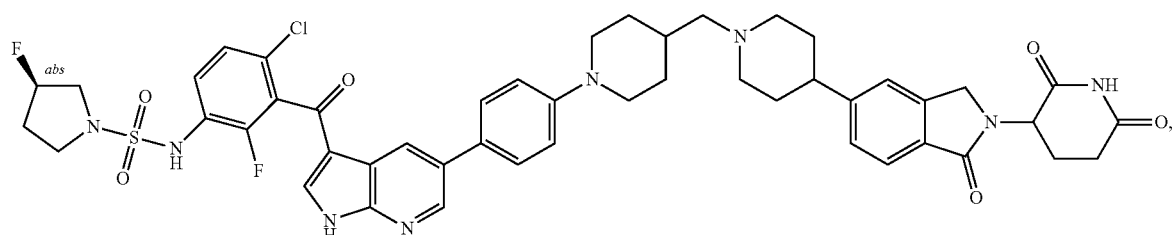
(268)
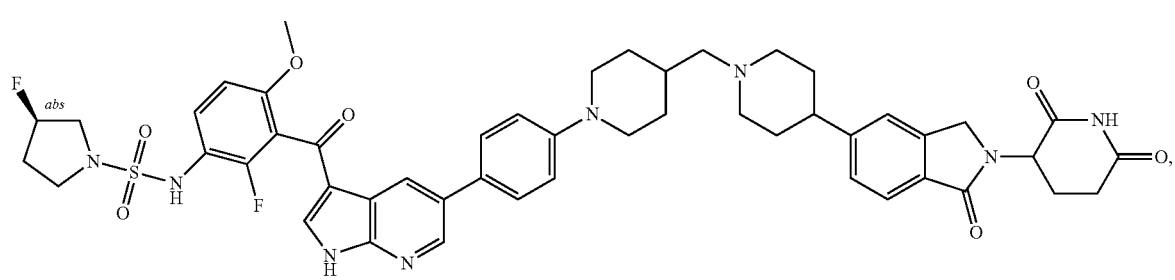
(269)
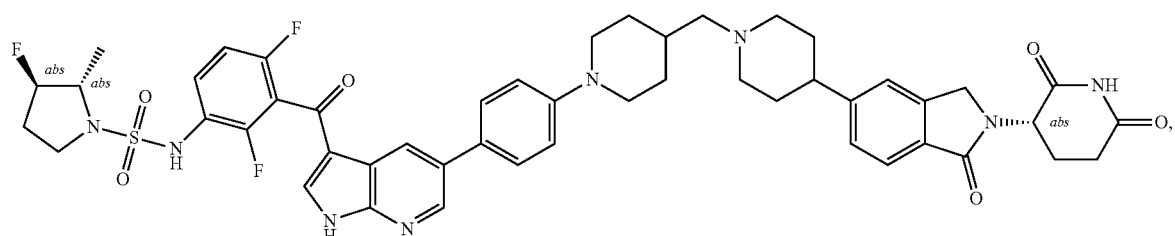
(270)
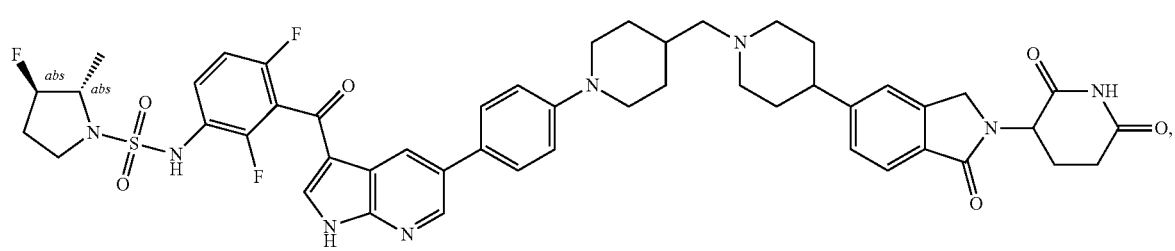
(271)

(272)
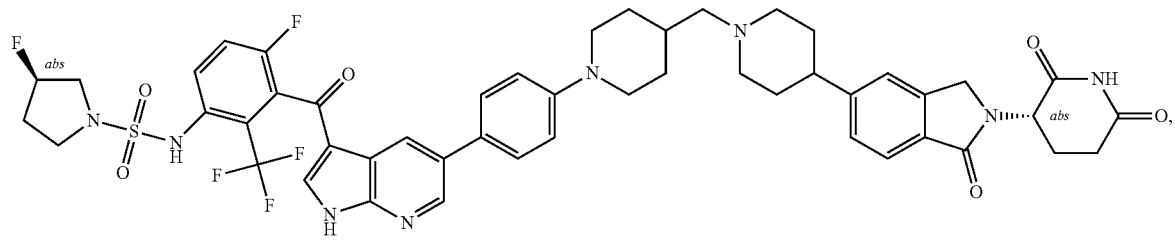
(273)
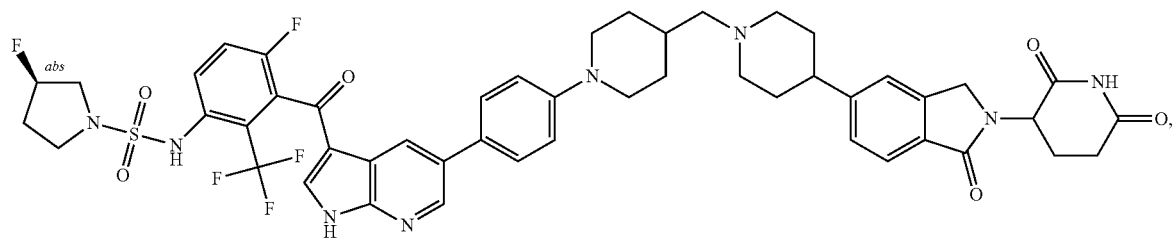
(274)
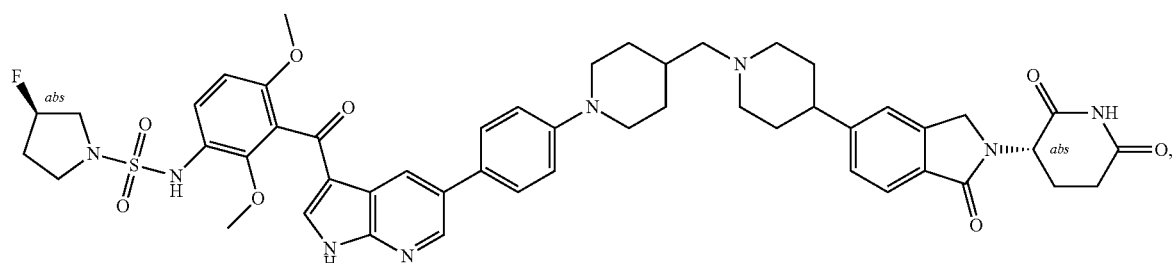
(275)
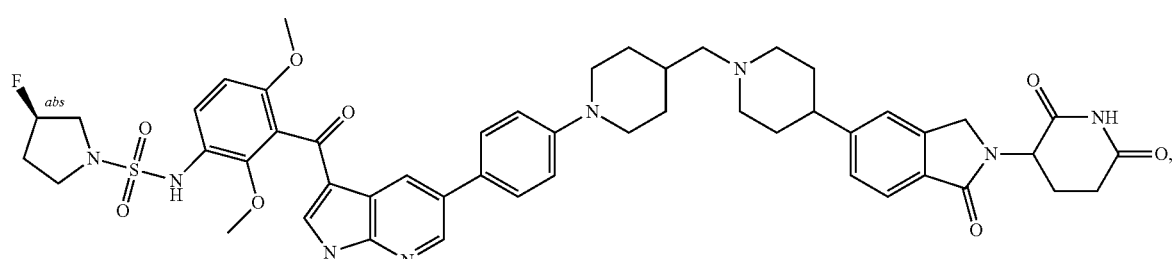
(276)
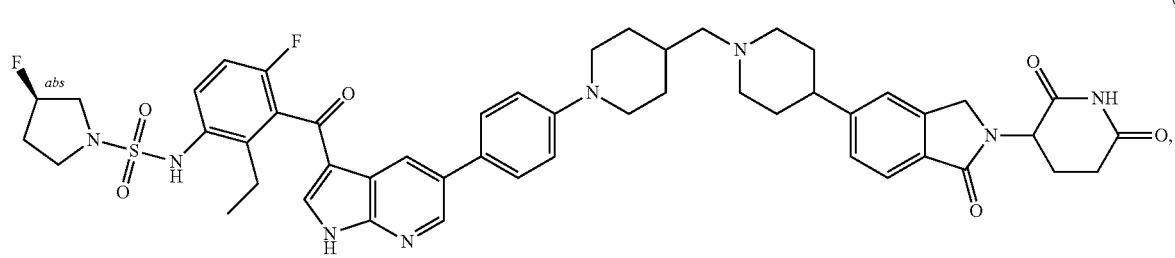
(277)
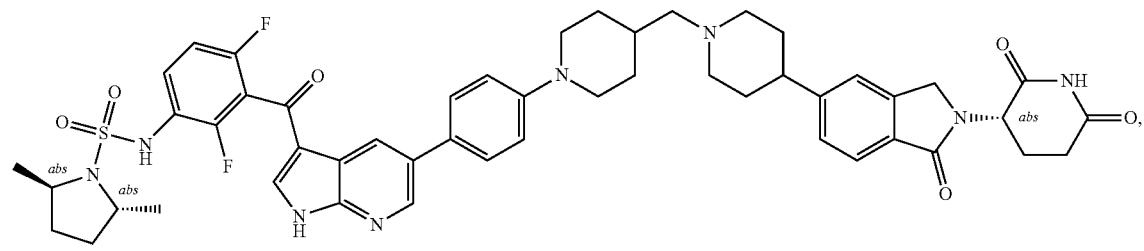 [SMILES: C[C@@H]1CC[C@@H](C)N1S(=O)(=O)Nc1ccc(F)c(C(=O)c2c[nH]c3ncc(-c4ccc(N5CCC(CN6CCC(c7ccc8c(c7)CN([C@H]7CCC(=O)NC7=O)C8=O)CC6)CC5)cc4)cc23)c1F]

-continued
(278)
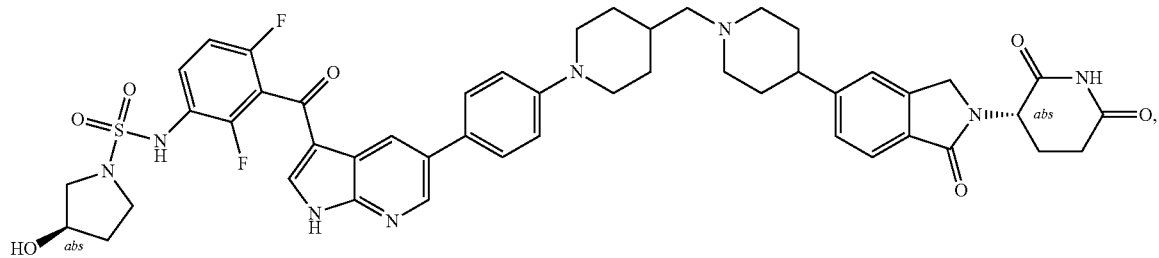
(279)
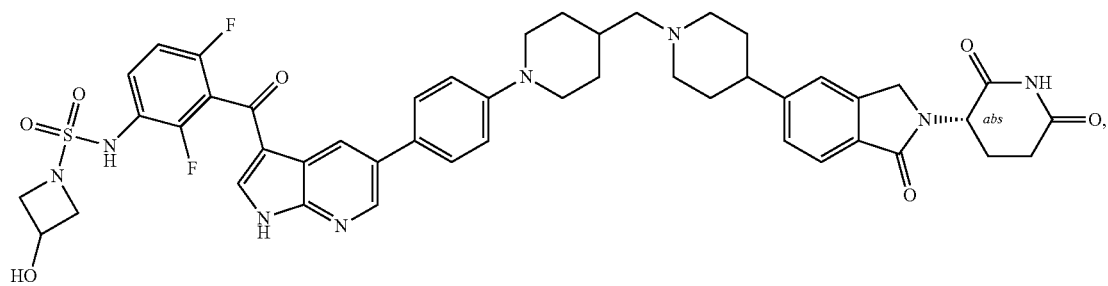 [SMILES: O=C1CC[C@H](N2Cc3cc(C4CCN(CC5CCN(c6ccc(-c7cnc8[nH]cc(C(=O)c9c(F)ccc(NS(=O)(=O)N%10CC(O)C%10)c9F)c8c7)cc6)CC5)CC4)ccc3C2=O)C(=O)N1]
(280)
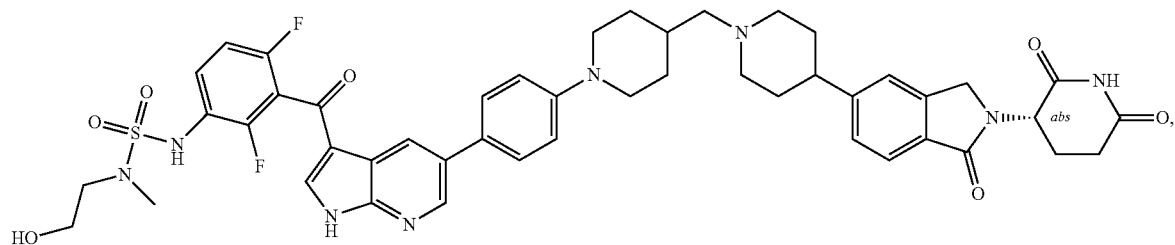 [SMILES: CN(CCO)S(=O)(=O)Nc1ccc(F)c(C(=O)c2c[nH]c3ncc(-c4ccc(N5CCC(CN6CCC(c7ccc8c(c7)CN([C@H]7CCC(=O)NC7=O)C8=O)CC6)CC5)cc4)cc23)c1F]
(281)
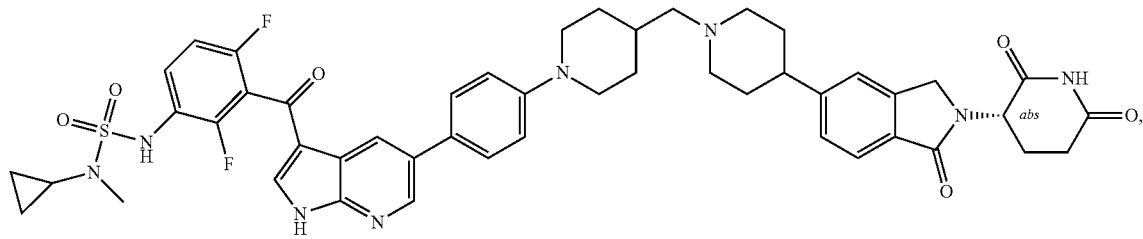 [SMILES: CN(C1CC1)S(=O)(=O)Nc1ccc(F)c(C(=O)c2c[nH]c3ncc(-c4ccc(N5CCC(CN6CCC(c7ccc8c(c7)CN([C@H]7CCC(=O)NC7=O)C8=O)CC6)CC5)cc4)cc23)c1F]
(282)
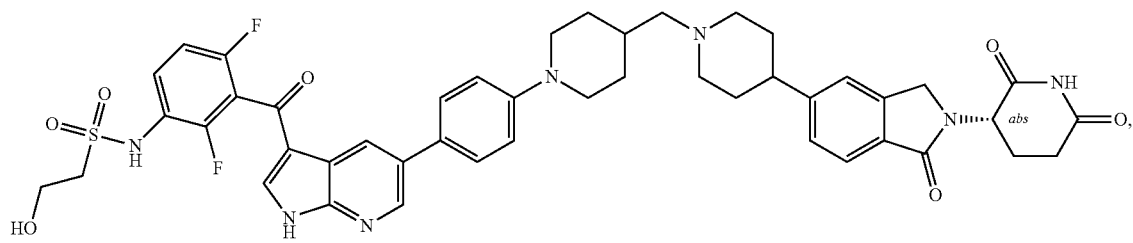

-continued
(283)
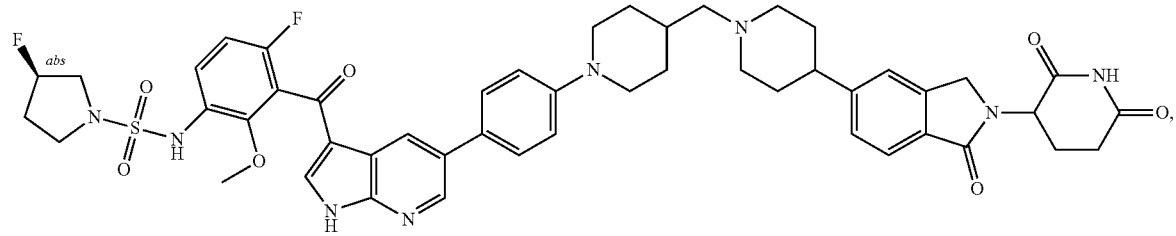
(284)
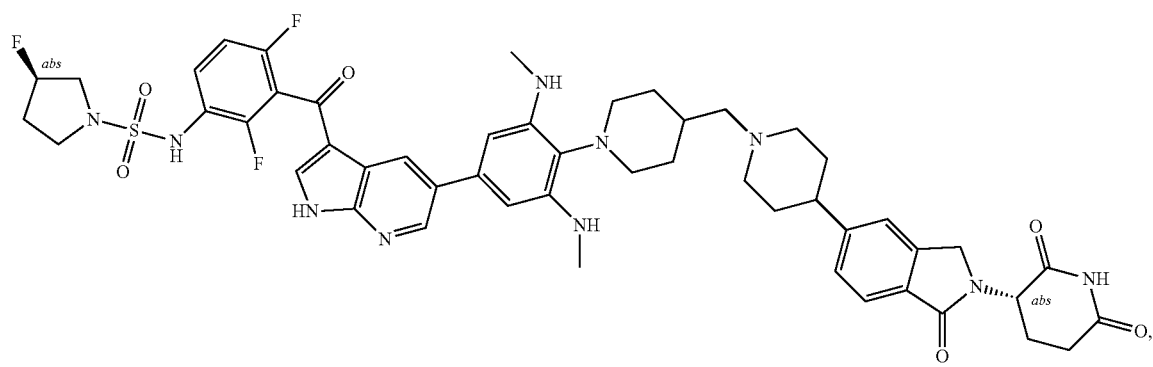
(285)
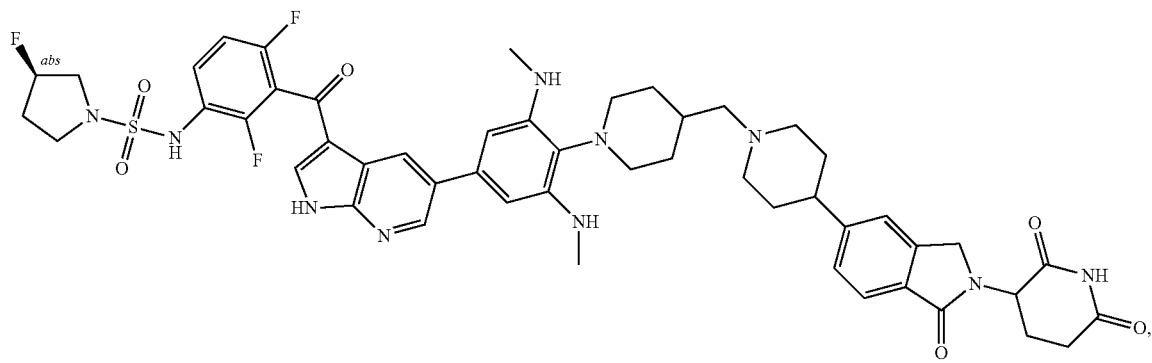
(286)
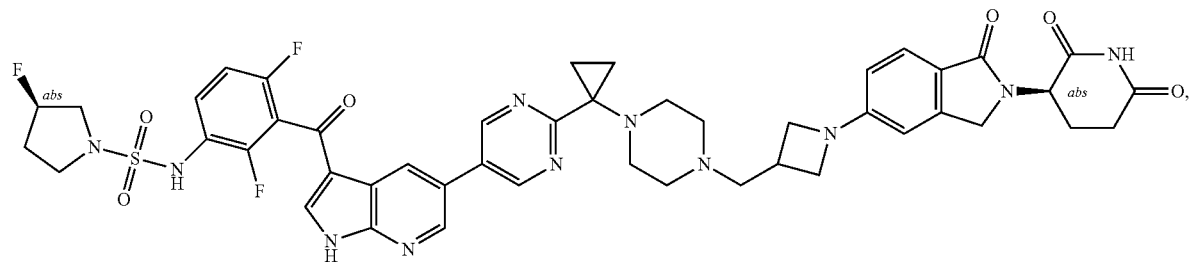
(287)
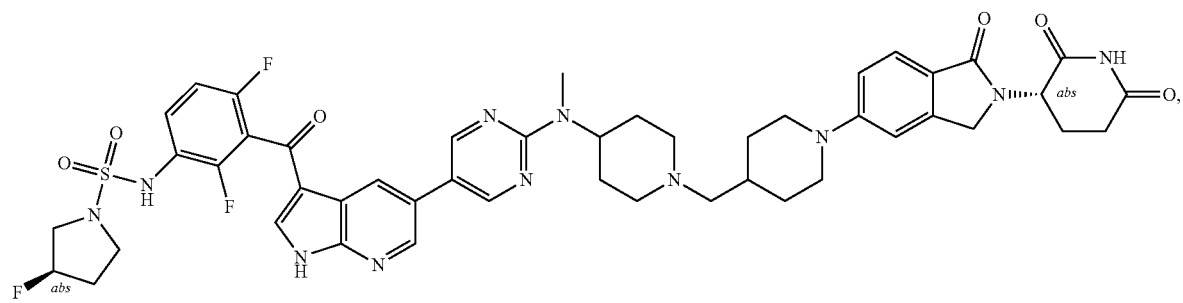

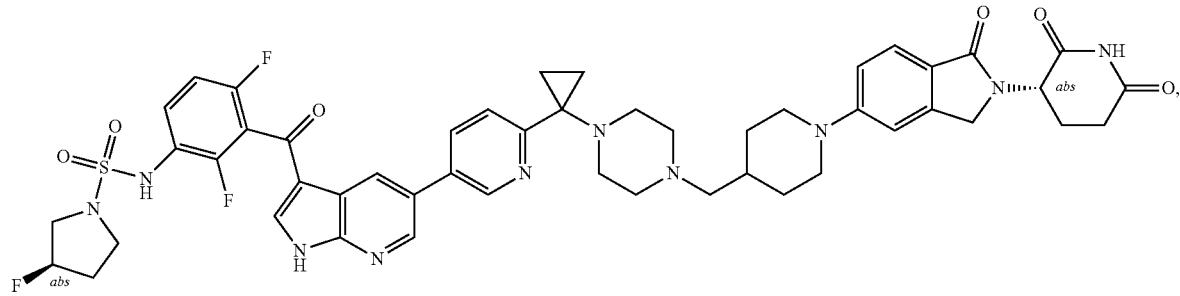
(288)
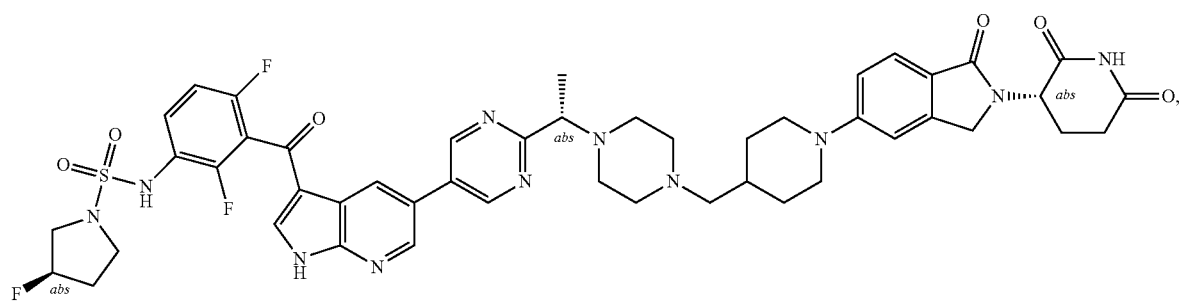
(289)
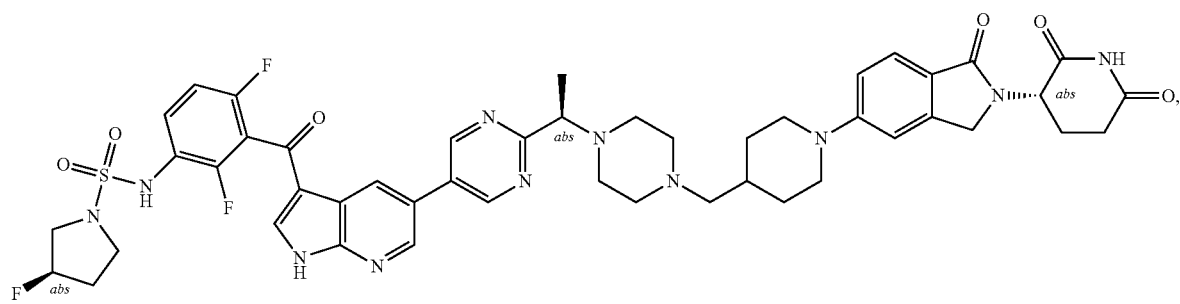
(290)
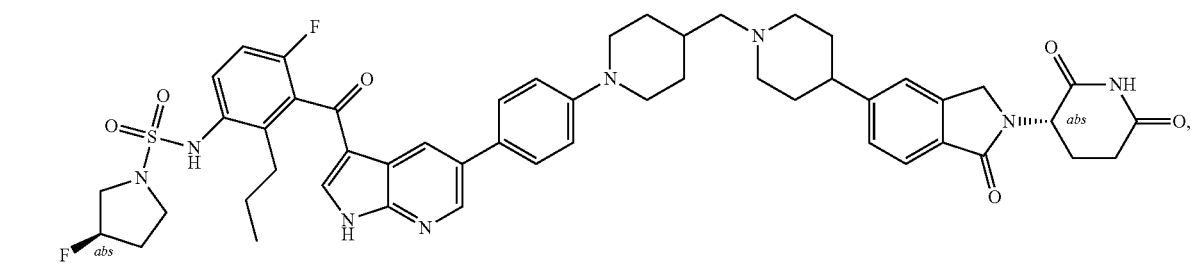
(291)
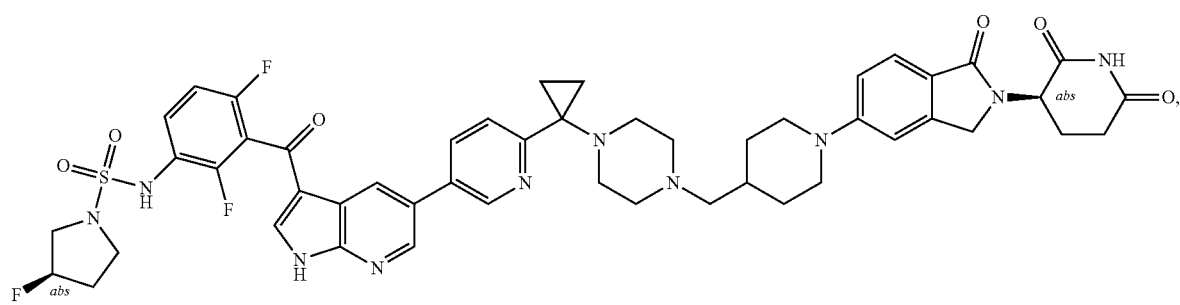
(292)

(293)
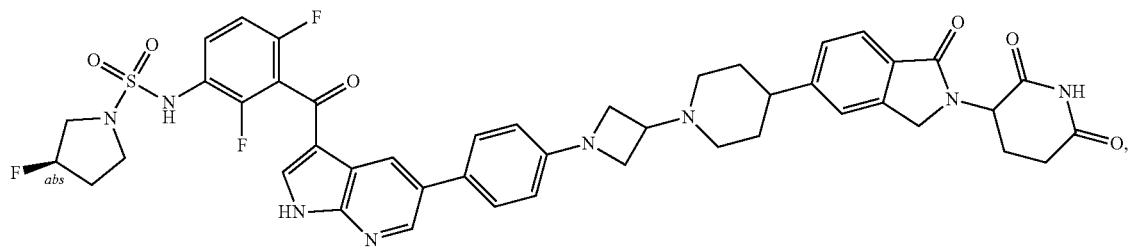
(294)
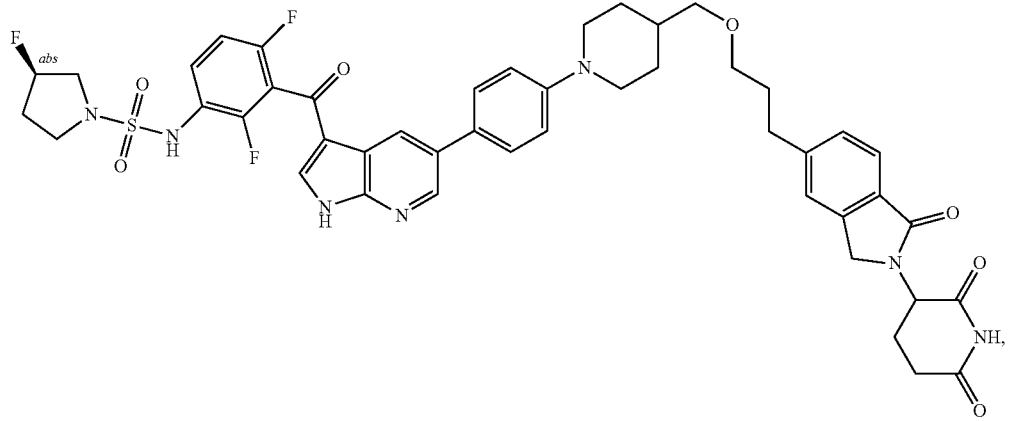
(295)
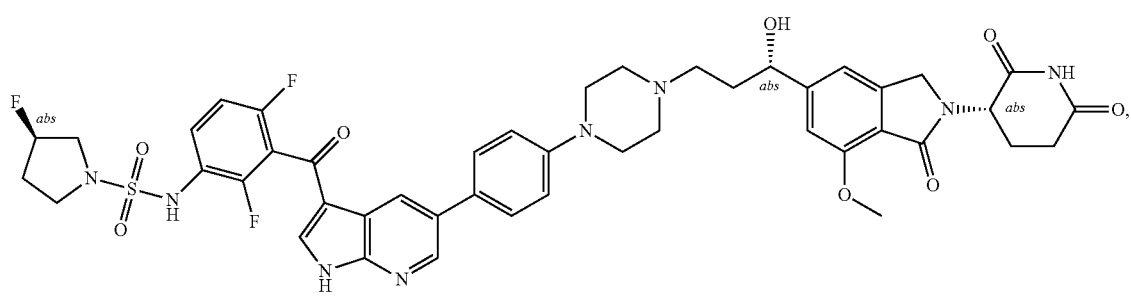
(296)
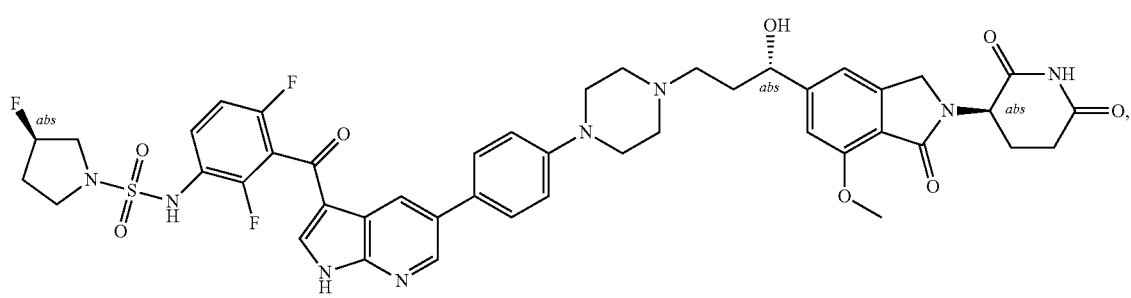
(297)
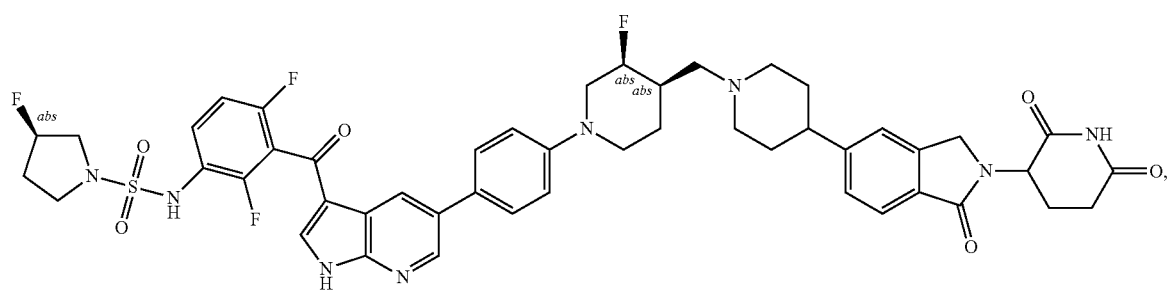

-continued
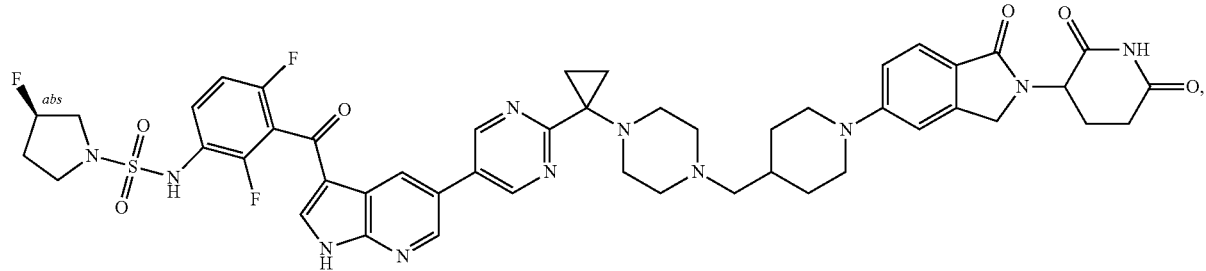
(298)
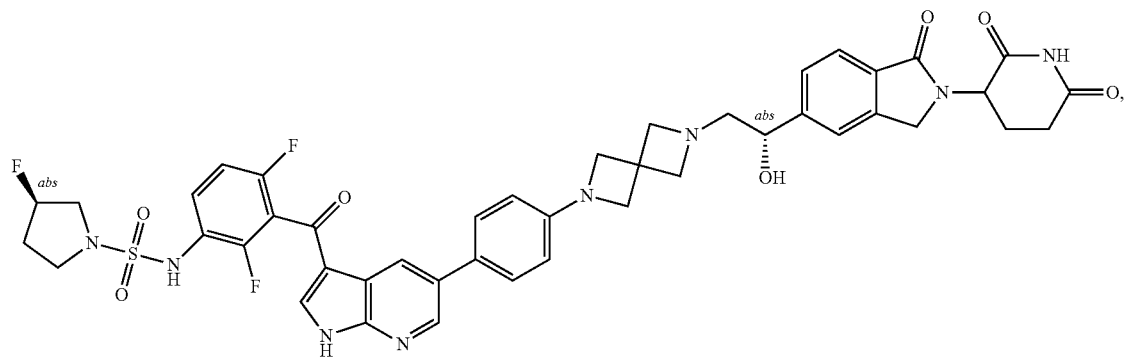
(299)
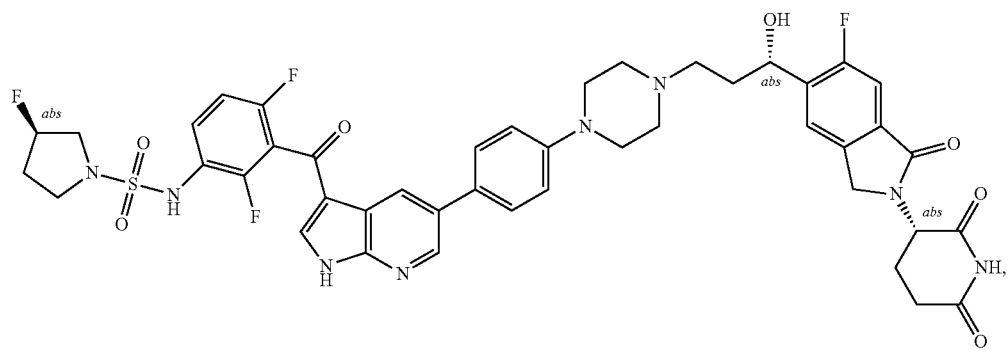
(300)
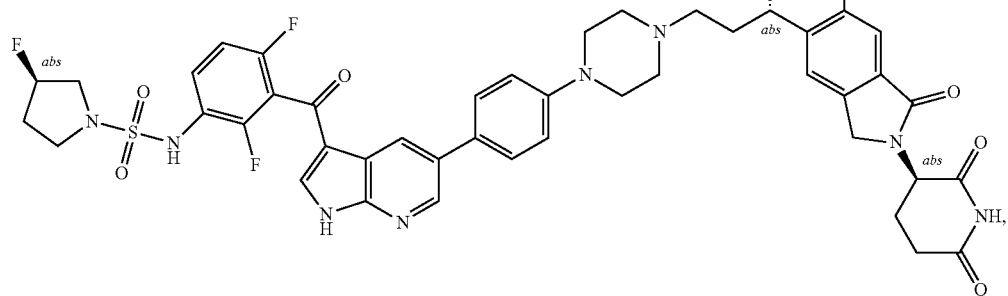
(301)

-continued
(302)
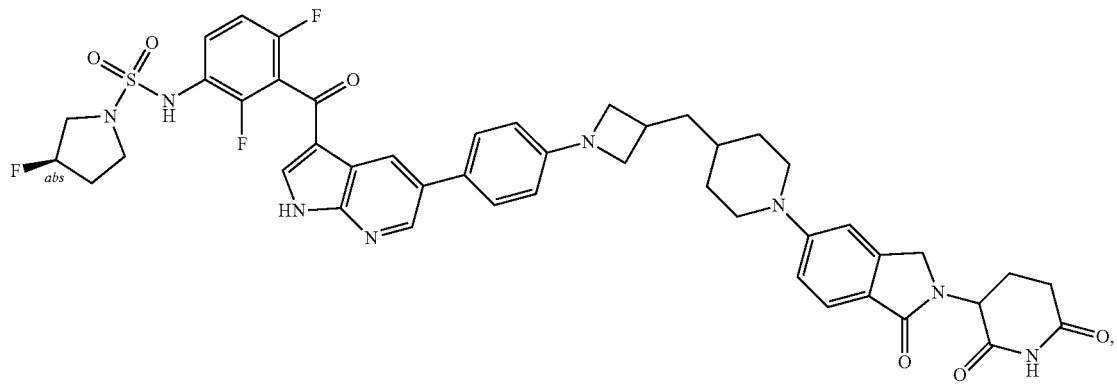
(303)
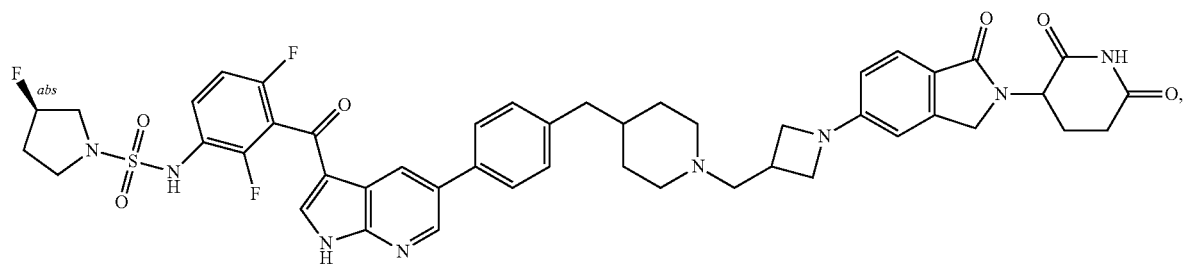
(304)
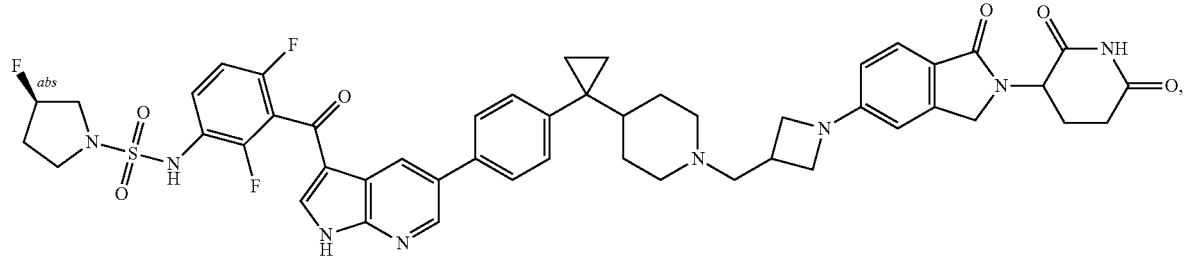
(305)
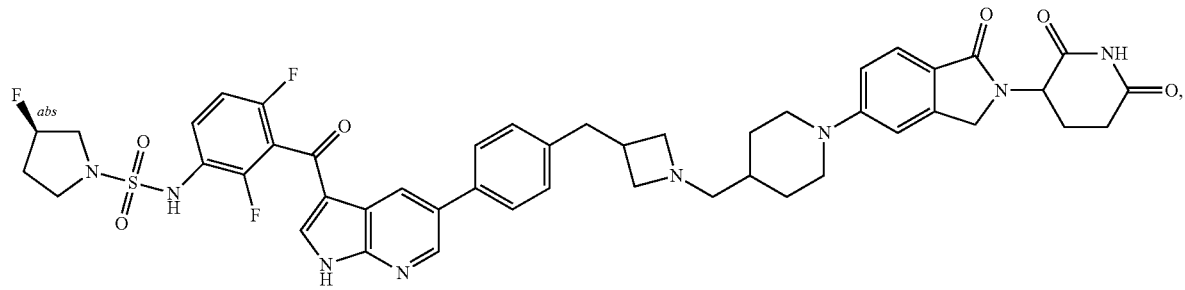

-continued
(306)
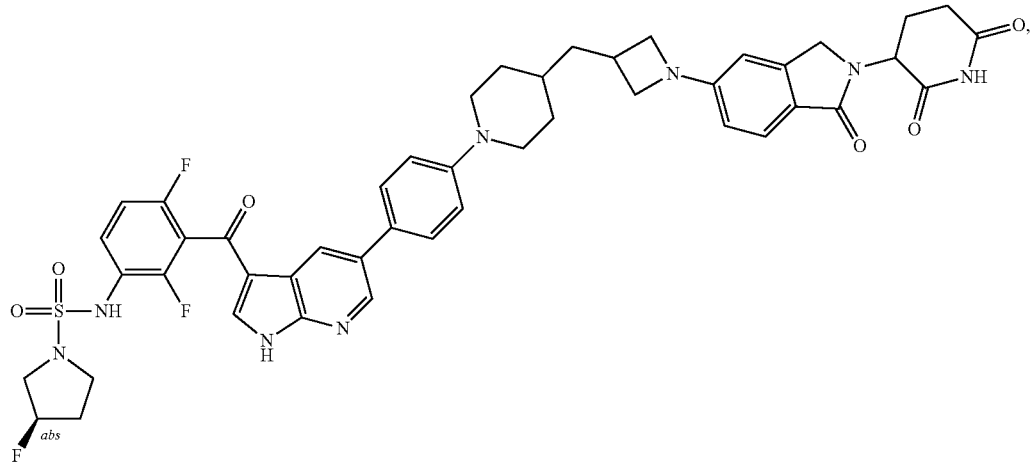
(307)
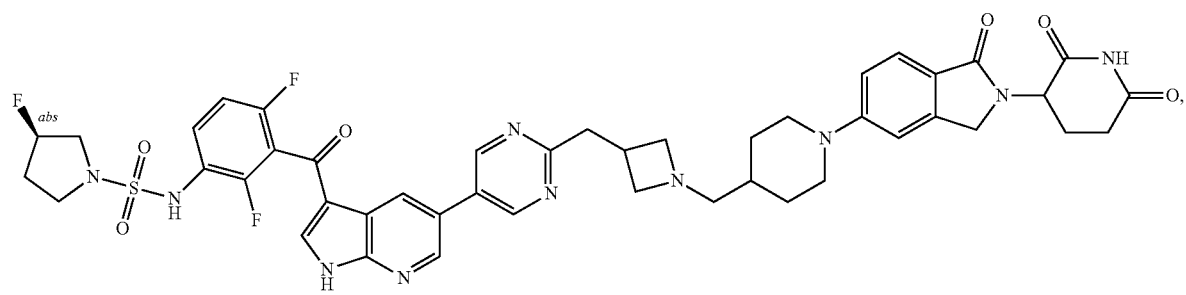
(308)
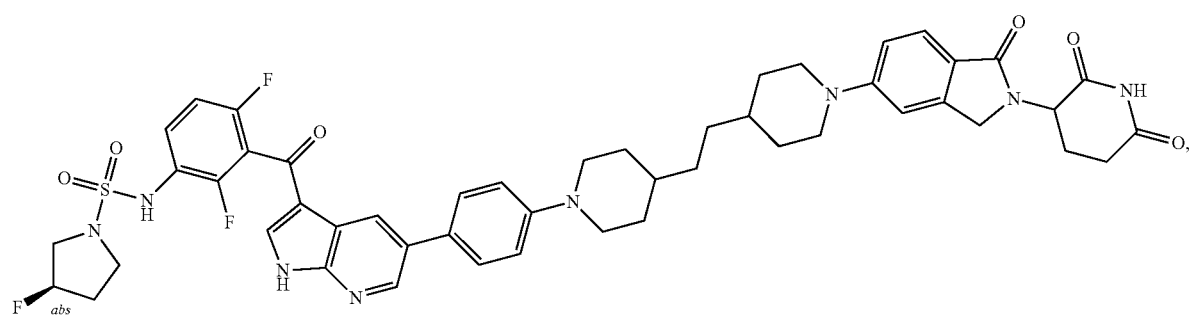
(309)
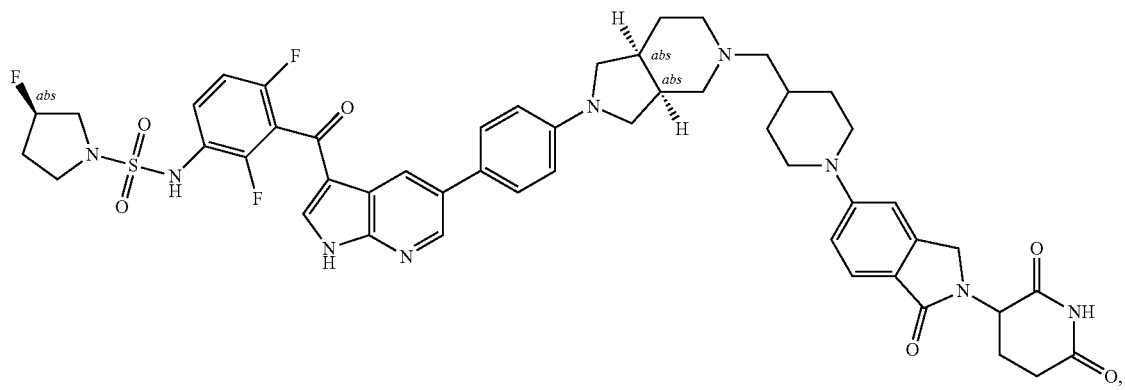

(310)
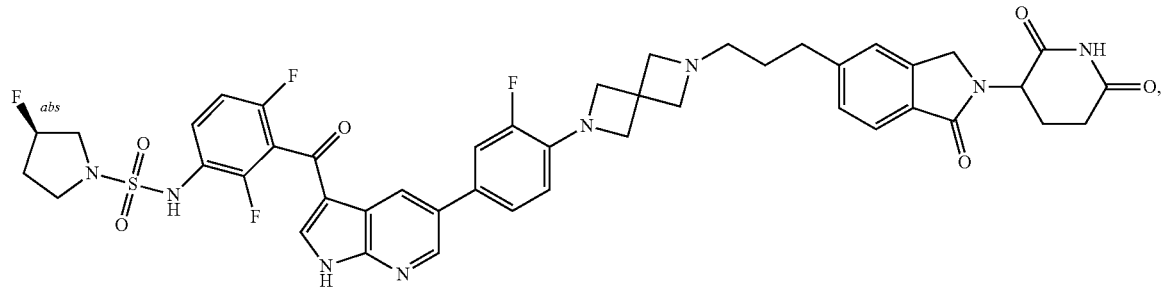
(311)
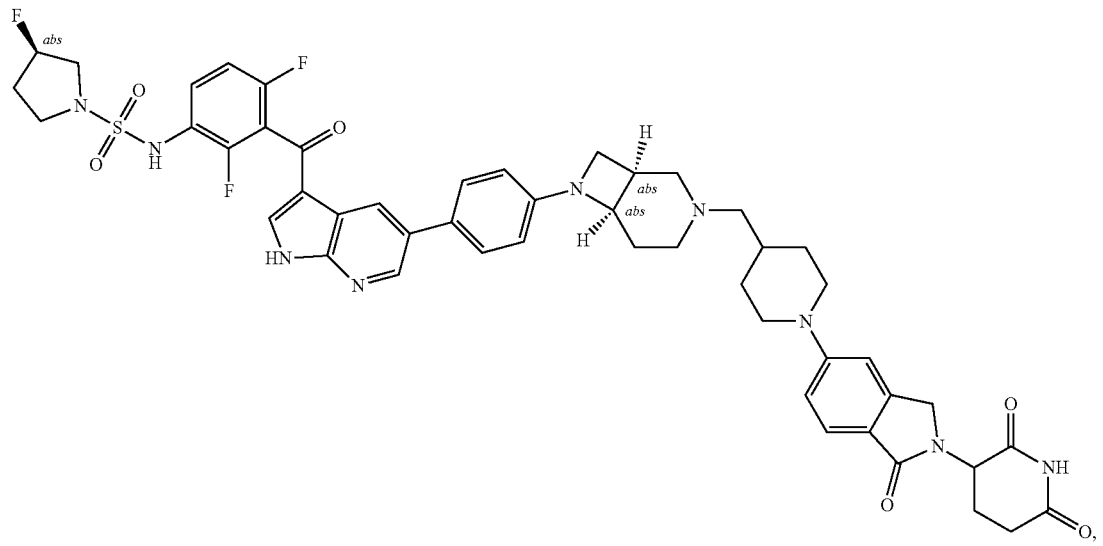
(312)
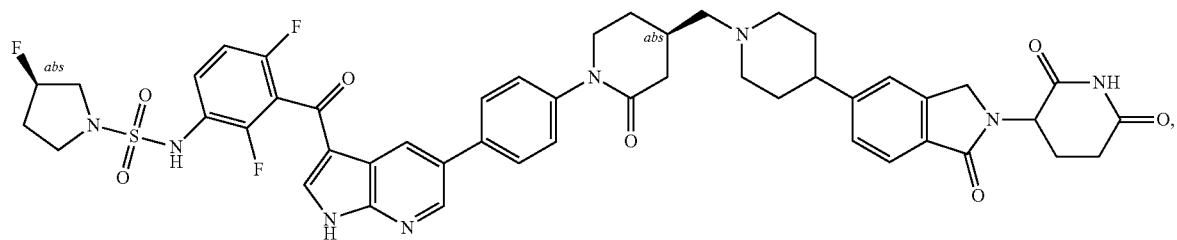
(313)
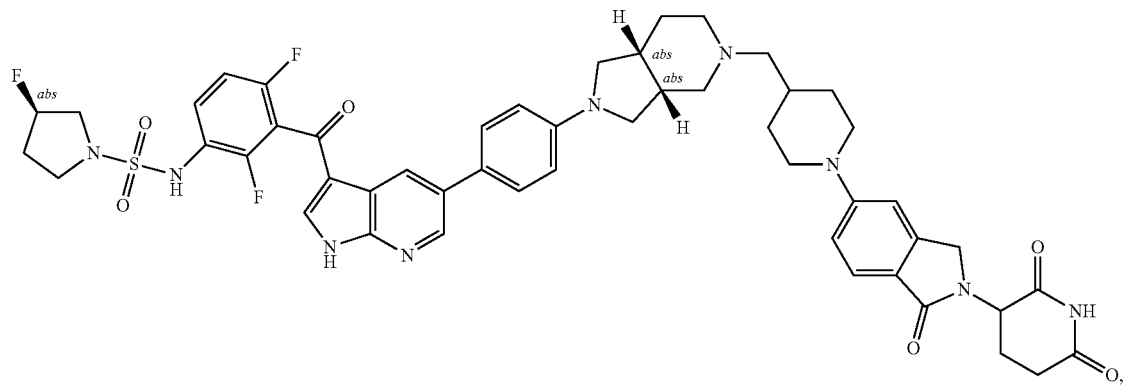

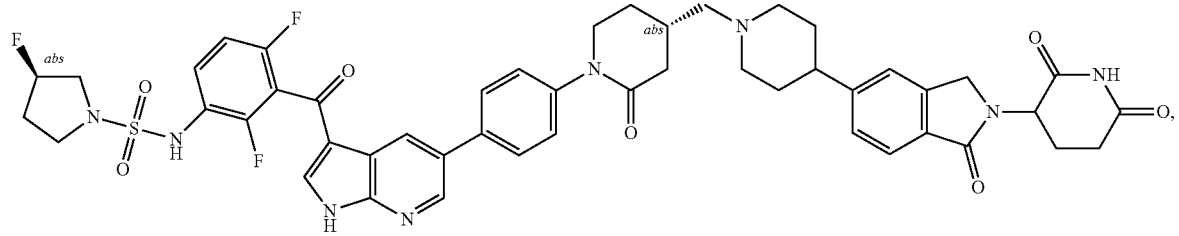
(314)
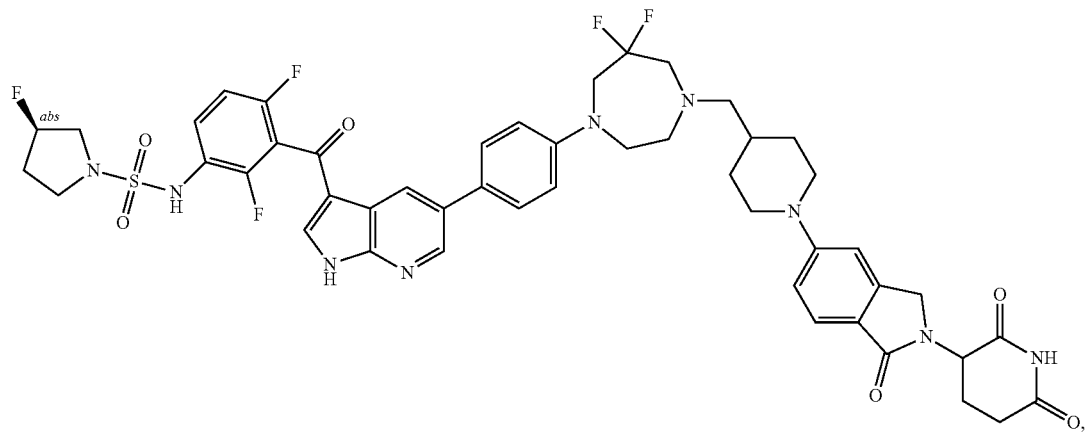
(315)
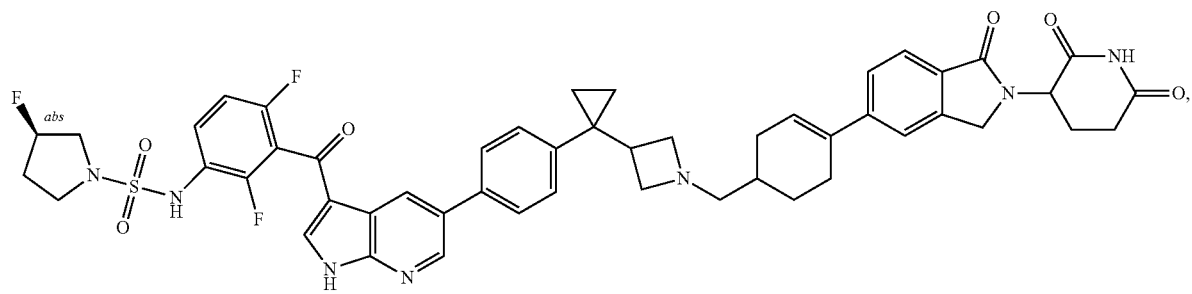
(316)
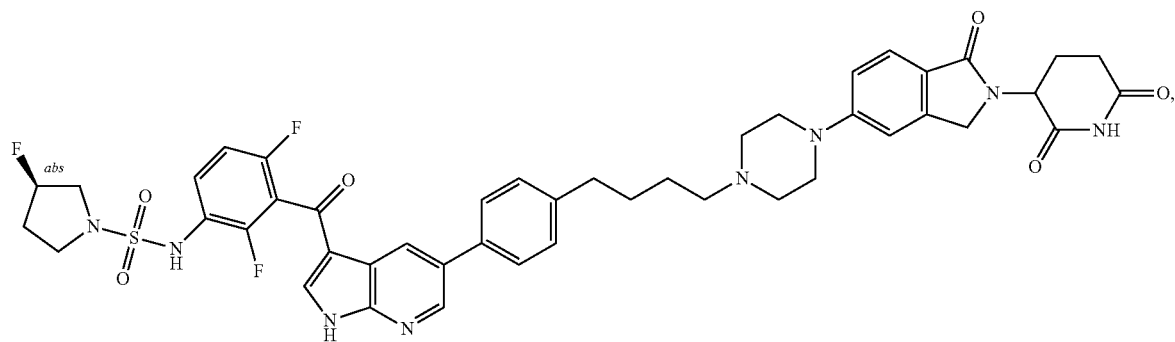
(317)

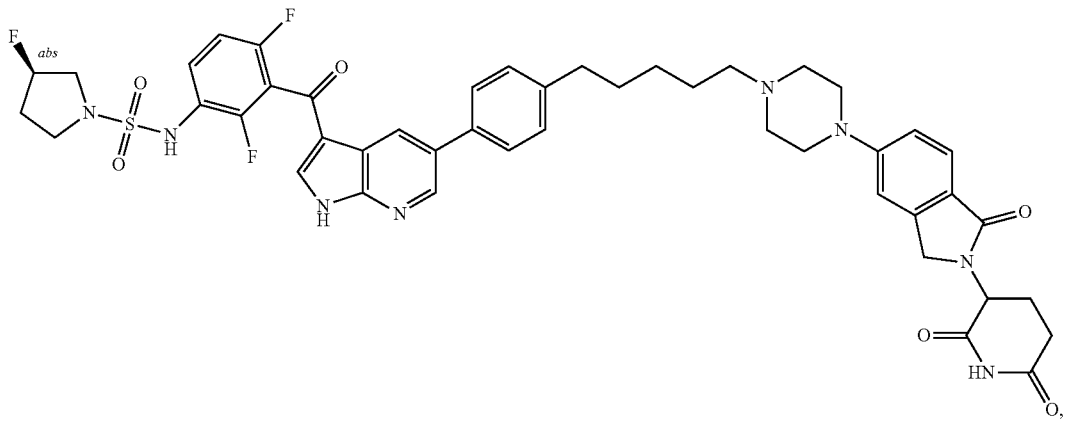
(318)
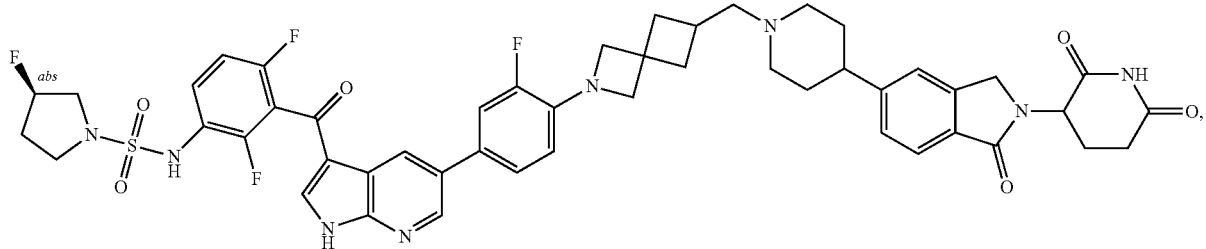
(319)
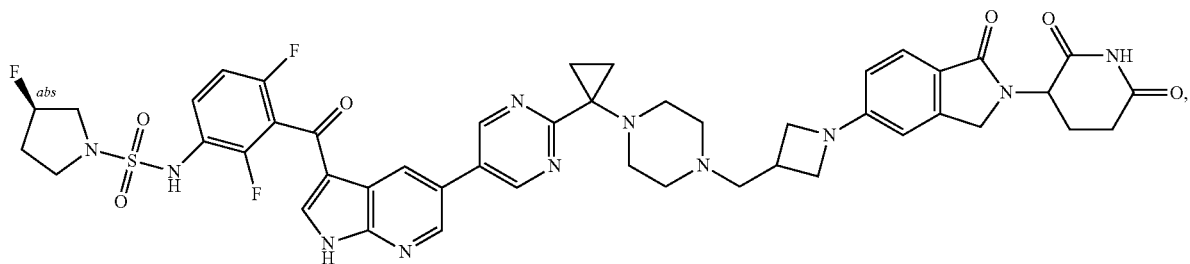
(320)
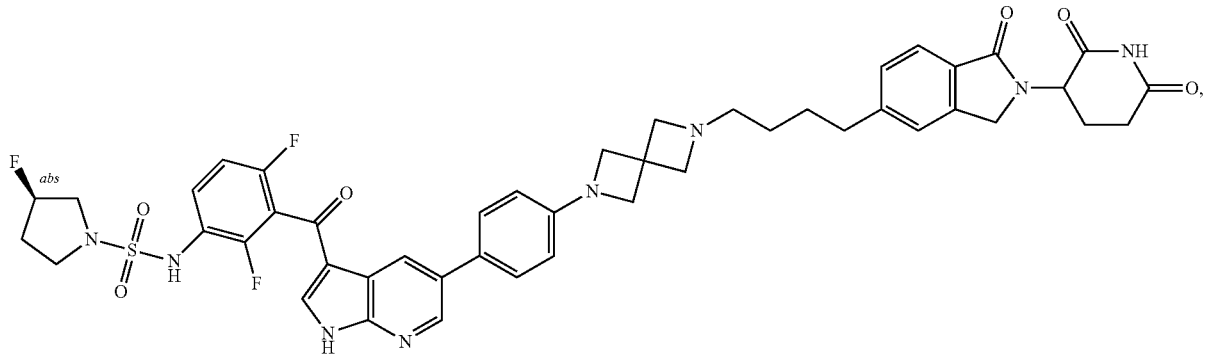
(321)

-continued
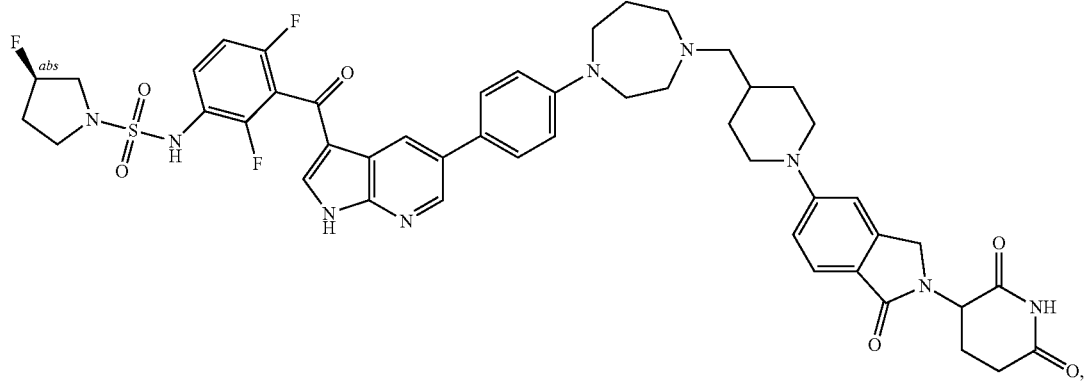
(322)
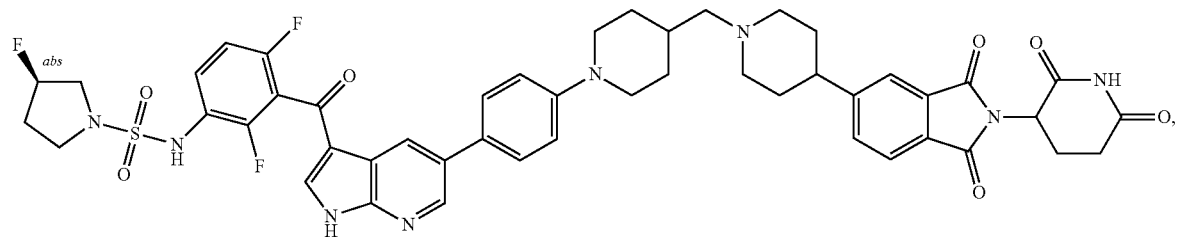
(323)
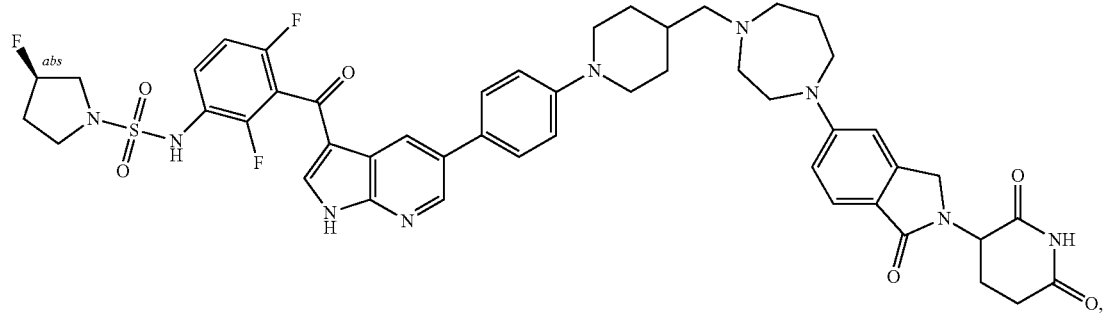
(324)
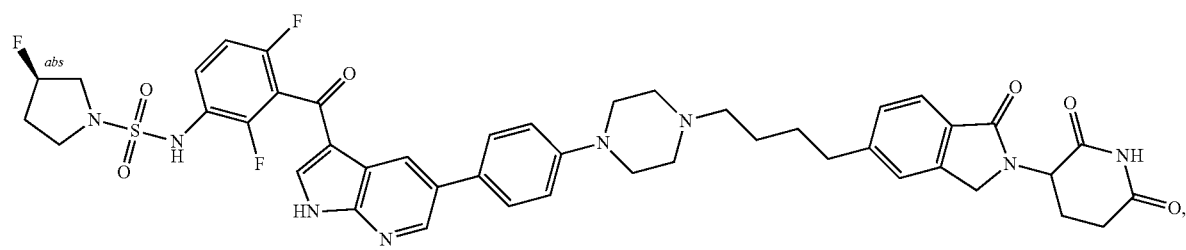
(325)

(326)
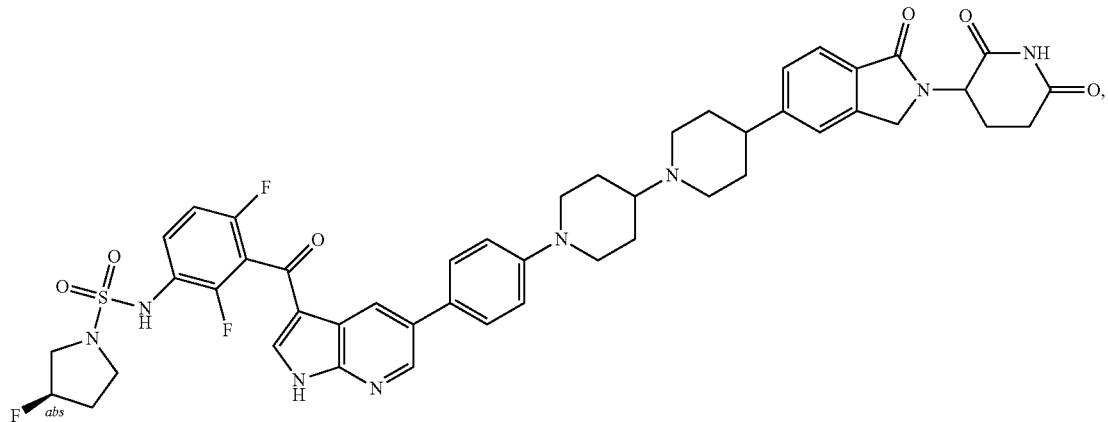
(327)
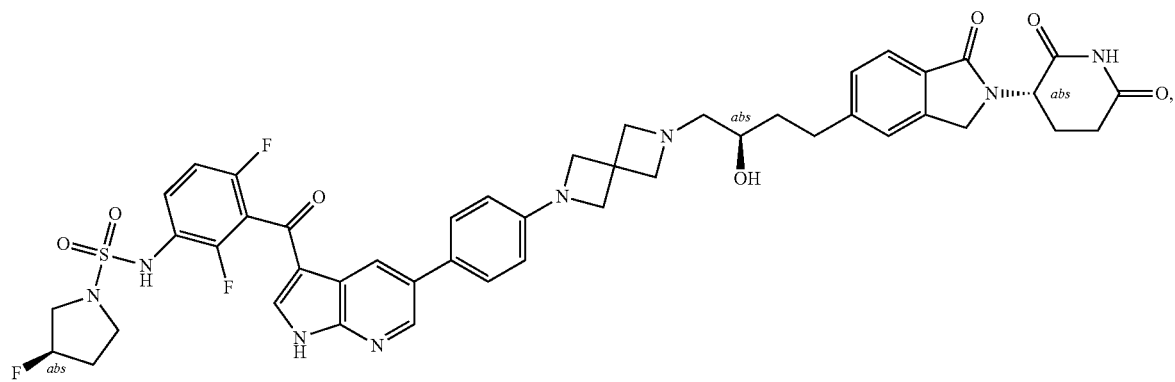
(328)
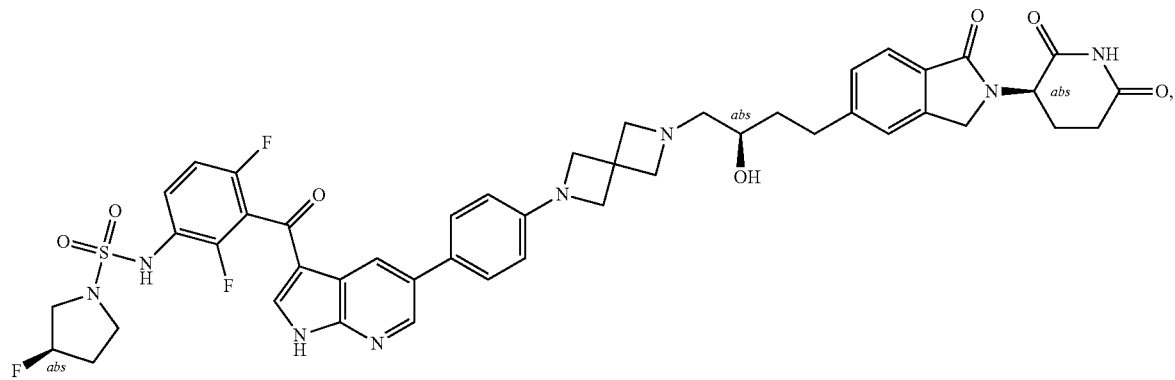

(329)
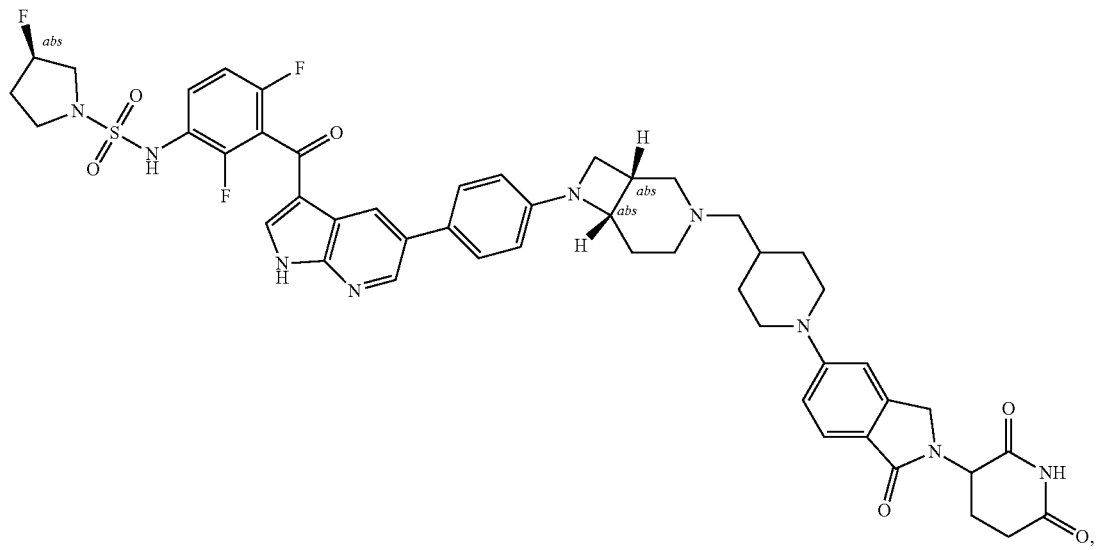
(330)
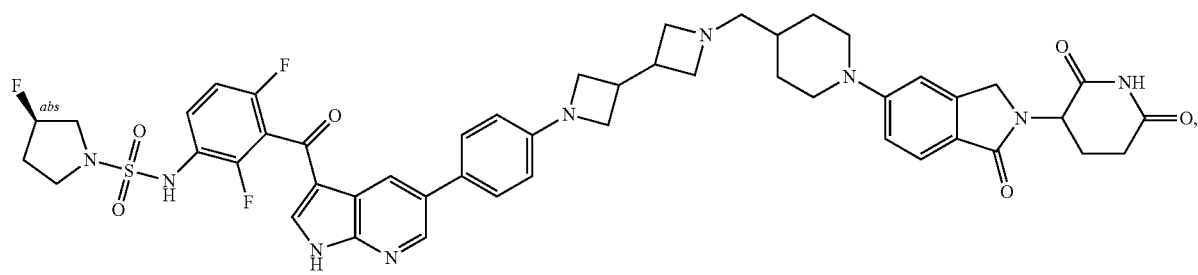
(331)
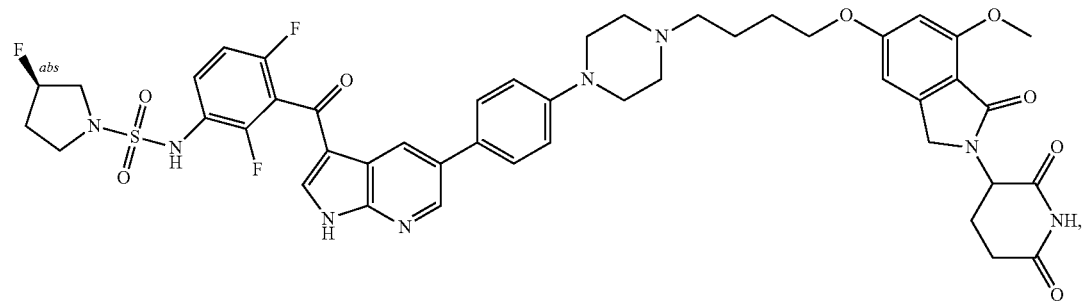
(332)
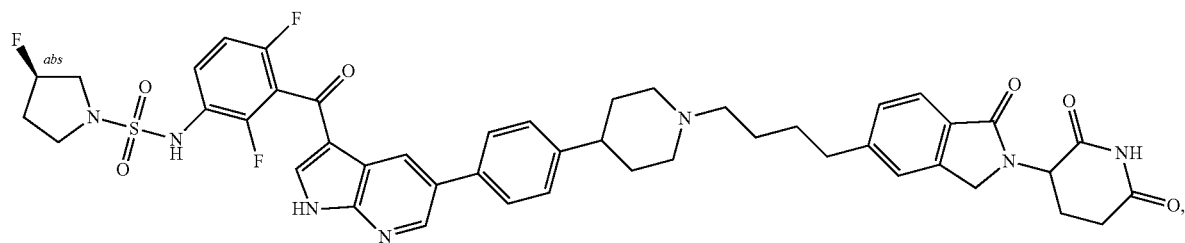

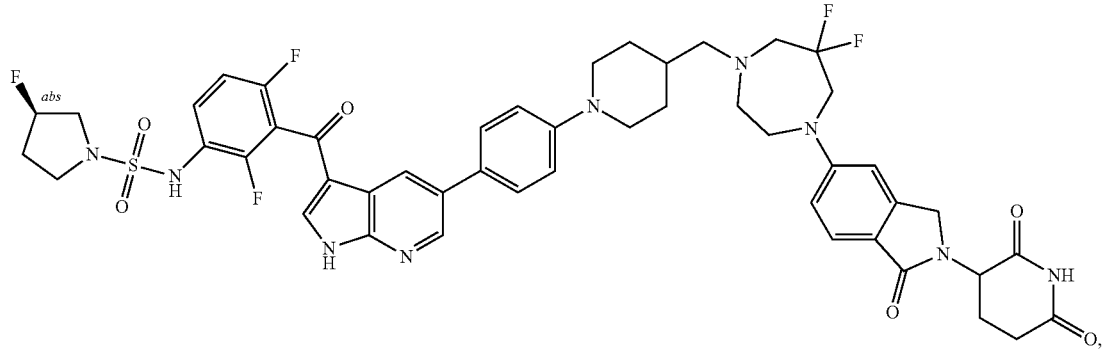
(333)
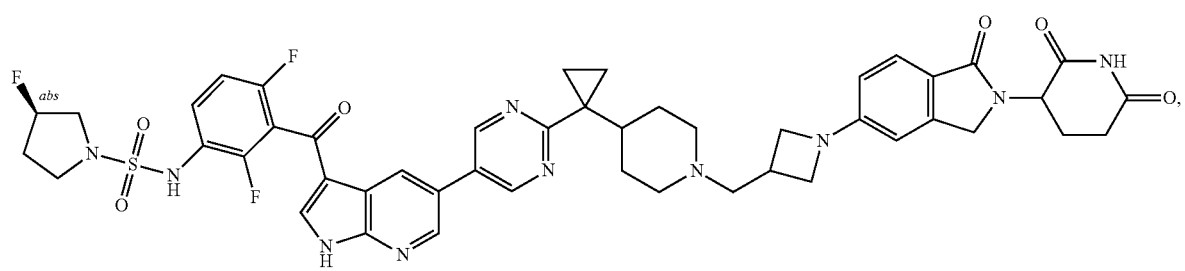
(334)
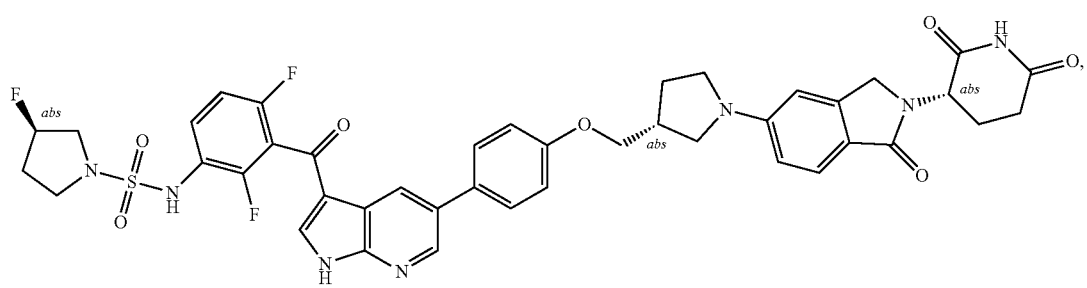
(335)
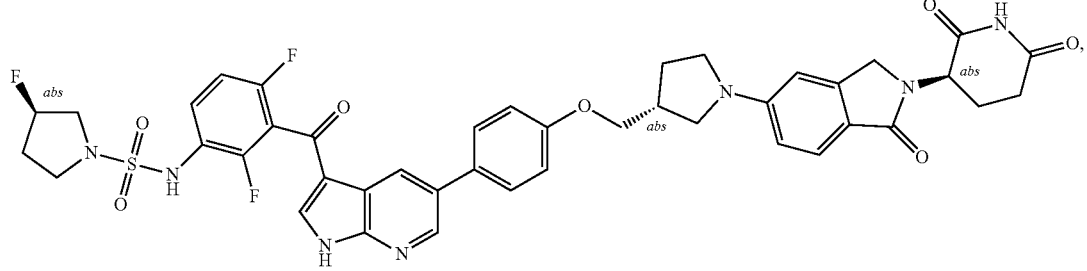
(336)
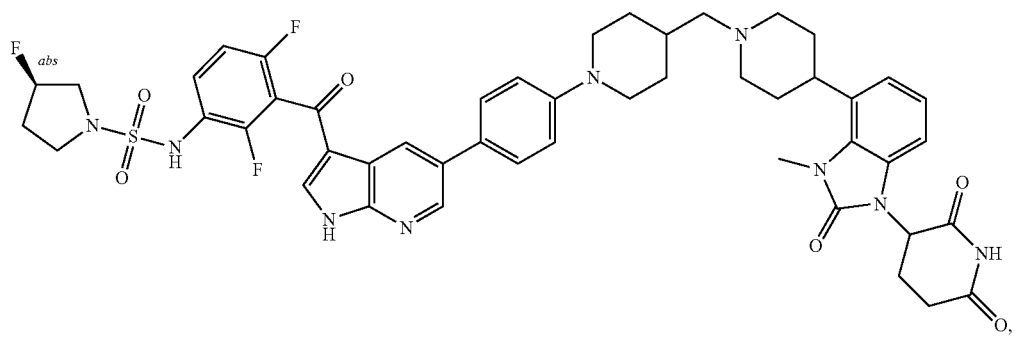
(337)

(338)
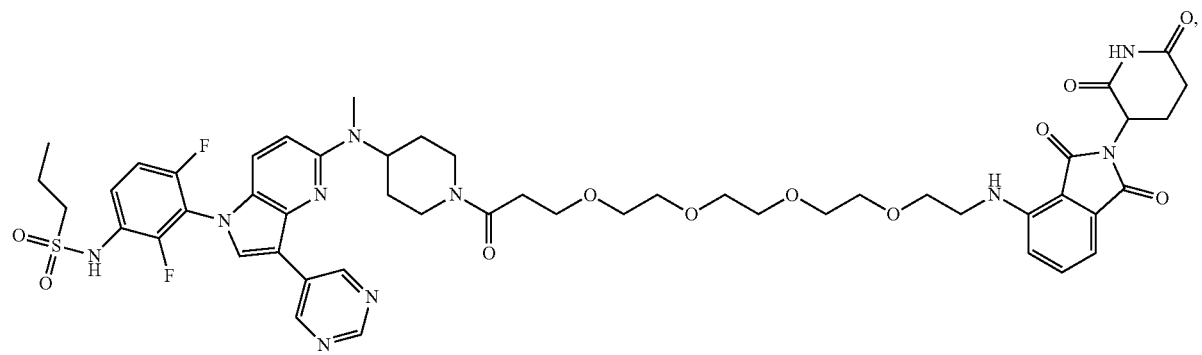 [SMILES: CCCS(=O)(=O)Nc1ccc(F)c(-n2cc(-c3cncnc3)c3nc(N(C)C4CCN(C(=O)CCOCCOCCOCCOCCNc5cccc6c5C(=O)N(C5CCC(=O)NC5=O)C6=O)CC4)ccc32)c1F]
(339)
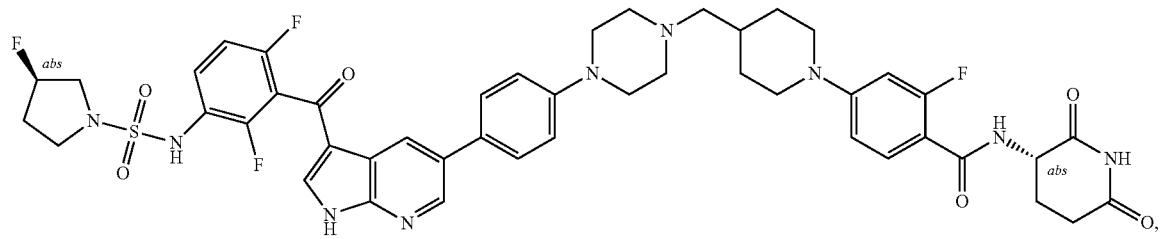
(340)
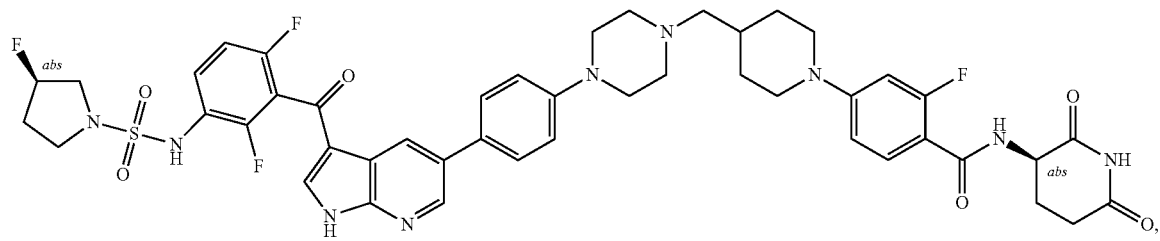
(341)
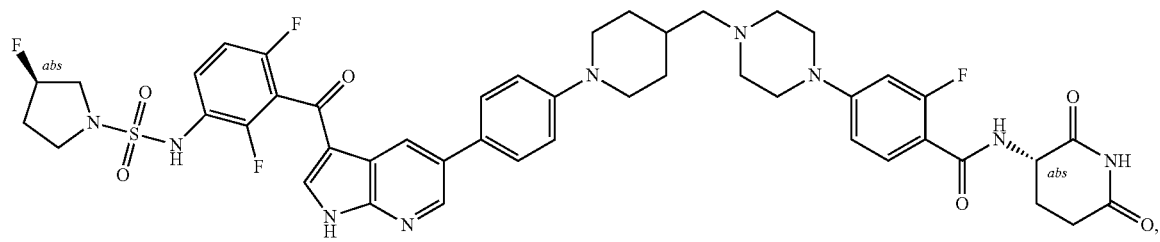
(342)
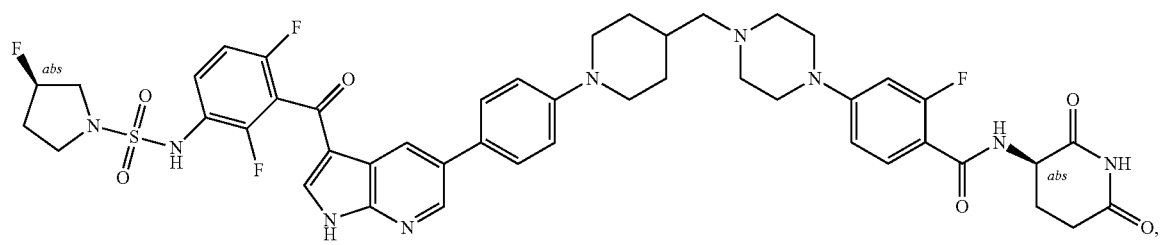

(343)
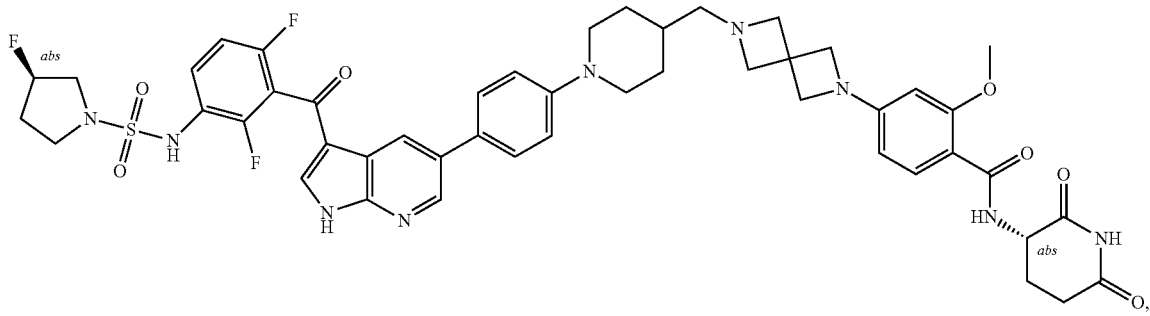
(344)
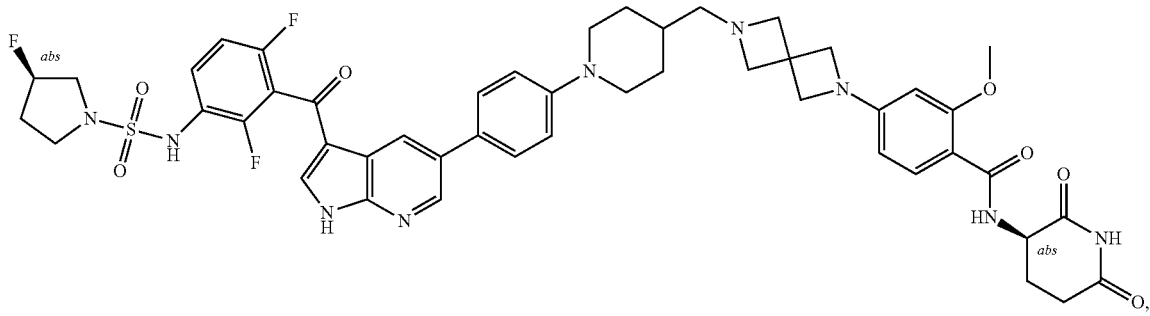
(345)
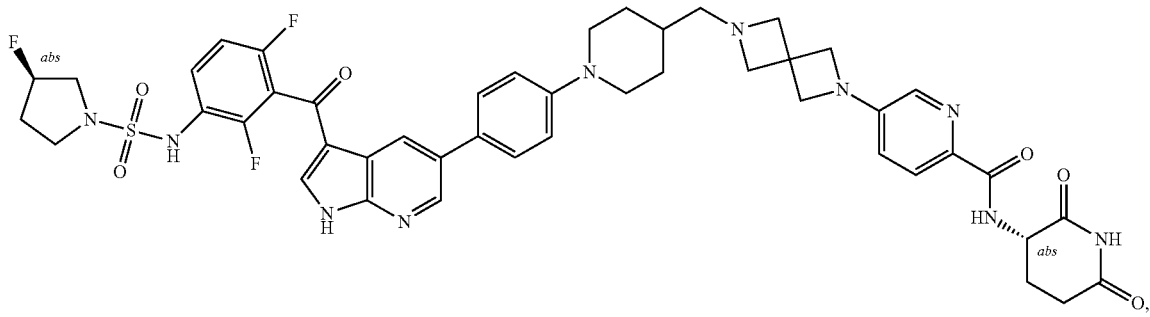
(346)
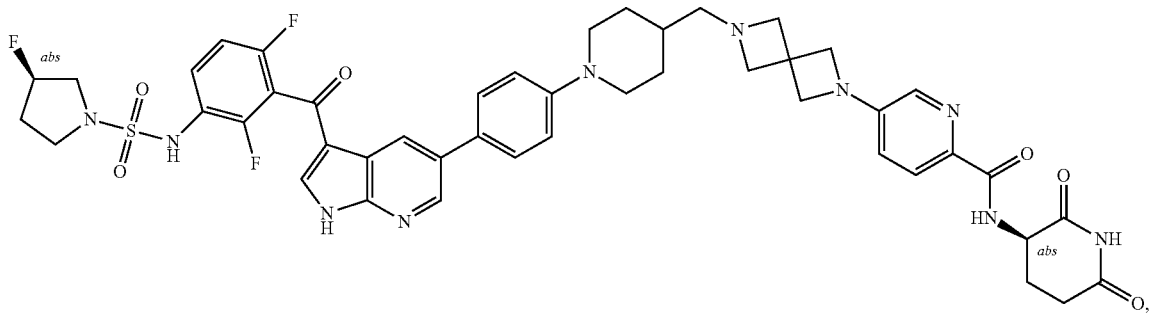

(347)
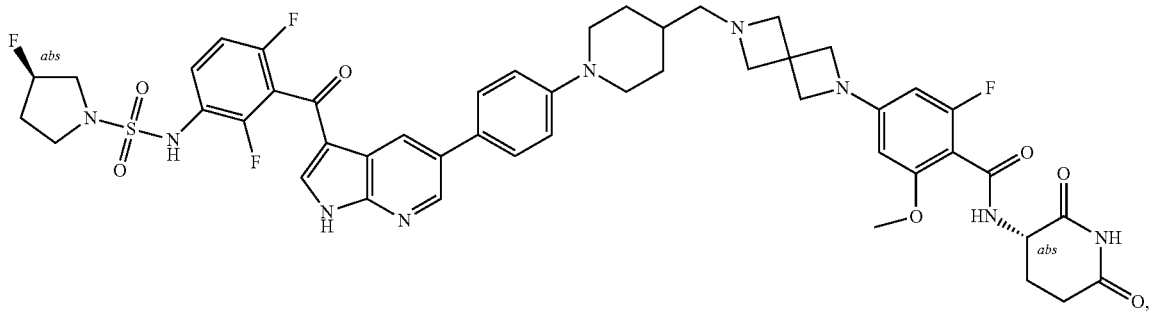
(348)
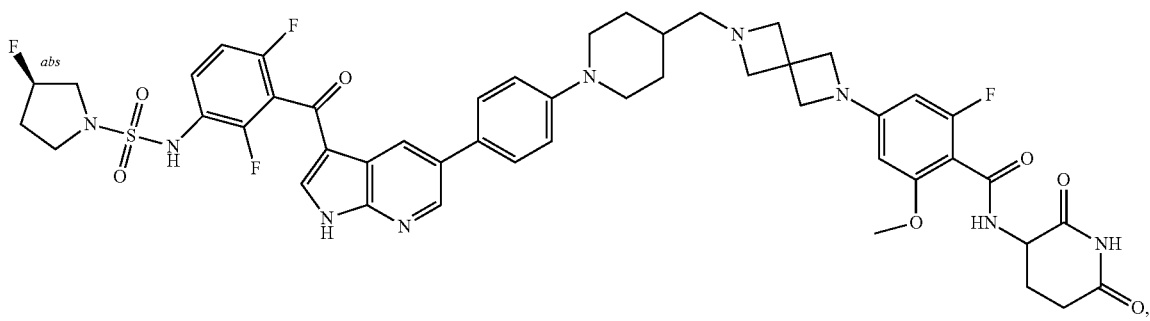
(349)
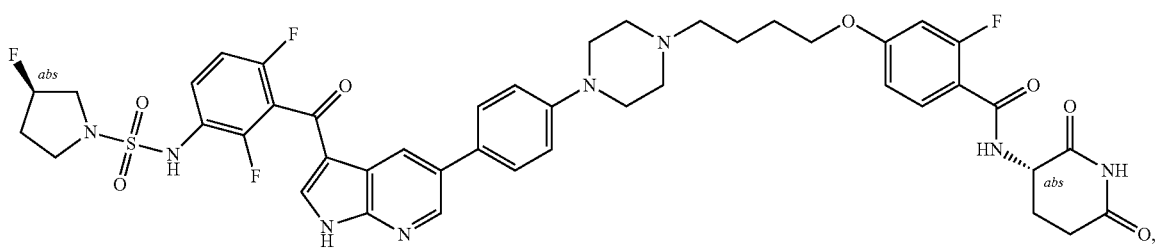
(350)
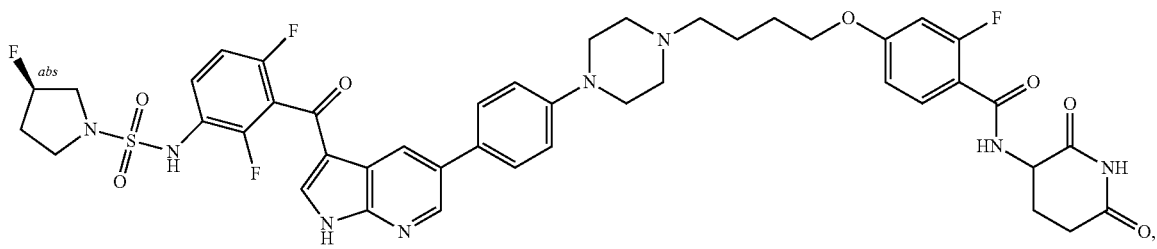
(351)
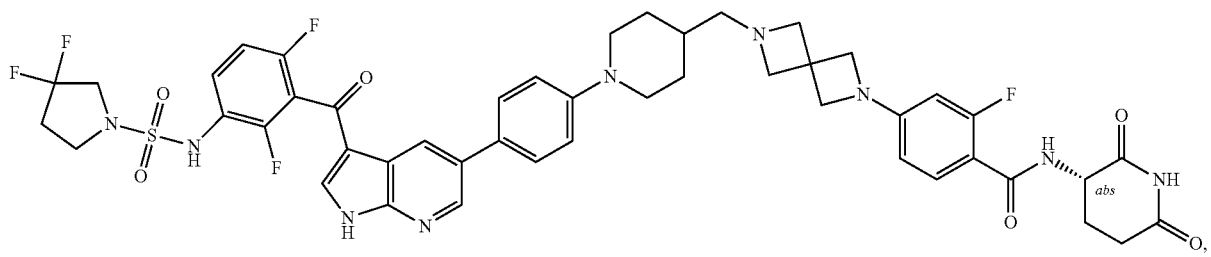

(352)
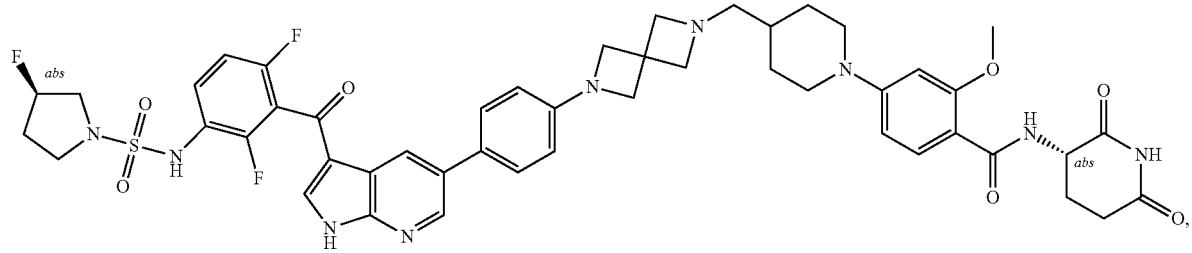
(353)
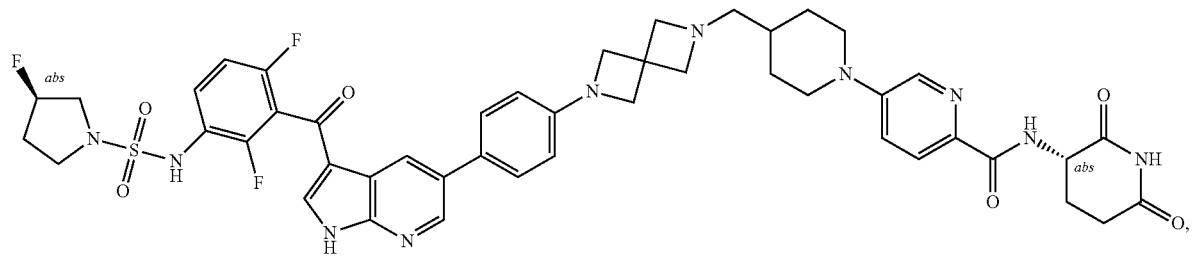
(354)
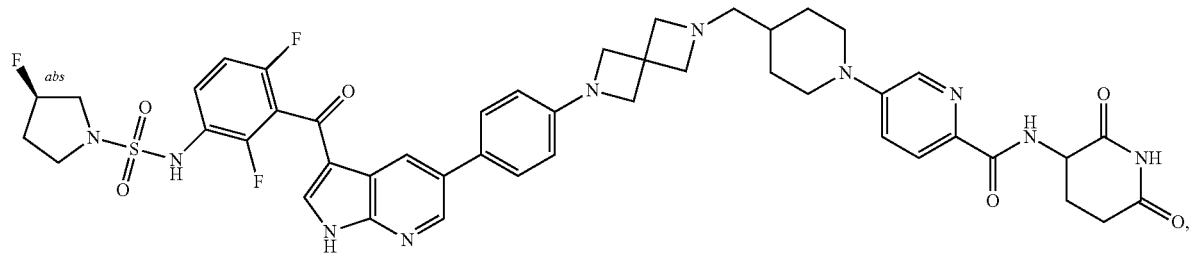
(355)
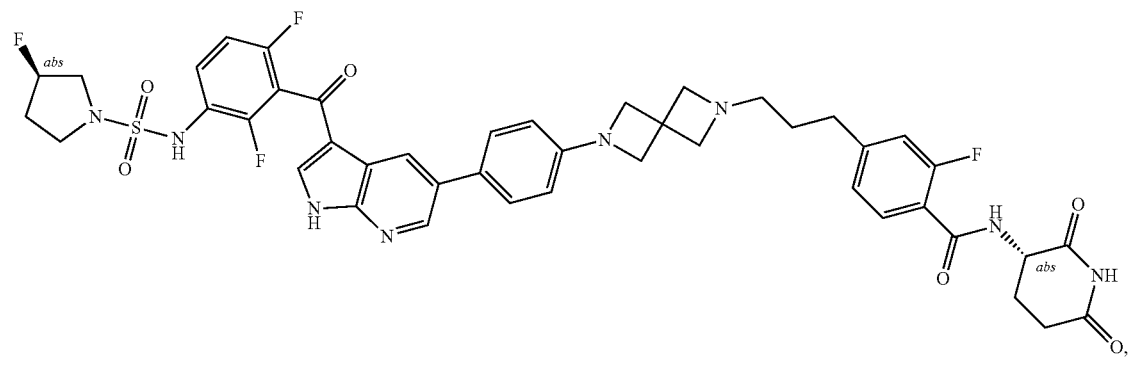
(356)
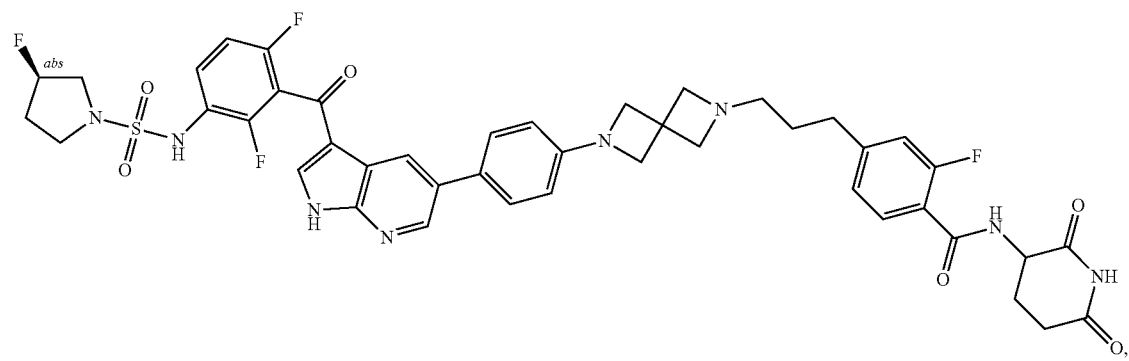

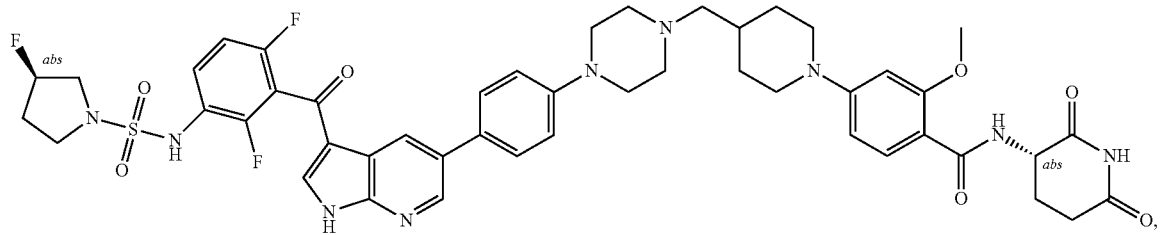
(357)
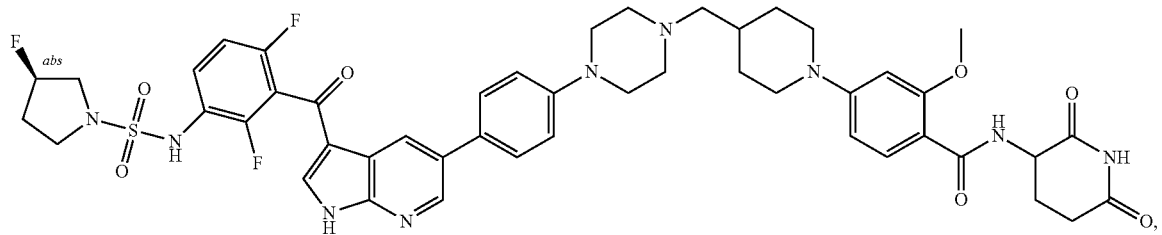
(358)
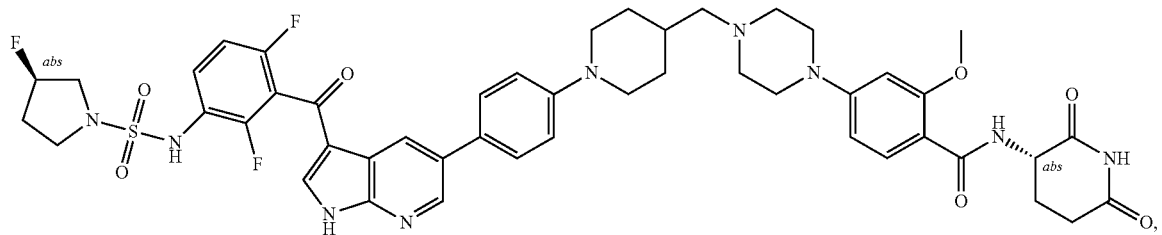
(359)
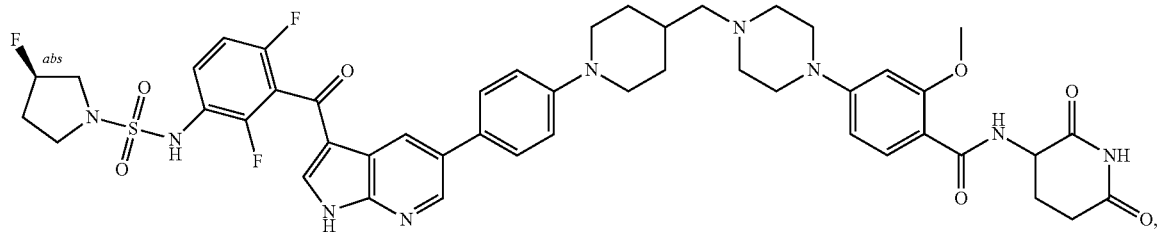
(360)
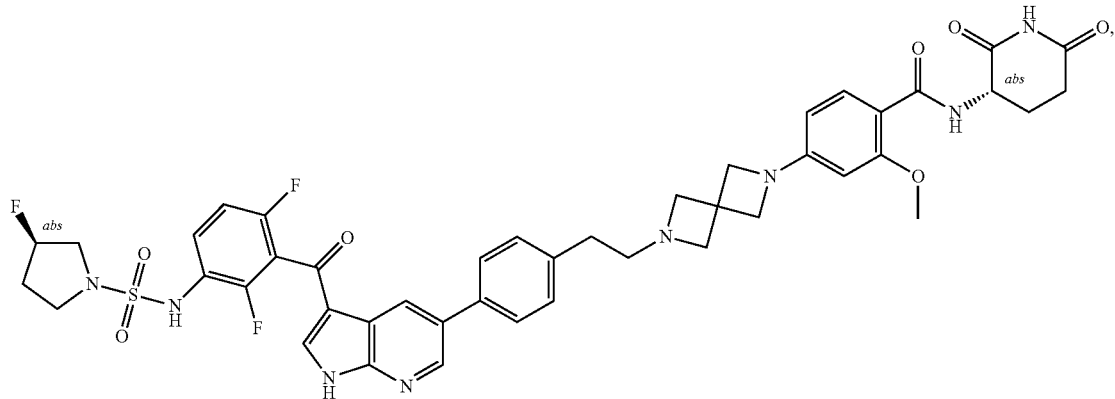
(361)

-continued
(362)
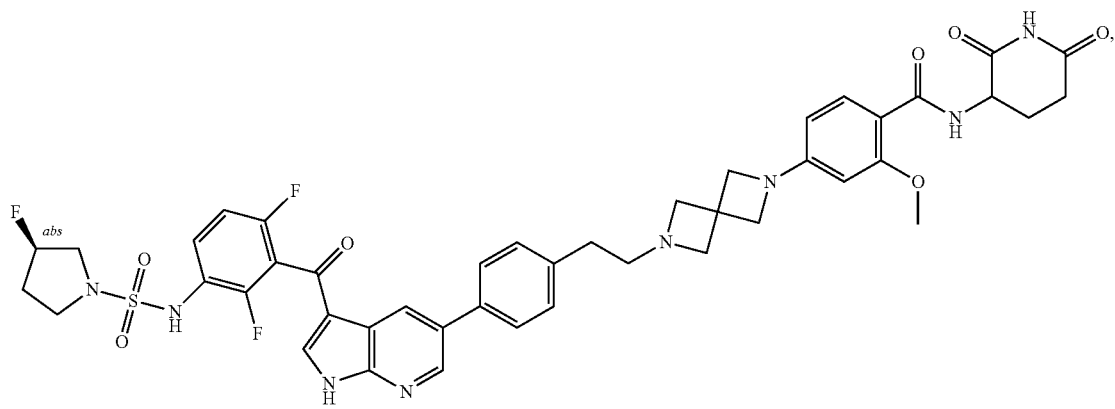
(363)
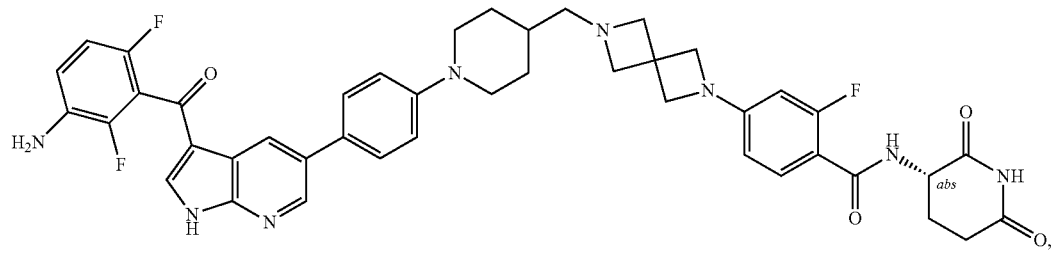
(364)
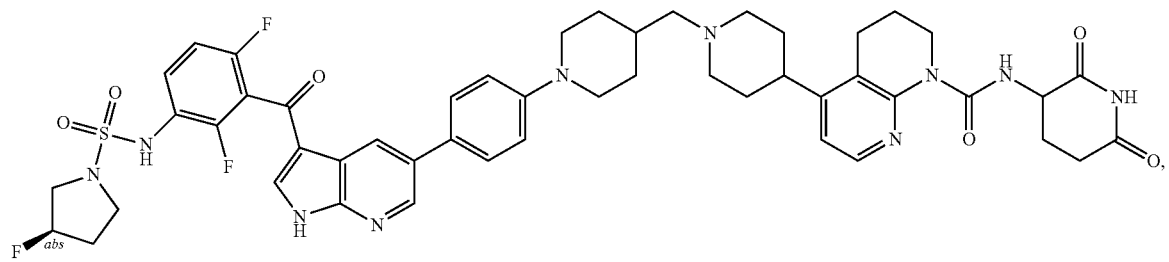
(365)
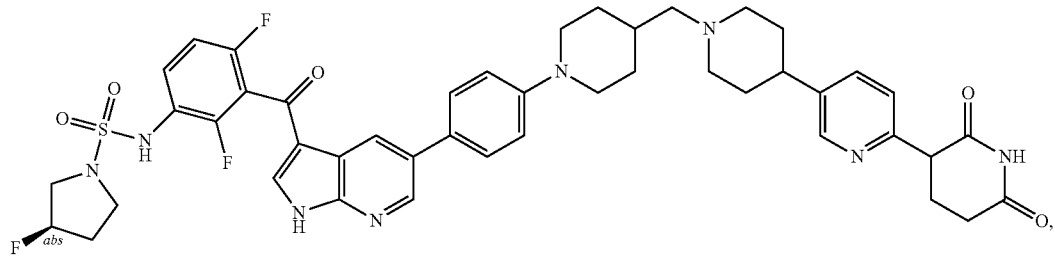
(366)
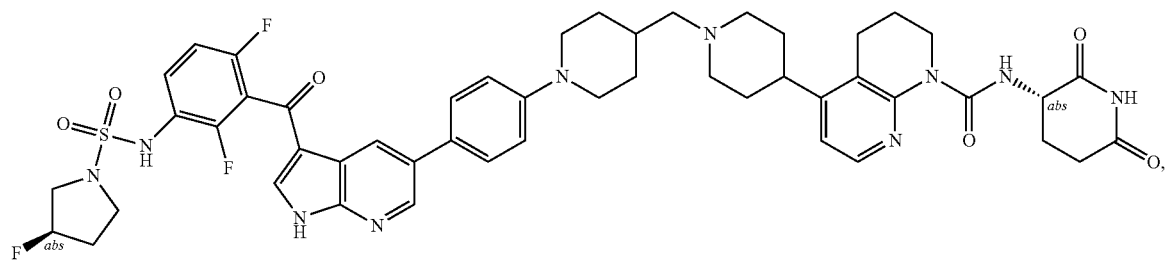

(367)
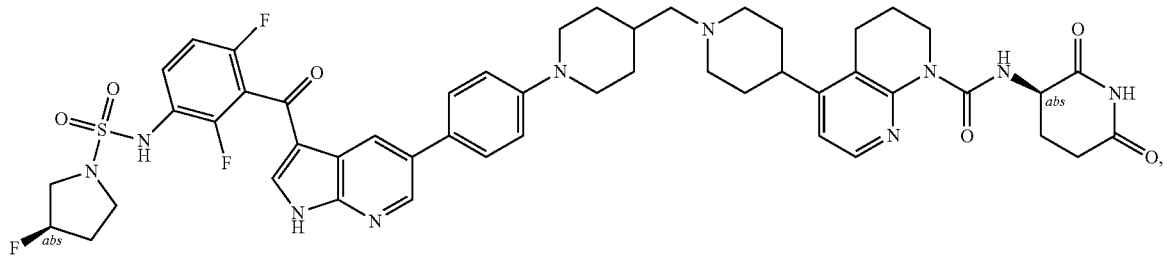
(368)
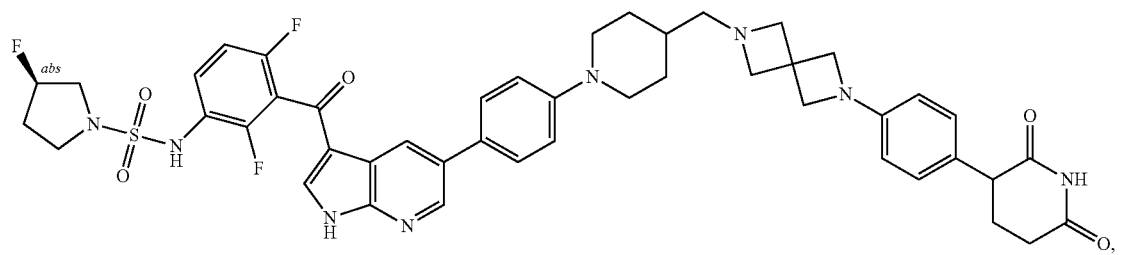
(369)
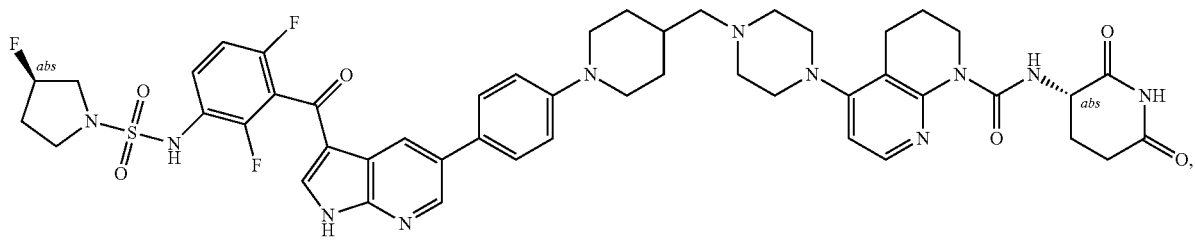
(370)
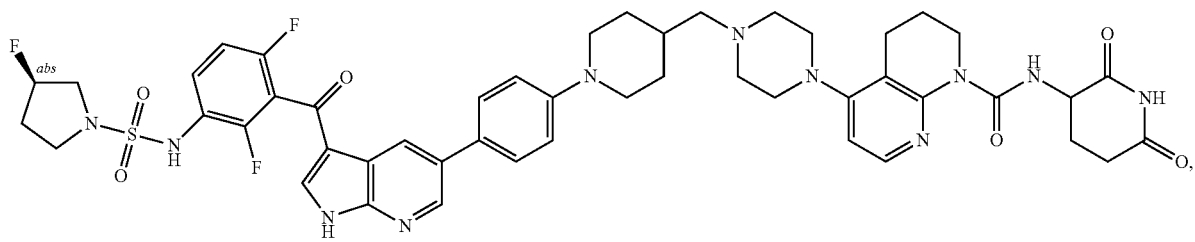
(371)
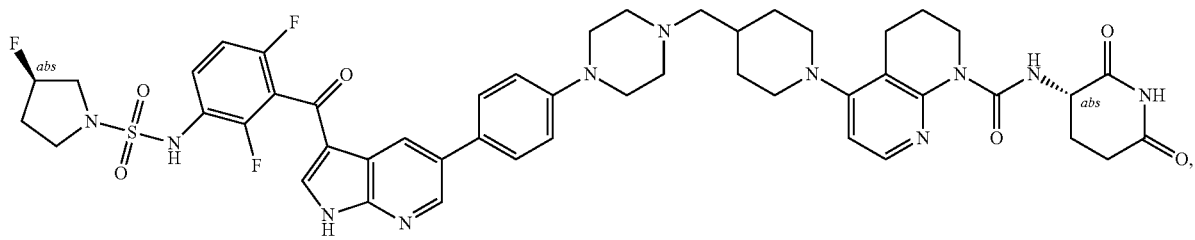
(372)
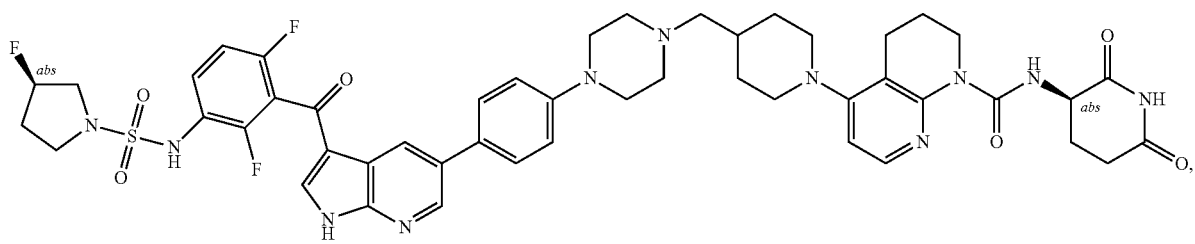

(373)
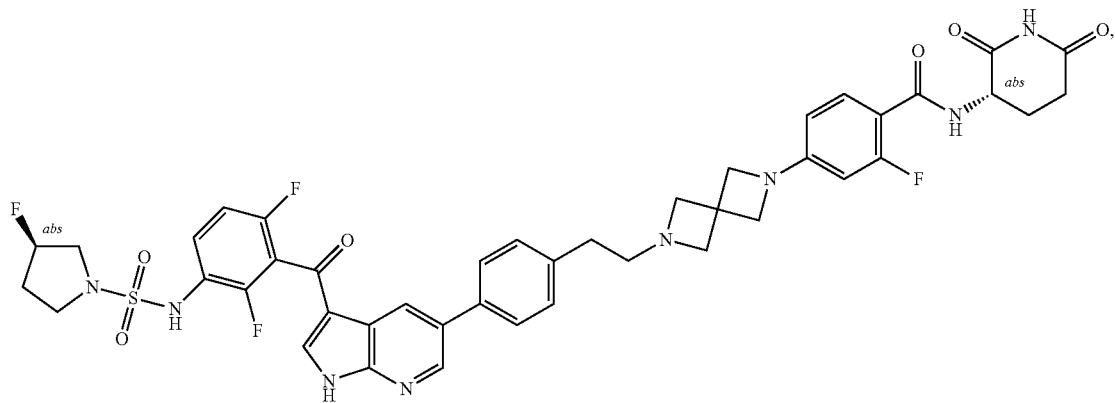
(374)
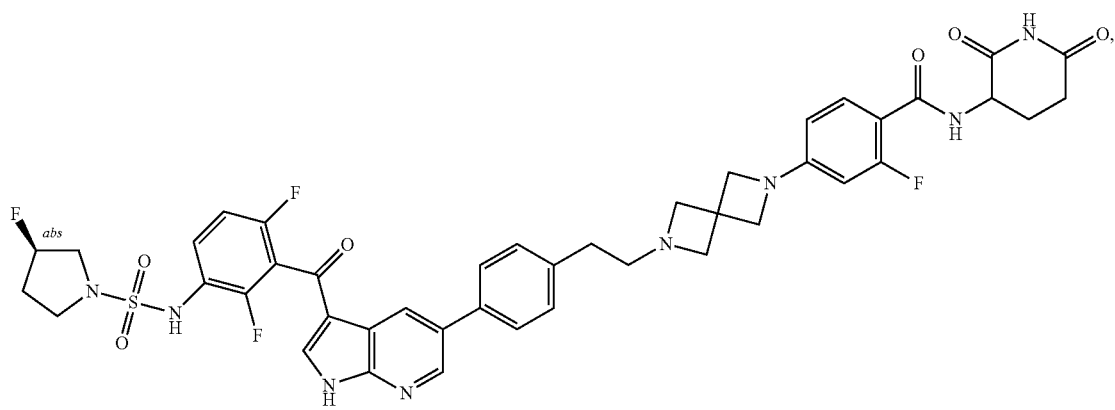
(375)
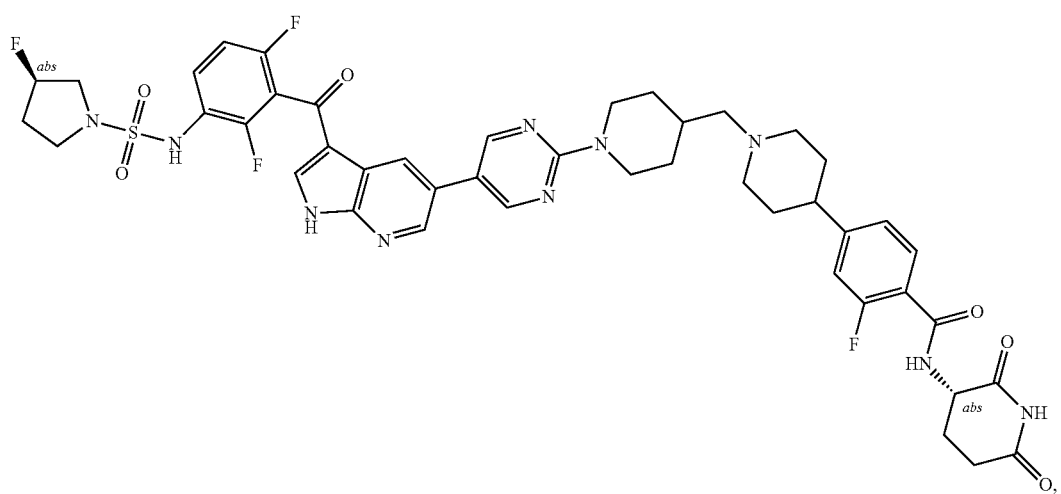

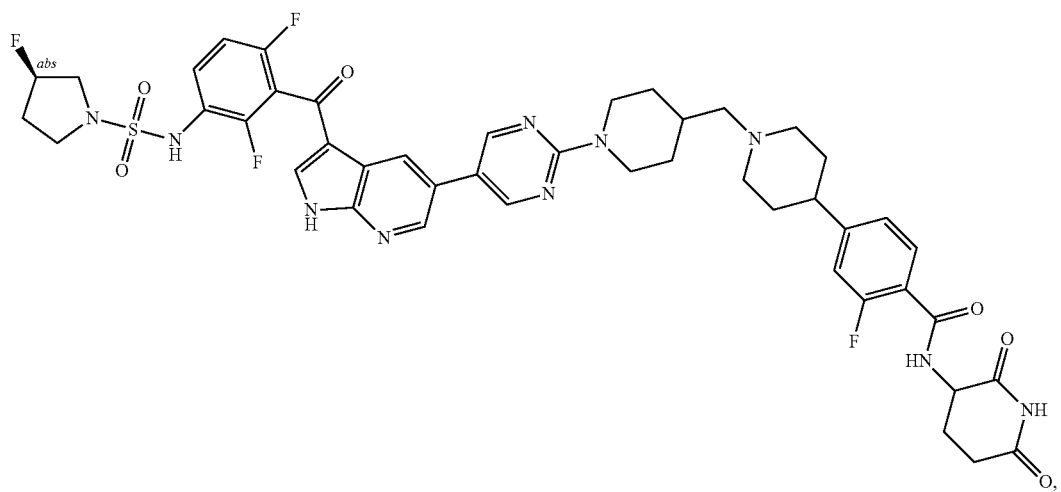
(376)
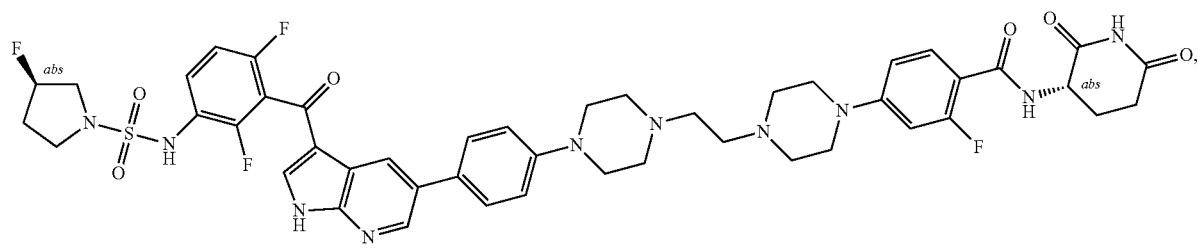
(377)
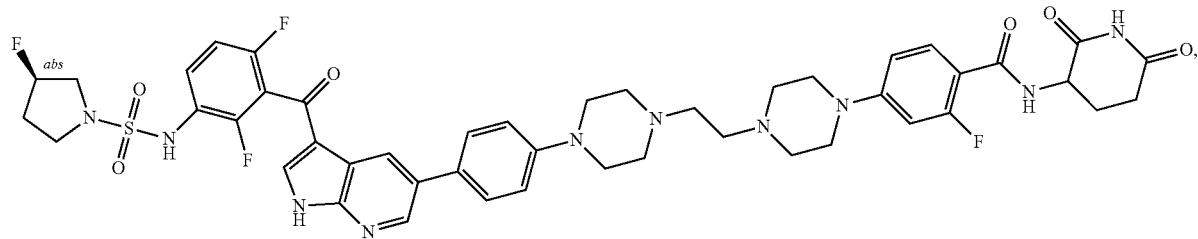
(378)
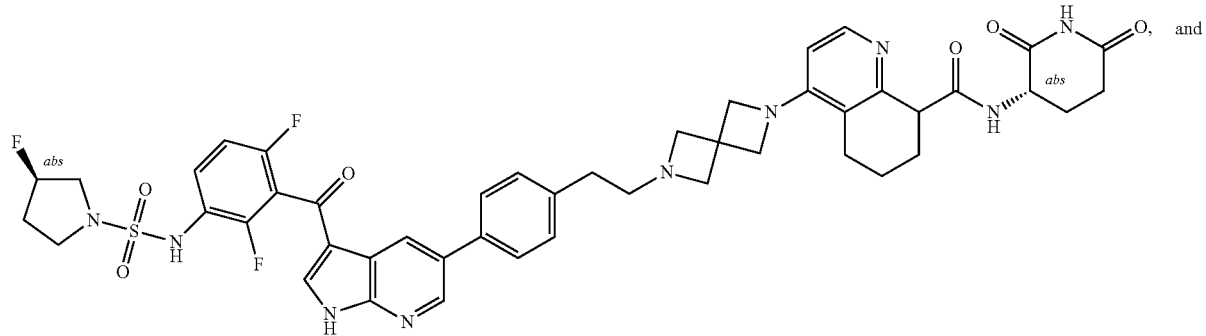
(379)

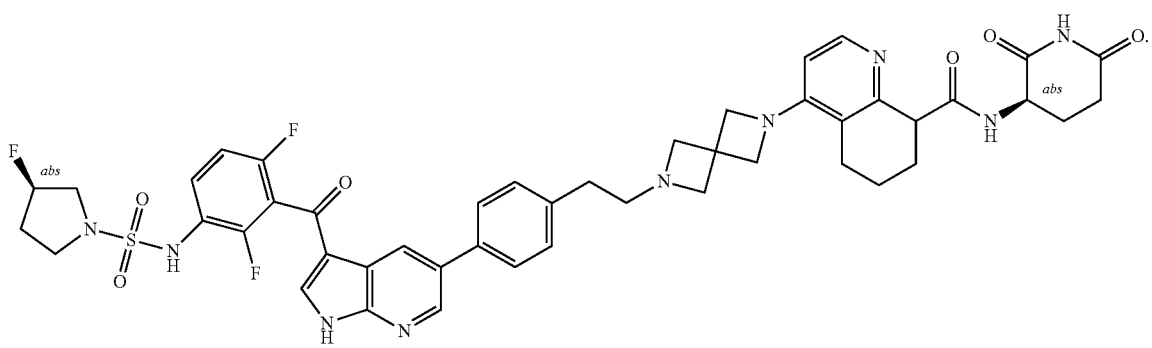
(380)
2. A composition comprising a compound of claim 1, and a pharmaceutically acceptable carrier.
3. The composition of claim 2, wherein the composition further comprises at least one additional bioactive agent.
4. The composition of claim 3, wherein the additional bioactive agent is an anti-cancer agent.
* * * * *

UNITED STATES PATENT AND TRADEMARK OFFICE
CERTIFICATE OF CORRECTION

PATENT NO. : 12,180,193 B2
APPLICATION NO. : 17/459179
DATED : December 31, 2024
INVENTOR(S) : Keith R. Hornberger and Jing Wang Page 1 of 3

It is certified that error appears in the above-identified patent and that said Letters Patent is hereby corrected as shown below:

In the Claims

In Claim 1, Columns 1019-1020, compound number (103), please replace the structure:

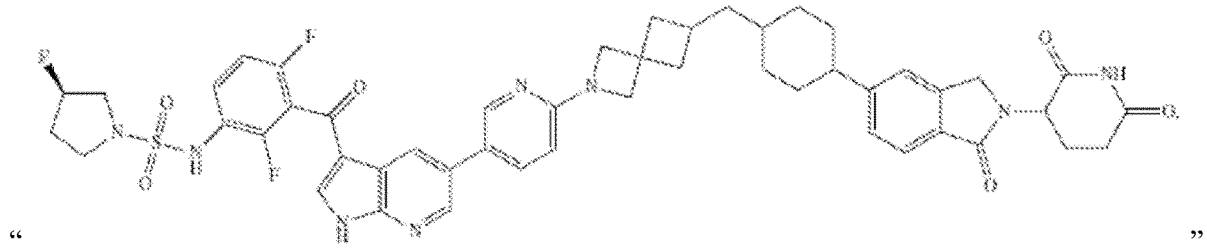

"

With the structure:

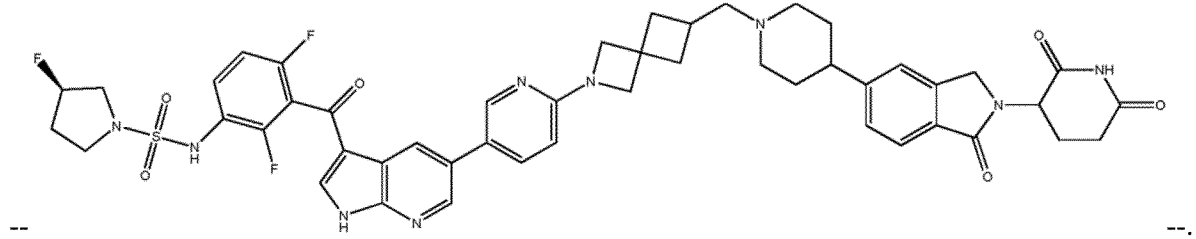

--                                                                                                                                                       --.

In Claim 1, Columns 1041-1042, compound number (151), please replace the structure:

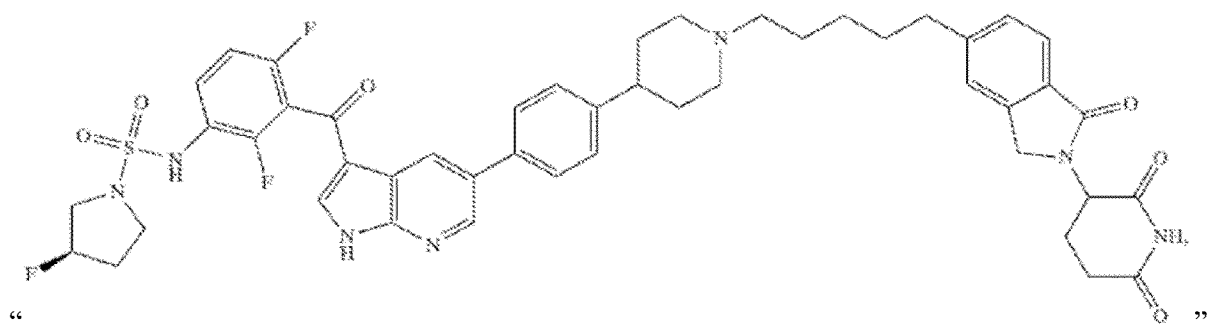

"

Signed and Sealed this
Sixth Day of May, 2025

Coke Morgan Stewart
*Acting Director of the United States Patent and Trademark Office*

CERTIFICATE OF CORRECTION (continued)
U.S. Pat. No. 12,180,193 B2

Page 2 of 3

With the structure:

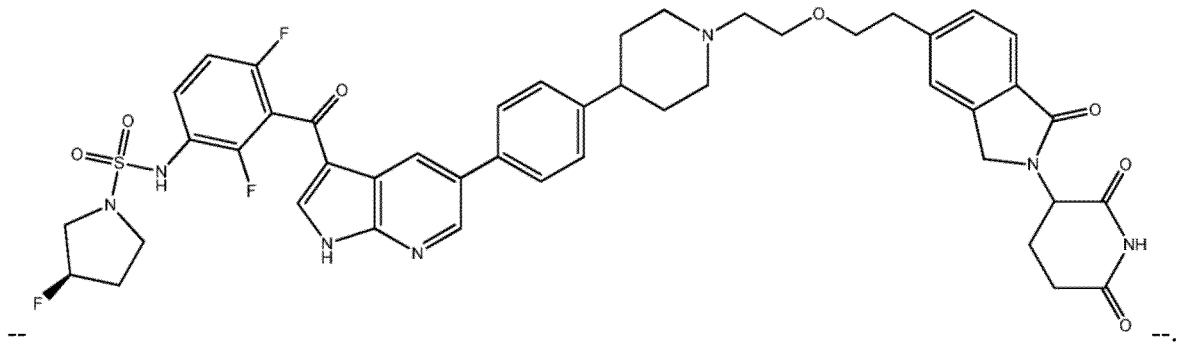

--.

In Claim 1, Columns 1087-1088, compound number (267), please replace the structure:

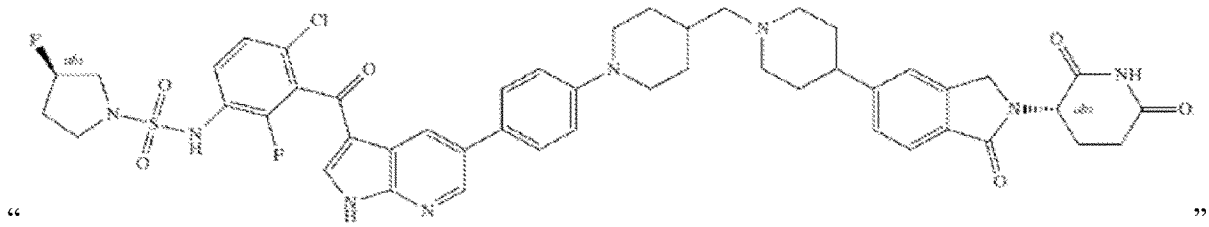

"                                                                                                                              "

With the structure:

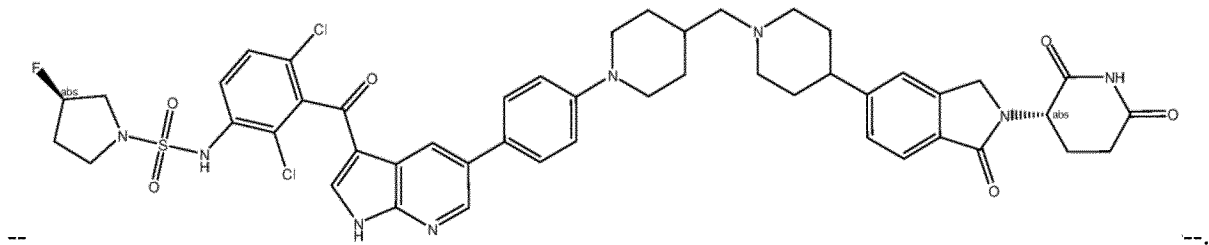

--                                                                                                                              --.

In Claim 1, Columns 1087-1088, compound number (268), please replace the structure:

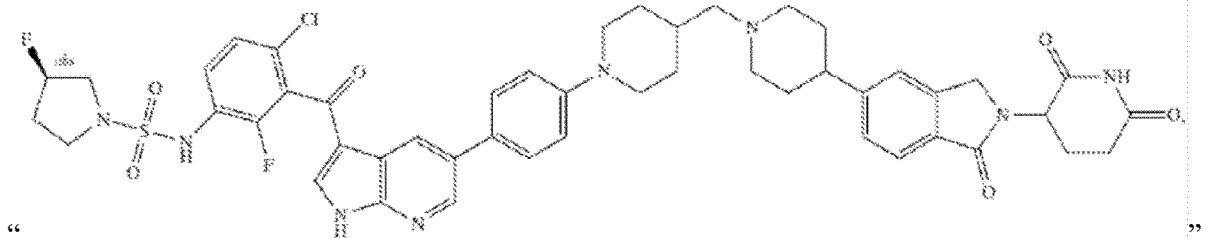

"                                                                                                                              "

With the structure:

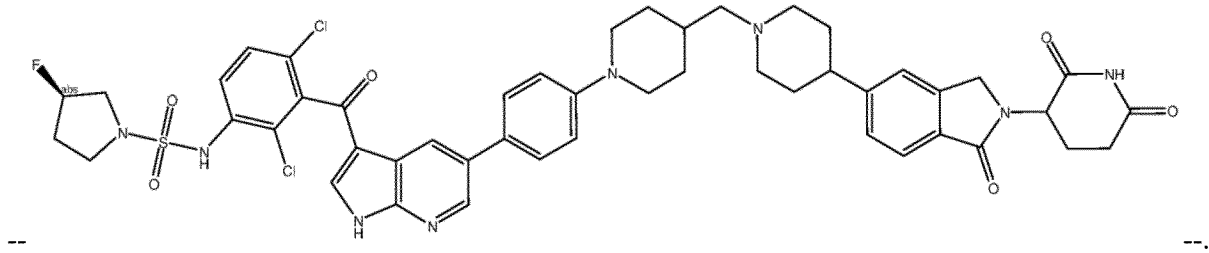

--                                                                                                                              --.

CERTIFICATE OF CORRECTION (continued)
U.S. Pat. No. 12,180,193 B2

In Claim 1, Columns 1095-1096, compound number (292), please replace the structure:

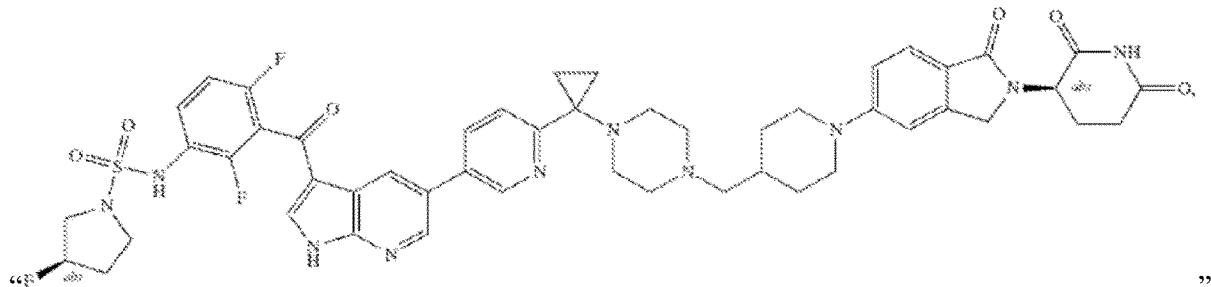

"

With the structure:

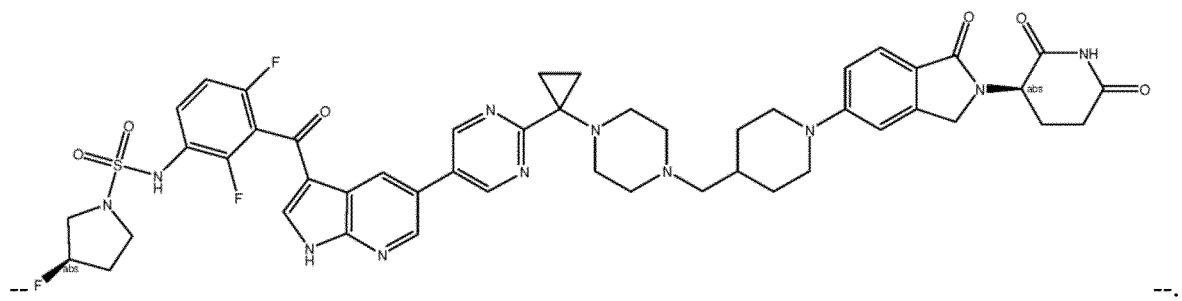

--.

In Claim 1, Columns 1107-1108, compound number (316), please replace the structure:

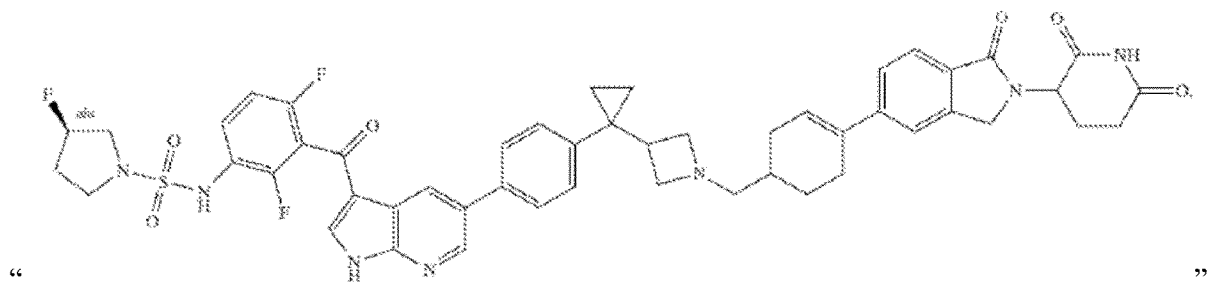

"

With the structure:

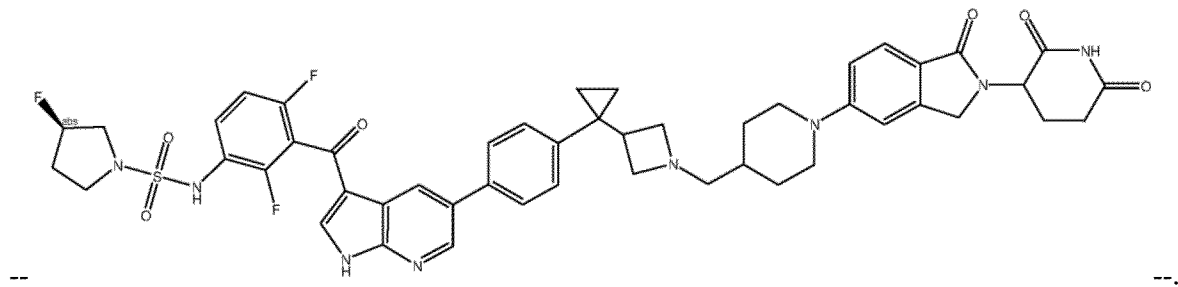

--.